US012471491B2

(12) United States Patent
Jeon et al.

(10) Patent No.: US 12,471,491 B2
(45) Date of Patent: Nov. 11, 2025

(54) HETEROCYCLIC COMPOUND, ORGANIC LIGHT-EMITTING DEVICE INCLUDING HETEROCYCLIC COMPOUND, AND ELECTRONIC APPARATUS INCLUDING ORGANIC LIGHT-EMITTING DEVICE

(71) Applicant: Samsung Electronics Co., Ltd., Suwon-si (KR)

(72) Inventors: Soonok Jeon, Suwon-si (KR); Eunkyung Lee, Seoul (KR); Jong Soo Kim, Hanam-si (KR); Juhyun Kim, Seoul (KR); Sooghang Ihn, Hwaseong-si (KR); Jun Chwae, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 909 days.

(21) Appl. No.: 17/315,629

(22) Filed: May 10, 2021

(65) Prior Publication Data

US 2022/0085297 A1 Mar. 17, 2022

(30) Foreign Application Priority Data

Sep. 10, 2020 (KR) ........................ 10-2020-0116214

(51) Int. Cl.

| | |
|---|---|
| ***H10K 85/60*** | (2023.01) |
| ***C07D 491/048*** | (2006.01) |
| ***C09K 11/06*** | (2006.01) |
| ***H10K 50/11*** | (2023.01) |
| ***H10K 101/10*** | (2023.01) |

(52) U.S. Cl.

CPC ....... *H10K 85/657* (2023.02); *C07D 491/048* (2013.01); *C09K 11/06* (2013.01); *H10K 85/654* (2023.02); *C09K 2211/1018* (2013.01); *H10K 50/11* (2023.02); *H10K 2101/10* (2023.02)

(58) Field of Classification Search

CPC .................................................... H10K 85/654

See application file for complete search history.

(56) References Cited

U.S. PATENT DOCUMENTS

| | | | | |
|---|---|---|---|---|
| 10,547,009 B2 | 1/2020 | Yoshida et al. | | |
| 2015/0053939 A1 | 2/2015 | Adamovich et al. | | |
| 2016/0181546 A1* | 6/2016 | Kang | C09K 11/06 257/40 | |
| 2019/0157603 A1* | 5/2019 | Kim | C07D 491/048 | |
| 2019/0305229 A1* | 10/2019 | Ihn | C07D 209/86 | |
| 2019/0312209 A1* | 10/2019 | Jeon | H10K 85/6572 | |
| 2020/0079760 A1* | 3/2020 | Yang | C07D 417/14 | |
| 2020/0083458 A1* | 3/2020 | Jeon | C07D 495/02 | |
| 2020/0131150 A1* | 4/2020 | Jung | C07D 417/10 | |

FOREIGN PATENT DOCUMENTS

| | | | |
|---|---|---|---|
| CN | 109912564 | A | 6/2019 |
| KR | 1020160126792 | A | 11/2016 |
| KR | 1020200023984 | A | 3/2020 |
| WO | 2016158540 | A1 | 10/2016 |
| WO | 2017043908 | A1 | 3/2017 |
| WO | 2018123924 | A1 | 7/2018 |

OTHER PUBLICATIONS

Jang et al. (Journal of Materials Chemistry C, 2019, 7, 12695) (Year: 2019).*
Machine Translation of WO 2017/043908 (Year: 2024).*
English abstract of KR 10-2016-0126792.
English abstract of WO 2017-043908.
English abstract of WO 2018-123924.
English Translation of Office Action dated Mar. 17, 2025, issued in corresponding KR Patent Application No. 10-2020-0116214, 6 pp.
Office Action dated Mar. 17, 2025, issued in corresponding KR Patent Application No. 10-2020-0116214, 9 pp.

* cited by examiner

*Primary Examiner* — Liam J Heincer
(74) *Attorney, Agent, or Firm* — CANTOR COLBURN LLP

(57) ABSTRACT

Provided are a heterocyclic compound represented by Formula 1, an organic light-emitting device including the heterocyclic compound, and an electronic apparatus including the organic light-emitting device:

Formula 1

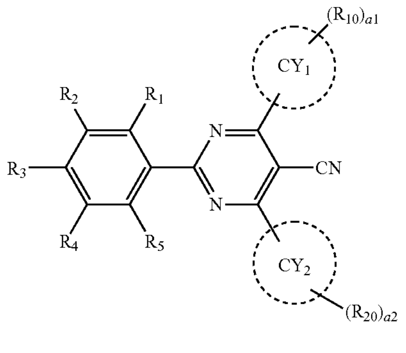

wherein Formula 1 may be understood by referring to the description of Formula 1 provided herein.

17 Claims, 1 Drawing Sheet

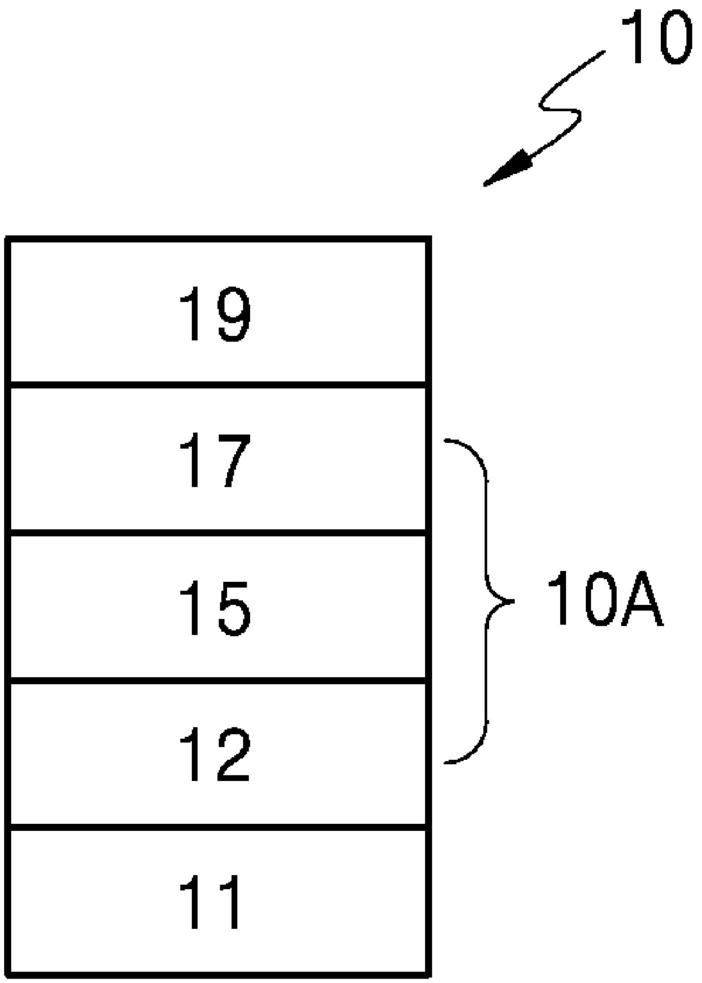
10
19
17
15
12
11
10A

HETEROCYCLIC COMPOUND, ORGANIC LIGHT-EMITTING DEVICE INCLUDING HETEROCYCLIC COMPOUND, AND ELECTRONIC APPARATUS INCLUDING ORGANIC LIGHT-EMITTING DEVICE

CROSS-REFERENCE TO RELATED APPLICATION

This application claims priority under 35 U.S.C. § 119 to Korean Patent Application No. 10-2020-0116214, filed on Sep. 10, 2020, in the Korean Intellectual Property Office, the content of which is incorporated by reference herein in its entirety.

BACKGROUND

1. Field

The present disclosure relates to a heterocyclic compound, an organic light-emitting device including the heterocyclic compound, and an electronic apparatus including the organic light-emitting device.

2. Description of Related Art

Organic light-emitting devices (OLEDs) are self-emissive devices which produce full-color images. In addition, OLEDs have wide viewing angles and exhibit excellent driving voltage and response speed characteristics.

OLEDs include an anode, a cathode, and an organic layer between the anode and the cathode and including an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transit from an excited state to a ground state to thereby generate light.

SUMMARY

Provided are a novel heterocyclic compound, an organic light-emitting device including the heterocyclic compound, and an electronic apparatus including the organic light-emitting device.

Additional aspects will be set forth in part in the description which follows and, in part, will be apparent from the description, or may be learned by practice of the presented embodiments of the disclosure.

According to one or more embodiments, a heterocyclic compound is represented by Formula 1:

Formula 1

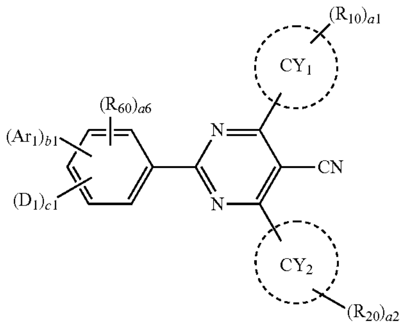

-continued

Formula 2

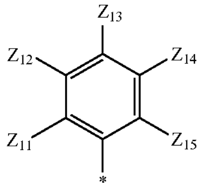

Formula 3

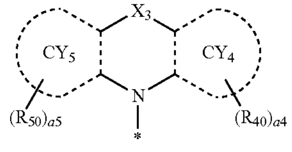

wherein, in Formula 1, $Ar_1$ is a group represented by Formula 2, and b1 is an integer from 1 to 3, in Formula 1, $D_1$ is a group represented by Formula 3, and c1 is an integer from 1 to 3, in Formulae 1 and 3, ring $CY_1$, ring $CY_2$, ring $CY_4$, and ring $CY_5$ are each independently a π electron-rich $C_3$-$C_{60}$ cyclic group, in Formula 3, $X_3$ may be a single bond, O, S, $N(R_{31})$, $C(R_{31})(R_{32})$, $Si(R_{31})(R_{32})$, or $Ge(R_{31})(R_{32})$, in Formulae 1 and 2, $R_{10}$, $R_{20}$, $R_{60}$, and $Z_1$ to $Z_{15}$ are each independently hydrogen, deuterium, —F, —Cl, —Br, —I, $—SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $—N(Q_1)(Q_2)$, $—Si(Q_3)(Q_4)(Q_5)$, $—Ge(Q_3)(Q_4)(Q_5)$, $—B(Q_6)(Q_7)$, $—P(=O)(Q_8)(Q_9)$, or $—P(Q_8)(Q_9)$, in Formula 3, $R_{31}$, $R_{32}$, $R_{40}$, and $R_{50}$ are each independently: hydrogen, deuterium, —F, or a cyano group; or a $C_1$-$C_{10}$ alkyl group, a $C_1$-$C_{10}$ alkoxy group, a π electron-rich $C_3$-$C_{60}$ cyclic group, or a pyridinyl group, each unsubstituted or substituted with deuterium, —F, a cyano group, a $C_1$-$C_{10}$ alkyl group, a $C_1$-$C_{10}$ alkoxy group, a π electron-rich $C_3$-$C_{60}$ cyclic group, a pyridinyl group, a biphenyl group, a terphenyl group, or any combination thereof, in Formulae 1 and 3, a1, a2, a4, and a5 are each independently an integer from 0 to 20, in Formula 1, a6 is an integer from 0 to 3, in Formulae 2 and 3, * indicates a binding site to an adjacent atom, and a substituent of the substituted $C_1$-$C_{10}$ alkyl group, the substituted $C_2$-$C_{60}$ alkenyl group, the substituted $C_2$-$C_{60}$ alkynyl group, the substituted $C_1$-$C_{10}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$Ge(Q_{13})(Q_{14})(Q_{15})$, —$B(Q_{16})(Q_{17})$, —$P(=O)(Q_{18})(Q_{19})$, —$P(Q_{18})(Q_{19})$, or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$Ge(Q_{23})(Q_{24})(Q_{25})$, —$B(Q_{26})(Q_{27})$, —$P(=O)(Q_{28})(Q_{29})$, —$P(Q_{28})(Q_{29})$, or any combination thereof; —$N(Q_{31})(Q_{32})$, —$Si(Q_{33})(Q_{34})(Q_{35})$, —$Ge(Q_{33})(Q_{34})(Q_{35})$, —$B(Q_{36})(Q_{37})$, —$P(=O)(Q_{38})(Q_{39})$, or —$P(Q_{38})(Q_{39})$; or any combination thereof, wherein $Q_1$ to $Q_9$, $Q_{11}$ to $Q_{19}$, $Q_{21}$ to $Q_{29}$, and $Q_{31}$ to $Q_{39}$ are each independently: hydrogen; deuterium; —F; —Cl; —Br; —I; a hydroxyl group; a cyano group; a nitro group; an amidino group; a hydrazine group; a hydrazone group; a carboxylic acid group or a salt thereof; a sulfonic acid group or a salt thereof; a phosphoric acid group or a salt thereof; a $C_1$-$C_{60}$ alkyl group unsubstituted or substituted with deuterium, a $C_1$-$C_{60}$ alkyl group, a $C_6$-$C_{60}$ aryl group, or any combination thereof; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group unsubstituted or substituted with deuterium, a $C_1$-$C_{60}$ alkyl group, a $C_6$-$C_{60}$ aryl group, or any combination thereof; a $C_6$-$C_{60}$ aryloxy group; a $C_6$-$C_{60}$ arylthio group; a $C_1$-$C_{60}$ heteroaryl group; a monovalent non-aromatic condensed polycyclic group; or a monovalent non-aromatic condensed heteropolycyclic group.

According to an aspect of another embodiment, an organic light-emitting device may include: a first electrode; a second electrode; and an organic layer located between the first electrode and the second electrode and including an emission layer and at least one heterocyclic compound.

According to an aspect of another embodiment, an electronic apparatus may include the organic light-emitting device.

BRIEF DESCRIPTION OF THE DRAWINGS

The above and other aspects, features, and advantages of certain embodiments of the disclosure will be more apparent from the following description taken in conjunction with the accompanying drawings, in which:

FIGURE illustrates a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween In contrast, when an element is referred to as being "directly on" another element, there are no intervening elements present It will be understood that, although the terms "first," "second," "third" etc. may be used herein to describe various elements, components, regions, layers and/or sections, these elements, components, regions, layers and/or sections should not be limited by these terms These terms are only used to distinguish one element, component, region, layer or section from another element, component, region, layer or section Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity and are intended to cover both the singular and plural, unless the context clearly indicates otherwise. For example, “an element” has the same meaning as “at least one element,” unless the context clearly indicates otherwise.

“Or” means “and/or.” As used herein, the term “and/or” includes any and all combinations of one or more of the associated listed items It will be further understood that the terms “comprises” and/or “comprising,” or “includes” and/or “including” when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as “lower” or “bottom” and “upper” or “top,” may be used herein to describe one element’s relationship to another element as illustrated in the FIGURES It will be understood that relative terms are intended to encompass different orientations of the device in addition to the orientation depicted in the FIGURES For example, if the device in one of the FIGURES is turned over, elements described as being on the “lower” side of other elements would then be oriented on “upper” sides of the other elements The exemplary term “lower,” can therefore, encompasses both an orientation of “lower” and “upper,” depending on the particular orientation of the FIGURE. Similarly, if the device in one of the FIGURES is turned over, elements described as “below” or “beneath” other elements would then be oriented “above” the other elements The exemplary terms “below” or “beneath” can, therefore, encompass both an orientation of above and below.

“About” or “approximately” as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, “about” can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments As such, variations from the shapes of the illustrations as a result, for example, of manufacturing techniques and/or tolerances, are to be expected Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features Moreover, sharp angles that are illustrated may be rounded Thus, the regions illustrated in the figures are schematic in nature and their shapes are not intended to illustrate the precise shape of a region and are not intended to limit the scope of the present claims.

A heterocyclic compound may be represented by Formula 1:

Formula 1

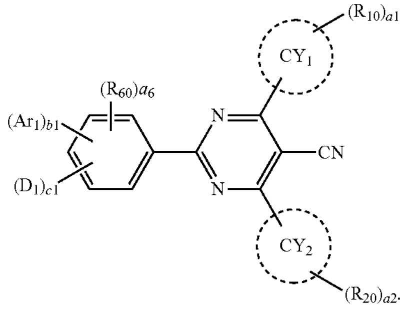

In Formula 1, $Ar_1$ may be a group represented by Formula 2, wherein b1 indicates the number of $Ar_1$(s), and b1 may be an integer from 1 to 3. In some embodiments, b1 may be 1 or 2. When b1 is 2 or greater, at least two $Ar_1$(s) may be identical to different from each other.

In Formula 1, $D_1$ may be a group represented by Formula 3, wherein c1 indicates the number of $D_1$(s), and c1 may be an integer from 1 to 3. In some embodiments, c1 may be 1. When c1 is 2 or greater, at least two $D_1$(s) may be identical to different from each other.

Formula 2

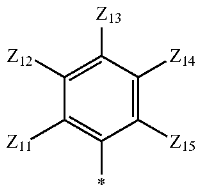

Formula 3

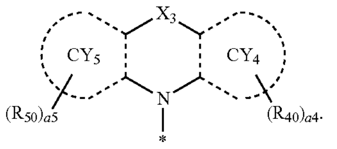

Formulae 2 and 3 may respectively be understood by referring to the descriptions Formulae 2 and 3 provided herein.

In Formulae 1 and 3, ring $CY_1$, ring $CY_2$, ring $CY_4$, and ring $CY_5$ may each independently be a π electron-rich $C_3$-$C_{60}$ cyclic group.

In some embodiments, ring $CY_1$, ring $CY_2$, ring $CY_4$, and ring $CY_5$ in Formulae 1 and 3 may each independently be a benzene group, a naphthalene group, a phenanthrene group, a furan group, a thiophene group, a pyrrole group, a cyclopentene group, a silole group, a germole group, a benzofuran group, a benzothiophene group, an indole group, an indene group, a benzosilole group, a benzogermole group, a dibenzofuran group, a dibenzothiophene group, a carbazole group, a fluorene group, a dibenzosilole group, a dibenzogermole group, an indolodibenzofuran group, an indolodibenzothiophene group, an indolocarbazole group, an indolofluorene group, an indolodibenzosilole group, an indolodibenzogermole group, or a 9,10-dihydroacridine group.

In some embodiments, in Formulae 1 and 3, ring $CY_1$, ring $CY_2$, and ring $CY_4$ may each independently be a benzene group or a naphthalene group.

In one or more embodiments, in Formula 3, ring $CY_5$ may be a benzene group, a naphthalene group, a dibenzofuran group, a dibenzothiophene group, a carbazole group, a fluorene group, a dibenzosilole group, a dibenzogermole group, an indolodibenzofuran group, an indolodibenzothiophene group, an indolocarbazole group, an indolofluorene group, an indolodibenzosilole group, an indolodibenzogermole group, or a 9,10-dihydroacridine group.

In Formula 3, $X_3$ may be a single bond, O, S, $N(R_{31})$, $C(R_{31})(R_{32})$, $Si(R_{31})(R_{32})$, or $Ge(R_{31})(R_{32})$.

In some embodiments, in Formula 3, $X_3$ may be a single bond or $C(R_{31})(R_{32})$.

In Formulae 1 and 2, $R_{10}$, $R_{20}$, $R_{60}$, and $Z_1$ to $Z_{15}$ may each independently be hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$Ge(Q_3)(Q_4)(Q_5)$, —$B(Q_6)(Q_7)$, —$P(=O)(Q_8)(Q_9)$, or —$P(Q_8)(Q_9)$.

For example, in Formulae 1 and 2, $R_{10}$, $R_{20}$, $R_{60}$, and $Z_1$ to $Z_{15}$ may each independently be:

hydrogen, deuterium, —F, or a cyano group; or a $C_1$-$C_{60}$ alkyl group, a $C_1$-$C_{60}$ alkoxy group, a $\pi$ electron-rich $C_3$-$C_{60}$ cyclic group, or a pyridinyl group, each unsubstituted or substituted with deuterium, —F, a cyano group, a $C_1$-$C_{60}$ alkyl group, a $C_1$-$C_{60}$ alkoxy group, a $\pi$ electron-rich $C_3$-$C_{60}$ cyclic group, a pyridinyl group, a biphenyl group, a terphenyl group, or any combination thereof.

In Formula 3, $R_{31}$, $R_{32}$, $R_{40}$, and $R_{50}$ may each independently be: hydrogen, deuterium, —F, or a cyano group; or a $C_1$-$C_{60}$ alkyl group, a $C_1$-$C_{60}$ alkoxy group, a $\pi$ electron-rich $C_3$-$C_{60}$ cyclic group, or a pyridinyl group, each unsubstituted or substituted with deuterium, —F, a cyano group, a $C_1$-$C_{60}$ alkyl group, a $C_1$-$C_{60}$ alkoxy group, a $\pi$ electron-rich $C_3$-$C_{60}$ cyclic group, a pyridinyl group, a biphenyl group, a terphenyl group, or any combination thereof.

In some embodiments, in Formulae 1 to 3, $R_{10}$, $R_{20}$, $R_{31}$, $R_{32}$, $R_{40}$, $R_{50}$, $R_{60}$, and $Z_1$ to $Z_{15}$ may each independently be:

hydrogen, deuterium, —F, or a cyano group; or a $C_1$-$C_{20}$ alkyl group, a phenyl group, a naphthyl group, a phenanthrenyl group, a furanyl group, a thiophenyl group, a pyrrolyl group, a cyclopentenyl group, a silolyl group, a benzofuranyl group, a benzothiophenyl group, an indolyl group, an indenyl group, a benzosilolyl group, a dibenzofuranyl group, a dibenzothiophenyl group, a carbazolyl group, a fluorenyl group, a dibenzosilolyl group, a benzonaphthofuranyl group, a benzonaphthothiophenyl group, a benzocarbazolyl group, a benzofluorenyl group, a benzonaphthosilolyl group, a dinaphthofuranyl group, a dinaphthothiophenyl group, a dibenzocarbazolyl group, a dibenzofluorenyl group, a dinaphthosilolyl group, a pyridinyl group, a biphenyl group, or a terphenyl group, each unsubstituted or substituted with deuterium, —F, a cyano group, a $C_1$-$C_{20}$ alkyl group, a phenyl group, a naphthyl group, a phenanthrenyl group, a furanyl group, a thiophenyl group, a pyrrolyl group, a cyclopentenyl group, a silolyl group, a benzofuranyl group, a benzothiophenyl group, an indolyl group, an indenyl group, a benzosilolyl group, a dibenzofuranyl group, a dibenzothiophenyl group, a carbazolyl group, a fluorenyl group, a dibenzosilolyl group, a benzonaphthofuranyl group, a benzonaphthothiophenyl group, a benzocarbazolyl group, a benzofluorenyl group, a benzonaphthosilolyl group, a dinaphthofuranyl group, a dinaphthothiophenyl group, a dibenzocarbazolyl group, a dibenzofluorenyl group, a dinaphthosilolyl group, a pyridinyl group, a biphenyl group, a terphenyl group, or any combination thereof.

In one or more embodiments, Formulae 1 to 3 may each satisfy at least one of Conditions (1) to (12):

Condition (1)

wherein, $R_{60}$ may include at least one carbon atom, and $R_{60}$ may be bound to a benzene group in Formula 1 via a carbon-carbon bond, Condition (2)

wherein, ring $CY_1$ may include at least one carbon atom, and ring $CY_1$ may be bound to a pyrimidine group in Formula 1 via a carbon-carbon bond, Condition (3)

wherein, $R_{10}$ may include at least one carbon atom, and $R_{10}$ may be bound to ring $CY_1$ in Formula 1 via a carbon-carbon bond, Condition (4)

wherein, ring $CY_2$ may include at least one carbon atom, and ring $CY_2$ may be bound to a pyrimidine group in Formula 1 via a carbon-carbon bond, Condition (5)

wherein, $R_{20}$ may include at least one carbon atom, and $R_{20}$ may be bound to ring $CY_2$ in Formula 1 via a carbon-carbon bond, Condition (6)

wherein, $Z_1$ may include at least one carbon atom, and $Z_{11}$ may be bound to a benzene group in Formula 2 via a carbon-carbon bond, Condition (7)

wherein, $Z_{12}$ may include at least one carbon atom, and $Z_{12}$ may be bound to a benzene group in Formula 2 via a carbon-carbon bond, Condition (8)

wherein, $Z_{13}$ may include at least one carbon atom, and $Z_{13}$ may be bound to a benzene group in Formula 2 via a carbon-carbon bond, Condition (9)

wherein, $Z_{14}$ may include at least one carbon atom, and $Z_{14}$ may be bound to a benzene group in Formula 2 via a carbon-carbon bond, Condition (10)

wherein, $Z_{15}$ may include at least one carbon atom, and $Z_{15}$ may be bound to a benzene group in Formula 2 via a carbon-carbon bond, Condition (11)

wherein, $R_{40}$ may include at least one carbon atom, and $R_{40}$ may be bound to ring $CY_4$ in Formula 3 via a carbon-carbon bond, and Condition (12)

wherein, $R_{60}$ may include at least one carbon atom, and $R_{60}$ may be bound to ring $CY_5$ in Formula 1 via a carbon-carbon bond.

In one or more embodiments, in Formula 3, $R_{50}$ may include at least one nitrogen atom, and the nitrogen atom in $R_{50}$ may be bound to a carbon atom in ring $CY_5$ in Formula 1 via a nitrogen-carbon bond.

In Formulae 1 and 3, a1, a2, a4, and a5 may respectively indicate the number of $R_{10}$(s), $R_{20}$(s), $R_{40}$(s), and $R_{60}$(s), and a1, a2, a4, and a5 may each independently be an integer from 0 to 20. When a1 is 2 or greater, at least two $R_{10}$(s) may be identical to or different from each other, when a2 is 2 or greater, at least two $R_{20}$(s) may be identical to or different from each other, when a4 is 2 is or greater, at least two $R_{40}$(s) may be identical to or different from each other, and when a5 is 20 is or greater, at least two $R_{50}$(s) may be identical to or different from each other. For example, in Formula 1, a1 and a2 may each independently be an integer from 0 to 5, and in Formula 3, a4 and a5 may each independently be an integer from 0 to 4.

In Formula 1, a6 indicates the number of $R_{60}$(s), and a6 may be an integer from 0 to 3. When a6 is an integer of 2 or greater, at least two $R_{60}$(s) may be identical to or different from each other.

In Formulae 2 and 3, * indicates a binding site to an adjacent atom.

In some embodiments, a group represented by

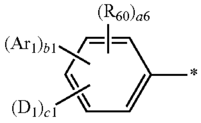

in Formula 1 may be represented by

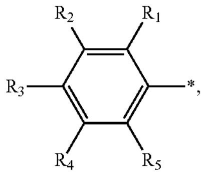

at least one of $R_1$ to $R_5$ may each be $Ar_1$, and the others in $R_1$ to $R_5$ other than $Ar_1$ may each be $D_1$, wherein the others in $R_1$ to $R_5$ other than $Ar_1$ and $D_1$ may each be understood by referring to the description of $R_{60}$ provided herein.

In an embodiment, a group represented by

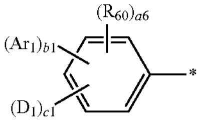

in Formula 1 may be represented by

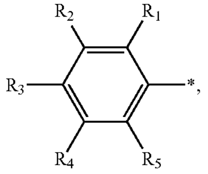

one, two, or three of $R_1$ to $R_5$ may each be $Ar_1$, one, two, or three of $R_1$ to $R_5$ other than $Ar_1$ may each be $D_1$, and one, two, or three of $R_1$ to $R_5$ other than $Ar_1$ and $D_1$ may each be understood by referring to the description of $R_{60}$, provided that a compound that satisfies Condition A, Condition B, and Condition C simultaneously is excluded from the heterocyclic compound represented by Formula 1:

Condition A wherein, $R_2$ may be $Ar_1$,

Condition B wherein, $R_4$ may be $D_1$, and

Condition C wherein, $R_1$, $R_3$, and $R_5$ may each be hydrogen.

In one or more embodiments, the group represented by

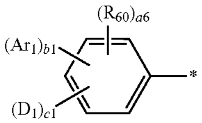

in Formula 1 may be represented by

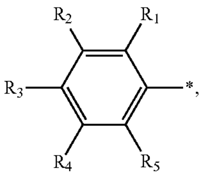

wherein $R_1$ may be $Ar_1$, and $R_4$ may be $D_1$;

$R_2$ may be $Ar_2$, and $R_5$ may be $D_1$; or $R_2$ and $R_4$ may each be $Ar_1$, $R_2$ and $R_4$ may be identical to or different from each other, and $R_3$ may be $D_1$.

In one or more embodiments, a group represented by

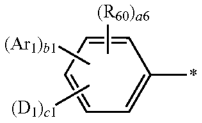

in Formula 1 may be a group represented by one of Formulae 1-1 to 1-25:

1-1

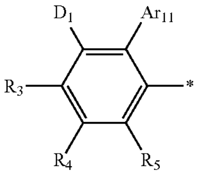

1-2

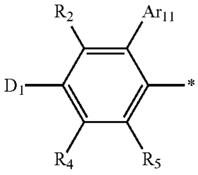

-continued
1-3
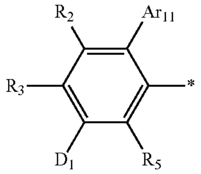
1-4
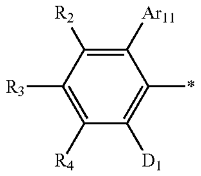
1-5
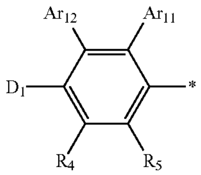
1-6
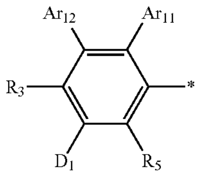
1-7
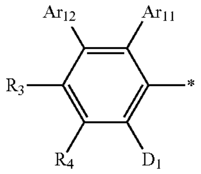
1-8
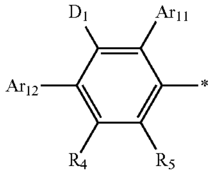
1-9
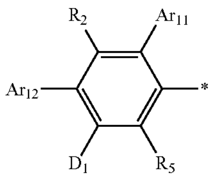
1-10
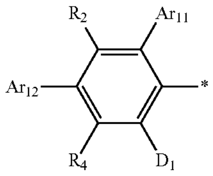
-continued
1-11
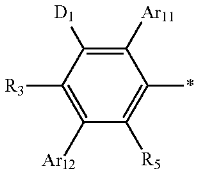
1-12
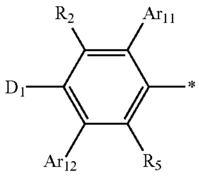
1-13
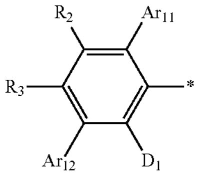
1-14
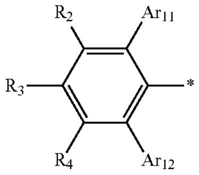
1-15
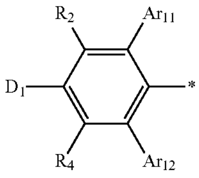
1-16
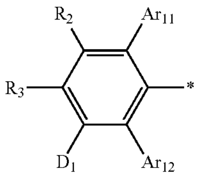
1-17
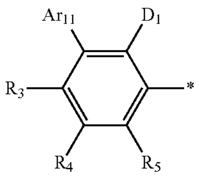
1-18
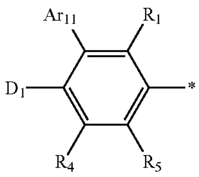

-continued 1-19

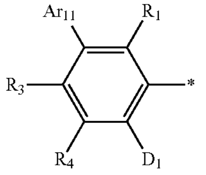

1-20

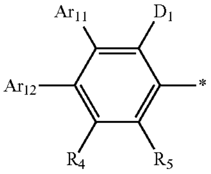

1-21

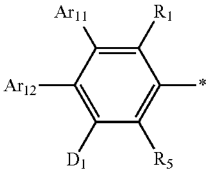

1-22

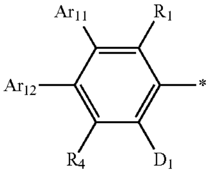

1-23

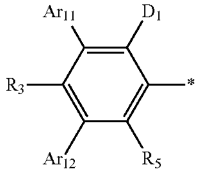

1-24

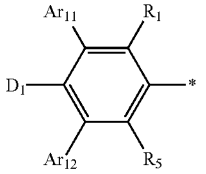

1-25

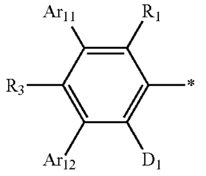

wherein, in Formulae 1-1 to 1-25, $D_1$ may be understood by referring to the description of $D_1$ provided herein, $R_1$ to $R_5$ may each be understood by referring to the description of $R_{50}$ provided herein, $Ar_{11}$ and $Ar_{12}$ may each be understood by referring to the description of $Ar_1$ provided herein, and

* indicates a binding site to an adjacent atom.

For example, in Formulae 1-1 to 1-25, $R_1$ to $R_5$ may each independently be hydrogen, deuterium, —F, a cyano group or a $C_1$-$C_{60}$ alkyl group.

In some embodiments, a group represented by

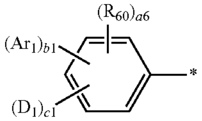

in Formula 1 may be represented by Formula 1-3, 1-19, or 1-24.

In one or more embodiments, the group represented by Formula 3 may be represented by one of Formulae 3-1 to 3-7:

3-1

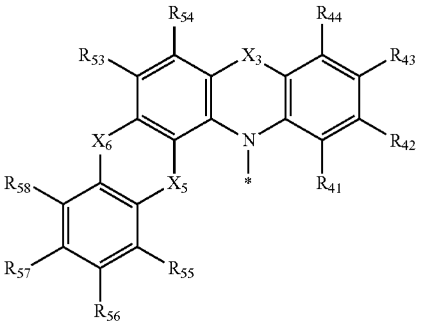

3-2

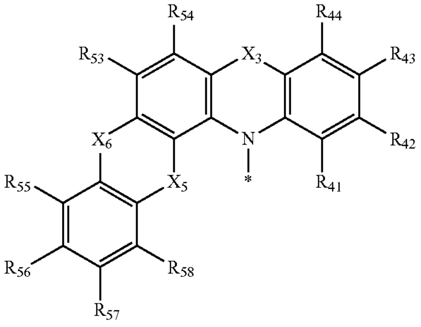

3-3

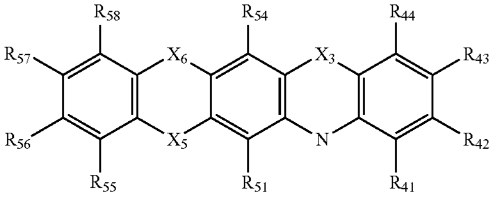

3-4

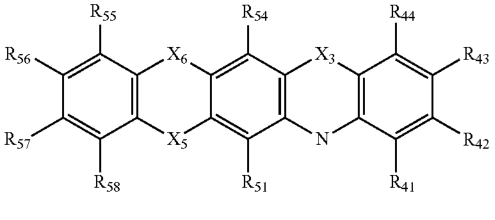

-continued 3-5

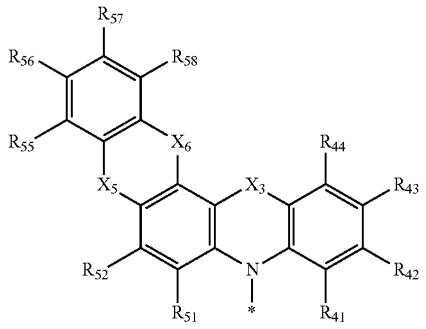

3-6

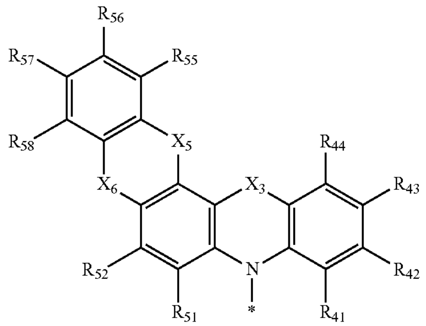

3-7

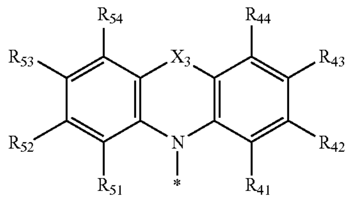

wherein, in Formulae 3-1 to 3-7, $X_3$ may be understood by referring to the description of $X_3$ provided herein, $X_5$ may be O, S, $N(R_{59})$, $C(R_{59a})(R_{59b})$, $Si(R_{59a})(R_{59b})$, or $Ge(R_{59a})(R_{59b})$, $X_6$ may be a single bond, O, S, $N(R_{59c})$, $C(R_{59d})(R_{59e})$, $Si(R_{59d})(R_{59e})$, or $Ge(R_{59a})(R_{59b})$, $R_{41}$ to $R_{44}$ may each be understood by referring to the description of $R_{40}$ provided herein, $R_{51}$ to $R_{59}$ and $R_{59a}$ to $R_{59e}$ may each be understood by referring to the description of $R_{50}$ provided herein,

* indicates a binding site to an adjacent atom.

For example, $X_6$ may be a single bond or $C(R_{59d})(R_{59e})$.

In one or more embodiments, the heterocyclic compound represented by Formula 1 may be any one of Compounds 1 to 238:

1

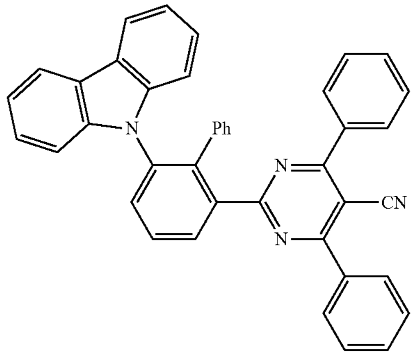

2

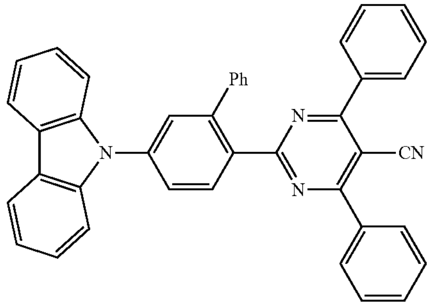

3

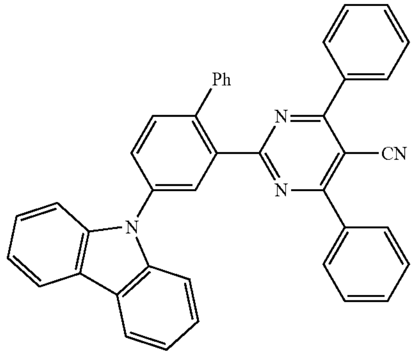

4

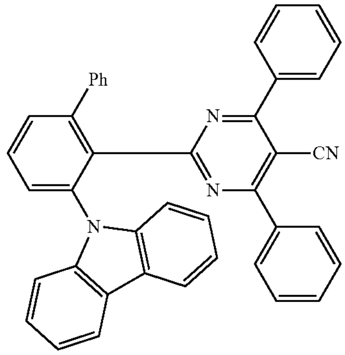

-continued
5
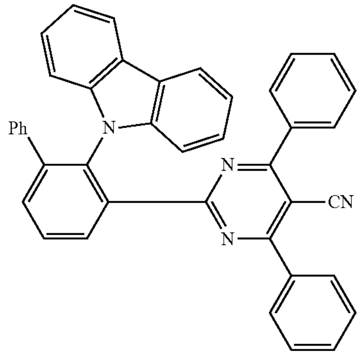
6
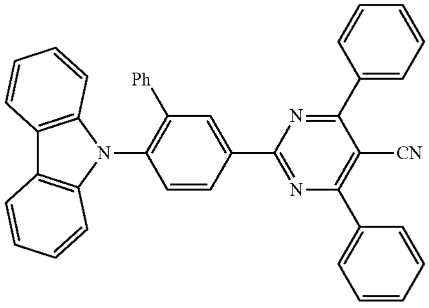
7
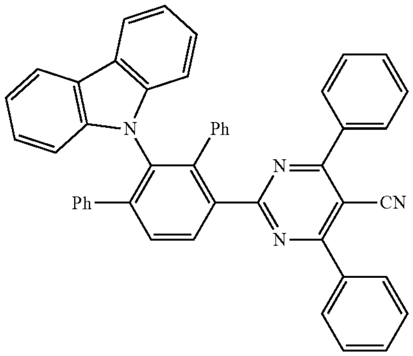
8
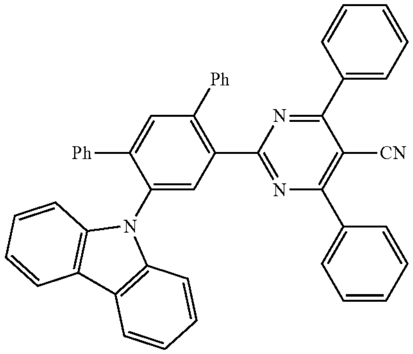
-continued
9
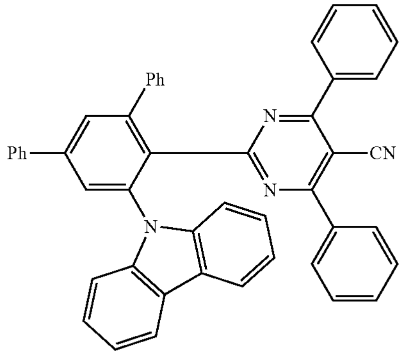
10
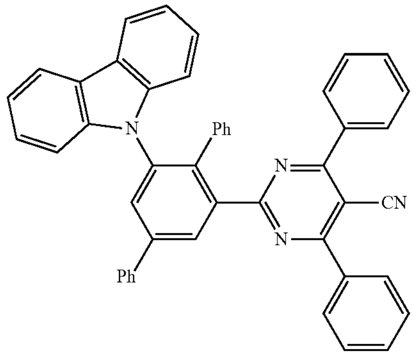
11
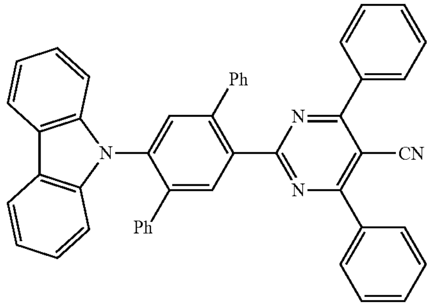
12
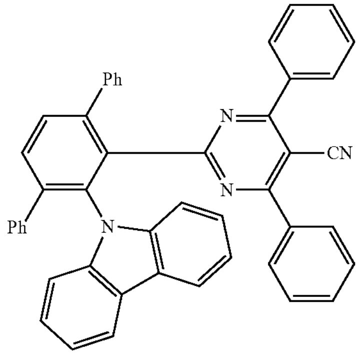

-continued
13
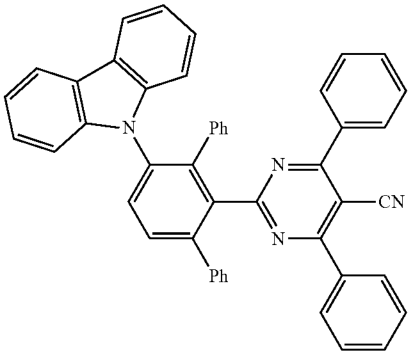
14
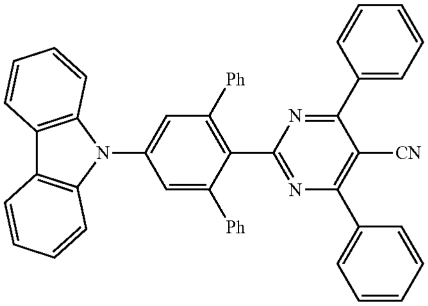
15
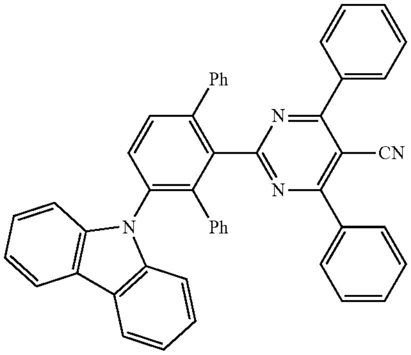
16
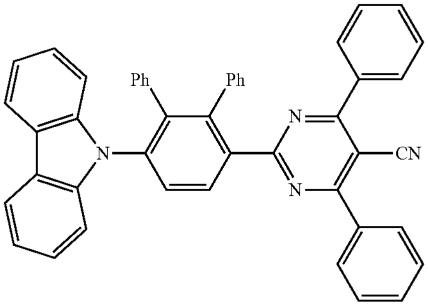
-continued
17
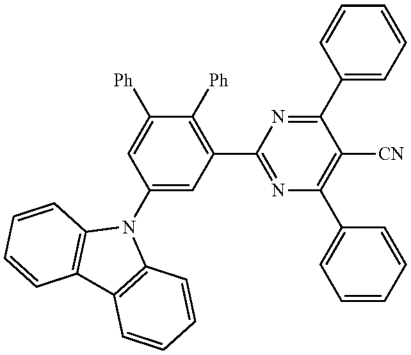
18
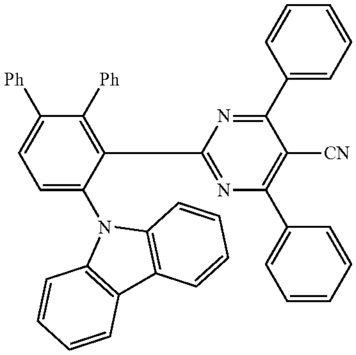
19
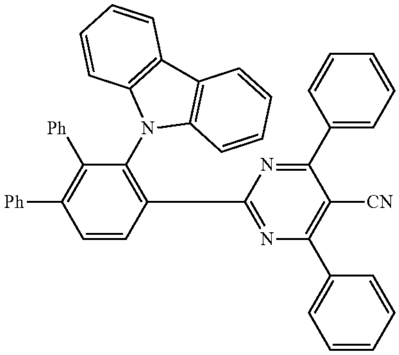
20
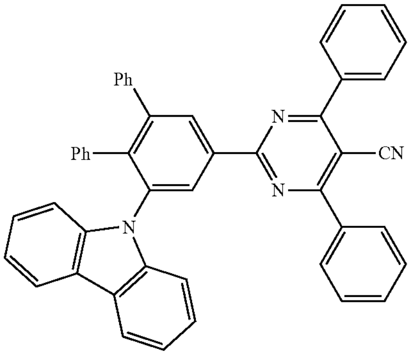

-continued
21
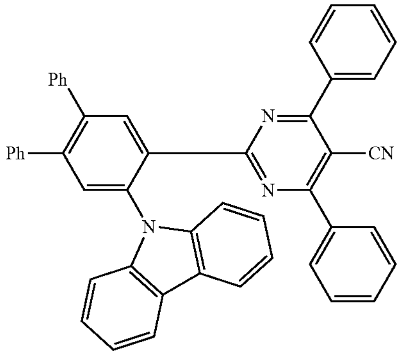
22
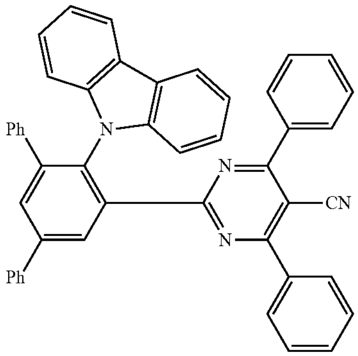
23
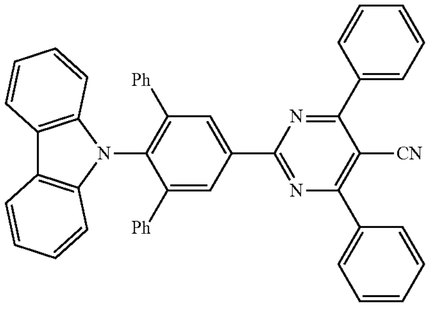
24
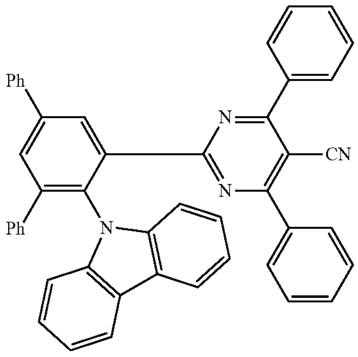
-continued
25
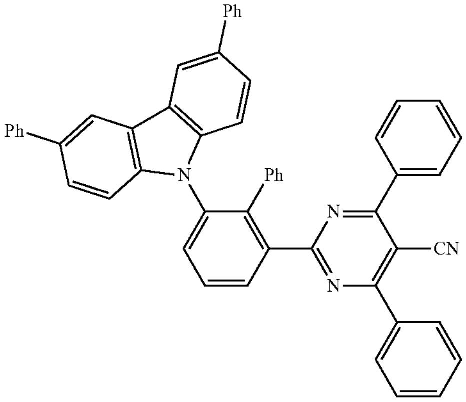
26
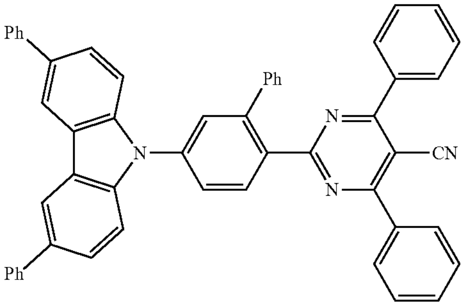
27
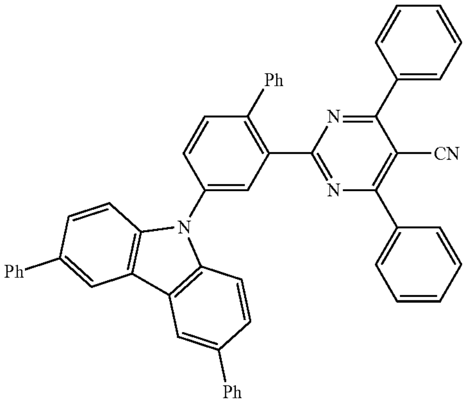
28
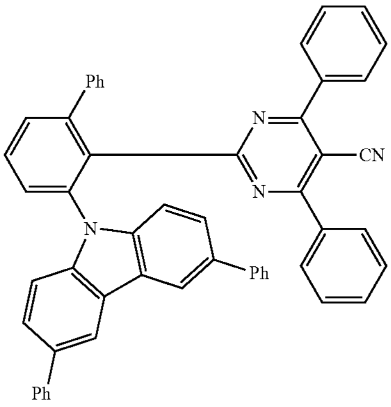

-continued
29
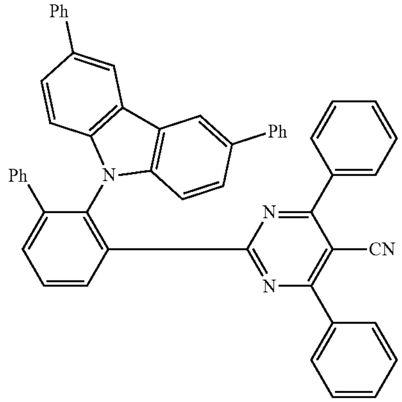
30
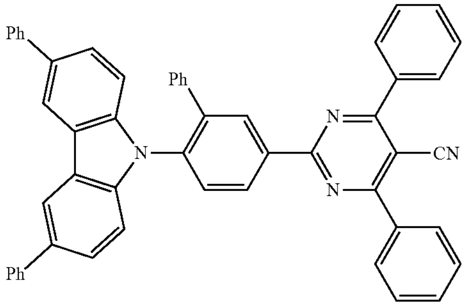
31
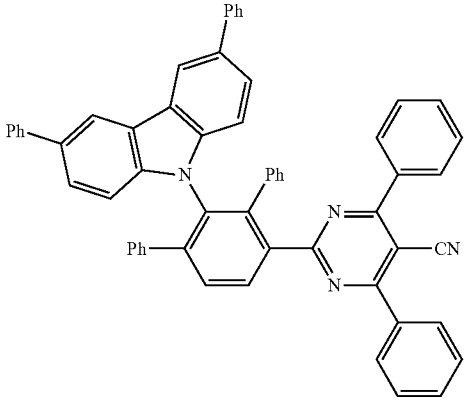
32
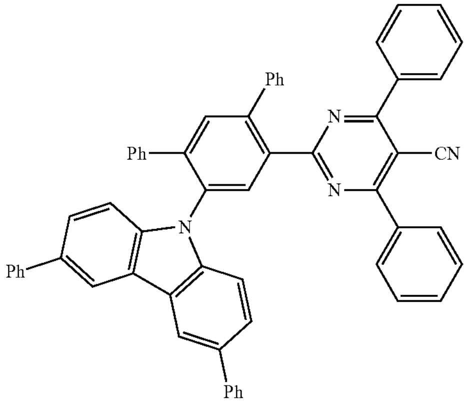
-continued
33
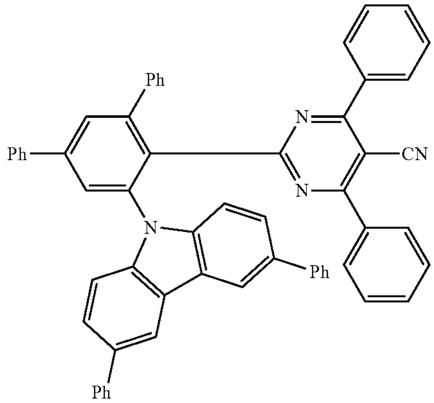
34
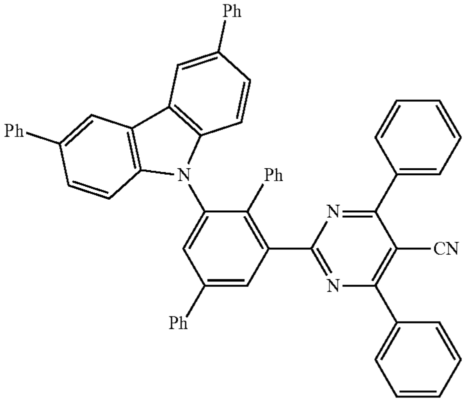
35
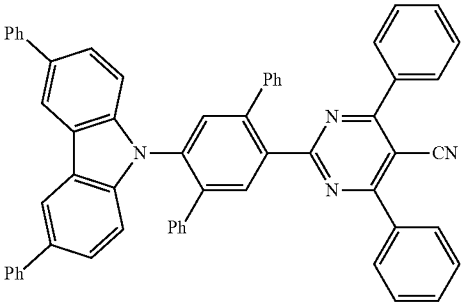
36
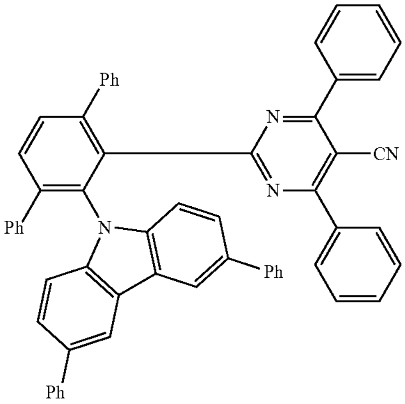

-continued
37
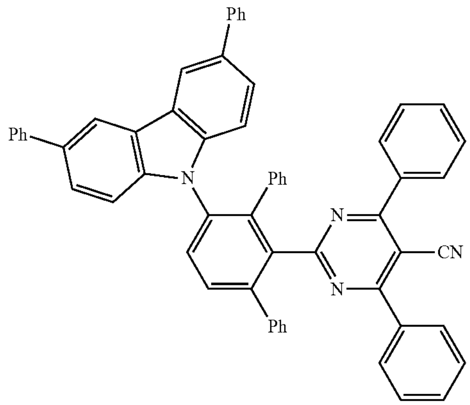
38
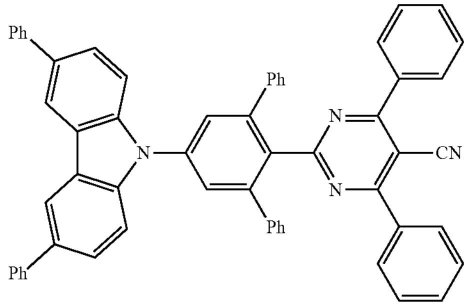
39
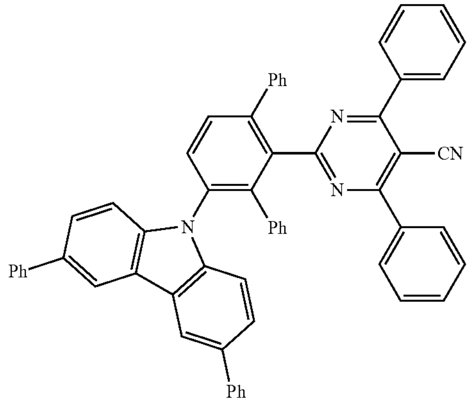
41
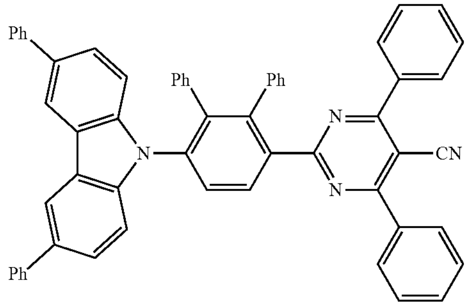
-continued
42
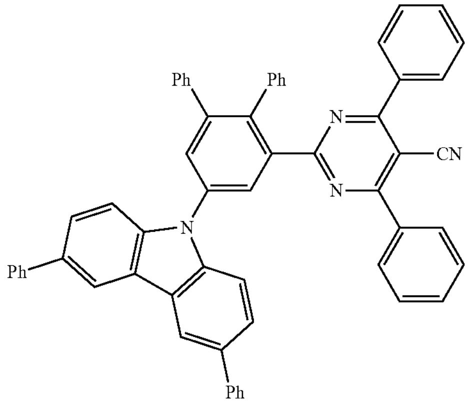
43
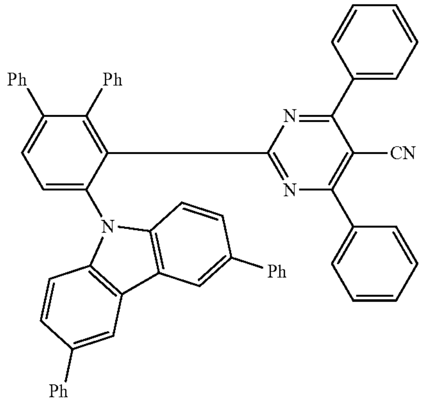
43
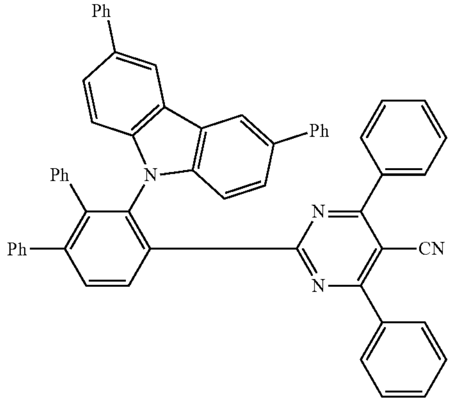
44
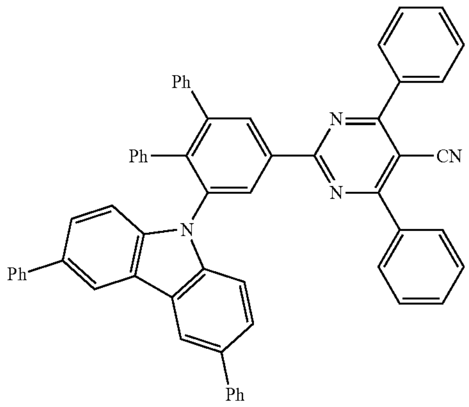

45
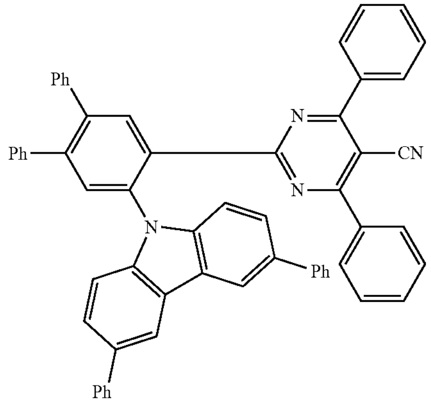
46
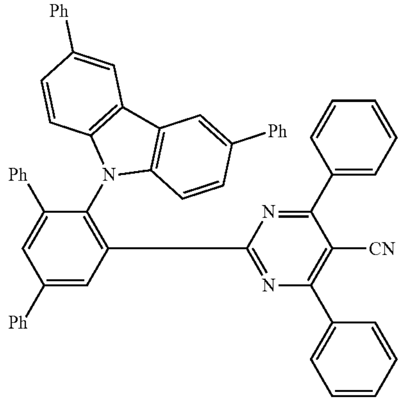
47
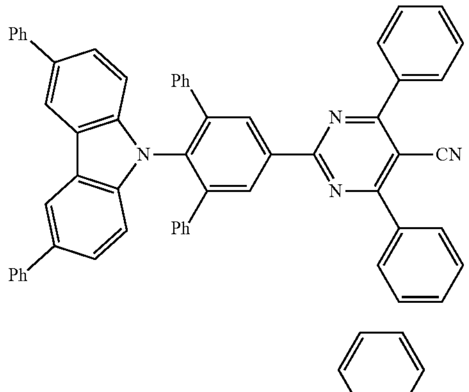
48
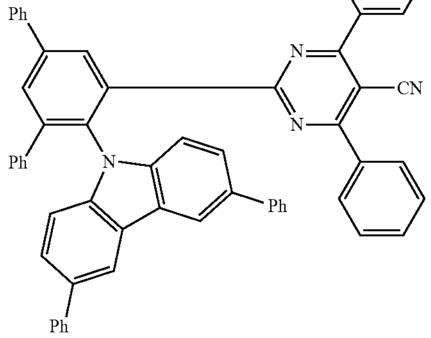
49
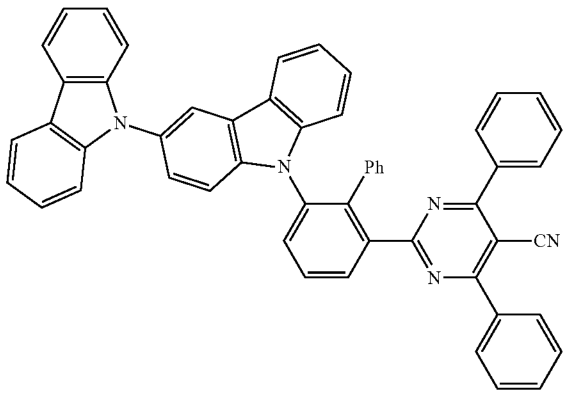
50
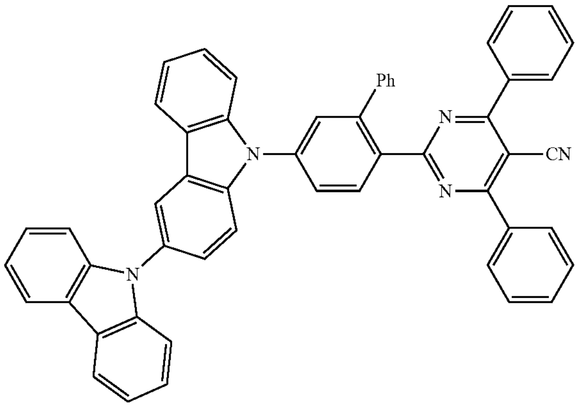
51
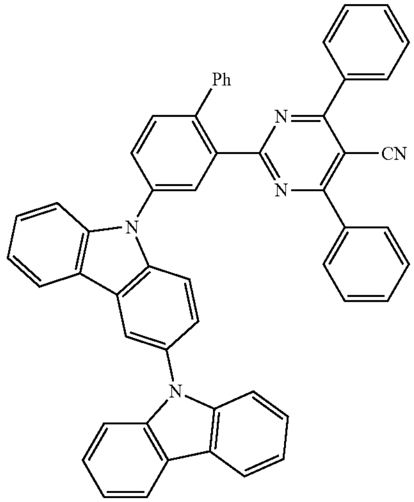

52
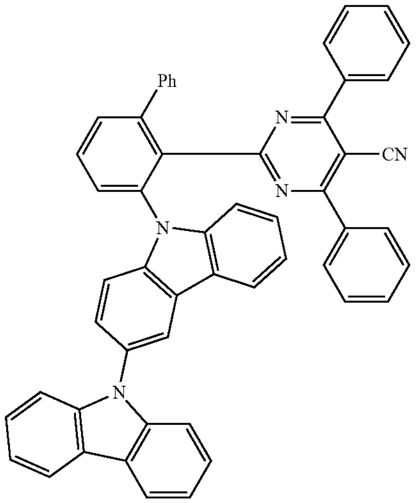
53
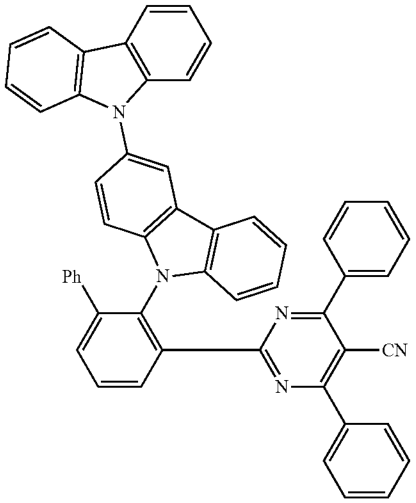
54
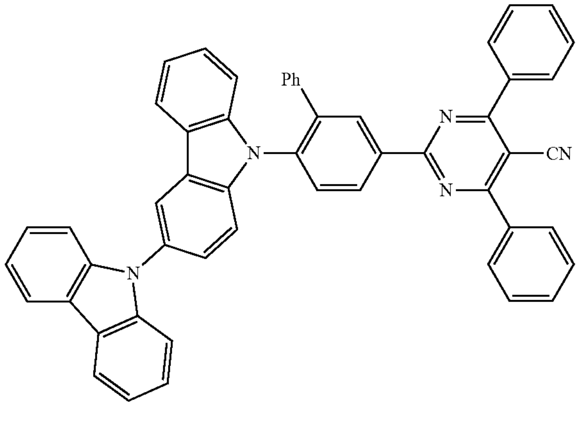
55
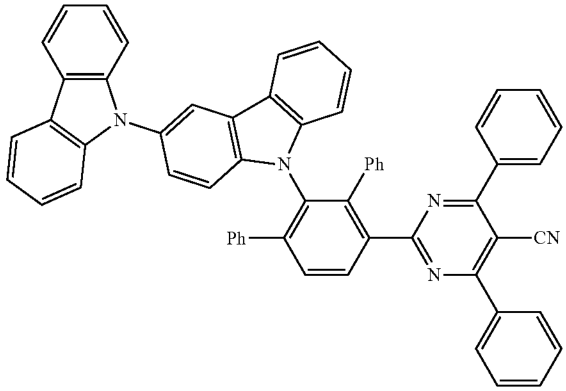
56
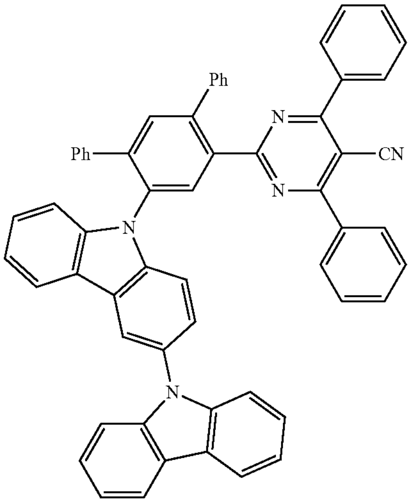
57
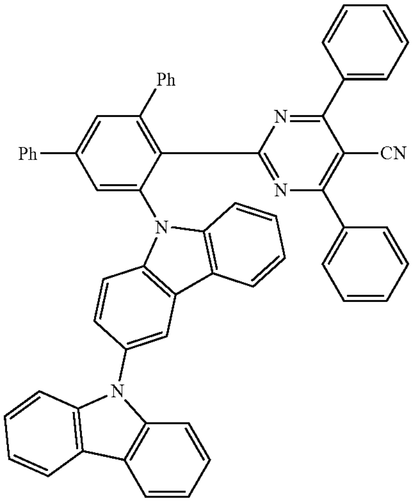

-continued
58
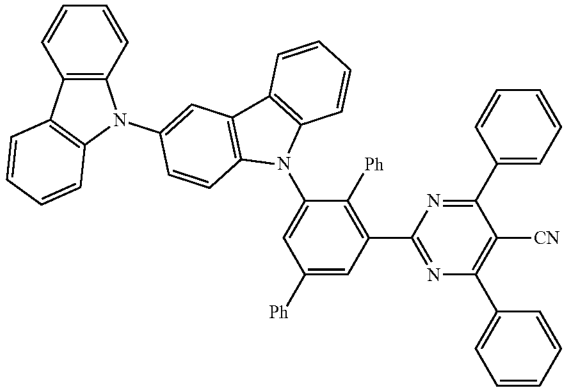
59
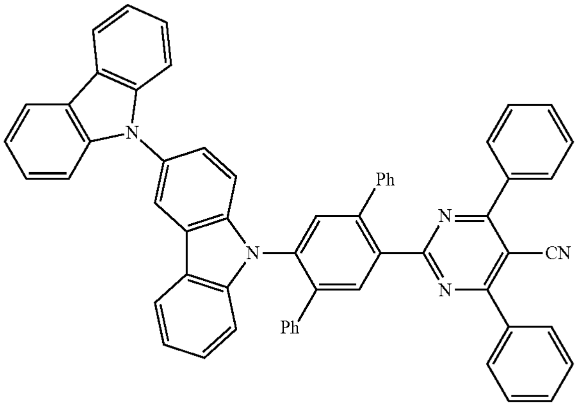
60
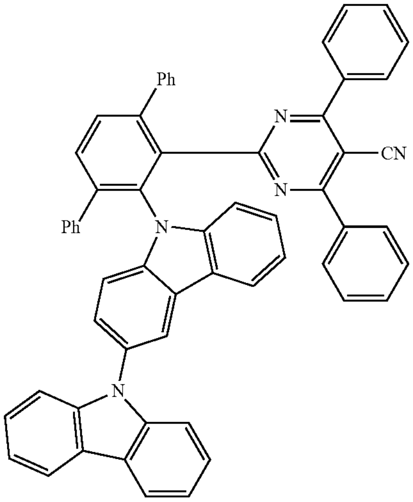
-continued
61
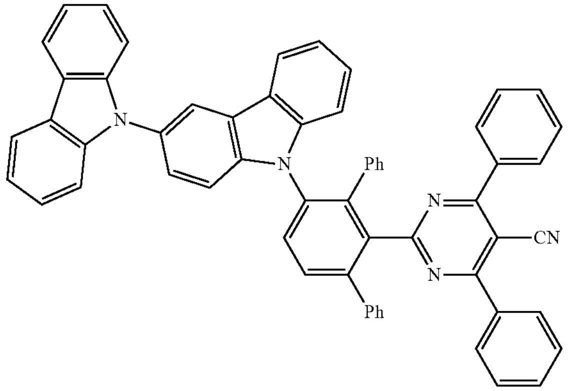
62
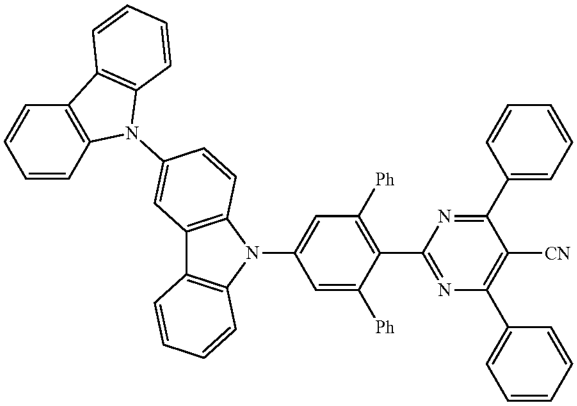
63
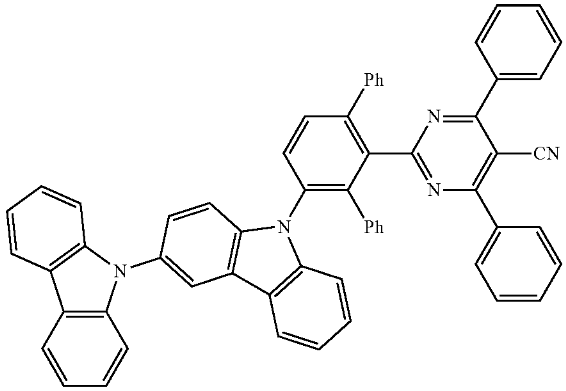

-continued
64
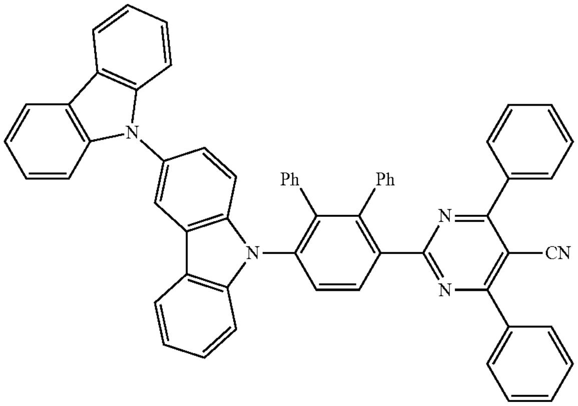
65
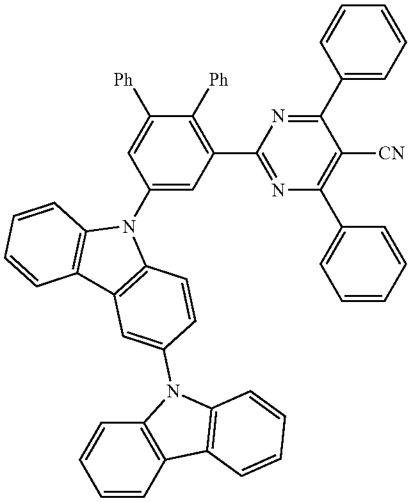
66
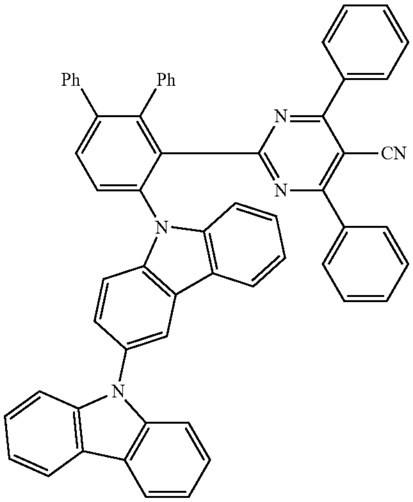
-continued
67
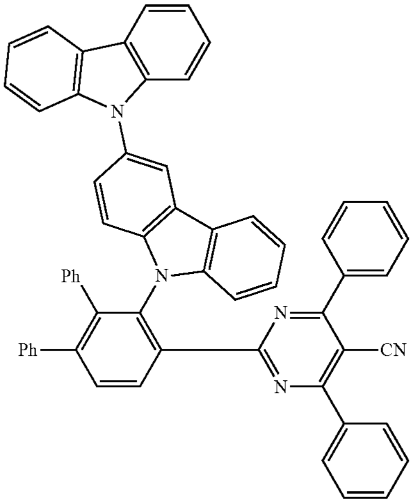
68
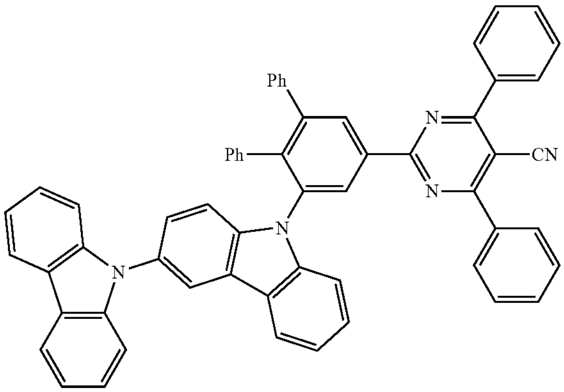
69
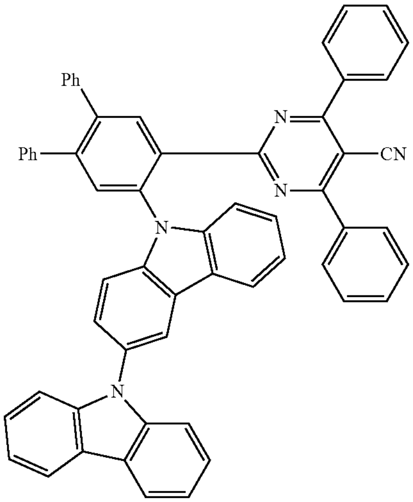

70
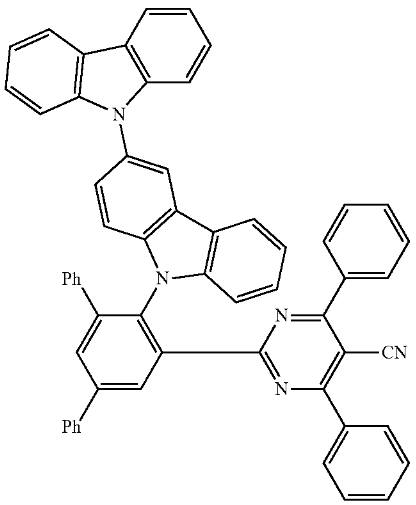
71
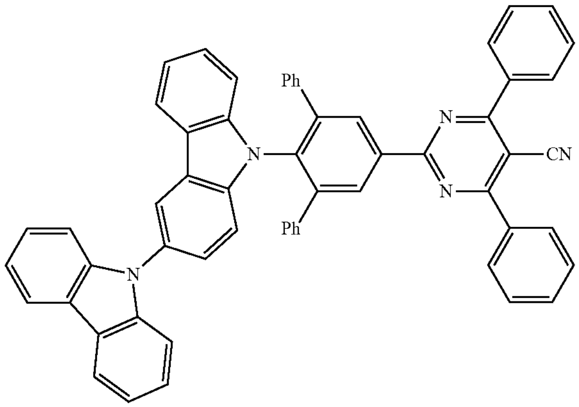
72
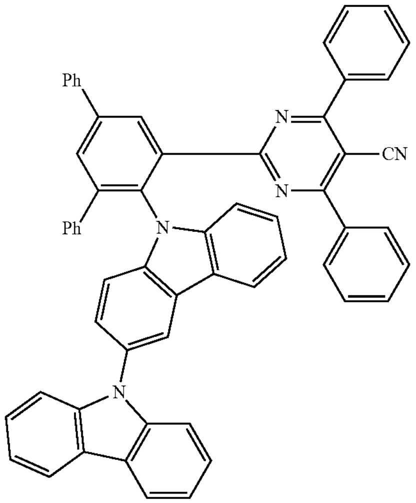
73
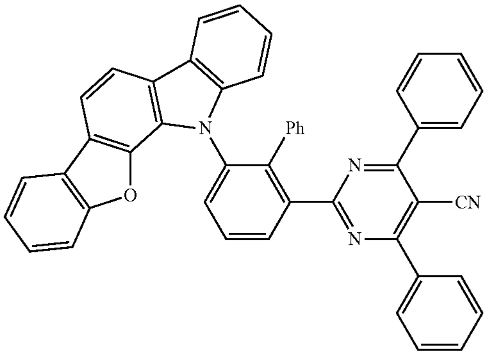
74
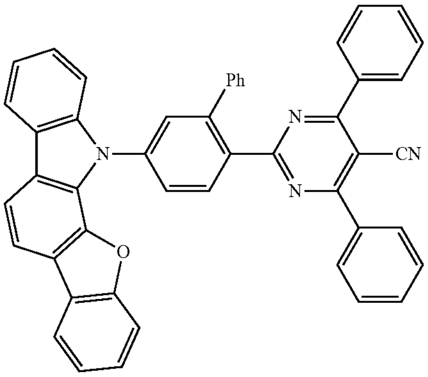
75
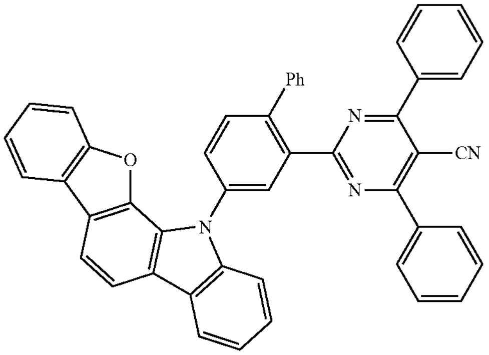
76
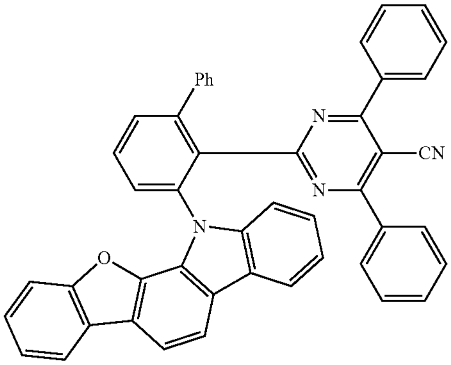

-continued
77
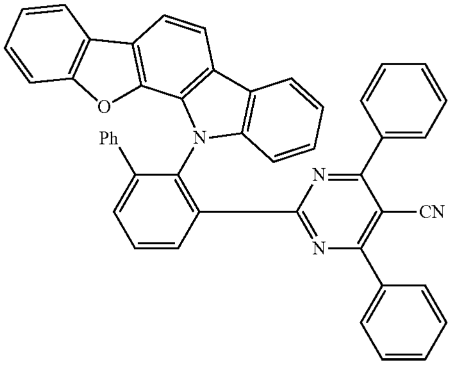
78
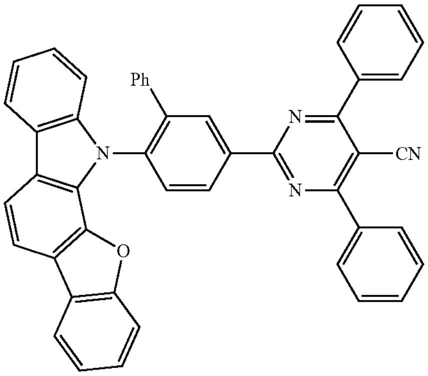
79
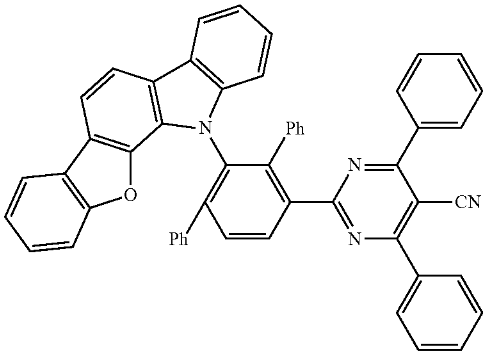
80
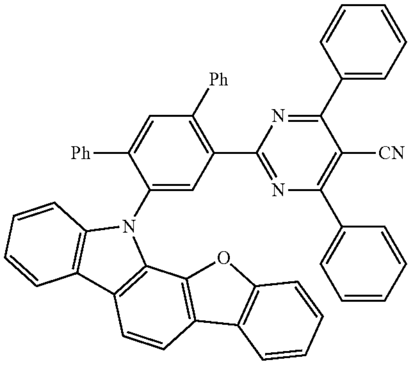
-continued
81
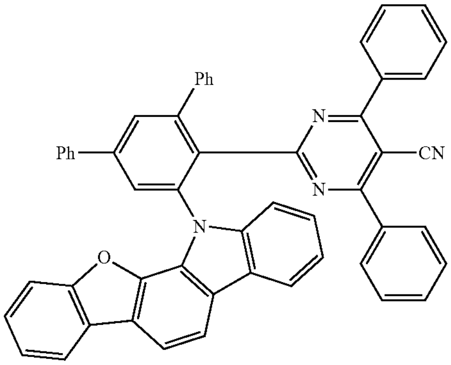
82
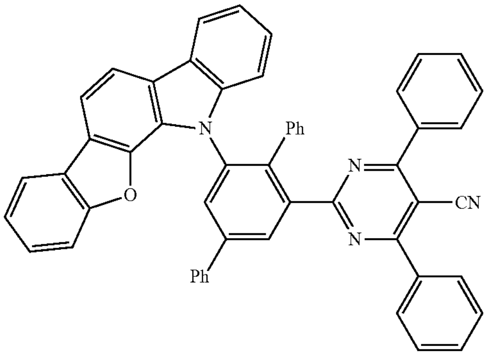
83
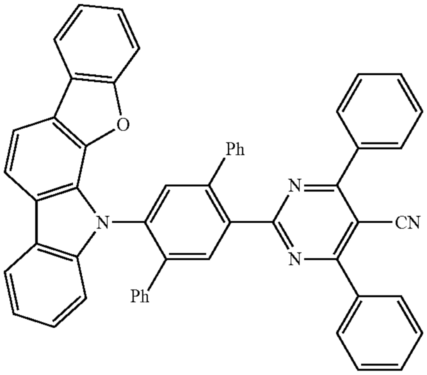
84
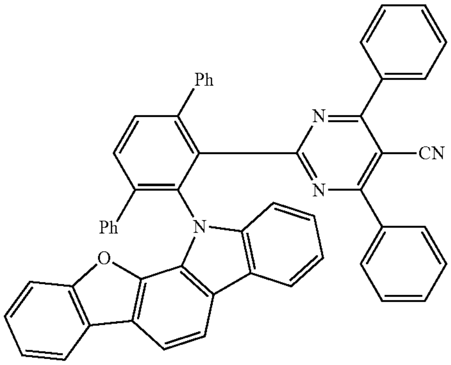

-continued
85
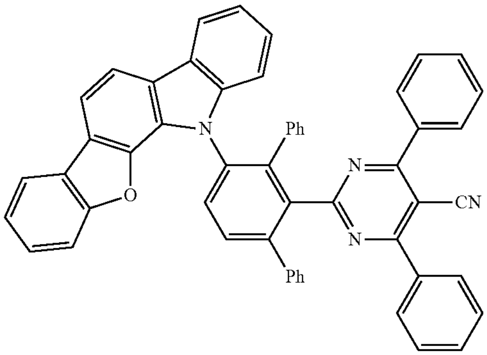
86
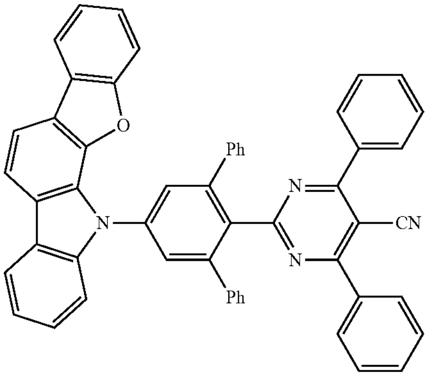
87
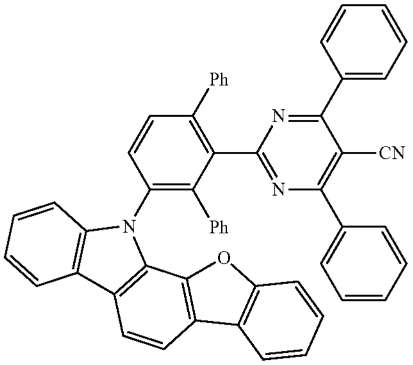
88
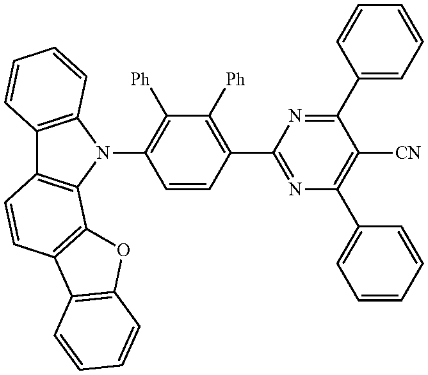
-continued
89
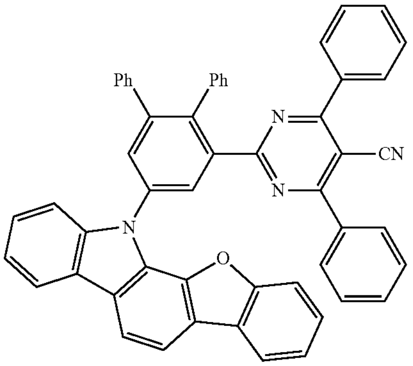
90
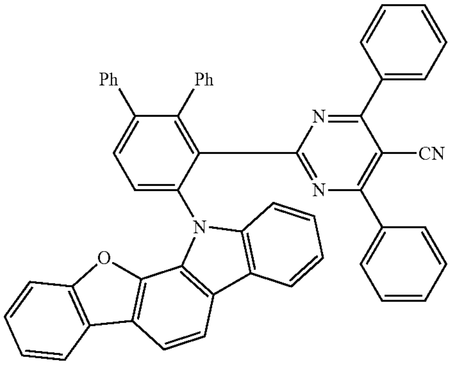
91
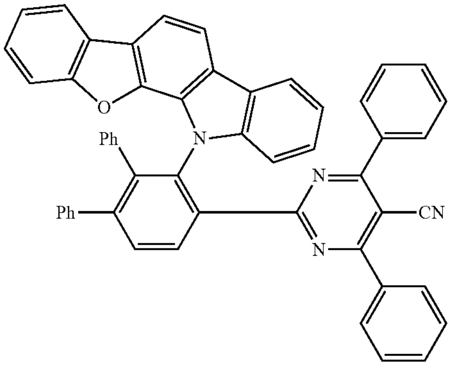
92
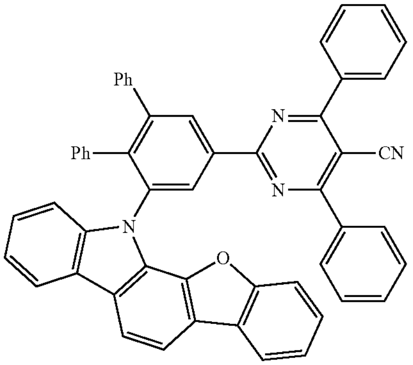

-continued
93
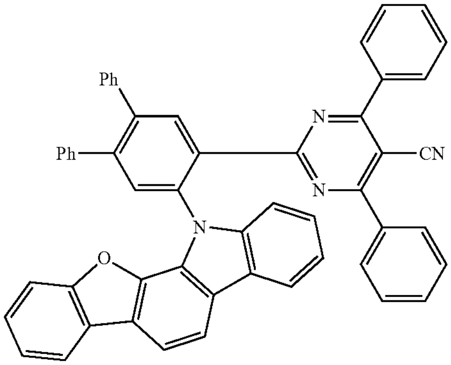
94
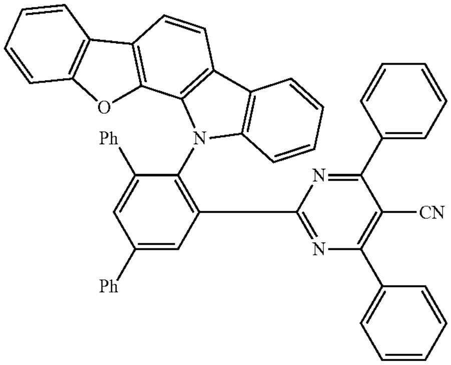
95
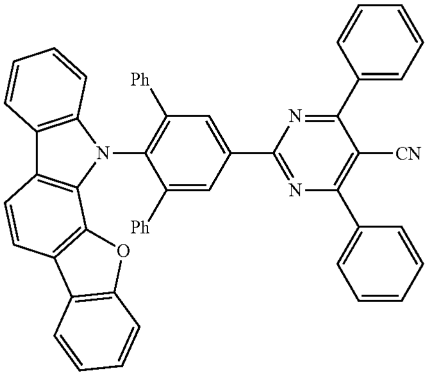
96
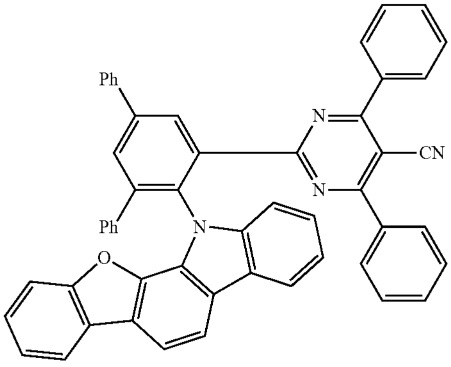
-continued
97
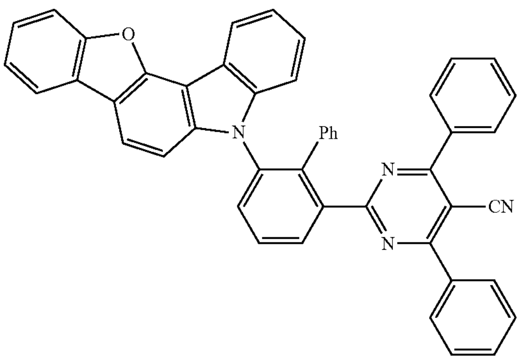
98
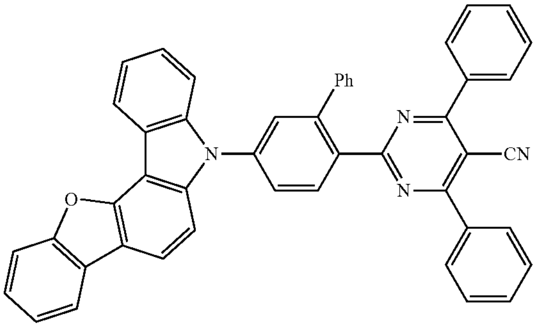
99
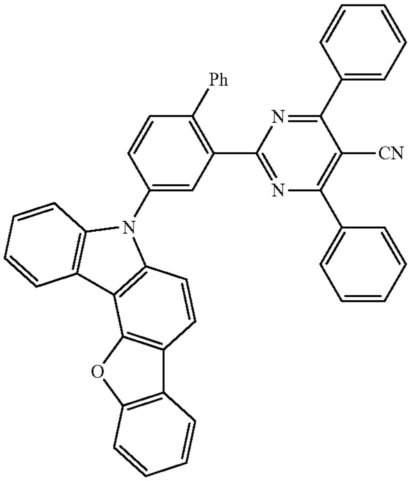

-continued
100
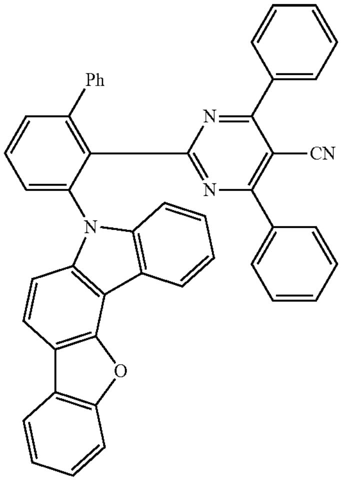
101
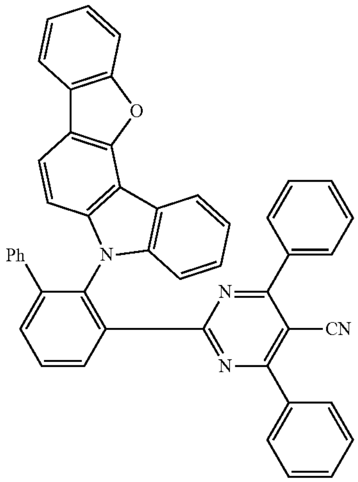
102
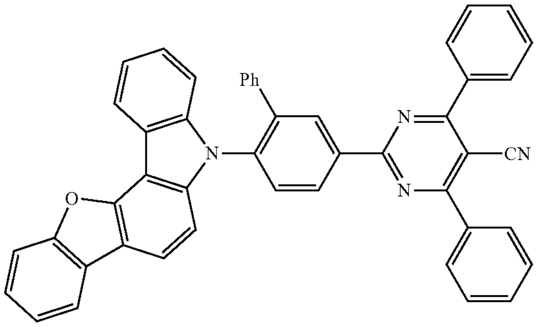
-continued
103
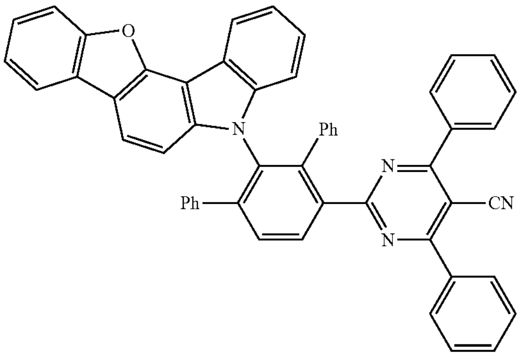
104
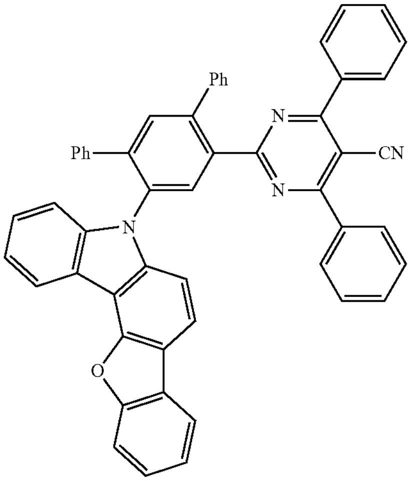
105
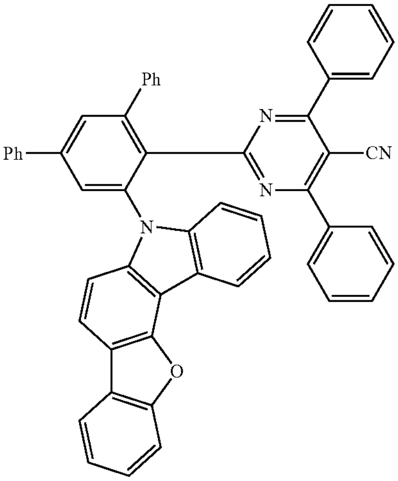

-continued
106
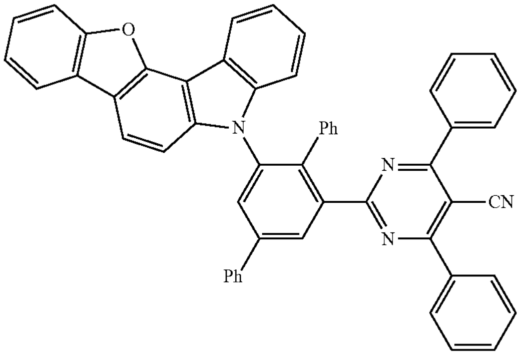
107
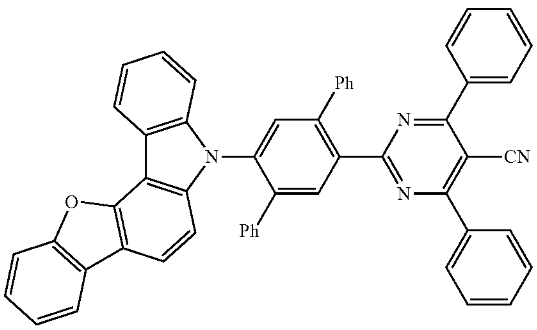
108
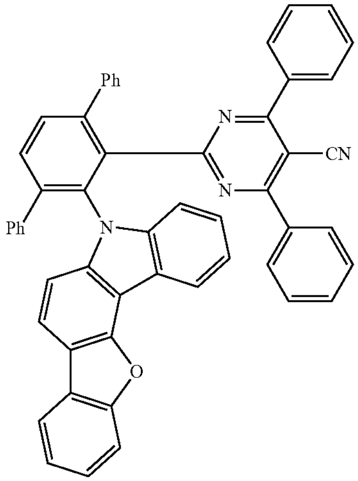
-continued
109
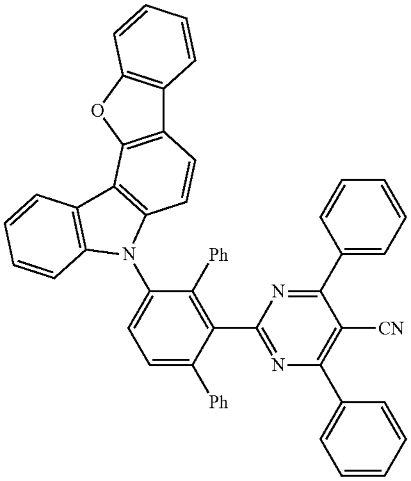
110
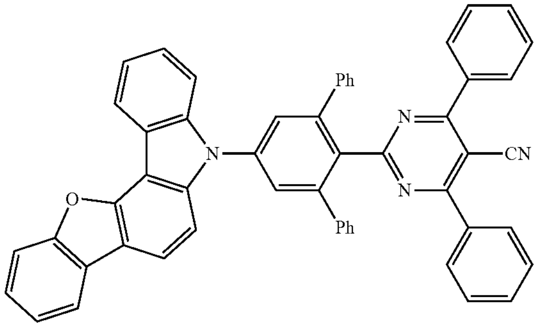
111
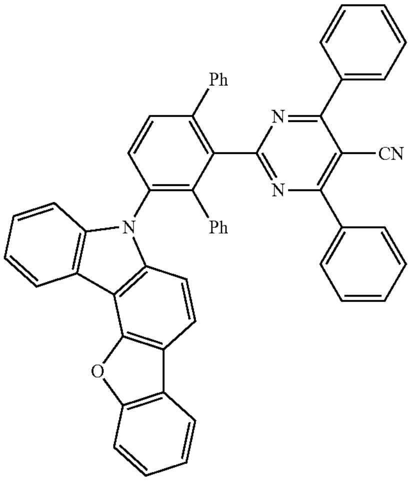
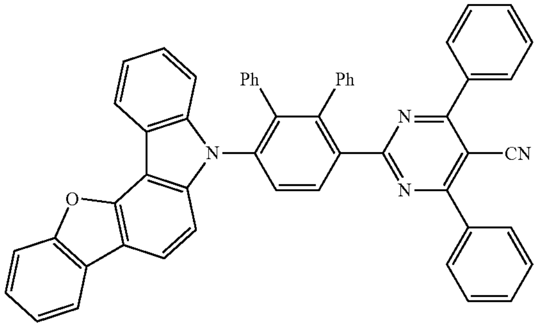

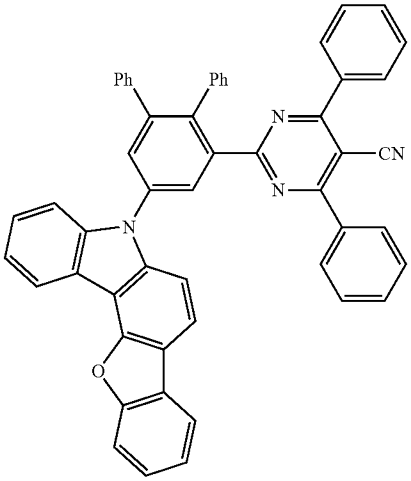
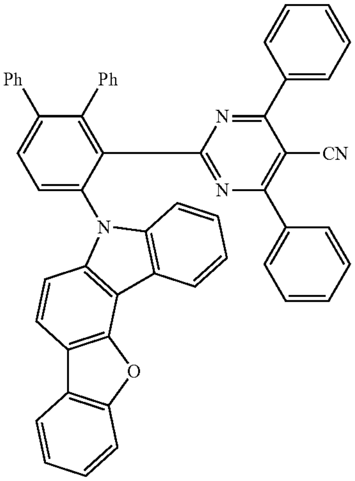
115
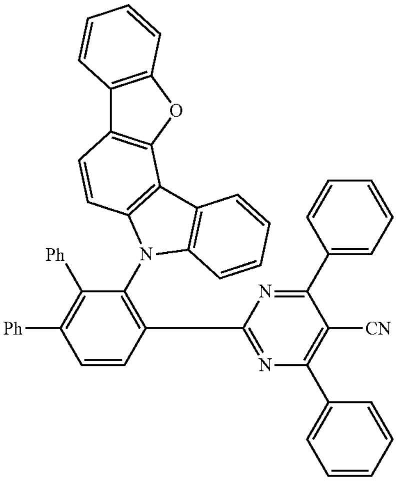
116
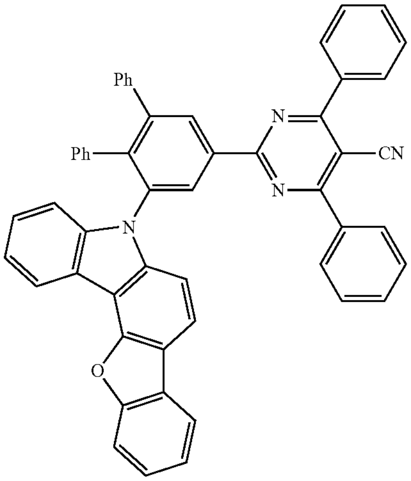
117
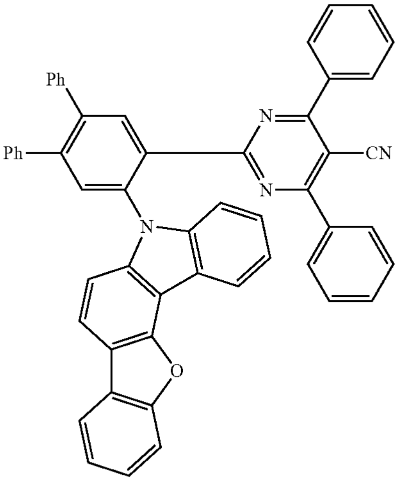
118
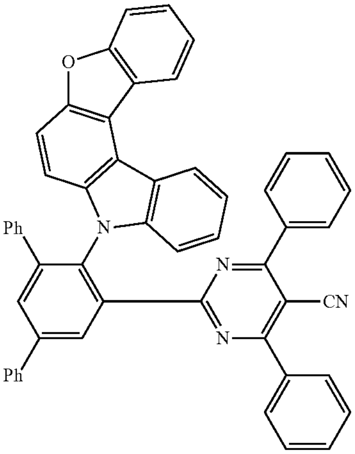

-continued
119
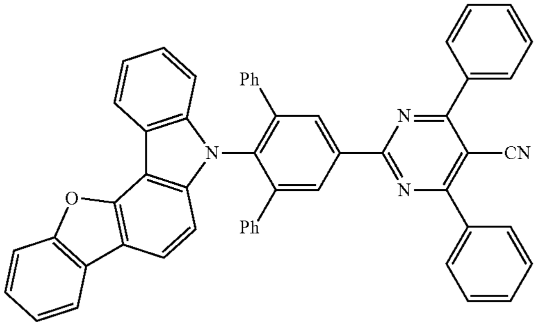
120
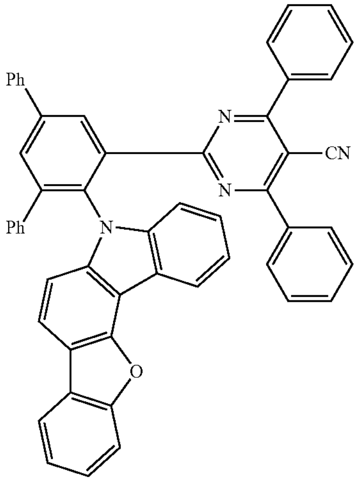
121
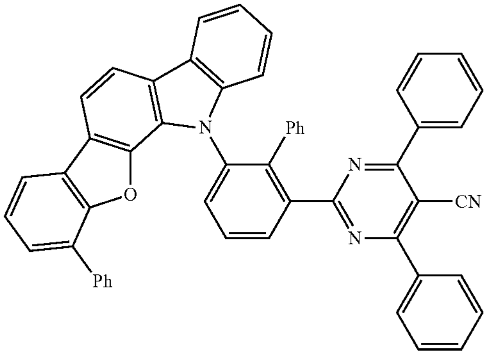
122
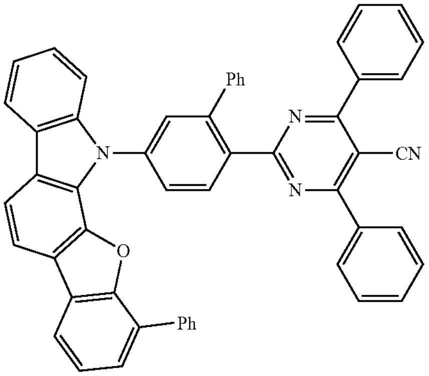
-continued
123
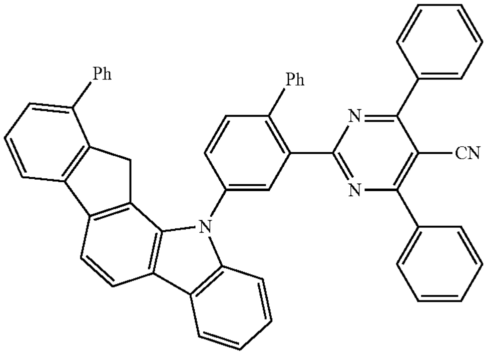
124
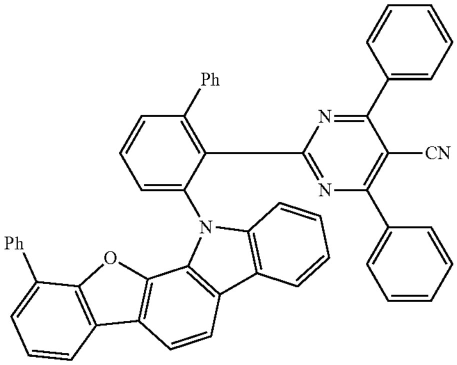
125
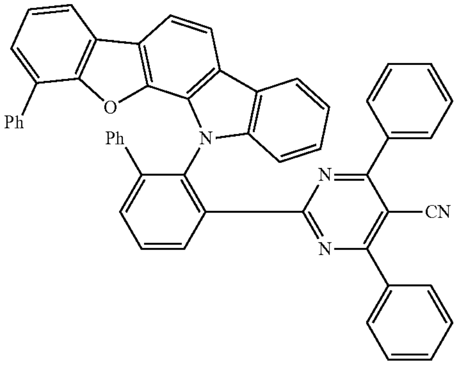
126
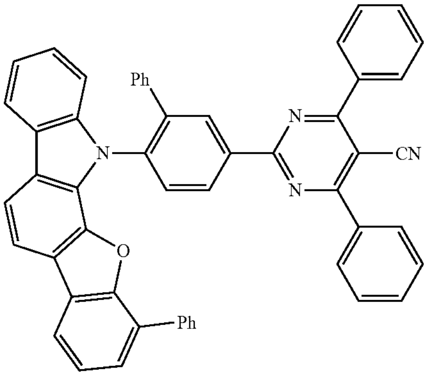

-continued
133
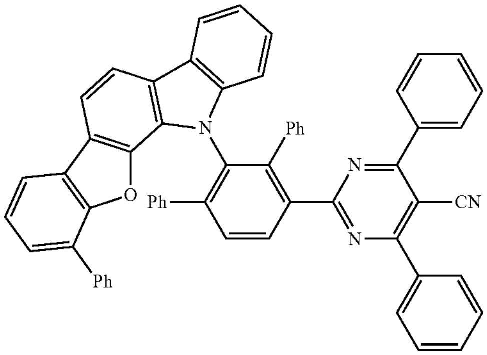
134
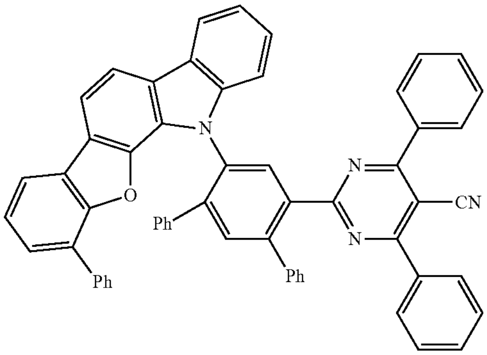
135
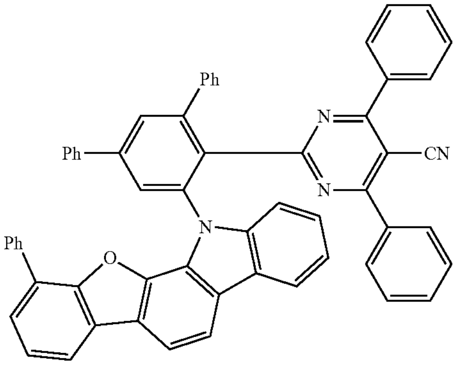
130
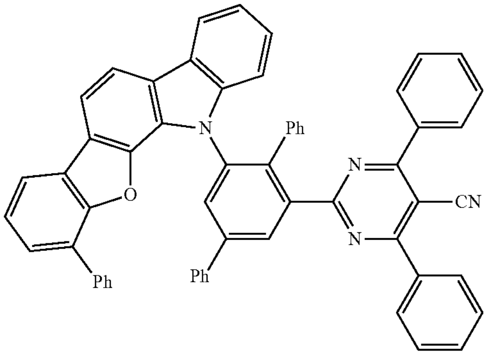
-continued
131
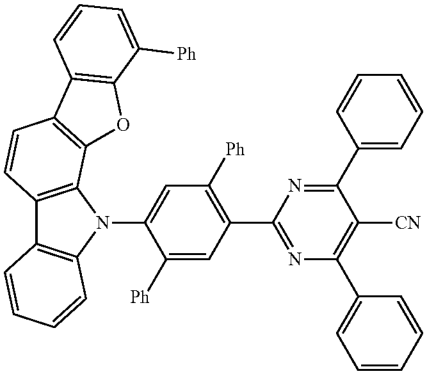
132
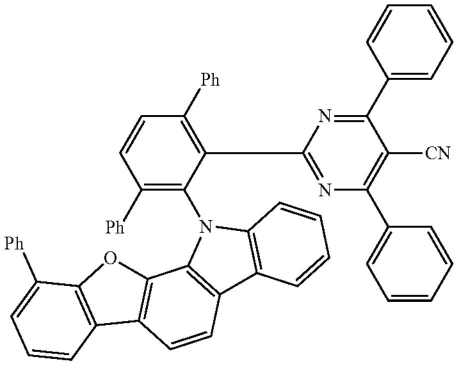
133
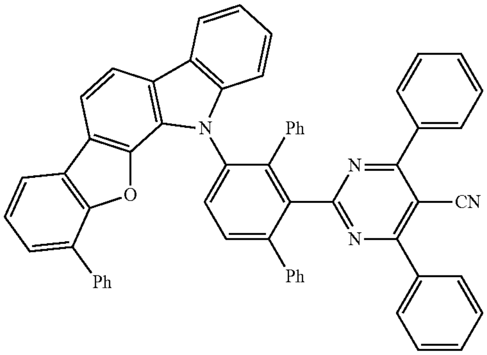
134
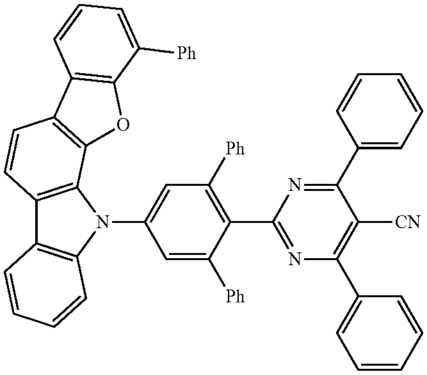

-continued
135
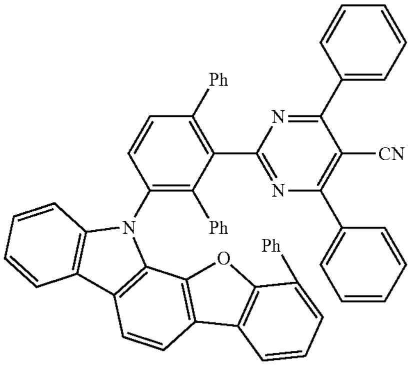
136
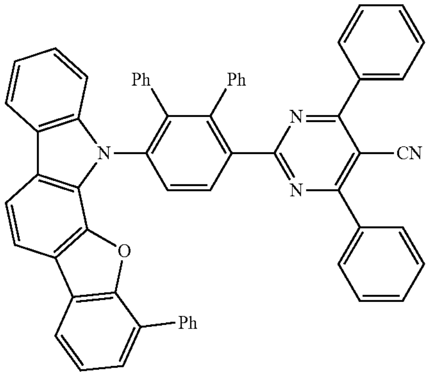
137
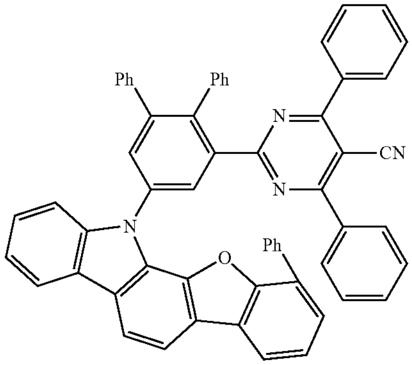
138
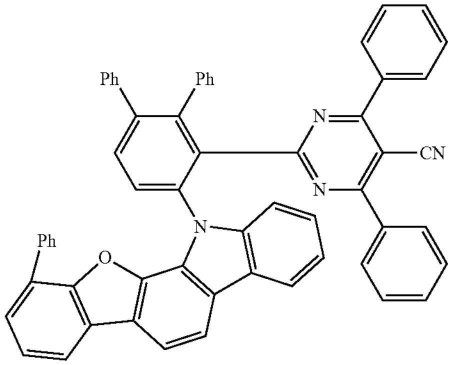
-continued
139
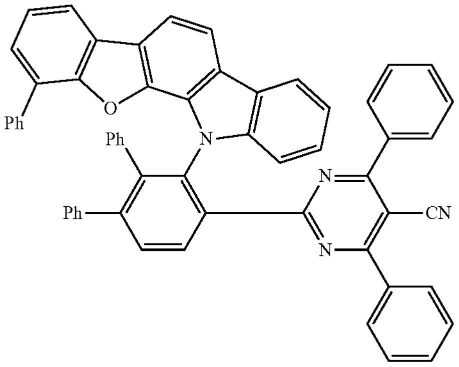
140
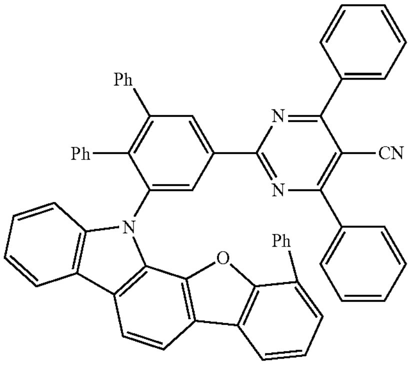
141
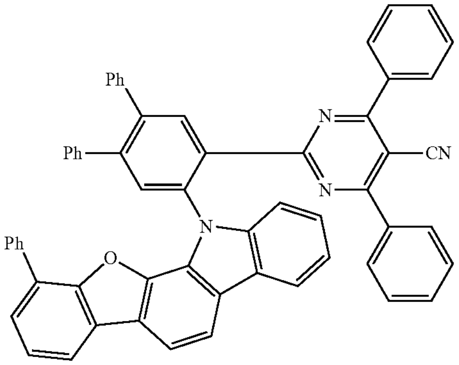
142
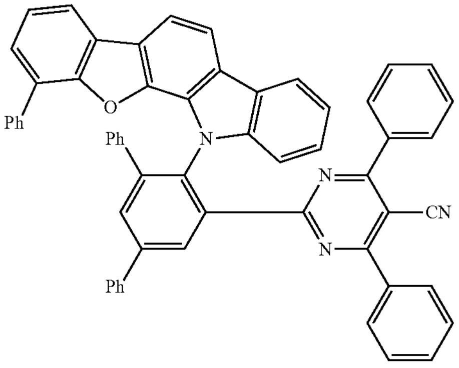

-continued
143
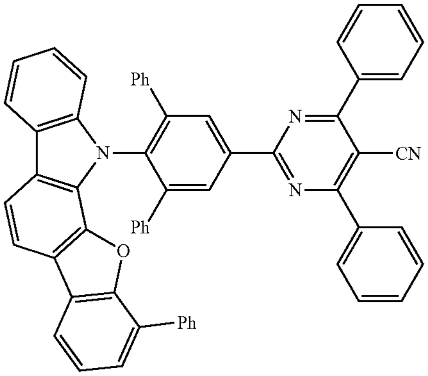
144
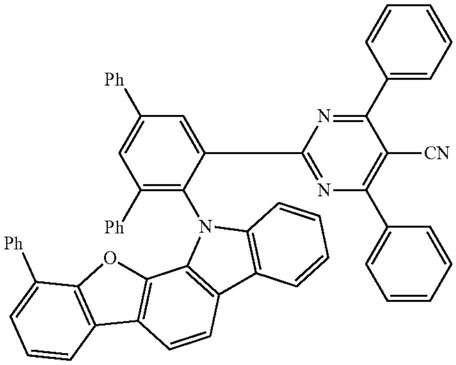
145
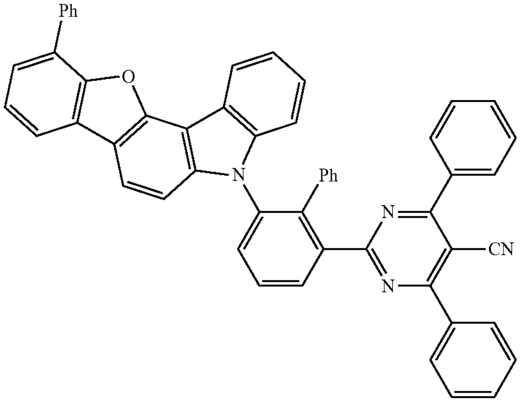
146
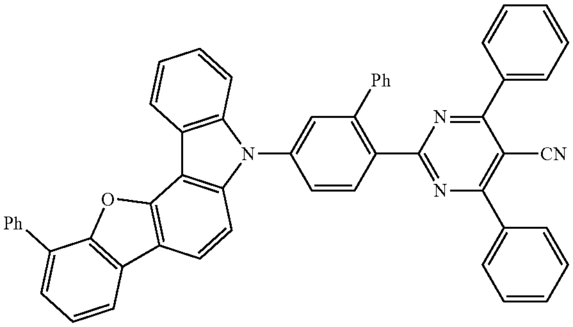
-continued
147
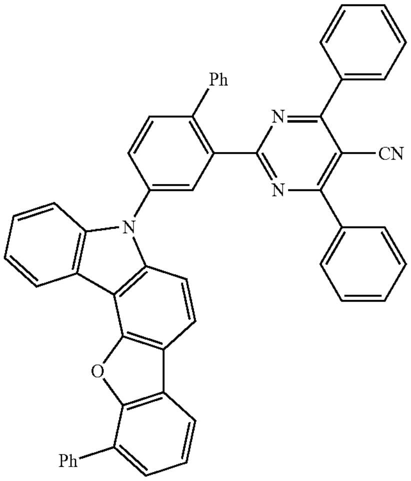
148
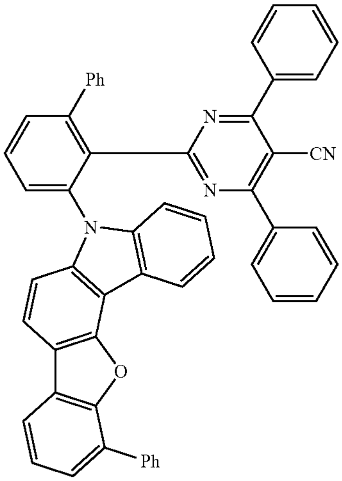
149
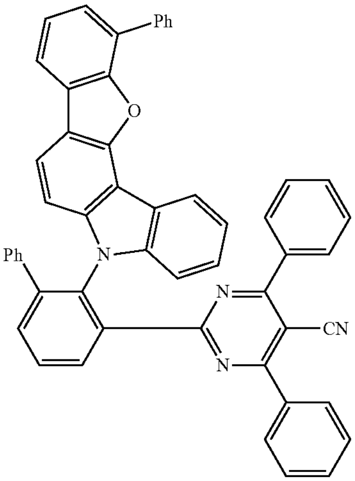

-continued
150
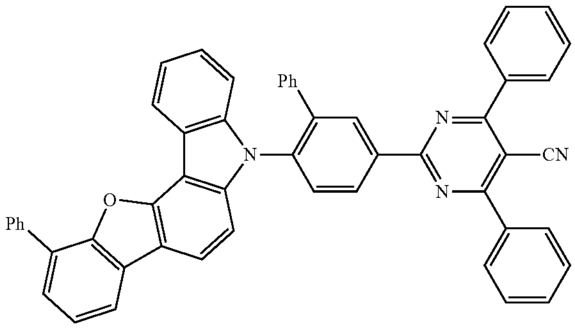
151
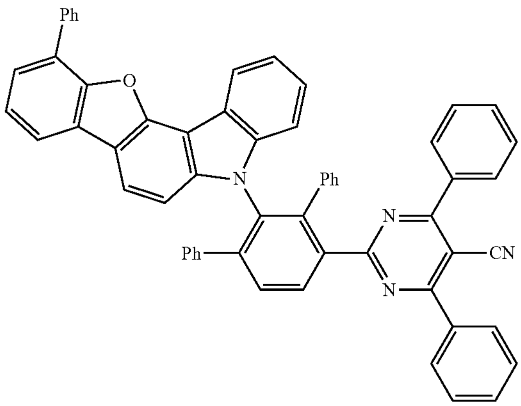
152
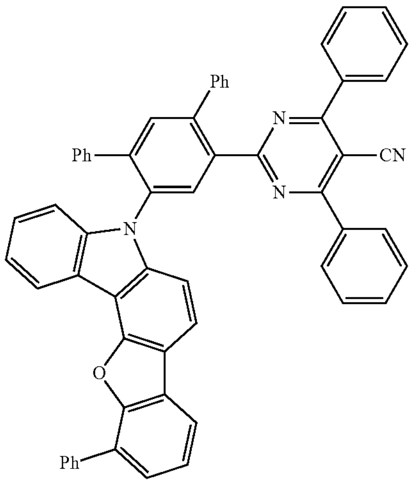
-continued
153
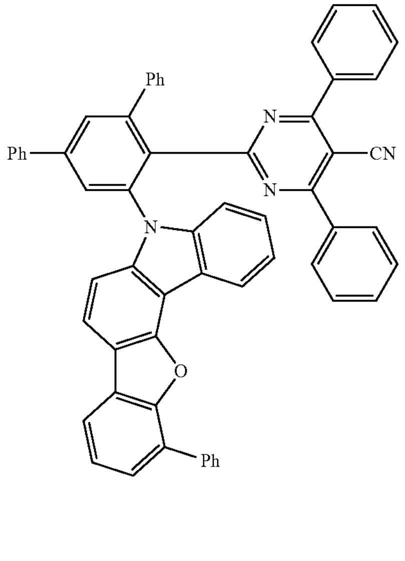
154
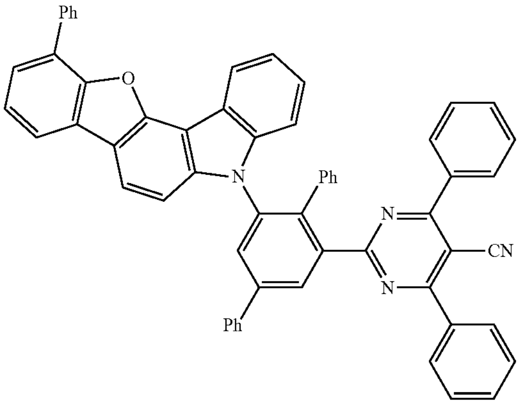
155
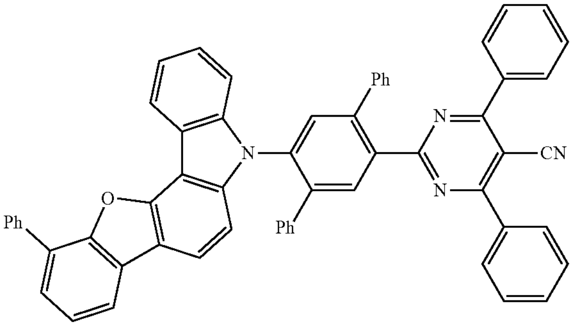

-continued
156
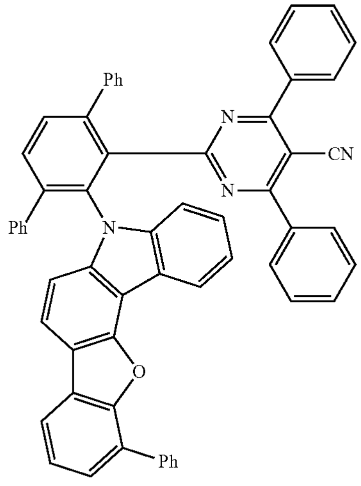
157
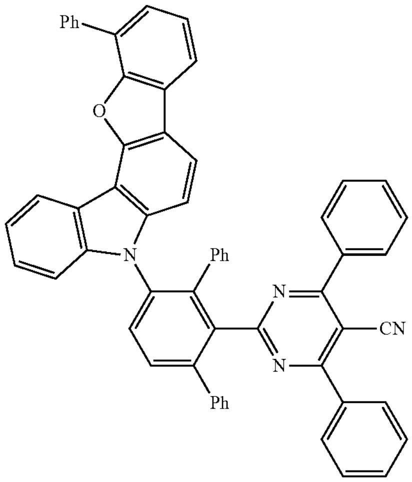
158
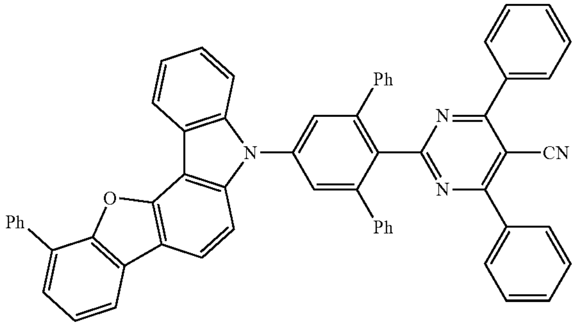
-continued
159
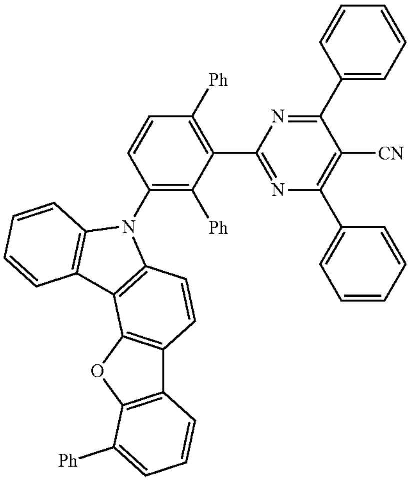
160
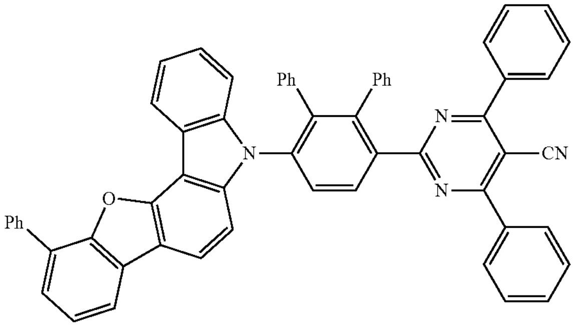
161
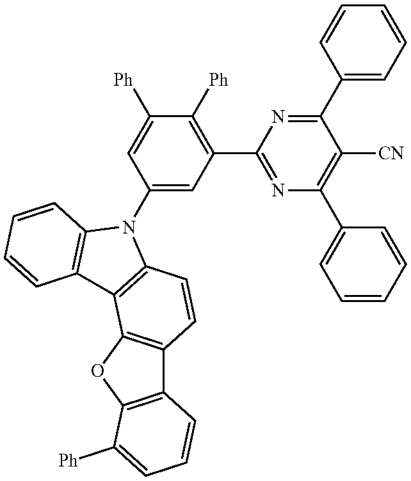

-continued
162
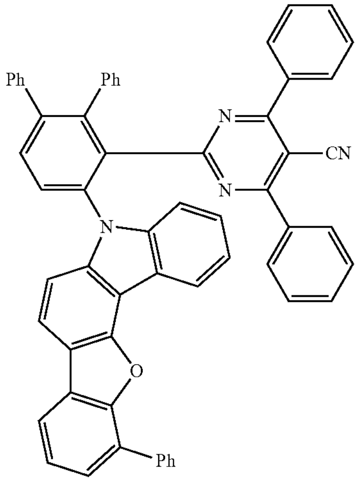
163
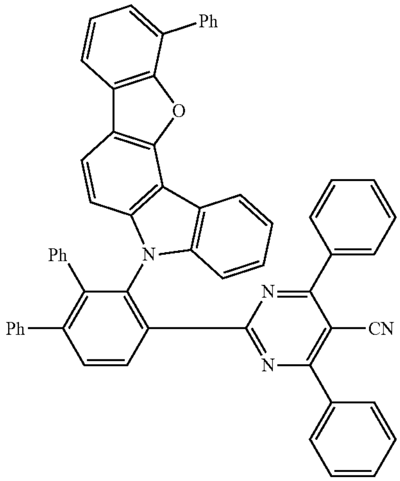
164
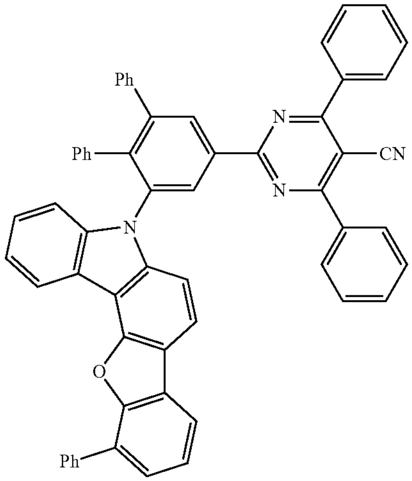
-continued
165
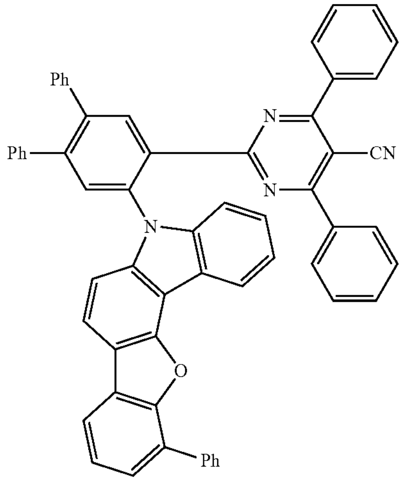
166
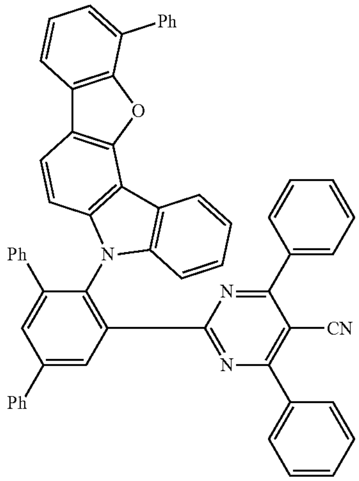
167
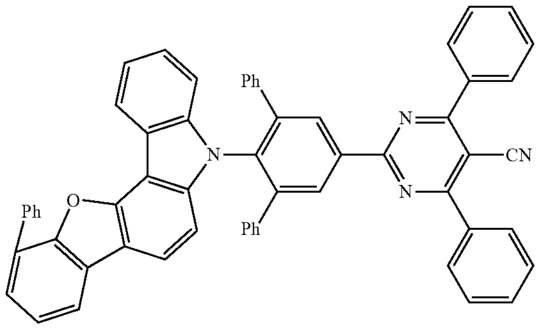

-continued
168
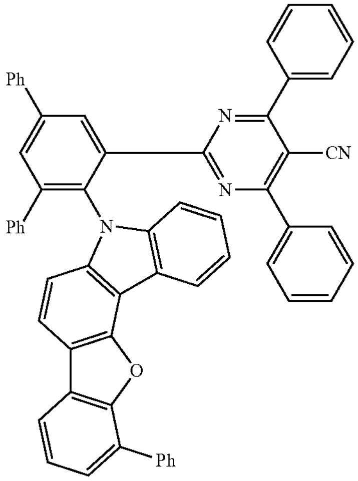
169
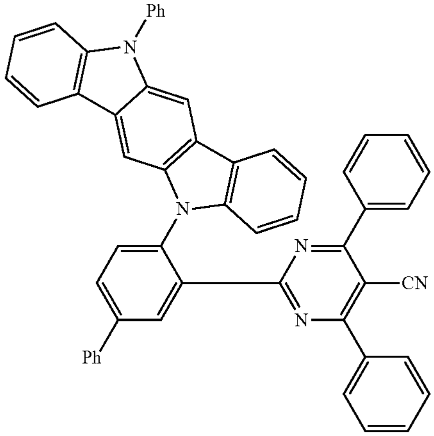
170
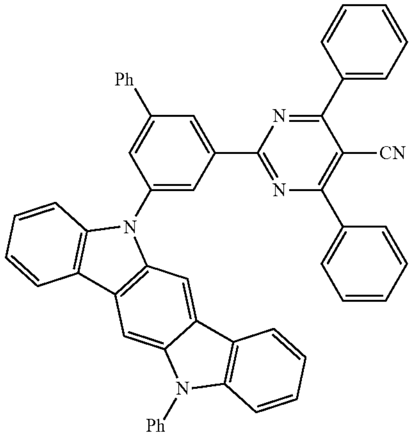
-continued
171
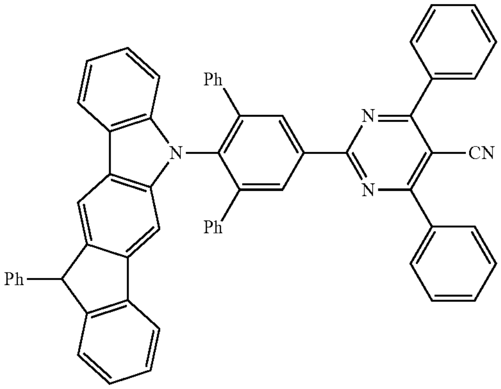
172
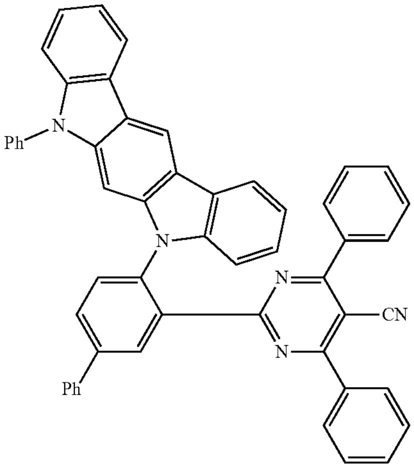
173
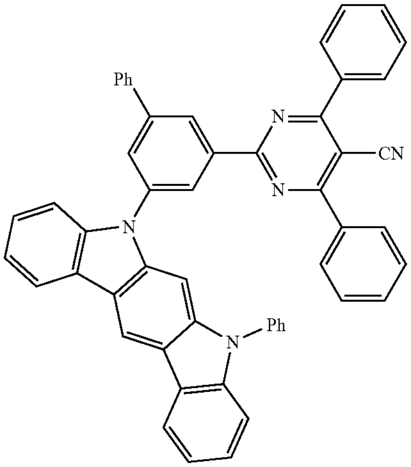

-continued
174
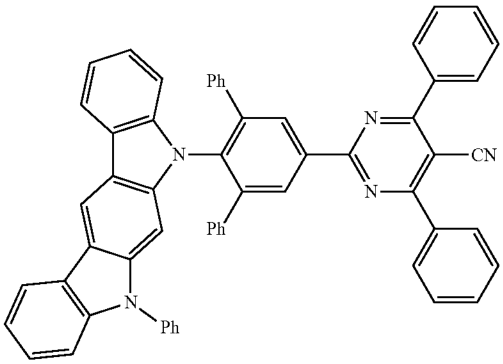
175
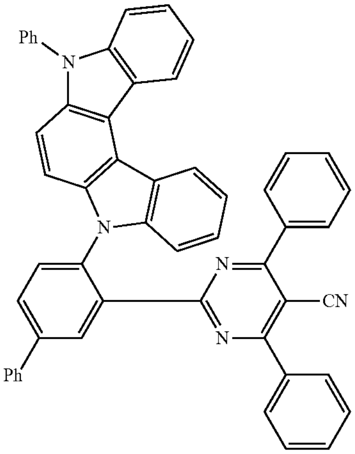
176
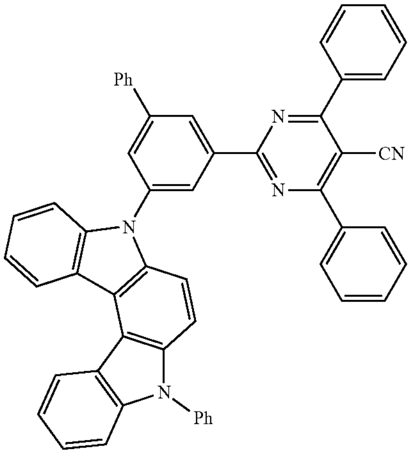
177
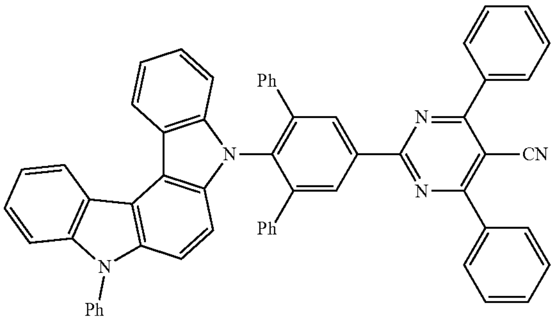
-continued
178
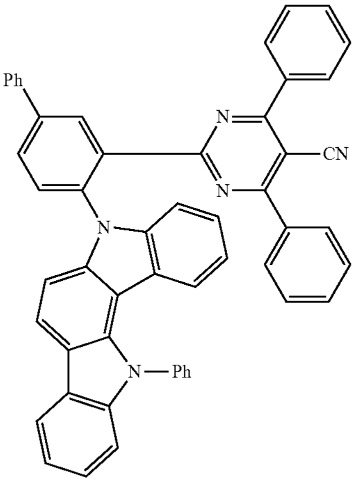
179
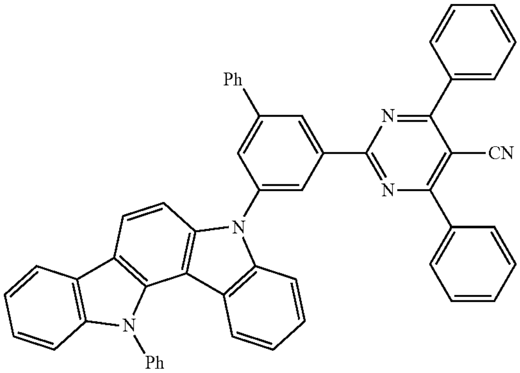
180
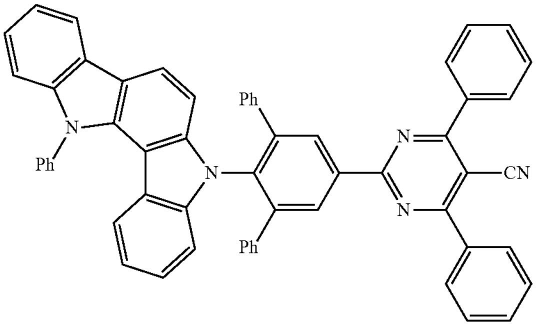
181
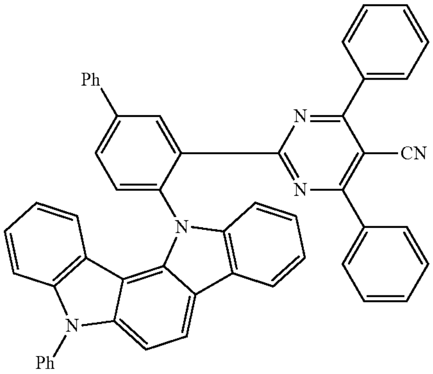

-continued
182
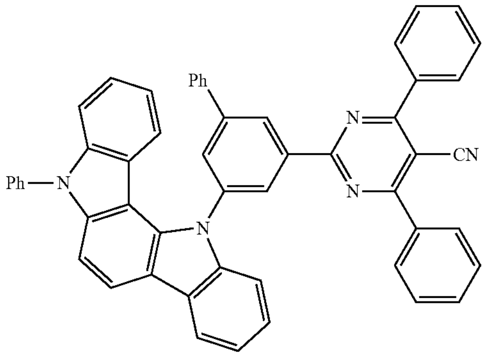
183
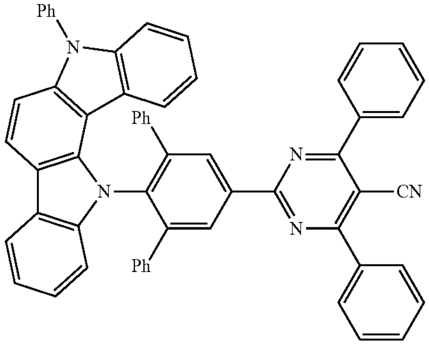
184
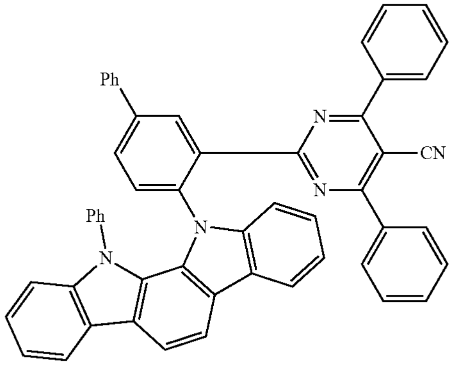
185
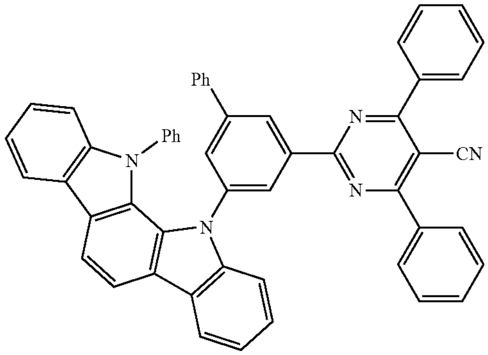
-continued
186
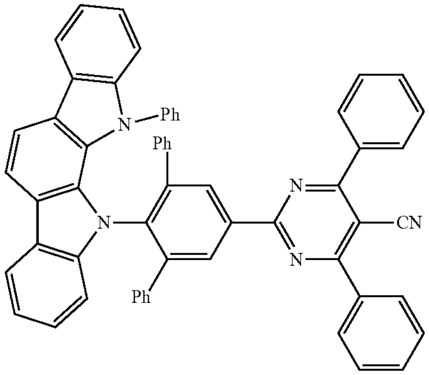
187
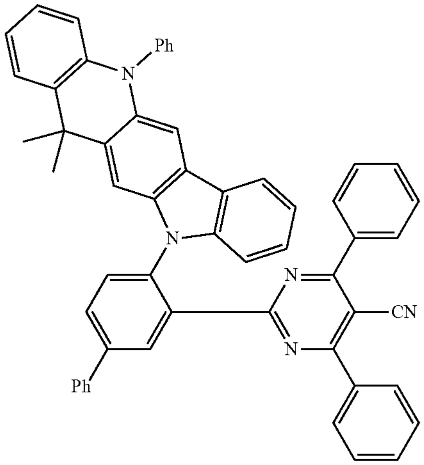
188
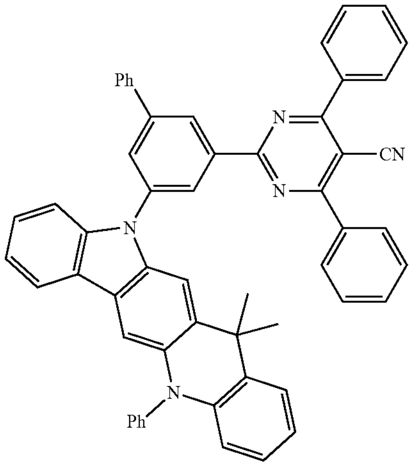

-continued
189
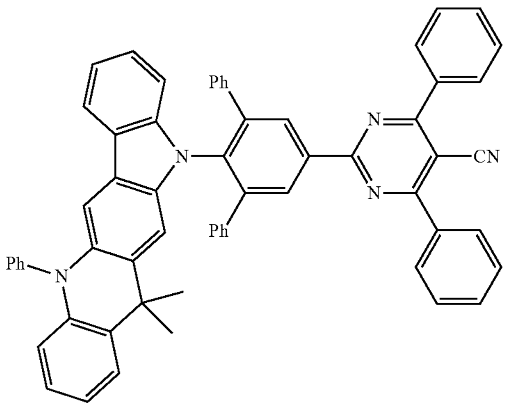
190
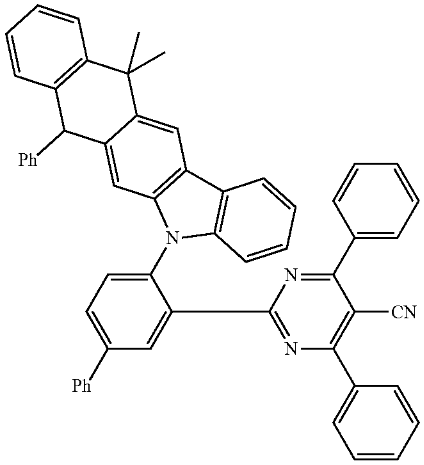
191
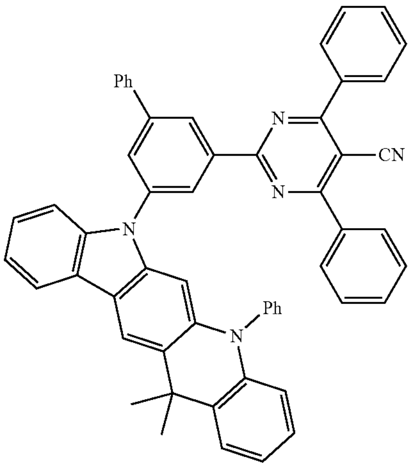
-continued
192
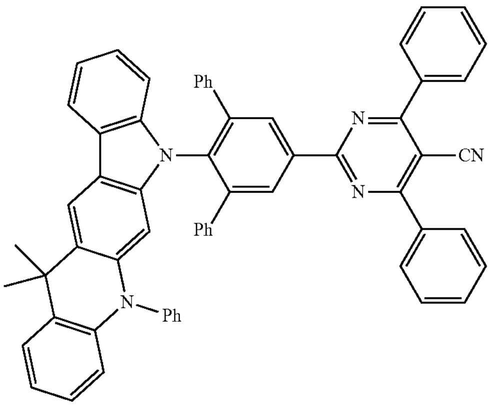
193
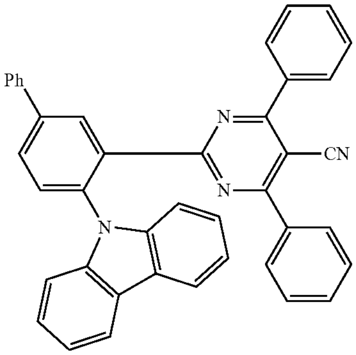
194
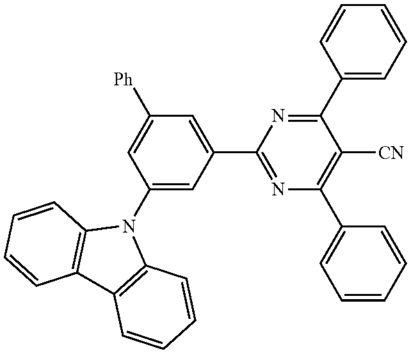
195
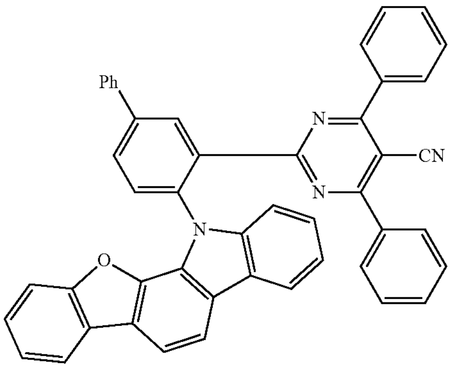

-continued
196
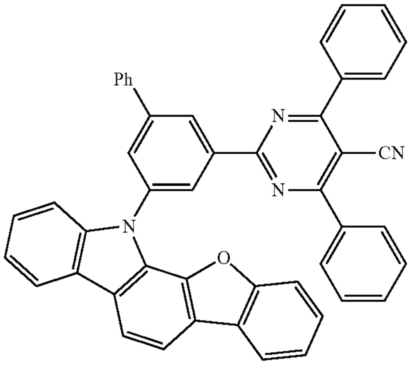
197
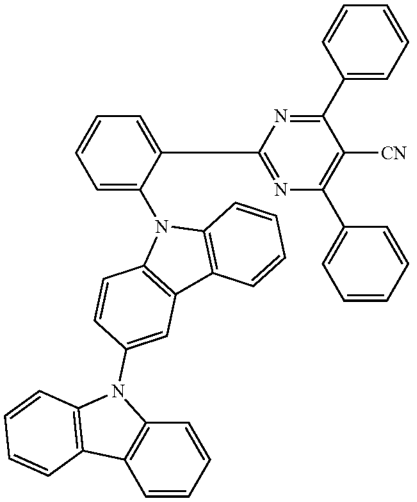
198
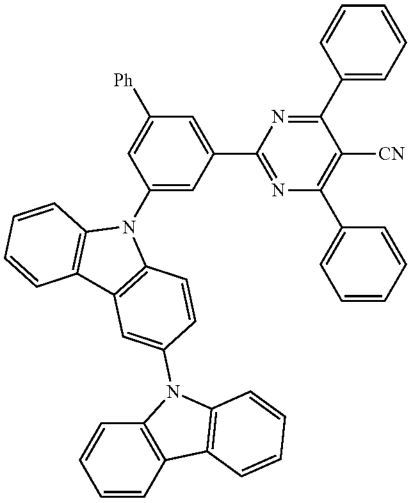
-continued
199
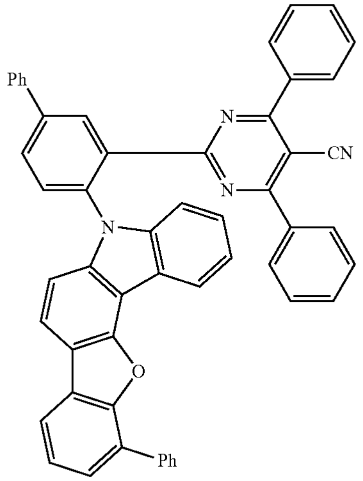
200
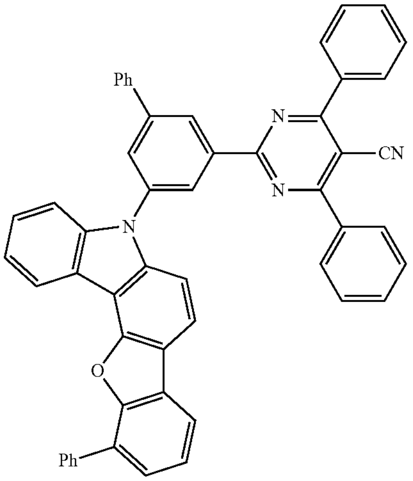
201
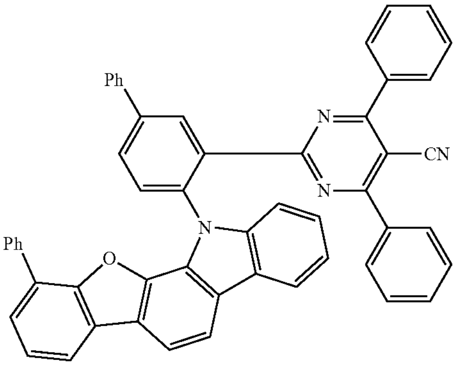

-continued
202
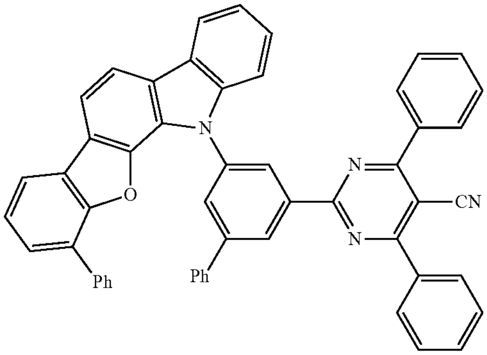
203
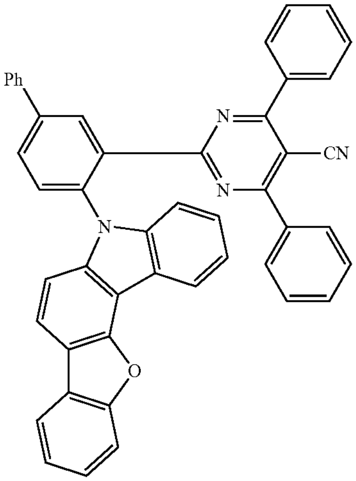
204
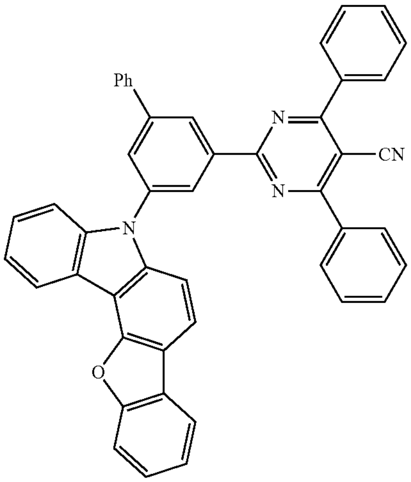
-continued
205
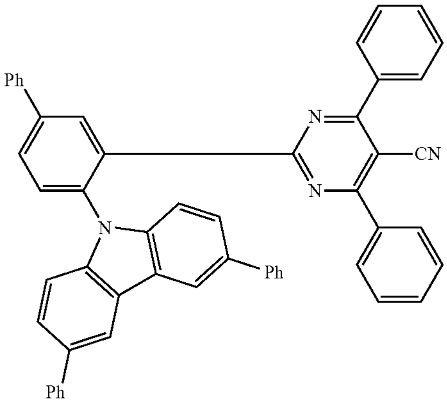
206
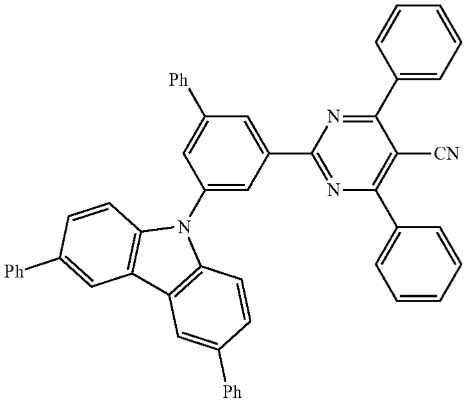
207
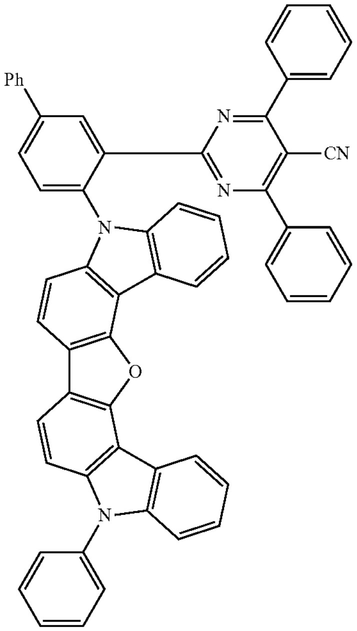

-continued
208
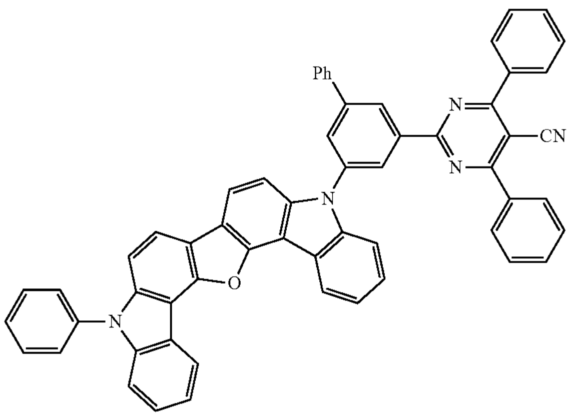
209
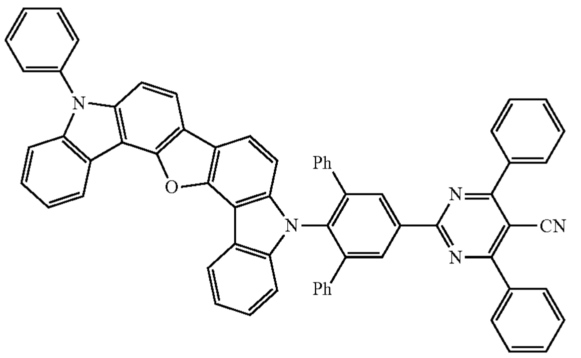
210
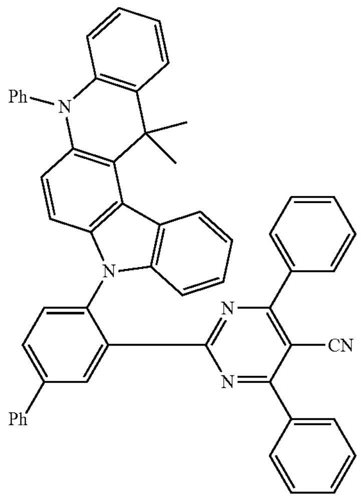
-continued
211
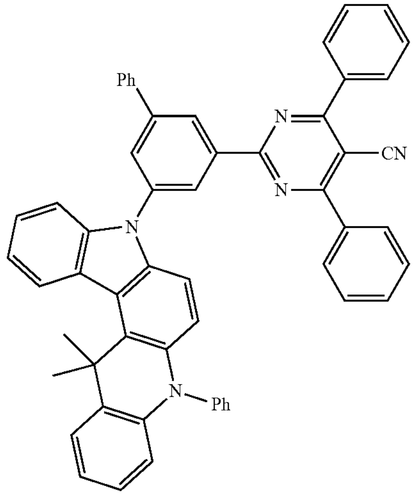
212
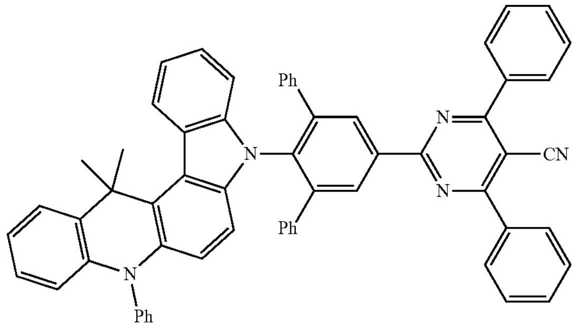
213
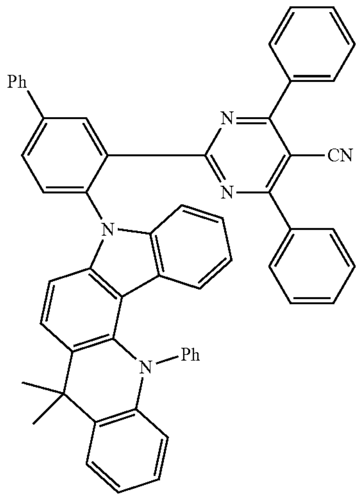

-continued
214
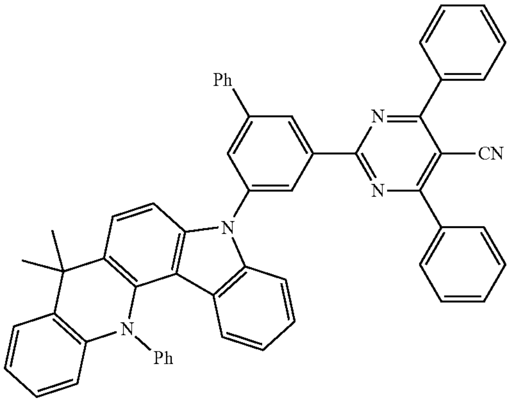
215
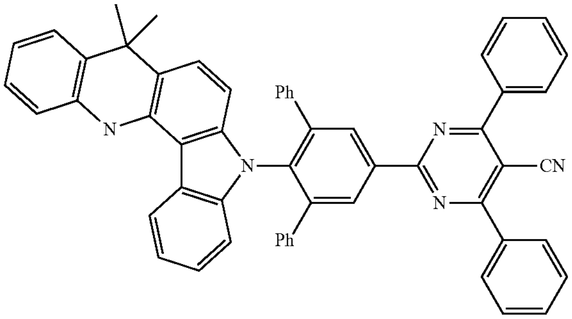
216
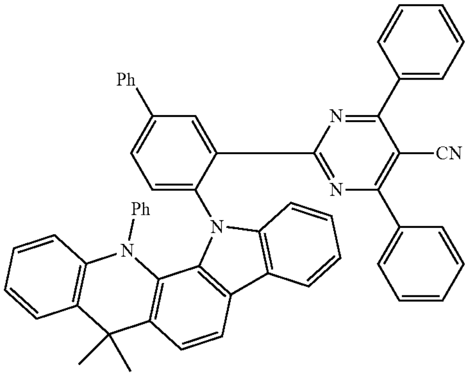
217
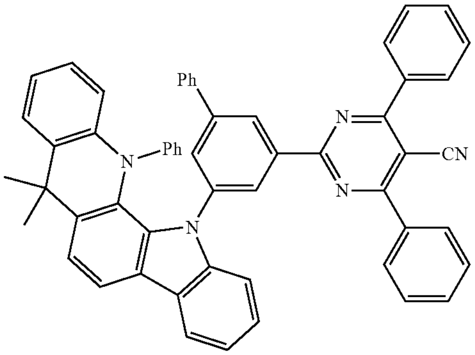
-continued
218
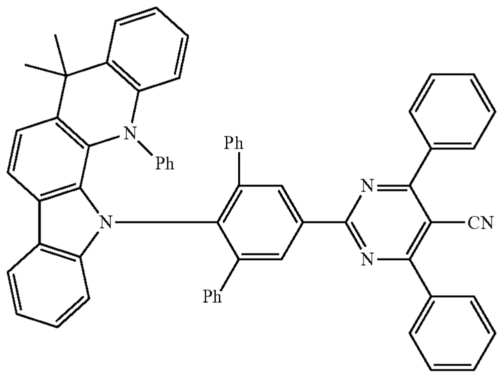
219
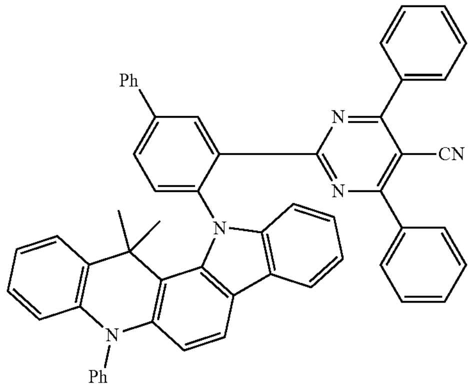
220
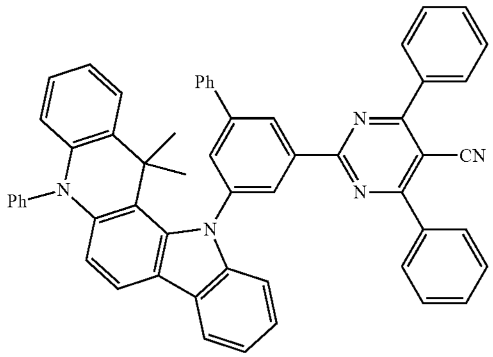
221
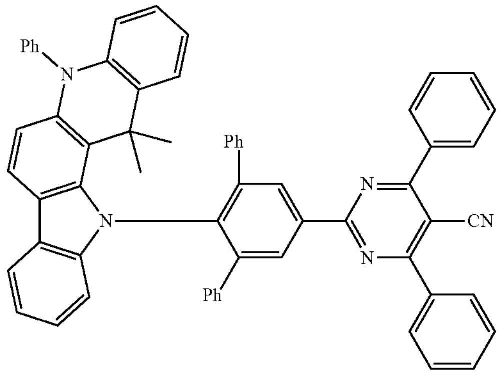

-continued
222
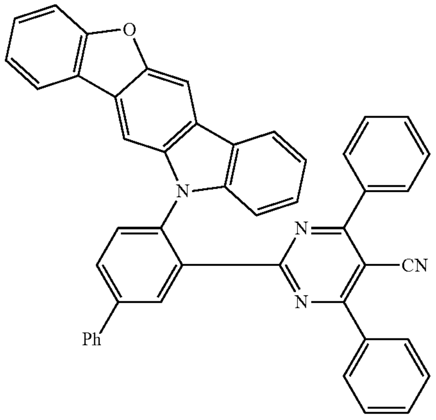
223
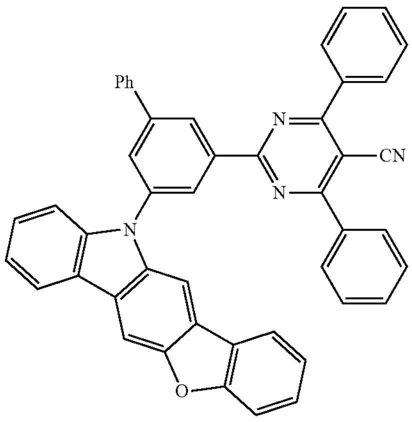
224
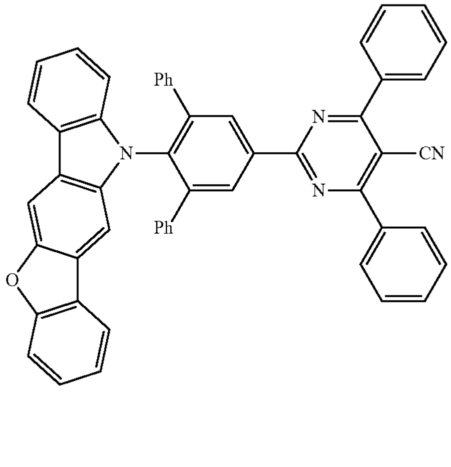
-continued
225
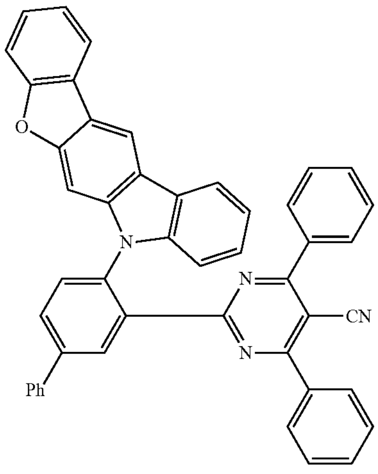
226
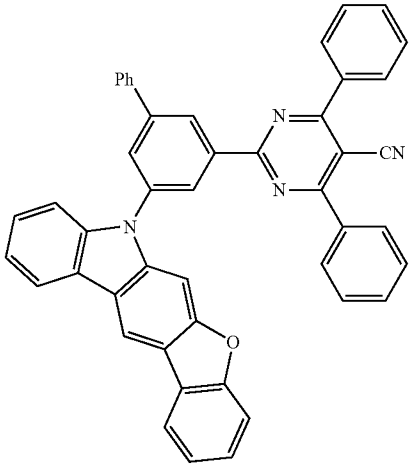
227
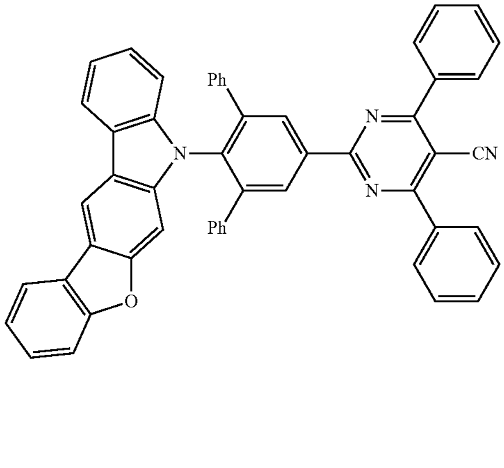

-continued
228
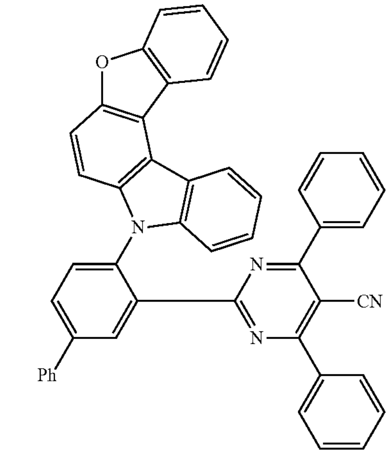
229
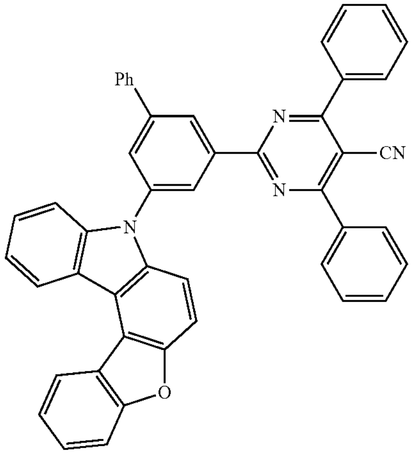
230
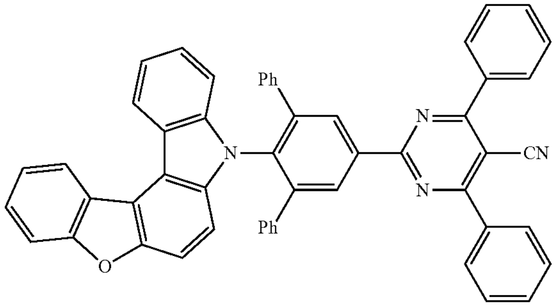
231
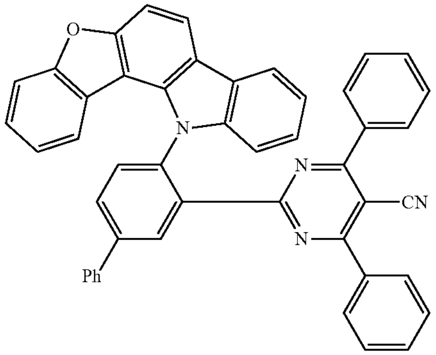
-continued
232
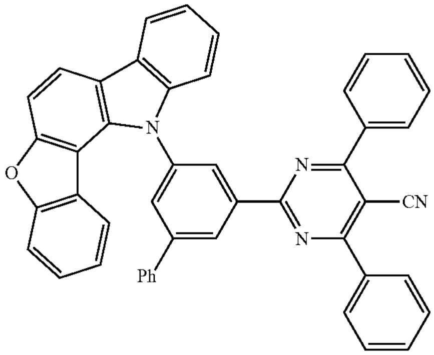
233
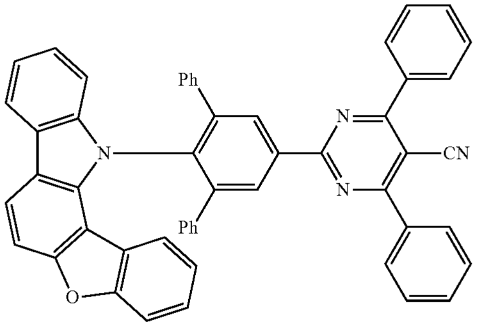
234
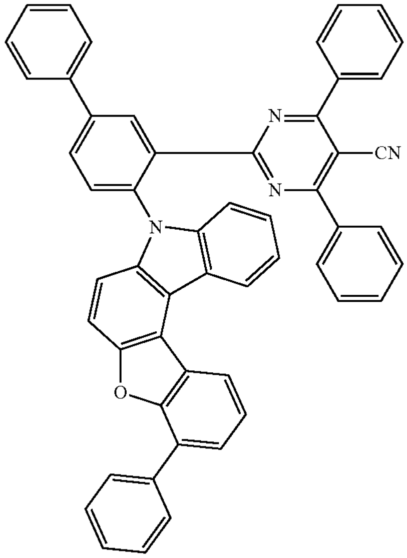
235
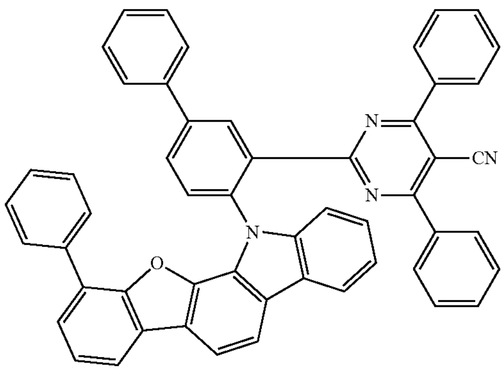

-continued

236

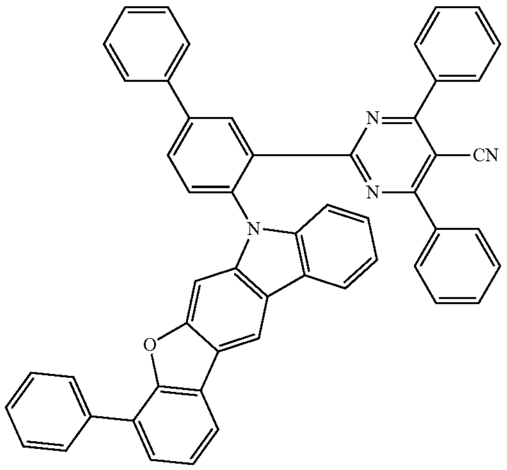

237

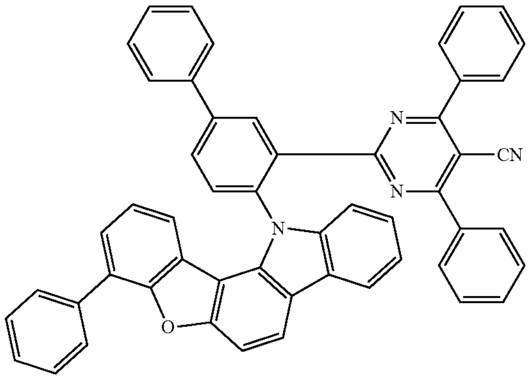

238

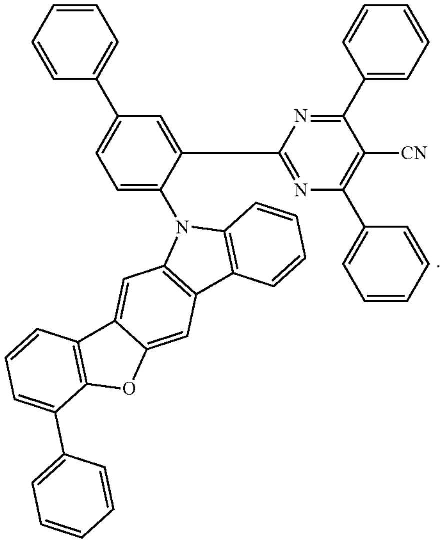

The heterocyclic compound represented by Formula 1 may include a pyrimidine group "substituted with a cyano group" (see Formula 1). Accordingly, as the heterocyclic compound represented by Formula 1 may have a deep highest occupied molecular orbital (HOMO) energy level (i.e., a large absolute value of HOMO energy level), excellent charge transport characteristics and charge balance maintaining characteristics may be obtained.

In addition, $Ar_1$ in Formula 1 may be a group represented by Formula 2, b1, which may be the number of $Ar_1$(s), may be an integer from 1 to 3, $D_1$ in Formula 1 may be the group represented by Formula 3, and c1, which may be the number of $D_1$(s), may be an integer from 1 to 3. That is, as b1 and c1 may not each be 0, a benzene group in the heterocyclic compound represented by Formula 1 may be essentially substituted with at least one $Ar_1$ and at least one $D_1$. Accordingly, an electron donor group and an electron acceptor group in the heterocyclic compound represented by Formula 1 may be effectively separated to thereby enlarge charge transfer characteristics of the heterocyclic compound.

Formula 1'

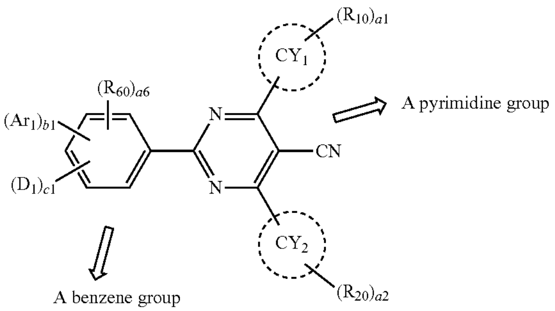

Formula 2

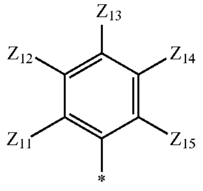

Formula 3

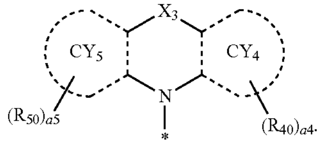

In some embodiments, the heterocyclic compound represented by Formula 1 may emit fluorescent light (fluorescence).

In one or more embodiments, the heterocyclic compound represented by Formula 1 may emit blue light. In some embodiments, the blue light may have a maximum emission wavelength in a range of about 400 nanometers (nm) to about 550 nm.

In one or more embodiments, a singlet energy level (eV) of the heterocyclic compound represented by Formula 1 may be about 2.5 electron volts (eV) or greater and about 3.0 eV or lower.

In one or more embodiments, a difference between a triplet energy level (eV) and a singlet energy level (eV) of the heterocyclic compound represented by Formula 1 may be about 0 eV or greater and 0.5 eV or lower. Accordingly, the heterocyclic compound represented by Formula 1 may emit delayed fluorescence having high emission efficiency and/or high luminescence. For example, the heterocyclic compound may emit thermally activated delayed fluorescence (TADF).

When a difference between a triplet energy level (eV) of the heterocyclic compound represented by Formula 1 and a singlet energy level (eV) of the TADF emitter is within this range, up-conversion from a triplet state to a singlet state may occur effectively, and thus, the heterocyclic compound may emit delayed fluorescence.

Here, the triplet energy level and the singlet energy level may be evaluated according to the density functional theory (DFT) method, wherein structure optimization is performed at a degree of B3LYP, and 6-31G(d,p), for example, according to Gaussian according to DFT method.

A method of synthesizing the heterocyclic compound represented by Formula 1 may be apparent to one of ordinary skill in the art by referring to Synthesis Examples provided herein.

According to an aspect of another embodiment, an organic light-emitting device may include: a first electrode; a second electrode; and an organic layer located between the first electrode and the second electrode and including an emission layer and at least one heterocyclic compound represented by Formula 1.

For example, the heterocyclic compound represented by Formula 1 may be included in the emission layer. The emission layer including the heterocyclic compound may be an emission layer according to one of the First to the Third Embodiments:

First Embodiment

The emission layer may consist of the heterocyclic compound represented by Formula 1. The emission layer consisting of the heterocyclic compound represented by Formula 1 may emit fluorescence from the heterocyclic compound, e.g., delayed fluorescence.

Second Embodiment

The emission layer may include a host and an emitter, the host may be different from the emitter, and the heterocyclic compound represented by Formula 1 may be included in the emitter. That is, the heterocyclic compound represented by Formula 1 may serve as an emitter. Accordingly, a ratio of emission components emitted from the heterocyclic compound may be in a range of about 70 percent (%) to about 100%, about 75% to about 100%, about 80% to about 100%, about 85% to about 100%, about 90% to about 100%, or about 95% to about 100%, based on total emission components emitted from the emission layer. In some embodiments, a content of the host may be greater than a content of the emitter. For example, light emitted from the emission layer may be fluorescence, e.g., delayed fluorescence (for example, TADF). In some embodiments, blue light emitted from the emission layer, e.g., blue light having a maximum emission wavelength of about 400 nm or greater and about 550 nm or lower may be obtained. As the heterocyclic compound represented by Formula 1 has excellent electrical characteristics and stability, an organic light-emitting device including an emission layer according to the Second Embodiment may have excellent emission efficiency and lifespan characteristics.

The emission layer according to the Second Embodiment may not include a phosphorescence emitter. In some embodiments, the emission layer according to the Second Embodiment may not include a transition metal. That is, the emission layer may not include a compound that may emit light according to a phosphorescence emission mechanism. Thus, the emission layer may not include a phosphorescence emitter and substantially may not emit phosphorescence. Instead, the emission layer may be, for example, a "delayed fluorescence" emission layer that may emit delayed fluorescence by transition to the ground state of triplet excitons of the heterocyclic compound represented by Formula 1 after reverse intersystem crossing (RISC) of the triplet excitons from a triplet state to a singlet state.

As described above, the "delayed fluorescence" emission layer described herein is different from a "phosphorescence" emission layer including a phosphorescence emitter (e.g., an iridium complex or a platinum complex) as an emitter, in which energy transfer to the phosphorescence emitter from a host may occur without delayed fluorescence emission by transition to the ground state of triplet excitons of the host after RISC to a singlet state.

The content of the emitter in the emission layer in the Second Embodiment may be in a range of about 0.01 parts to about 30 parts by weight, about 0.5 parts to about 20 parts by weight, or about 1 part to about 10 parts by weight, based on 100 parts by weight of the emission layer. When the content of the emitter is within any of these ranges, an organic light-emitting device having high emission efficiency and long lifespan without concentration quenching may be realized.

Third Embodiment

The emission layer may include a host, an emitter, and a sensitizer, wherein the host, the emitter, and the sensitizer may be different from each other, and the heterocyclic compound represented by Formula 1 may be included in the sensitizer. That is, the emission layer may include three different types of compounds, and the heterocyclic compound represented by Formula 1 may serve as a sensitizer that transfers energy to the emitter, not as an emitter.

In the Third Embodiment, the emitter in the emission layer may be a fluorescence emitter. For example, 25% of the energy of singlet excitons generated from the host may be transferred to a sensitizer by Förster energy transfer, and 75% of energy of triplet excitons generated from the host may be transferred to a singlet excited state and a triplet excited state of the sensitizer. In this embodiment, after the triplet excitons transferred to a triplet excited state undergo RISC to a singlet excited state, the singlet excitons of the sensitizer may be transferred to a singlet excited state of the fluorescence emitter by Förster energy transfer. Accordingly, as both singlet excitons and triplet excitons generated from the emission layer may be transferred to a singlet excited state of the fluorescent emitter, an organic light-emitting device including the emission layer according to the Third Embodiment may have excellent emission efficiency and lifespan characteristics.

Accordingly, a ratio of emission components emitted from the emitter may be in a range of about 70% to about 100%, about 75% to about 100%, about 80% to about 100%, about 85% to about 100%, about 90% to about 100%, or about 95% to about 100%, based on total emission components emitted from the emission layer according to the Third Embodiment. For example, light emitted from the emission layer may be red light, green light, or blue light. In some embodiments, blue light emitted from the emission layer, e.g., blue light having a maximum emission wavelength of about 400 nm or greater and about 550 nm or lower may be obtained.

The content of the emitter and the sensitizer in the emission layer in the Third Embodiment may be in a range of about 0.5 parts to about 50 parts by weight, about 1 part to about 30 parts by weight, or about 5 part to about 20 parts by weight, based on 100 parts by weight of the emission layer. The content ratio of the emitter to the sensitizer may be in a range of about 10:90 to about 90:10, for example, about 30:70 to about 70:30. When the content of the emitter and the sensitizer is within any of these ranges, and/or when the content ratio of the emitter to the sensitizer is within any of these ranges, an organic light-emitting device having high emission efficiency and long lifespan without concentration quenching may be realized.

The host that may be used in the Second Embodiment and the Third Embodiment and the emitter that may be used in the Third Embodiment may be understood by referring to the descriptions thereof provided herein.

DESCRIPTION OF FIGURE

FIGURE illustrates a schematic cross-sectional view of an organic light-emitting device 10 according to an embodiment. Hereinafter, a structure of an organic light-emitting device according to one or more embodiments and a method of manufacturing the organic light-emitting device will be described with reference to FIGURE.

In FIGURE, an organic light-emitting device 10 includes a first electrode 11, a second electrode 19 facing the first electrode 11, and an organic layer 10A between the first electrode 11 and the second electrode 19.

In FIGURE, the organic layer 10A includes an emission layer 15, a hole transport region 12 between the first electrode 11 and an emission layer 15, and an electron transport region 17 between the emission layer 15 and the second electrode 19.

A substrate may be additionally disposed under the first electrode 11 or on the second electrode 19. The substrate may be any substrate used in organic light-emitting devices, e.g., a glass substrate or a transparent plastic substrate, each having excellent mechanical strength, thermal stability, transparency, surface smoothness, ease of handling, and water repellency.

First Electrode 11

The first electrode 11 may be formed by depositing or sputtering, onto the substrate, a material for forming the first electrode 11. The first electrode 11 may be an anode. The material for forming the first electrode 11 may include a material with a high work function for easy hole injection.

The first electrode 11 may be a reflective electrode, a semi-transmissive electrode, or a transmissive electrode. When the first electrode 11 is a transmissive electrode, a material for forming the first electrode 110 may include indium tin oxide (ITO), indium zinc oxide (IZO), tin oxide ($SnO_2$), zinc oxide (ZnO), or any combinations thereof. In some embodiments, when the first electrode 110 is a semi-transmissive electrode or a reflective electrode, a material for forming the first electrode 110 may include magnesium (Mg), silver (Ag), aluminum (Al), aluminum-lithium (Al—Li), calcium (Ca), magnesium-indium (Mg—In), magnesium-silver (Mg—Ag), or any combination thereof.

The first electrode 11 may have a single-layered structure or a multi-layered structure including a plurality of layers.

Emission Layer 15

The emission layer 15 may include the heterocyclic compound represented by Formula 1. The emission layer 15 may further include a host in addition to the heterocyclic compound represented by Formula 1.

The thickness of the emission layer may be in a range of about 100 Å to about 1,000 Å, and in some embodiments, about 200 Å to about 600 Å. When the thickness of the emission layer is within any of these ranges, improved luminescence characteristics may be obtained without a substantial increase in driving voltage.

For example, the emission layer 15 may be an emission layer according to any one of the First Embodiment, the Second Embodiment, and the Third Embodiment. The host that may be used in the Second Embodiment and the Third Embodiment and the emitter that may be used in the Third Embodiment will be described hereinafter.

Host in Emission Layer 15

The host may not include a transition metal.

The host may consist of one type of compound or a mixture of two different types of compounds.

The host may be any suitable host.

In some embodiments, the host may include a bipolar host, an electron transporting host, a hole transporting host, or any combination thereof. The bipolar host, the electron transporting host, and the hole transporting host may be identical to each other.

The electron transporting host may include at least one electron transporting group.

The hole transporting host may not include an electron transporting group.

The term "electron transporting group" as used herein may include a cyano group, a π electron-depleted nitrogen-containing $C_1$-$C_{60}$ cyclic group, a group represented by one of the following Formulae, or any combination thereof:

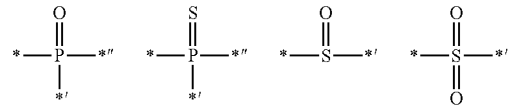

wherein, in the Formulae above, *, *', and *" may each indicate a binding site to an adjacent atom.

In some embodiments, the electron transporting host in the emission layer 15 may include a cyano group, a π electron-depleted nitrogen-containing $C_1$-$C_{60}$ cyclic group, or any combination thereof.

In one or more embodiments, the electron transporting host in the emission layer 15 may include a cyano group.

In one or more embodiments, the electron transporting host in the emission layer 15 may include at least one cyano group and a π electron-depleted nitrogen-containing $C_1$-$C_{60}$ cyclic group.

In one or more embodiments, the host may include a bipolar host.

In one or more embodiments, the host may include an electron transporting host.

In one or more embodiments, the host may include a hole transporting host.

In one or more embodiments, the hole transporting host may not be 1,3-bis(9-carbazolyl)benzene (mCP), tris(4-carbazoyl-9-ylphenyl)amine (TCTA), 4,4'-bis(N-carbazolyl)-1,1'-biphenyl (CBP), 3,3-bis(carbazol-9-yl)biphenyl (mCBP), N,N'-di(1-naphthyl)-N,N'-diphenyl-(1,1'-biphenyl)-4,4'-diamine (NPB), 4,4',4"-tris[phenyl(m-tolyl)amino]triphenylamine (m-MTDATA), or N,N'-bis(3-methylphenyl)-N,N'-diphenylbenzidine (TPD).

In one or more embodiments, the host may include an electron transporting host and a hole transporting host, the electron transporting host may include at least one π electron-rich $C_3$-$C_{60}$ cyclic group and at least one electron transporting group, the hole transporting host may include at least one π electron-rich $C_3$-$C_{60}$ cyclic group and not include an electron transporting group, and the electron transporting group may include a cyano group, a π electron-depleted nitrogen-containing $C_1$-$C_{60}$ cyclic group, or any combination thereof.

In one or more embodiments, the electron transporting host may include i) a cyano group, a pyrimidine group, a pyrazine group, a triazine group, or any combination thereof and ii) a triphenylene group, a carbazole group, or any combination thereof.

In one or more embodiments, the hole transporting host may include at least one carbazole group.

In one or more embodiments, the electron transporting host may include a compound represented by Formula E-1, and the hole transporting host may include a compound represented by Formula H-1:

$$[Ar_{301}]_{xb11}\text{-}[(L_{301})_{xb1}\text{-}R_{301}]_{xb21} \qquad \text{Formula E-1}$$

wherein, in Formula E-1, $Ar_{301}$ may be a $C_5$-$C_{60}$ carbocyclic group unsubstituted or substituted with at least one $R_{301a}$ or a $C_1$-$C_{60}$ heterocyclic group unsubstituted or substituted with at least one $R_{301a}$, xb11 may be 1, 2, or 3, $L_{301}$ may each independently be a single bond, a group represented by one of the following Formulae, a $C_5$-$C_{60}$ carbocyclic group unsubstituted or substituted with at least one $R_{301a}$ or a $C_1$-$C_{60}$ heterocyclic group unsubstituted or substituted with at least one $R_{301a}$, wherein in Formulae, *, *', and *" each indicate a binding site to an adjacent atom,

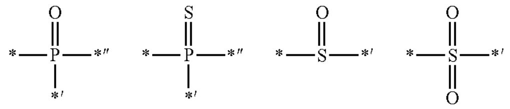

xb1 may be an integer from 1 to 5, $R_{301a}$ and $R_{301}$ may each independently be hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_{301})(Q_{302})(Q_{303})$, —$N(Q_{301})(Q_{302})$, —$B(Q_{301})(Q_{302})$, —$C(=O)(Q_{301})$, —$S(=O)_2(Q_{301})$, —$S(=O)(Q_{301})$, —$P(=O)(Q_{301})(Q_{302})$ or —$P(=S)(Q_{301})(Q_{302})$, xb21 may be an integer from 1 to 5, wherein $Q_{301}$ to $Q_{303}$ may each independently be a $C_1$-$C_{10}$ alkyl group, a $C_1$-$C_{10}$ alkoxy group, a phenyl group, a biphenyl group, a terphenyl group, or a naphthyl group, and at least one of Conditions 1 to 3 may be satisfied:

Condition 1 wherein, at least one of $Ar_{301}$, $L_{301}$, and $R_{301}$ in Formula E-1 may each independently include a π electron-depleted nitrogen-containing $C_1$-$C_{60}$ cyclic group, Condition 2 wherein, $L_{301}$ in Formula E-1 may be a group represented by one of the following Formulae, and

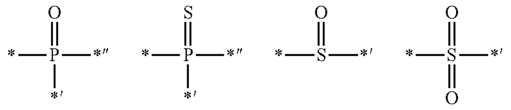

Condition 3 wherein, $R_{301}$ in Formula E-1 may be a cyano group, —$S(=O)_2(Q_{301})$, —$S(=O)(Q_{301})$, —$P(=O)(Q_{301})(Q_{302})$, or —$P(=S)(Q_{301})(Q_{302})$.

Formula H-1 is shown below.

$$Ar_{401}\text{-}(L_{401})_{xc1}\text{-}(Ar_{402})_{xc11}$$

11

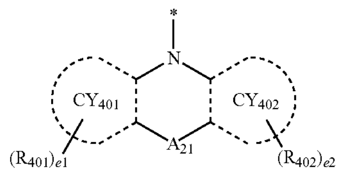

12

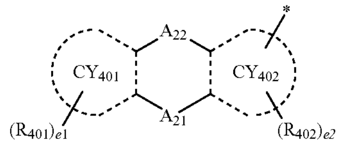

In Formulae H-1, 11 and 12, $L_{401}$ may be:

a single bond; or a π electron-rich $C_3$-$C_{60}$ cyclic group unsubstituted or substituted with deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, —$Si(Q_{401})(Q_{402})(Q_{403})$, or any combination thereof, xc1 may be an integer from 1 to 10, and when xc1 is 2 or greater, at least two $L_{401}$(s) may be identical to or different from each other, $Ar_{401}$ may be a group represented by Formula 11 or Formula 12, $Ar_4O_2$ may be:

a group represented by Formula 11 or Formula 12; or a π electron-rich $C_3$-$C_{60}$ cyclic group (e.g., a phenyl group, a naphthyl group, a fluorenyl group, a carbazolyl group, a dibenzofuranyl group, a dibenzothiophenyl group, a biphenyl group, a terphenyl group, or a triphenylenyl group), unsubstituted or substituted with deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, or any combination thereof, xc11 may be an integer from 1 to 10, and when xc11 is 2 or greater, at least two $Ar_{402}$(s) may be identical to or different from each other, $CY_{401}$ and $CY_{402}$ may each independently be a π electron-rich $C_3$-$C_{60}$ cyclic group (a benzene group, a naphthalene group, a fluorene group, a carbazole group, a benzocarbazole group, an indolocarbazole group, a dibenzofuran group, a dibenzothiophene group, a dibenzosilole group, a benzonaphthofuran group, a benzonapthothiophene group, or a benzonaphthosilole group), $A_{21}$ may be a single bond, O, S, $N(R_{411})$, $C(R_{411})(R_{412})$, or $Si(R_{411})(R_{412})$, $A_{22}$ may be a single bond, O, S, $N(R_{411})$, $C(R_{411})(R_{412})$, or $Si(R_{411})(R_{412})$, at least one of $A_{21}$ and $A_{22}$ in Formula 12 may not be a single bond, $R_{401}$, $R_{402}$, $R_{411}$, and $R_{412}$ may each independently be:

hydrogen, deuterium, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, a phenyl group, a naphthyl group, a fluorenyl group, a carbazolyl group, a dibenzofuranyl group, a dibenzothiophenyl group, or any combination thereof;

a π electron-rich $C_3$-$C_{60}$ cyclic group unsubstituted or substituted with deuterium, a $C_1$-$C_{20}$ alkyl group, a $C_1$-$C_{20}$ alkoxy group, a phenyl group, a naphthyl group, a fluorenyl group, a carbazolyl group, a dibenzofuranyl group, a dibenzothiophenyl group, a biphenyl group, or any combination thereof; or —$Si(Q_{404})(Q_{405})(Q_{406})$, and e1 and e2 may each independently be an integer from 0 to 10, wherein $Q_{401}$ to $Q_{406}$ may each independently be hydrogen, deuterium, a $C_1$-$C_{20}$alkyl group, a phenyl group, a naphthyl group, a fluorenyl group, a carbazolyl group, a dibenzofuranyl group, a dibenzothiophenyl group, a biphenyl group, a terphenyl group, or a triphenylenyl group, and

* indicates a binding site to an adjacent atom.

In some embodiments, in Formula E-1, $Ar_{301}$ and $L_{301}$ may each independently be a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group, each unsubstituted or substituted with deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl) triazinyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, —$P(=O)(Q_{31})(Q_{32})$, or any combination thereof, at least one of $L_{301}$(s) in the number of xb1 may each independently be an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group, each unsubstituted or substituted with deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl) triazinyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, —$P(=O)(Q_{31})(Q_{32})$, or any combination thereof, and $R_{301}$ may be hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a tetraphenyl group, a naphthyl group, a cyano group-containing phenyl group, a cyano group-containing biphenyl group, a cyano group-containing terphenyl group, a cyano group-containing tetraphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl) triazinyl group, $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, or $-P(=O)(Q_{31})(Q_{32})$, wherein $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group.

In some embodiments, $Ar_{301}$ may be a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, or a dibenzothiophene group, each unsubstituted or substituted with deuterium, —F, —Cl, —Br, —I, $-SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl) triazinyl group, $-Si(Q_{31})(Q_{32})(Q_{33})$, $-N(Q_{31})(Q_{32})$, $-B(Q_{31})(Q_{32})$, $-C(=O)(Q_{31})$, $-S(=O)_2(Q_{31})$, $-P(=O)(Q_{31})(Q_{32})$, or any combination thereof; or a group represented by one of Formulae 5-1 to 5-3 and Formulae 6-1 to 6-33, and $L_{301}$ may be a group represented by one of Formulae 5-1 to 5-3 and Formulae 6-1 to 6-33:

5-1

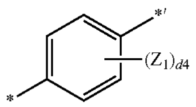

-continued 5-2

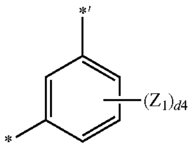

5-3

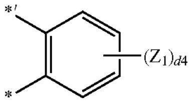

6-1

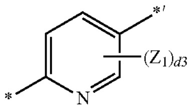

6-2

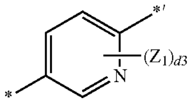

6-3

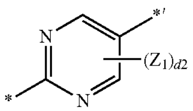

6-4

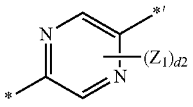

6-5

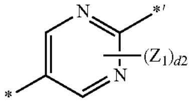

6-6

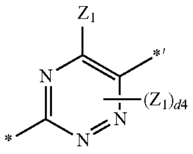

6-7

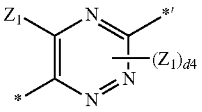

6-8

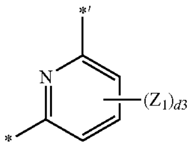

6-9

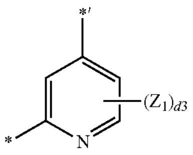

6-10

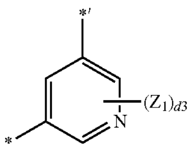

-continued
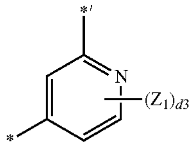
6-11
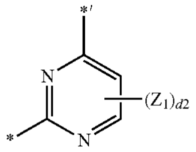
6-12
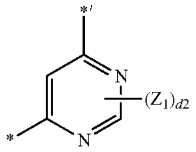
6-13
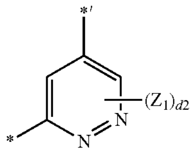
6-14
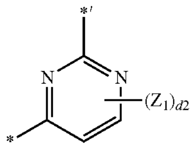
6-15
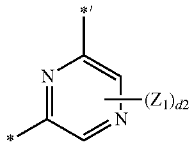
6-16
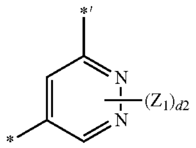
6-17
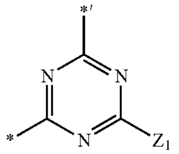
6-18
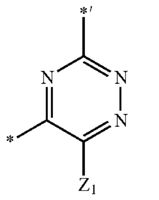
6-19
-continued
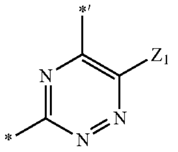
6-20
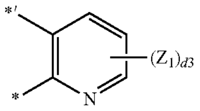
6-21
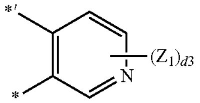
6-22
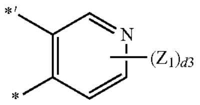
6-23
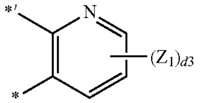
6-24
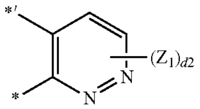
6-25
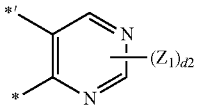
6-26
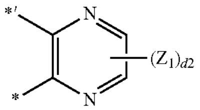
6-27
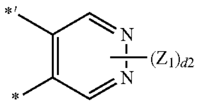
6-28
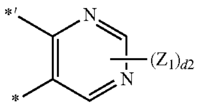
6-29
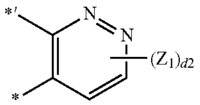
6-30
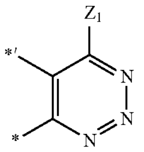
6-31
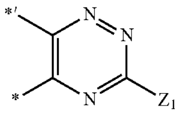
6-32

-continued 6-33

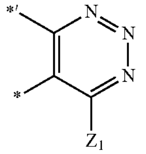

wherein, in Formulae 5-1 to 5-3 and 6-1 to 6-33, $Z_1$ may be hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a cyano group-containing phenyl group, a cyano group-containing biphenyl group, a cyano group-containing terphenyl group, a cyano group-containing naphthyl group, a pyridinyl group, a phenylpyridinyl group, a diphenylpyridinyl group, a biphenylpyridinyl group, a di(biphenyl)pyridinyl group, a pyrazinyl group, a phenylpyrazinyl group, a diphenylpyrazinyl group, a biphenylpyrazinyl group, a di(biphenyl)pyrazinyl group, a pyridazinyl group, a phenylpyridazinyl group, a diphenylpyridazinyl group, a biphenylpyridazinyl group, a di(biphenyl)pyridazinyl group, a pyrimidinyl group, a phenylpyrimidinyl group, a diphenylpyrimidinyl group, a biphenylpyrimidinyl group, a di(biphenyl)pyrimidinyl group, a triazinyl group, a phenyltriazinyl group, a diphenyltriazinyl group, a biphenyltriazinyl group, a di(biphenyl) triazinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), or —P(=O)($Q_{31}$)($Q_{32}$), d4 may be 0, 1, 2, 3, or 4, d3 may be 0, 1, 2, or 3, d2 may be 0, 1, or 2, and

* and *' each indicate a binding site to an adjacent atom.

$Q_{31}$ to $Q_{33}$ may respectively be understood by referring to the descriptions of $Q_{31}$ to $Q_{33}$ provided herein.

In one or more embodiments, $L_{301}$ may be a group represented by one of Formulae 5-2, 5-3, and 6-8 to 6-33.

In one or more embodiments, $R_{301}$ may be a cyano group or a group represented by one of Formulae 7-1 to 7-18, and at least one of $Ar_{402}$(s) in the number of xc11 may be represented by one of Formulae 7-1 to 7-18:

7-1

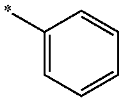

7-2

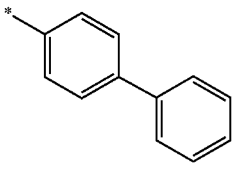

7-3

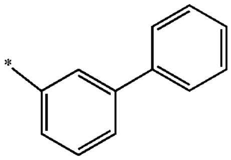

-continued 7-4

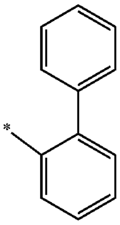

7-5

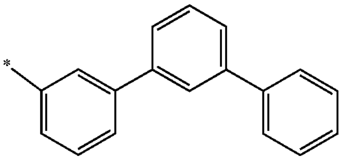

7-6

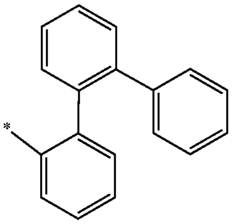

7-7

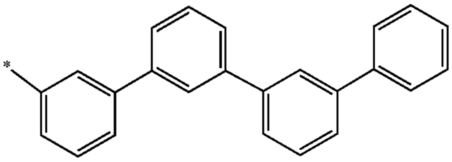

7-8

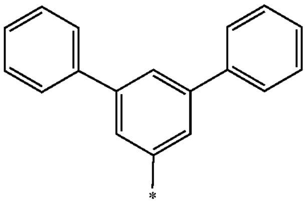

7-9

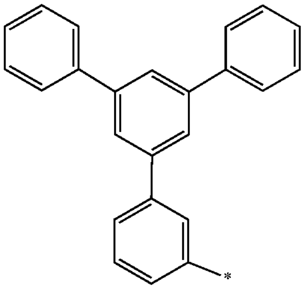

7-10

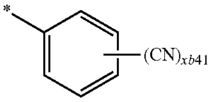

7-11

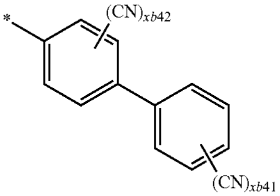

-continued 7-12

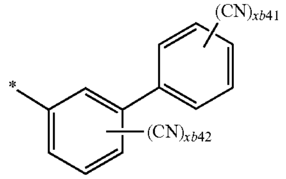

7-13

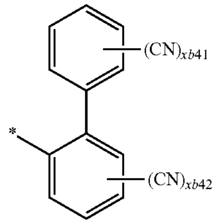

7-14

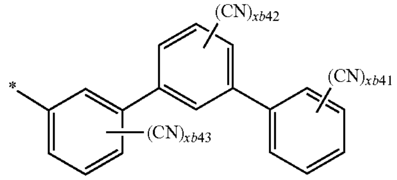

7-15

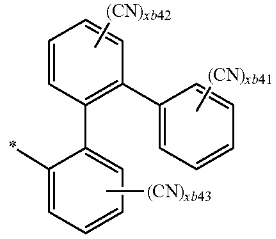

7-16

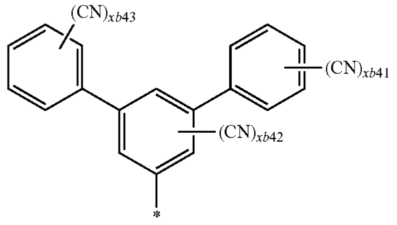

7-17

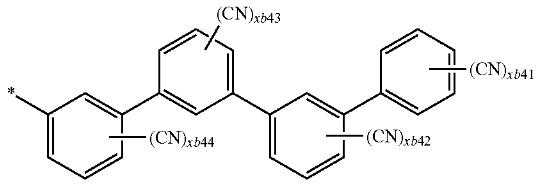

7-18

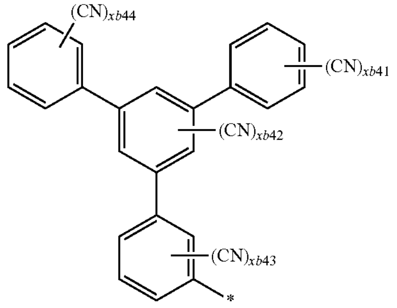

wherein, in Formulae 7-1 to 7-18, xb41 to xb44 may each be 0, 1, or 2, provided that xb41 in Formula 7-10 may not be 0, xb41+xb42 in Formulae 7-11 to 7-13 may not be 0, xb41+xb42+xb43 in Formulae 7-14 to 7-16 may not be 0, xb41+xb42+xb43+xb44 in Formulae 7-17 and 7-18 may not be 0, and * indicates a binding site to an adjacent atom.

In Formula E-1, at least two $Ar_{301}$(s) may be identical to or different from each other, and at least two $L_{301}$(s) may be identical to or different from each other. In Formula H-1, at least two $L_{401}$(s) may be identical to or different from each other, and at least two $Ar_{402}$(s) may be identical to or different from each other.

Examples of the electron transporting host may include compounds of Groups HE1 to HE7:

Group HE1

H-E1

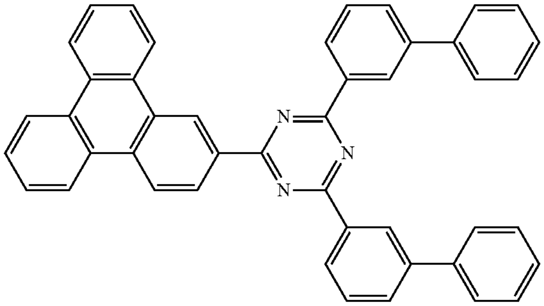

H-E2

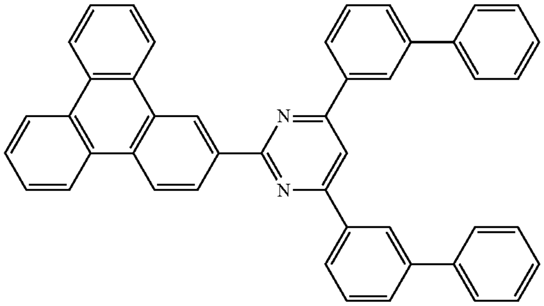

H-E3

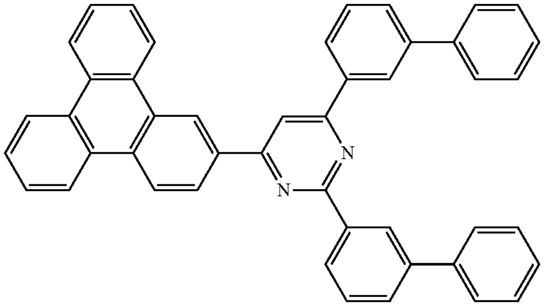

-continued
H-E4
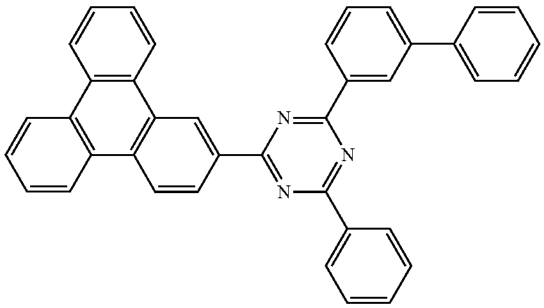
H-E5
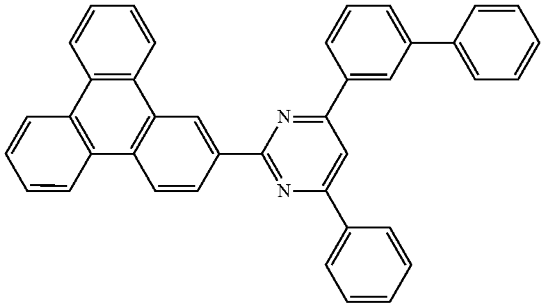
H-E6
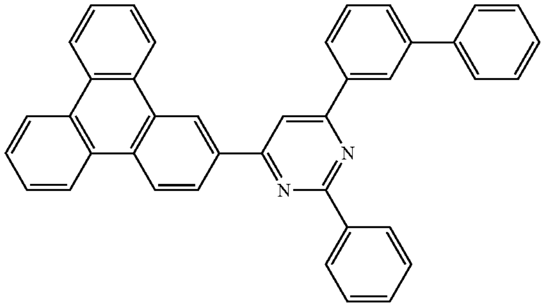
H-E7
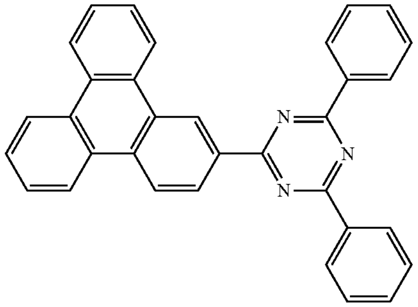
H-E8
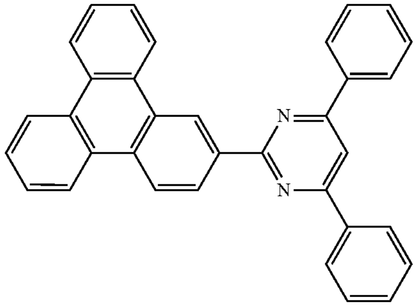
-continued
H-E9
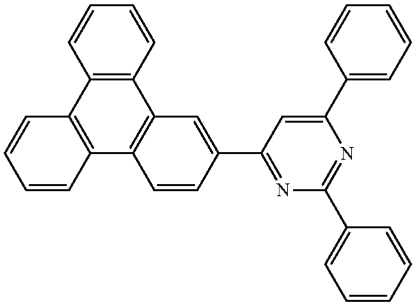
H-E10
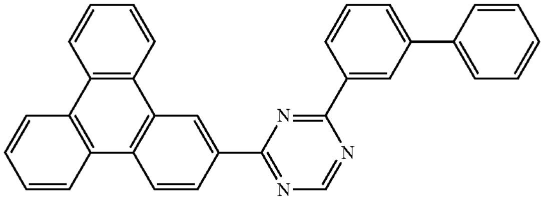
H-E11
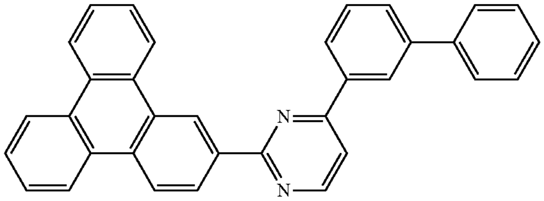
H-E12
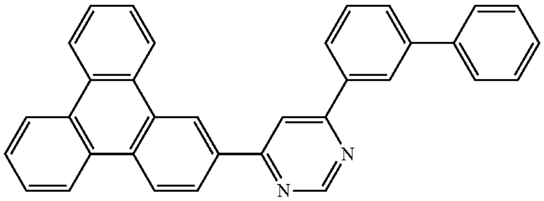
H-E13
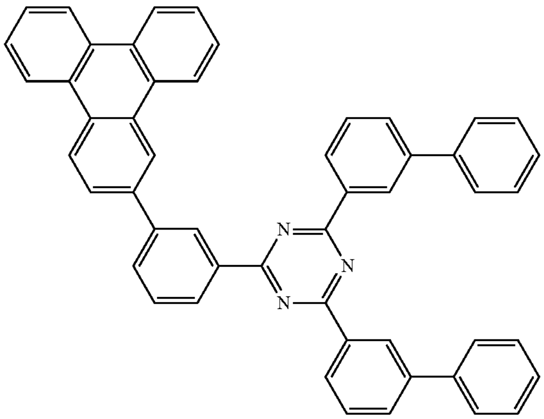

-continued
H-E14
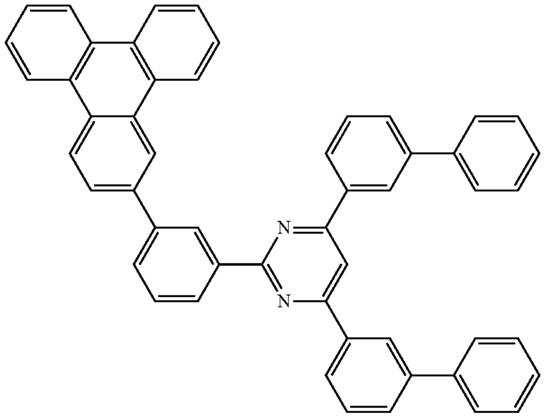
H-E15
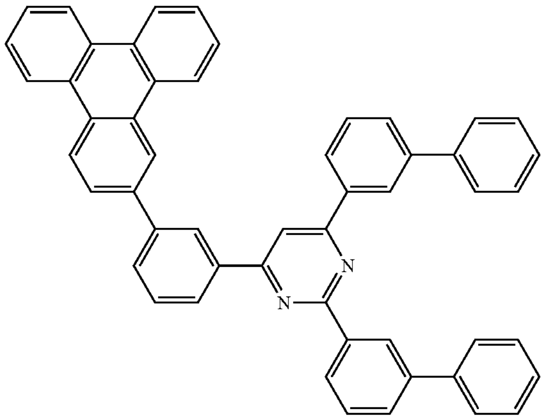
H-E16
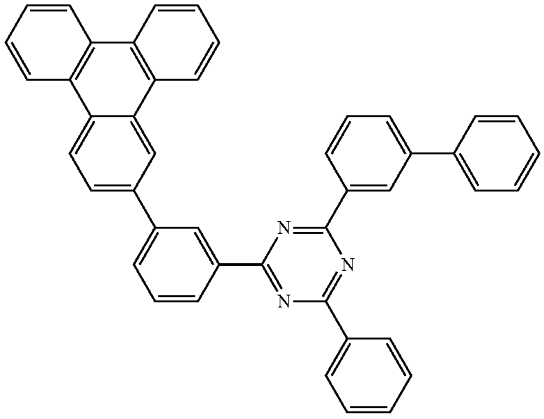
-continued
H-E17
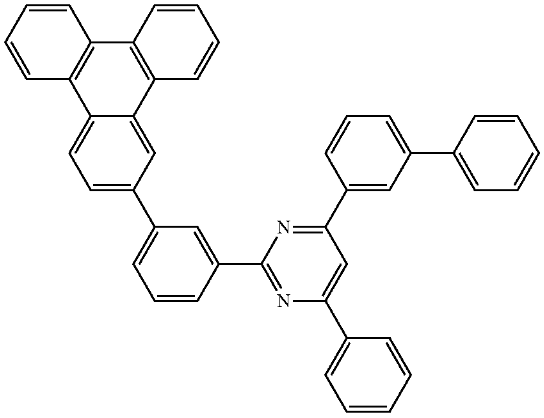
H-E18
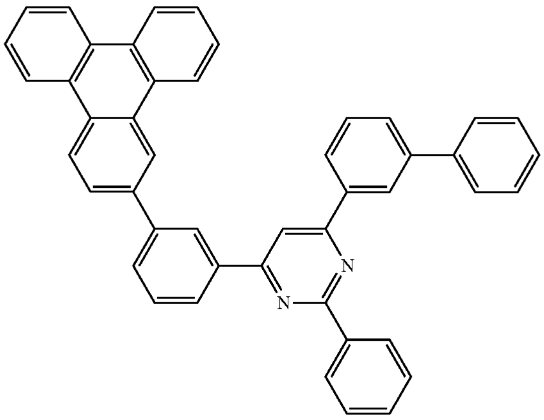
H-E19
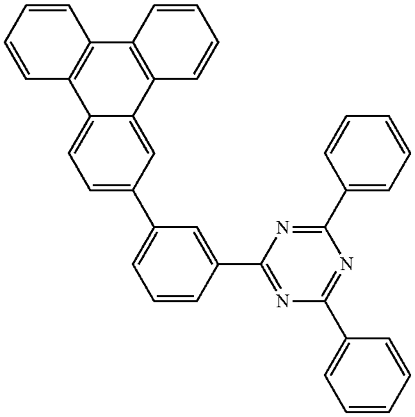

-continued
H-E20
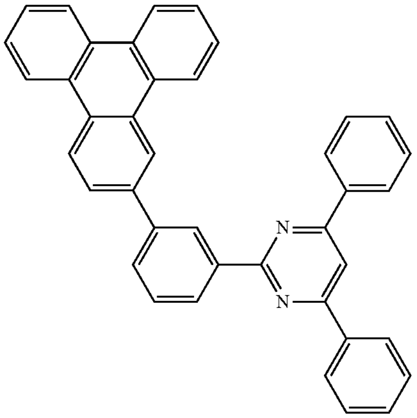
H-E21
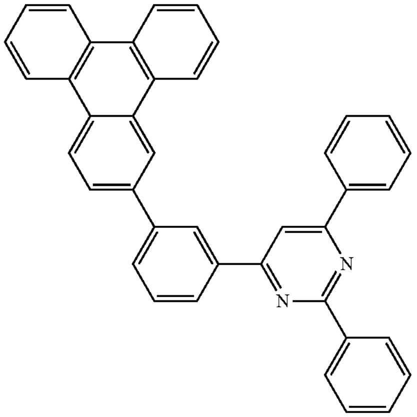
H-E22
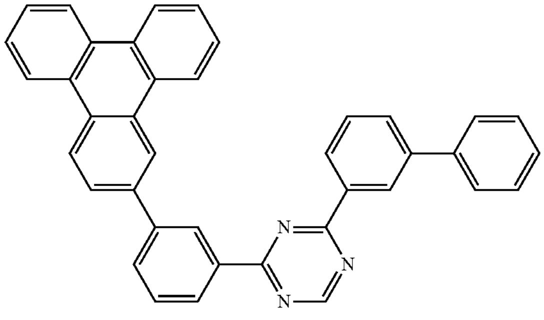
H-E23
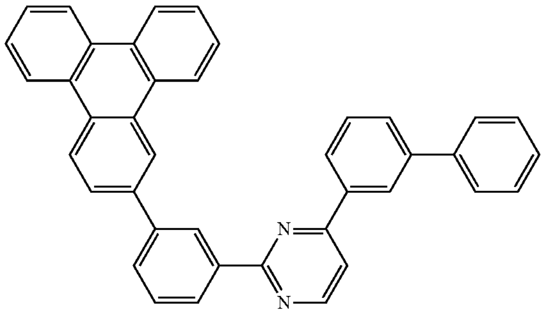
-continued
H-E24
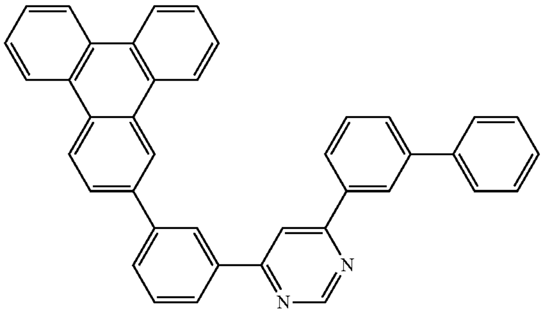
H-E25
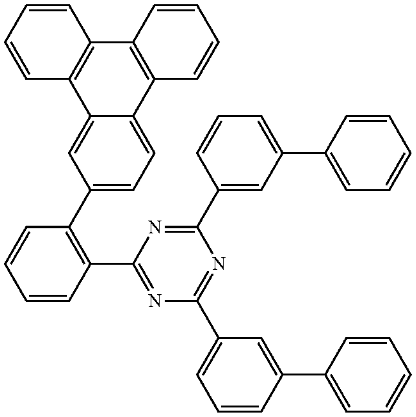
H-E26
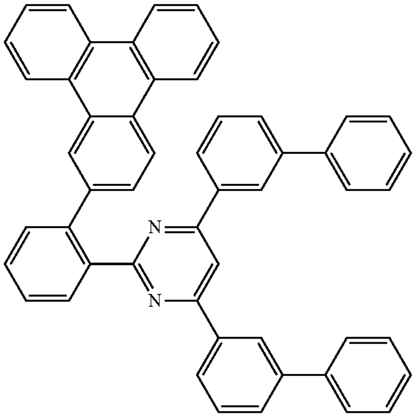
H-E27
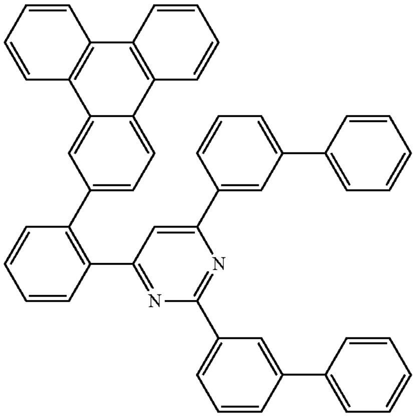

-continued
H-E28
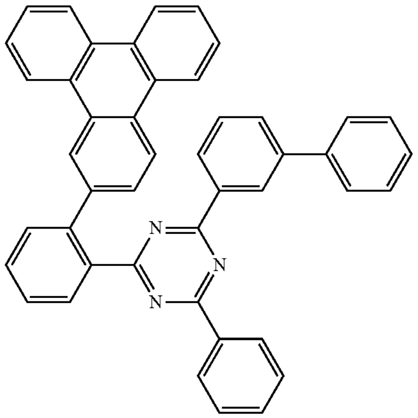
H-E29
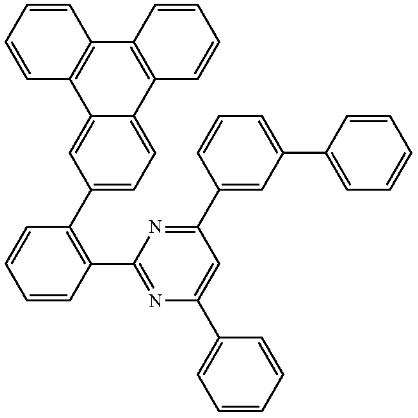
H-E30
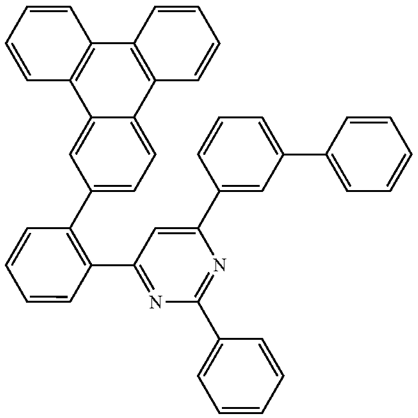
-continued
H-E31
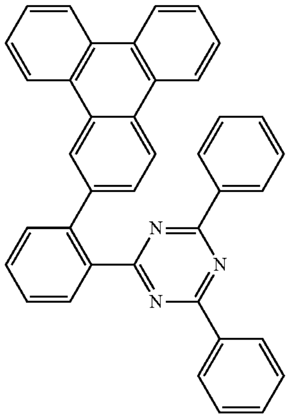
H-E32
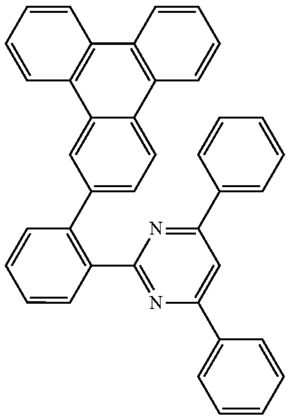
H-E33
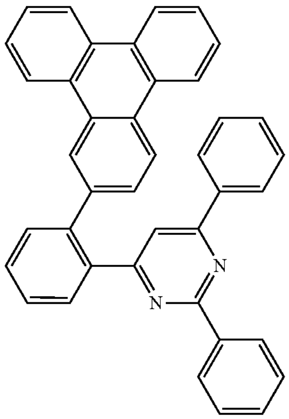
H-E34
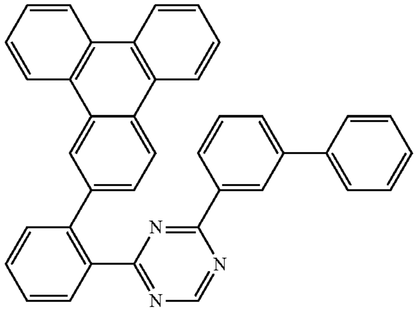

H-E35
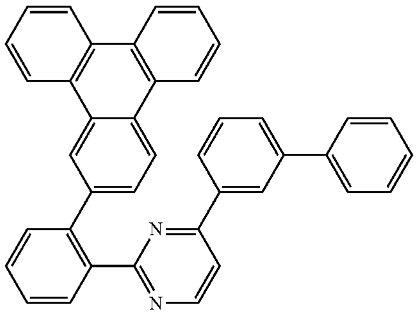
H-E36
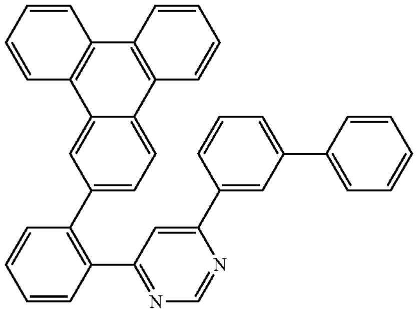
H-E37
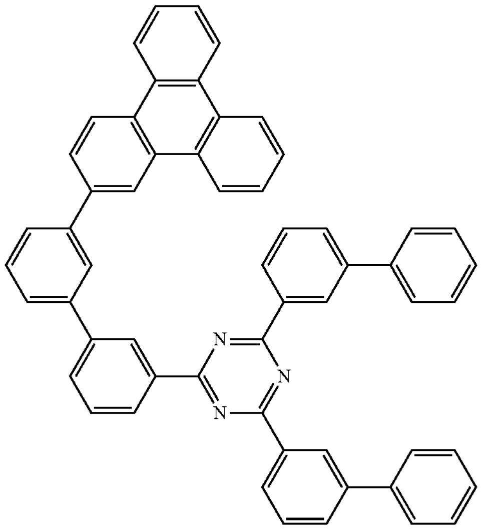
H-E38
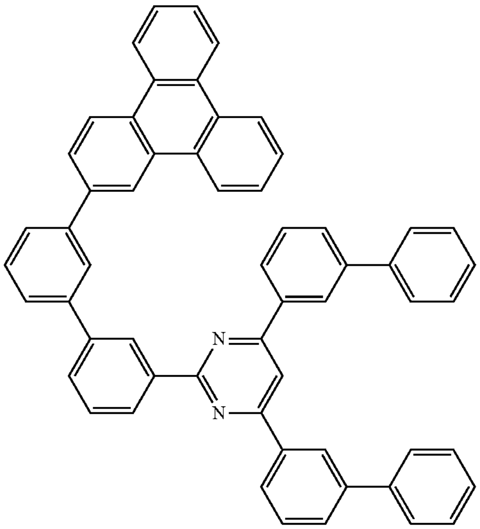
H-E39
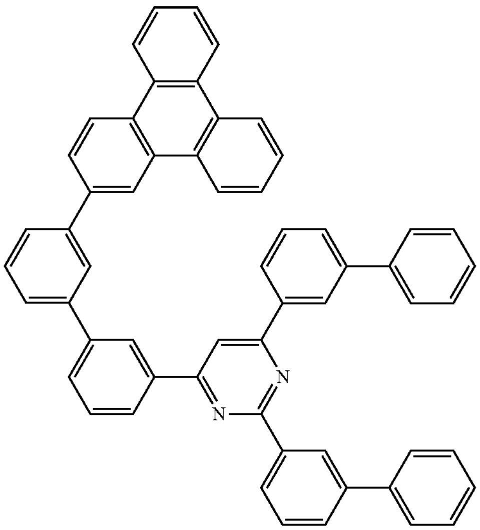
H-E40
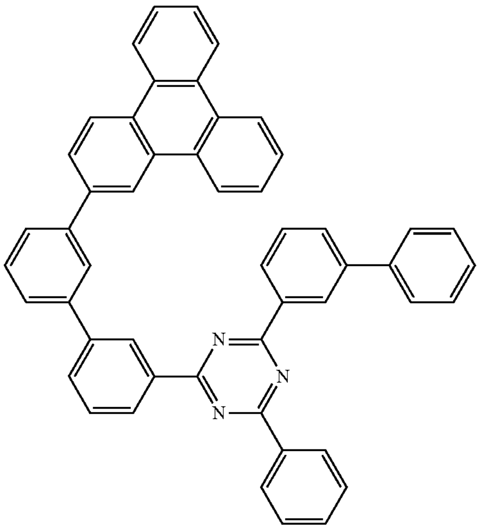

-continued
H-E41
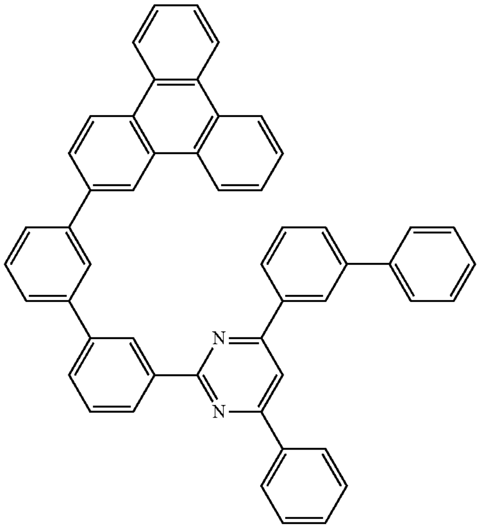
H-E42
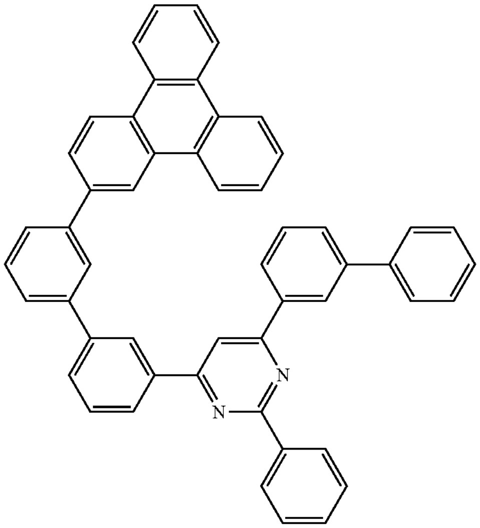
H-E43
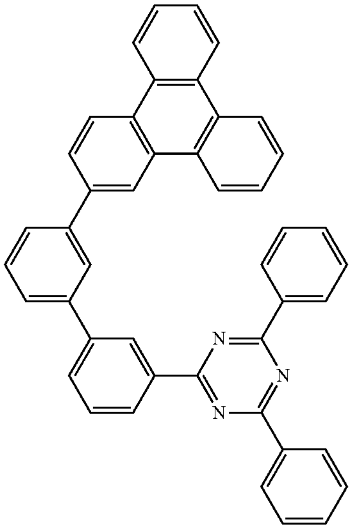
-continued
H-E44
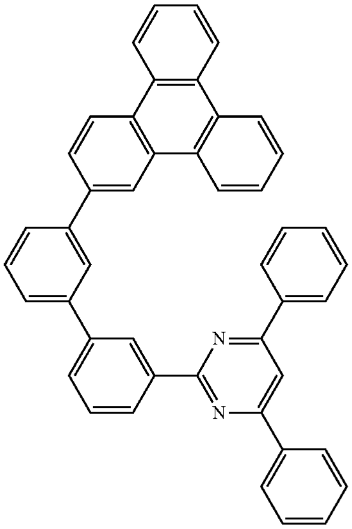
H-E45
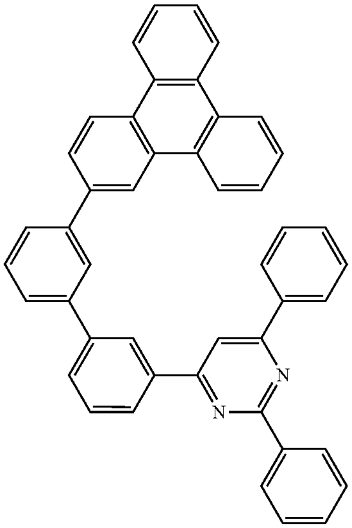
H-E46
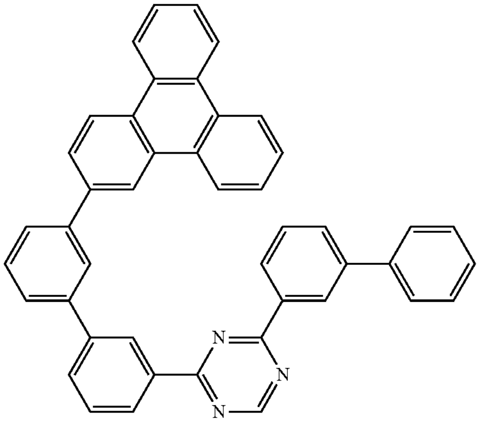

-continued
H-E47
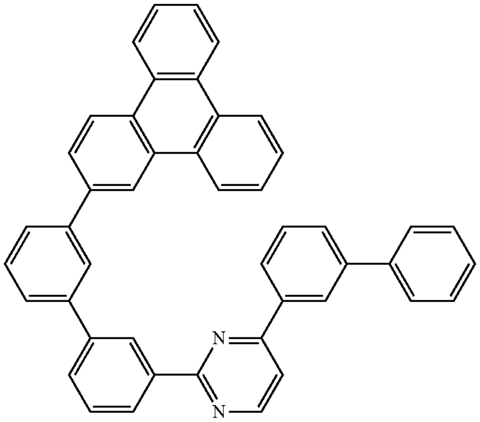
H-E48
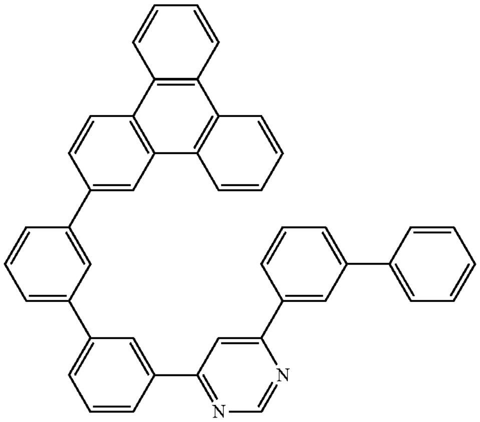
H-E49
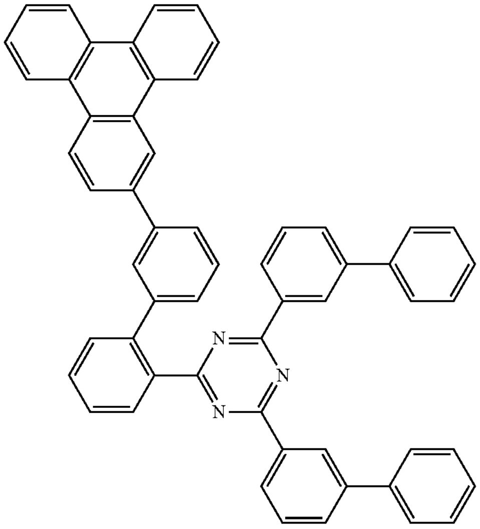
-continued
H-E50
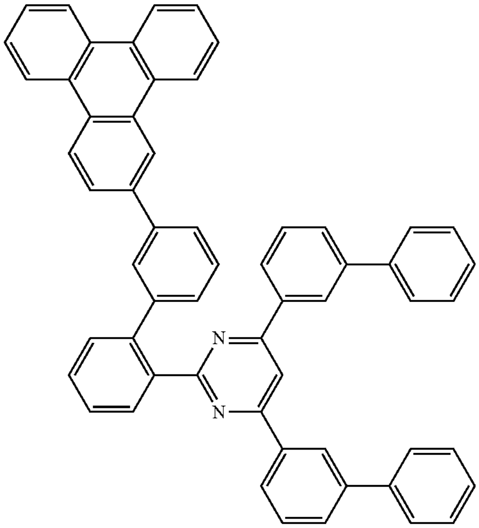
H-E51
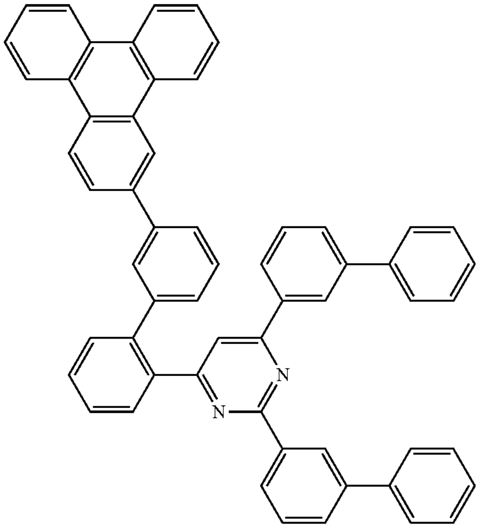
H-E52
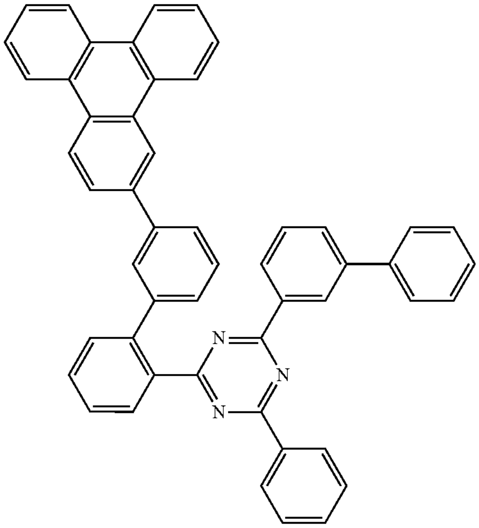

-continued
H-E53
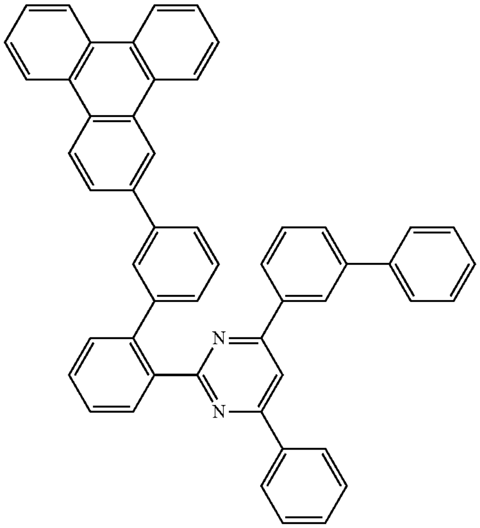
H-E54
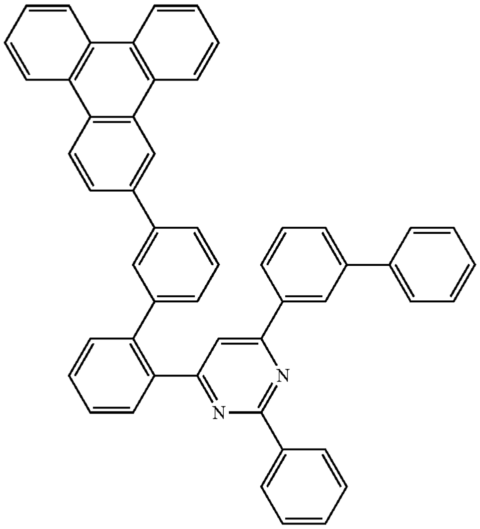
H-E55
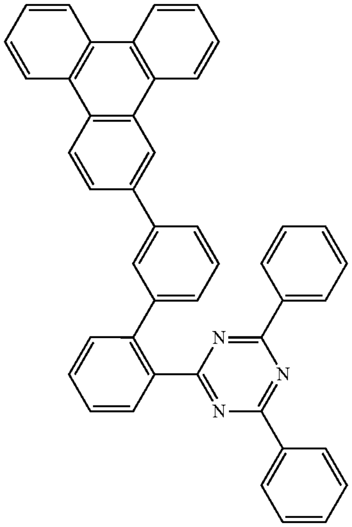
-continued
H-E56
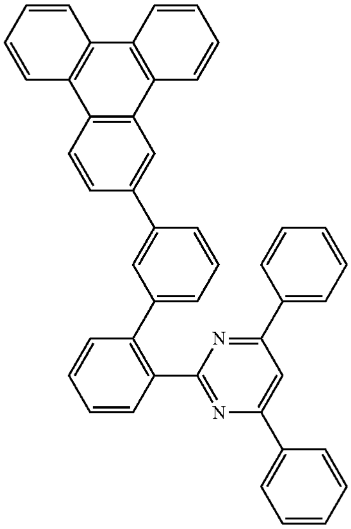
H-E57
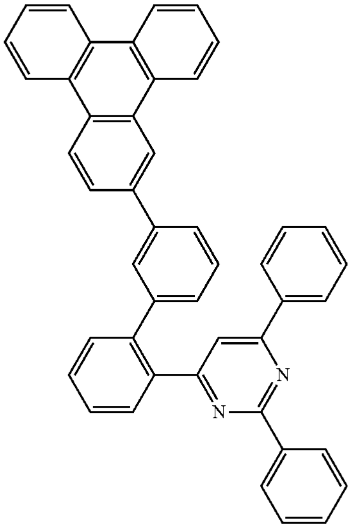
H-E58
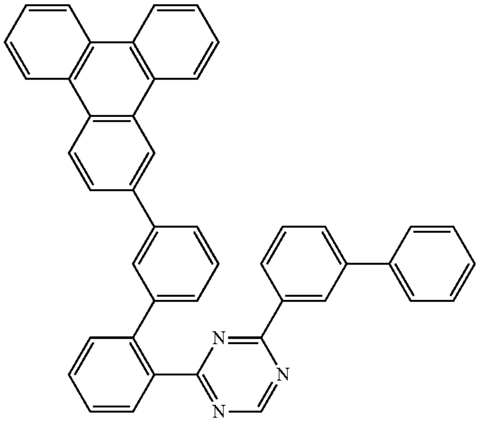

-continued
H-E59
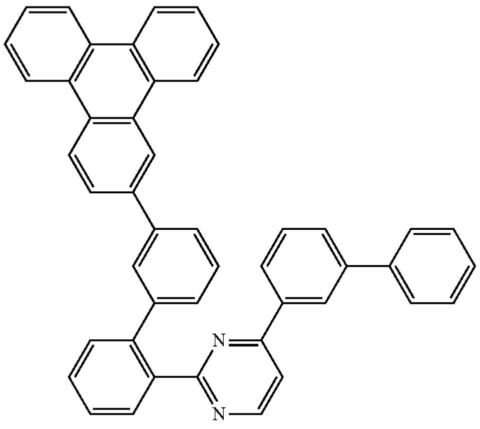
H-E60
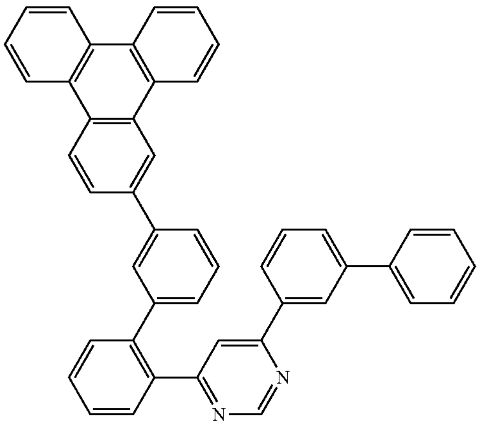
H-E61
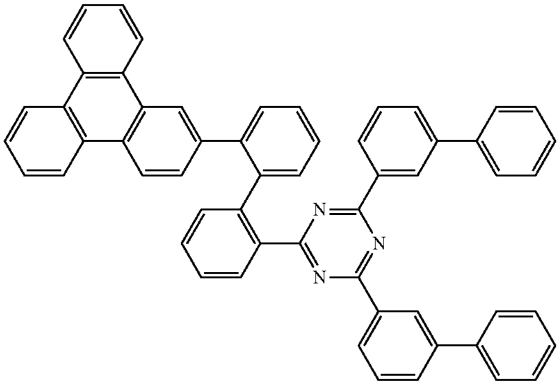
-continued
H-E62
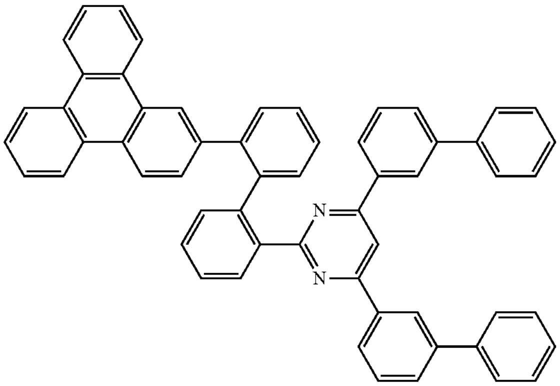
H-E63
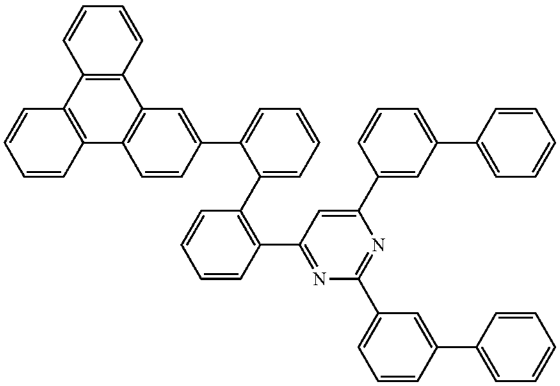
H-E64
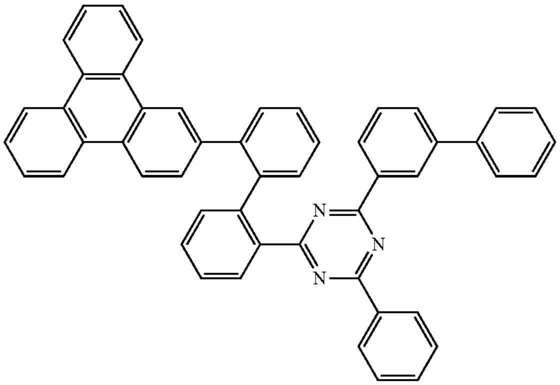
H-E65
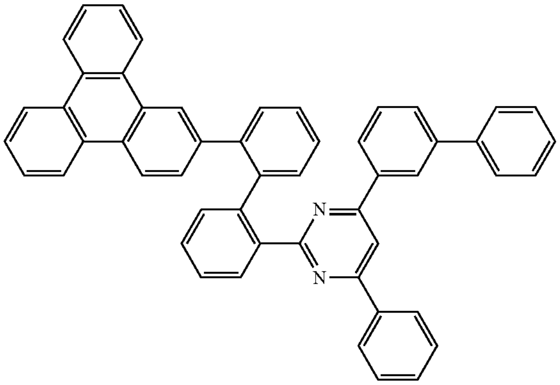

-continued
H-E66
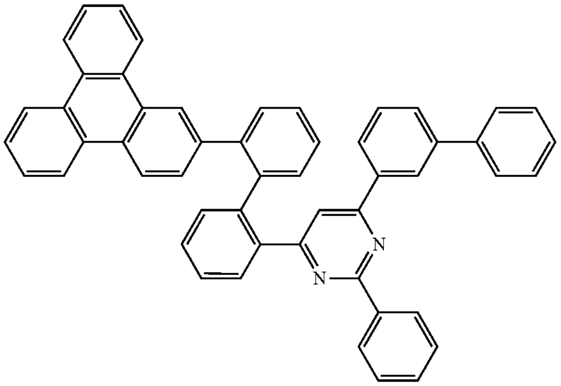
H-E67
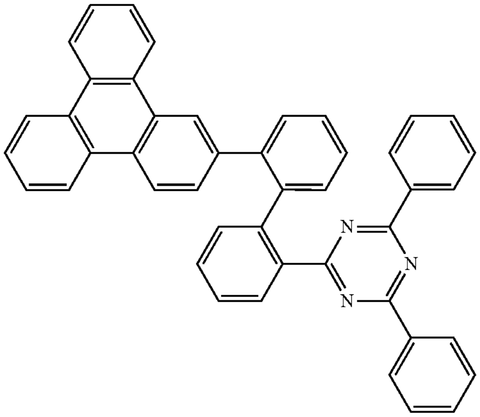
H-E68
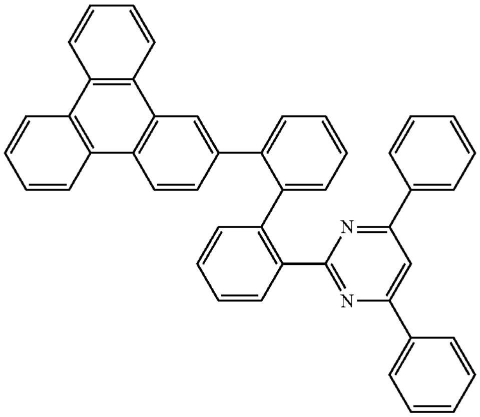
-continued
H-E69
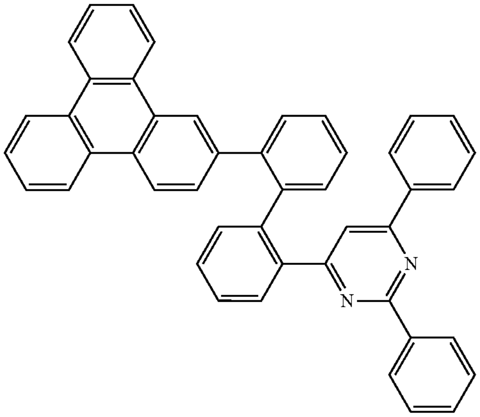
H-E70
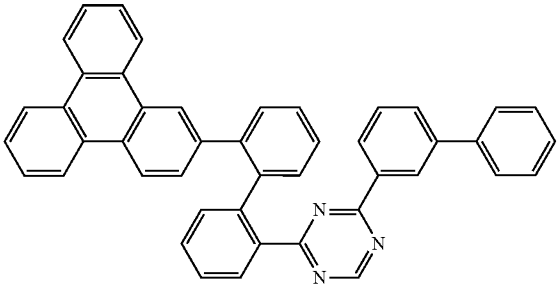
H-E71
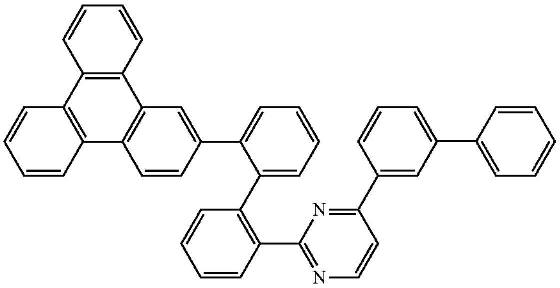
H-E72
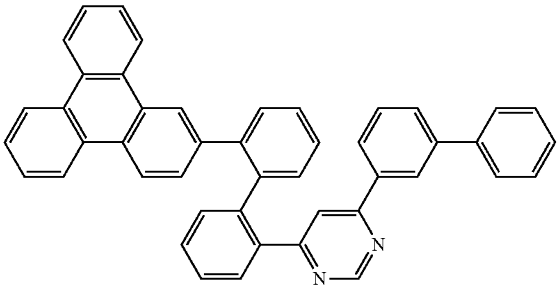

-continued
H-E73
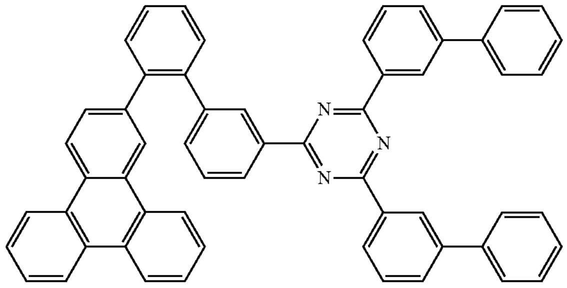
H-E74
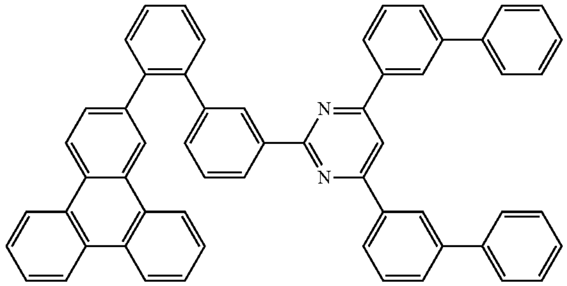
H-E75
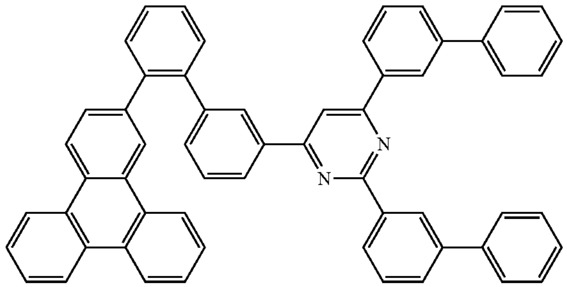
H-E76
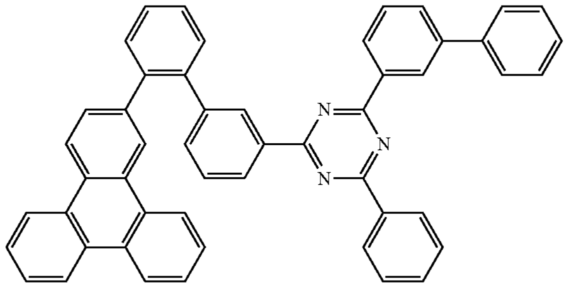
H-E77
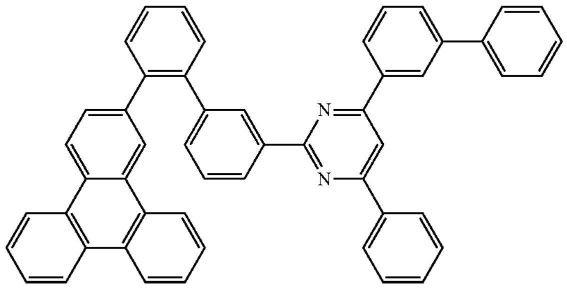
-continued
H-E78
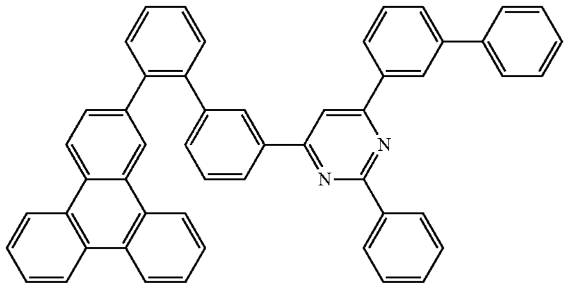
H-E79
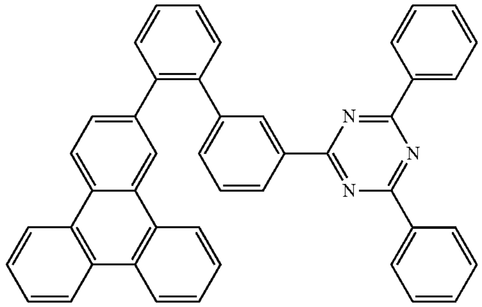
H-E80
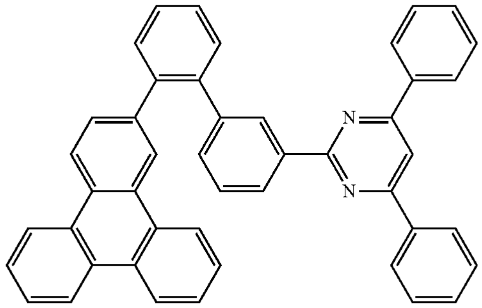
H-E81
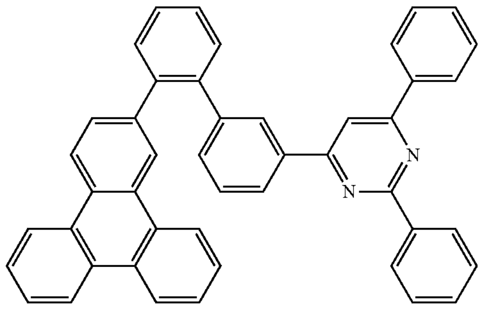
H-E82
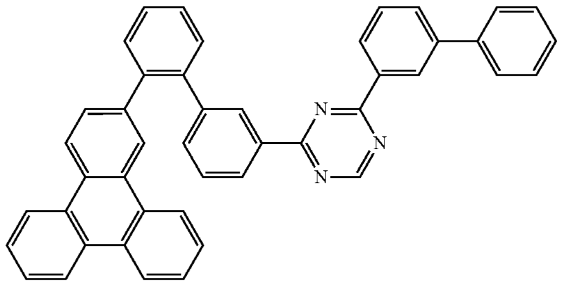

-continued
H-E83
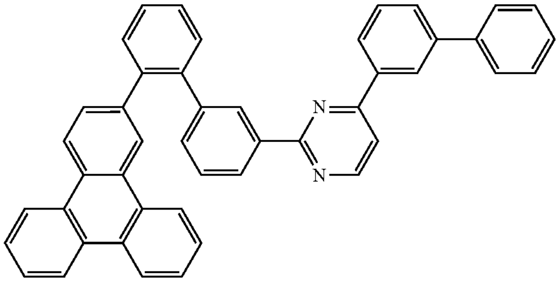
H-E84
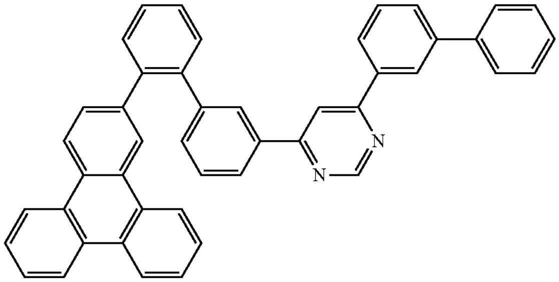
H-E(1)
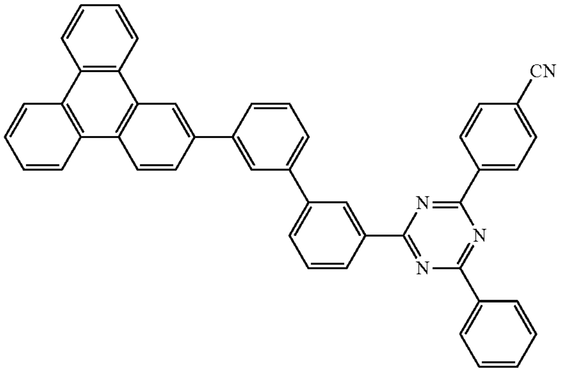
H-E(2)
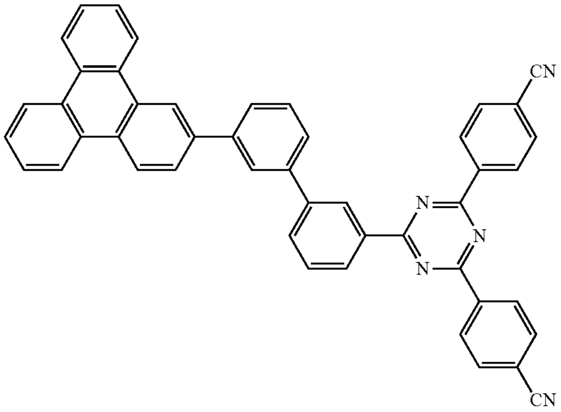
-continued
H-E(3)
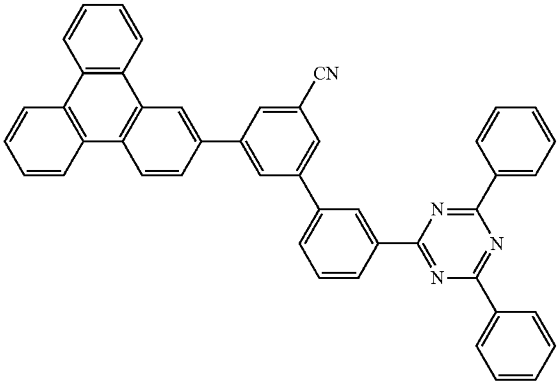
H-E(4)
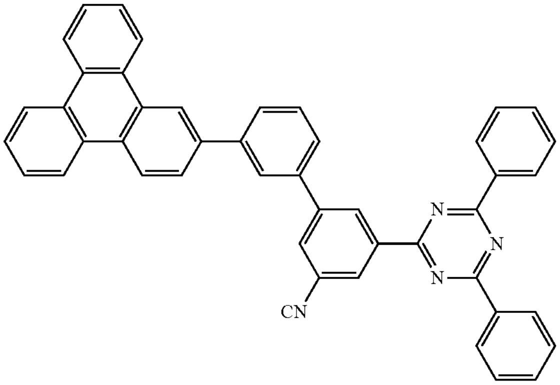
A-1
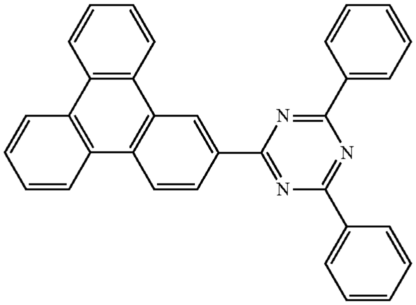
A-2
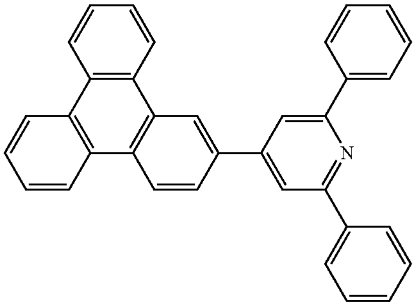

-continued
A-3
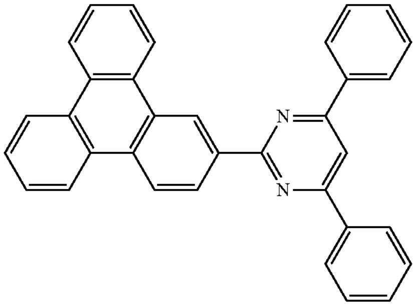
A-4
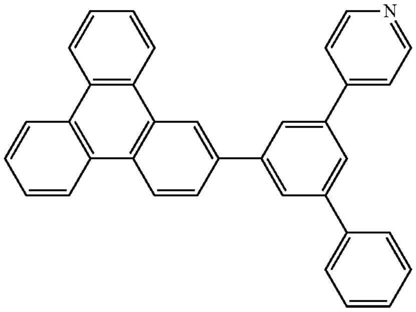
A-5
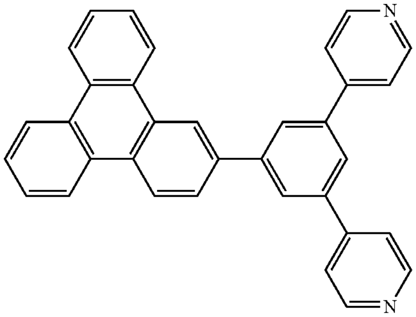
A-6
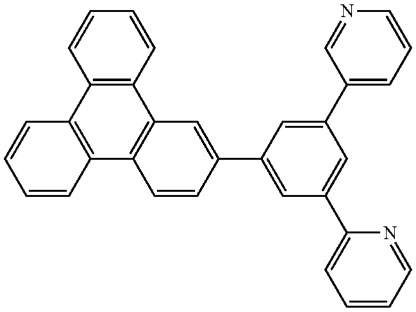
A-7
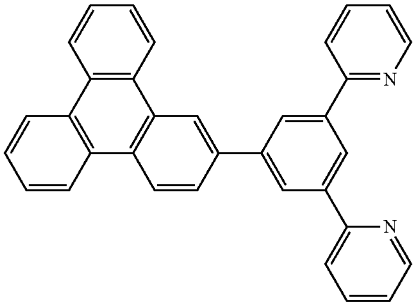
-continued
A-8
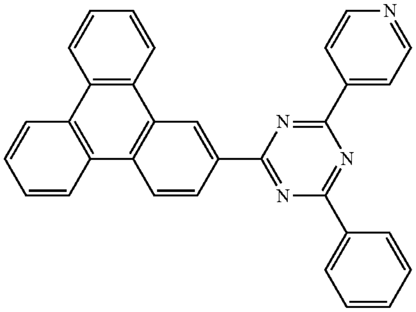
A-9
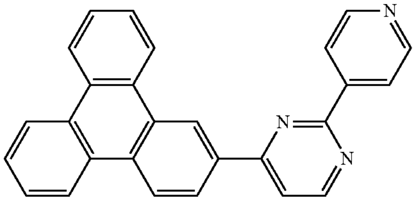
A-10
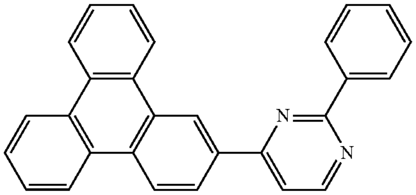
A-11
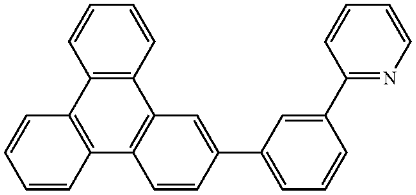
A-12
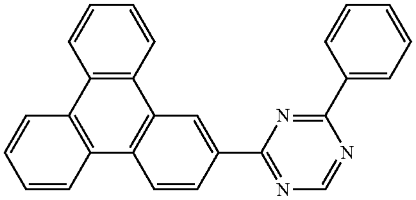
A-13
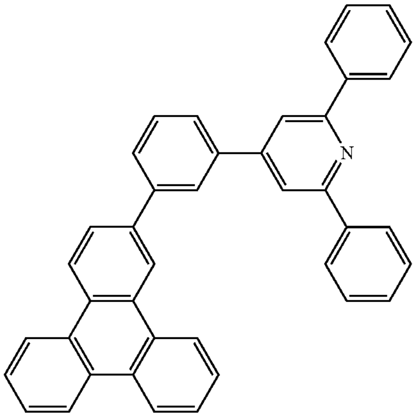

-continued
A-14
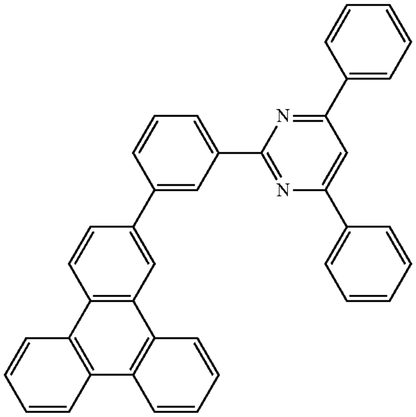
A-15
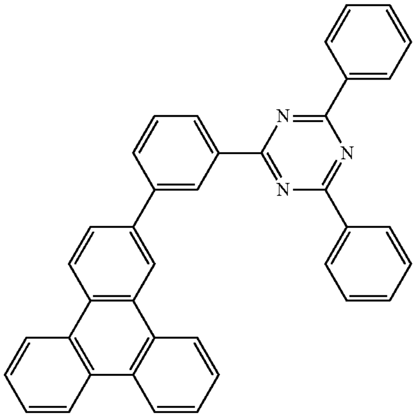
A-16
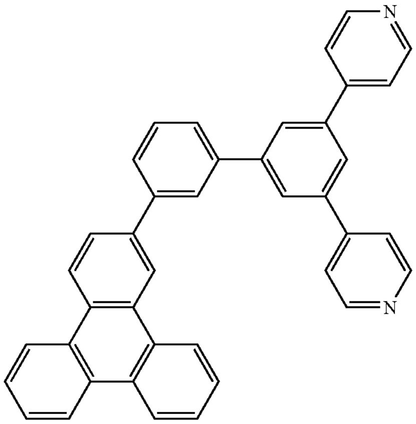
-continued
A-17
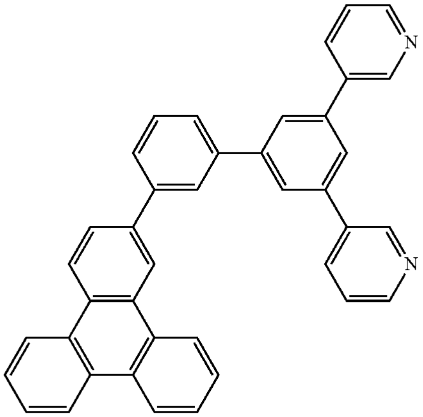
A-18
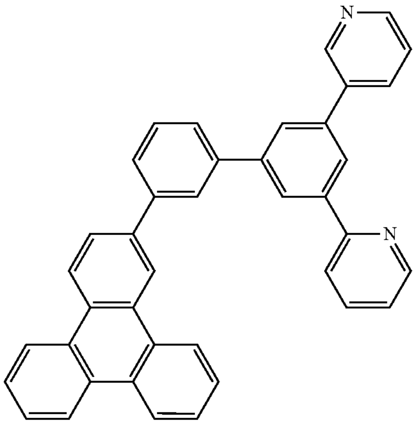
A-19
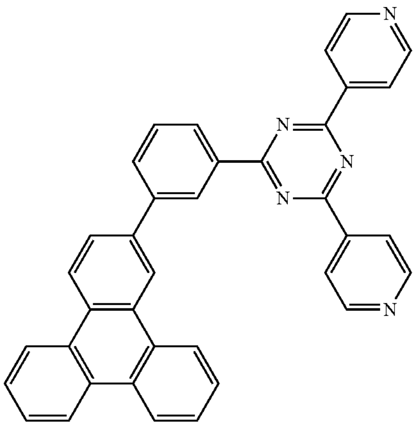

-continued
A-20
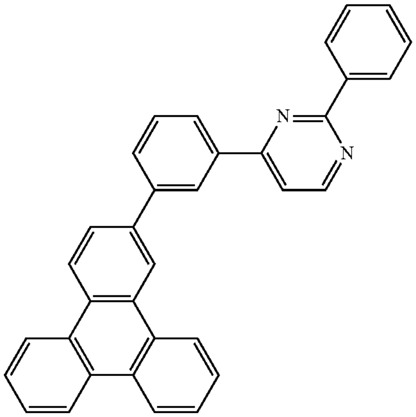
A-21
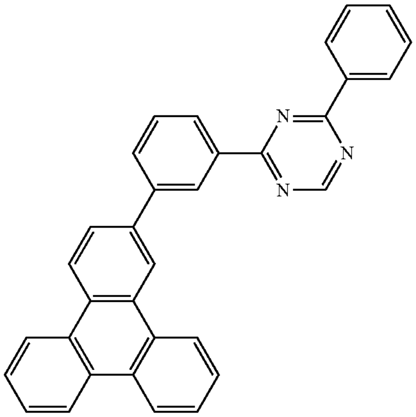
A-22
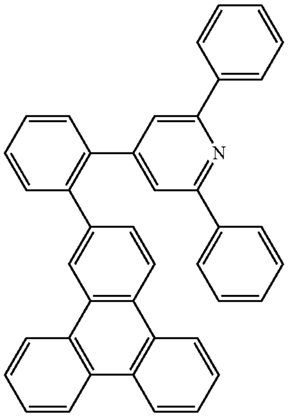
-continued
A-23
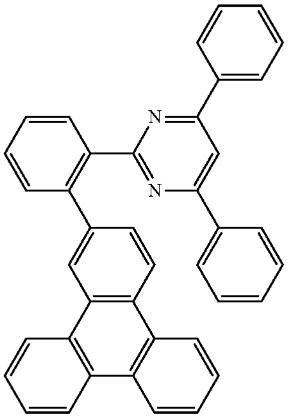
A-24
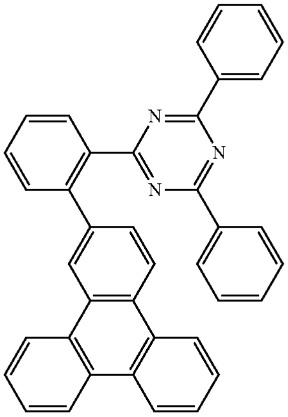
A-25
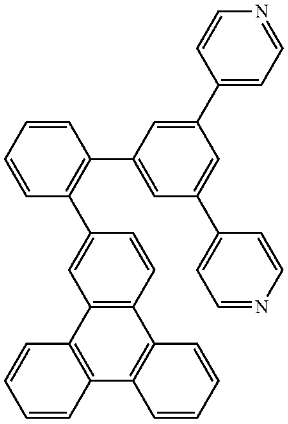

A-26
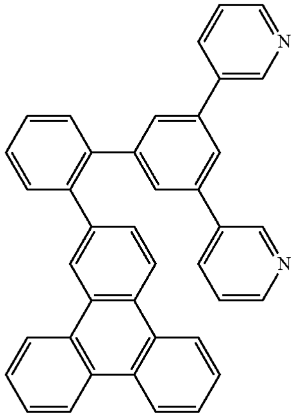
A-27
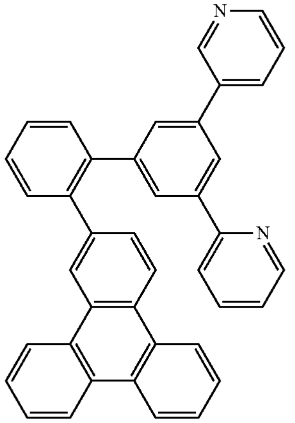
A-28
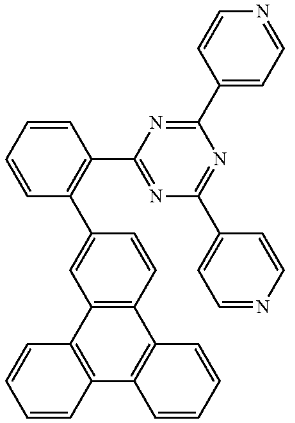
A-29
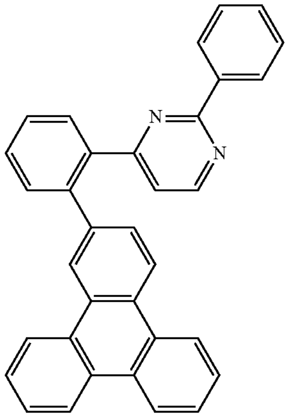
A-30
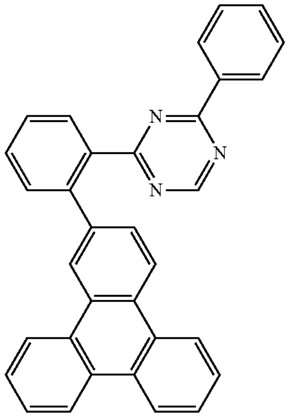
A-31
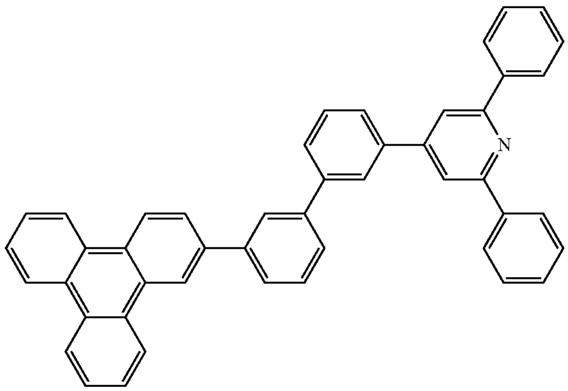

-continued
A-32
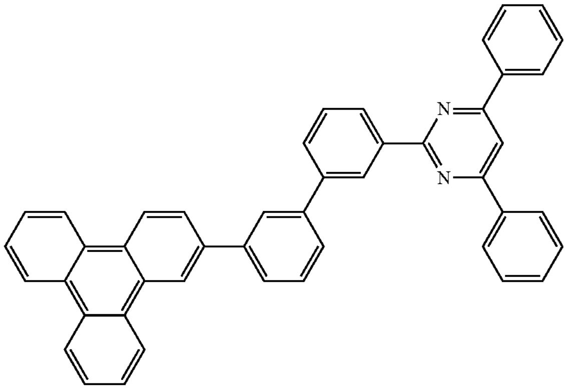
A-33
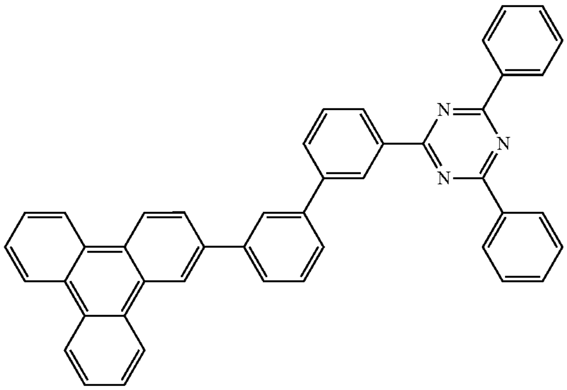
A-34
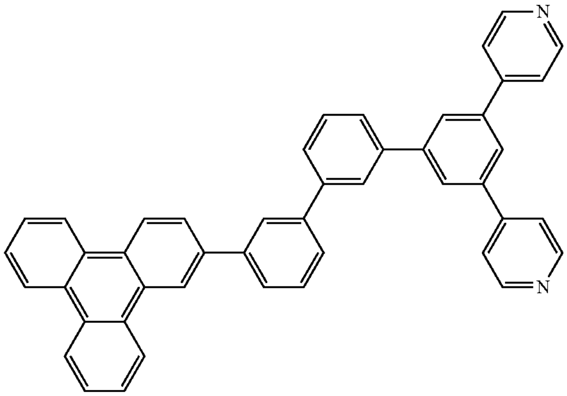
A-35
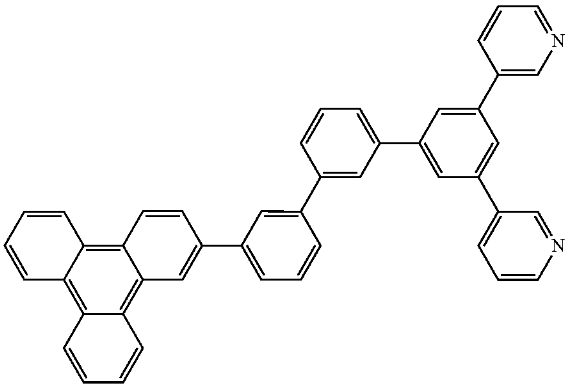
-continued
A-36
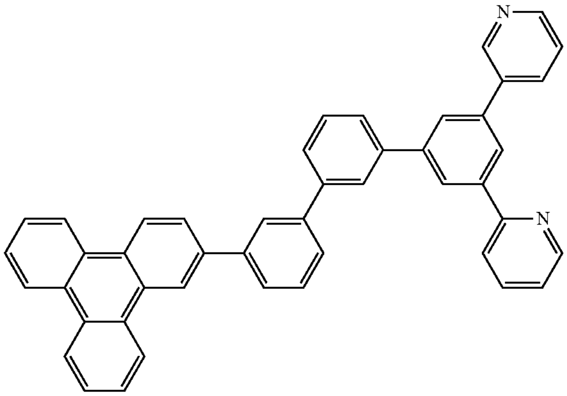
A-37
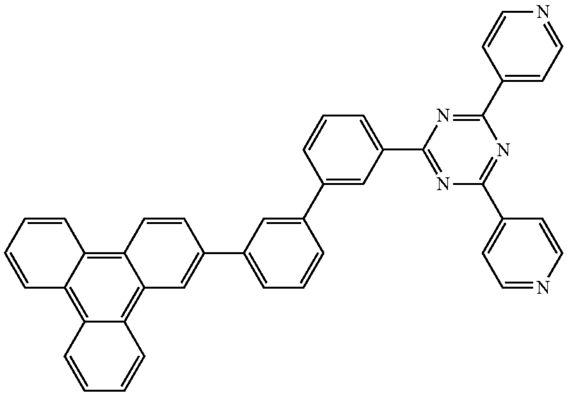
A-38
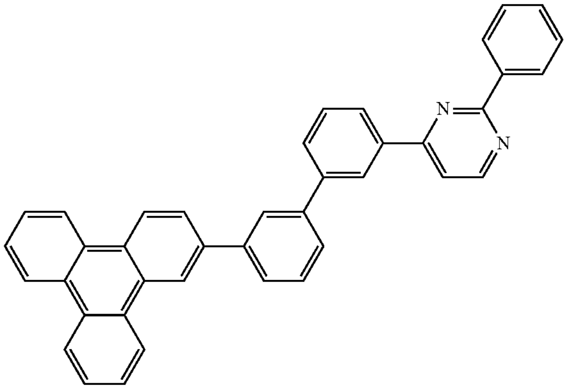
A-39
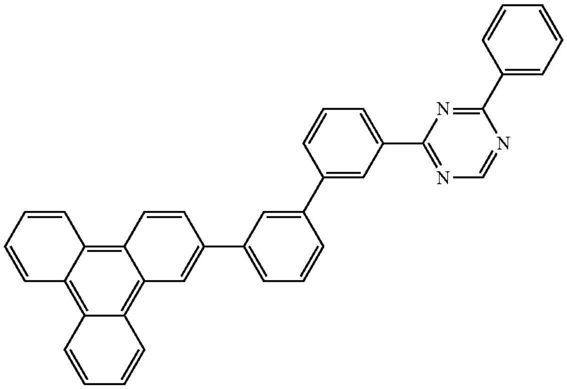

-continued
A-40
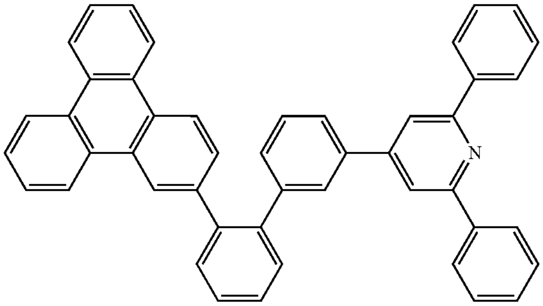
A-41
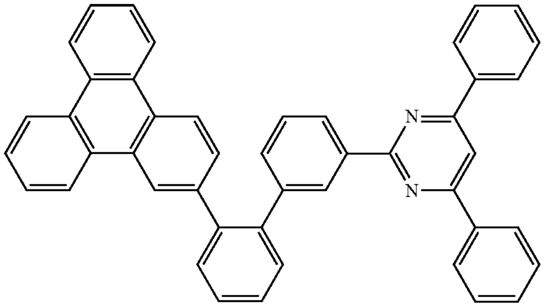
A-42
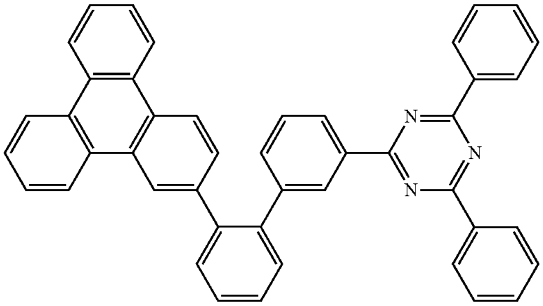
A-43
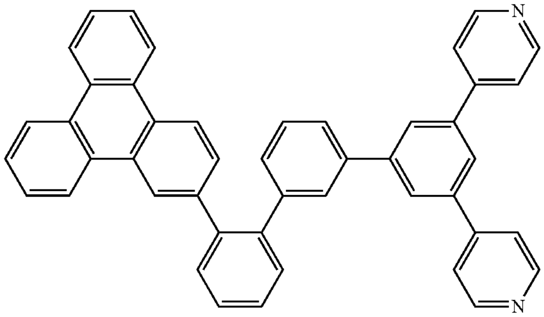
-continued
A-44
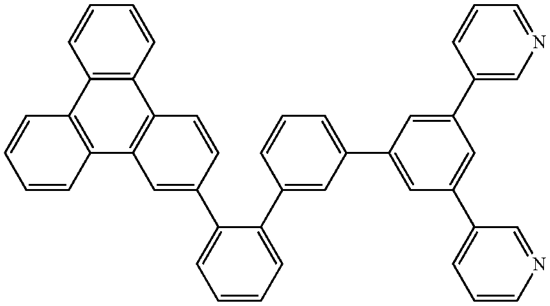
A-45
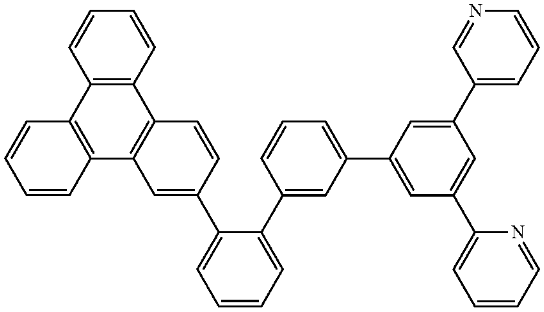
A-46
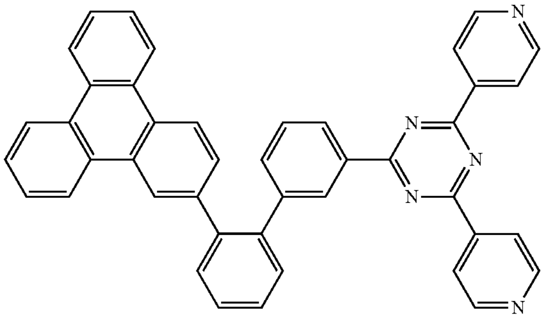
A-47
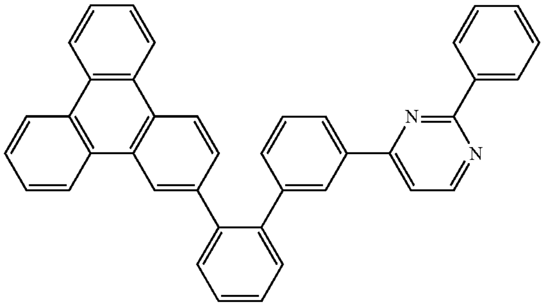

-continued
A-48
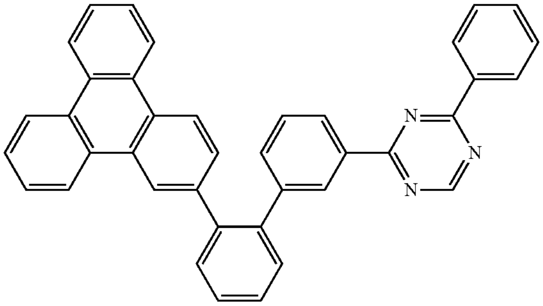
A-49
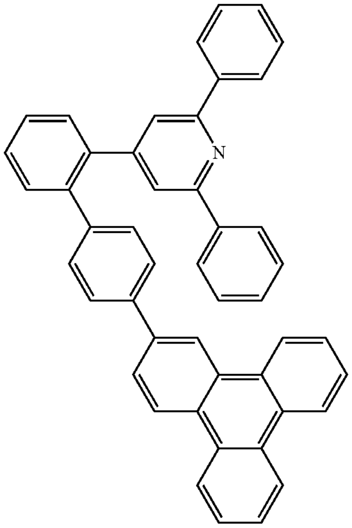
A-50
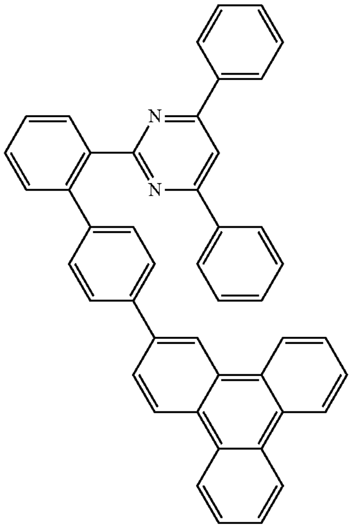
-continued
A-51
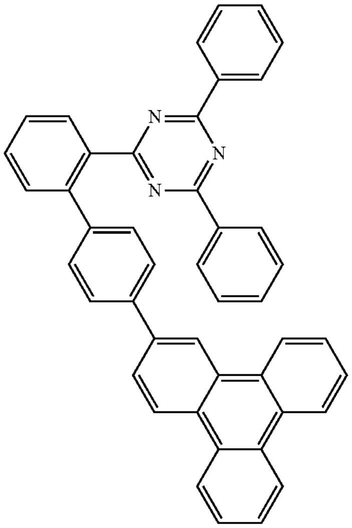
A-52
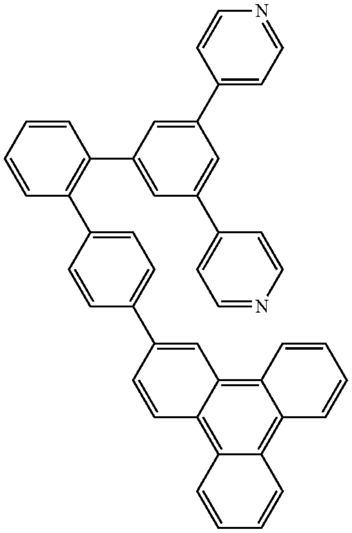
A-53
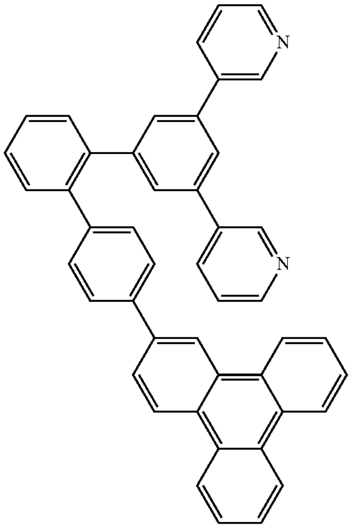

-continued
A-54
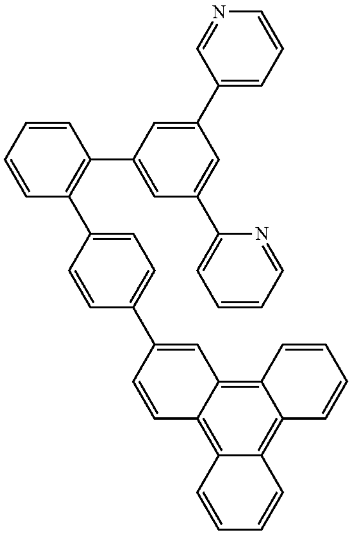
A-55
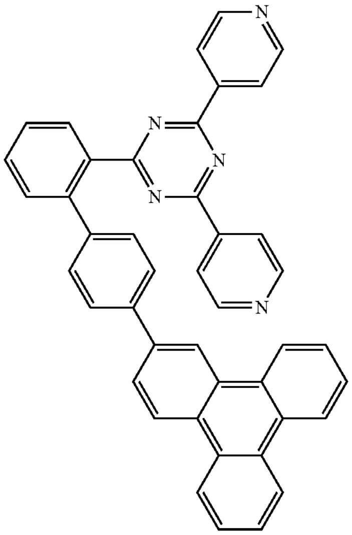
A-56
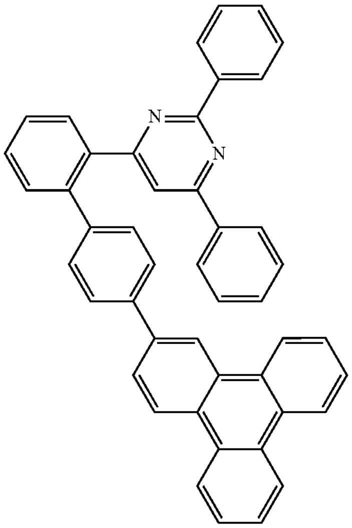
-continued
A-57
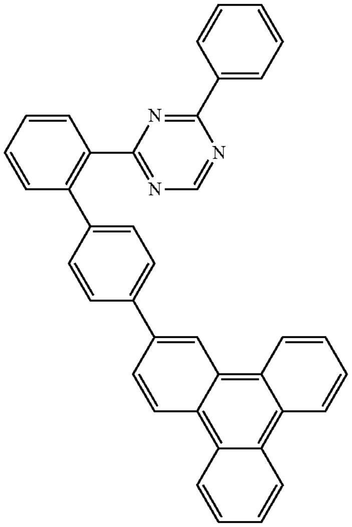
A-58
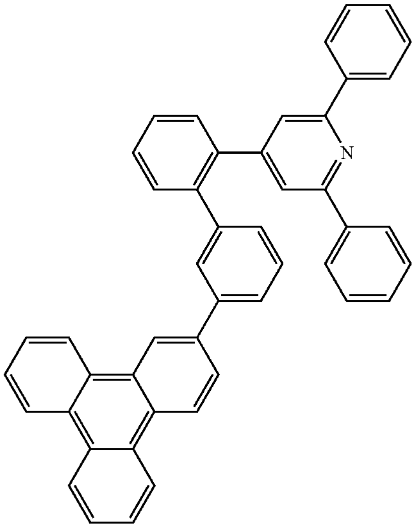
A-59
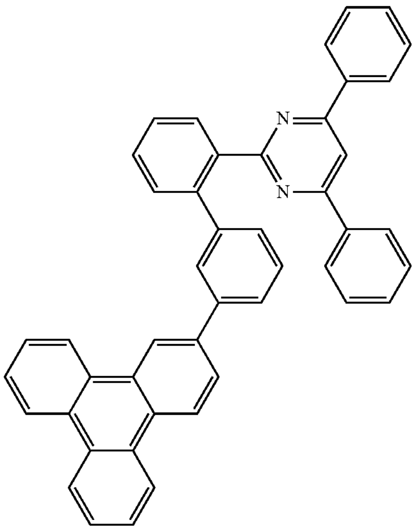

-continued
A-60
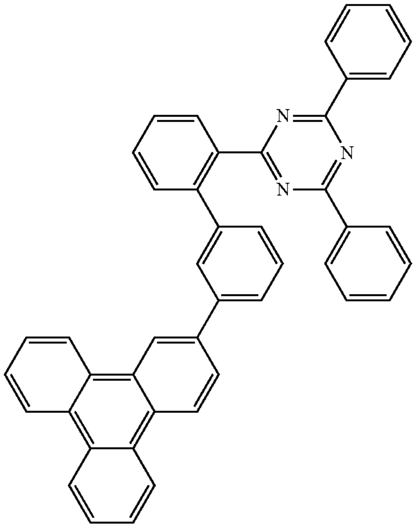
A-61
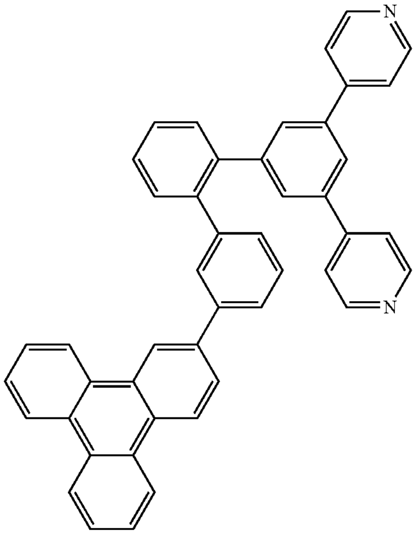
A-62
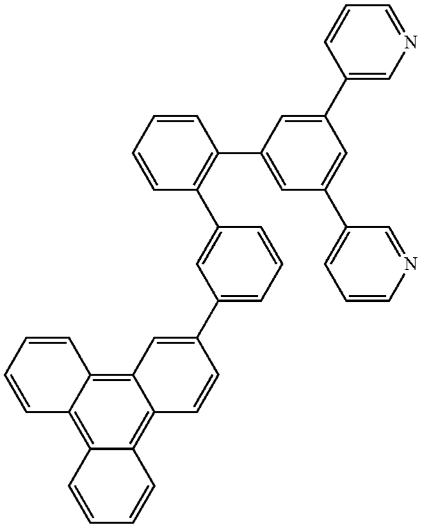
-continued
A-63
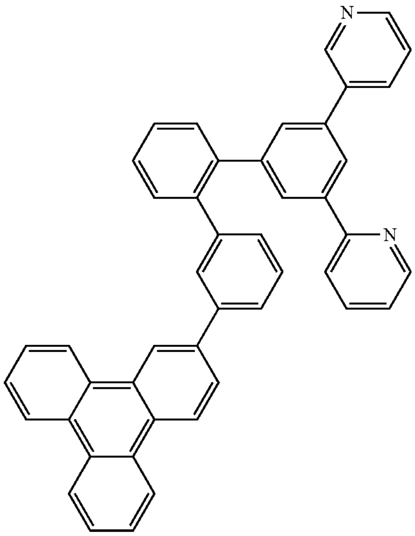
A-64
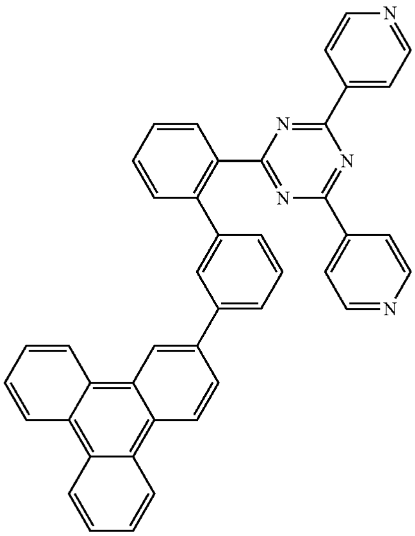
A-65
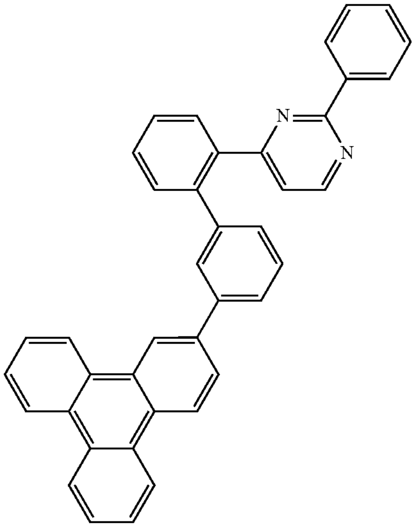

-continued
A-66
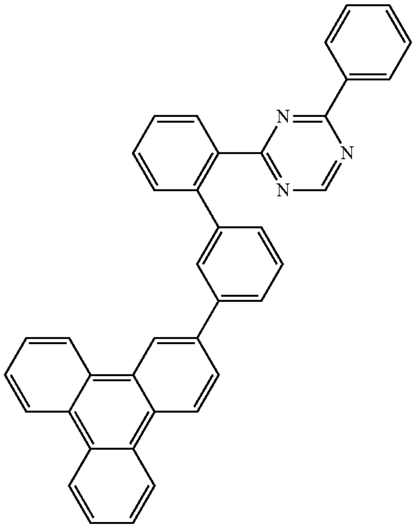
A-67
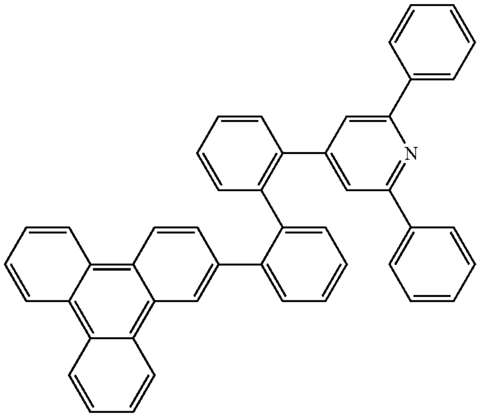
A-68
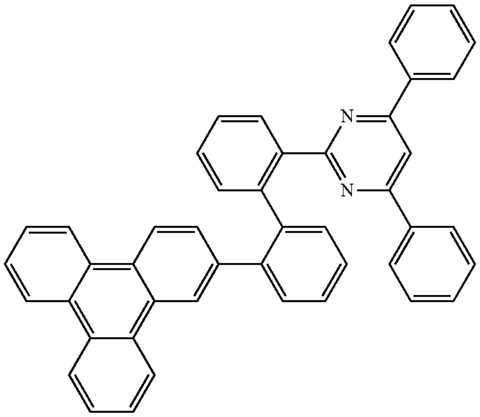
-continued
A-69
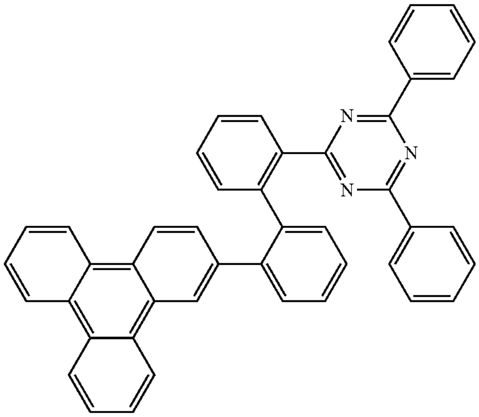
A-70
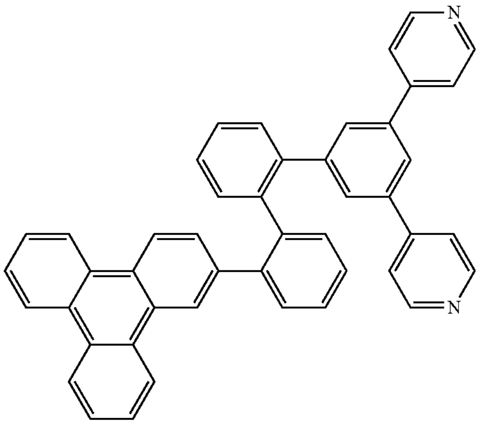
A-71
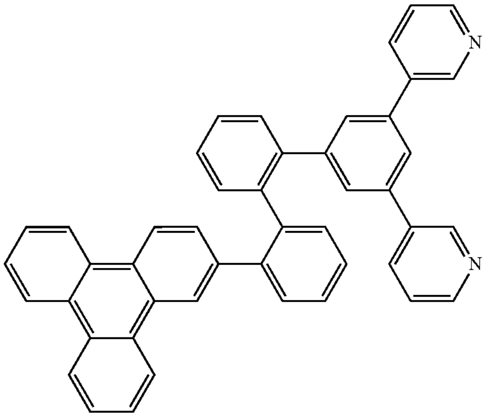

-continued
A-72
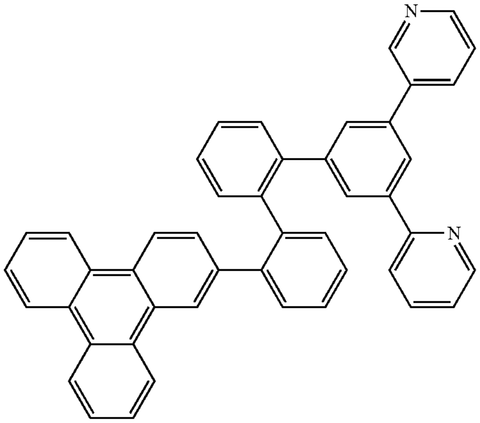
A-73
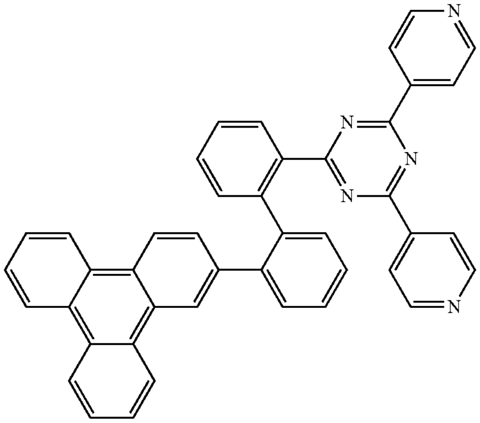
A-74
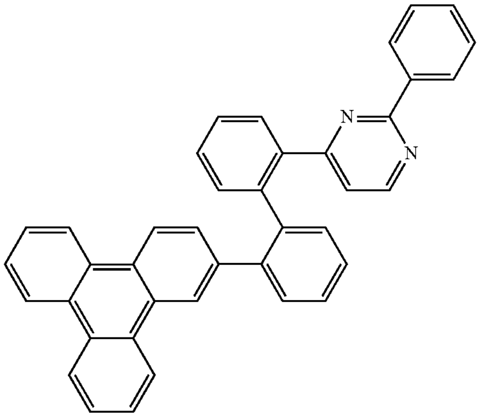
-continued
A-75
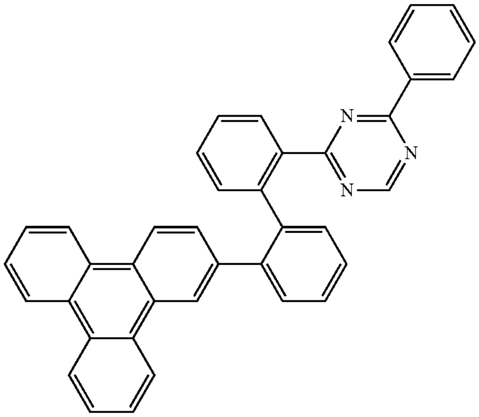
A-76
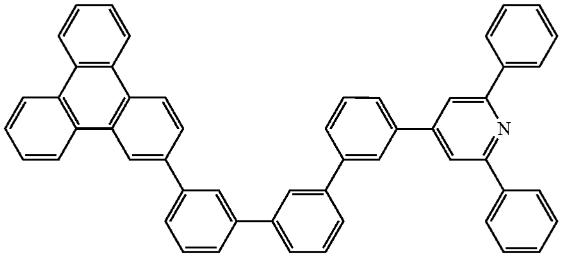
A-77
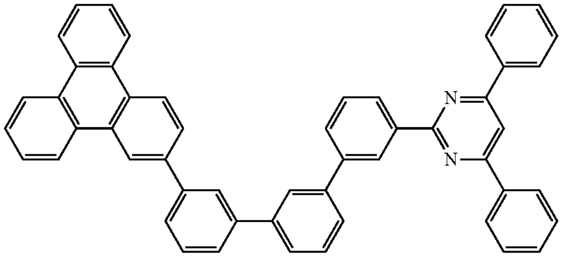
A-78
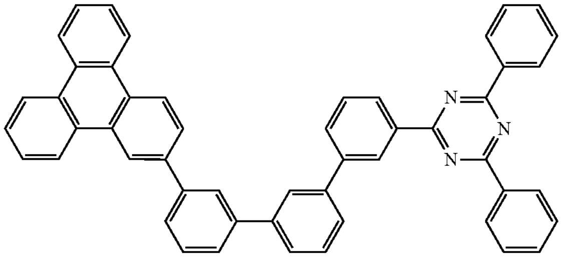
A-79
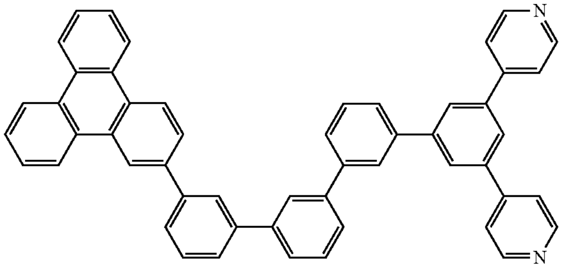

A-80
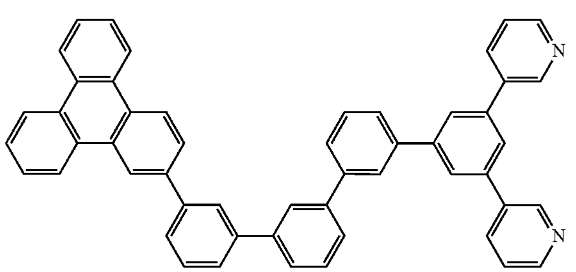
A-81
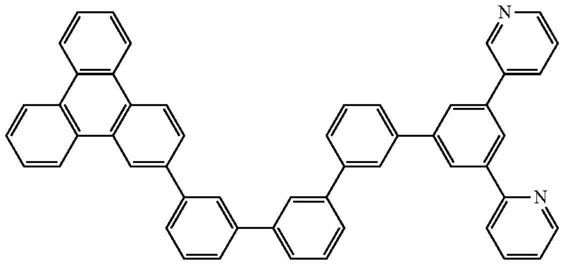
A-82
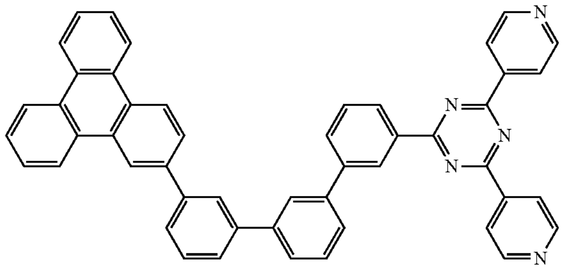
A-83
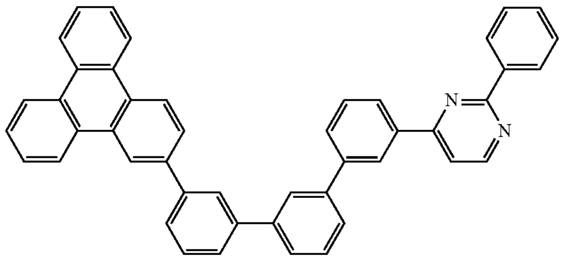
A-84
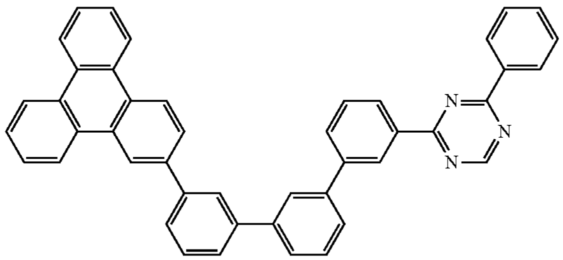
A-85
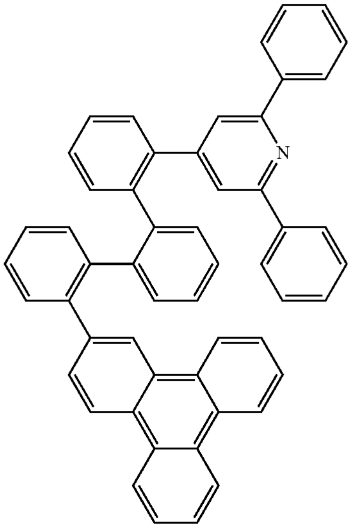
A-86
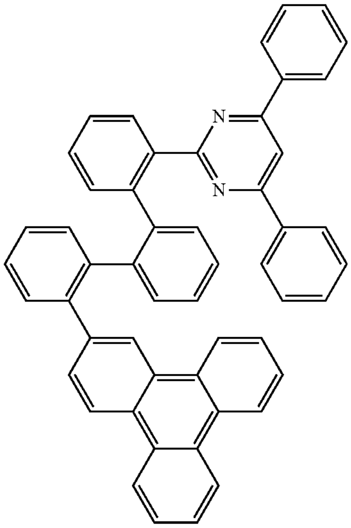
A-87
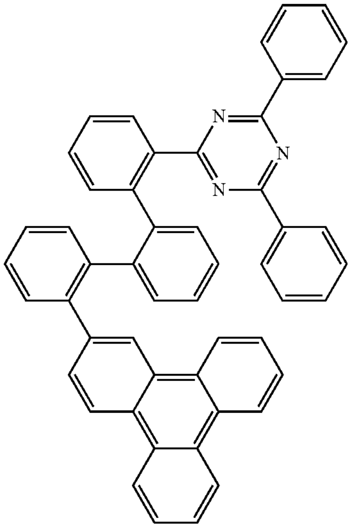

-continued
A-88
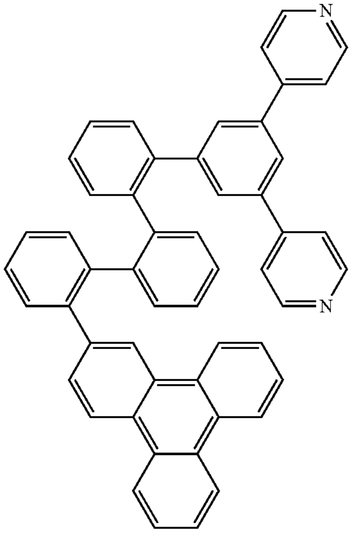
A-89
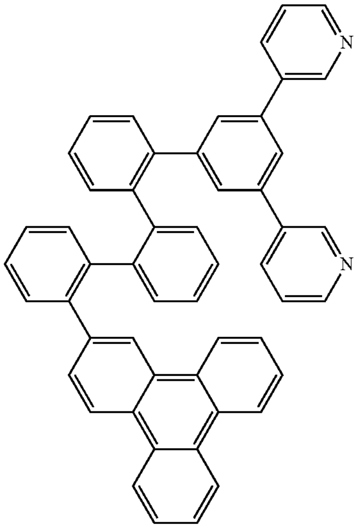
A-90
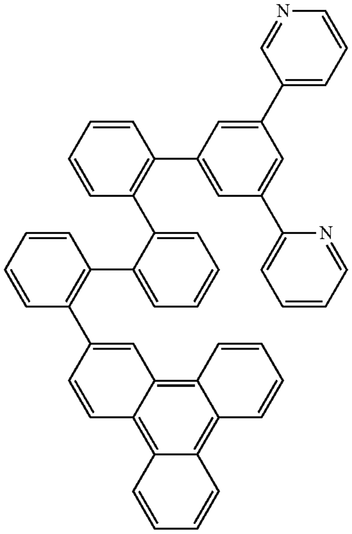
-continued
A-91
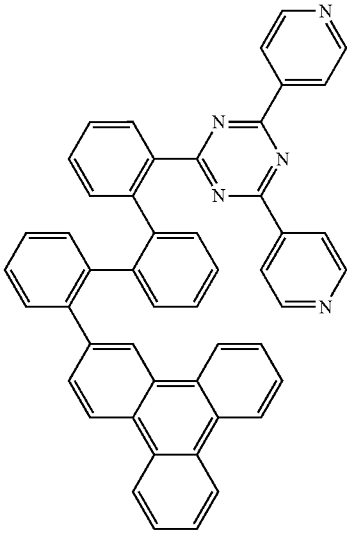
A-92
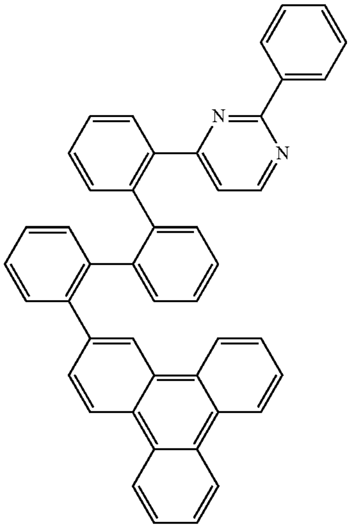
A-93
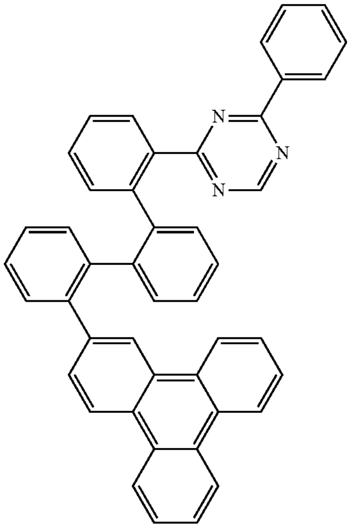

-continued
A-94
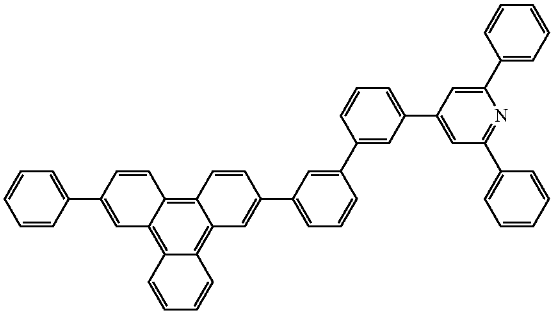
A-95
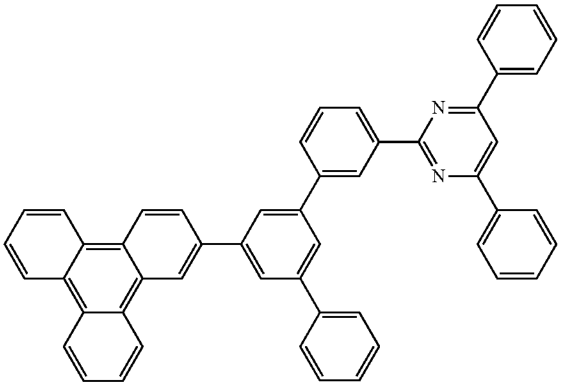
A-96
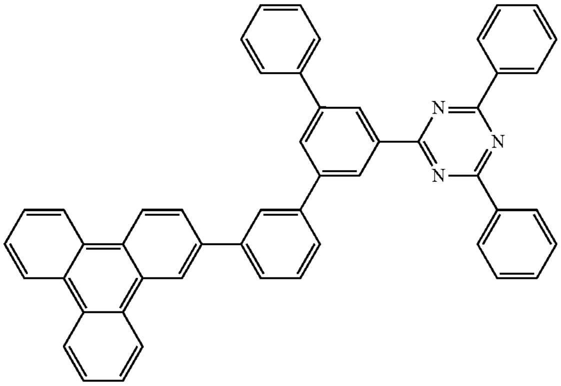
A-97
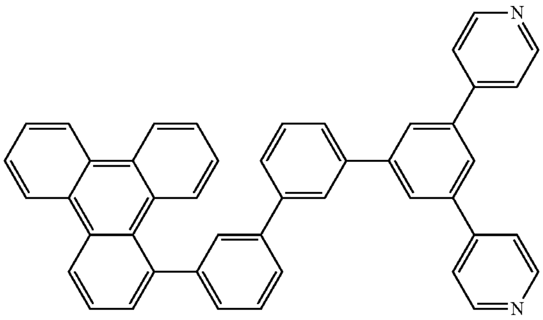
-continued
A-98
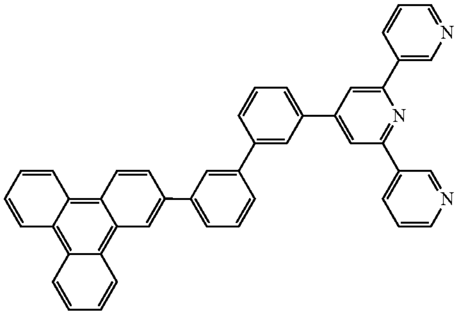
A-99
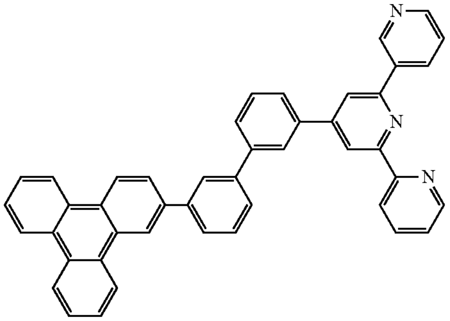
A-100
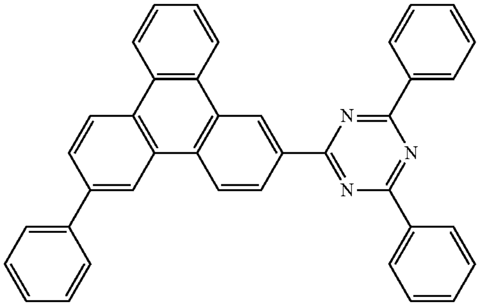
A-101
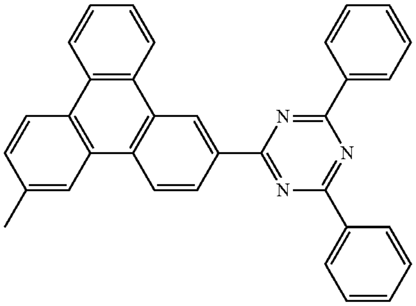
A-102
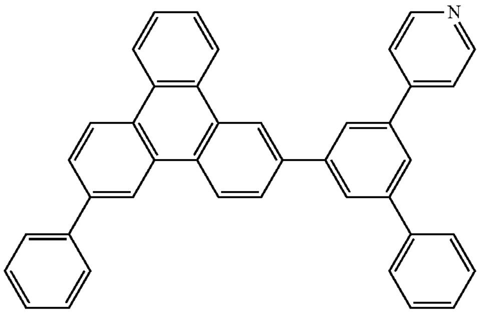

-continued
A-103
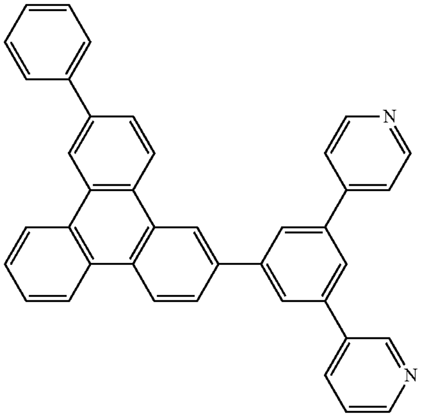
A-104
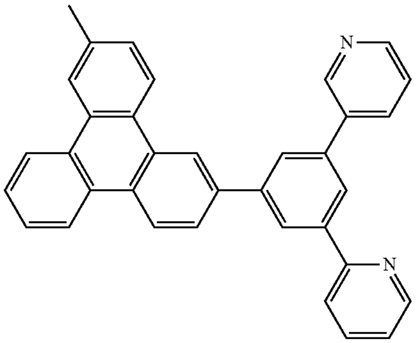
A-105
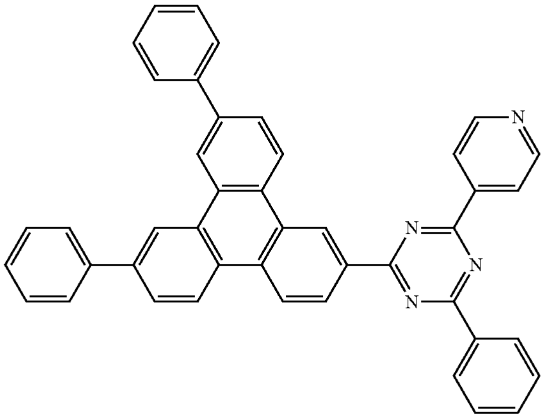
A-106
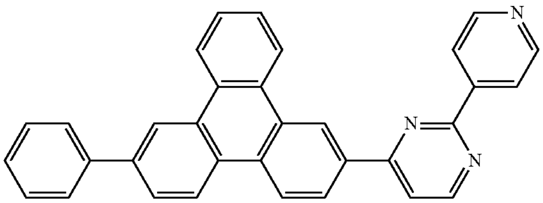
-continued
A-107
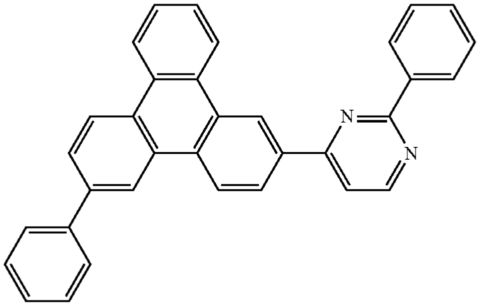
A-108
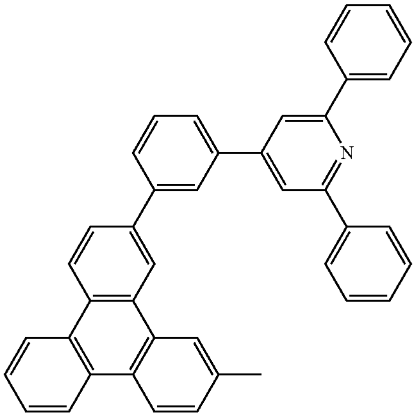
A-109
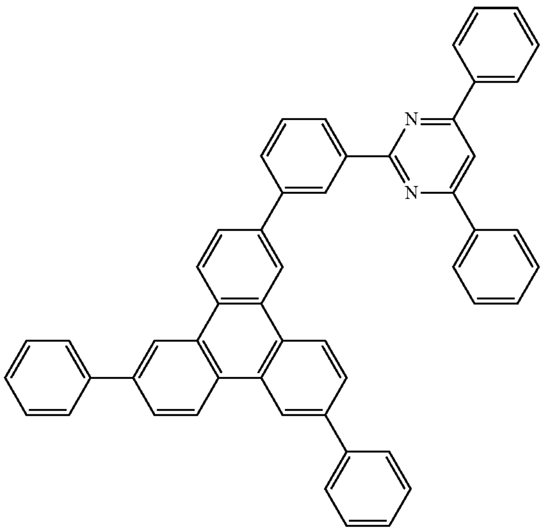

-continued
A-110
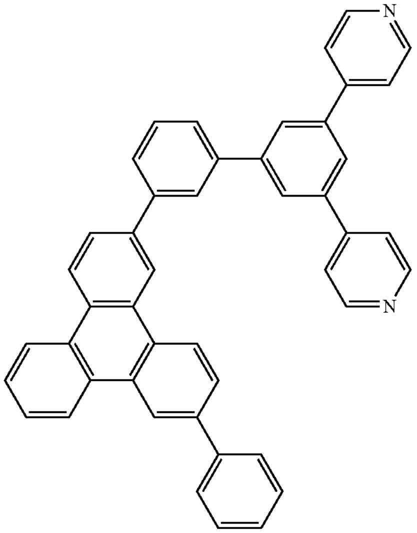
A-111
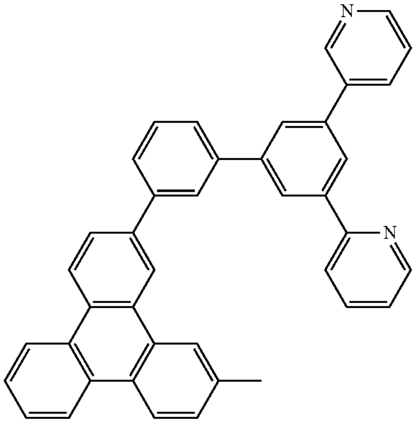
A-112
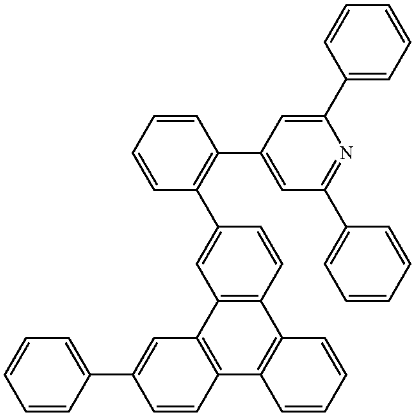
A-113
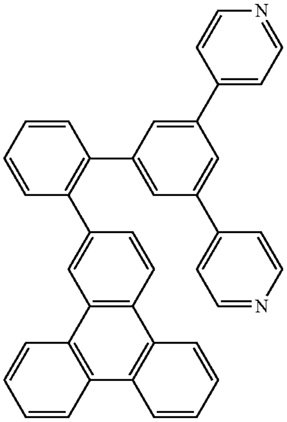
A-114
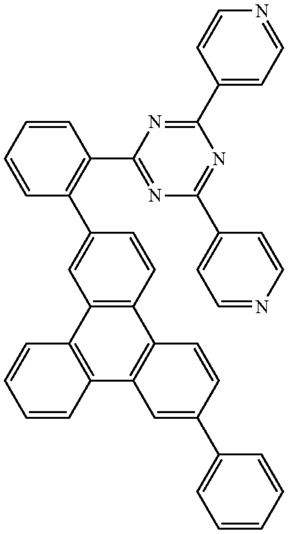
A-115
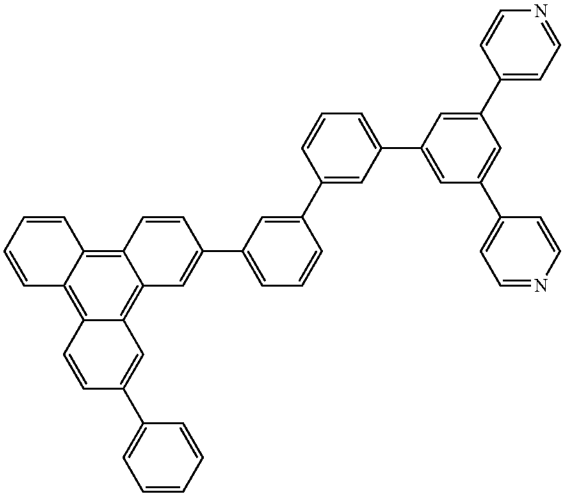

-continued
A-116
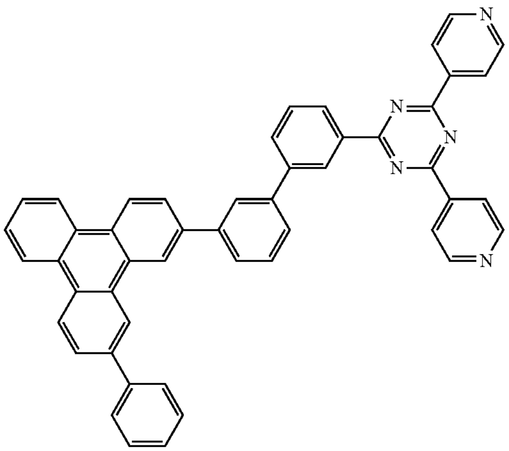
A-117
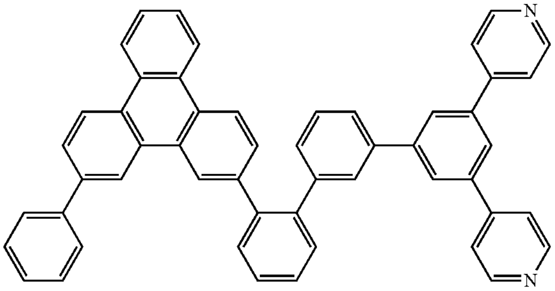
A-118
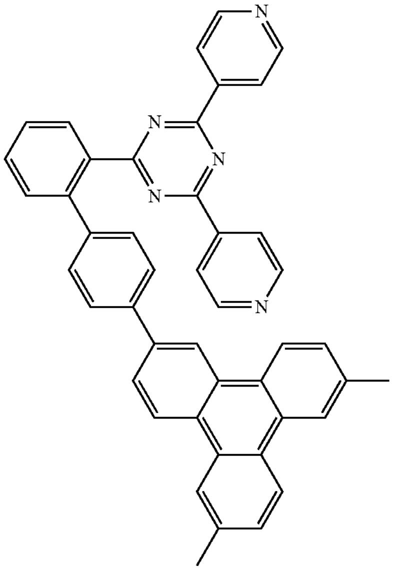
A-119
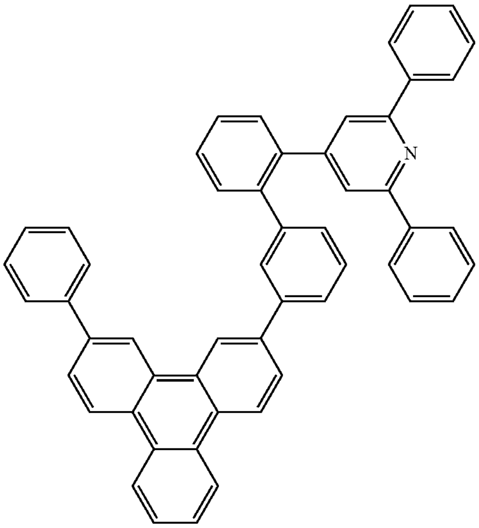
A-120
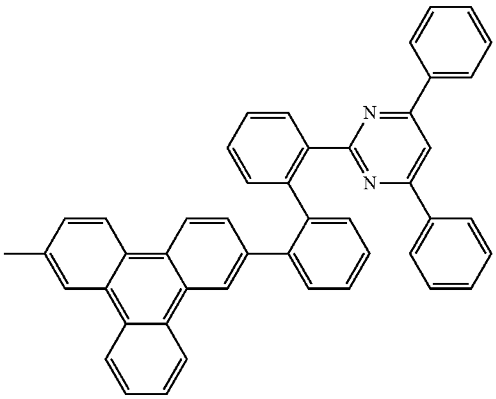
A-121
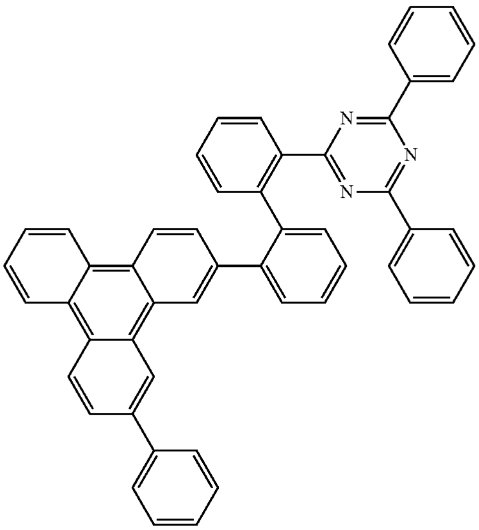

-continued
A-122
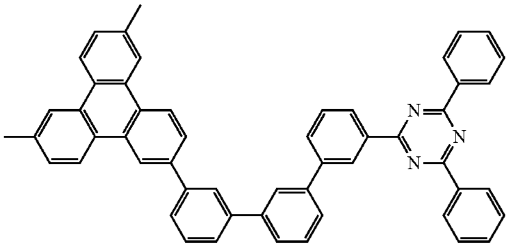
A-123
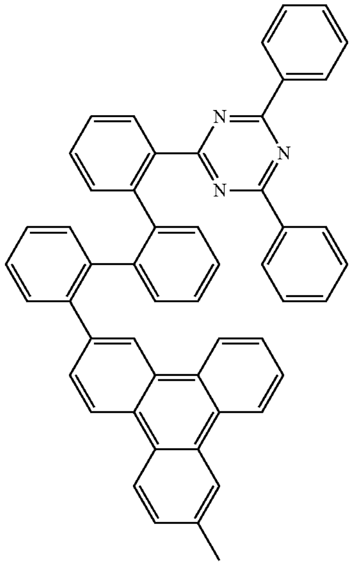
A-124
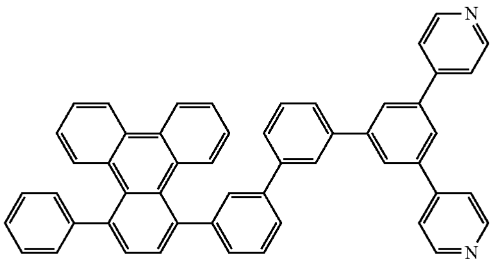
A-125
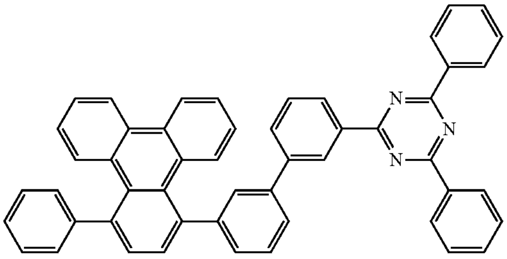
A(1)
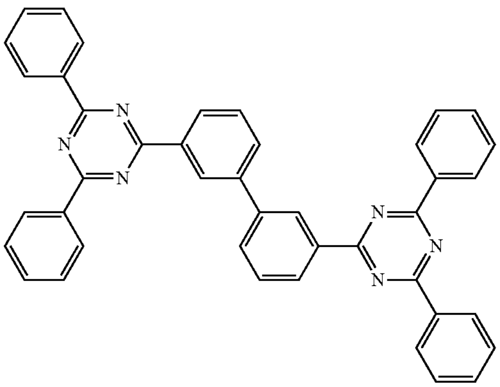
A(2)
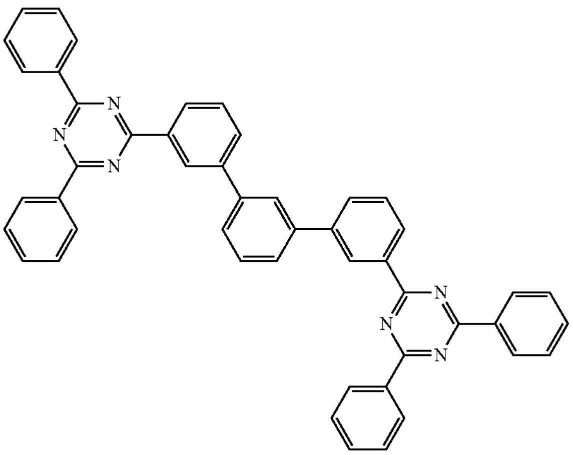

-continued
A(3)
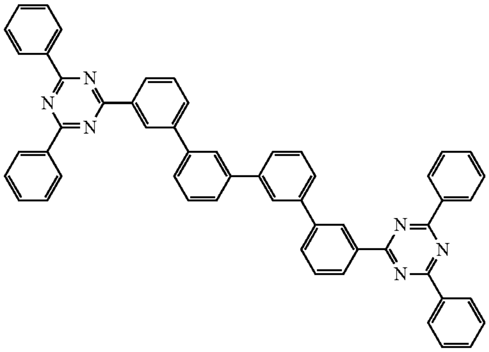
A(4)
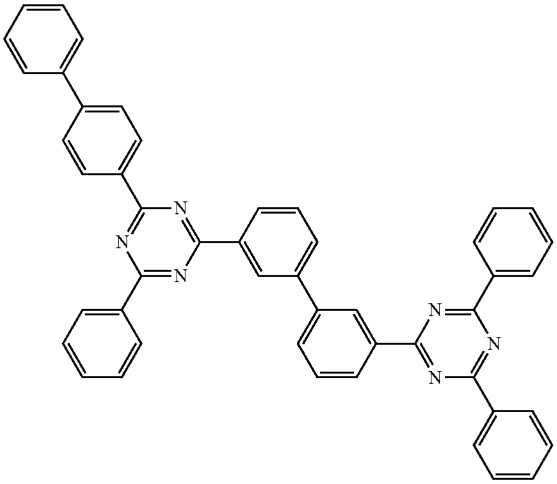
A(5)
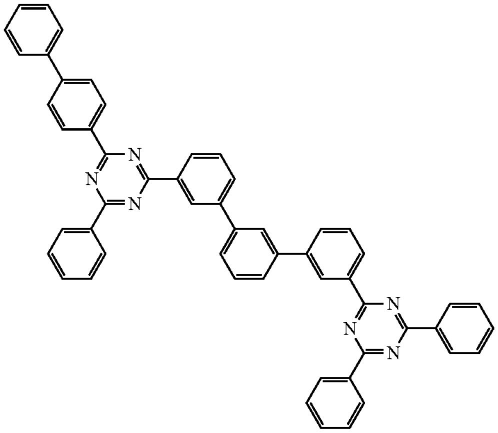
A(6)
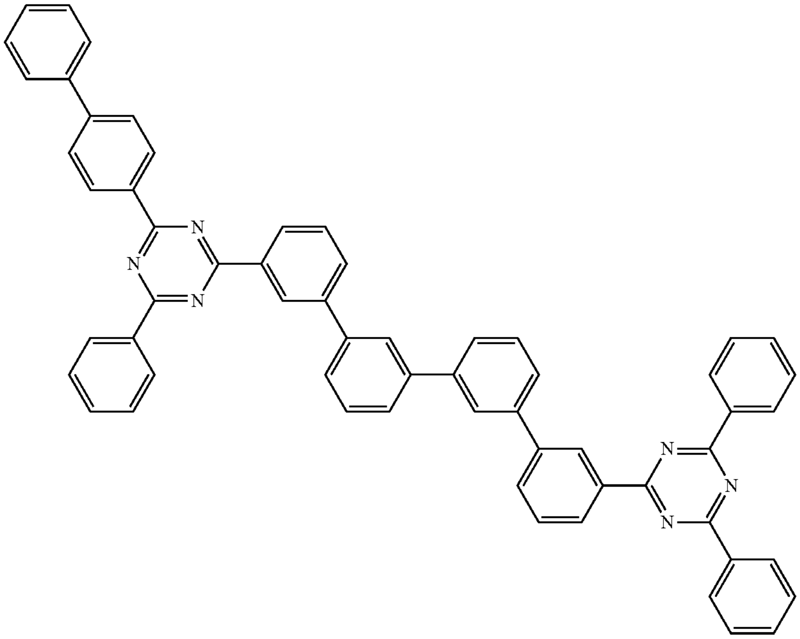

-continued
A(7)
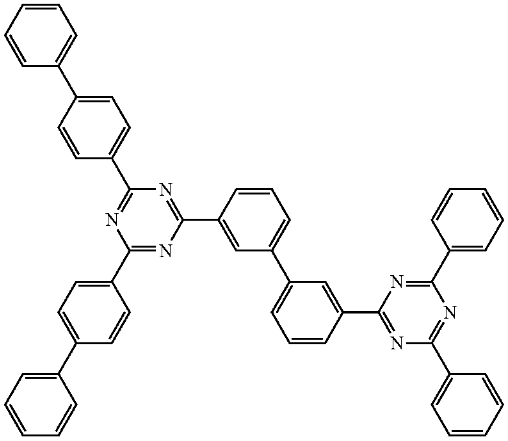
A(8)
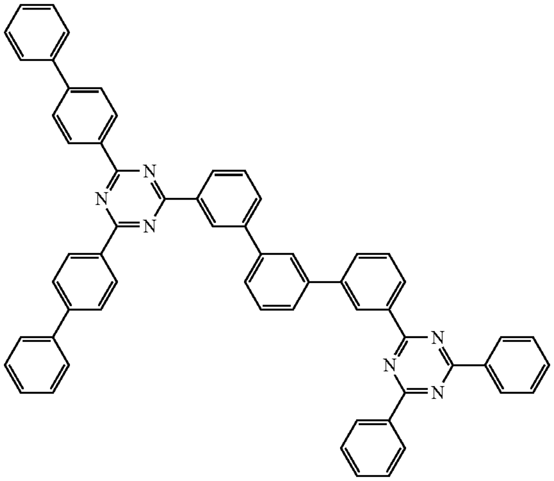
A(9)
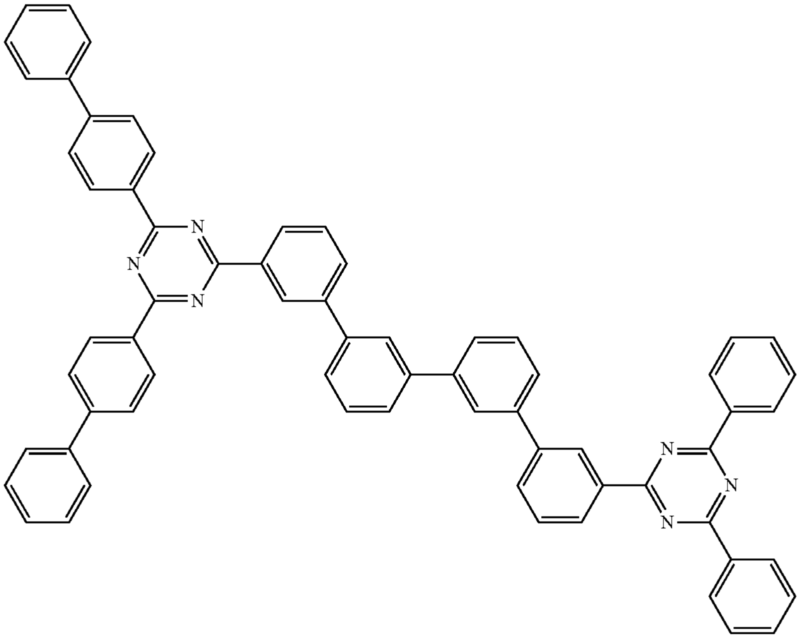

-continued
A(10)
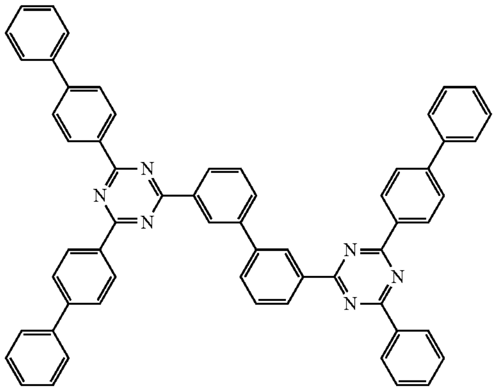
A(11)
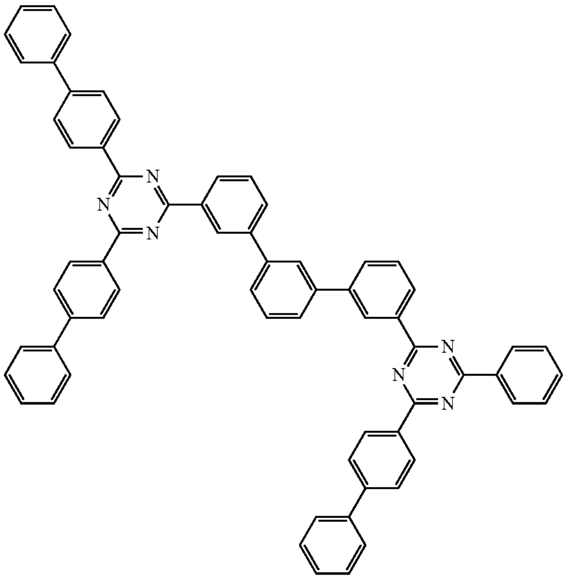
A(12)
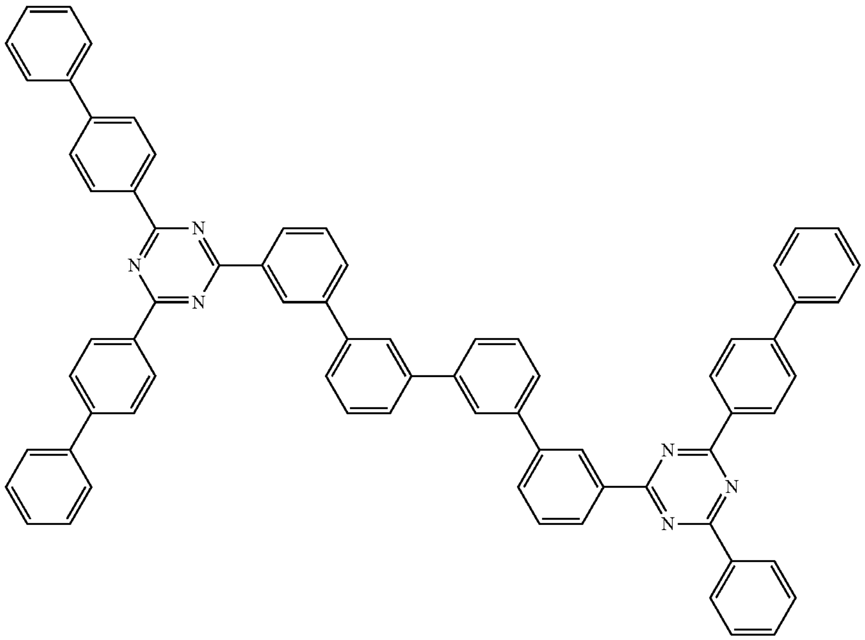

-continued
A(13)
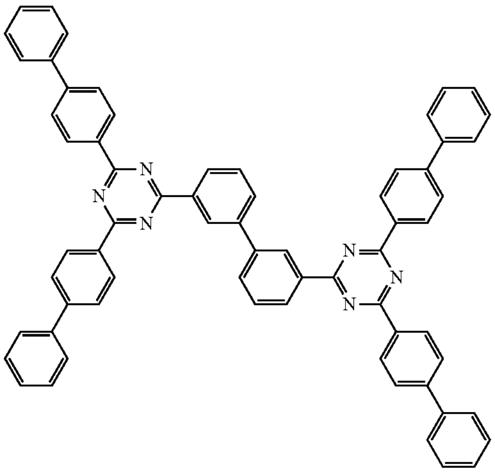
A(14)
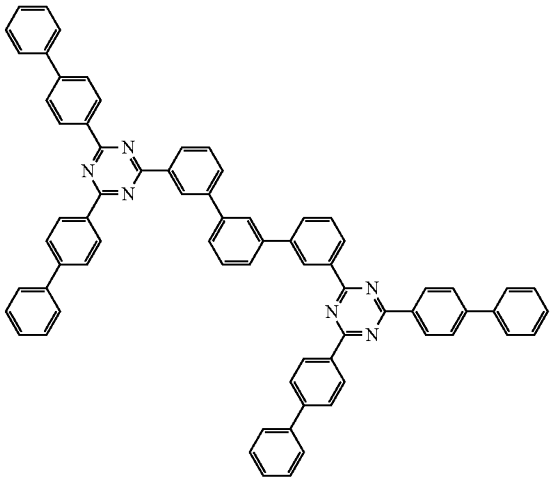
A(15)
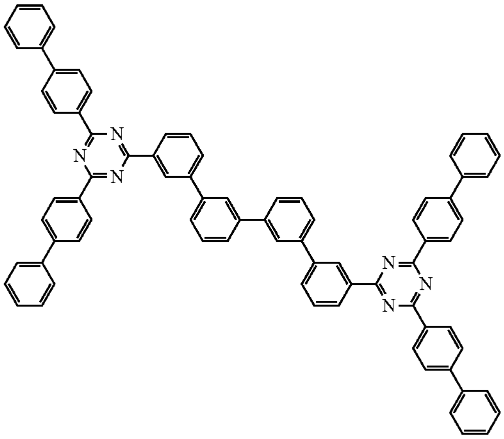
A(16)
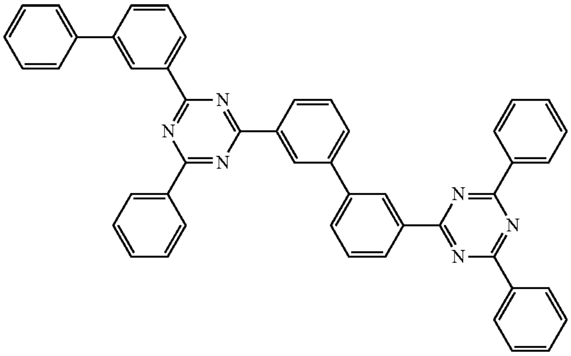
A(17)
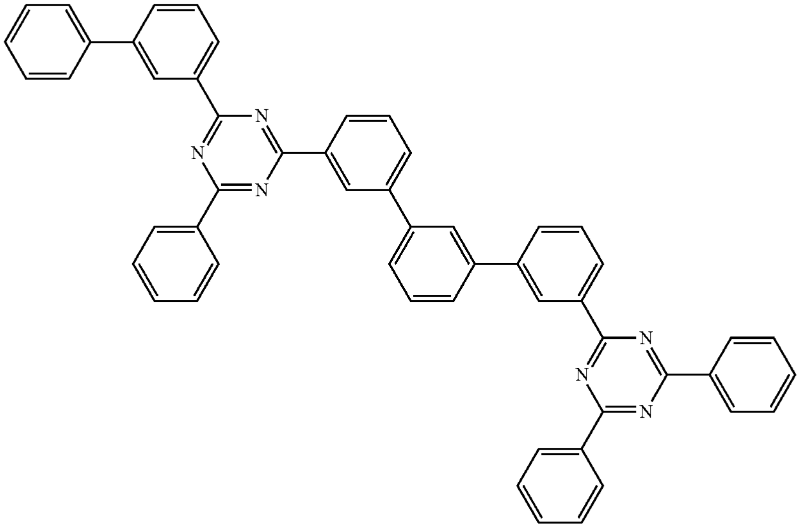

-continued
A(18)
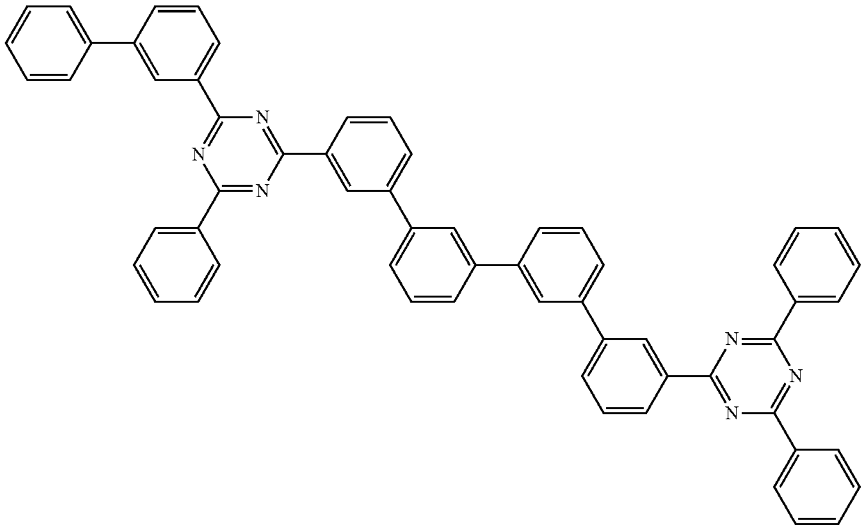
A(19)
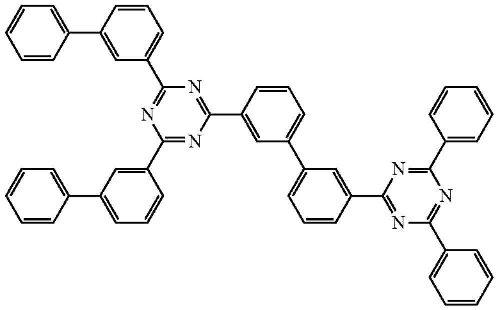
A(20)
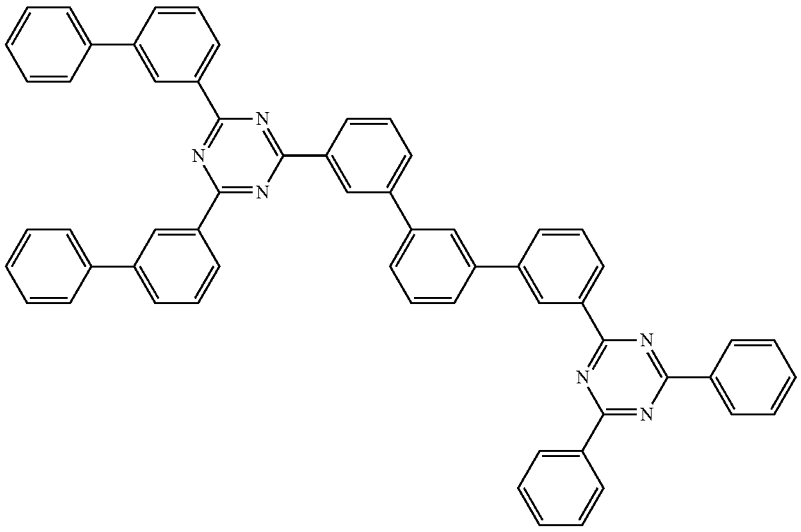

-continued
A(21)
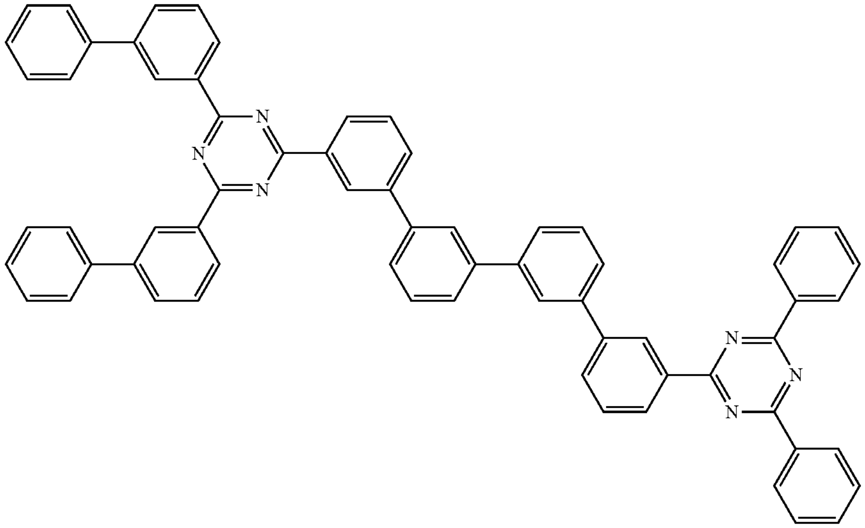
A(22)
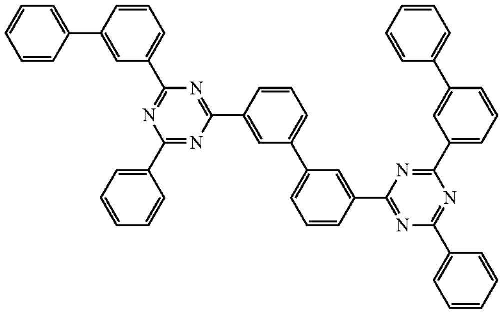
A(23)
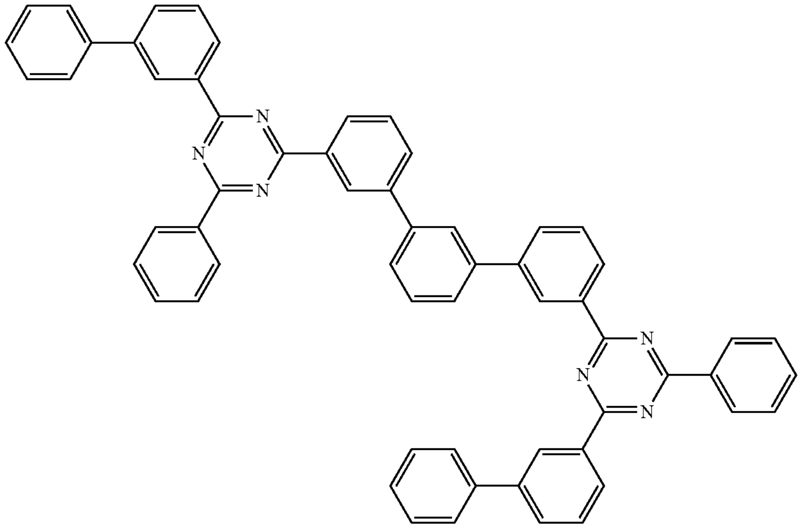

-continued
A(24)
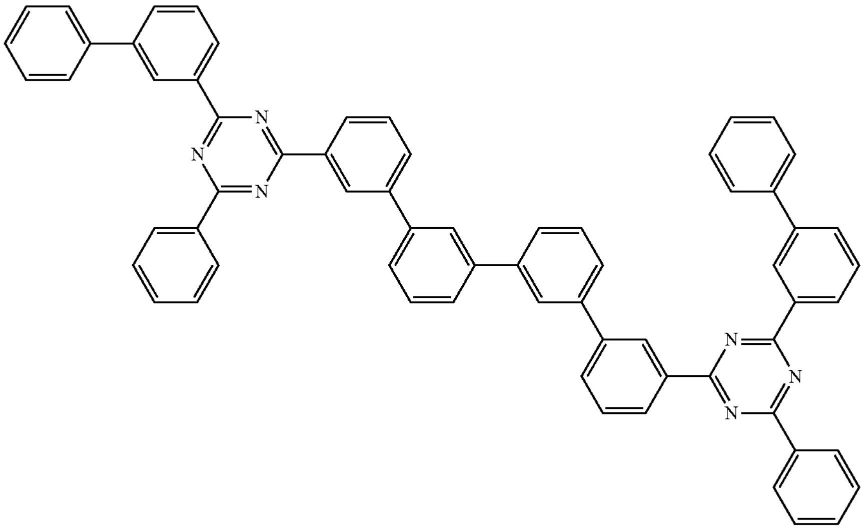
A(25)
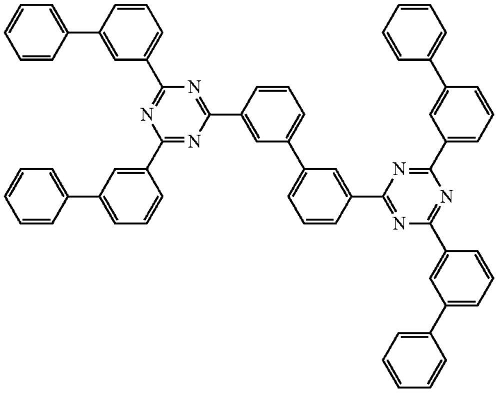
A(26)
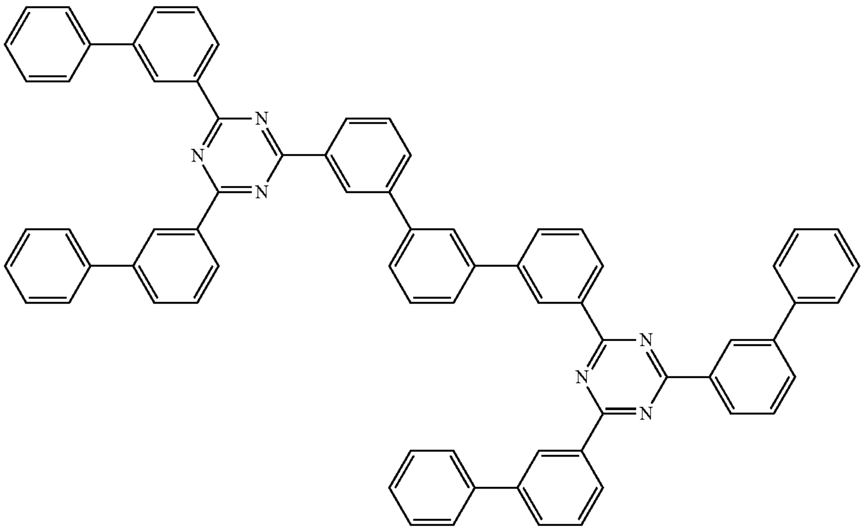

-continued
A(27)
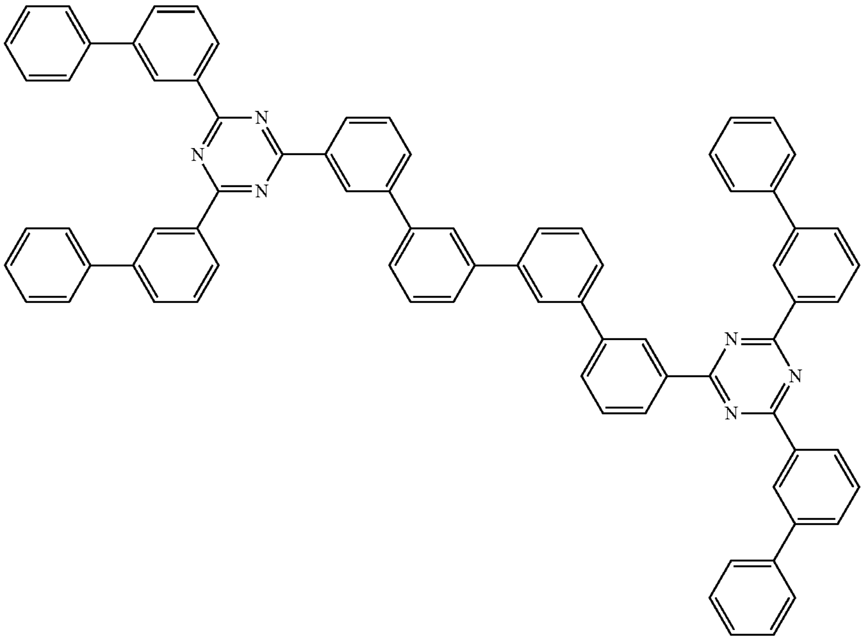
A(28)
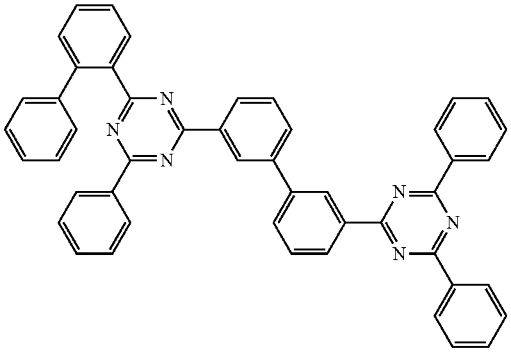
A(29)
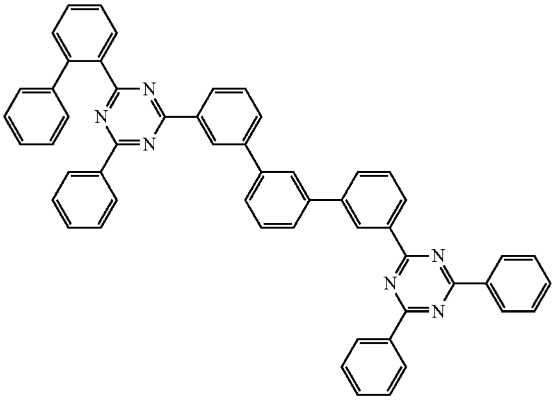
A(30)
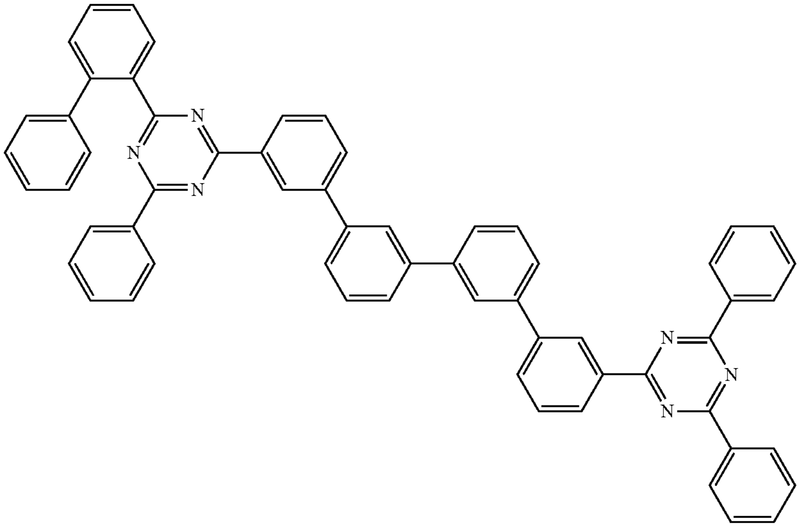

-continued
A(31)
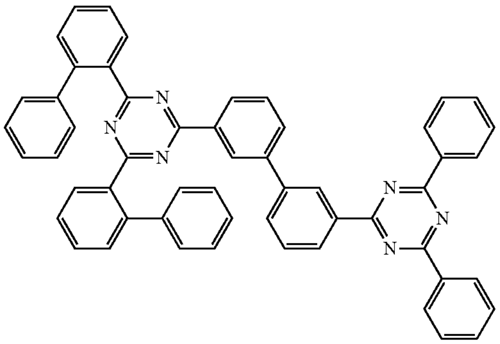
A(32)
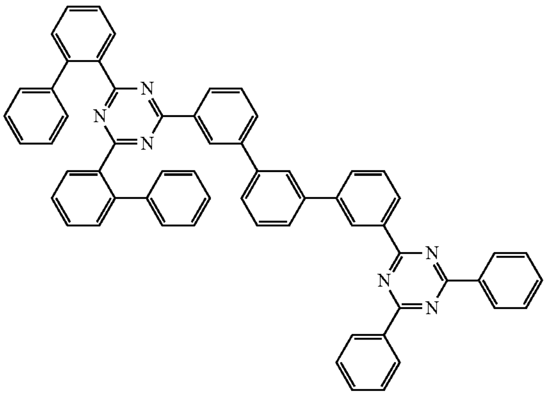
A(33)
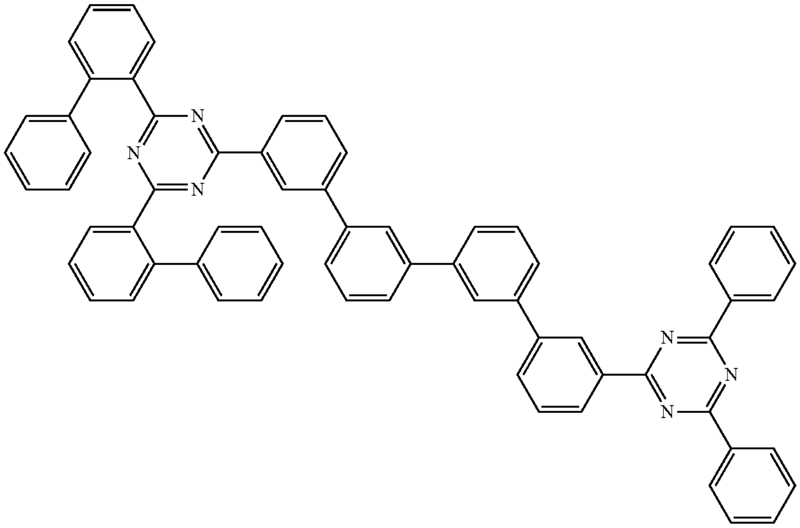
A(34)
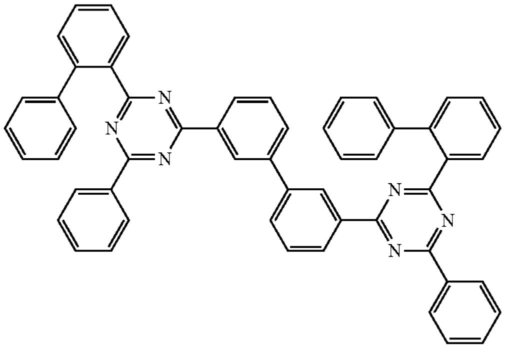

-continued
A(35)
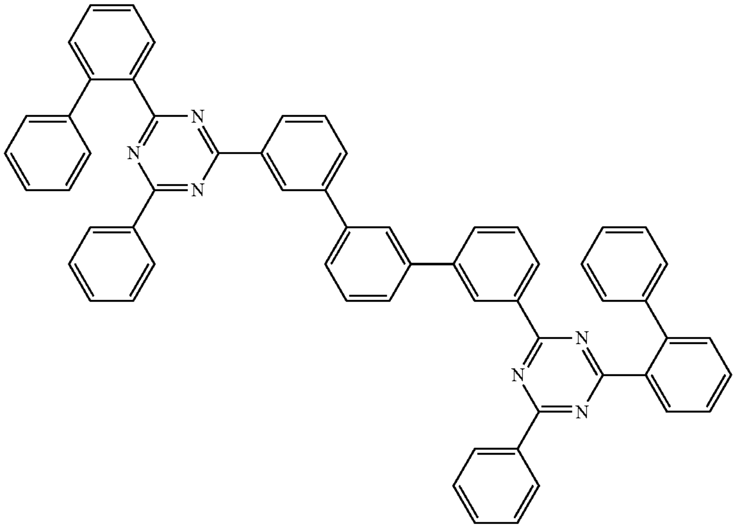
A(36)
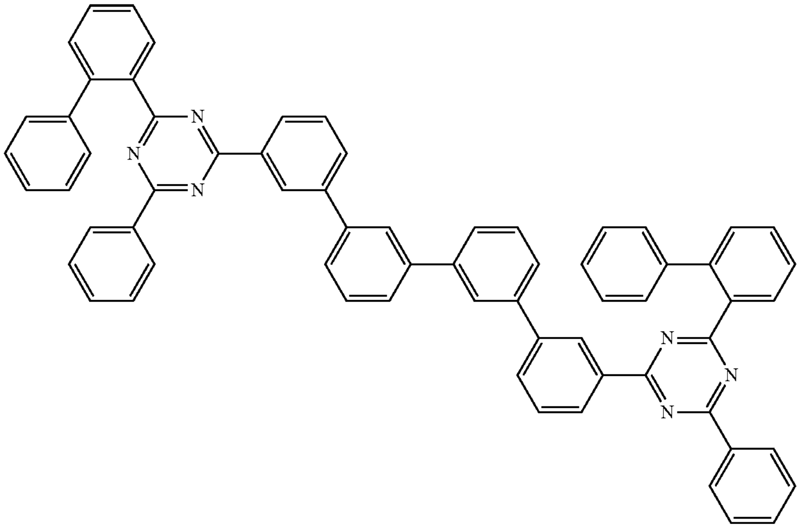
A(37)
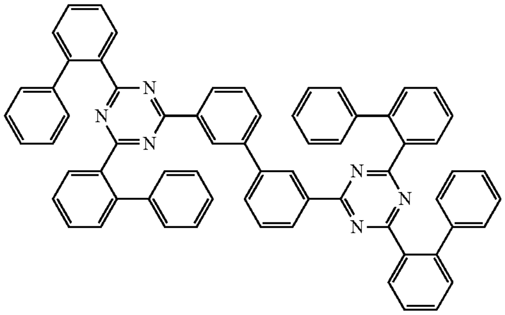
A(38)
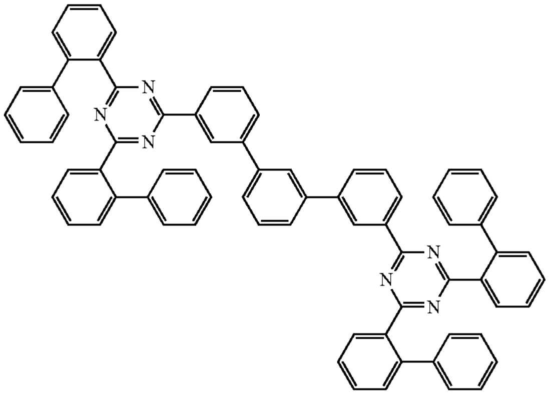

-continued
A(39)
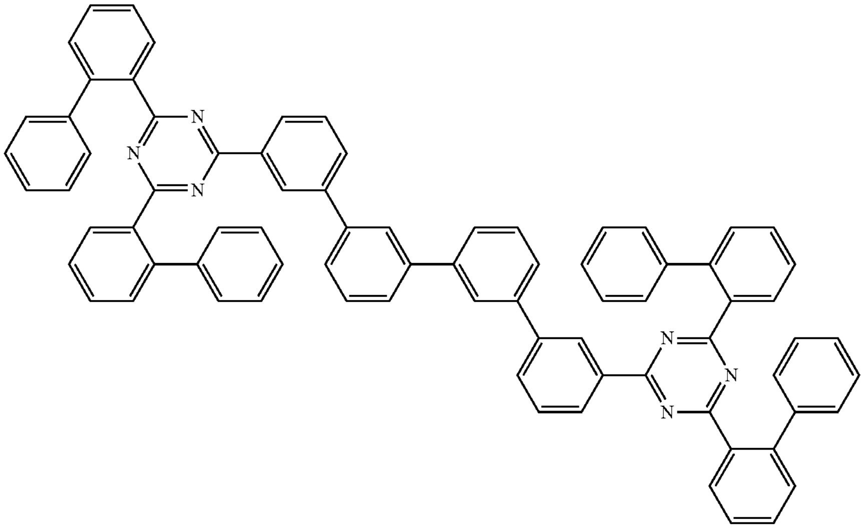
A(40)
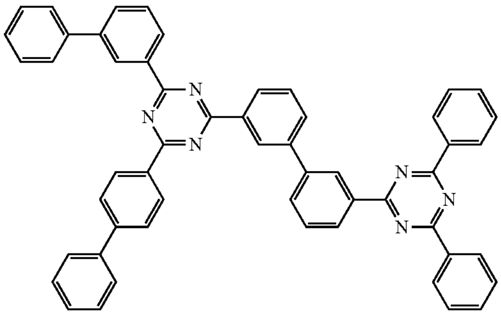
A(41)
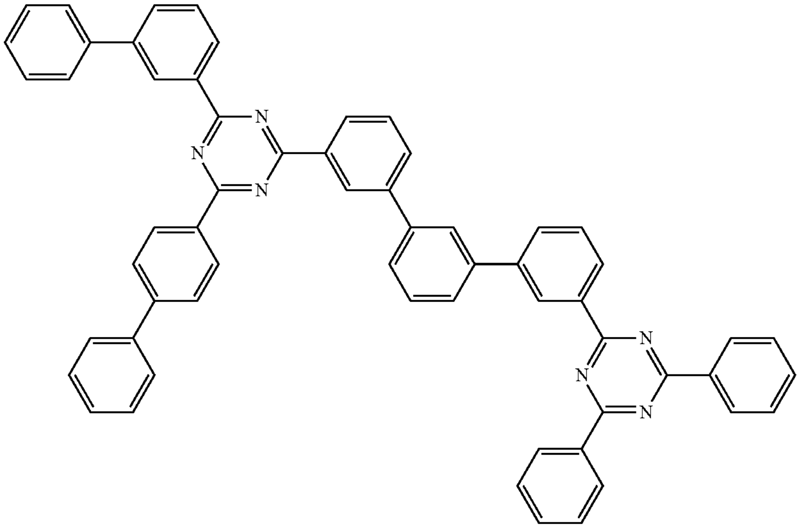

-continued
A(42)
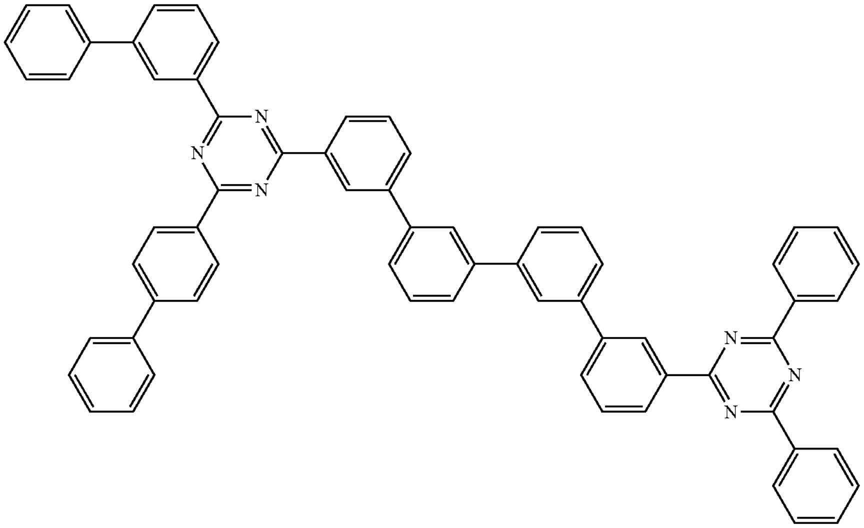
A(43)
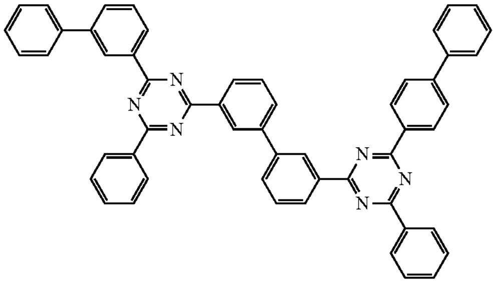
A(44)
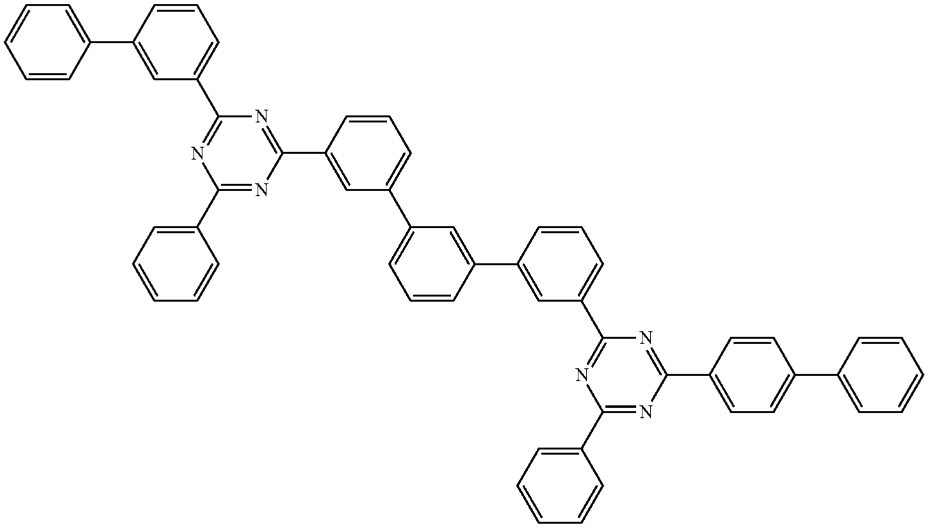

-continued
A(45)
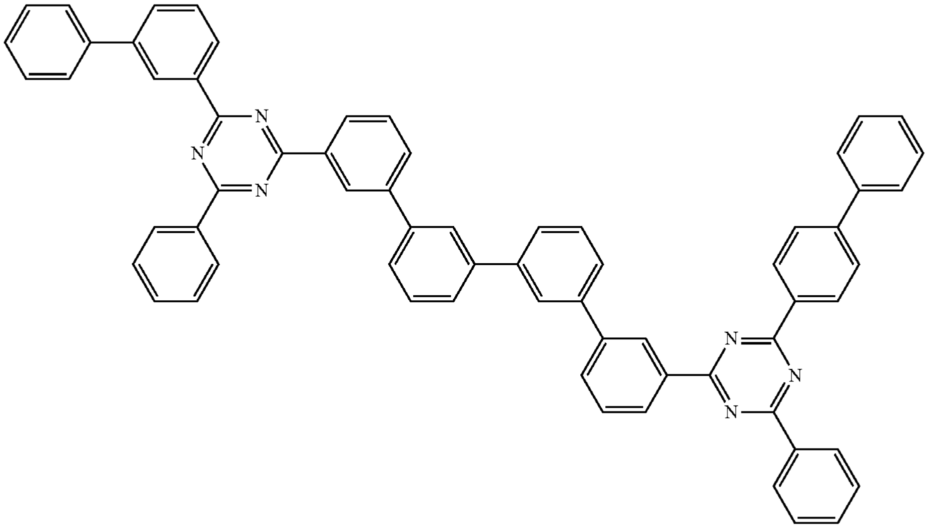
A(46)
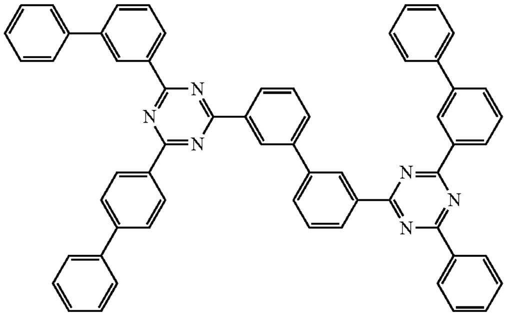
A(47)
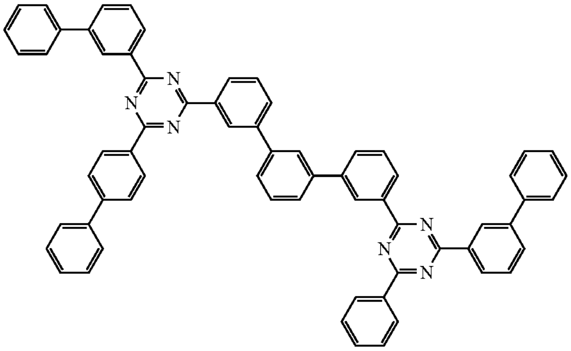
A(48)
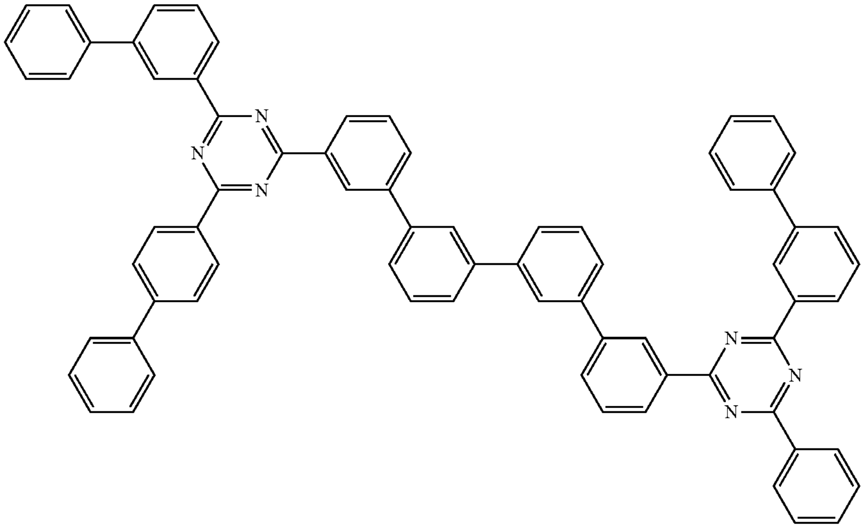

-continued
A(49)
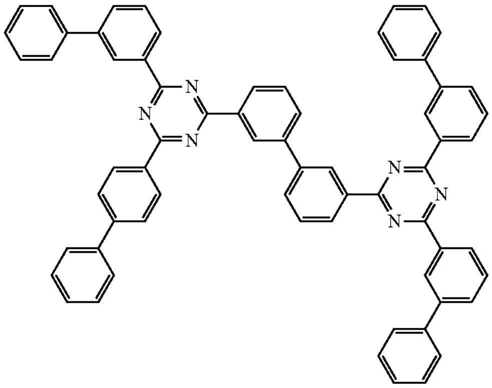
A(50)
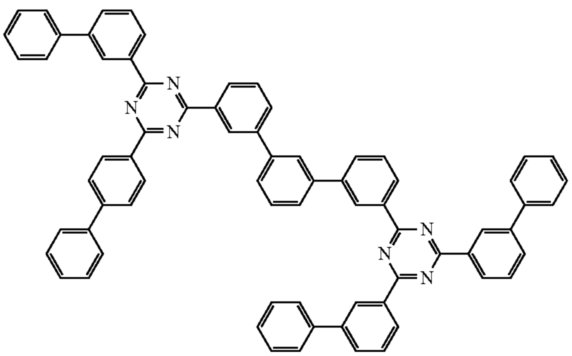
A(51)
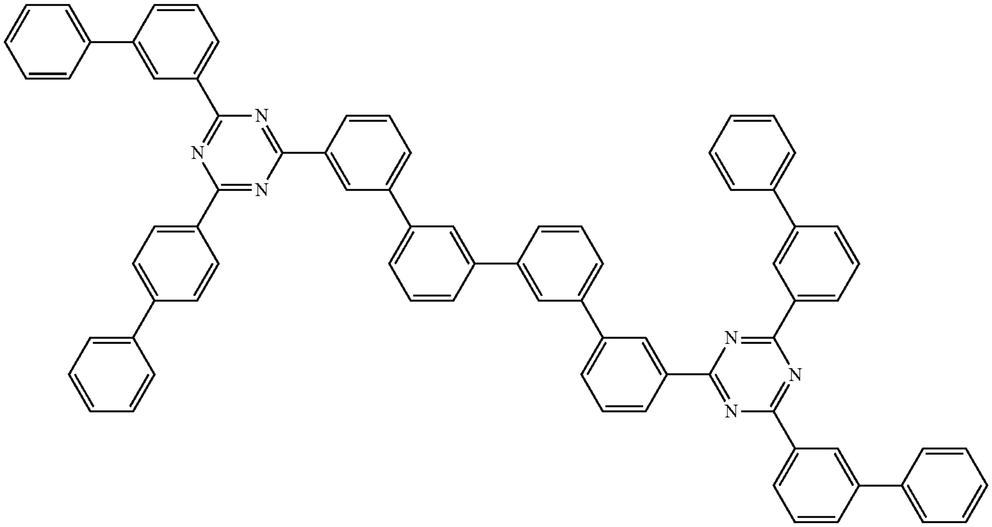
A(52)
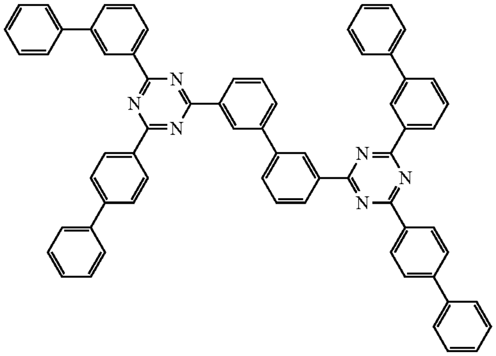

-continued
A(53)
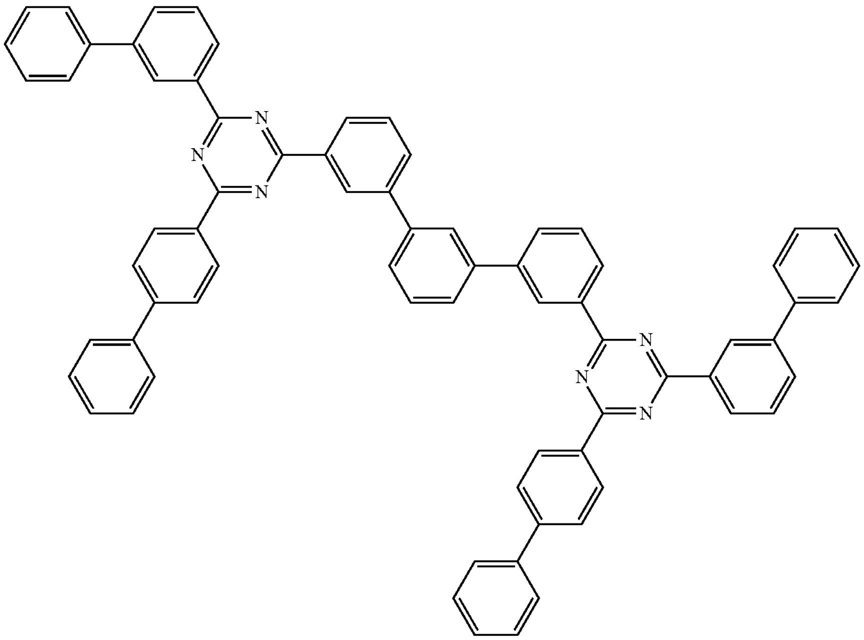
A(54)
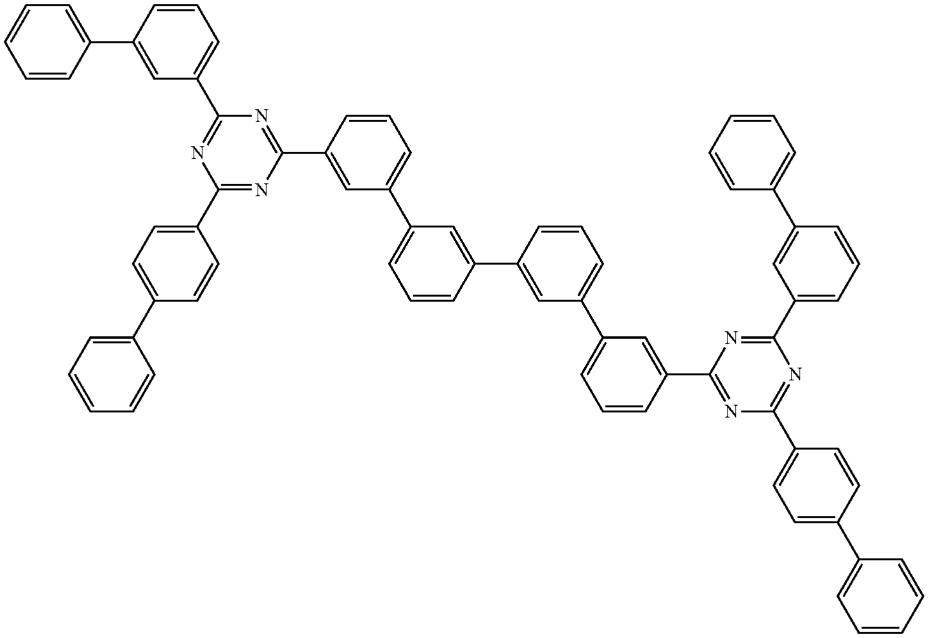

-continued
A(55)
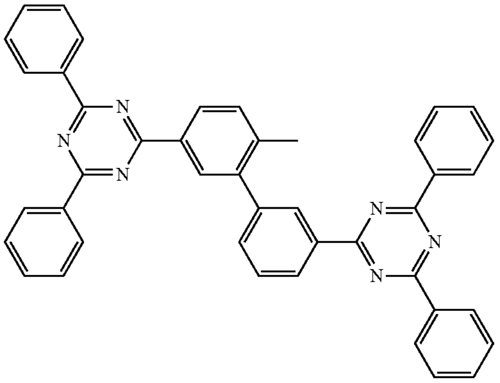
A(56)
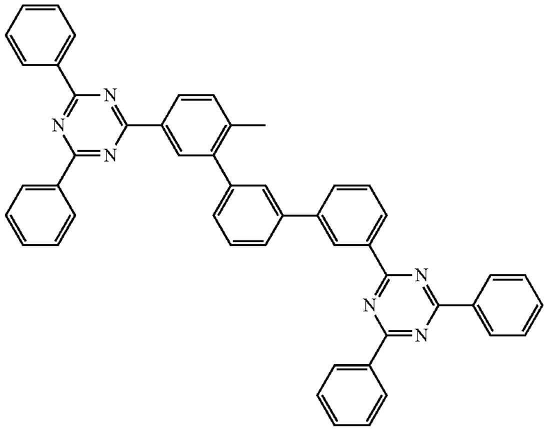
A(57)
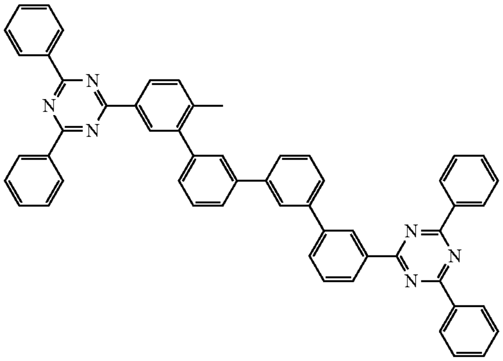
A(58)
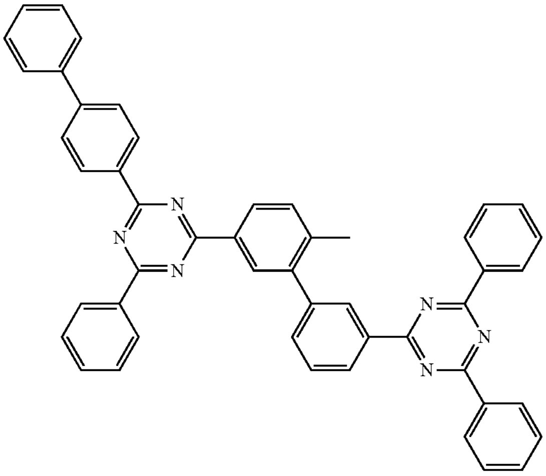
A(59)
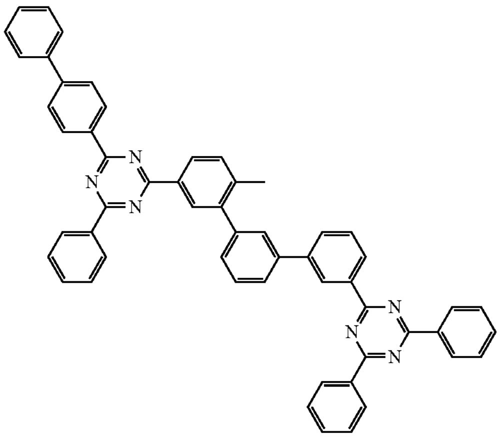

-continued
A(60)
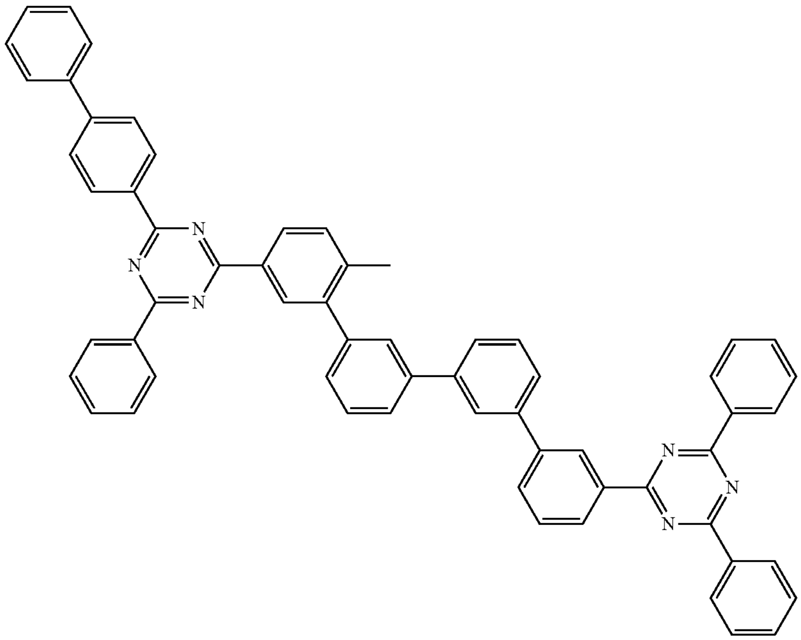
A(61)
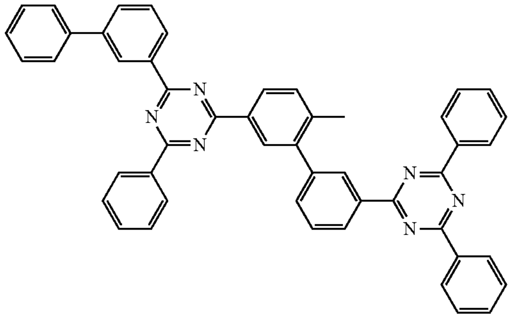
A(62)
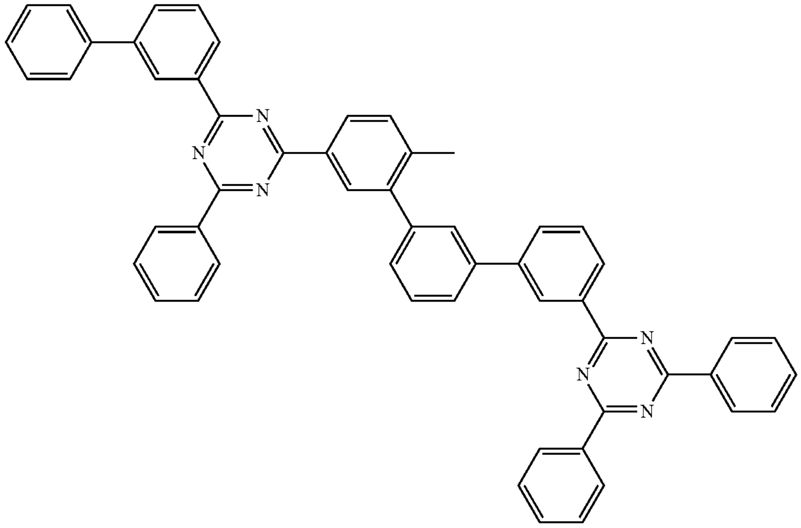

-continued
A(63)
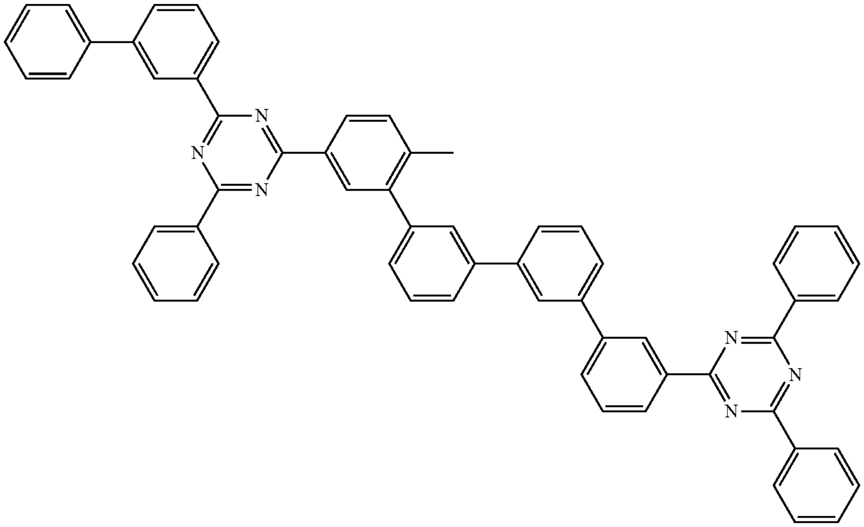
A(64)
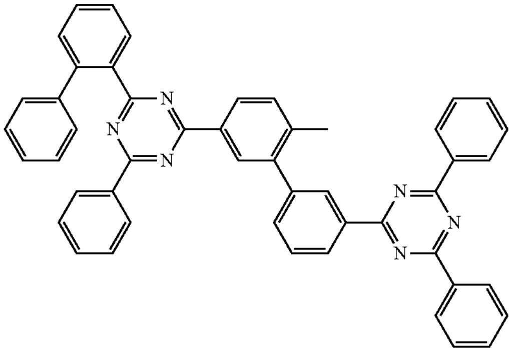
A(65)
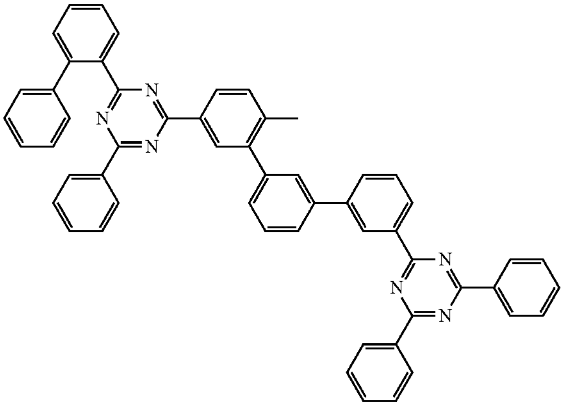
A(66)
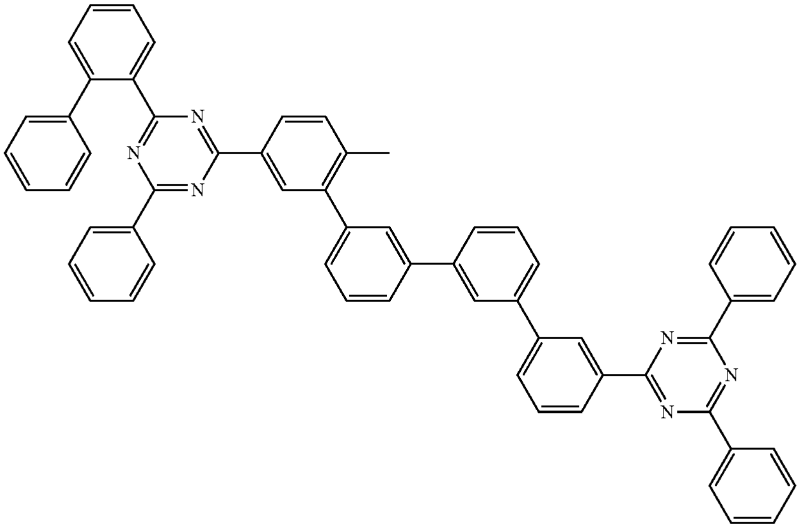

-continued
A(67)
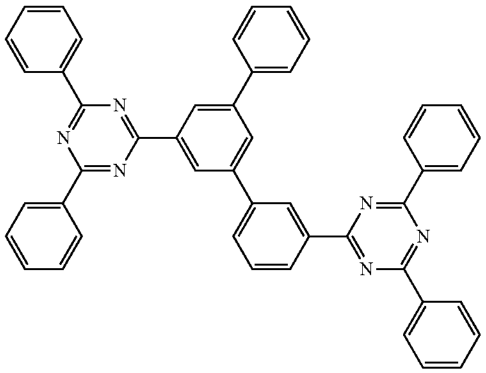
A(68)
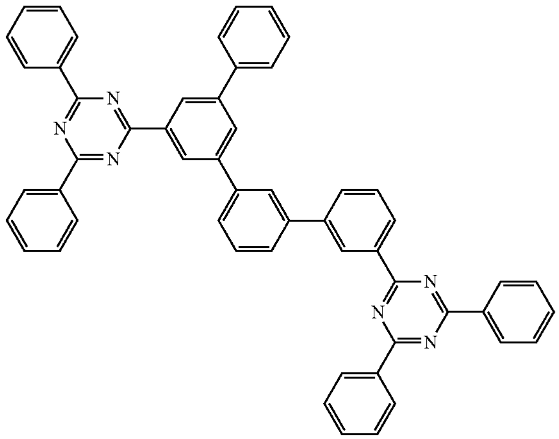
A(69)
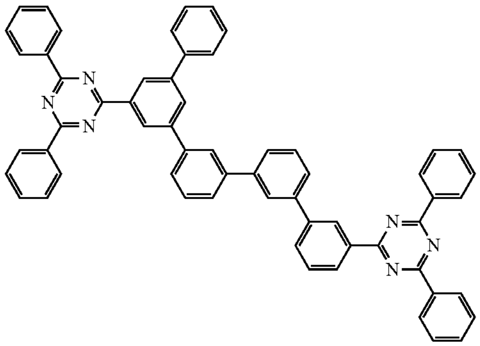
A(70)
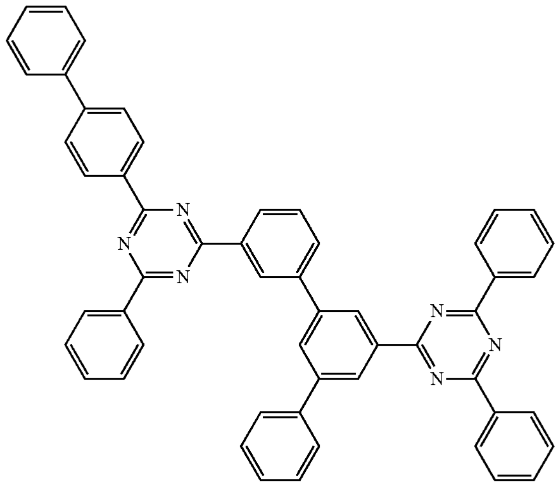
A(71)
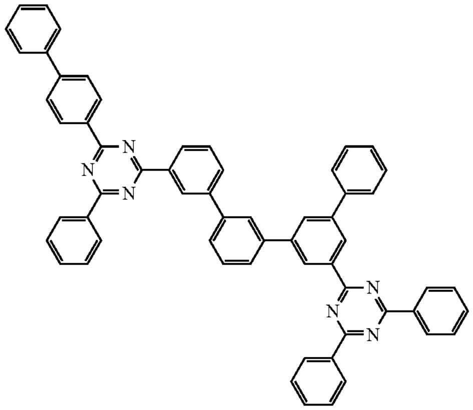

-continued
A(72)
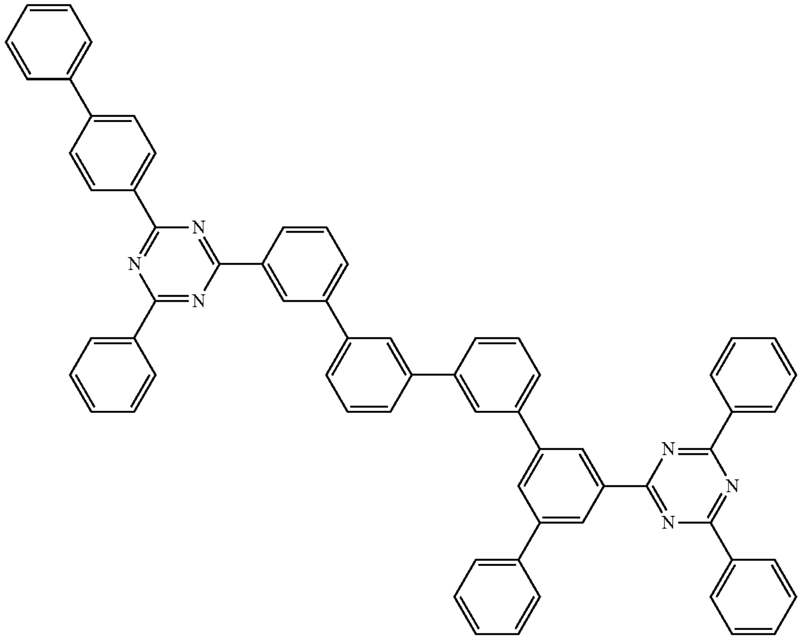
A(73)
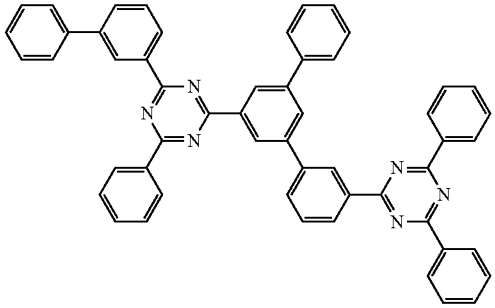
A(74)
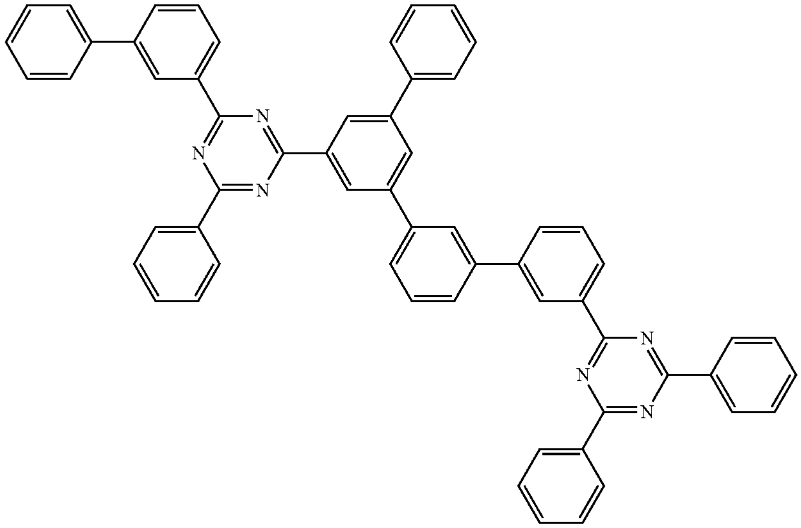

-continued
A(75)
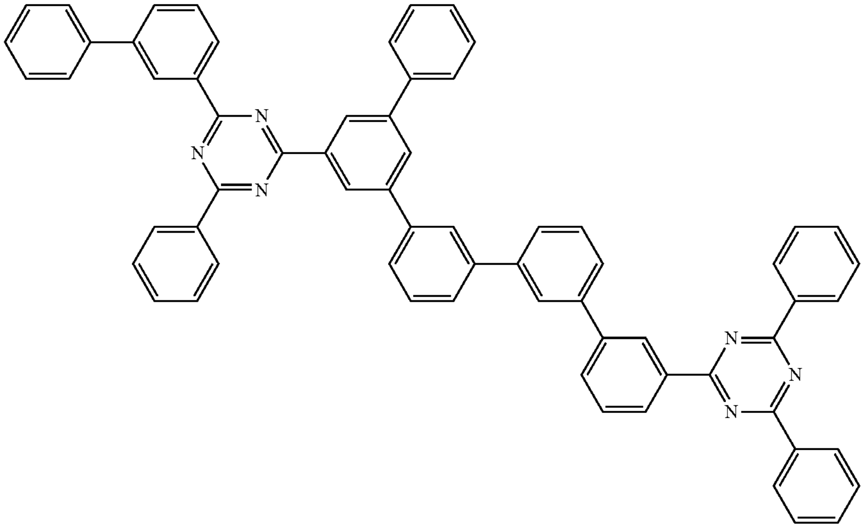
A(76)
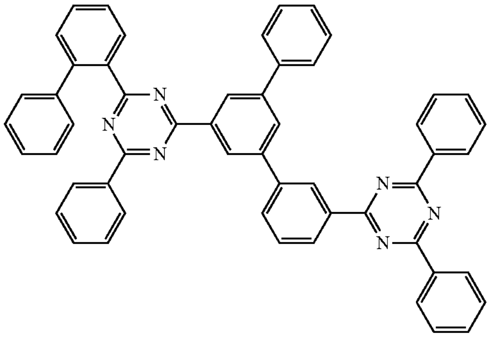
A(77)
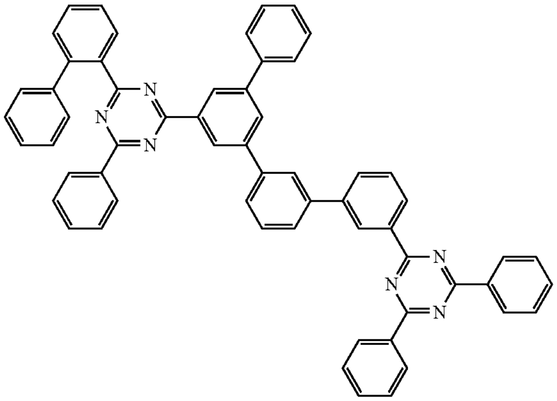
A(78)
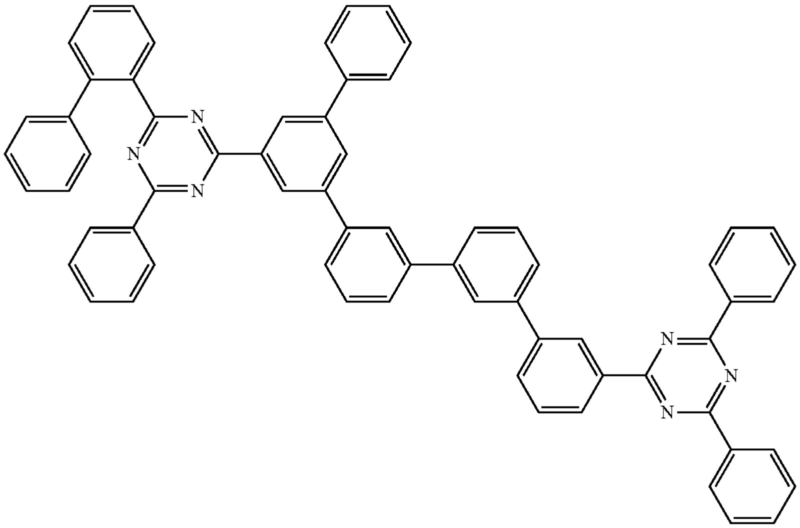

-continued
A(79)
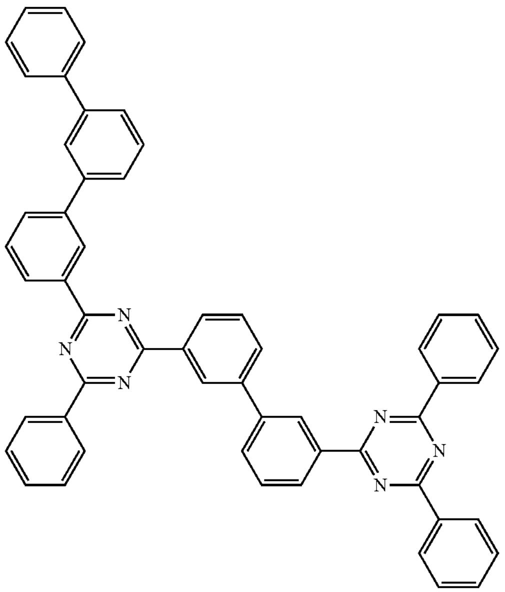
A(80)
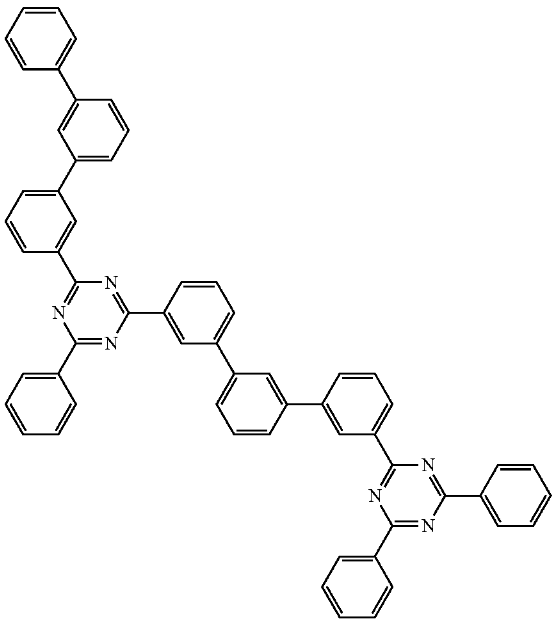
A(81)
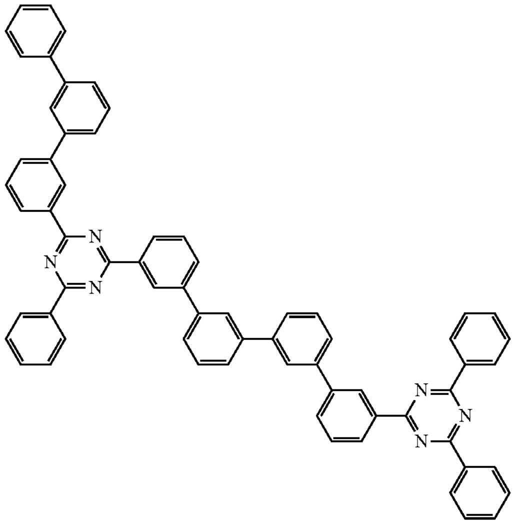
A(82)
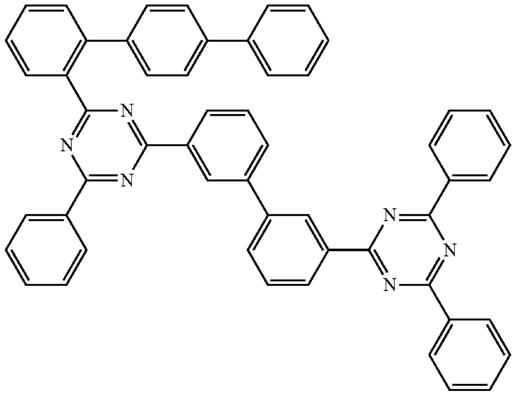
A(83)
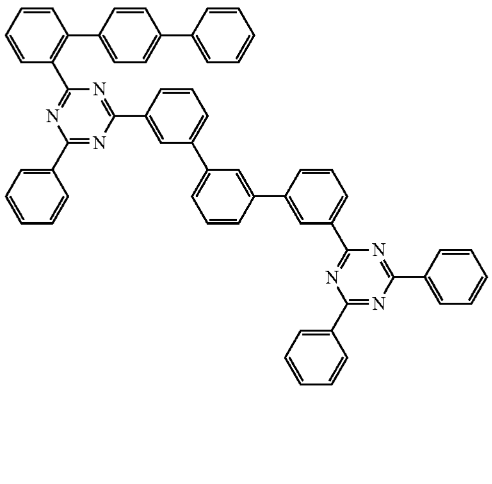
A(84)
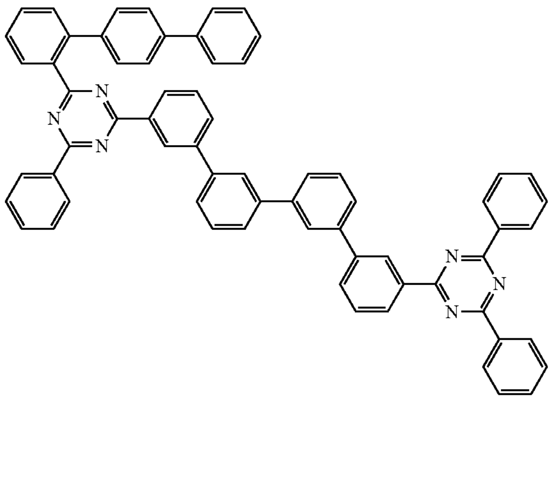

-continued
A(85)
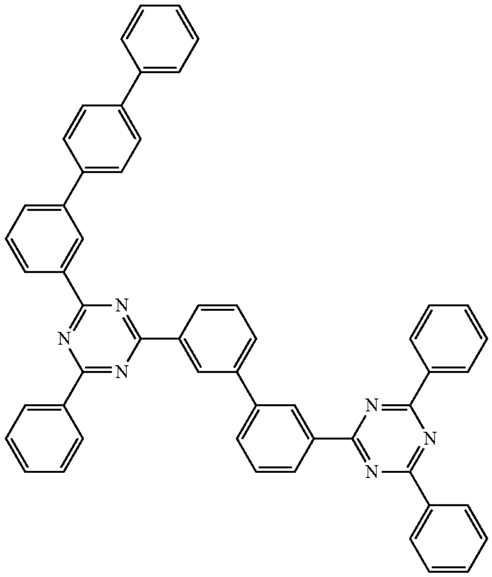
A(86)
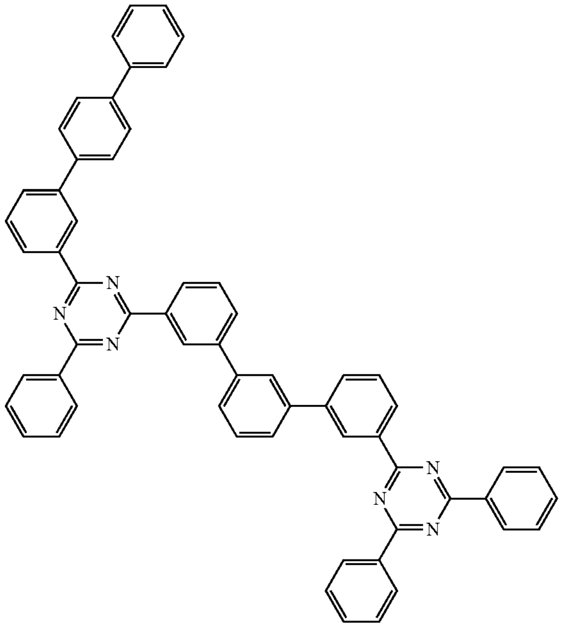
A(87)
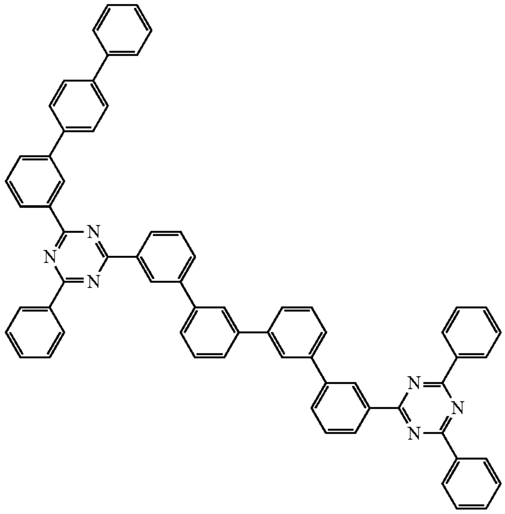
A(88)
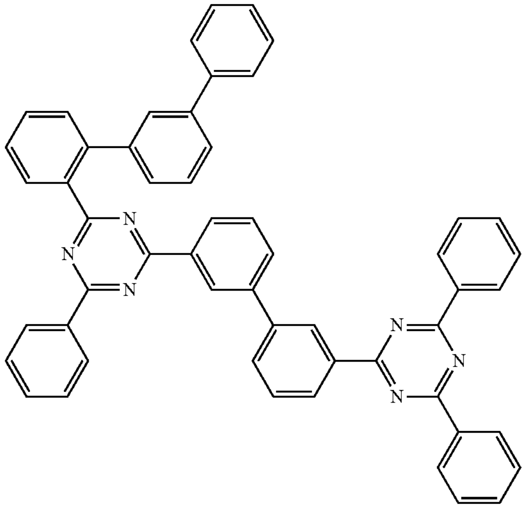

-continued
A(89)
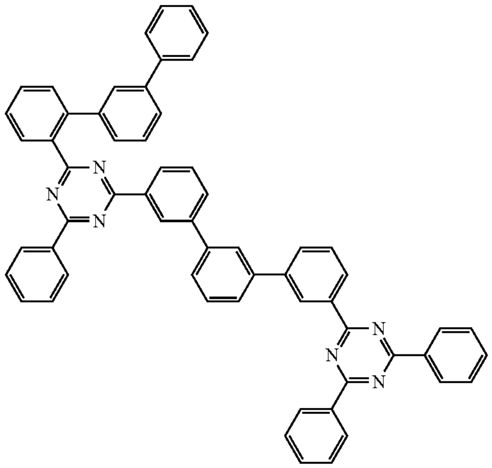
A(90)
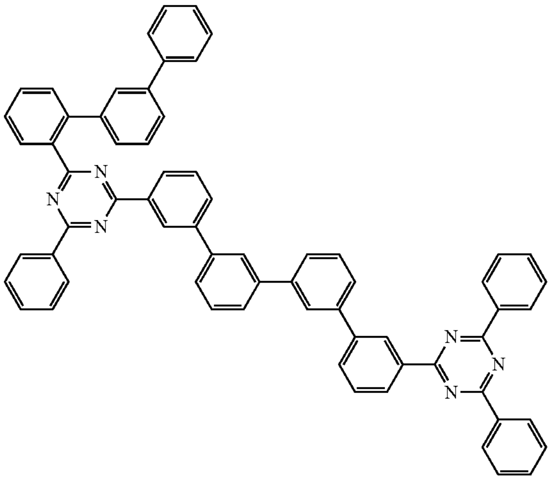
A(91)
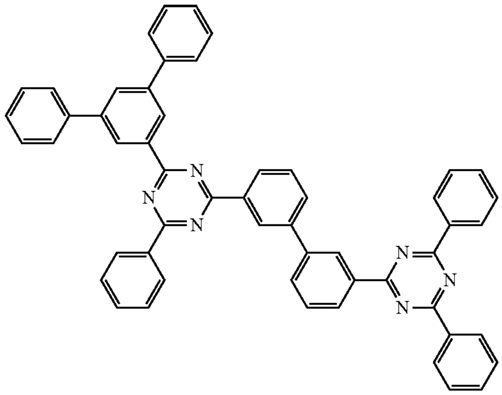
A(92)
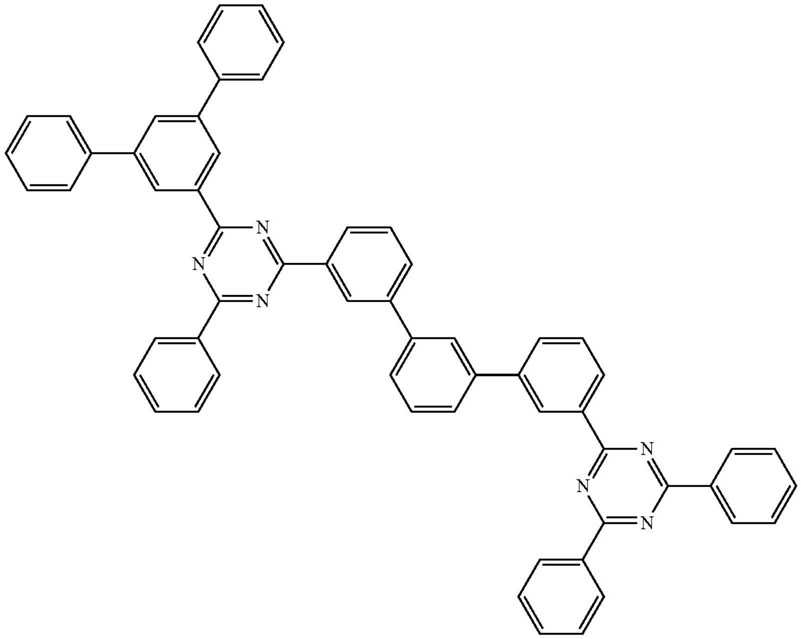

-continued
A(93)
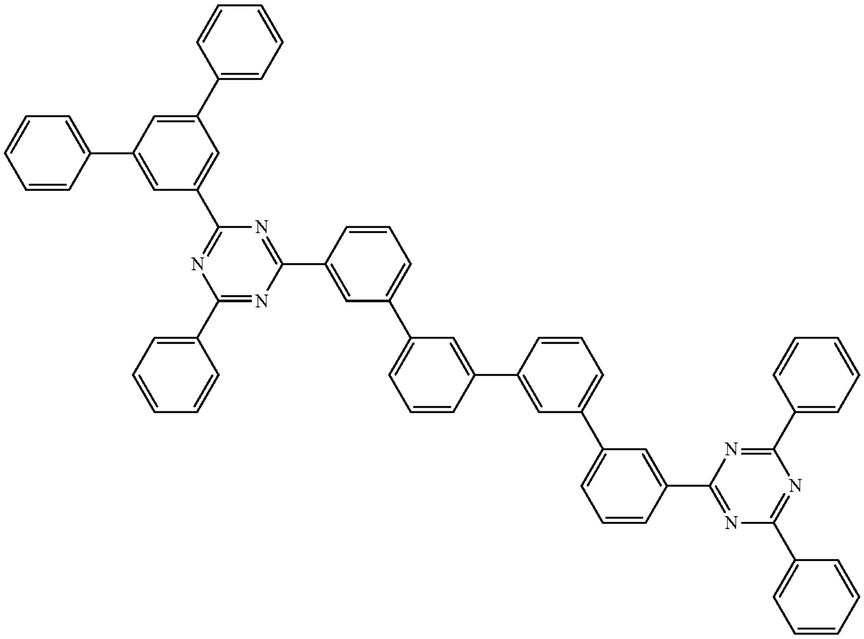
A(94)
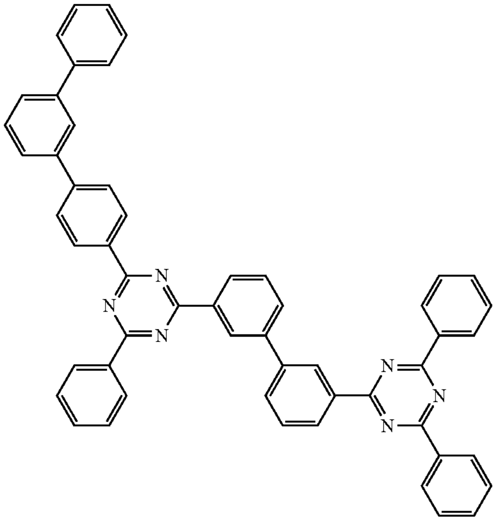
A(95)
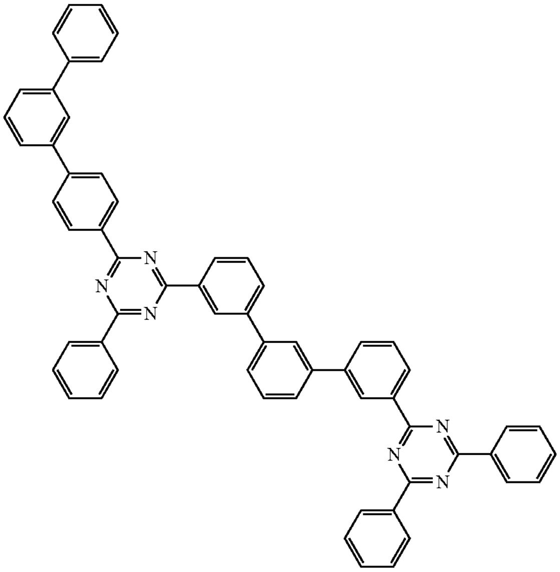

-continued
A(96)
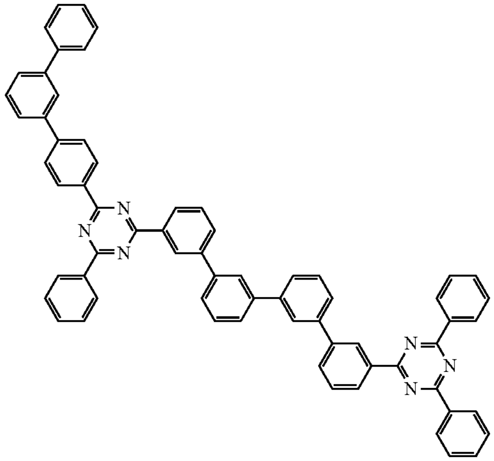
A(97)
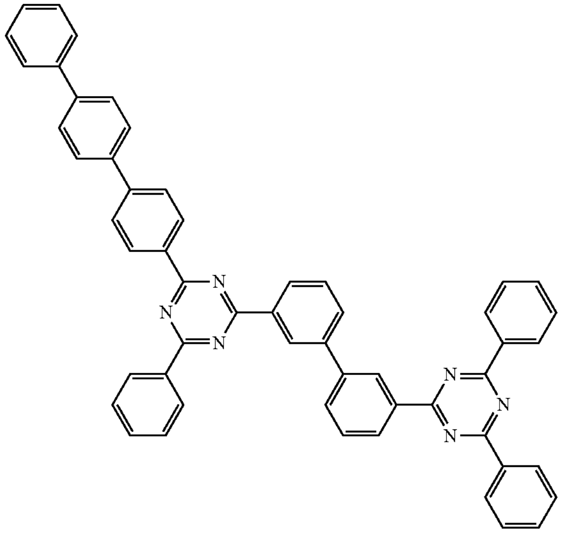
A(98)
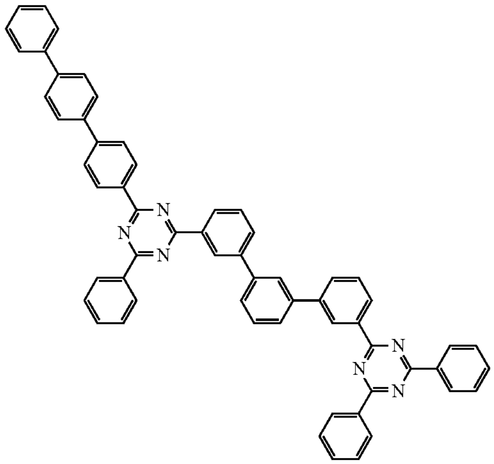
A(99)
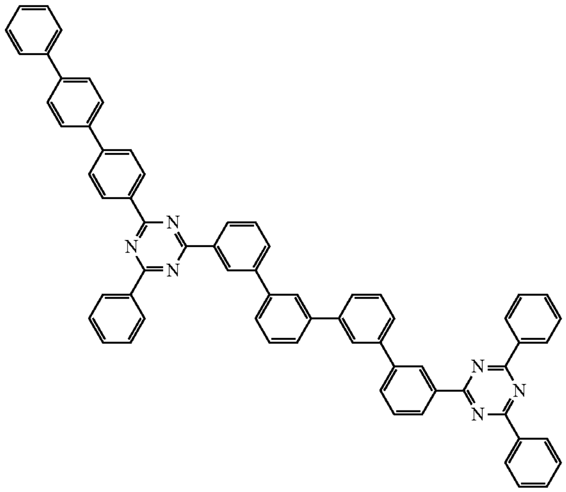

-continued
A(100)
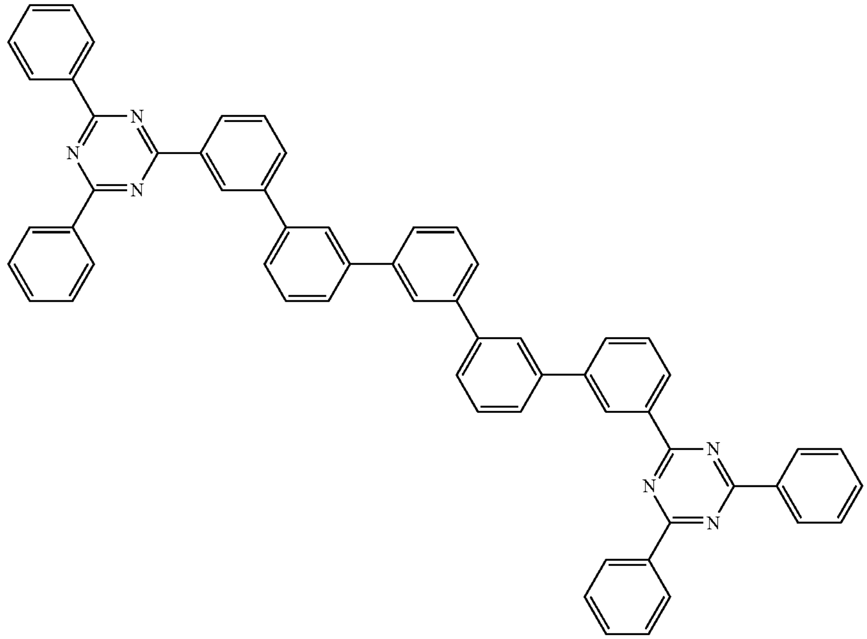
A(101)
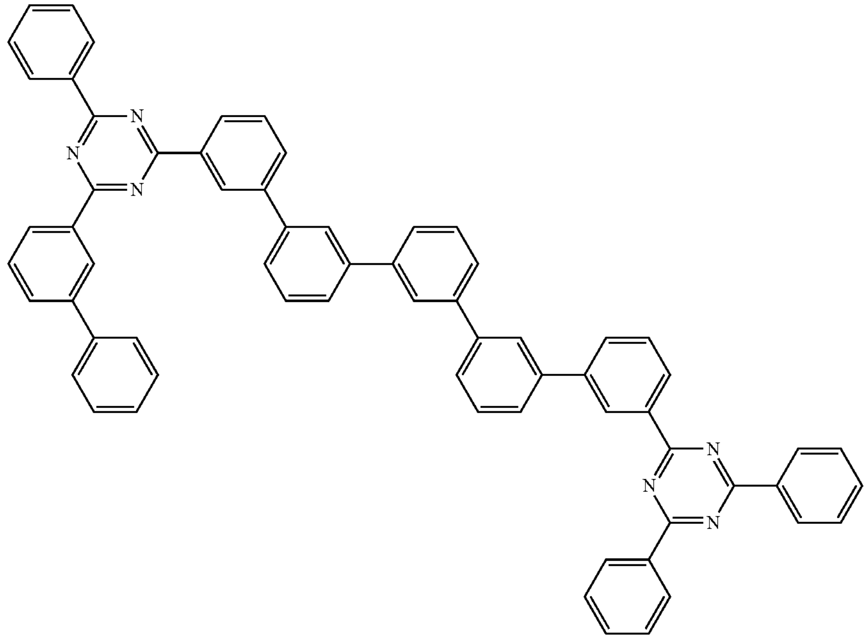

-continued
A(102)
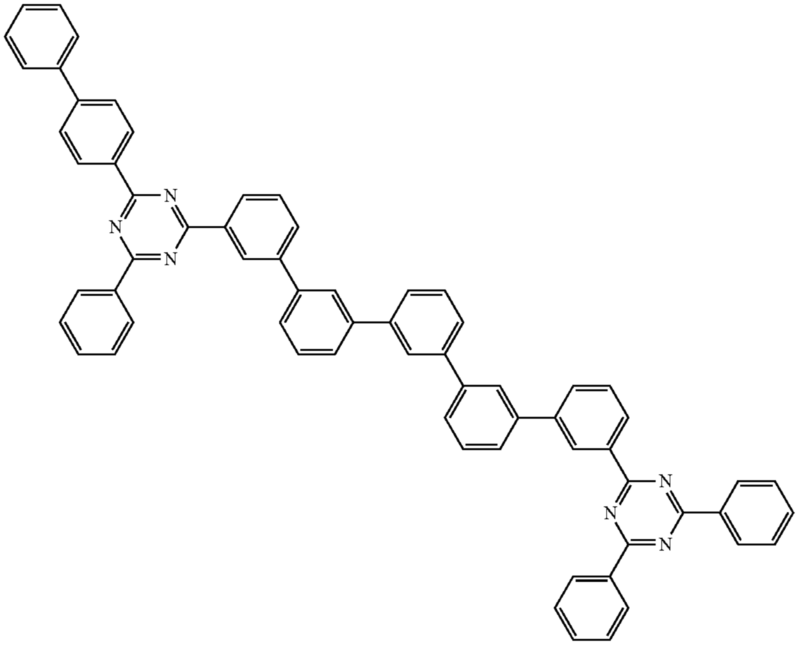
A(103)
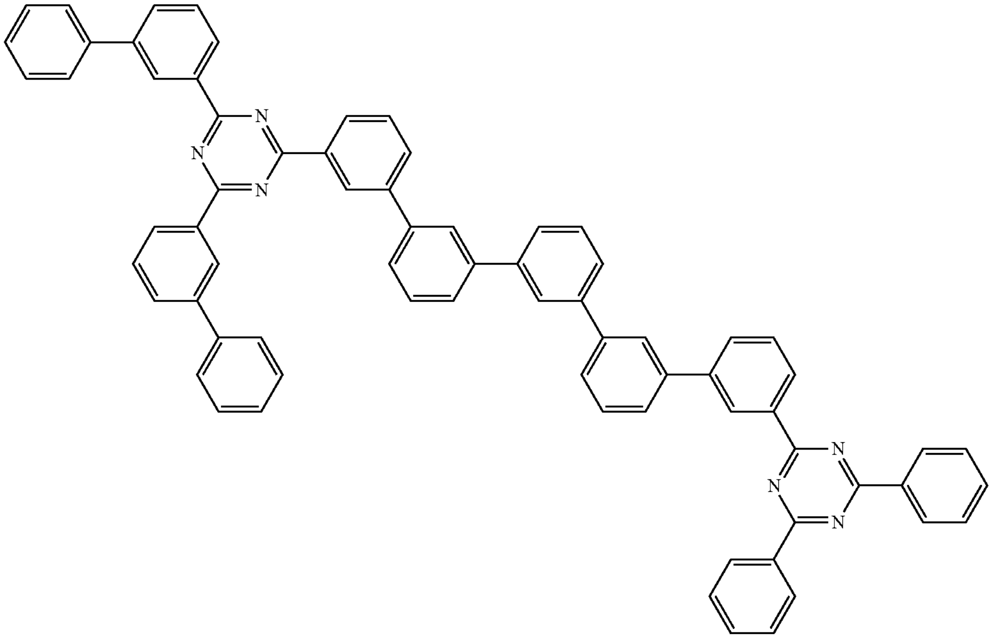

-continued
A(104)
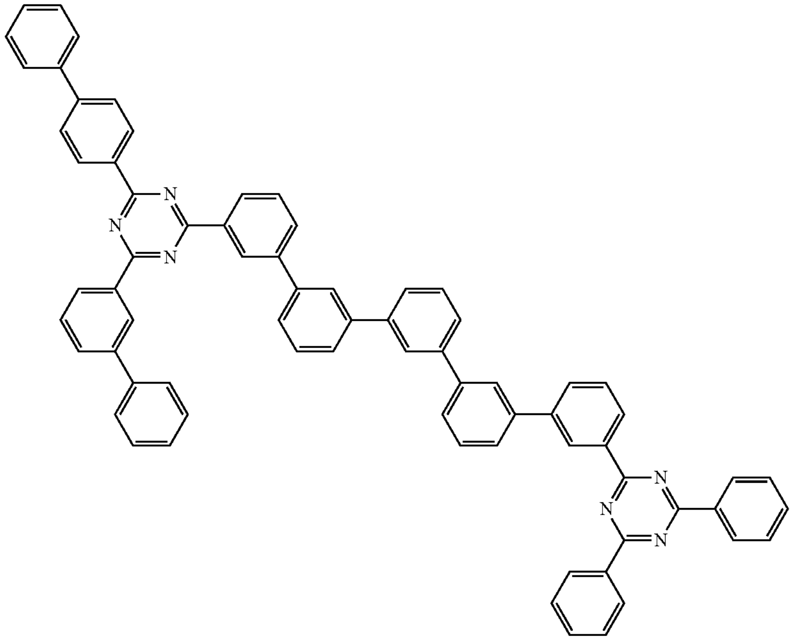
A(105)
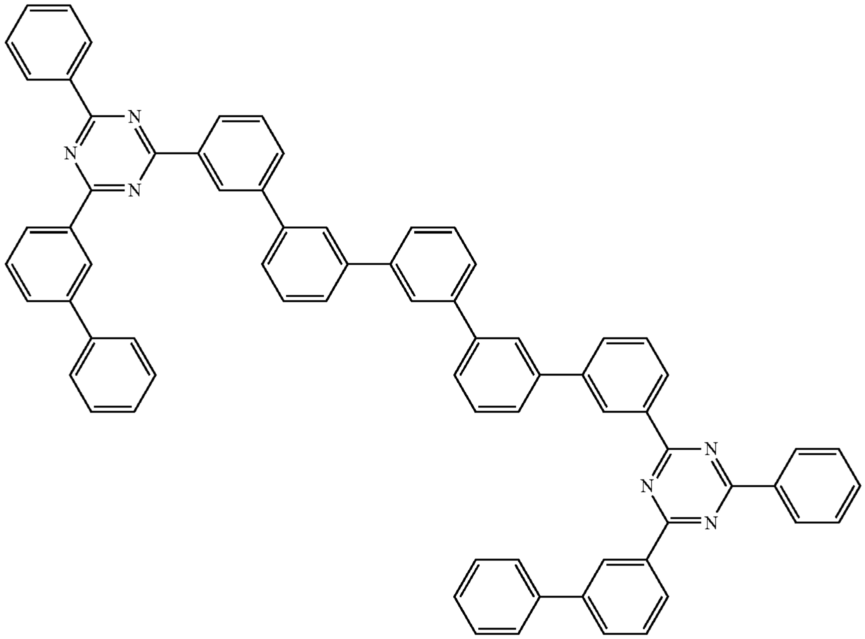

-continued
A(106)
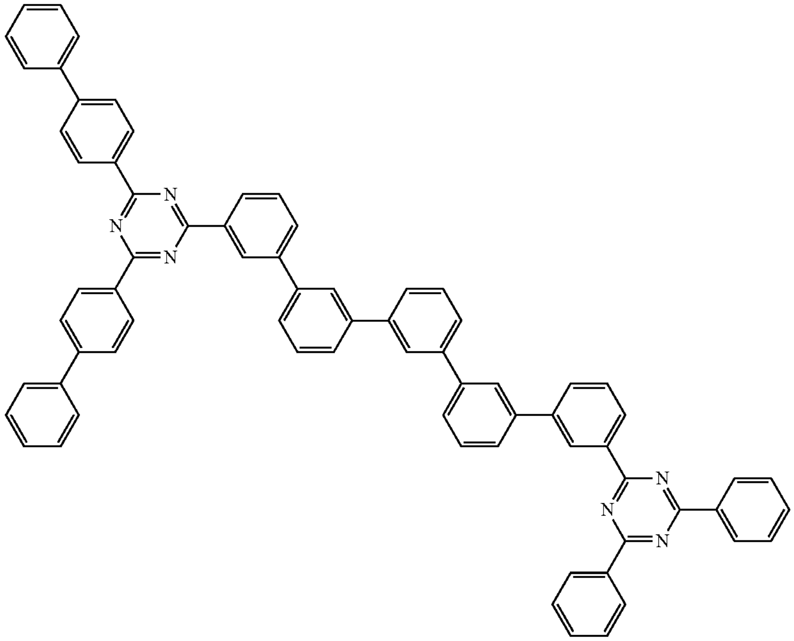
A(107)
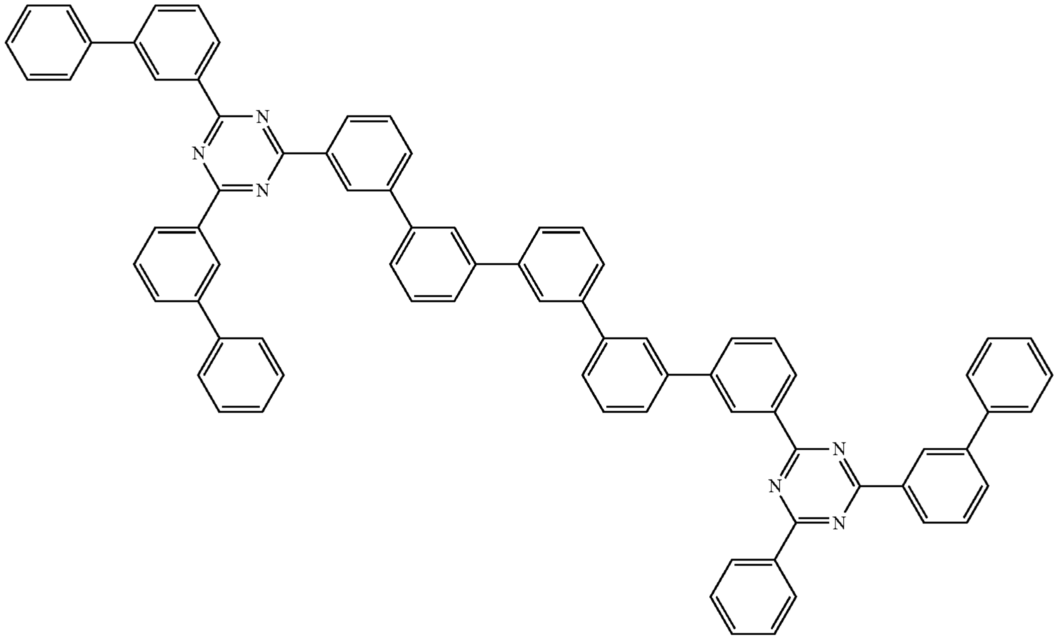

-continued
A(108)
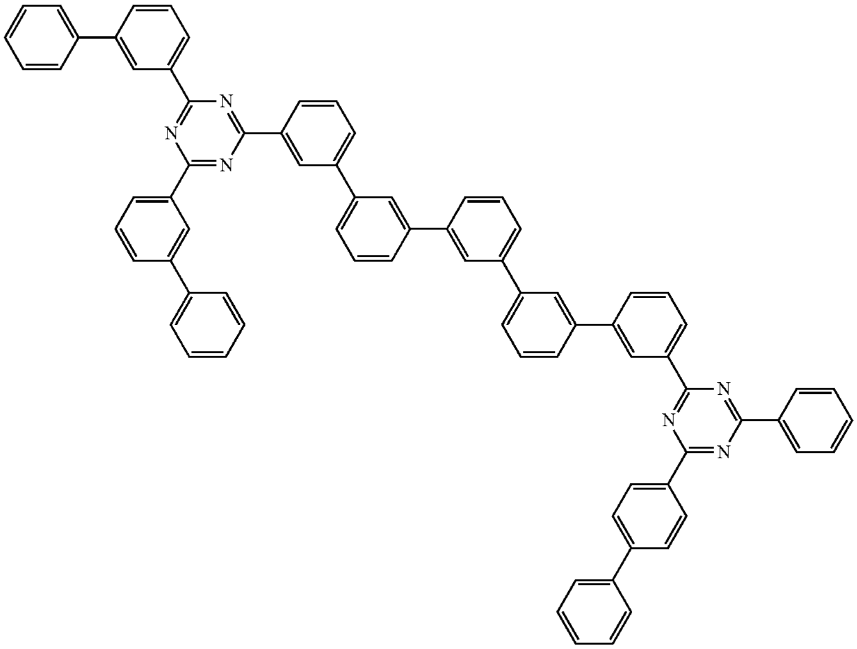
A(109)
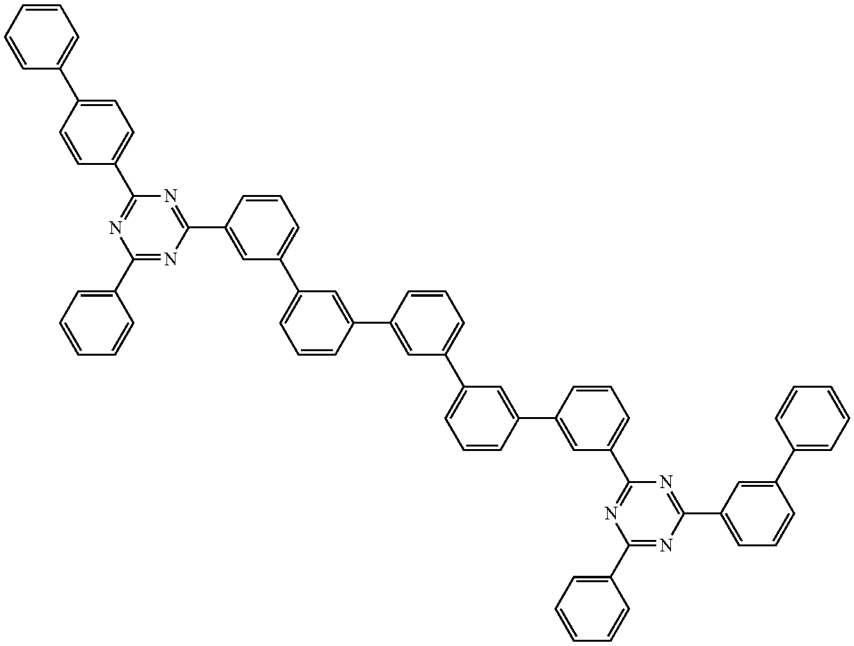

-continued
A(110)
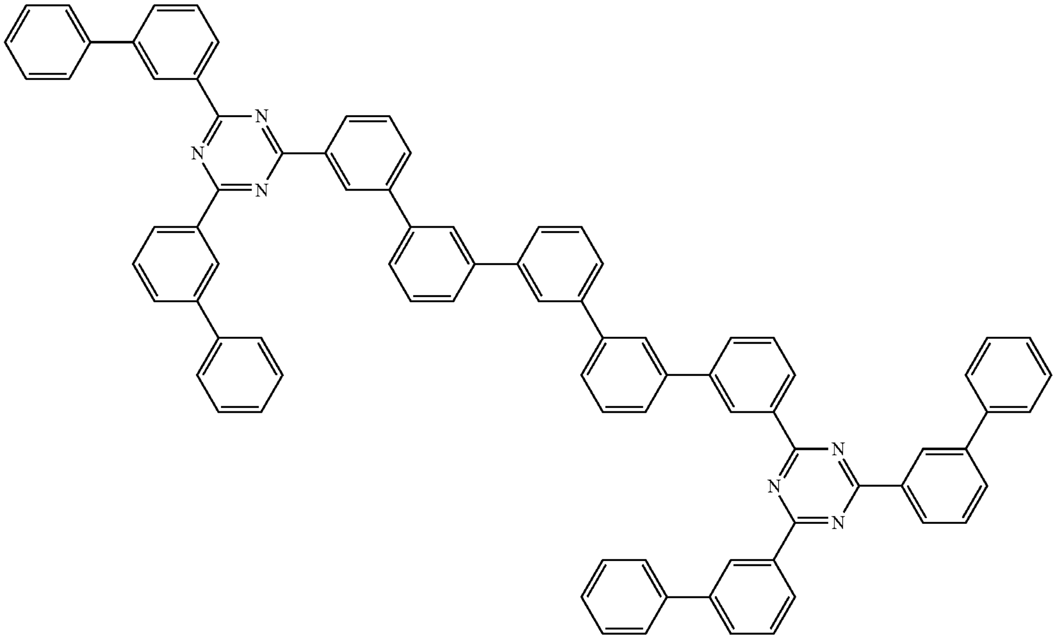
A(111)
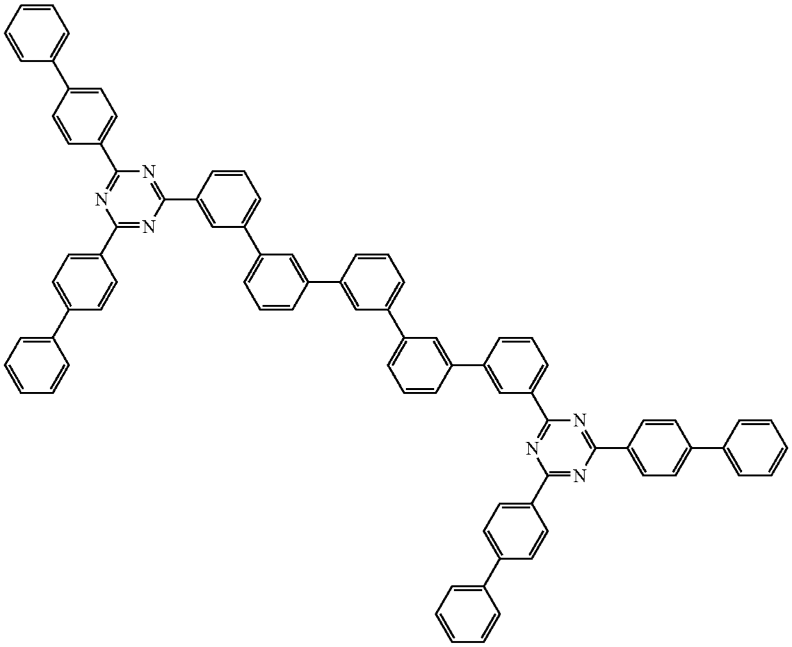

-continued
A(112)
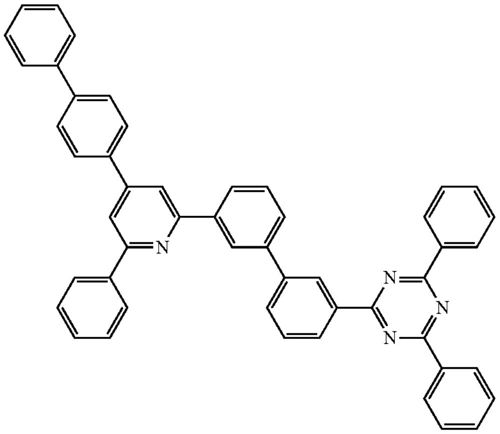
A(113)
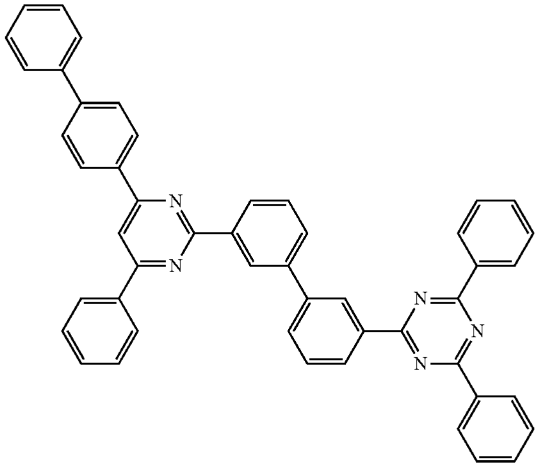
A(114)
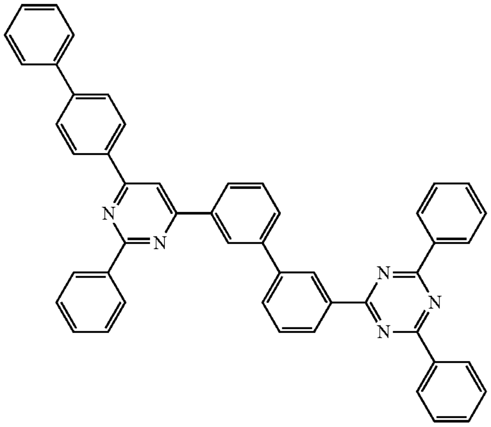
A(115)
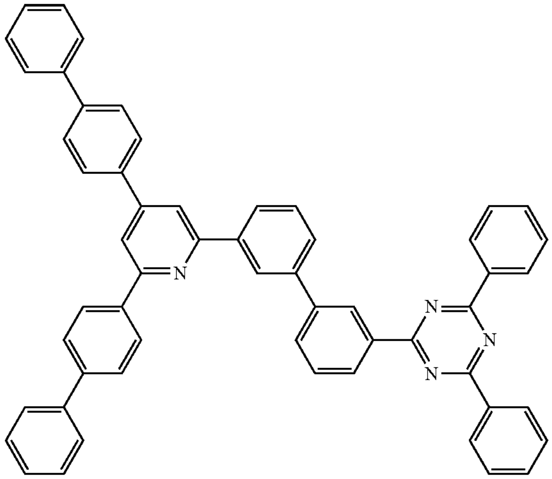
A(116)
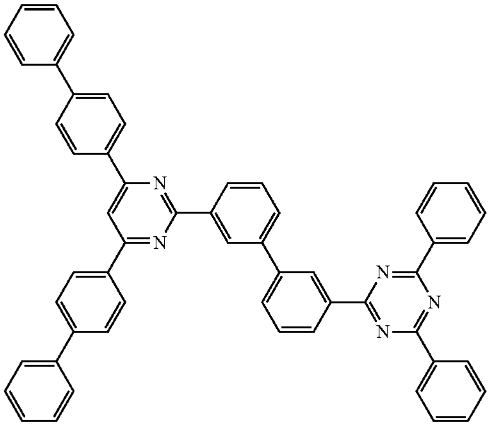
A(117)
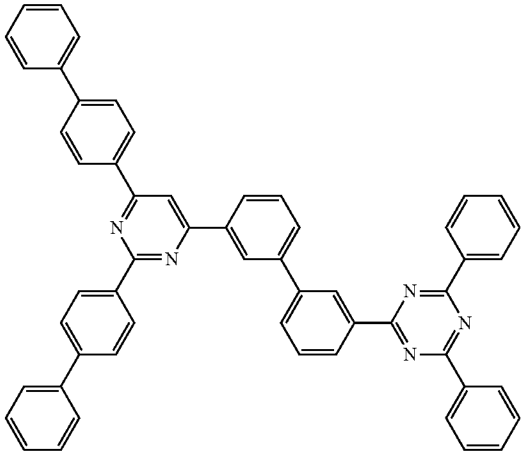

-continued
A(118)
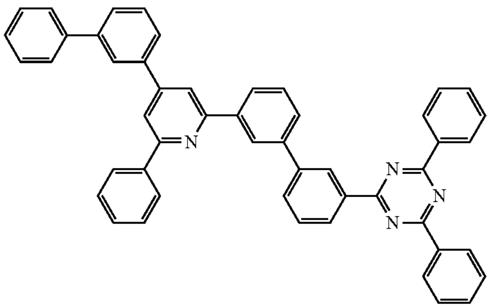
A(119)
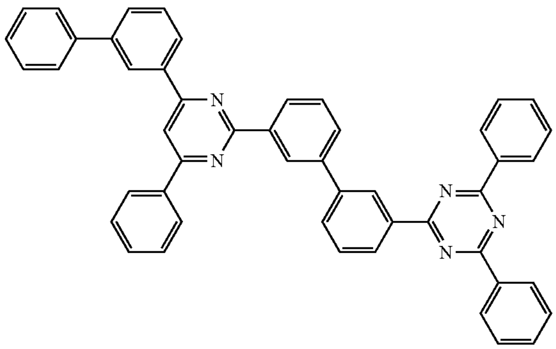
A(120)
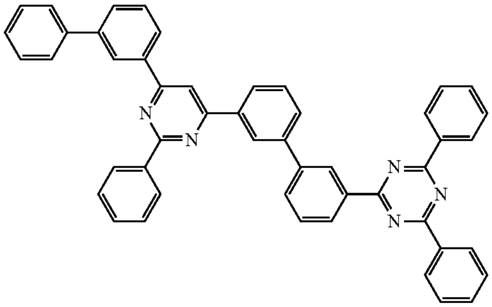
A(121)
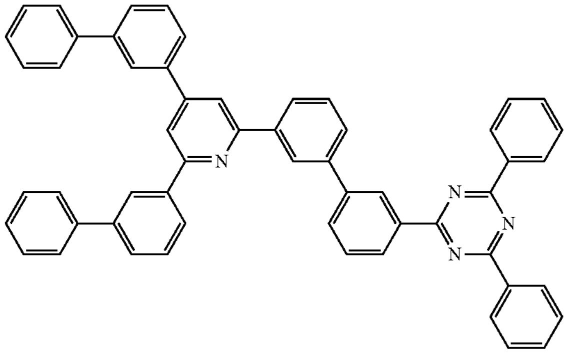
A(122)
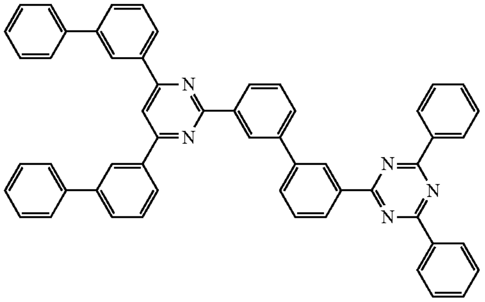
A(123)
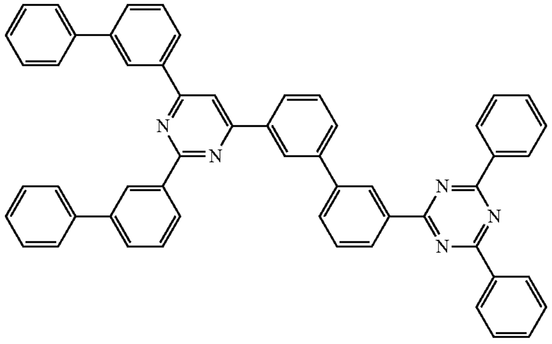
A(124)
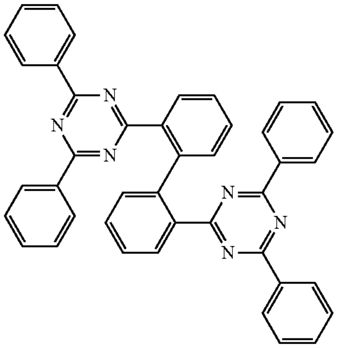
A(125)
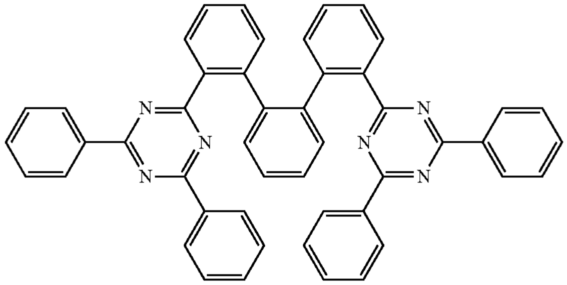

-continued
A(126)
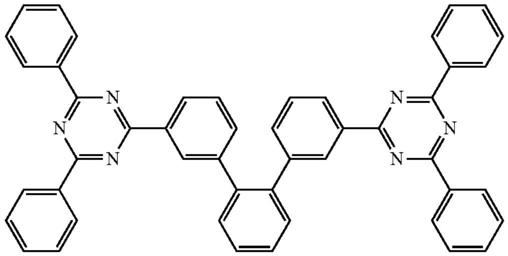
A(127)
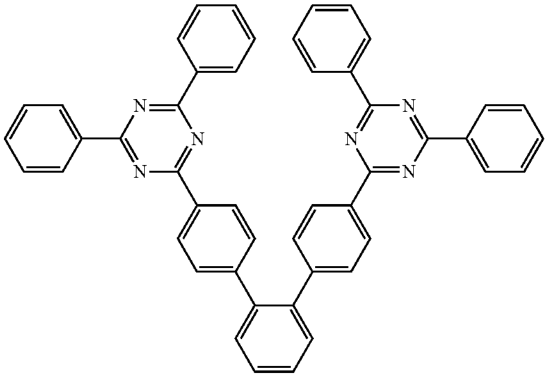
A(128)
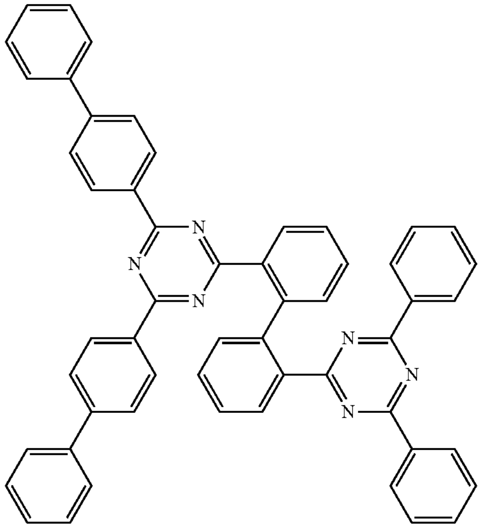
A(129)
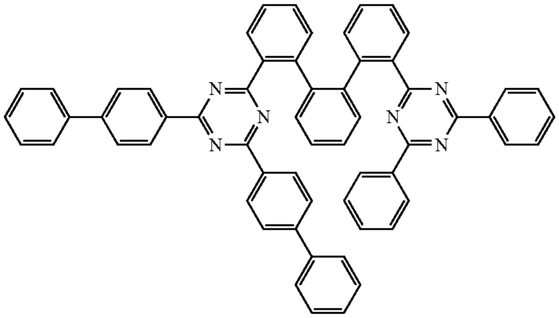
A(130)
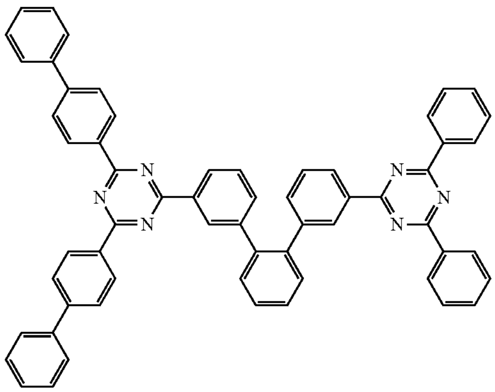
A(131)
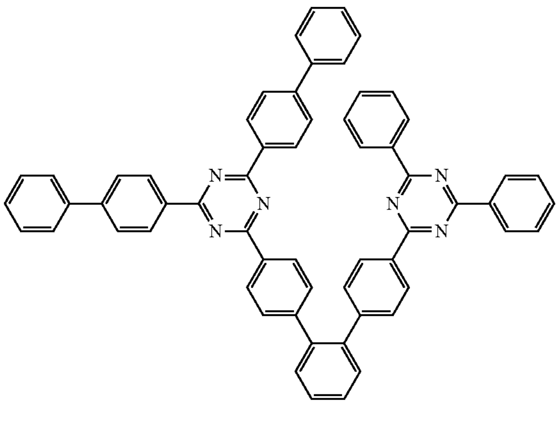

-continued
A(132)
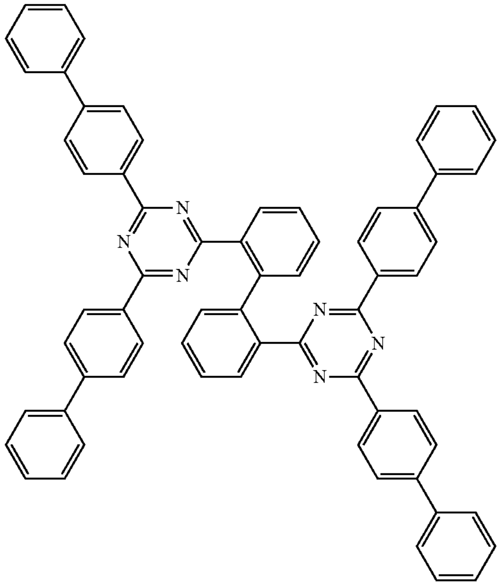
A(133)
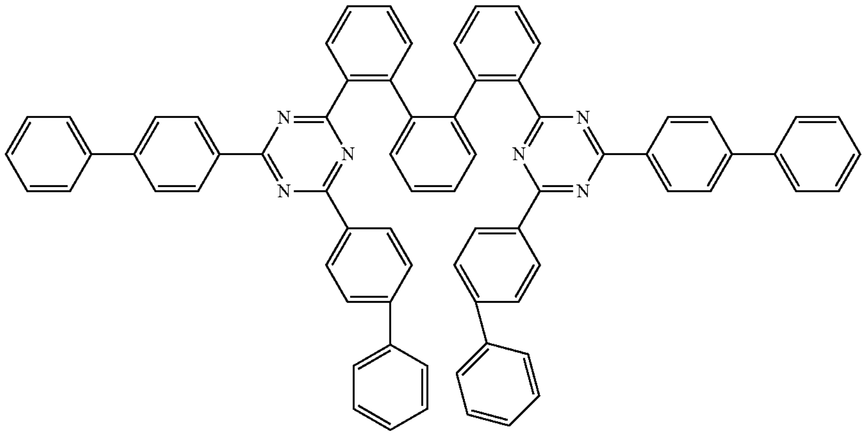
A(134)
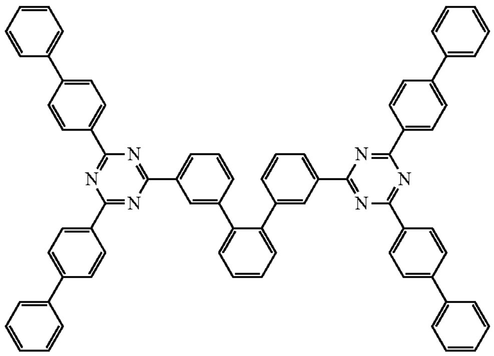

-continued
A(135)
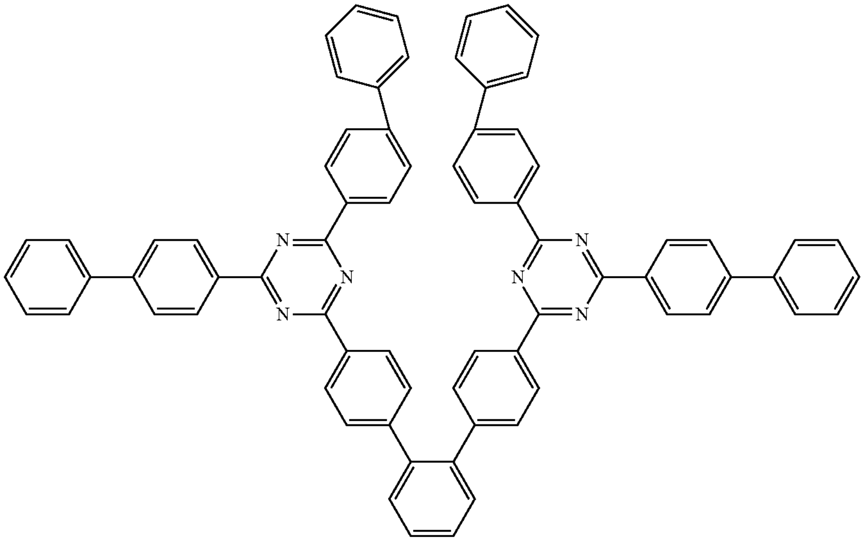
A(136)
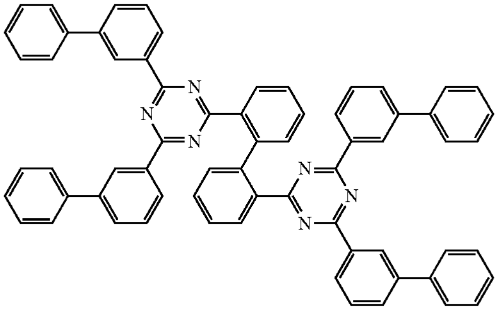
A(137)
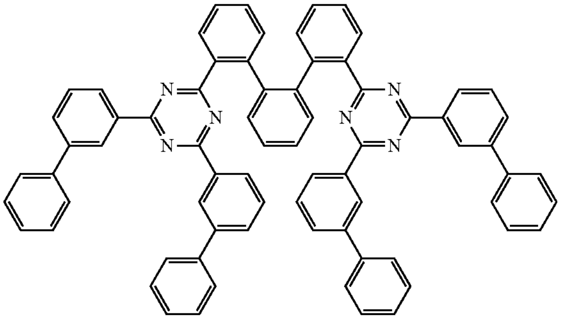
A(138)
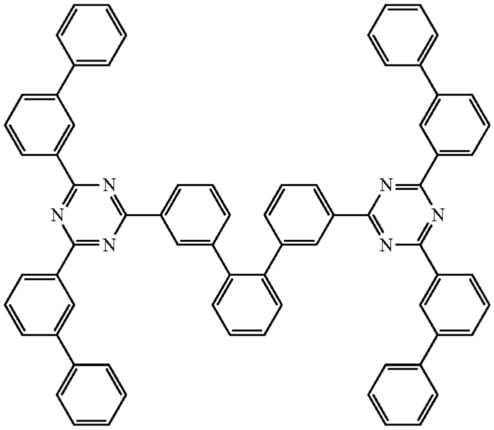
A(139)
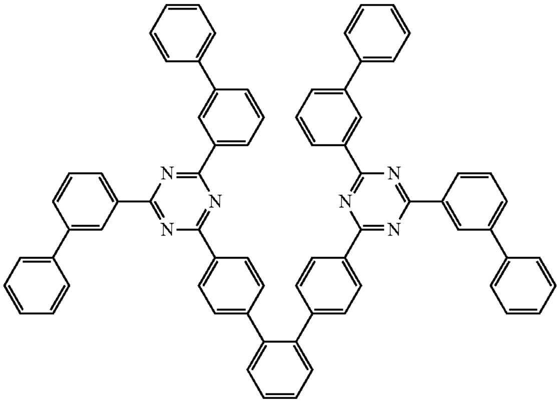
A(140)
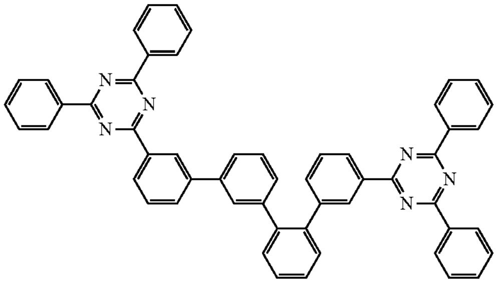
A(141)
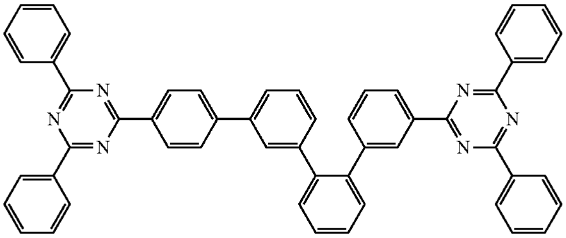

-continued
A(142)
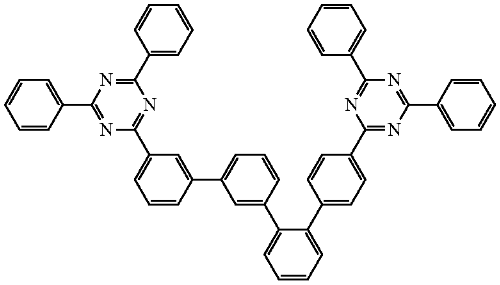
A(143)
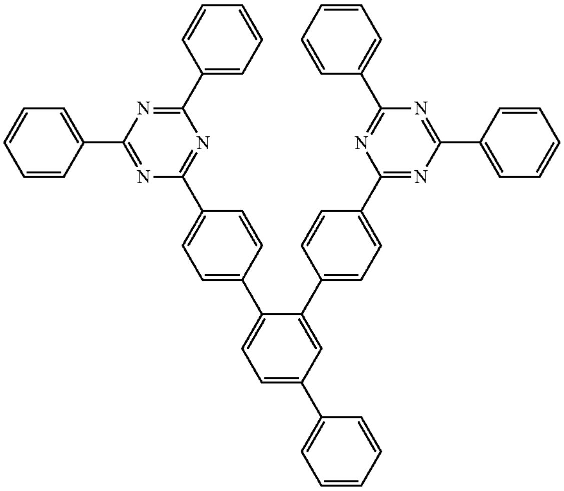
A(144)
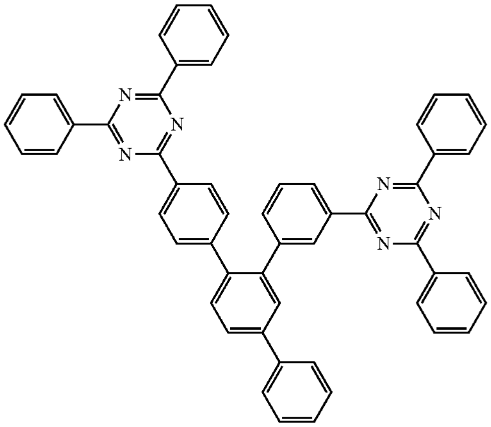
A(145)
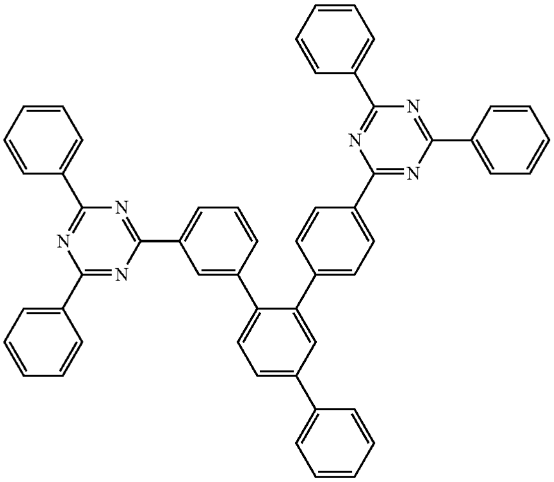
A(146)
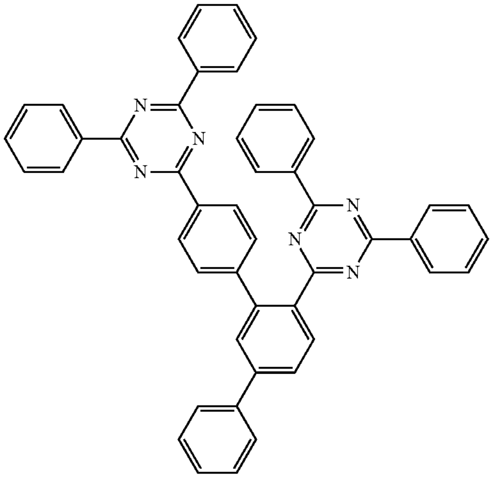
A(147)
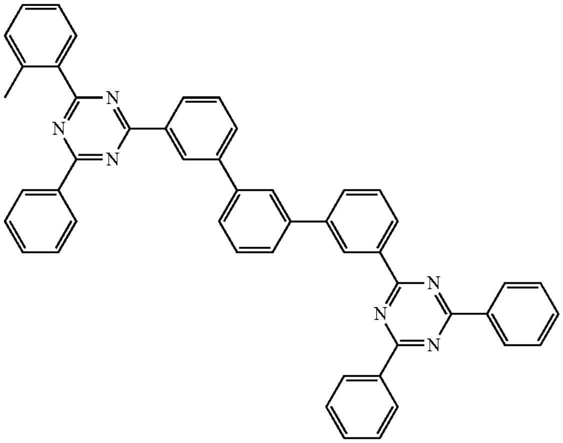

-continued
A(148)
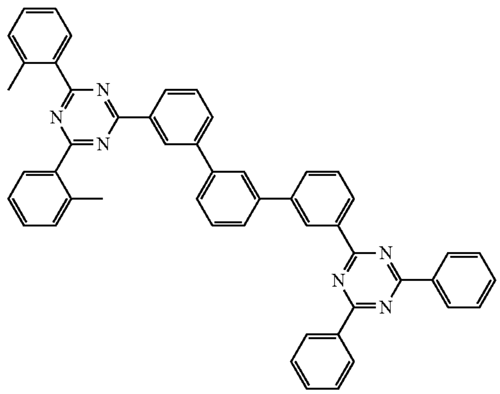
A(149)
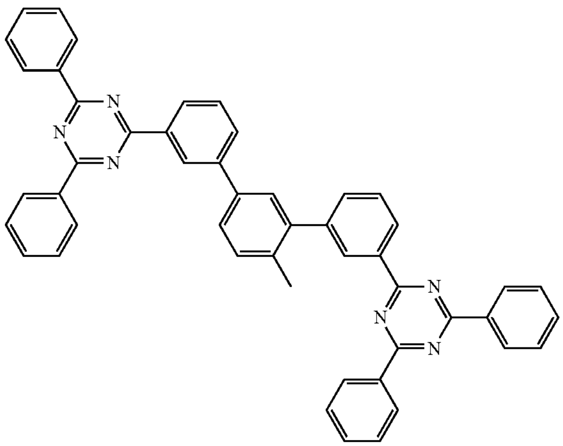
A(150)
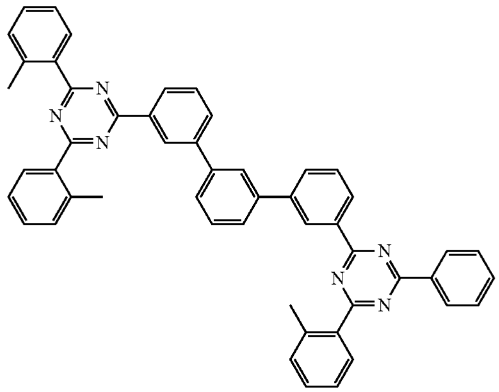
A(151)
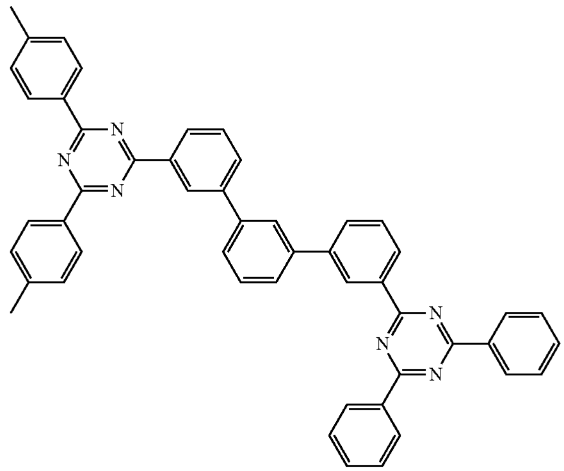
A(152)
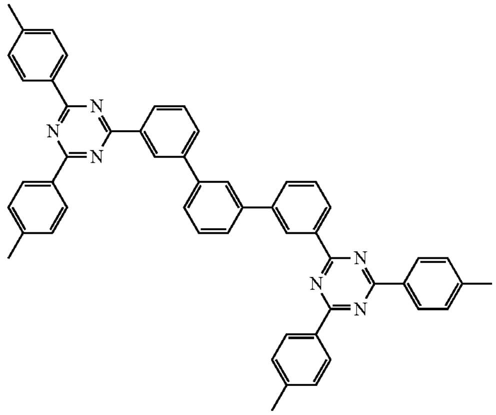
A(153)
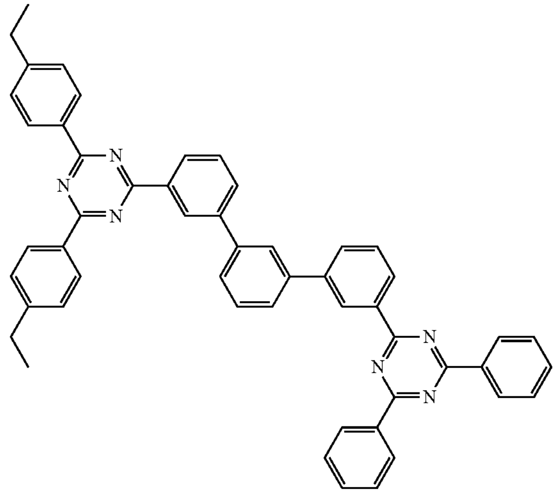

-continued
A(154)
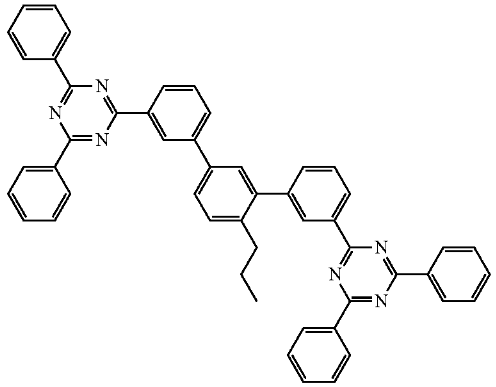
Group HE2
1
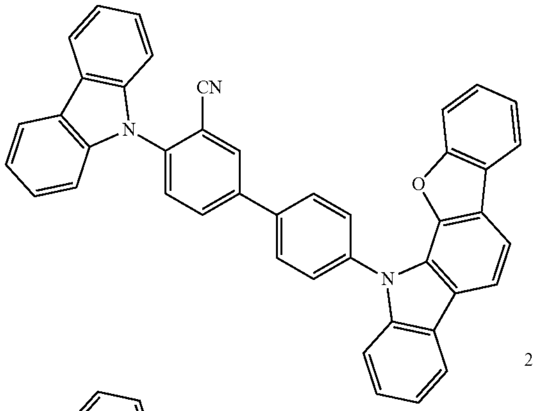
2
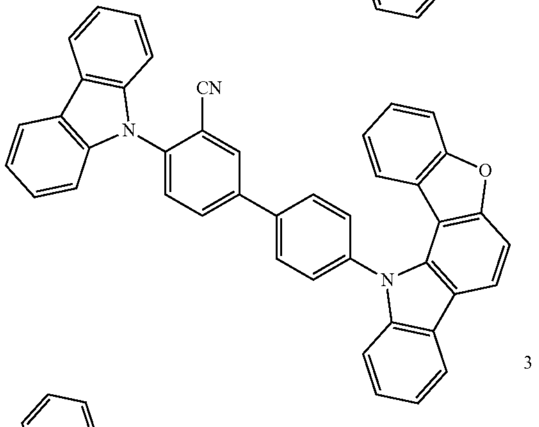
3
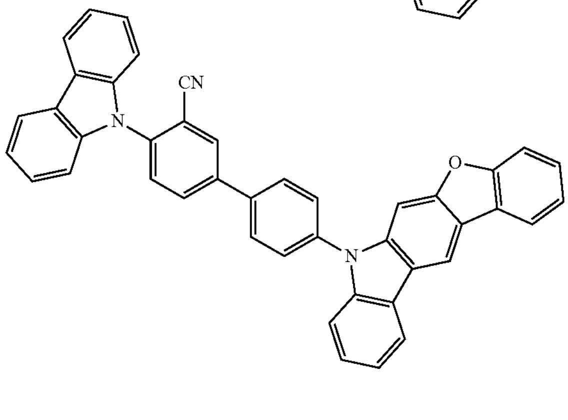
-continued
4
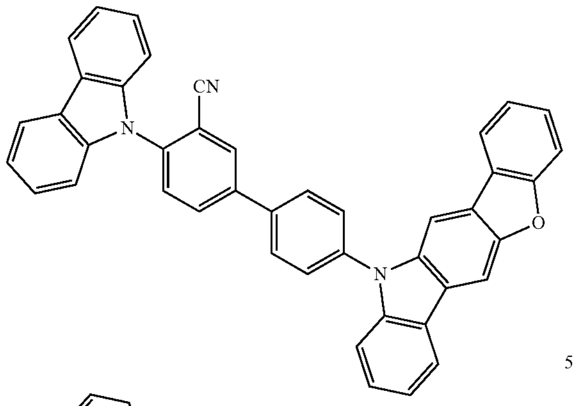
5
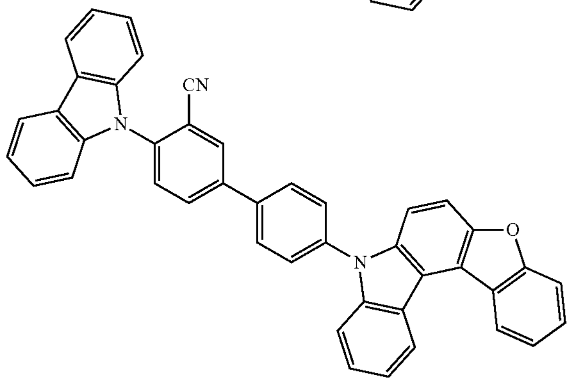
6
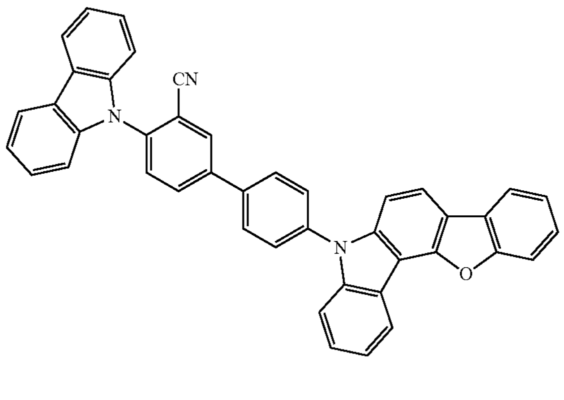

7
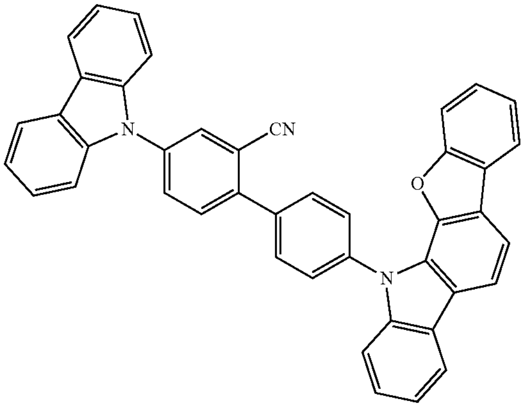
8
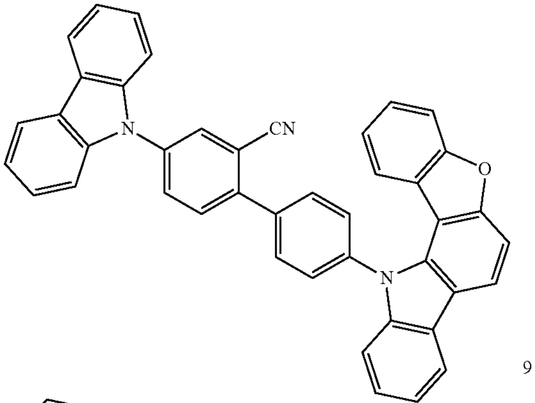
9
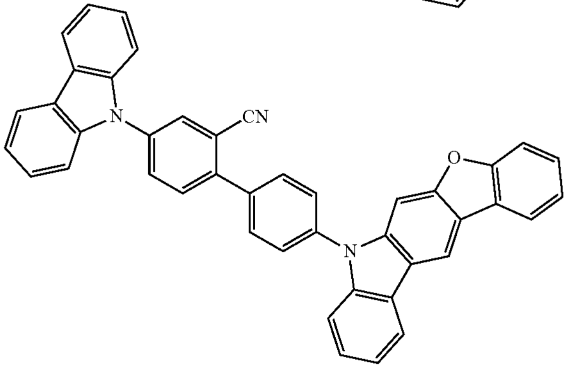
10
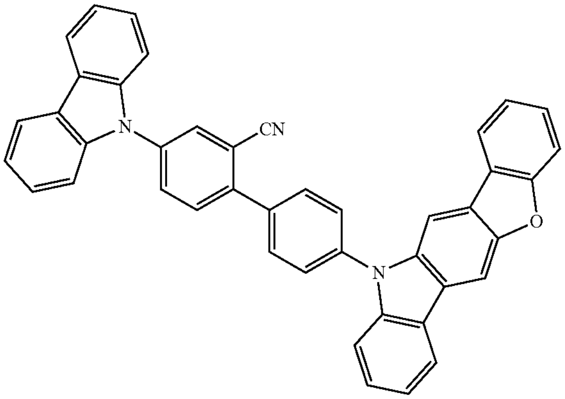
-continued
11
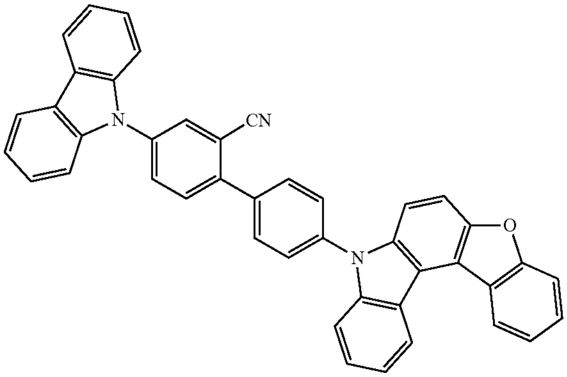
12
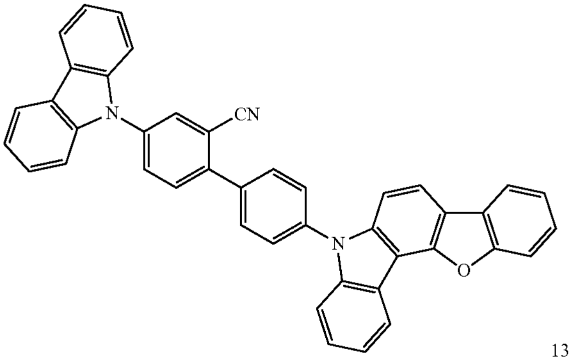
13
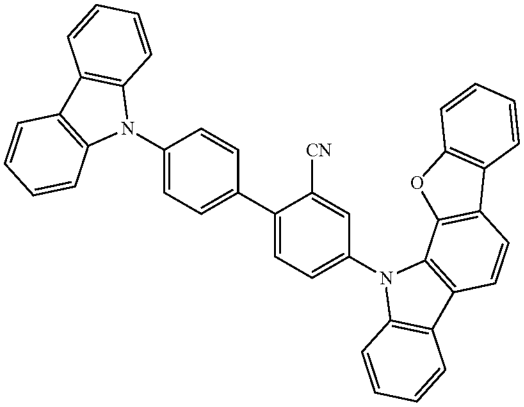
14
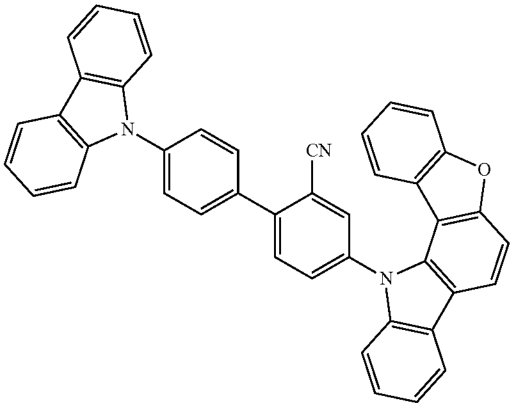

-continued
15
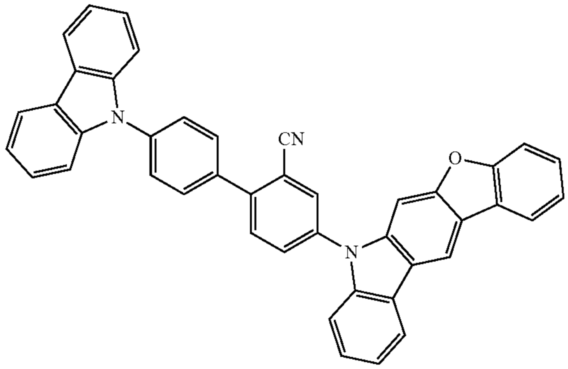
16
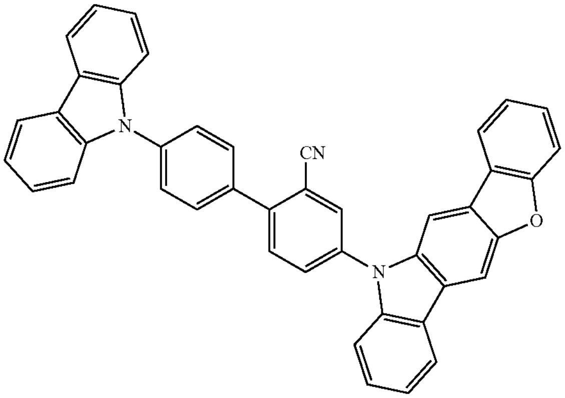
17
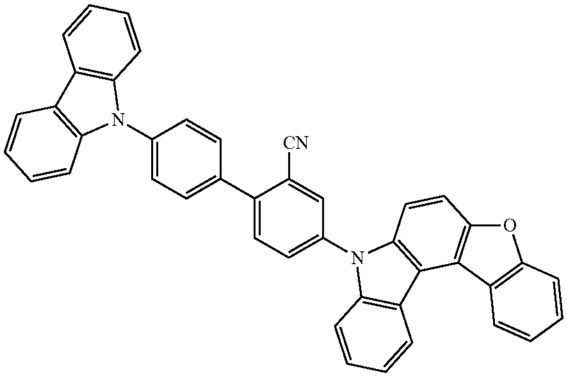
18
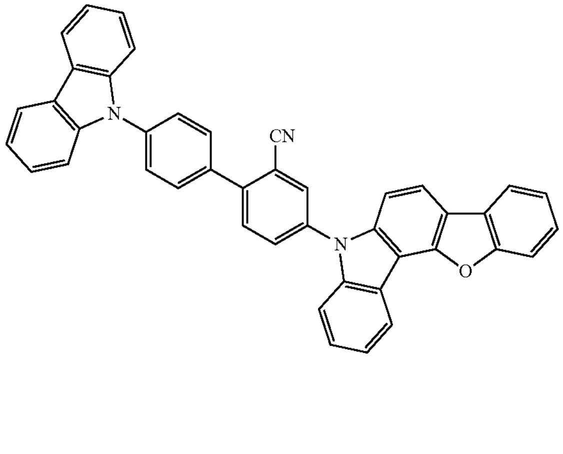
-continued
19
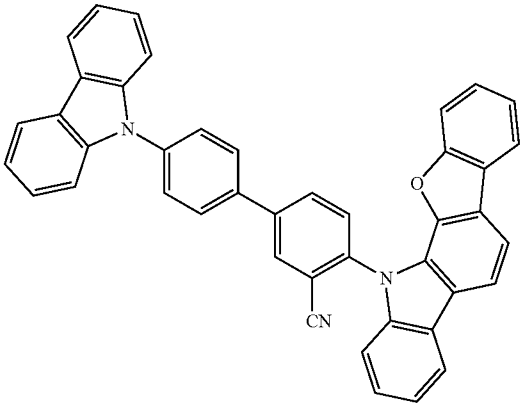
20
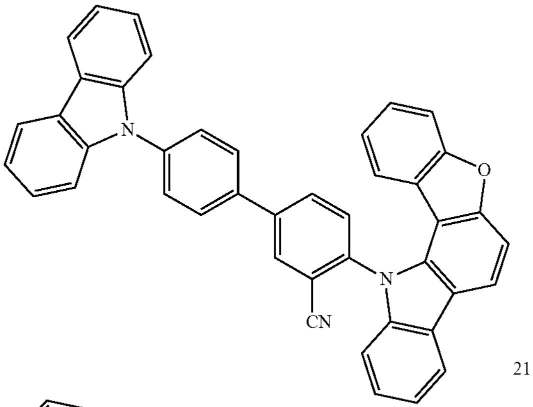
21
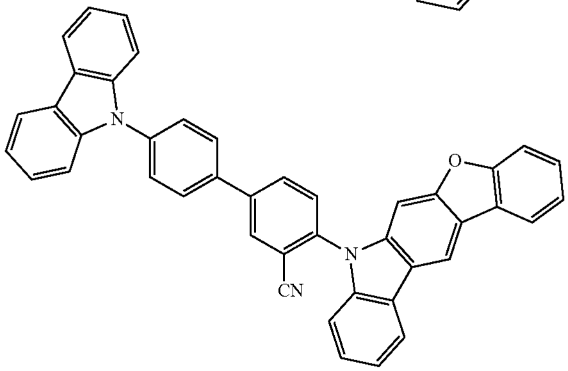
22
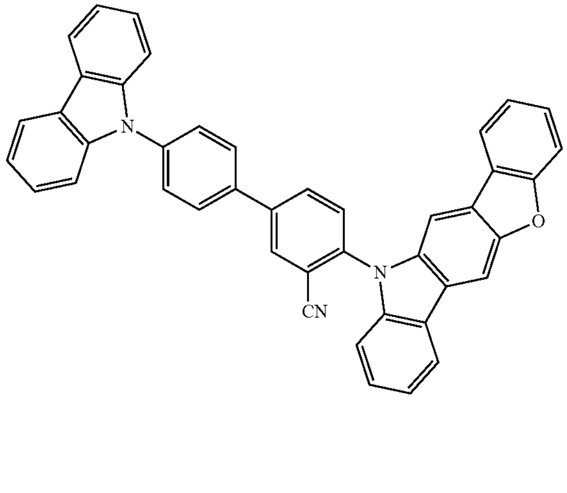

-continued
23
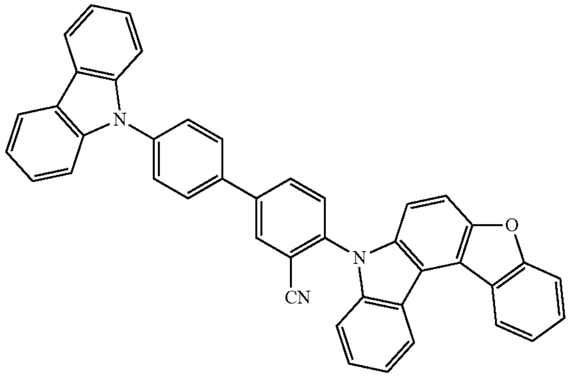
24
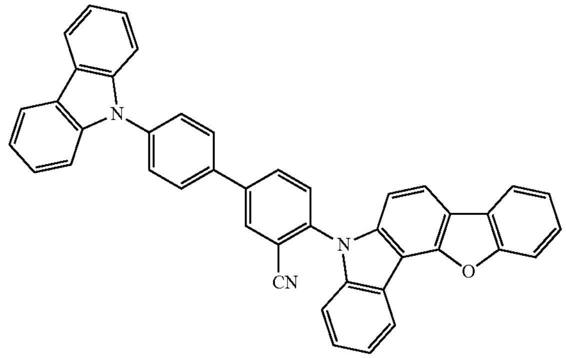
25
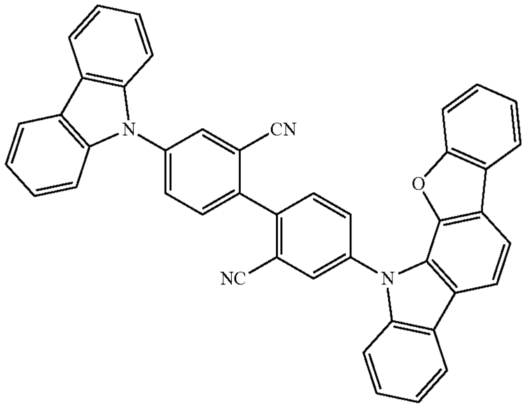
26
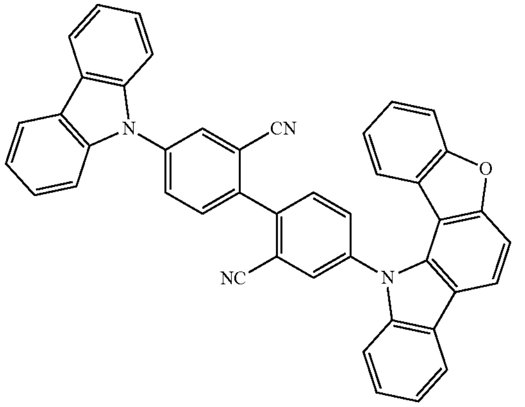
-continued
27
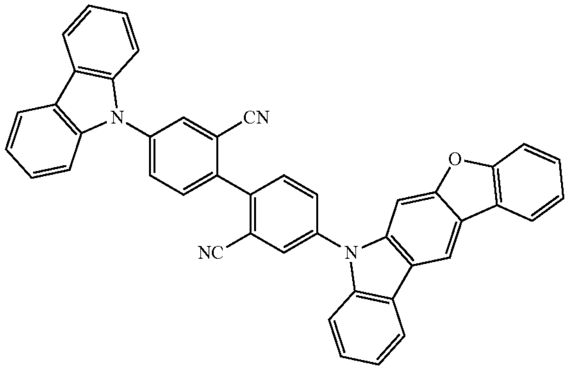
28
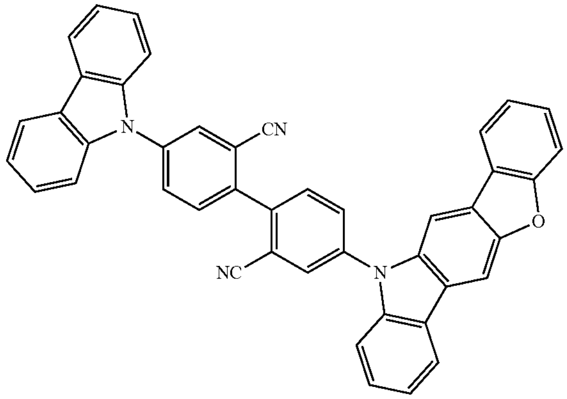
29
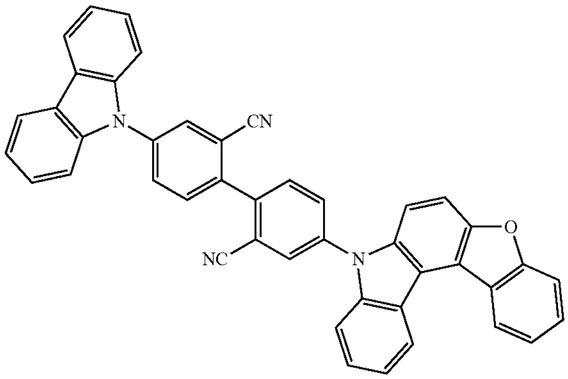
30
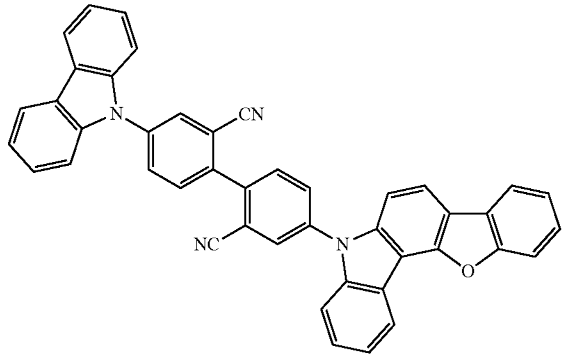

-continued
31
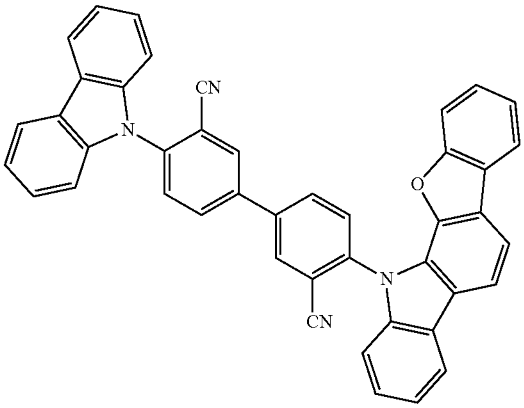
32
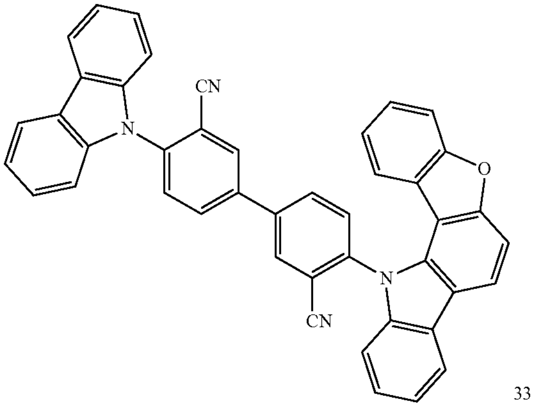
33
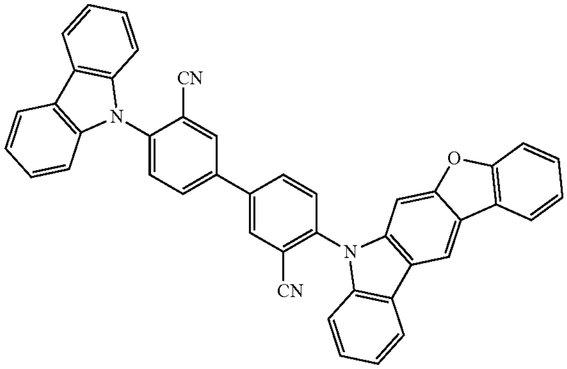
34
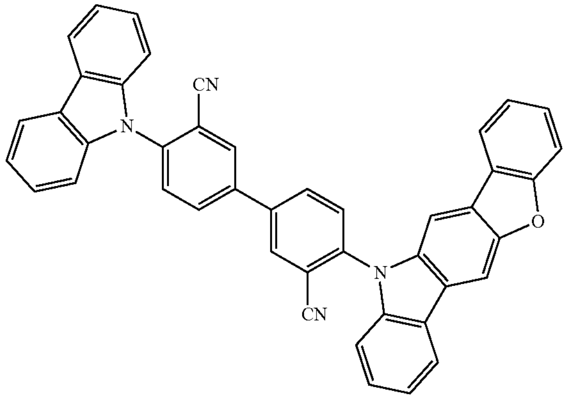
-continued
35
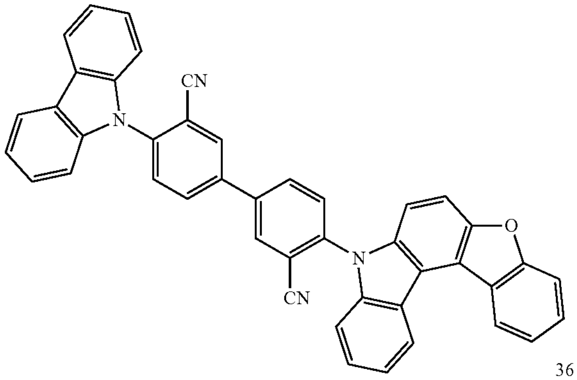
36
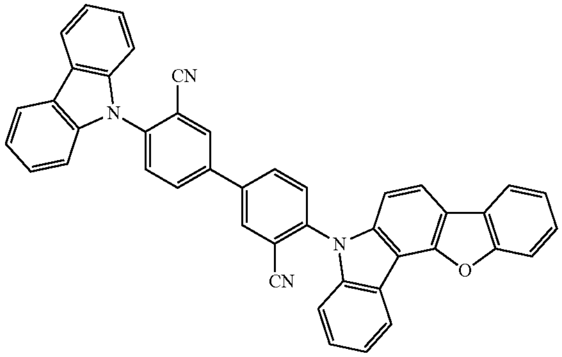
37
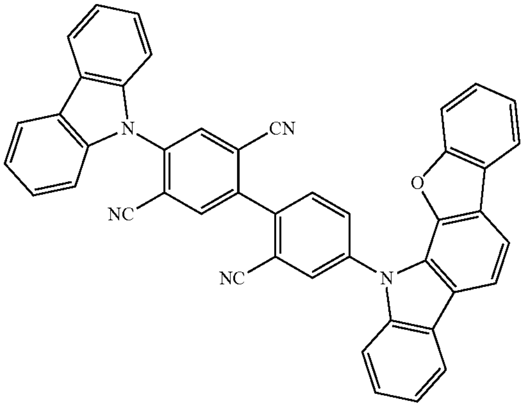
38
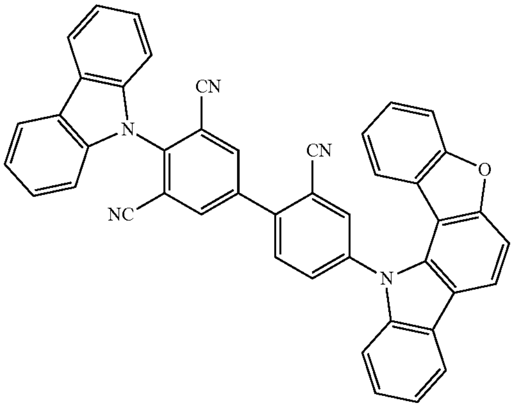

39
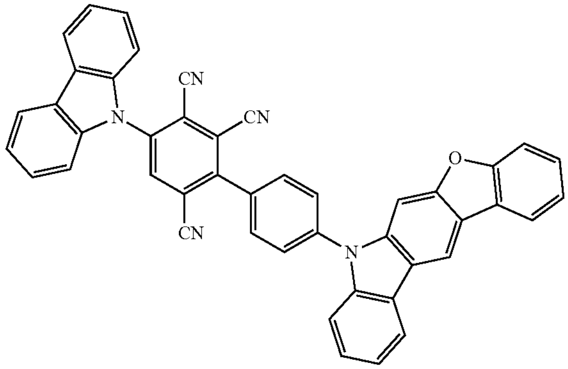
40
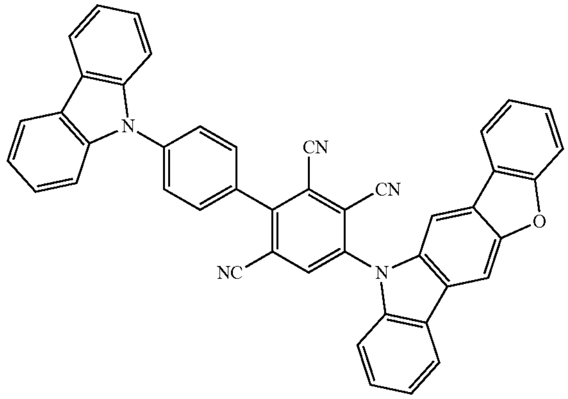
41
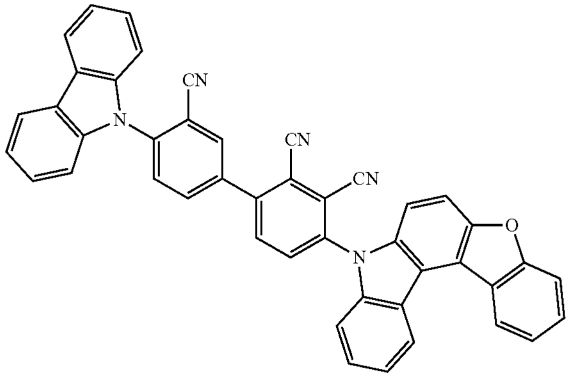
42
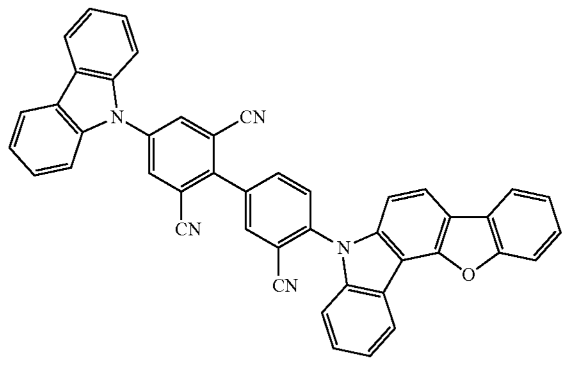
43
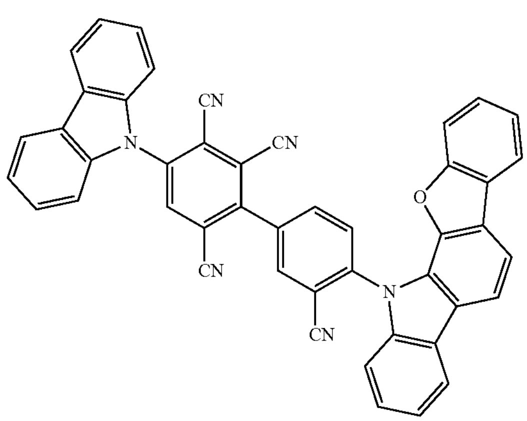
44
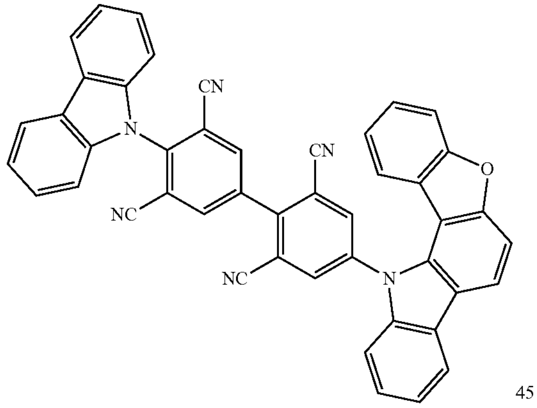
45
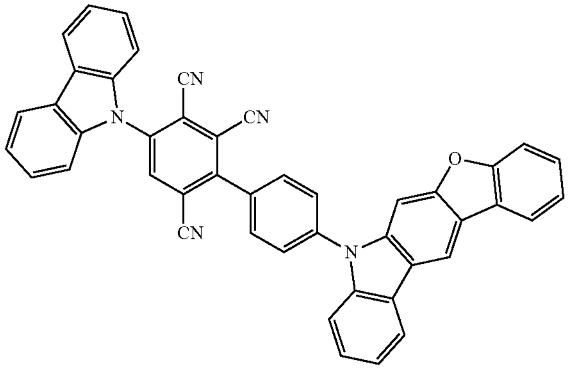
46
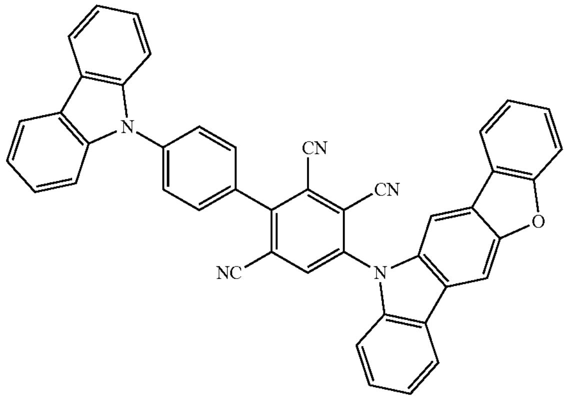

-continued
47
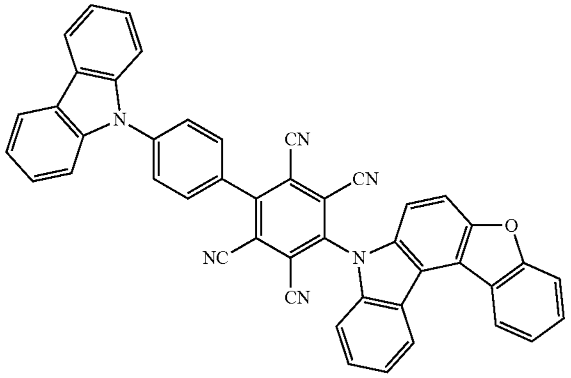
48
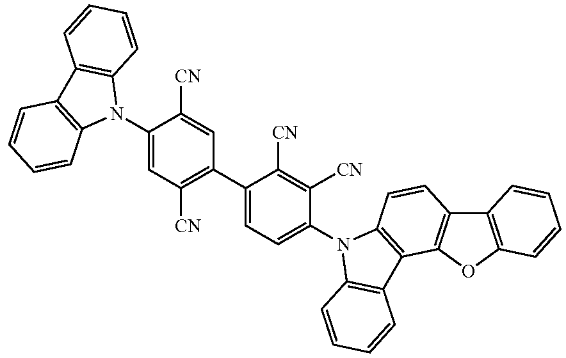
49
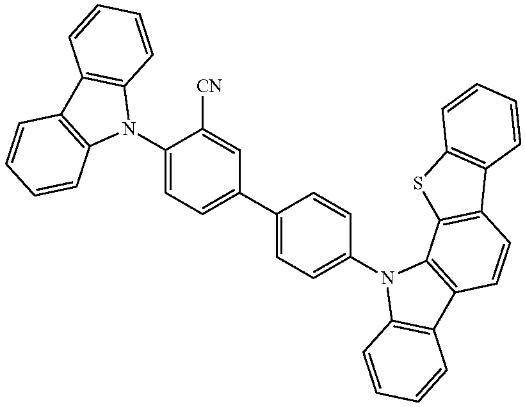
50
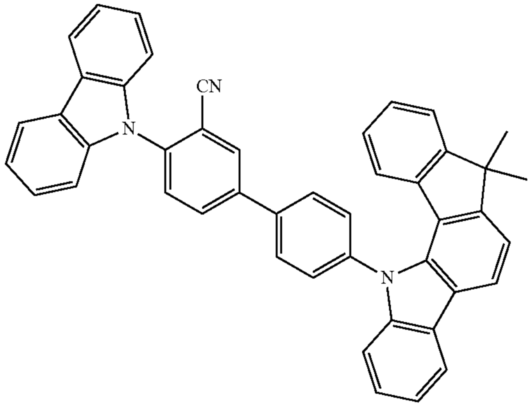
-continued
51
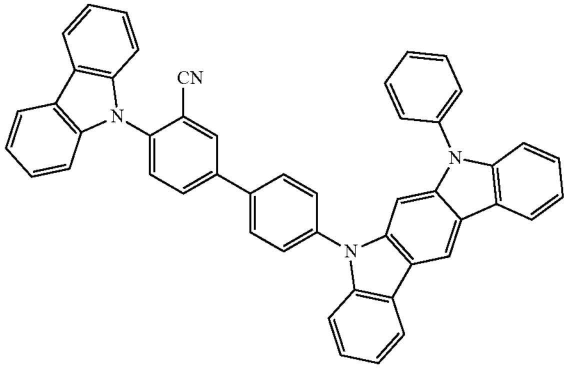
52
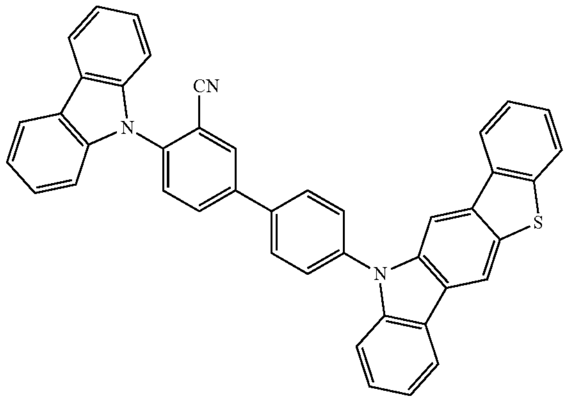
53
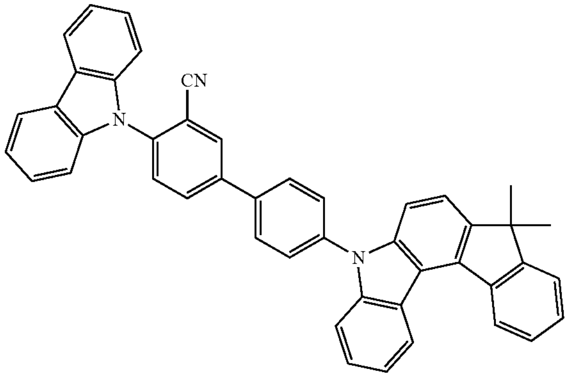
54
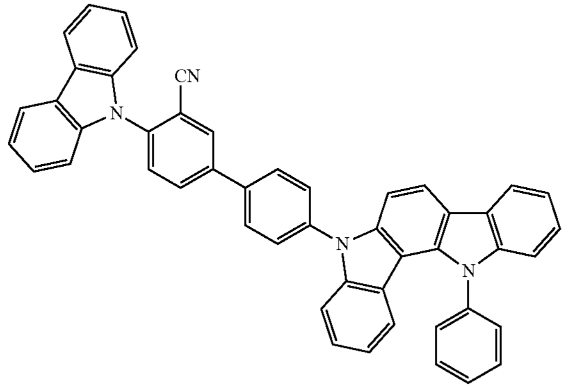

-continued
55
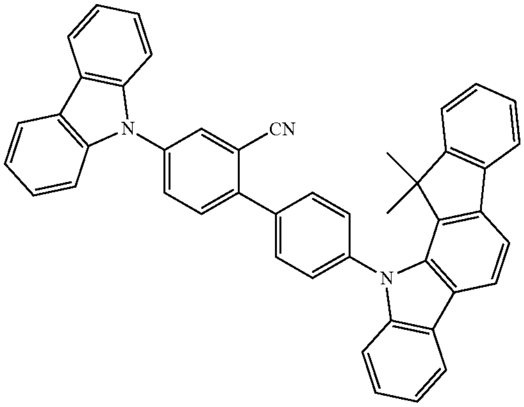
56
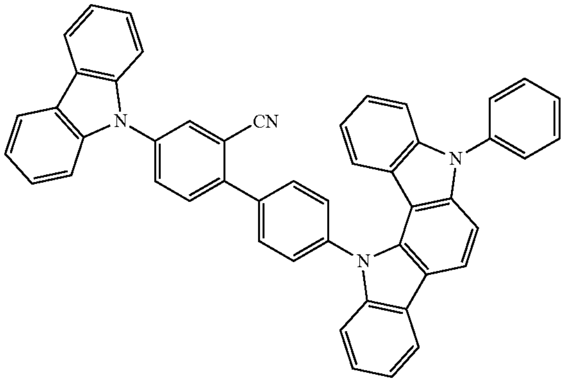
57
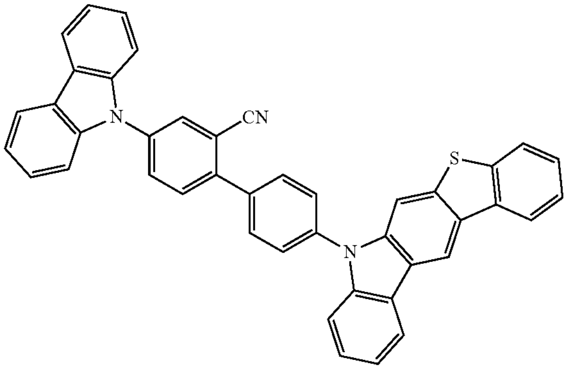
58
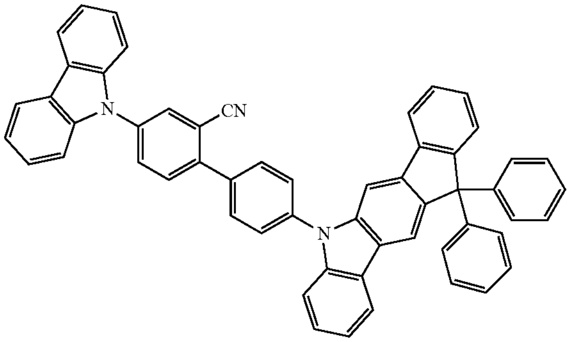
-continued
59
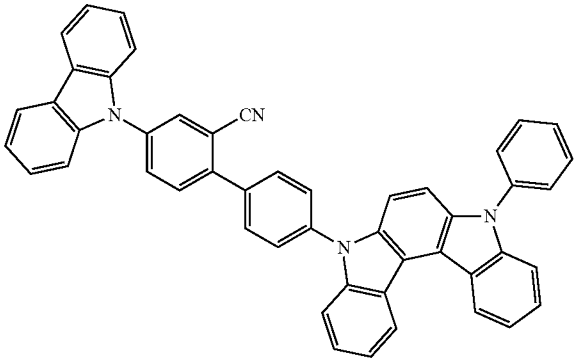
60
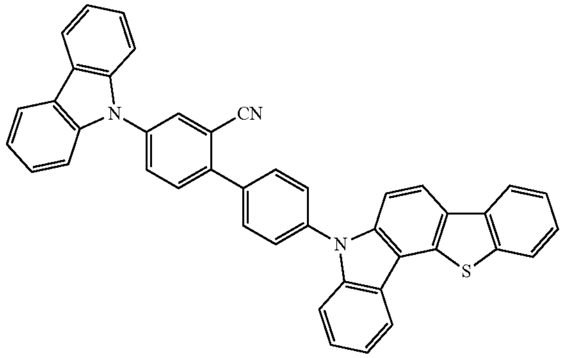
61
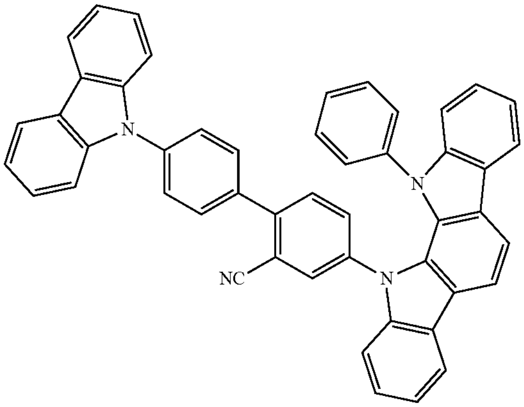
62
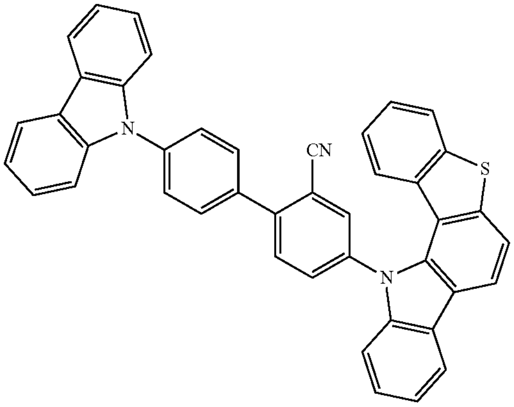

-continued
63
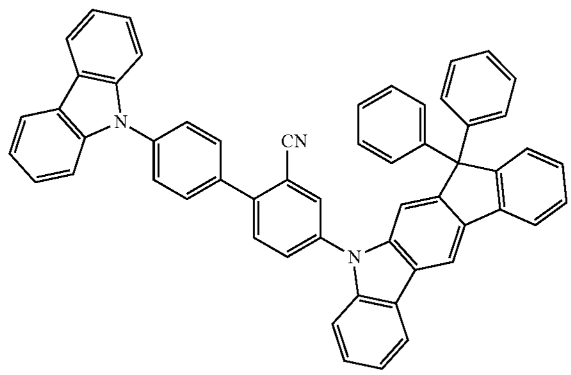
64
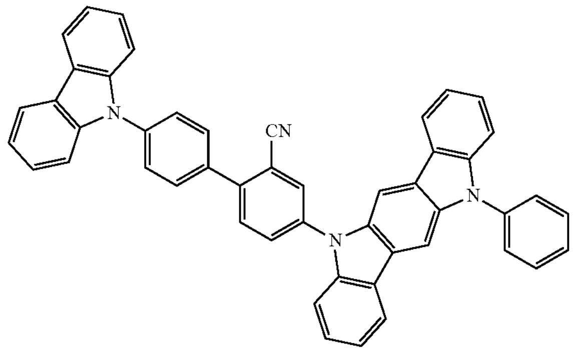
65
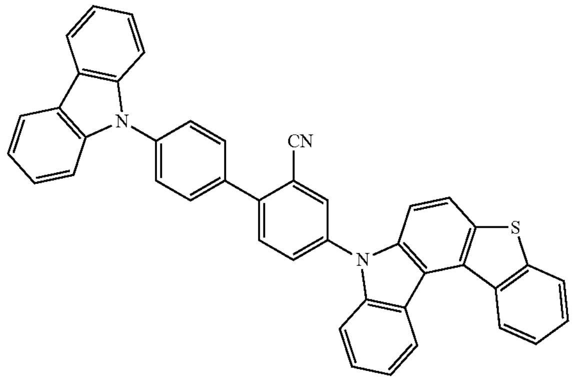
66
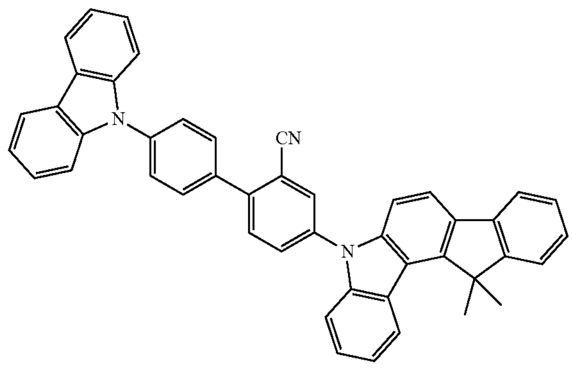
-continued
67
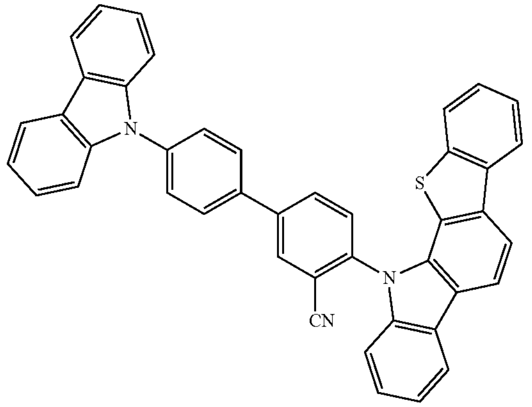
68
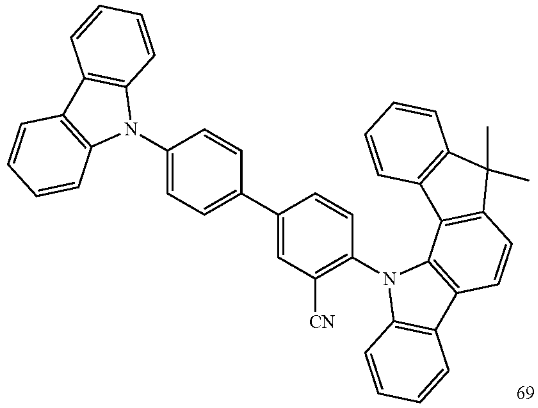
69
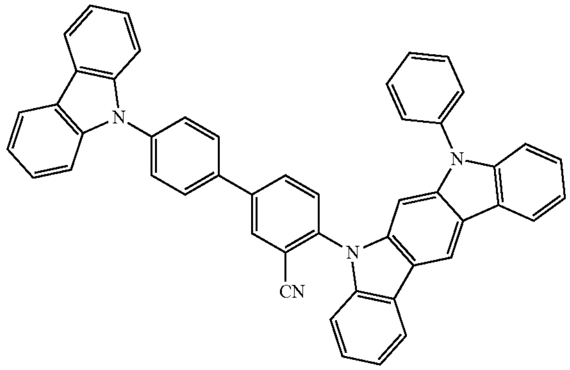
70
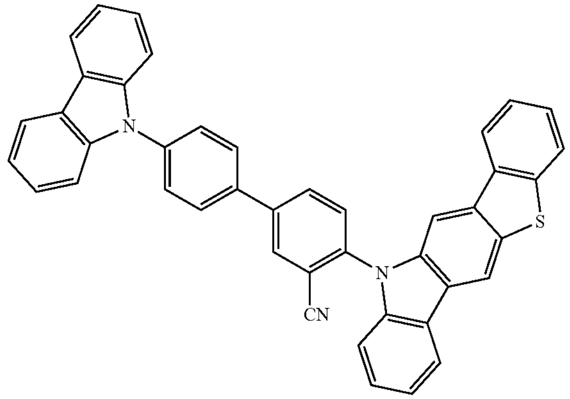

-continued
71
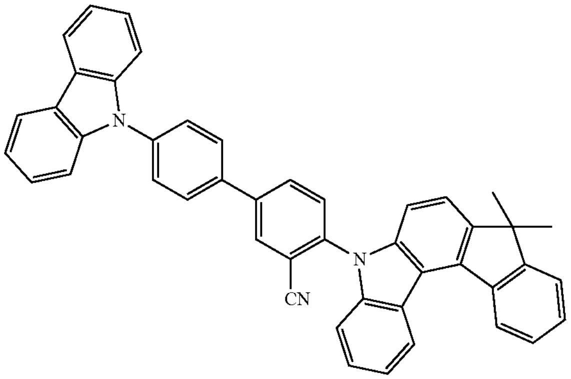
72
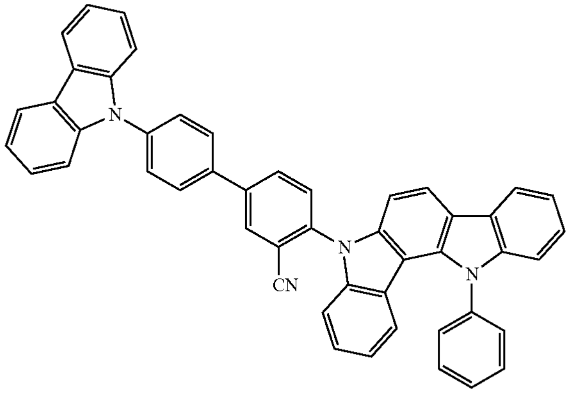
73
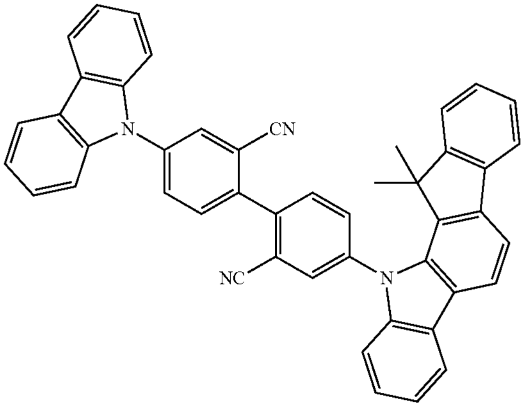
74
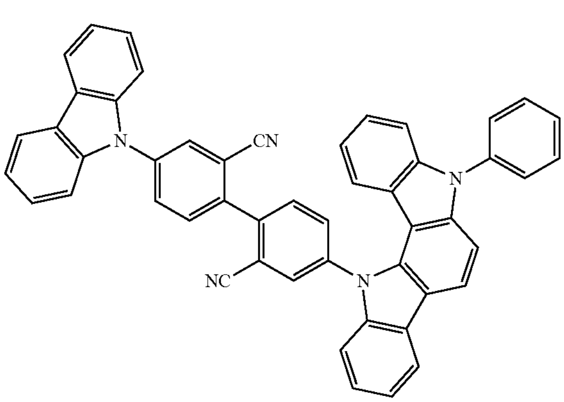
-continued
75
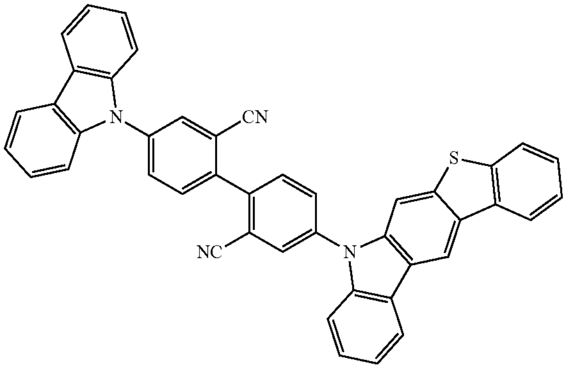
76
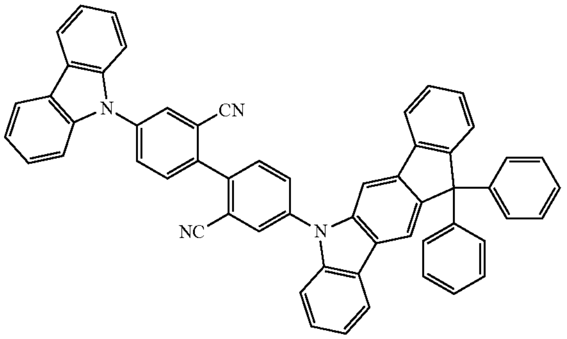
77
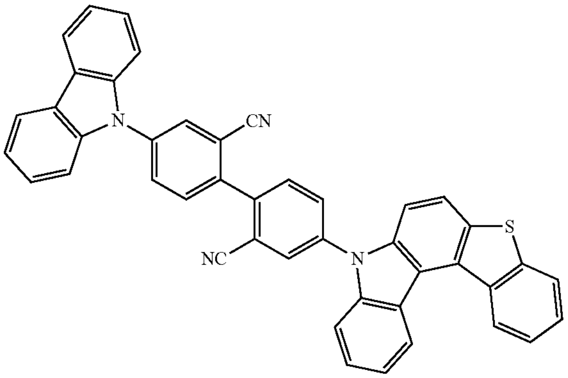
78
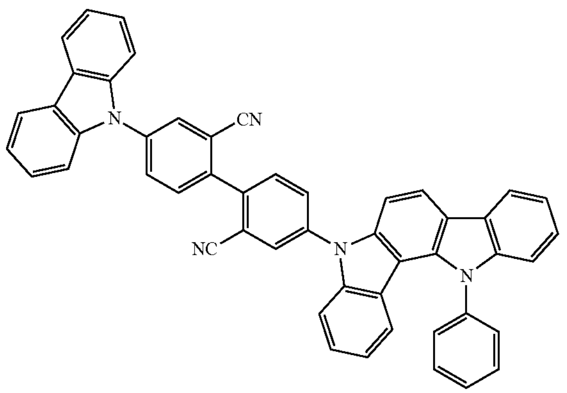

-continued
79
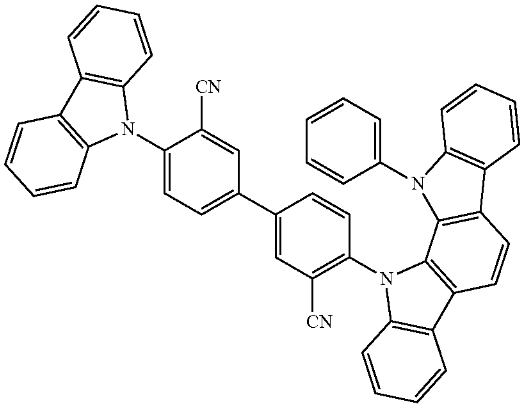
80
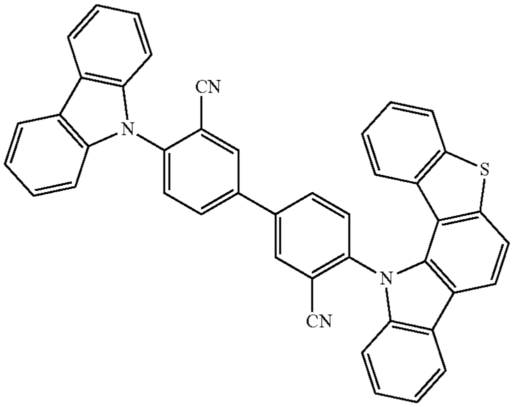
81
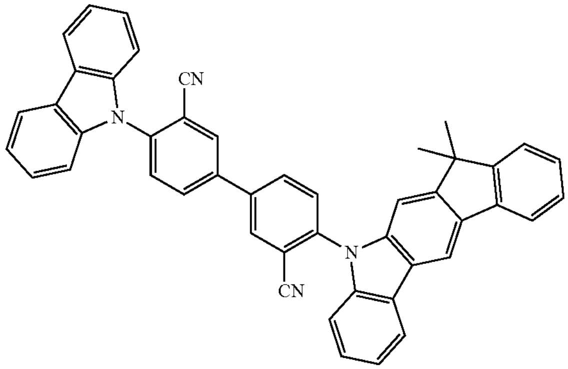
82
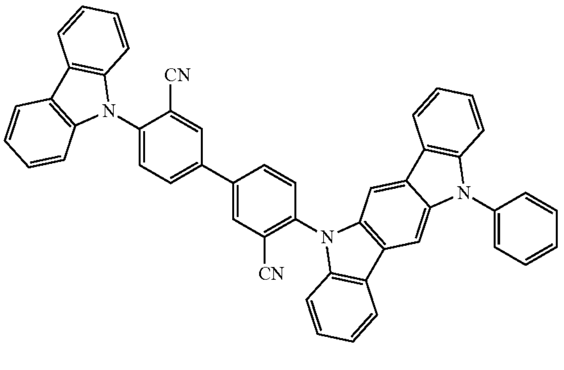
-continued
83
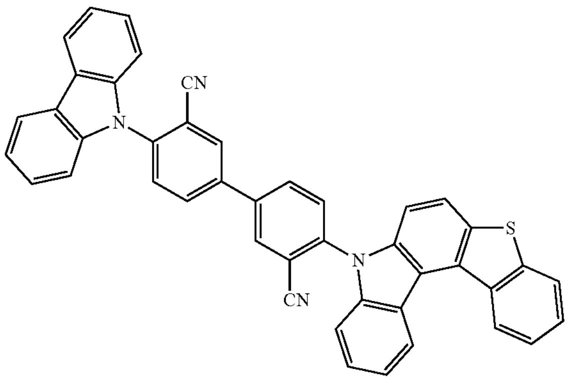
84
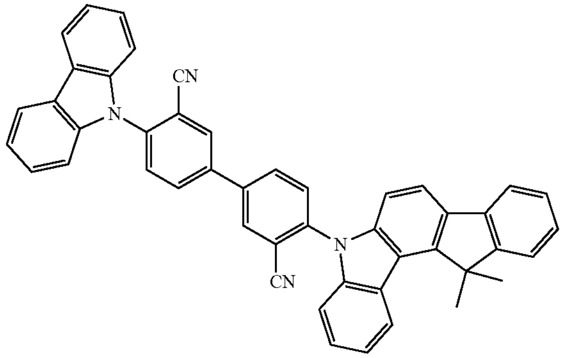
85
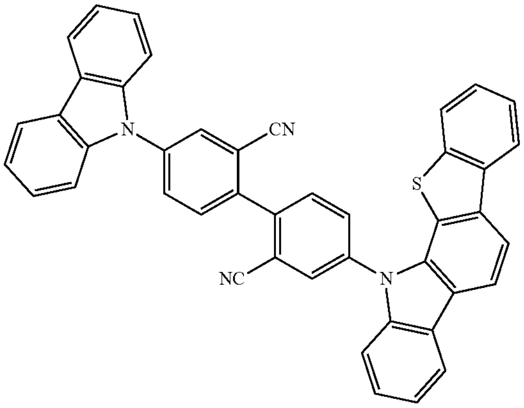
86
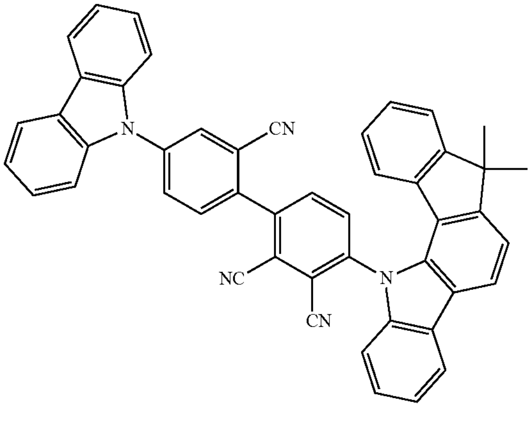

-continued
87
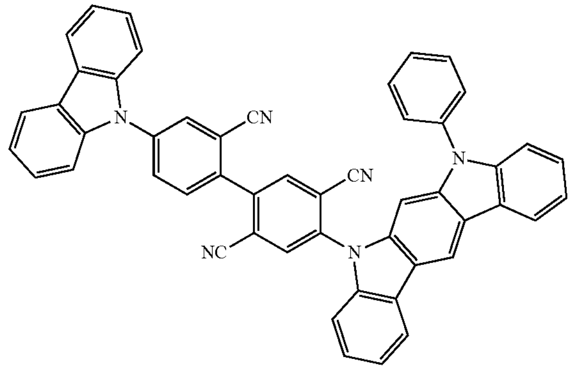
88
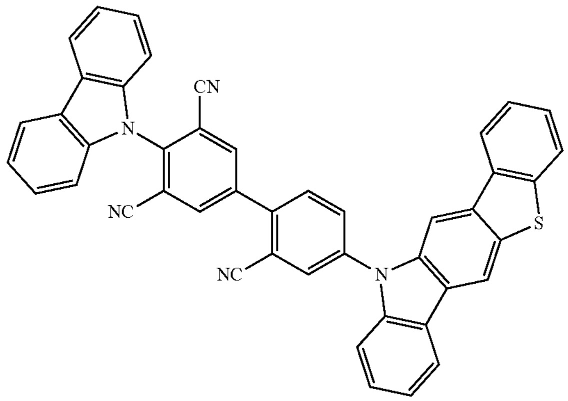
89
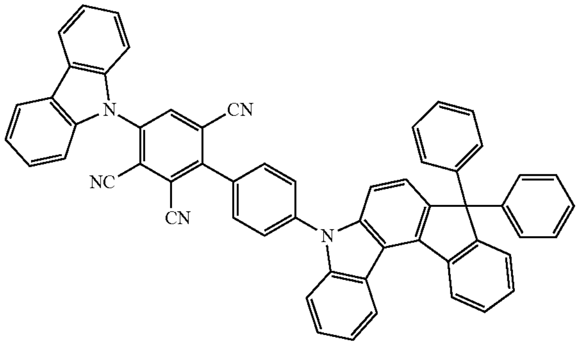
90
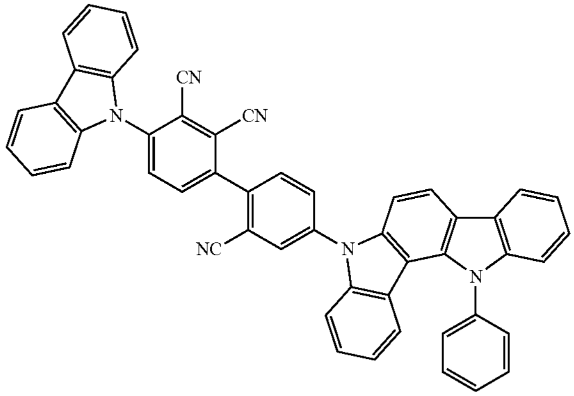
-continued
91
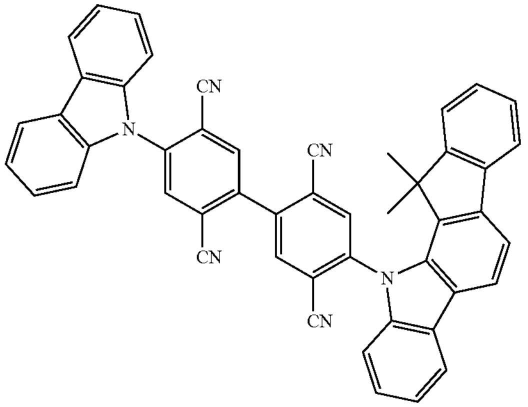
92
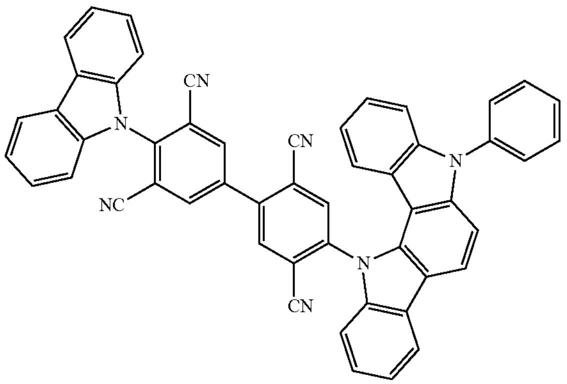
93
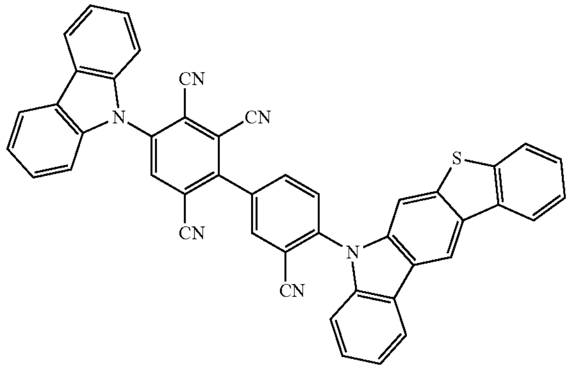
94
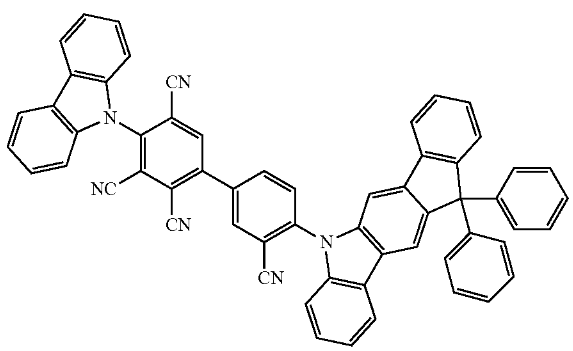

-continued
95
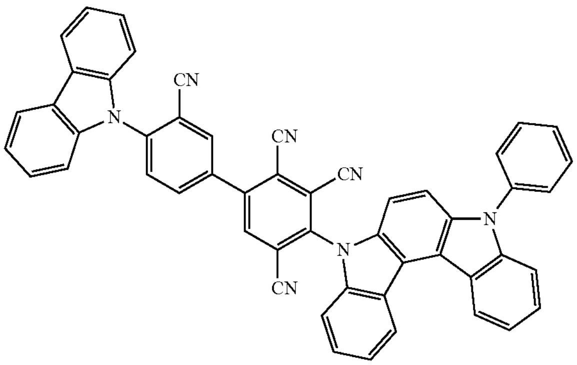
96
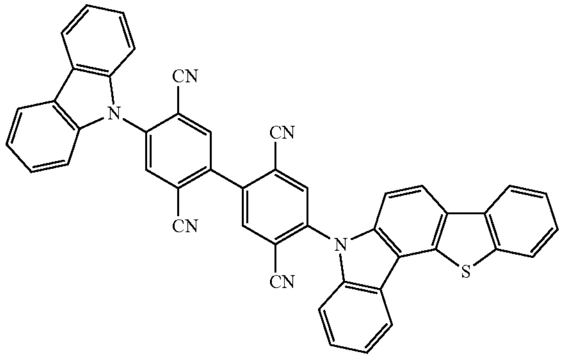
97
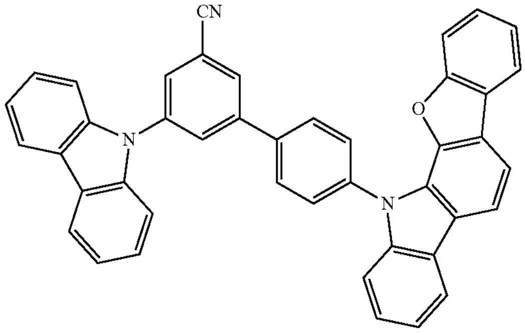
98
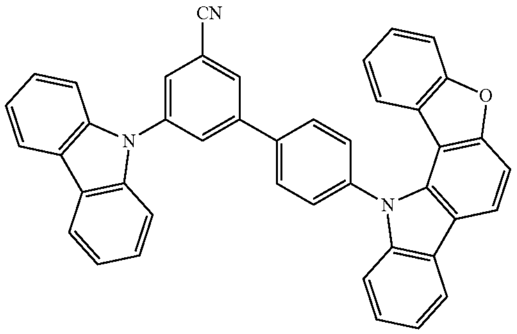
-continued
99
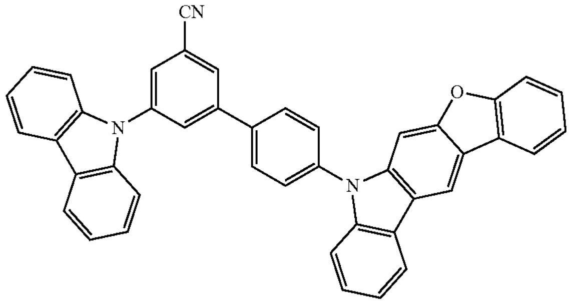
100
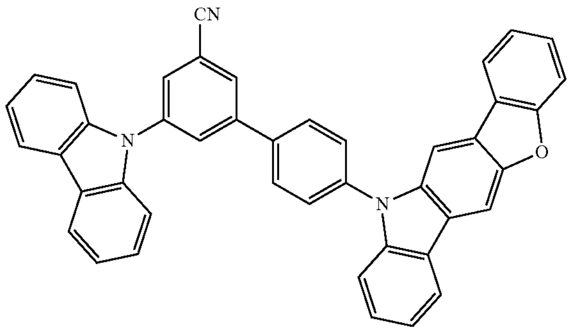
101
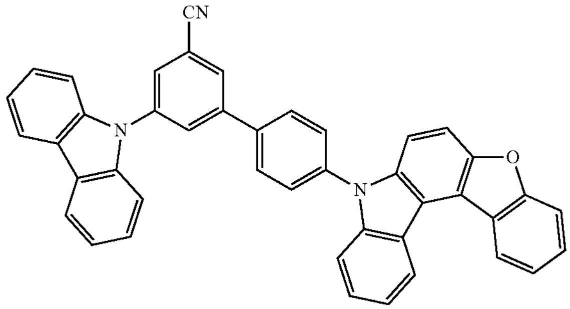
102
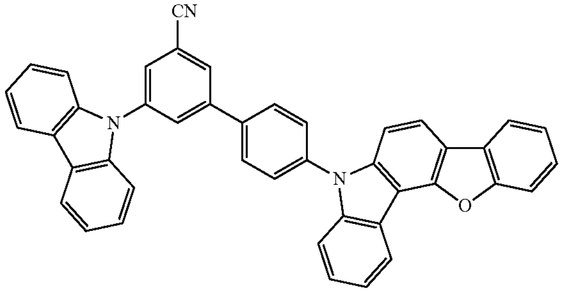

-continued
103
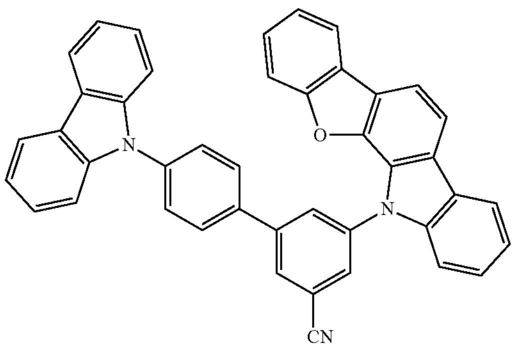
104
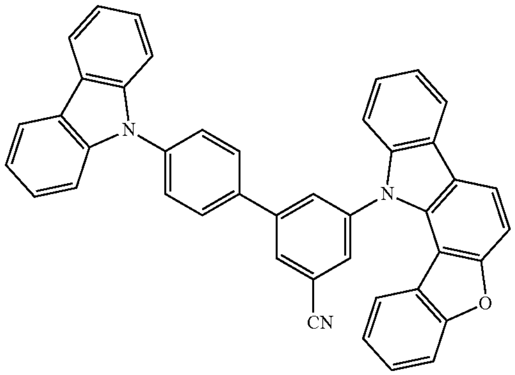
105
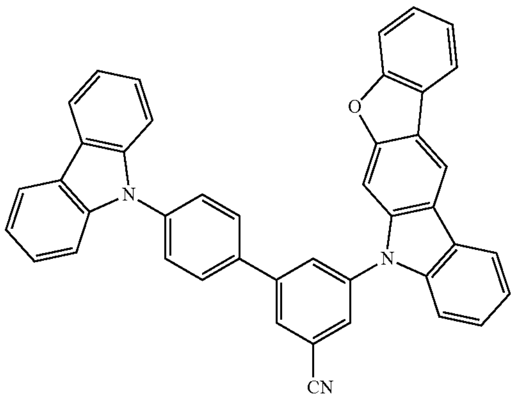
106
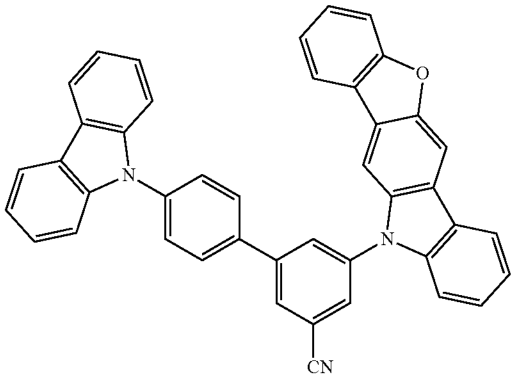
-continued
107
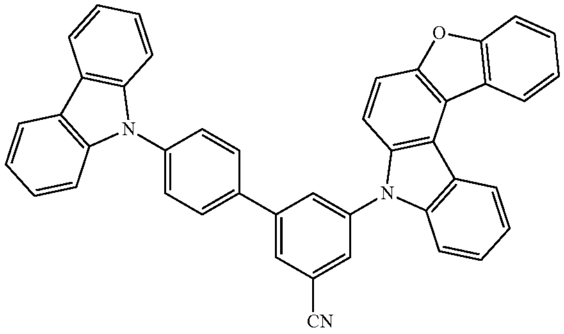
108
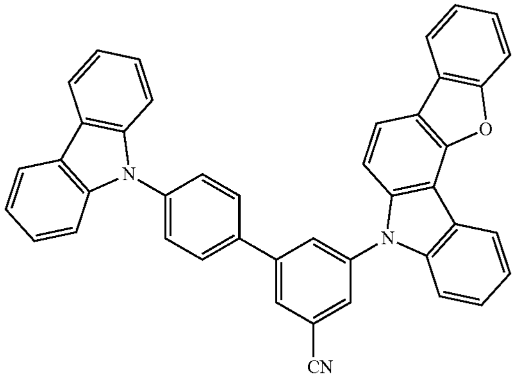
109
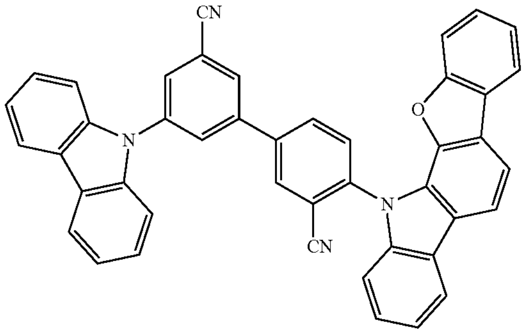
110
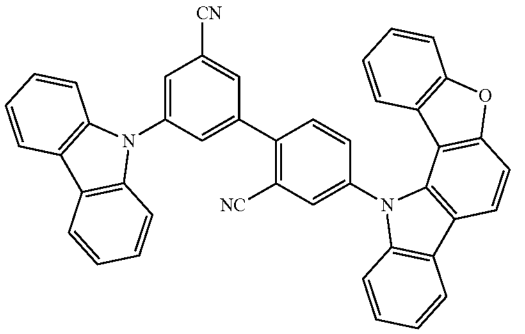

-continued
111
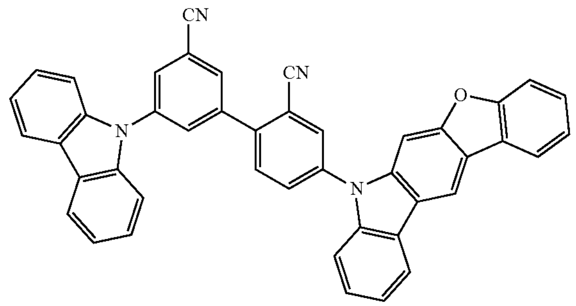
112
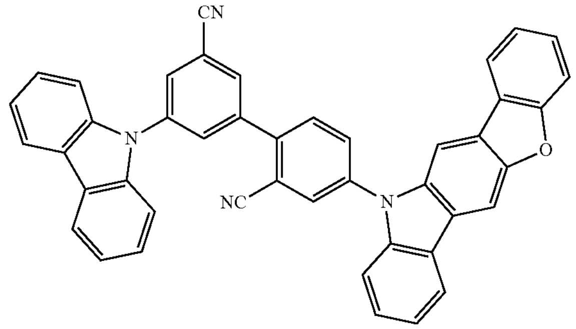
113
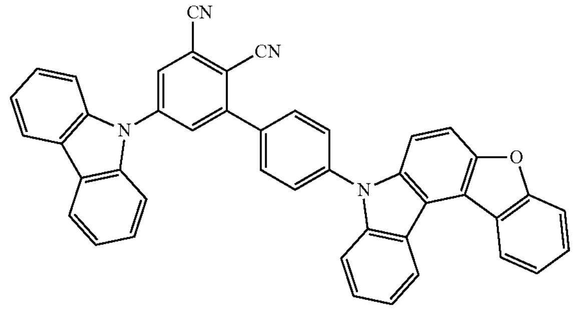
114
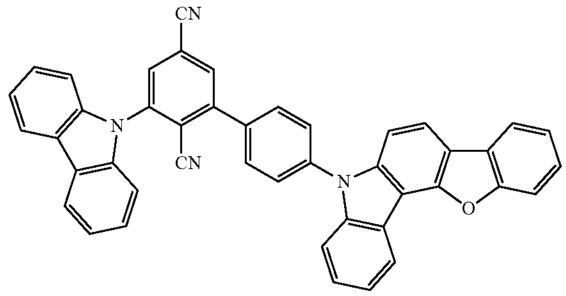
-continued
115
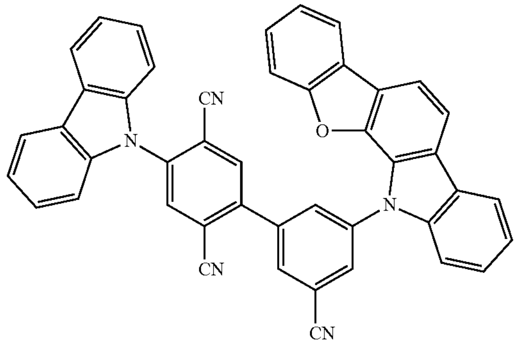
116
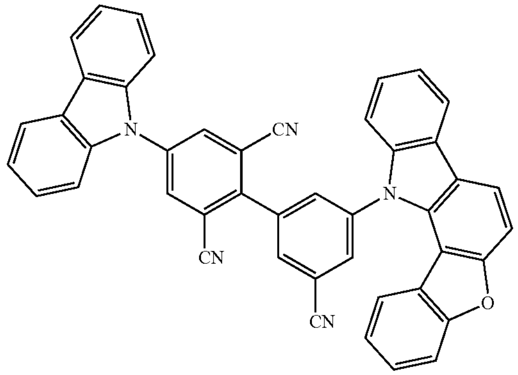
117
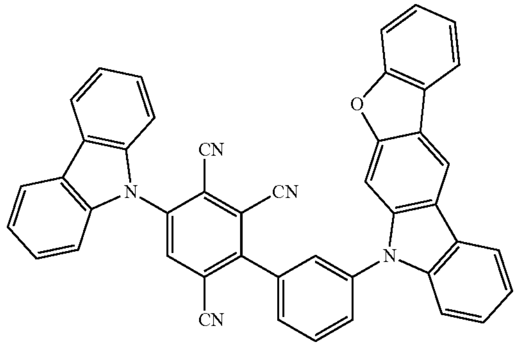
118
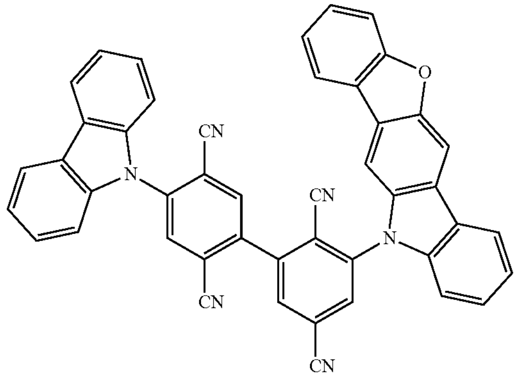

-continued
119
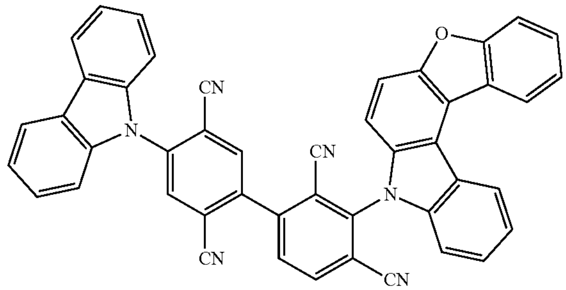
120
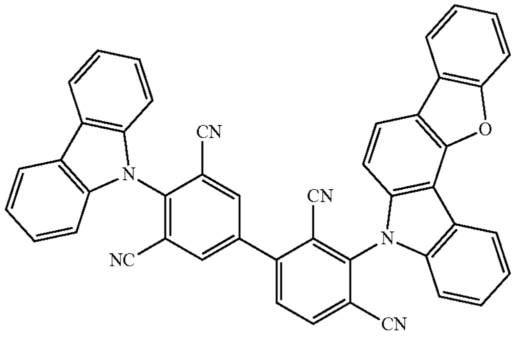
121
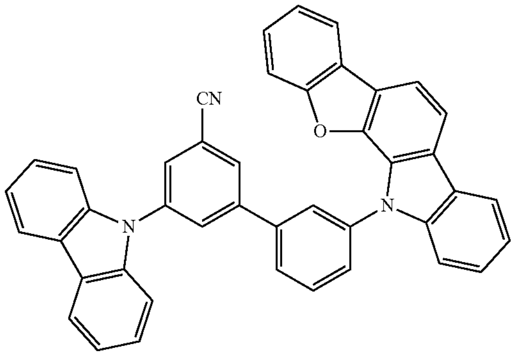
122
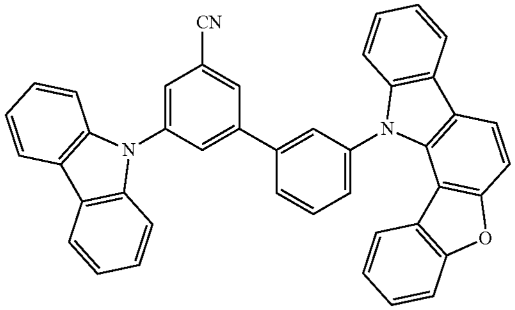
-continued
123
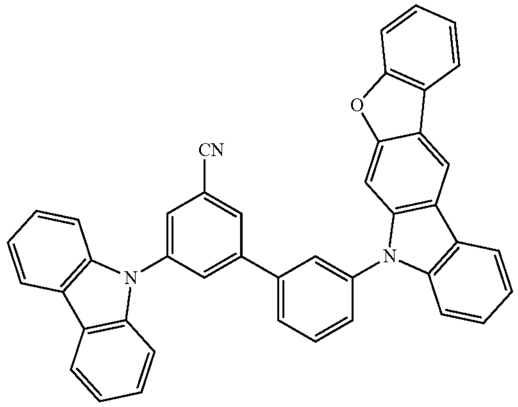
124
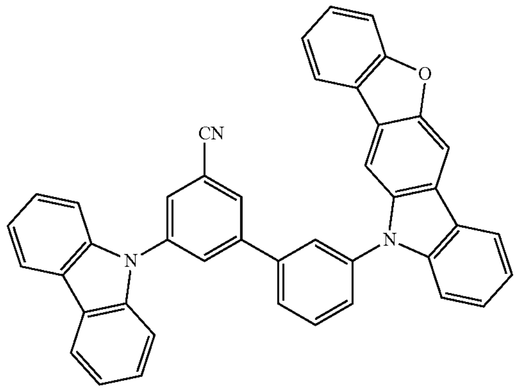
125
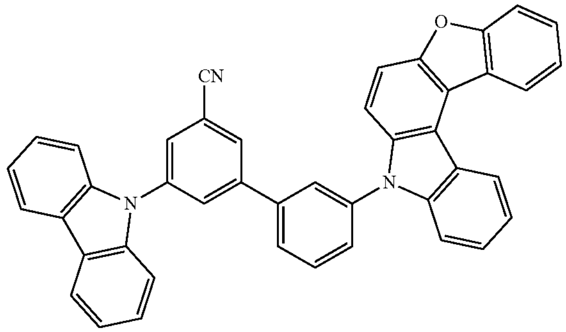
126
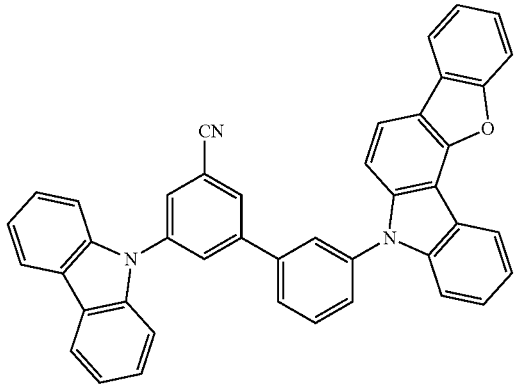

-continued
127
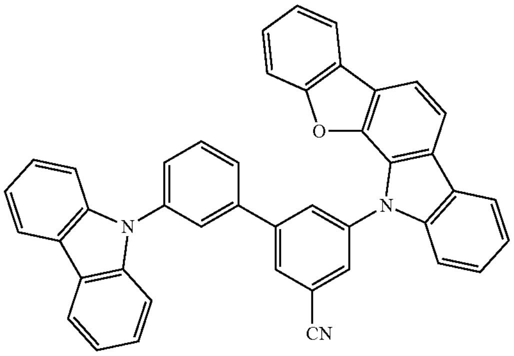
128
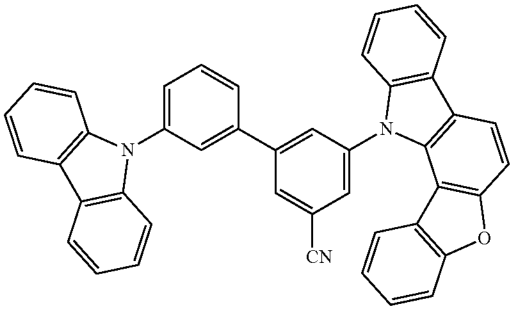
129
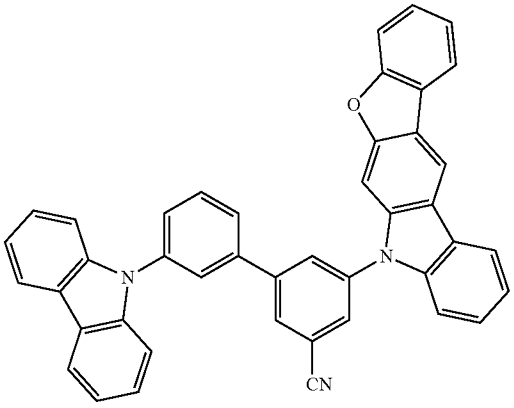
130
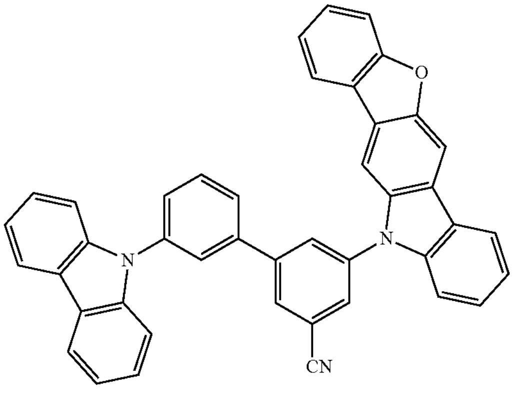
-continued
131
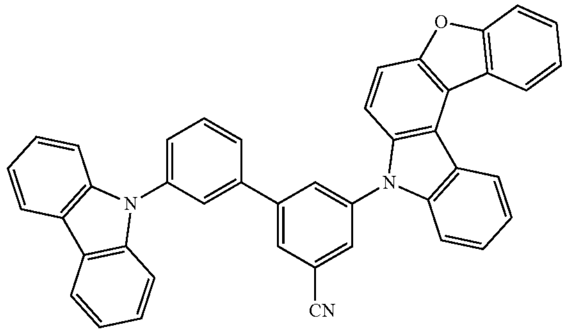
132
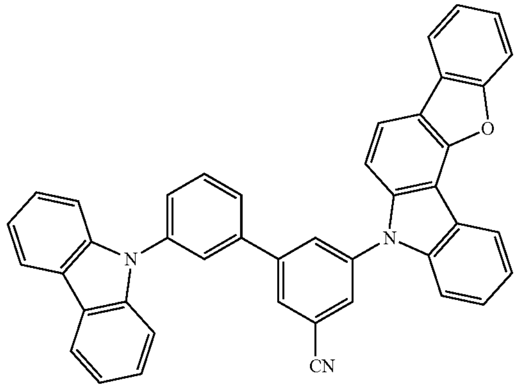
133
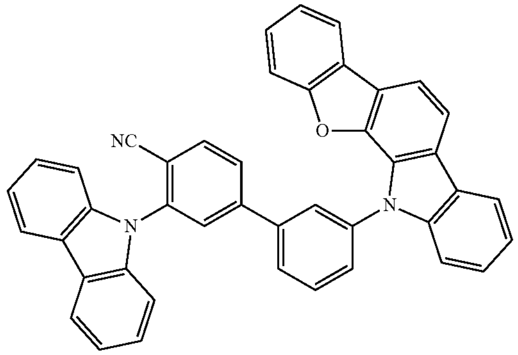
134
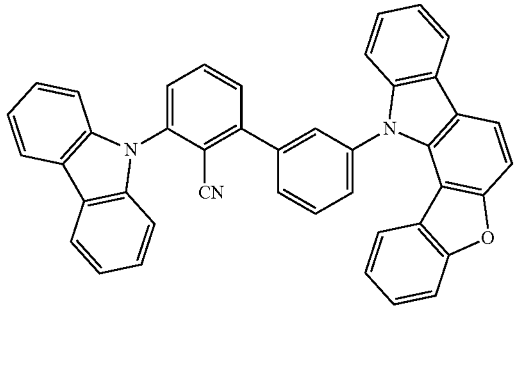

-continued
135
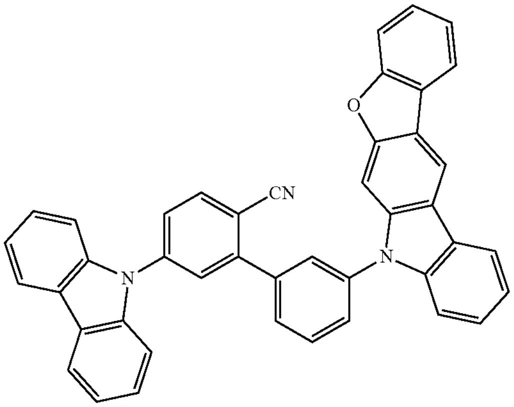
136
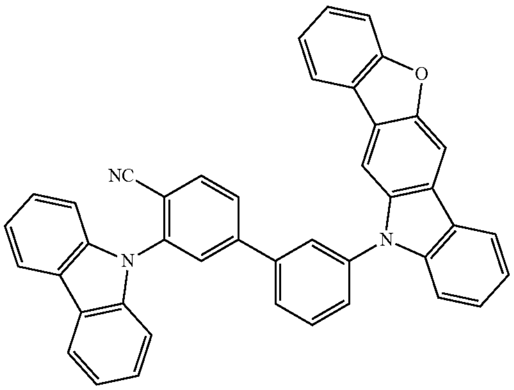
137
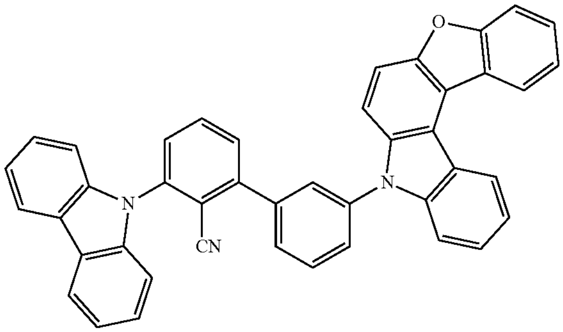
138
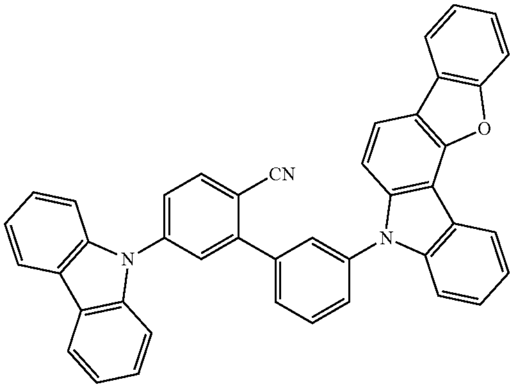
-continued
139
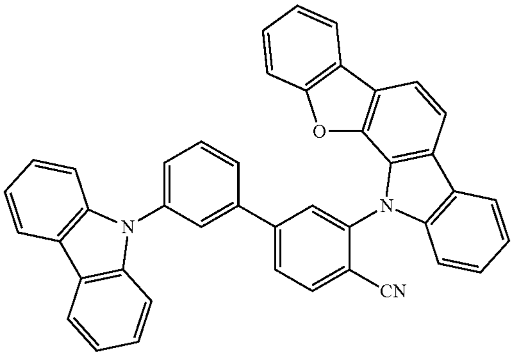
140
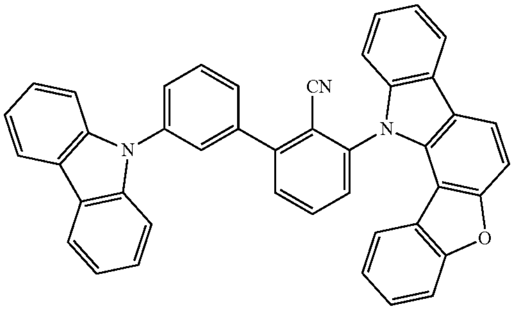
141
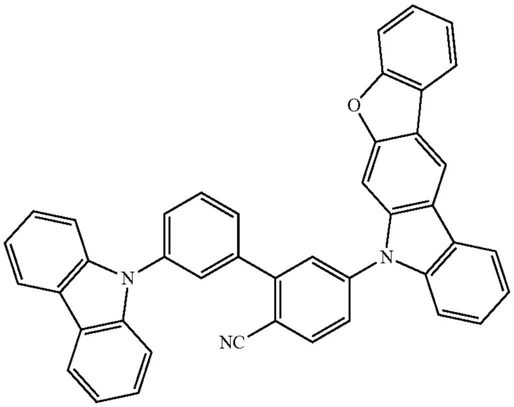
142
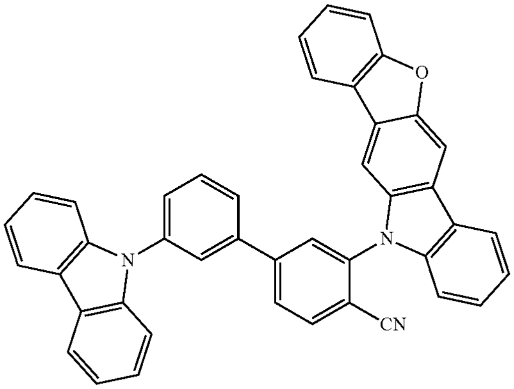

-continued
143
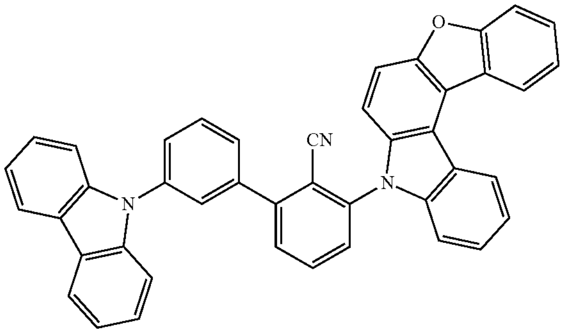
144
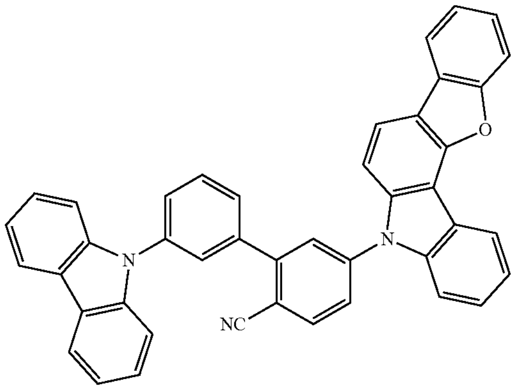
145
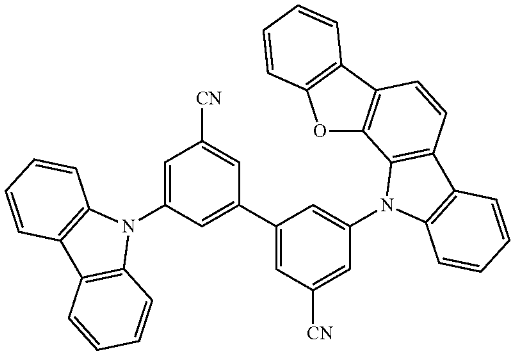
146
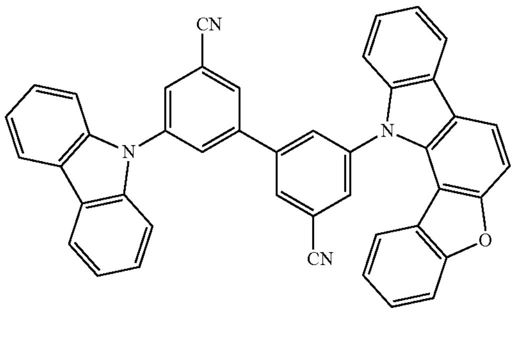
-continued
147
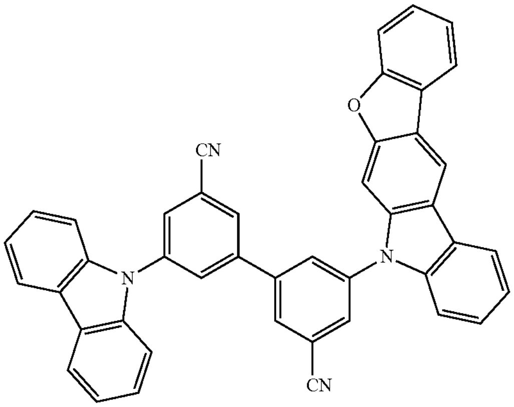
148
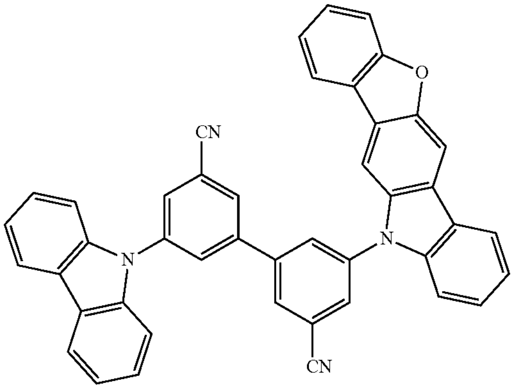
149
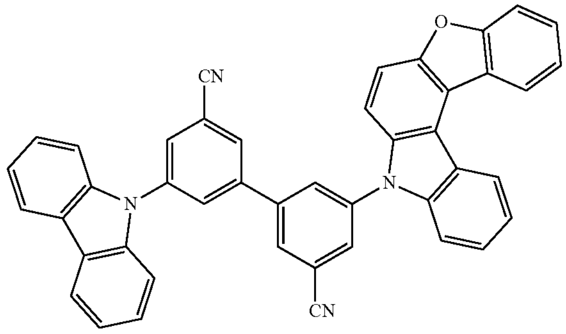
150
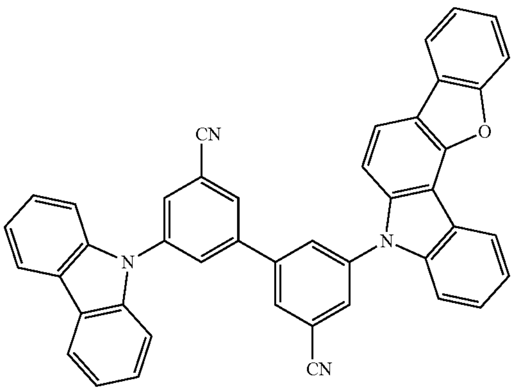

-continued
151
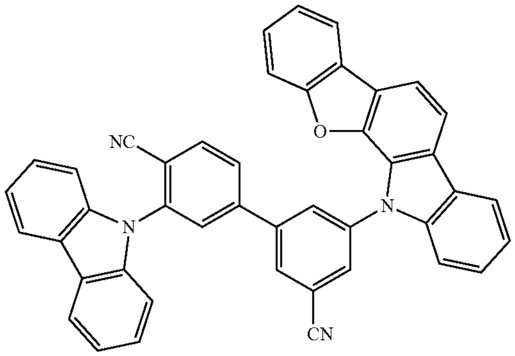
152
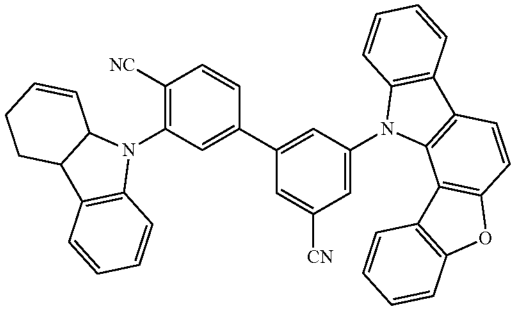
153
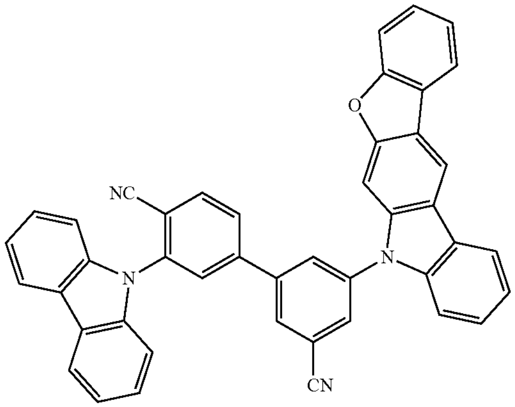
154
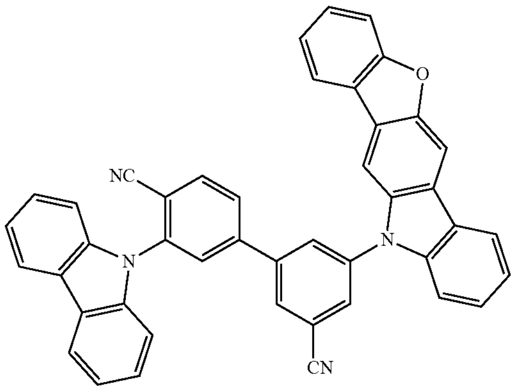
-continued
155
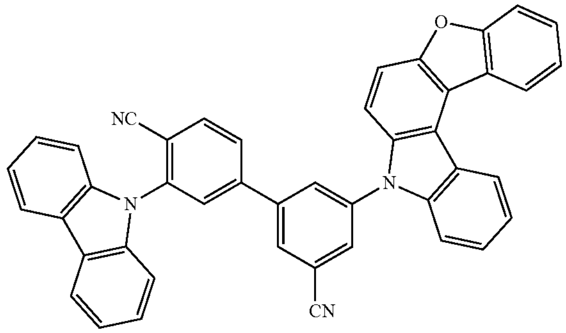
156
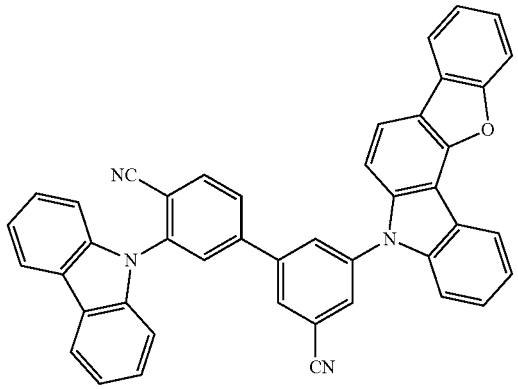
157
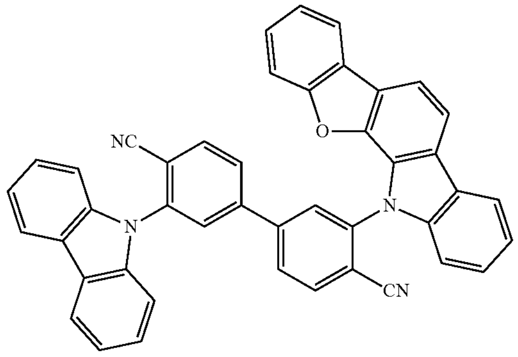
158
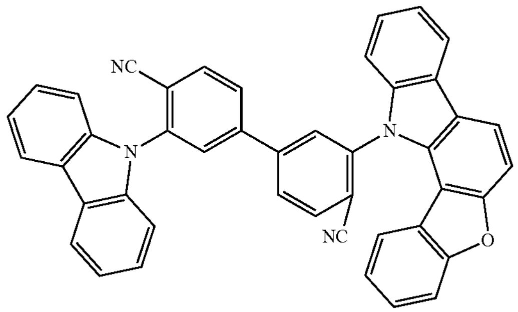

-continued
159
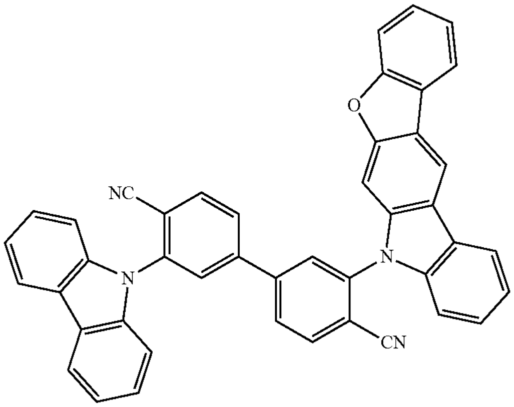
160
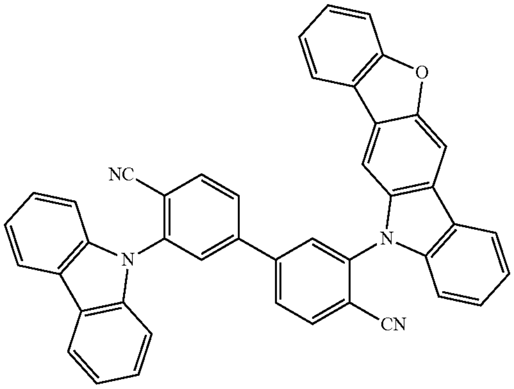
161
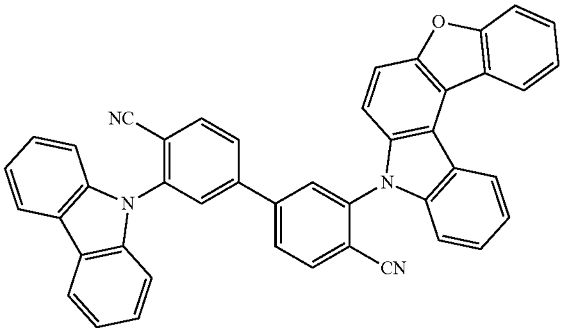
162
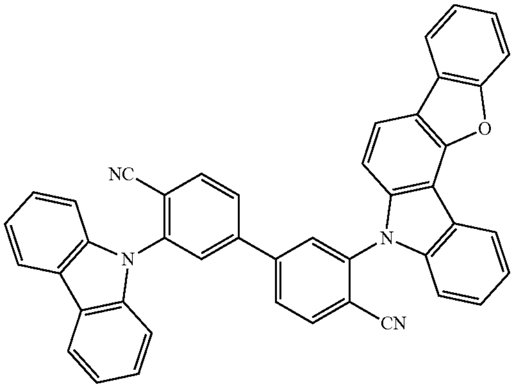
-continued
163
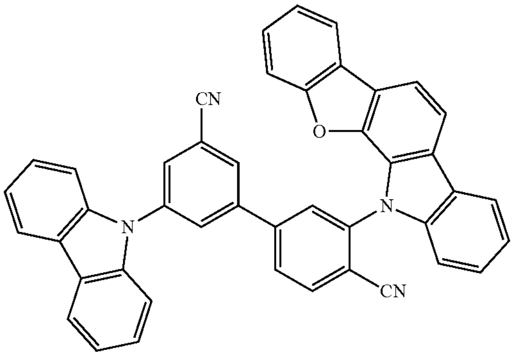
164
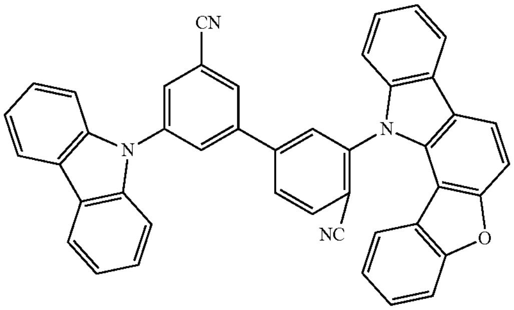
165
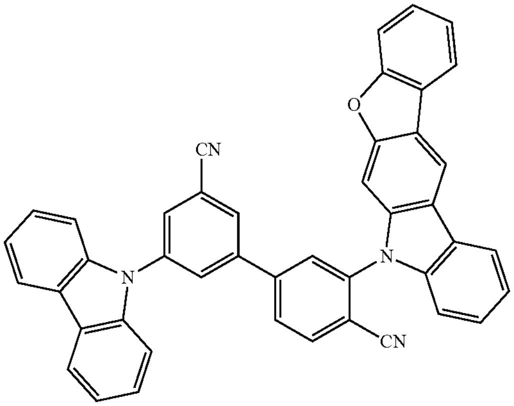
166
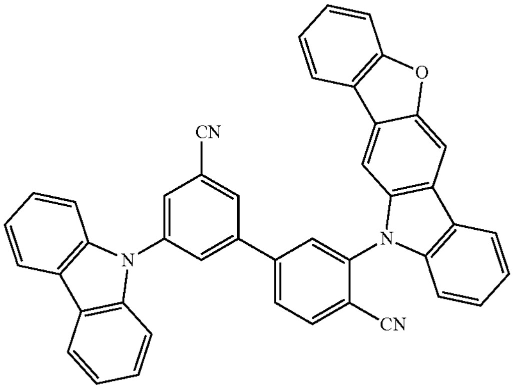

167
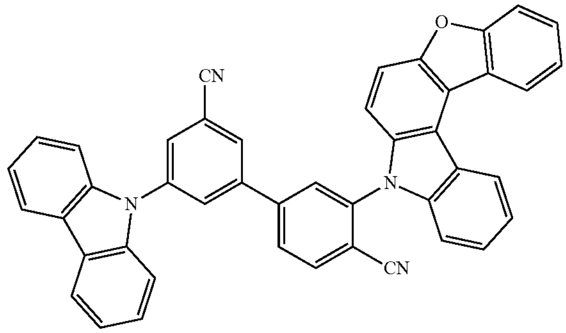
168
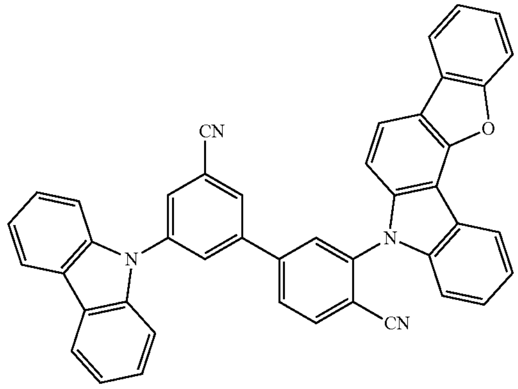
169
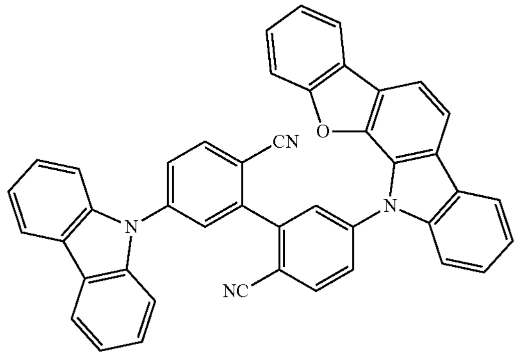
170
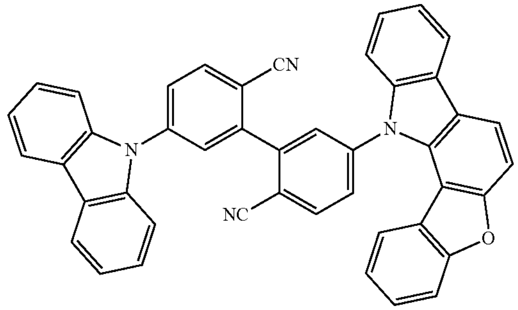
171
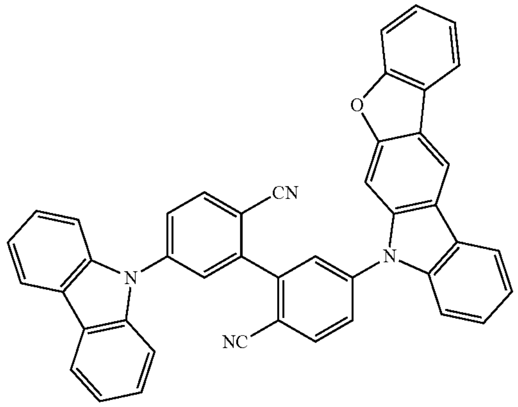
172
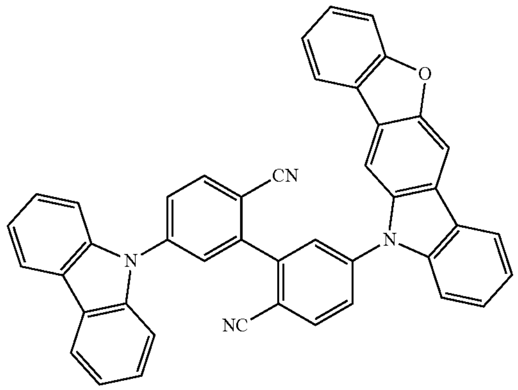
173
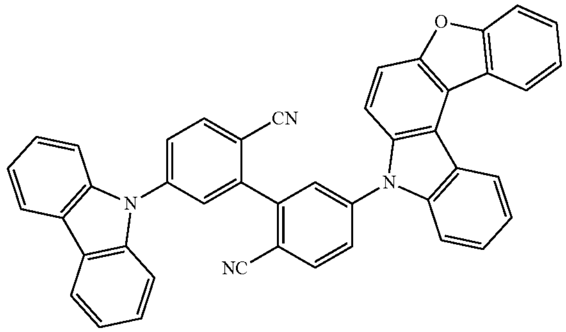
174
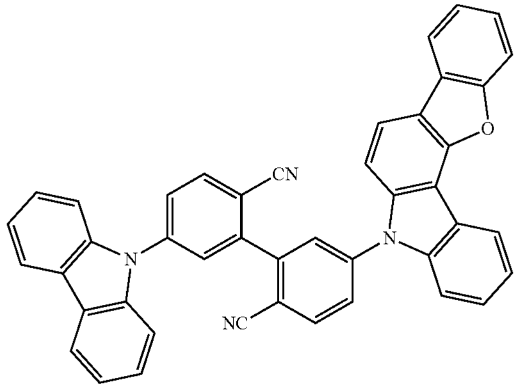

-continued
175
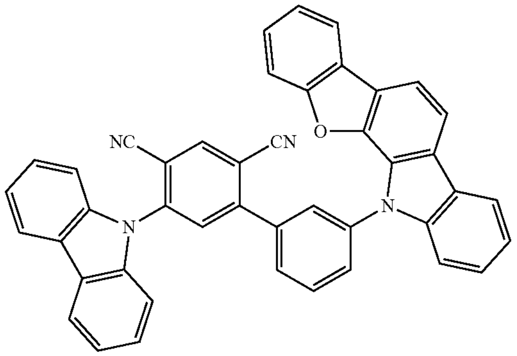
176
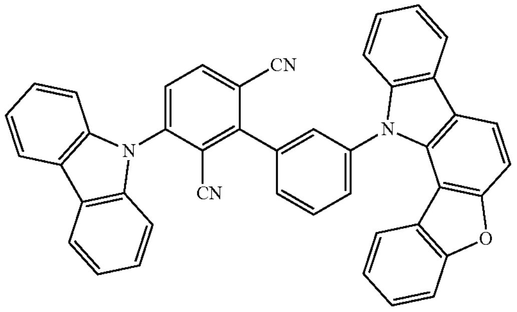
177
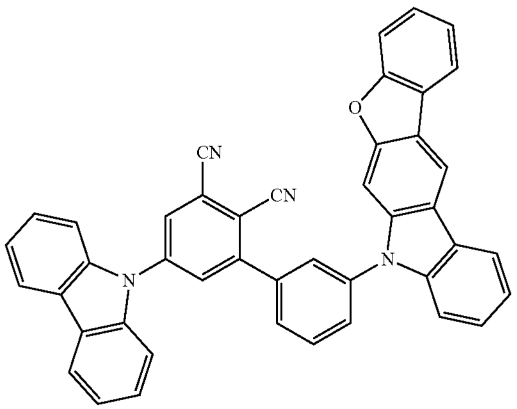
178
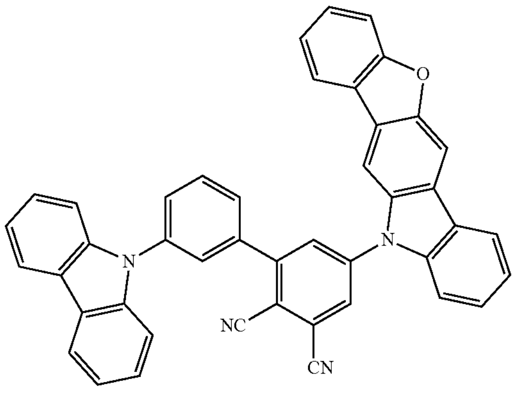
-continued
179
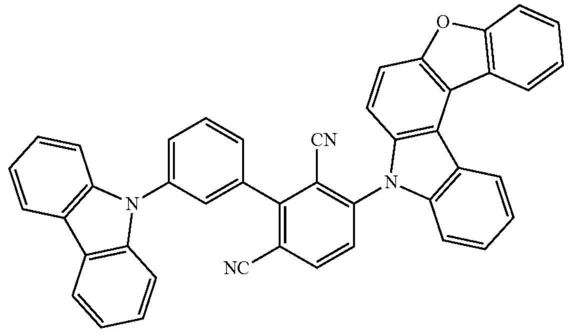
180
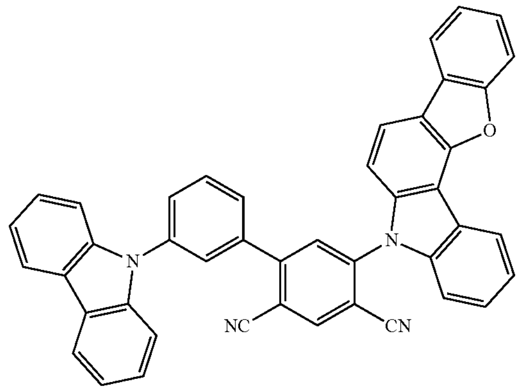
181
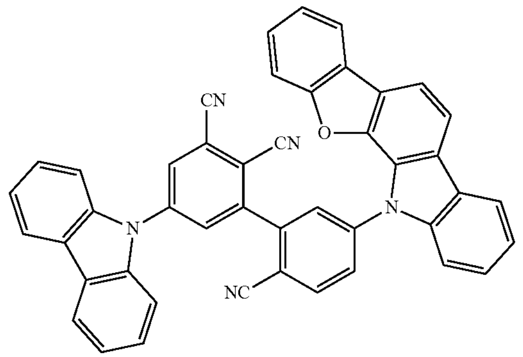
182
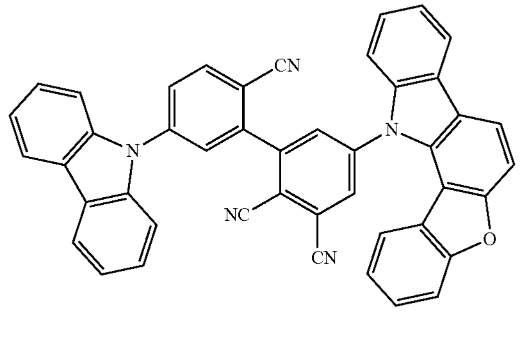

-continued
183
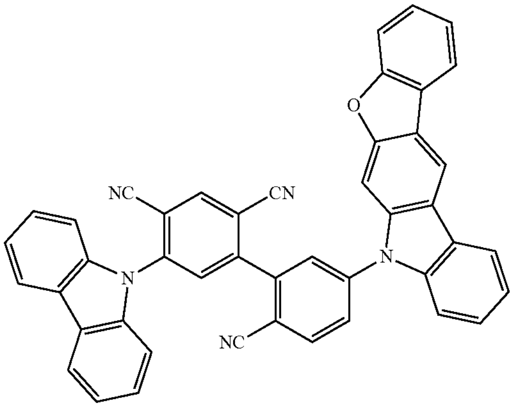
184
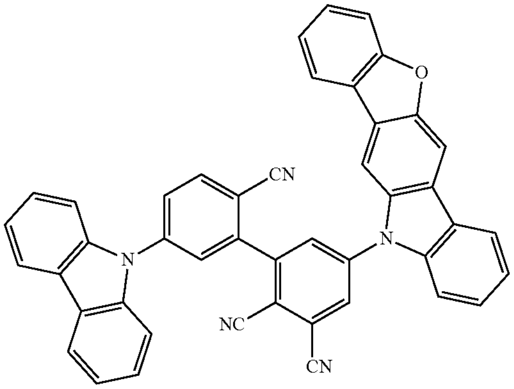
185
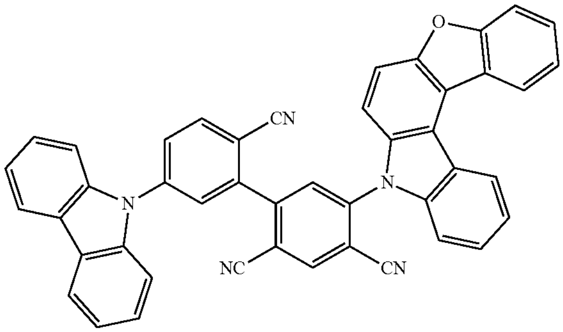
186
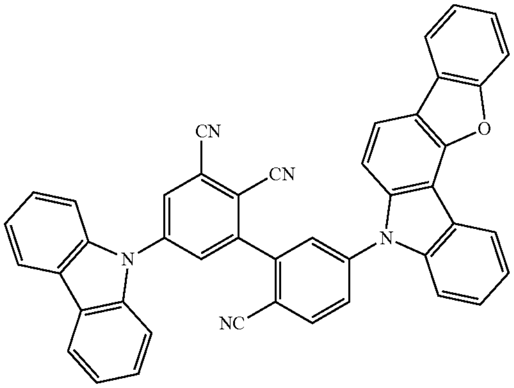
-continued
187
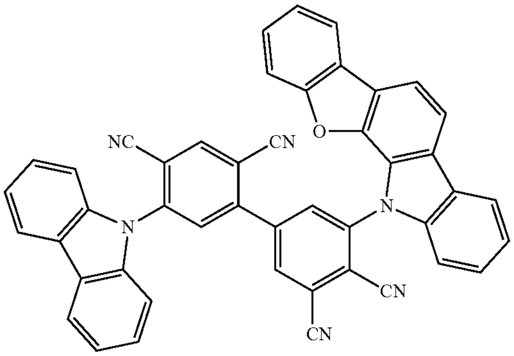
188
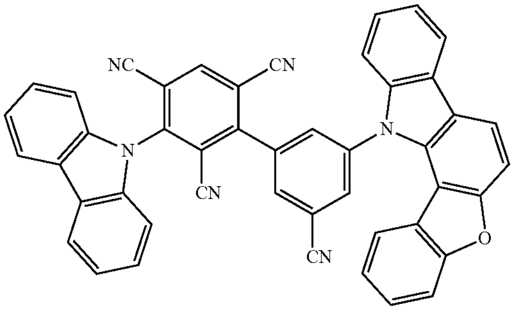
189
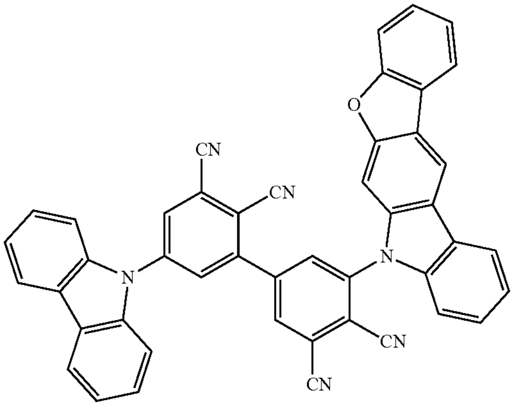
190
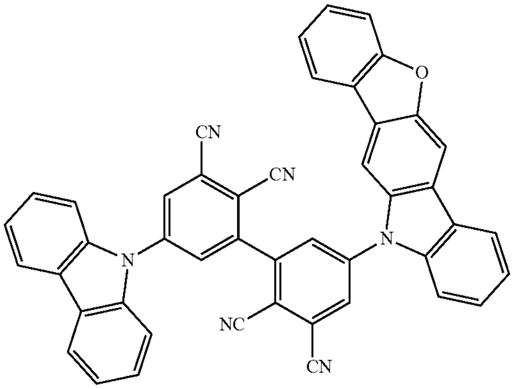

-continued
191
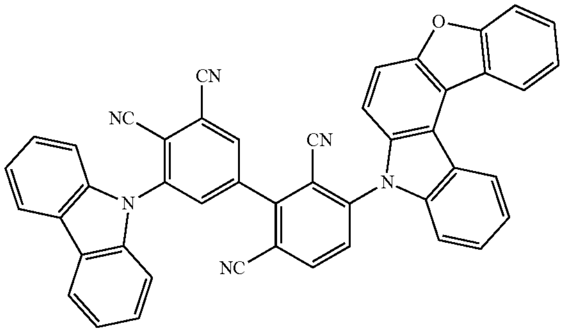
192
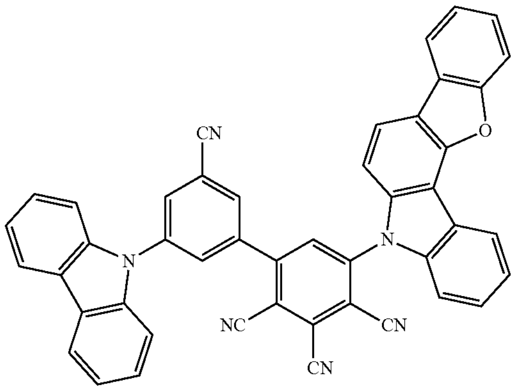
193
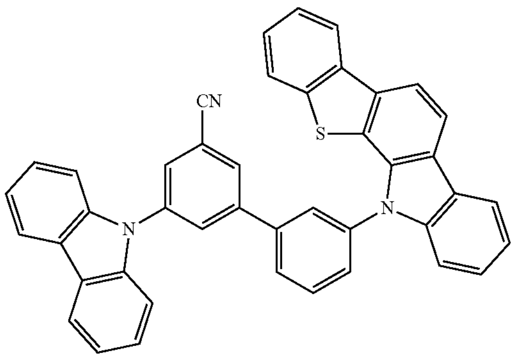
194
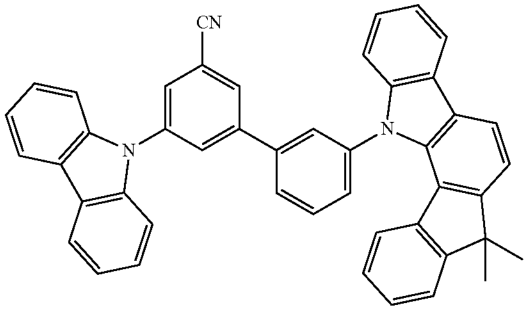
-continued
195
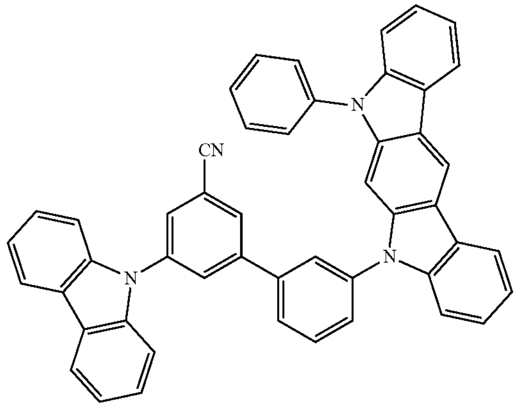
196
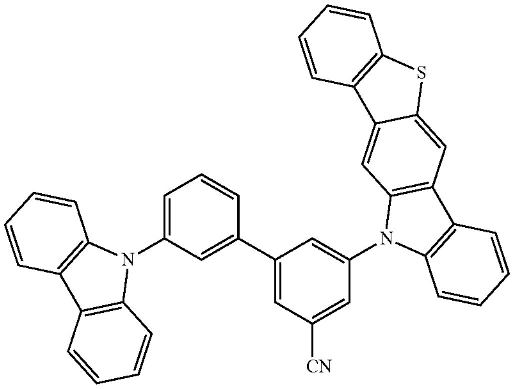
197
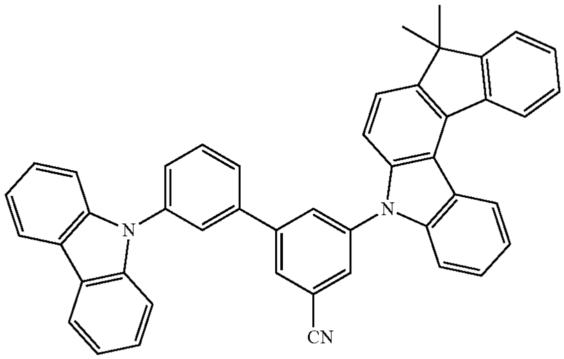
198
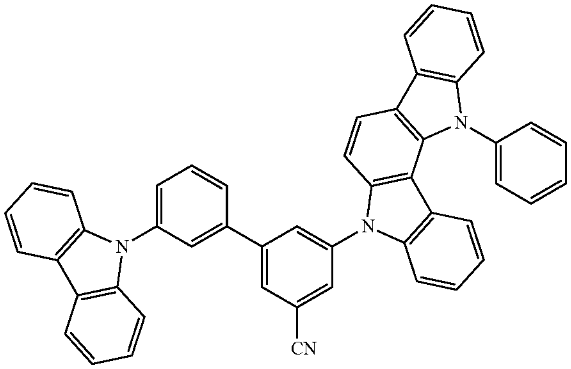

-continued
199
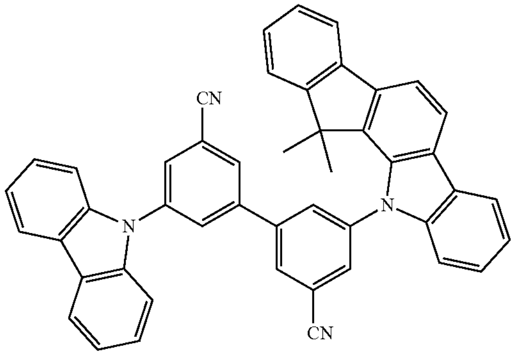
200
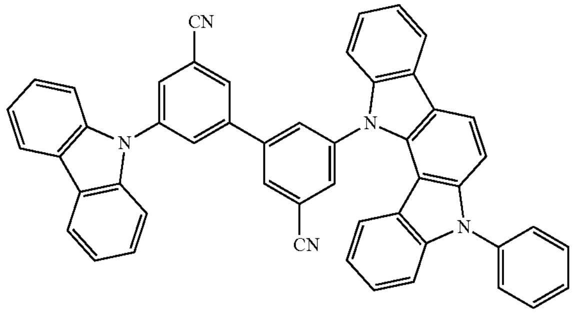
201
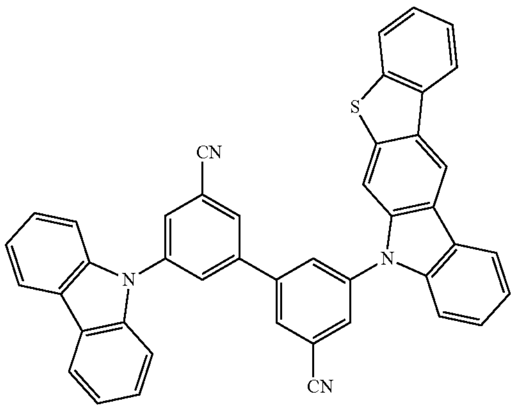
202
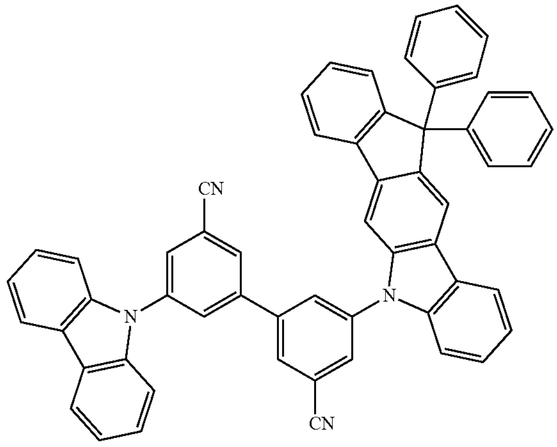
-continued
203
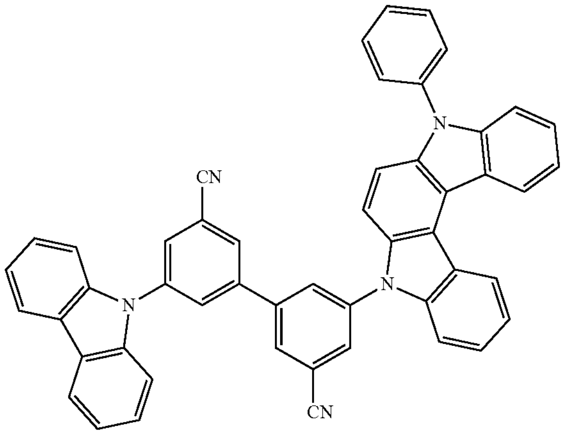
204
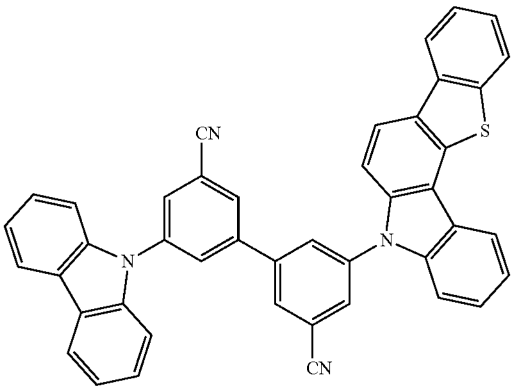
205
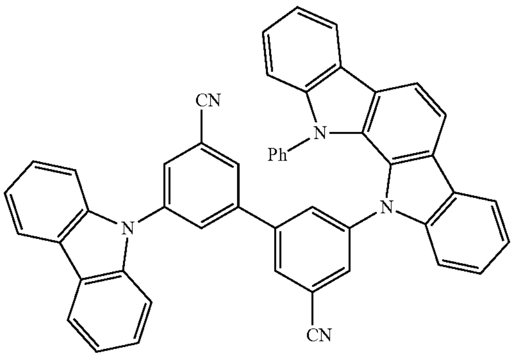
206
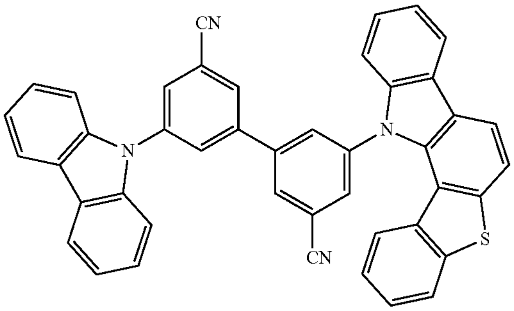

-continued
207
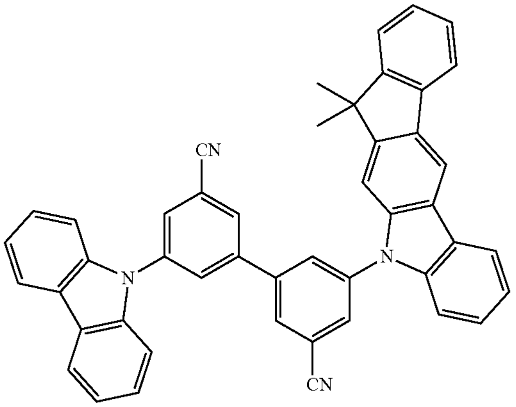
208
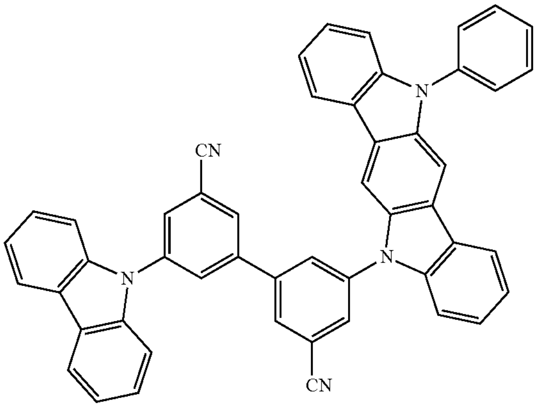
209
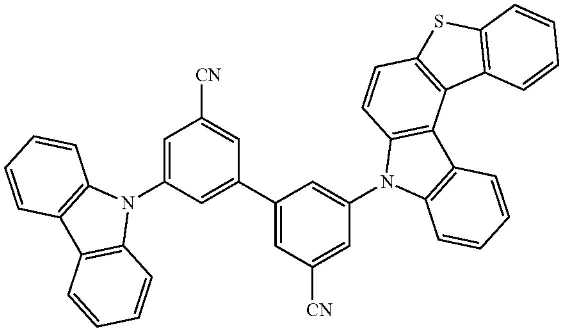
210
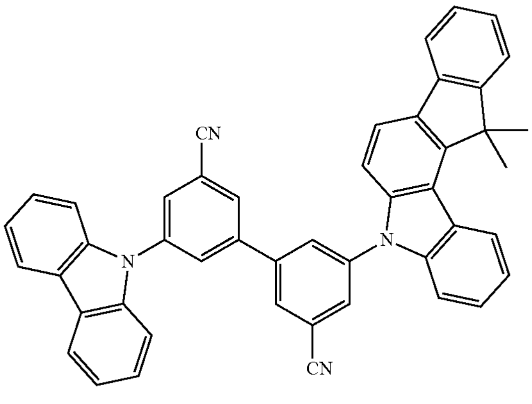
-continued
211
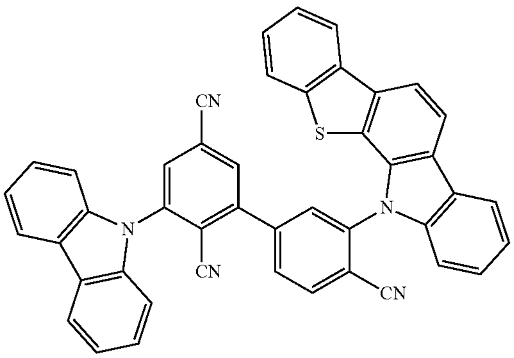
212
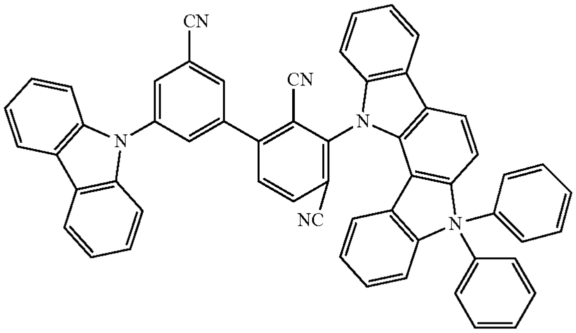
213
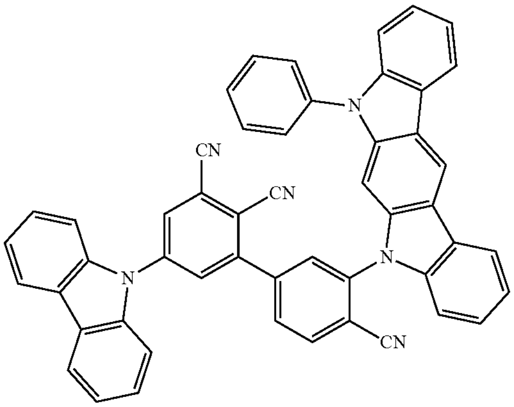
214
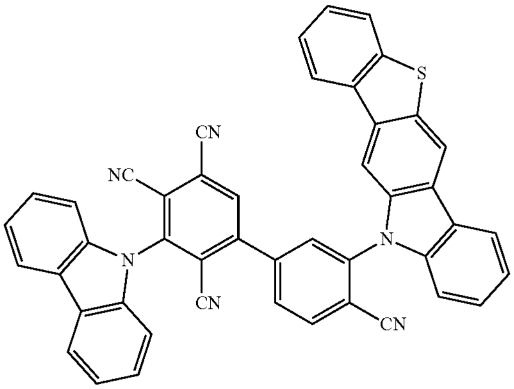

-continued
215
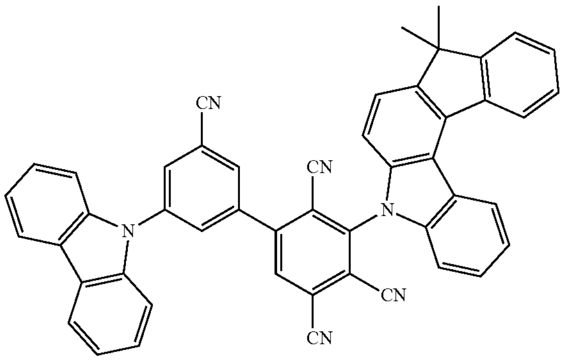
216
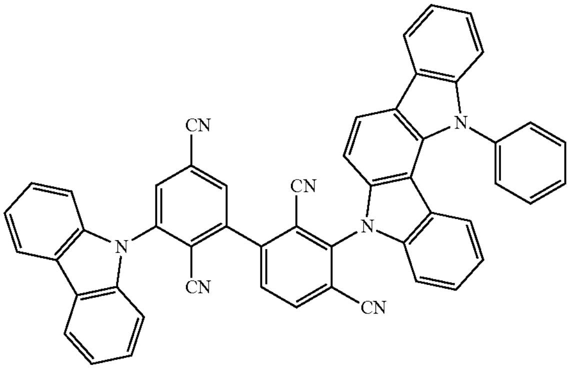
217
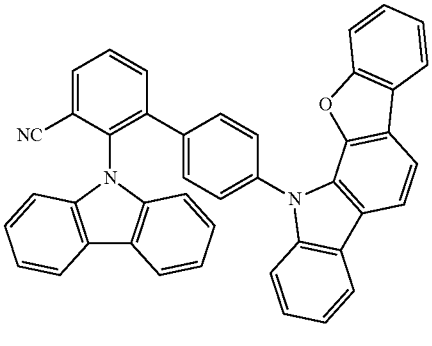
218
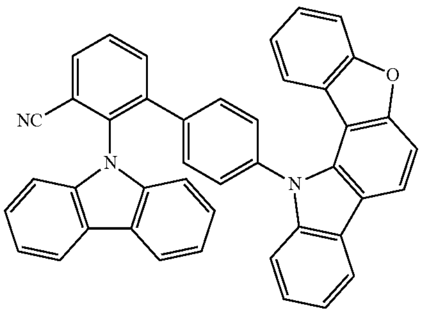
-continued
219
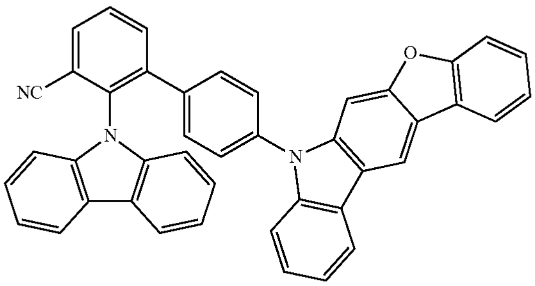
220
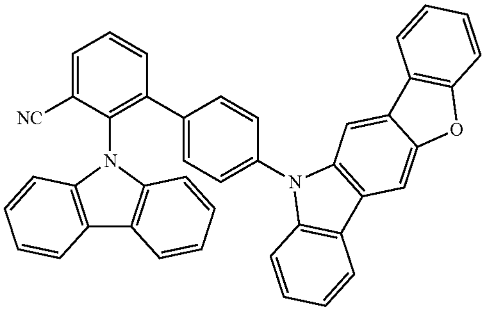
221
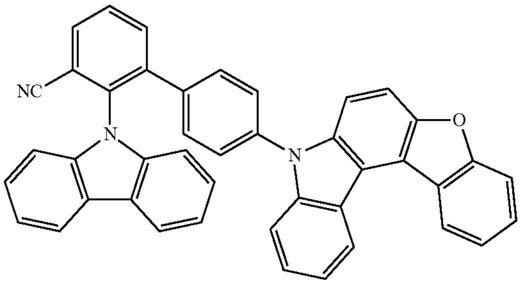
222
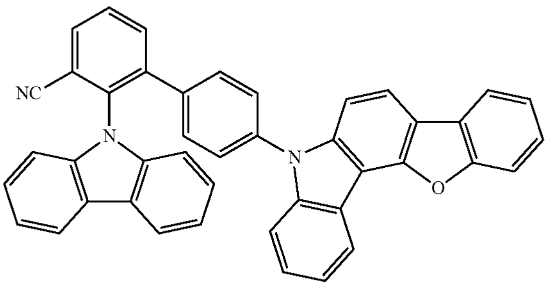
223
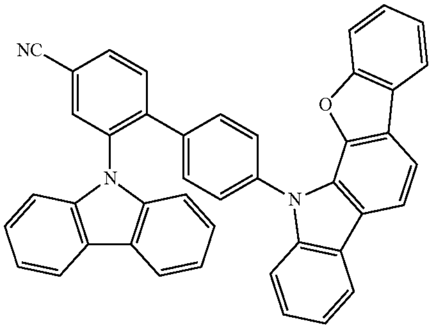

-continued
224
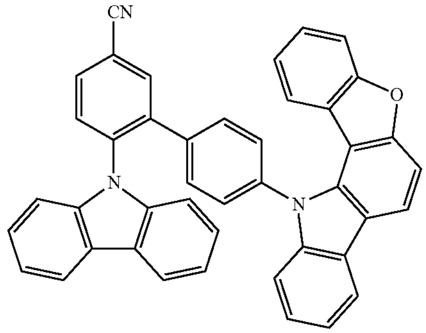
225
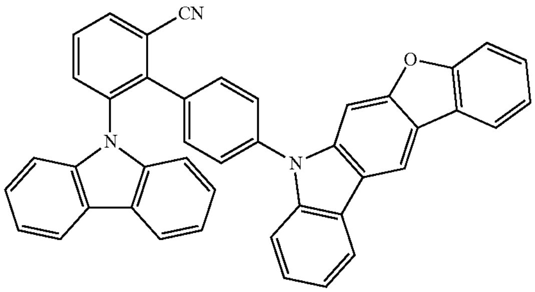
226
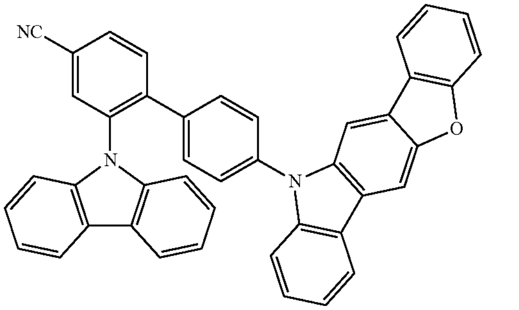
227
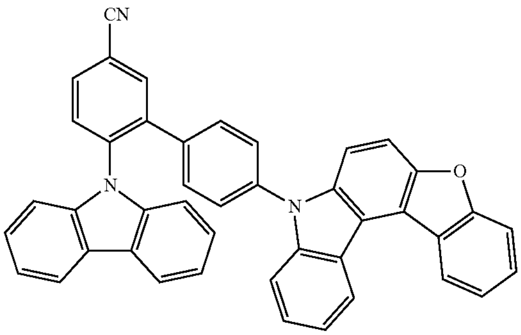
228
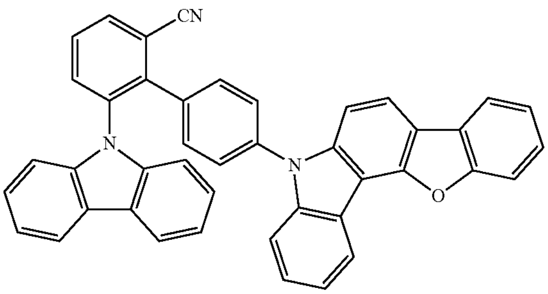
-continued
229
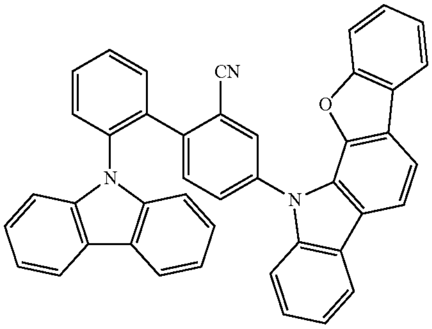
230
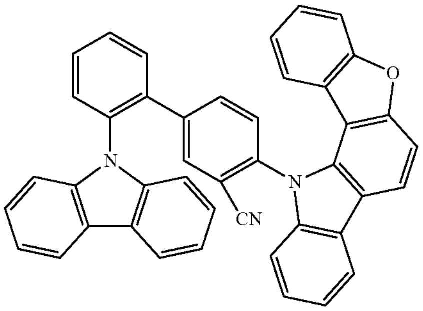
231
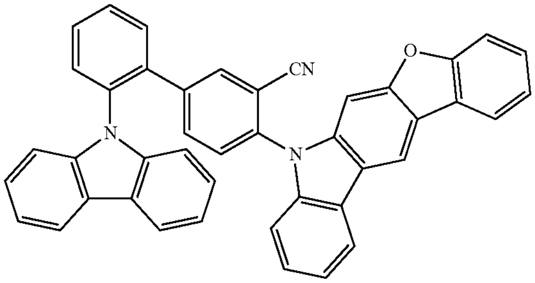
232
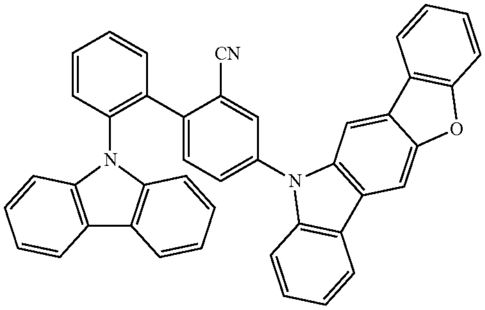
223
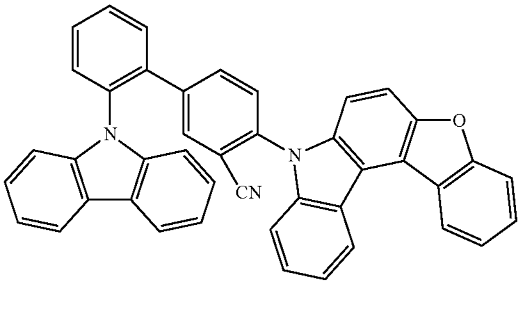

-continued
234
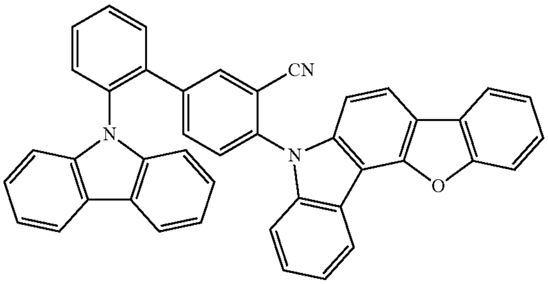
235
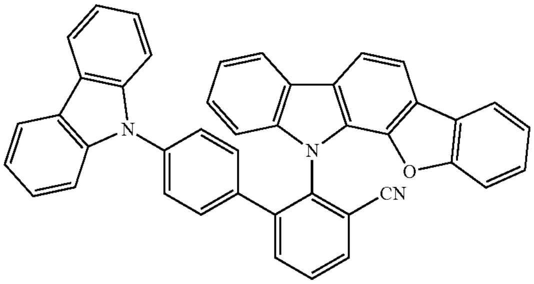
236
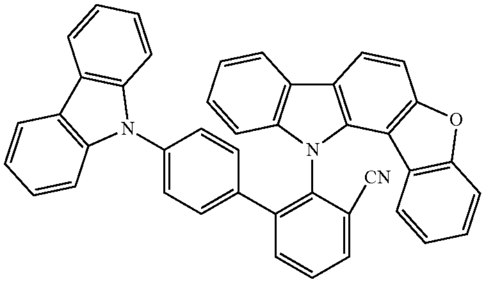
237
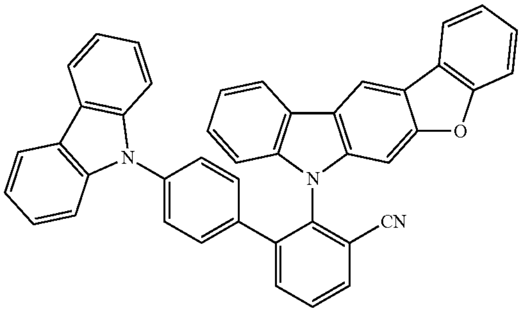
238
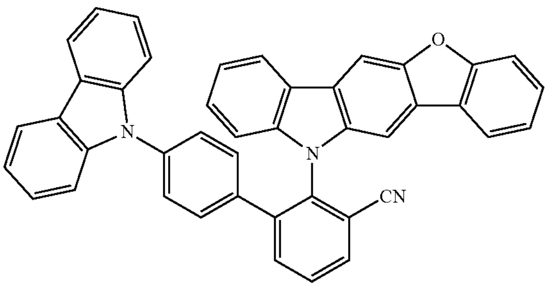
-continued
239
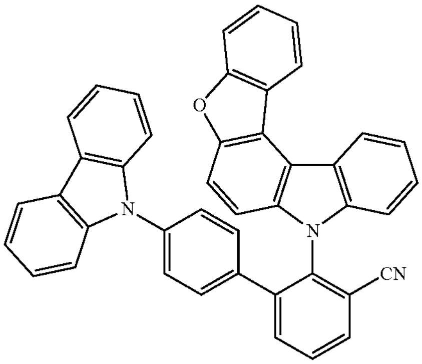
240
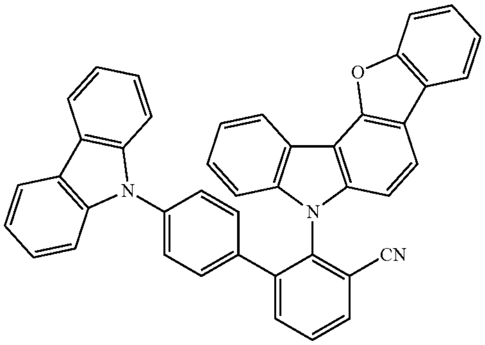
241
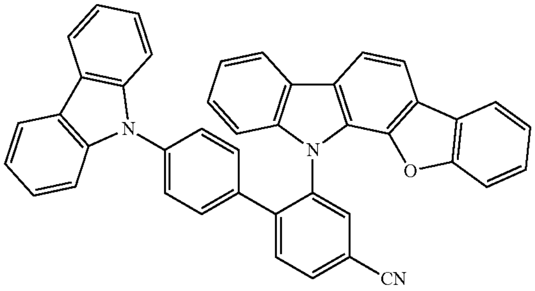
242
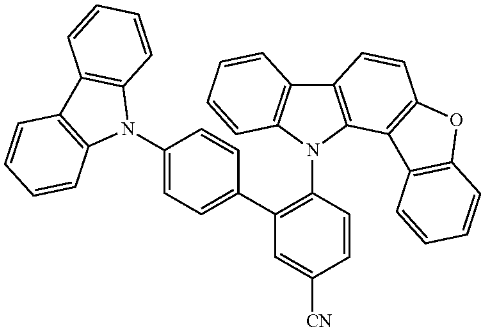

-continued
243
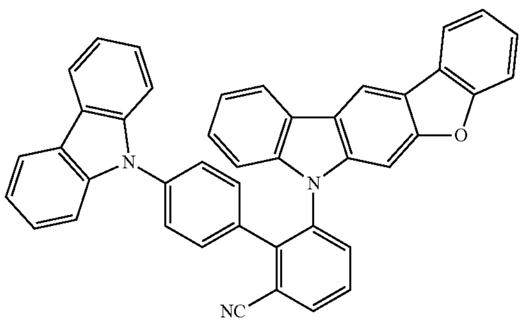
244
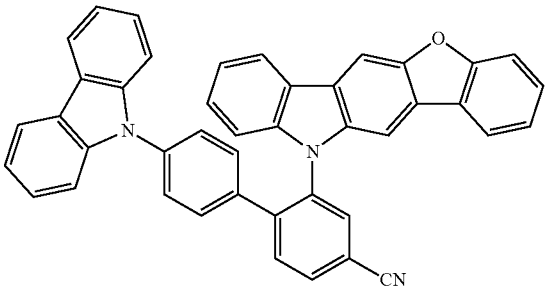
245
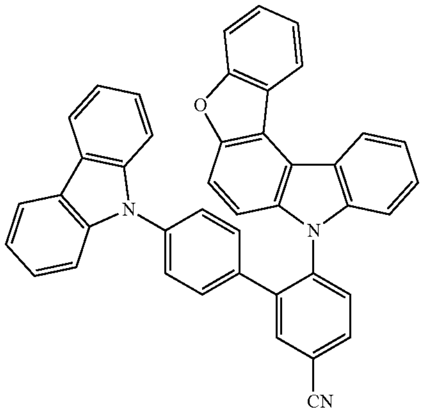
246
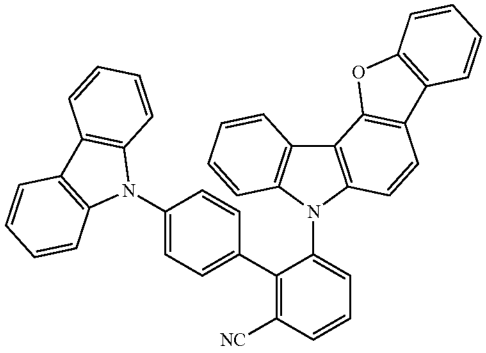
-continued
247
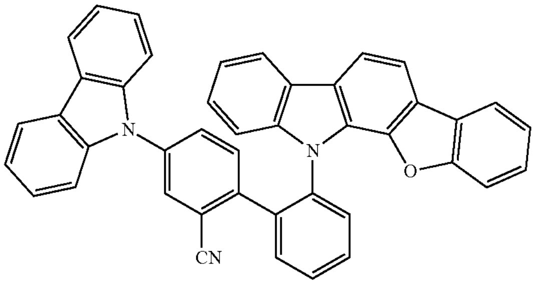
248
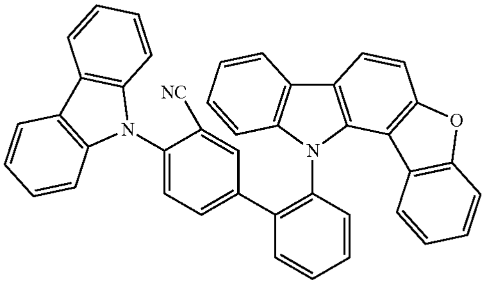
249
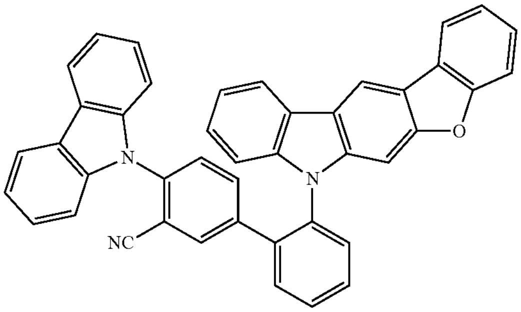
250
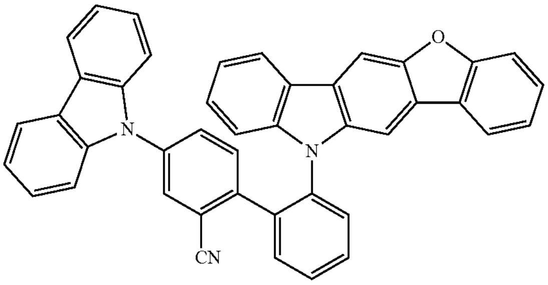
251
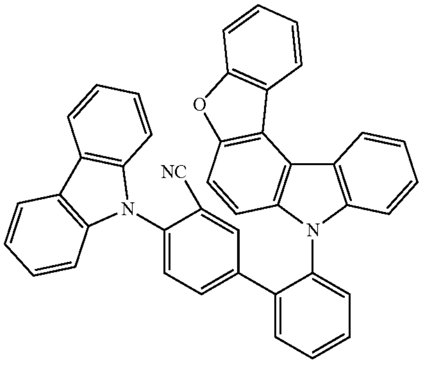

-continued
252
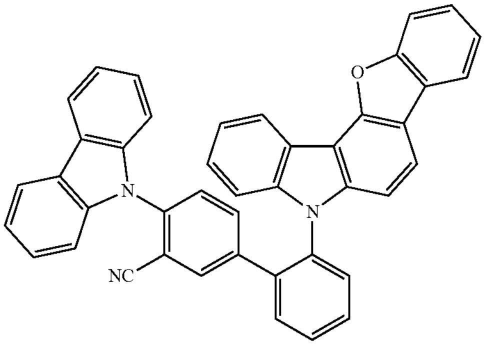
253
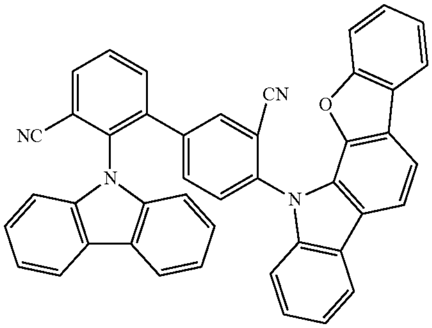
254
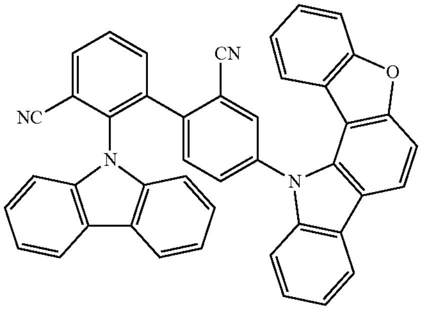
255
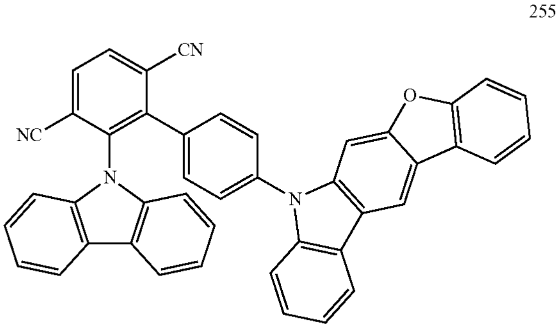
-continued
256
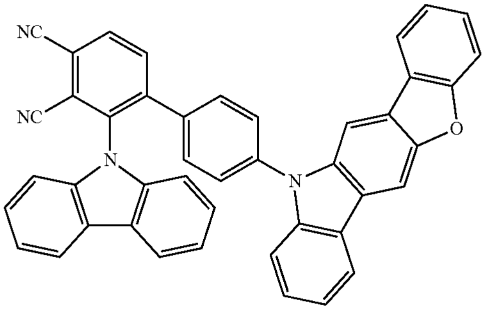
257
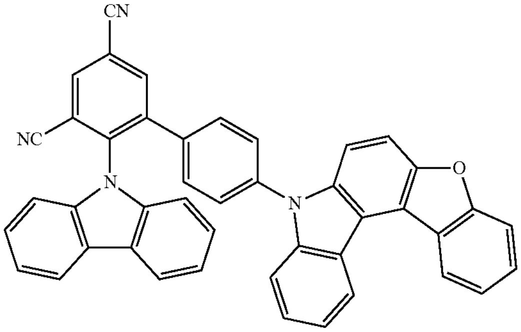
258
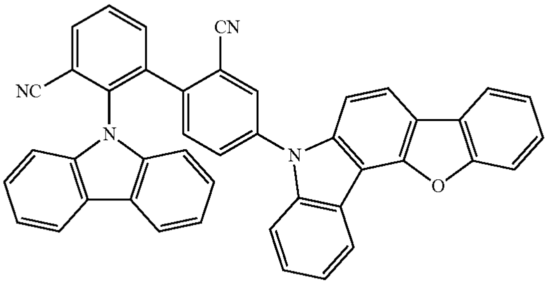
259
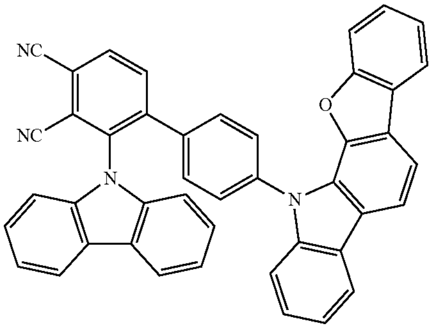
260
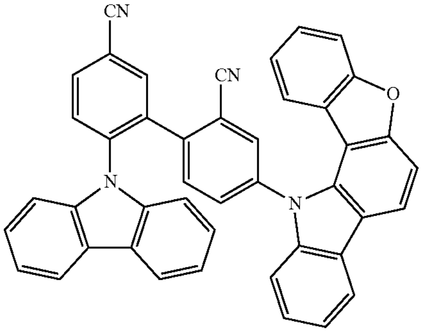

261
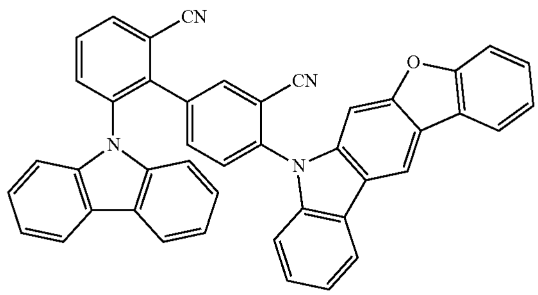
262
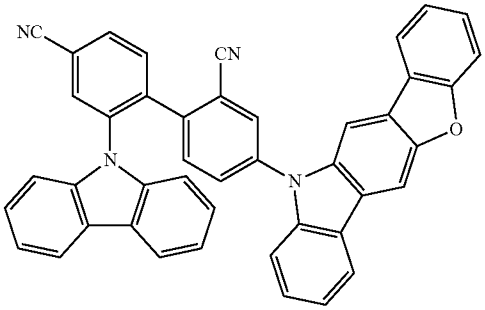
263
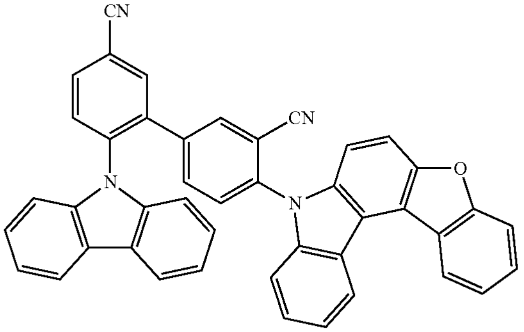
264
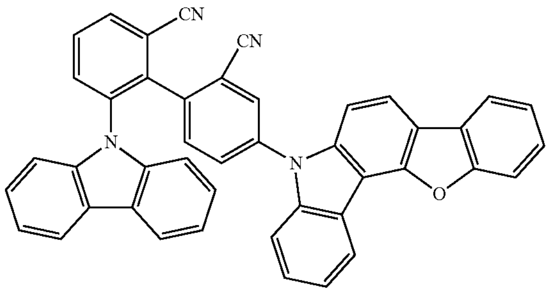
265
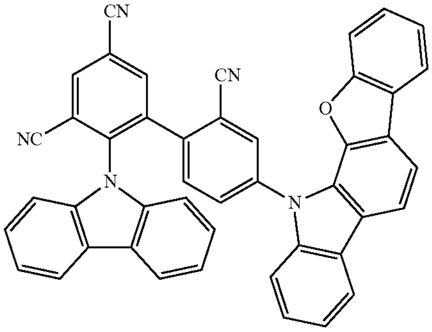
266
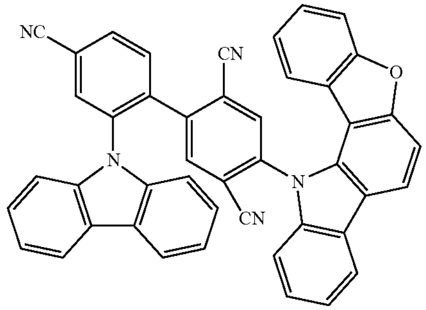
267
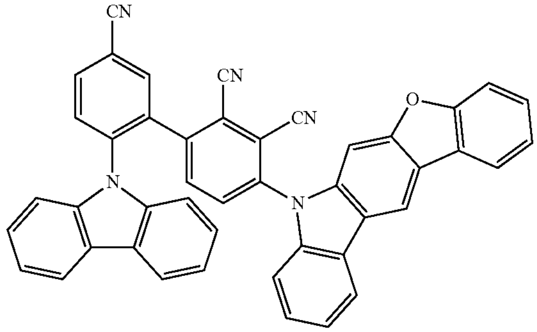
268
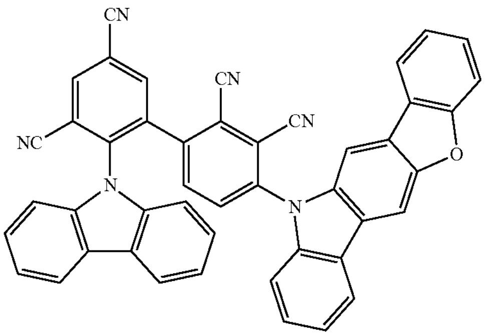
269
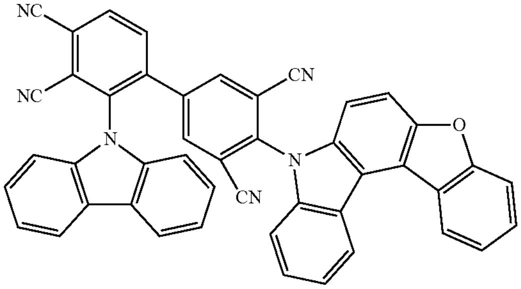

-continued
270
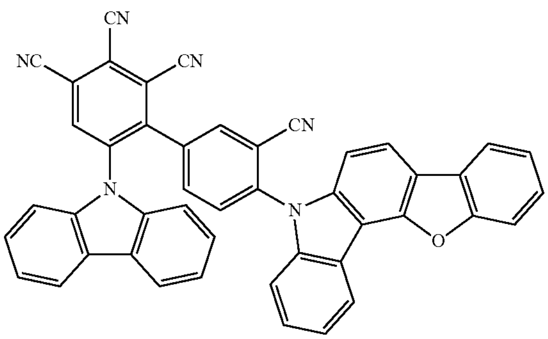
271
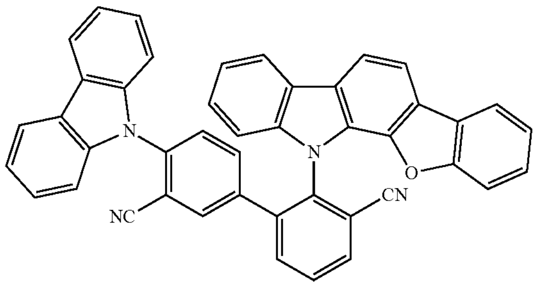
272
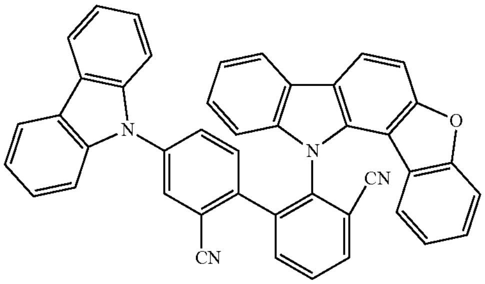
273
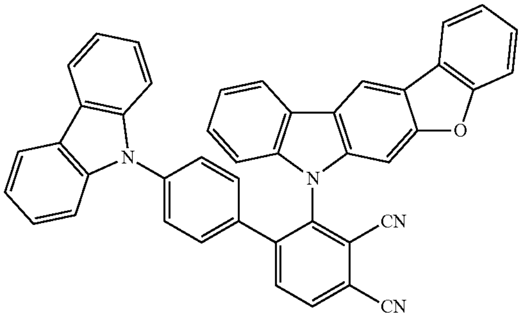
274
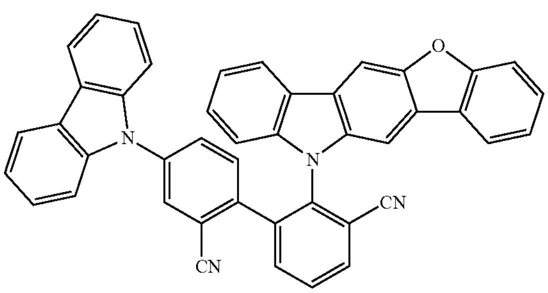
-continued
275
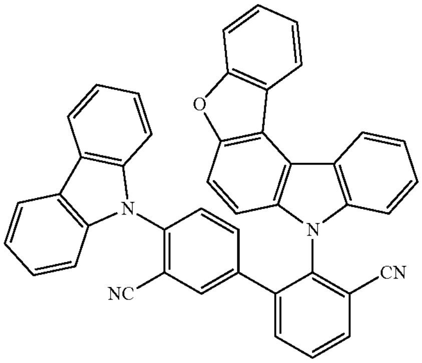
276
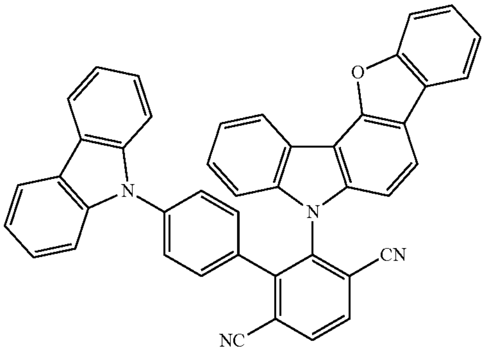
277
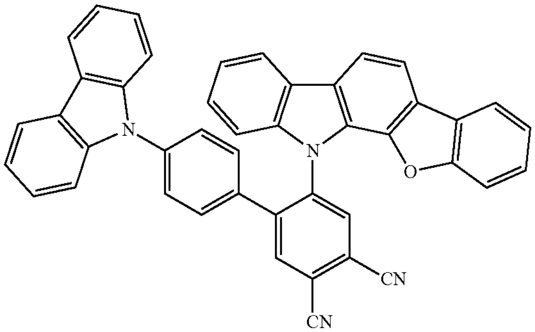
278
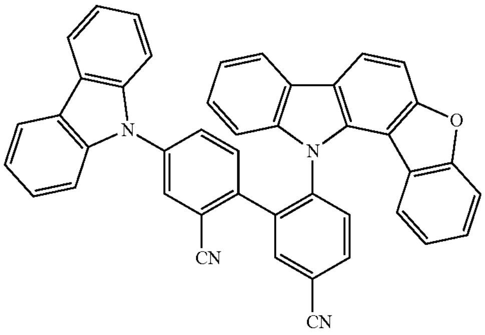

-continued
279
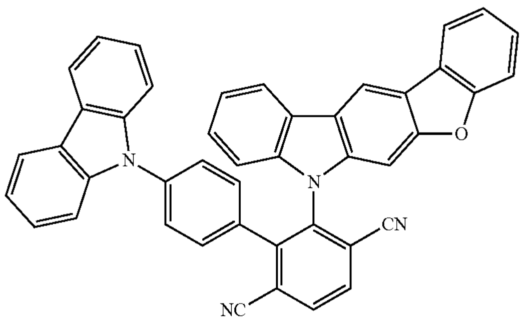
280
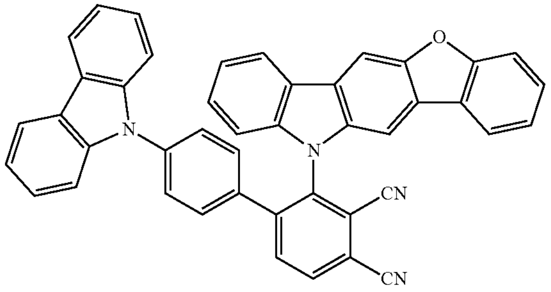
281
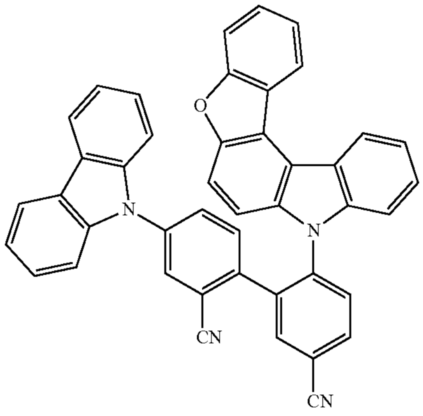
282
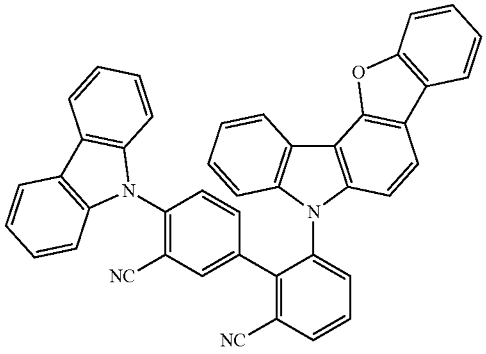
-continued
283
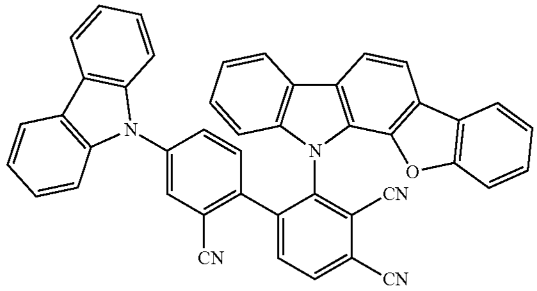
284
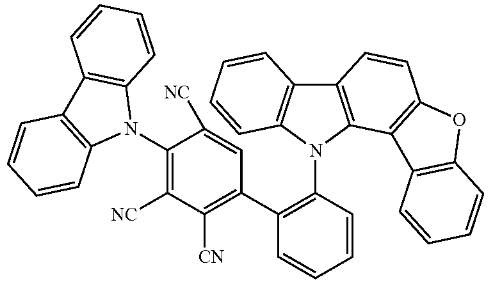
285
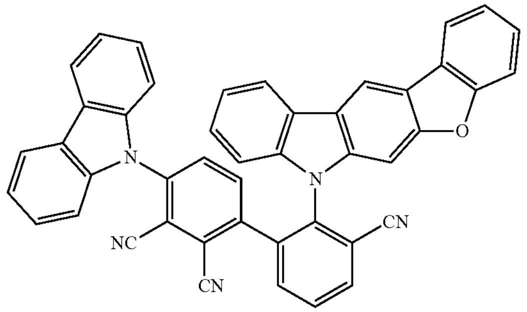
286
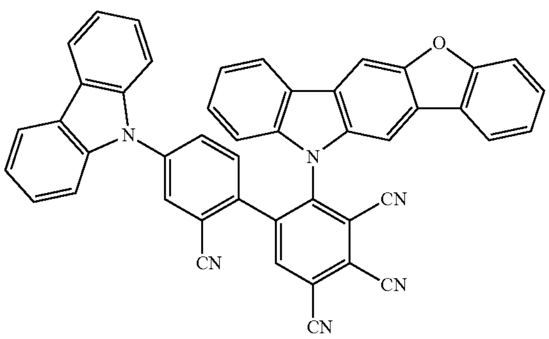

-continued
287
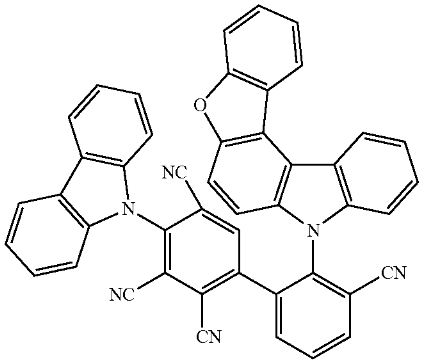
288
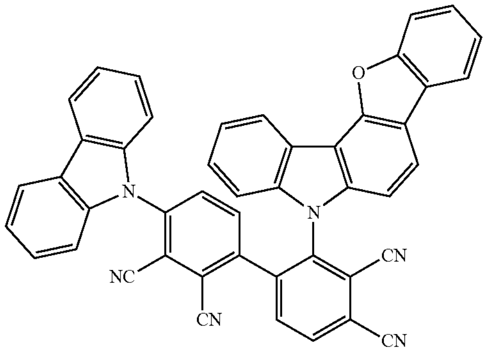
289
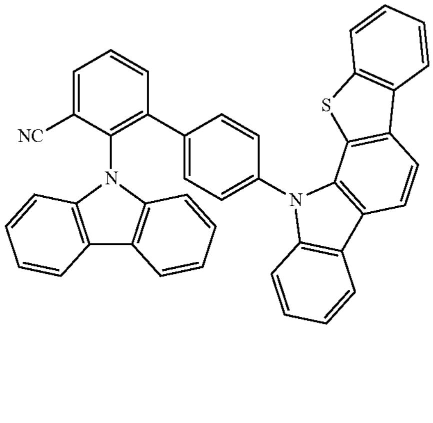
290
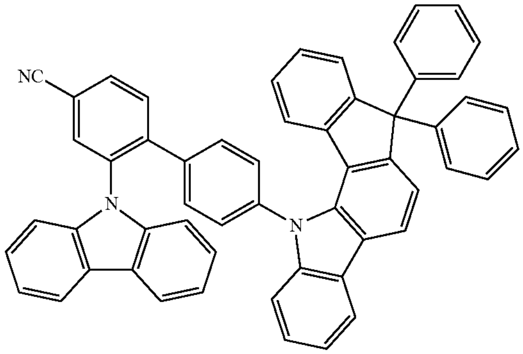
-continued
291
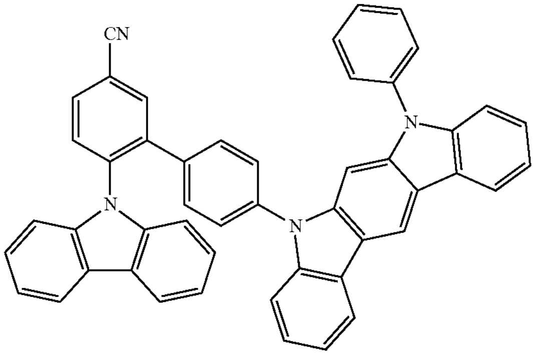
292
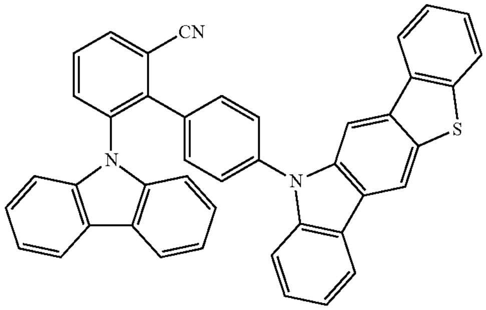
293
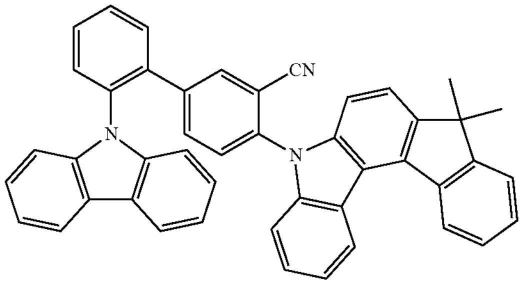
294
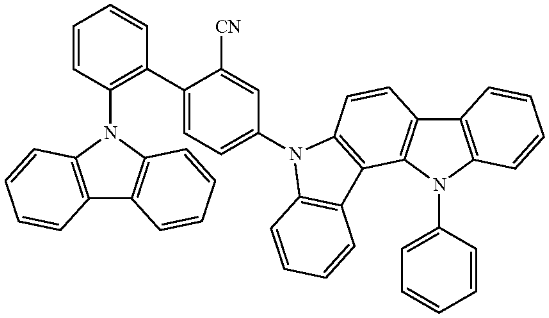

-continued
295
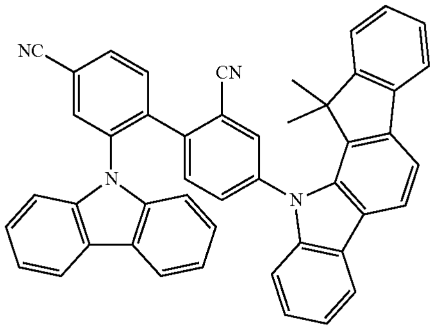
296
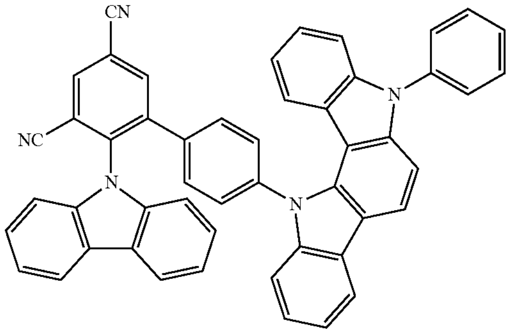
297
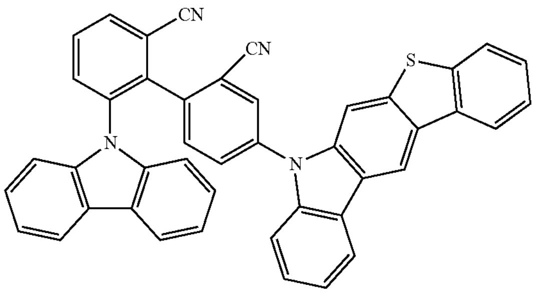
298
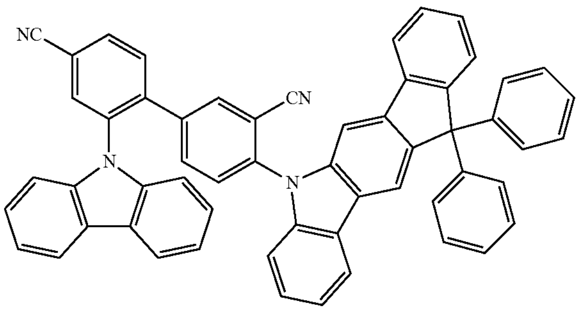
-continued
299
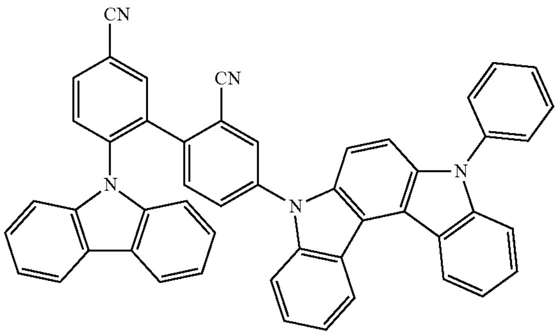
300
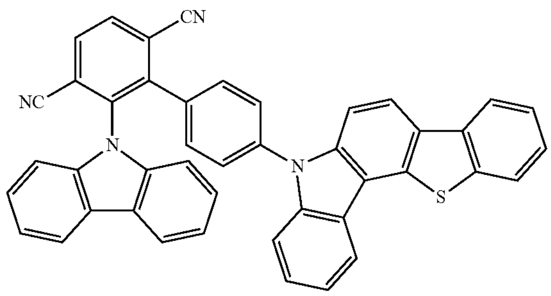
301
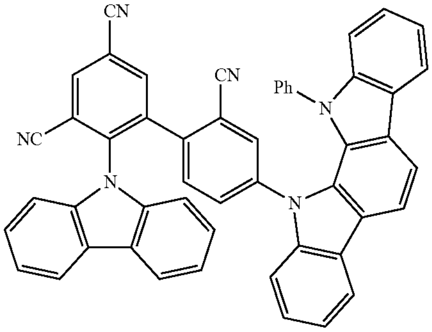
302
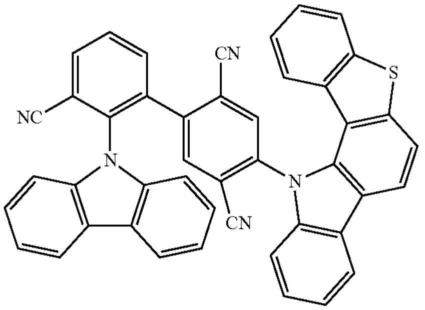
303
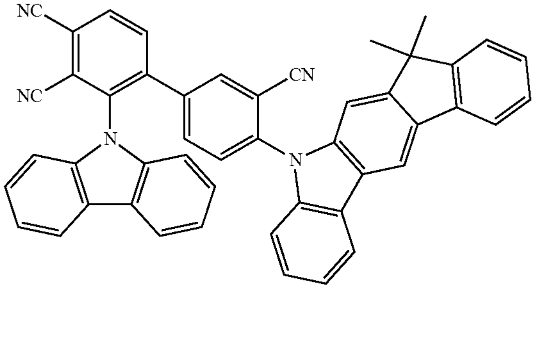

-continued
304
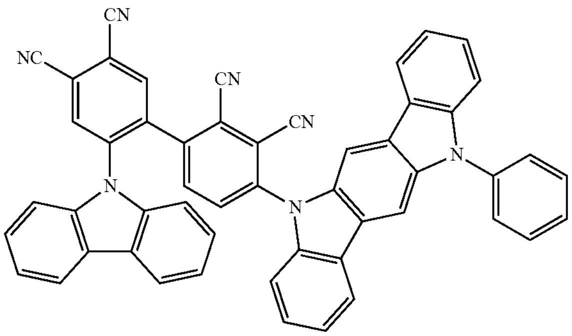
305
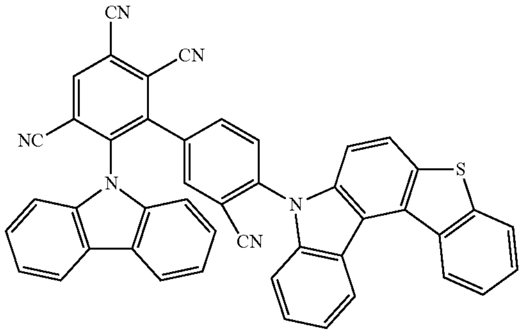
306
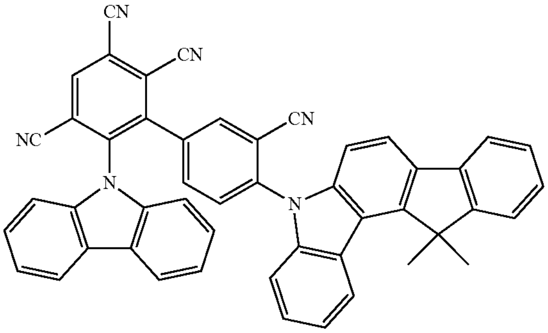
307
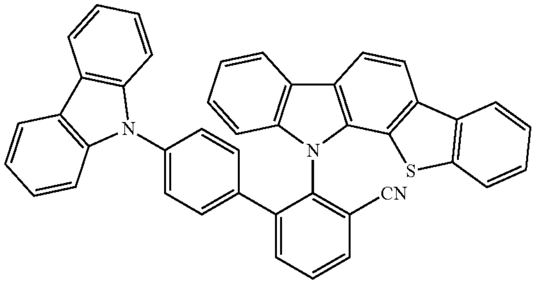
-continued
308
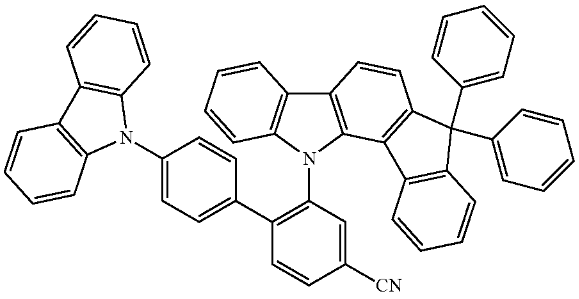
309
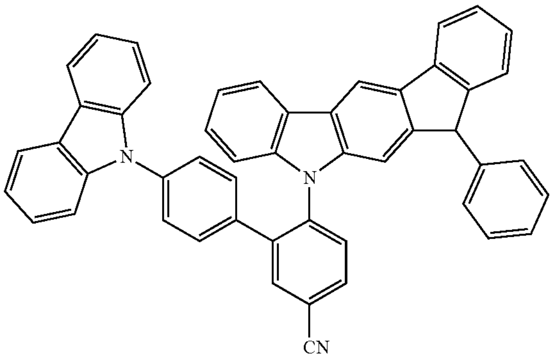
310
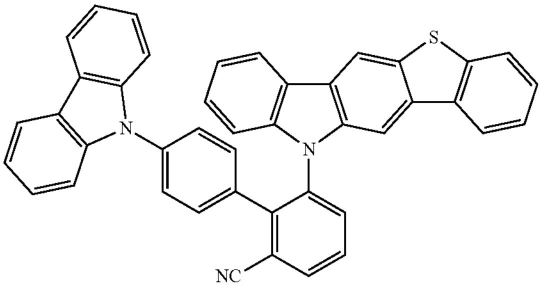
311
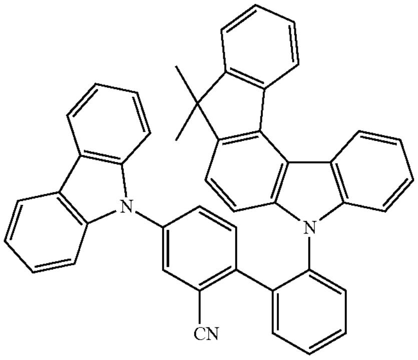

-continued
312
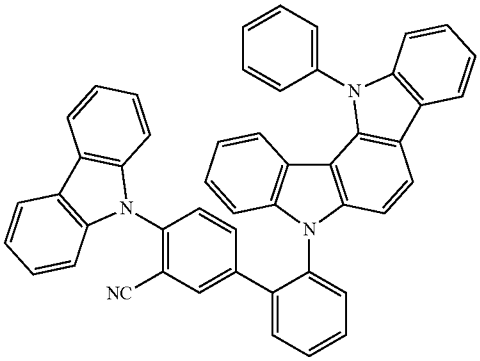
313
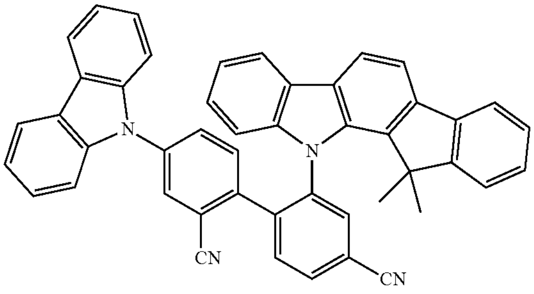
314
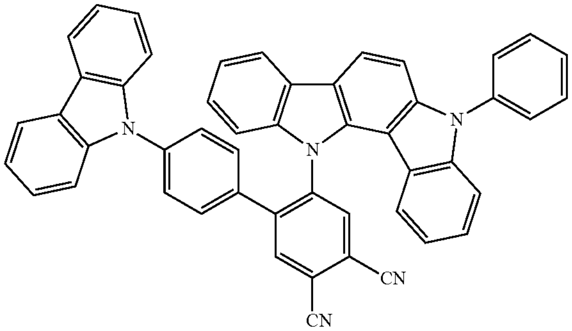
315
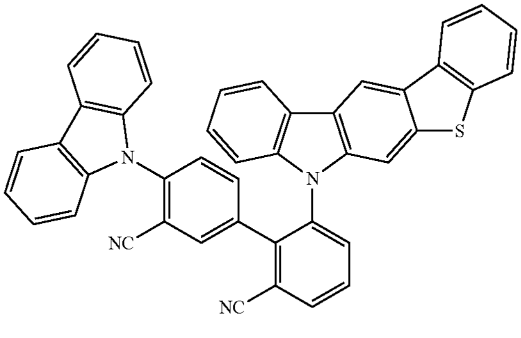
-continued
316
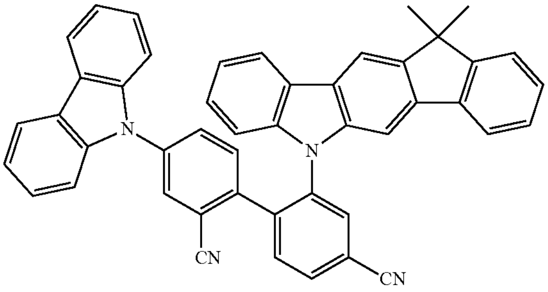
317
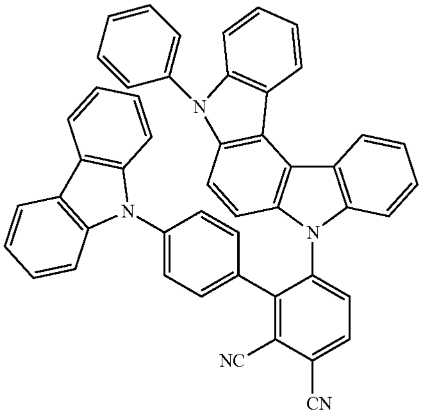
318
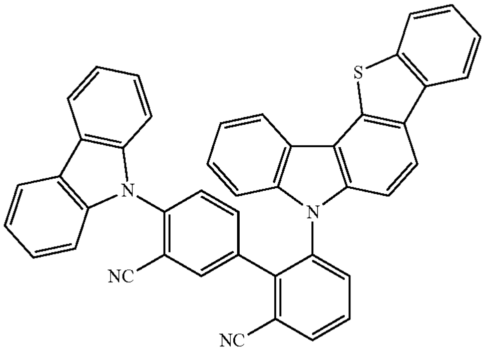
319
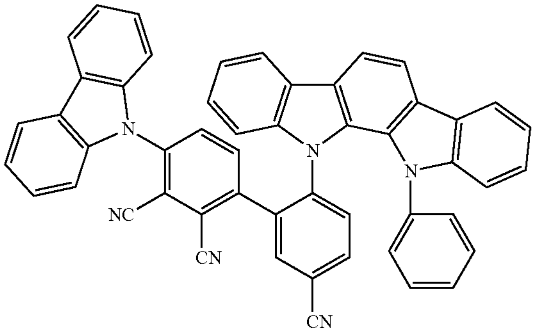

320
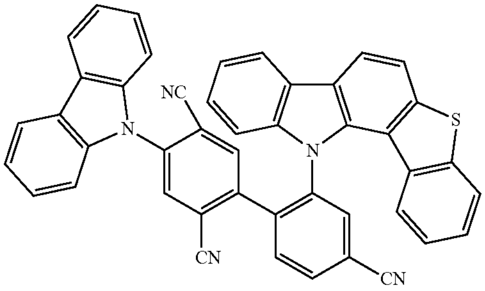
321
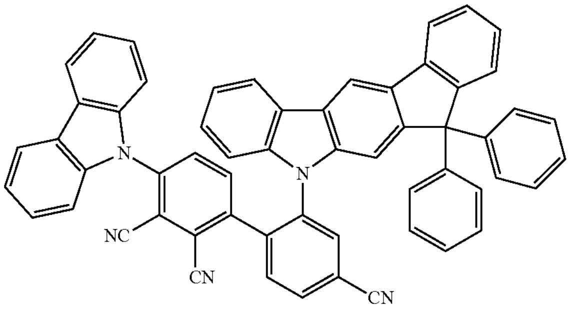
322
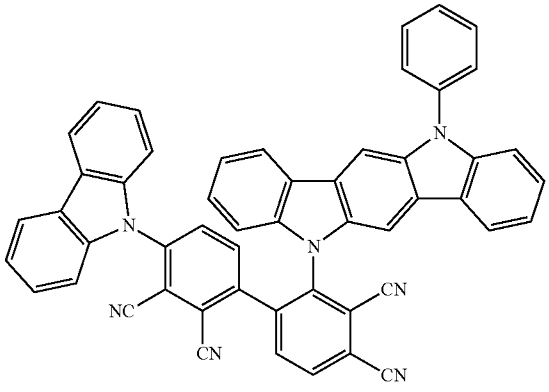
323
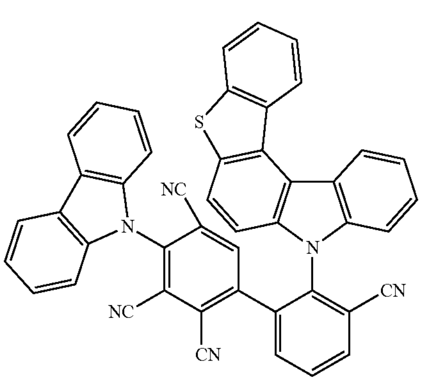
324
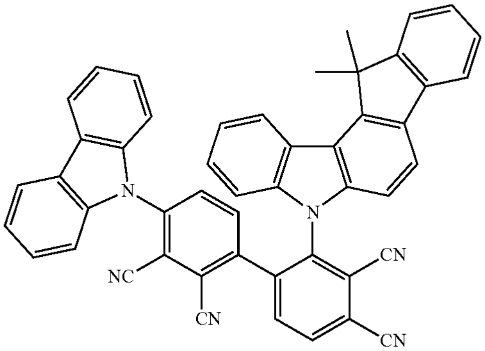
325
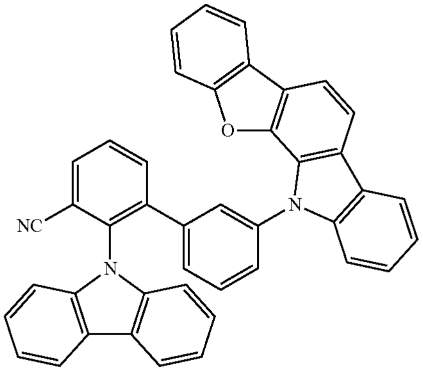
326
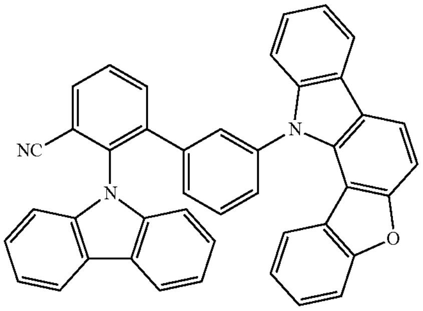
327
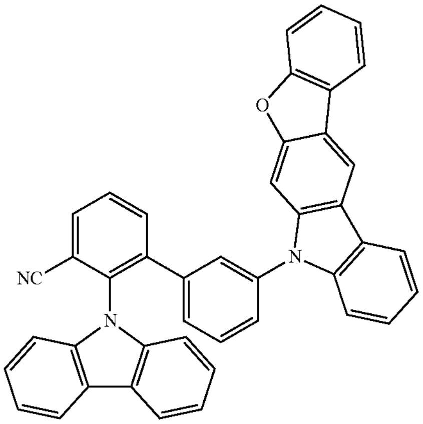

-continued
328
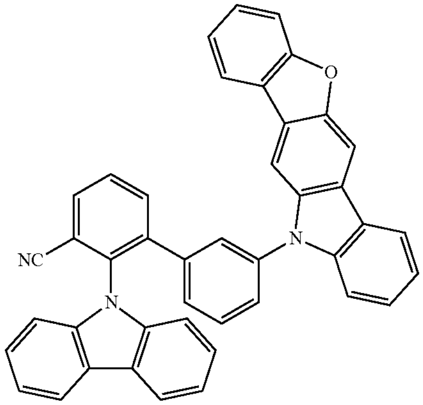
329
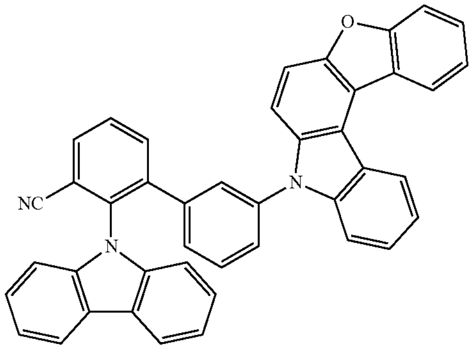
330
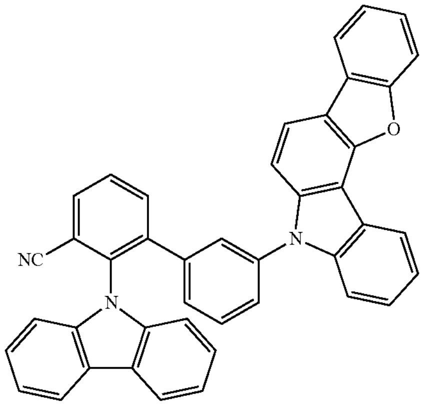
331
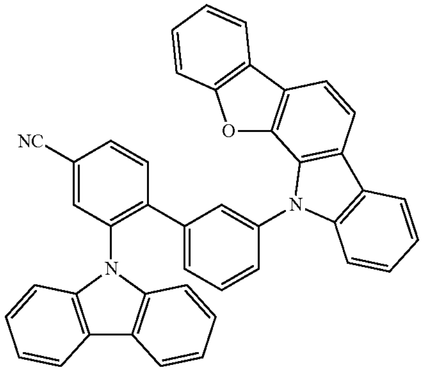
-continued
332
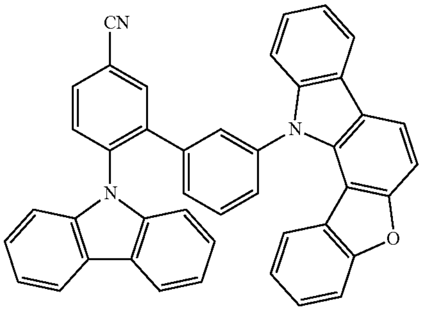
333
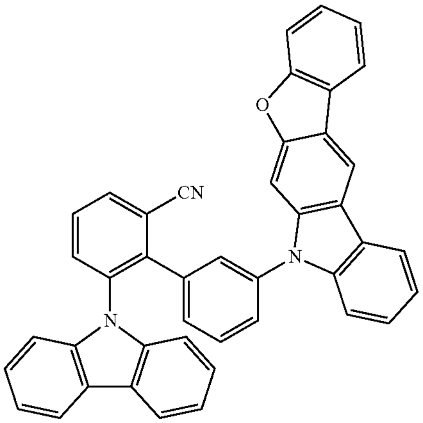
334
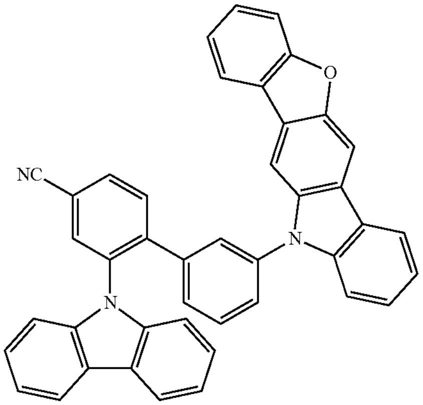
335
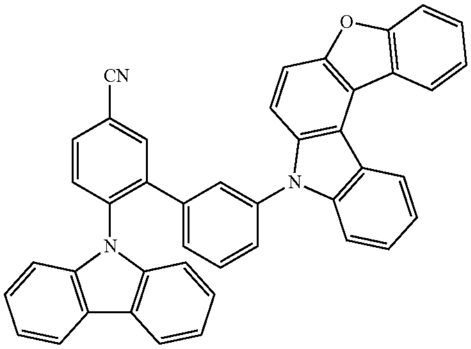

336
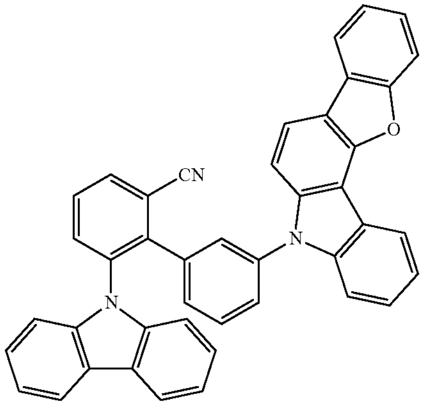
337
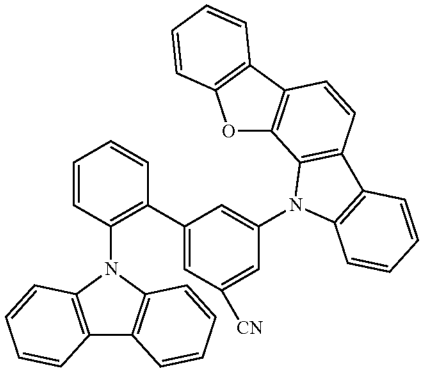
338
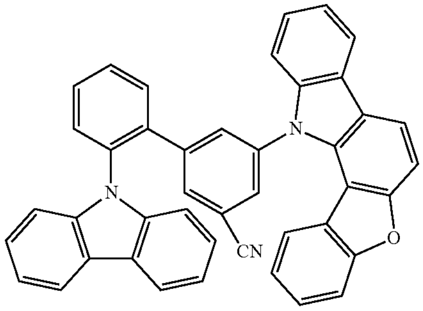
339
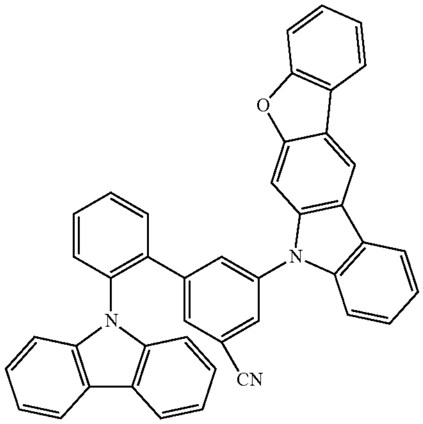
340
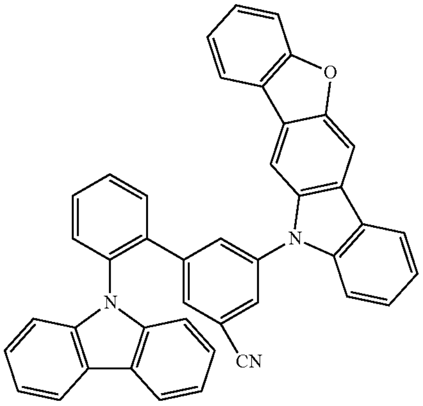
341
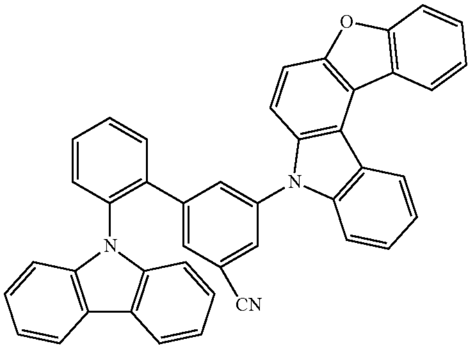
342
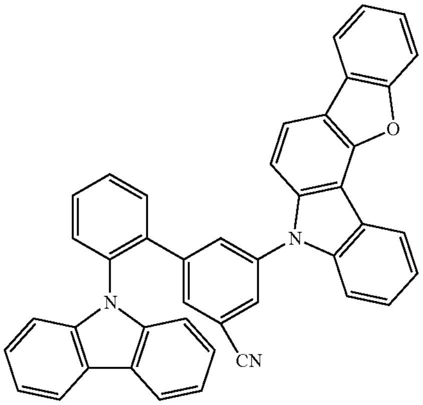
343
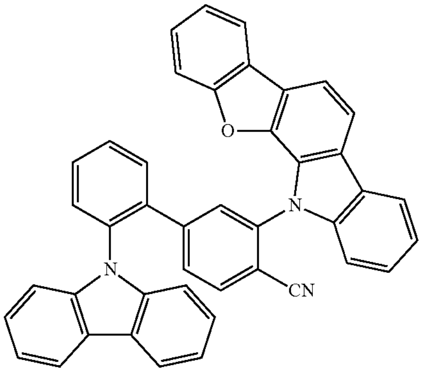

-continued
344
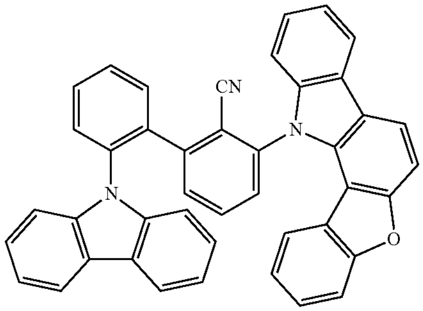
345
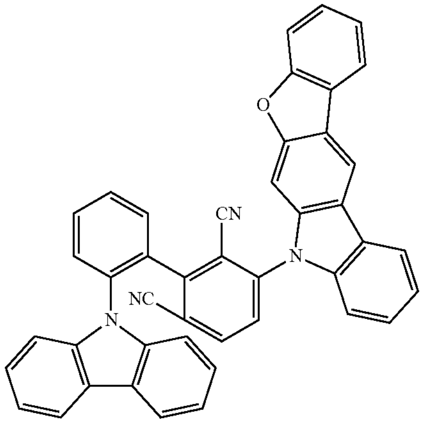
346
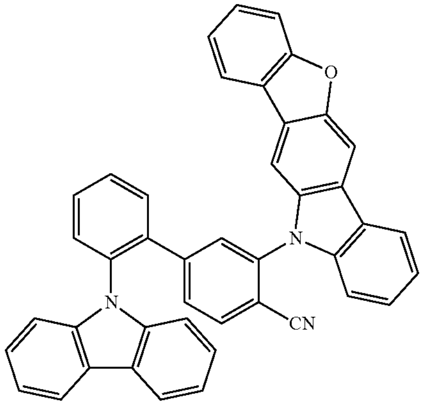
347
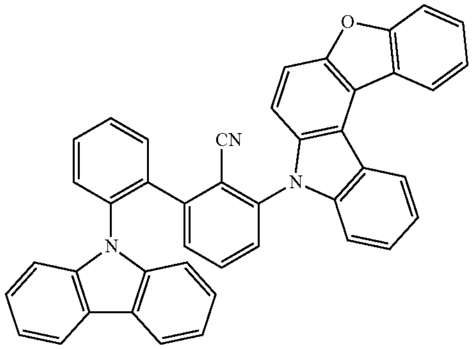
-continued
348
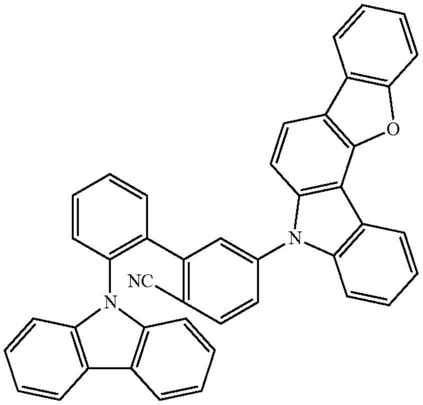
349
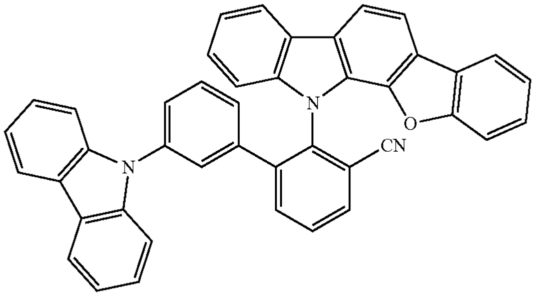
350
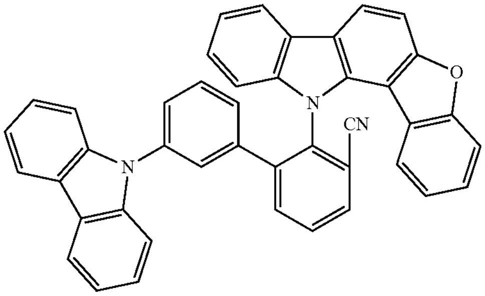
351
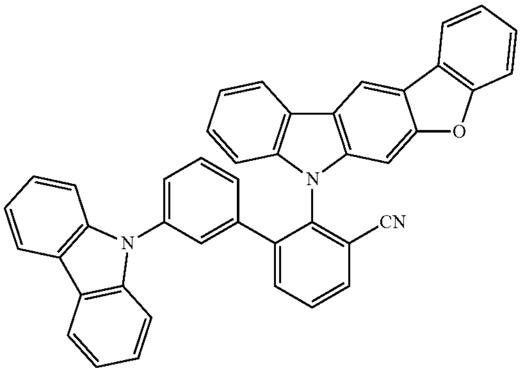

-continued
352
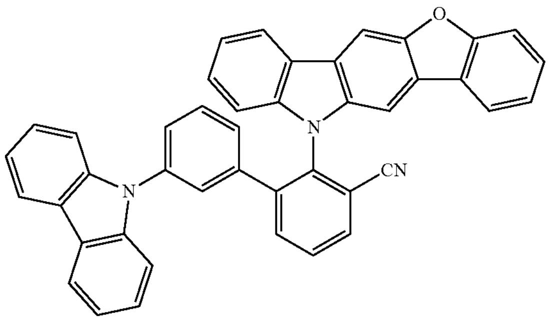
353
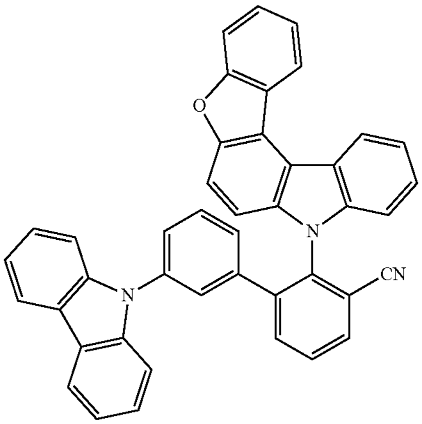
354
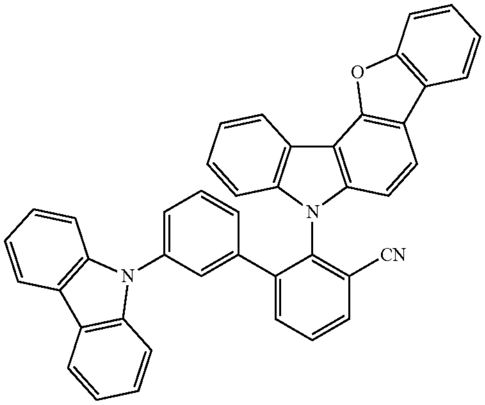
355
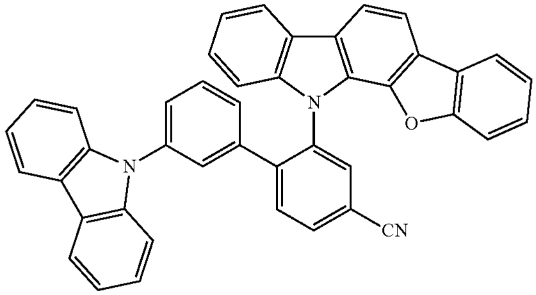
-continued
356
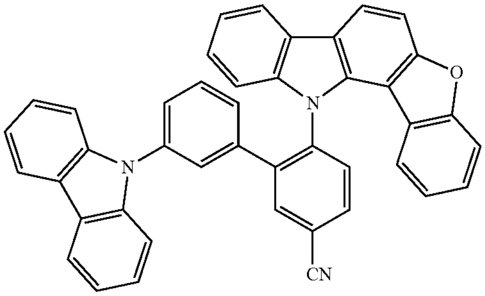
357
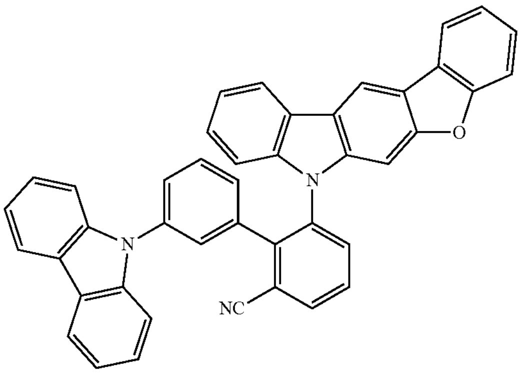
358
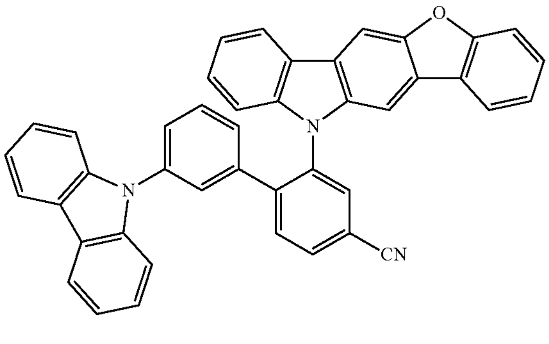
359
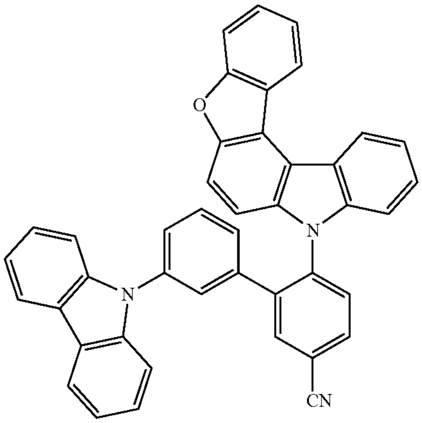

-continued
360
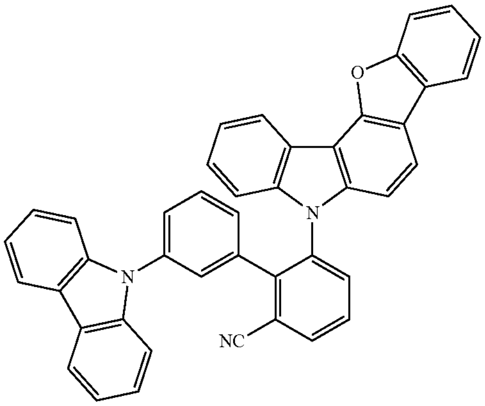
361
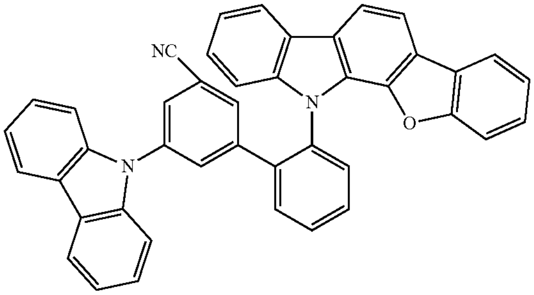
362
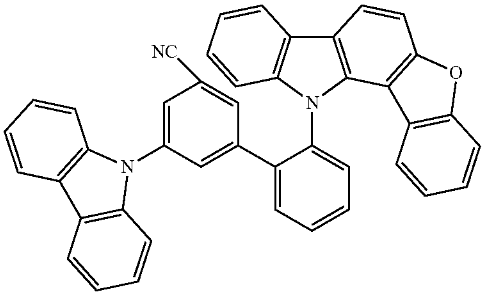
363
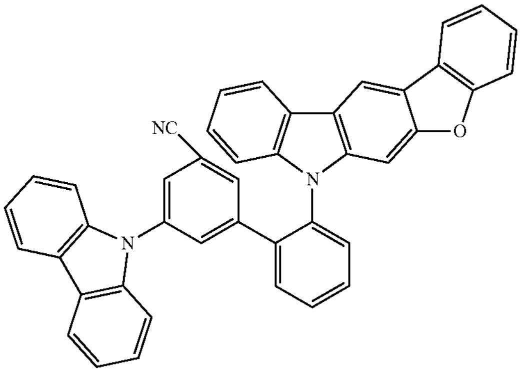
-continued
364
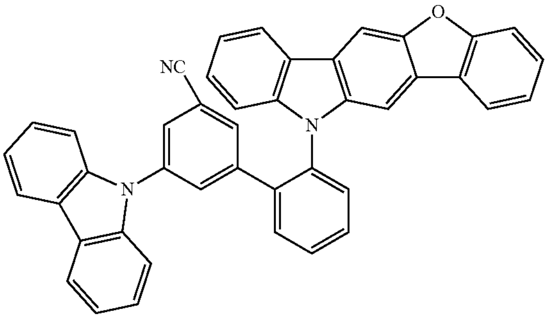
365
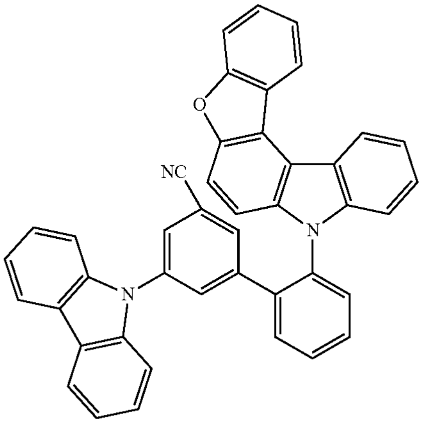
366
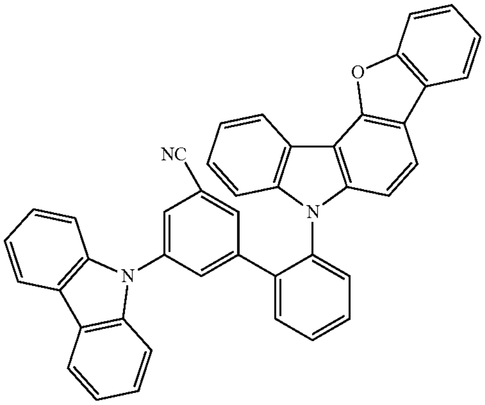
367
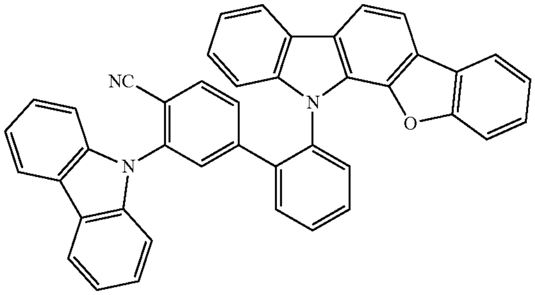

-continued
368
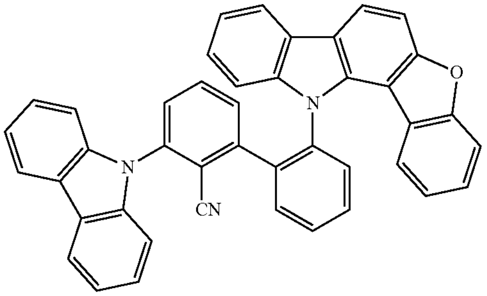
369
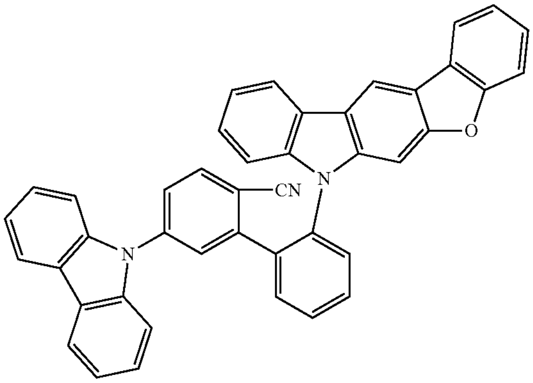
370
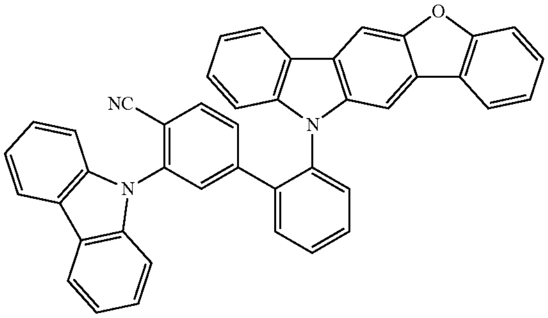
371
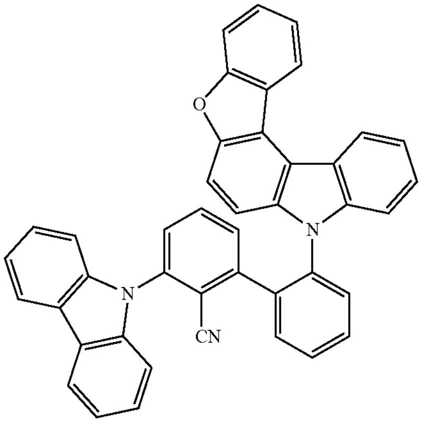
-continued
372
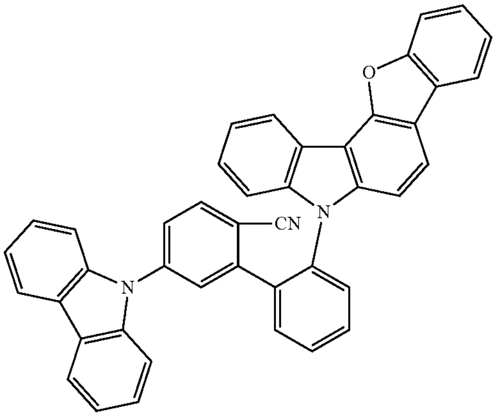
373
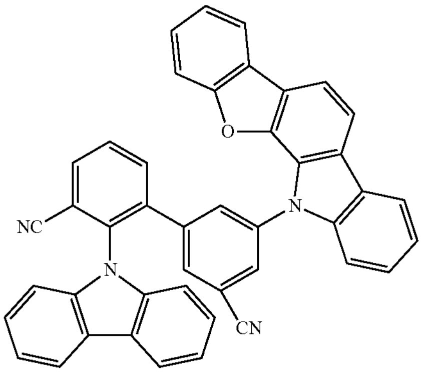
374
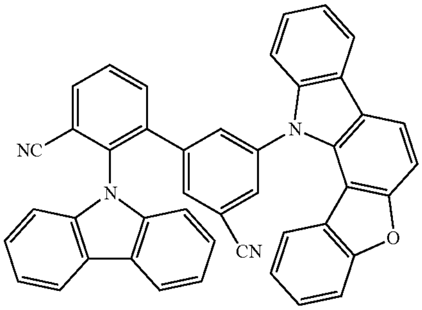
375
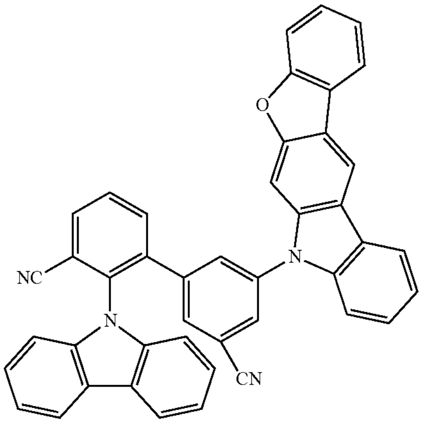

-continued
376
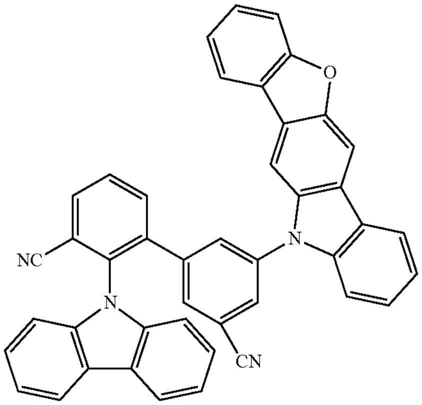
377
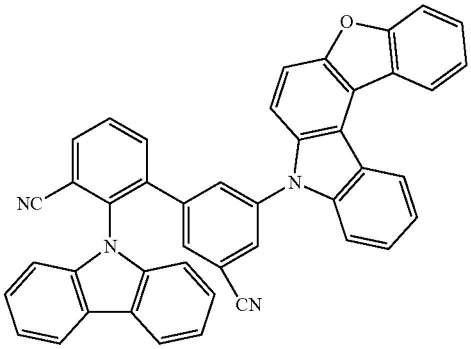
378
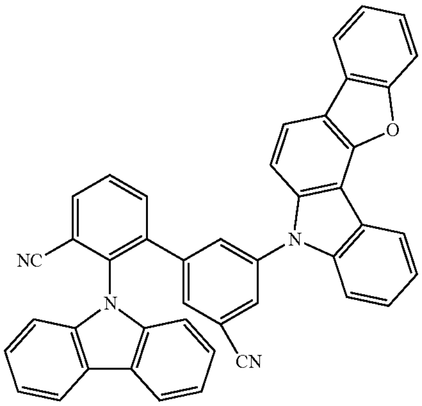
379
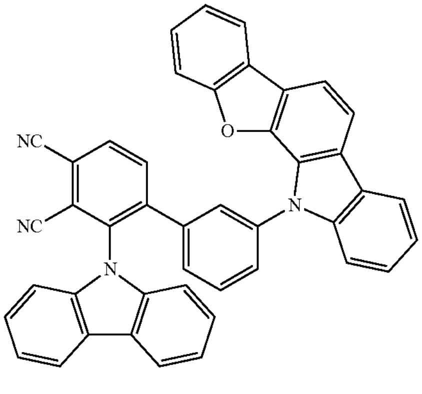
-continued
380
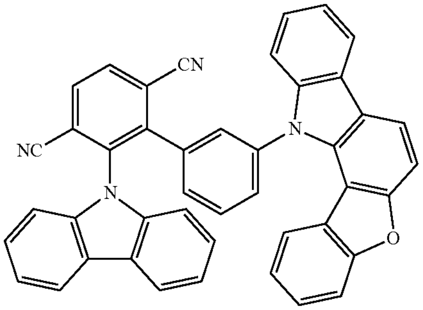
381
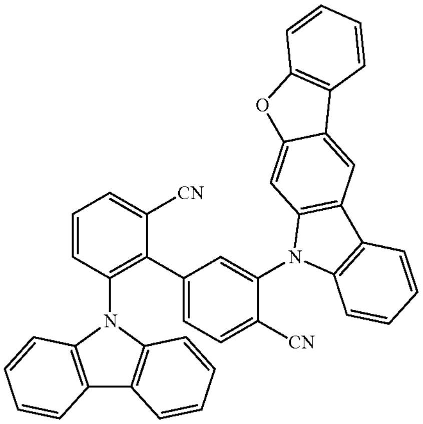
382
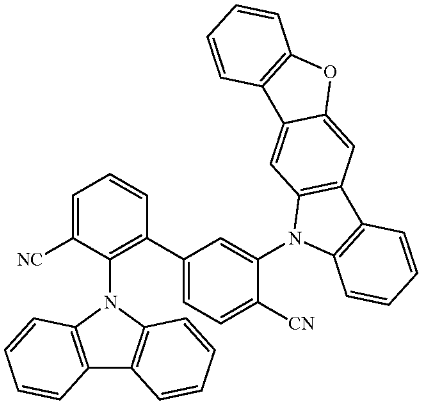
383
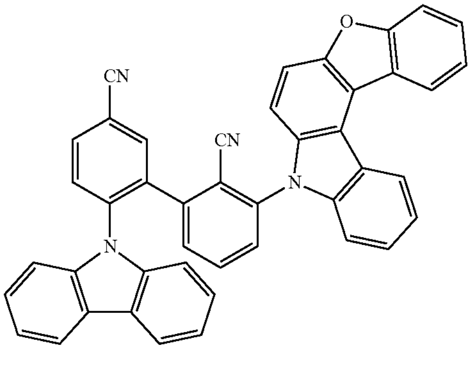

384
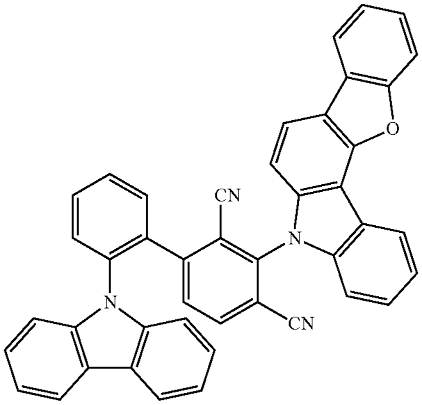
385
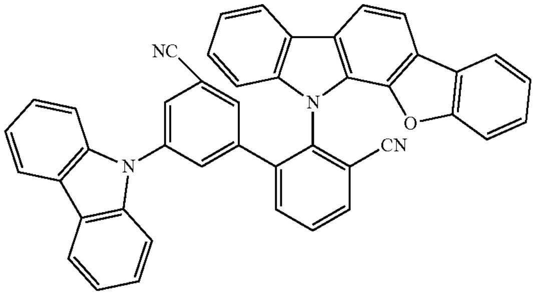
386
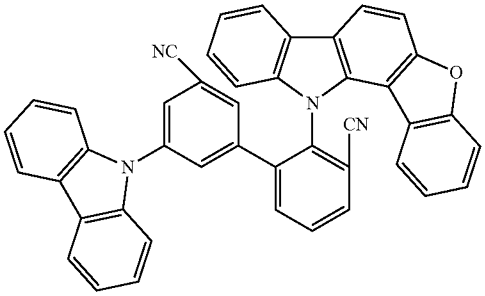
387
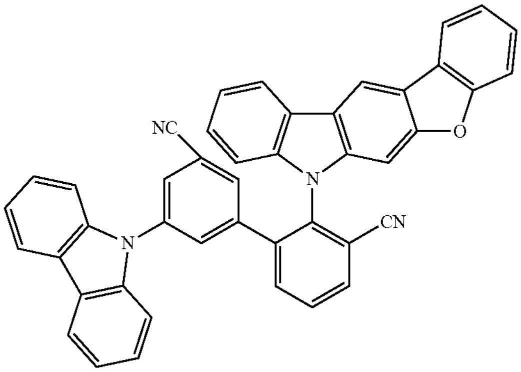
388
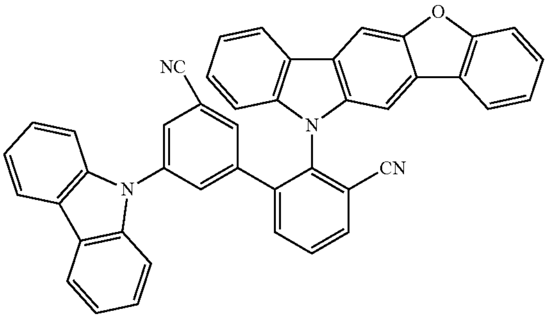
389
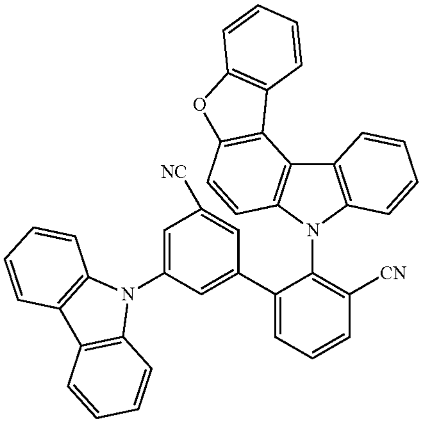
390
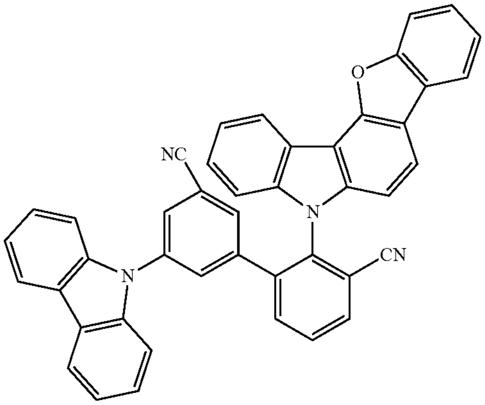
391
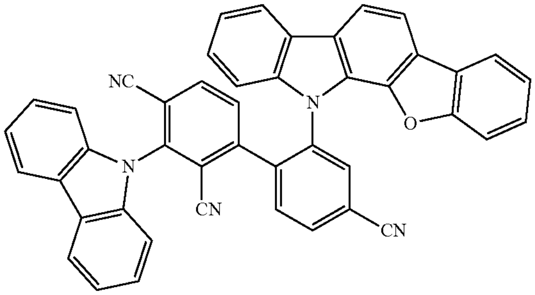

-continued
392
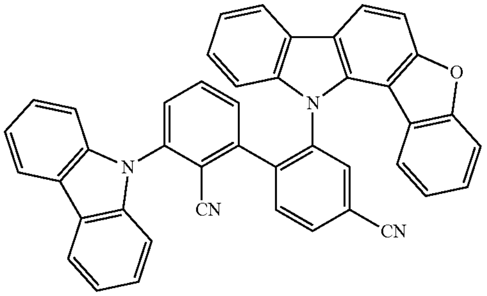
393
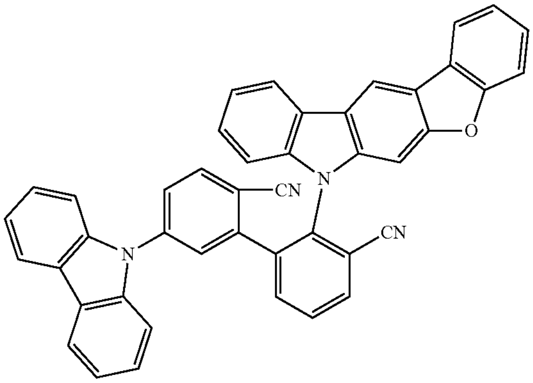
394
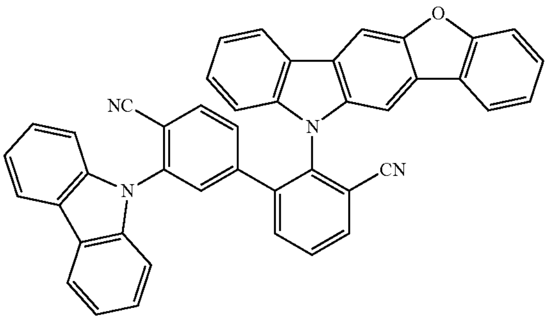
395
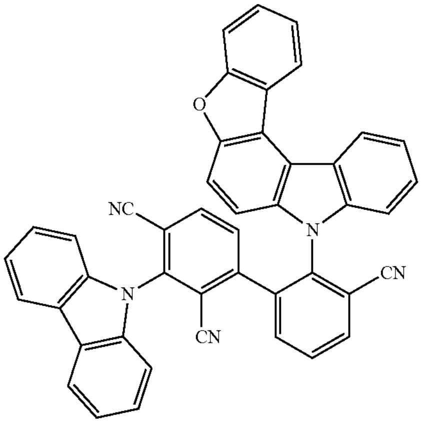
-continued
396
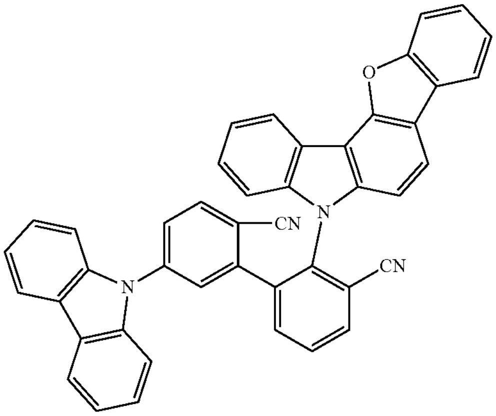
397
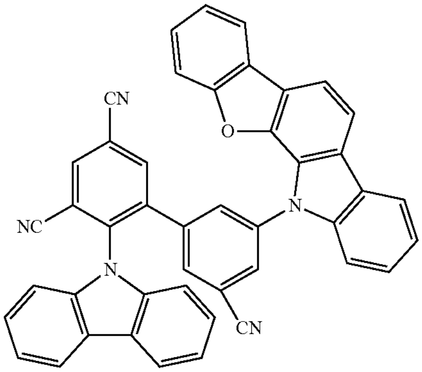
398
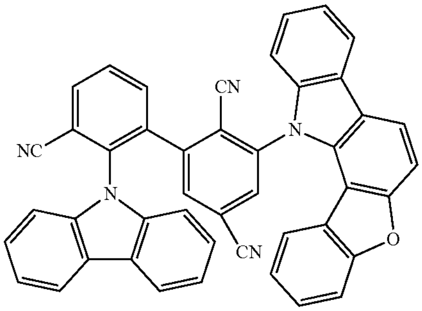
399
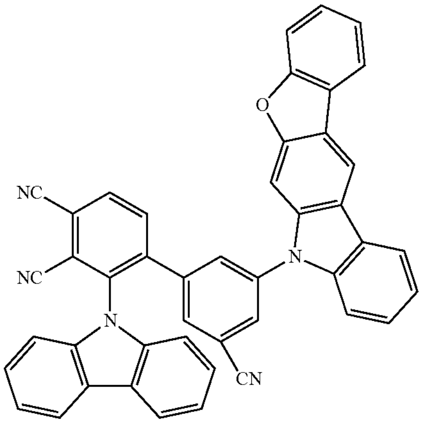

-continued
400
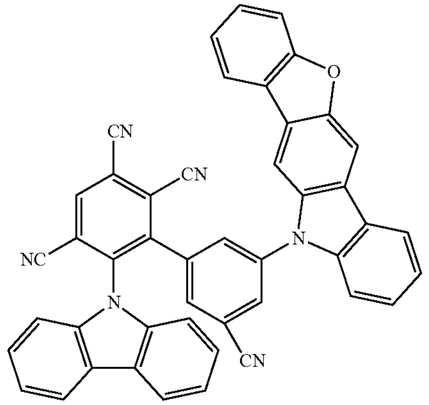
401
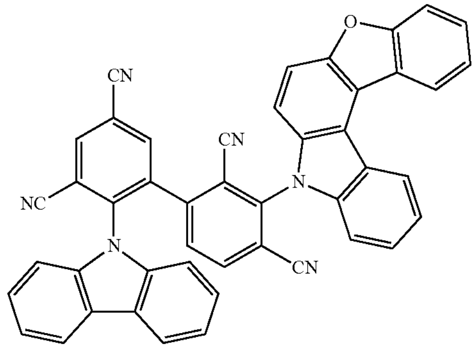
402
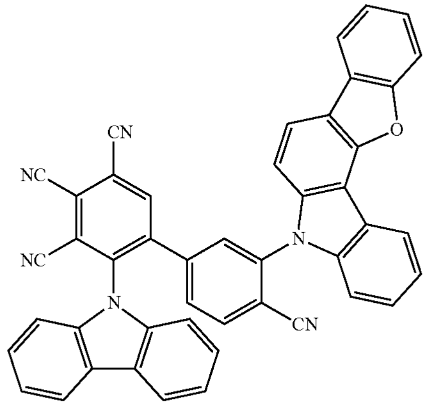
403
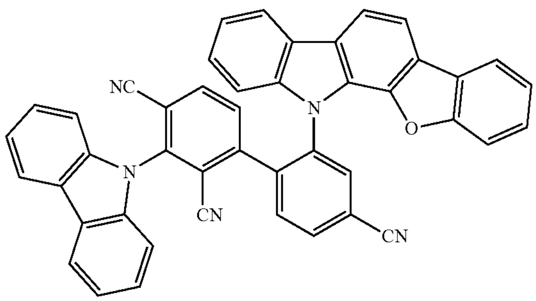
-continued
404
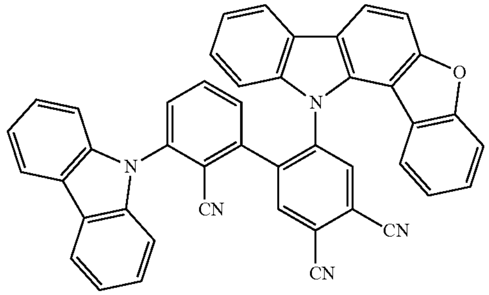
405
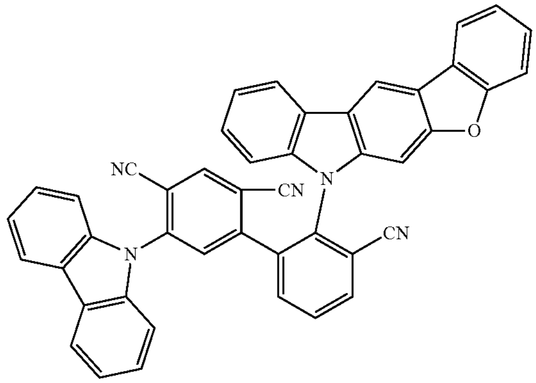
406
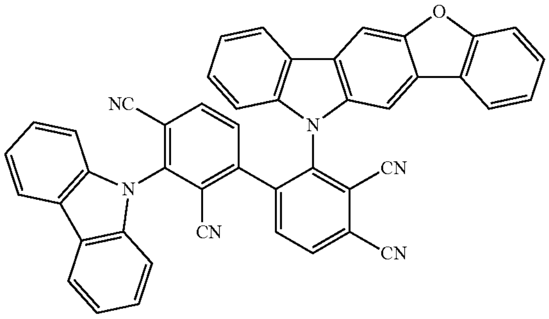
407
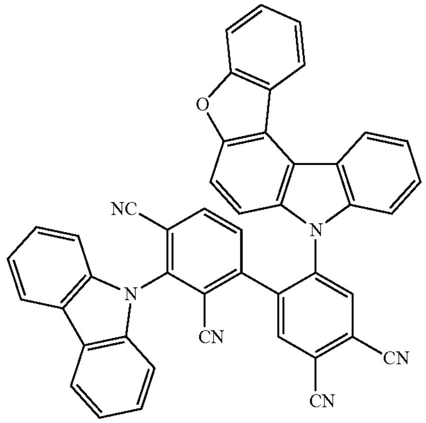

-continued
408
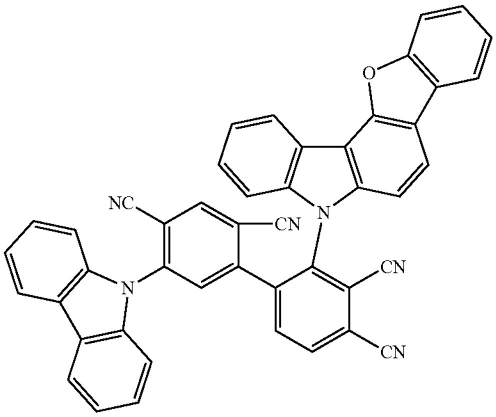
409
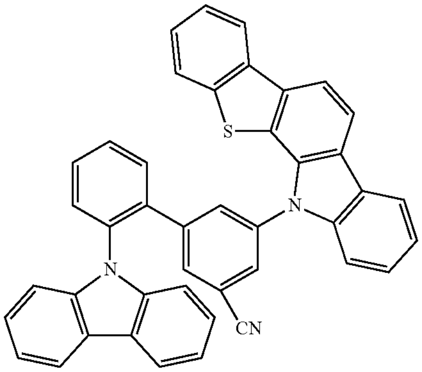
410
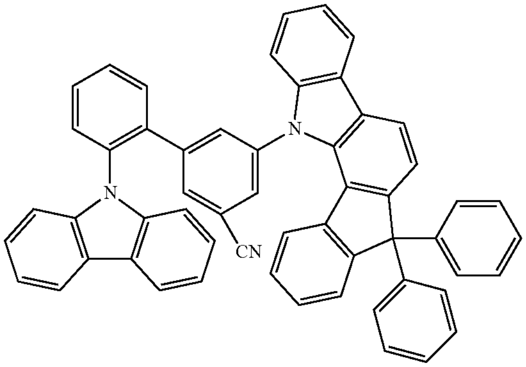
411
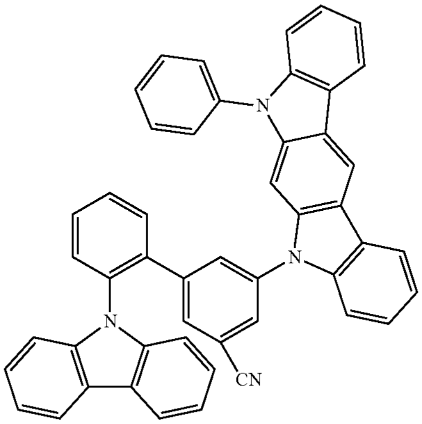
-continued
412
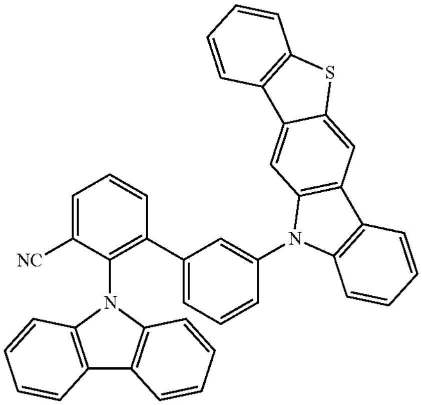
413
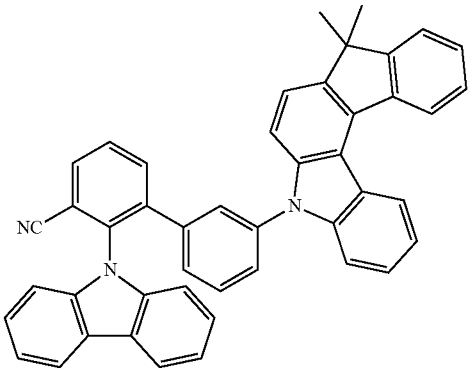
414
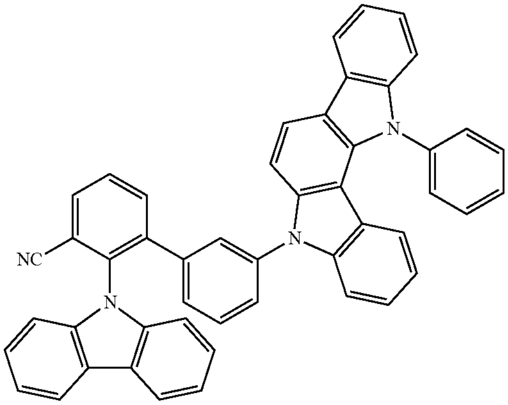
415
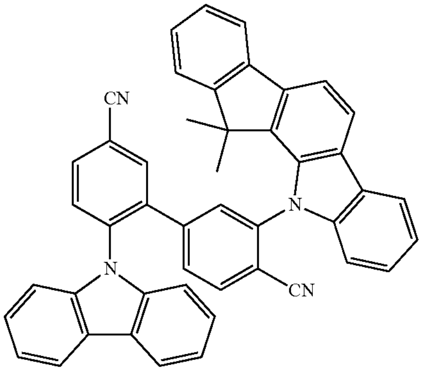

-continued
416
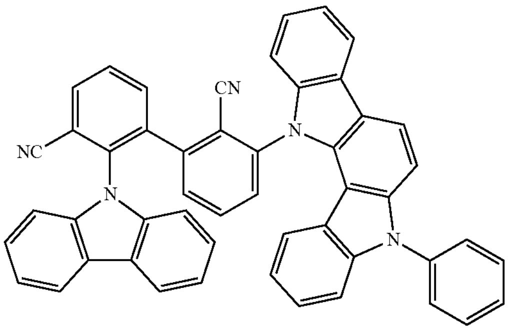
417
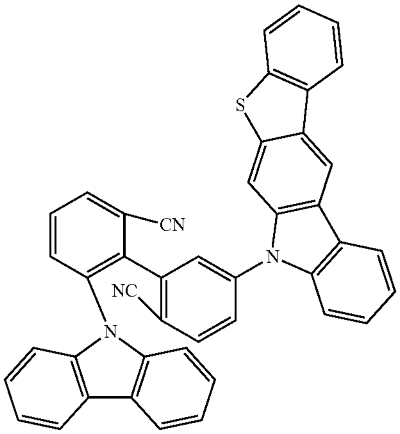
418
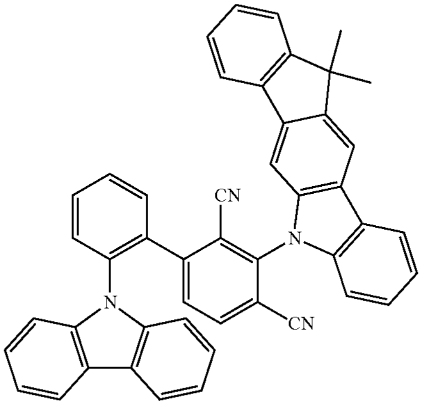
419
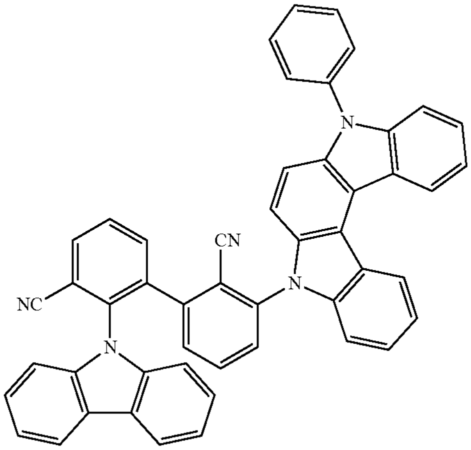
-continued
420
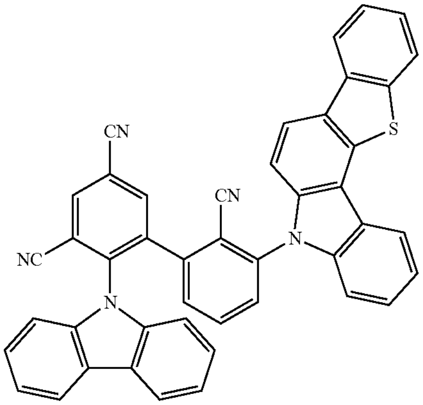
421
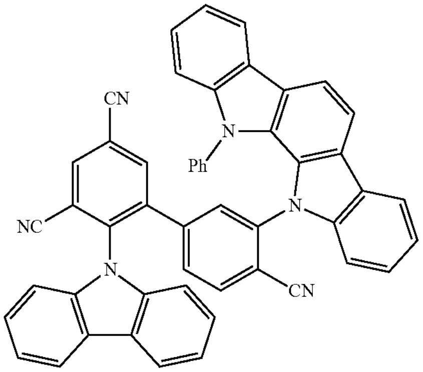
422
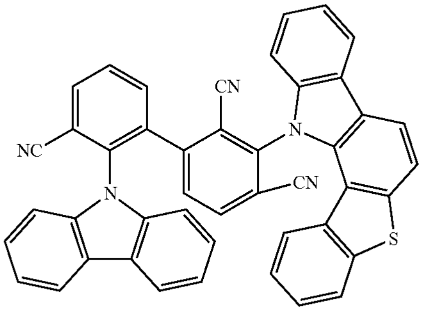
423
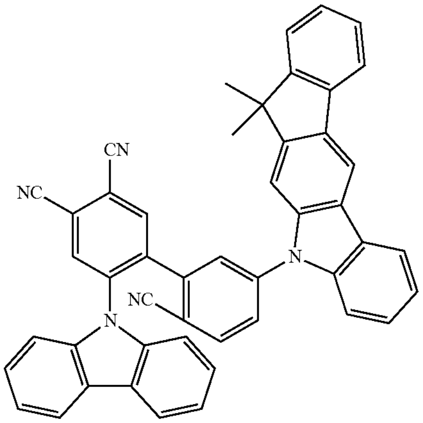

-continued
424
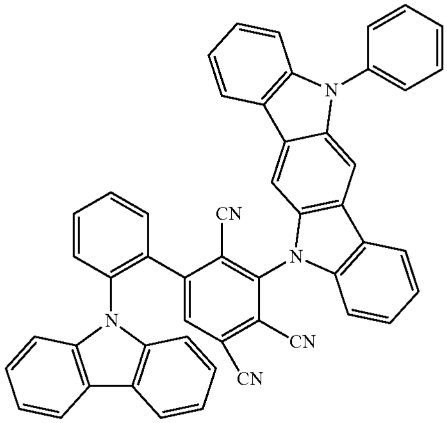
425
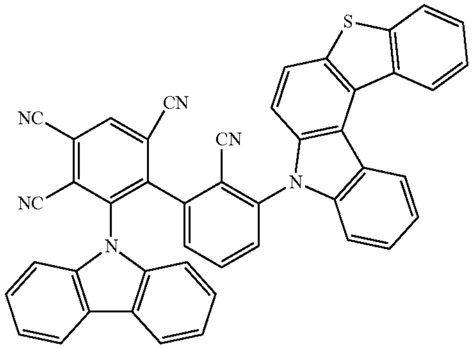
426
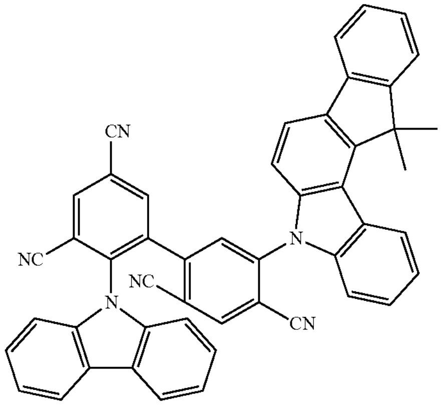
427
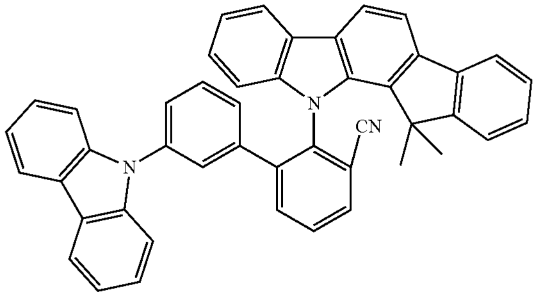
-continued
428
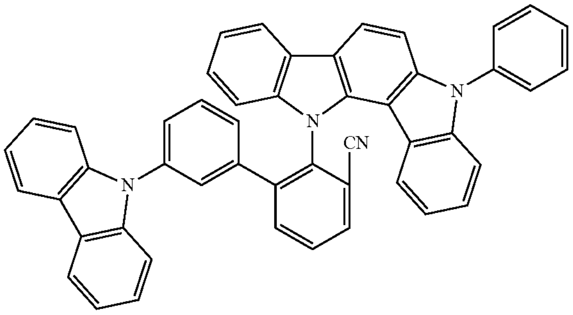
429
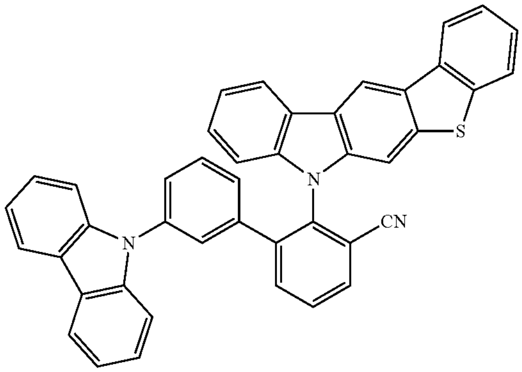
430
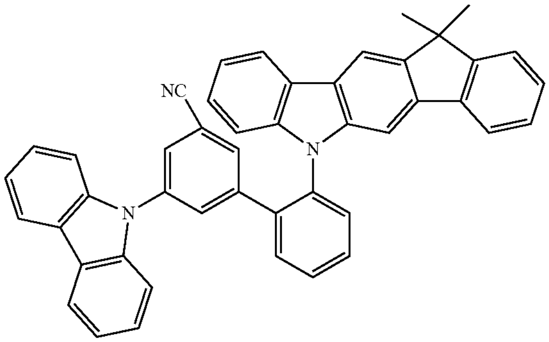
431
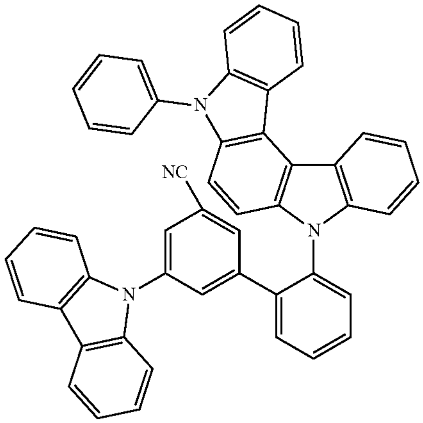

432
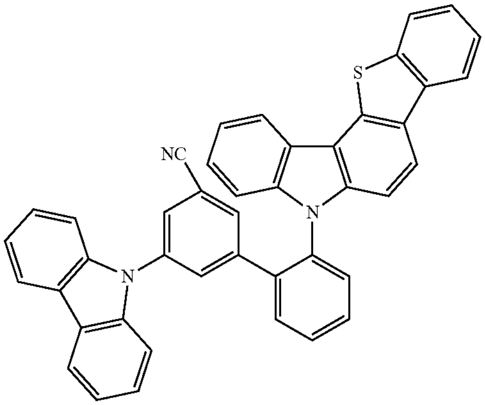
433
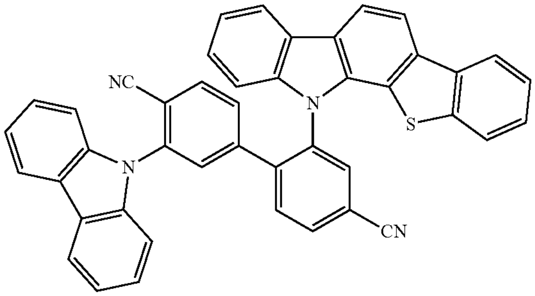
434
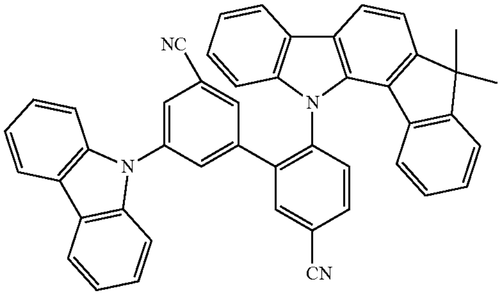
435
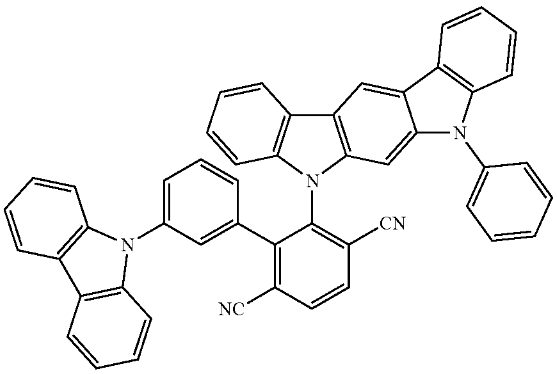
436
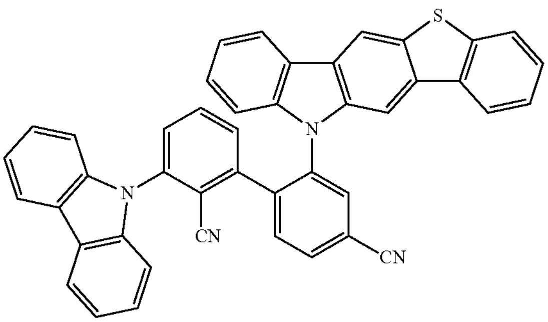
437
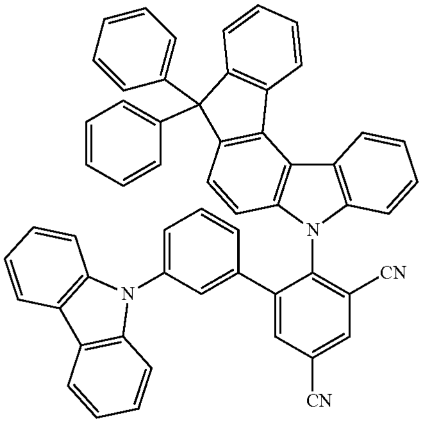
438
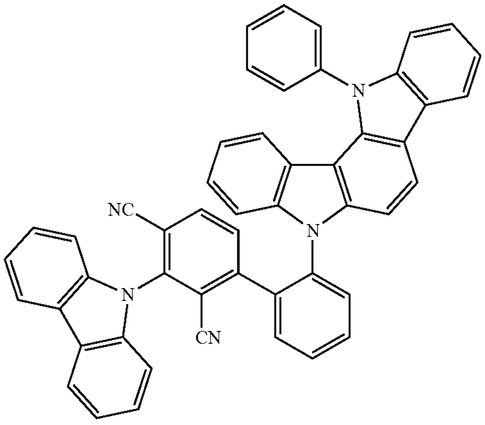
439
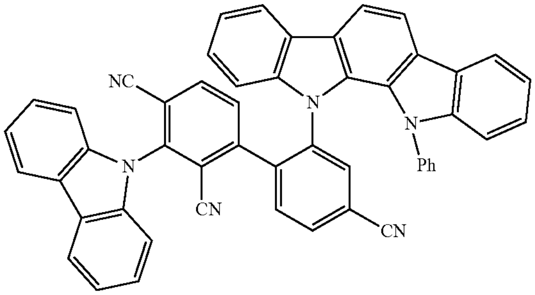

-continued
440
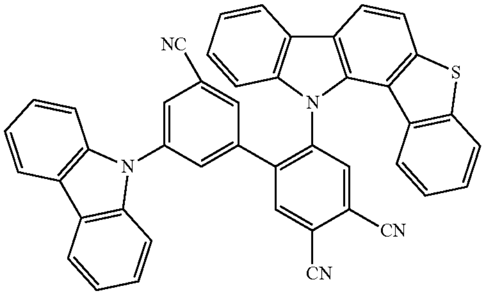
441
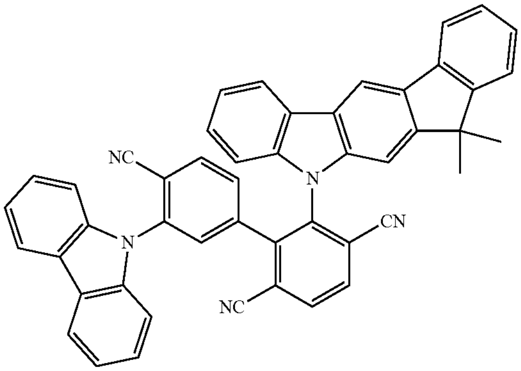
442
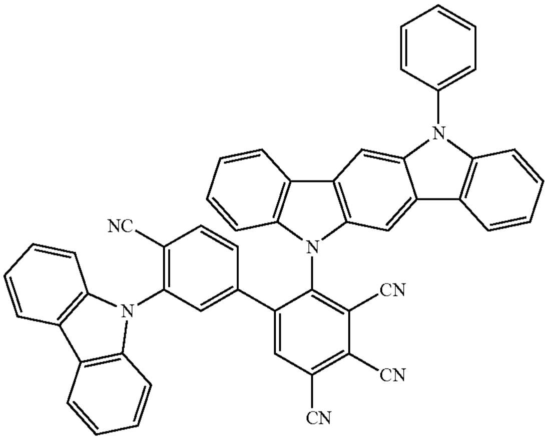
443
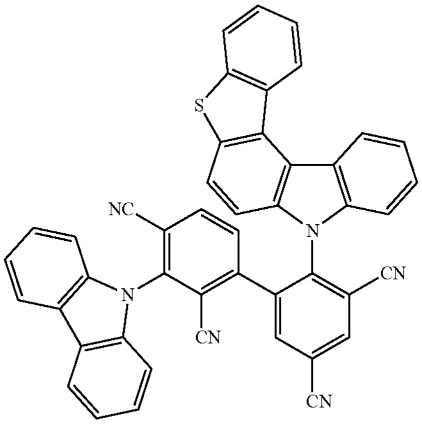
-continued
444
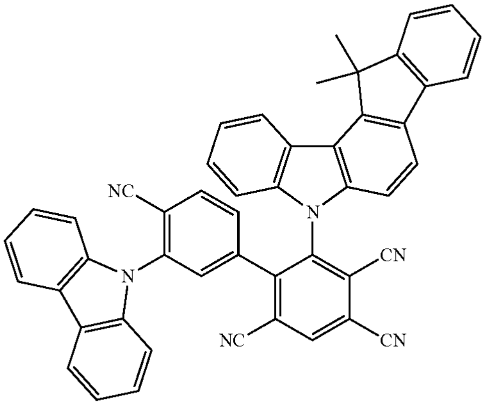
445
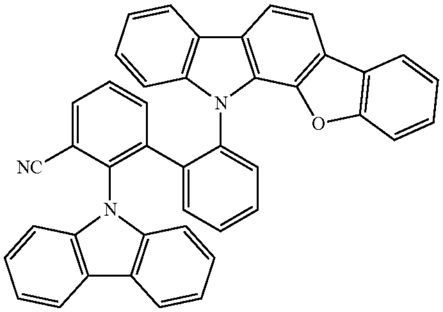
446
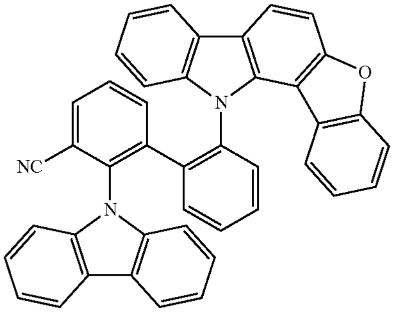
447
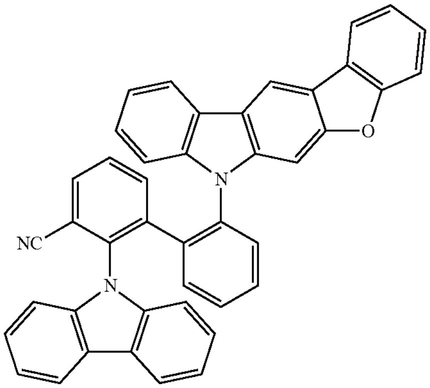

-continued
448
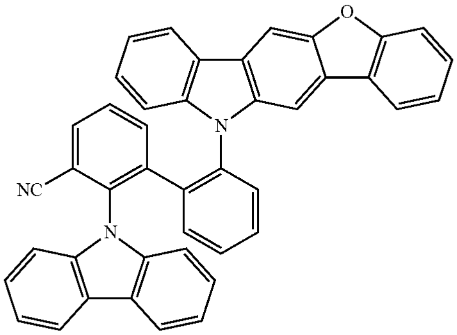
449
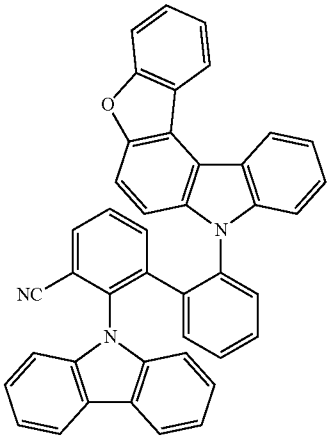
450
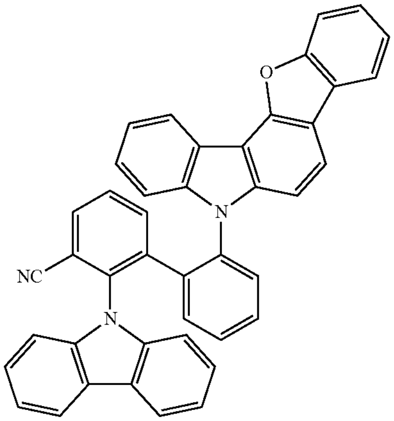
451
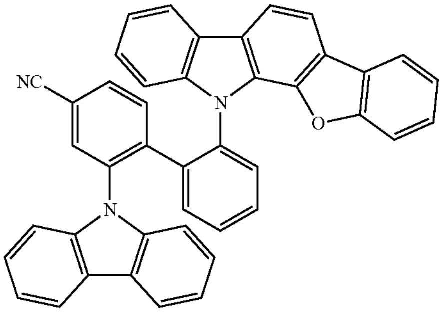
-continued
452
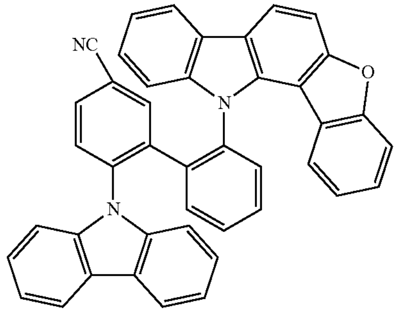
453
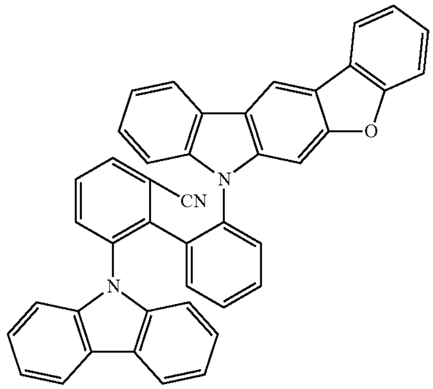
454
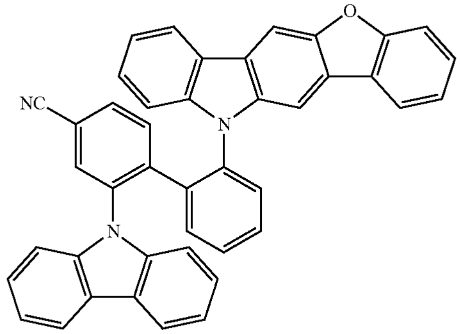
455
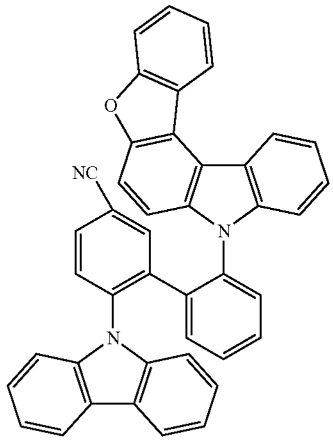

-continued
456
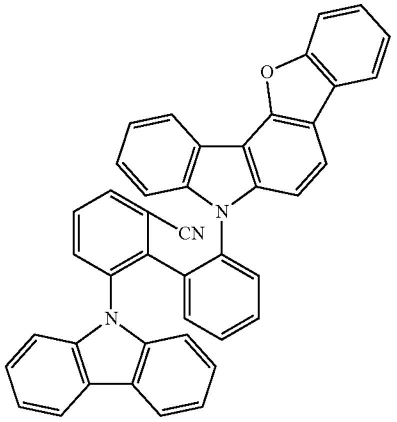
457
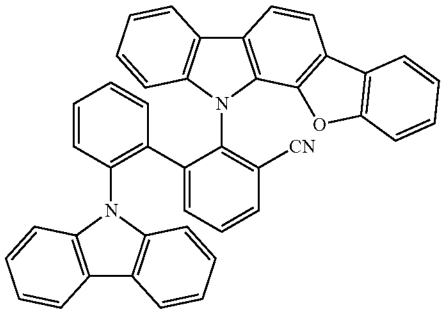
458
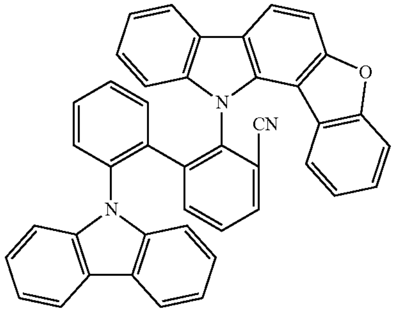
459
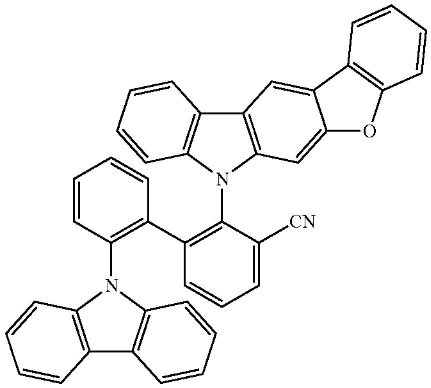
-continued
460
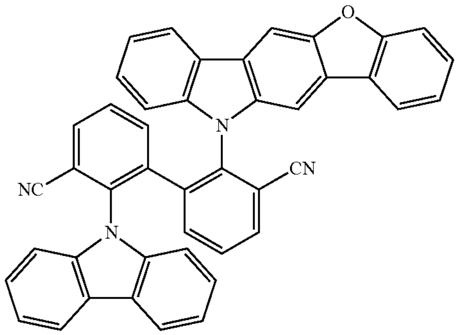
461
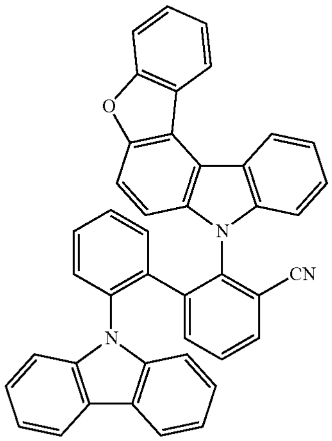
462
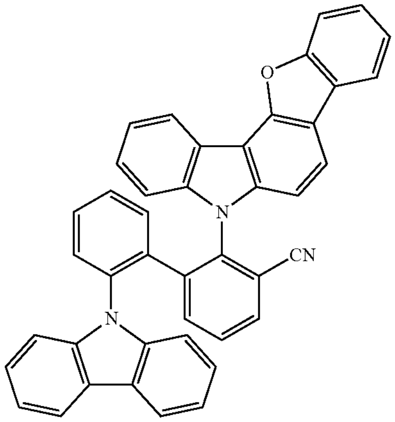
463
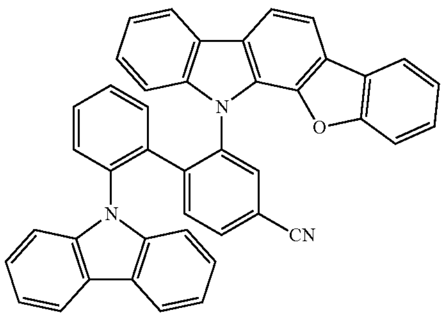

-continued
464
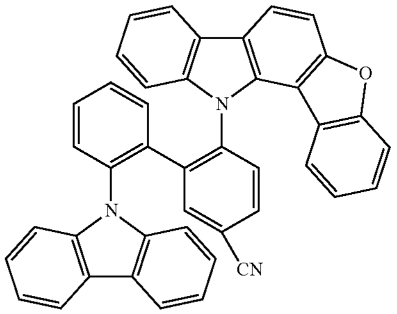
465
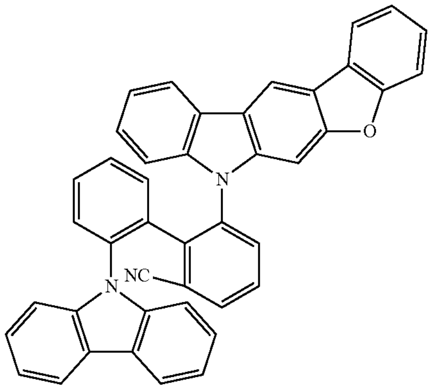
466
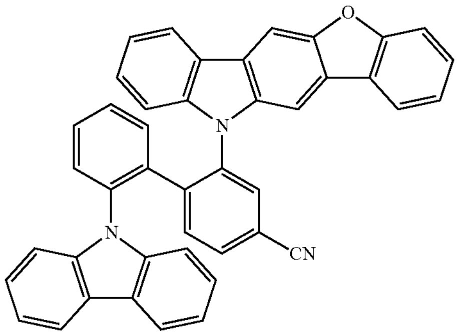
467
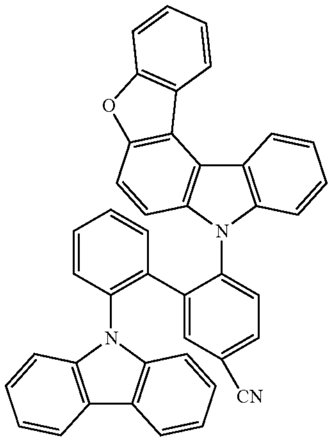
-continued
468
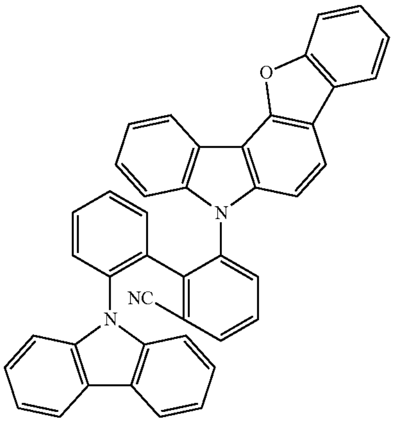
469
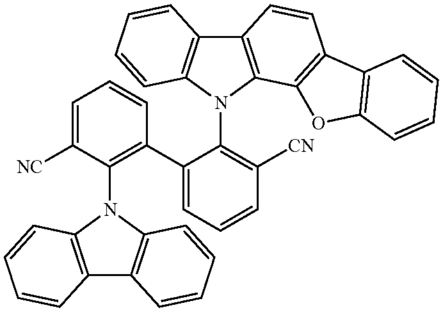
470
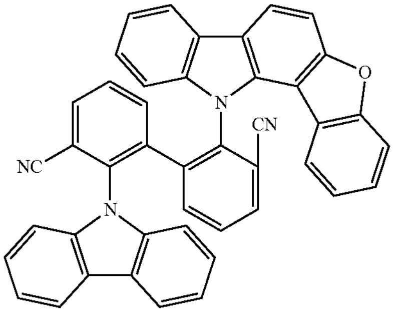
471
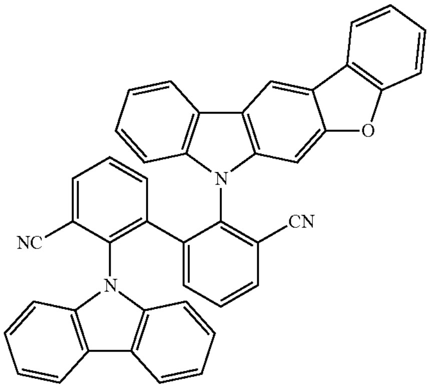

-continued
472
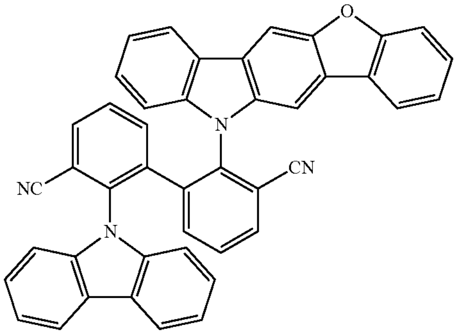
473
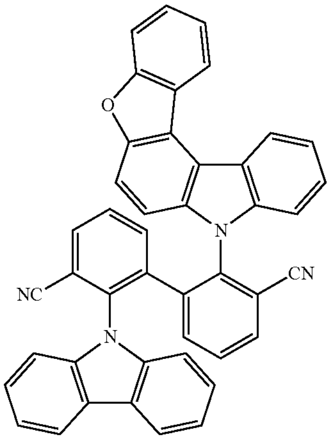
474
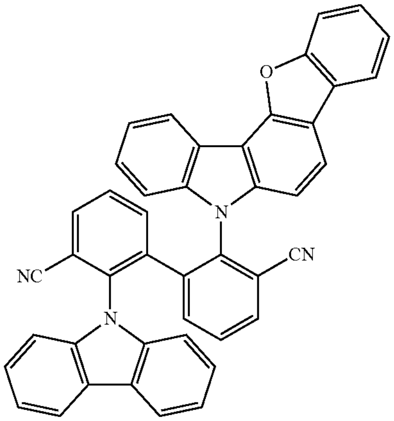
475
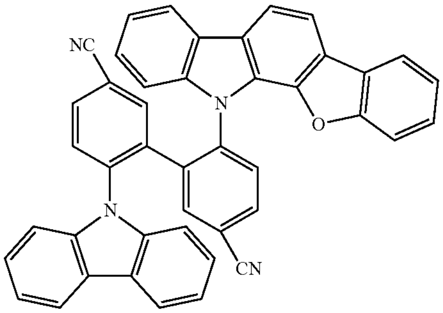
-continued
476
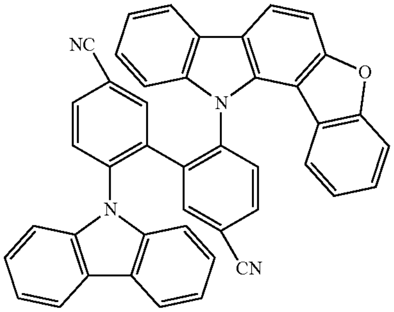
477
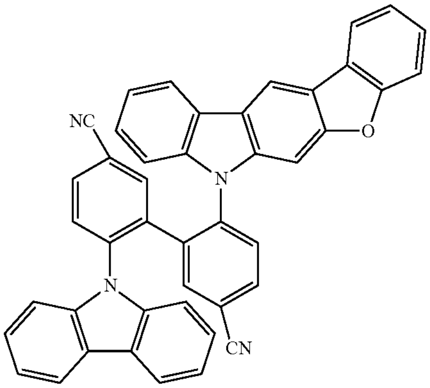
478
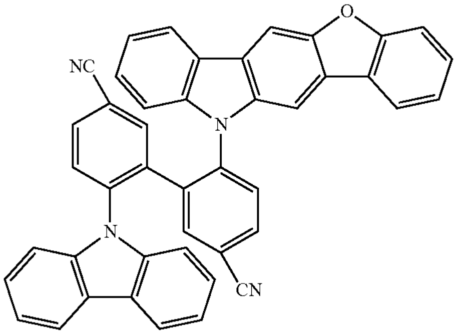
479
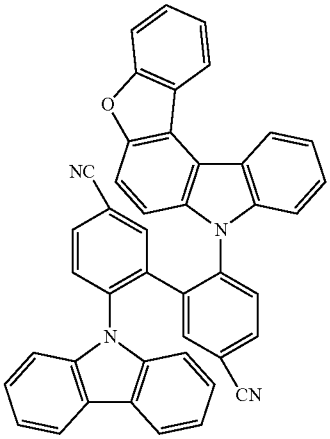

-continued
480
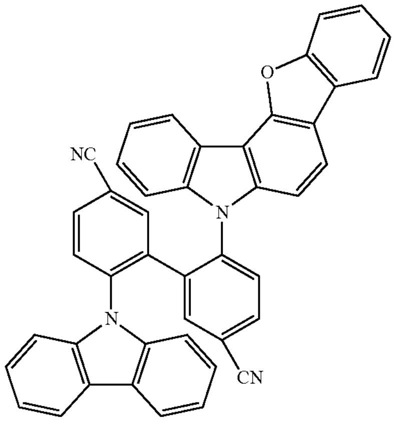
481
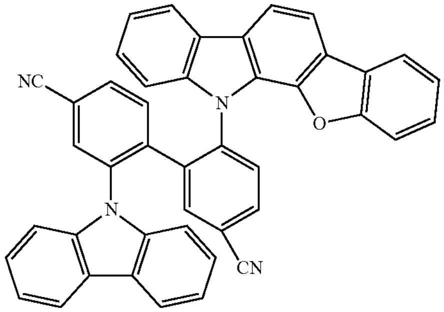
482
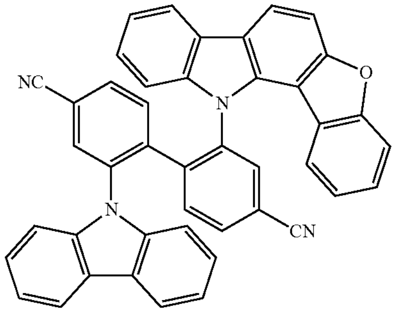
483
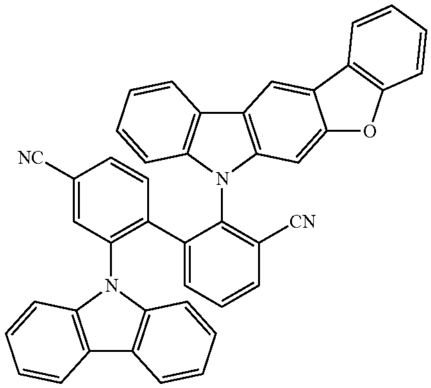
-continued
484
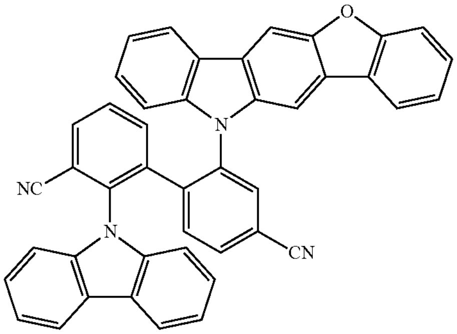
485
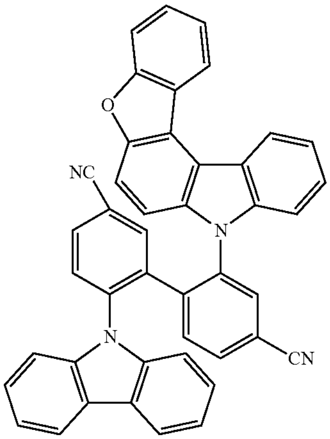
486
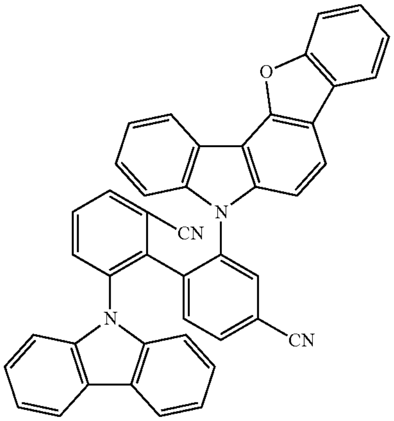
487
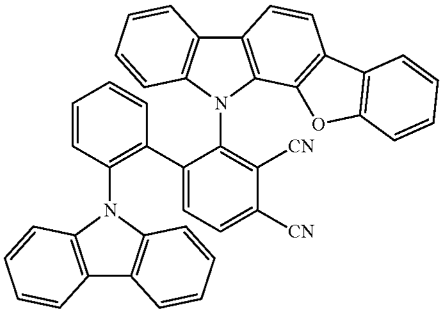

-continued
488
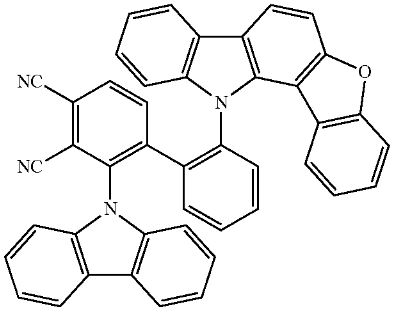
489
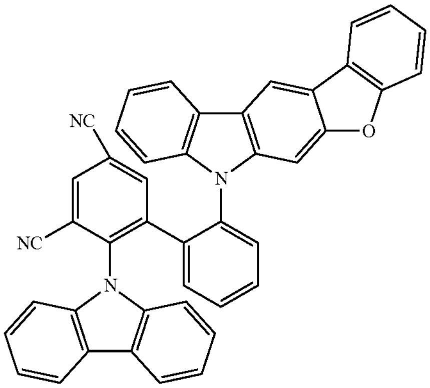
490
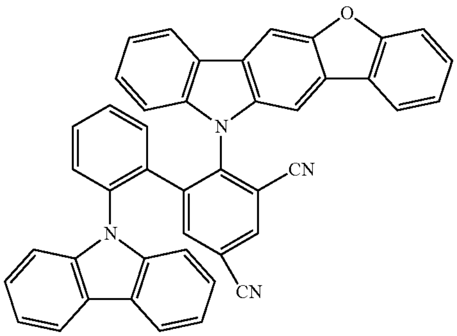
491
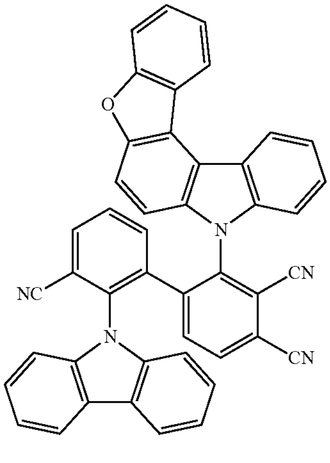
-continued
492
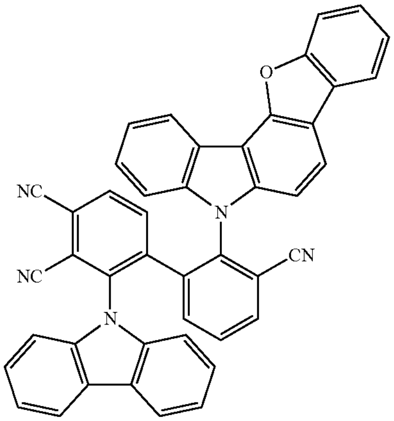
493
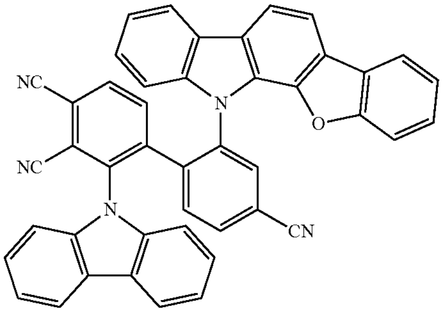
494
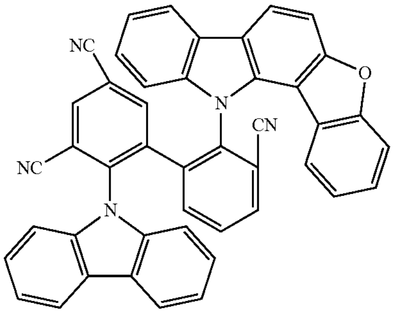
495
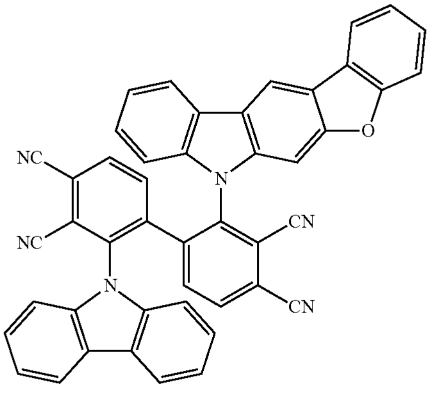

-continued
496
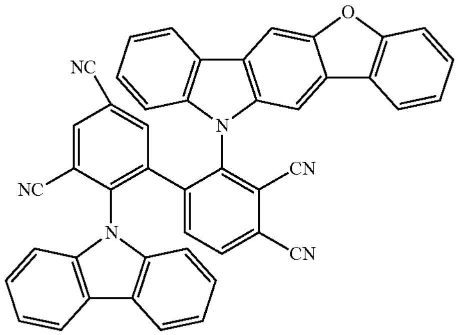
497
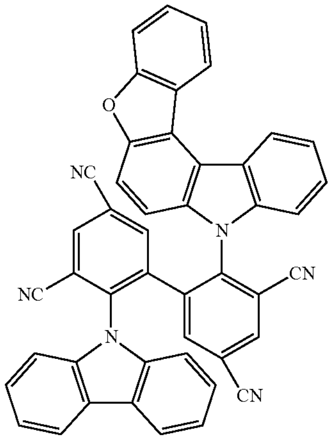
498
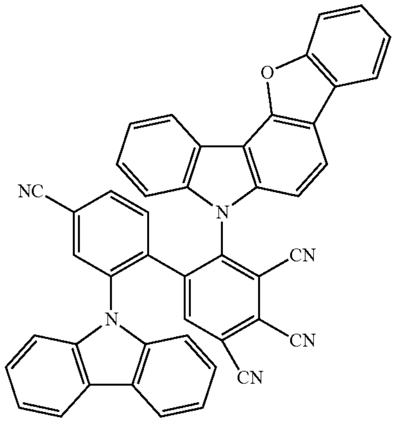
499
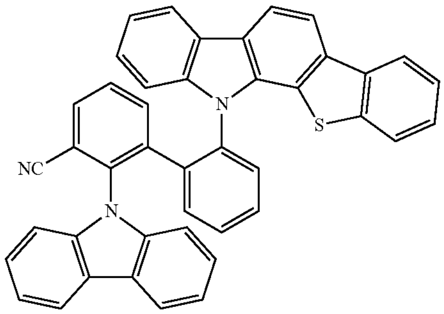
-continued
500
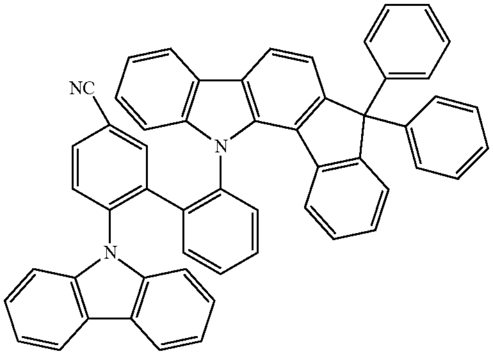
501
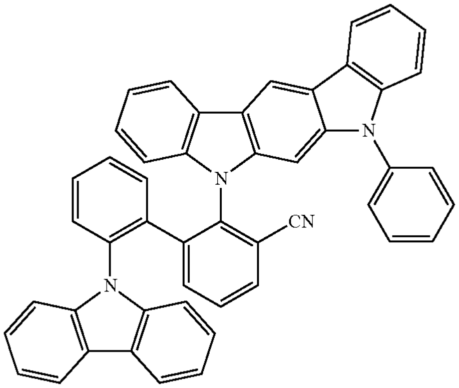
502
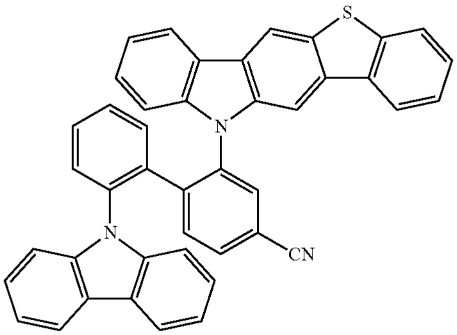
503
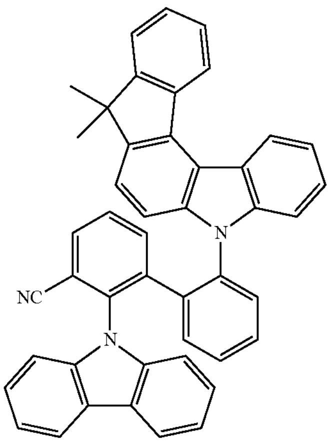

-continued
504
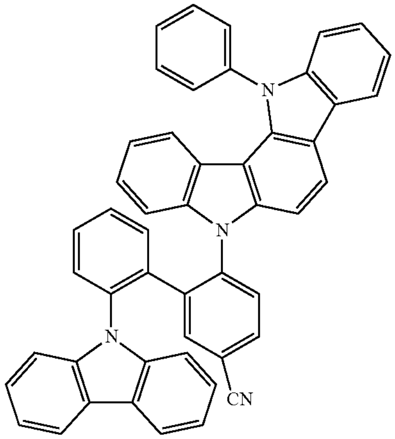
505
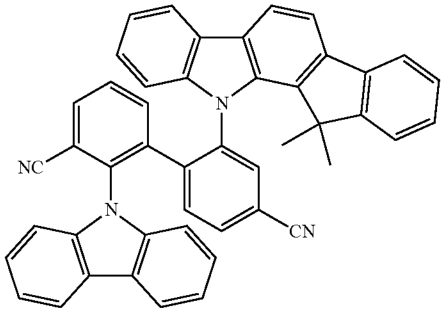
506
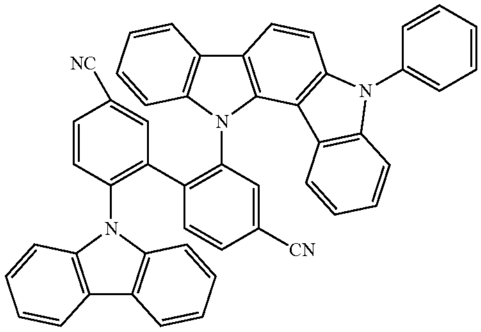
507
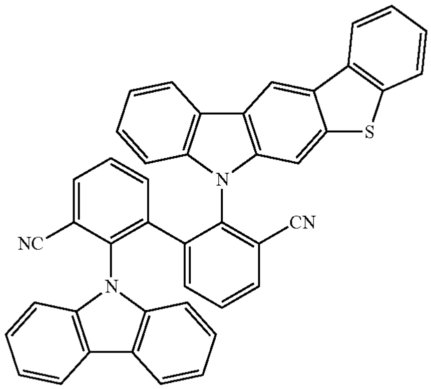
-continued
508
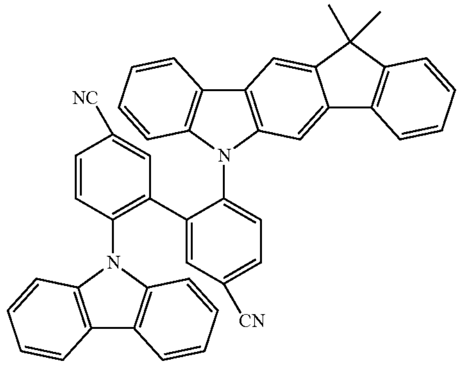
509
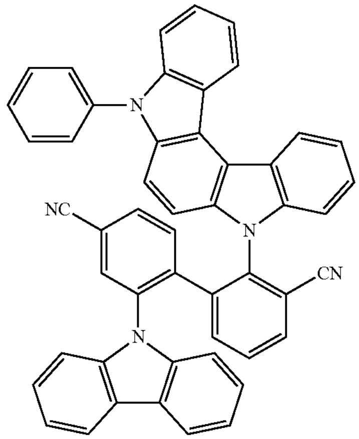
510
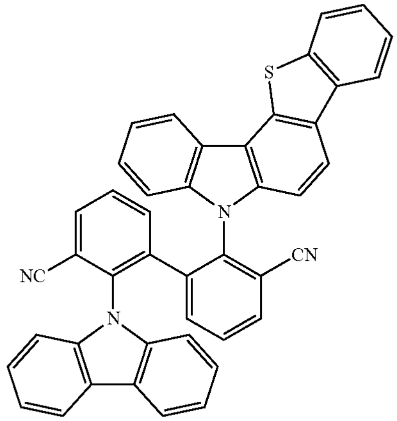
511
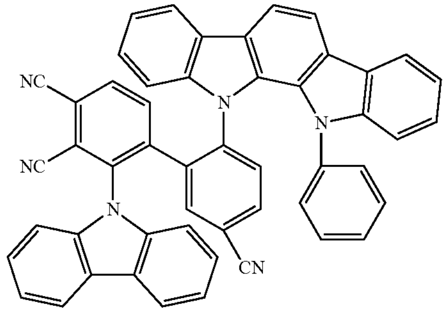

-continued
512
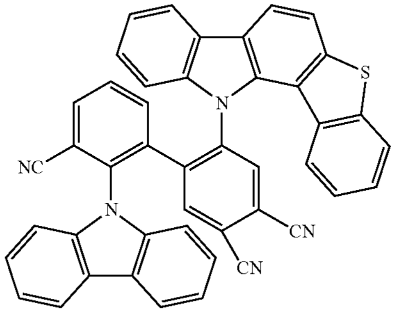
513
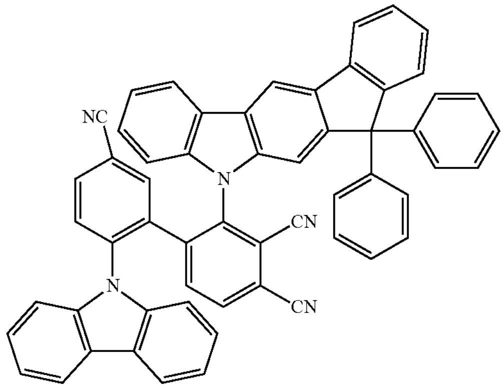
514
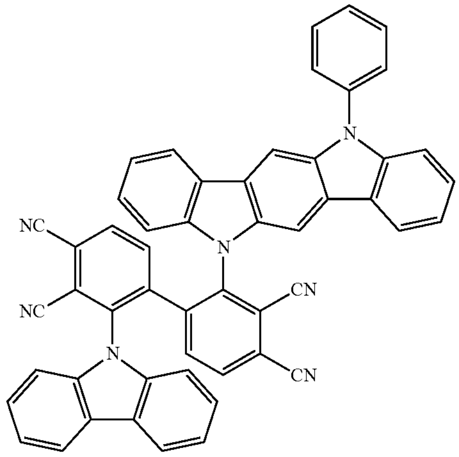
515
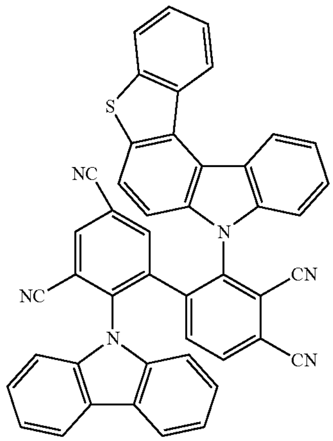
-continued
516
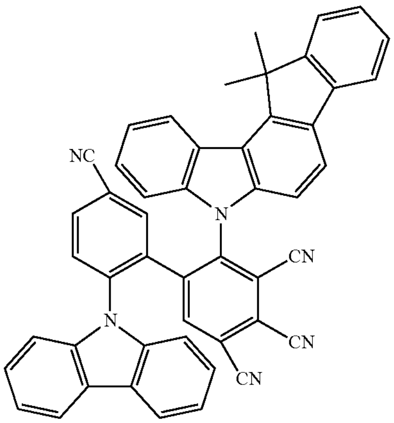
517
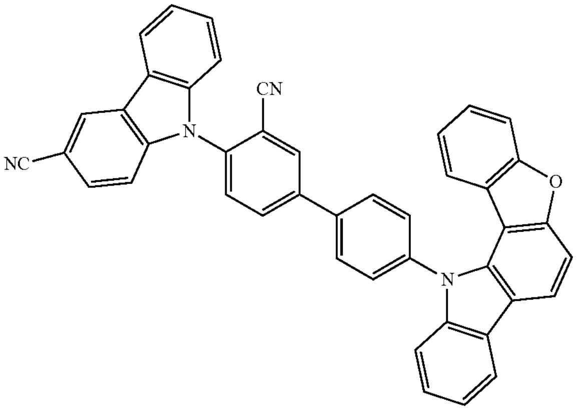
518
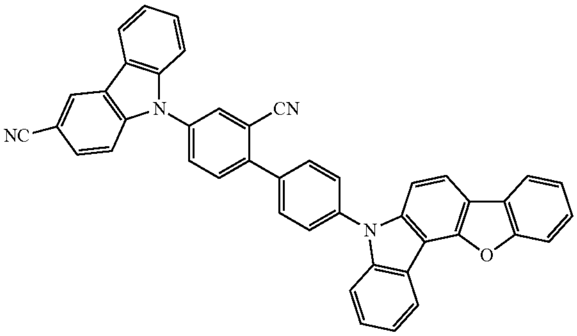
519
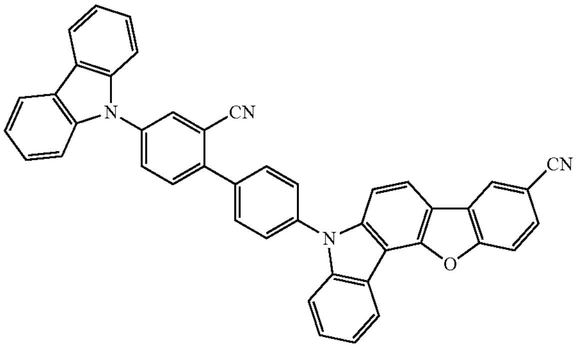

-continued
520
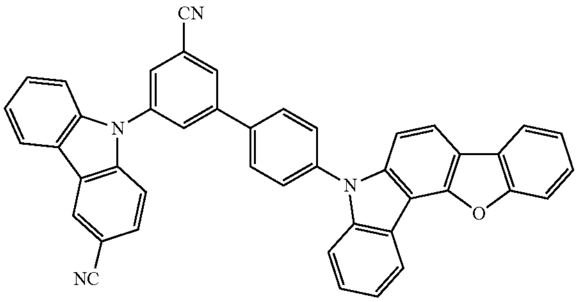
521
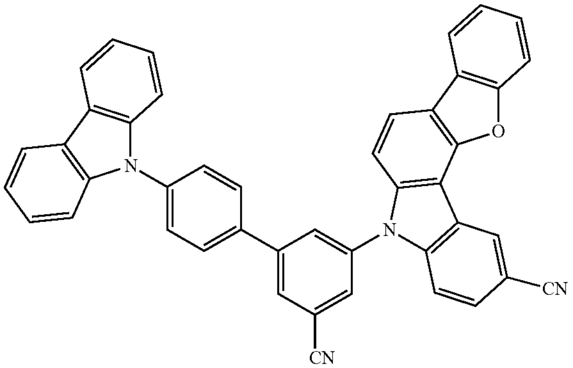
522
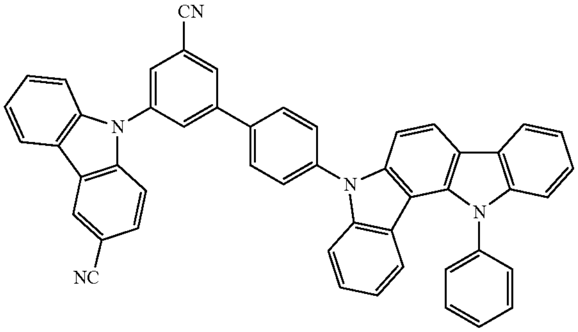
523
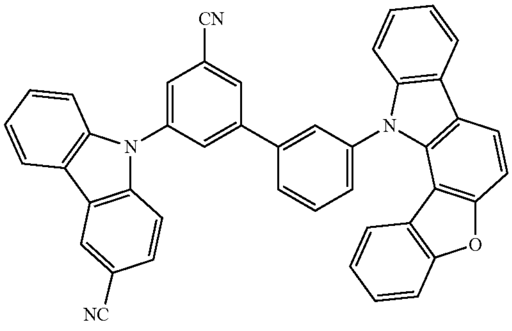
-continued
524
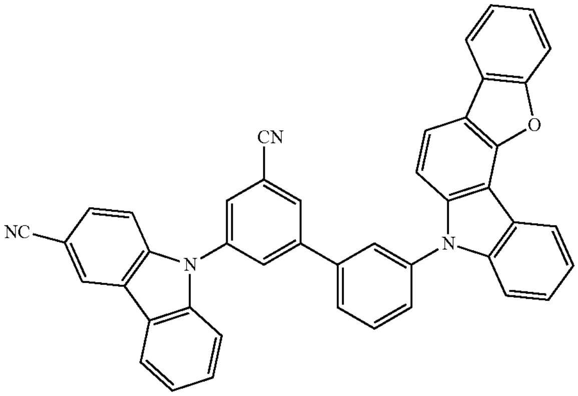
525
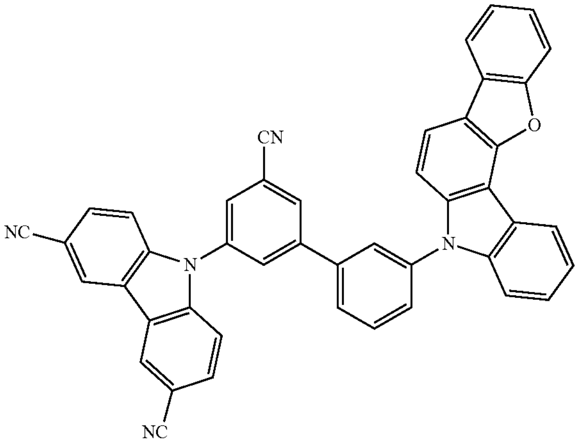
526
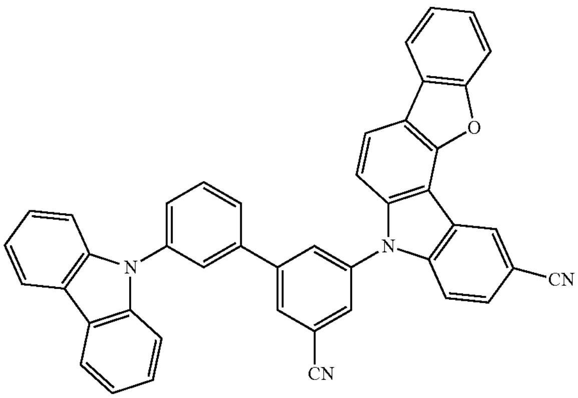

-continued
527
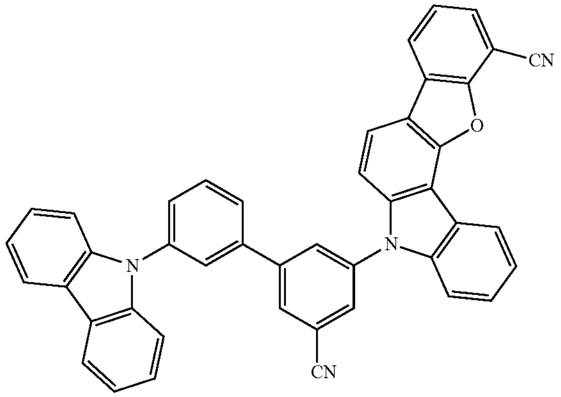
528
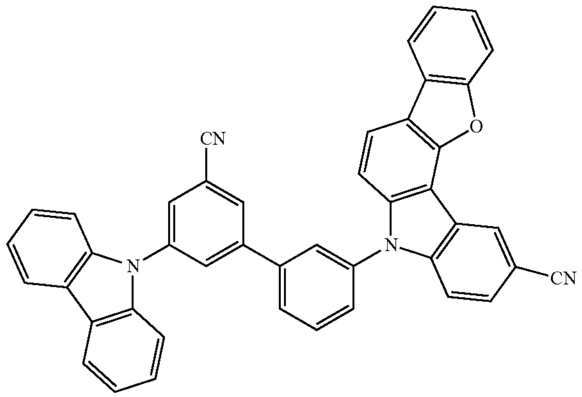
529
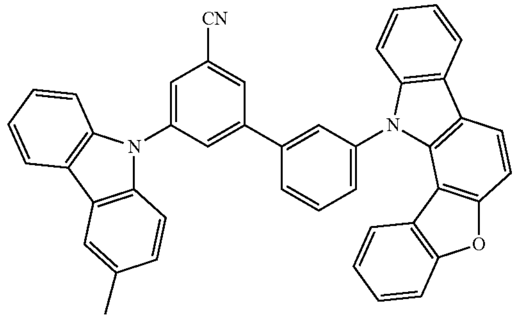
530
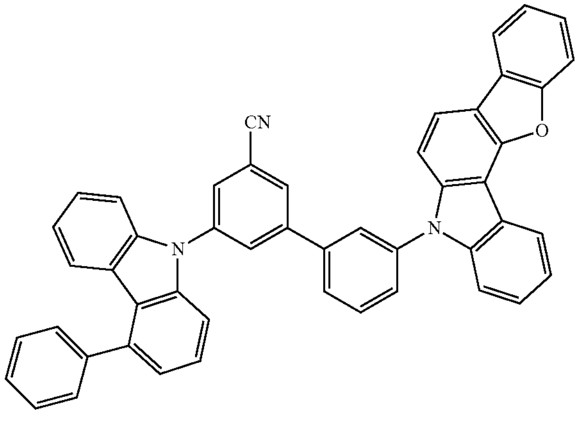
-continued
531
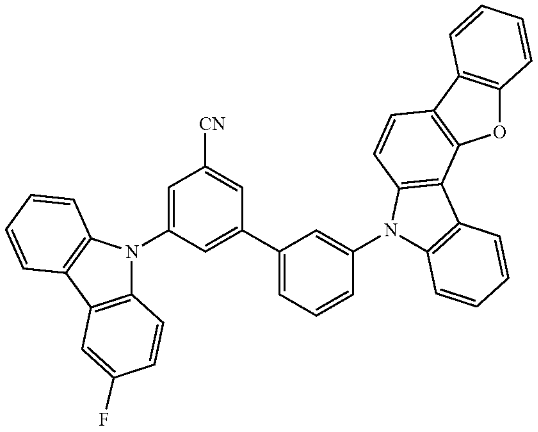
532
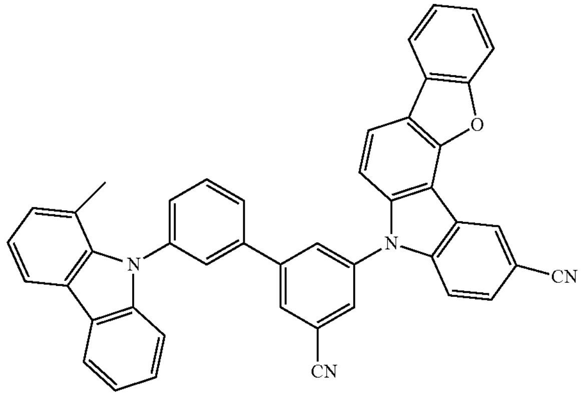
533
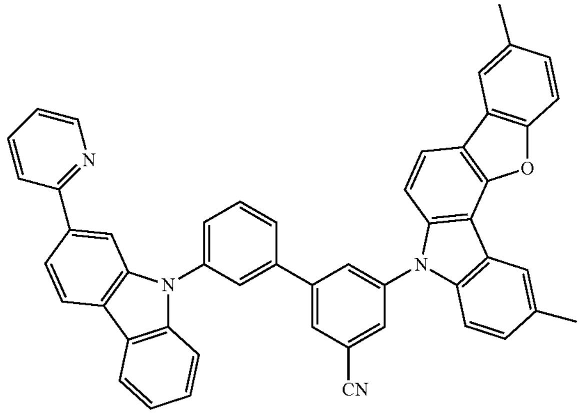

-continued
534
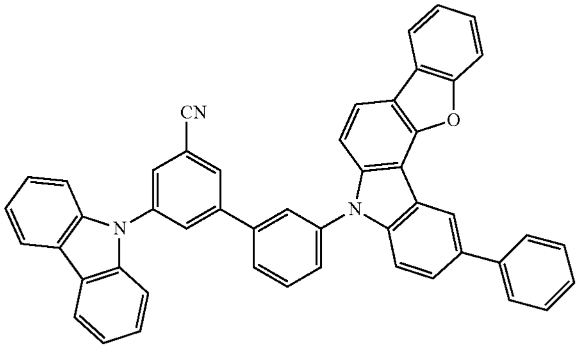
535
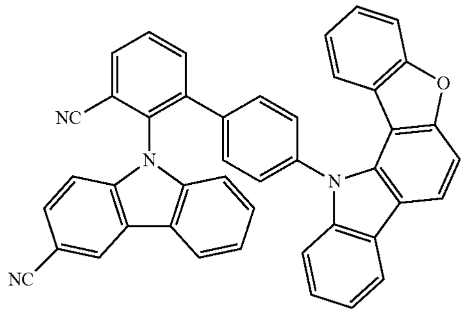
536
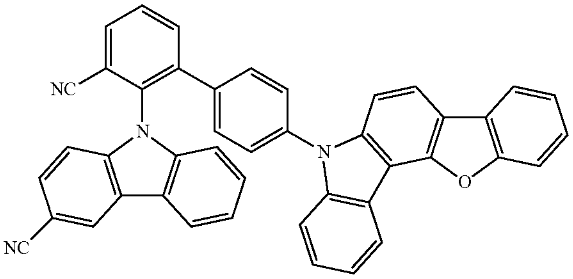
537
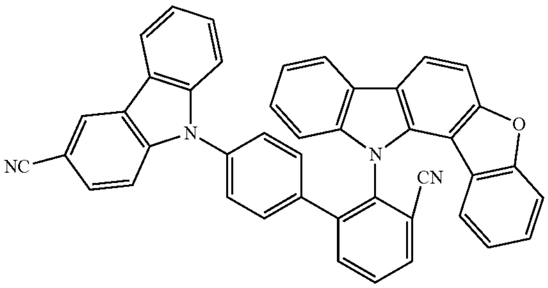
-continued
538
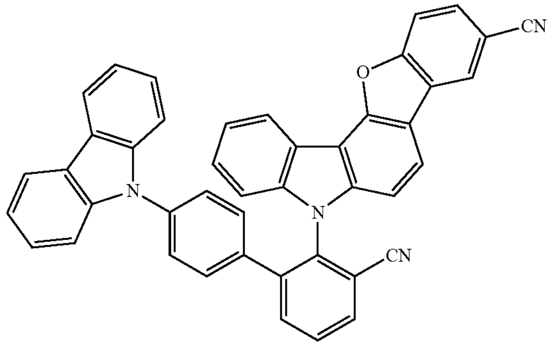
539
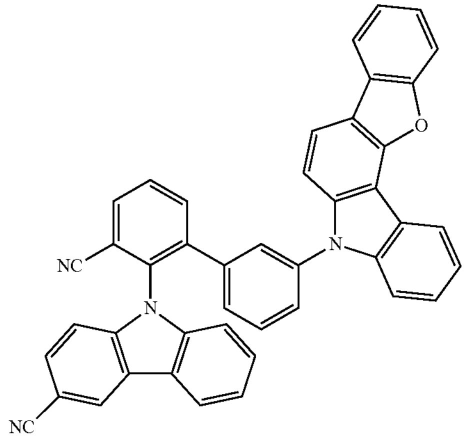
540
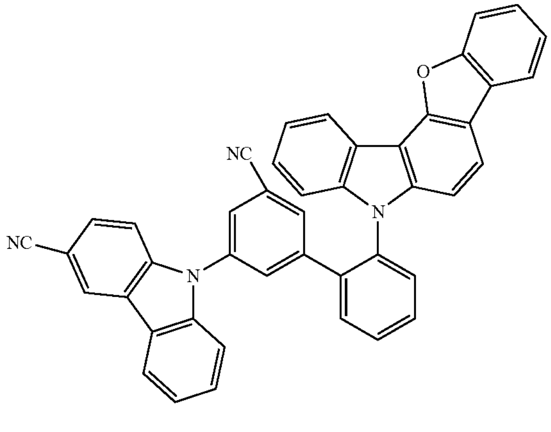
541
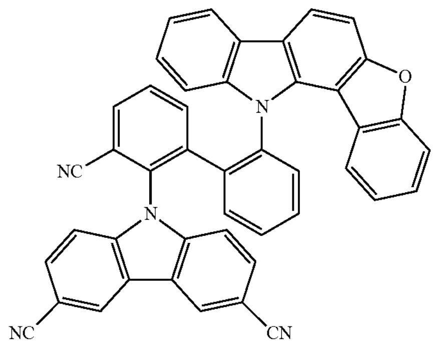

-continued
542
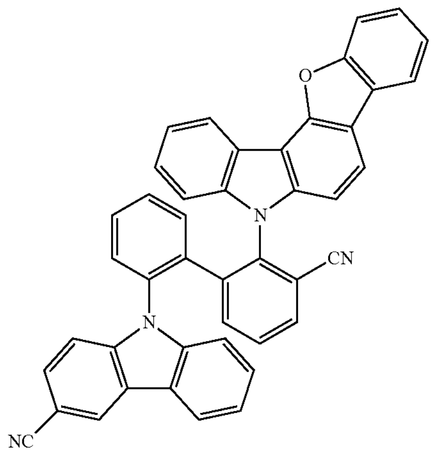
543
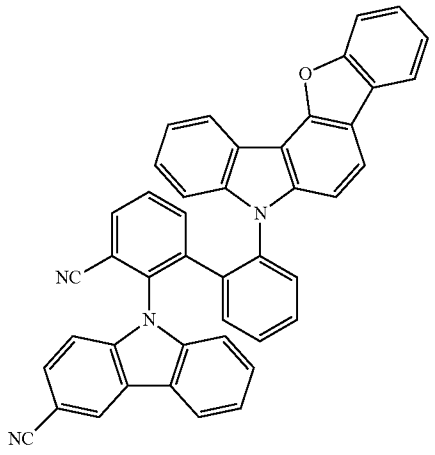
544
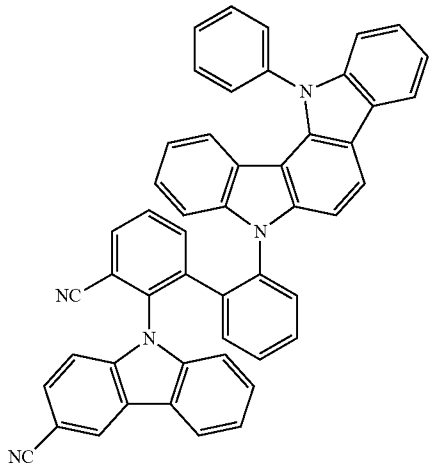
-continued
545
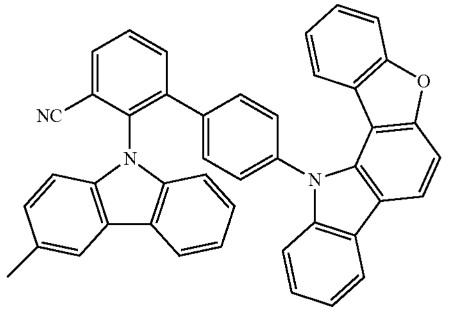
546
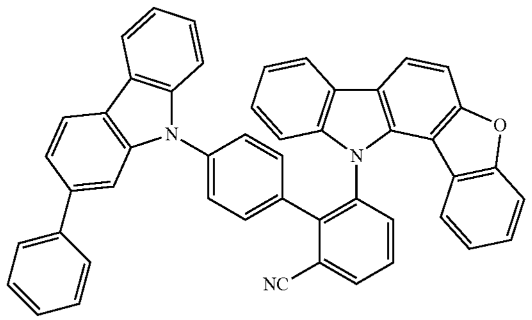
547
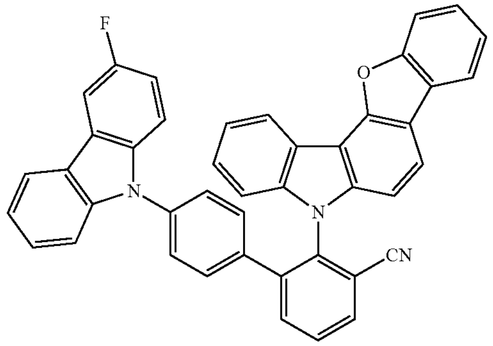
548
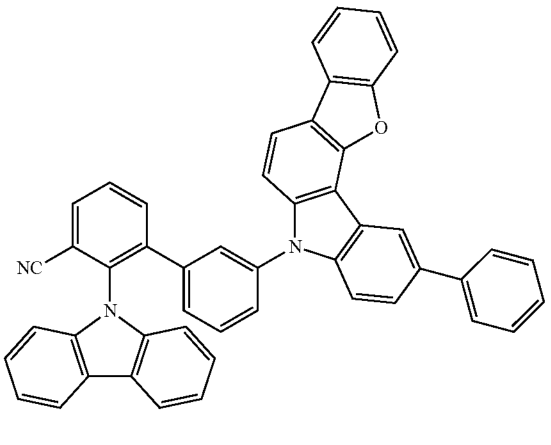

549
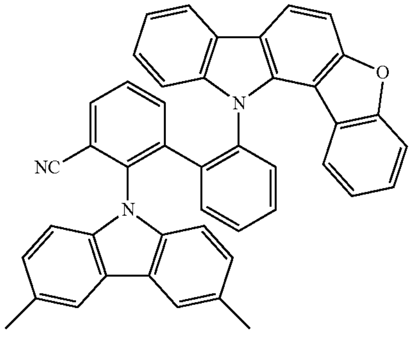
550
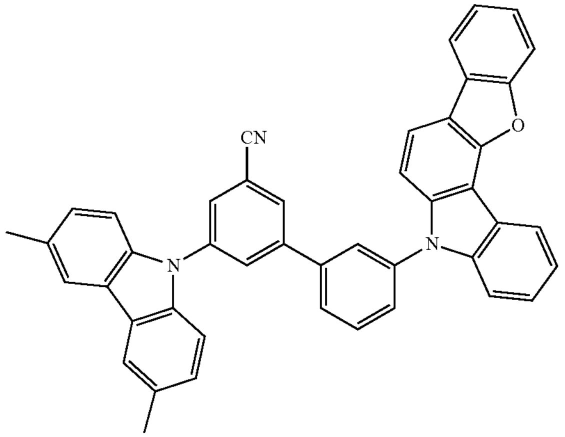
551
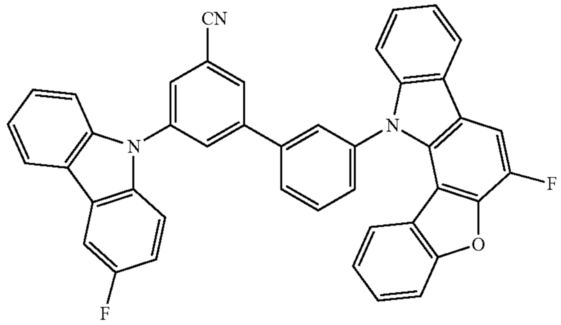
552
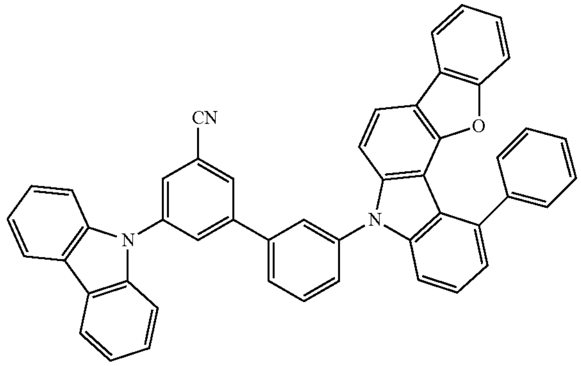
553
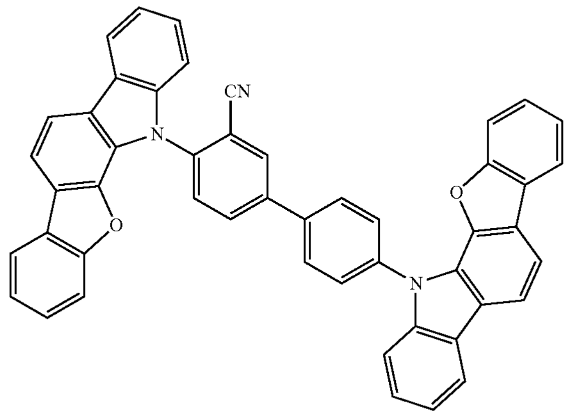
554
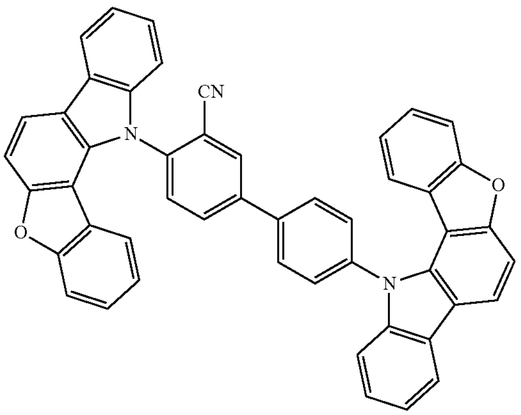
555
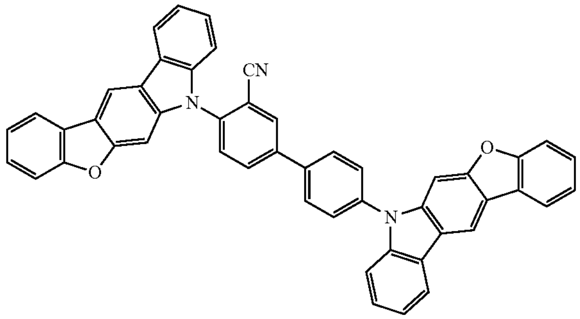
556
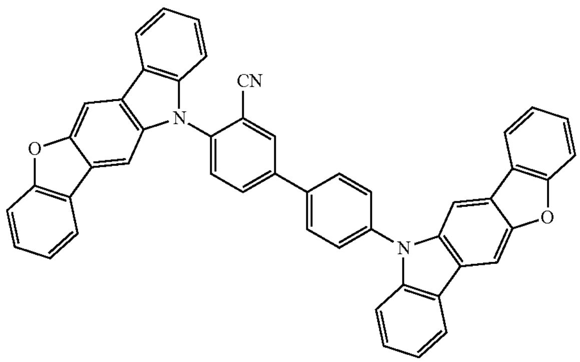

-continued
557
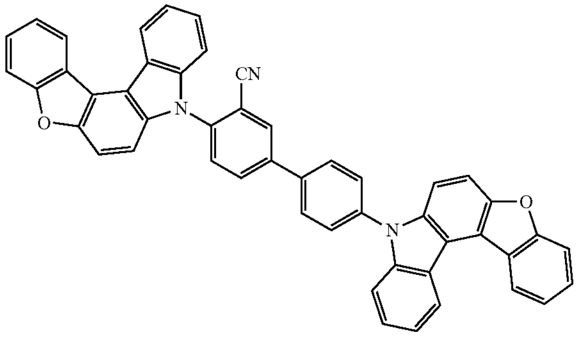
558
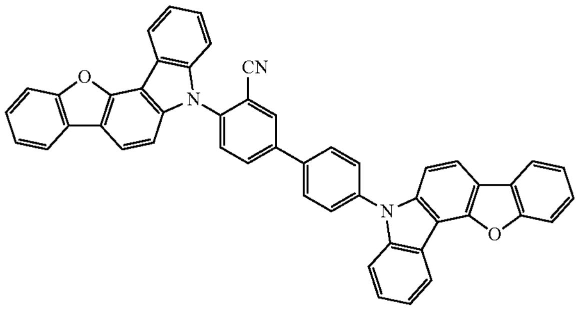
559
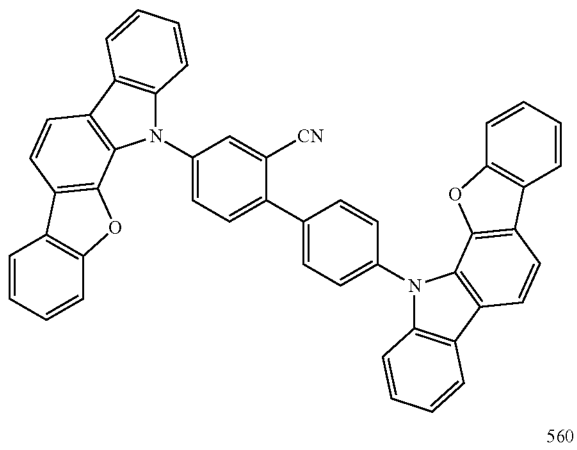
560
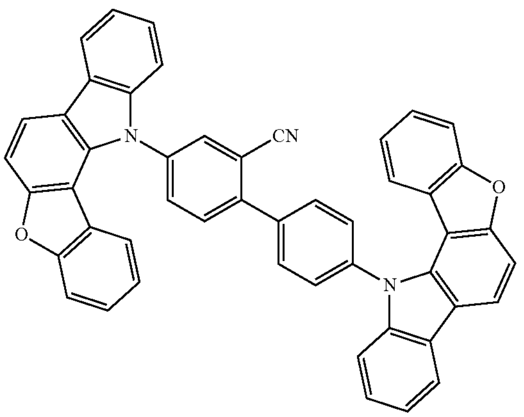
-continued
561
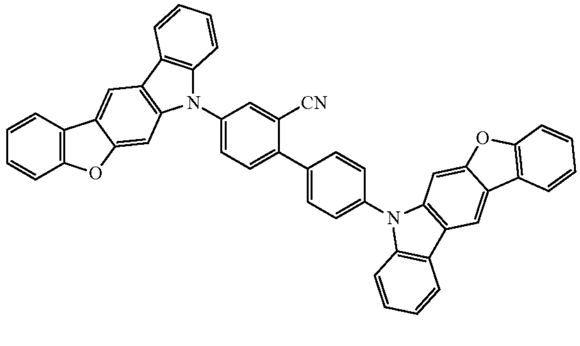
562
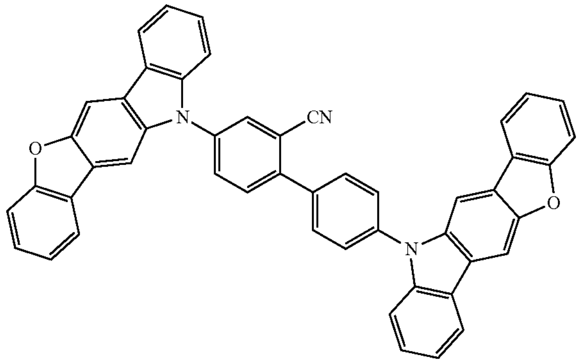
563
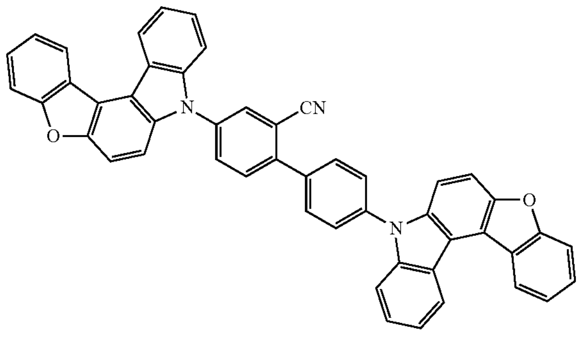
564
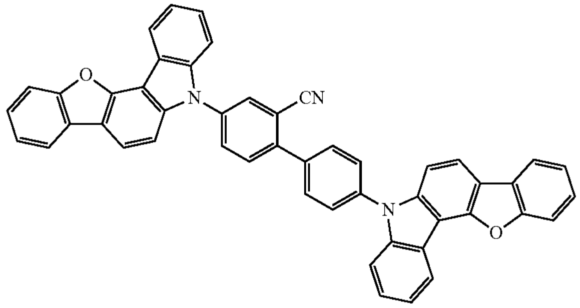

565
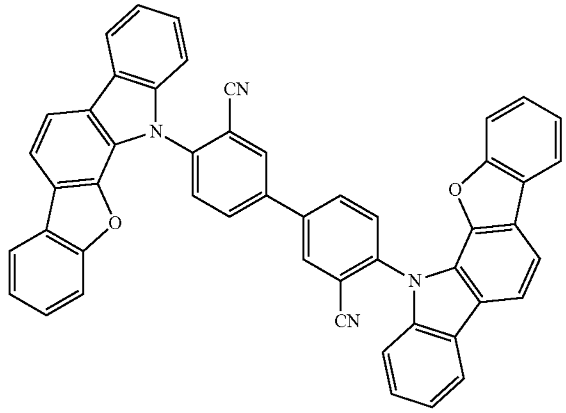
566
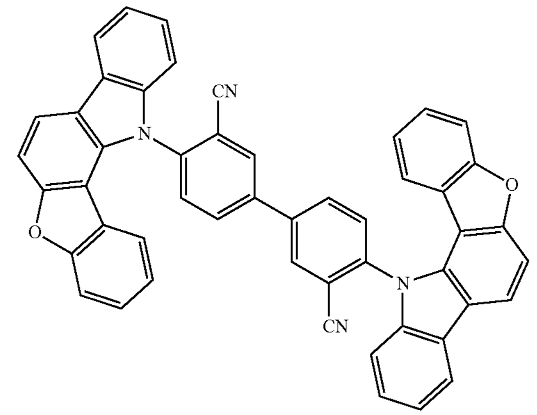
567
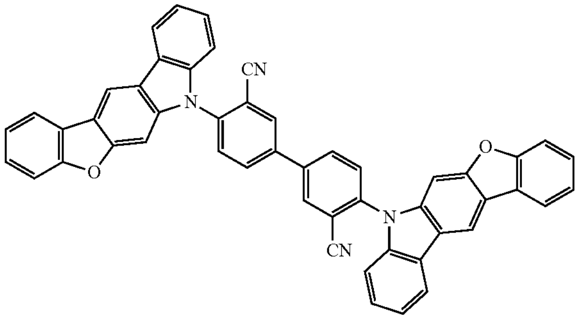
568
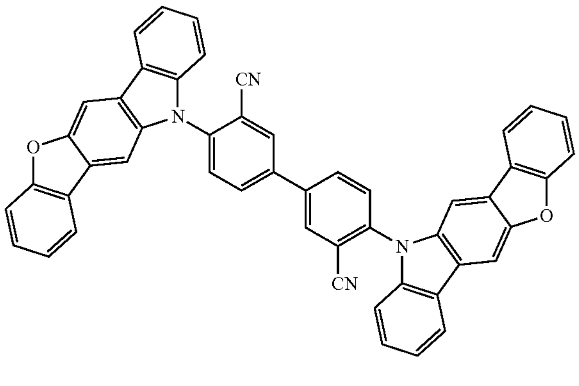
569
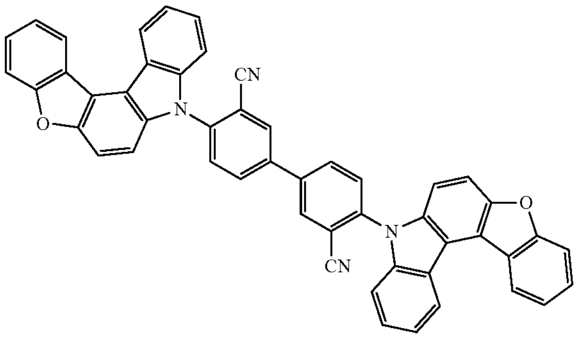
670
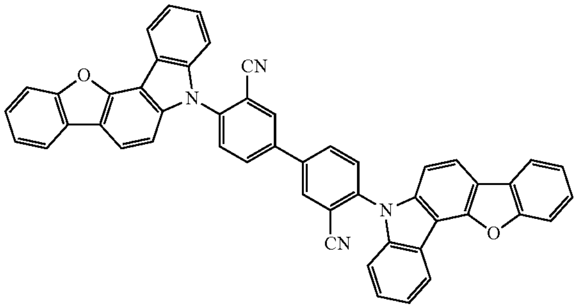
571
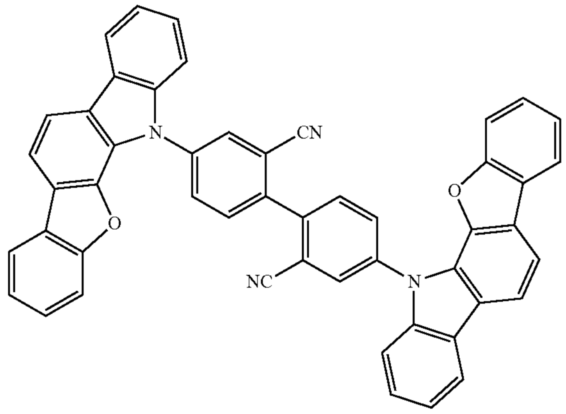
572
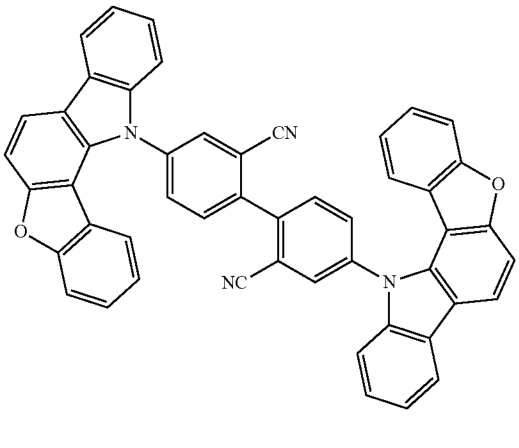

-continued
573
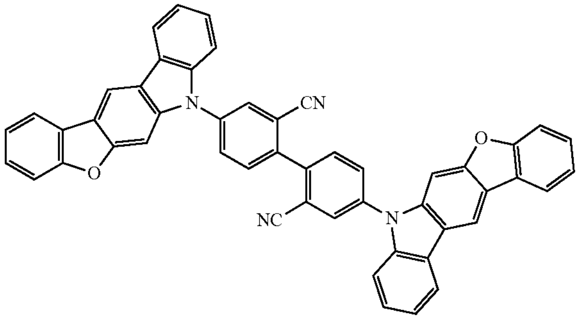
574
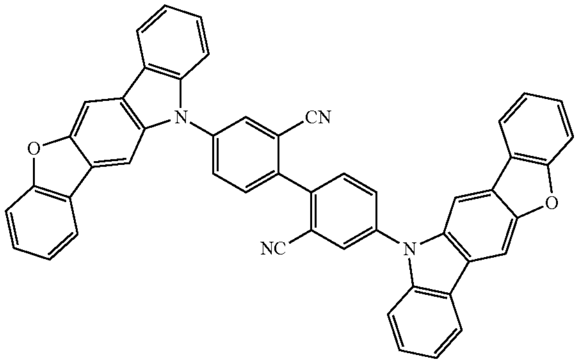
575
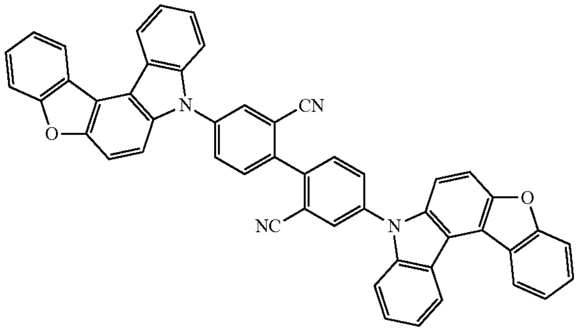
576
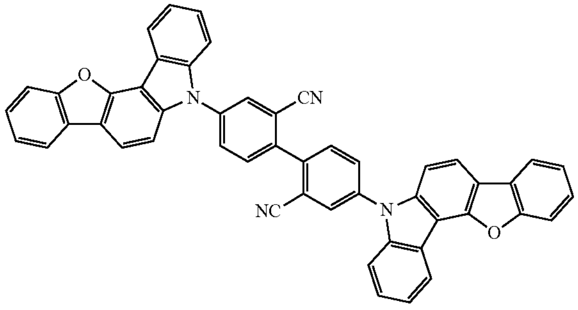
-continued
577
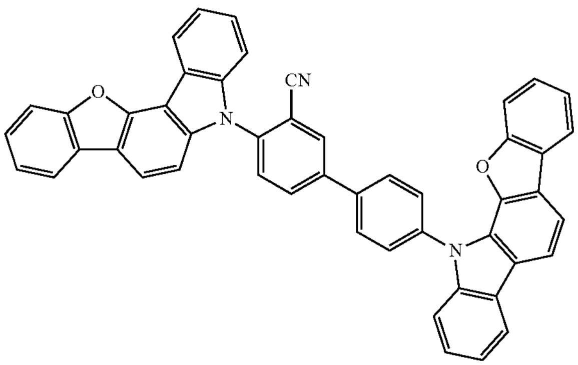
578
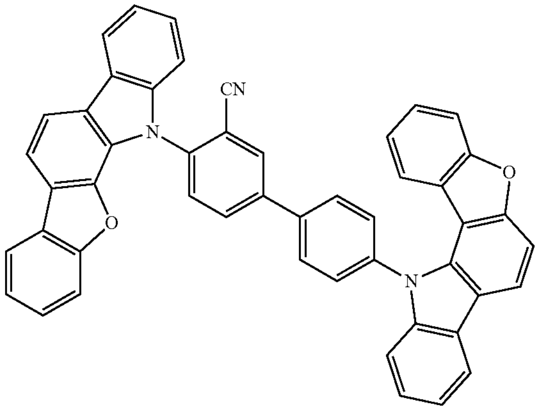
579
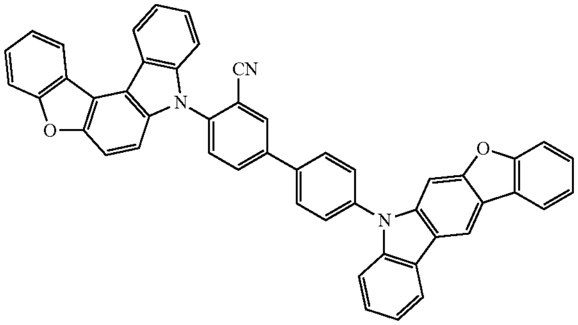
580
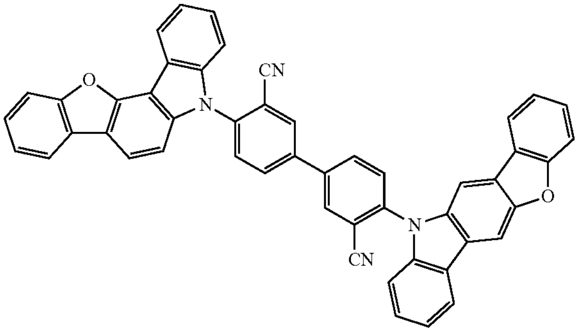

-continued
581
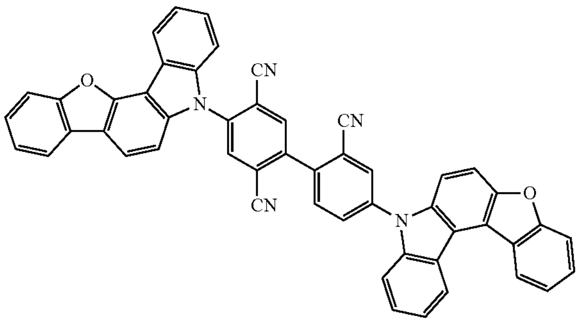
582
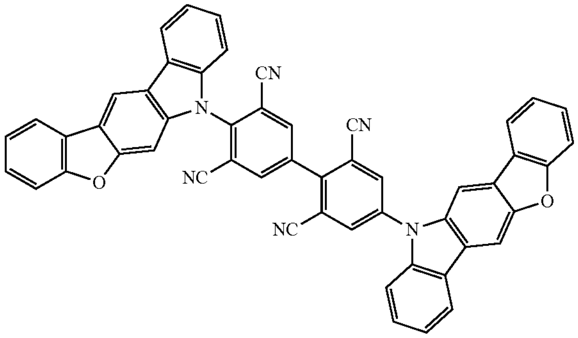
583
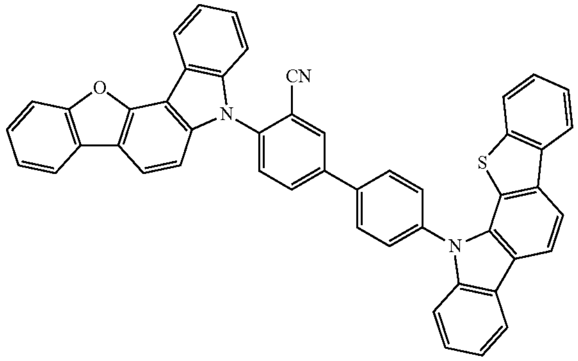
584
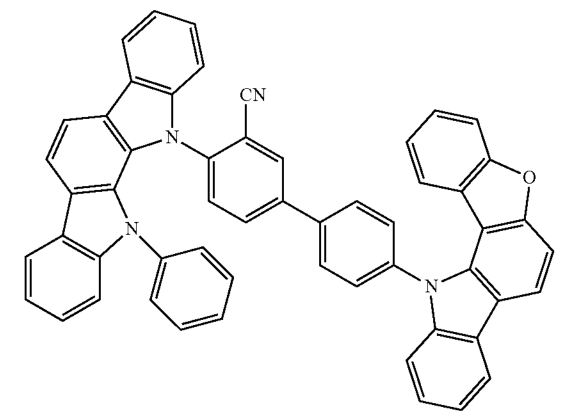
-continued
585
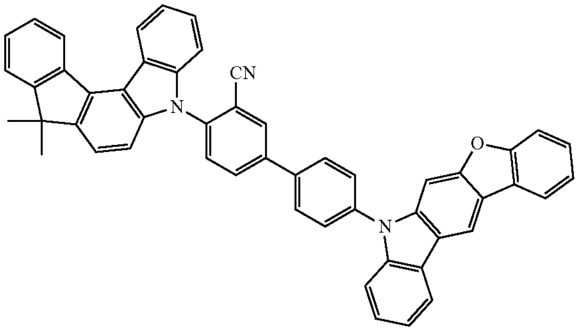
586
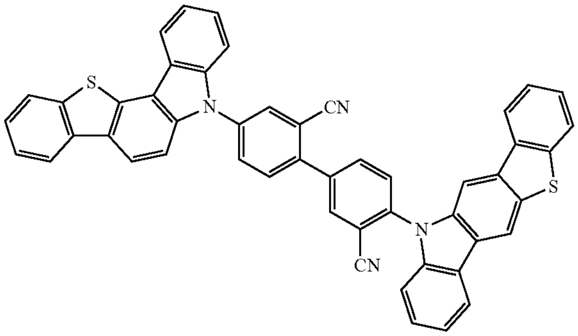
587
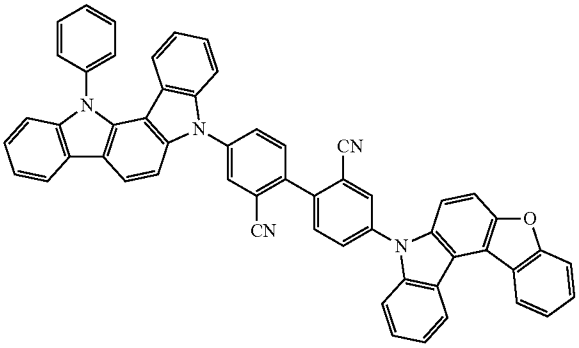
588
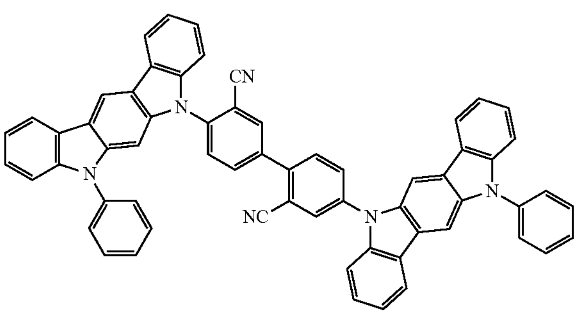

-continued
589
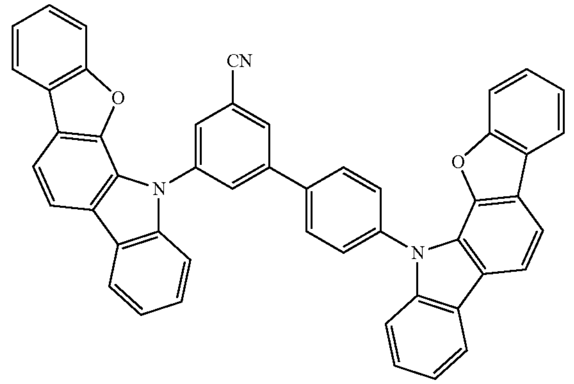
590
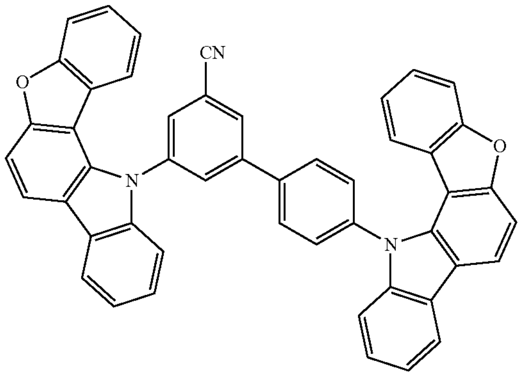
591
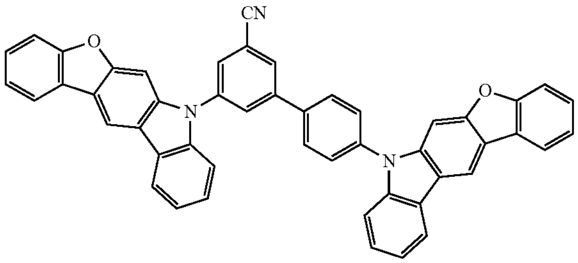
592
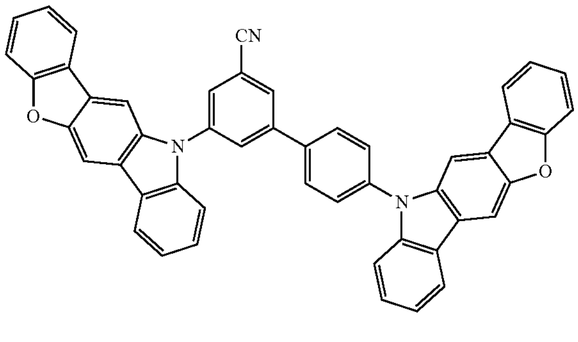
-continued
593
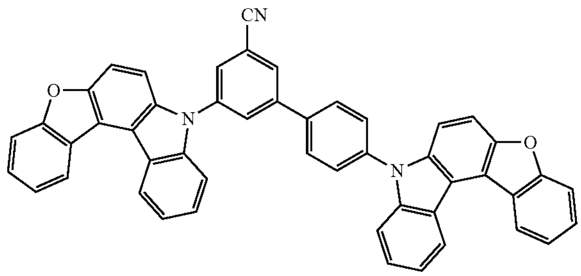
594
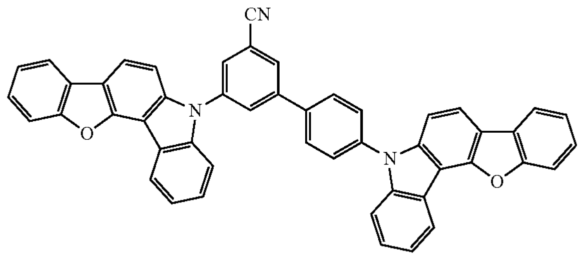
595
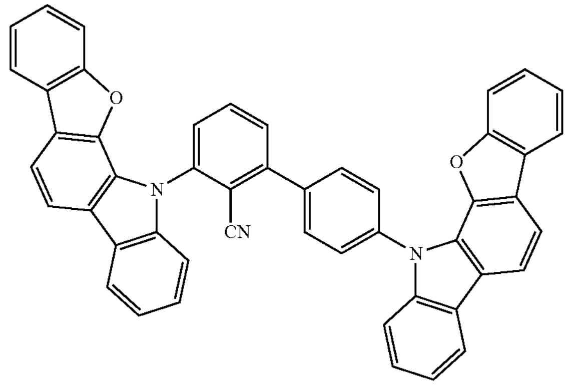
596
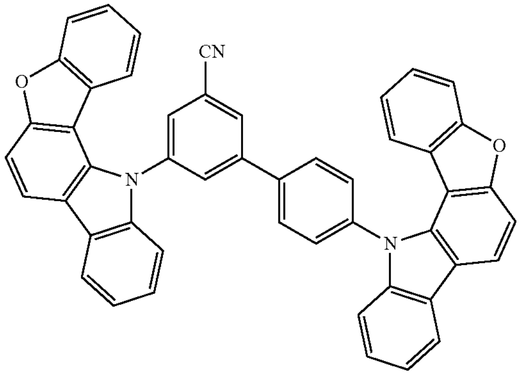
597
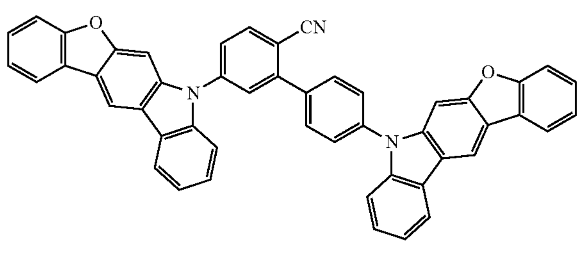

-continued
598
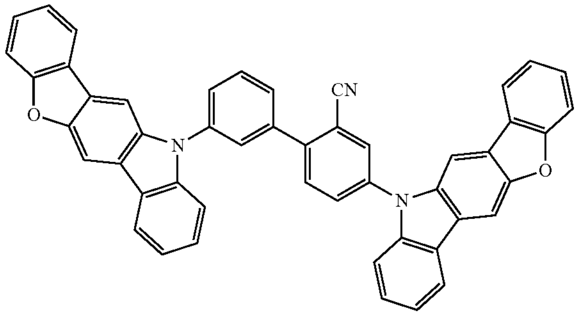
599
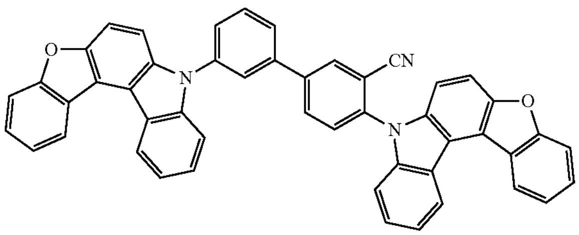
600
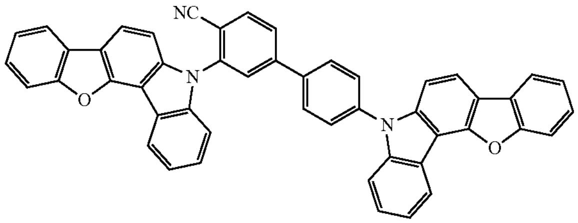
601
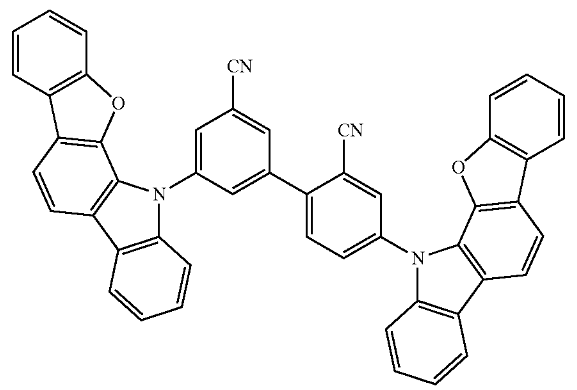
602
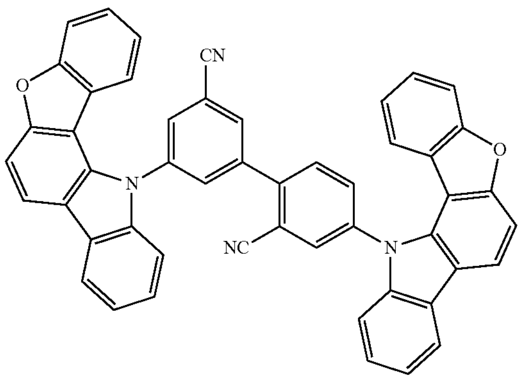
-continued
603
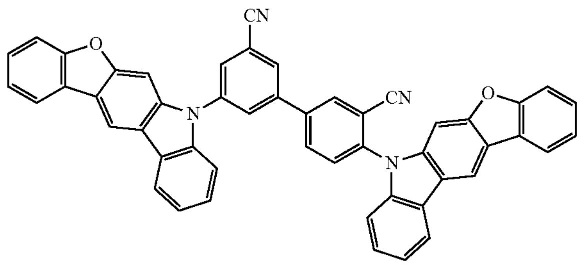
604
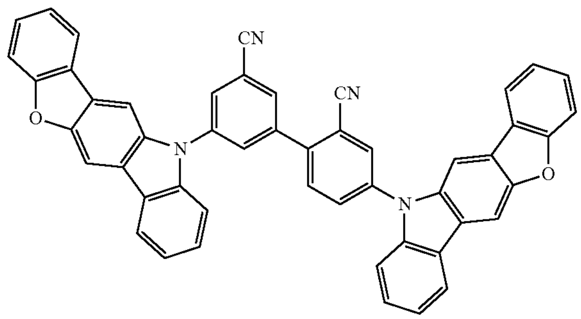
605
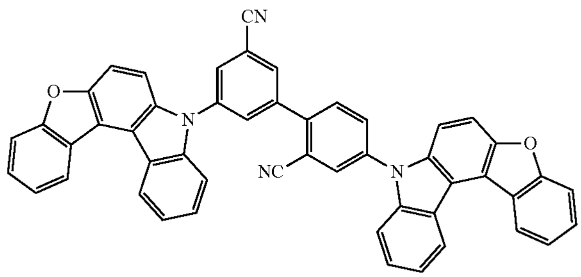
606
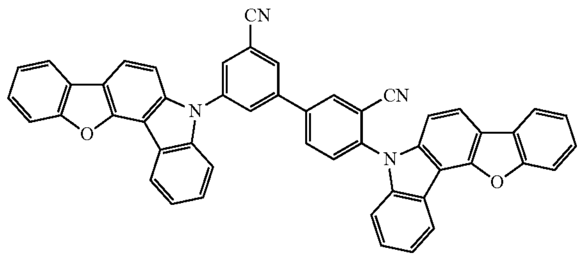
607
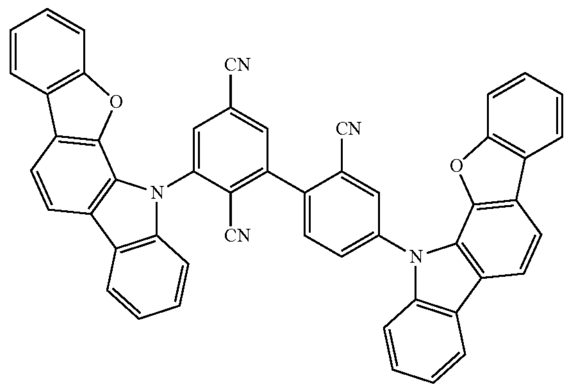

-continued
608
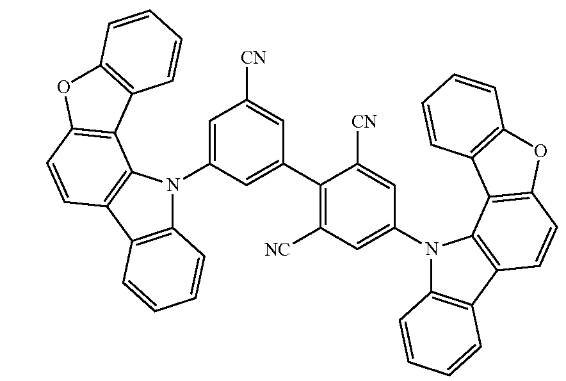
609
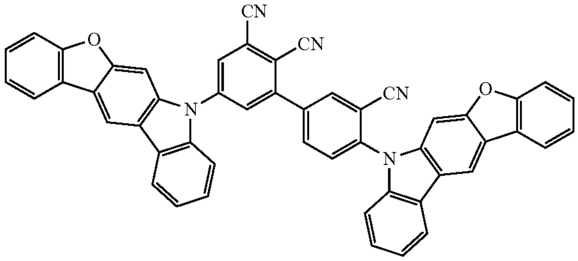
610
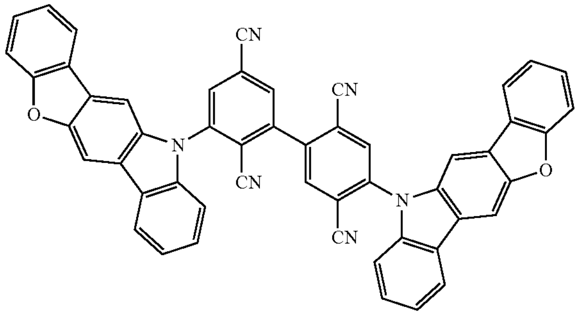
611
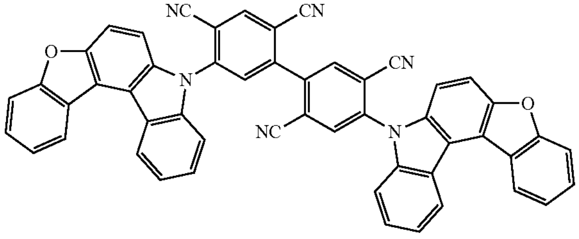
612
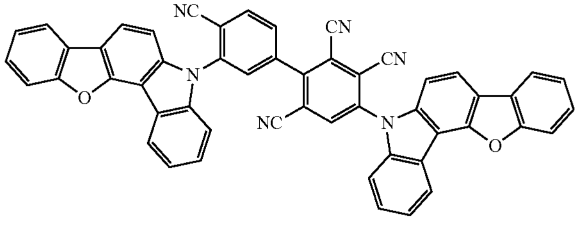
-continued
613
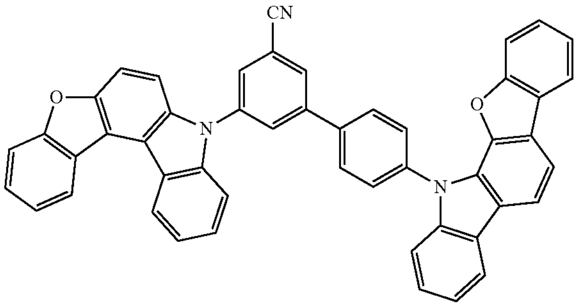
614
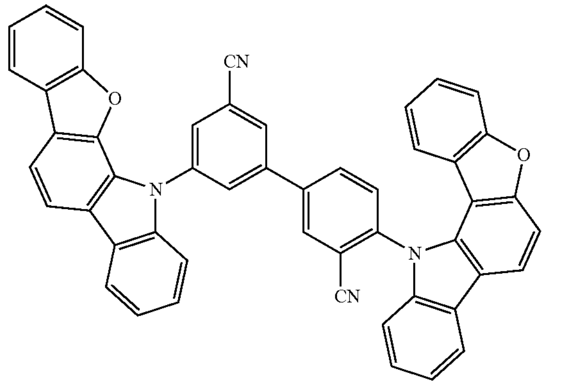
615
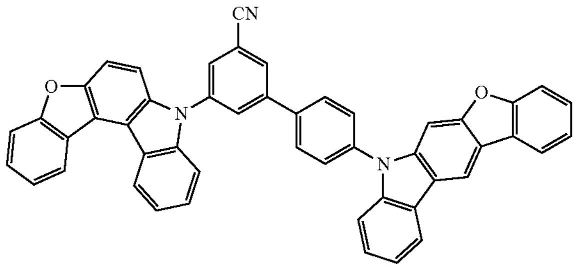
616
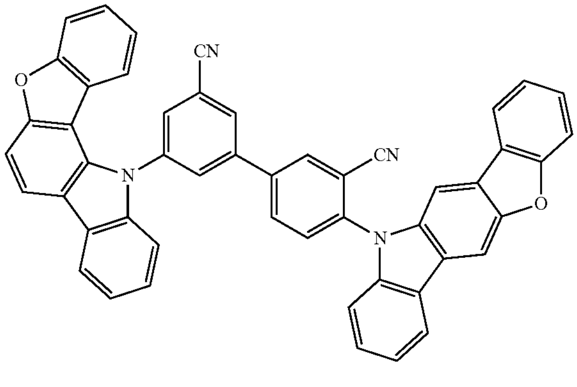

-continued
617
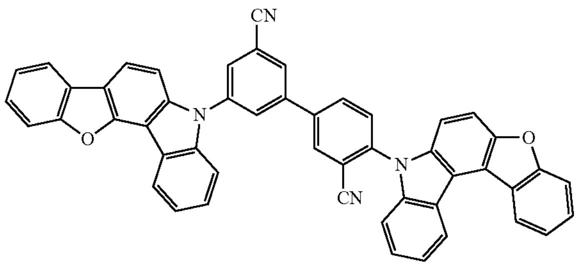
618
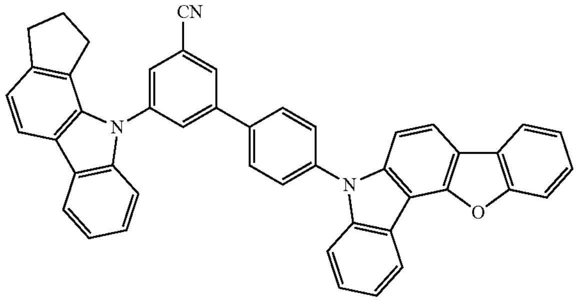
619
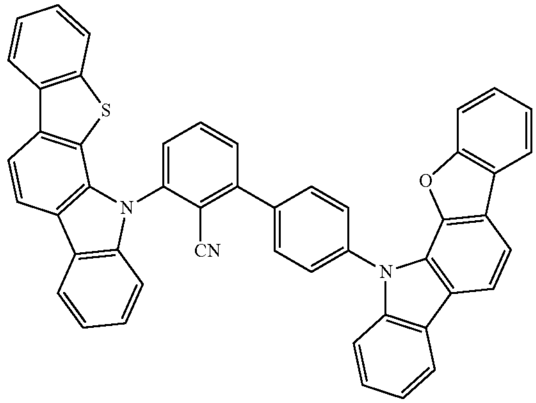
620
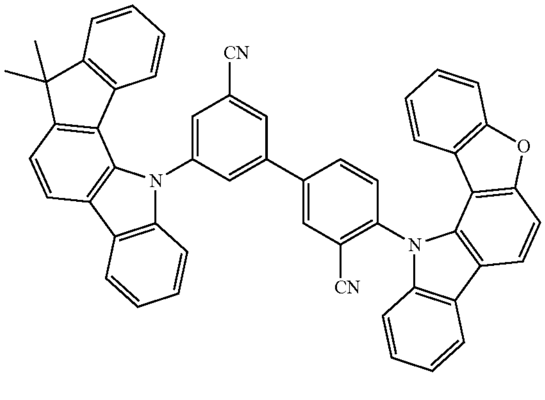
-continued
621
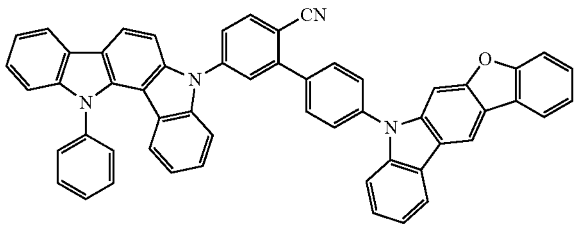
622
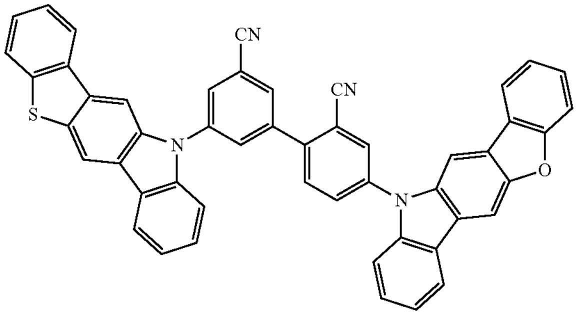
623
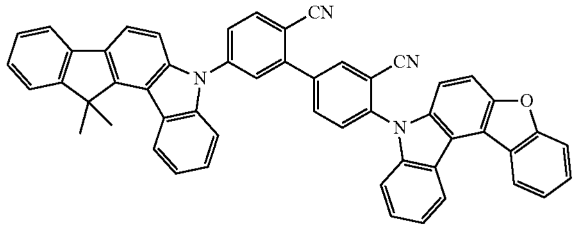
624
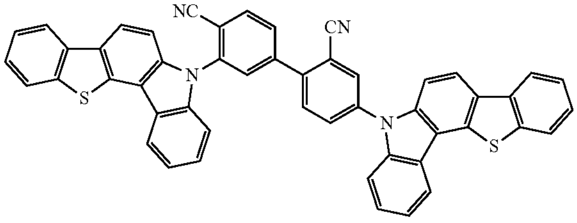
625
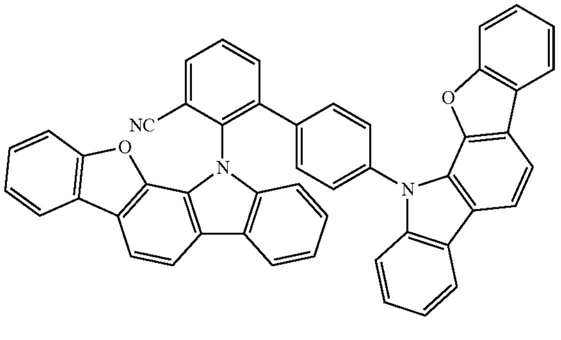

-continued
626
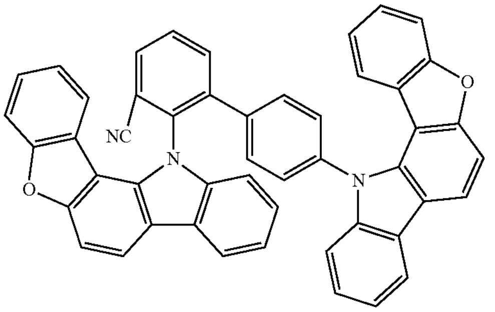
627
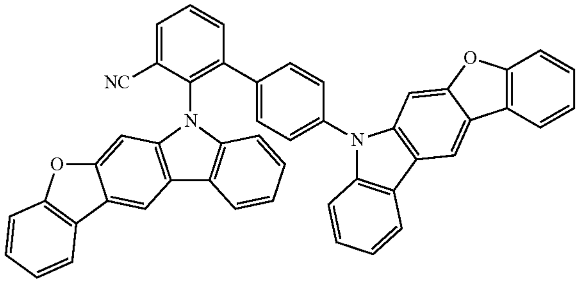
628
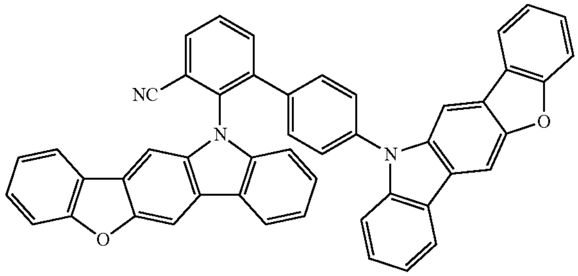
629
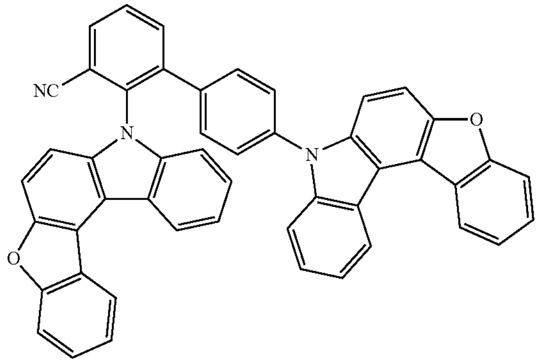
-continued
630
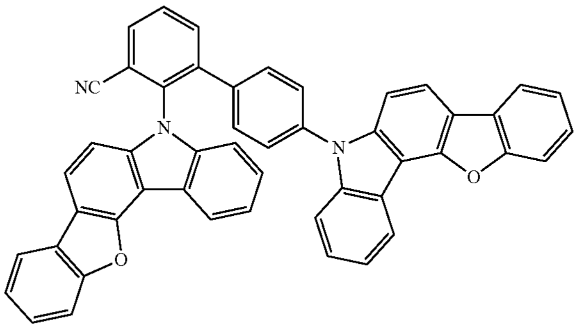
631
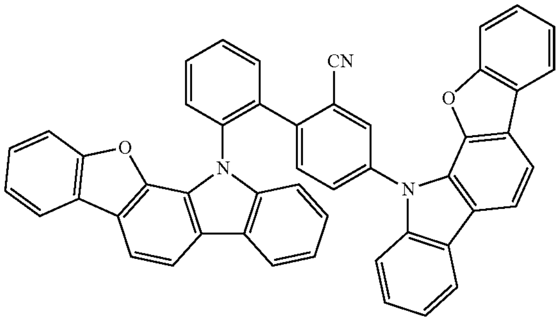
632
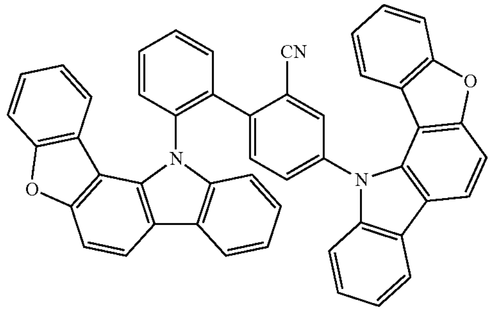
633
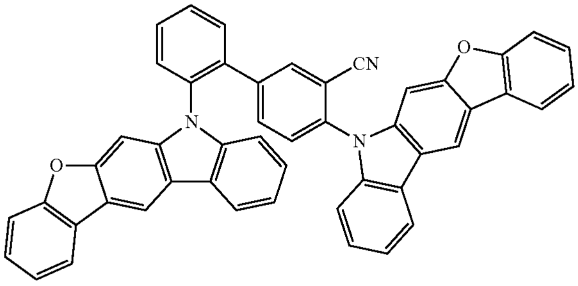
634
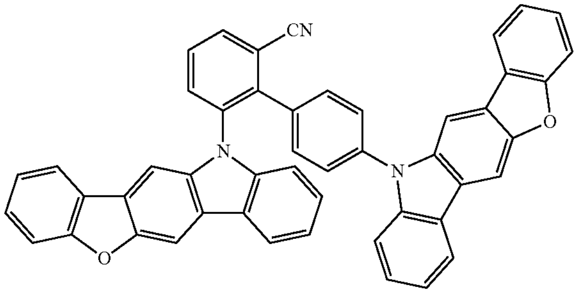

-continued
635
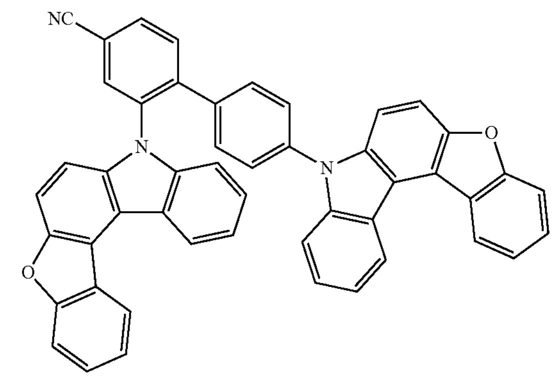
636
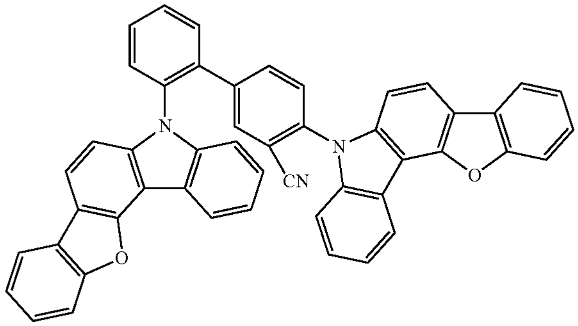
637
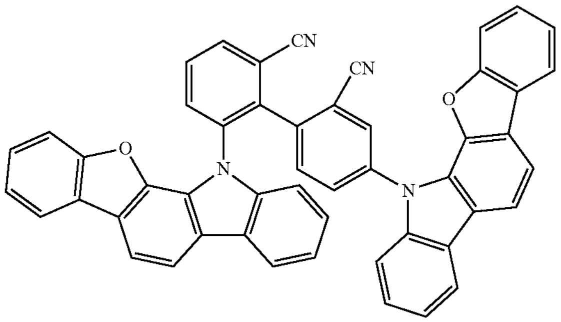
638
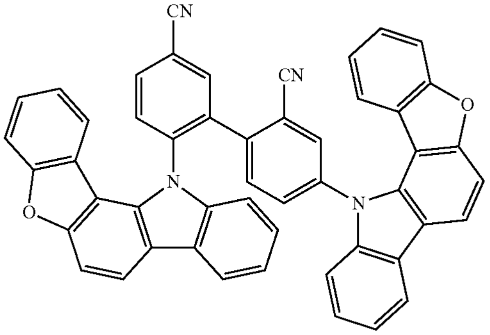
-continued
639
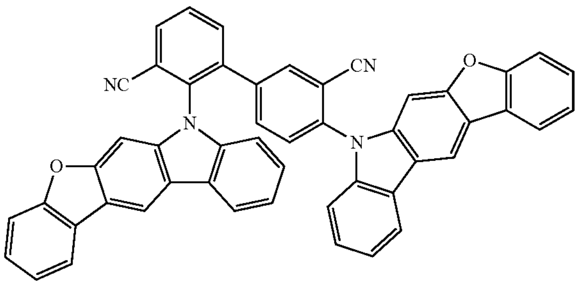
640
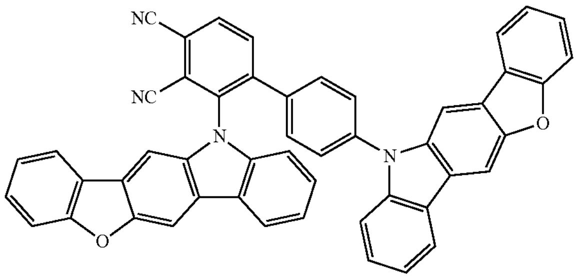
641
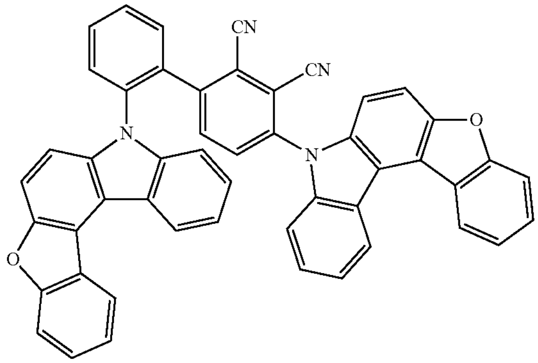
642
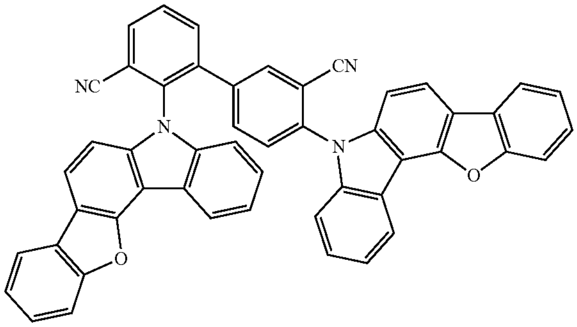

-continued
643
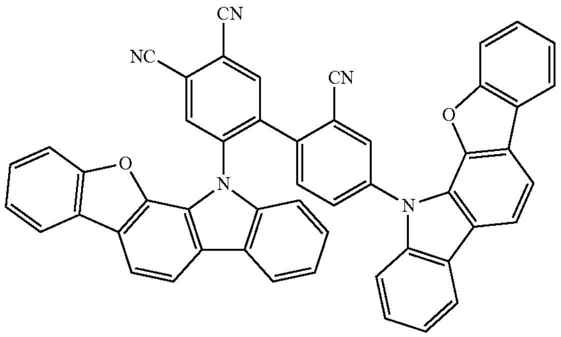
644
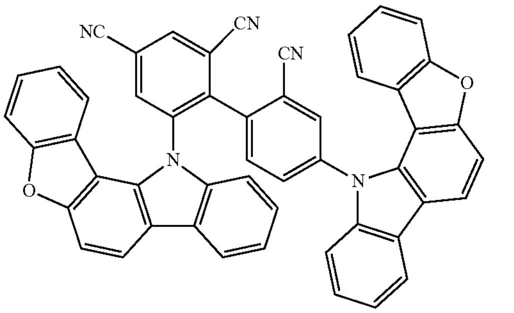
645
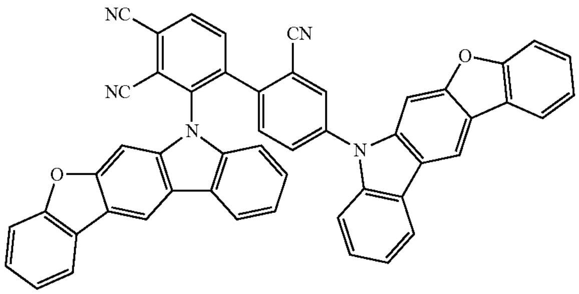
646
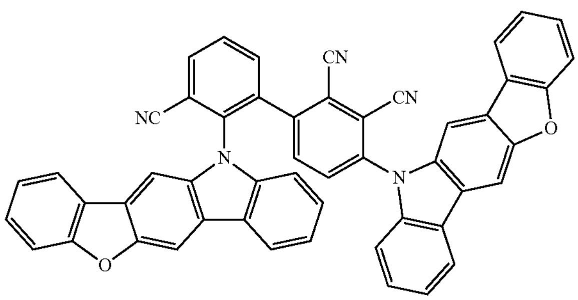
-continued
647
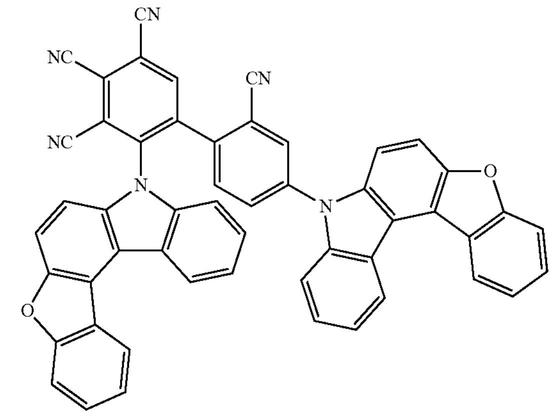
648
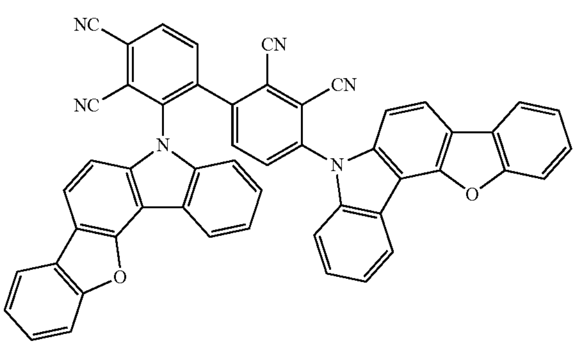
649
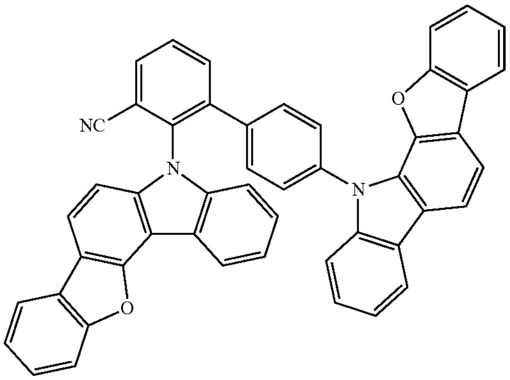
650
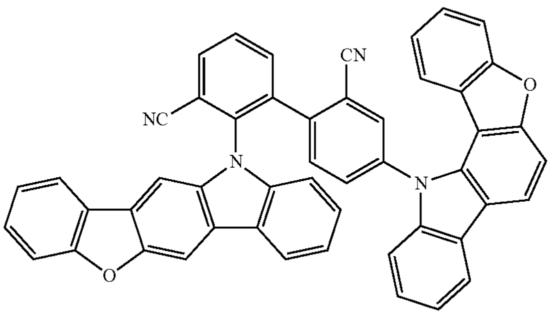

-continued
651
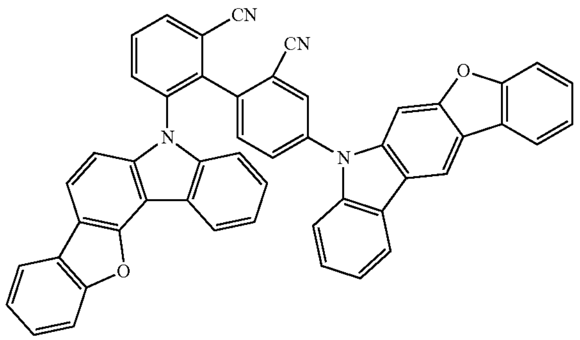
652
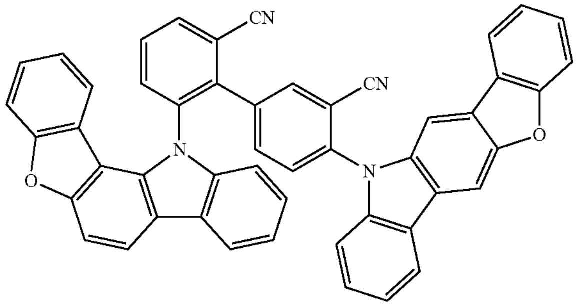
653
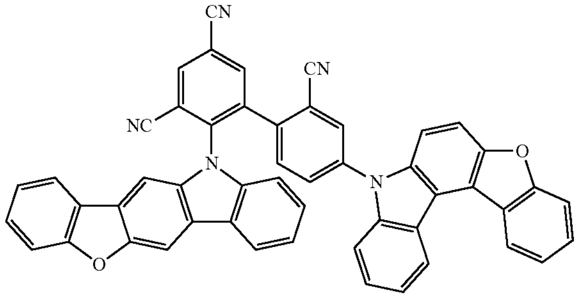
654
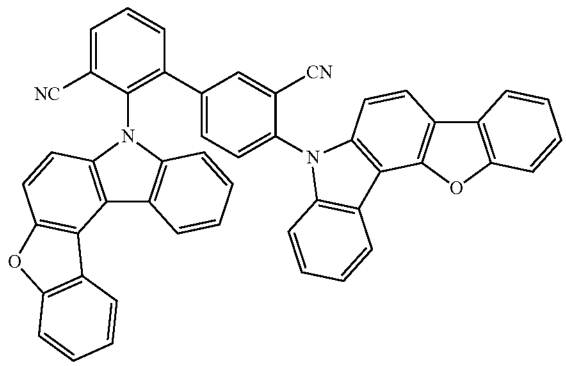
-continued
655
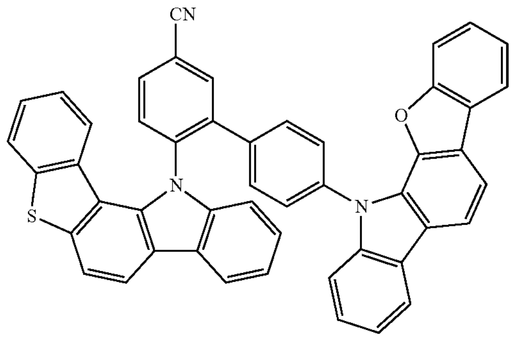
656
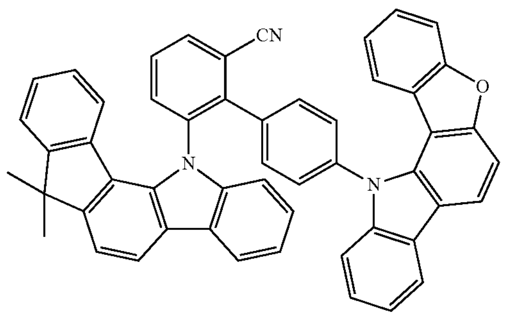
657
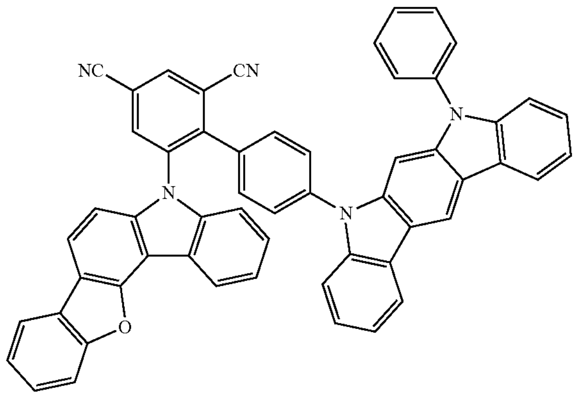
658
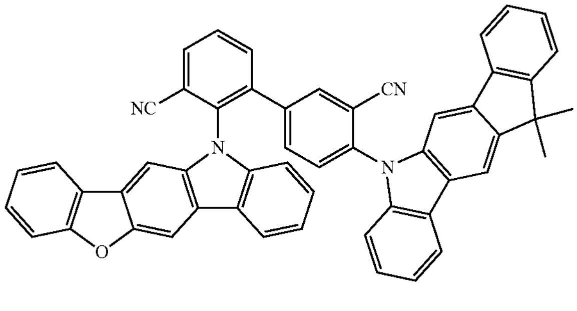

-continued
659
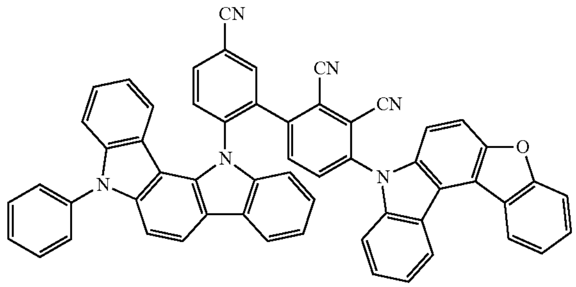
660
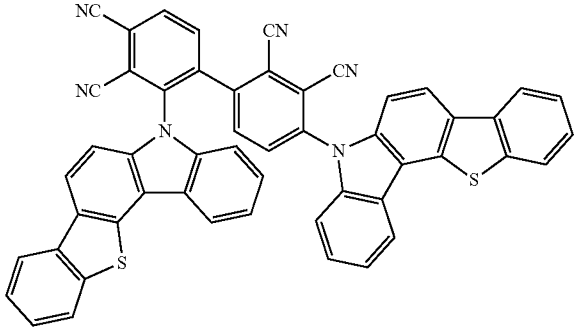
661
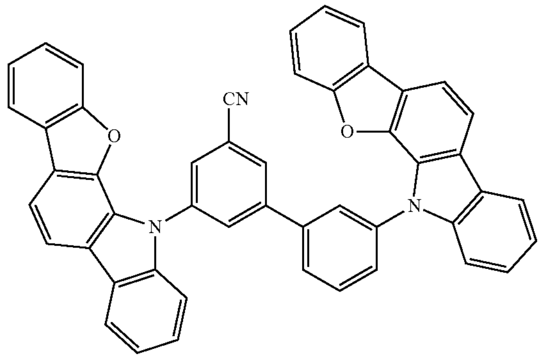
662
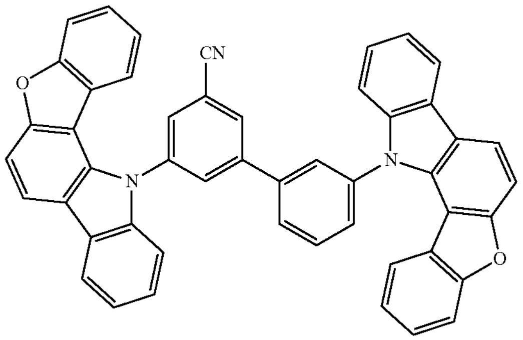
-continued
663
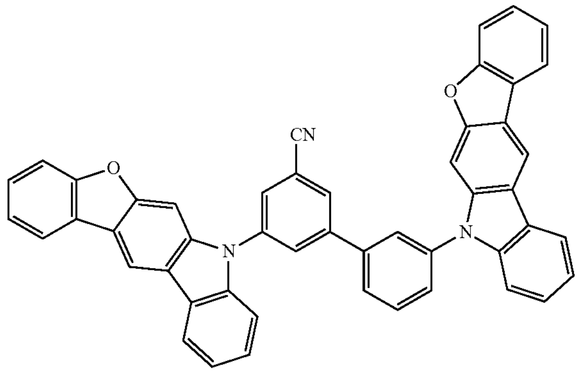
664
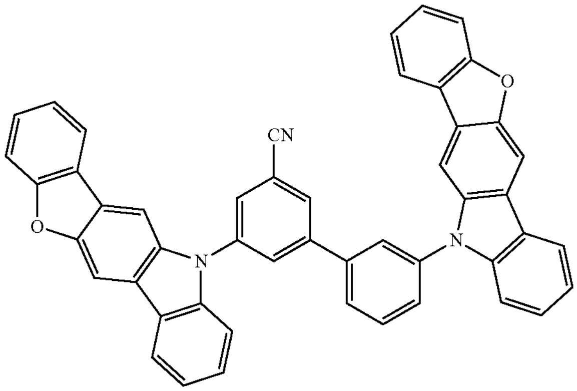
665
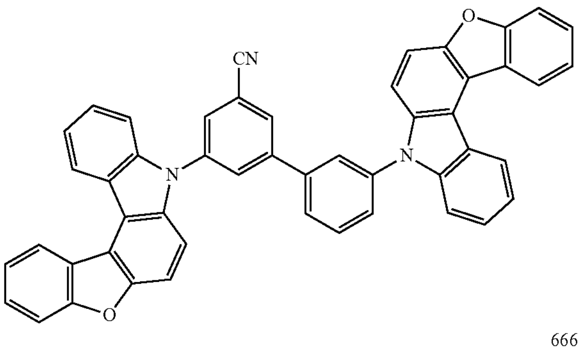
666
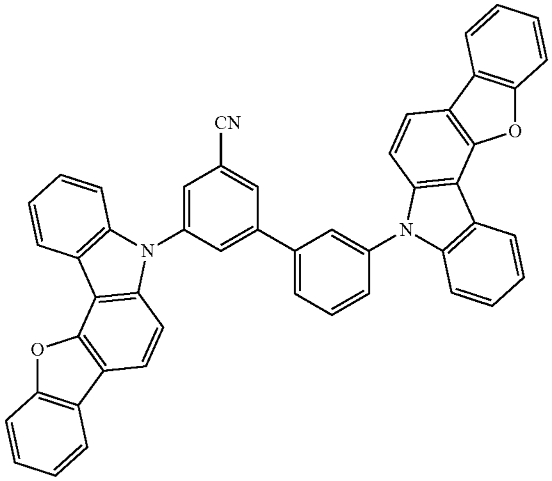

-continued
667
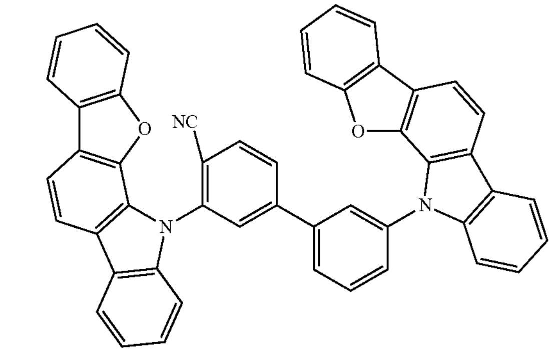
668
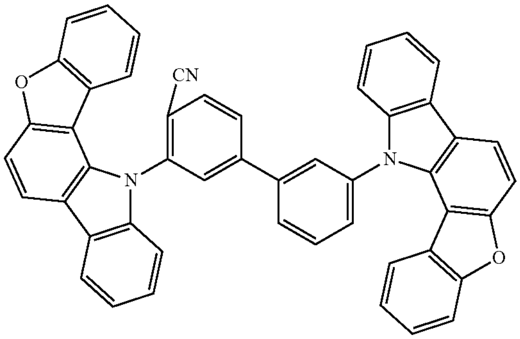
669
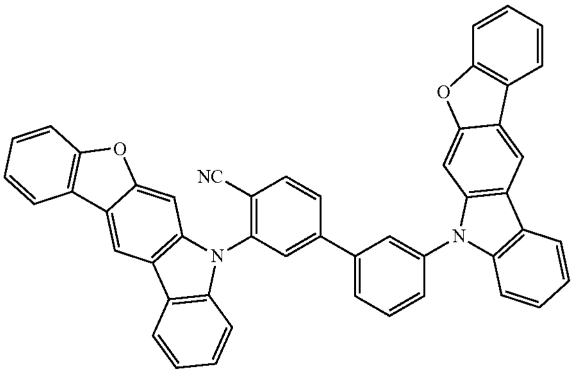
670
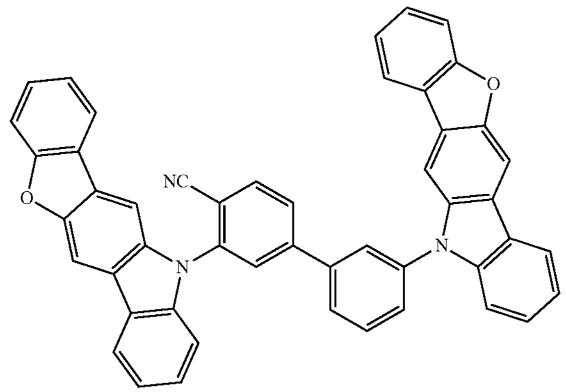
-continued
671
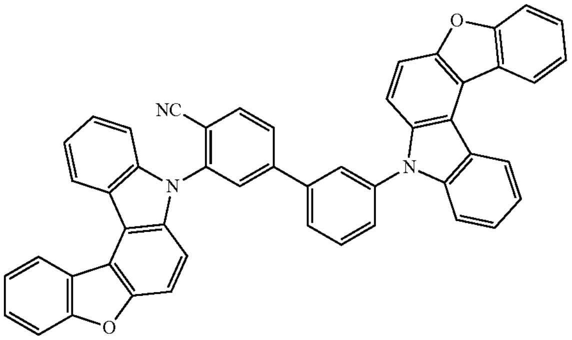
672
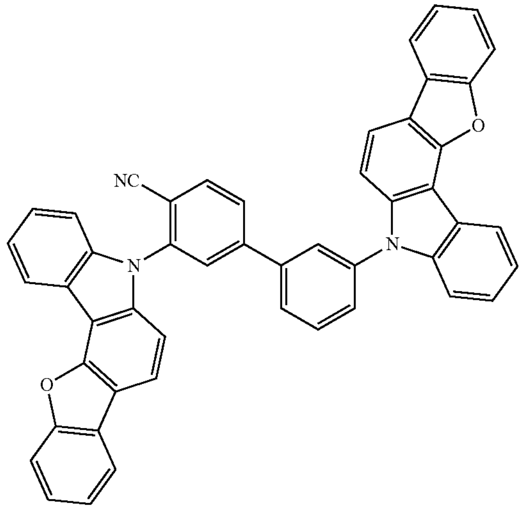
673
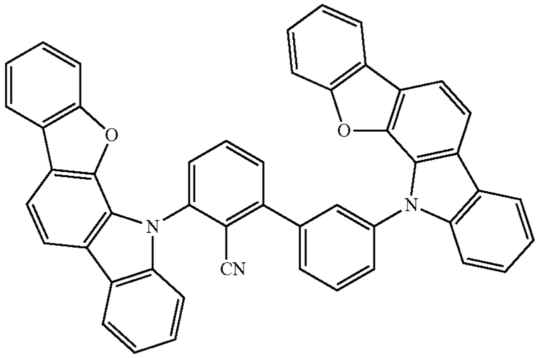
674
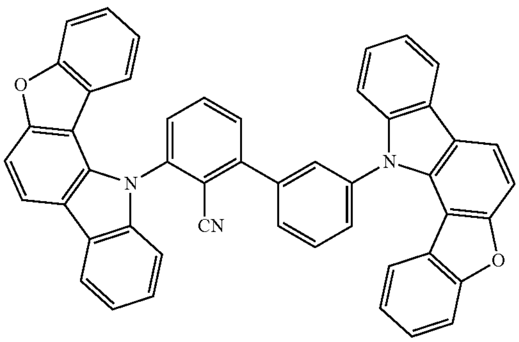

-continued
675
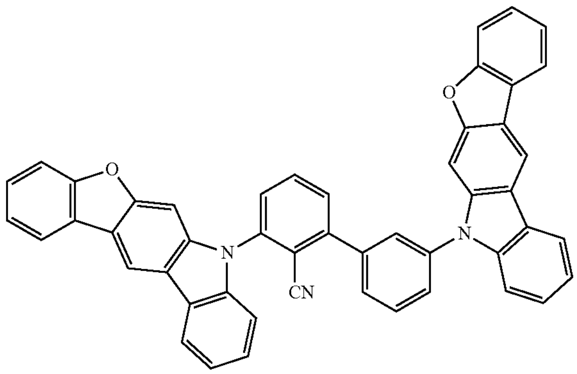
676
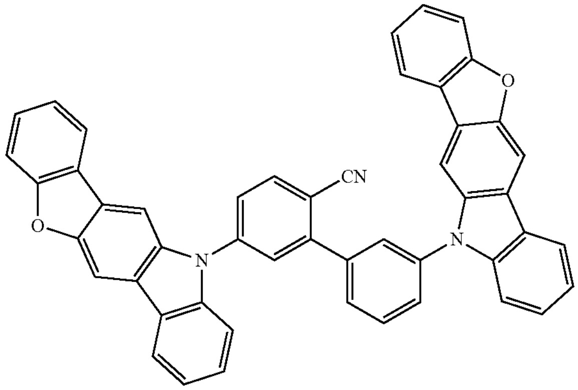
677
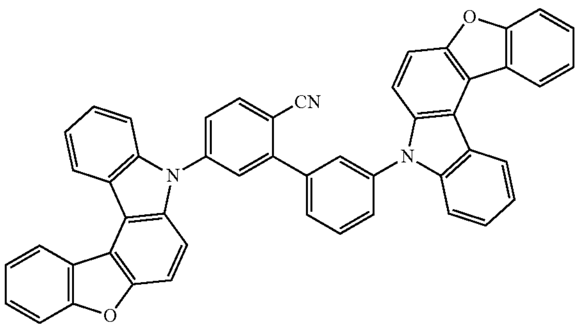
678
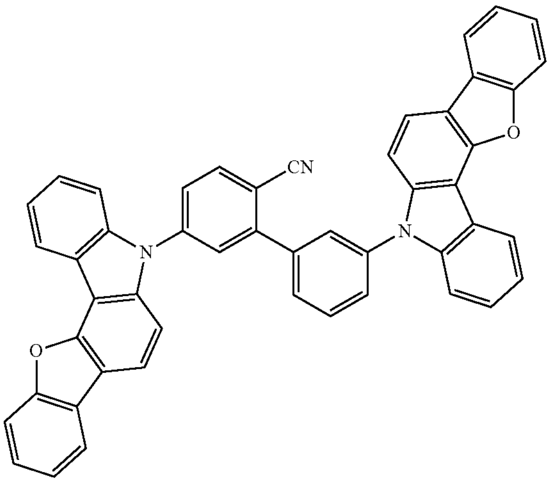
-continued
679
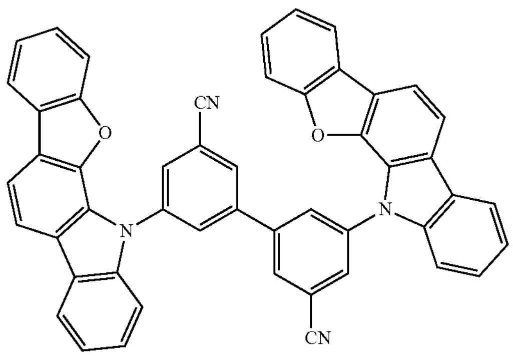
680
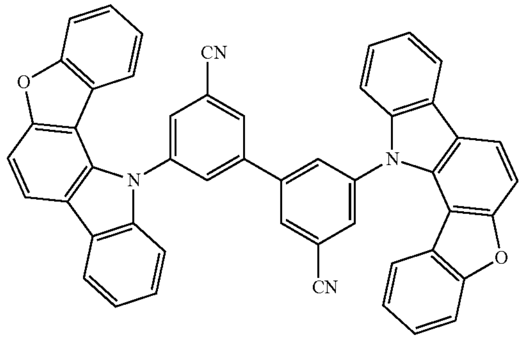
681
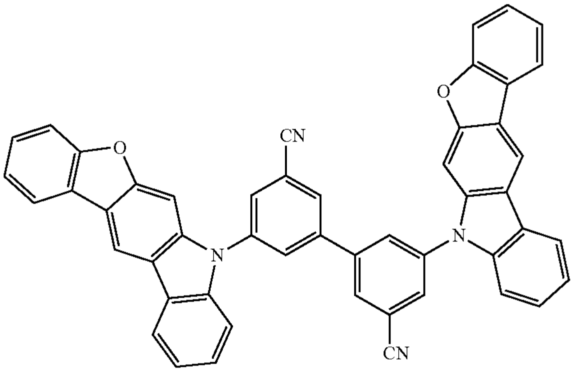
682
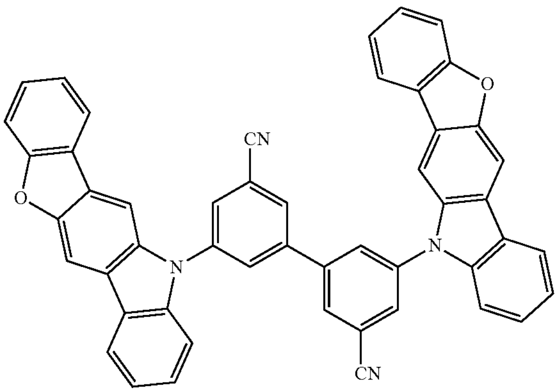

-continued
683
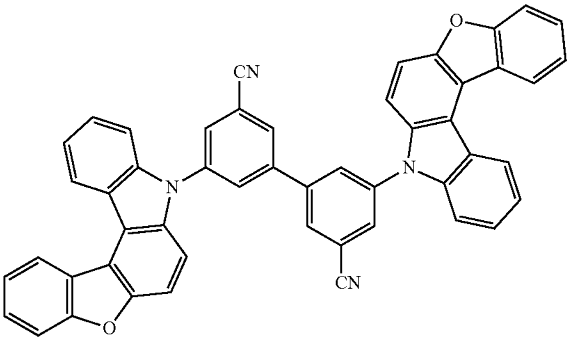
684
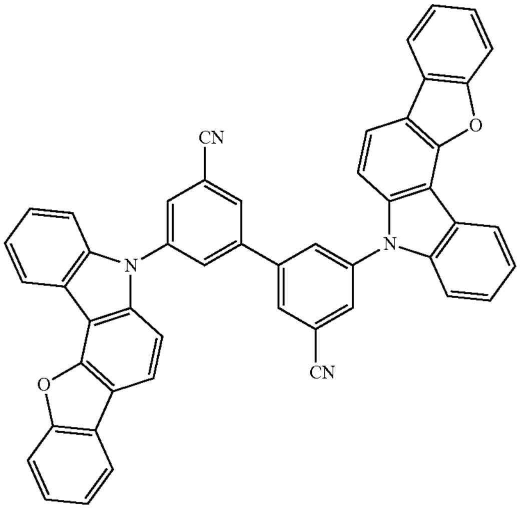
685
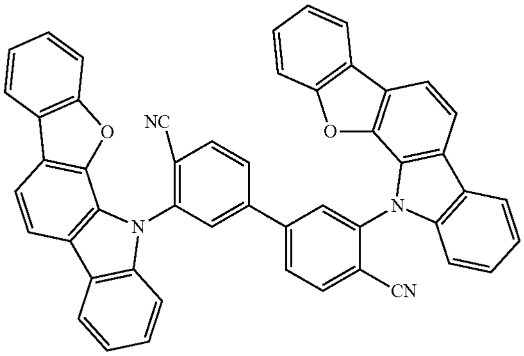
-continued
686
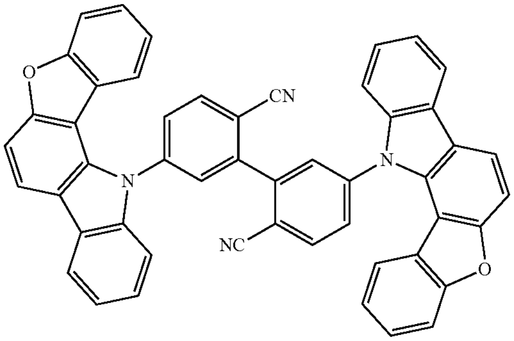
687
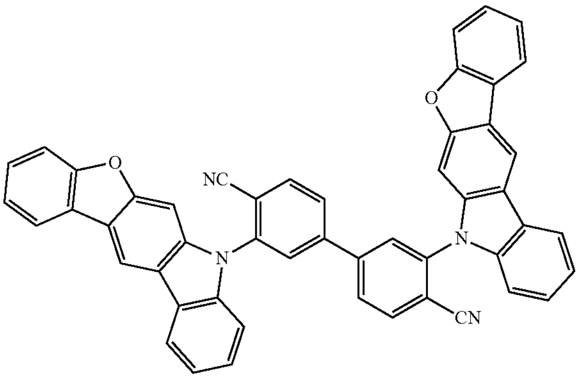
688
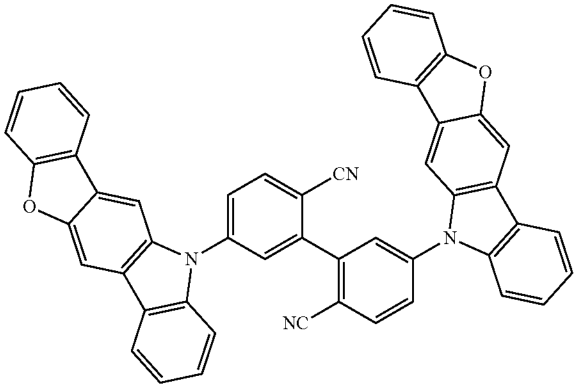
689
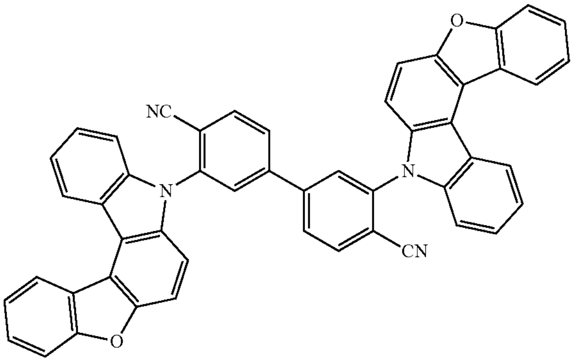

-continued
690
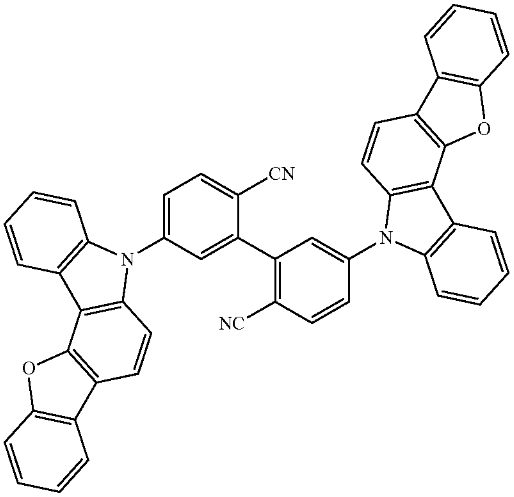
691
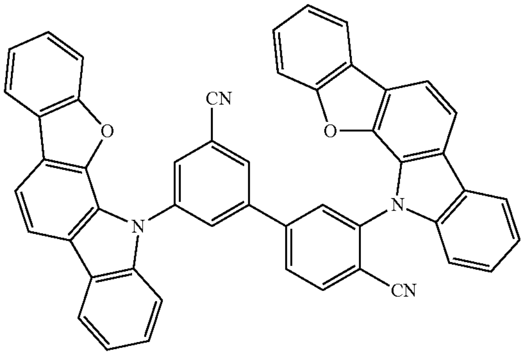
692
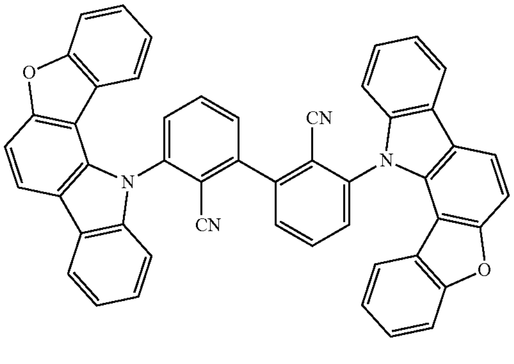
-continued
693
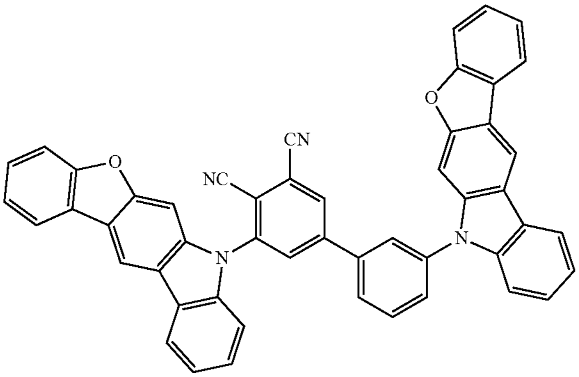
694
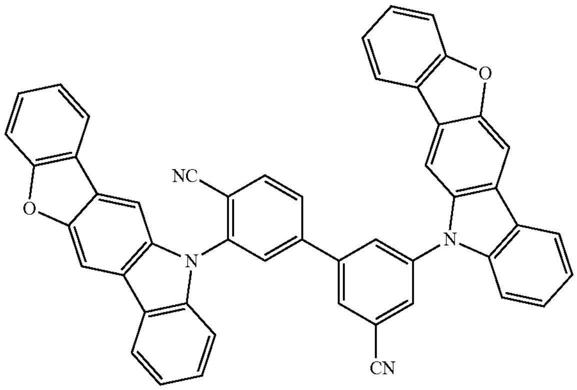
695
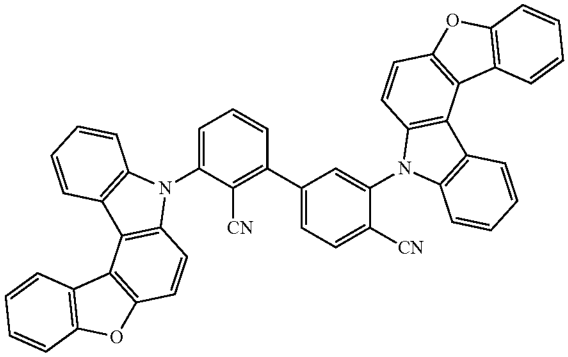

-continued
696
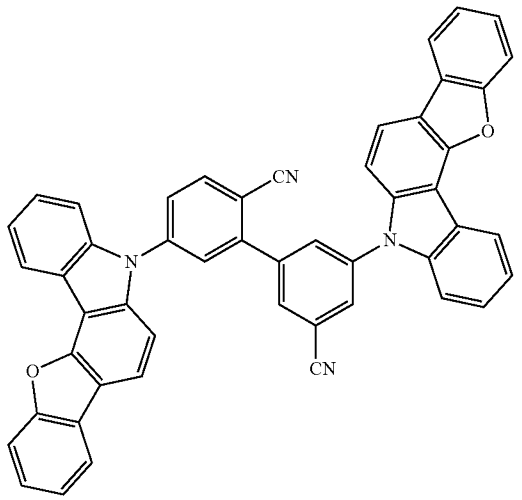
697
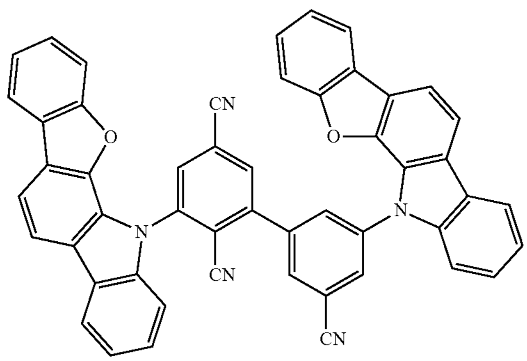
698
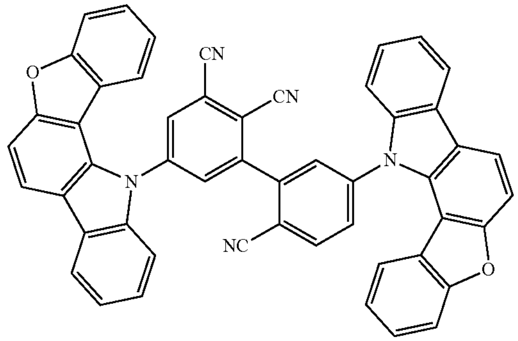
699
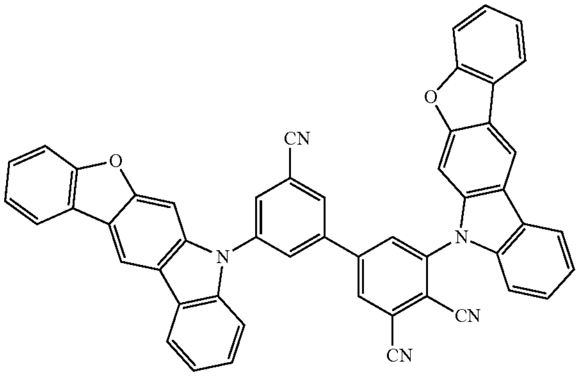
-continued
700
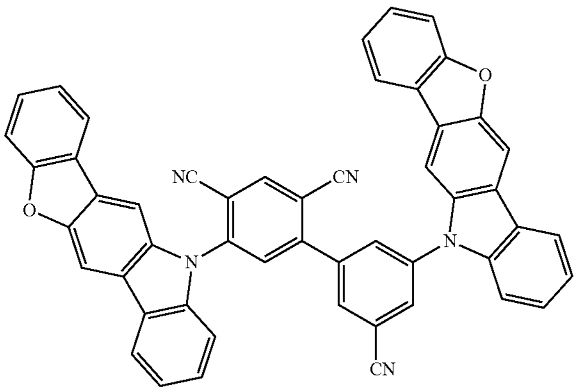
701
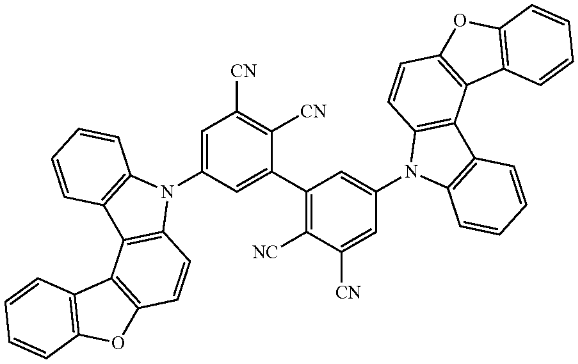
702
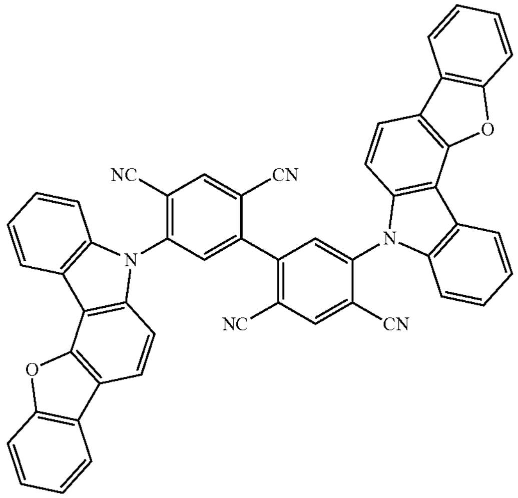
703
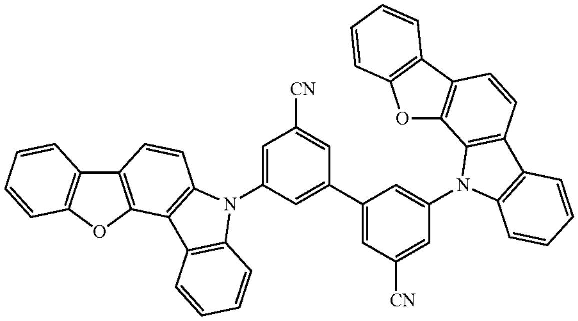

-continued
704
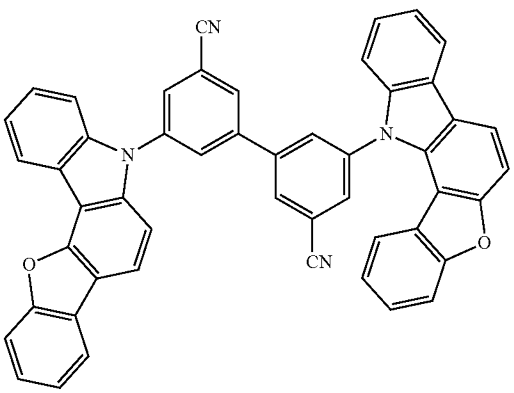
705
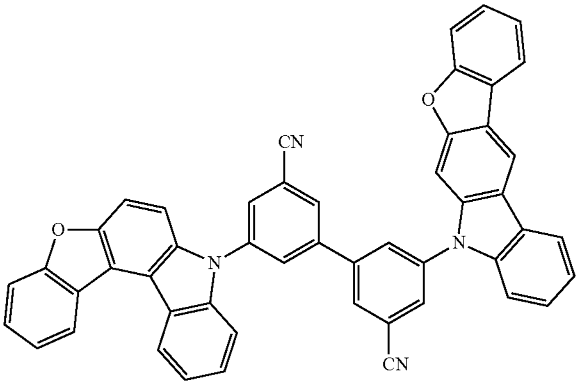
706
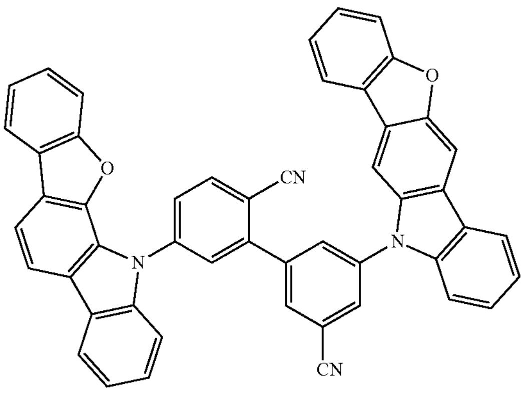
707
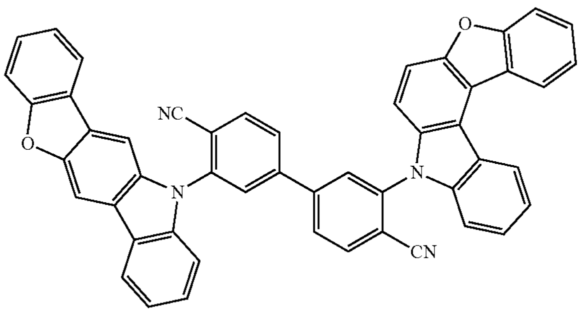
-continued
708
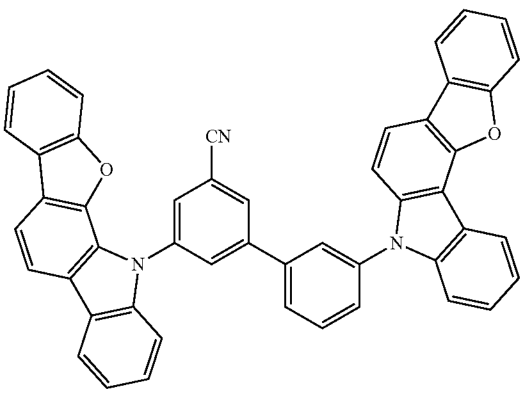
709
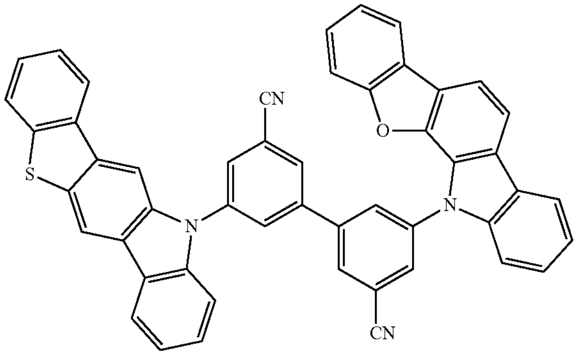
710
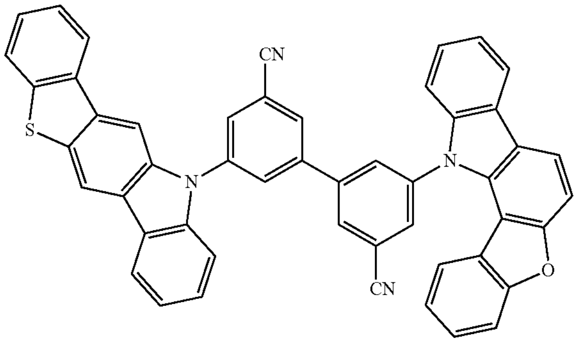
711
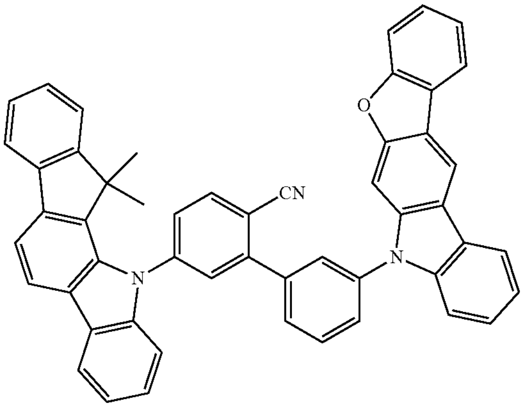

712
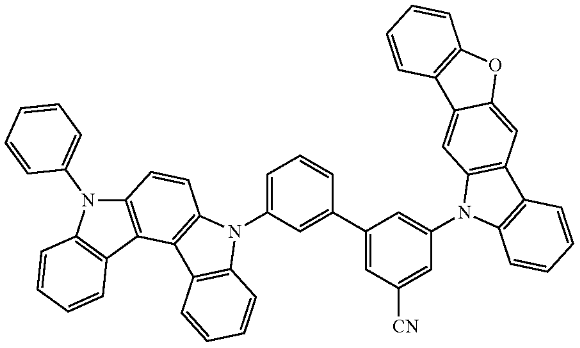
713
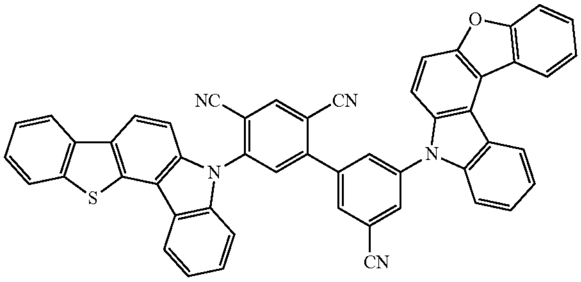
714
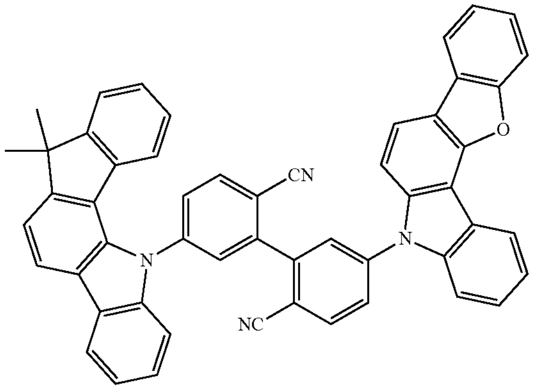
715
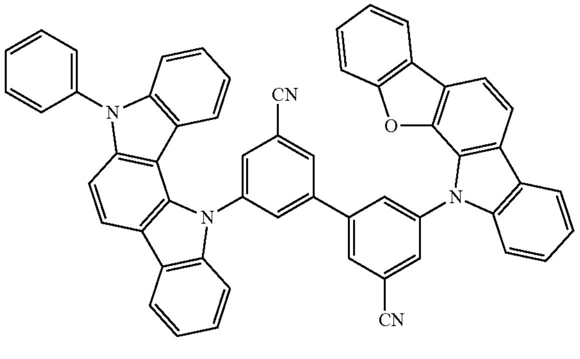
716
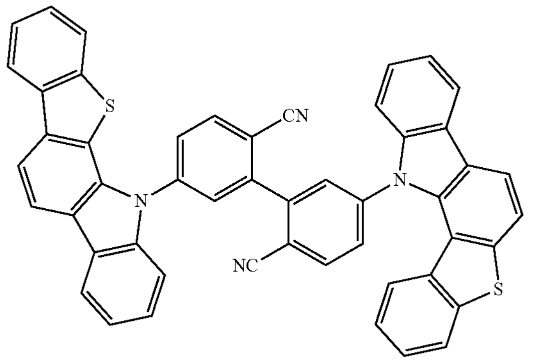
717
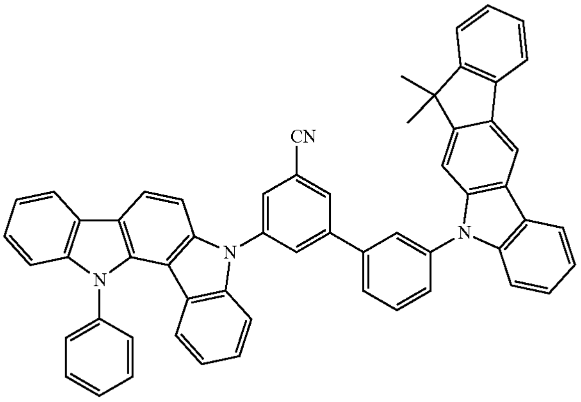
718
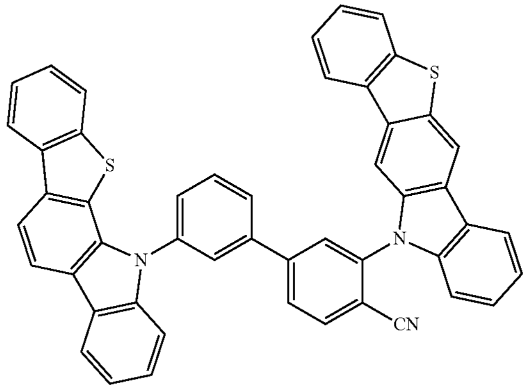
719
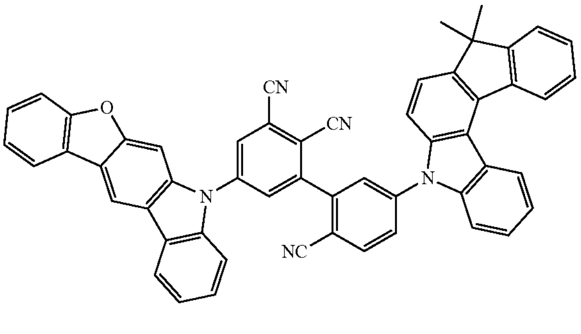

-continued
720
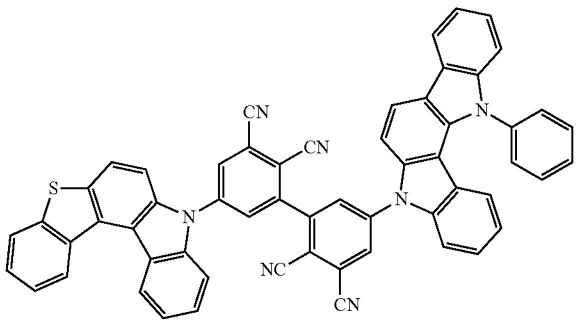
721
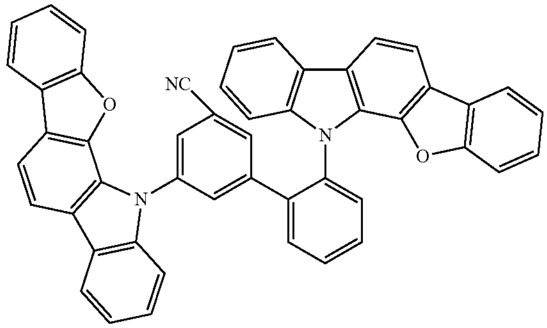
722
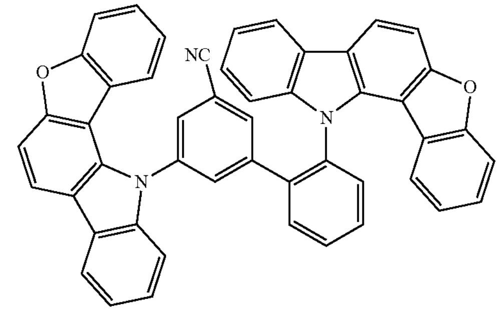
723
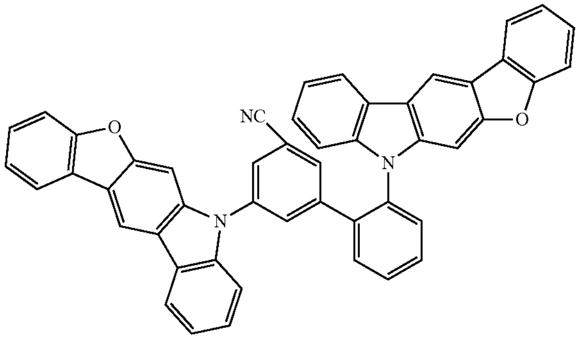
-continued
724
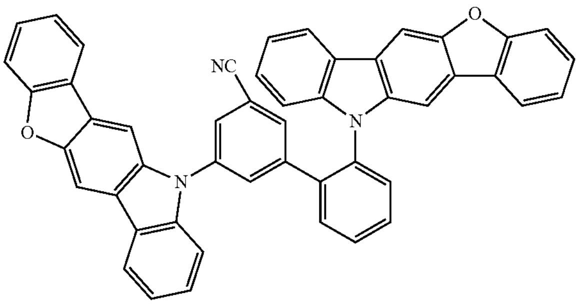
725
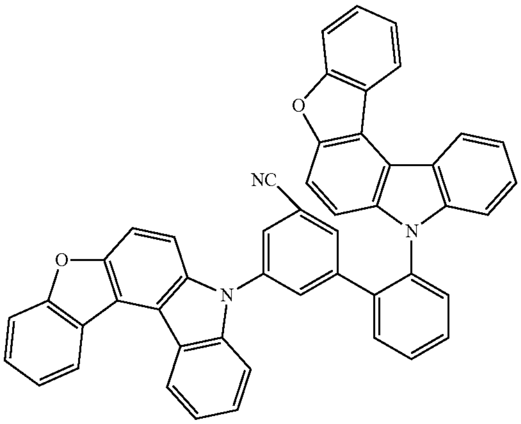
726
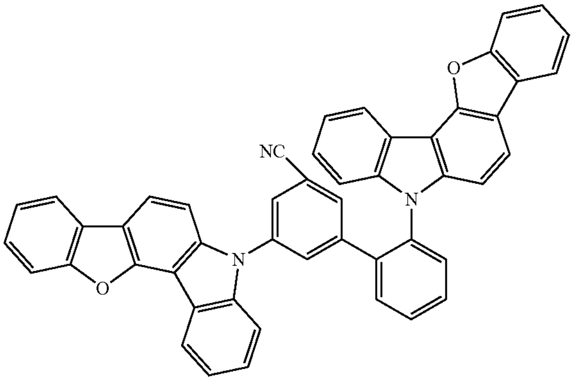
727
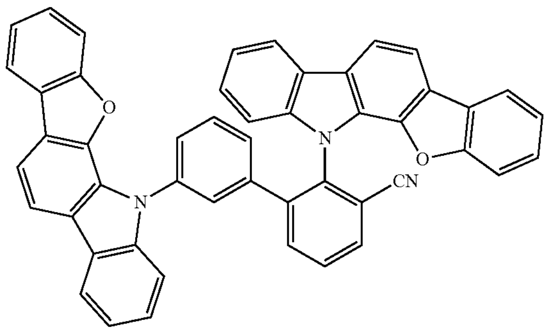

-continued
728
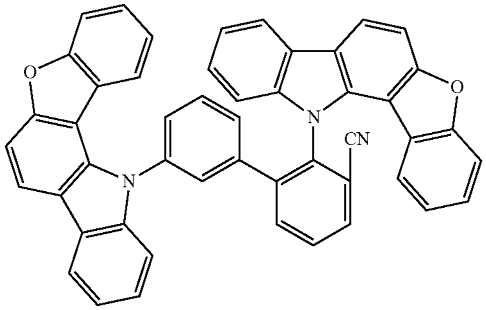
729
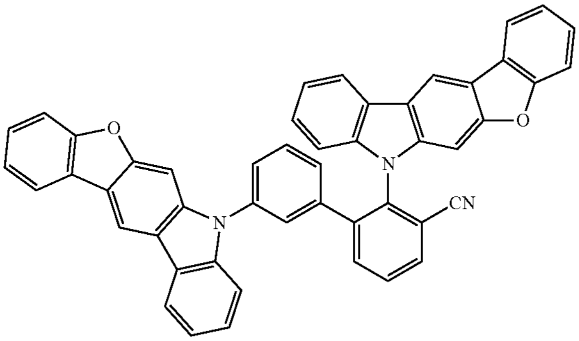
730
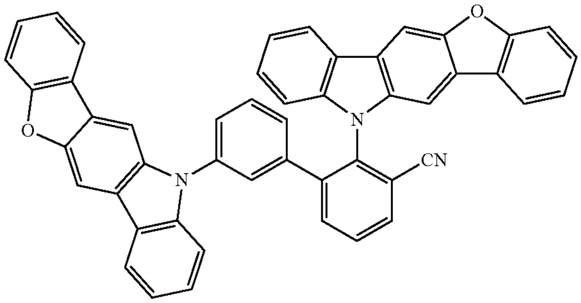
731
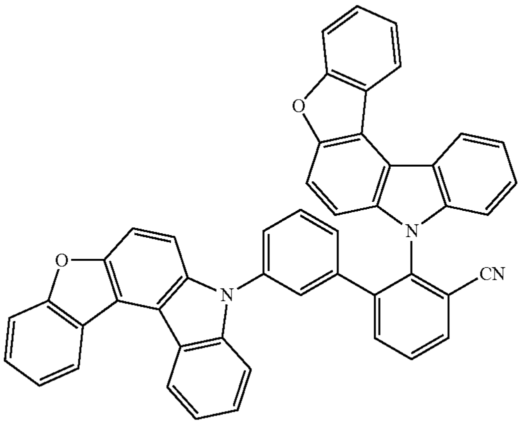
-continued
732
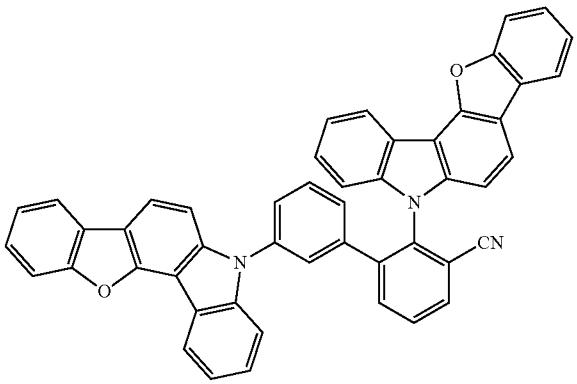
733
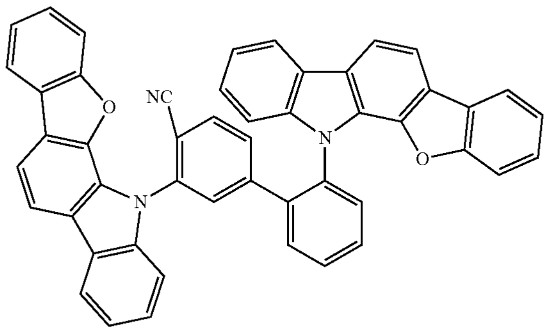
734
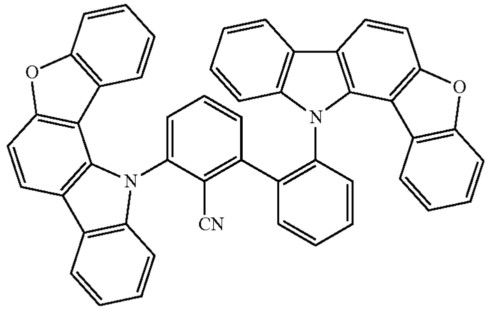
735
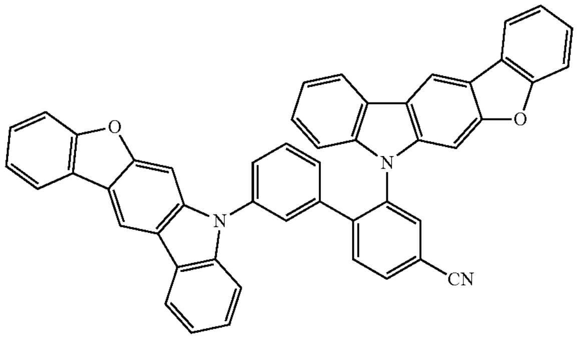

-continued
736
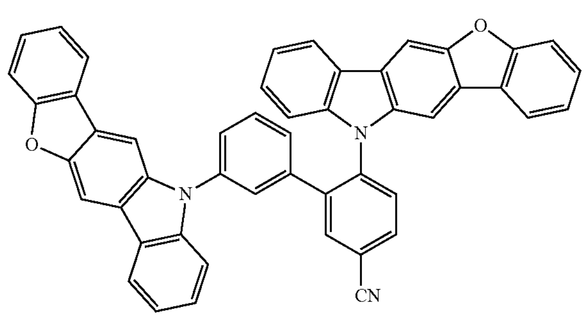
737
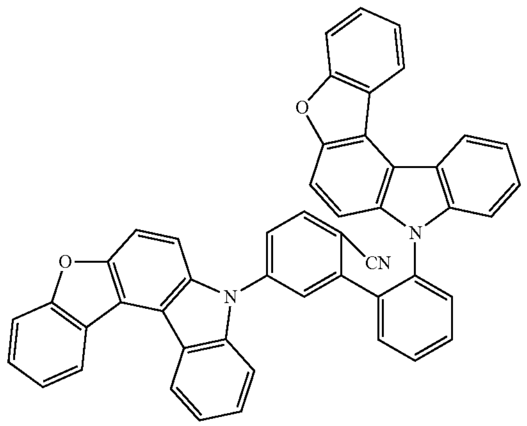
738
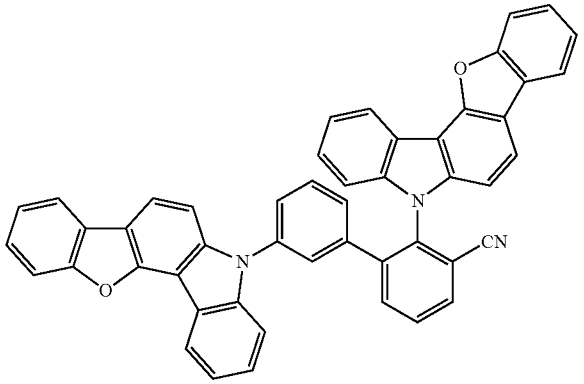
739
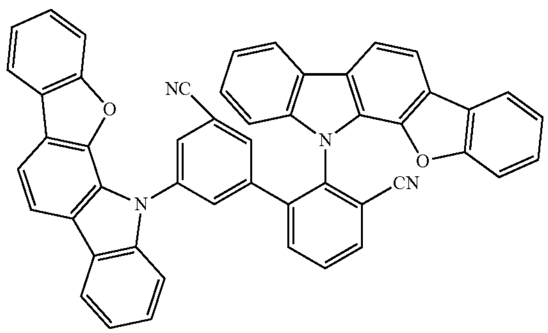
-continued
740
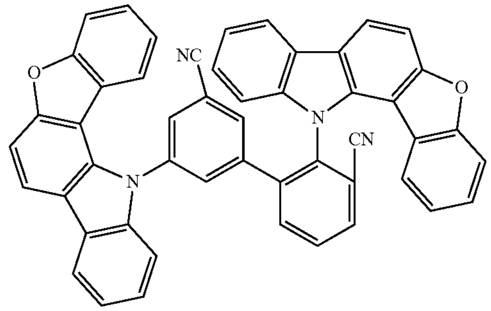
741
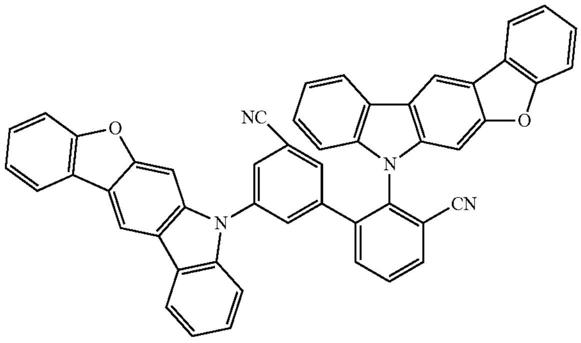
742
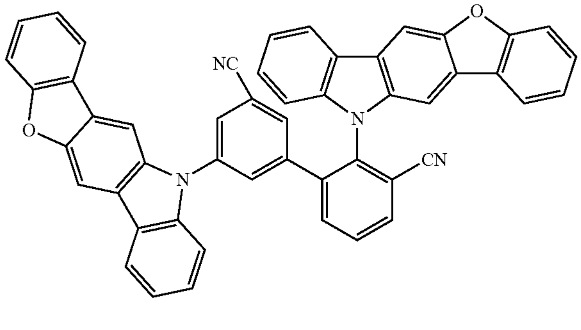
743
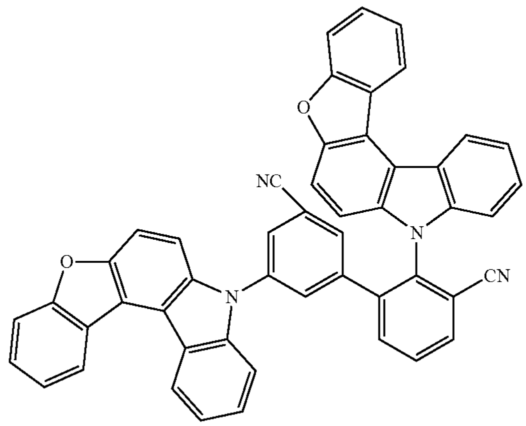

-continued
744
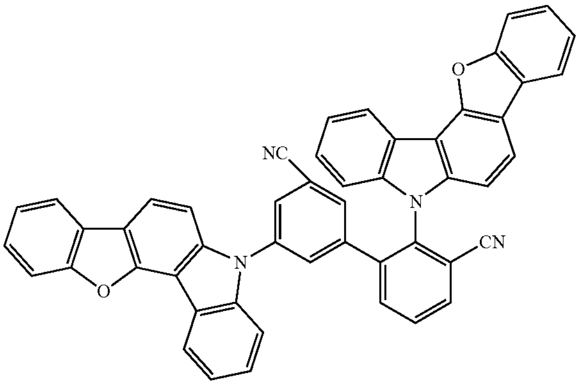
745
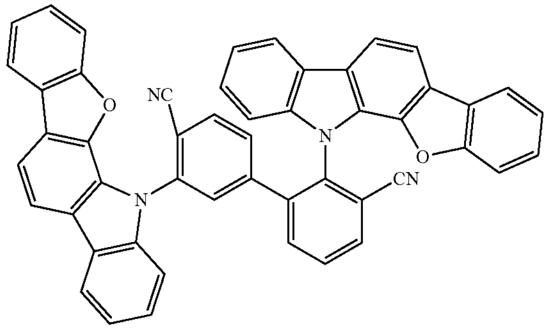
746
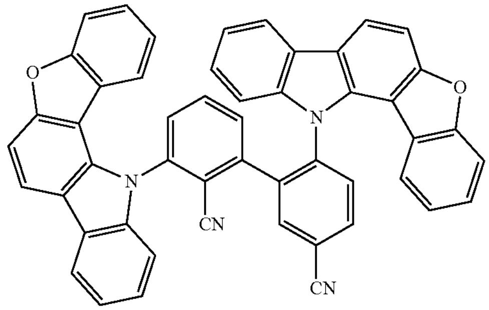
747
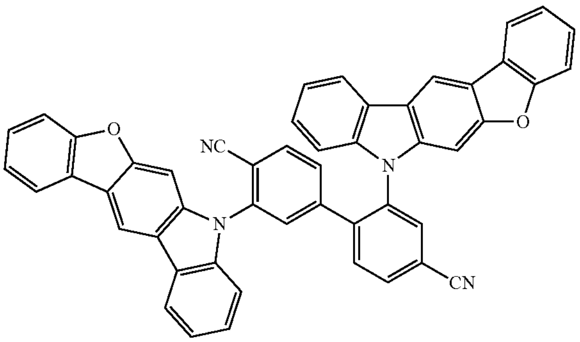
-continued
748
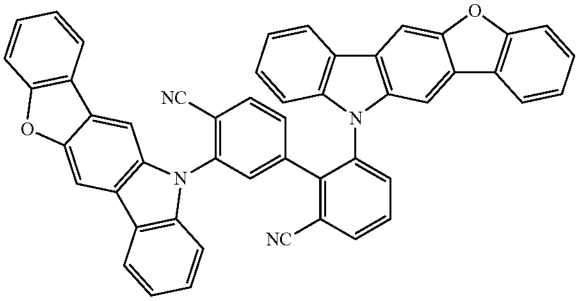
749
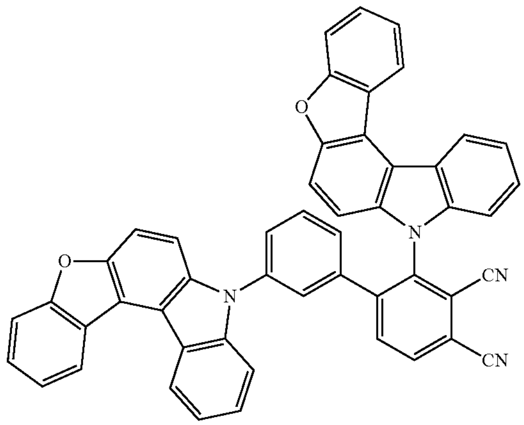
750
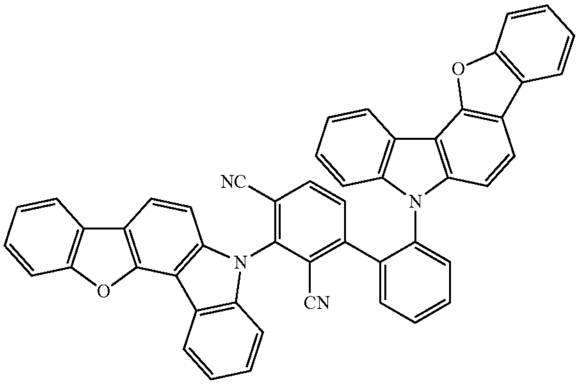
751
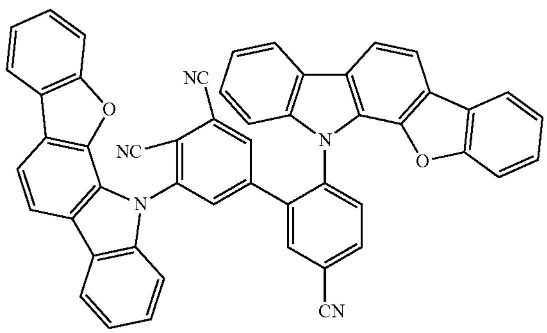

-continued
752
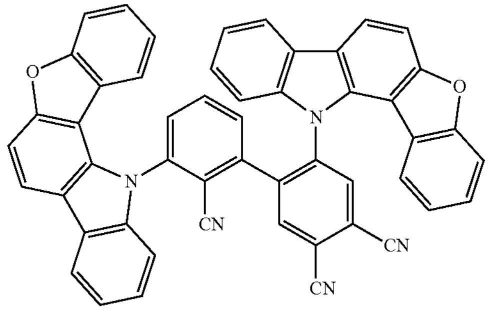
753
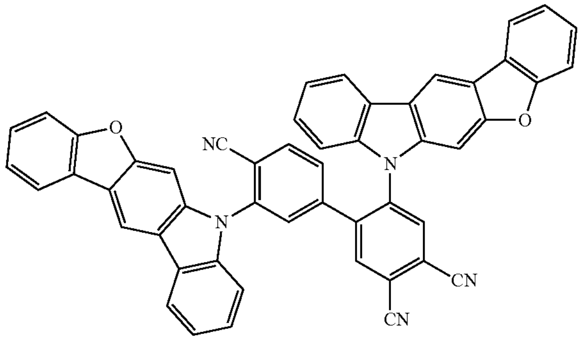
754
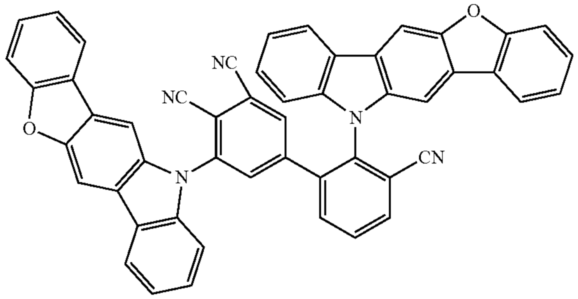
755
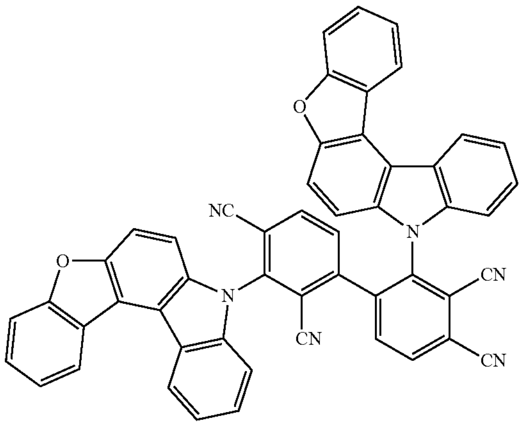
-continued
756
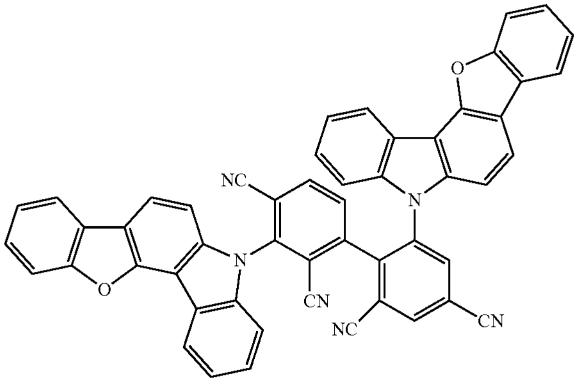
757
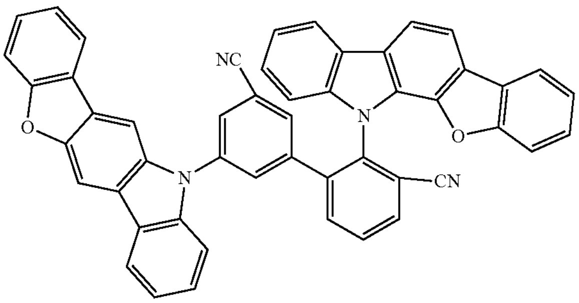
758
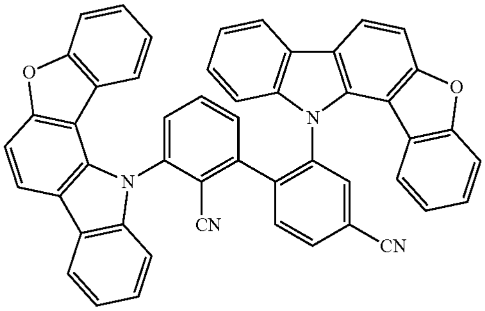
759
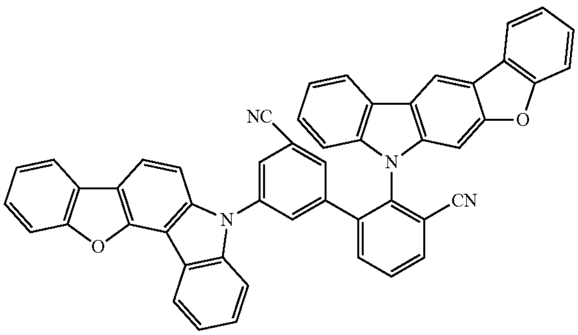

-continued
760
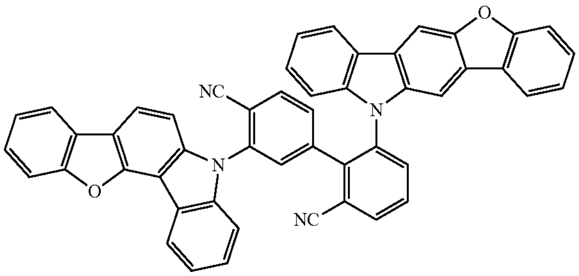
761
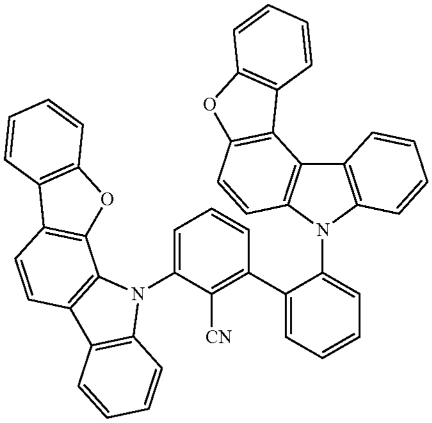
762
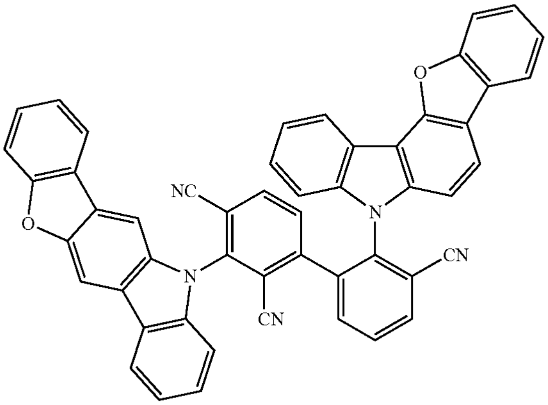
763
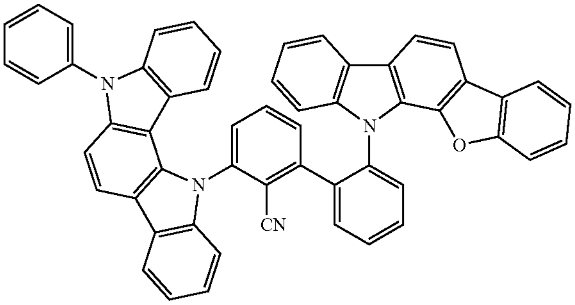
-continued
764
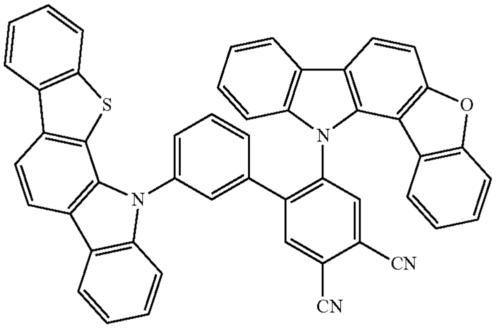
765
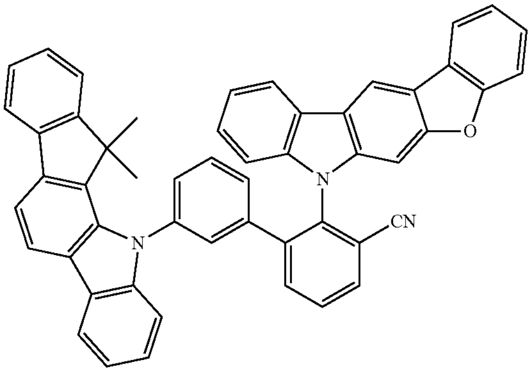
766
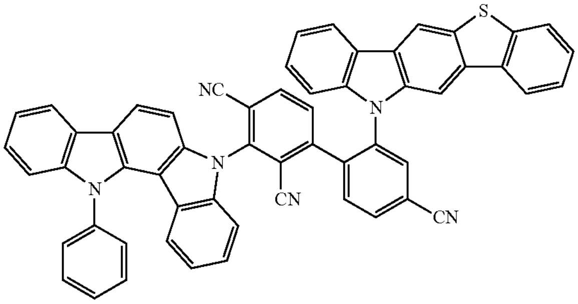
767
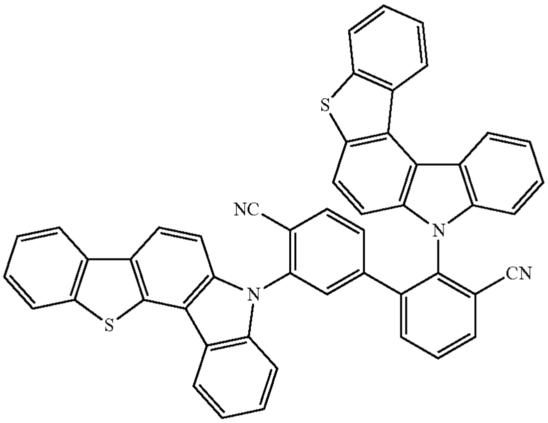

-continued
768
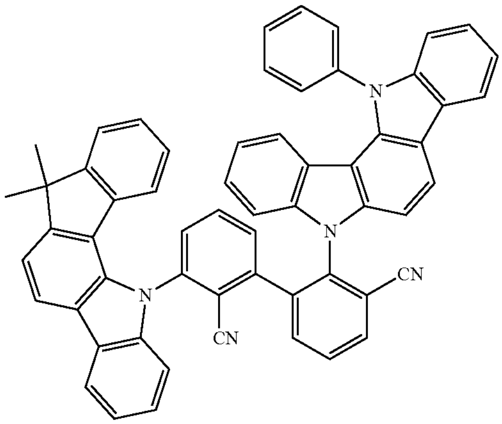
769
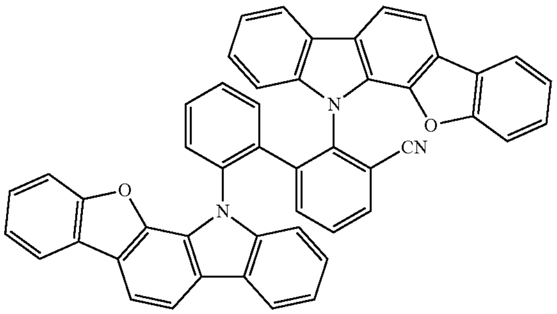
770
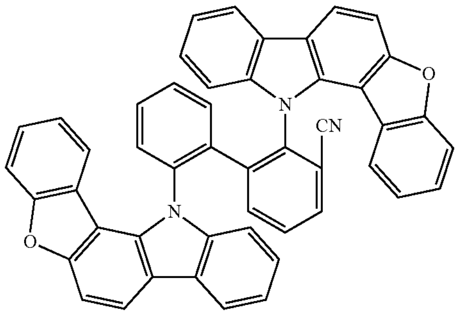
771
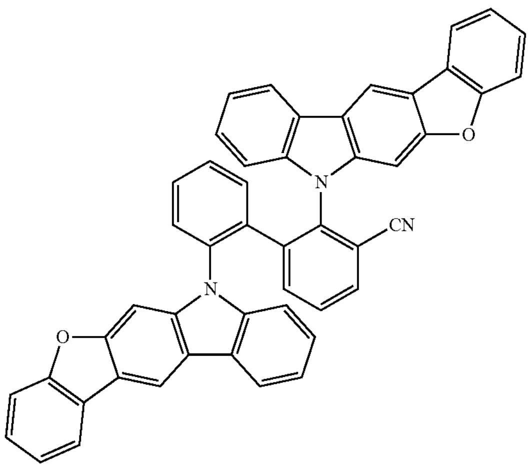
-continued
772
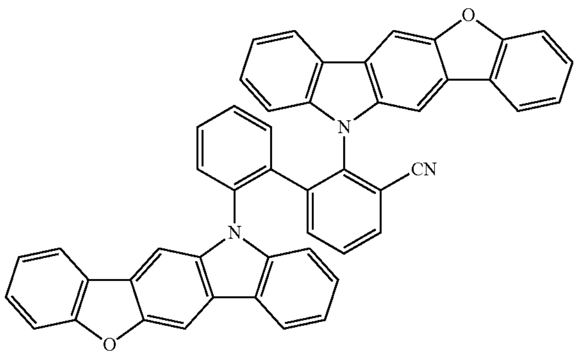
773
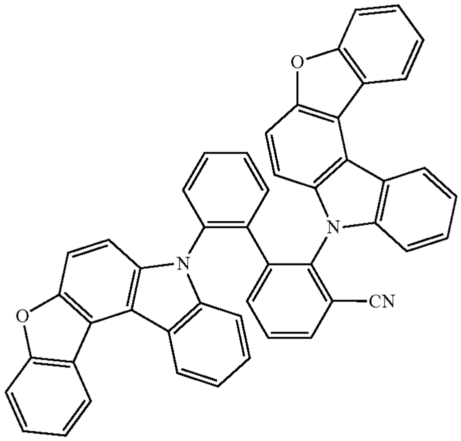
774
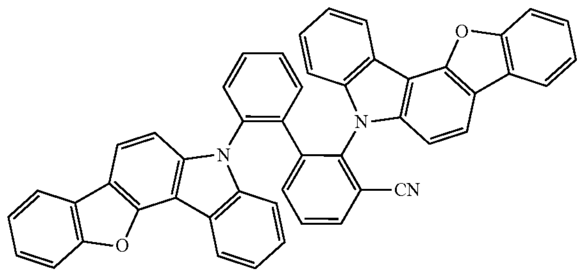
775
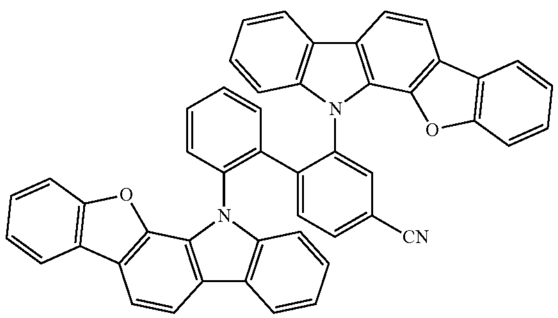

-continued
776
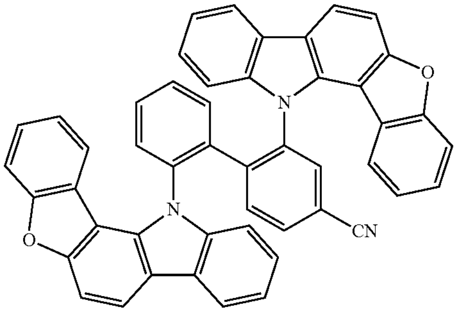
777
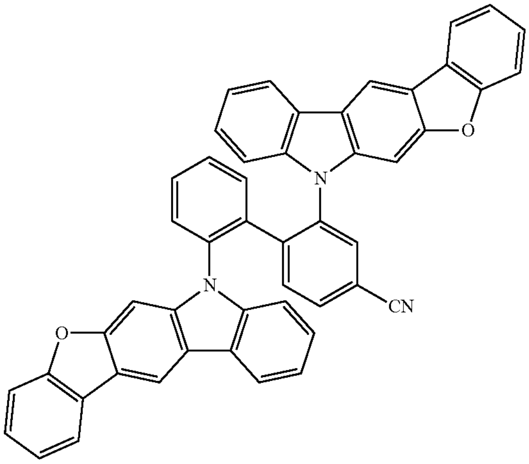
778
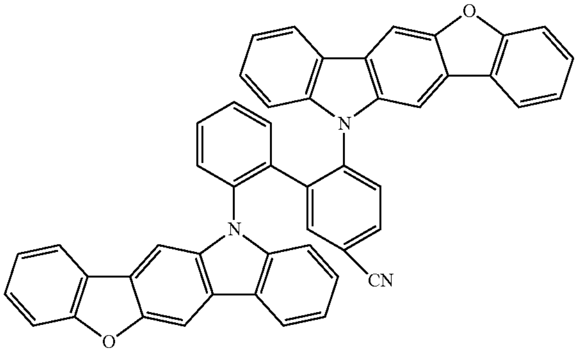
779
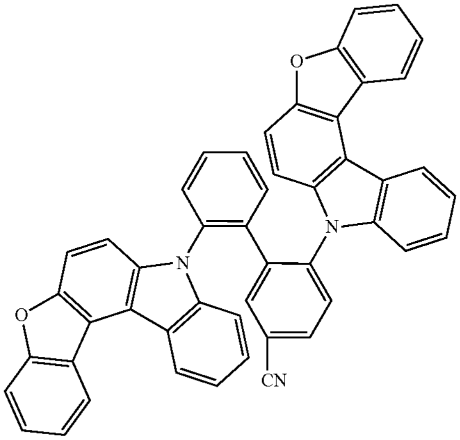
-continued
780
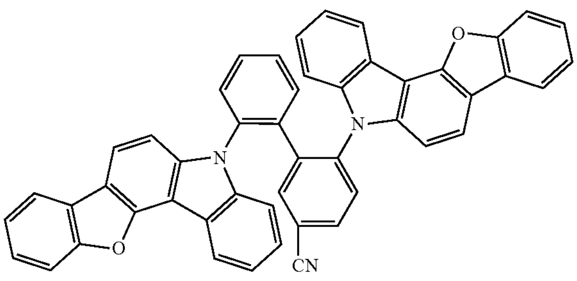
781
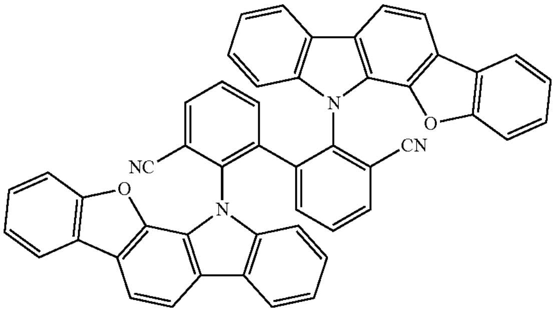
782
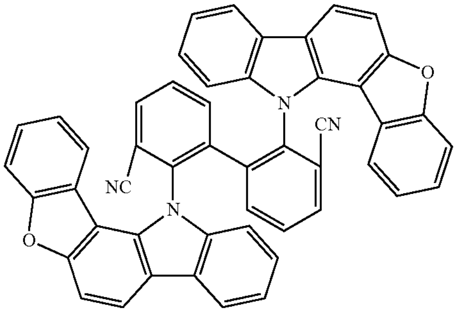
783
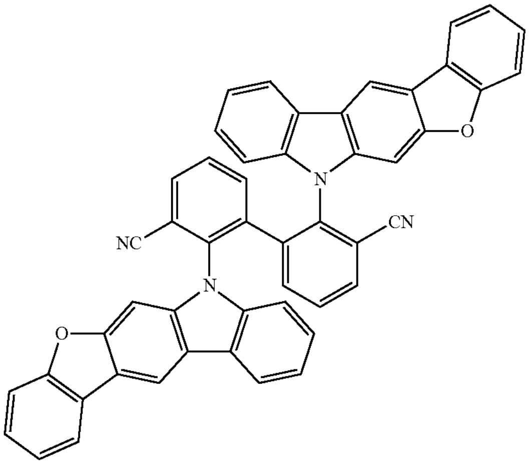

-continued
784
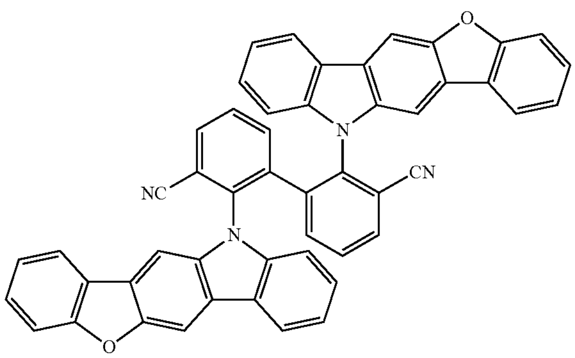
785
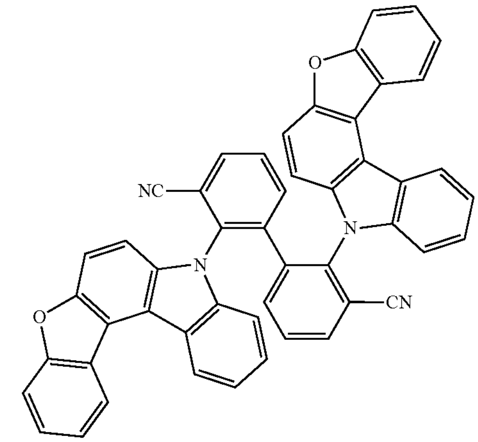
786
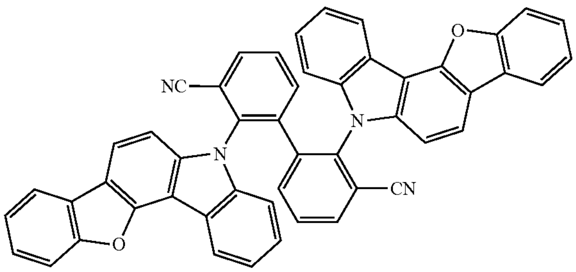
787
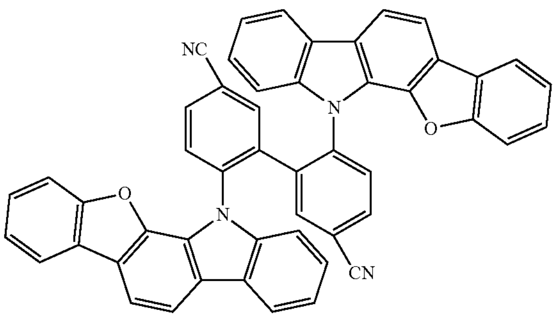
-continued
788
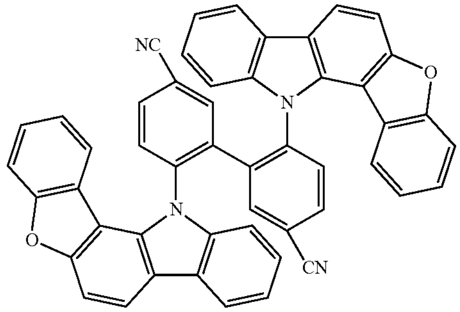
789
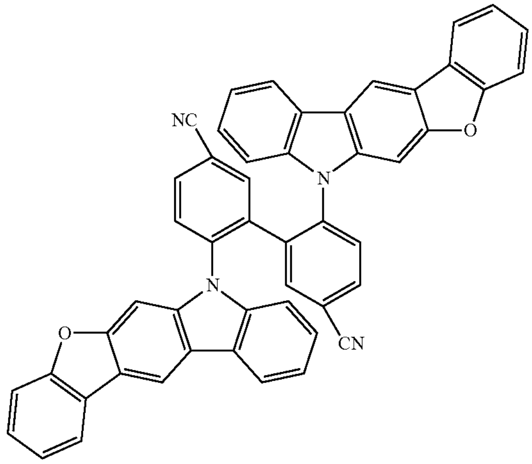
790
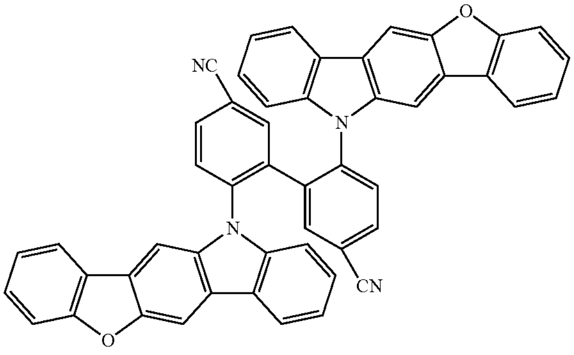
791
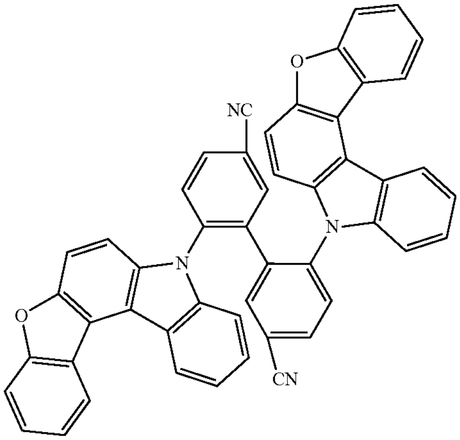

-continued
792
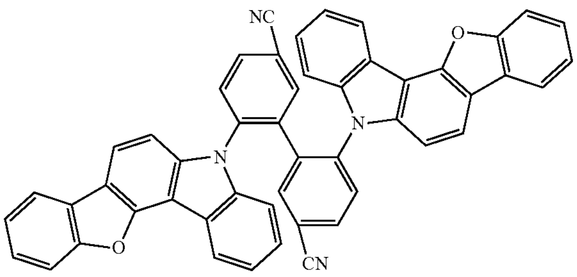
793
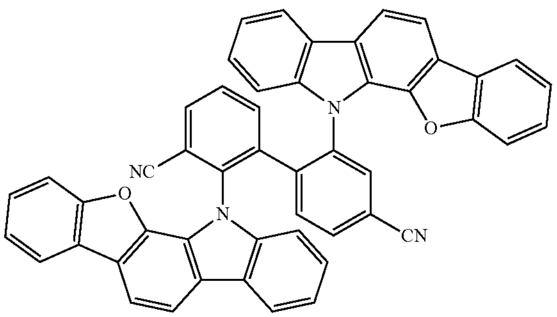
794
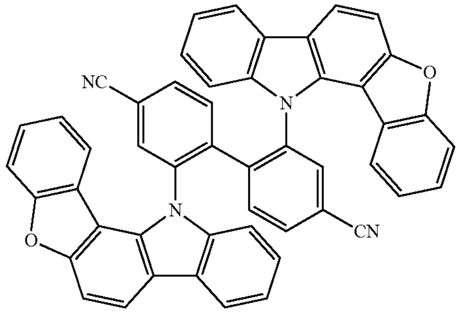
795
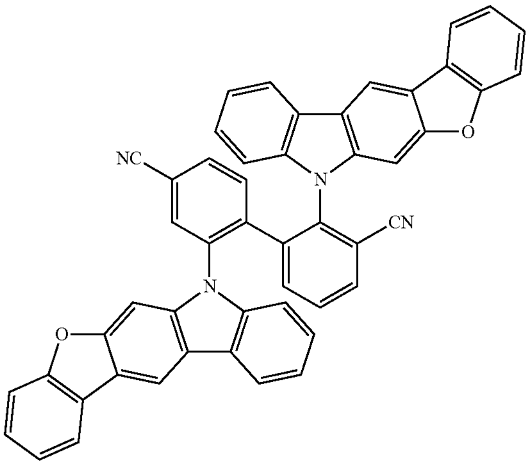
-continued
796
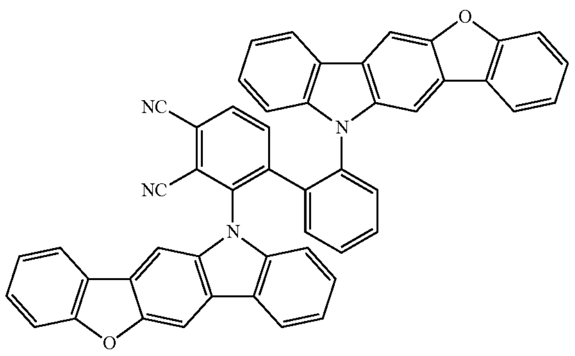
797
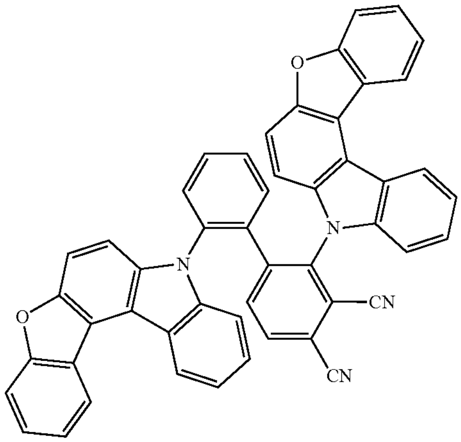
798
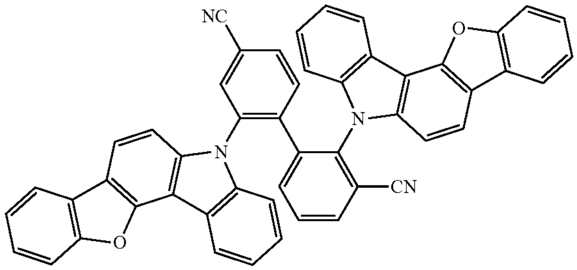
799
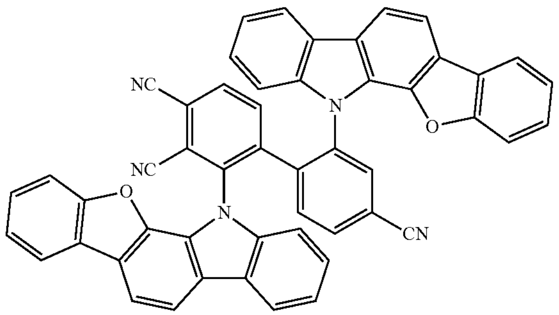

-continued
800
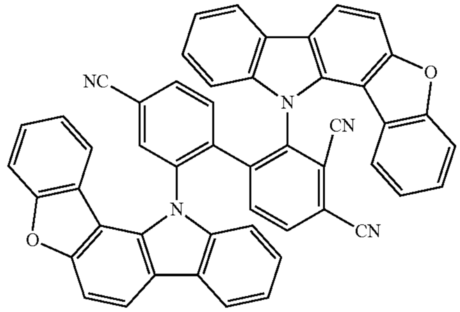
801
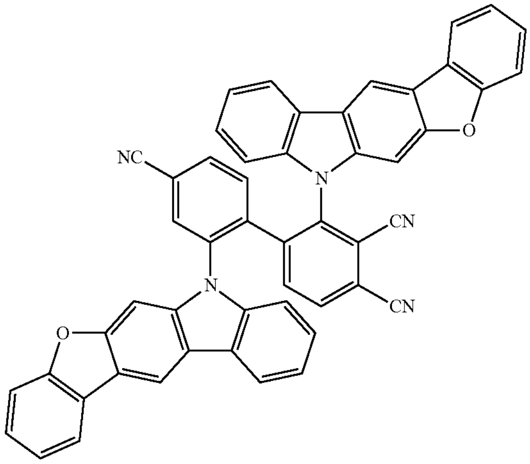
802
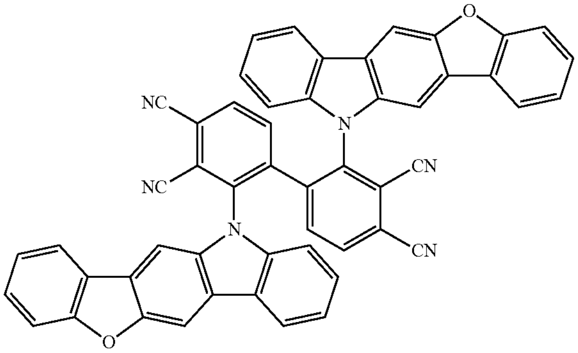
803
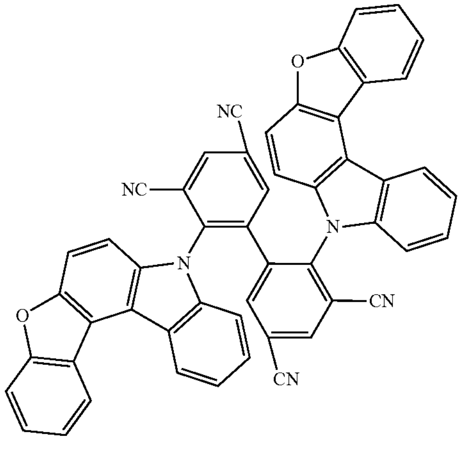
-continued
804
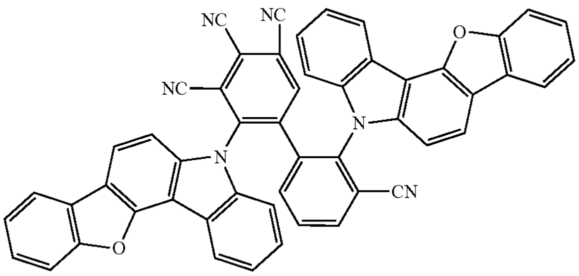
805
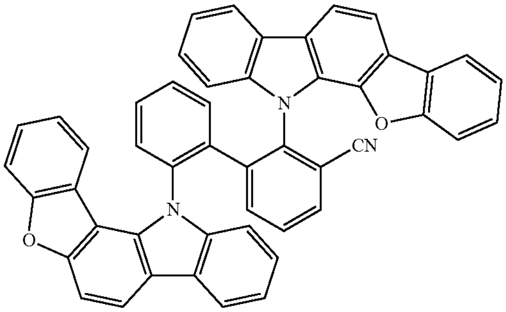
806
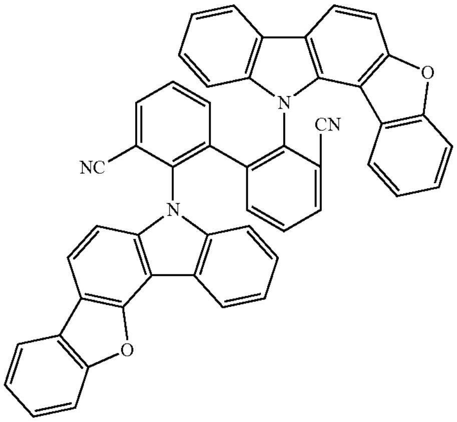
807
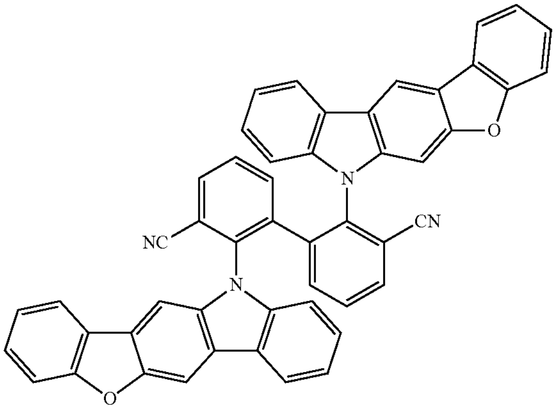

-continued
808
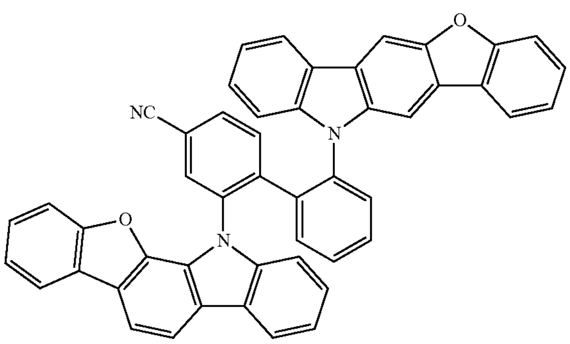
809
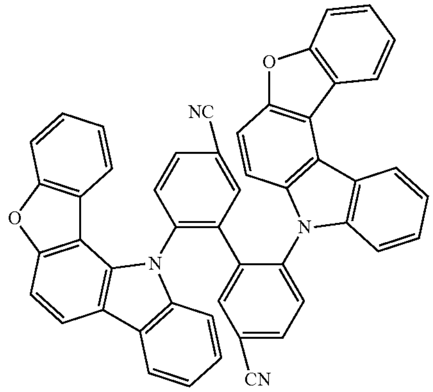
810
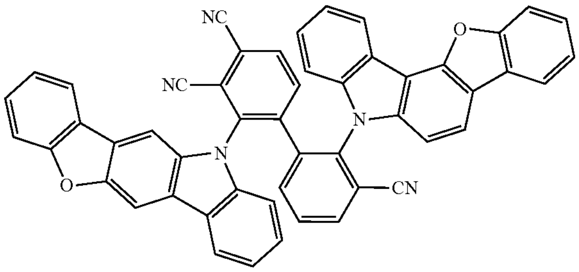
811
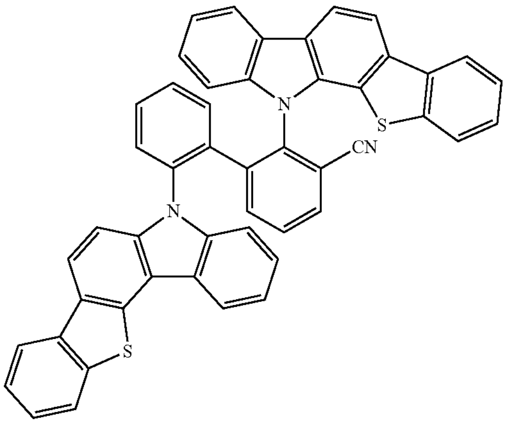
-continued
812
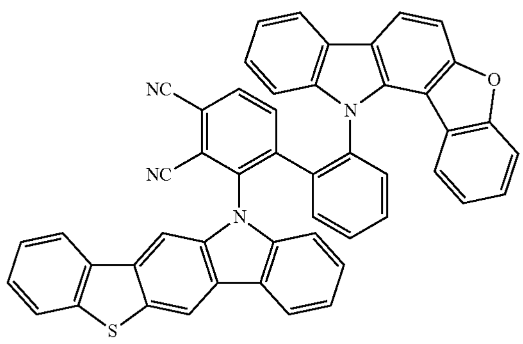
813
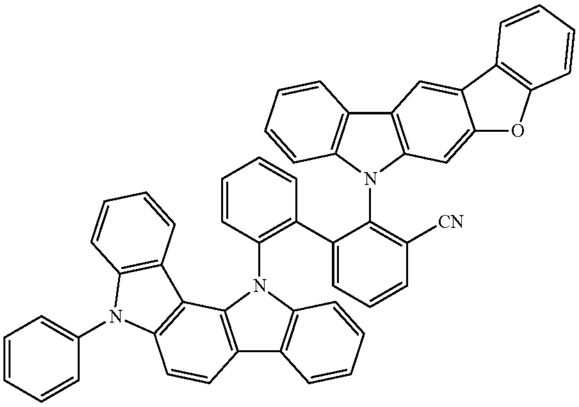
814
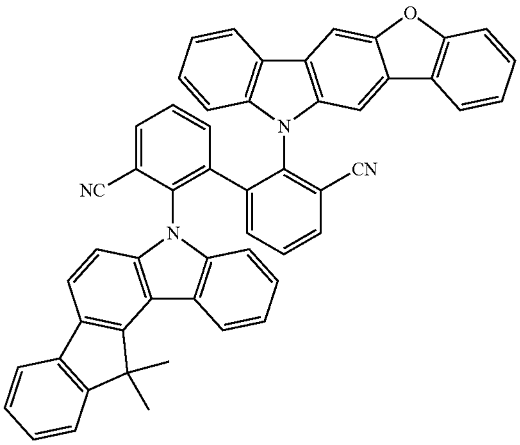

-continued
815
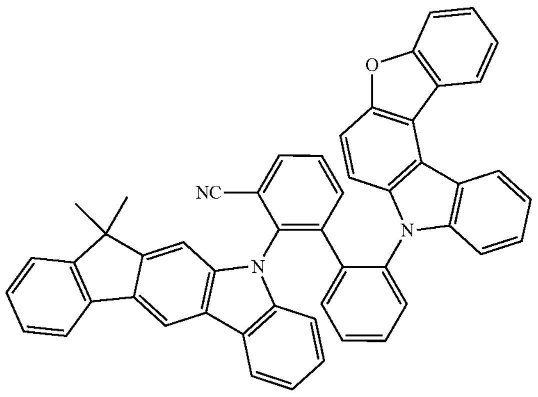
816
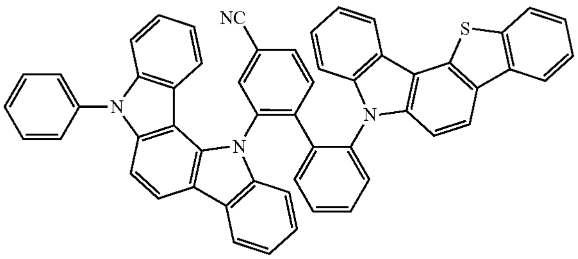
817
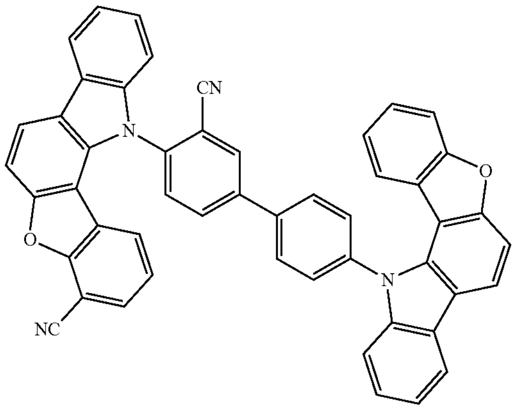
818
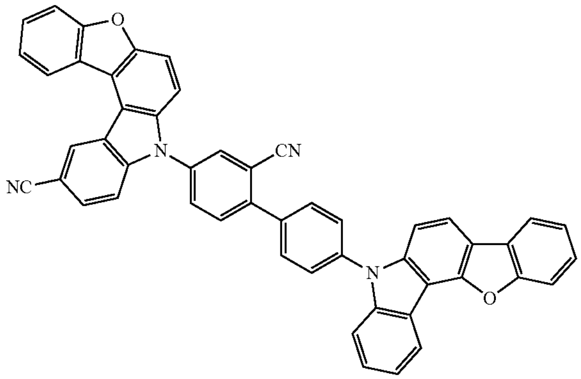
-continued
819
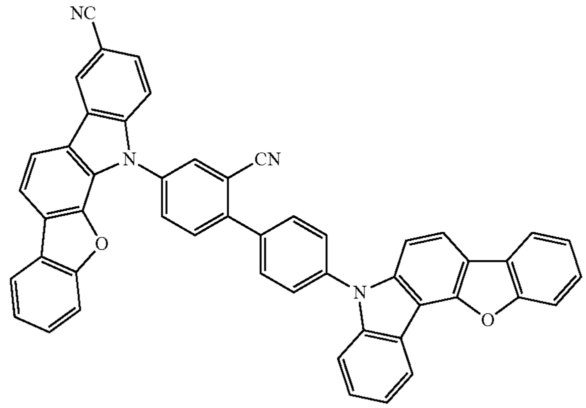
820
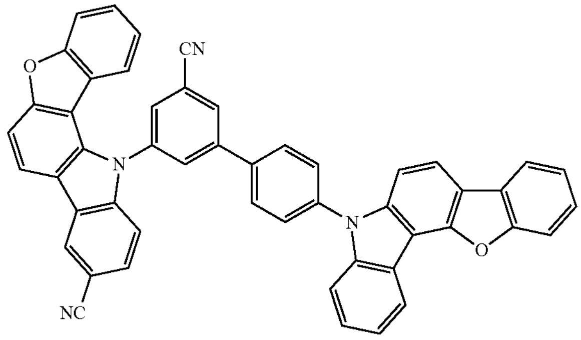
821
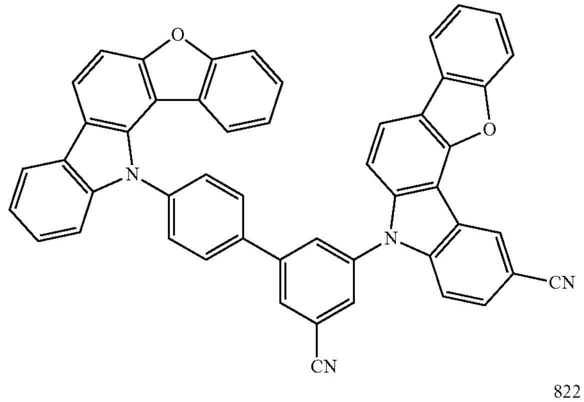
822
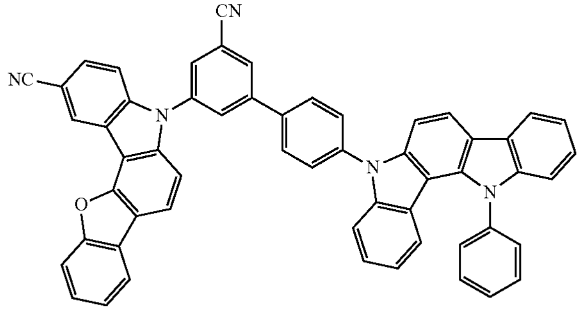

-continued
823
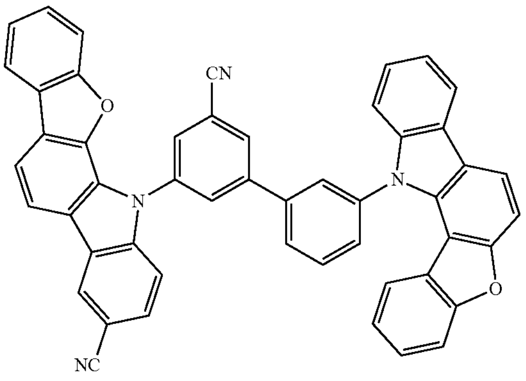
824
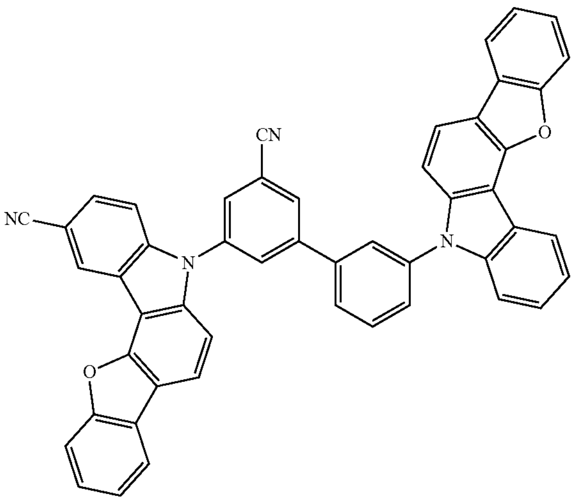
825
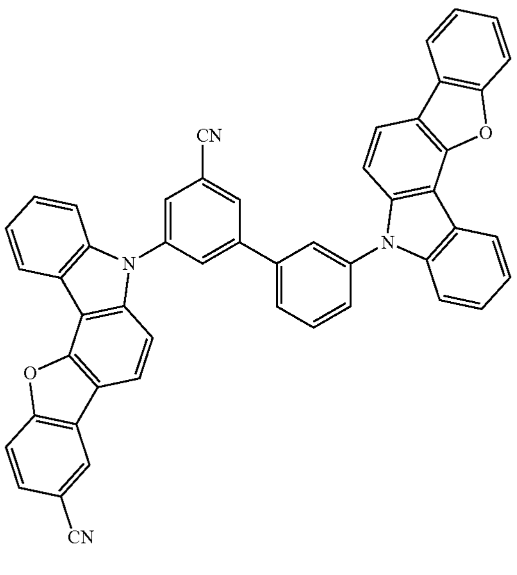
-continued
826
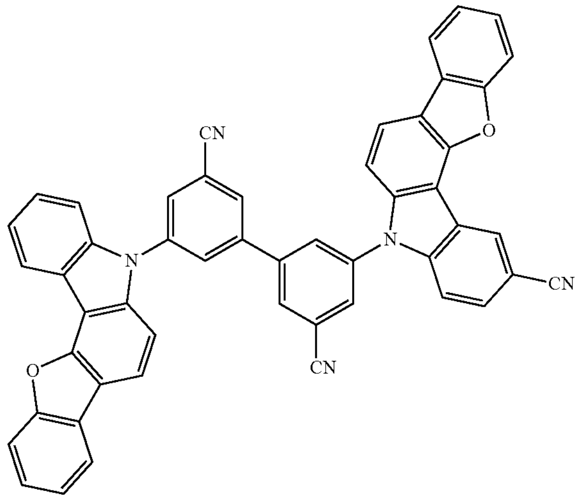
827
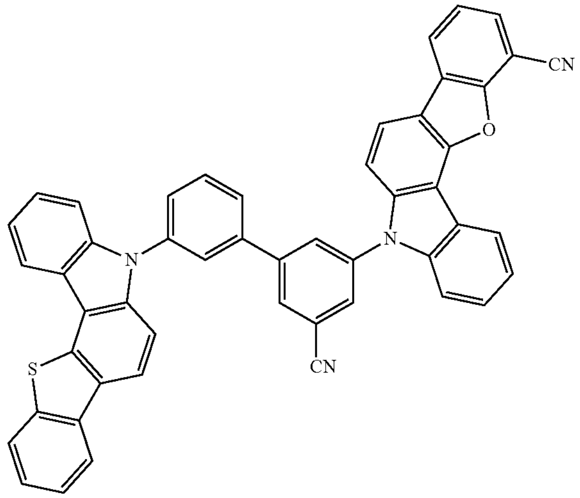
828
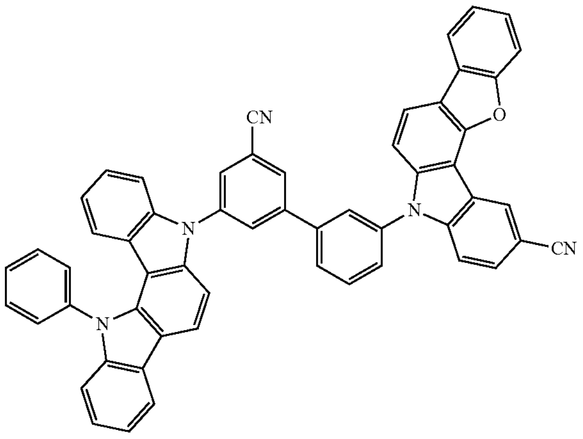

-continued
829
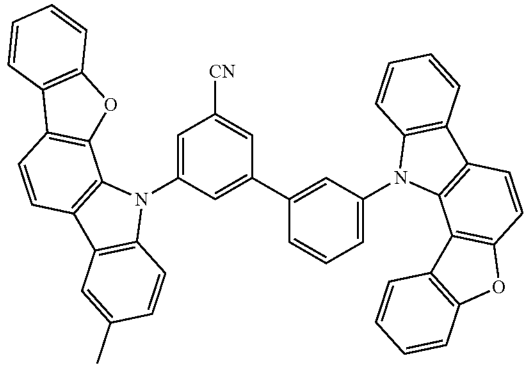
830
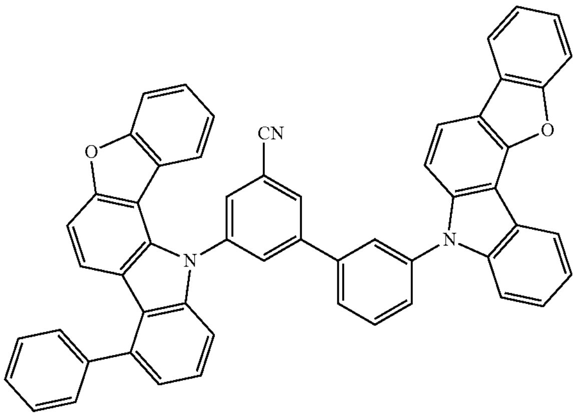
831
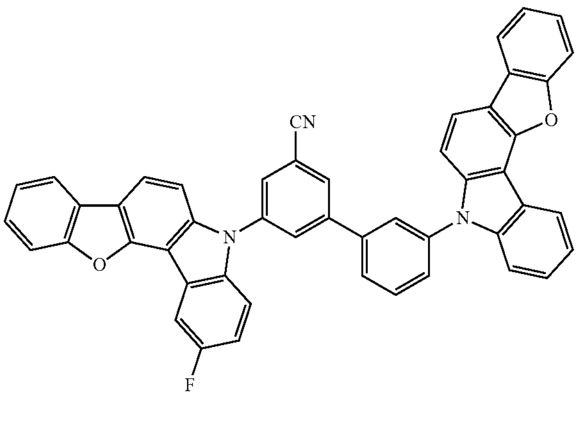
-continued
832
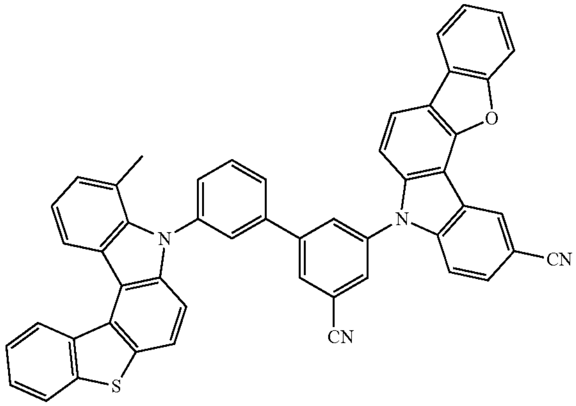
833
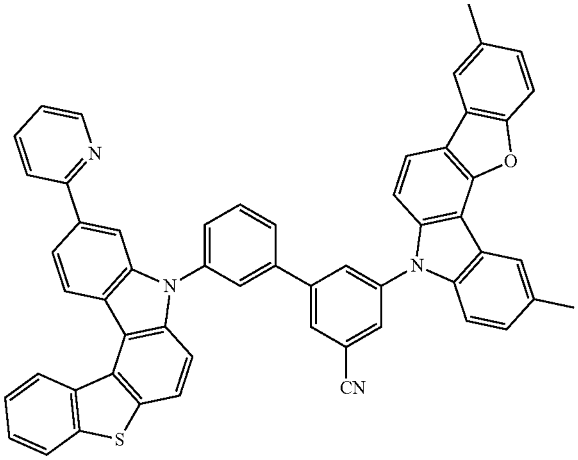
834
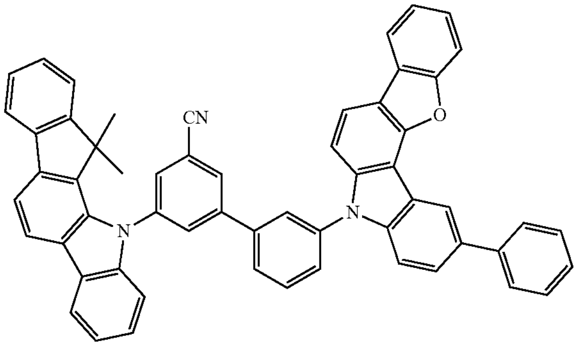
835
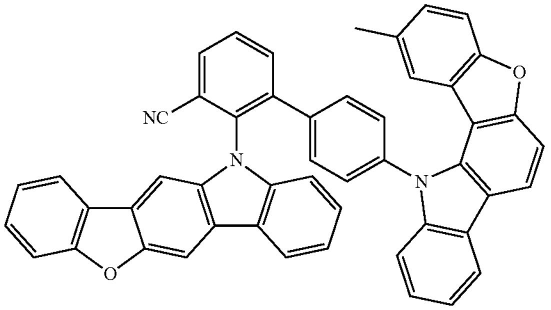

-continued
836
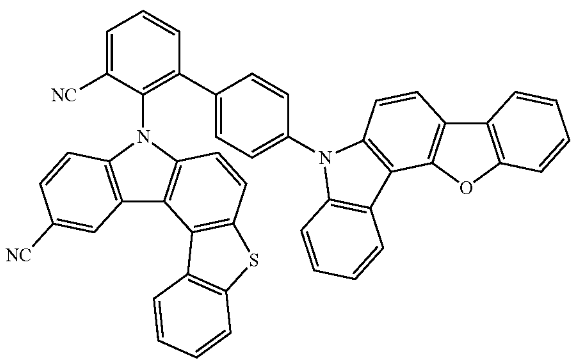
837
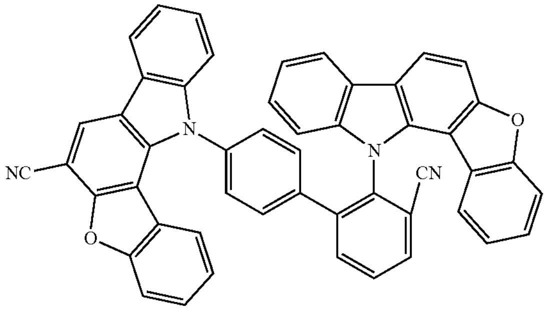
838
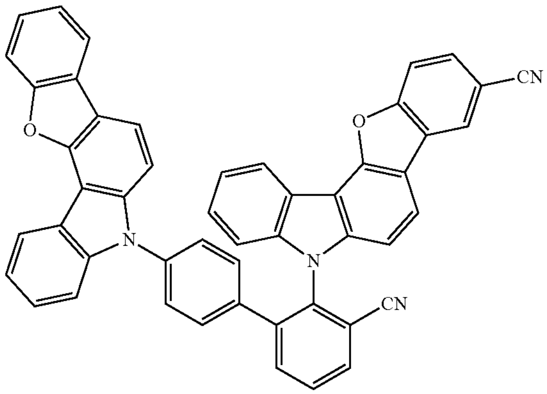
839
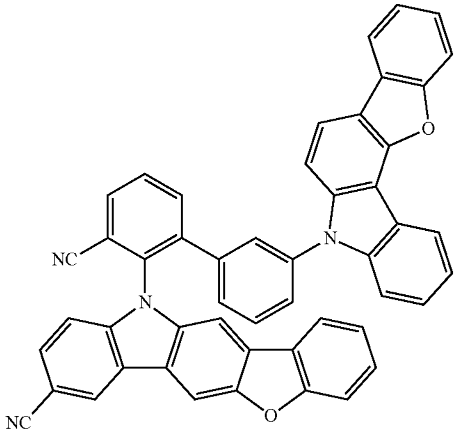
-continued
840
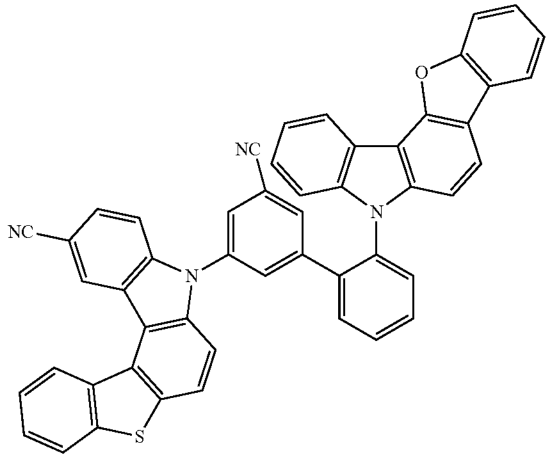
841
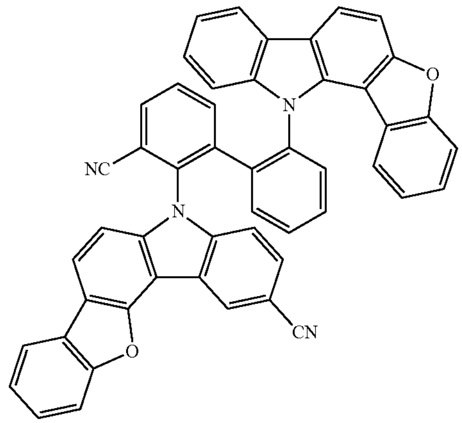
842
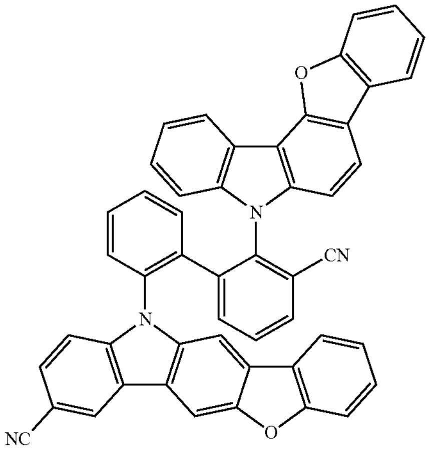

-continued
843
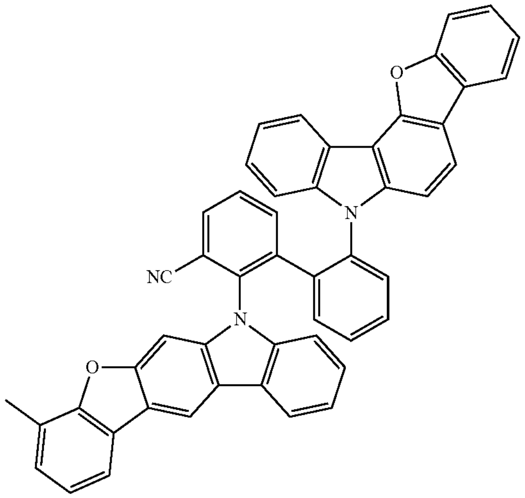
844
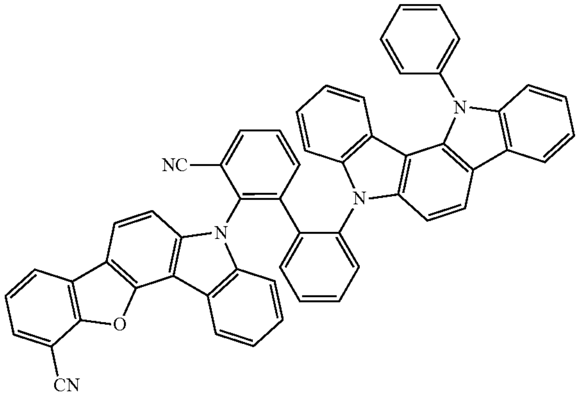
845
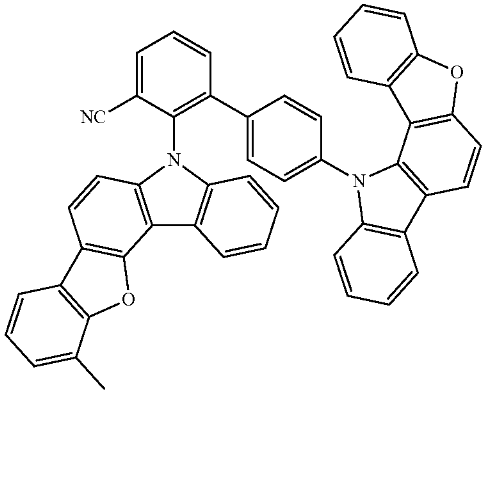
-continued
846
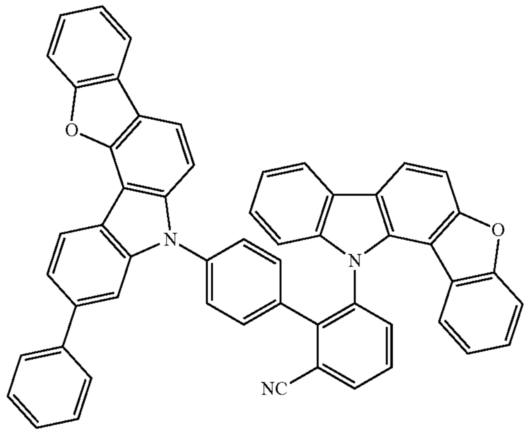
847
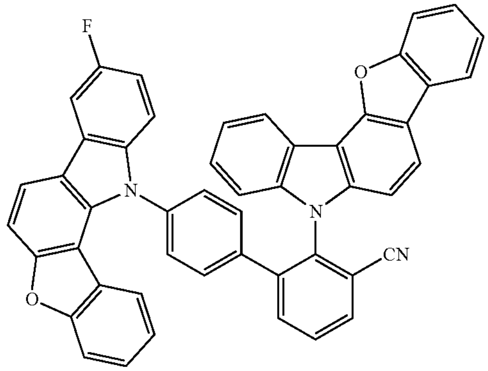
848
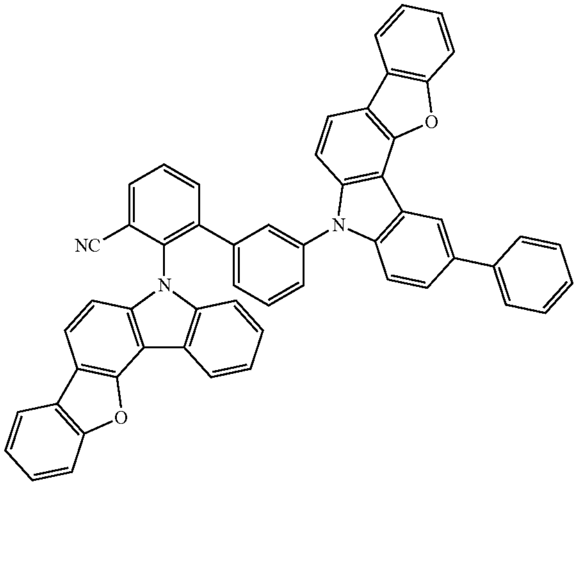

-continued
849
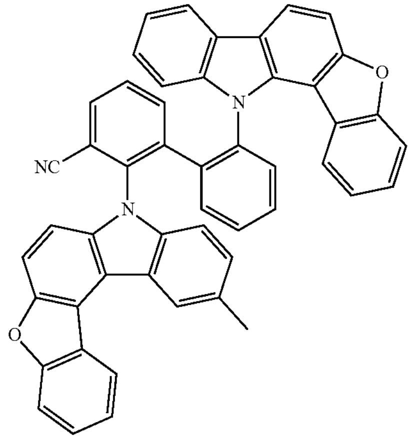
850
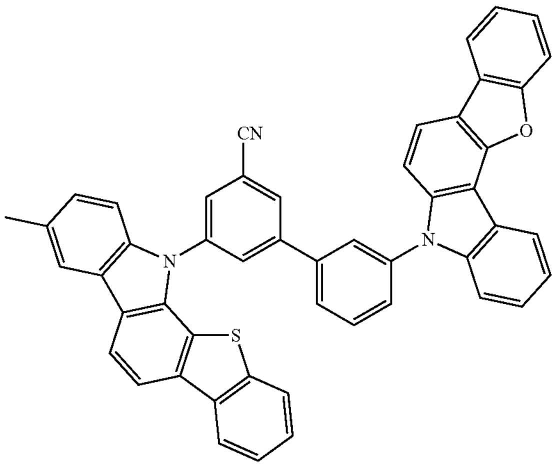
851
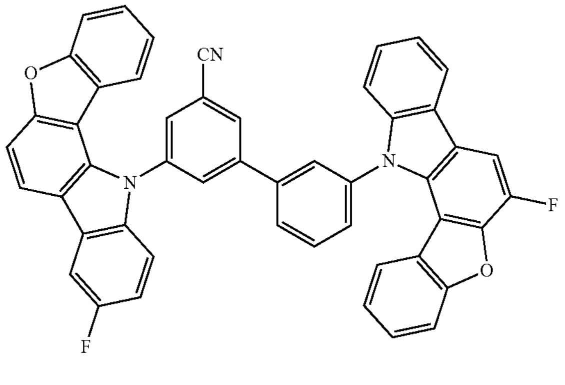
-continued
852
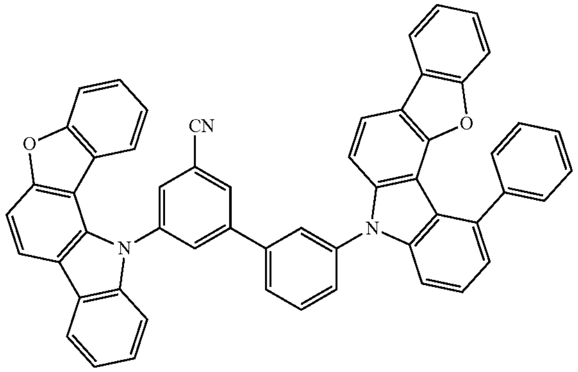
Group HE3
1
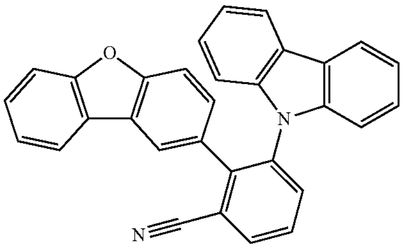
2
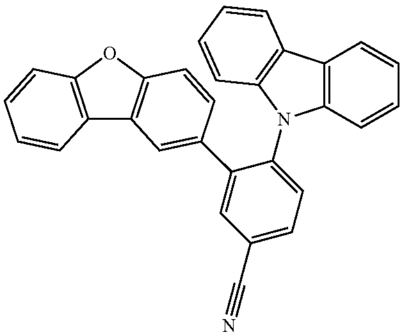
3
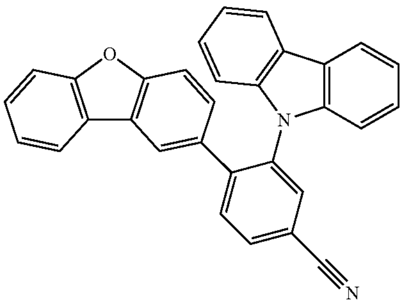

-continued
4
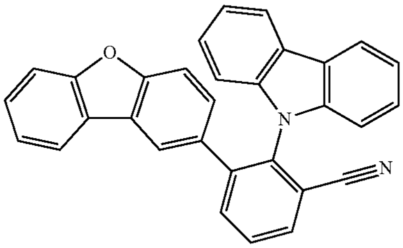
5
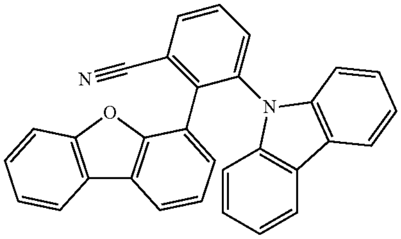
6
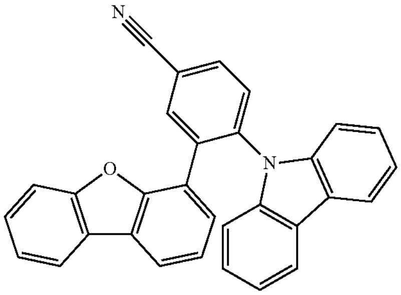
7
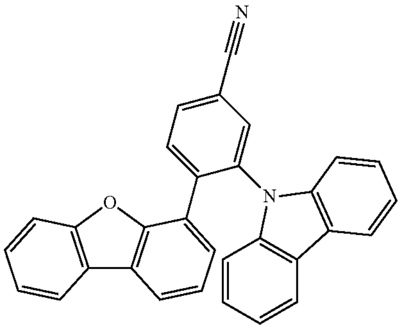
8
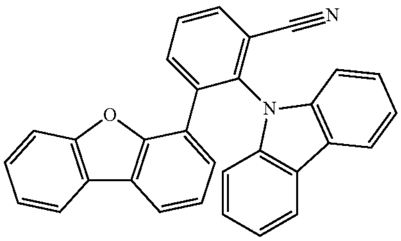
9
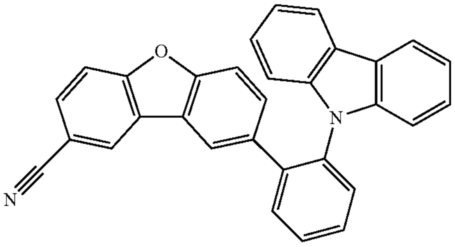
-continued
10
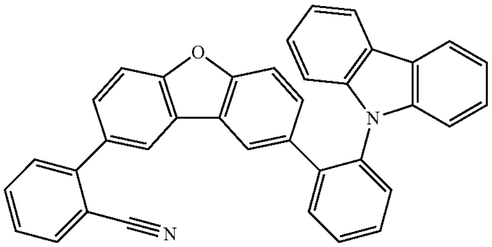
11
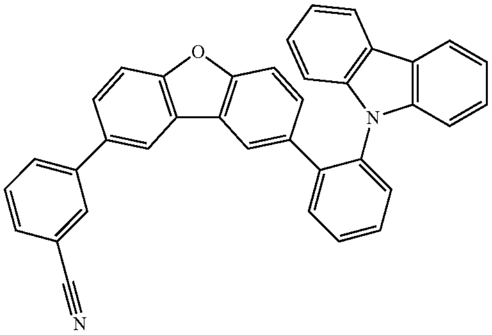
12
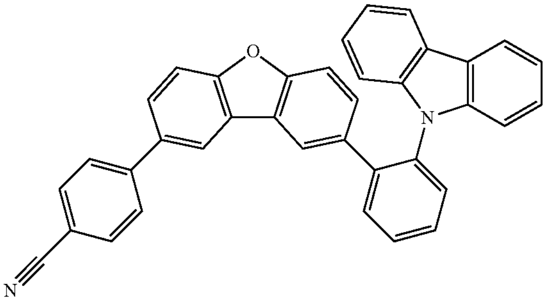
13
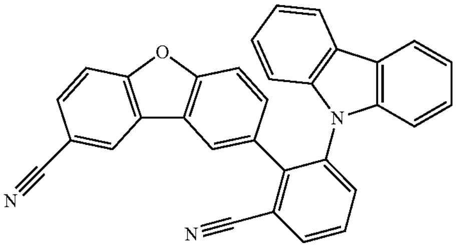
14
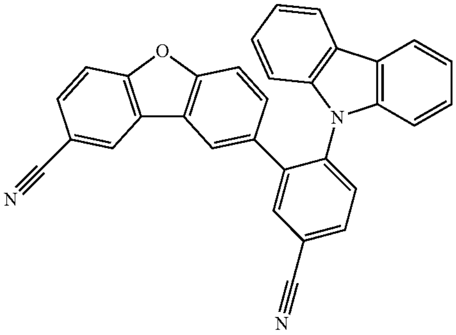

-continued
15
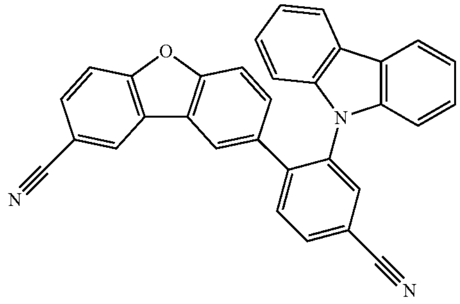
16
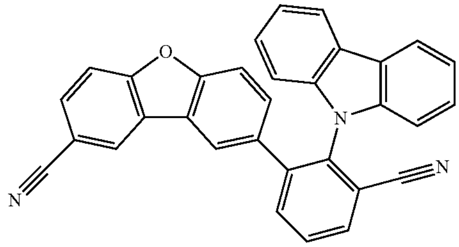
17
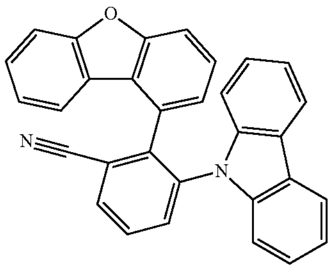
18
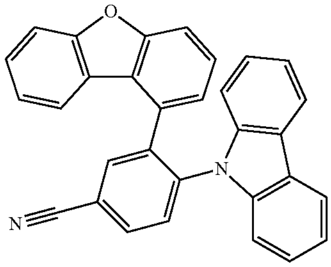
19
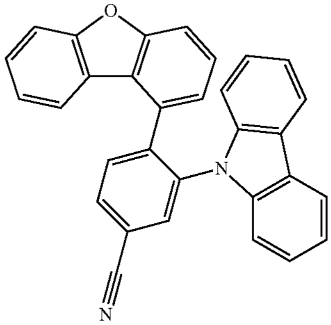
-continued
20
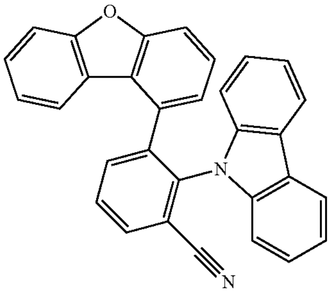
21
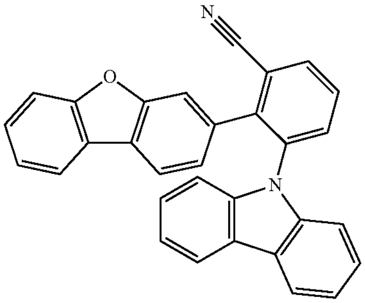
22
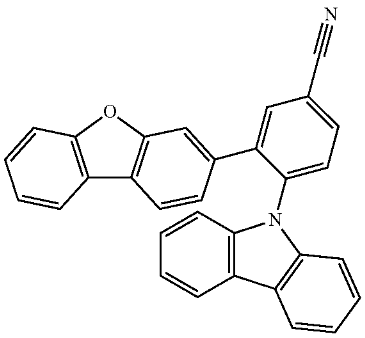
23
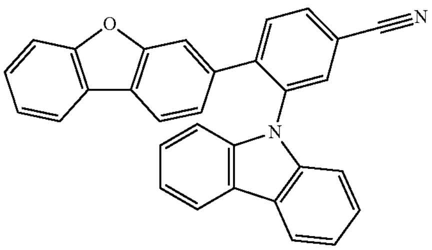
24
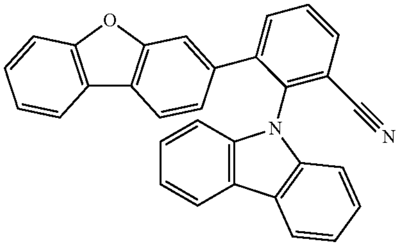

-continued
25
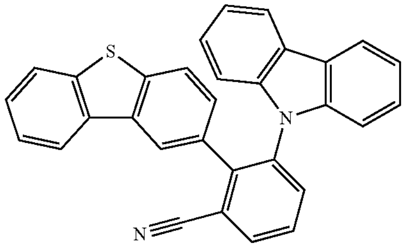
26
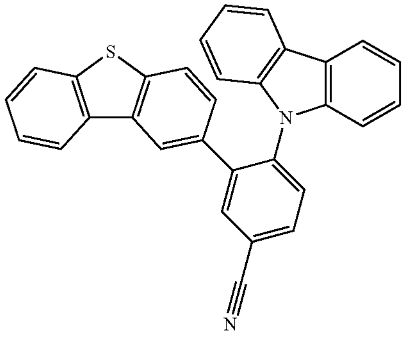
27
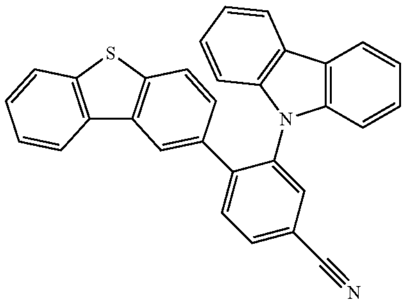
28
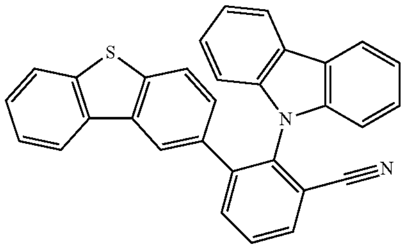
29
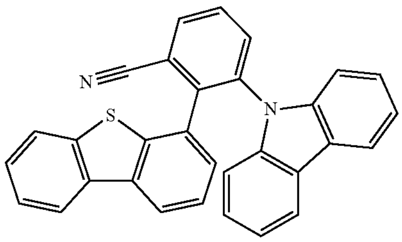
-continued
30
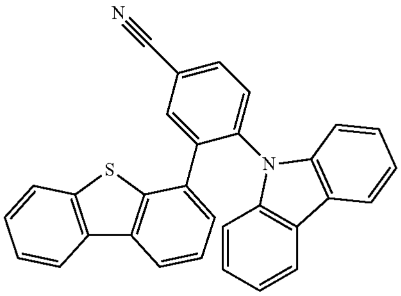
31
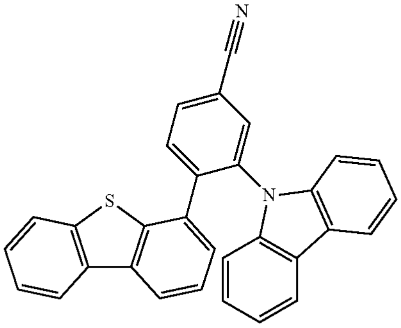
32
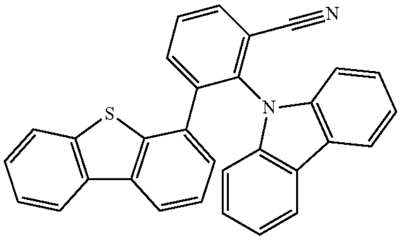
33
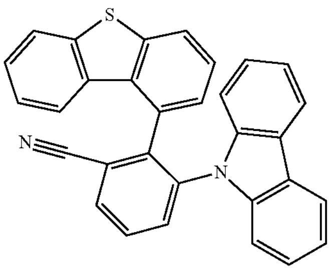
34
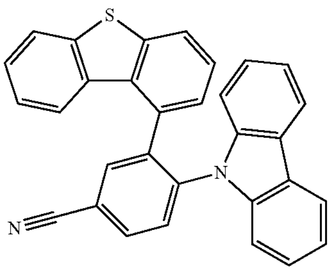

-continued
35
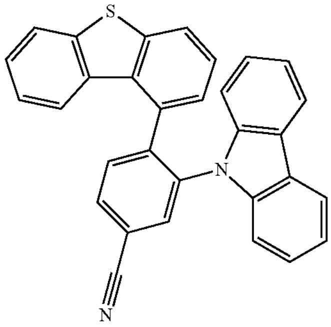
36
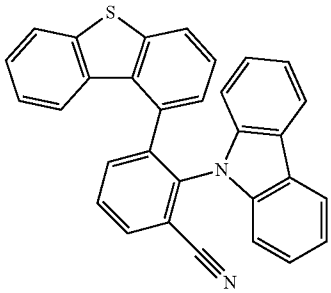
37
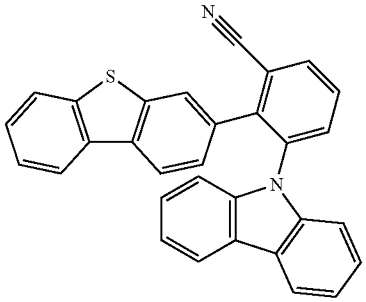
38
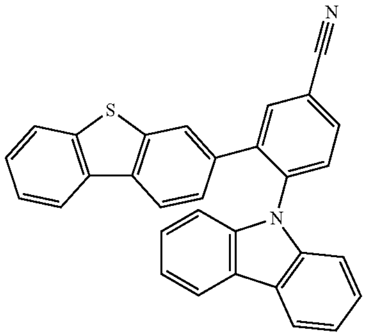
39
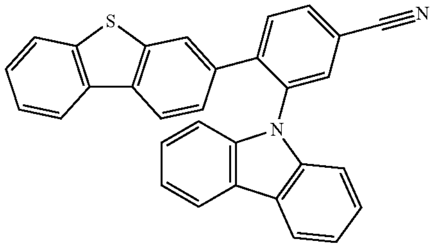
-continued
40
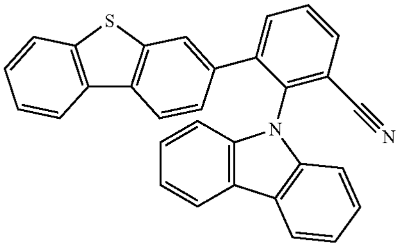
41
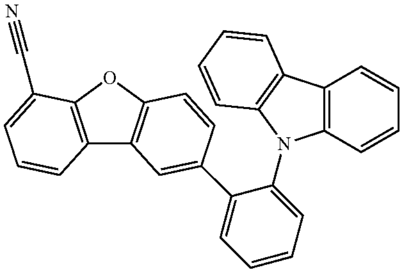
42
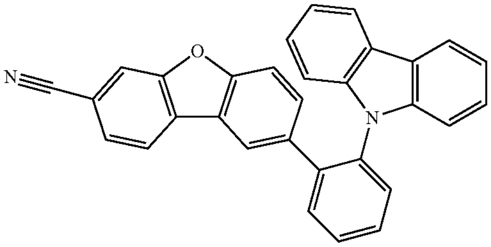
43
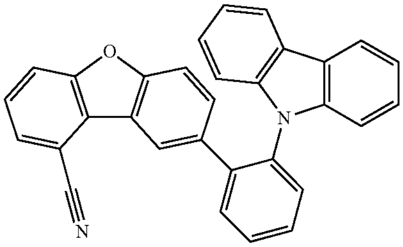
44
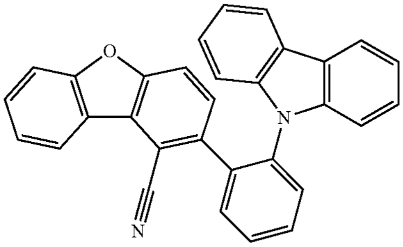
45
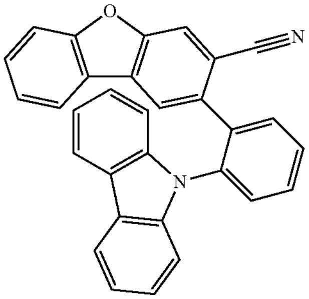

-continued
46
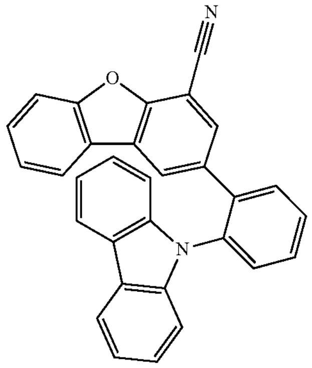
47
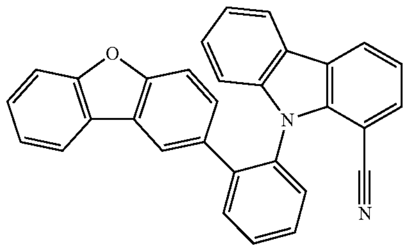
48
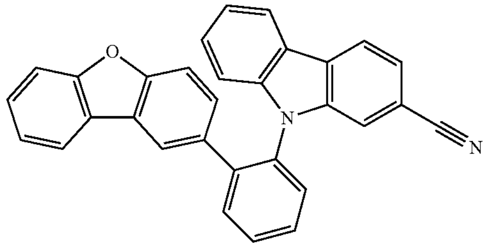
49
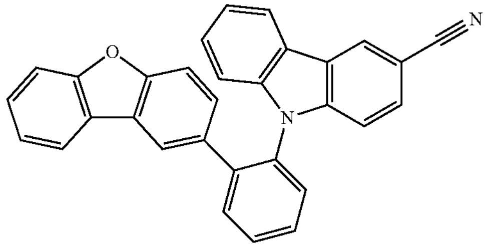
50
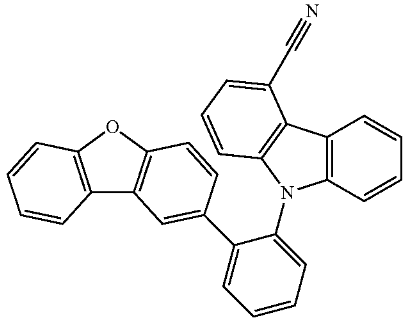
-continued
51
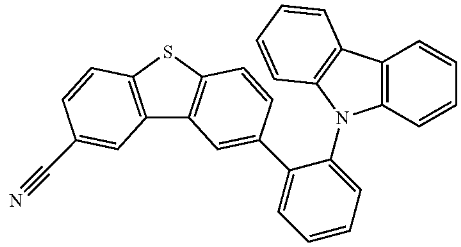
52
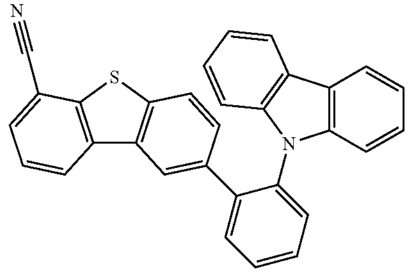
53
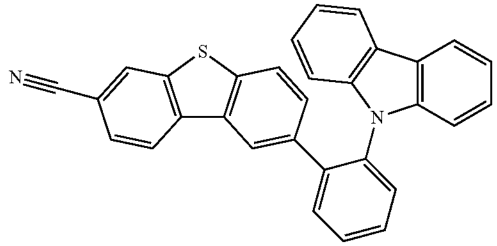
54
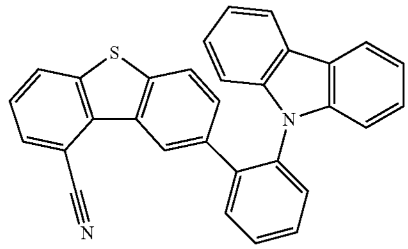
55
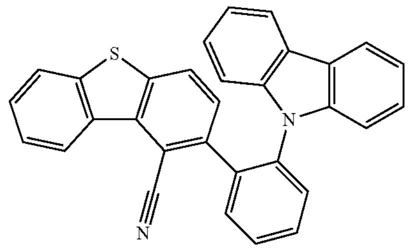
56
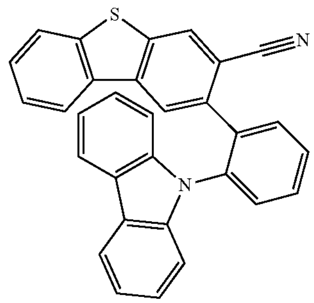

-continued
57
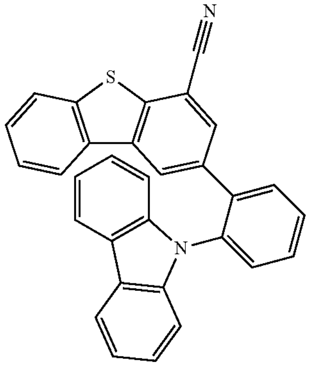
58
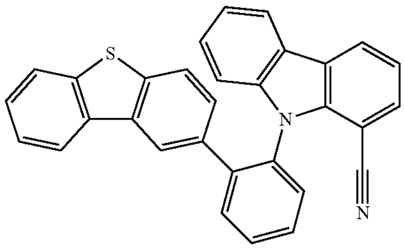
59
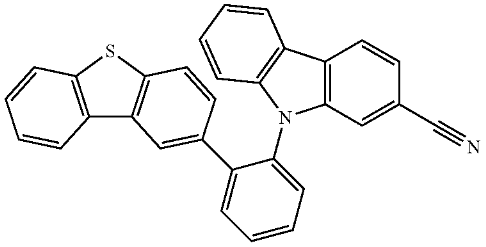
60
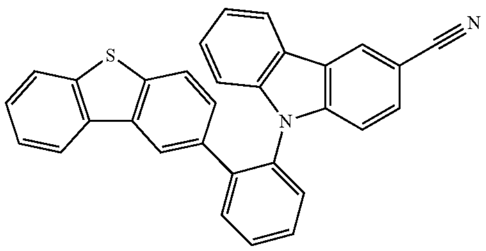
61
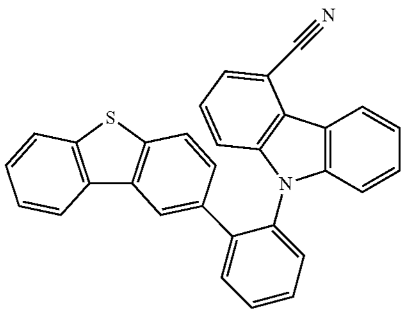
-continued
62
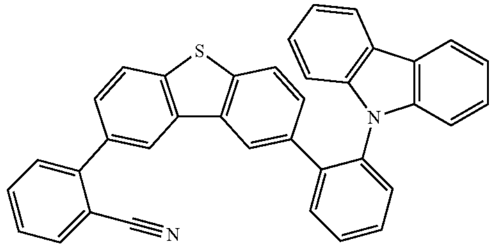
63
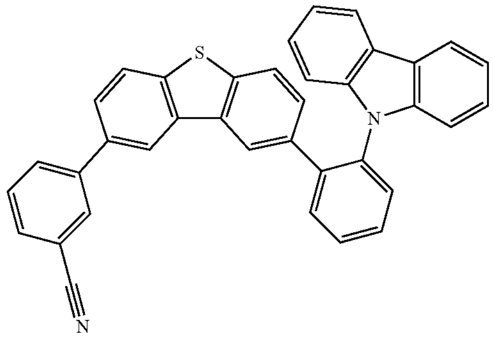
64
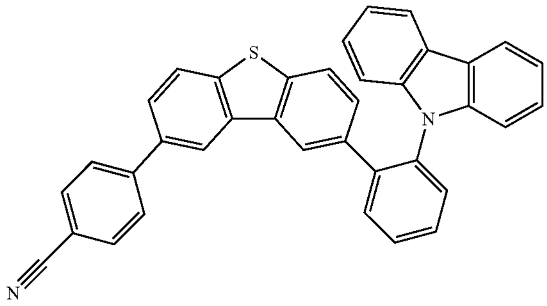
65
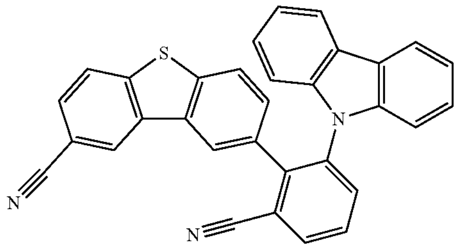
66
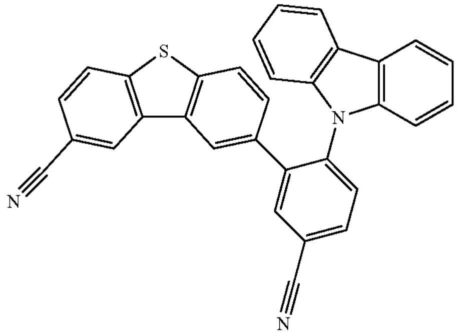

67
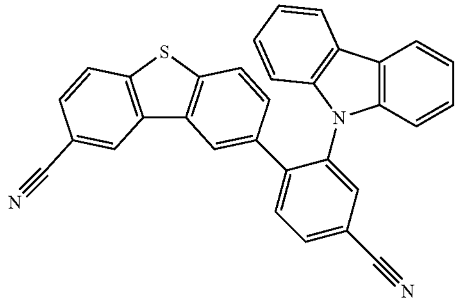
68
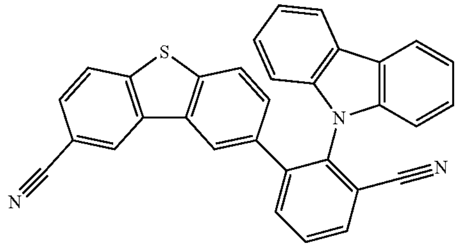
69
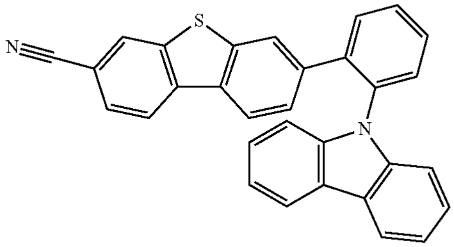
70
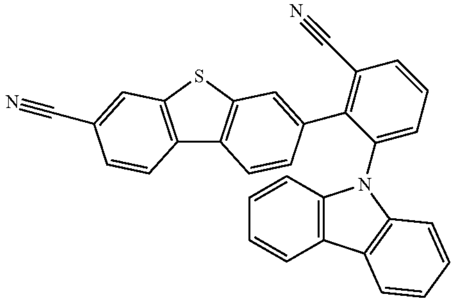
71
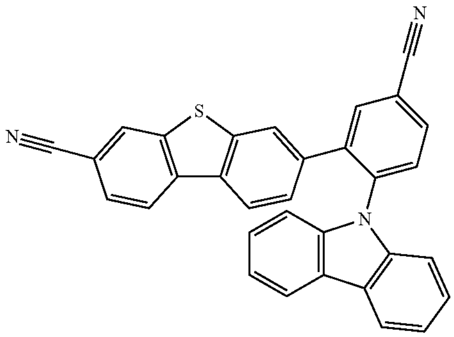
72
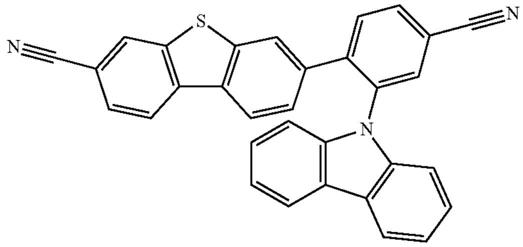
73
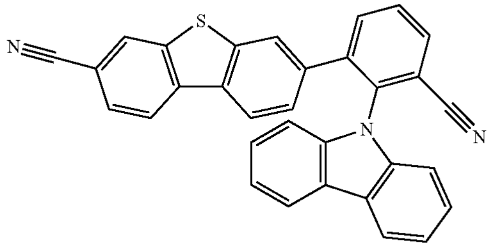
74
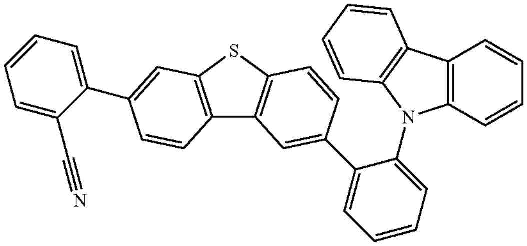
75
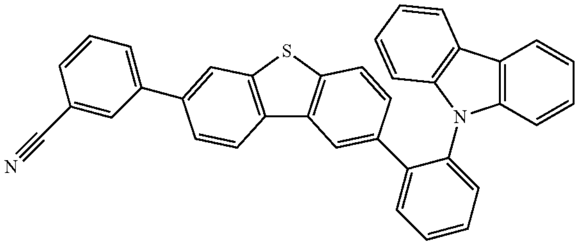
76
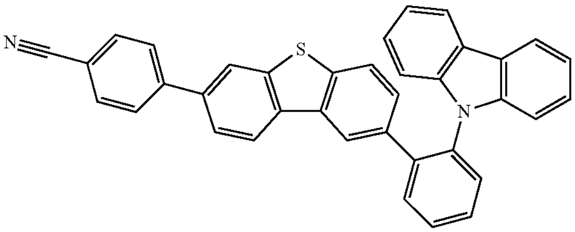

-continued
77
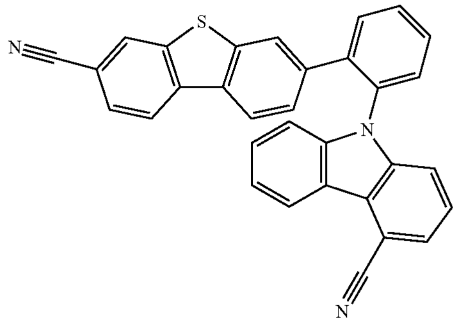
78
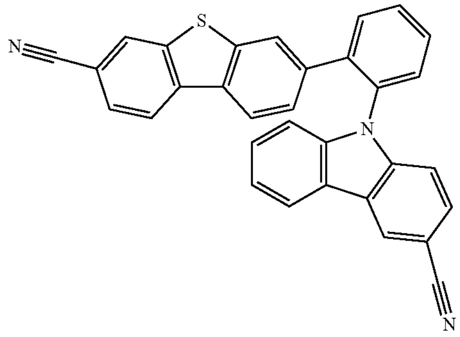
79
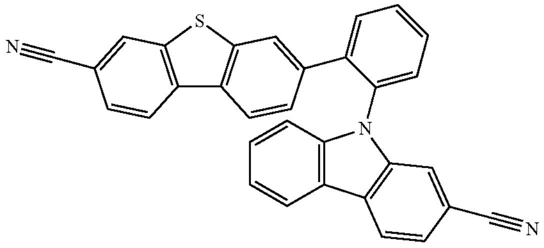
80
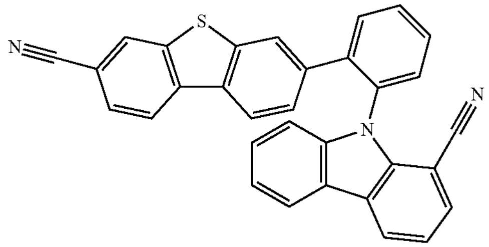
-continued
81
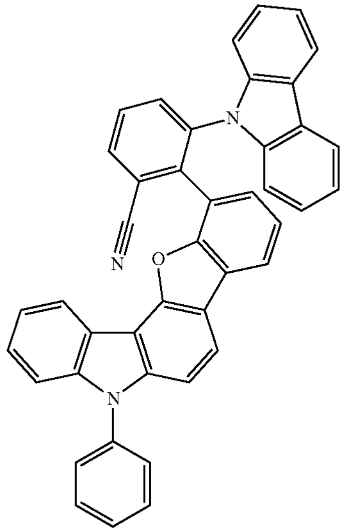
82
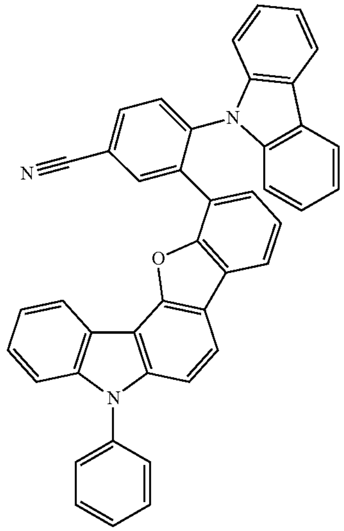
83
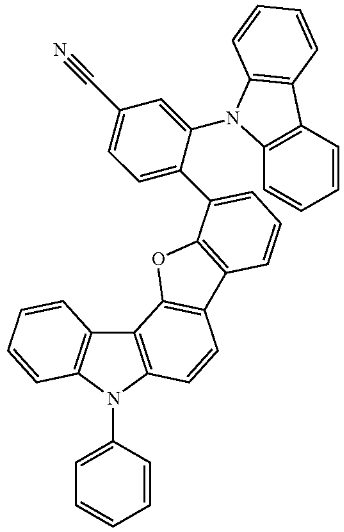

84
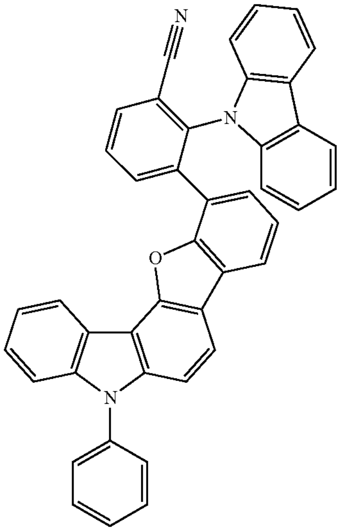
85
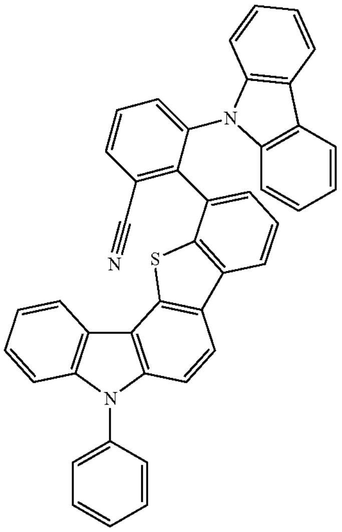
86
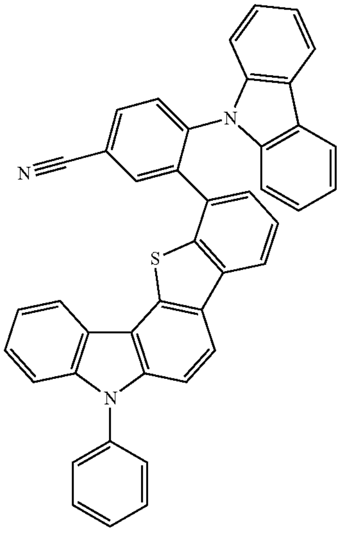
87
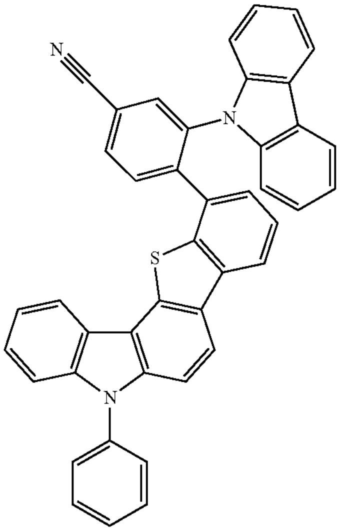
88
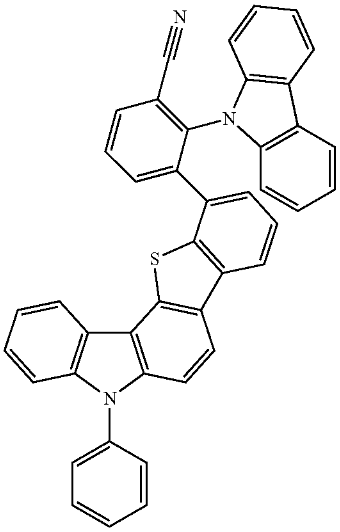
89
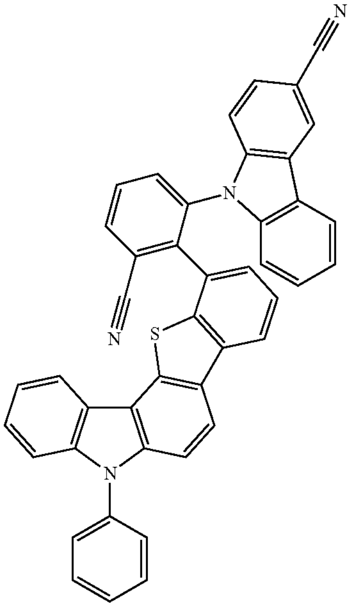

-continued
90
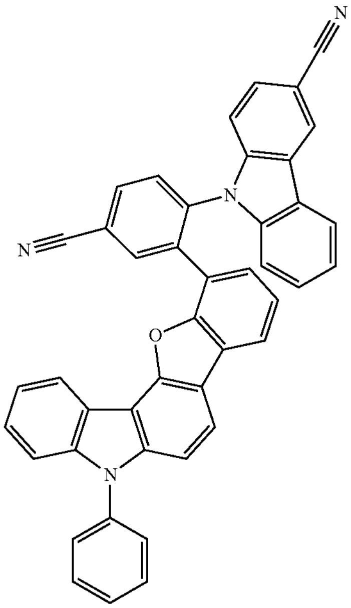
91
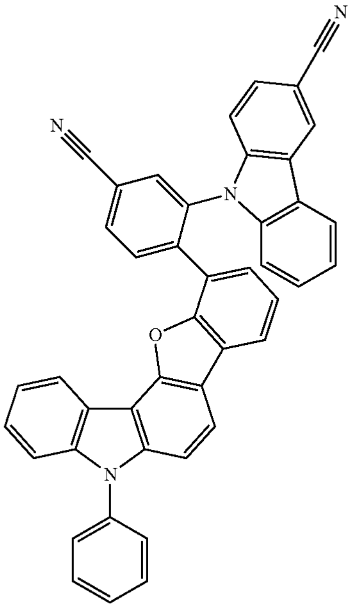
-continued
92
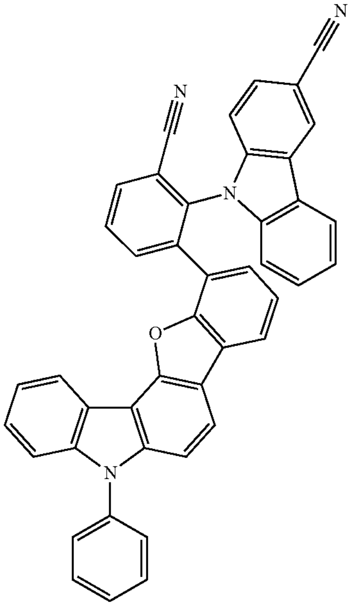
93
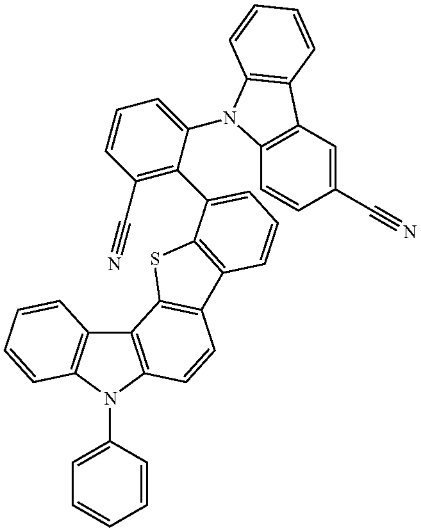
94
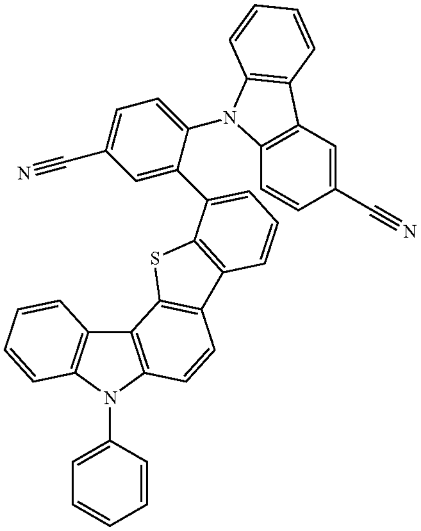

-continued
95
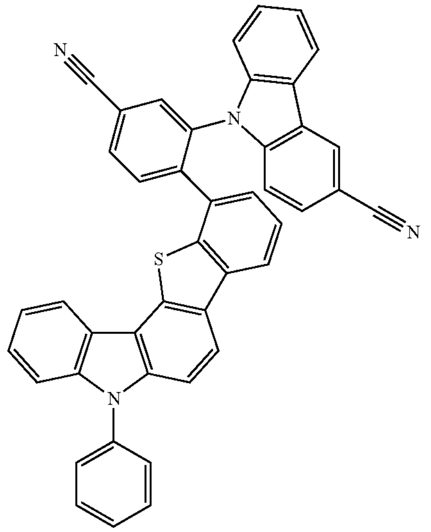
96
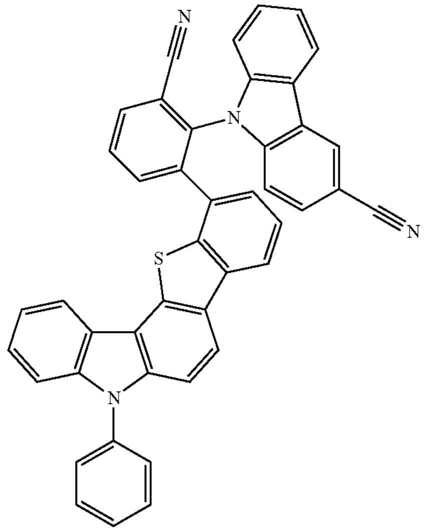
97
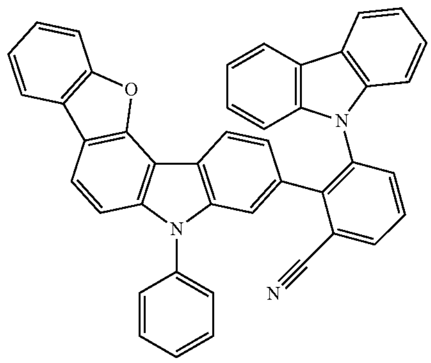
-continued
98
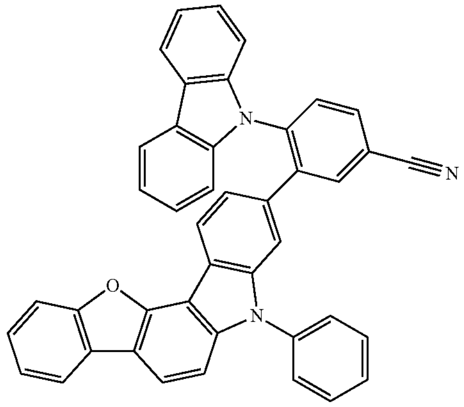
99
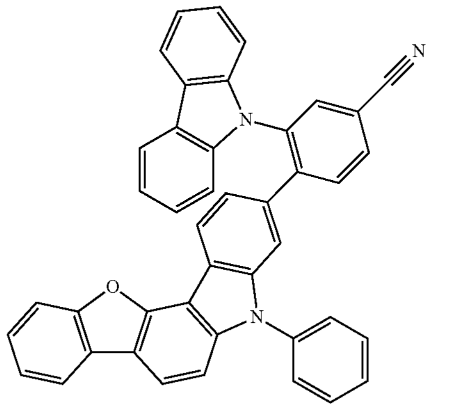
100
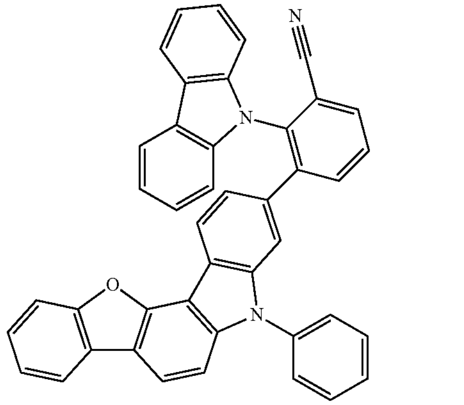
101
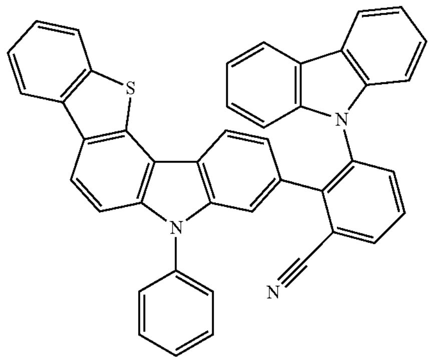

-continued
102
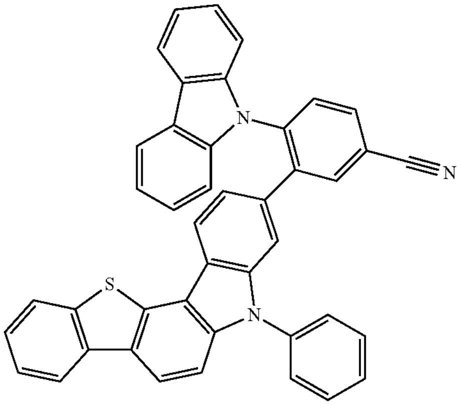
103
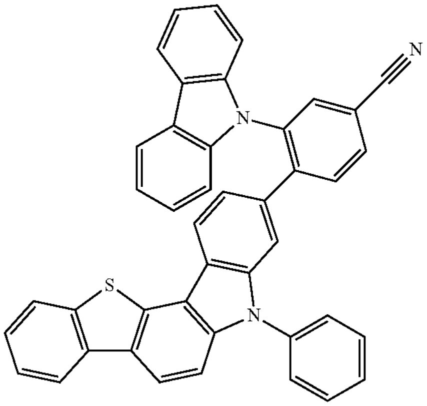
104
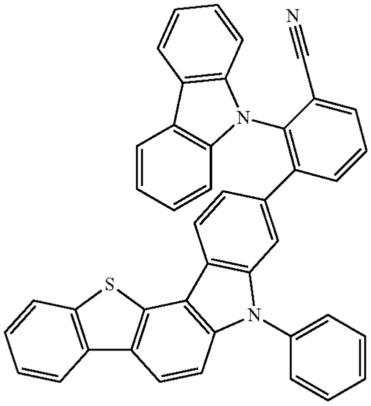
105
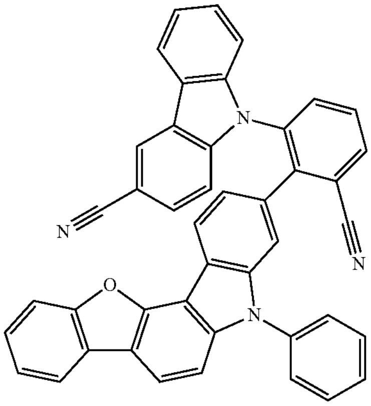
-continued
106
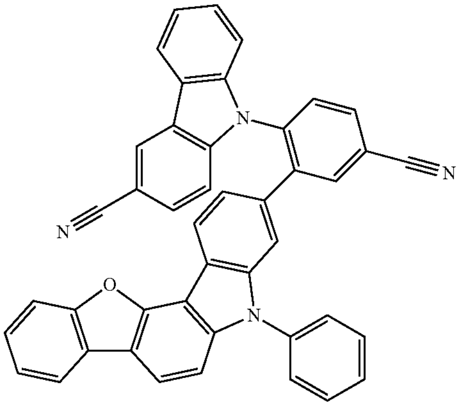
107
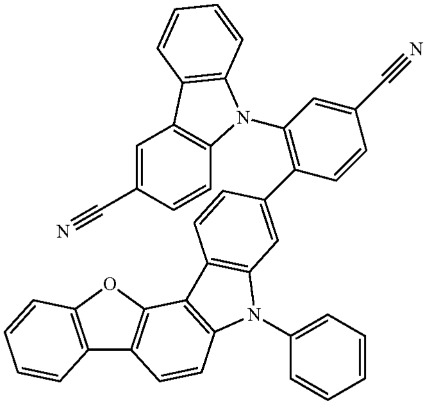
108
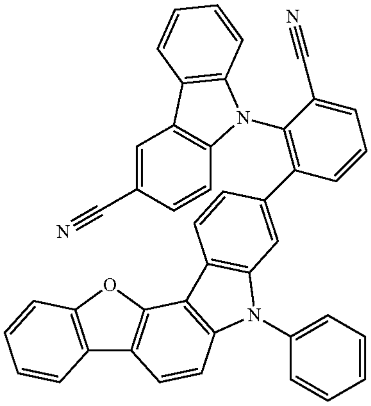
109
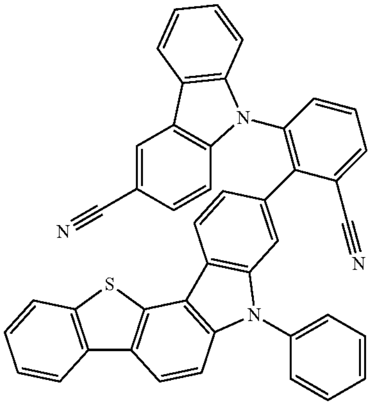

-continued
110
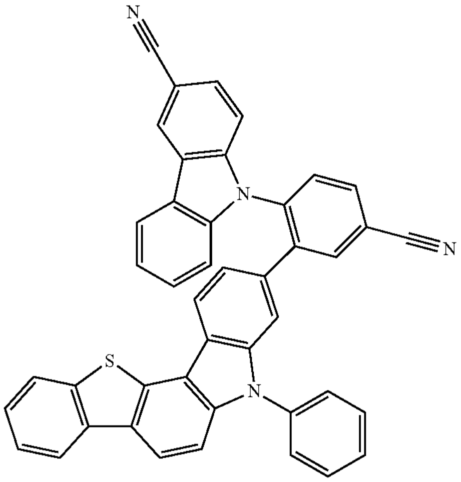
111
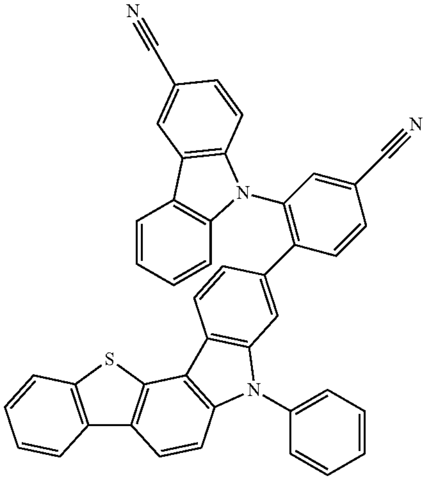
112
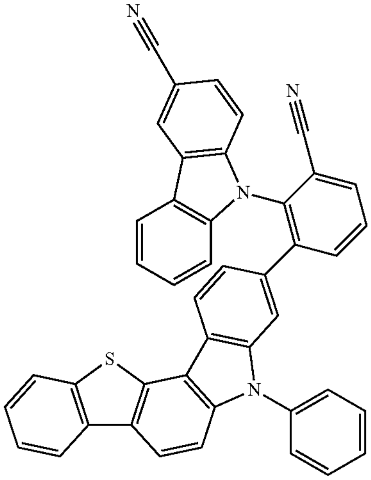
-continued
113
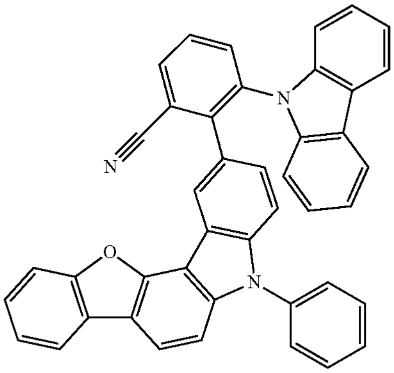
114
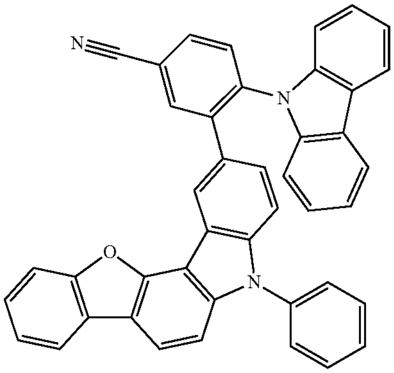
115
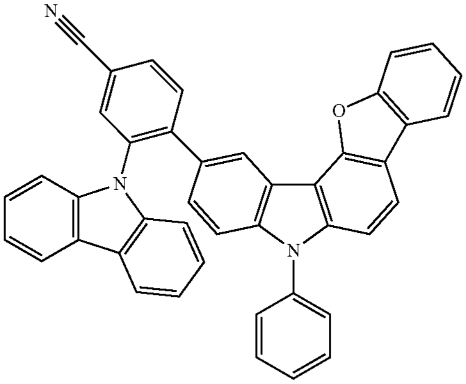
116
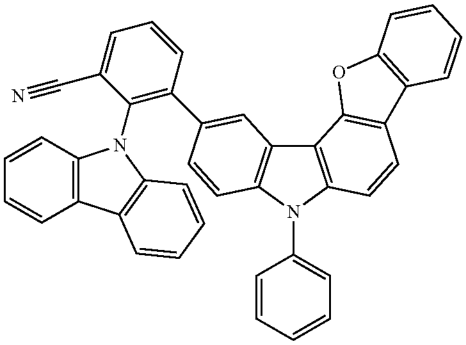

-continued
117
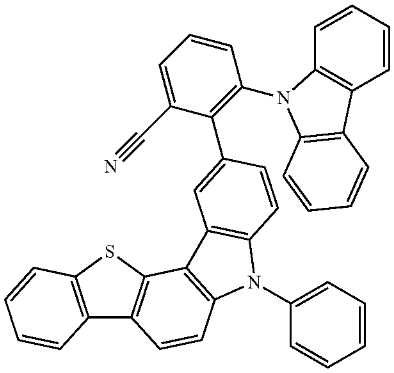
118
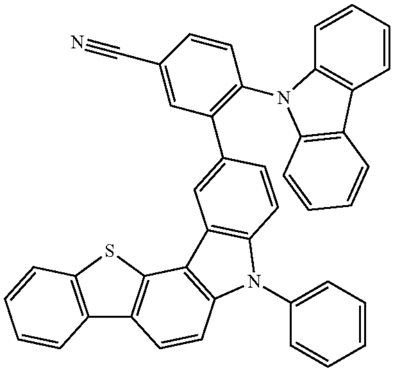
119
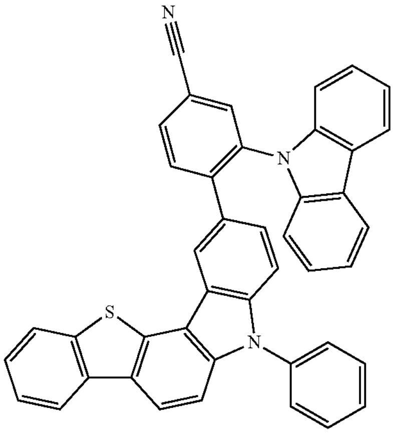
120
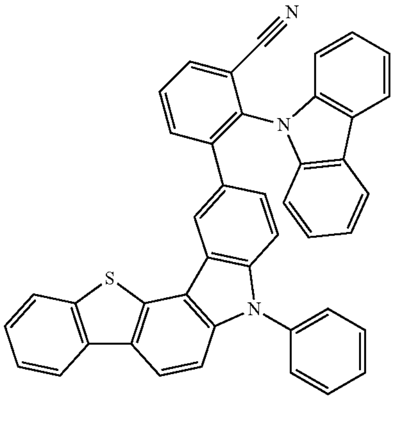
-continued
121
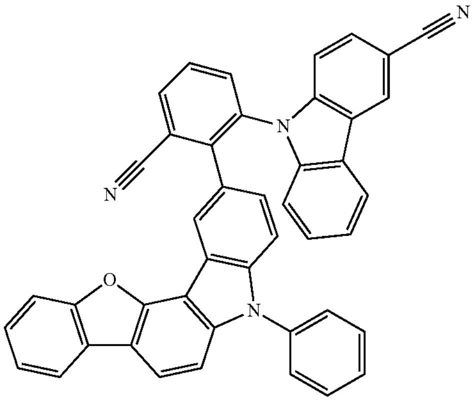
122
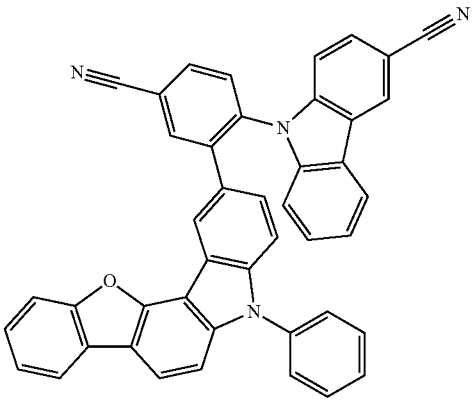
123
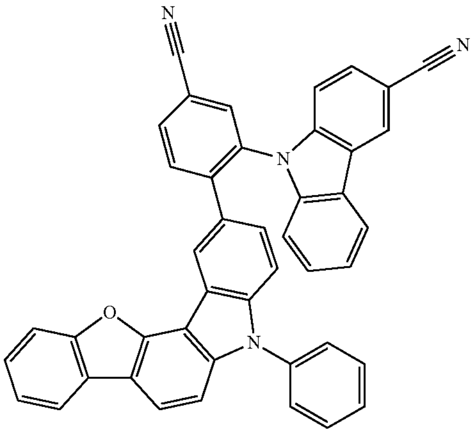
124
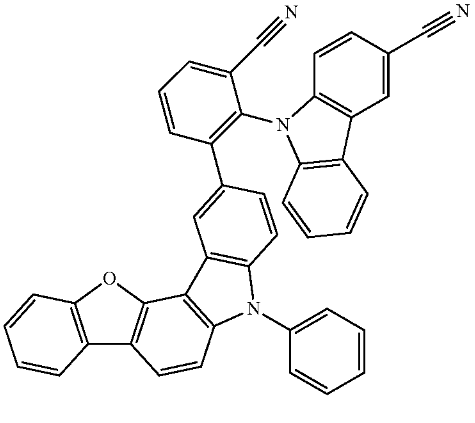

-continued
125
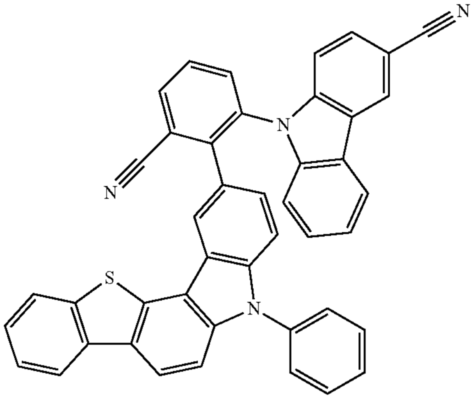
126
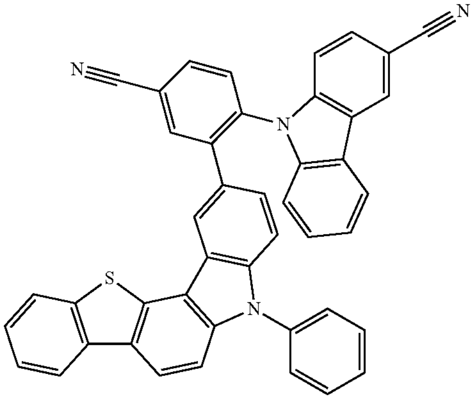
127
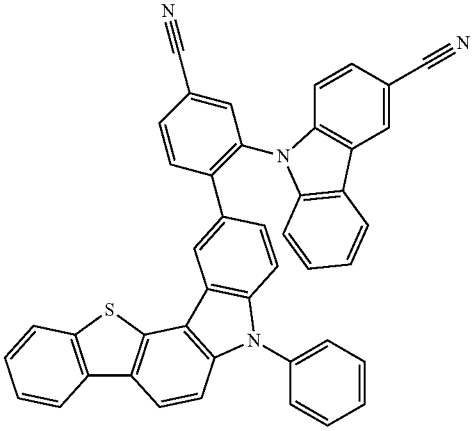
128
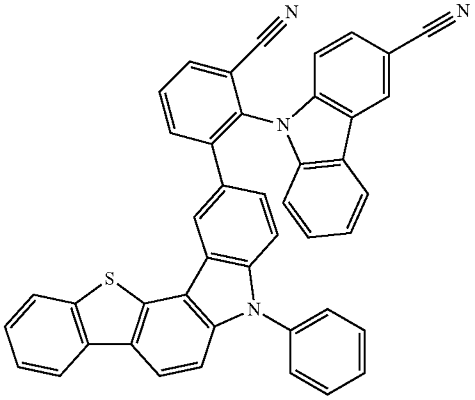
-continued
129
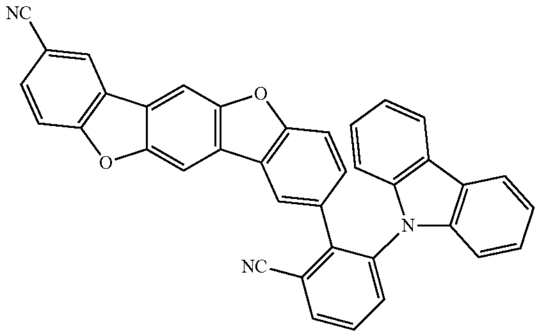
130
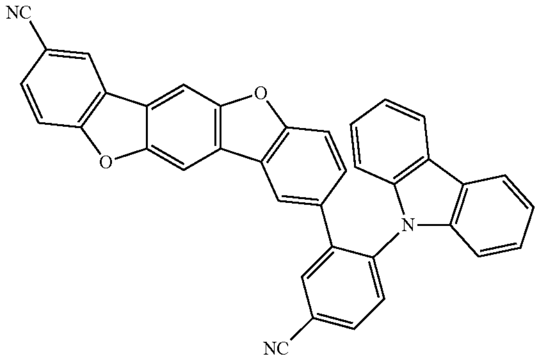
131
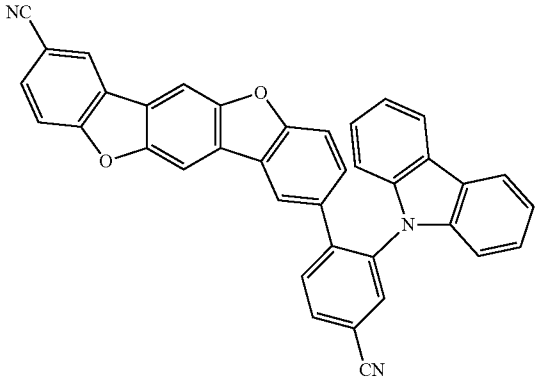
132
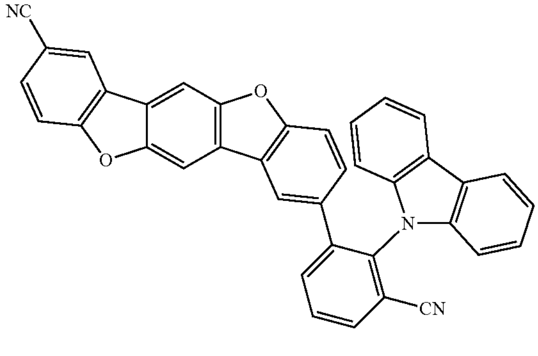

-continued
133
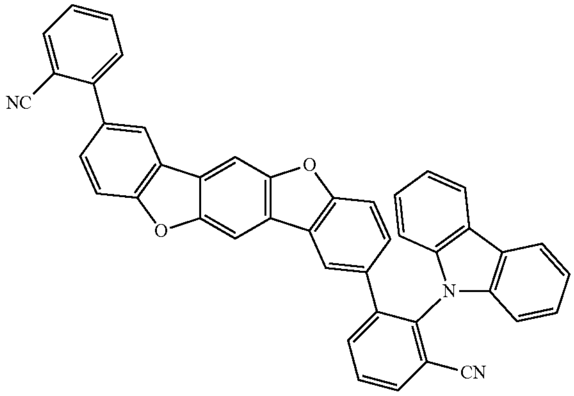
134
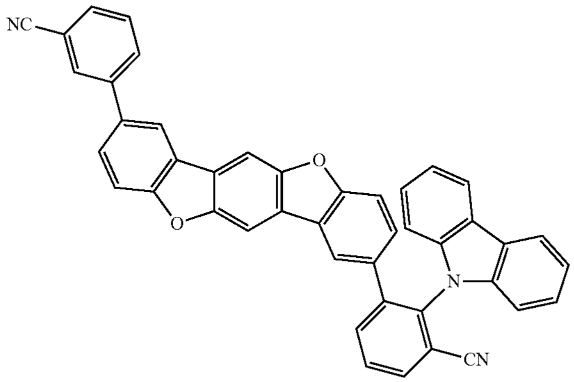
135
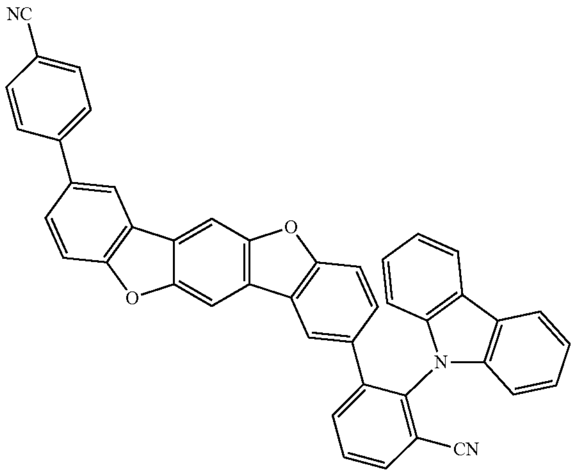
-continued
136
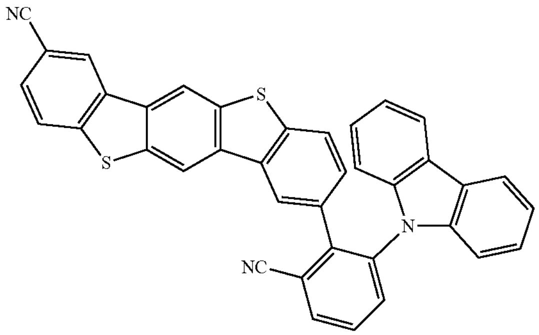
137
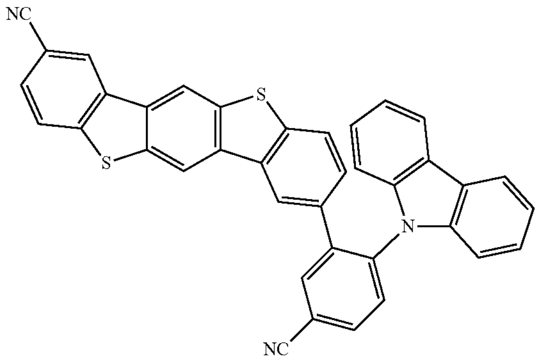
138
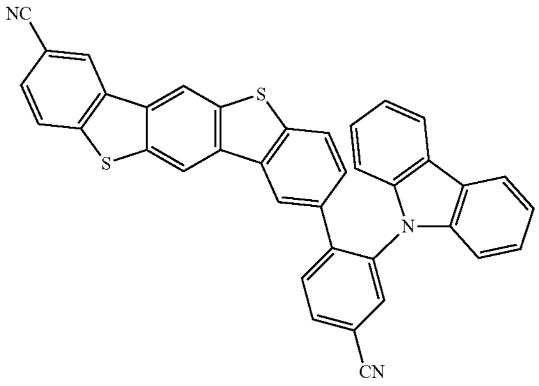
139
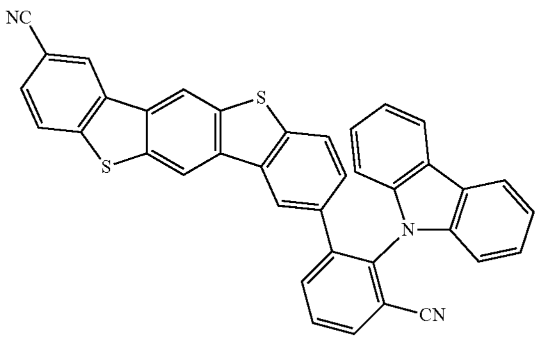

-continued
140
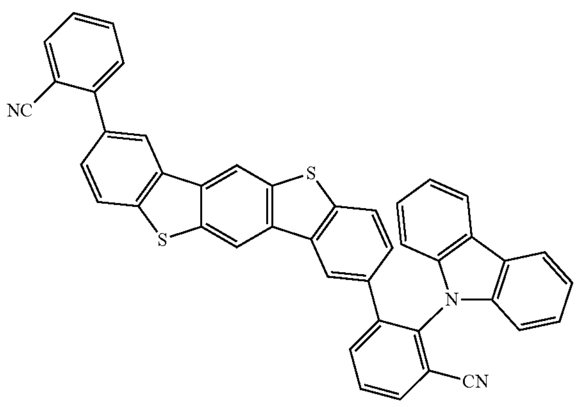
141
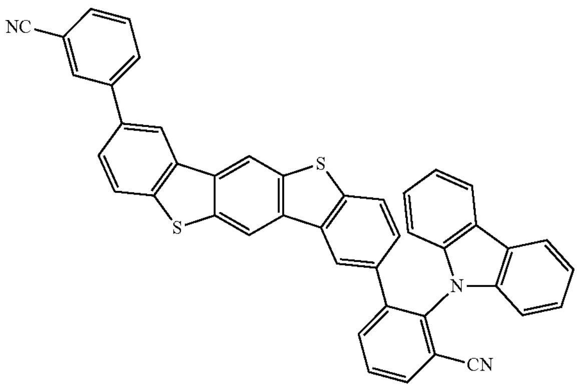
142
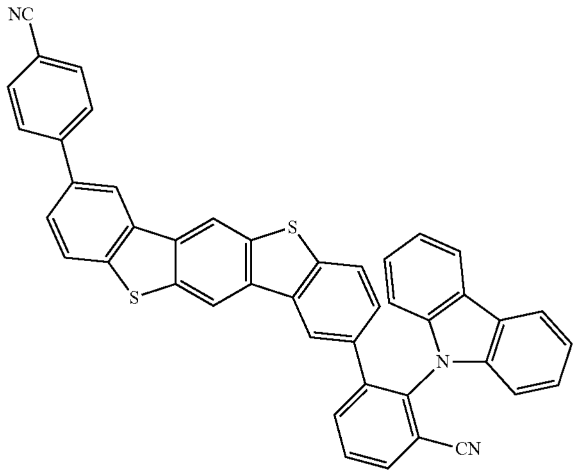
143
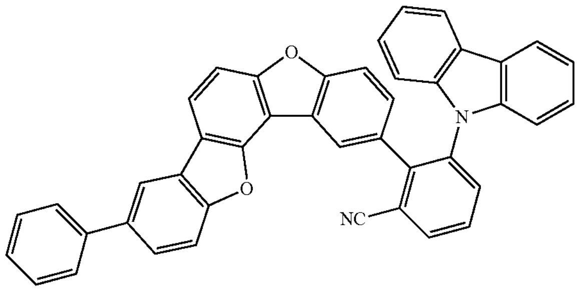
-continued
144
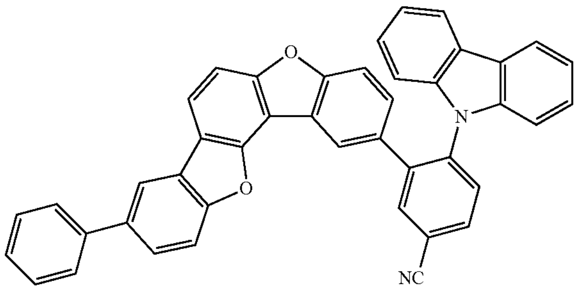
145
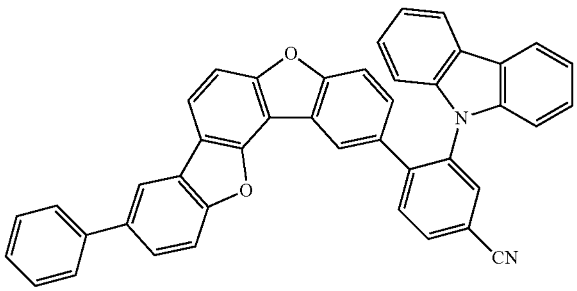
146
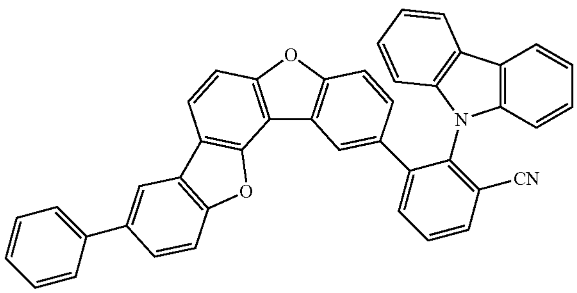
147
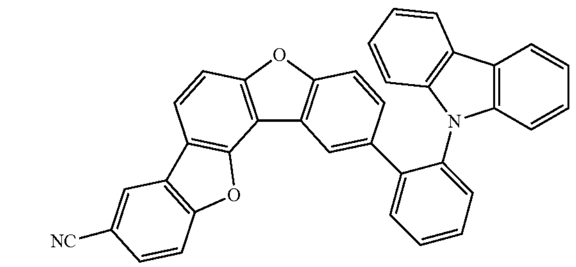
148
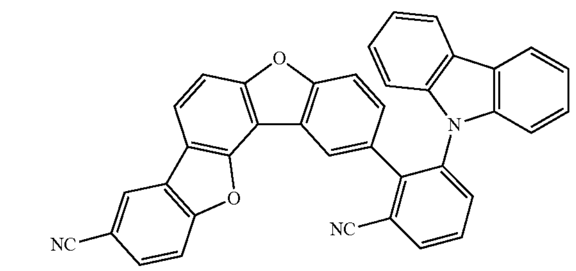

149
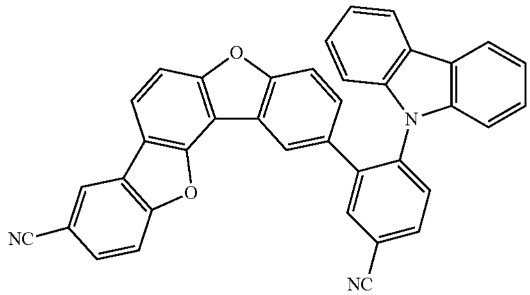
150
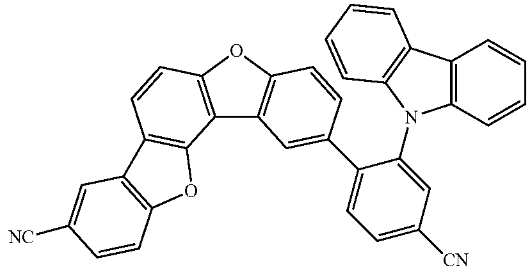
151
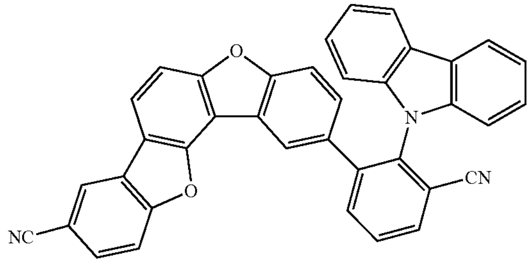
152
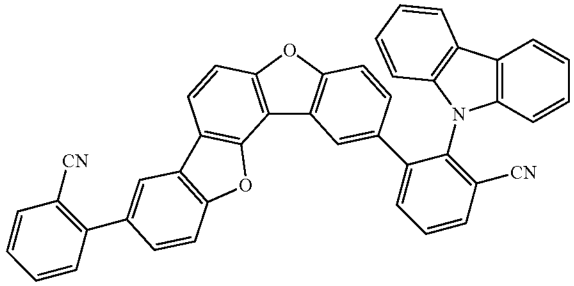
153
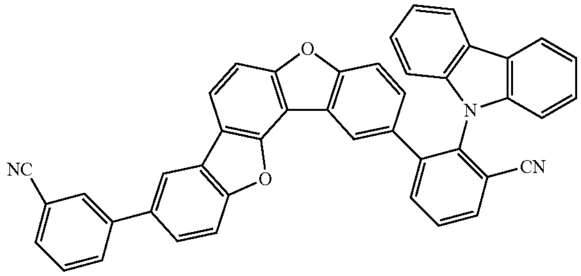
154
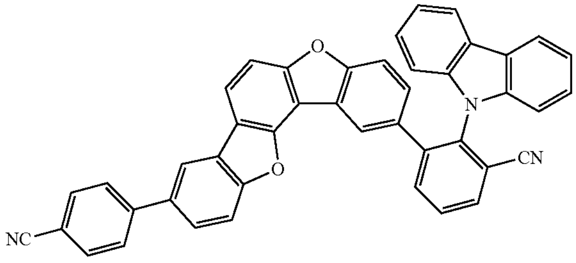
155
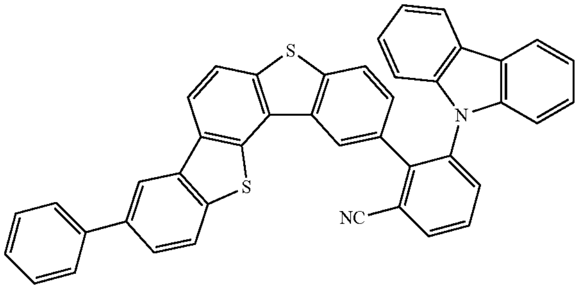
156
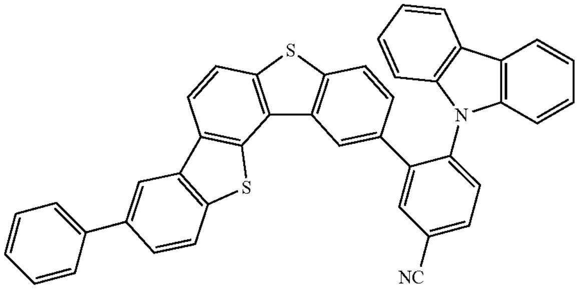
157
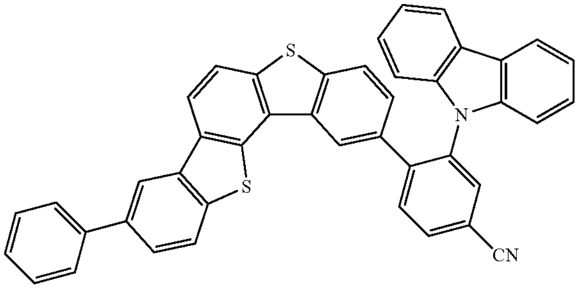
158
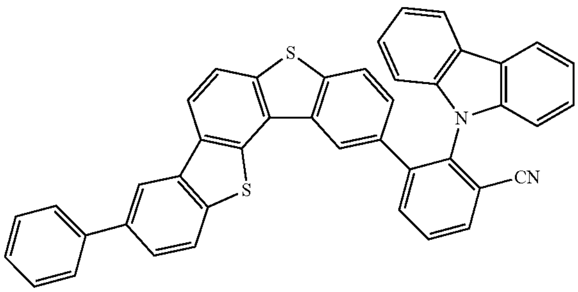

-continued
159
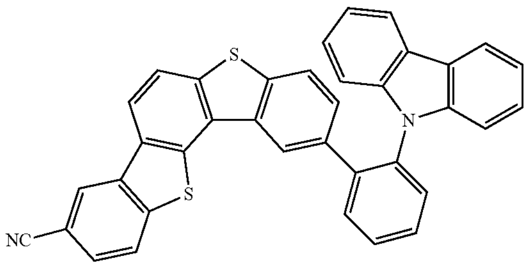
160
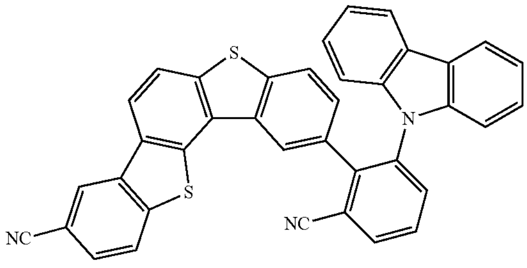
161
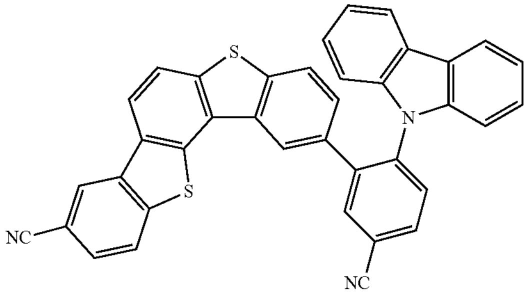
162
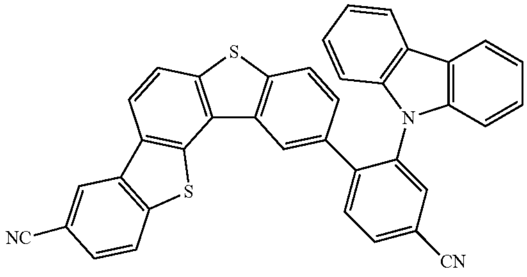
163
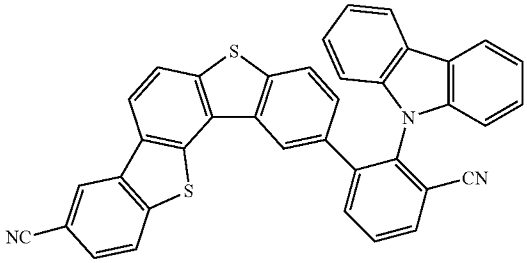
-continued
164
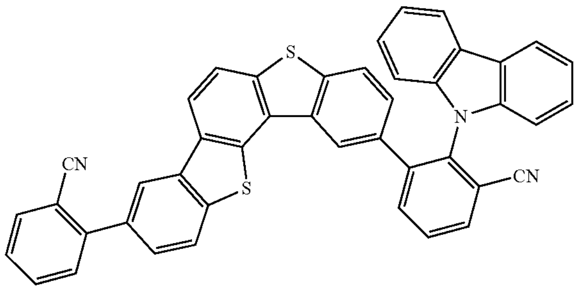
165
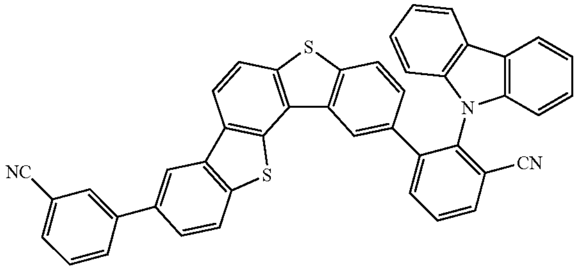
166
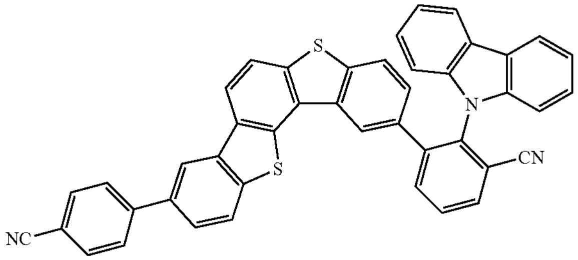
167
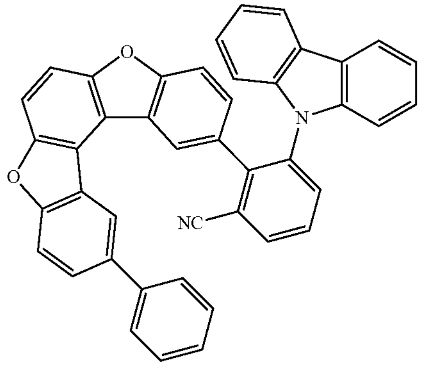
168
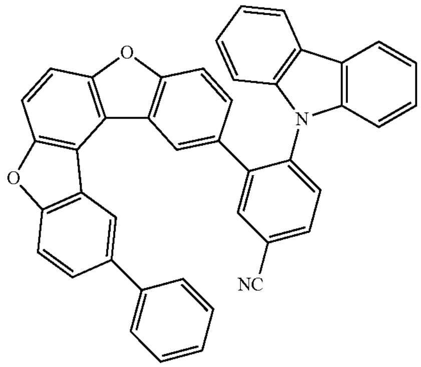

-continued
169
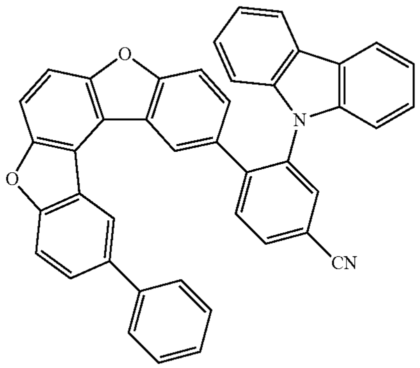
170
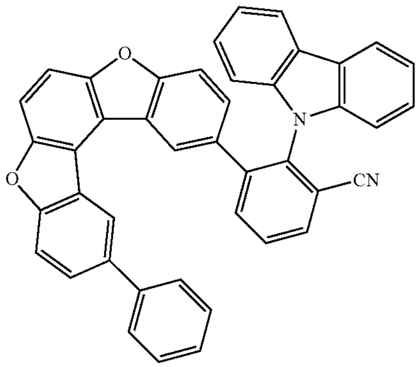
171
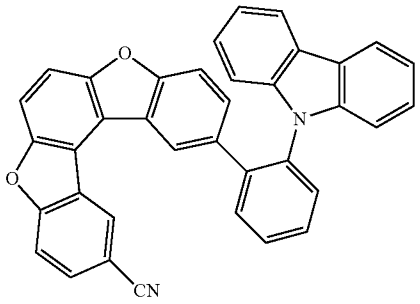
172
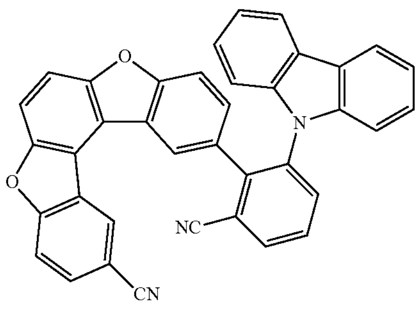
-continued
173
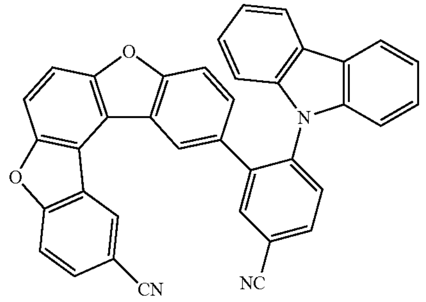
174
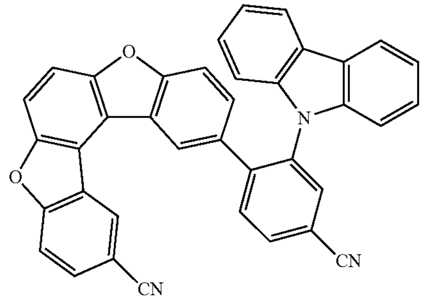
175
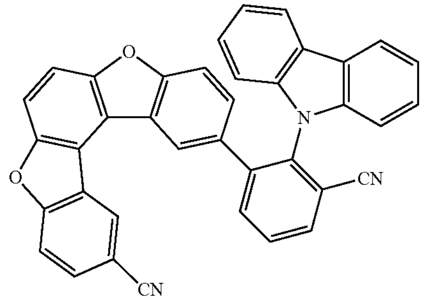
176
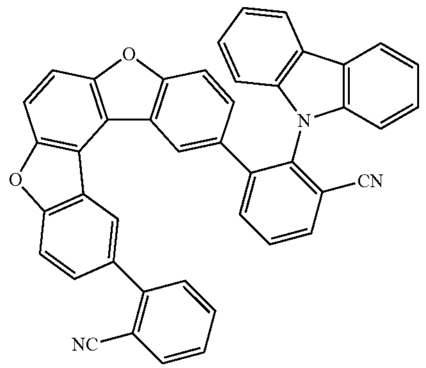

-continued
177
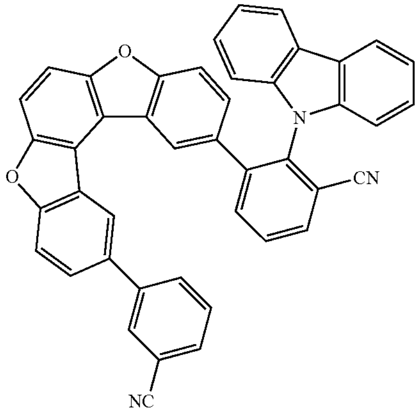
178
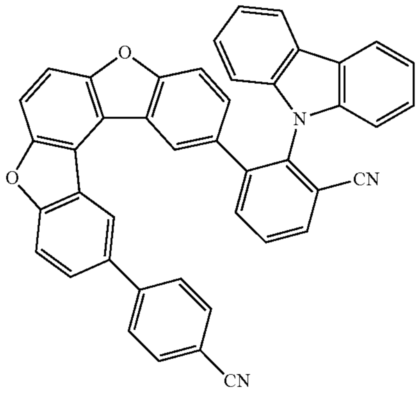
179
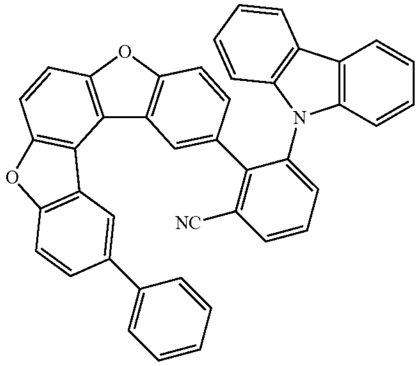
180
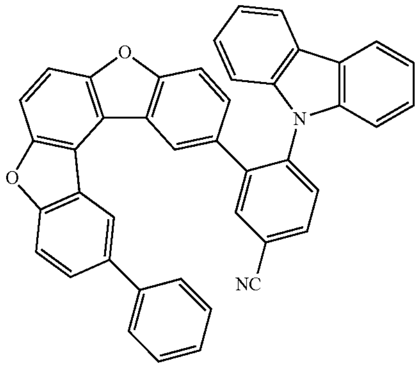
-continued
181
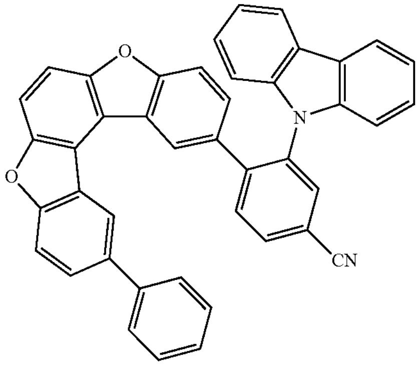
182
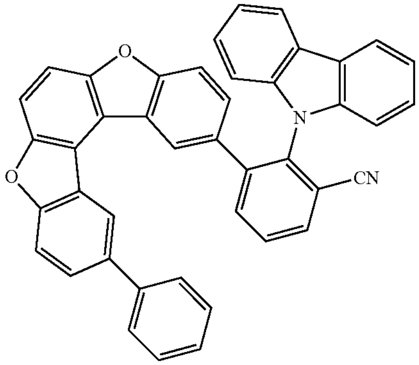
183
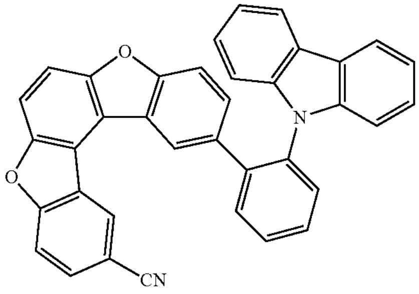
184
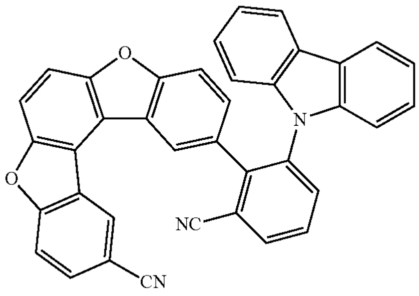
185
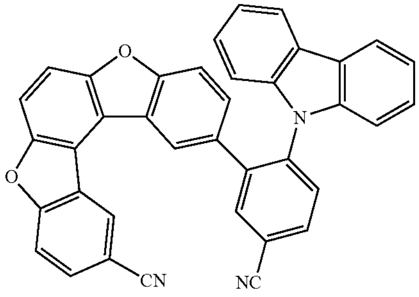

-continued
186
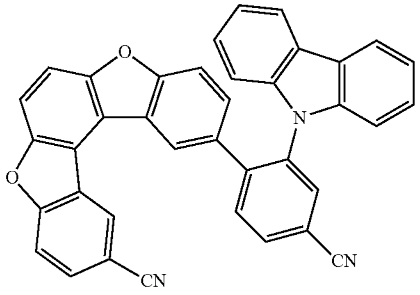
187
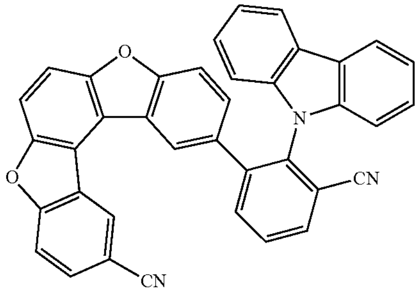
188
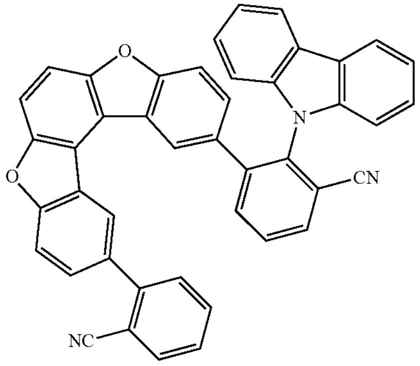
189
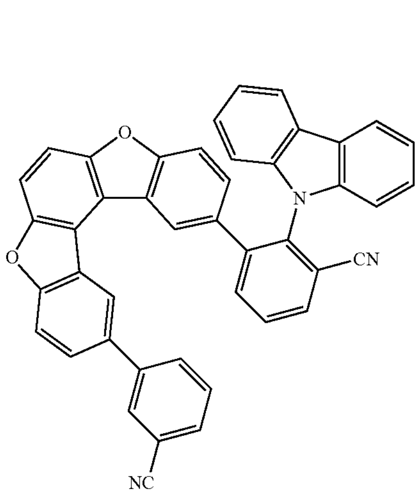
-continued
190
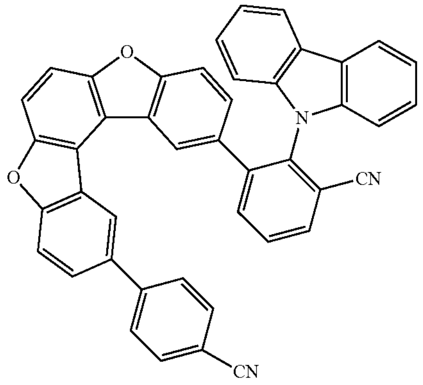
191
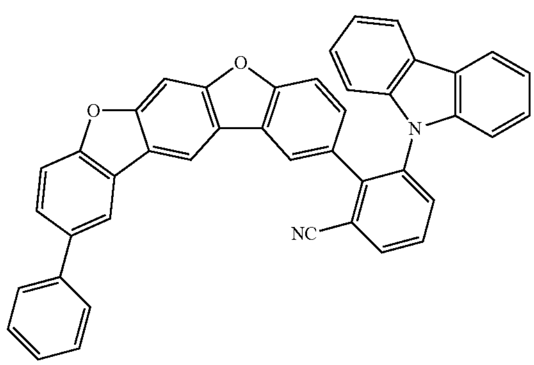
192
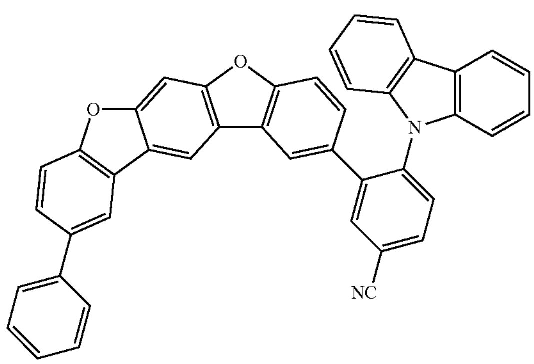
193
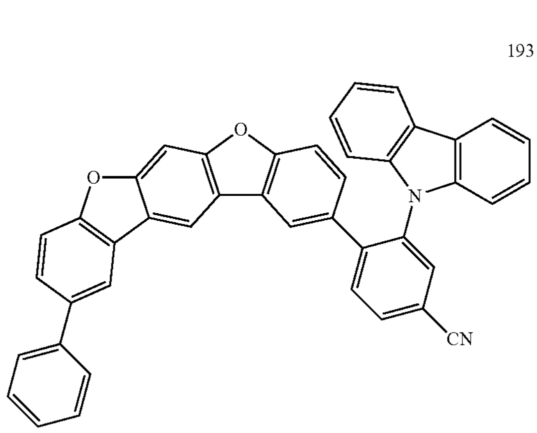

194
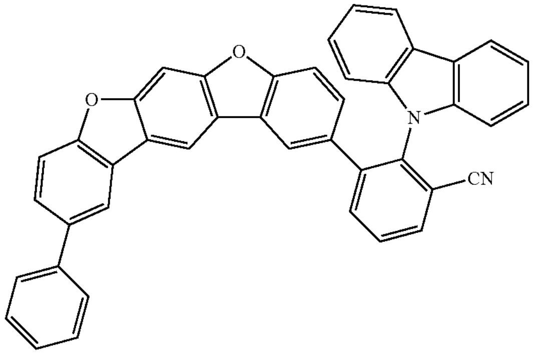
195
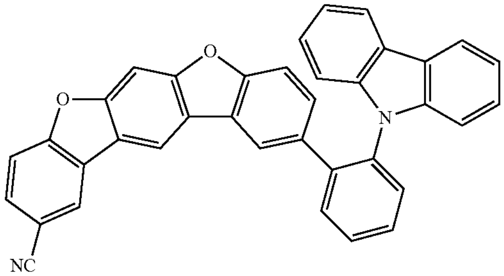
196
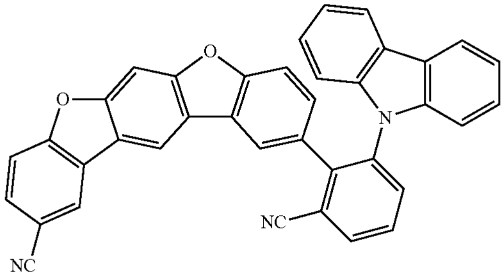
197
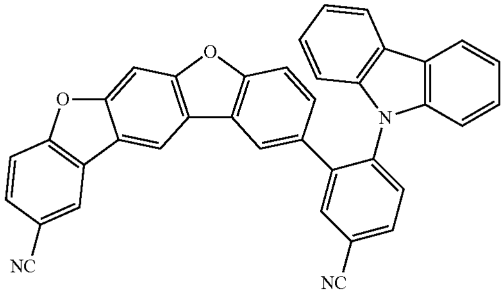
198
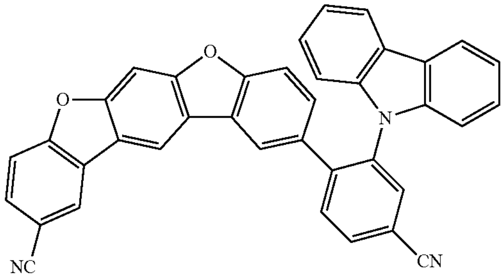
199
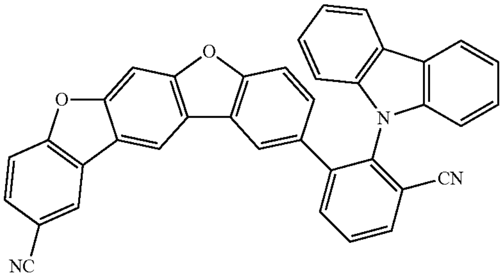
200
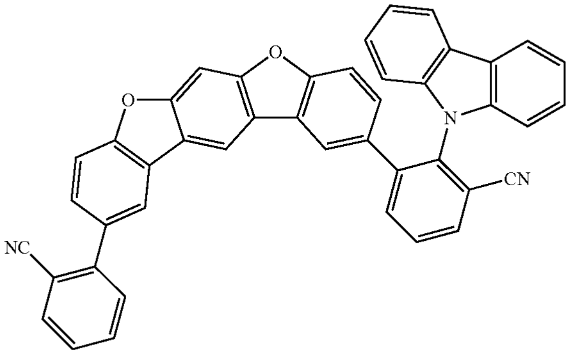
201
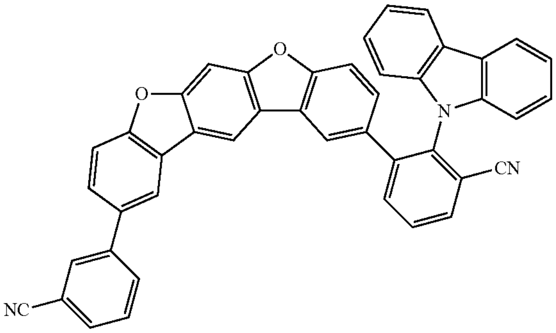
202
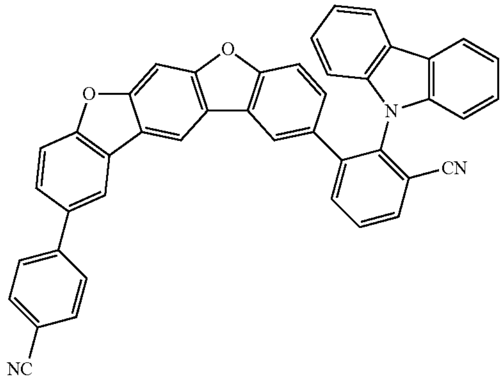

-continued
203
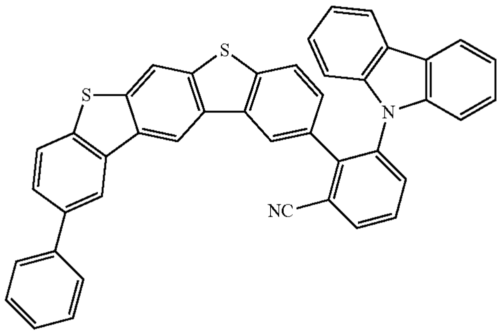
204
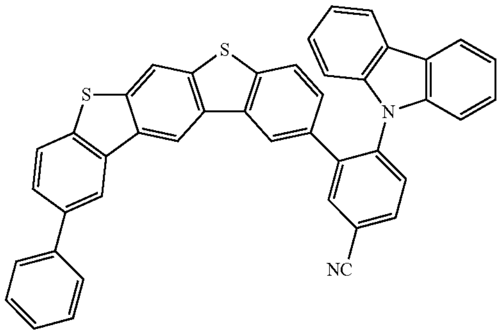
205
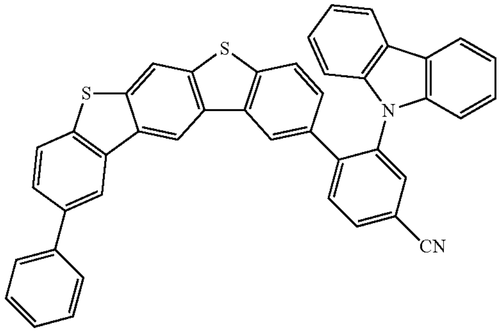
206
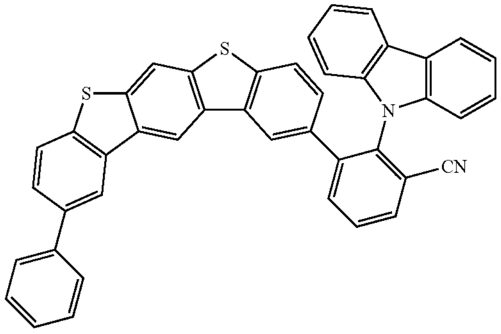
207
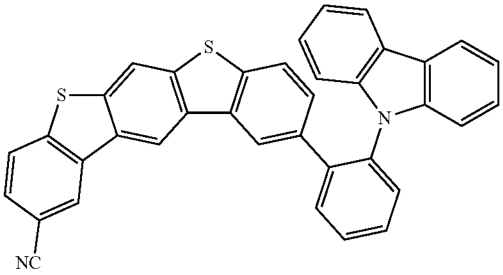
208
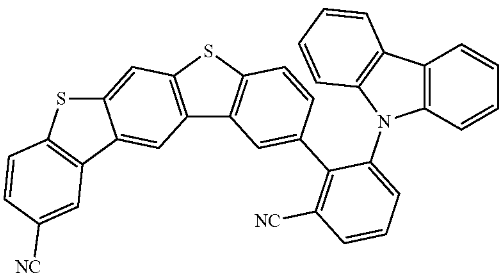
209
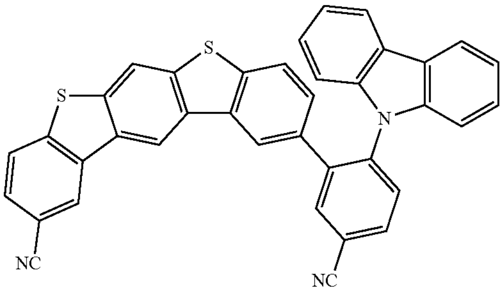
210
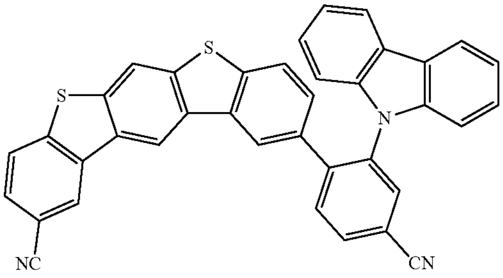
211
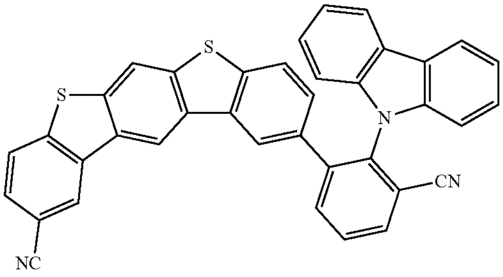

-continued
212
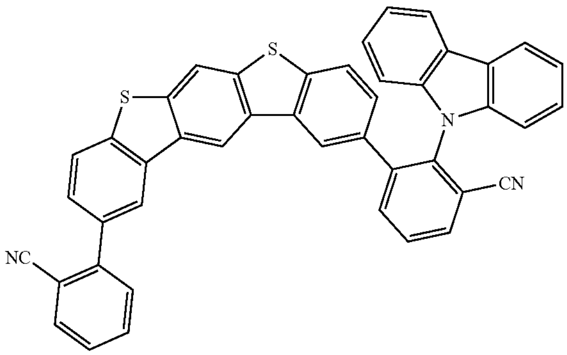
213
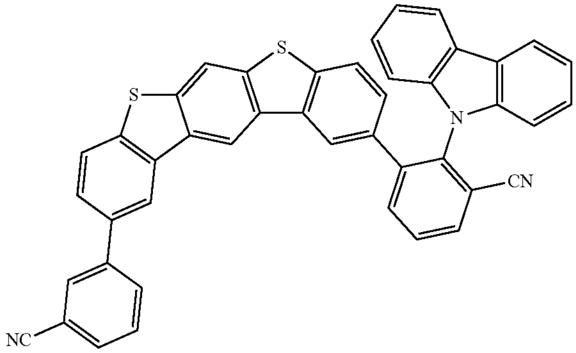
214
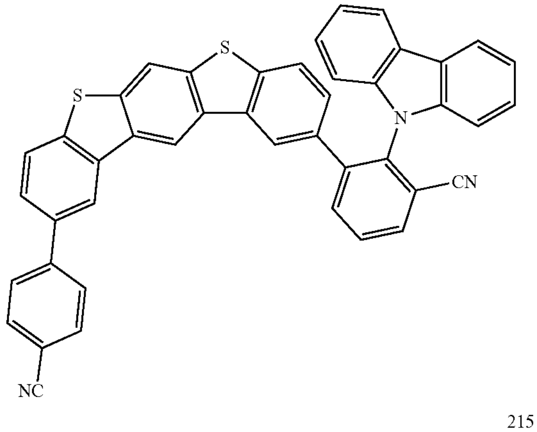
215
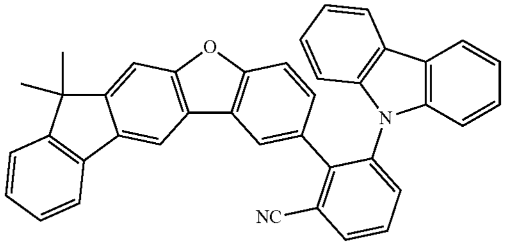
-continued
216
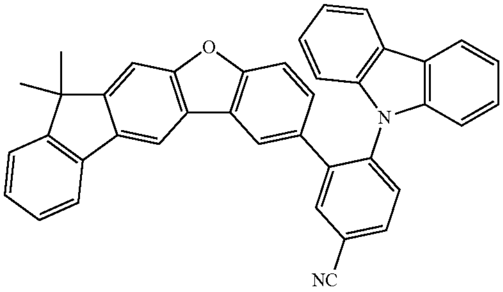
217
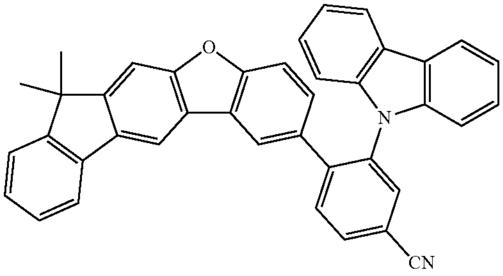
218
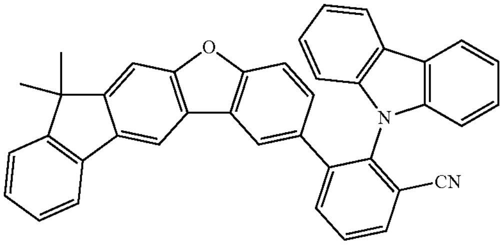
219
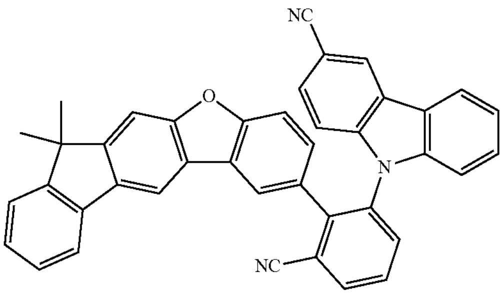
220
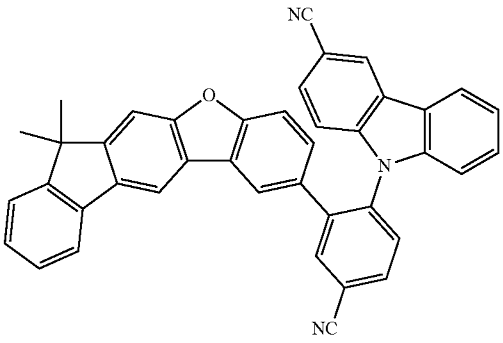

-continued
221
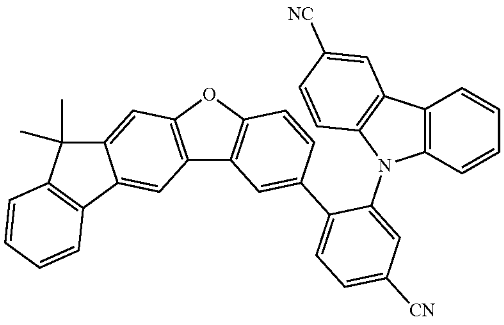
222
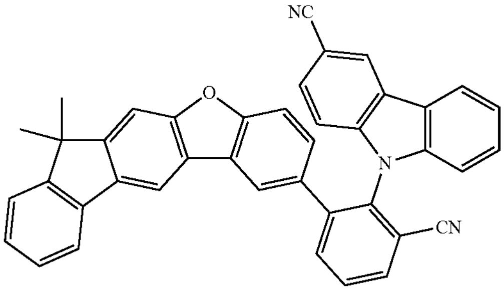
223
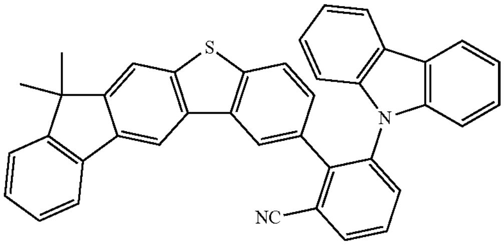
224
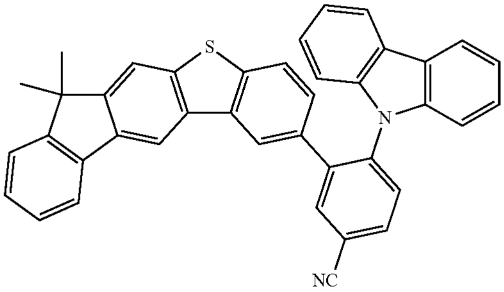
225
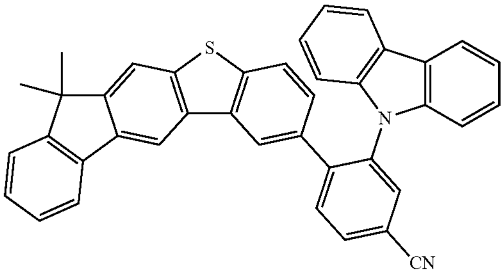
-continued
226
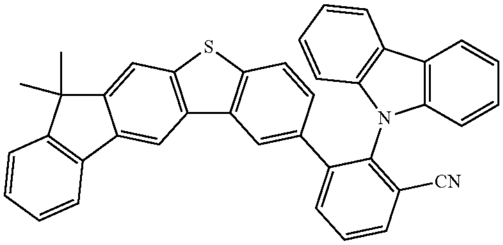
227
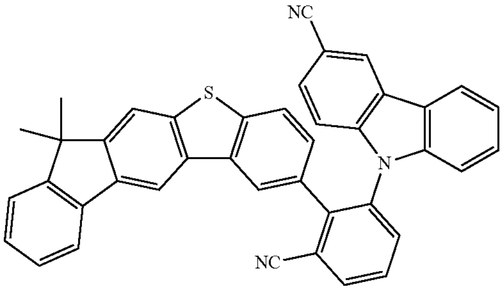
228
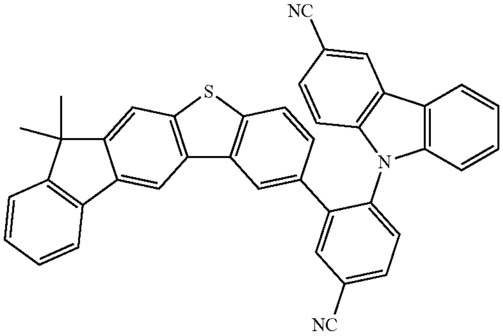
229
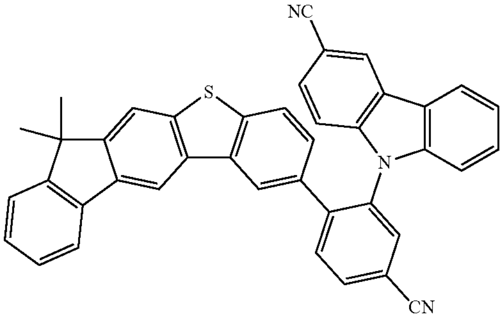
230
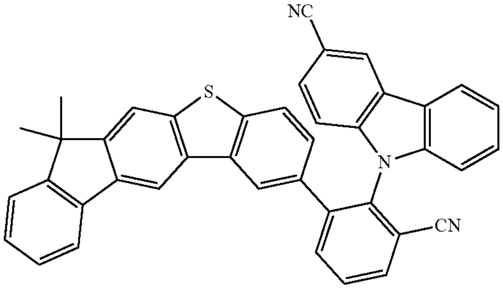

-continued
231
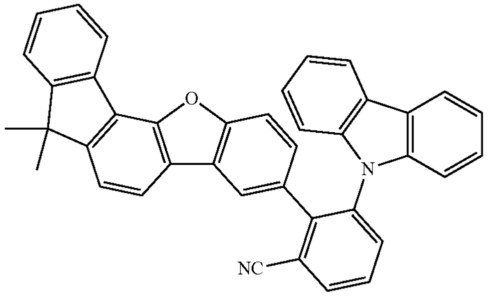
232
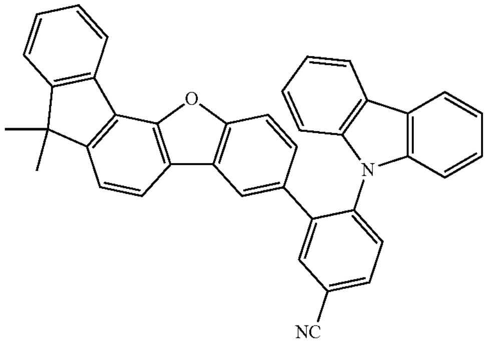
233
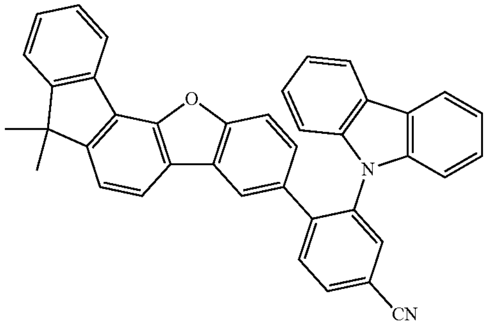
234
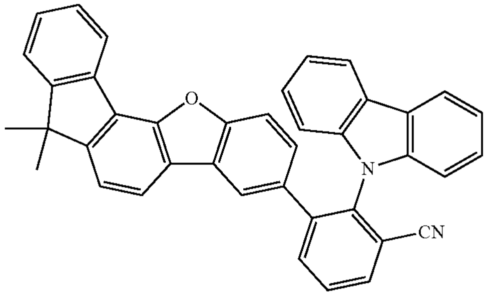
235
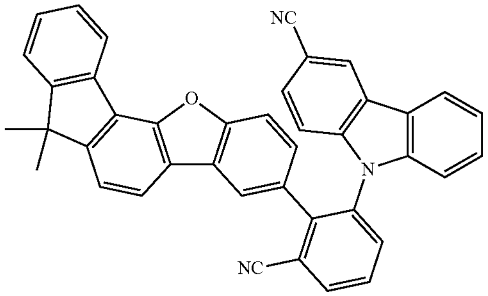
-continued
236
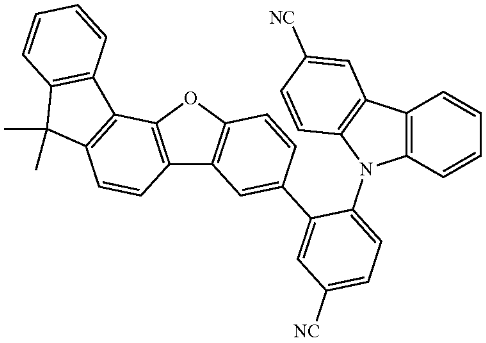
237
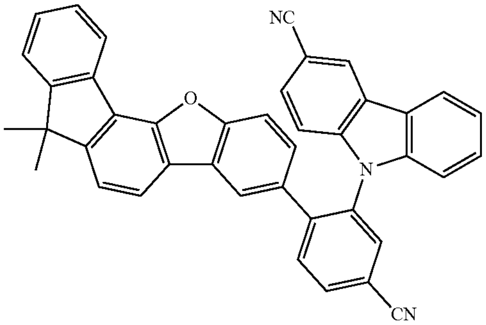
238
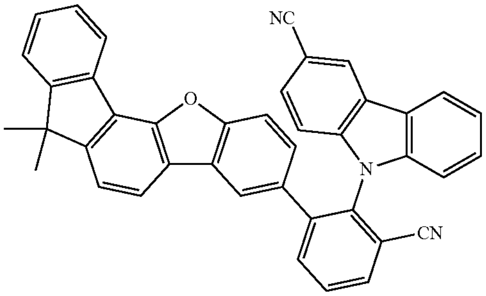
239
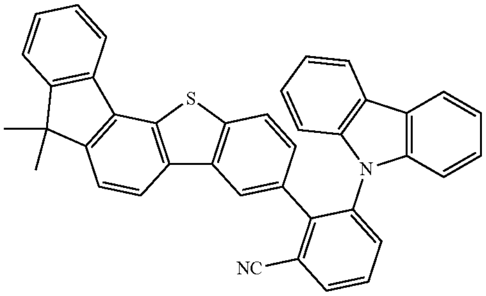
240
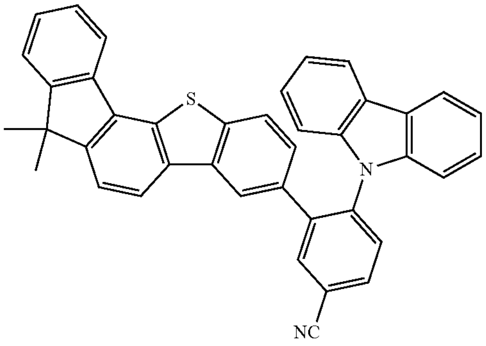

-continued
241
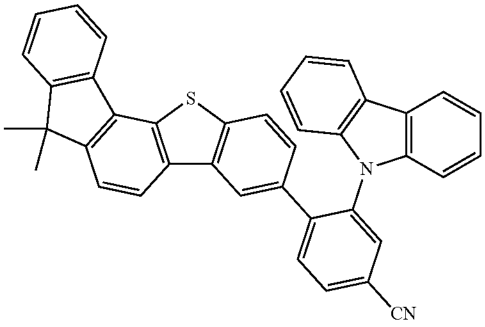
242
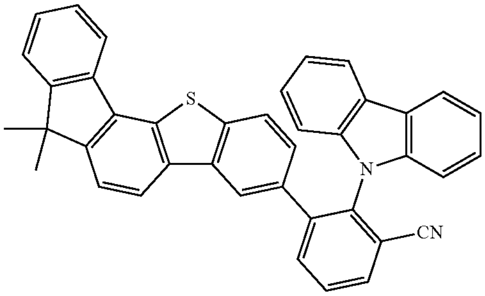
243
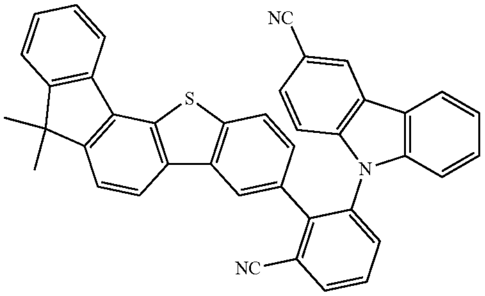
244
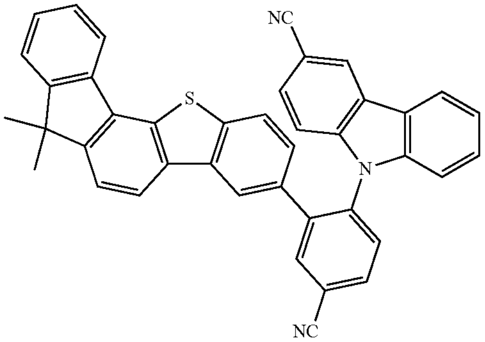
245
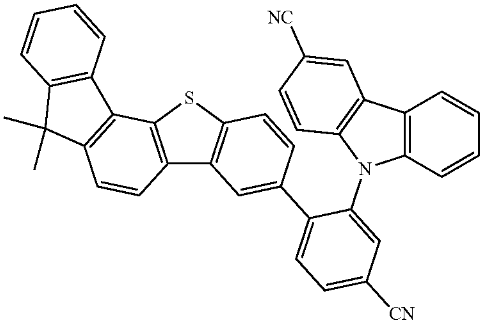
-continued
246
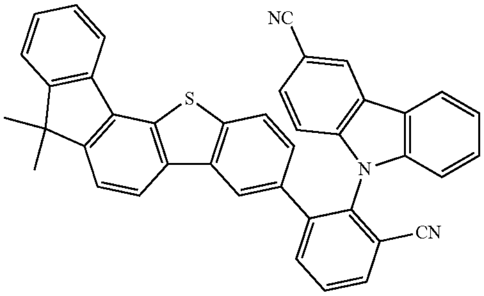
247
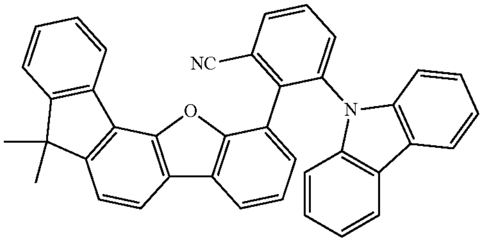
248
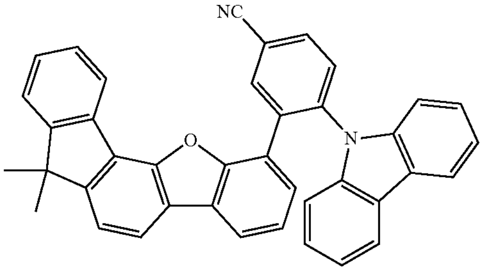
249
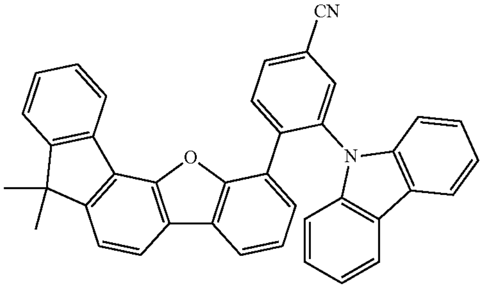
250
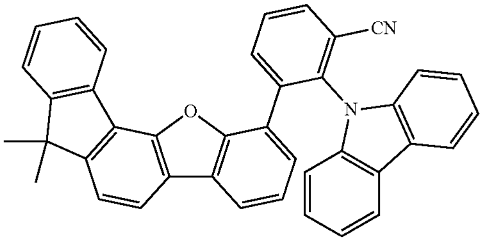

-continued
251
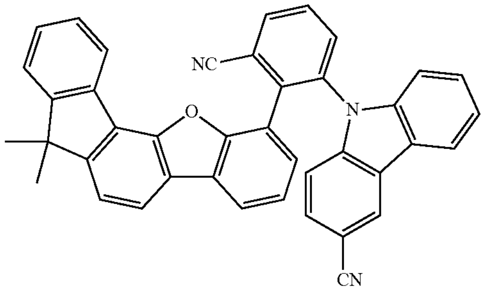
252
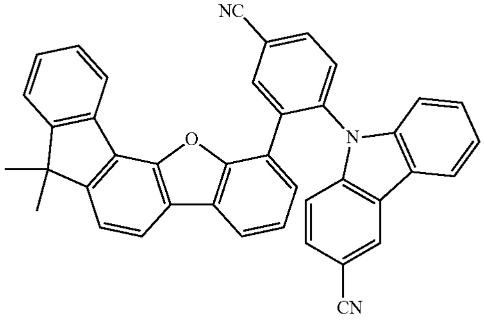
253
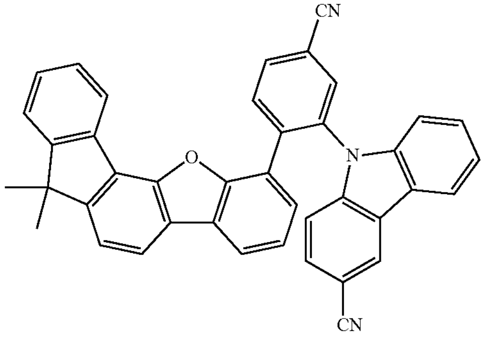
254
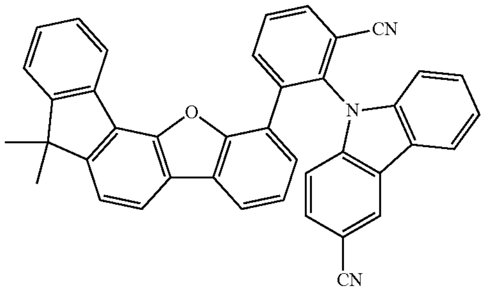
255
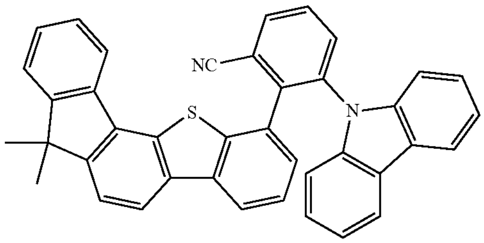
-continued
256
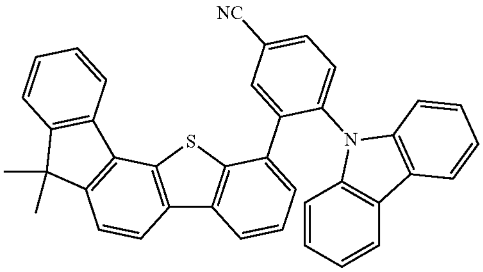
257
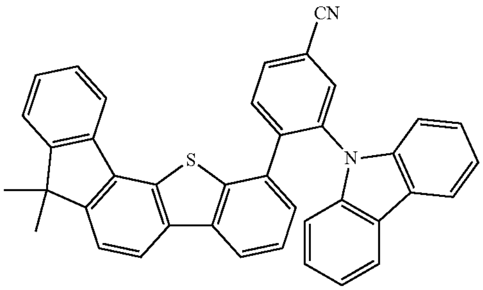
258
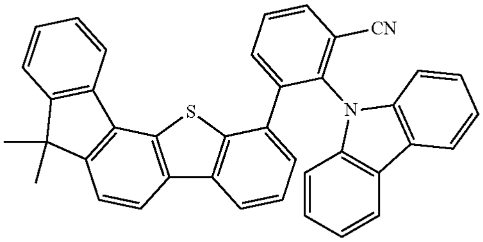
259
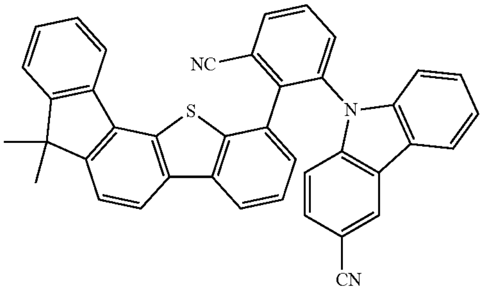
260
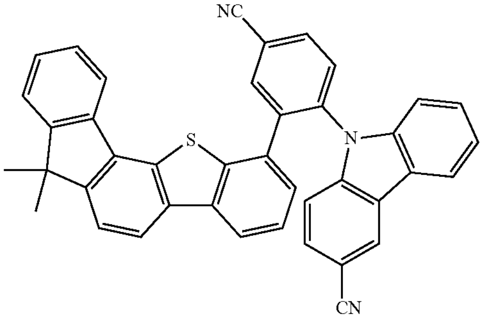

261
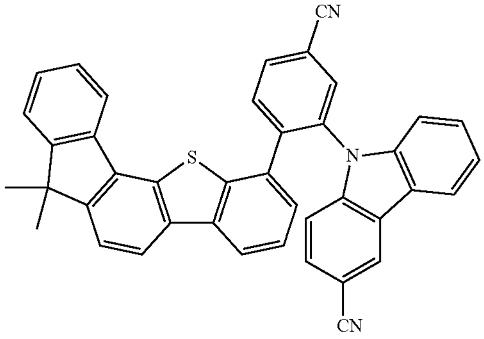
262
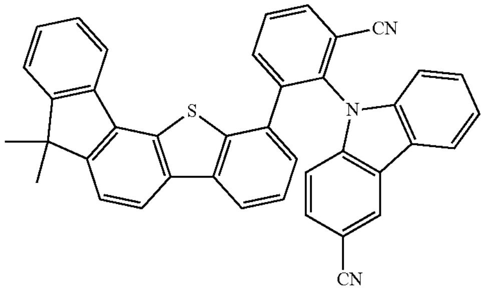
263
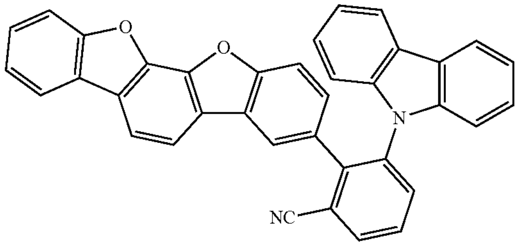
264
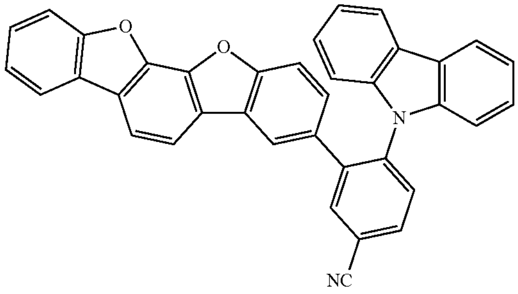
265
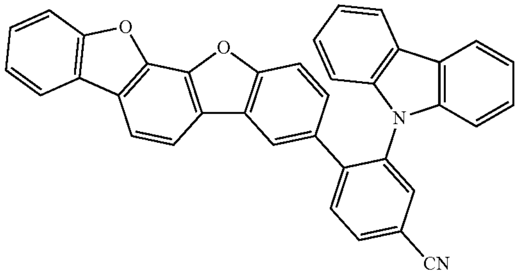
266
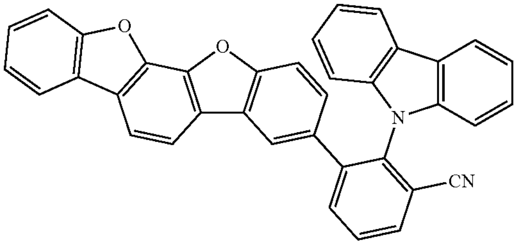
267
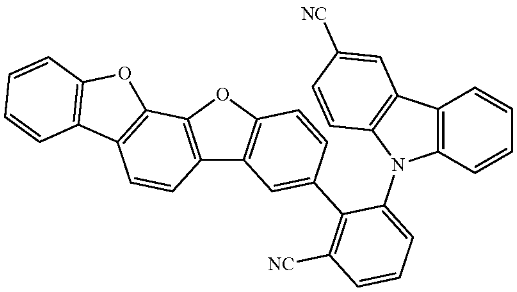
268
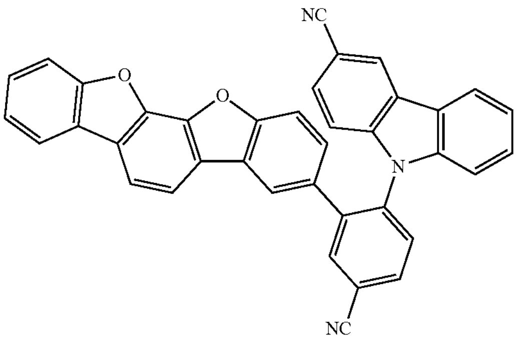
269
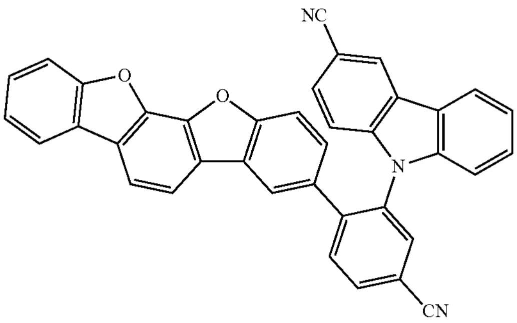
270
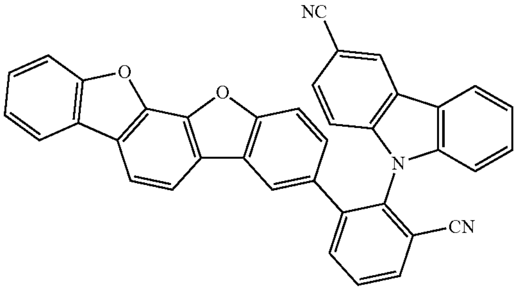

-continued
271
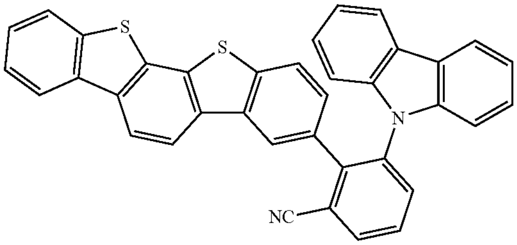
272
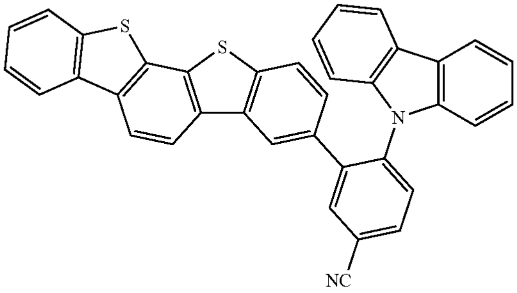
273
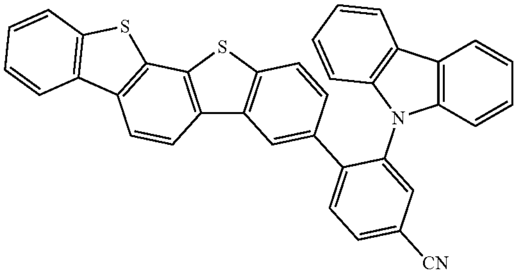
274
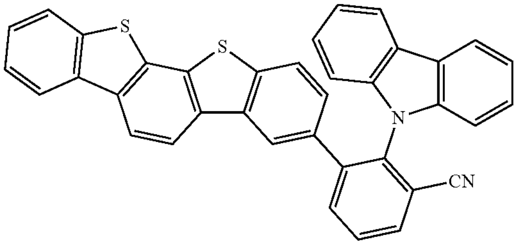
275
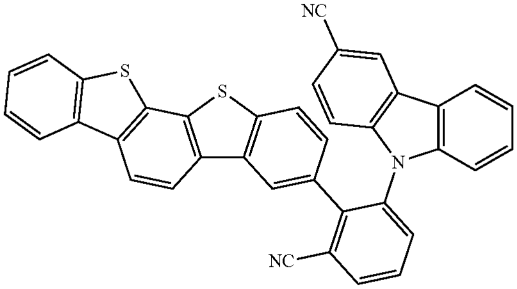
-continued
276
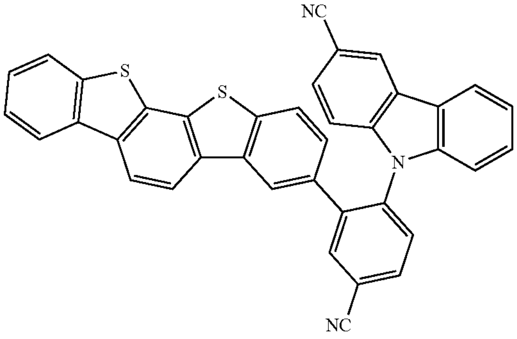
277
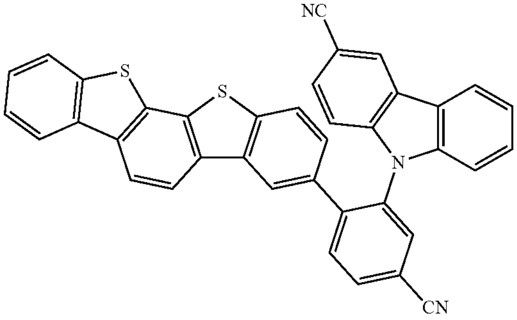
278
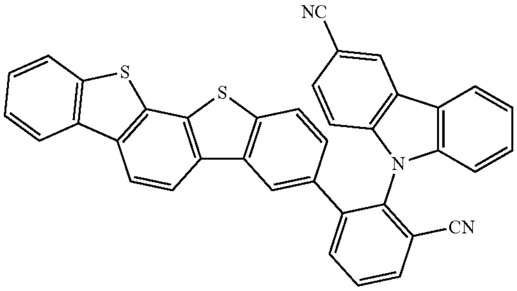
279
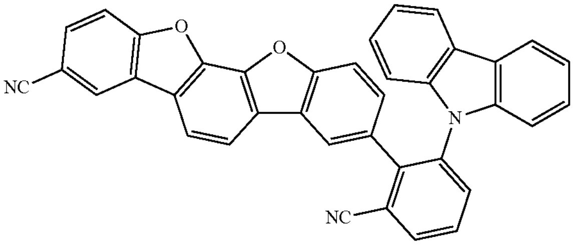
280
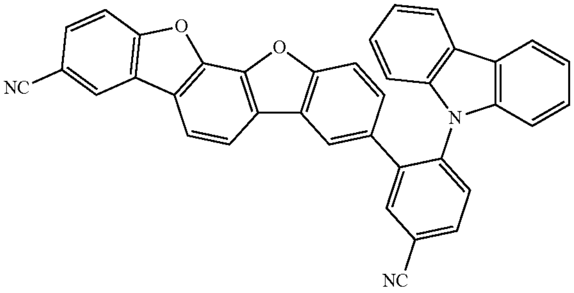

-continued
281
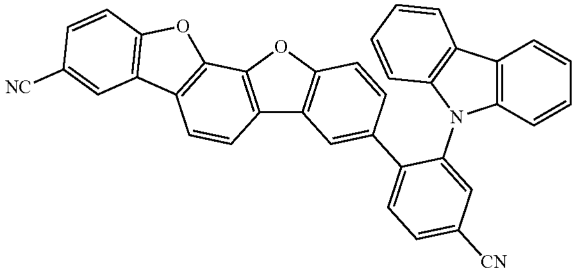
282
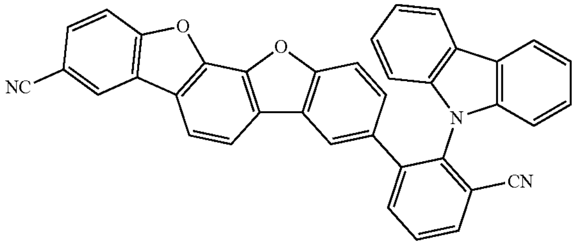
283
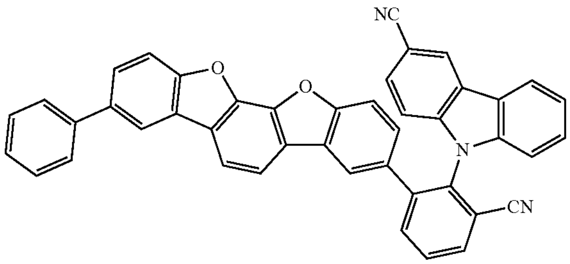
284
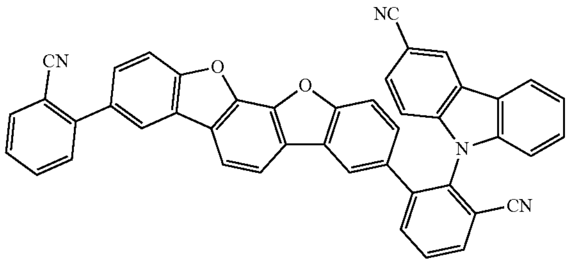
285
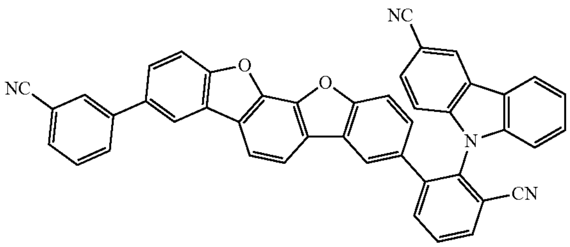
-continued
286
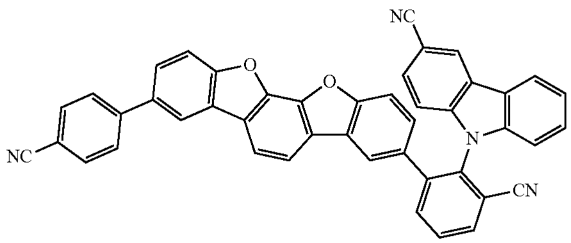
287
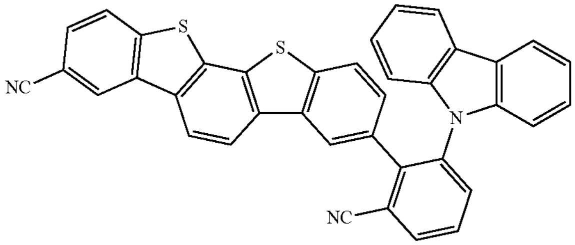
288
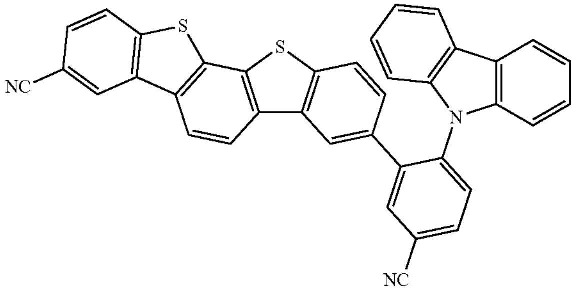
289
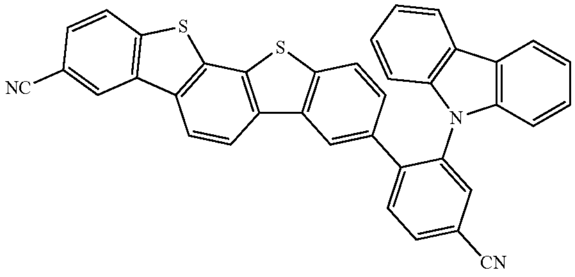
290
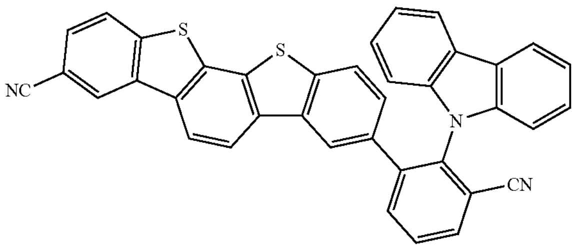

-continued
291
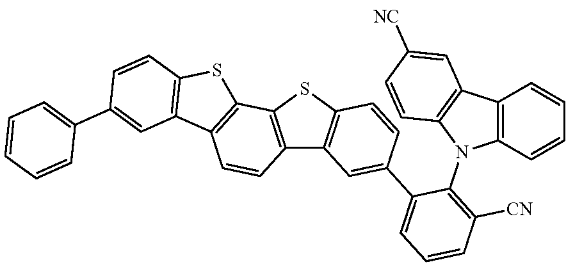
292
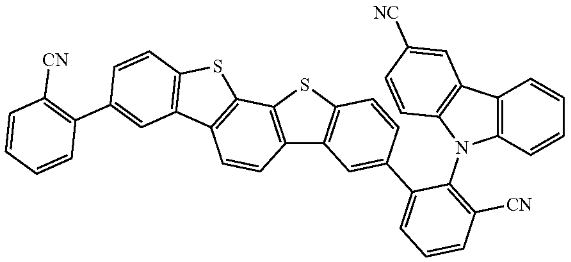
293
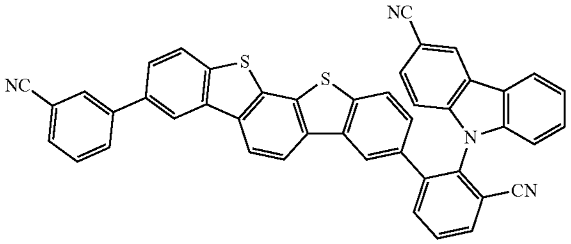
294
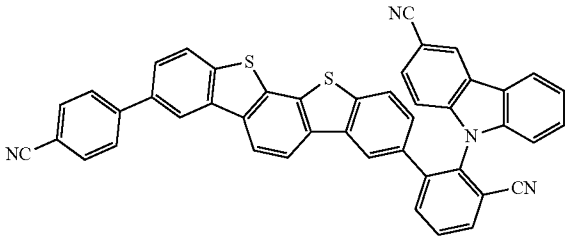
295
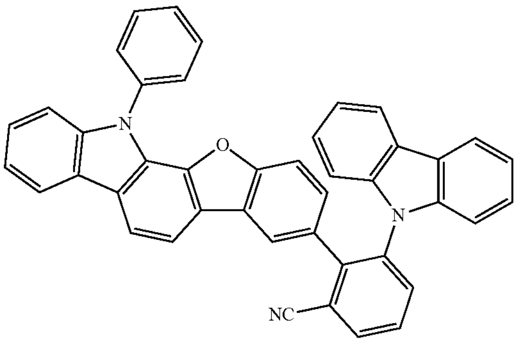
-continued
296
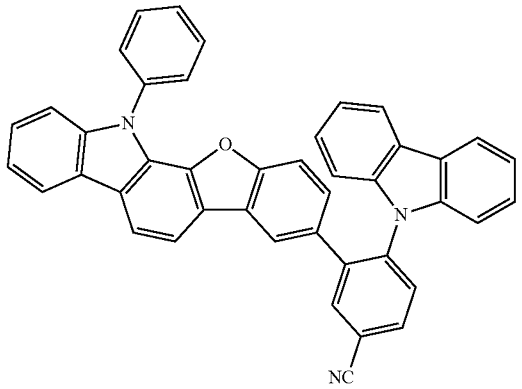
297
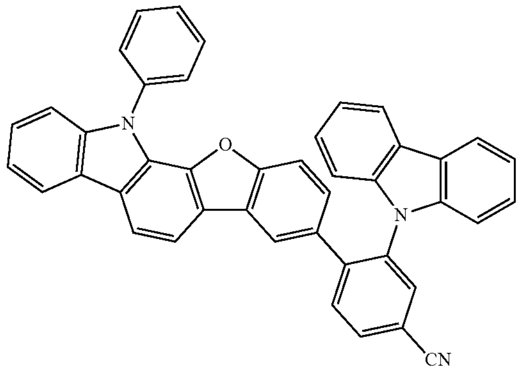
298
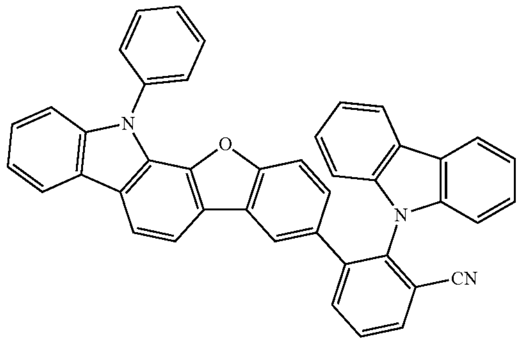
299
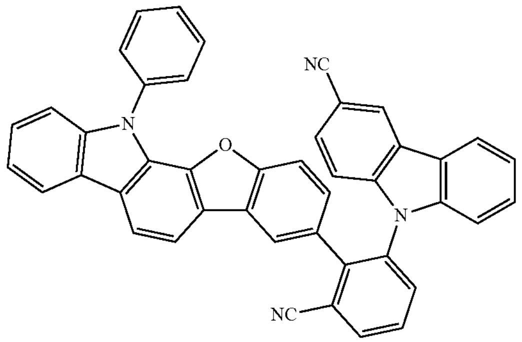

-continued
300
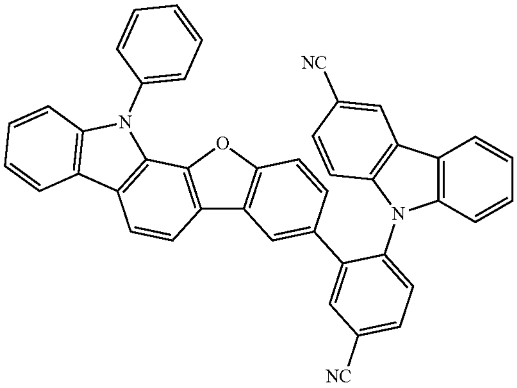
301
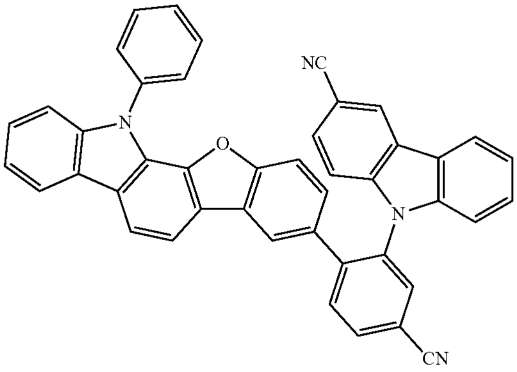
302
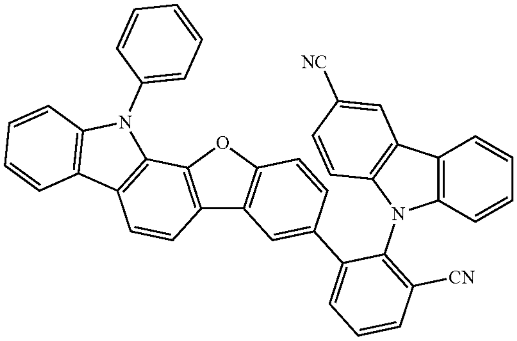
303
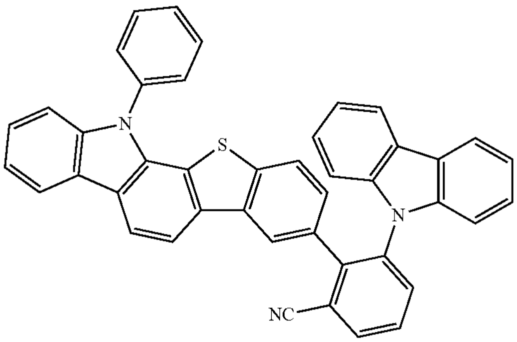
-continued
304
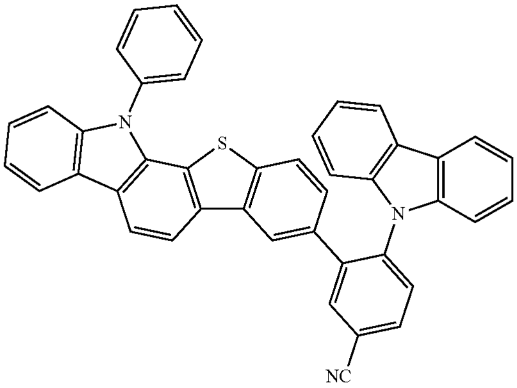
305
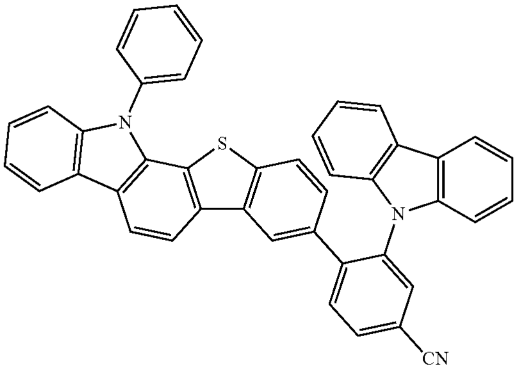
306
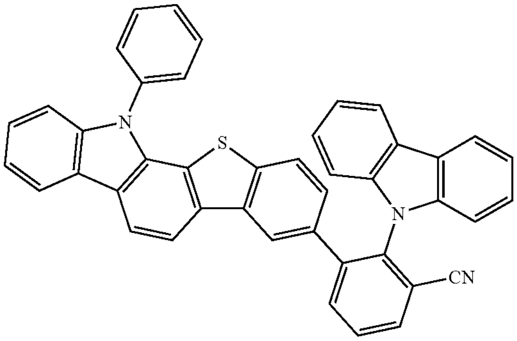
307
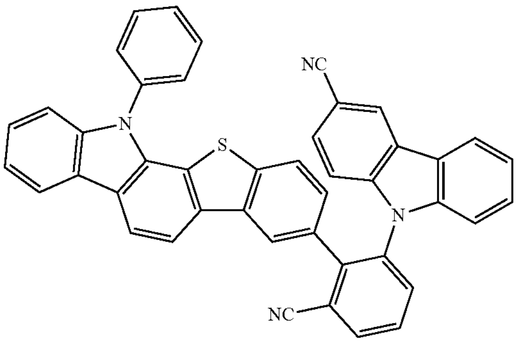

-continued
308
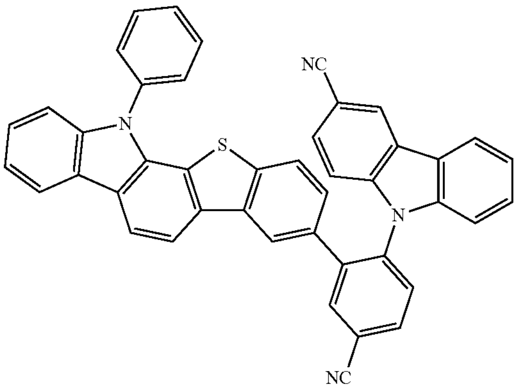
309
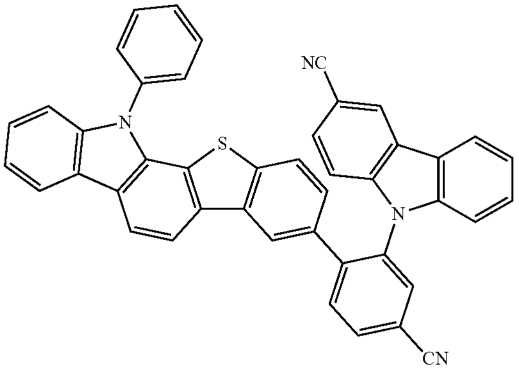
310
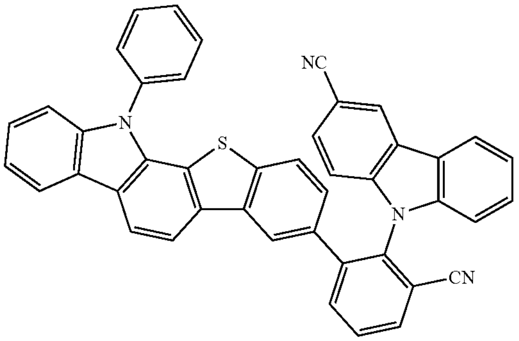
311
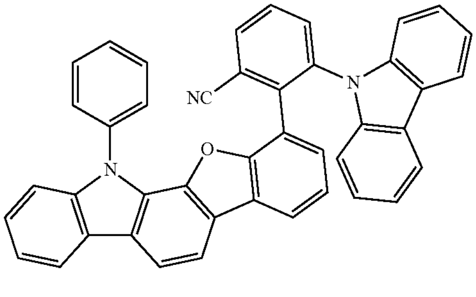
-continued
312
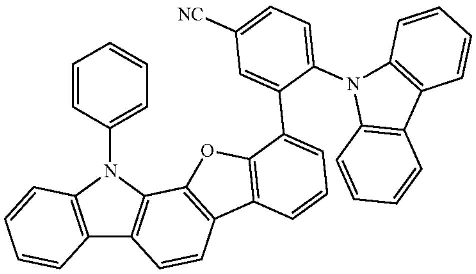
313
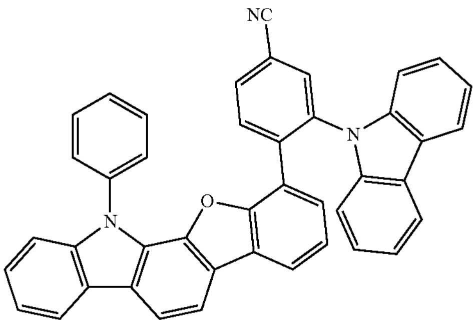
314
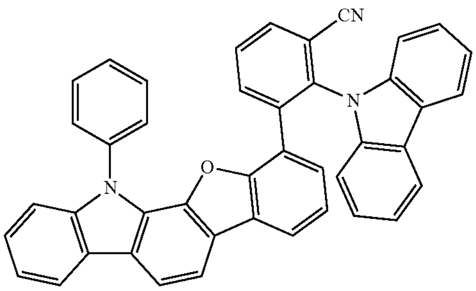
315
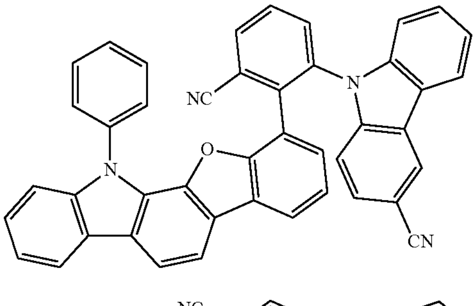
316
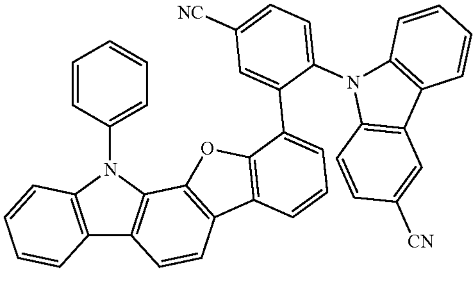

-continued
317
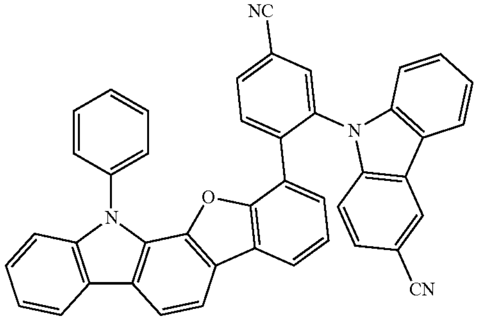
318
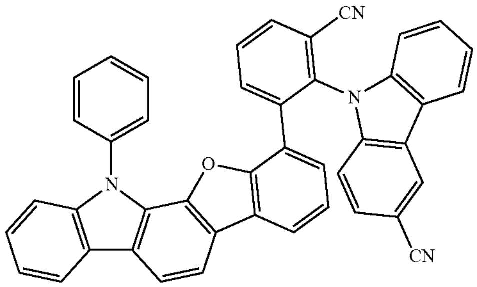
319
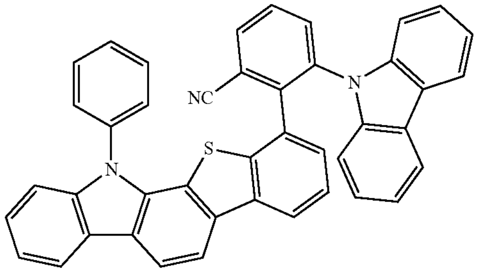
320
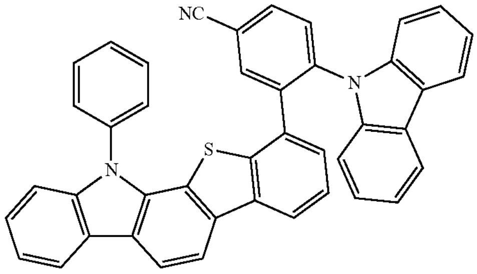
321
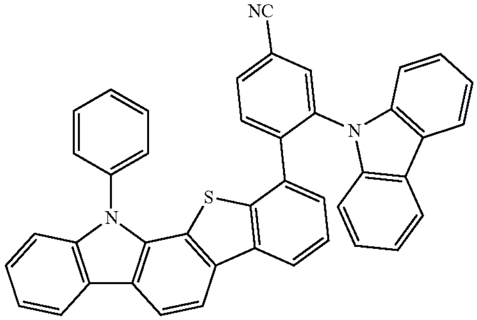
-continued
322
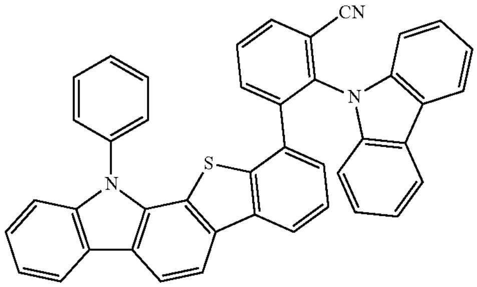
323
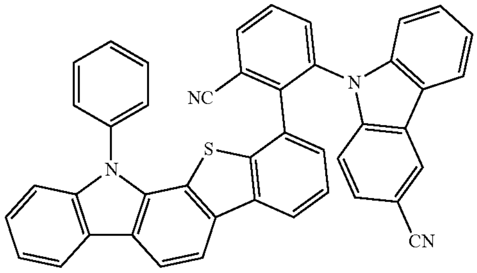
324
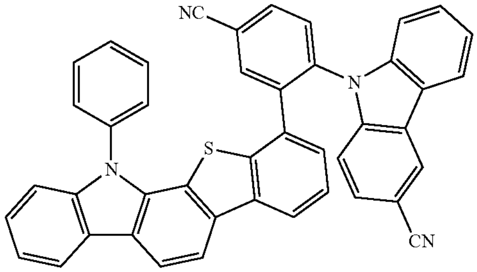
325
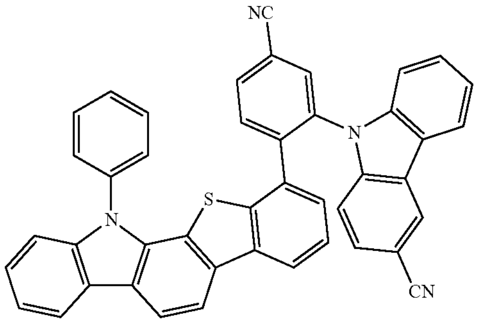
326
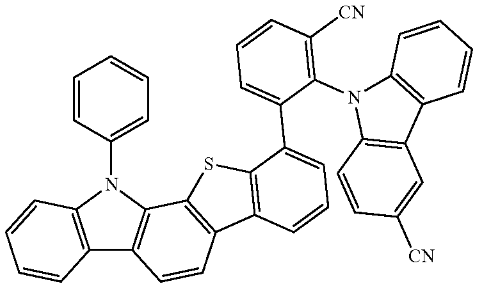

-continued
327
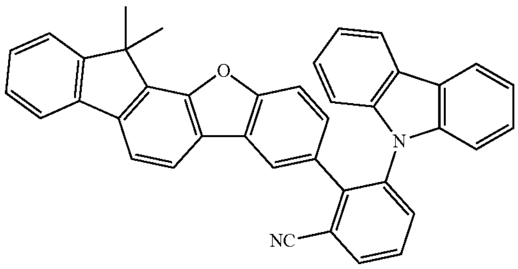
328
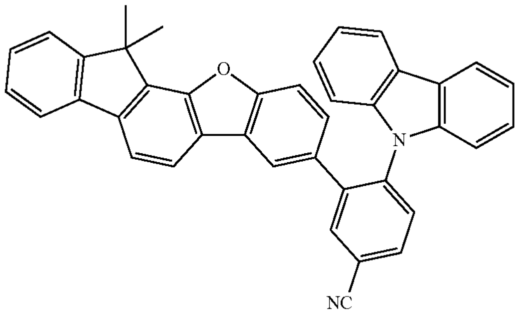
329
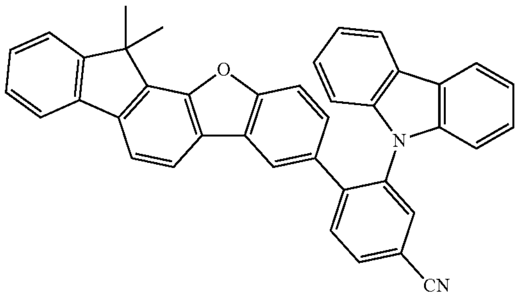
330
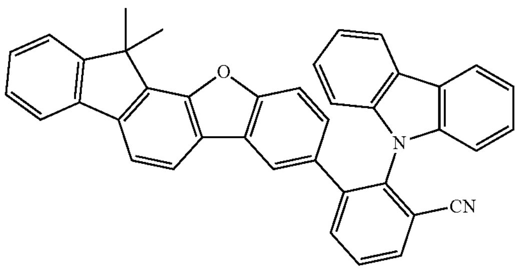
331
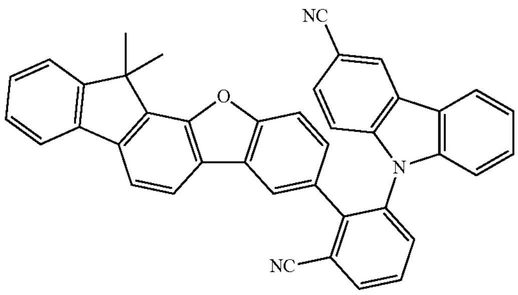
-continued
332
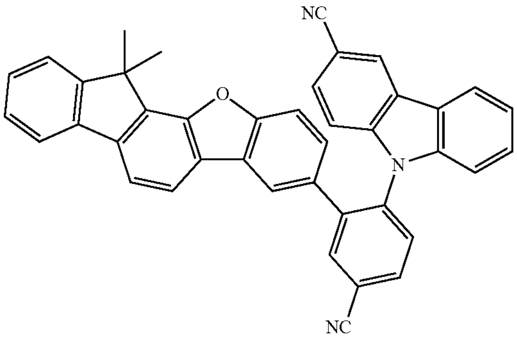
333
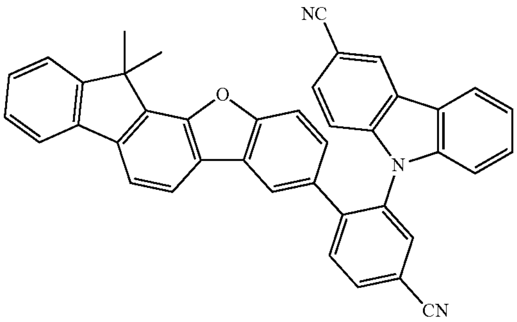
334
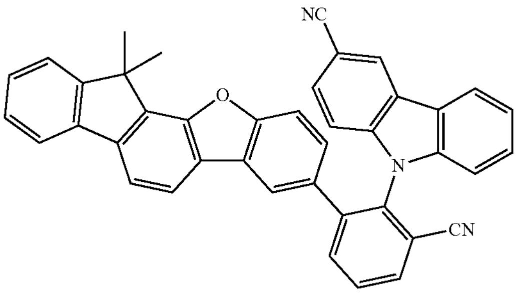
335
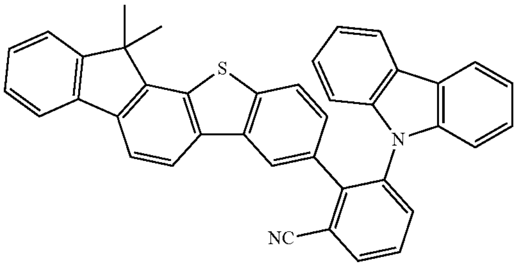
336
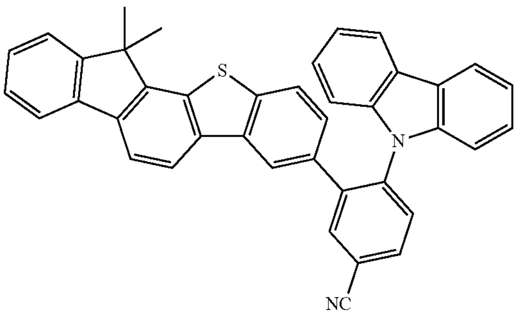

-continued
337
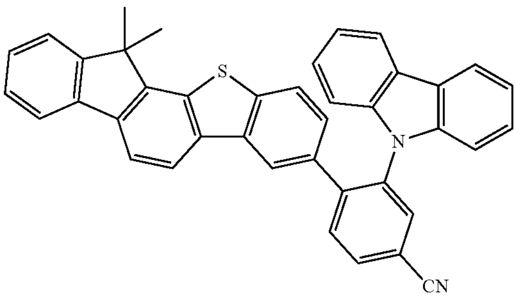
338
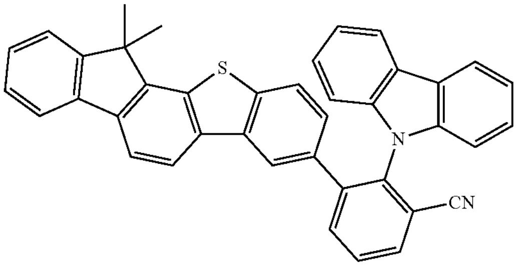
339
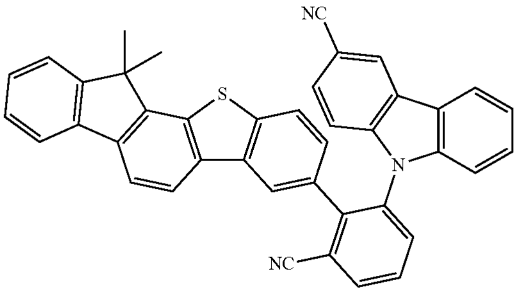
340
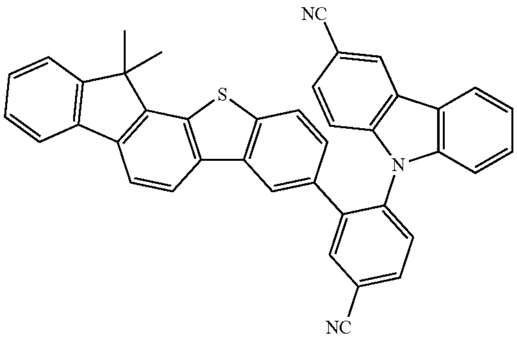
341
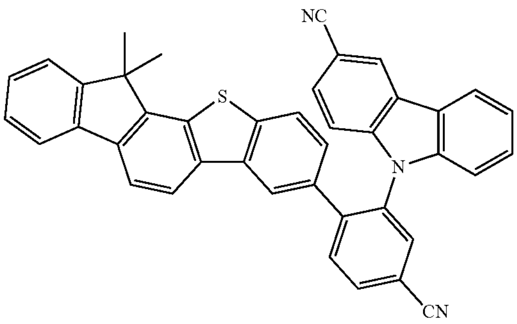
-continued
342
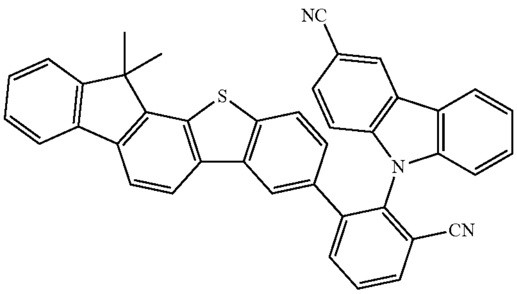
343
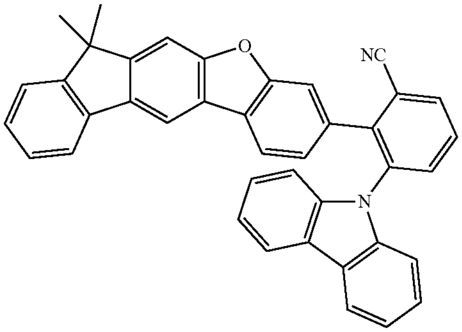
344
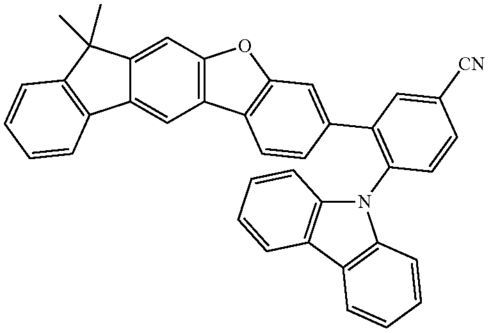
345
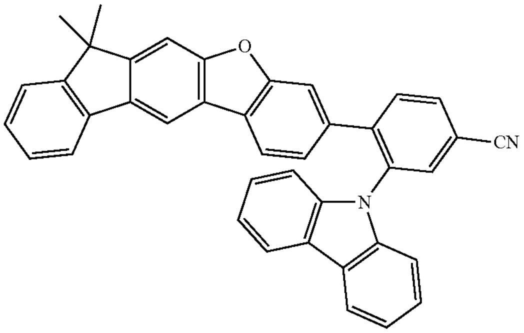

-continued
346
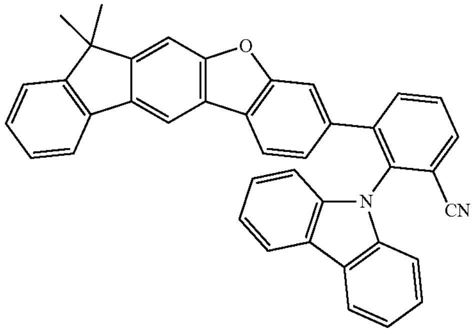
347
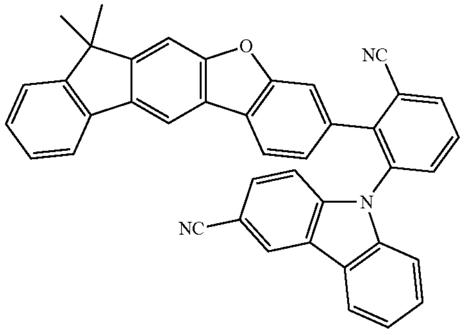
348
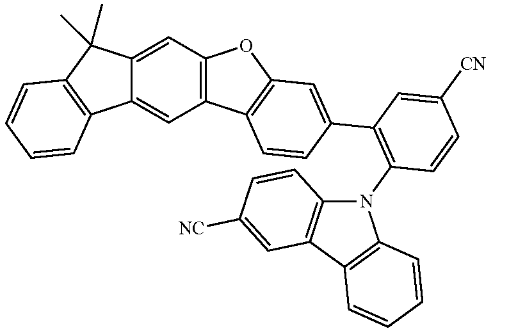
349
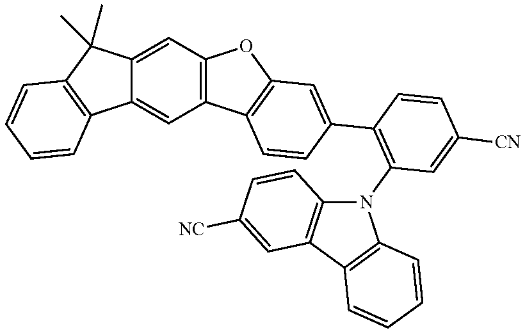
-continued
350
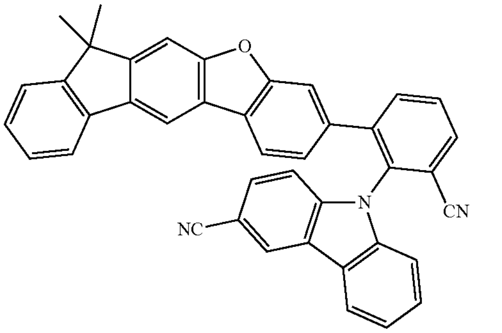
351
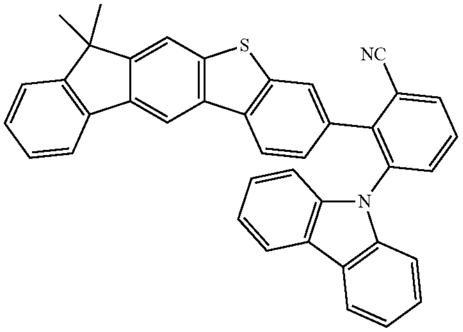
352
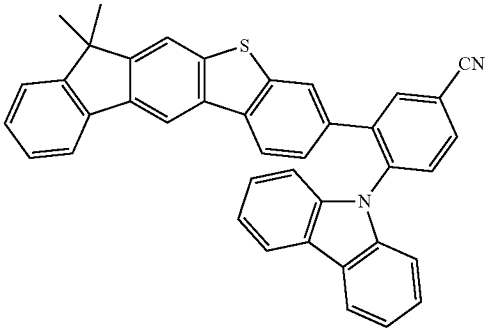
353
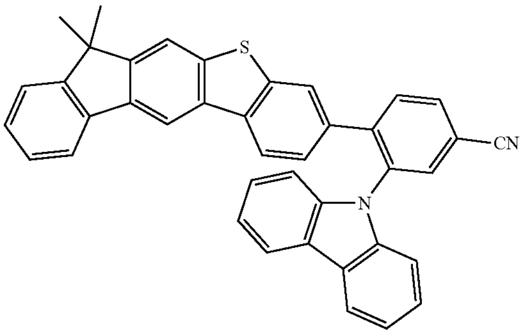

-continued
354
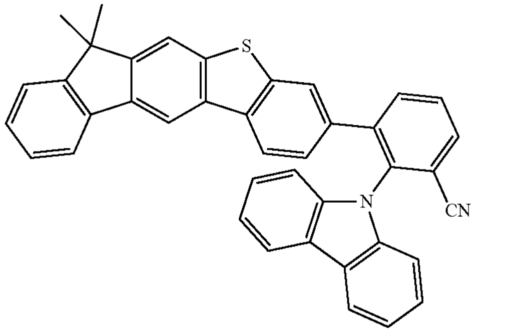
355
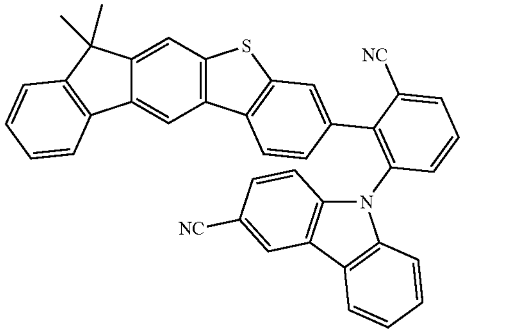
356
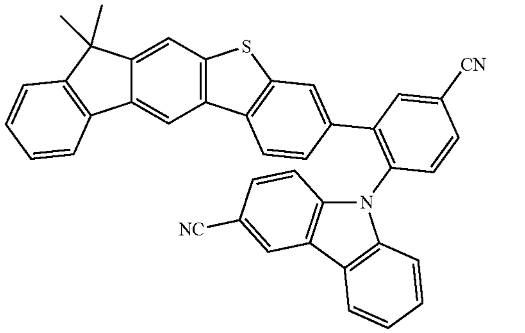
357
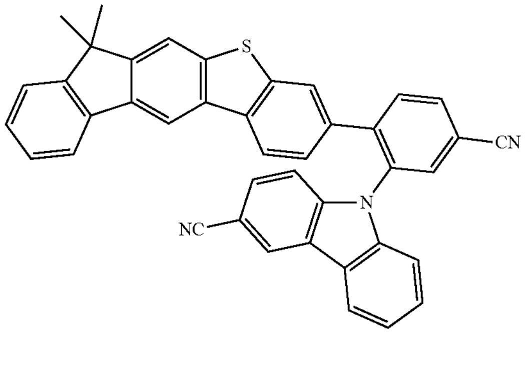
-continued
358
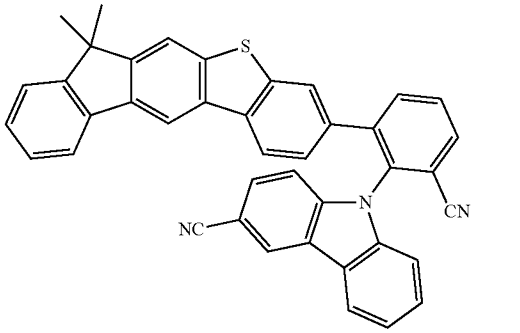
359
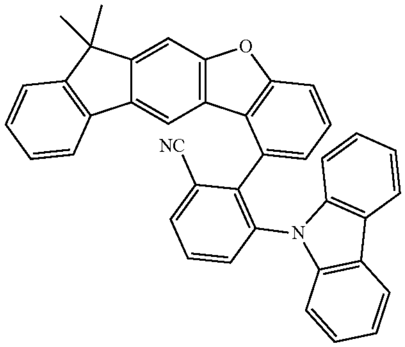
360
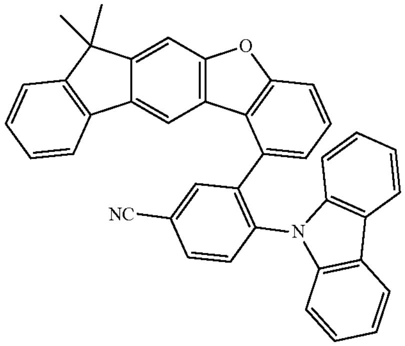
361
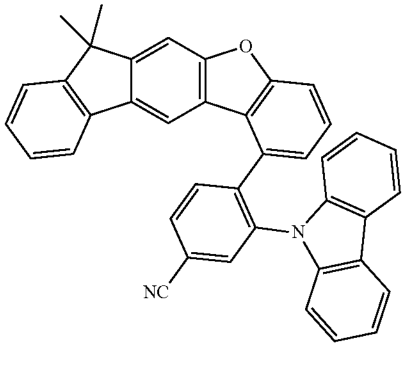

-continued
362
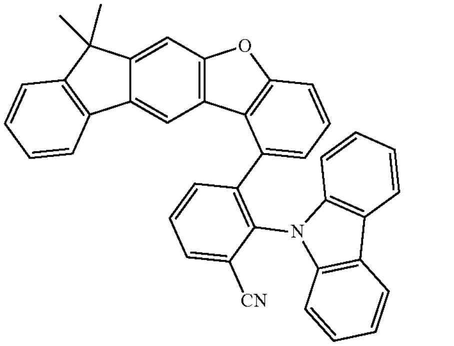
363
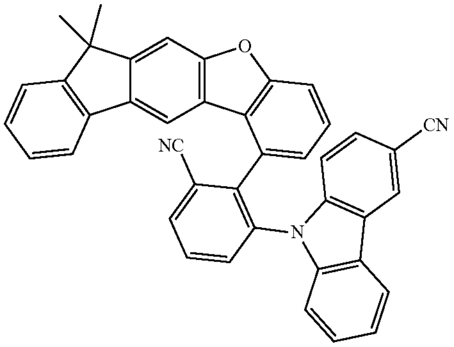
364
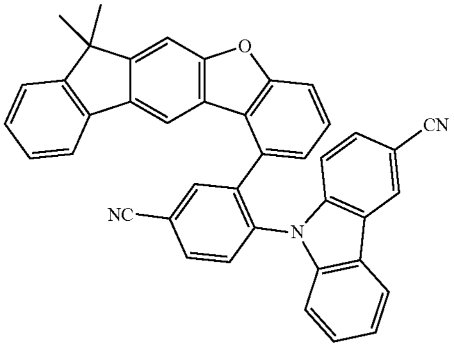
365
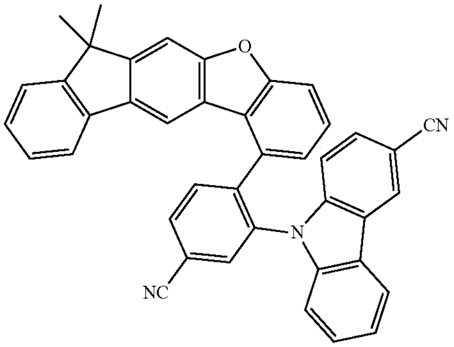
-continued
366
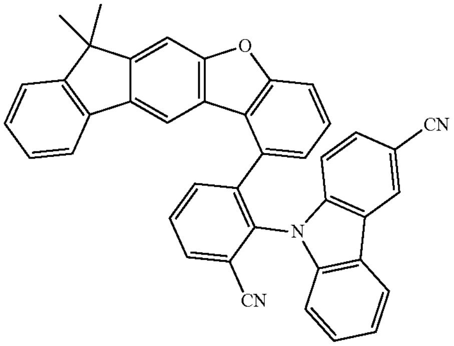
367
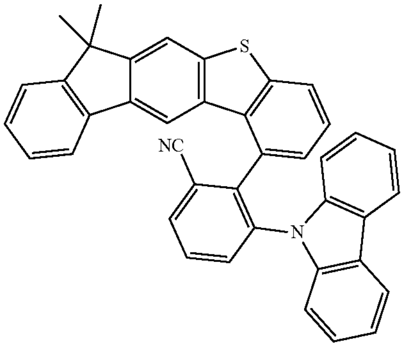
368
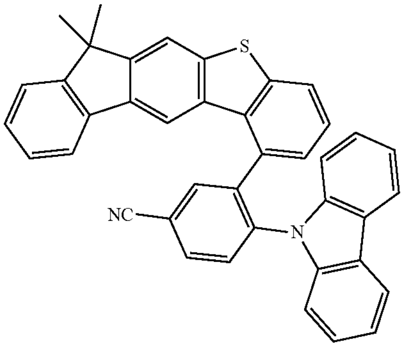
369
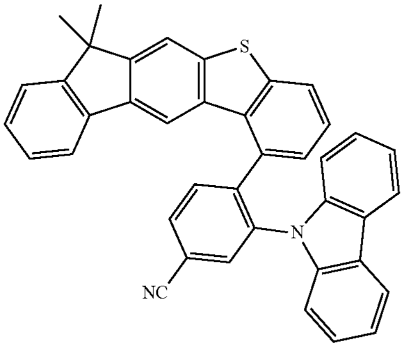

-continued
370
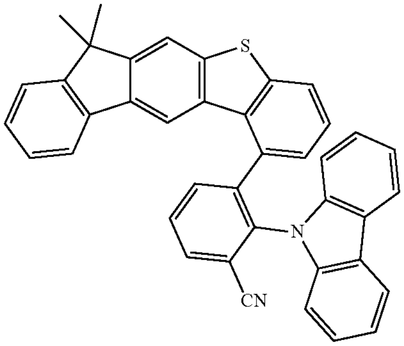
371
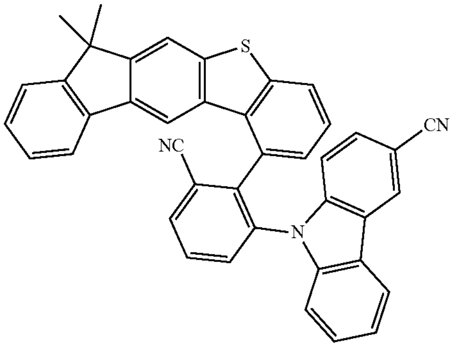
372
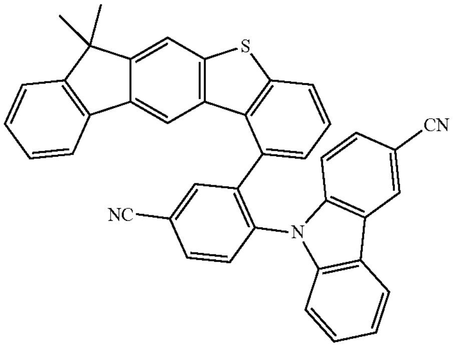
373
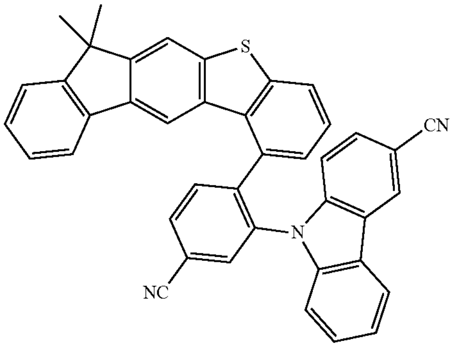
-continued
374
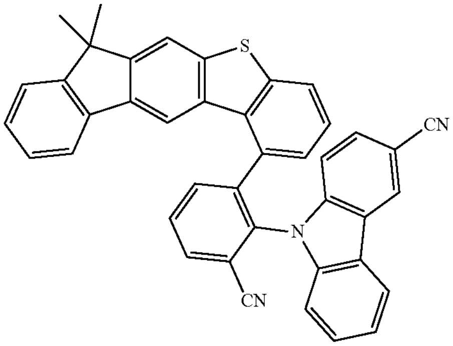
375
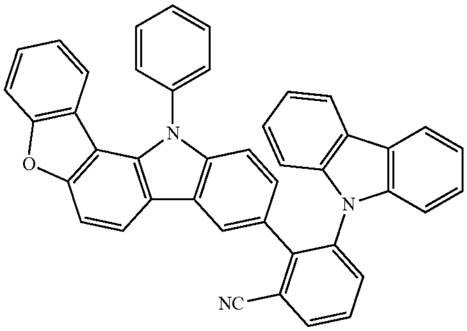
376
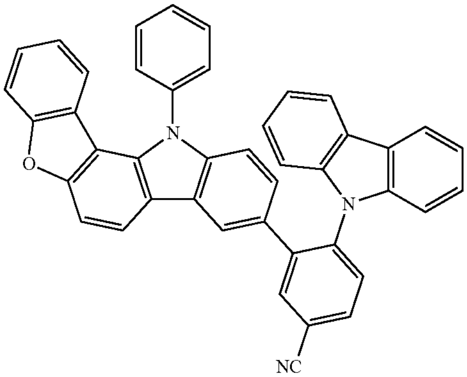
377
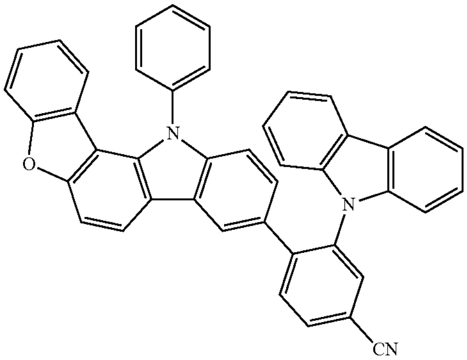

-continued
378
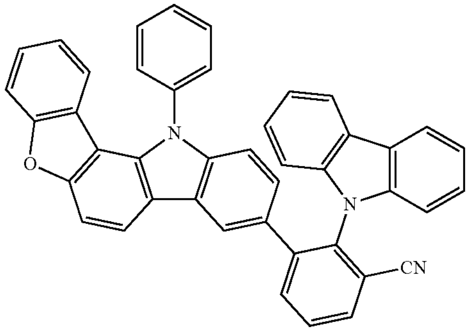
379
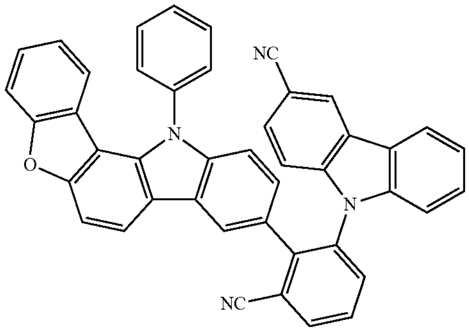
380
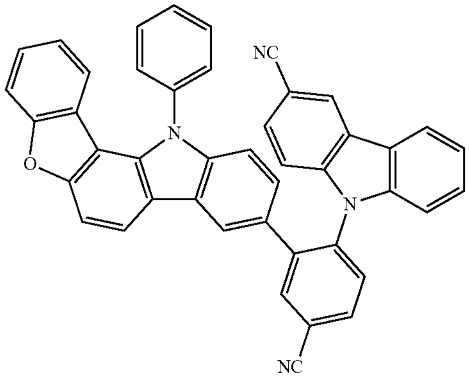
381
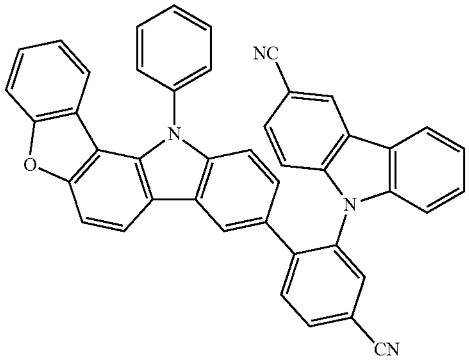
-continued
382
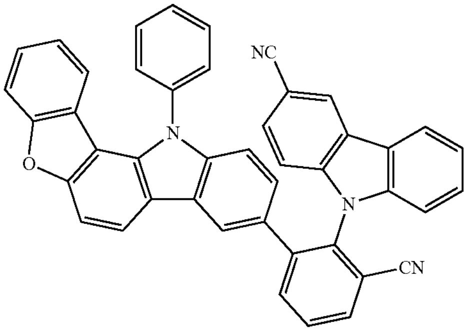
383
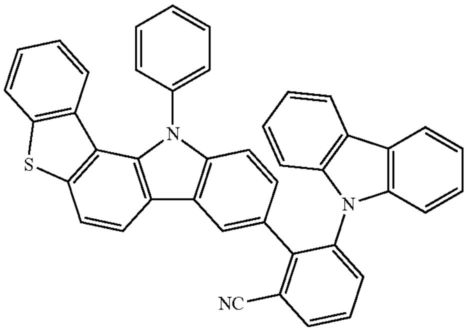
384
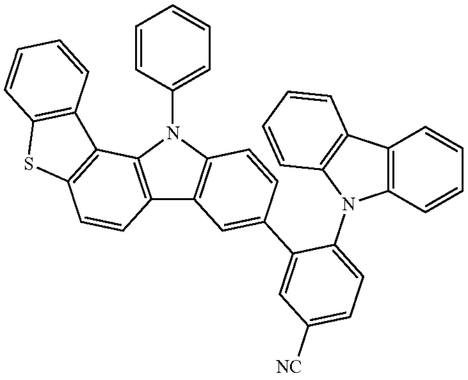
385
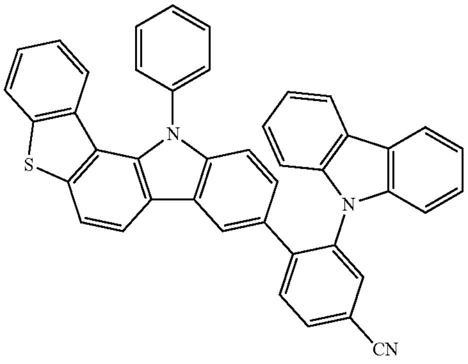

386
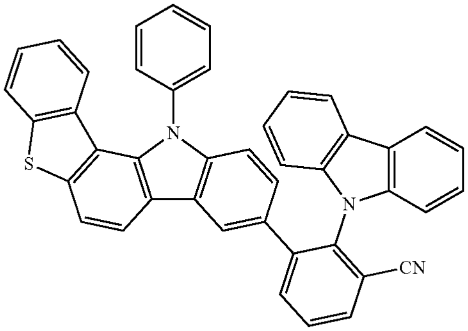
387
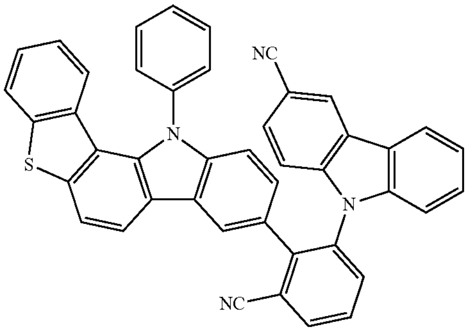
388
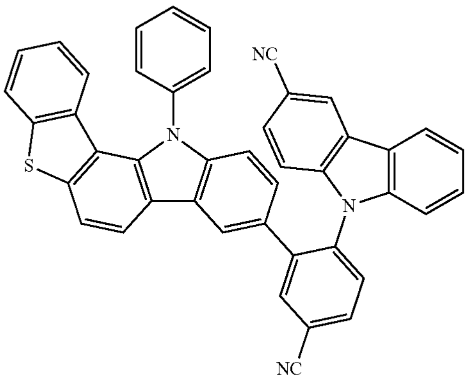
389
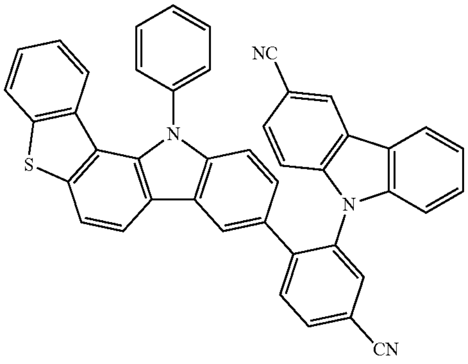
390
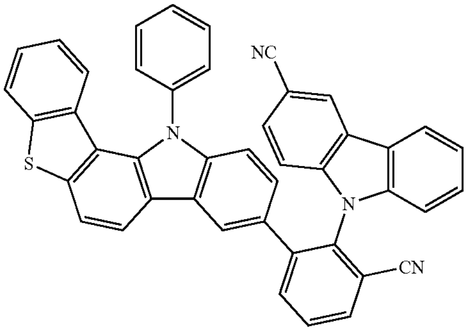
391
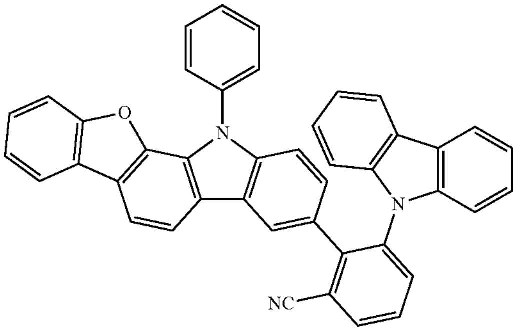
392
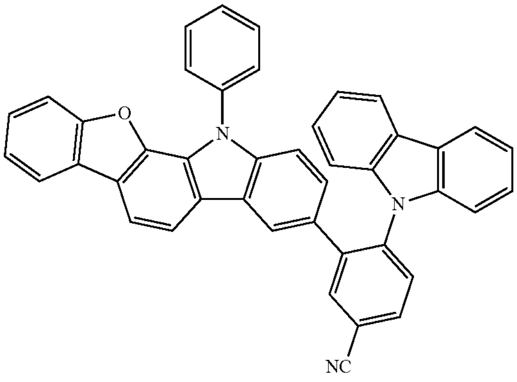
393
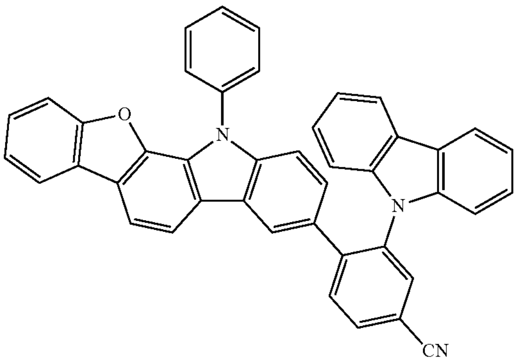

-continued
394
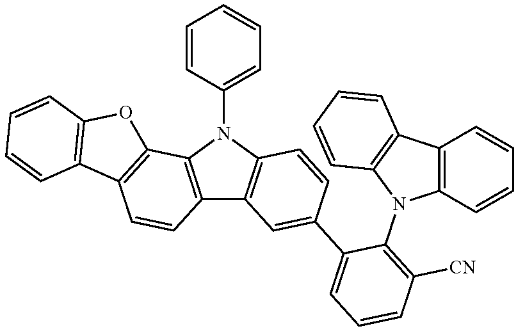
395
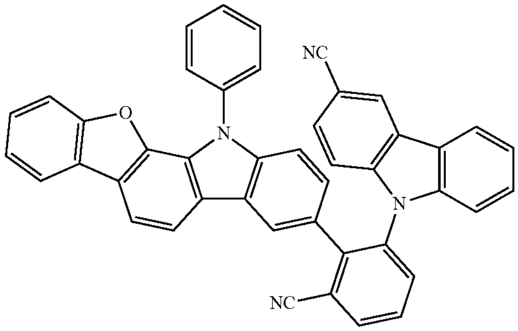
396
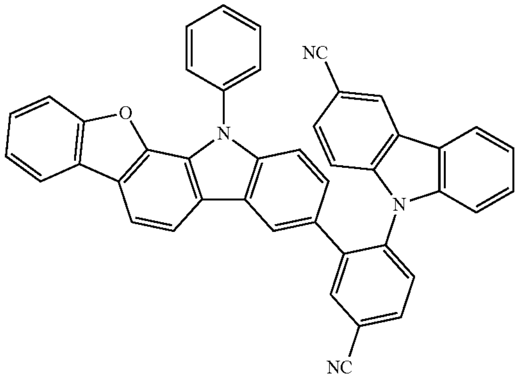
397
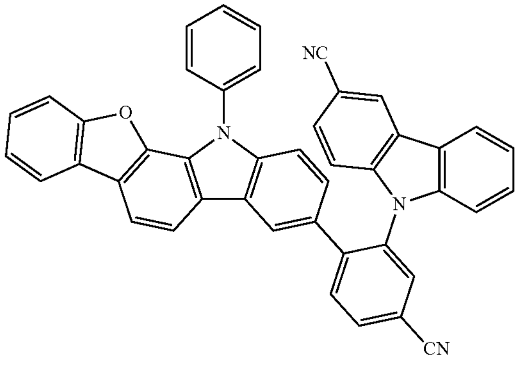
-continued
398
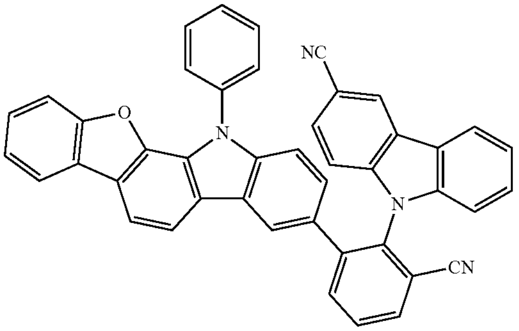
399
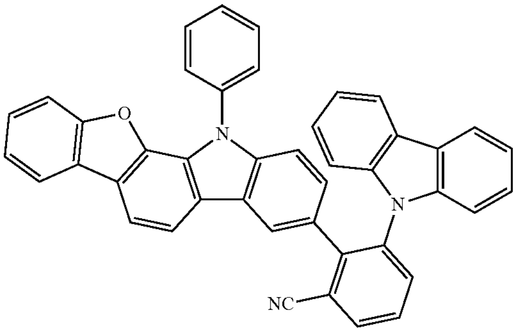
400
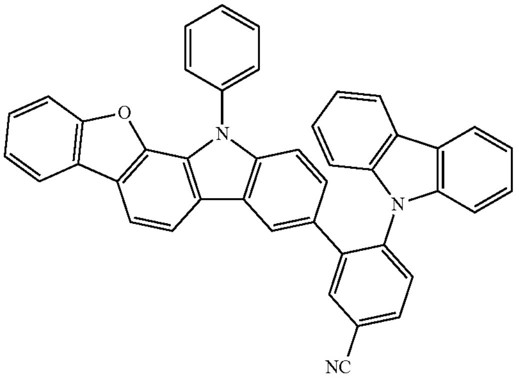
401
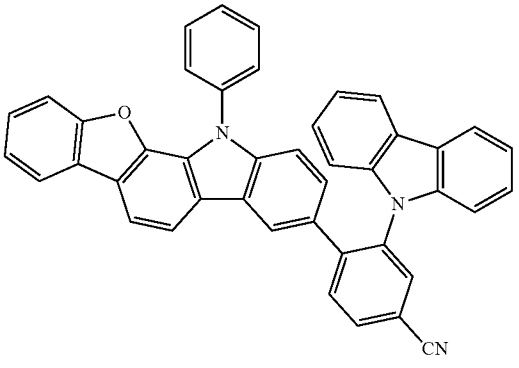

-continued
402
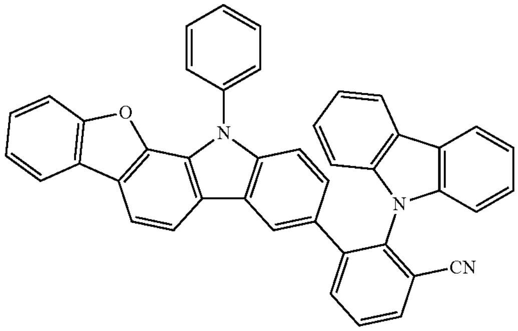
403
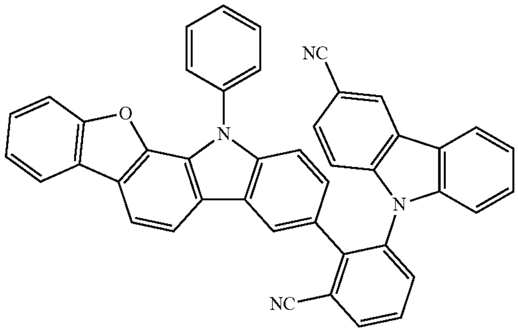
404
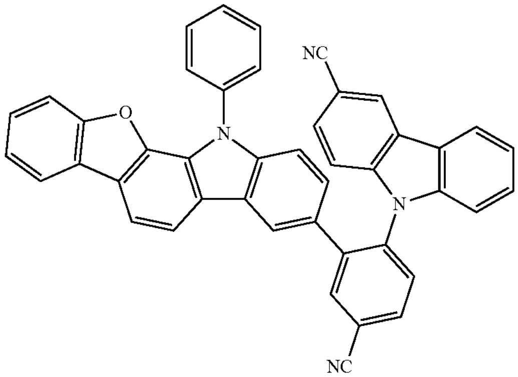
405
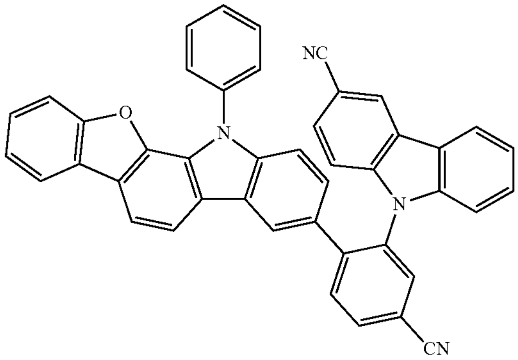
-continued
406
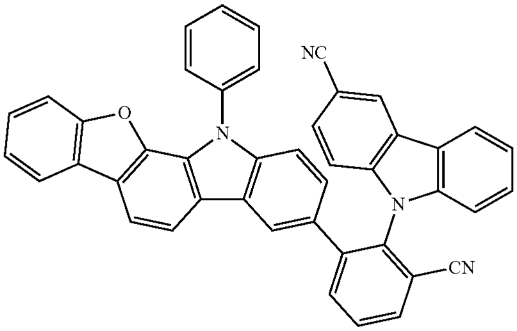
407
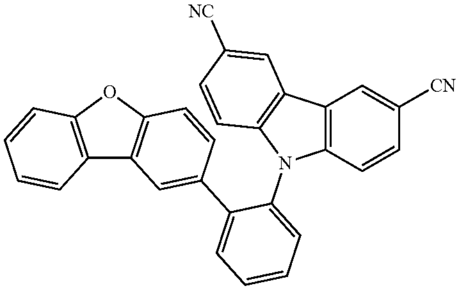
408
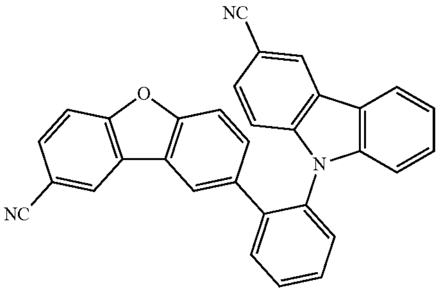
409
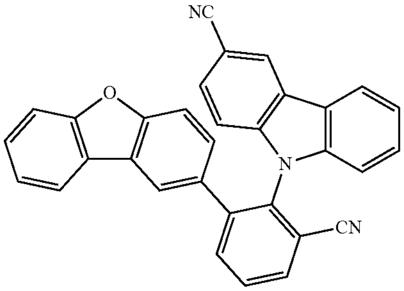
410
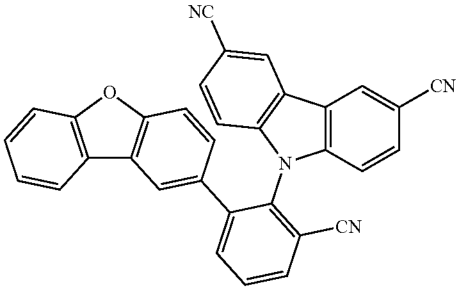

-continued
411
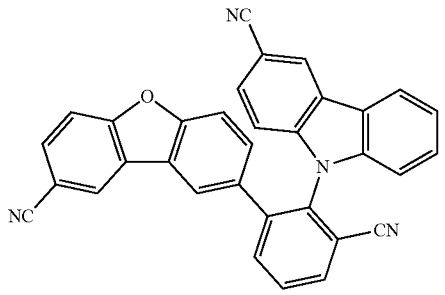
412
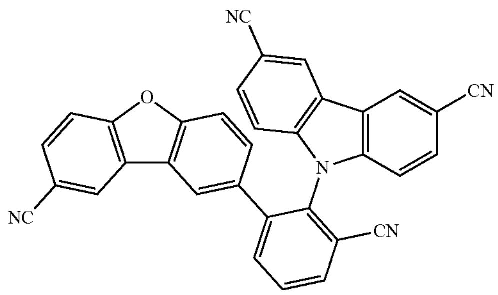
413
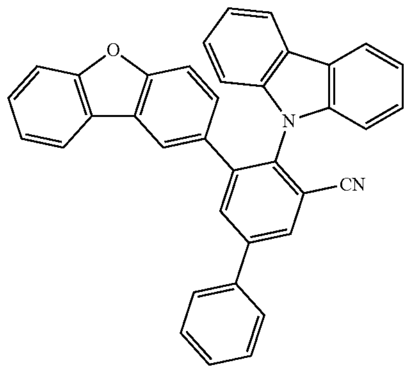
414
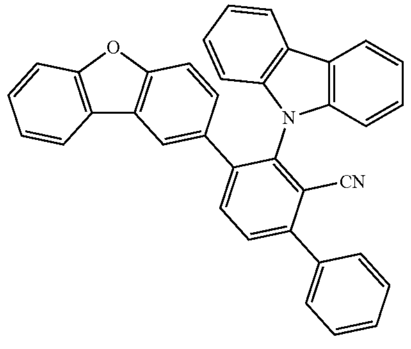
-continued
415
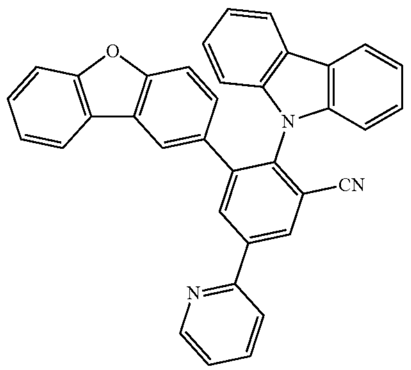
416
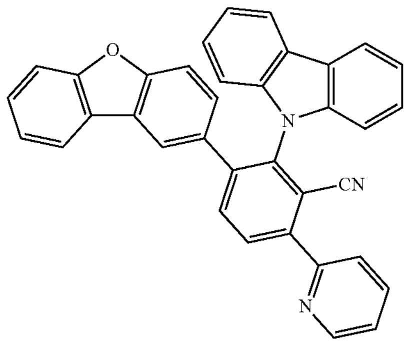
417
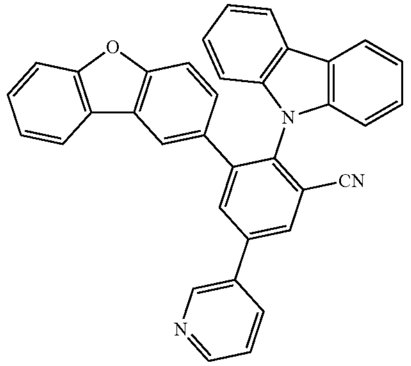
418
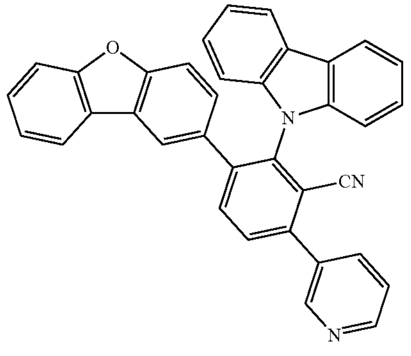

-continued
419
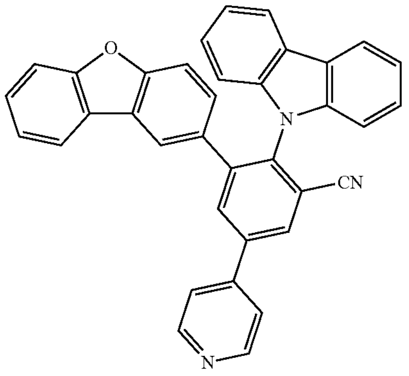
420
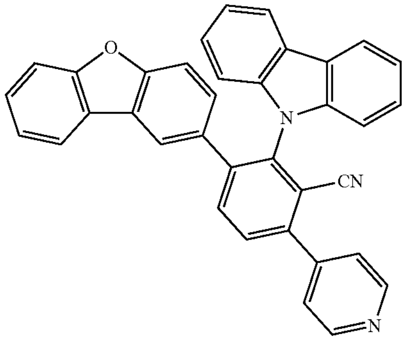
421
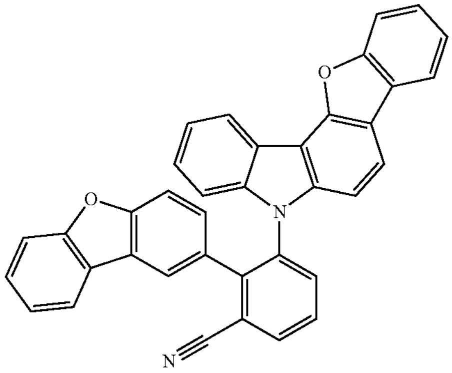
422
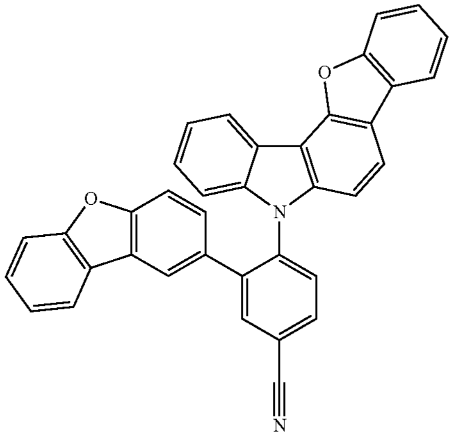
-continued
423
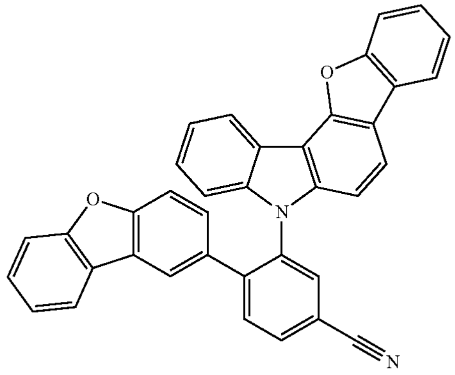
424
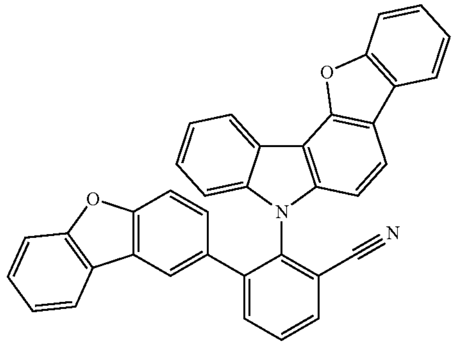
425
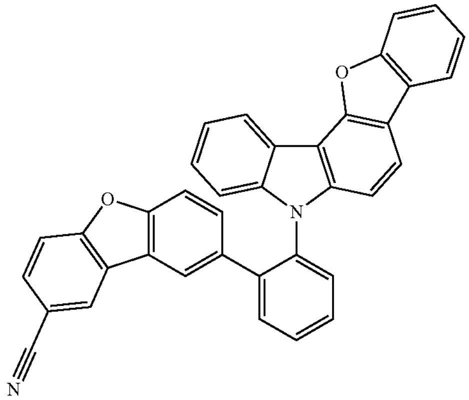
426
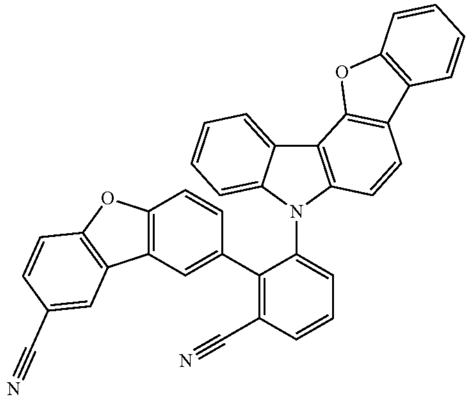

-continued
427
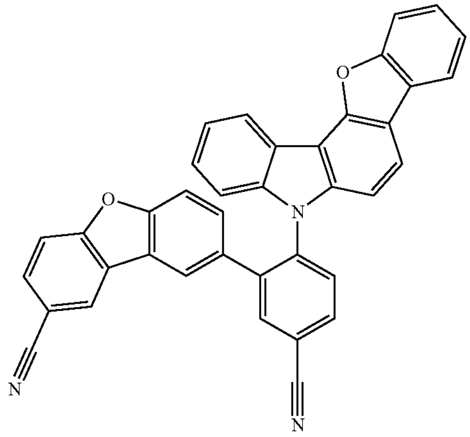
428
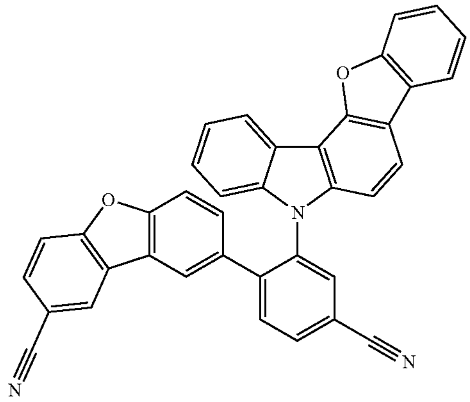
429
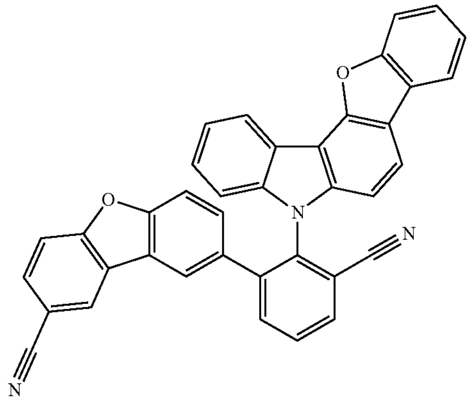
-continued
430
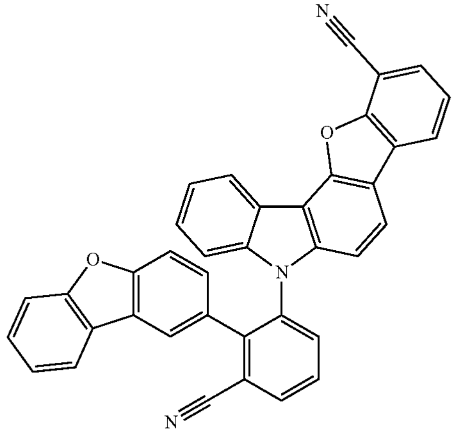
431
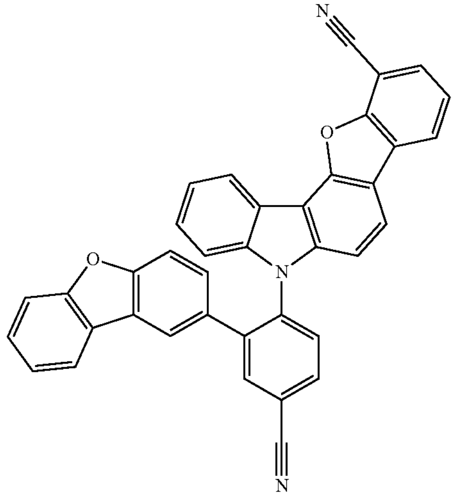
432
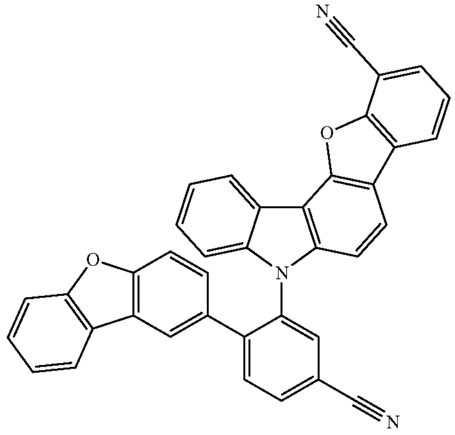

-continued
433
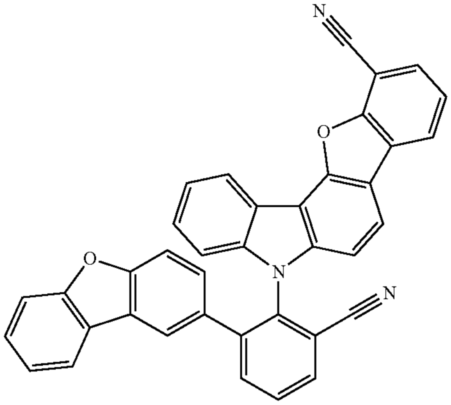
434
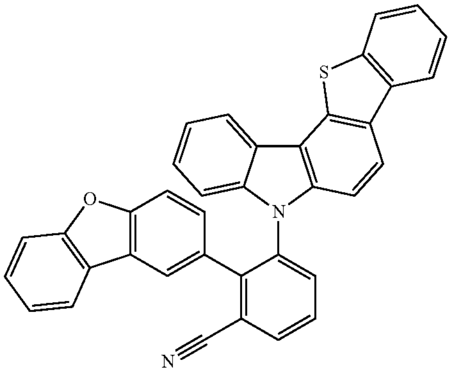
435
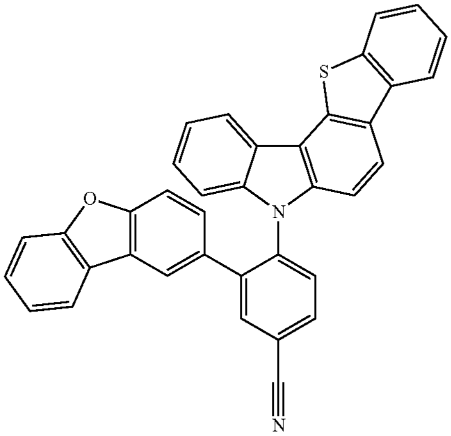
436
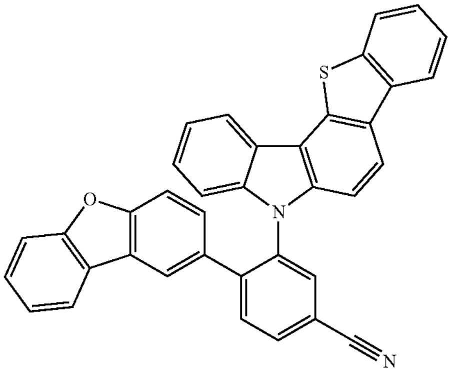
-continued
437
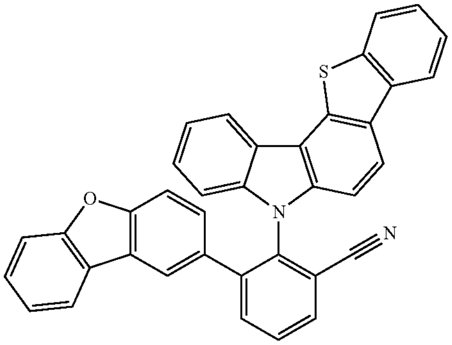
438
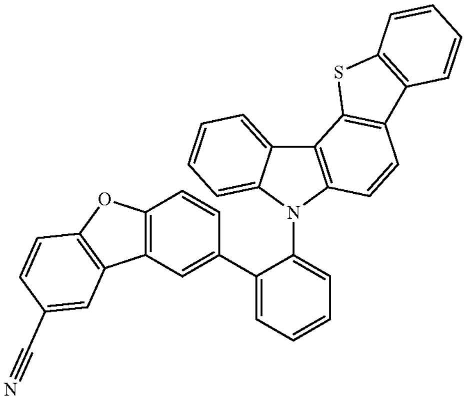
439
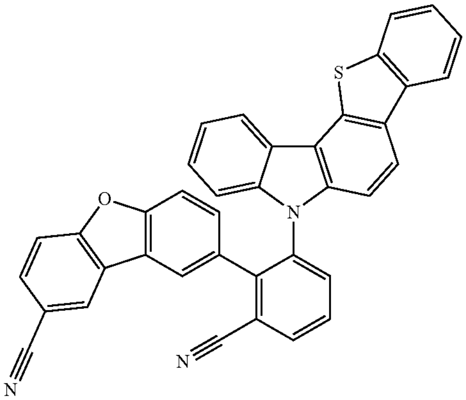
440
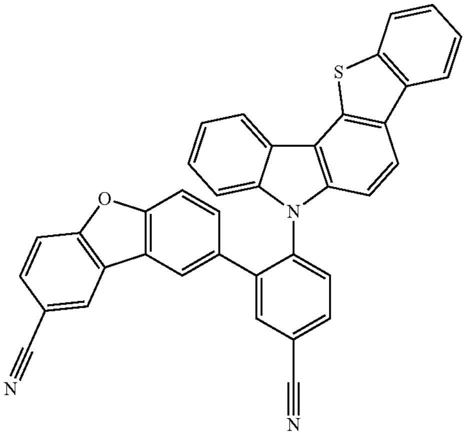

441
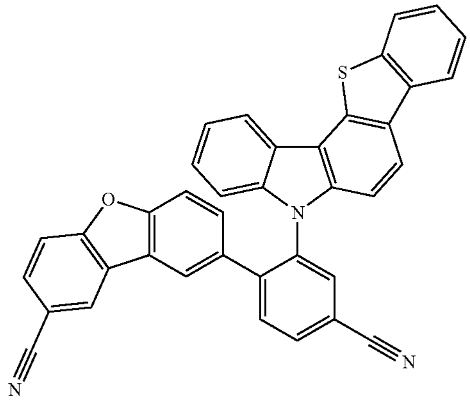
442
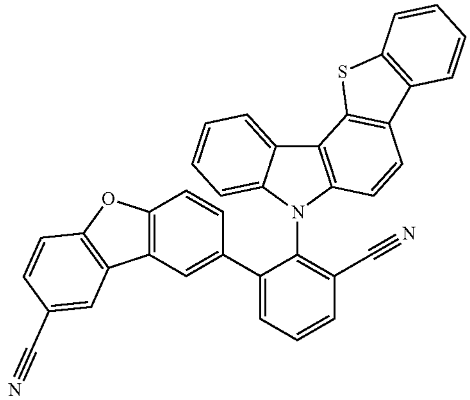
443
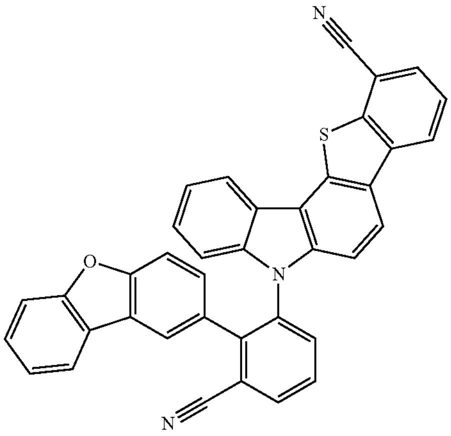
444
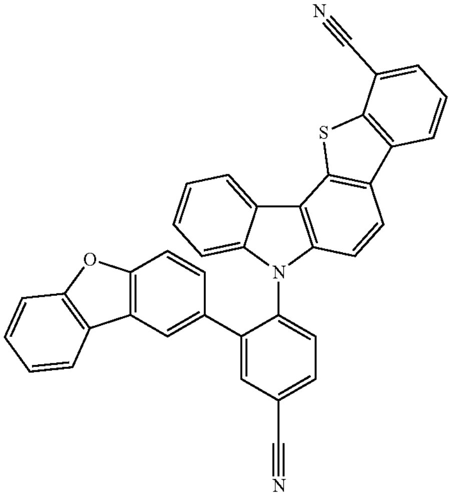
445
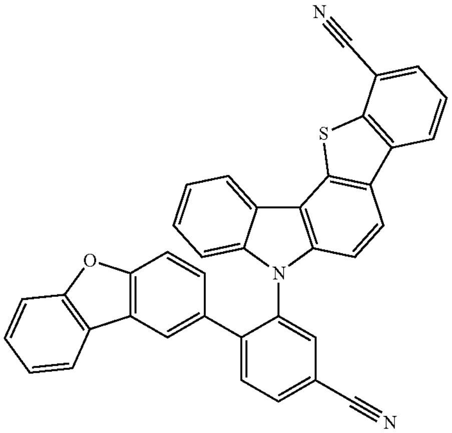
446
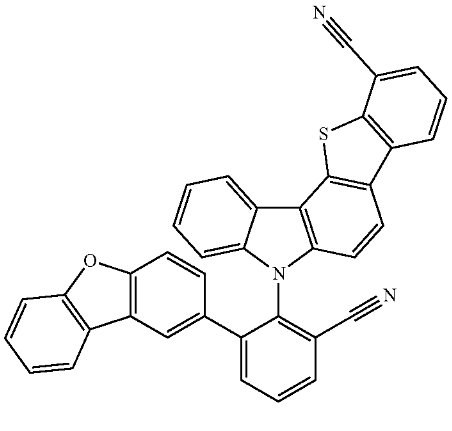

-continued
447
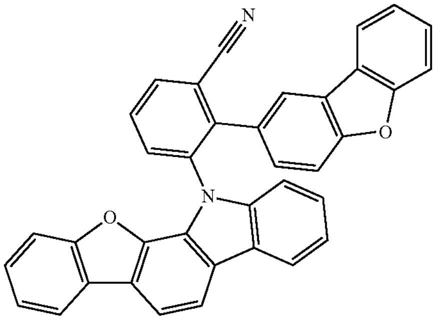
448
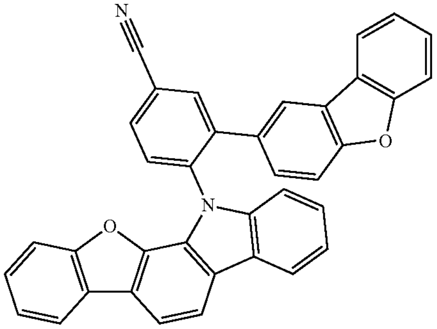
449
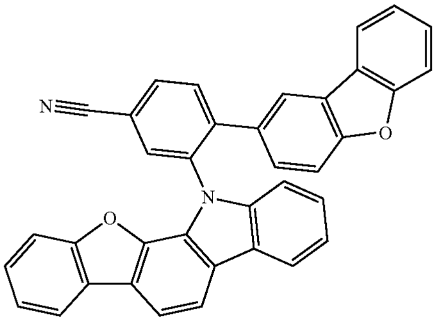
450
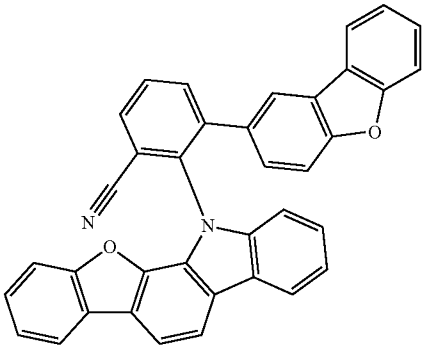
-continued
451
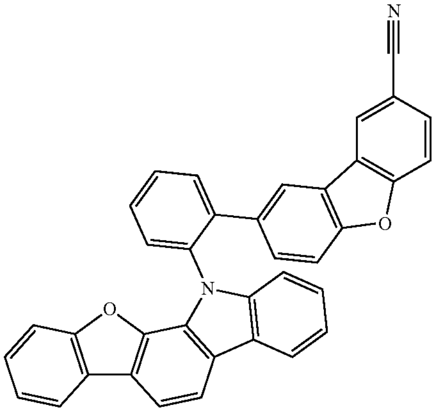
452
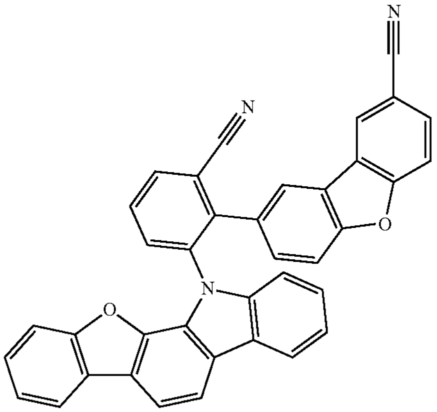
453
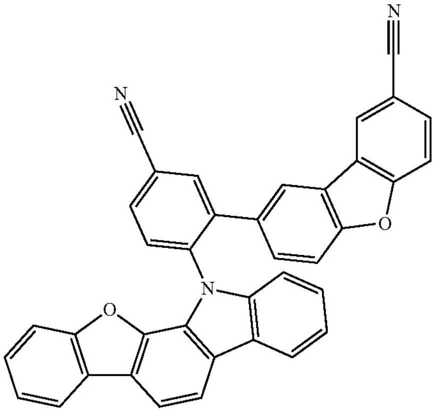
454
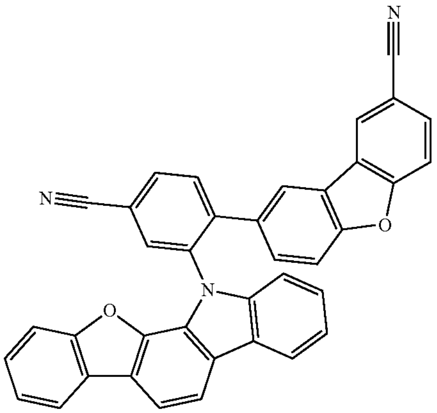

-continued
455
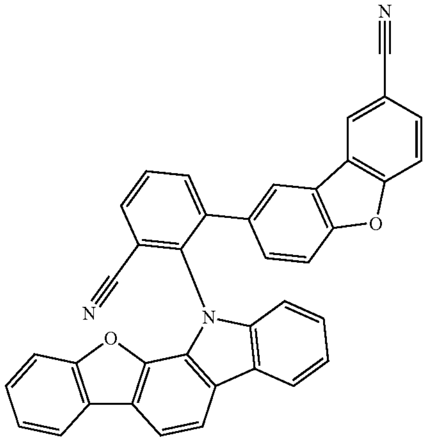
456
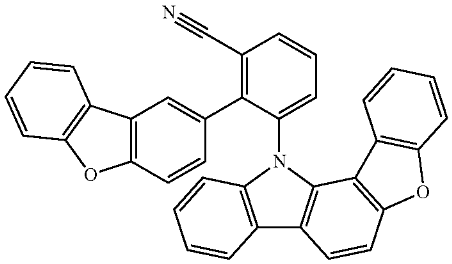
457
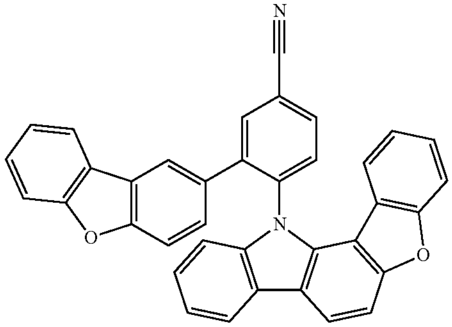
458
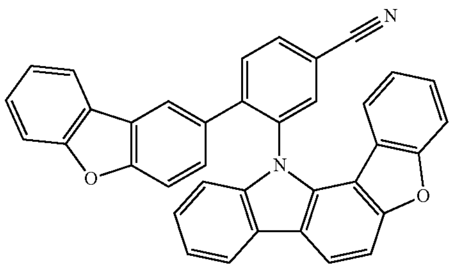
-continued
459
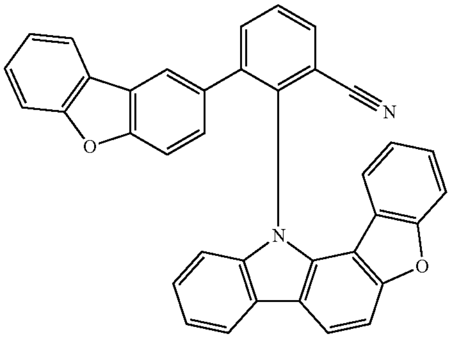
460
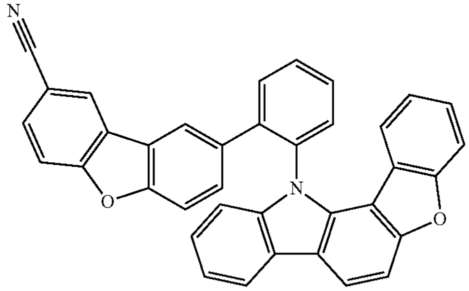
461
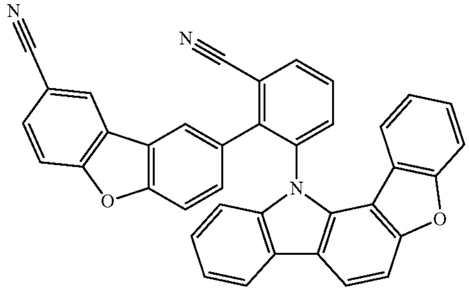
462
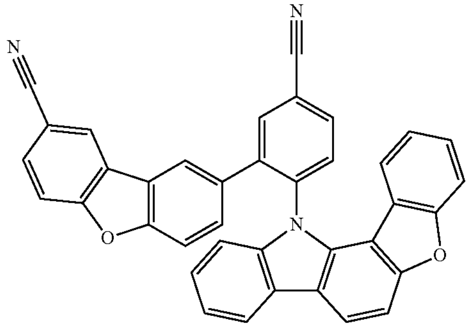
463
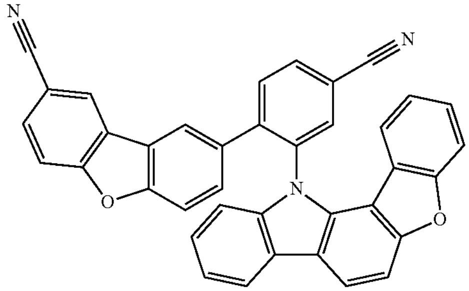

-continued
464
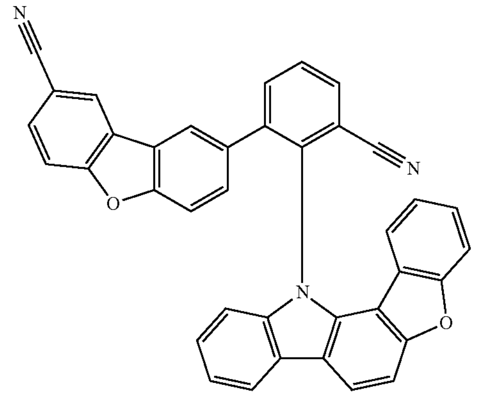
465
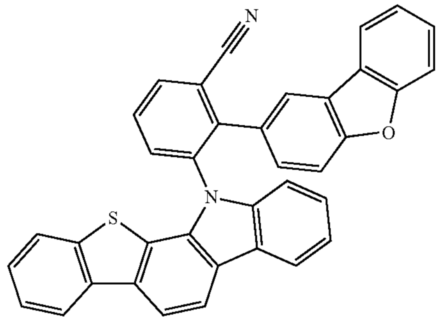
466
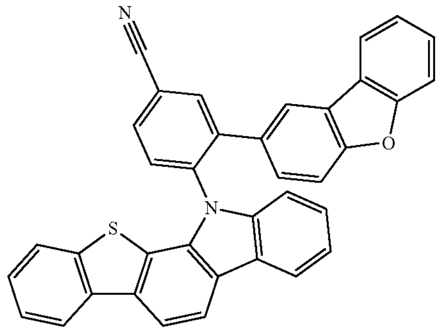
467
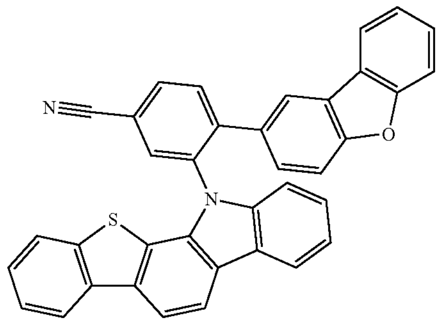
-continued
468
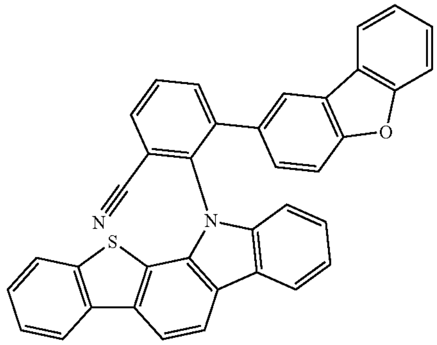
469
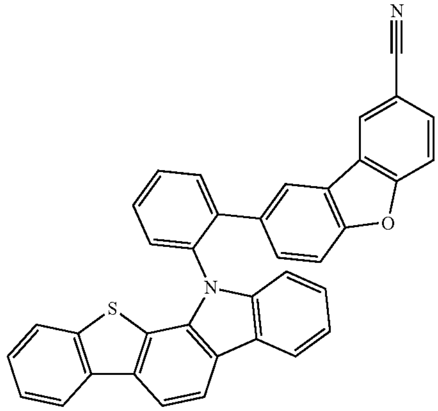
470
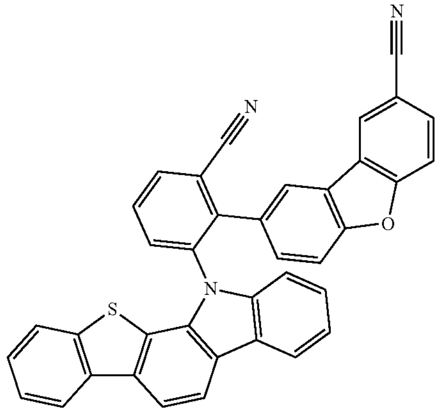
471
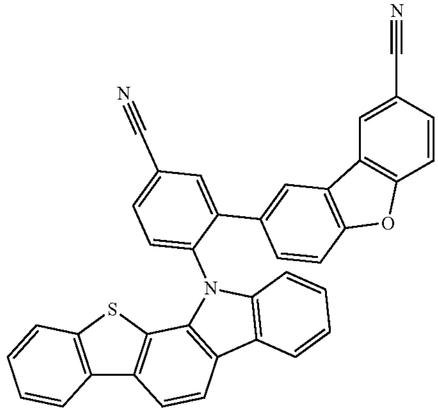

-continued
472
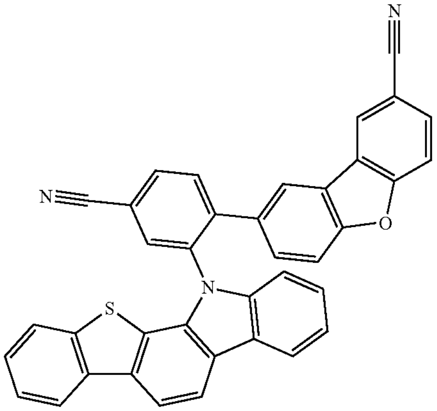
473
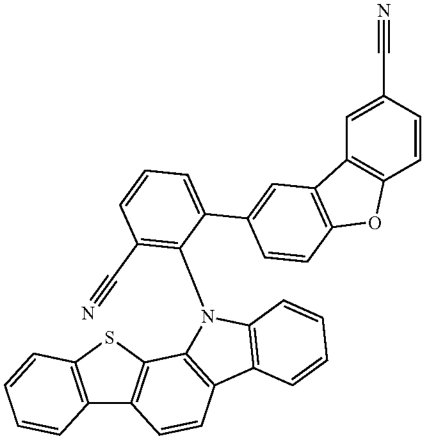
474
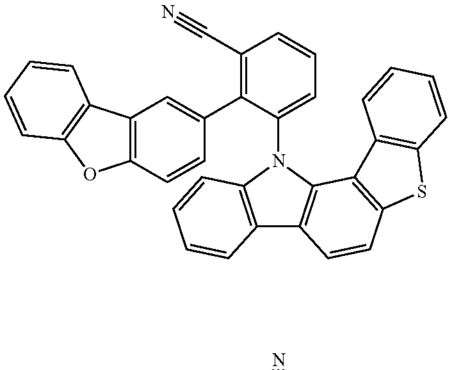
475
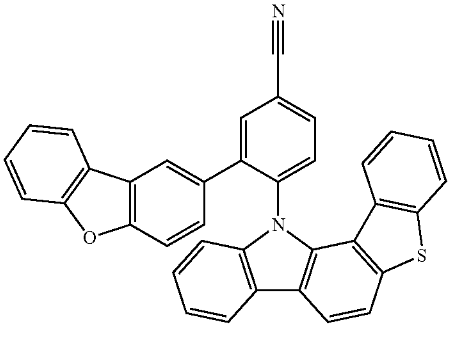
-continued
476
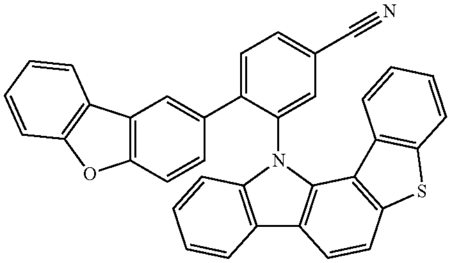
477
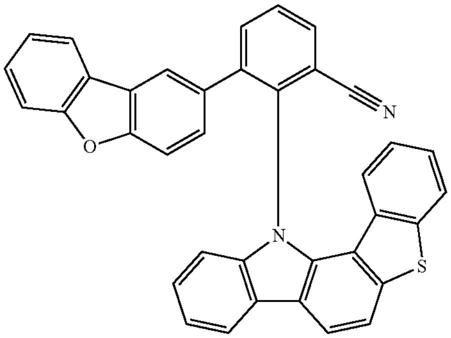
478
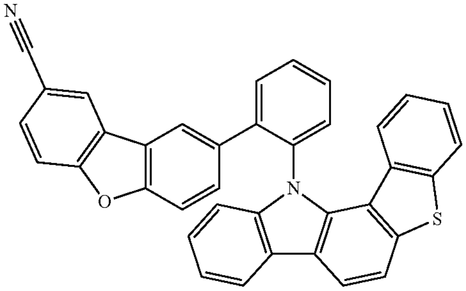
479
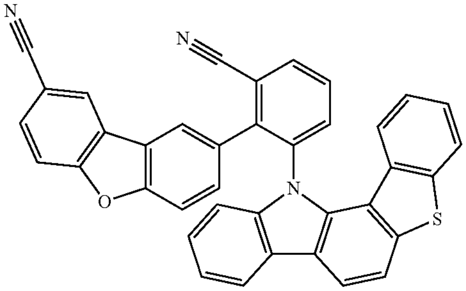
480
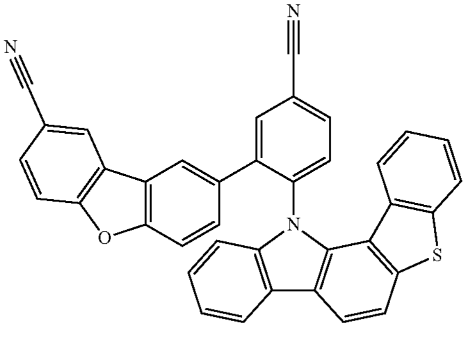

-continued
481
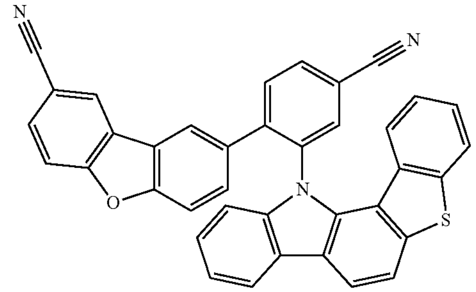
482
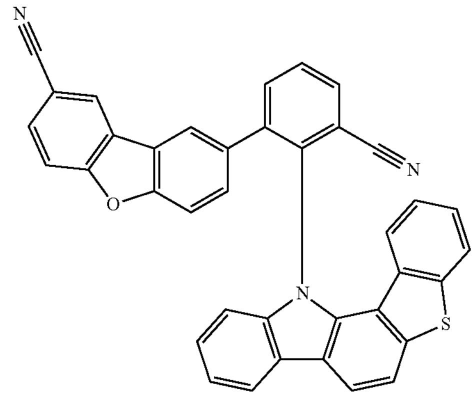
Group HE4
1
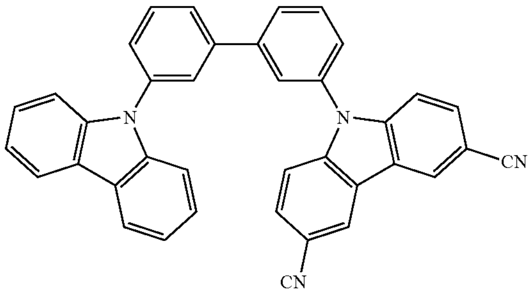
2
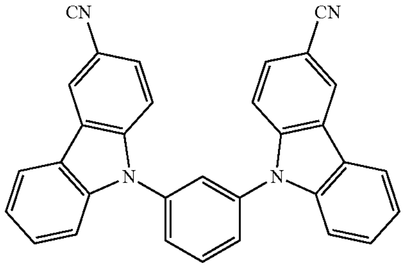
-continued
3
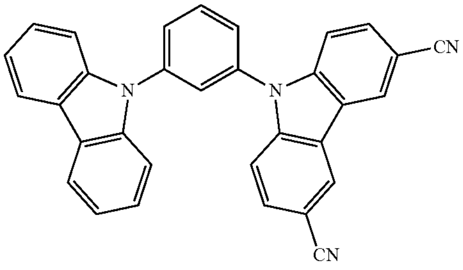
4
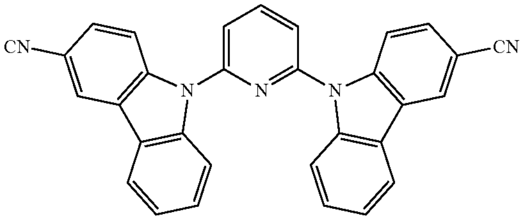
5
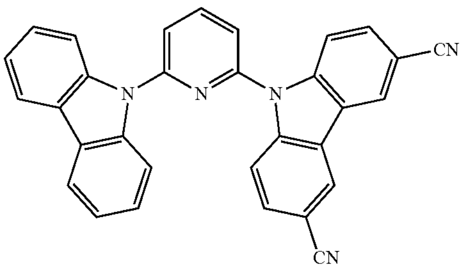
6
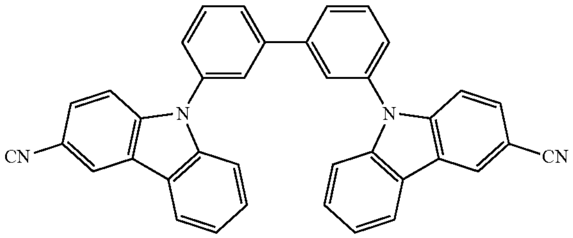
7
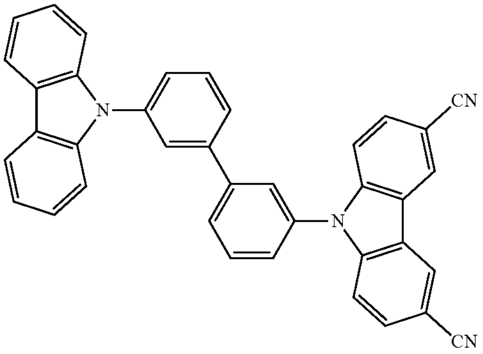

-continued
8
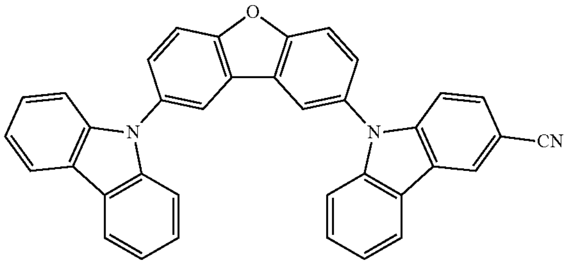
9
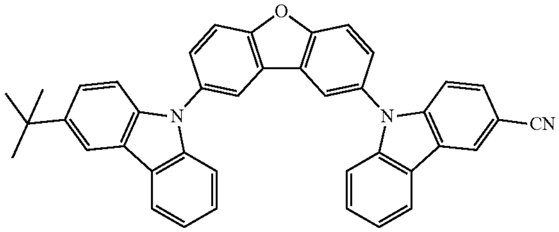
10
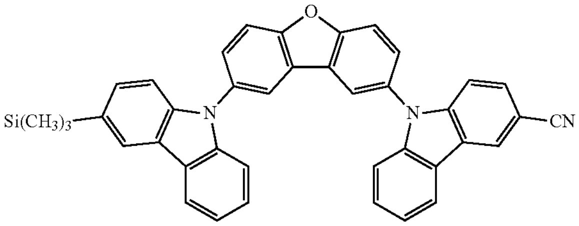
11
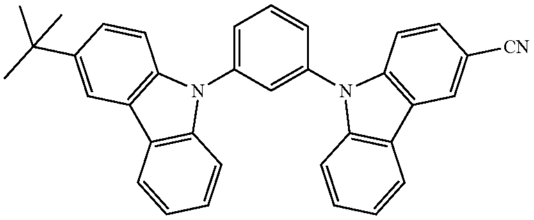
12
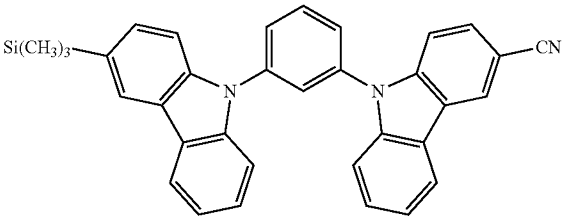
13
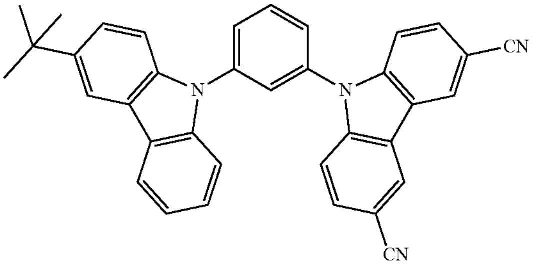
-continued
14
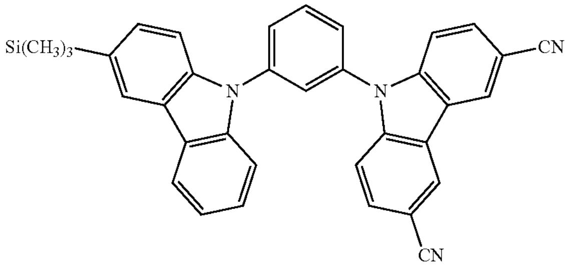
15
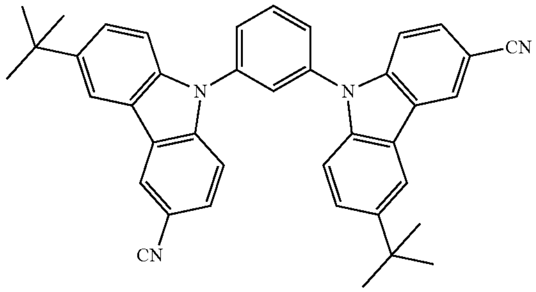
16
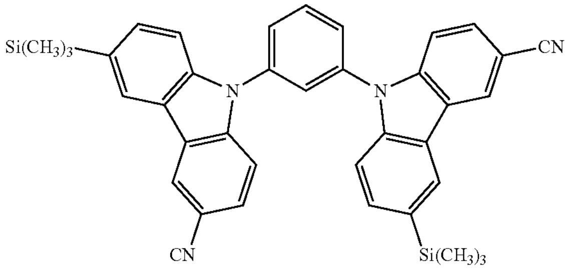
17
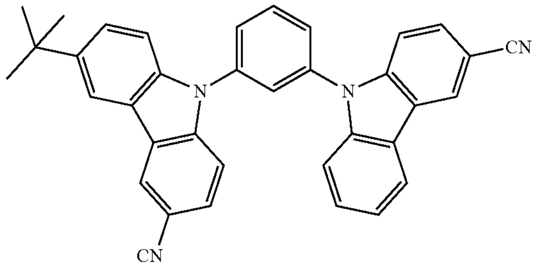
18
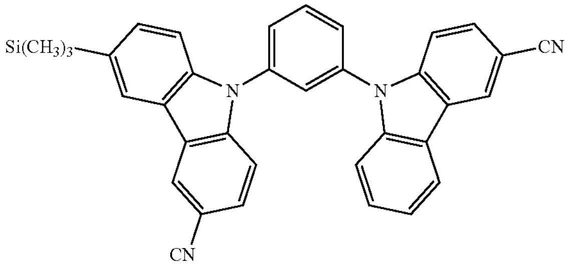

-continued
19
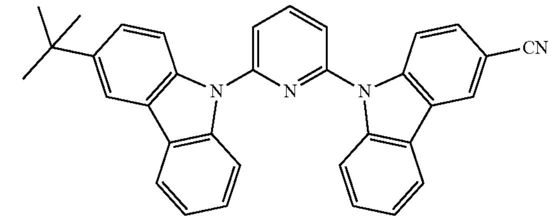
20
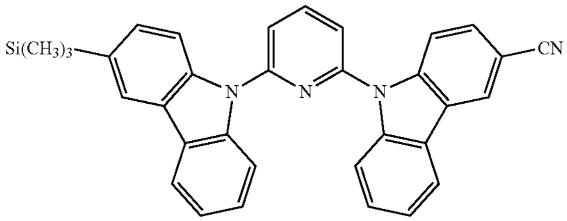
21
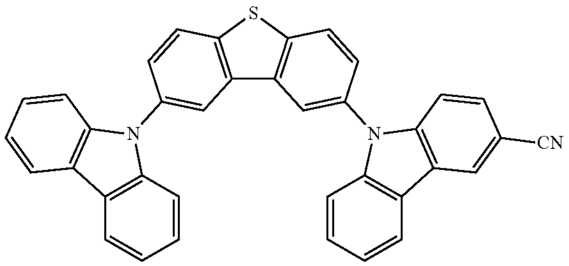
22
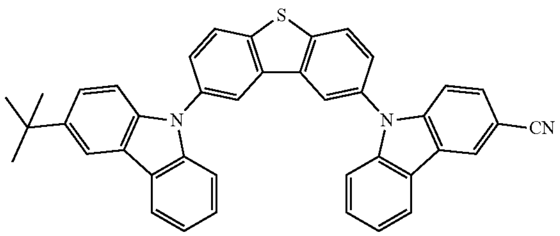
23
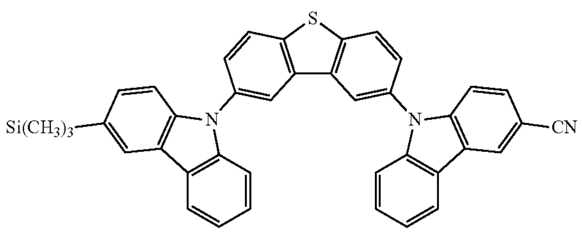
24
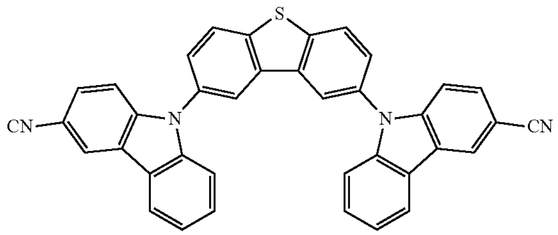
-continued
25
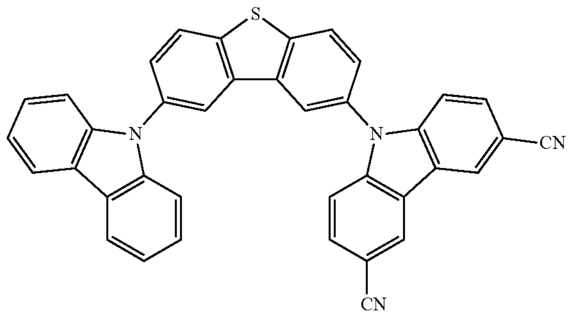
26
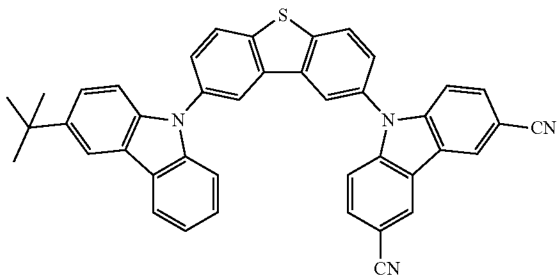
27
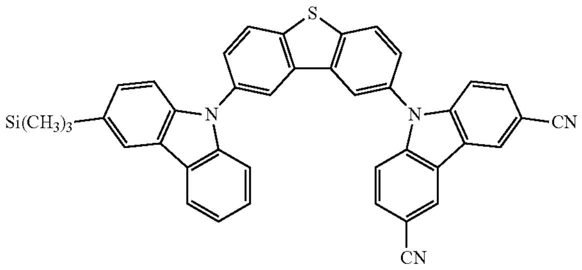
28
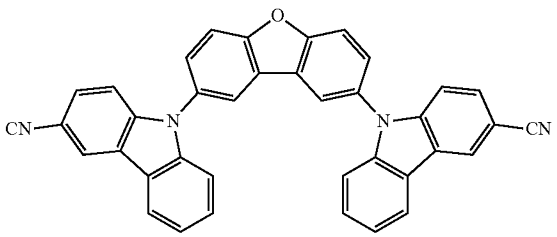
29
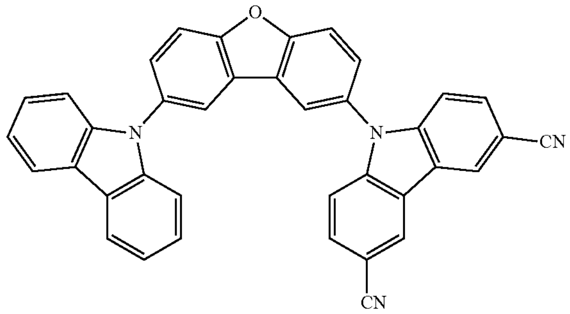

-continued
30
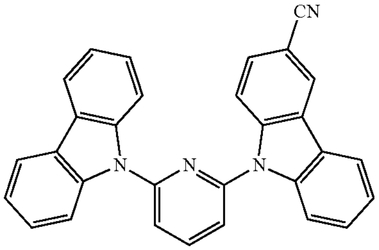
31
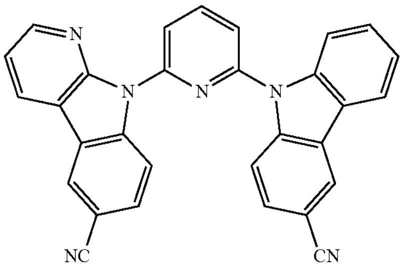
32
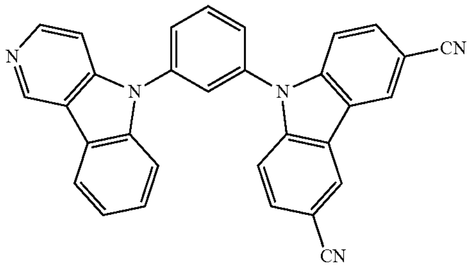
33
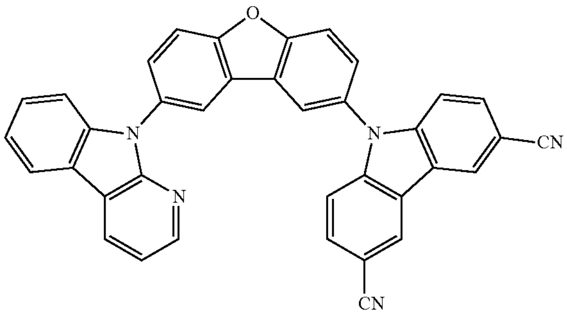
34
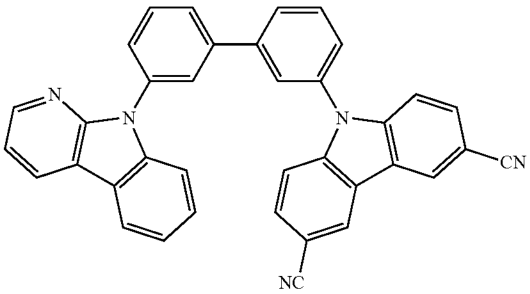
-continued
35
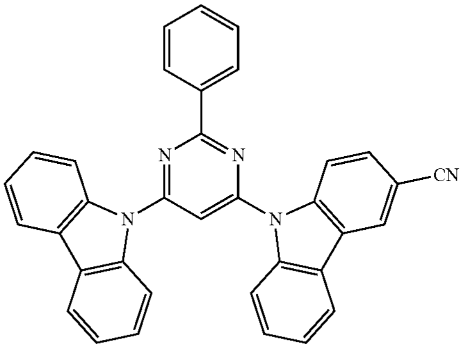
36
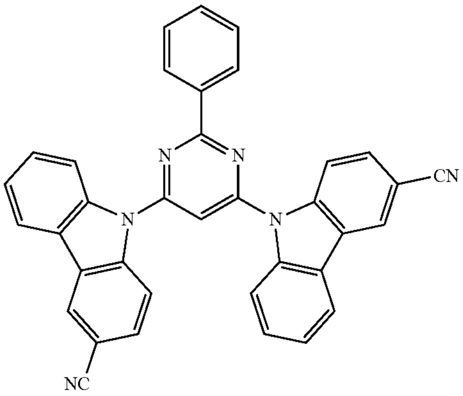
37
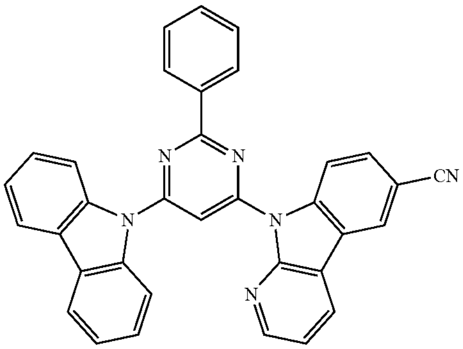
38
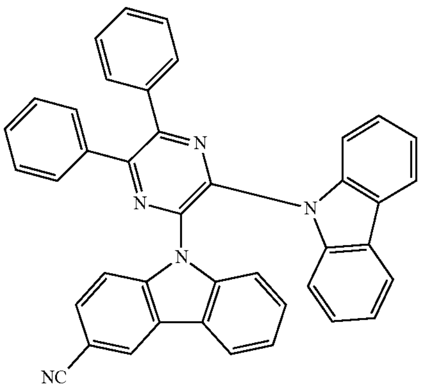

-continued
39
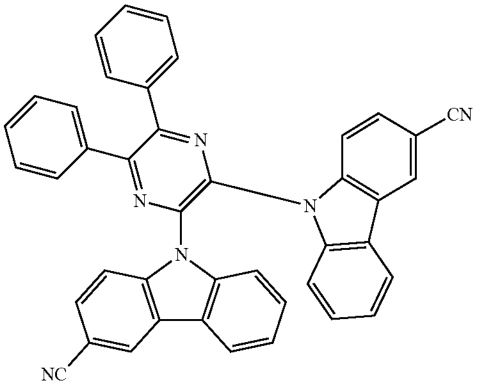
40
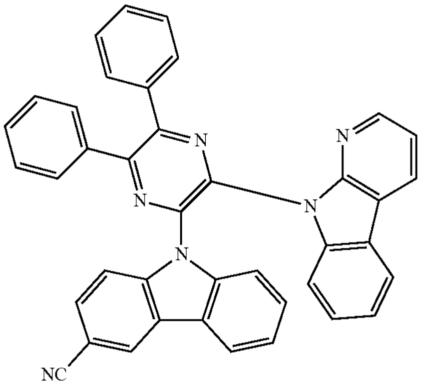
41
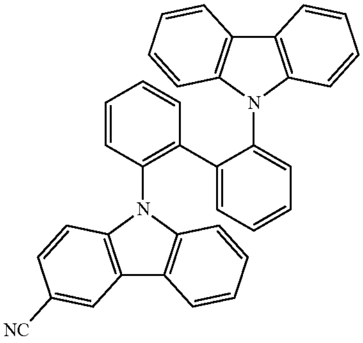
42
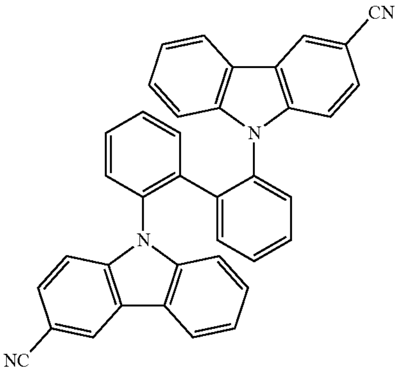
-continued
43
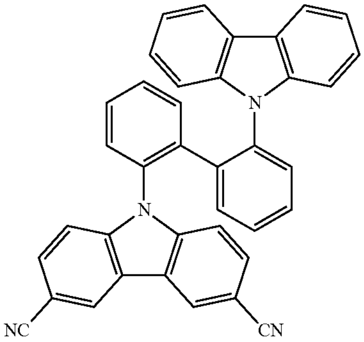
44
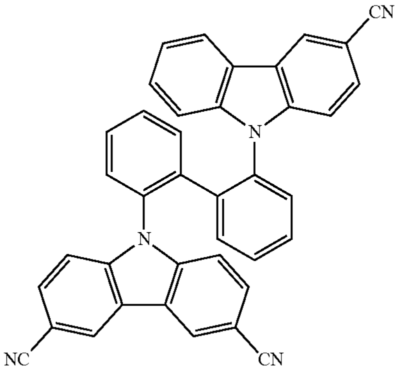
45
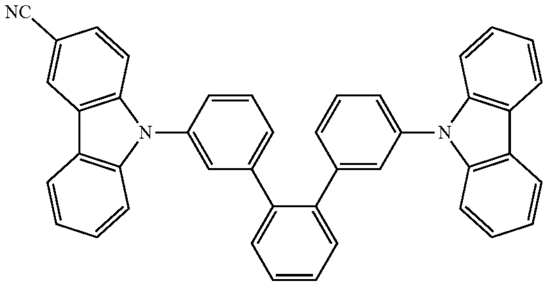
46
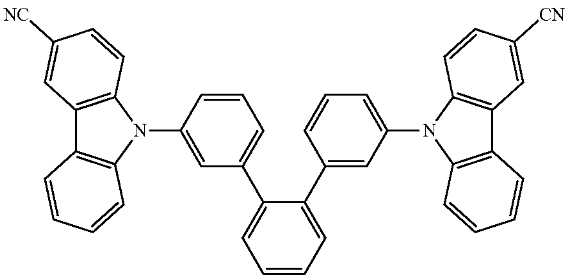
47
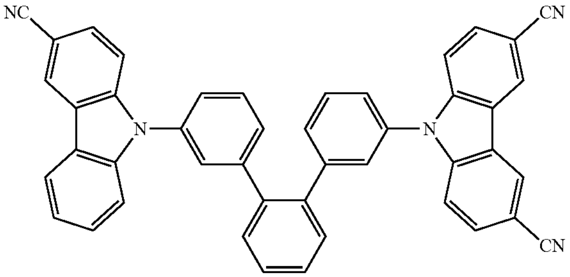

-continued
48
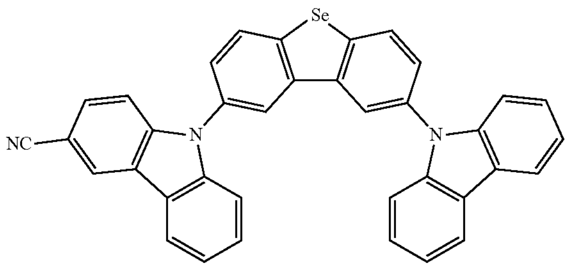
49
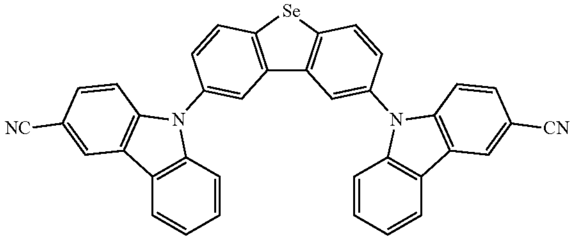
50
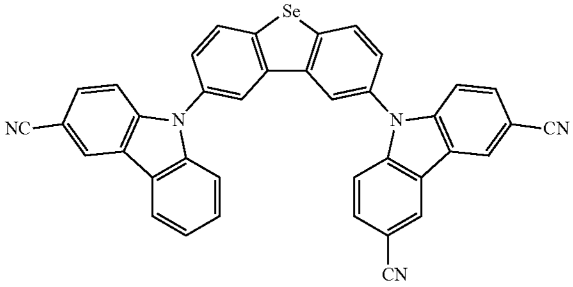
51
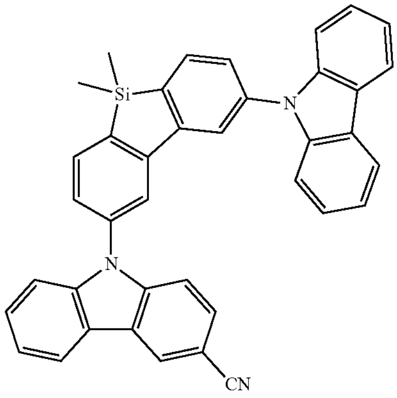
-continued
52
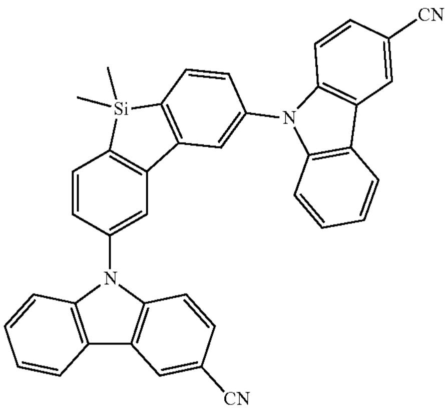
53
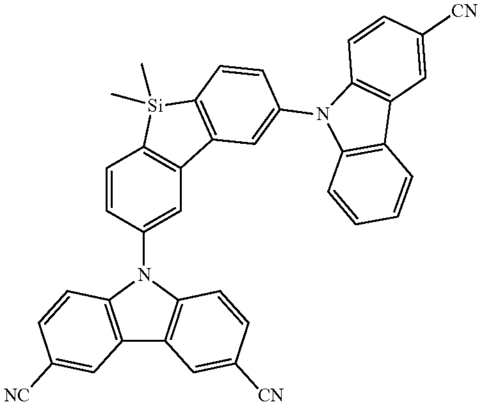
54
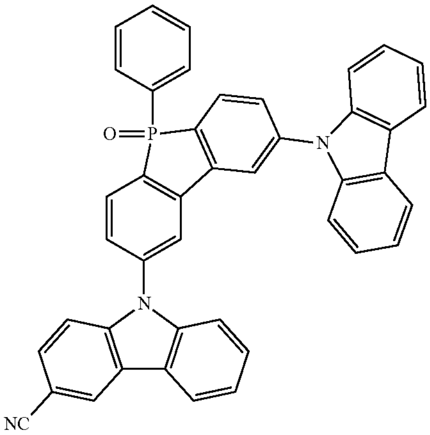

-continued
55
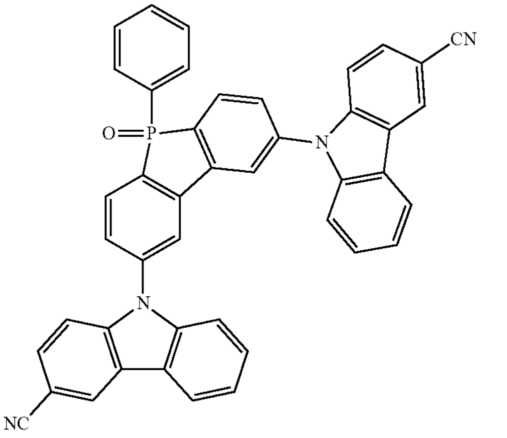
56
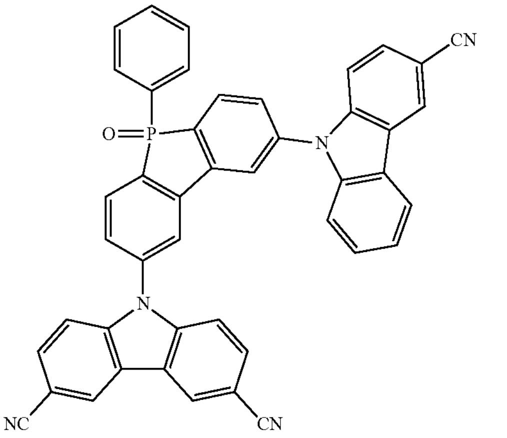
Group HE5
1
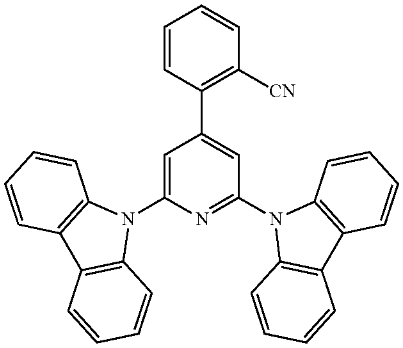
-continued
1
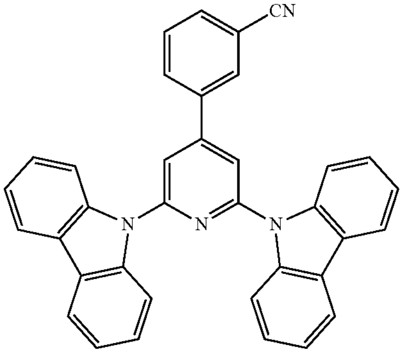
2
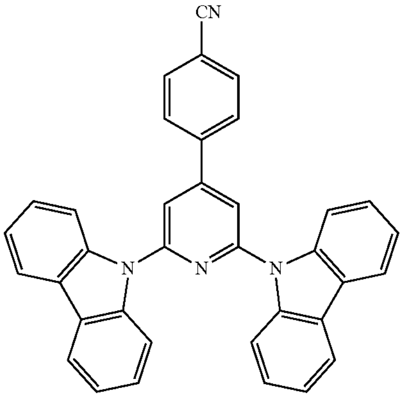
3
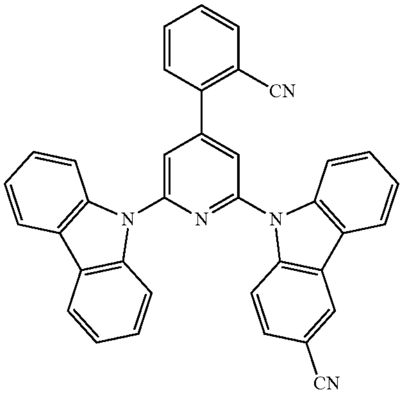
5
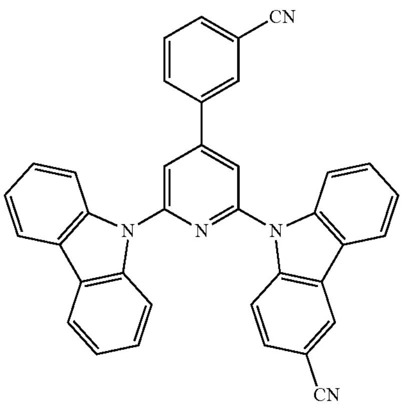

-continued
6
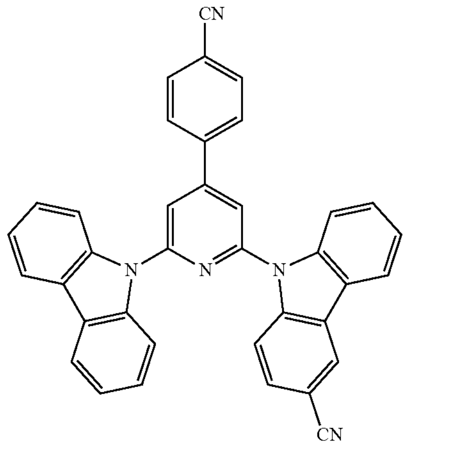
7
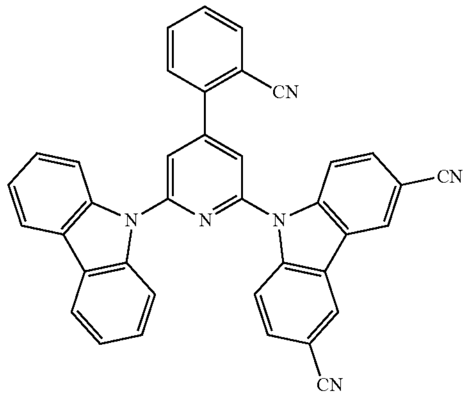
8
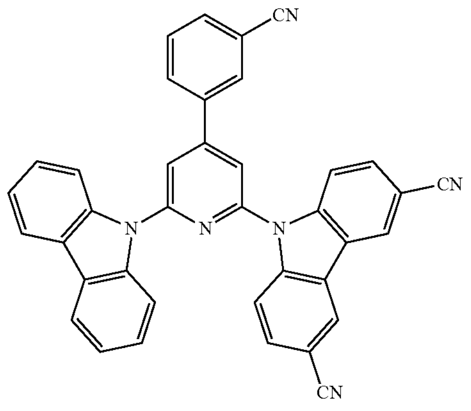
-continued
9
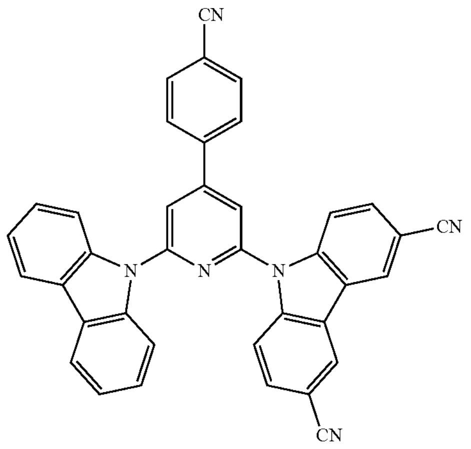
10
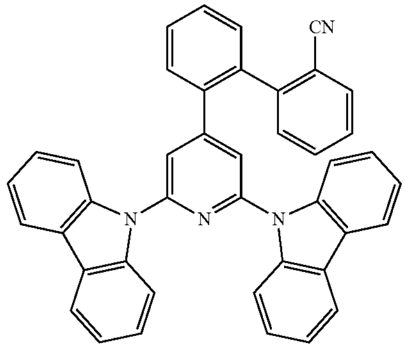
11
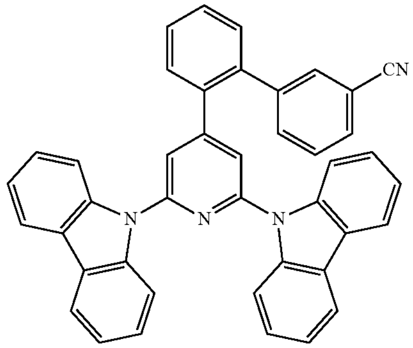
12
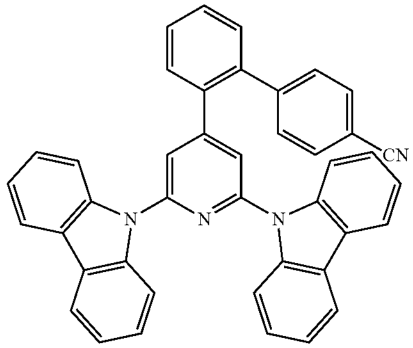

-continued
13
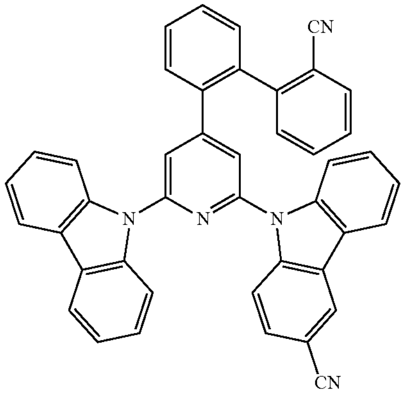
14
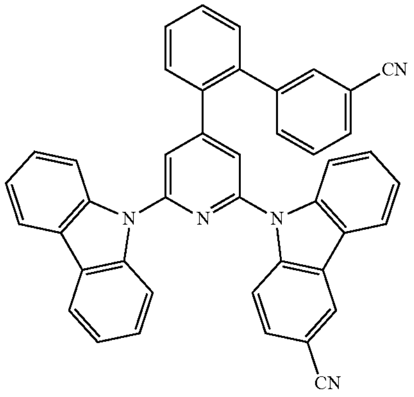
15
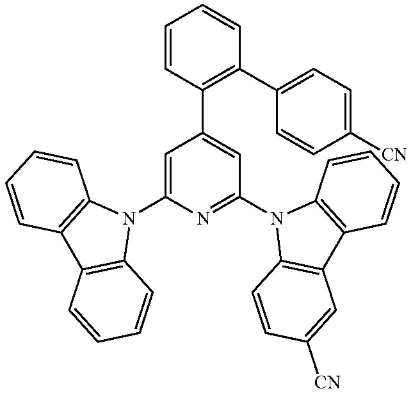
16
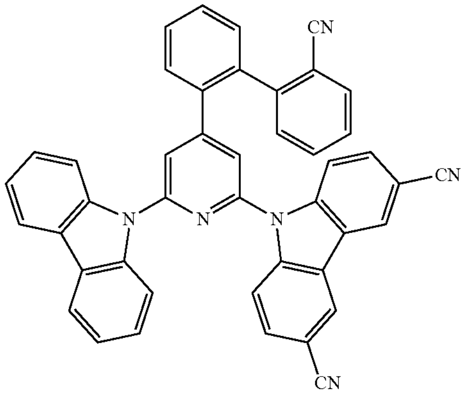
-continued
17
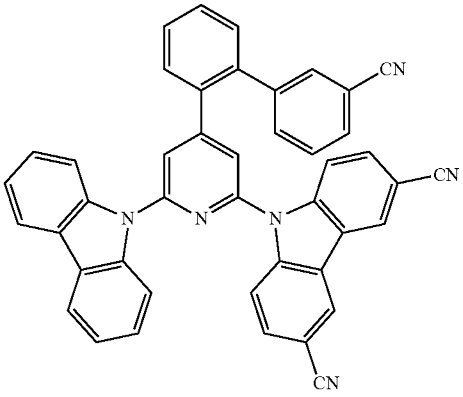
18
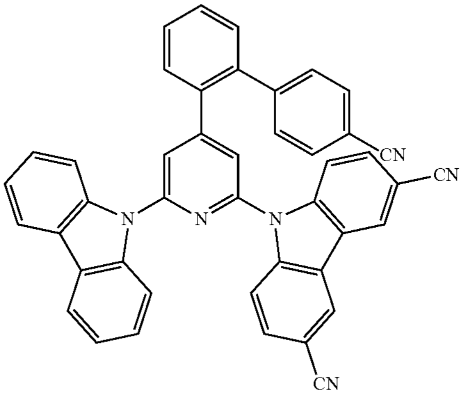
19
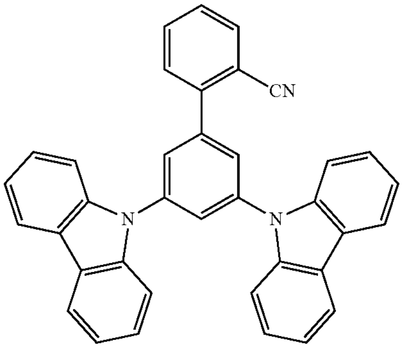
20
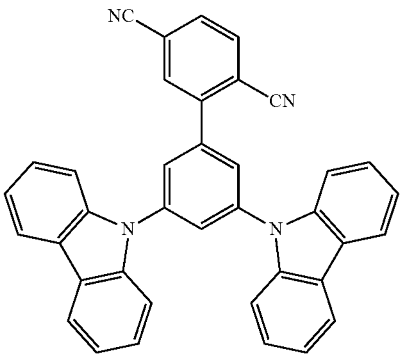

-continued
21
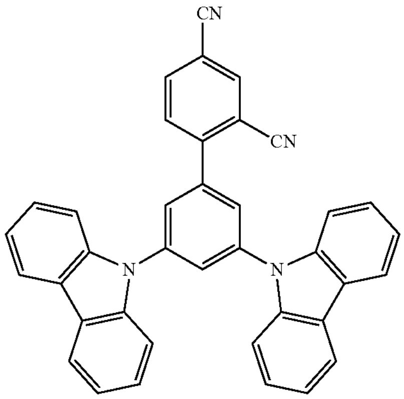
22
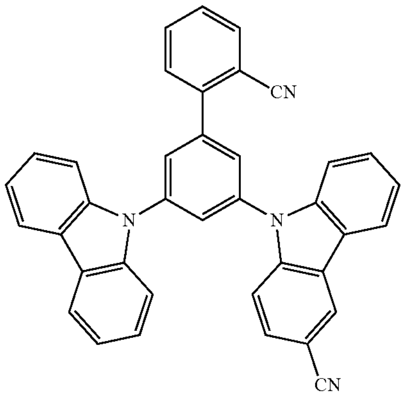
23
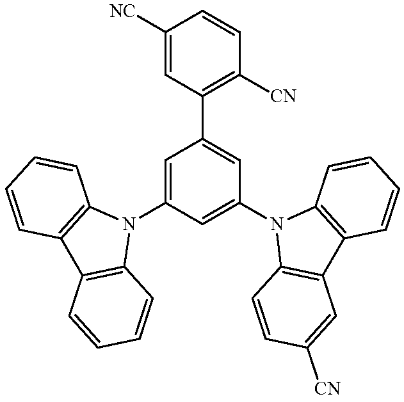
24
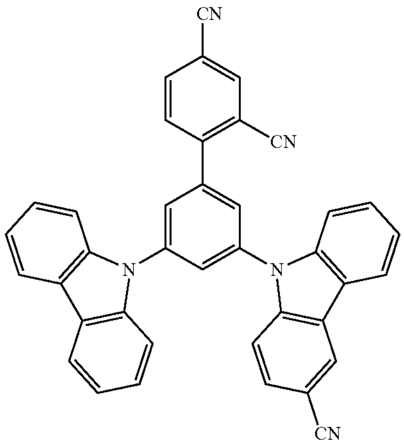
-continued
25
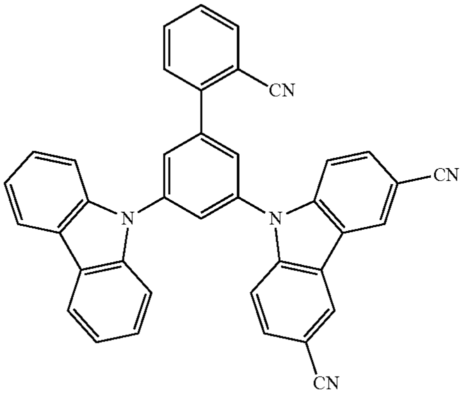
26
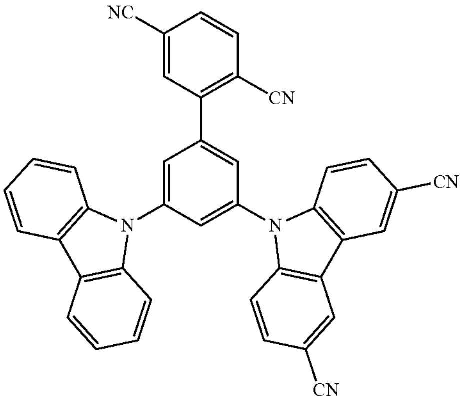
27
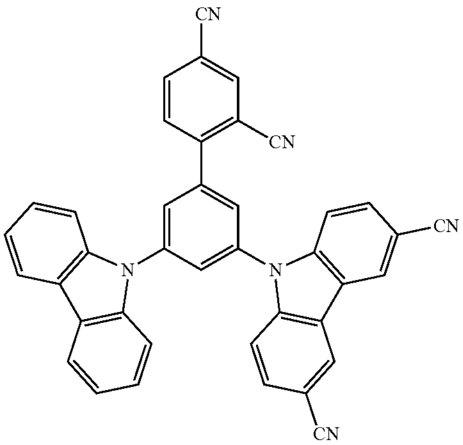
28
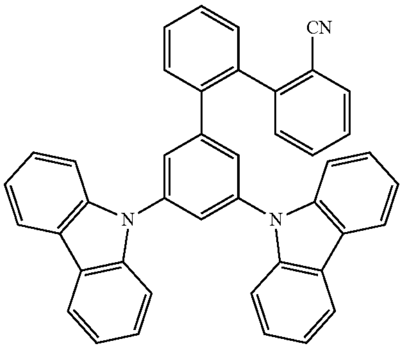

29
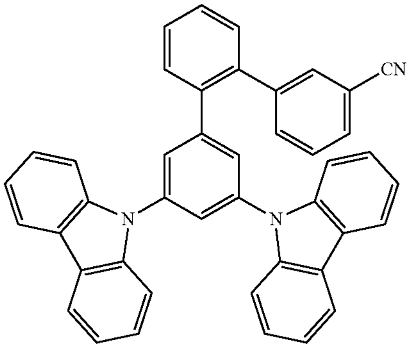
30
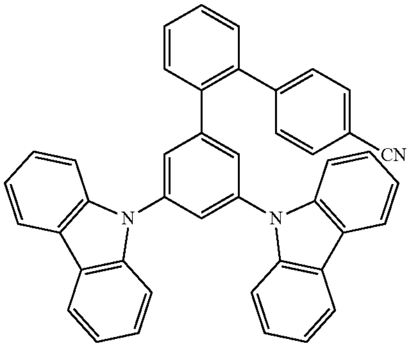
31
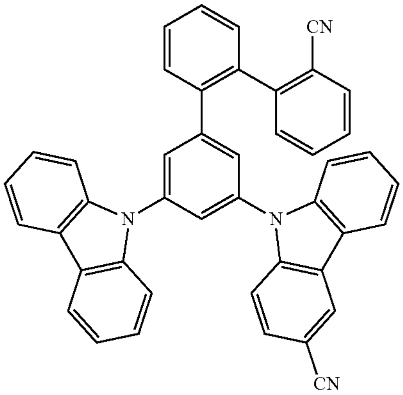
32
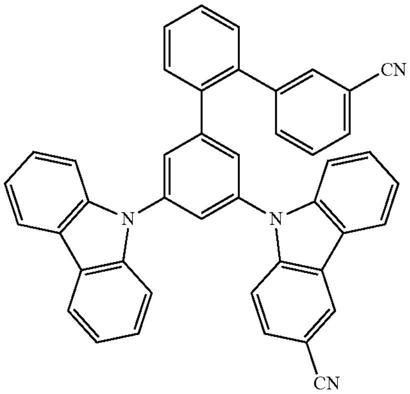
33
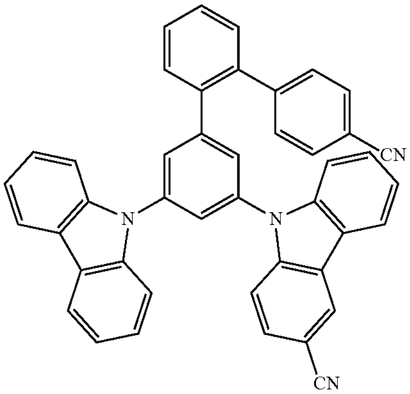
34
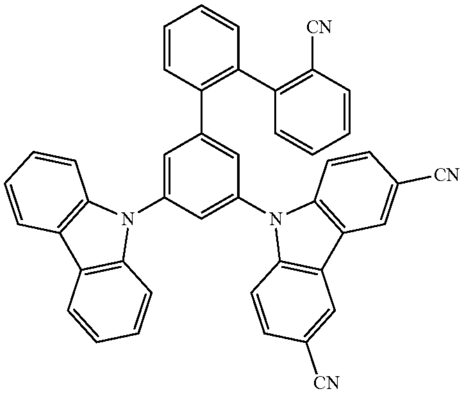
35
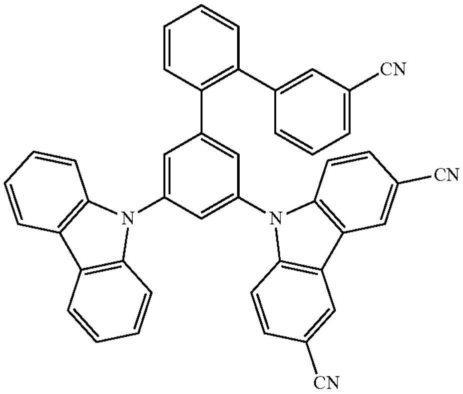
36
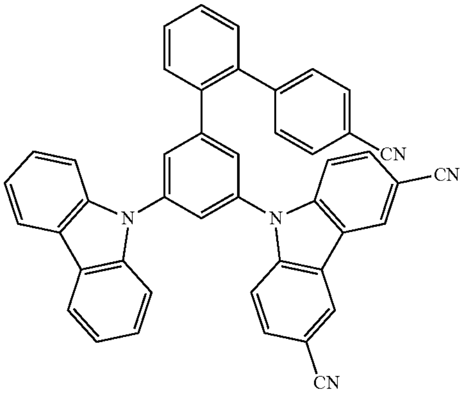

-continued
37
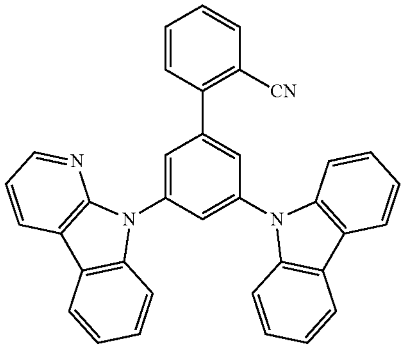
38
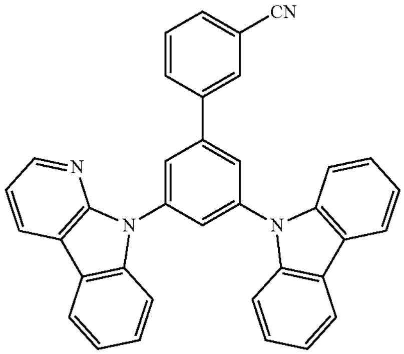
39
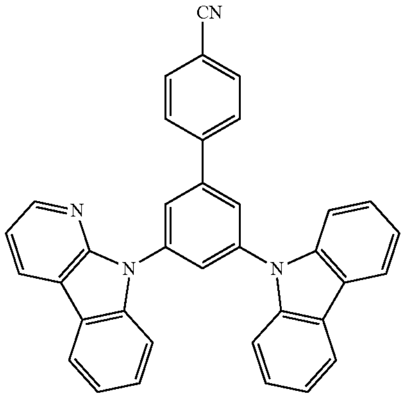
40
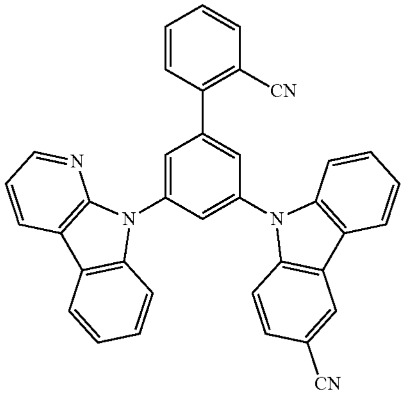
-continued
41
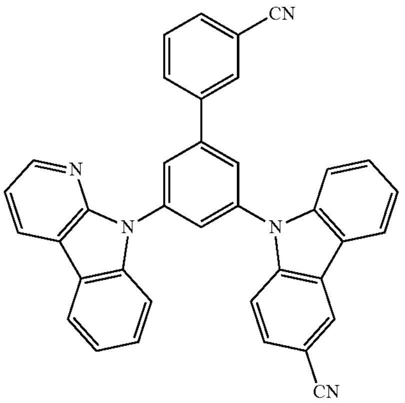
42
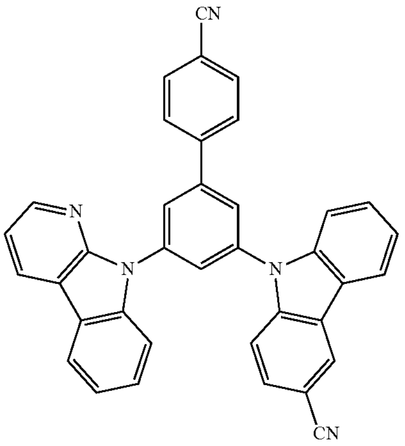
43
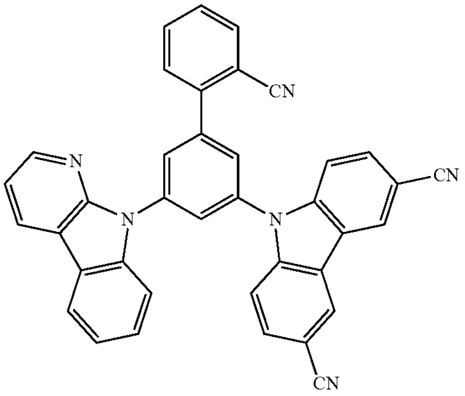
44
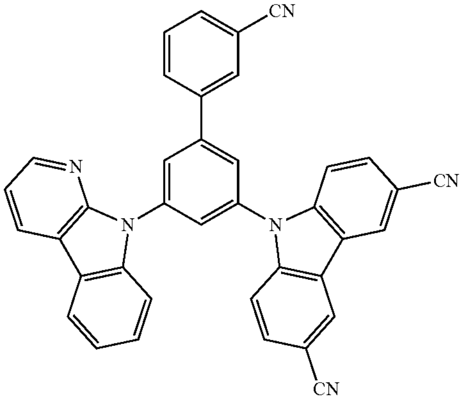

-continued
45
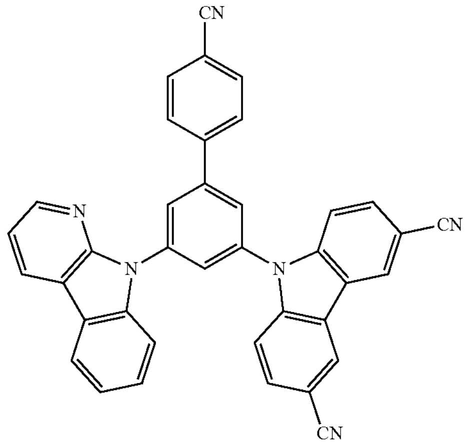
46
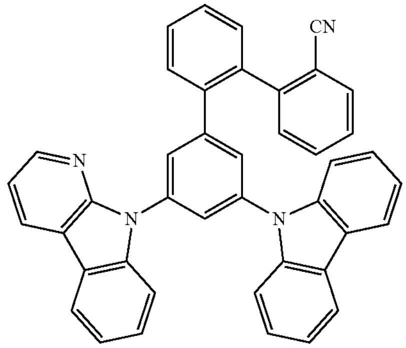
47
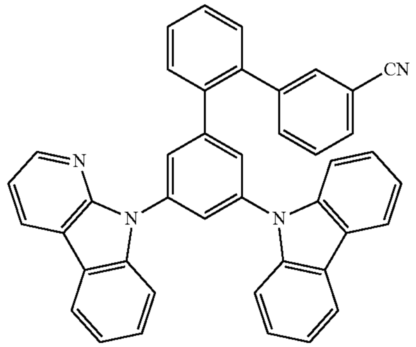
48
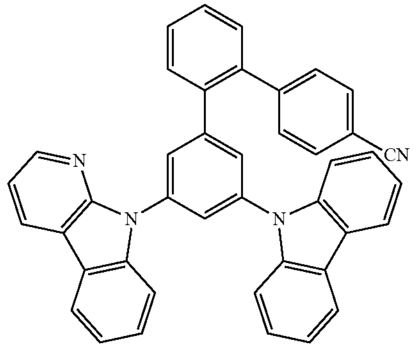
-continued
49
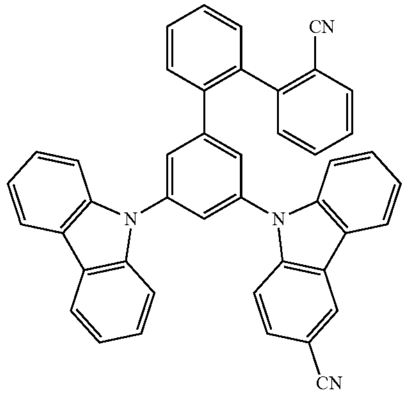
50
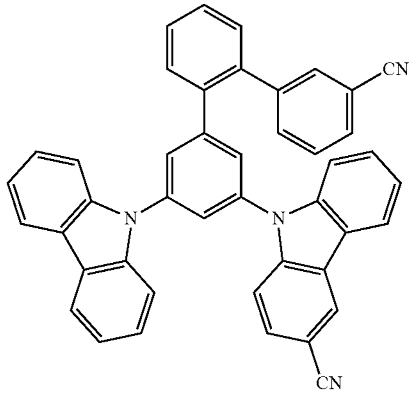
51
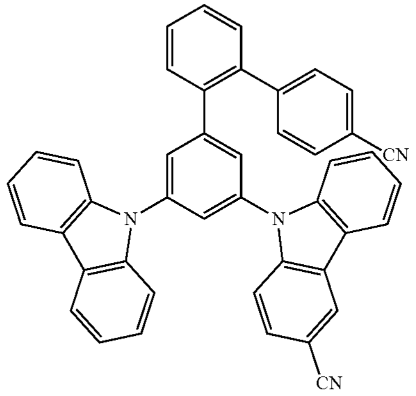
52
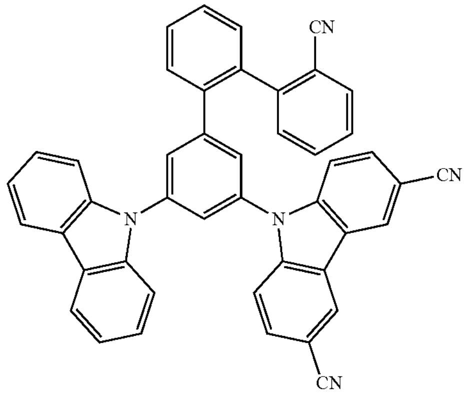

-continued
53
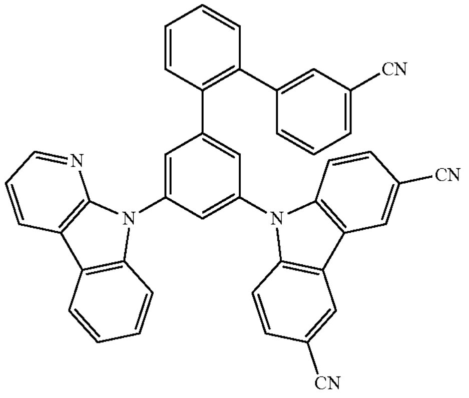
54
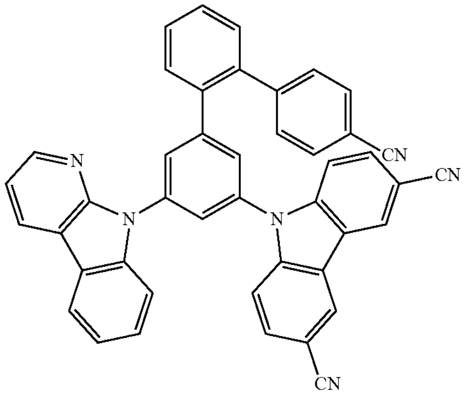
55
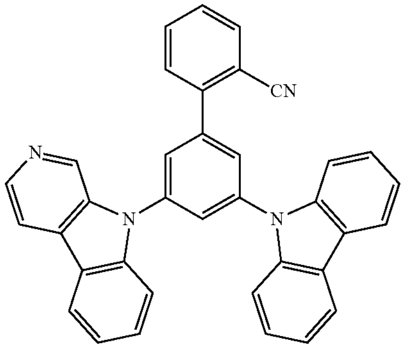
56
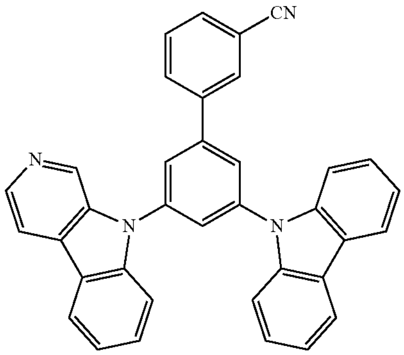
-continued
57
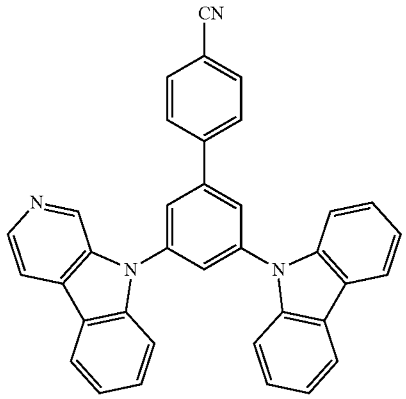
58
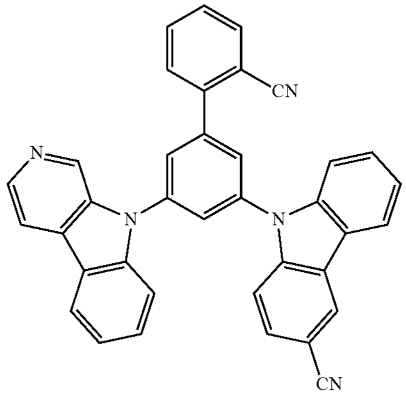
59
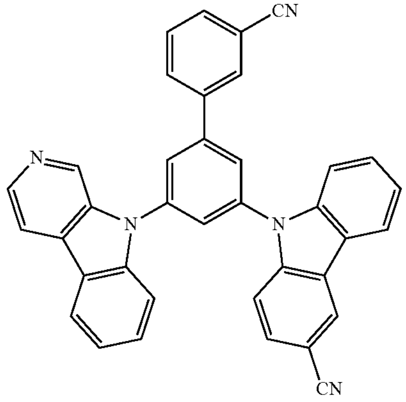
60
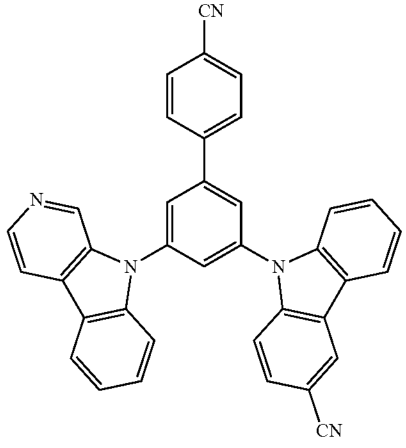

-continued
61
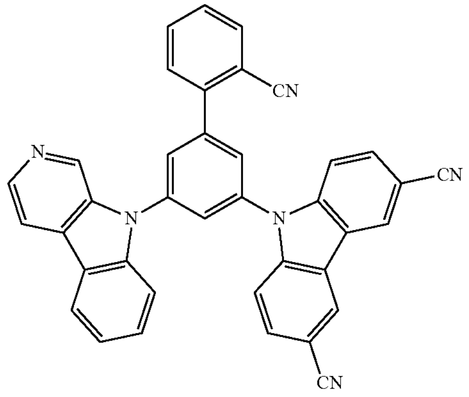
62
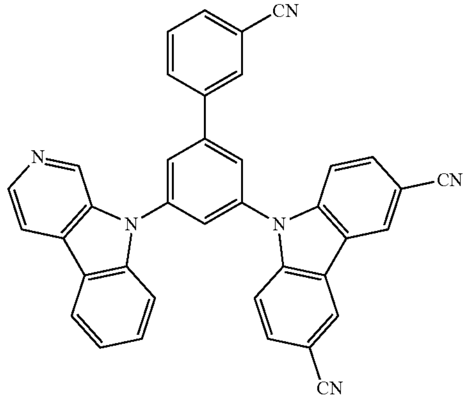
63
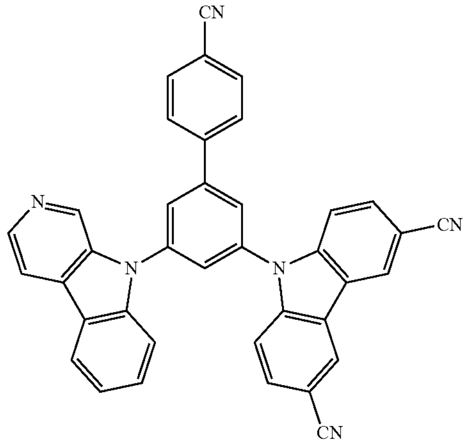
64
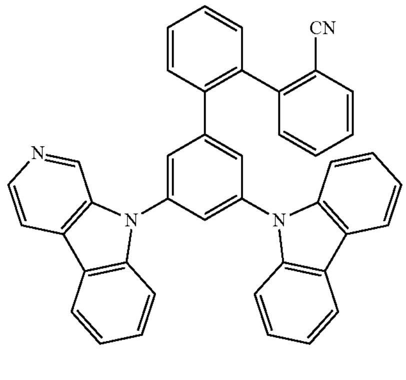
-continued
65
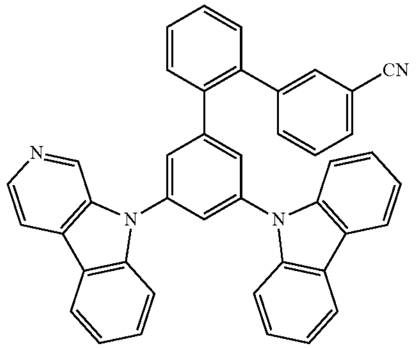
66
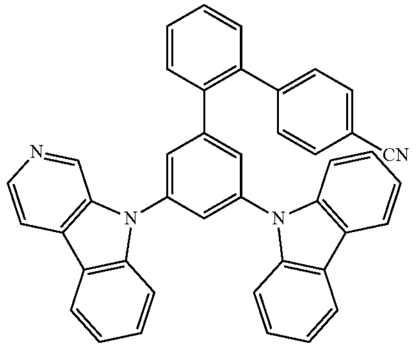
67
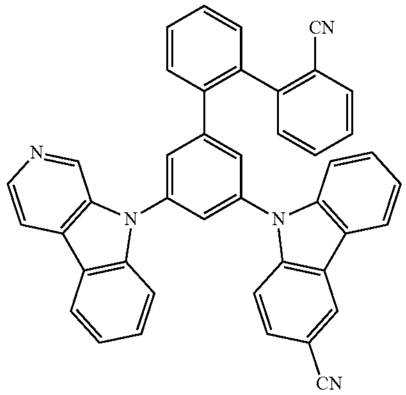
68
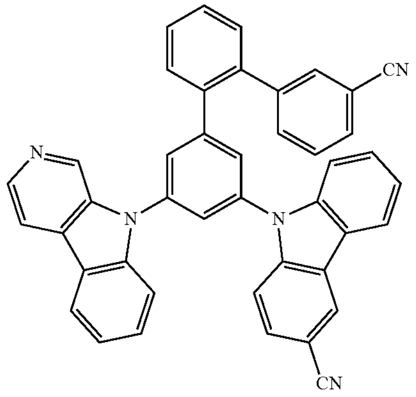

-continued
69
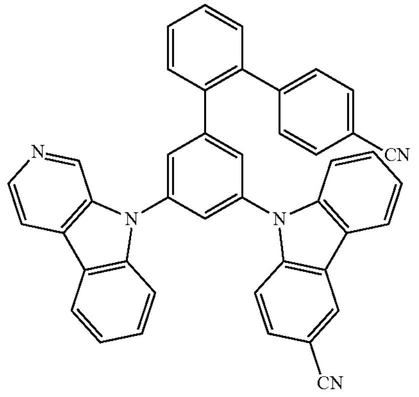
70
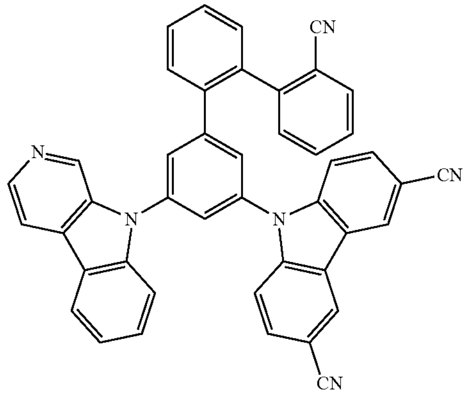
71
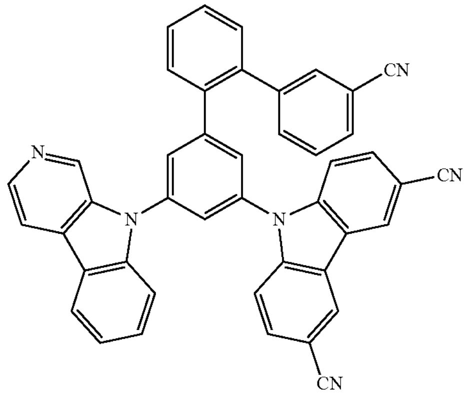
72
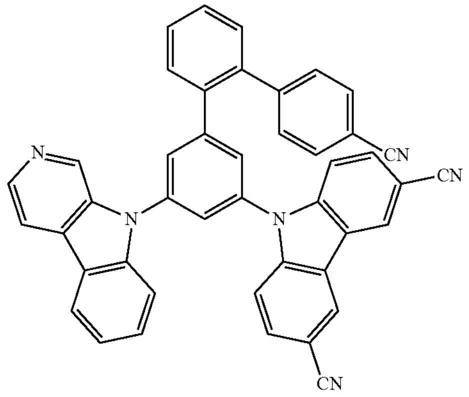
-continued
73
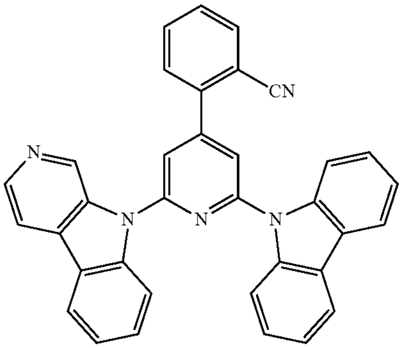
74
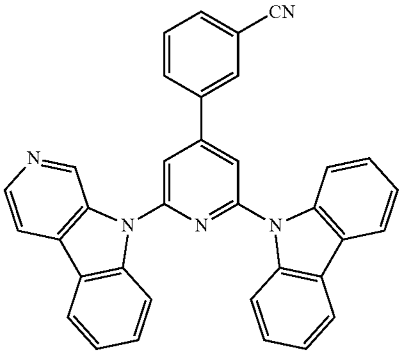
75
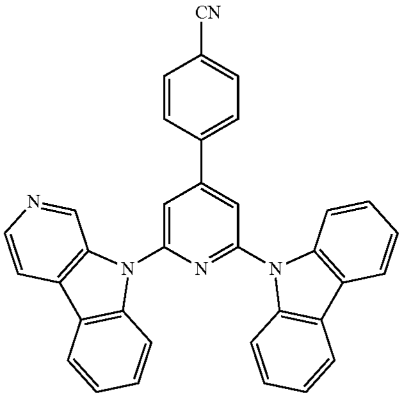
76
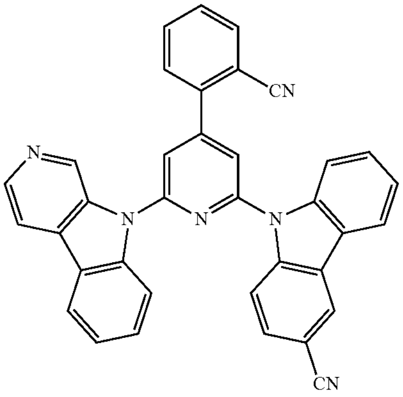

77
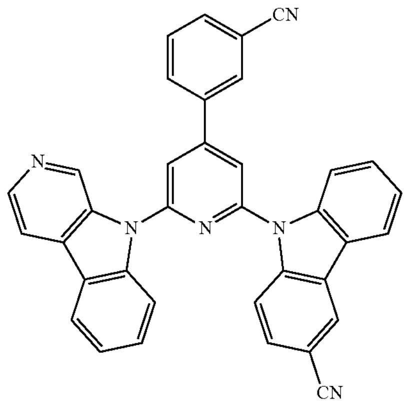
78
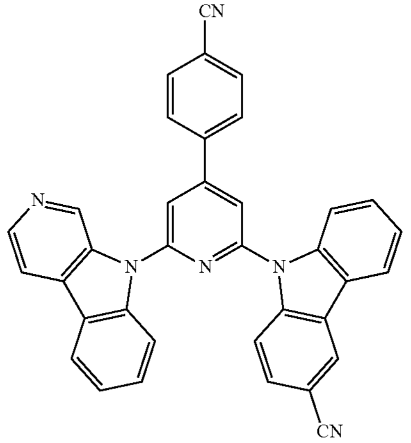
79
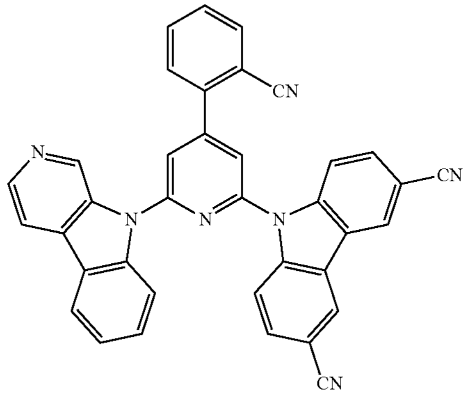
80
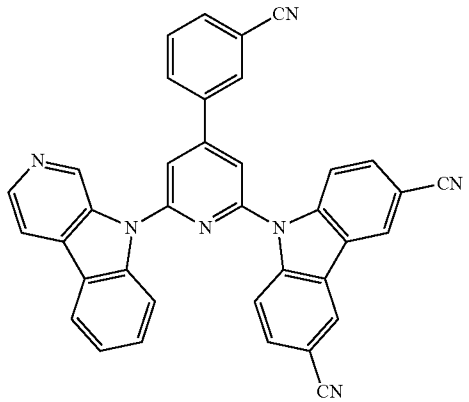
81
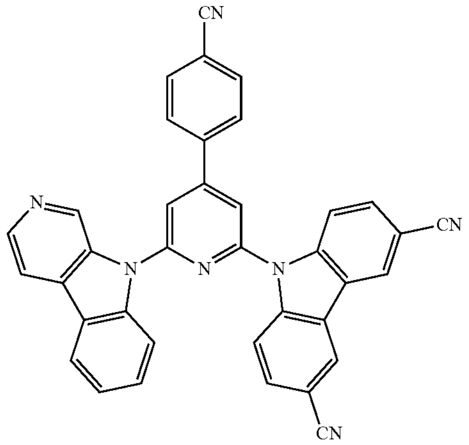
82
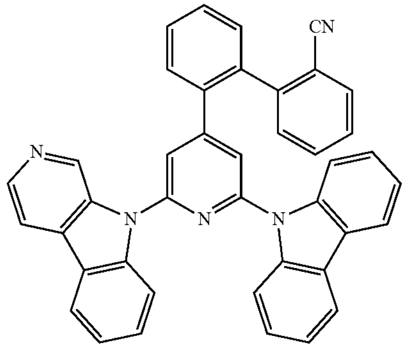
83
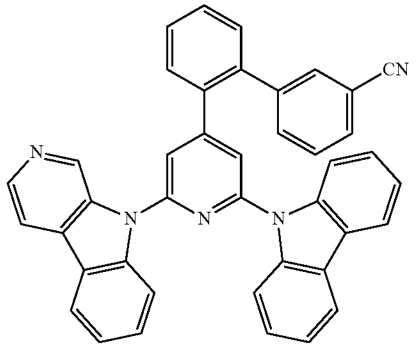
84
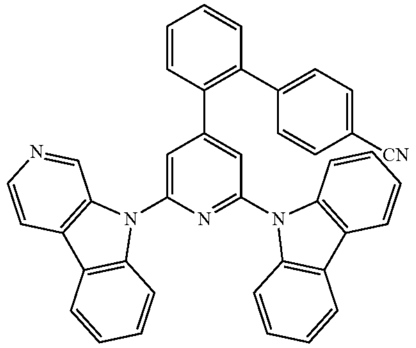

-continued
85
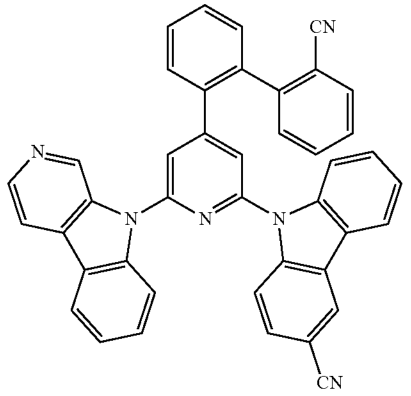
86
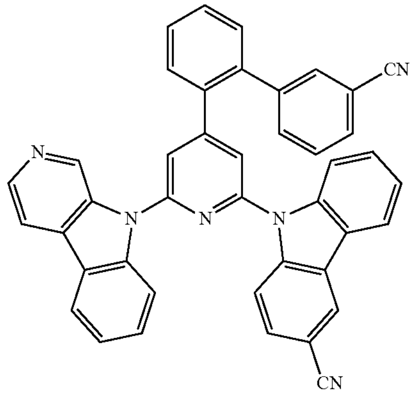
87
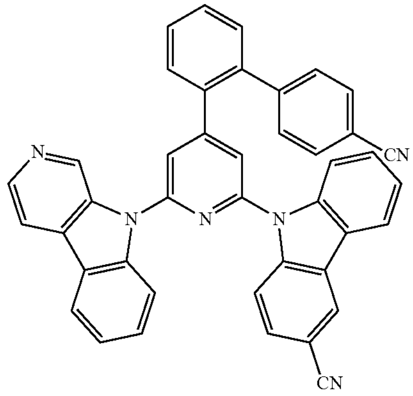
88
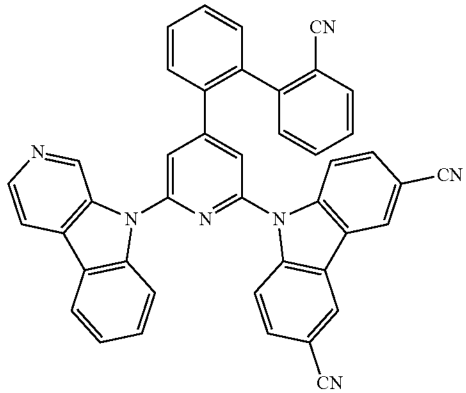
-continued
89
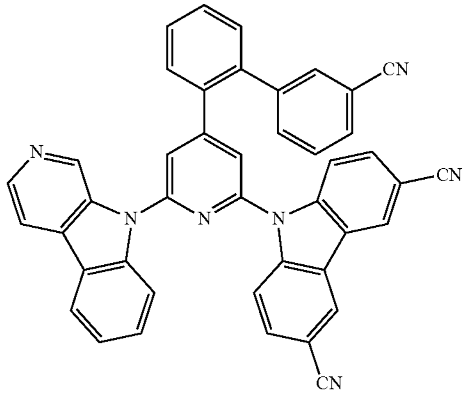
90
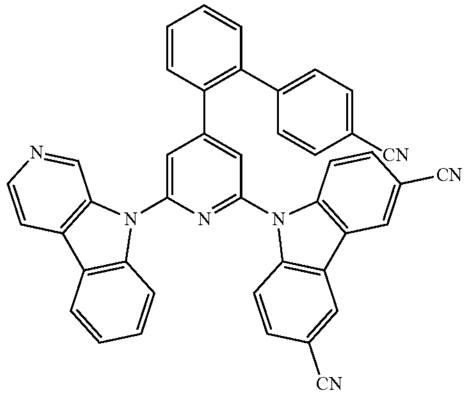
91
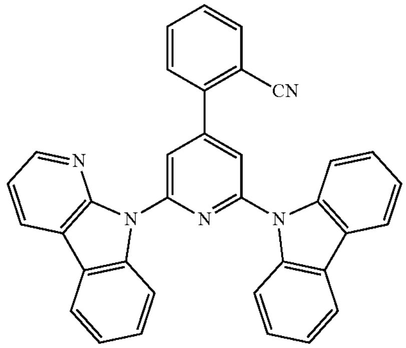
92
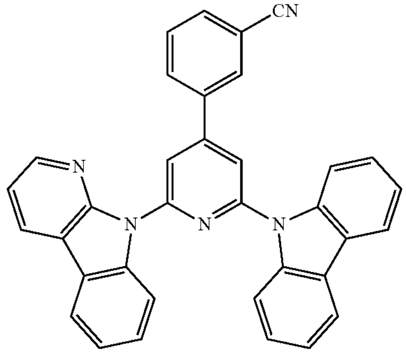

-continued
93
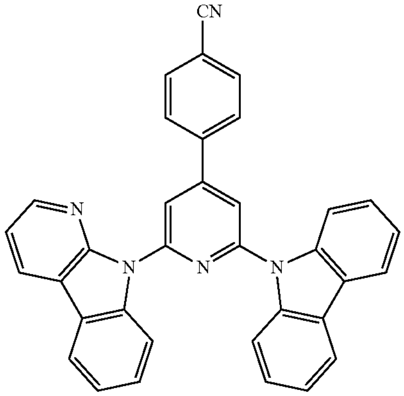
94
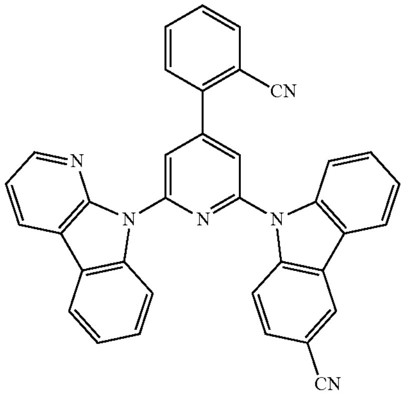
95
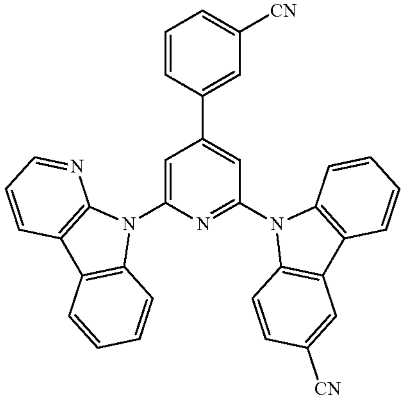
96
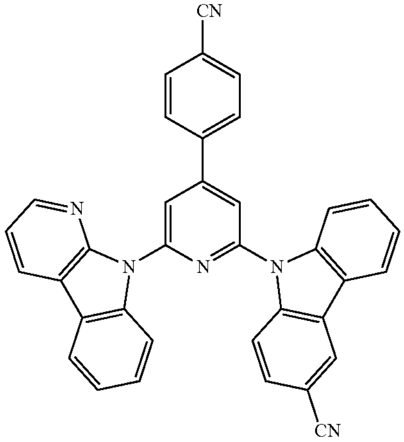
-continued
97
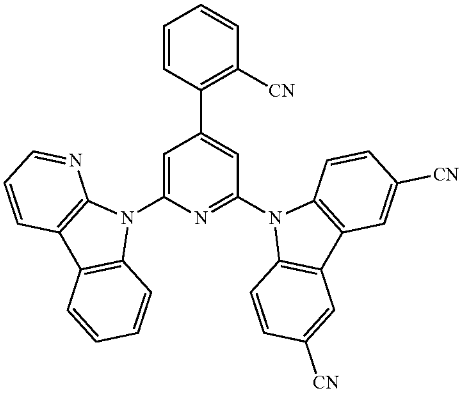
98
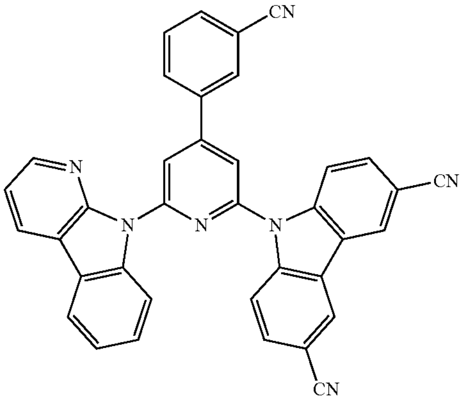
99
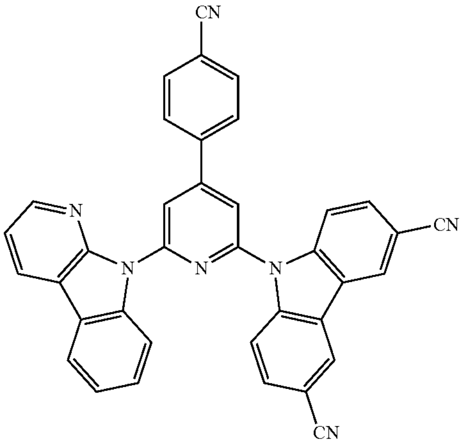
100
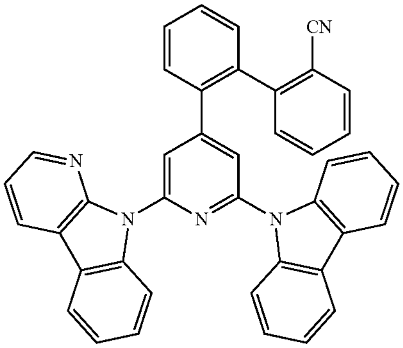

-continued
101
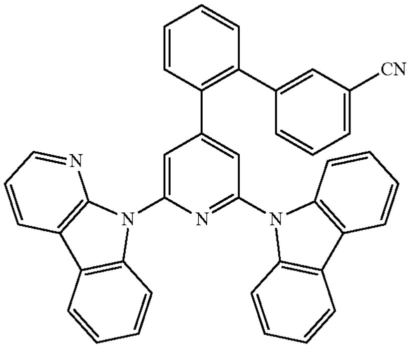
102
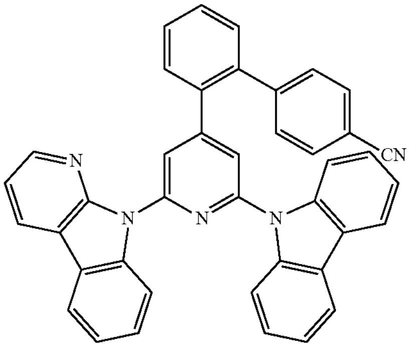
103
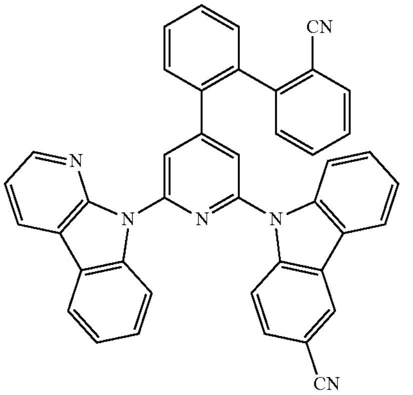
104
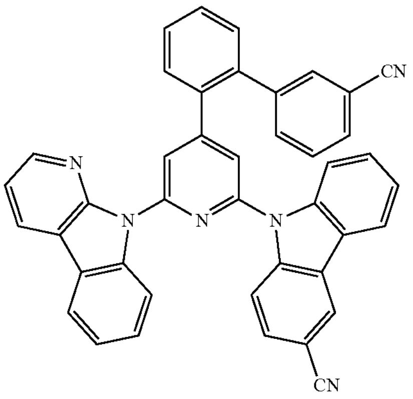
-continued
105
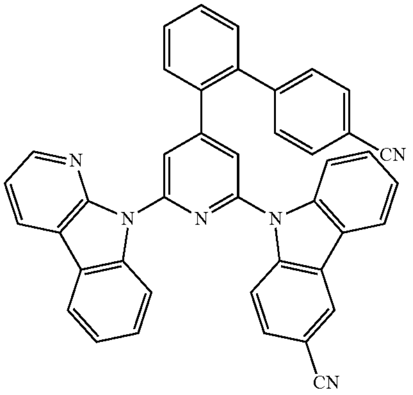
106
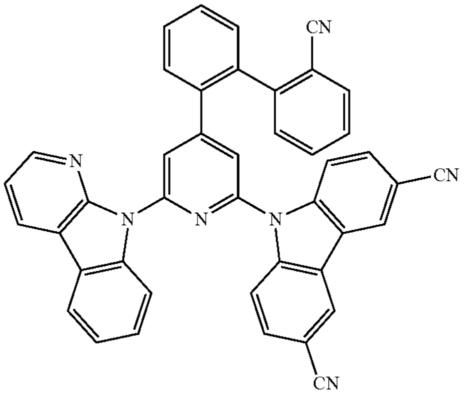
107
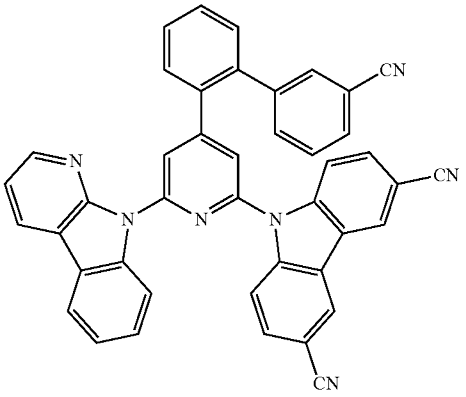
108
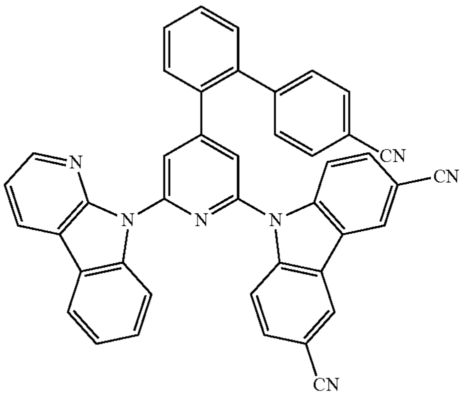

-continued
109
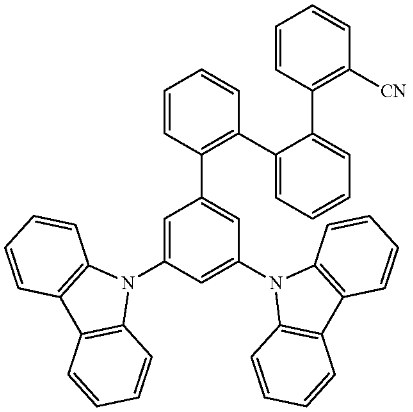
110
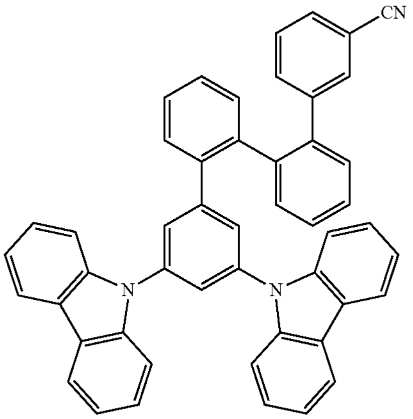
111
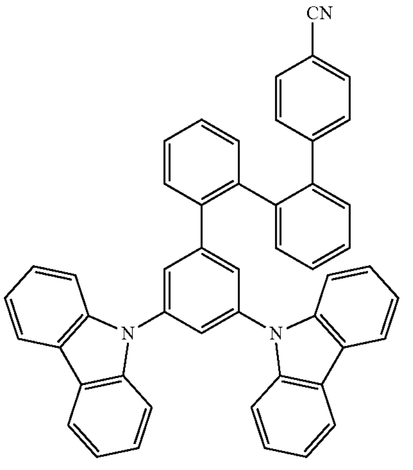
-continued
112
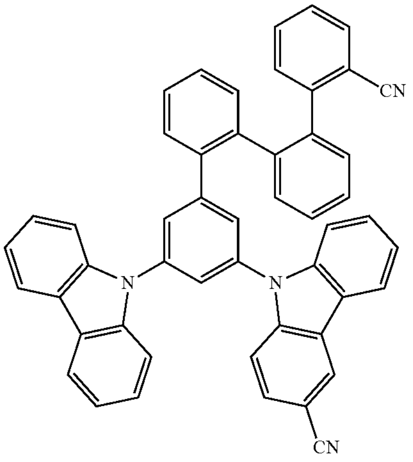
113
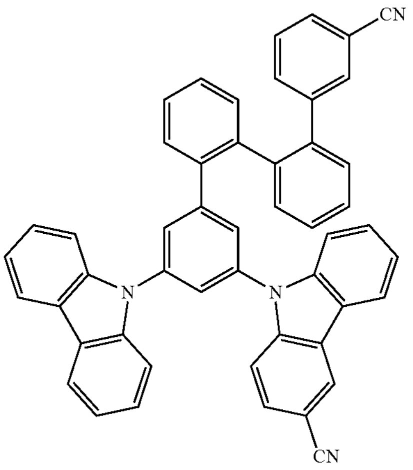
114
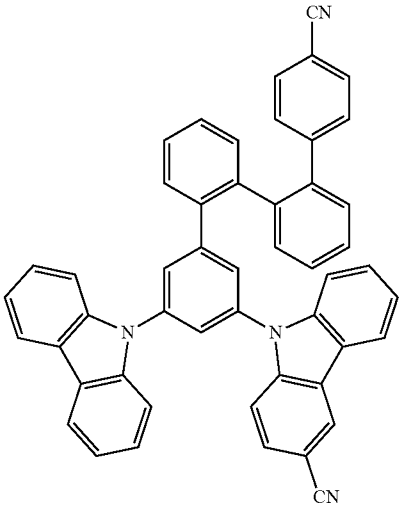

115
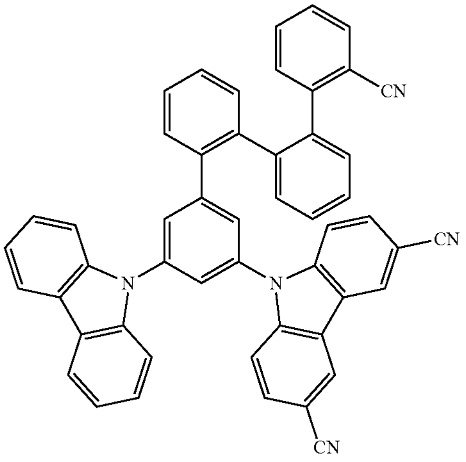
116
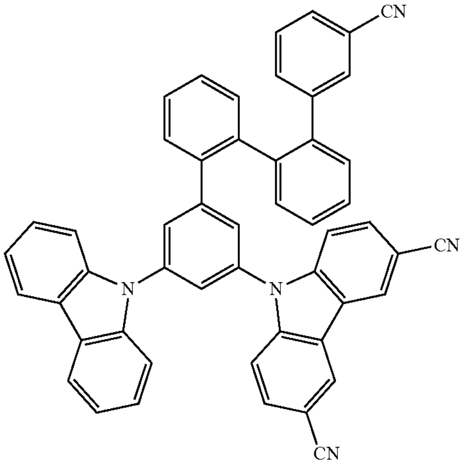
117
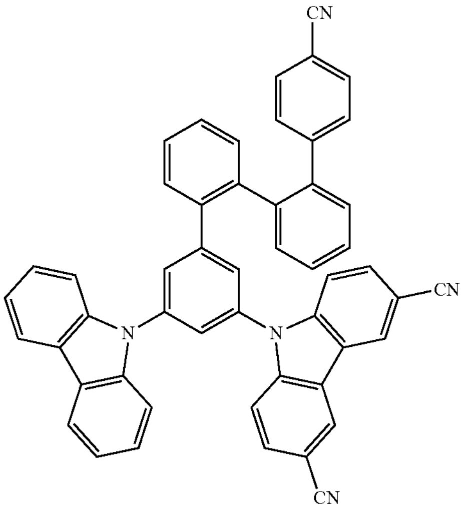
118
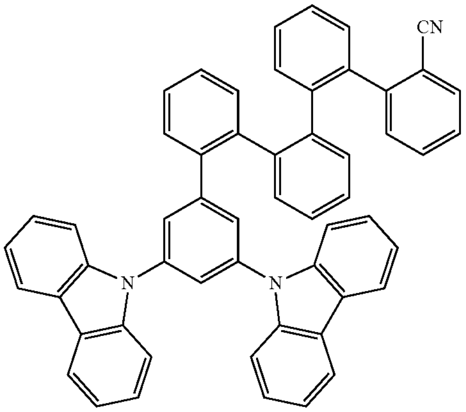
119
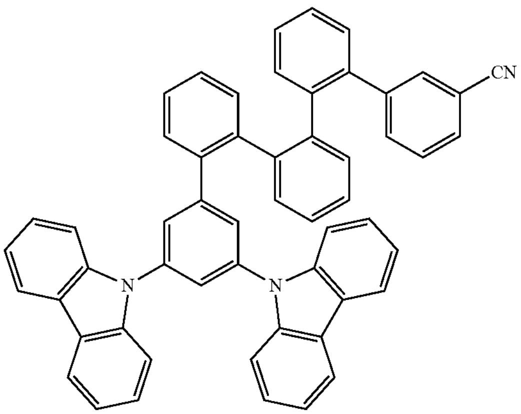
120
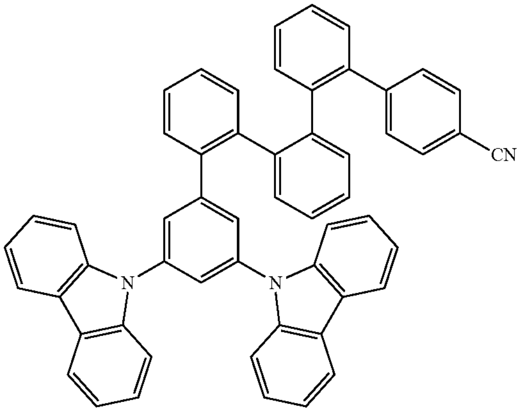

-continued
121
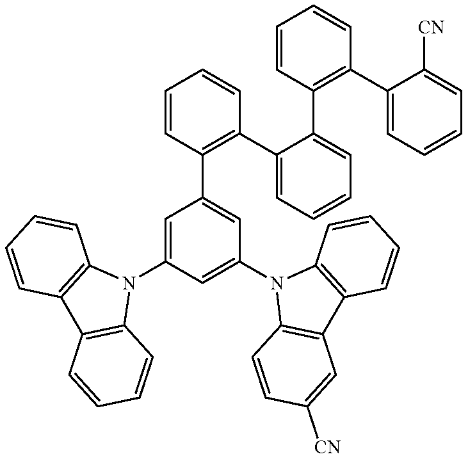
122
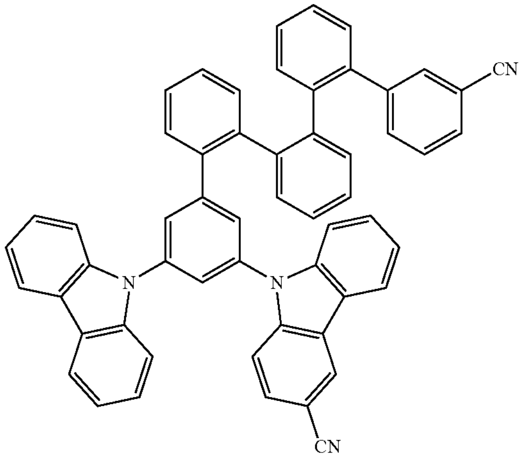
123
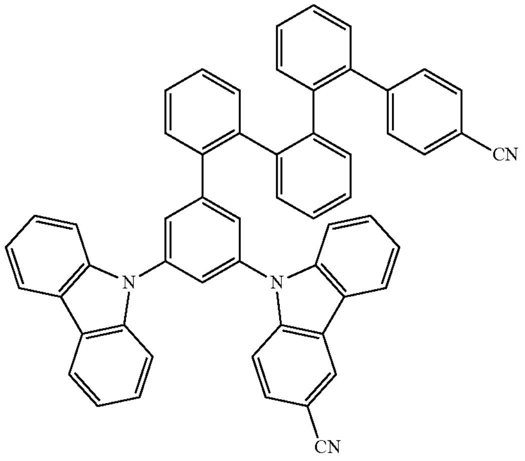
-continued
124
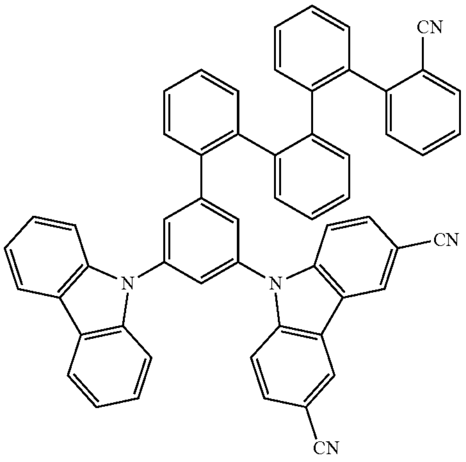
125
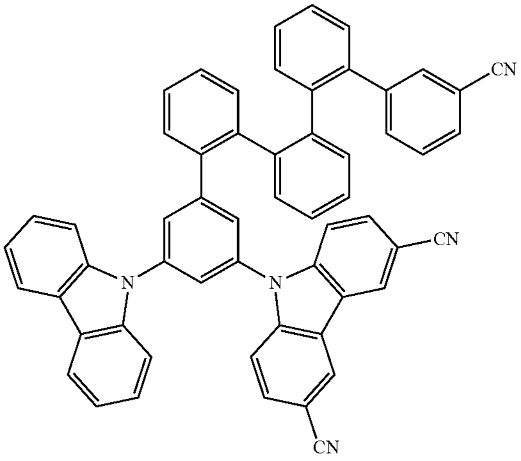
126
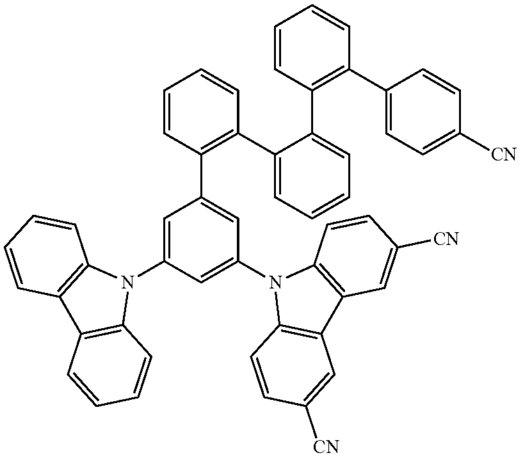

-continued
127
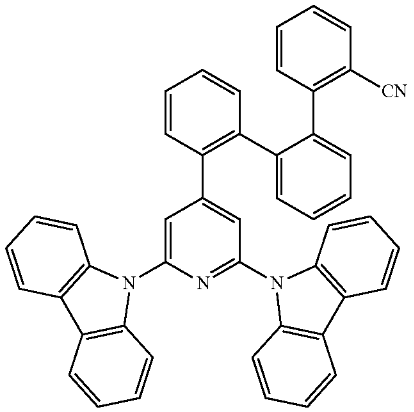
128
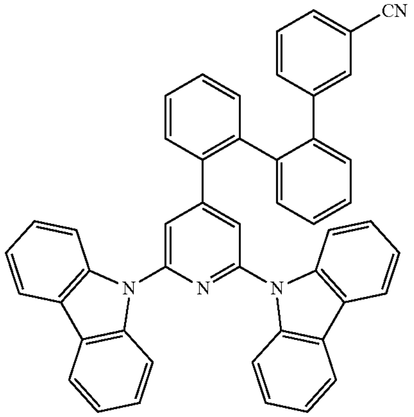
129
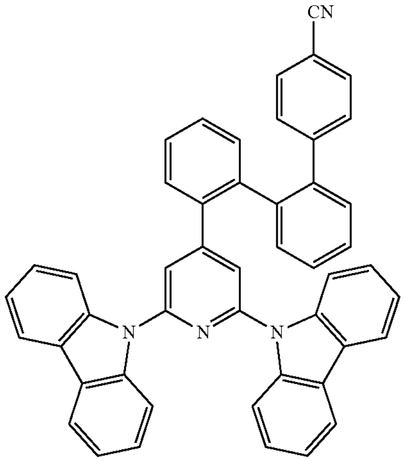
-continued
130
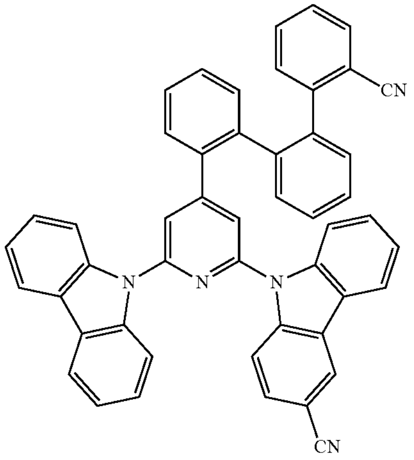
131
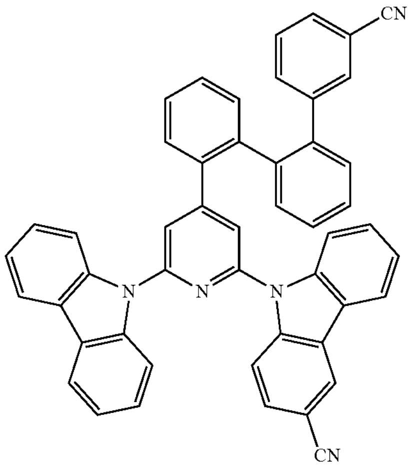
132
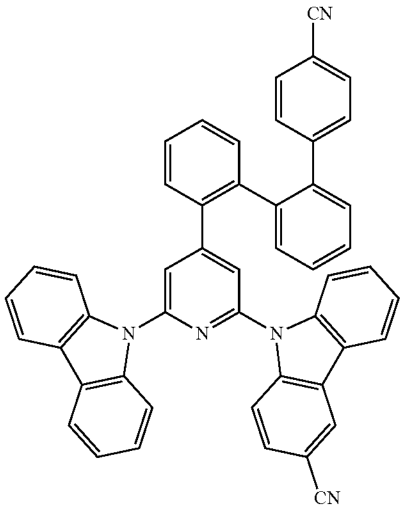

133
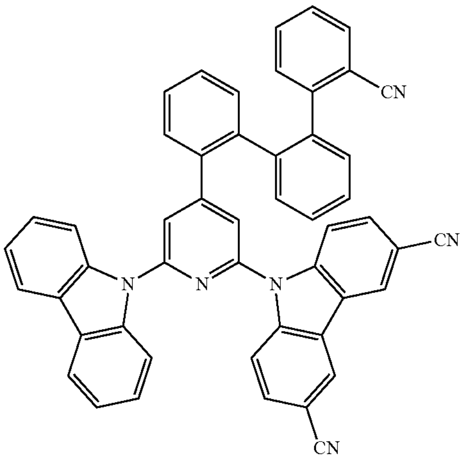
134
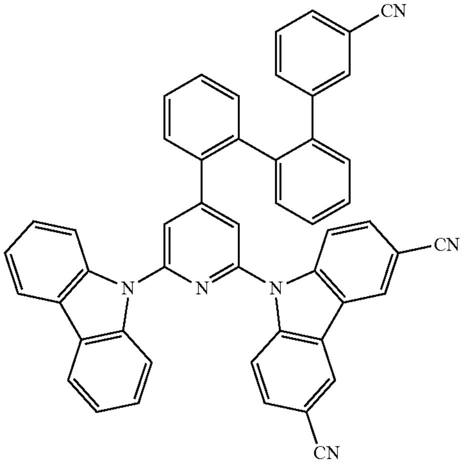
135
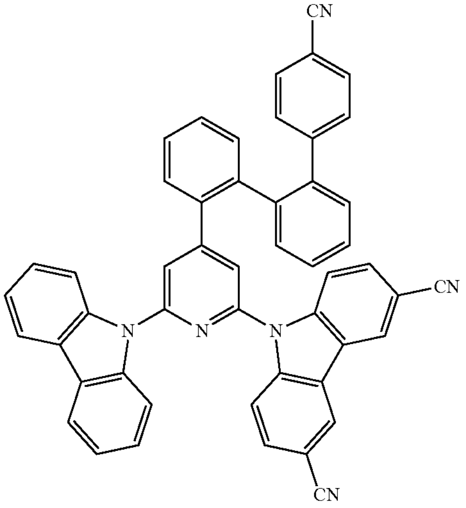
136
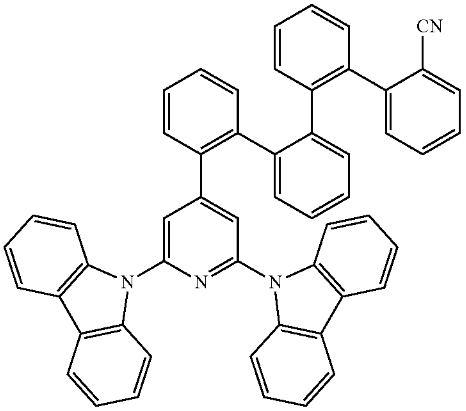
137
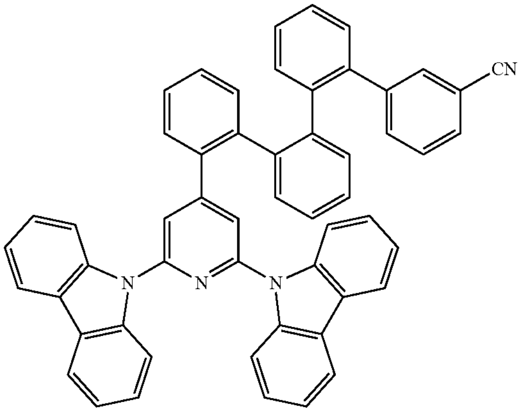
138
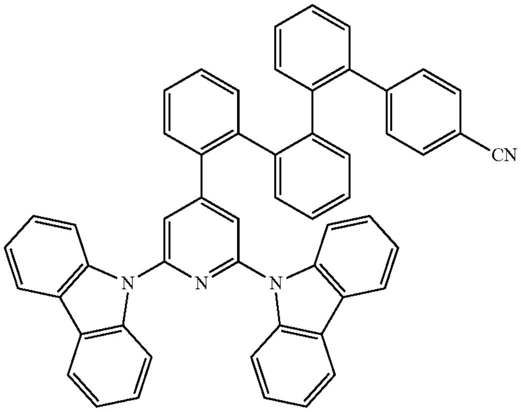

-continued
139
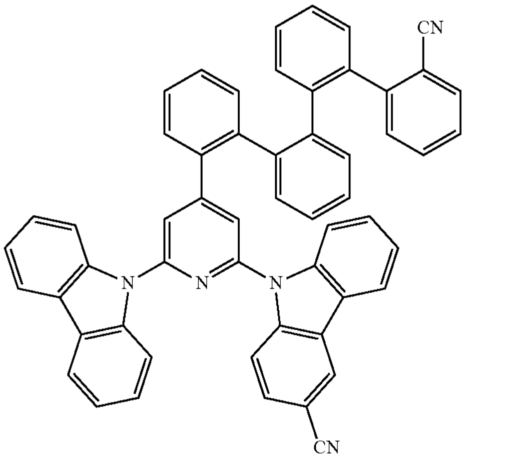
140
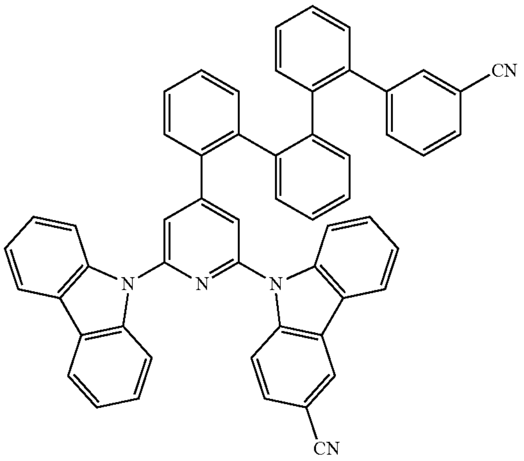
141
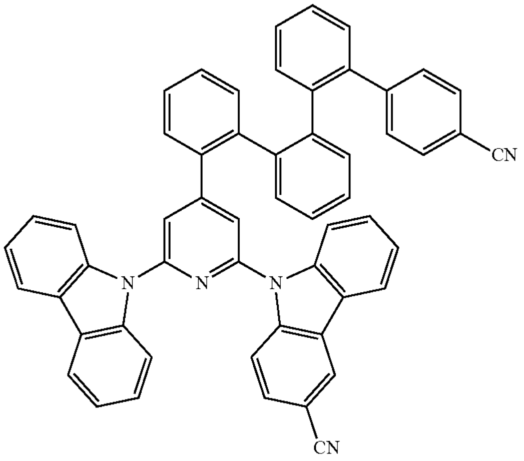
-continued
142
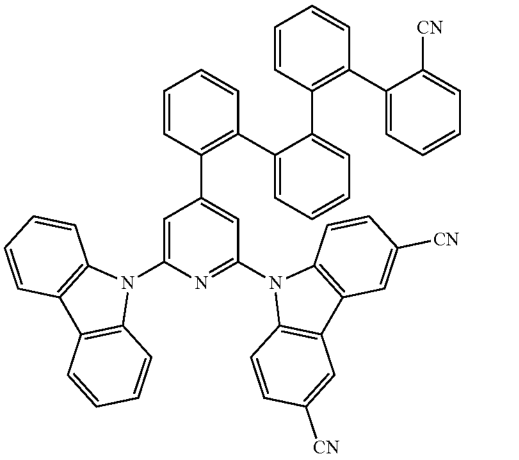
143
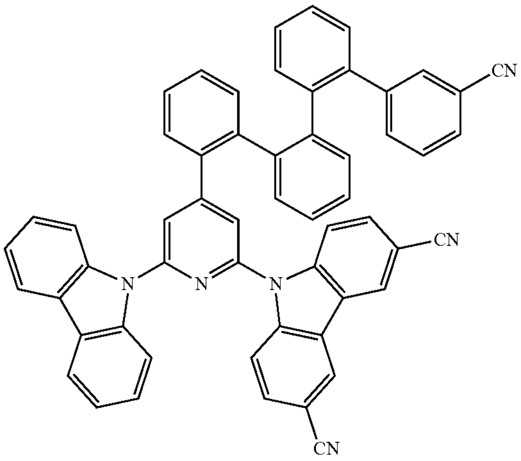
144
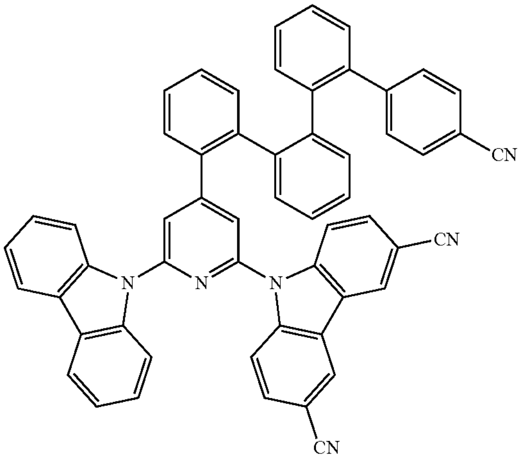

-continued
145
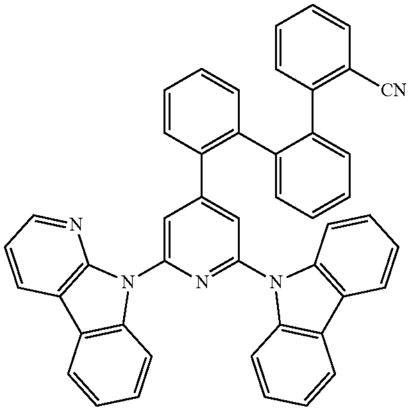
146
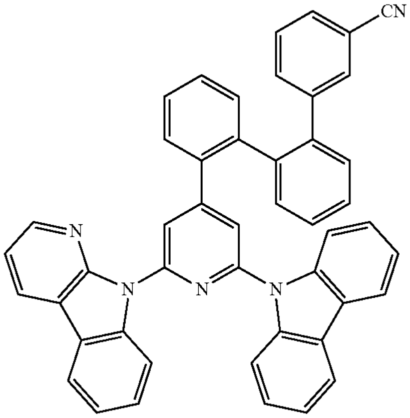
147
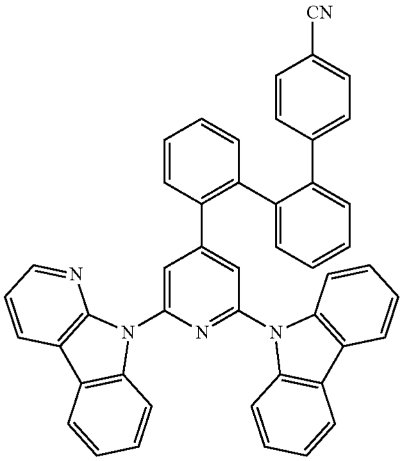
-continued
148
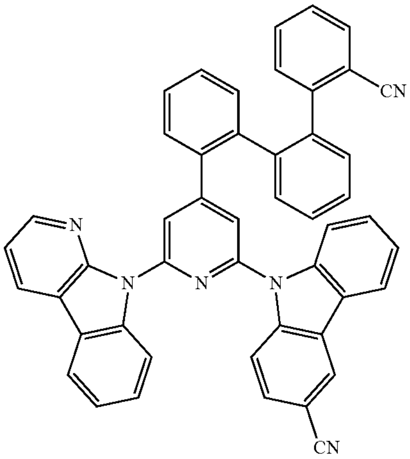
149
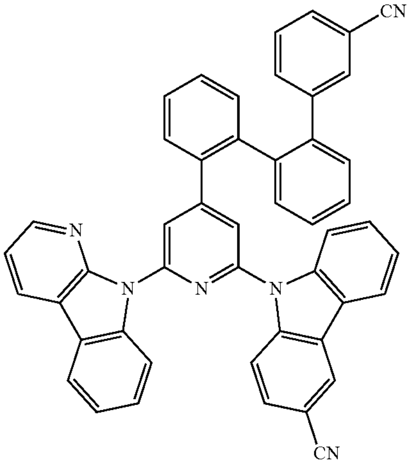
150
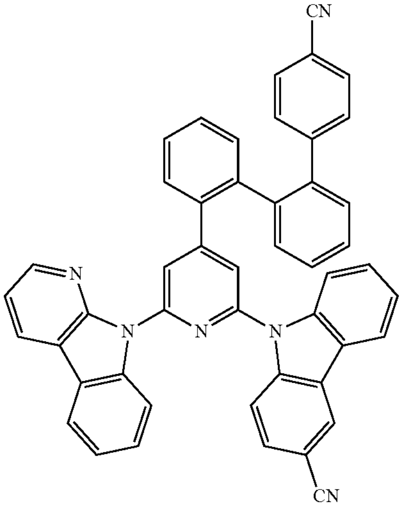

-continued
151
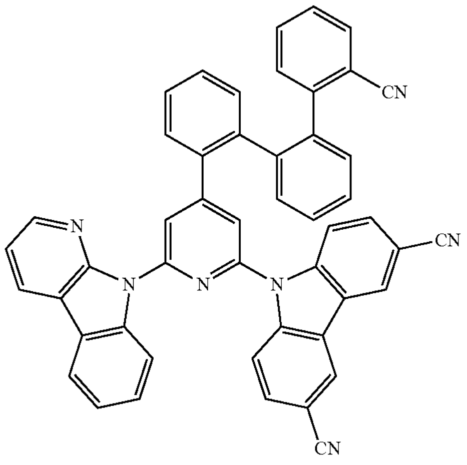
152
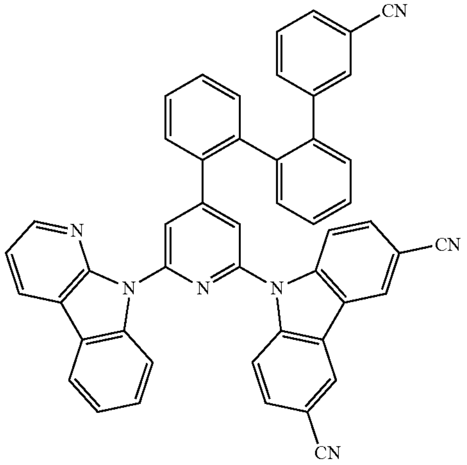
153
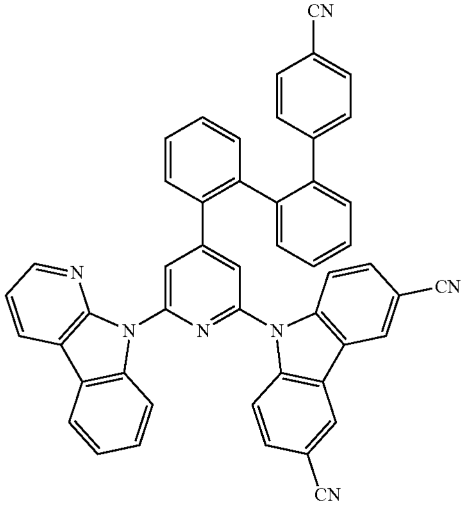
-continued
154
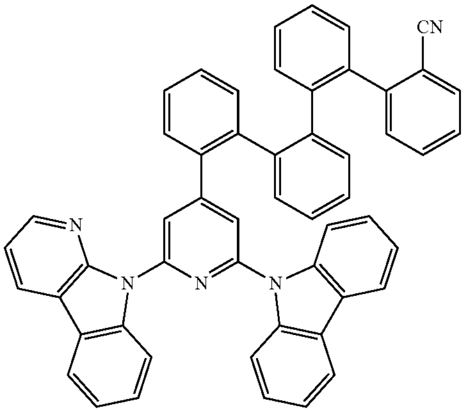
155
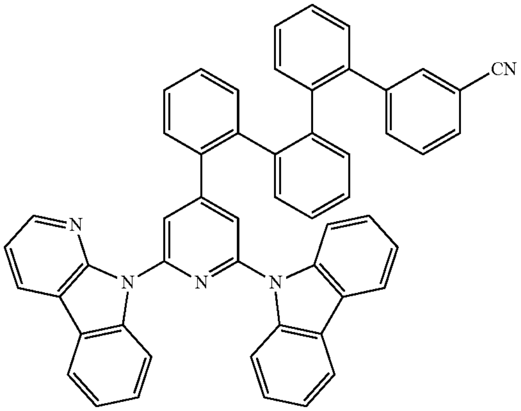
156
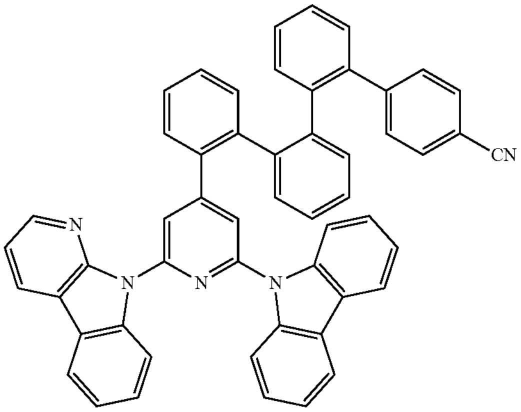

-continued
157
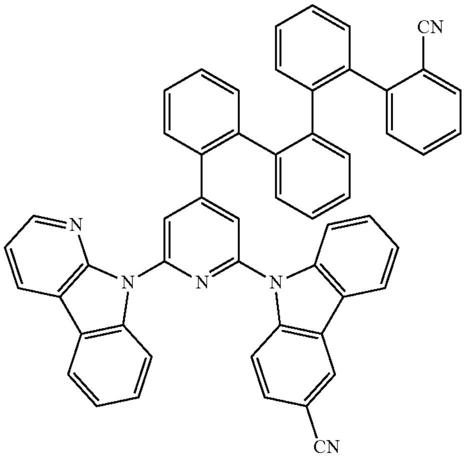
158
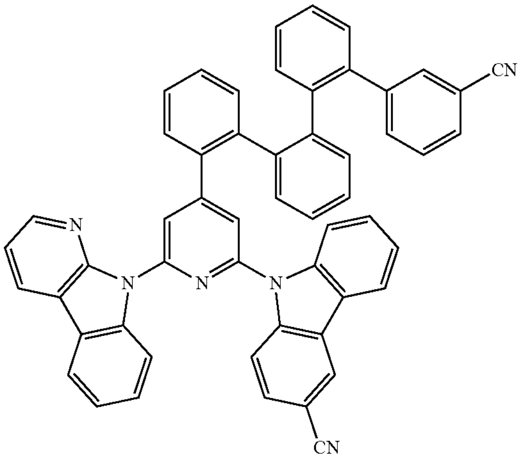
159
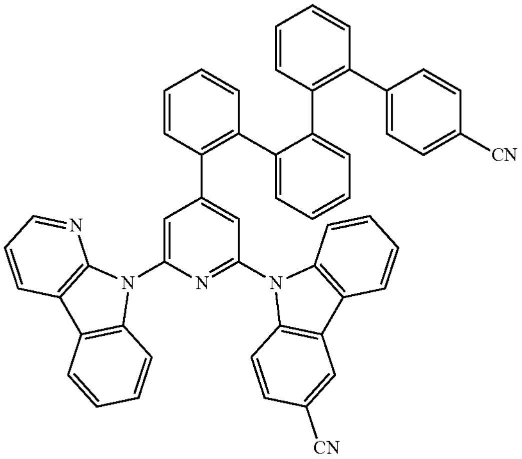
-continued
160
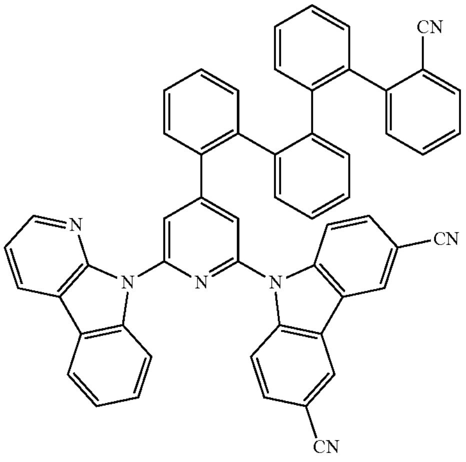
161
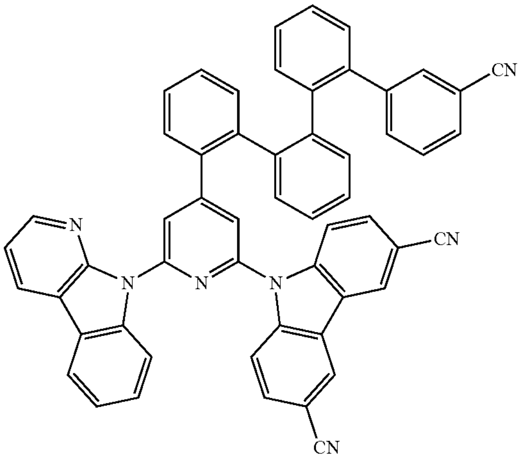
162
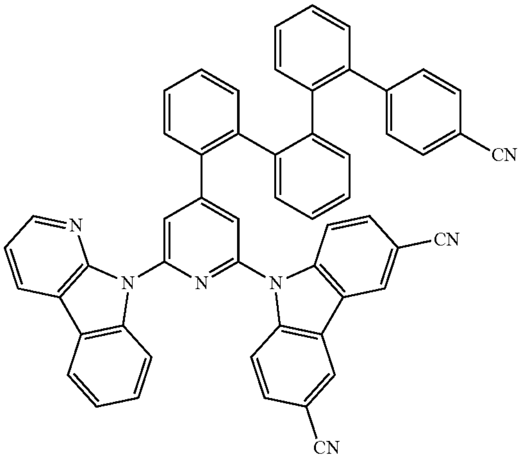

-continued
163
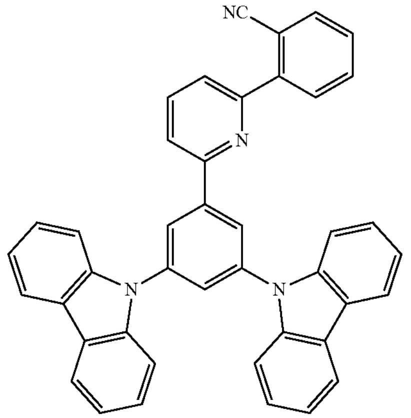
164
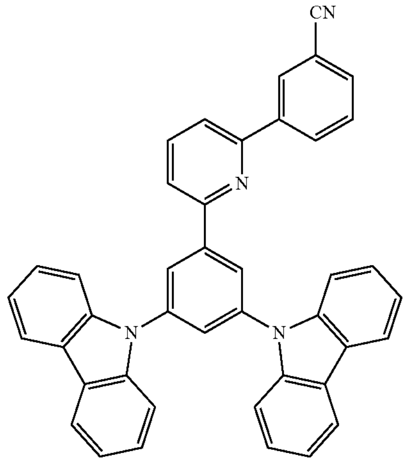
165
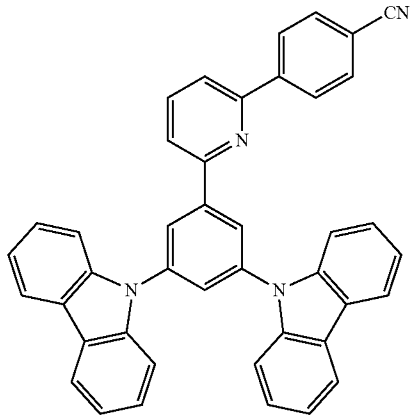
-continued
166
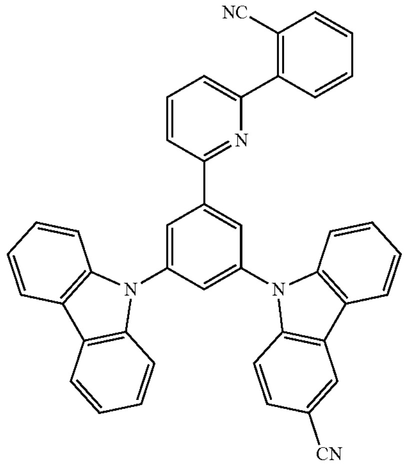
167
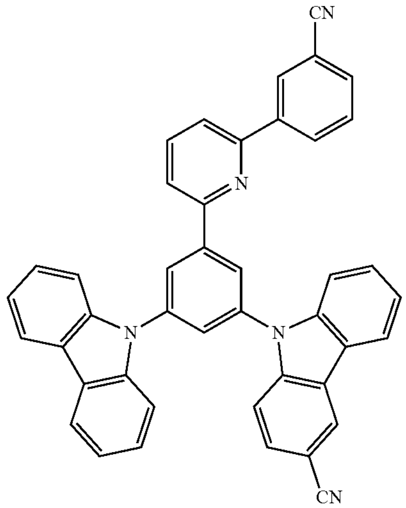
168
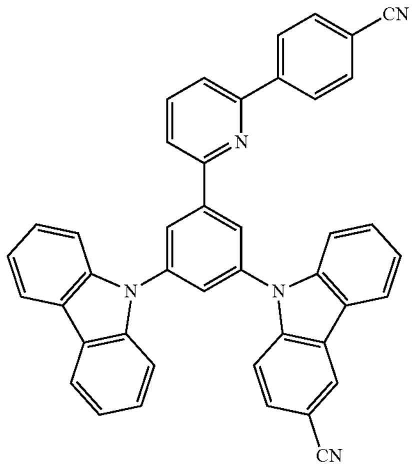

-continued
169
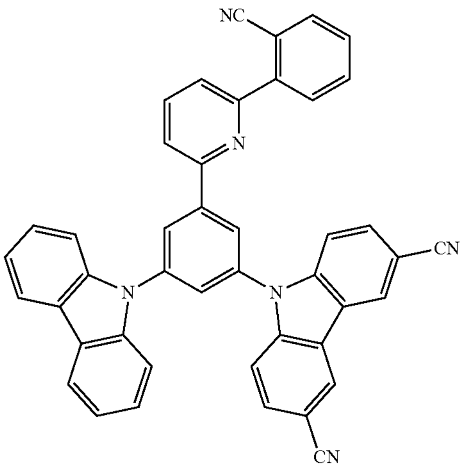
170
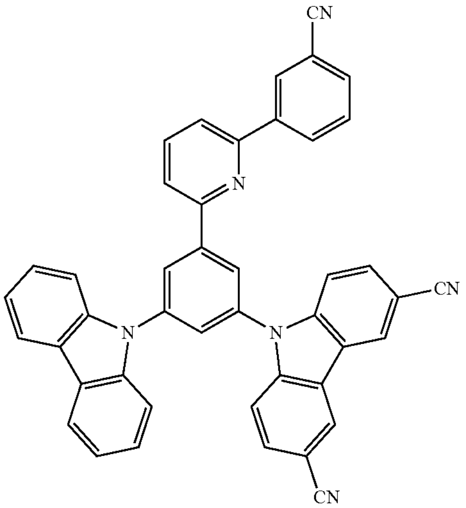
171
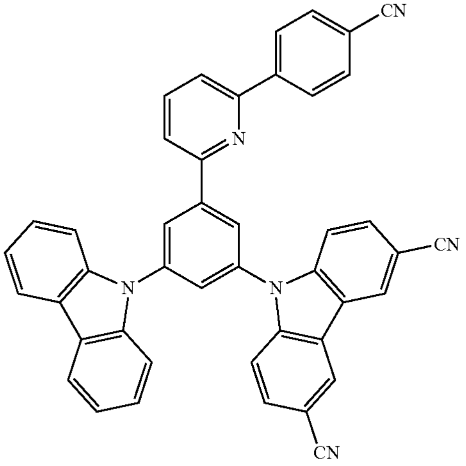
-continued
172
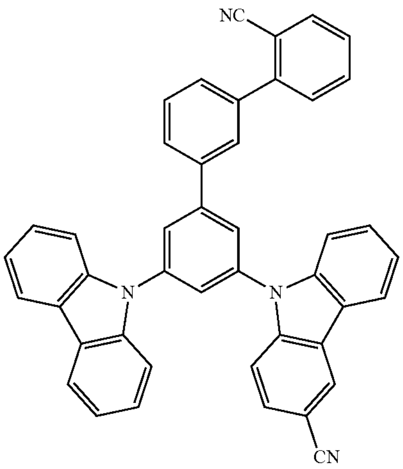
173
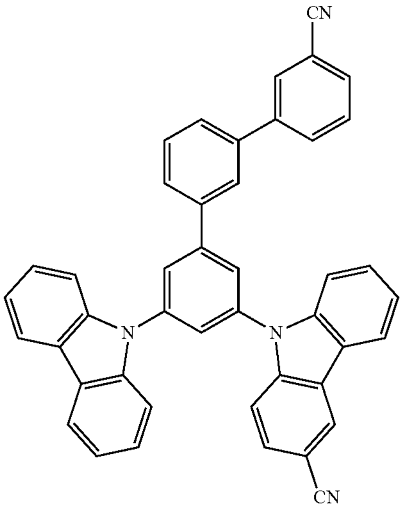
174
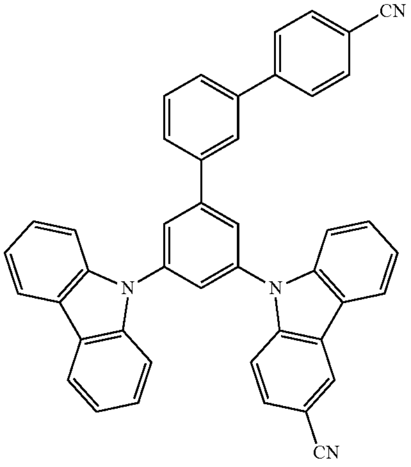

-continued
175
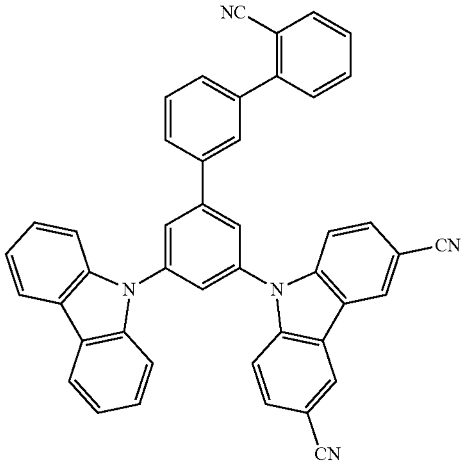
176
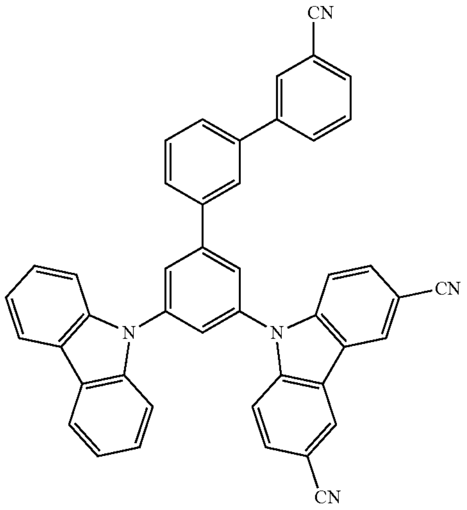
177
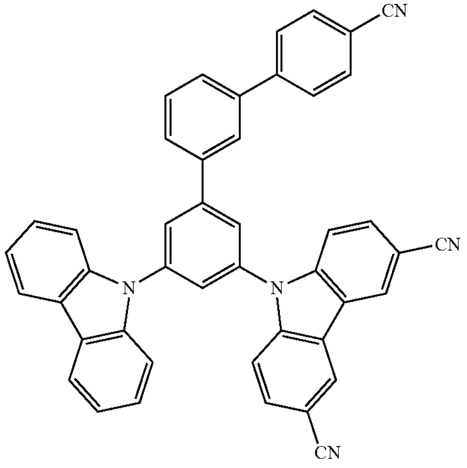
-continued
178
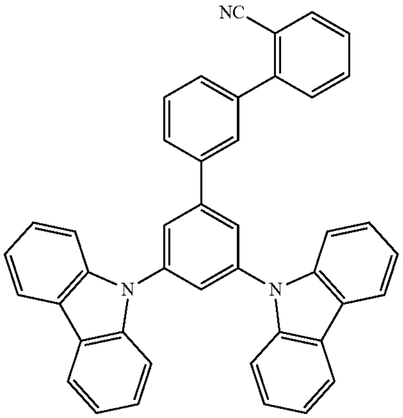
179
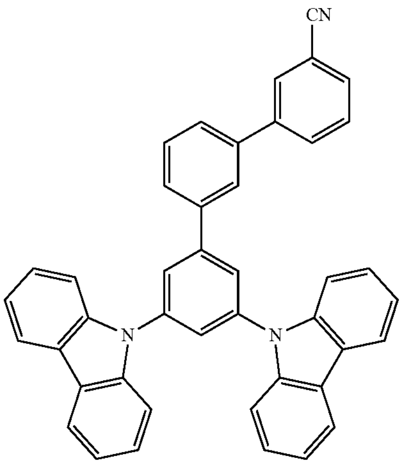
180
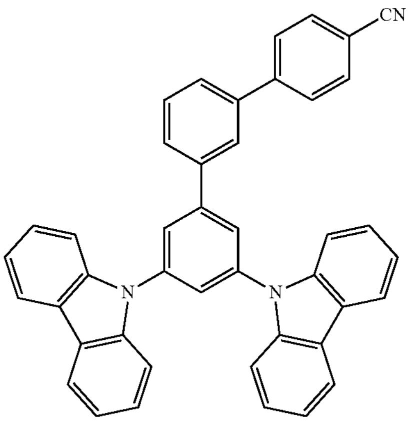

-continued
181
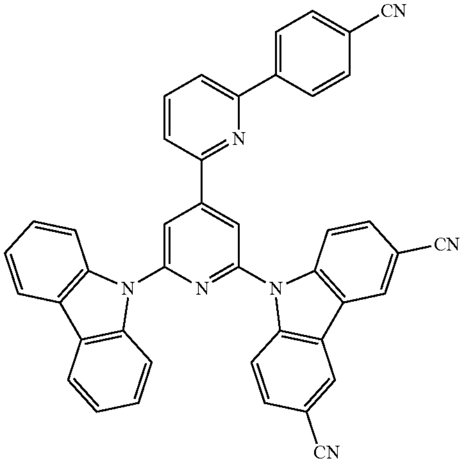
182
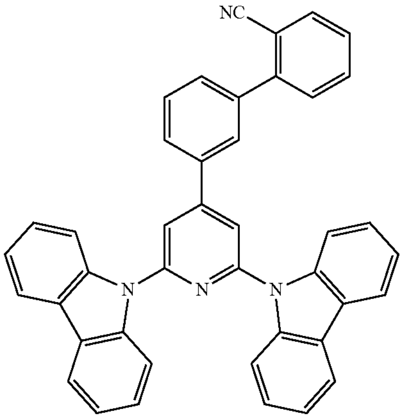
183
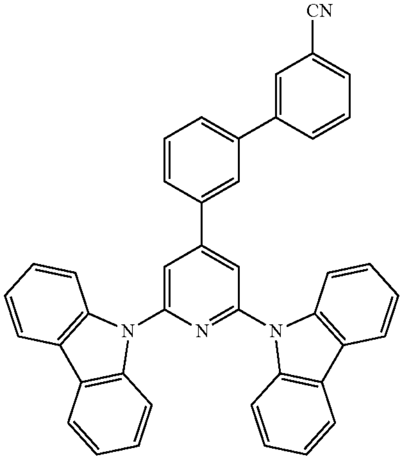
-continued
184
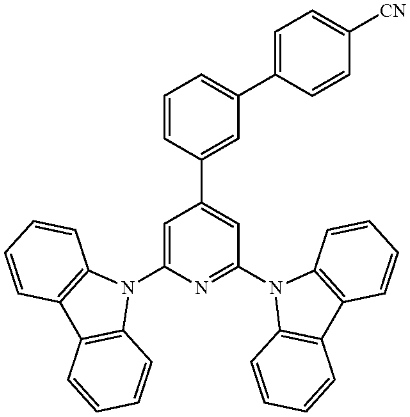
185
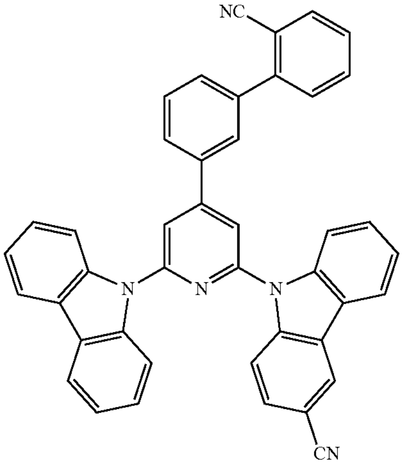
186
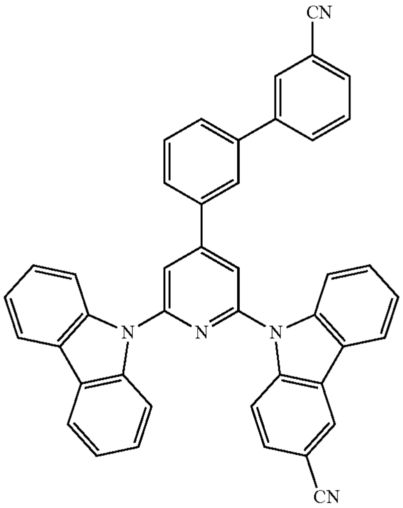

-continued
187
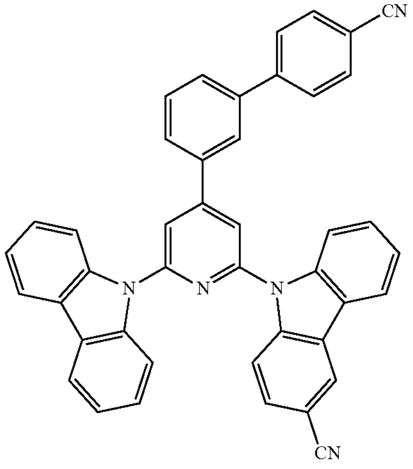
188
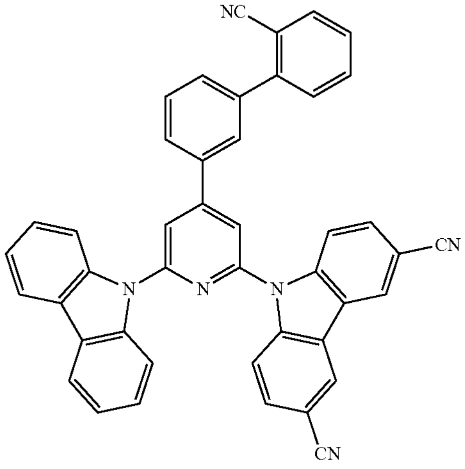
189
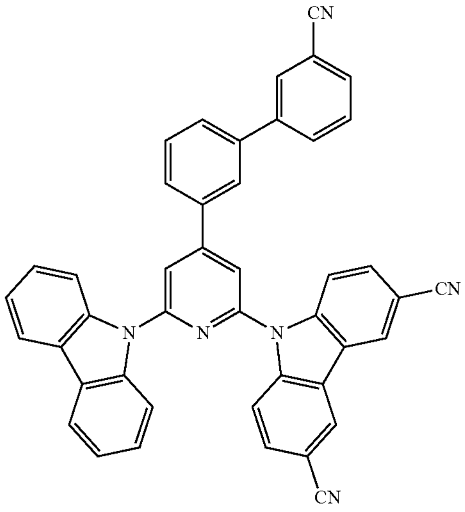
-continued
190
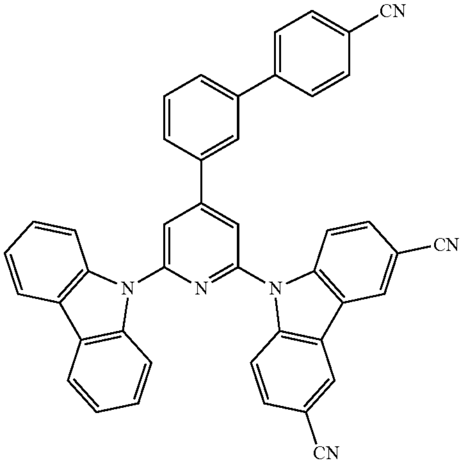
191
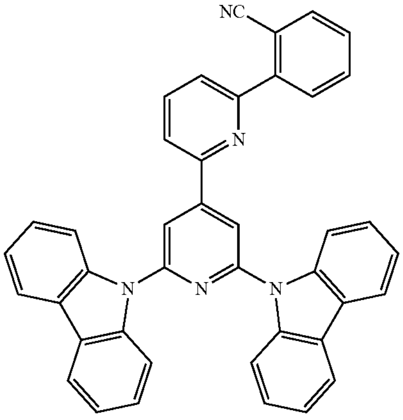
192
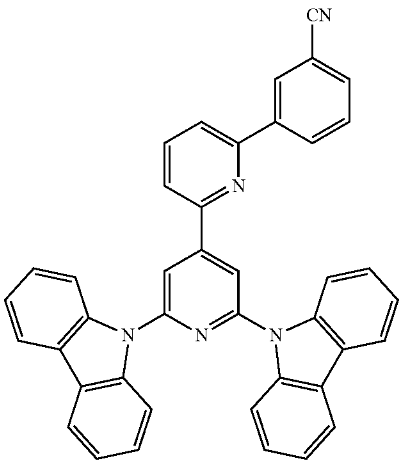

-continued
193
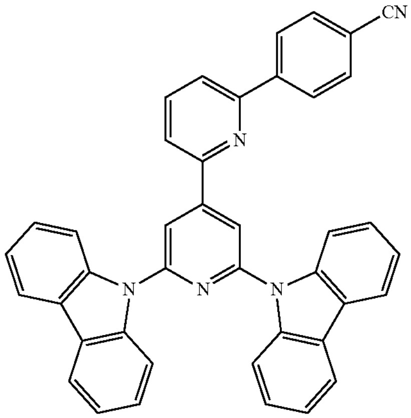
194
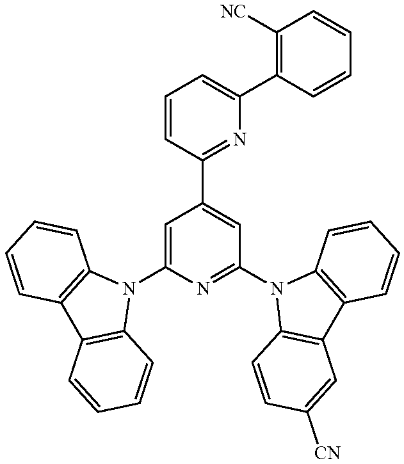
195
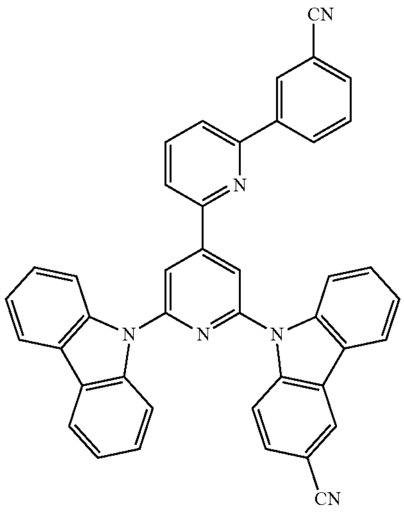
-continued
196
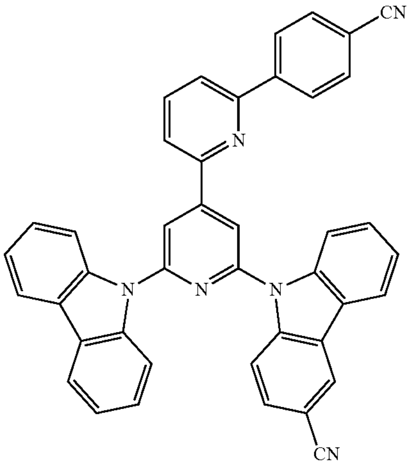
197
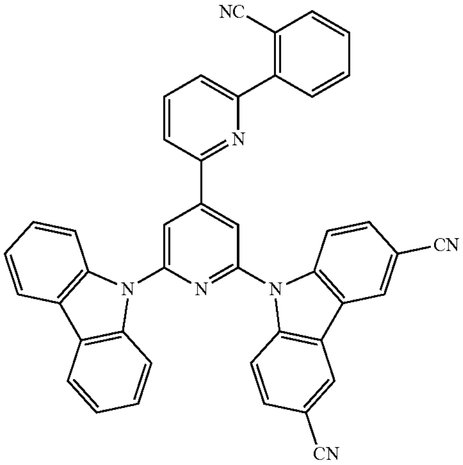
198
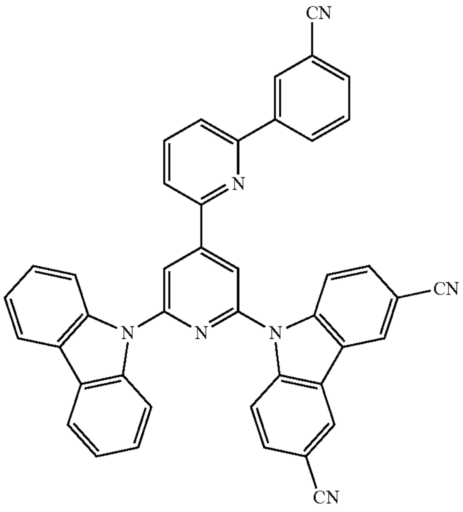

-continued
199
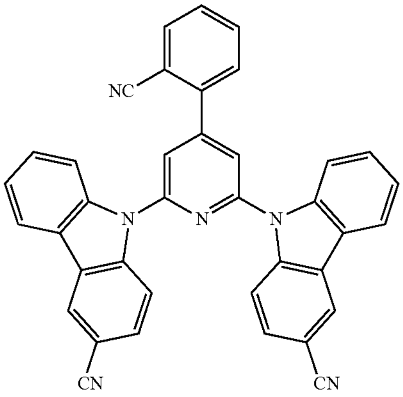
200
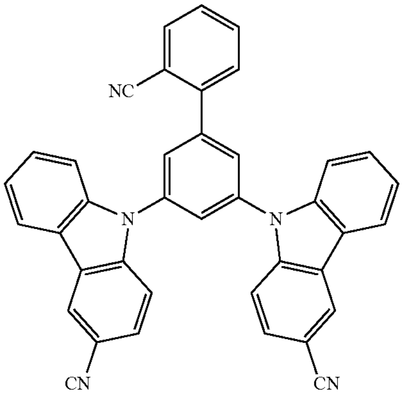
201
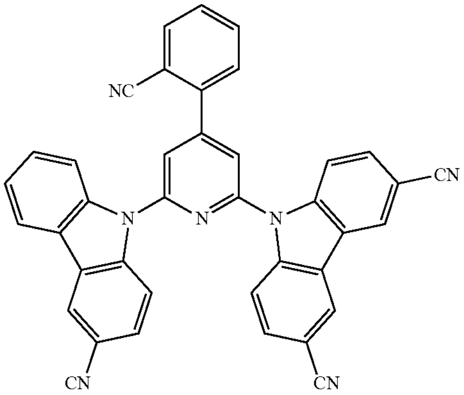
202
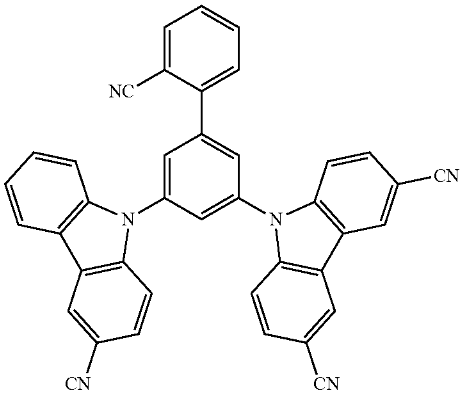
Group HE6
1
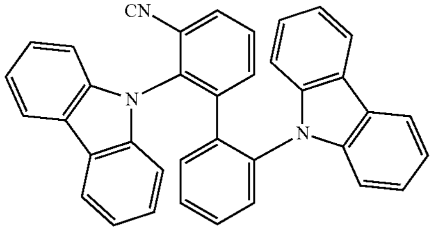
2
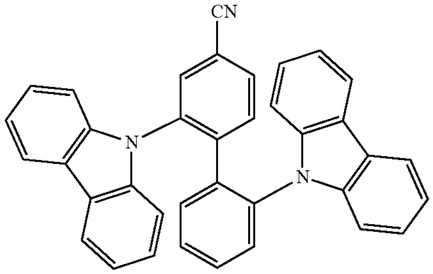
3
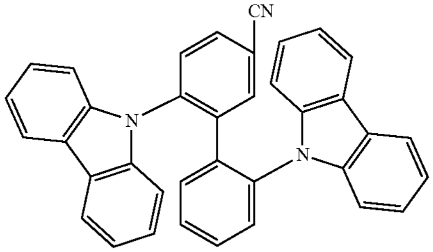
4
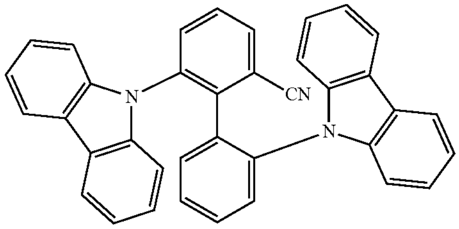
5
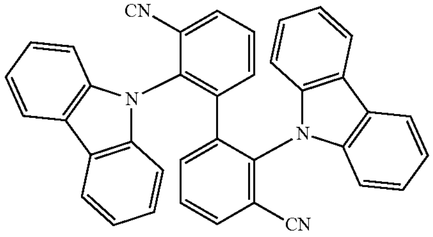
6
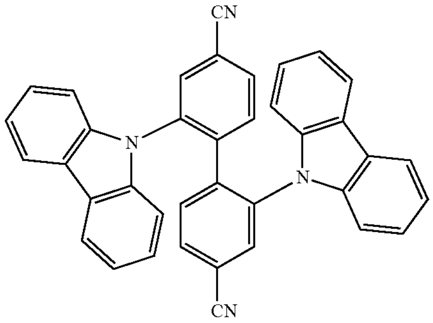

-continued
7
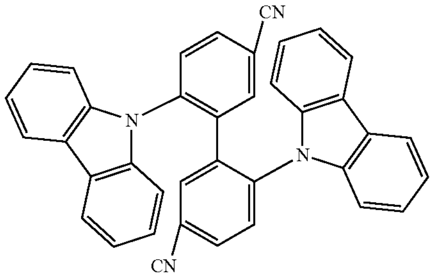
8
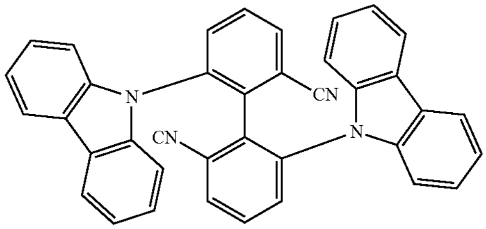
9
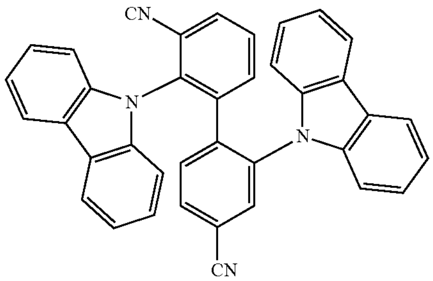
10
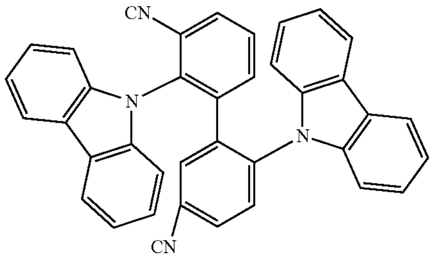
11
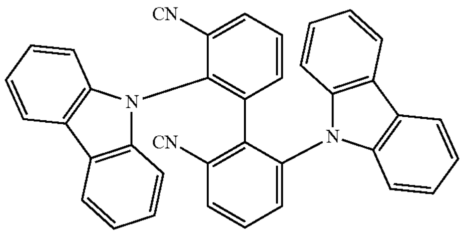
12
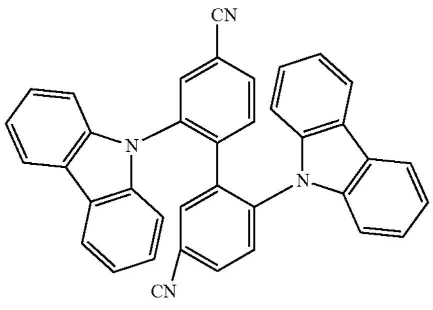
-continued
13
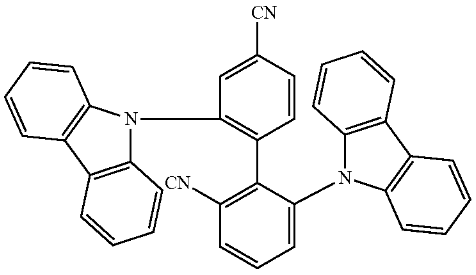
14
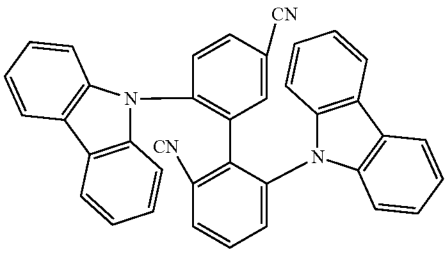
15
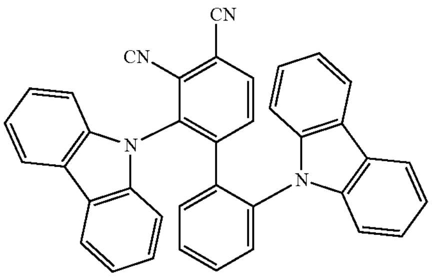
16
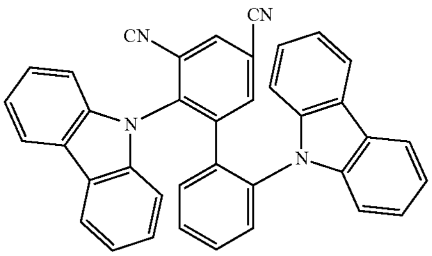
17
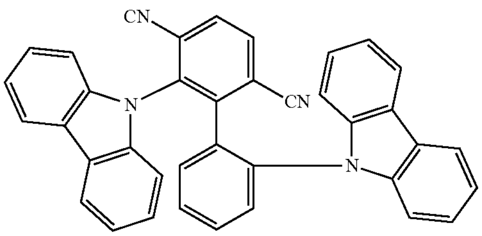
18
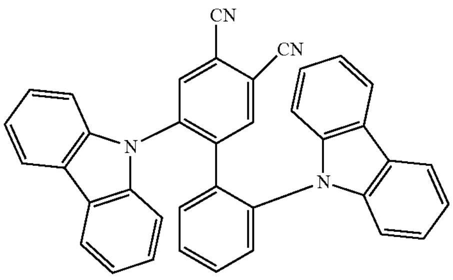

19
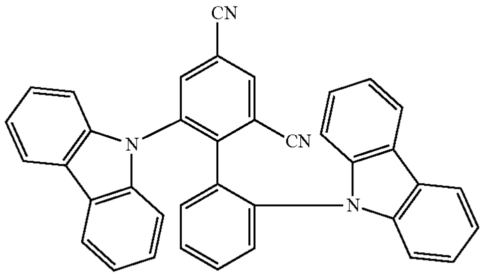
20
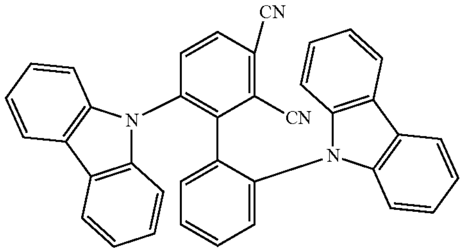
21
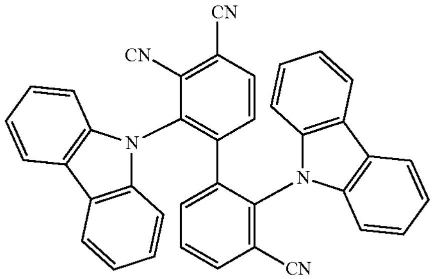
22
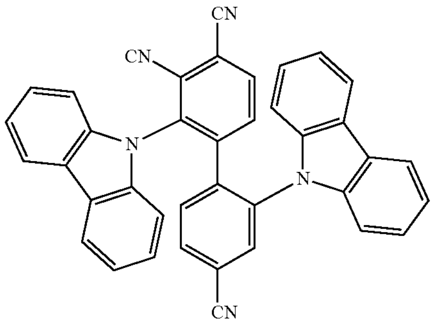
23
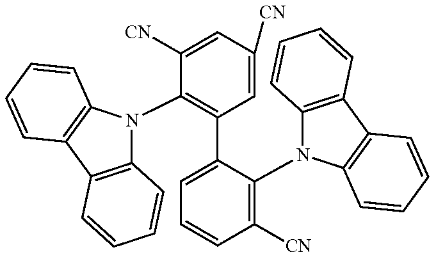
24
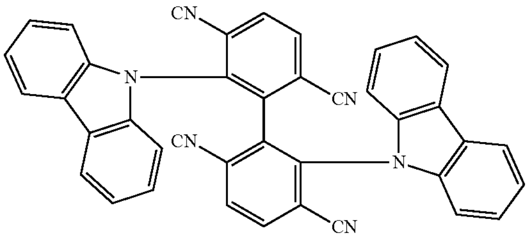
25
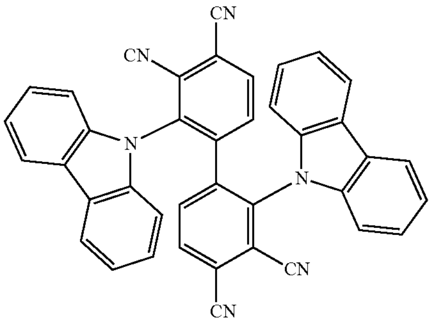
26
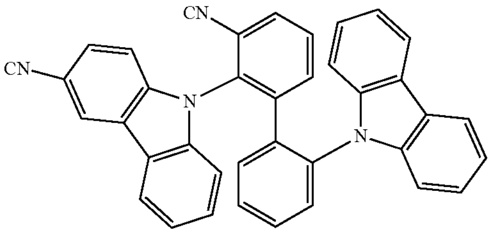
27
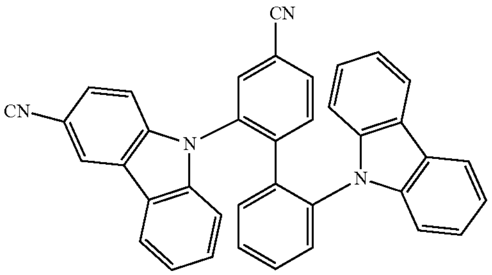
28
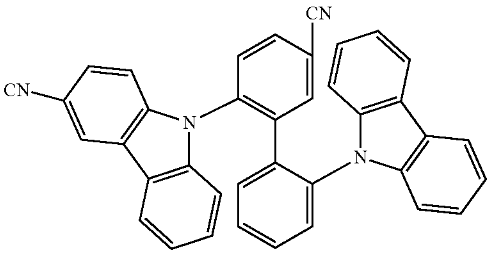
29
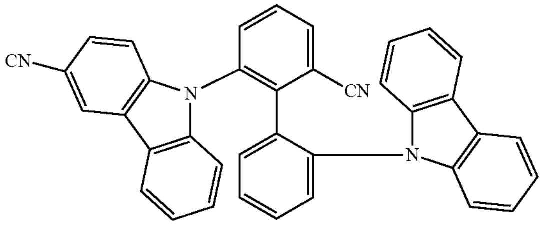

-continued
30
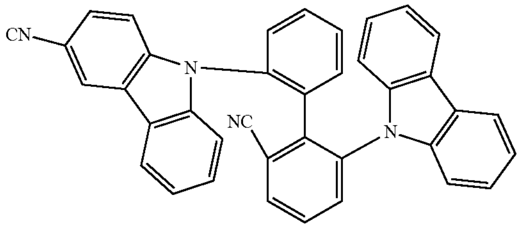
31
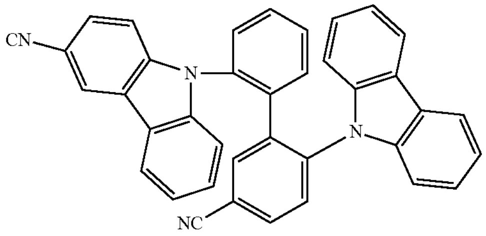
32
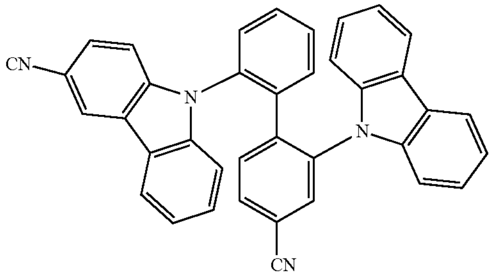
33
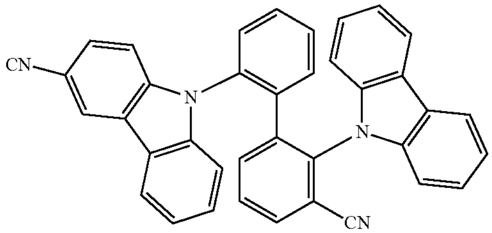
34
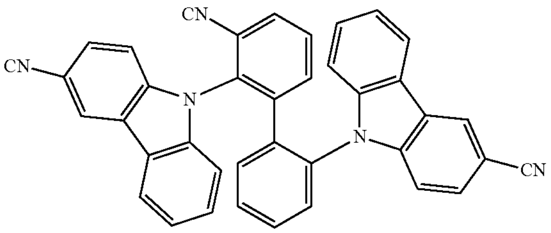
35
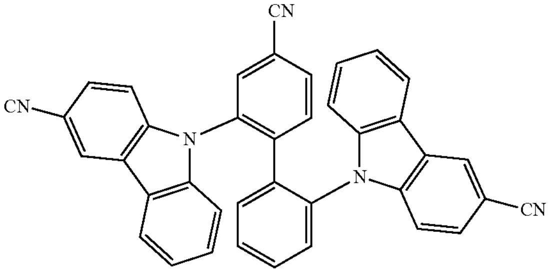
-continued
36
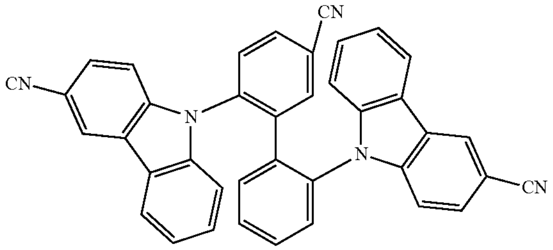
37
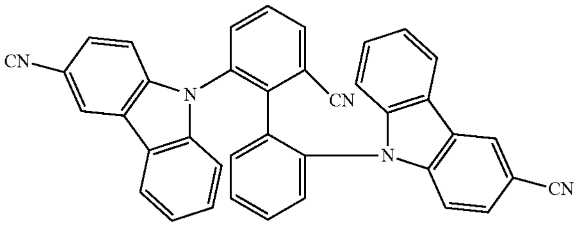
38
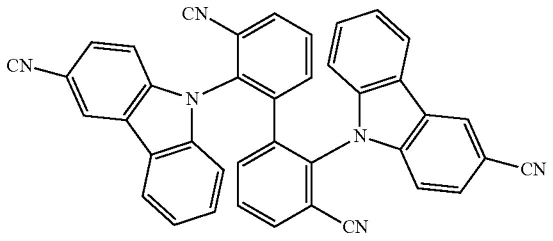
39
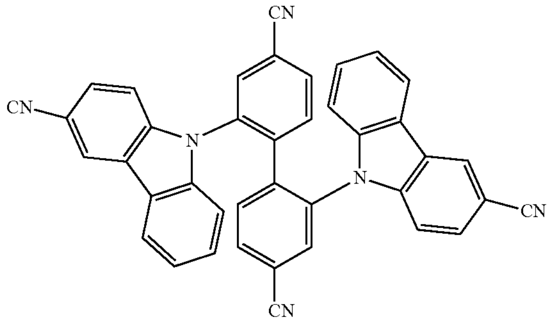
40
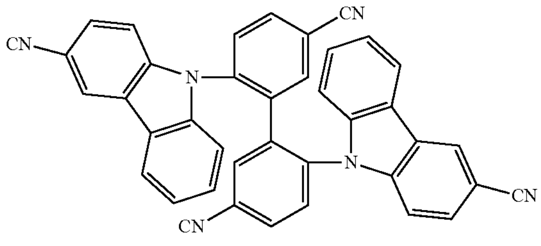

-continued
41
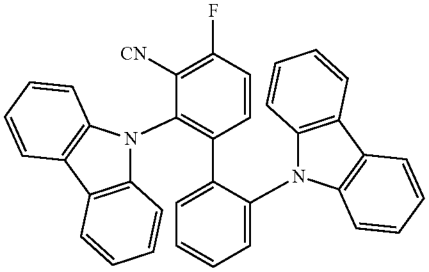
42
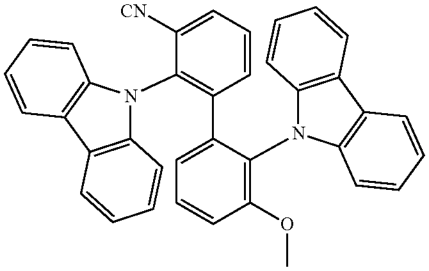
43
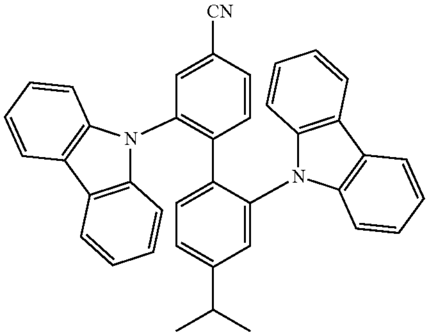
44
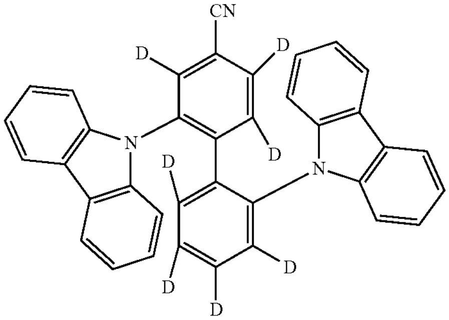
45
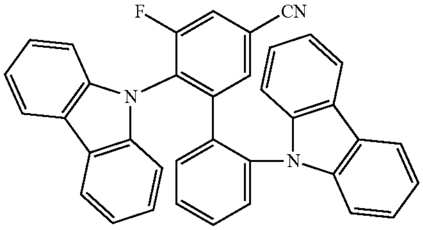
-continued
46
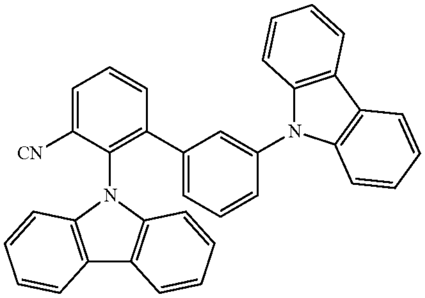
47
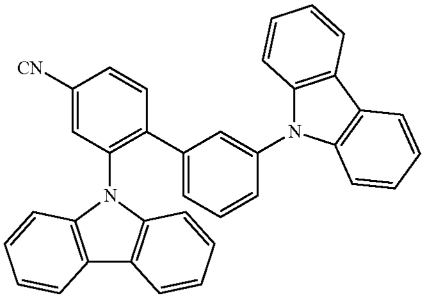
48
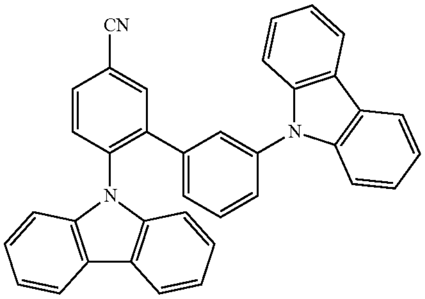
49
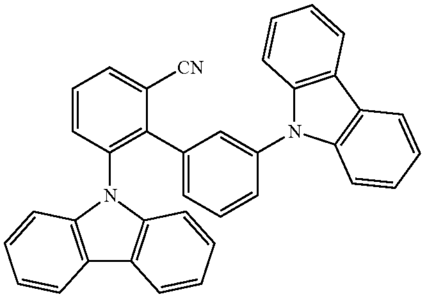
50
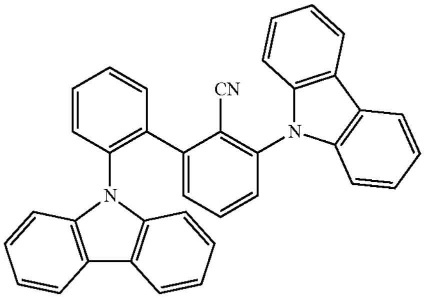

-continued
51
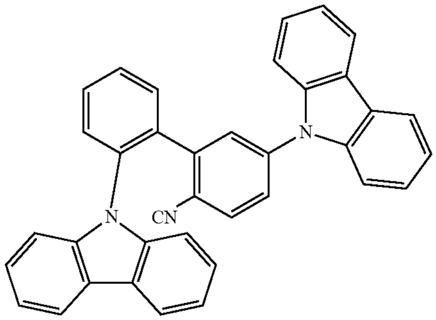
52
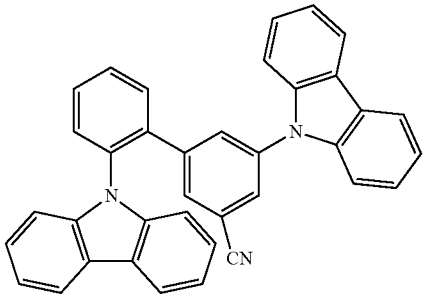
53
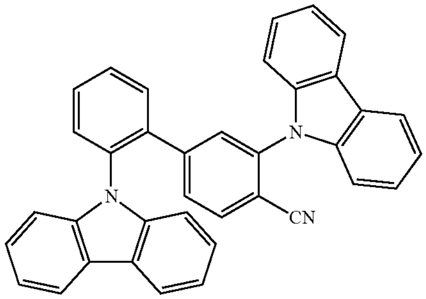
54
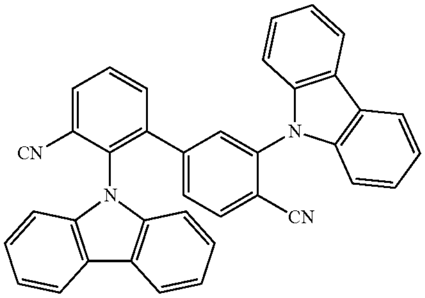
55
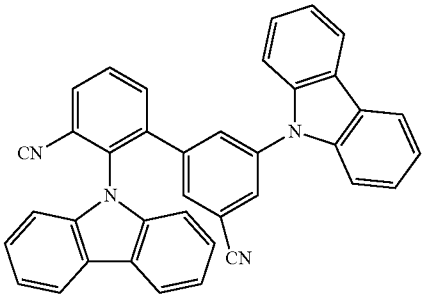
-continued
56
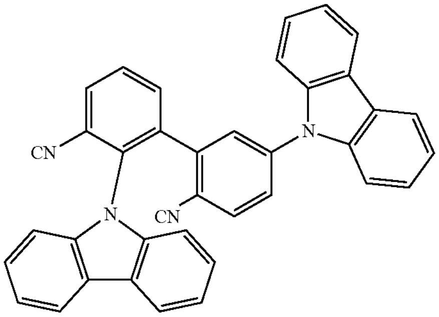
57
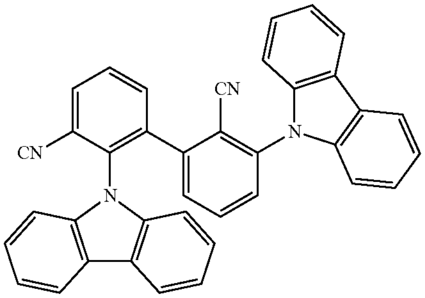
58
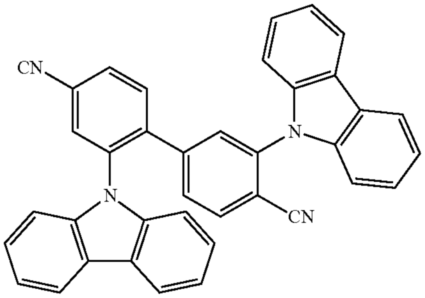
59
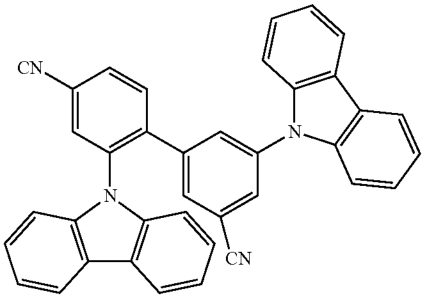
60
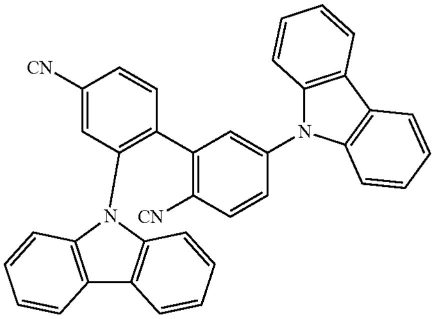

61
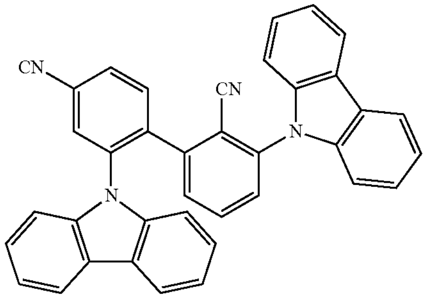
62
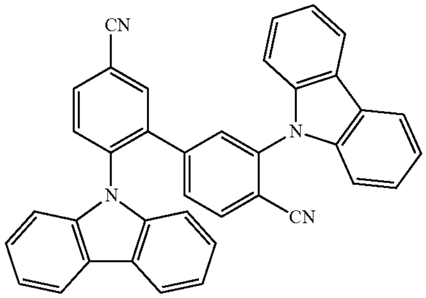
63
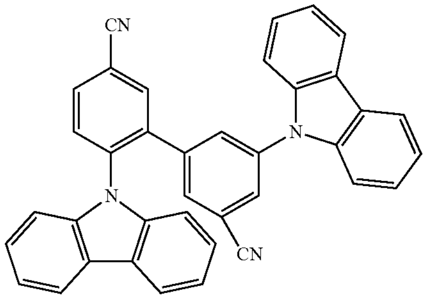
64
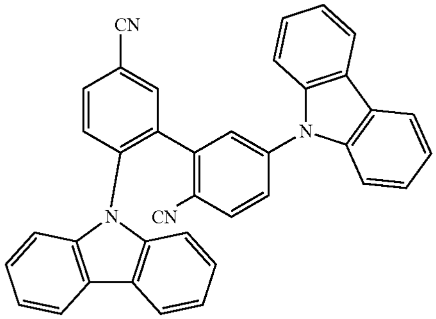
65
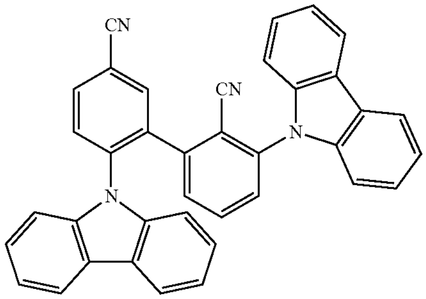
66
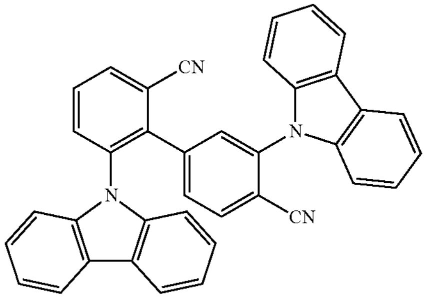
67
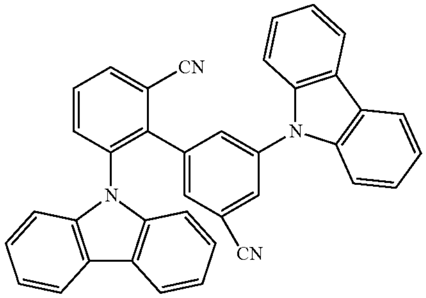
68
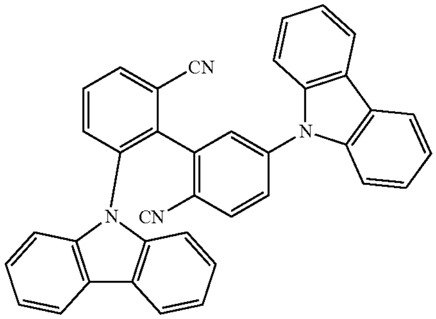
69
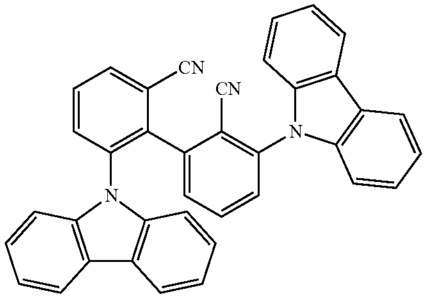
70
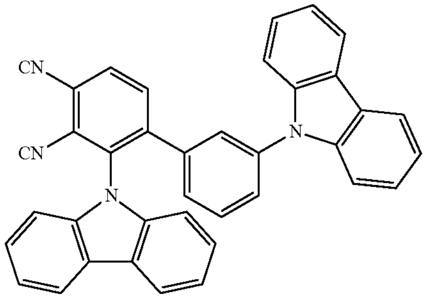

-continued
71
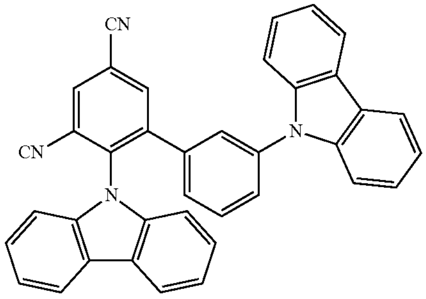
72
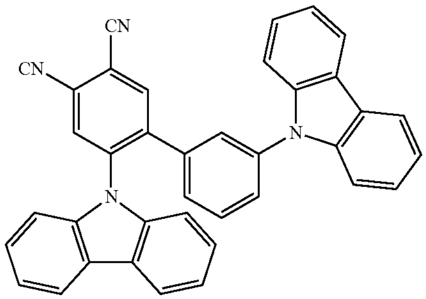
73
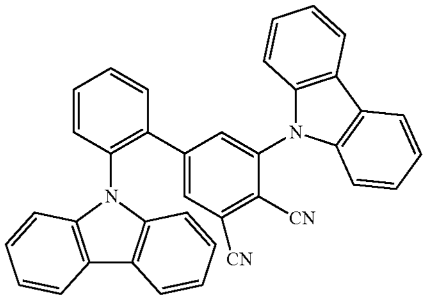
74
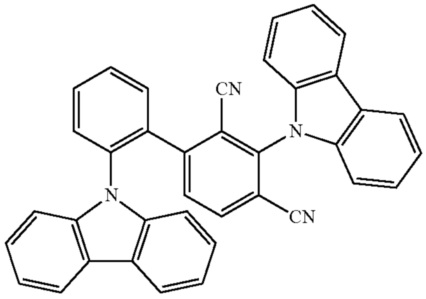
75
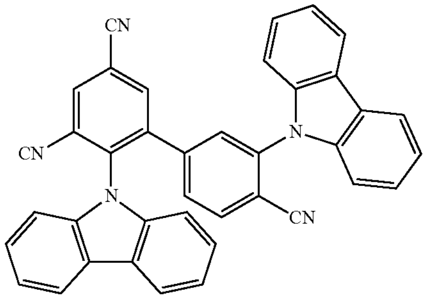
-continued
76
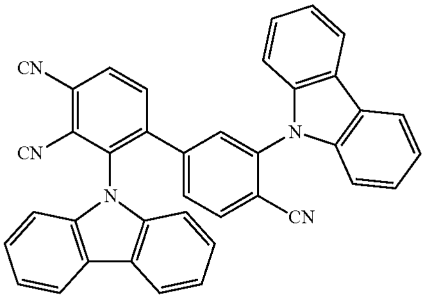
77
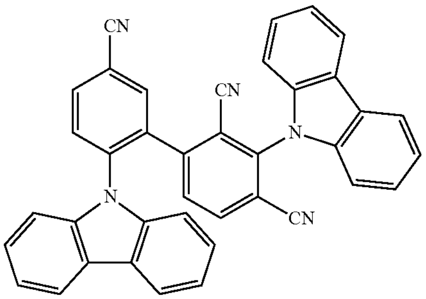
78
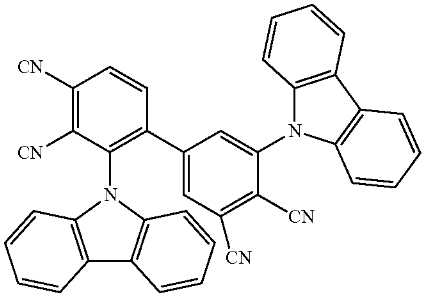
79
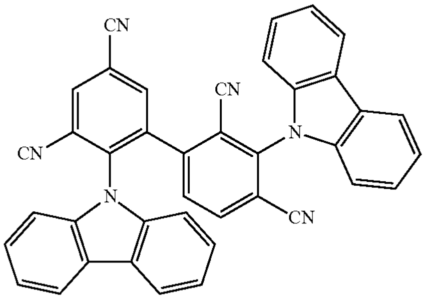
80
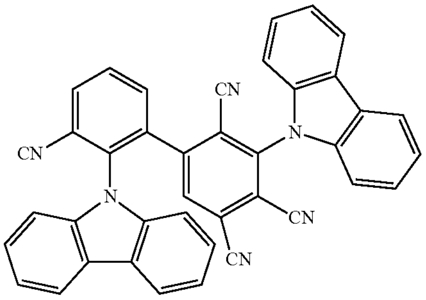

-continued
81
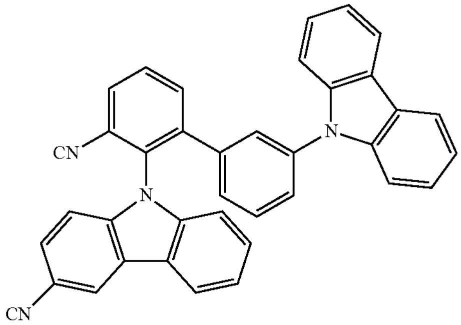
82
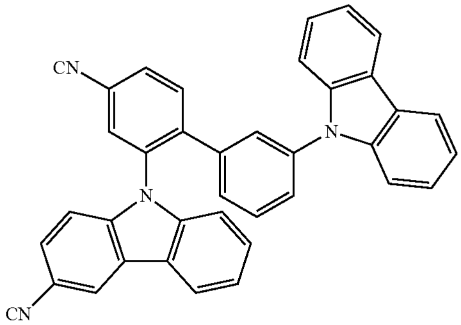
83
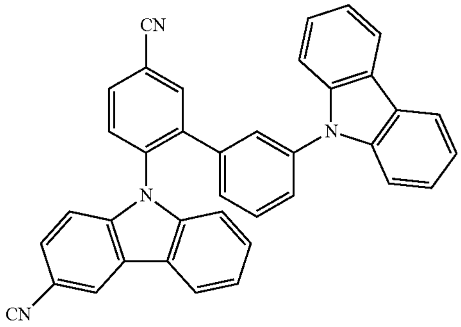
84
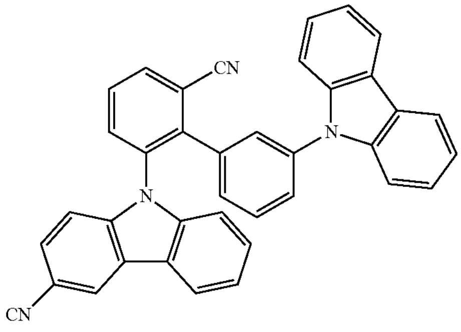
-continued
85
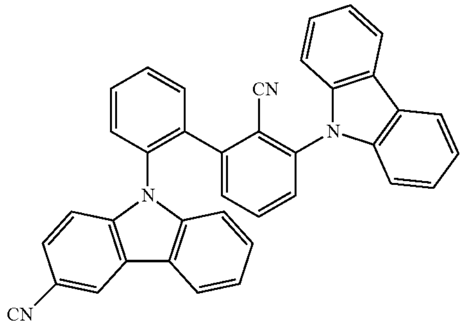
86
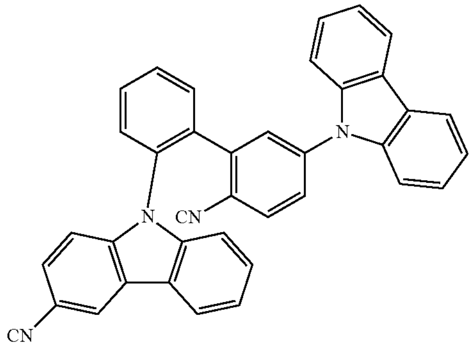
87
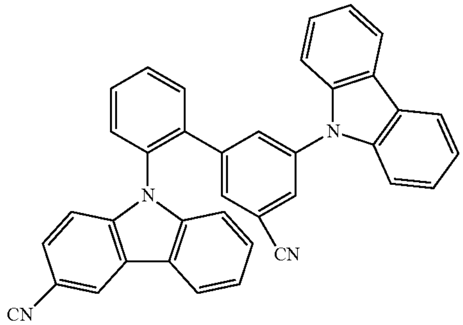
88
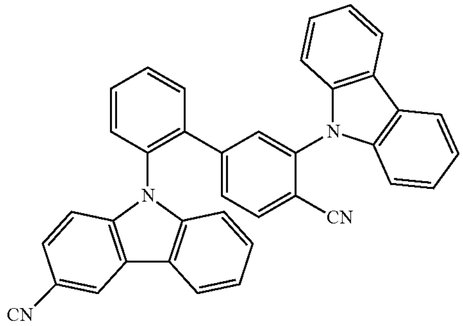
89
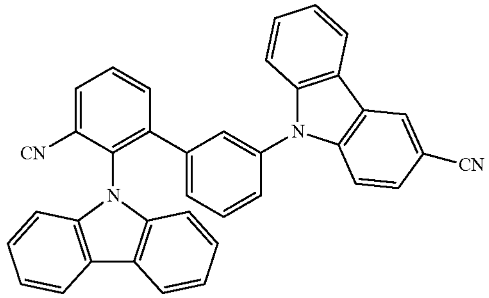

-continued
90
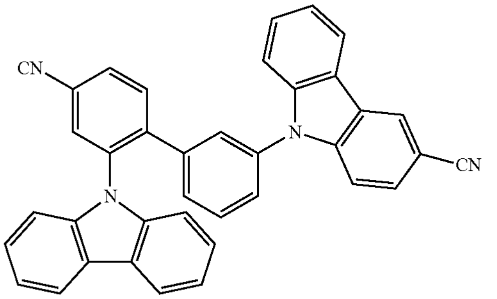
91
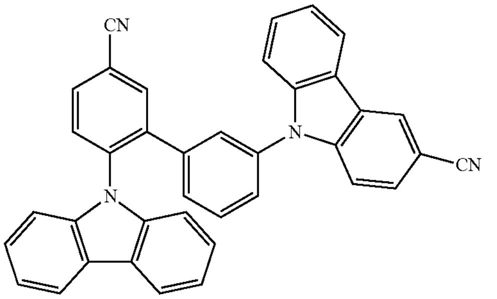
92
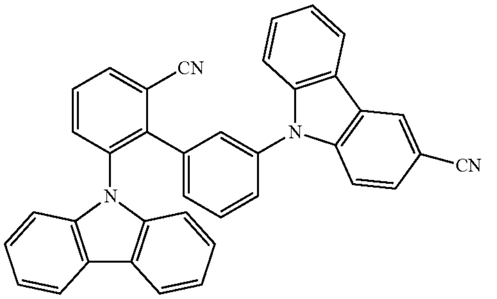
93
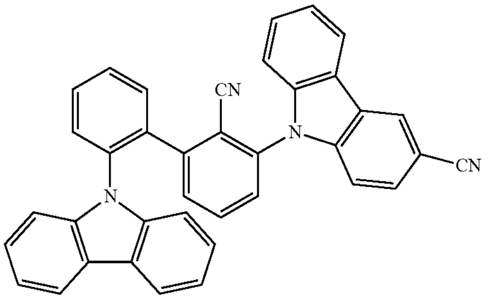
94
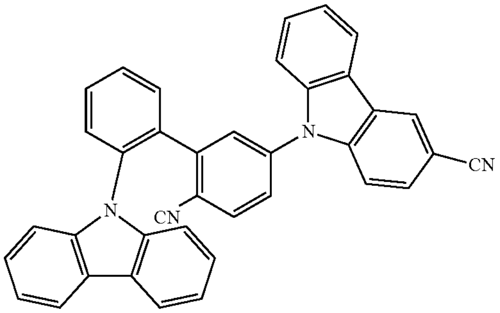
-continued
95
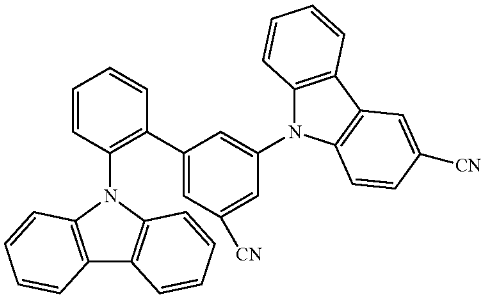
96
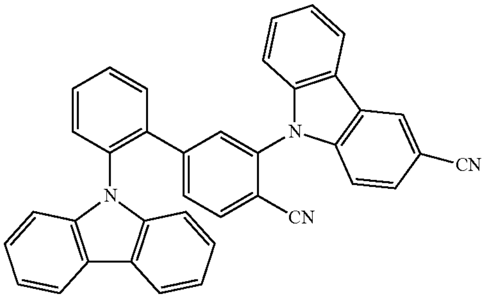
97
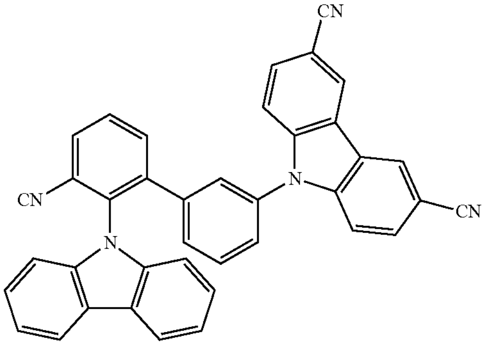
98
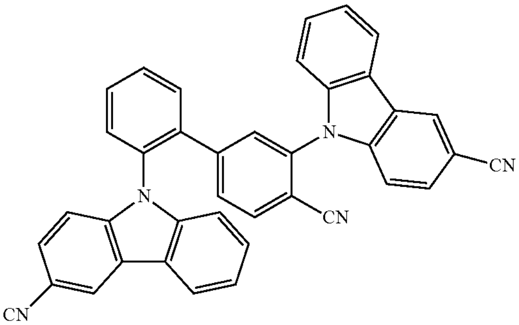

-continued
99
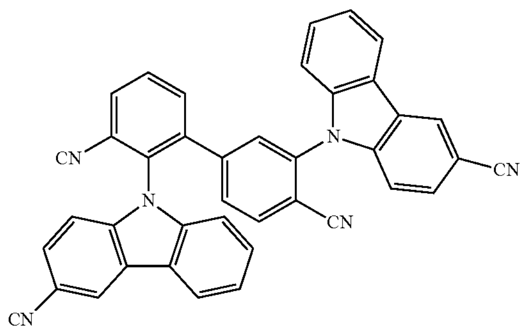
100
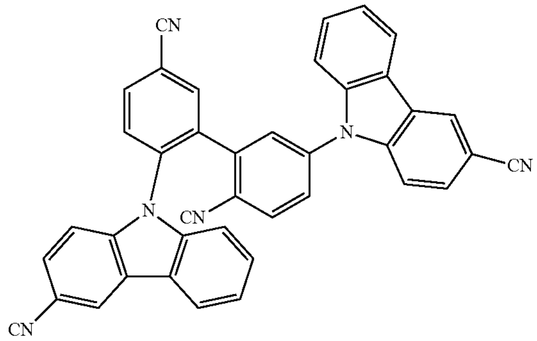
101
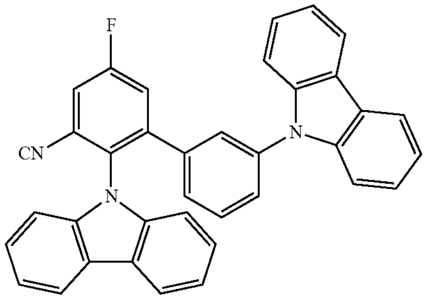
102
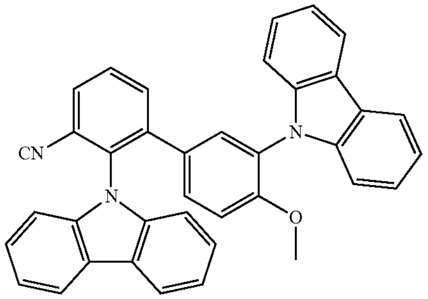
103
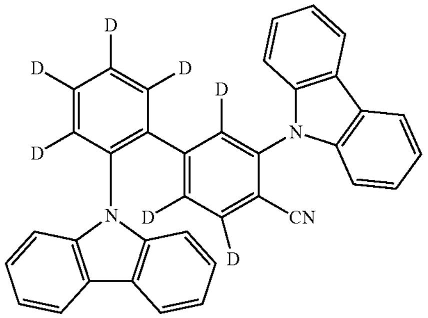
-continued
104
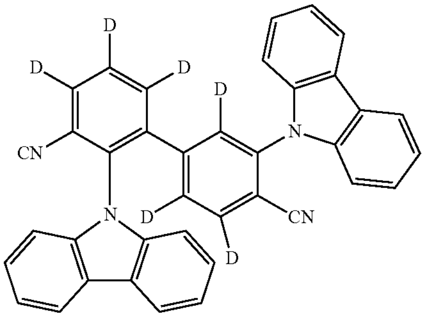
105
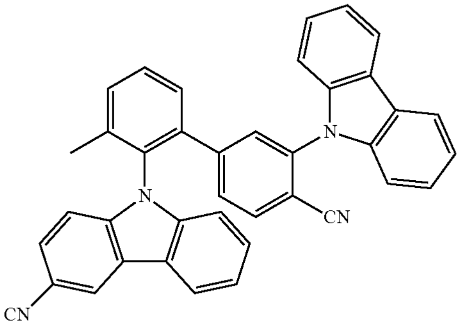
106
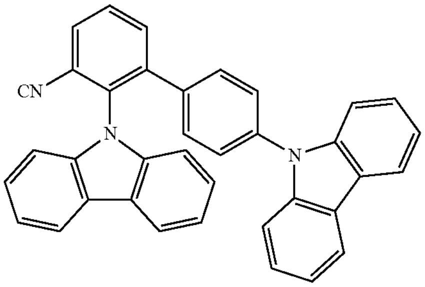
107
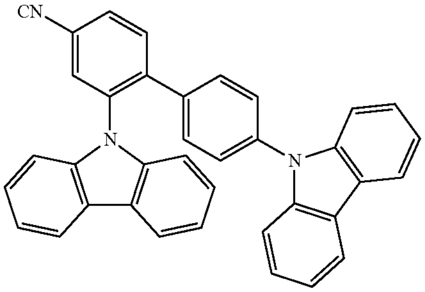
108
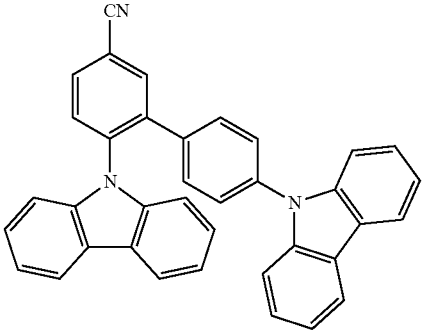

-continued
109
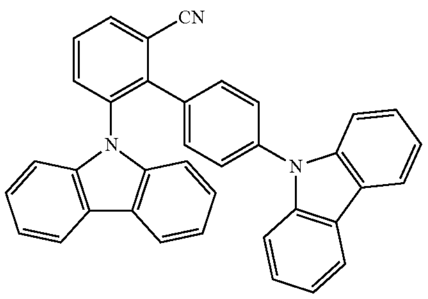
110
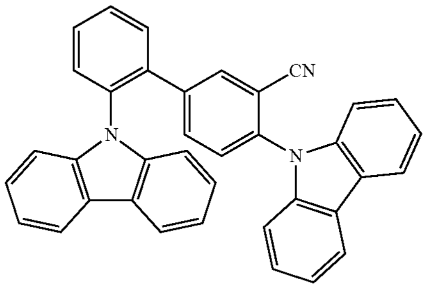
111
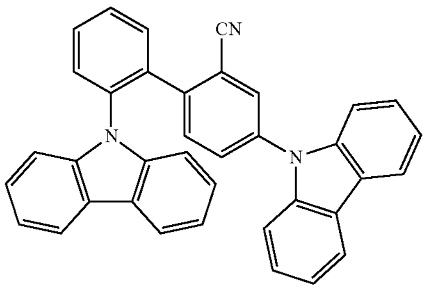
112
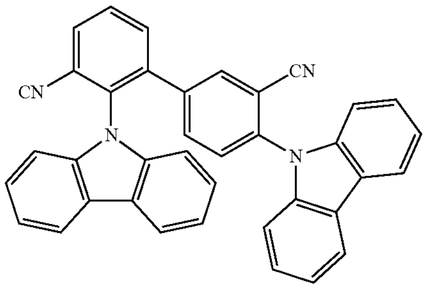
113
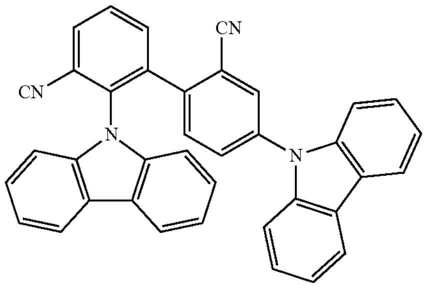
-continued
114
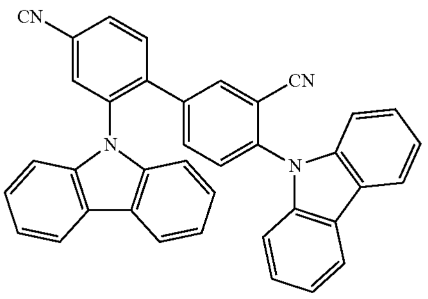
115
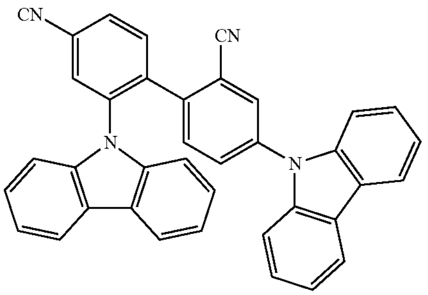
116
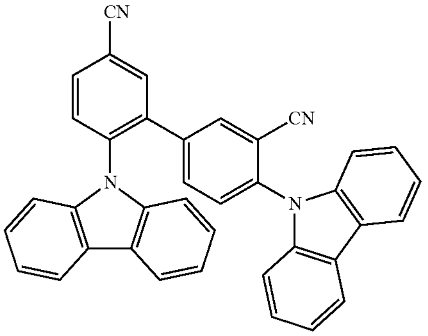
117
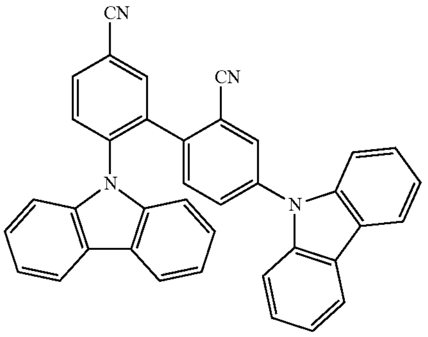
118
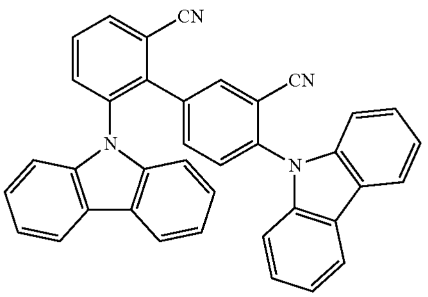

-continued
119
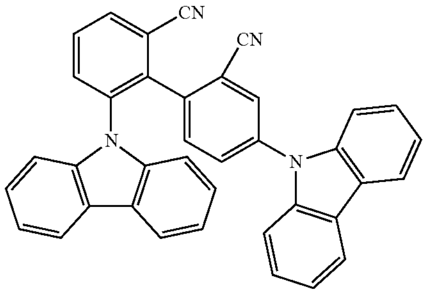
120
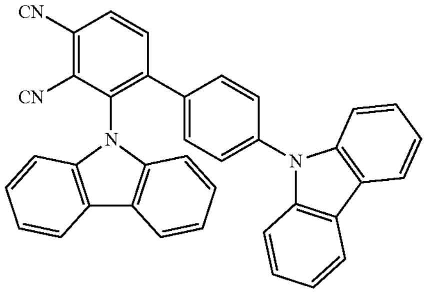
121
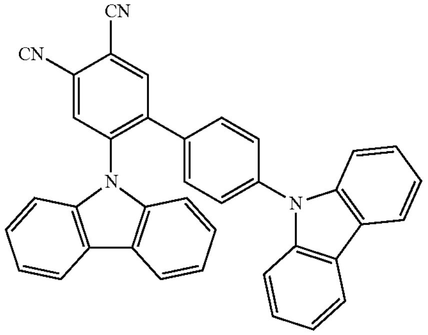
122
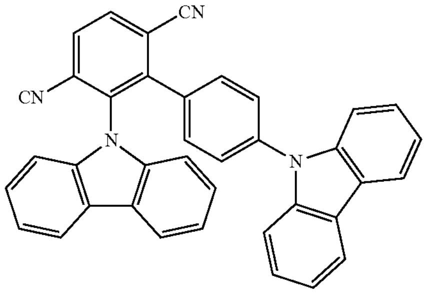
123
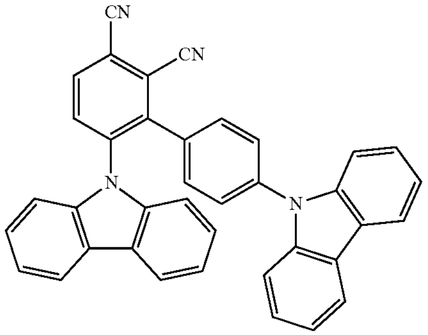
-continued
124
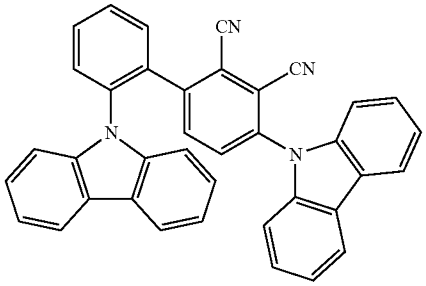
125
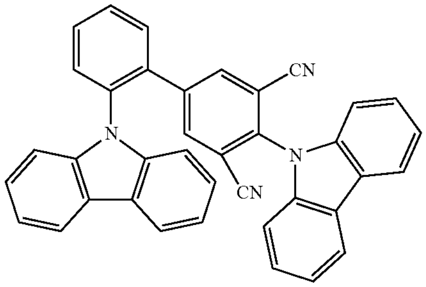
126
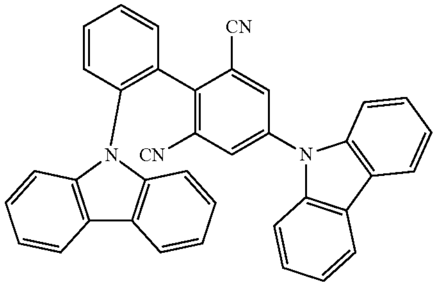
127
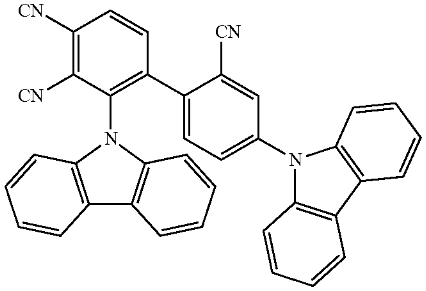
128
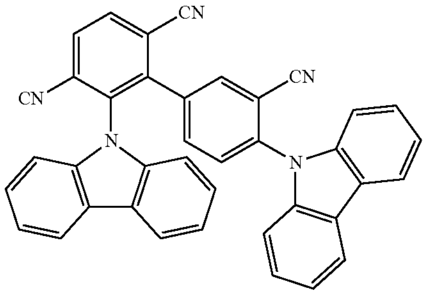

-continued
129
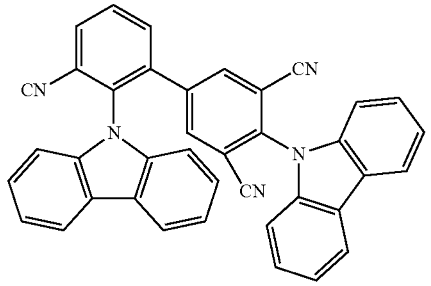
130
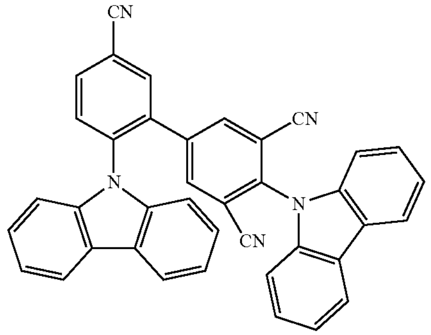
131
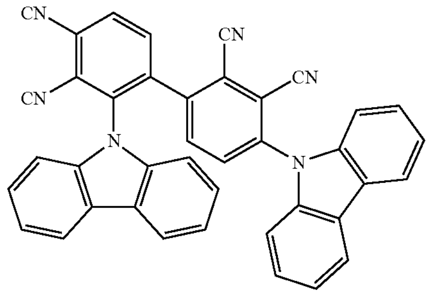
132
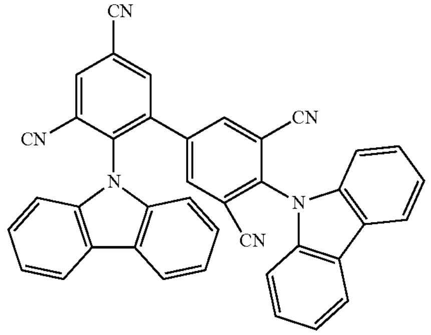
133
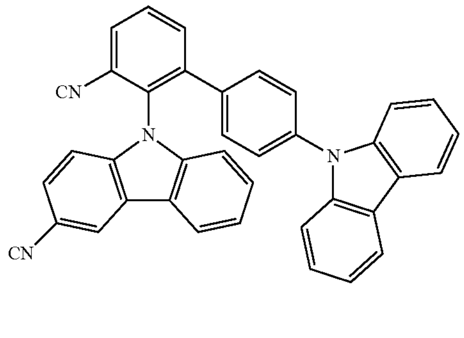
-continued
134
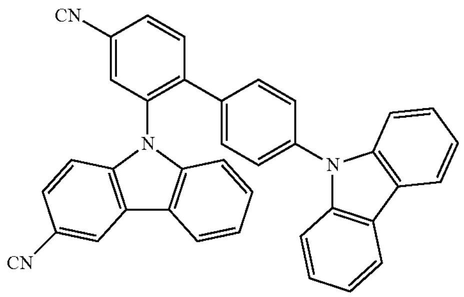
135
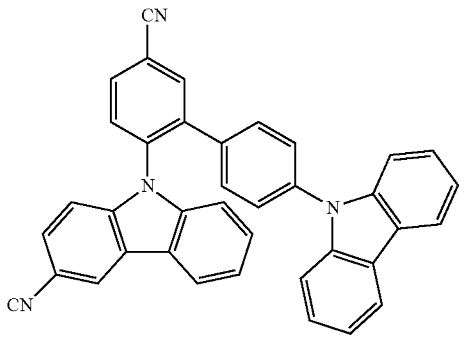
136
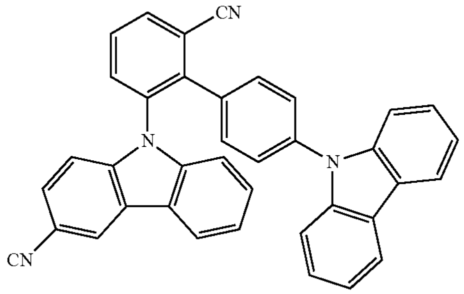
137
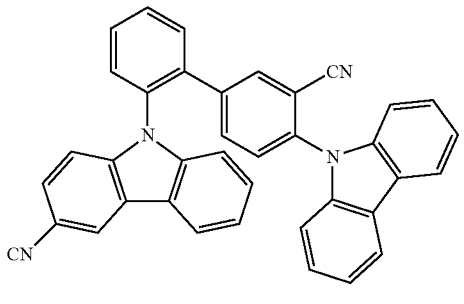
138
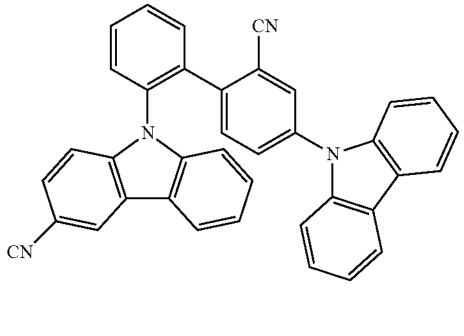

-continued
139
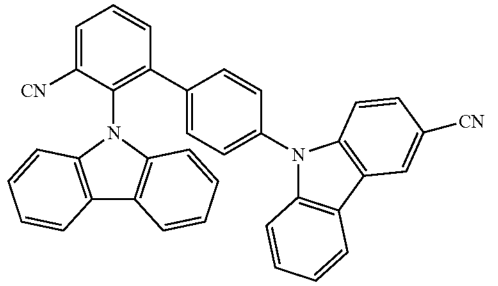
140
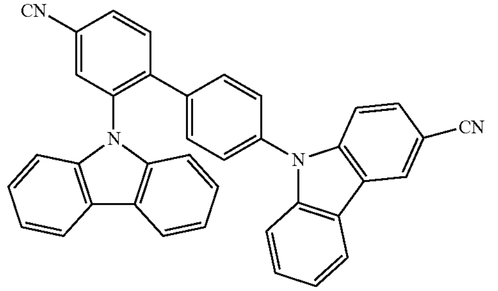
141
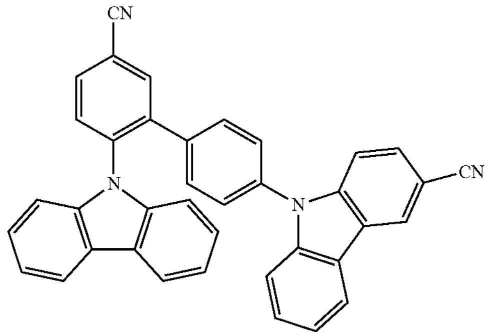
142
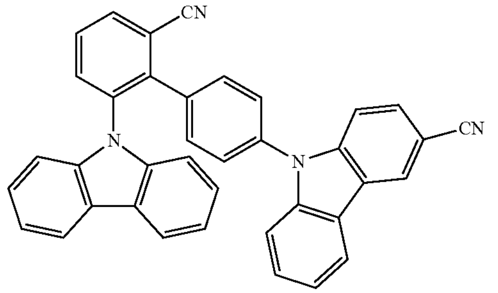
143
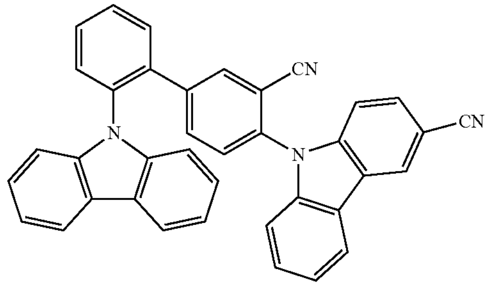
-continued
144
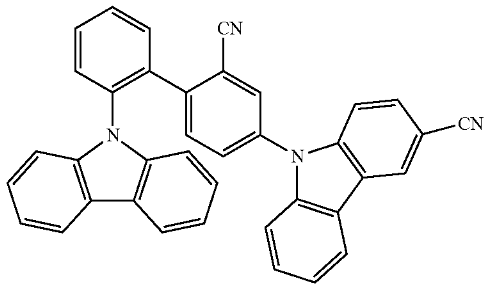
145
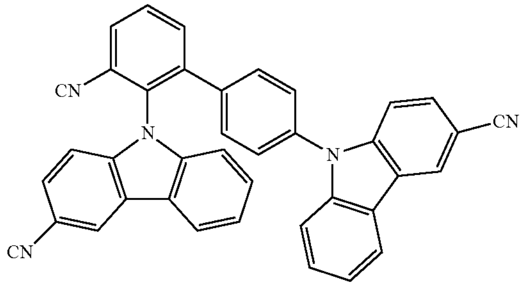
146
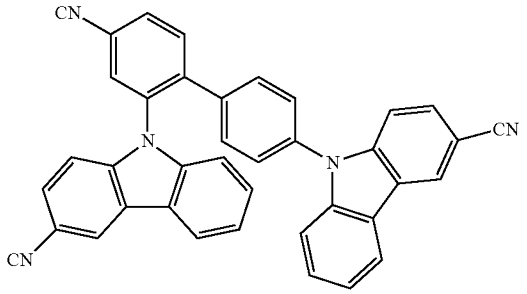
147
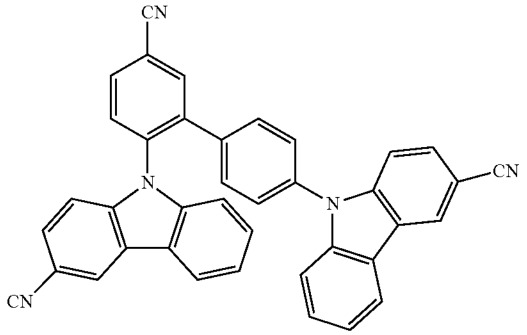
148
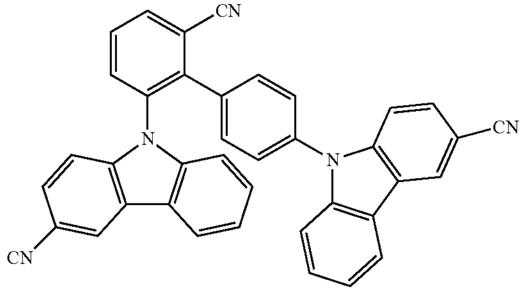

-continued
149
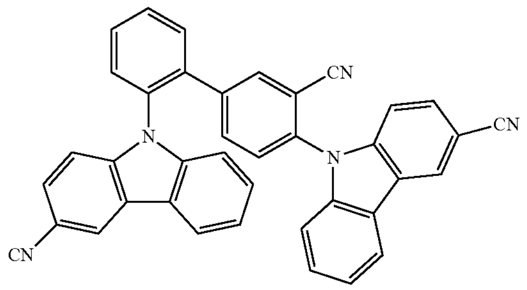
150
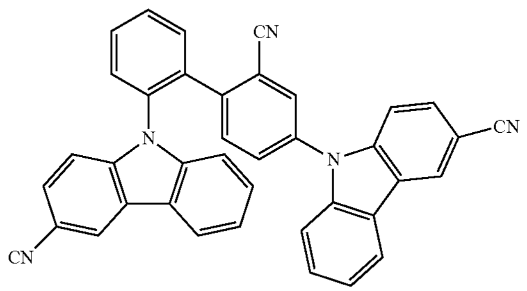
151
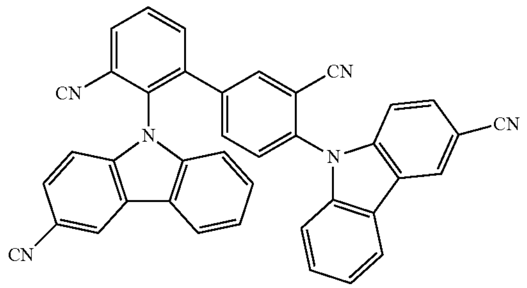
152
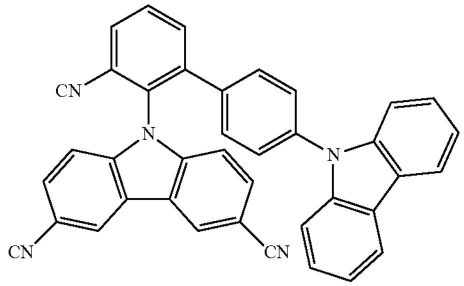
153
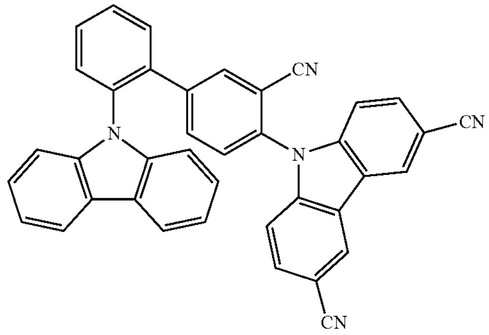
-continued
154
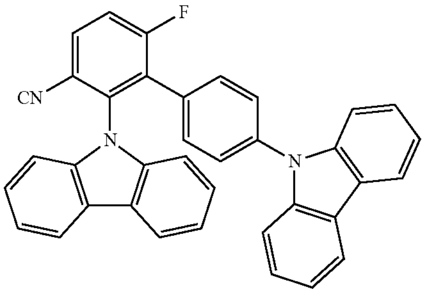
155
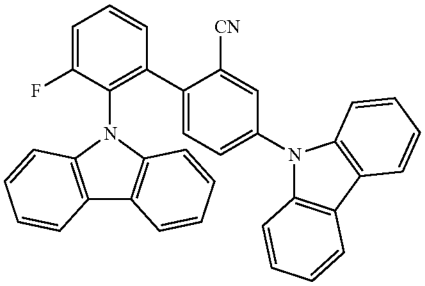
156
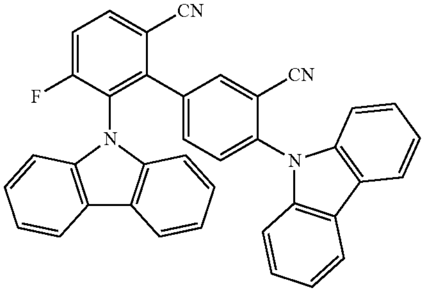
157
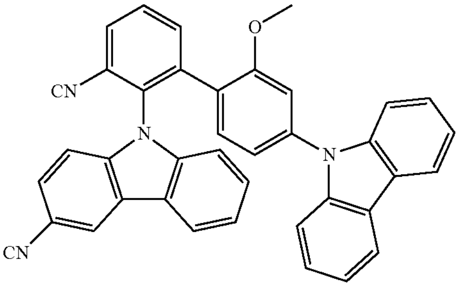
158
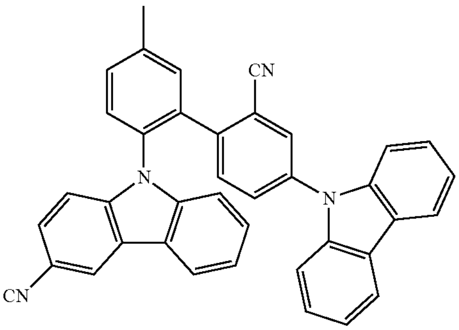

-continued
159
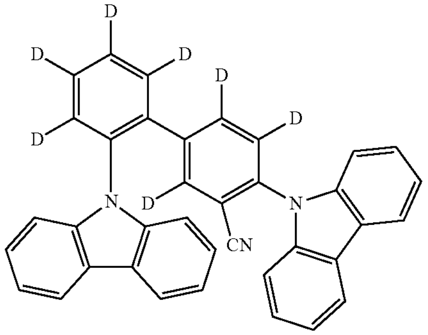
160
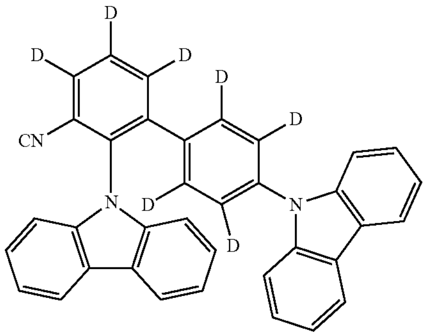
161
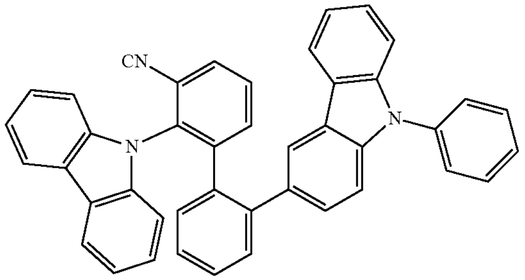
162
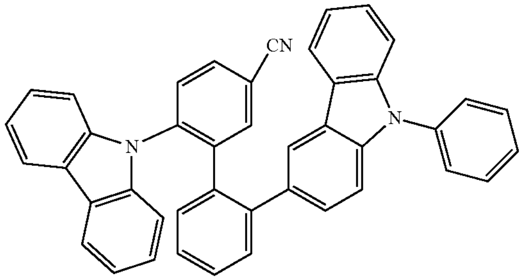
163
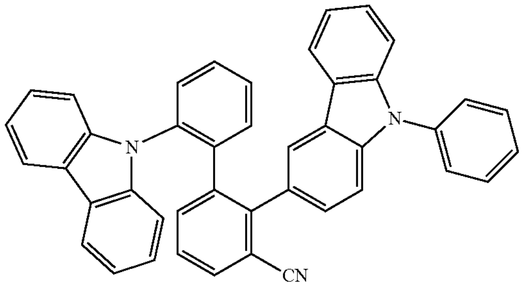
-continued
164
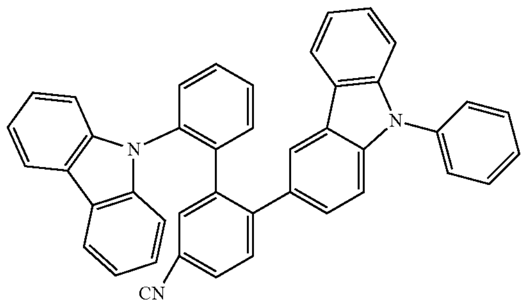
165
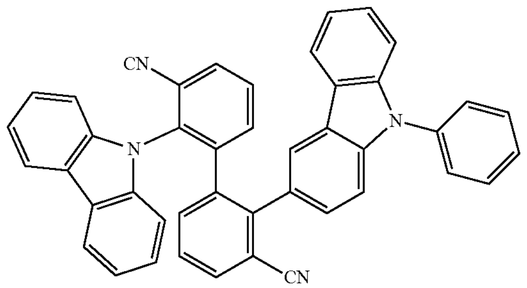
166
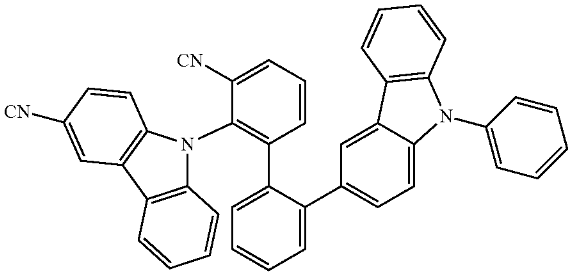
167
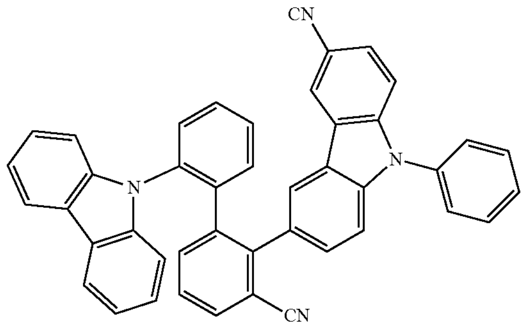
168
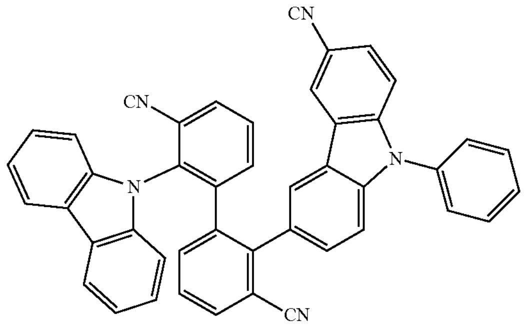

-continued
169
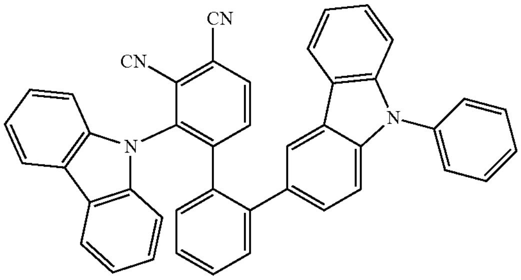
170
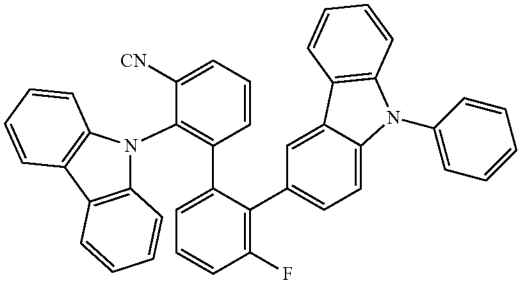
171
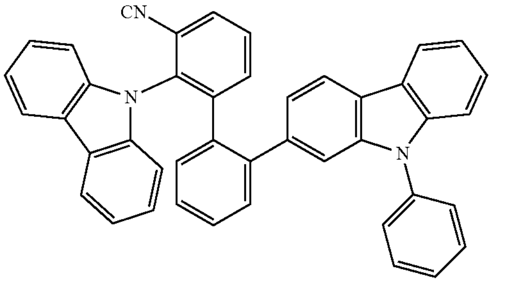
172
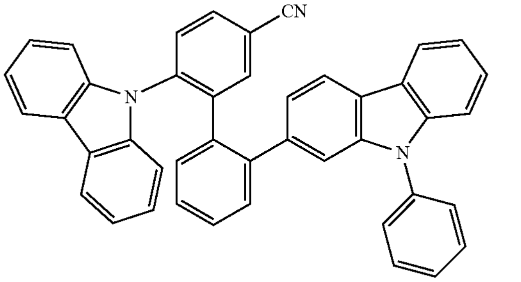
173
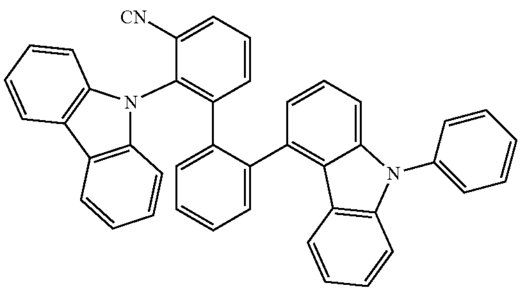
-continued
174
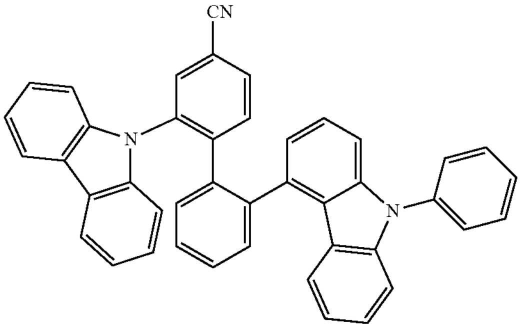
175
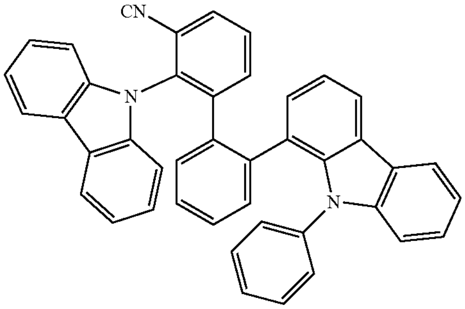
176
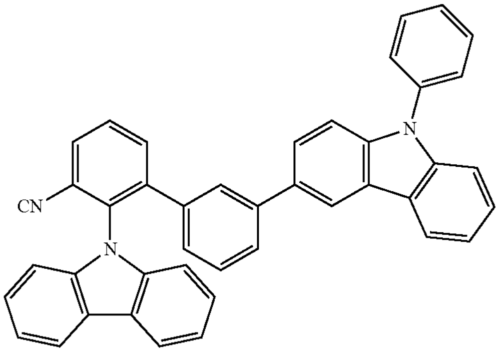
177
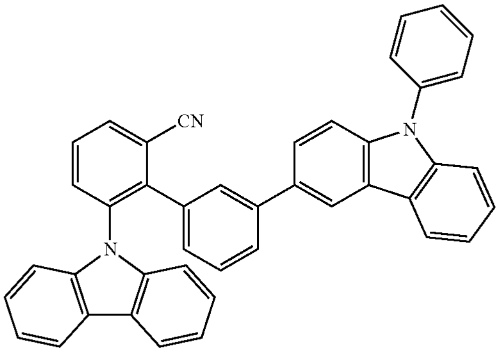

-continued
178
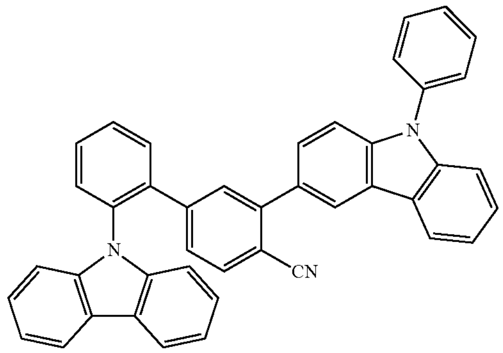
179
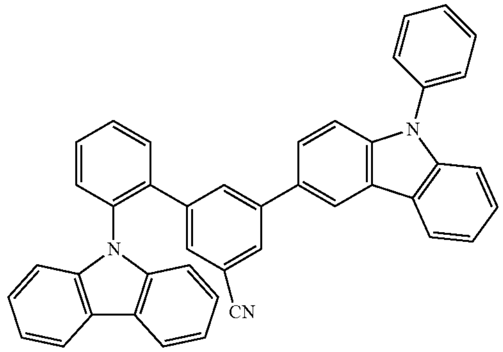
180
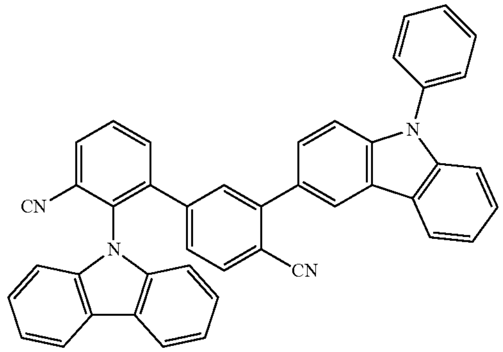
181
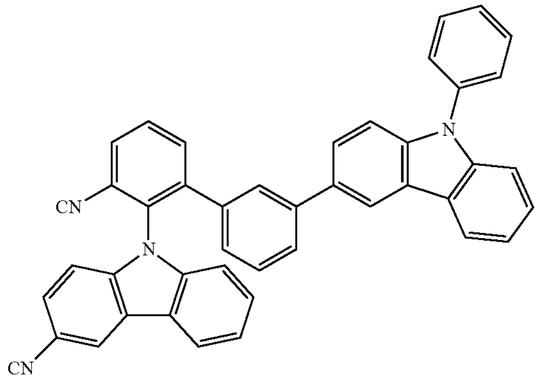
-continued
182
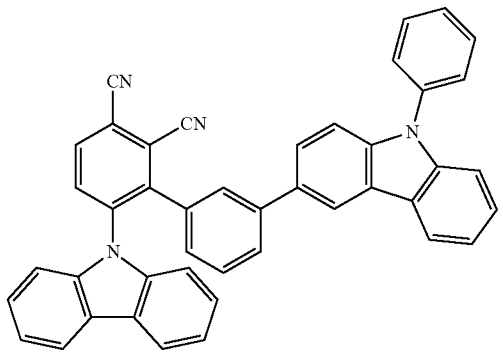
183
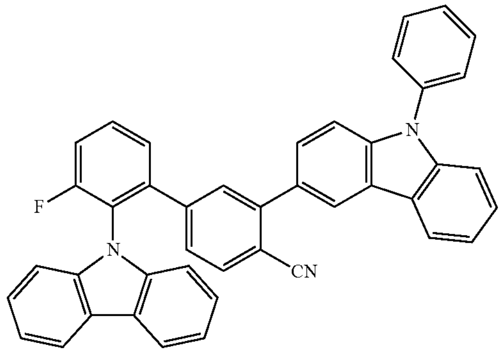
184
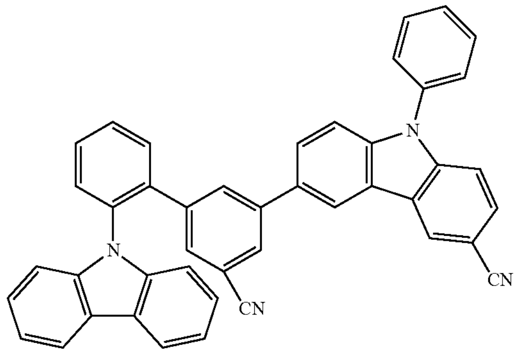
185
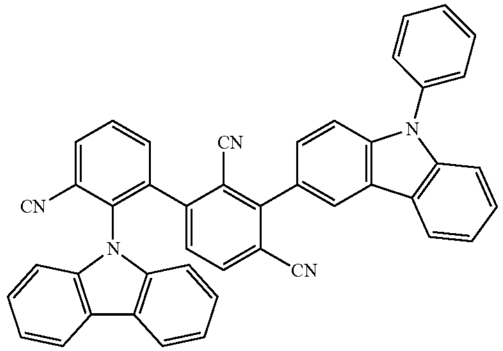

-continued
186
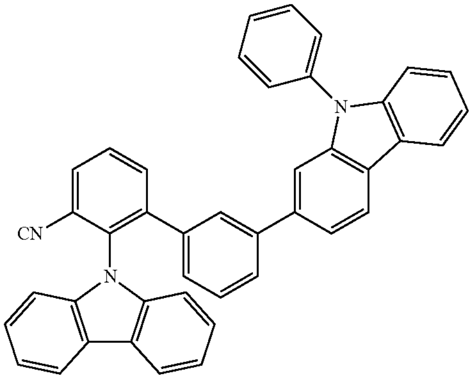
187
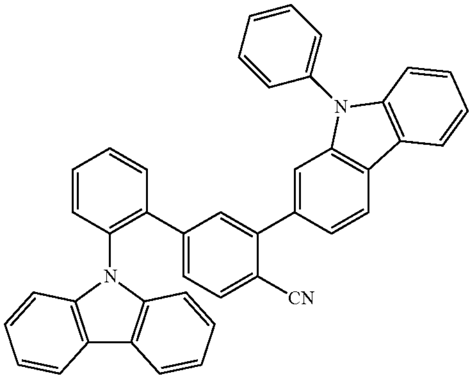
188
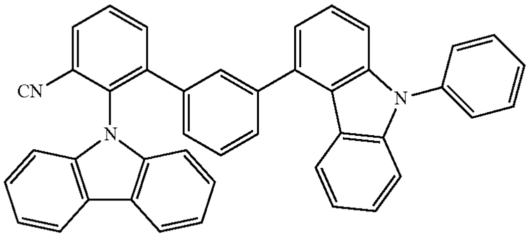
189
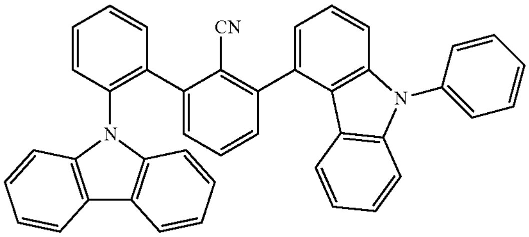
190
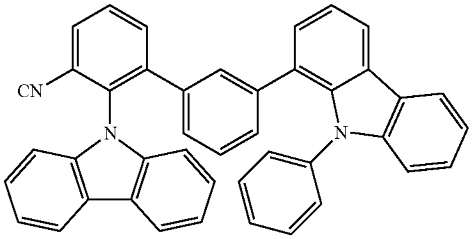
-continued
191
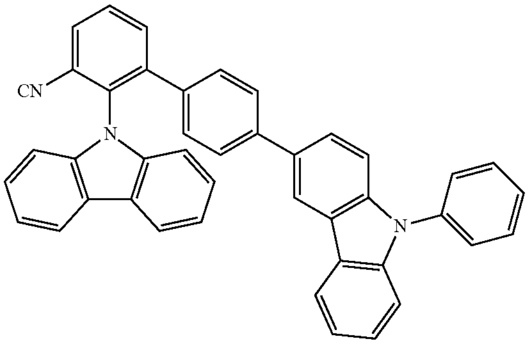
192
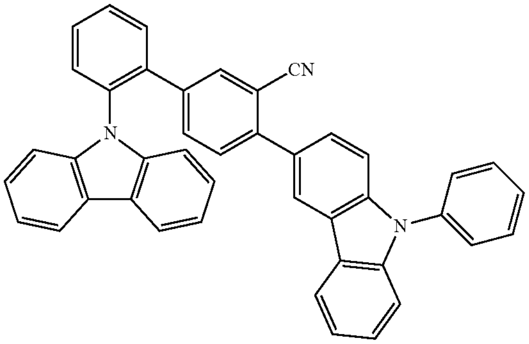
193
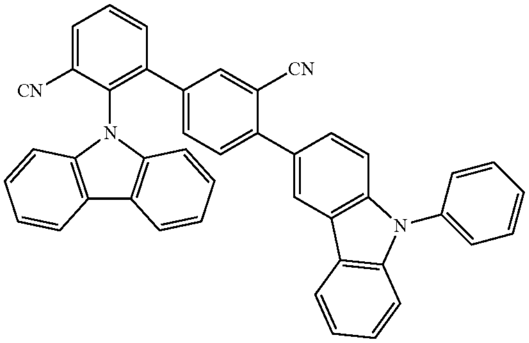
194
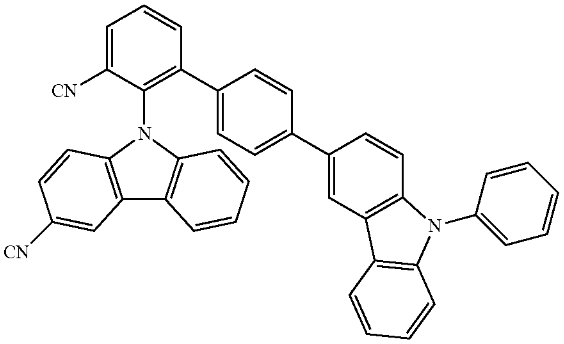

-continued
195
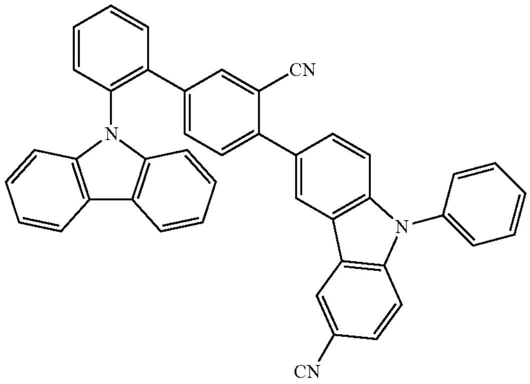
196
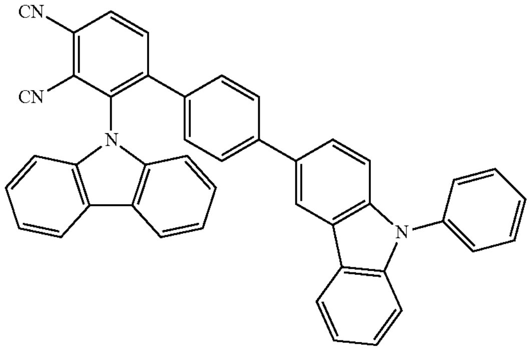
197
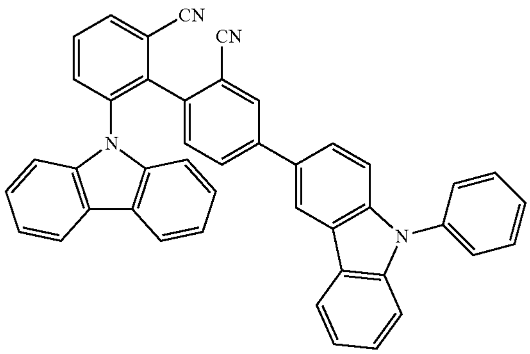
198
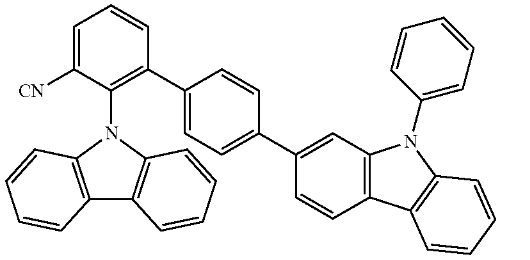
-continued
199
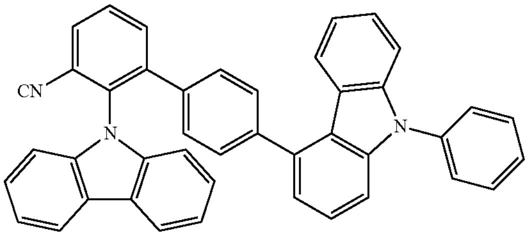
200
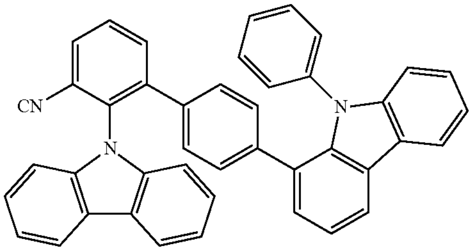
201
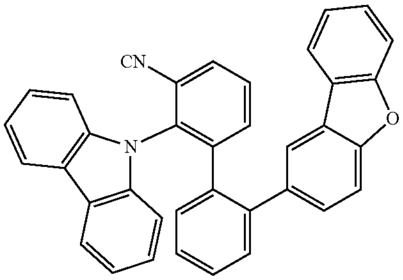
202
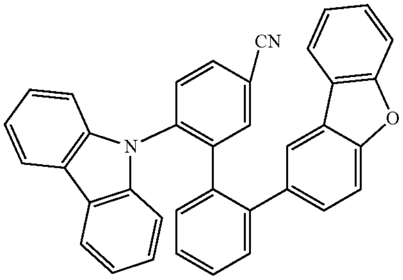
203
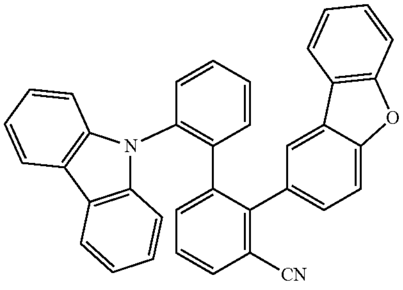

-continued
204
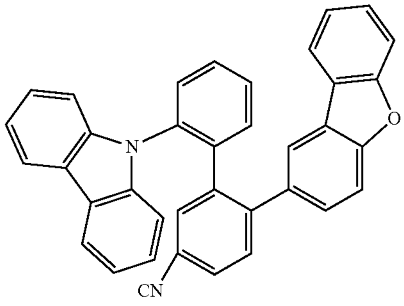
205
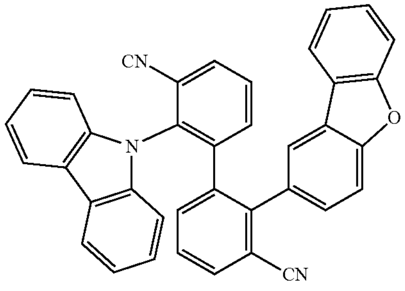
206
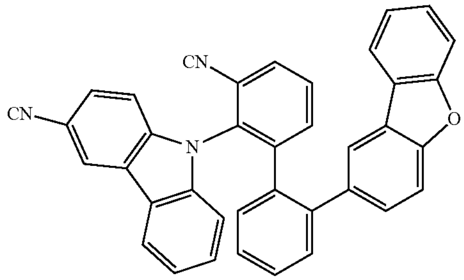
207
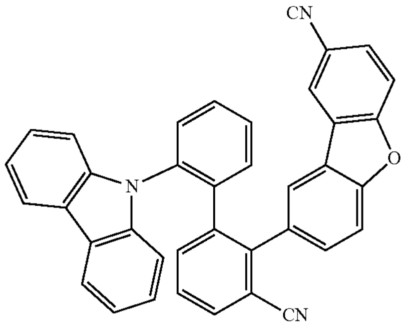
208
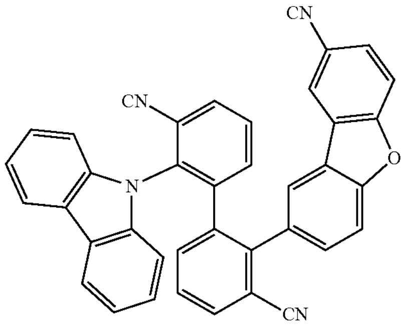
-continued
209
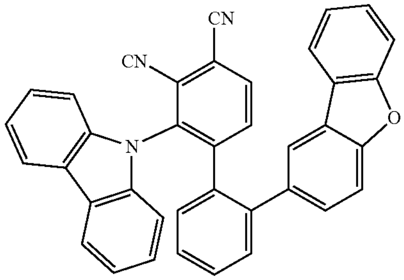
210
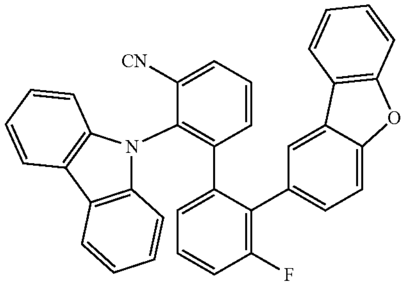
211
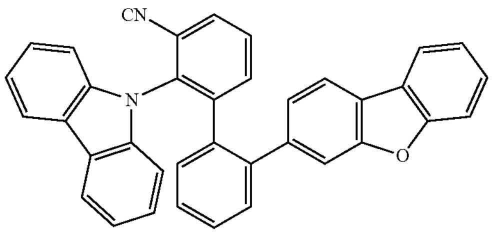
212
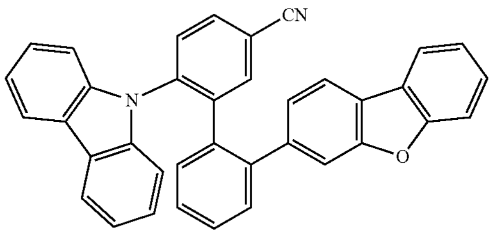
213
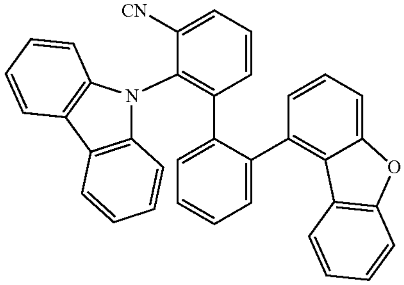

214
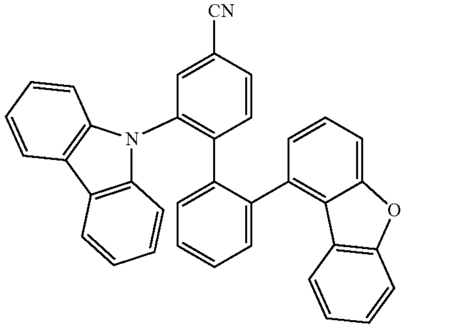
215
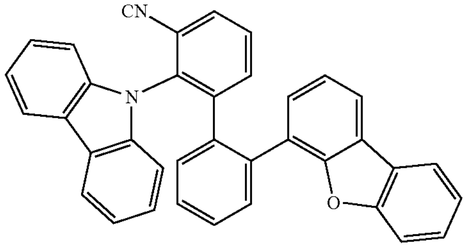
216
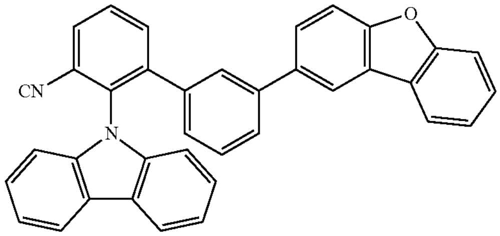
217
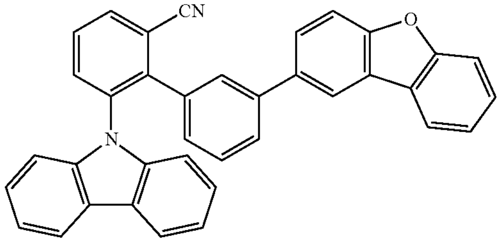
218
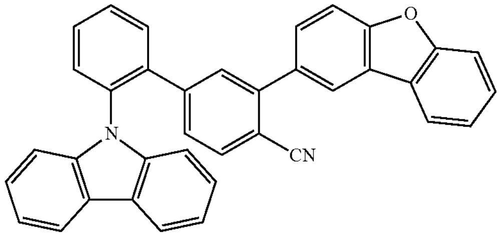
219
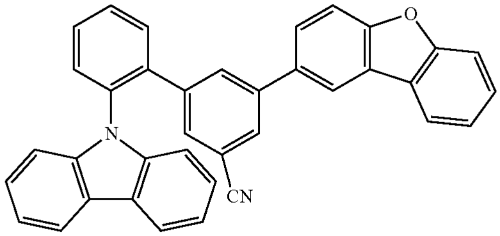
220
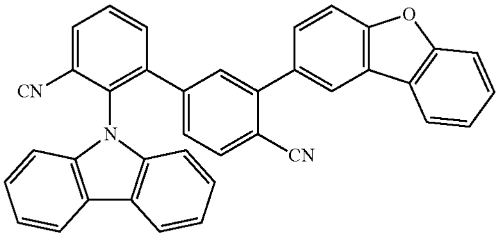
221
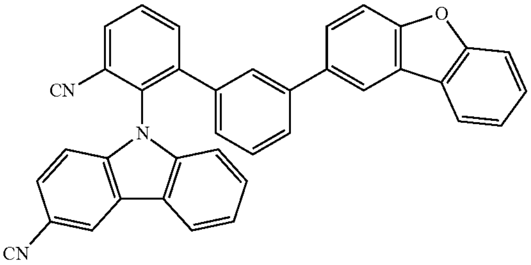
222
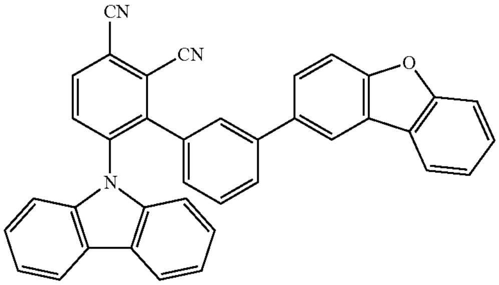
223
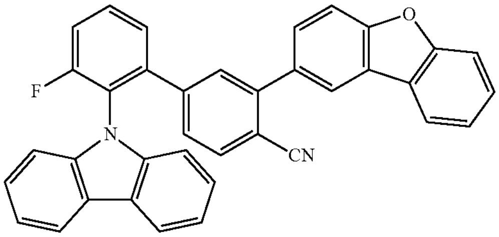
224
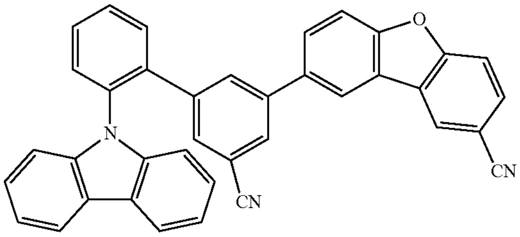

-continued
225
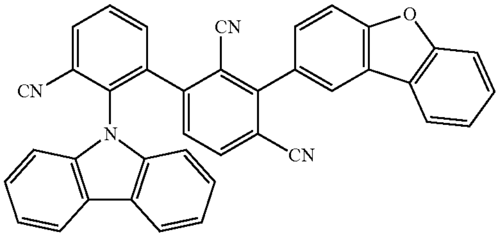
226
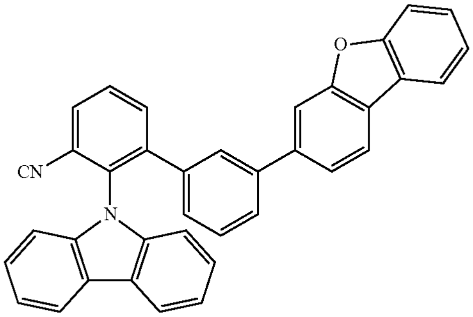
227
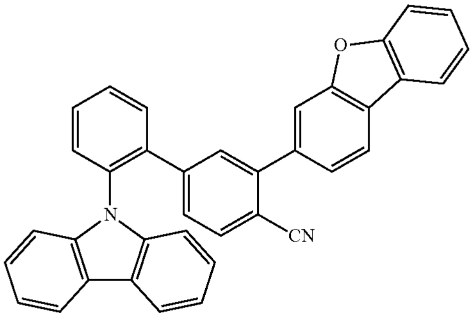
228
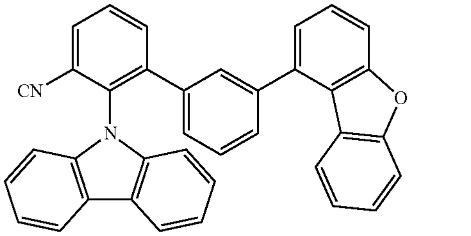
229
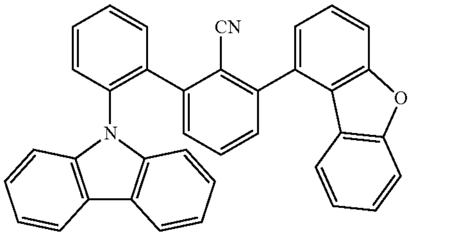
230
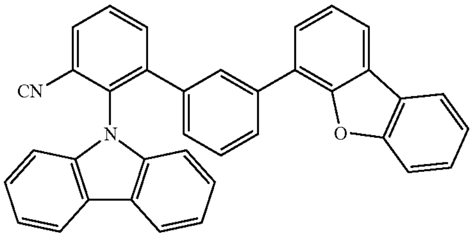
-continued
231
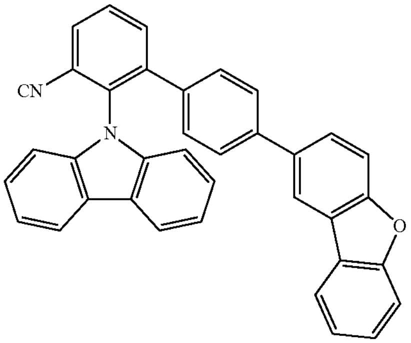
232
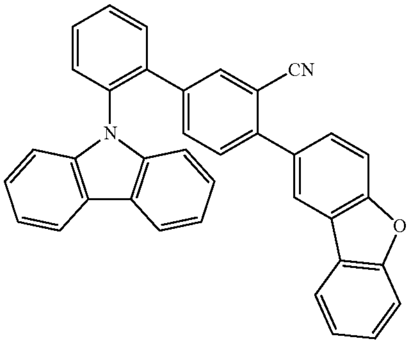
233
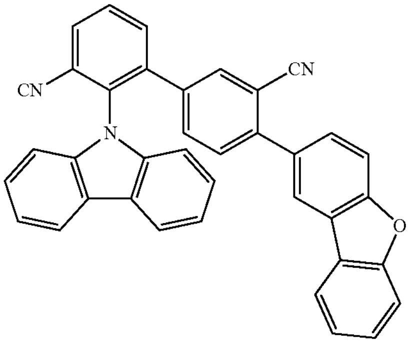
234
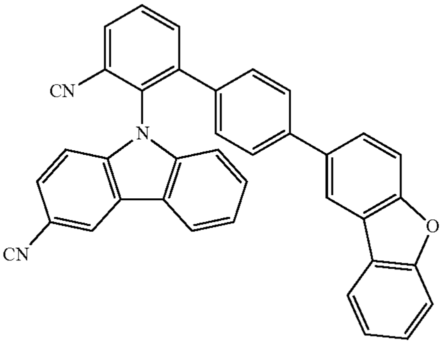

-continued
235
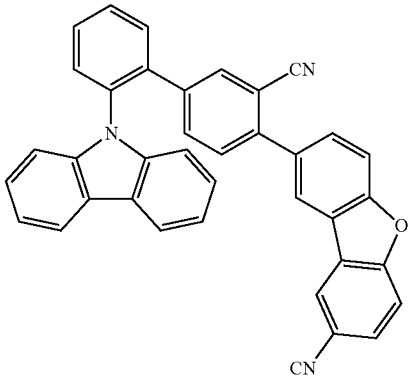
236
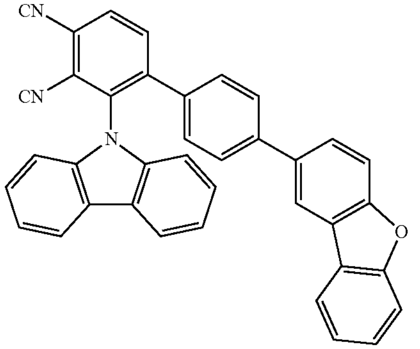
237
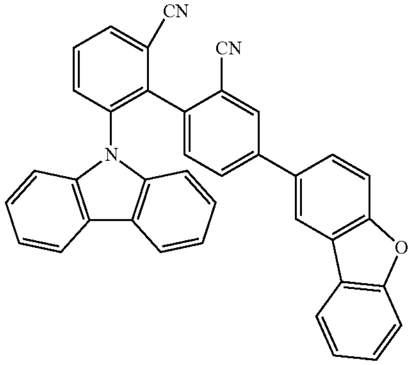
238
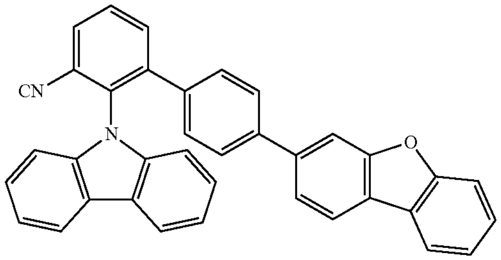
239
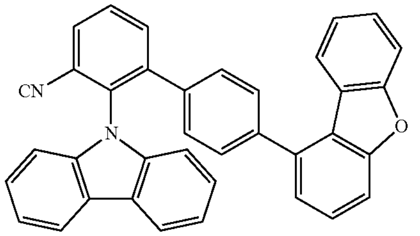
-continued
240
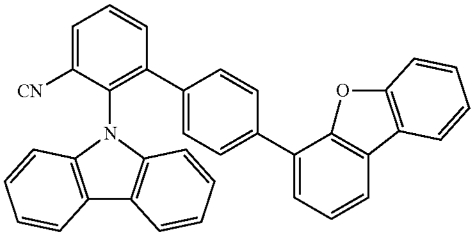
241
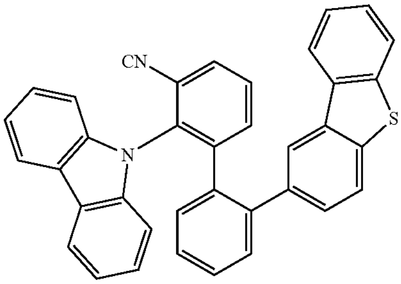
242
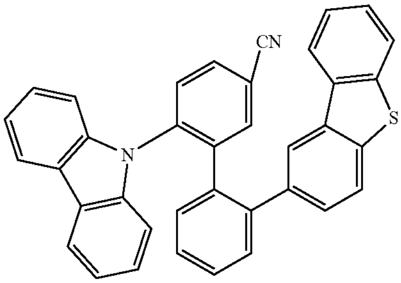
243
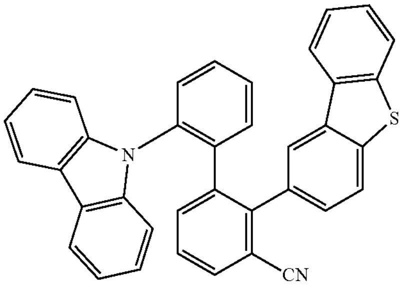
244
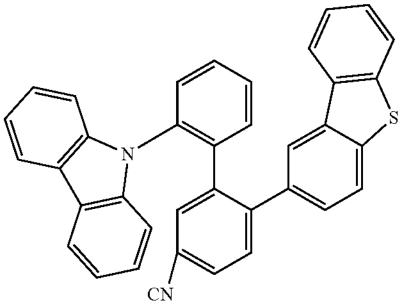

-continued
245
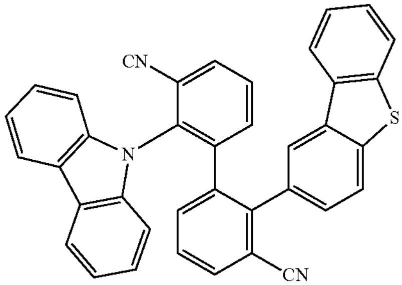
246
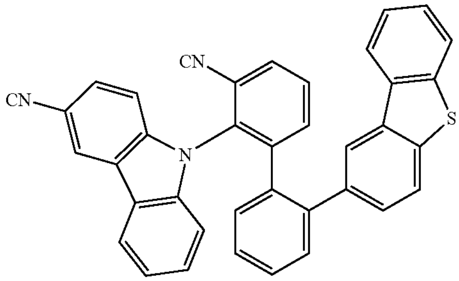
247
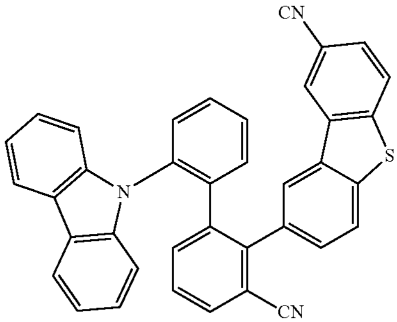
248
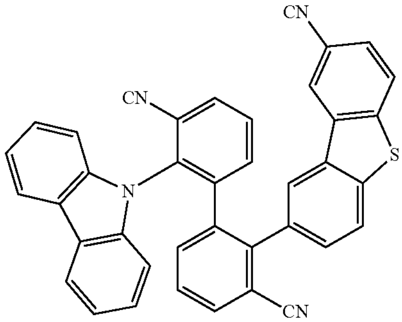
249
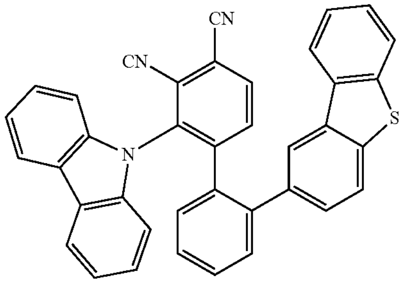
-continued
250
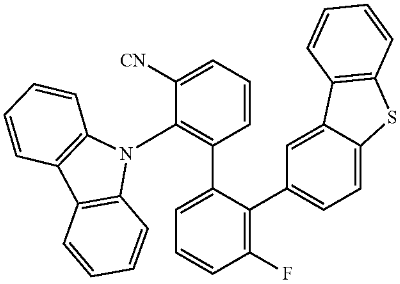
251
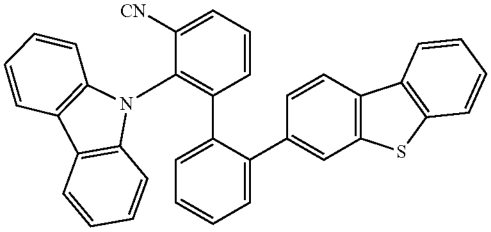
252
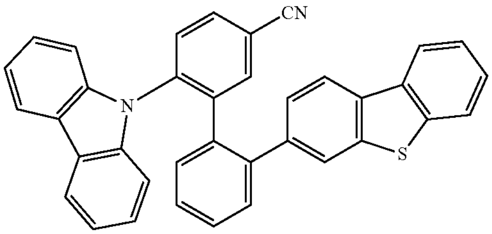
253
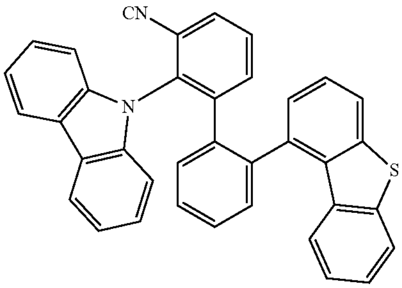
254
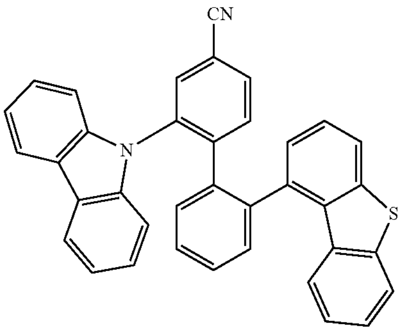

-continued
255
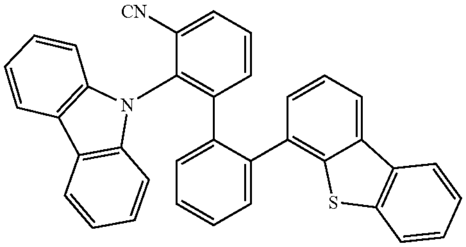
256
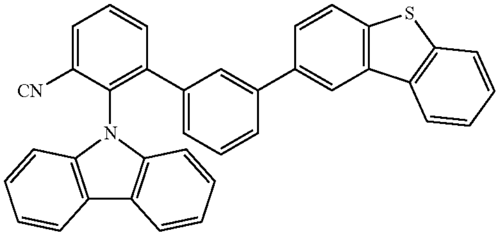
257
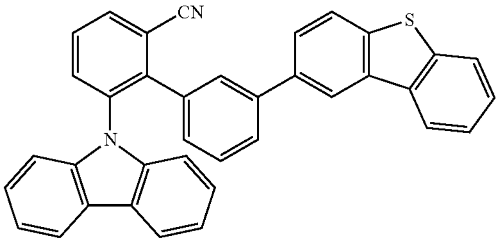
258
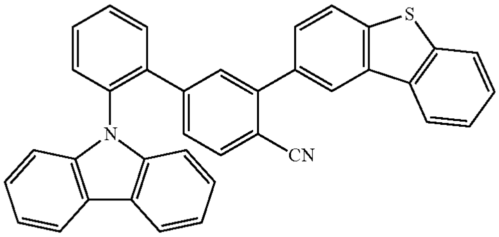
259
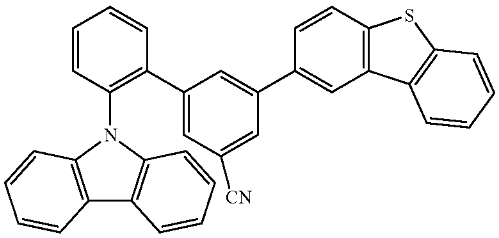
260
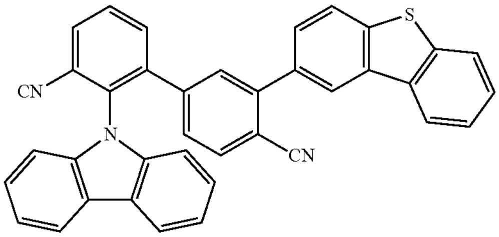
-continued
261
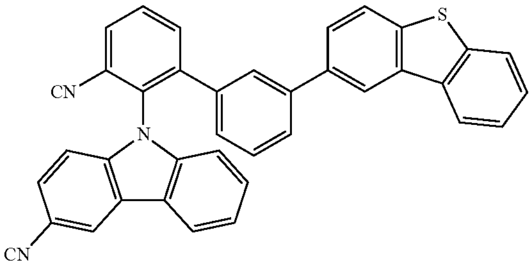
262
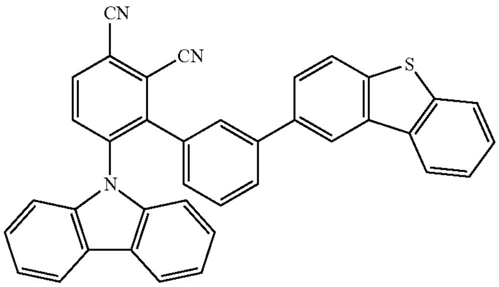
263
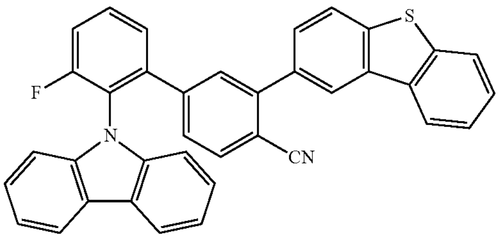
264
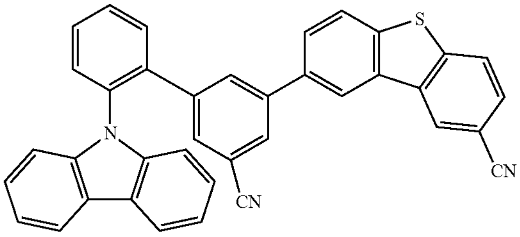
265
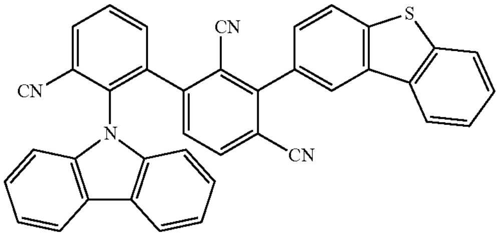

-continued
266
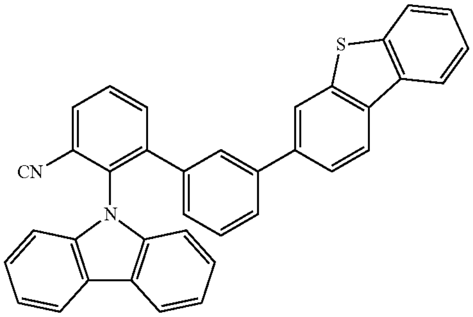
267
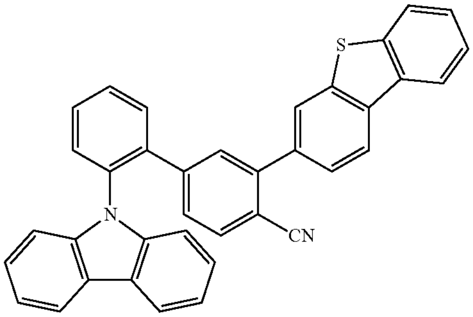
268
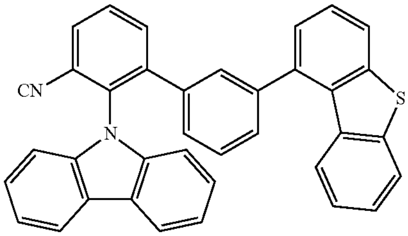
269
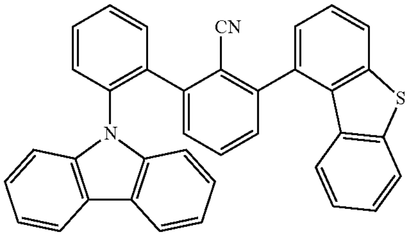
270
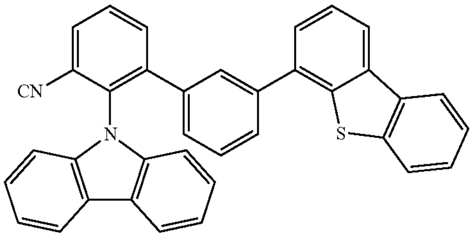
-continued
271
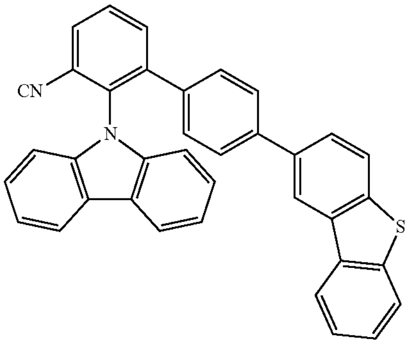
272
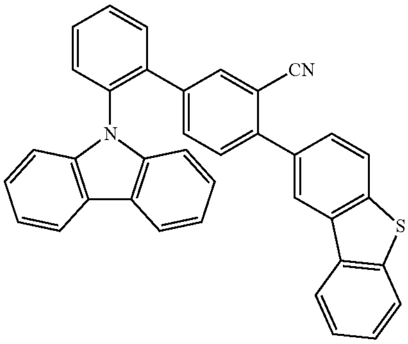
273
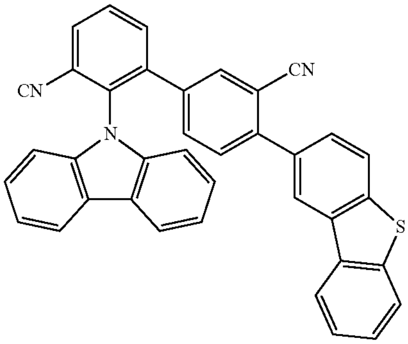
274
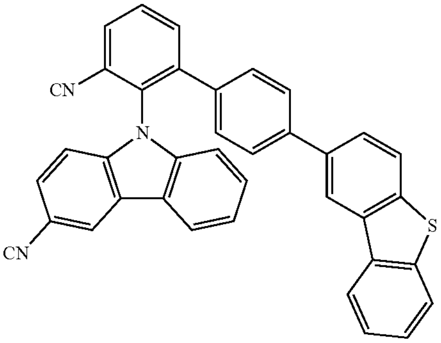

-continued
275
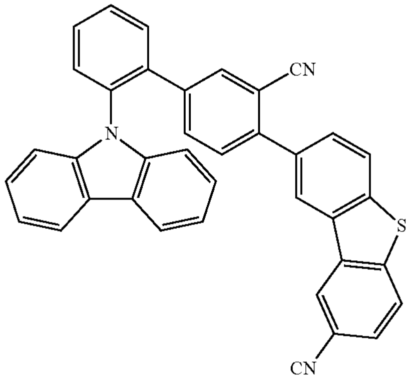
276
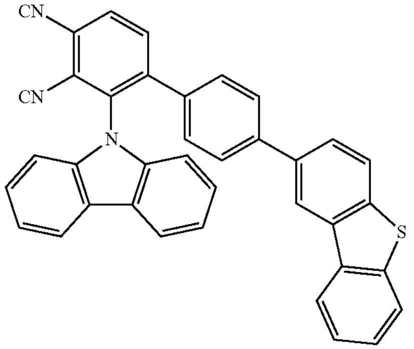
277
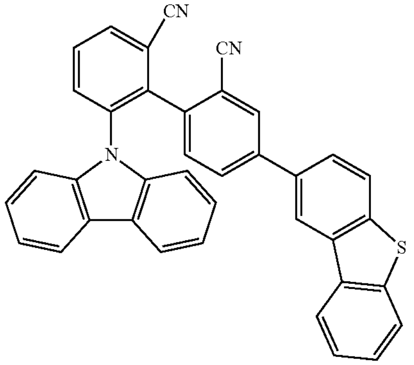
278
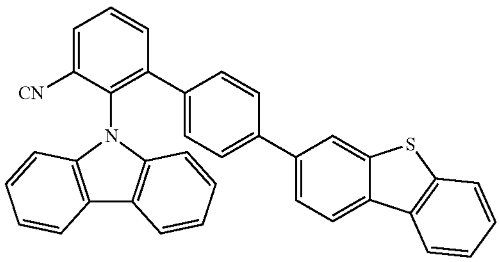
279
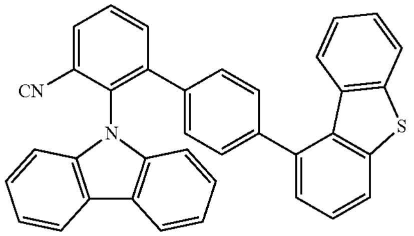
-continued
280
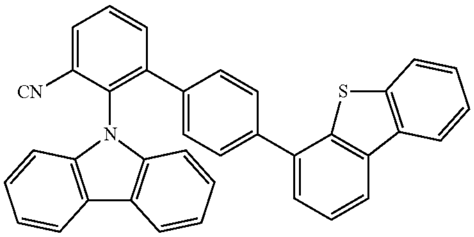
281
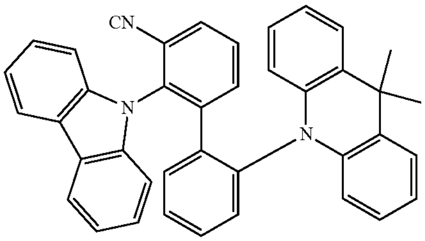
282
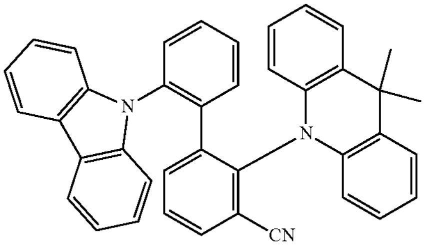
283
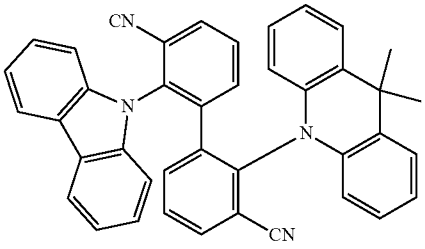
284
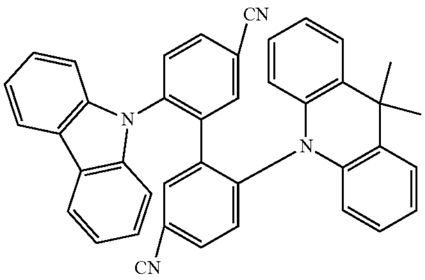
285
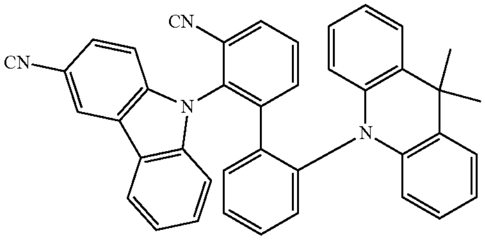

-continued
286
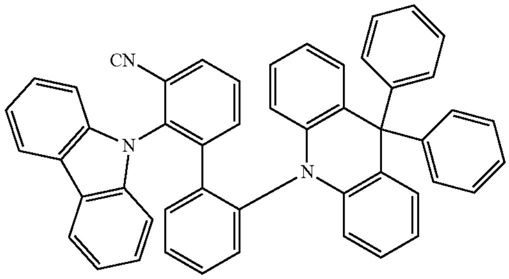
287
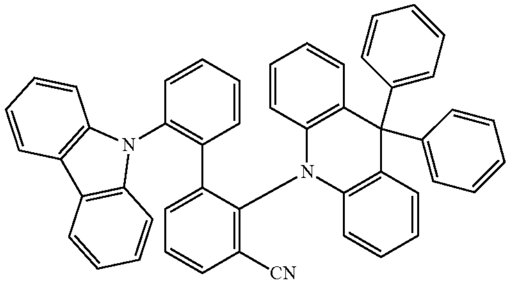
288
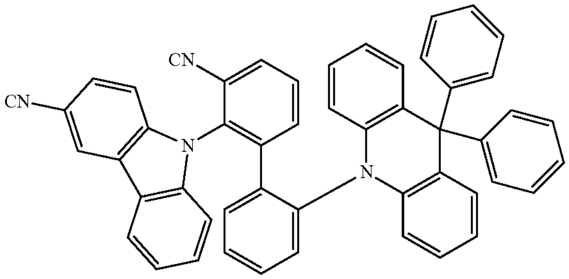
289
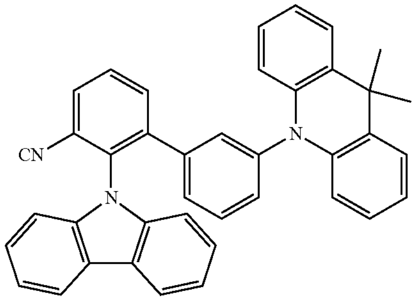
290
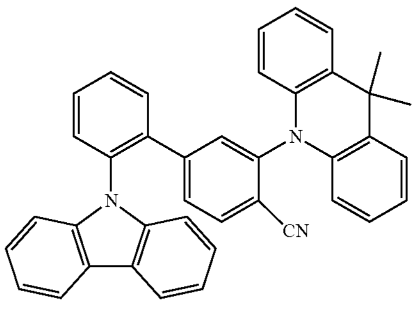
-continued
291
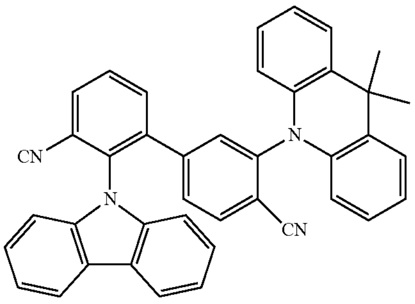
292
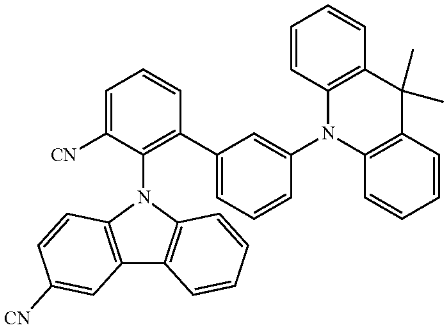
293
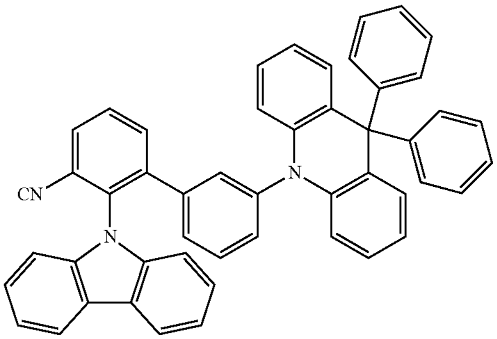
294
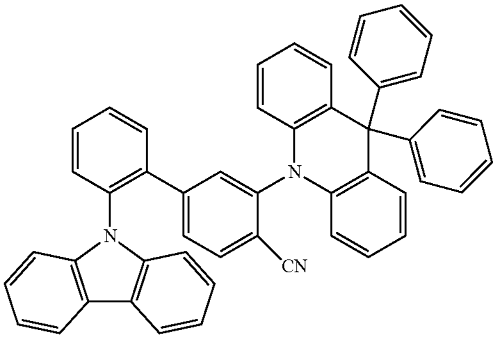

-continued
295
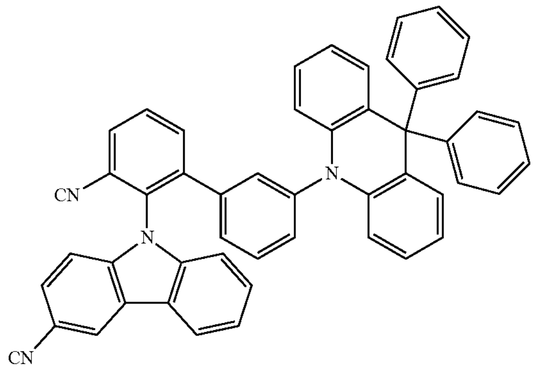
296
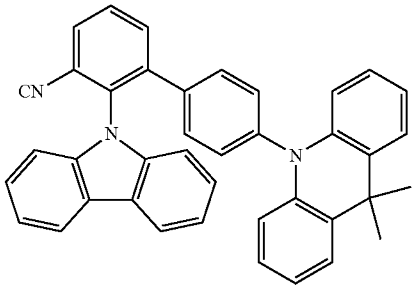
297
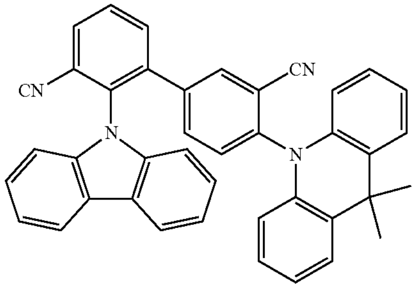
298
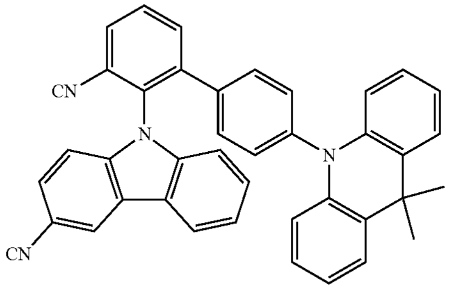
299
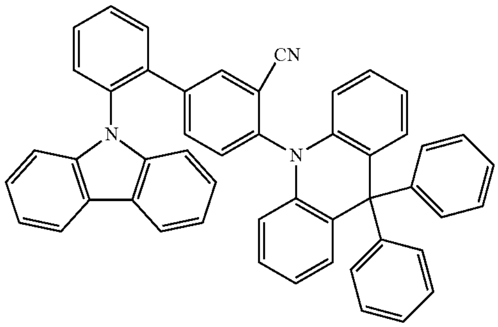
-continued
300
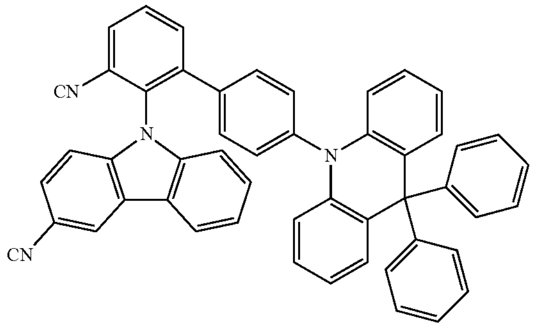
301
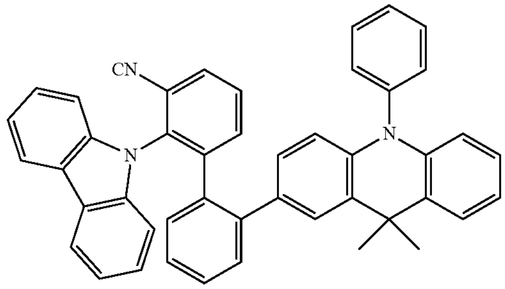
302
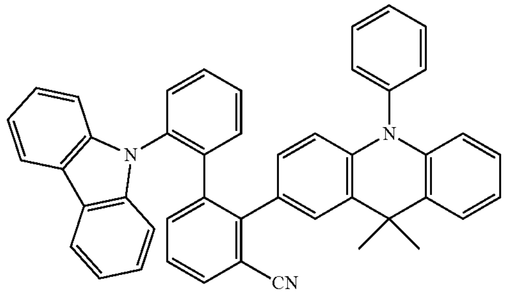
303
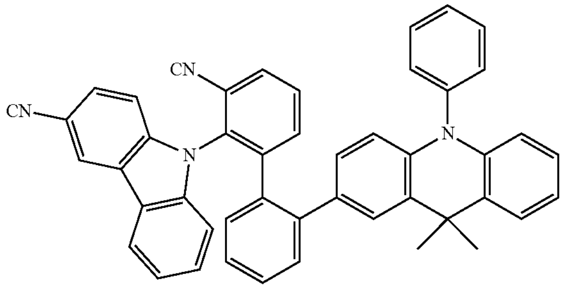
304
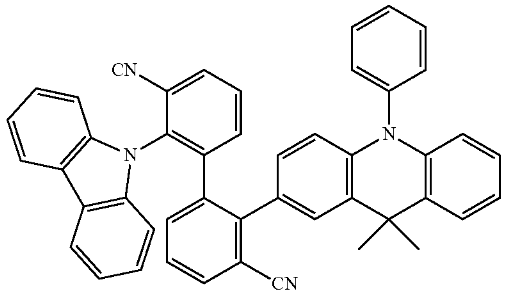

-continued
305
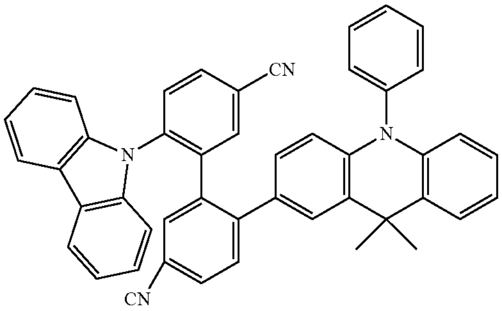
306
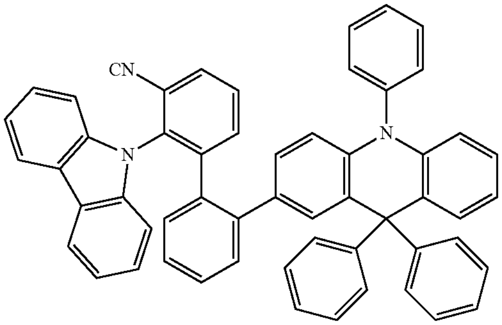
307
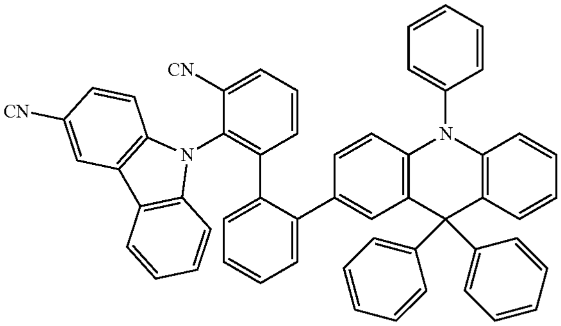
308
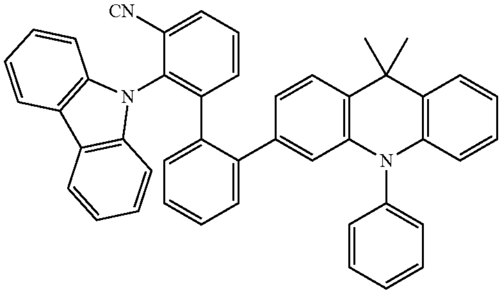
-continued
309
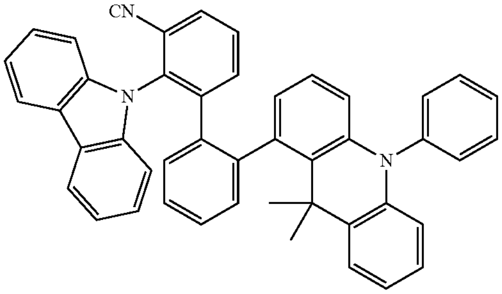
310
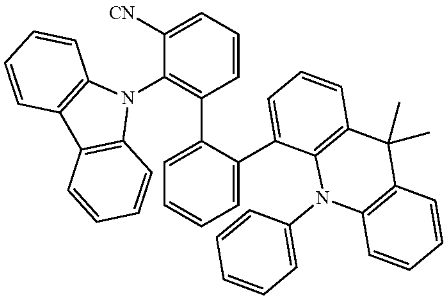
311
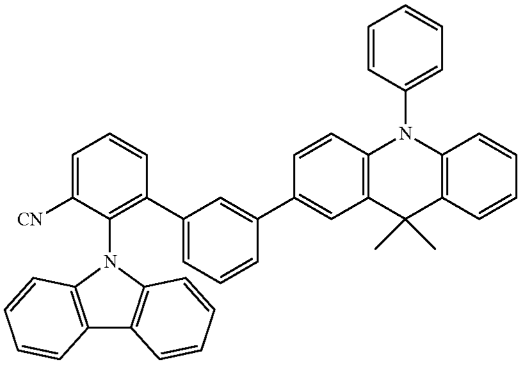
312
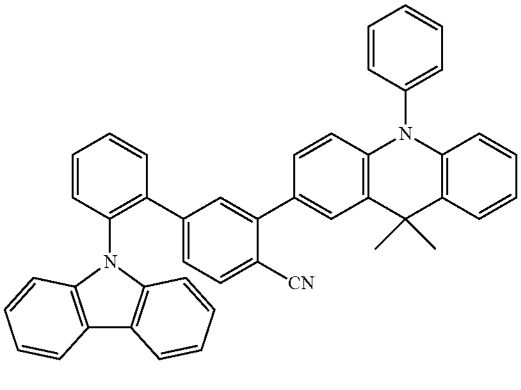

-continued
313
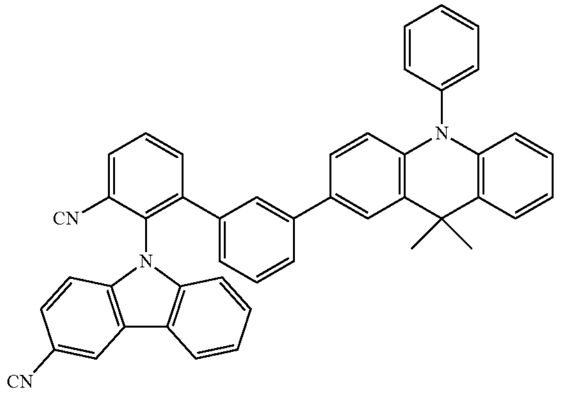
314
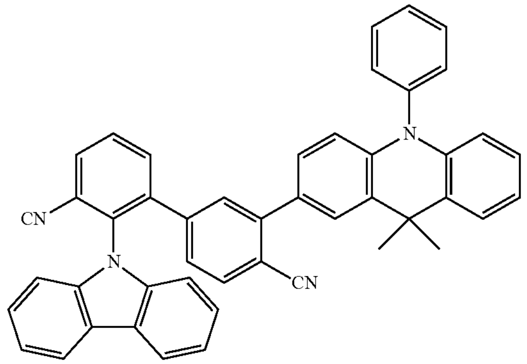
315
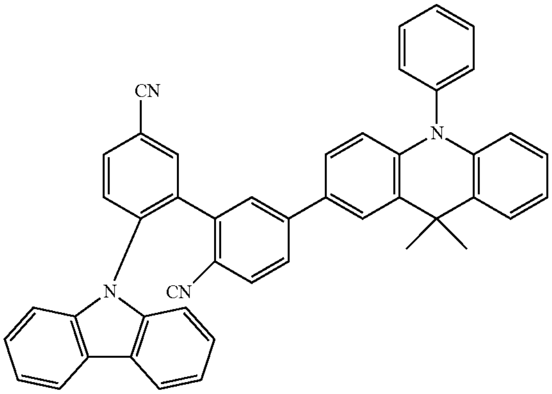
316
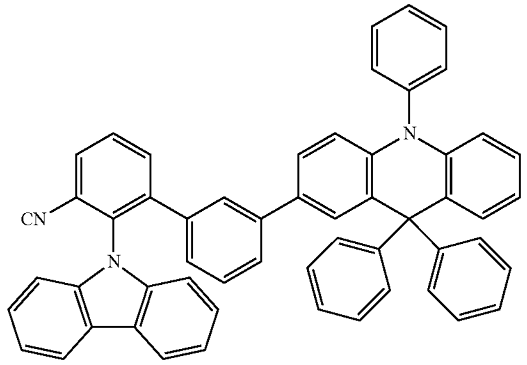
-continued
317
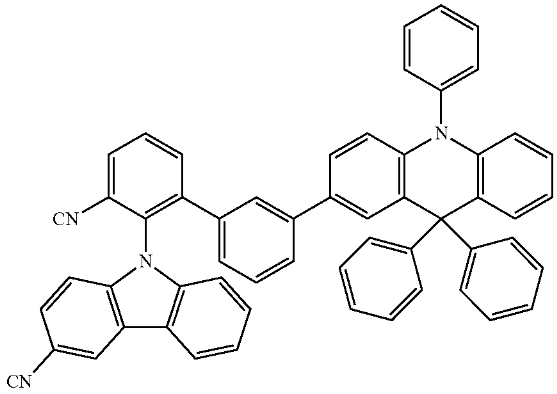
318
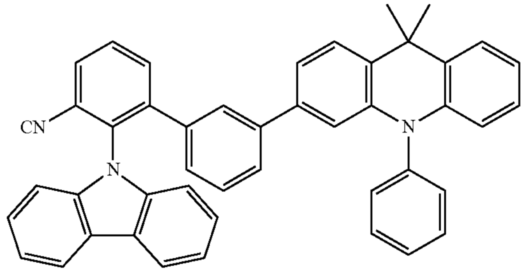
319
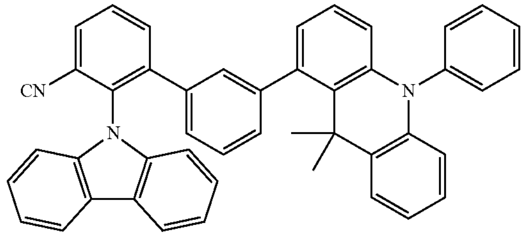
320
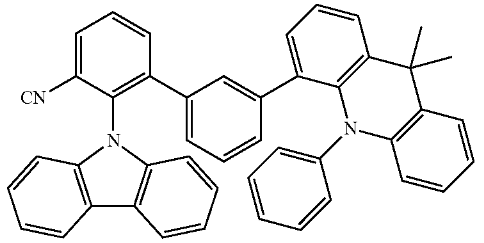
321
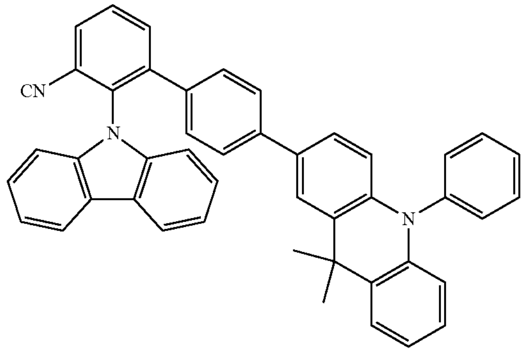

-continued
322
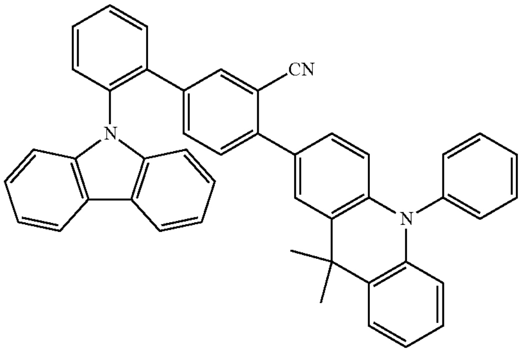
323
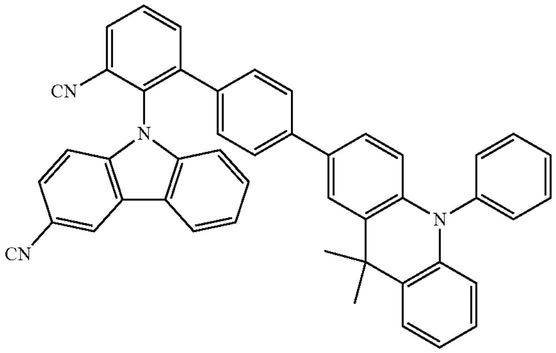
324
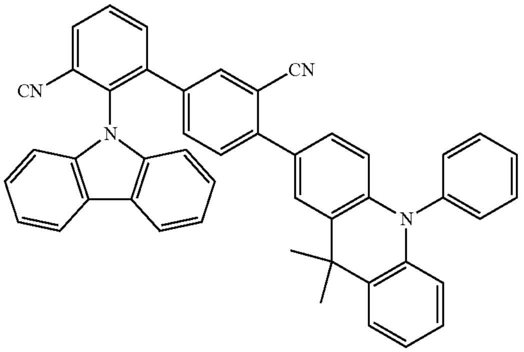
325
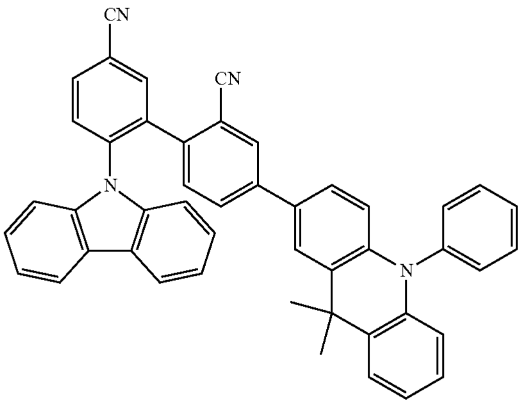
-continued
326
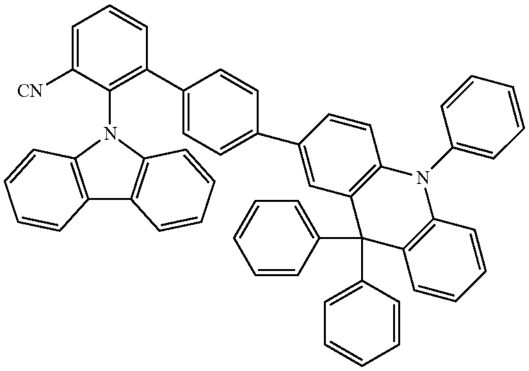
327
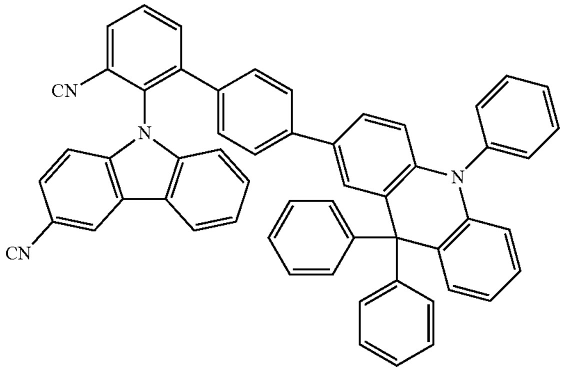
328
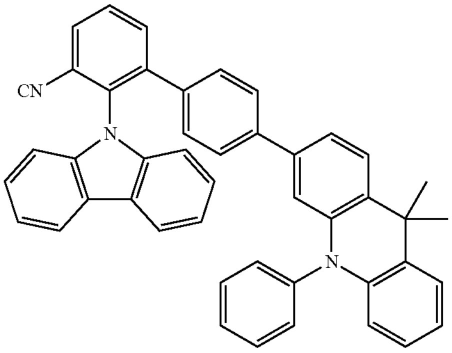
329
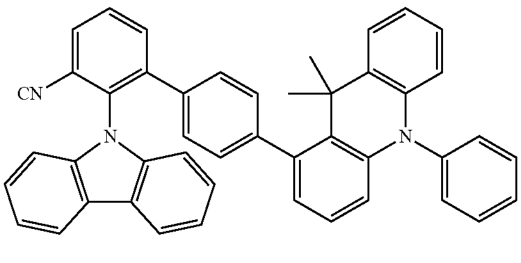

330
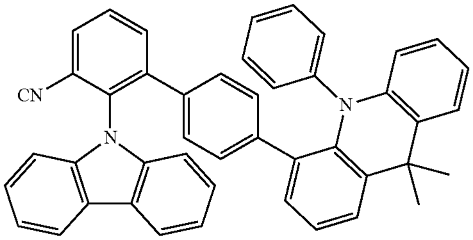
Group HE7
1
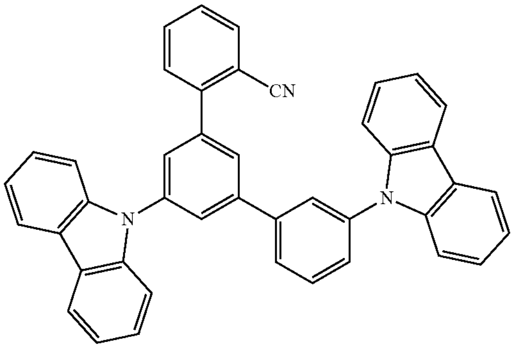
2
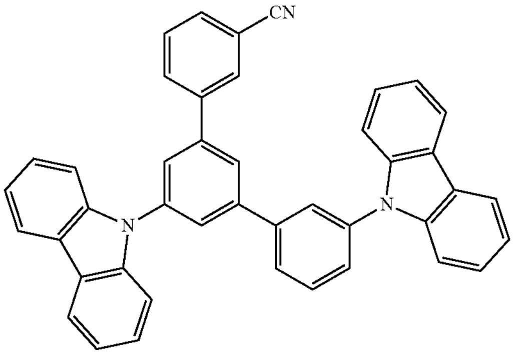
3
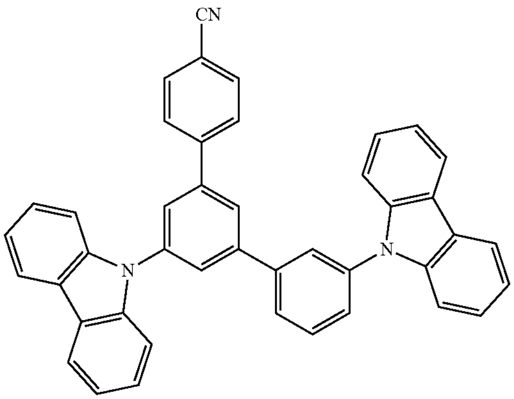
4
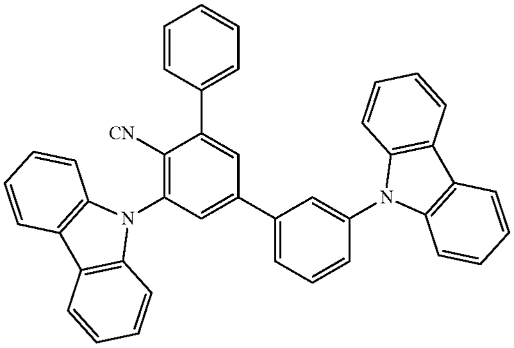
5
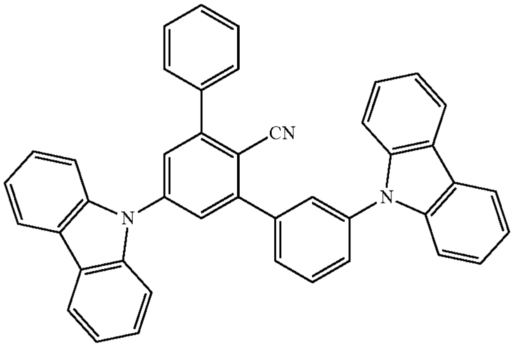
6
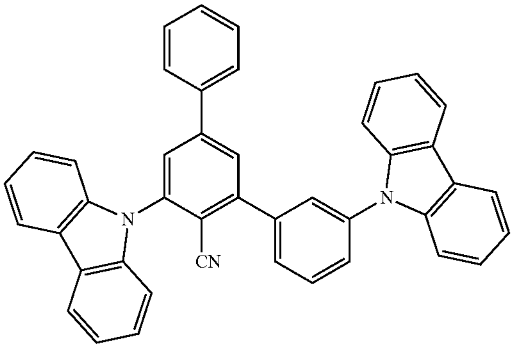
7
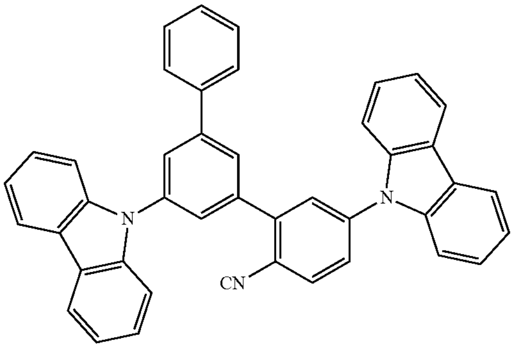

-continued
8
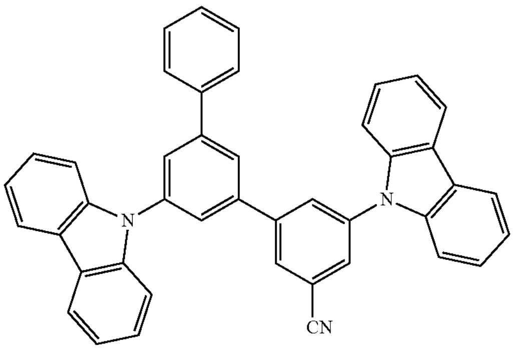
9
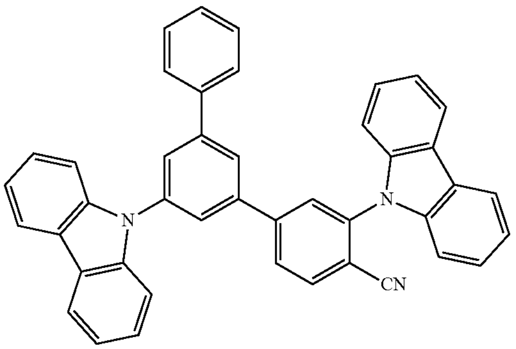
10
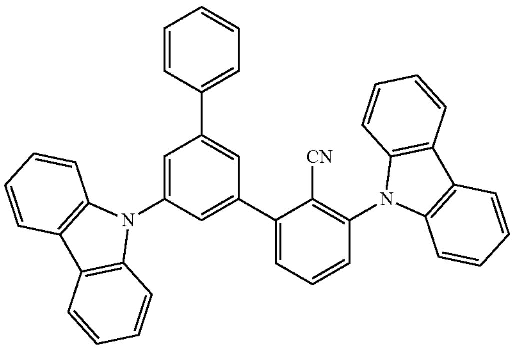
11
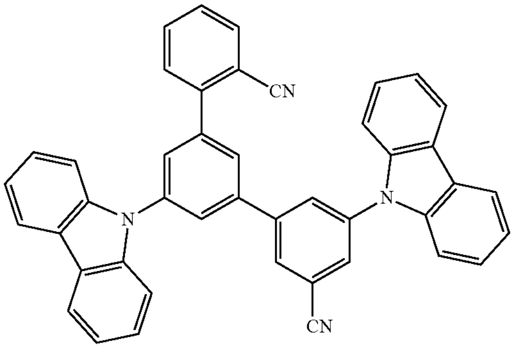
-continued
12
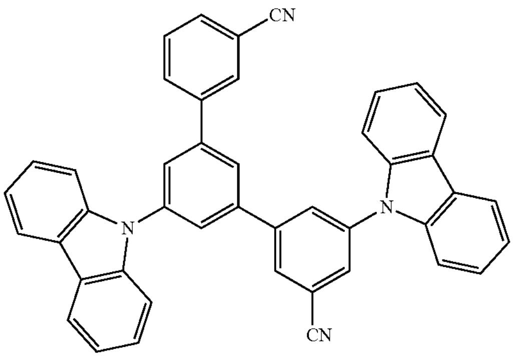
13
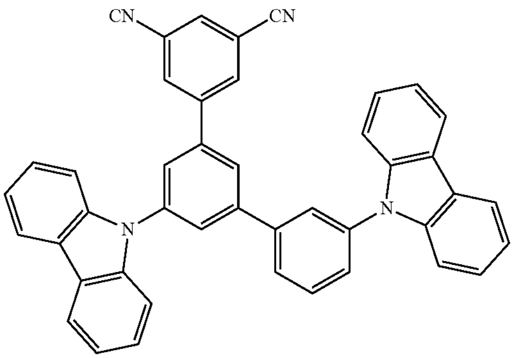
14
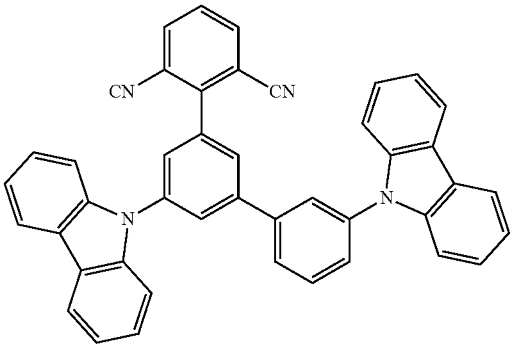
15
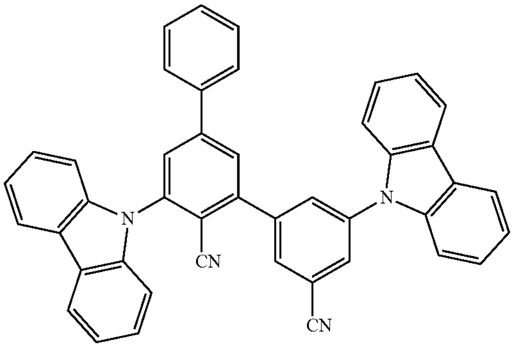

-continued
16
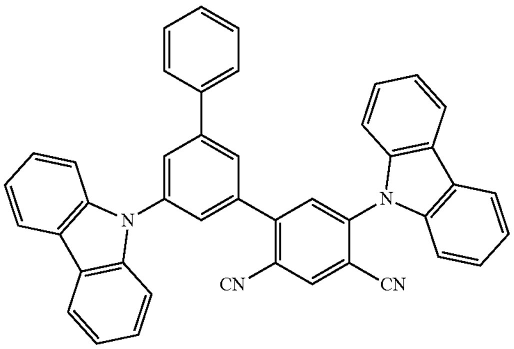
17
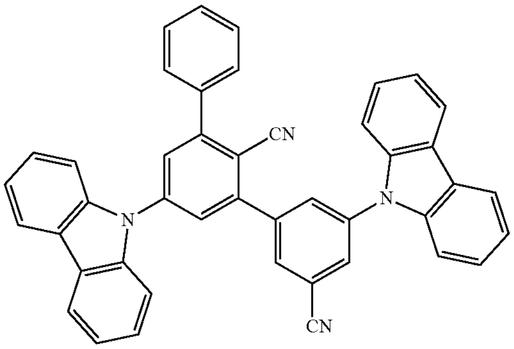
18
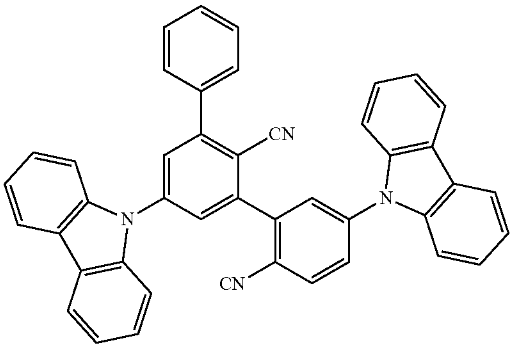
19
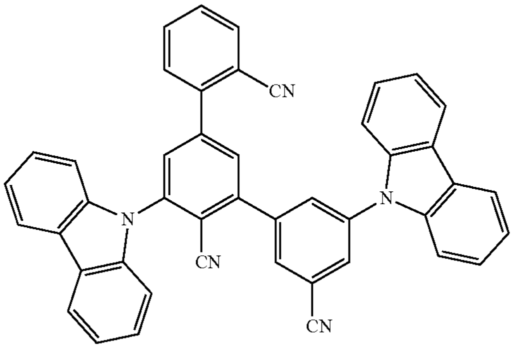
-continued
20
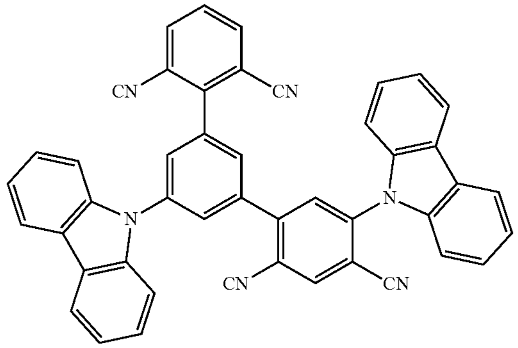
21
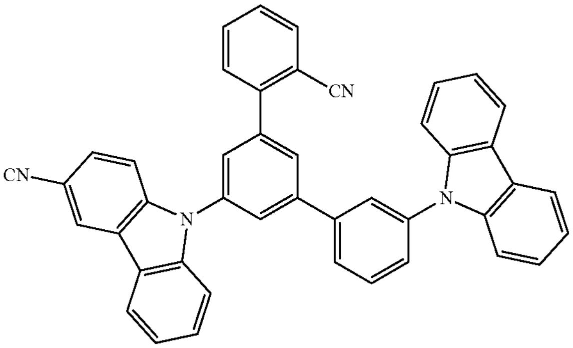
22
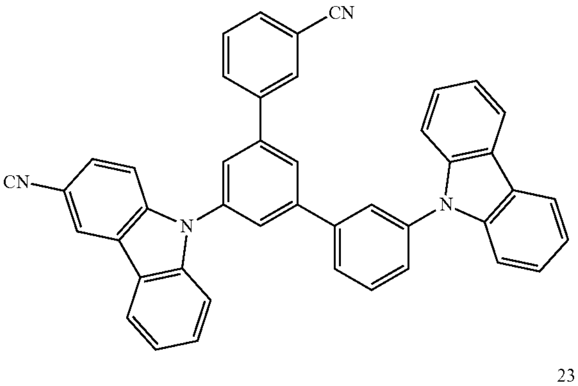
23
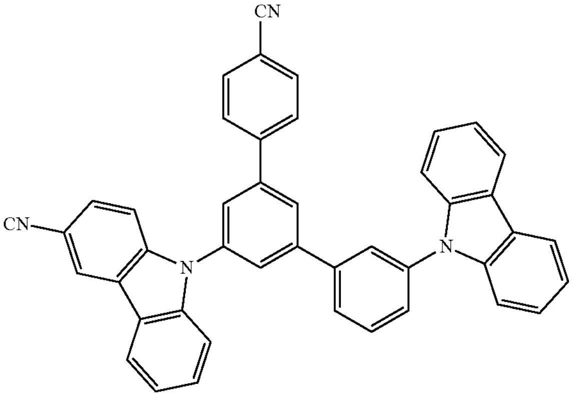

24
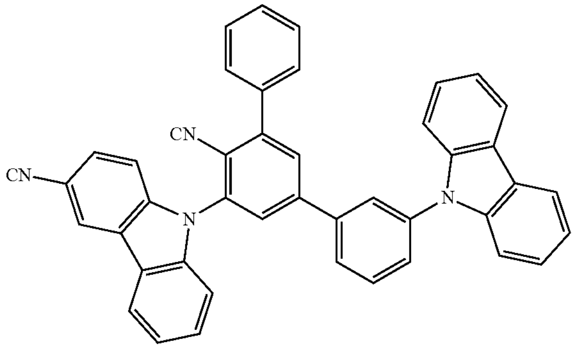
25
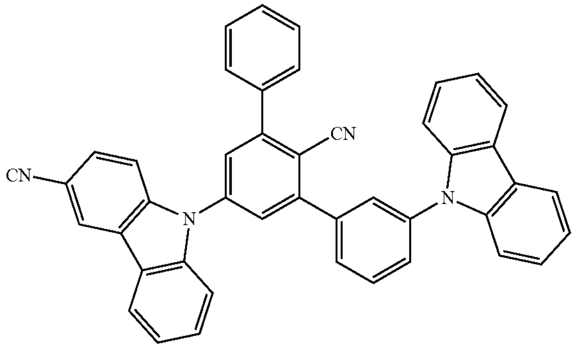
26
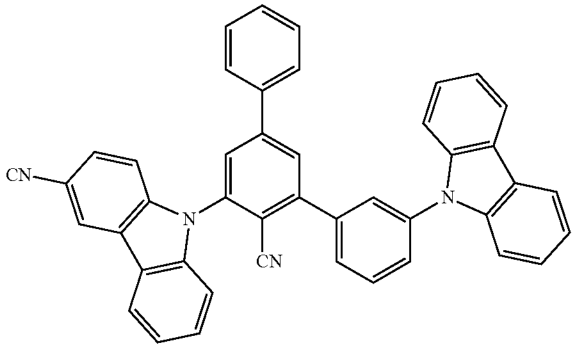
27
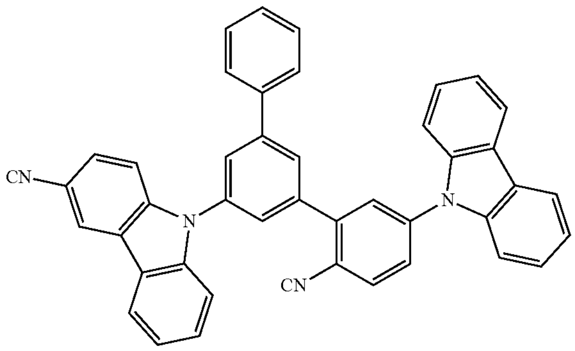
28
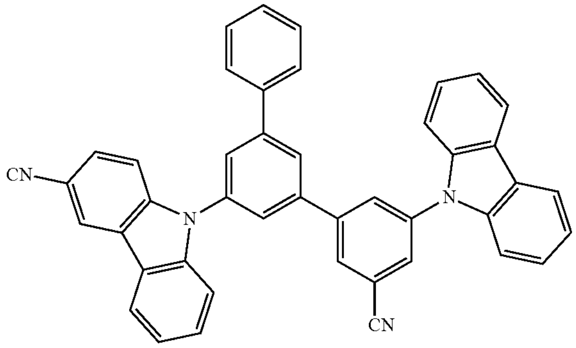
29
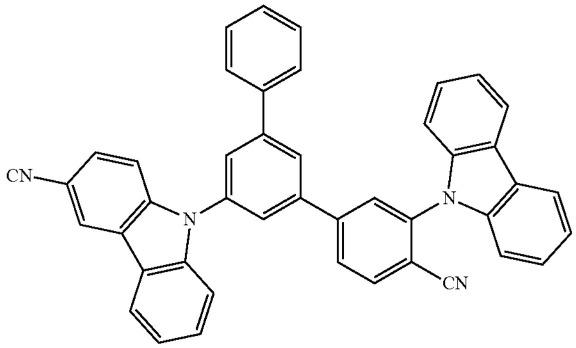
30
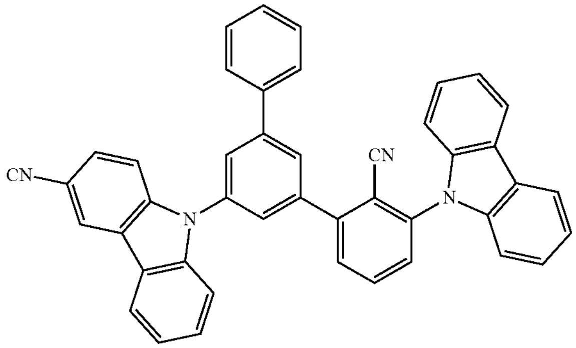
31
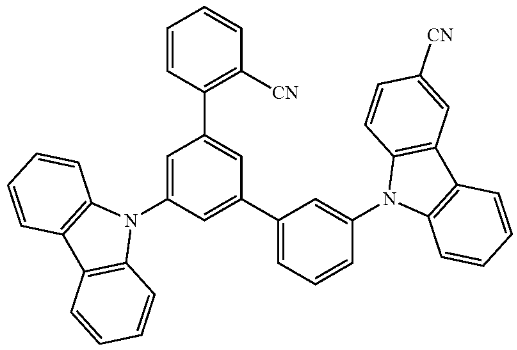

-continued
32
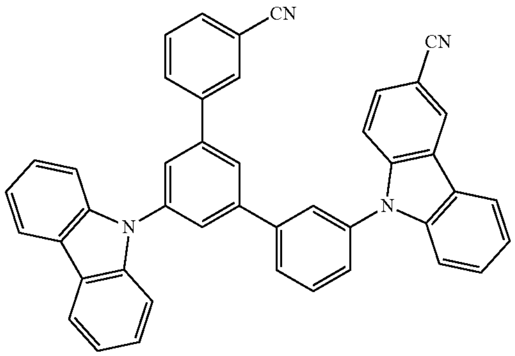
33
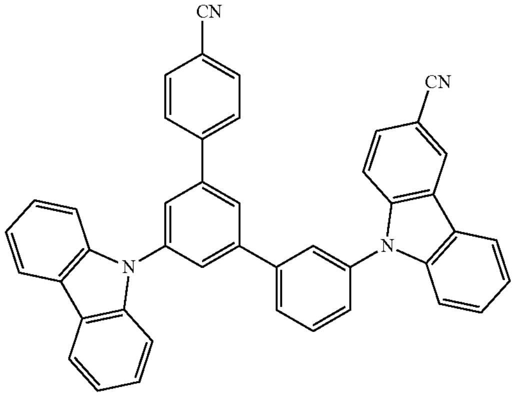
34
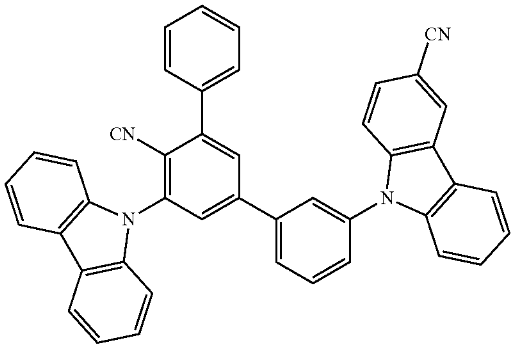
35
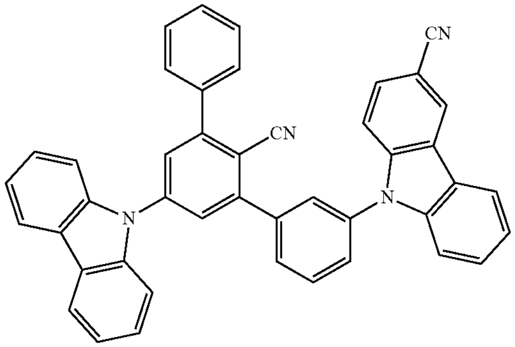
-continued
36
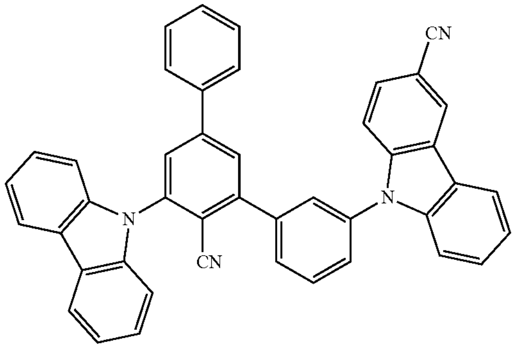
37
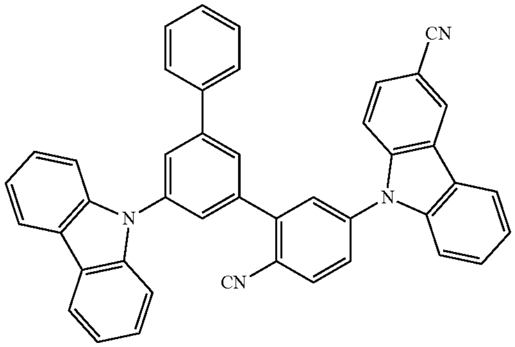
38
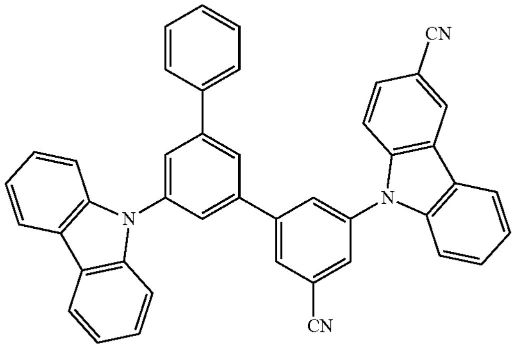
39
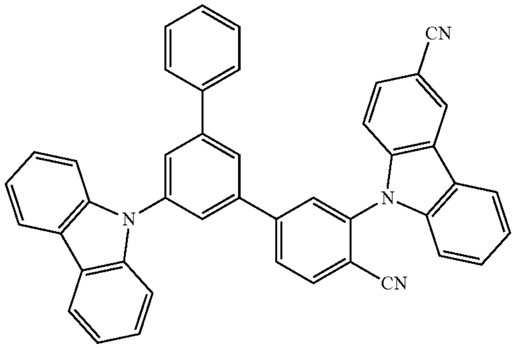

-continued
40
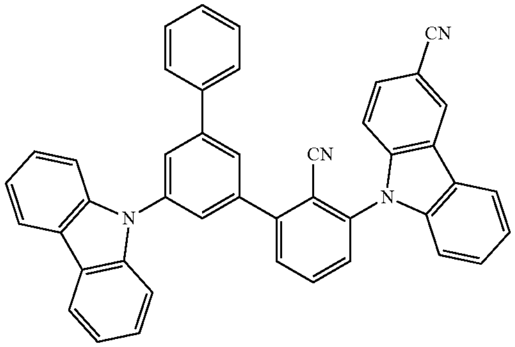
41
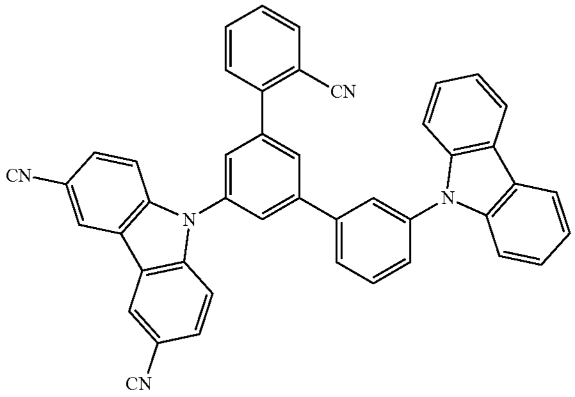
42
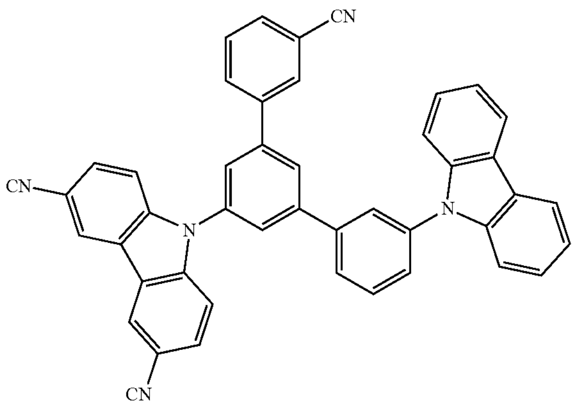
-continued
43
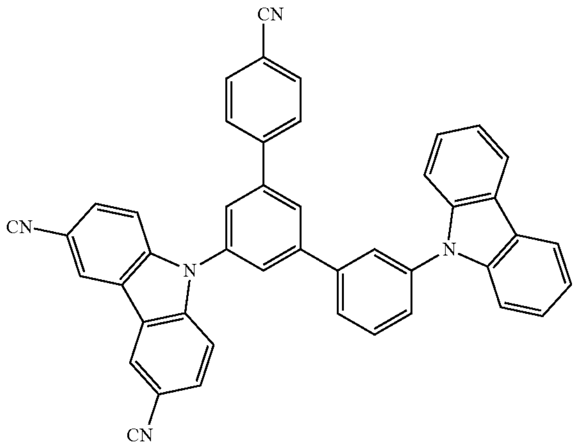
44
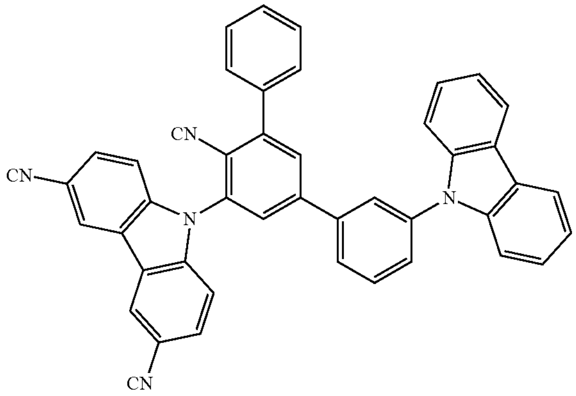
45
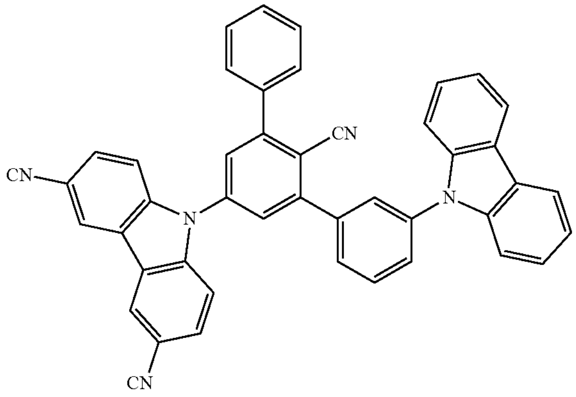

-continued
46
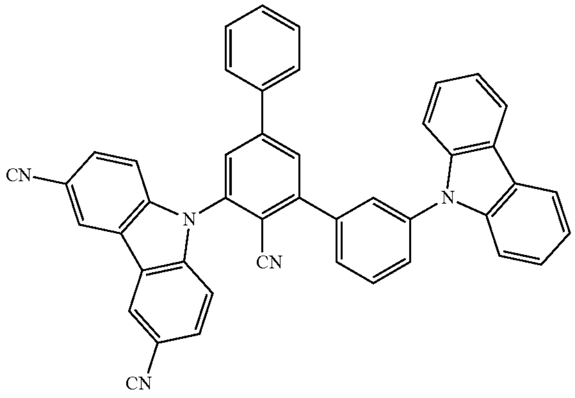
47
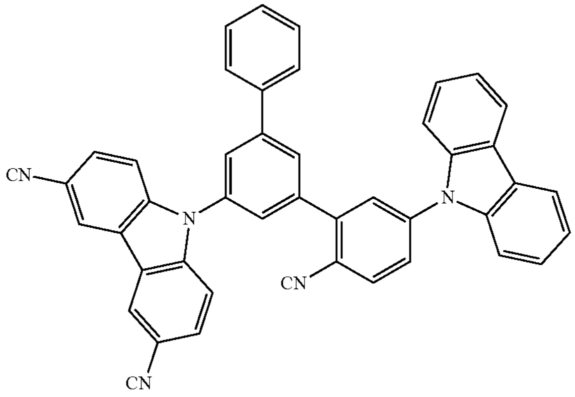
48
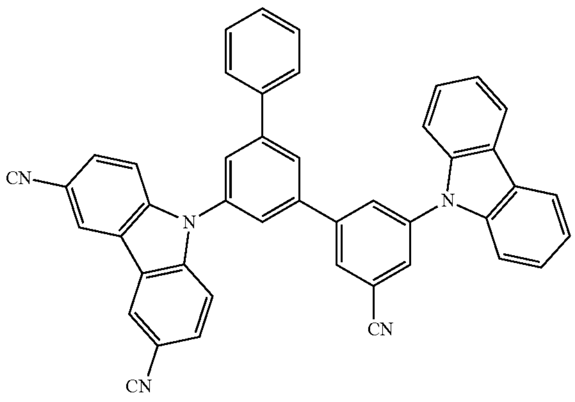
-continued
49
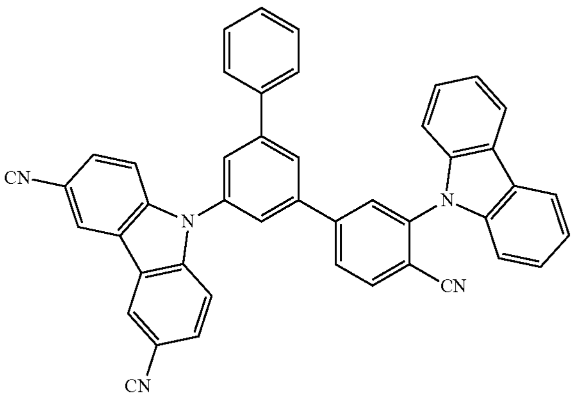
50
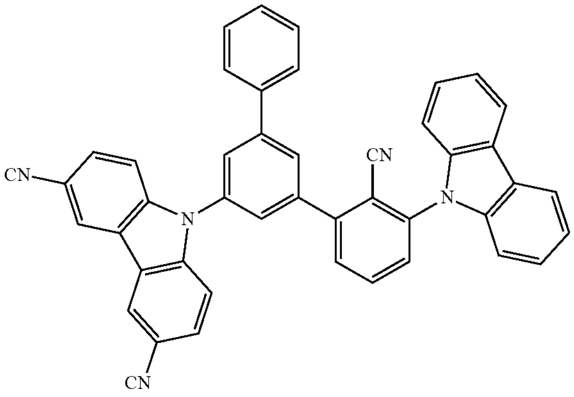
51
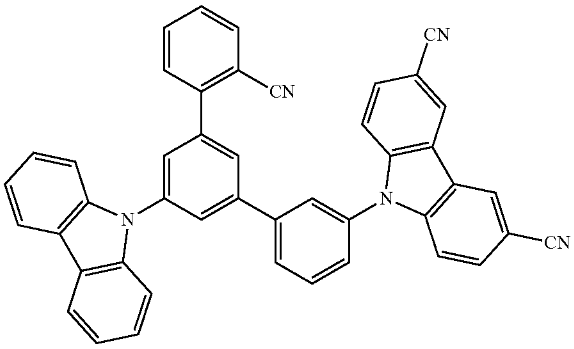
52
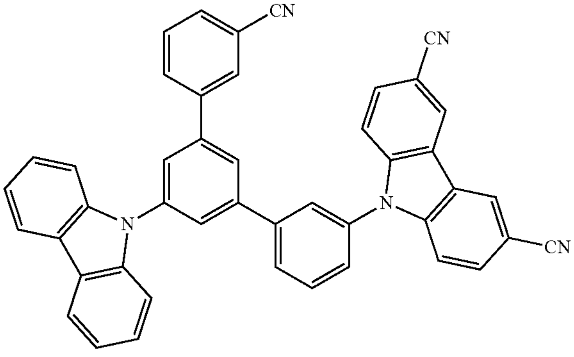

-continued
53
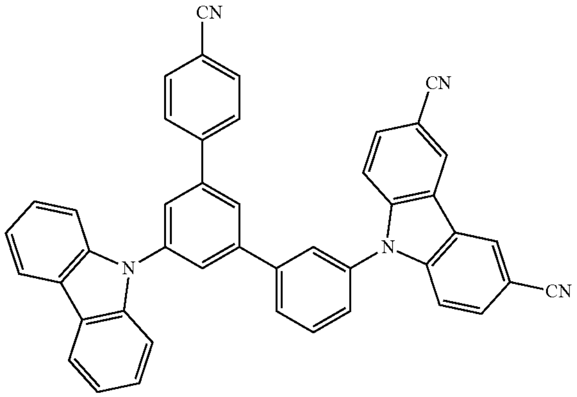
54
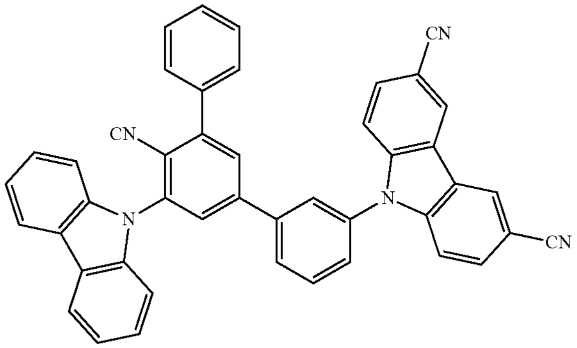
55
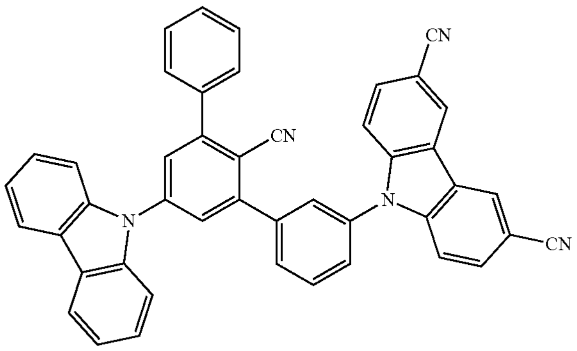
56
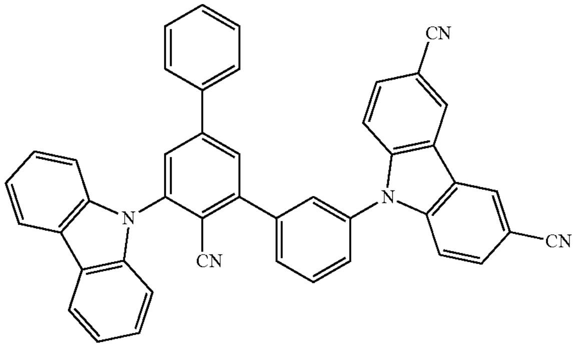
-continued
57
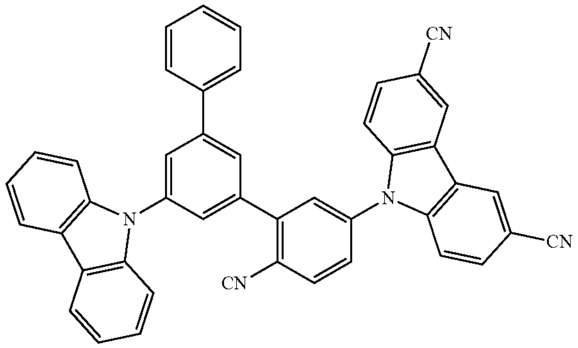
58
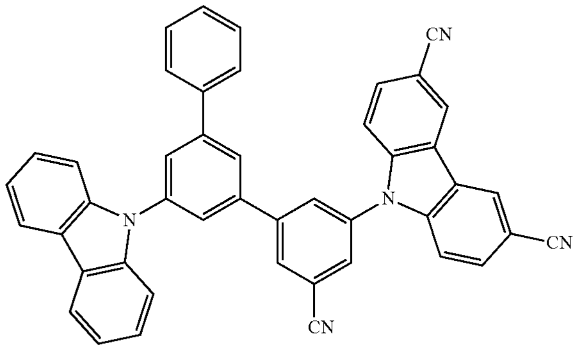
59
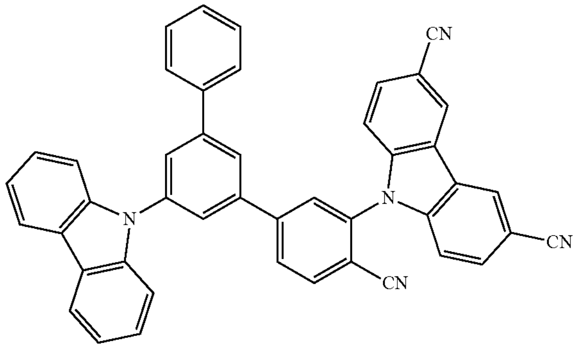
60
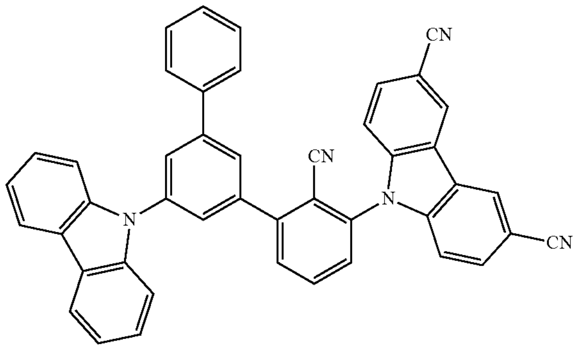

-continued
61
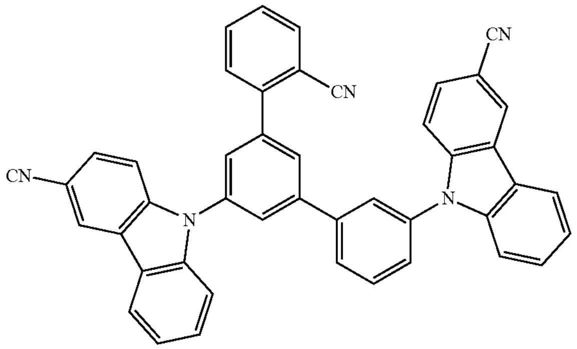
62
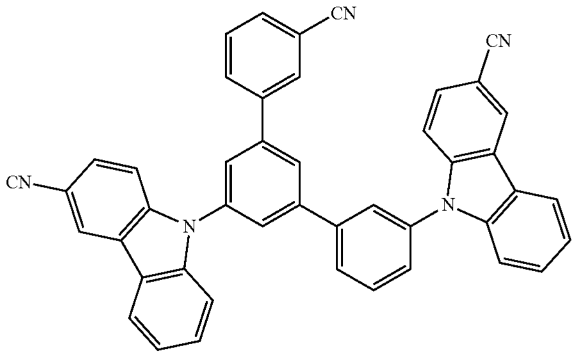
63
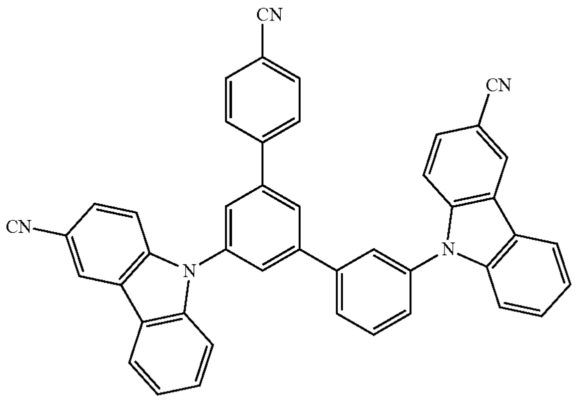
64
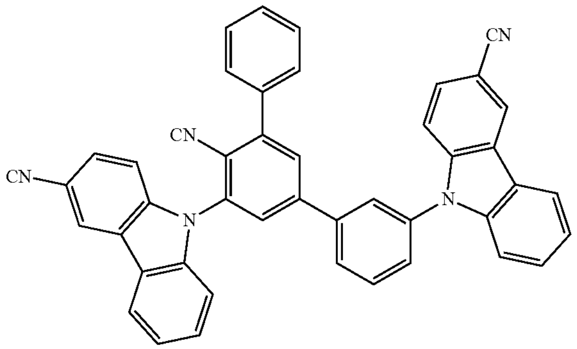
-continued
65
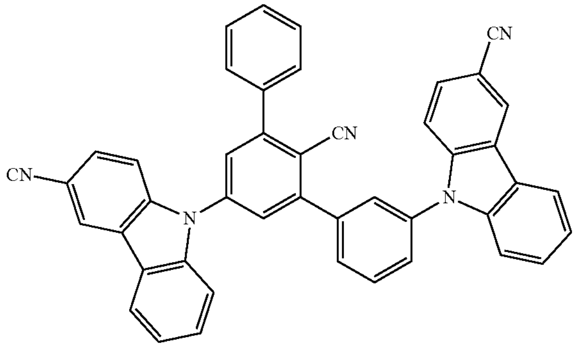
66
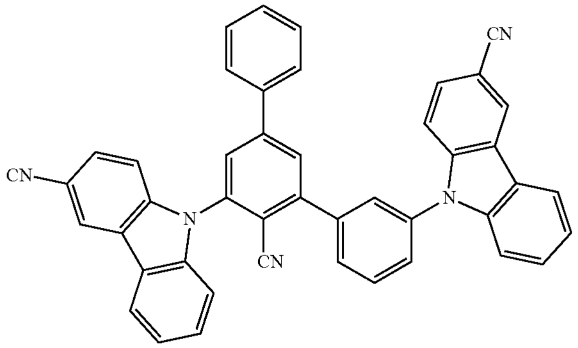
67
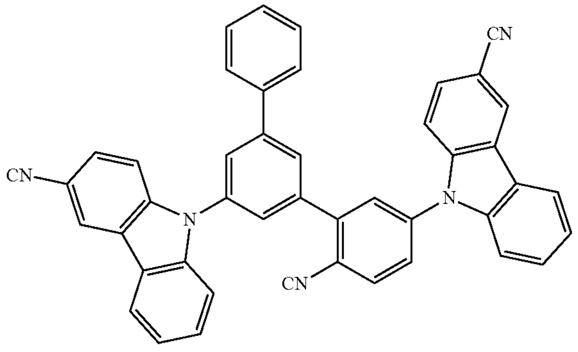
68
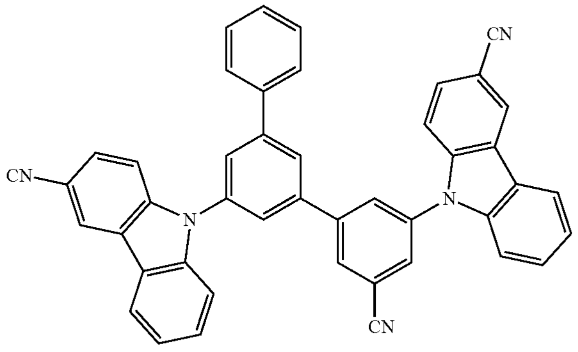

-continued
69
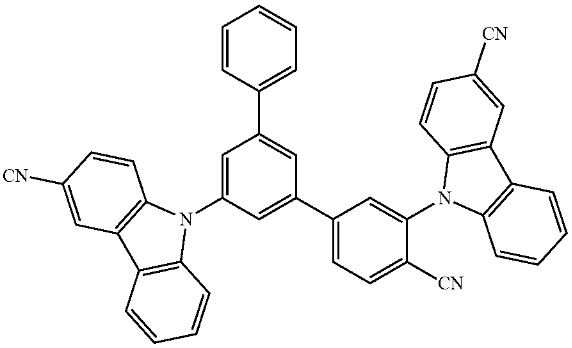
70
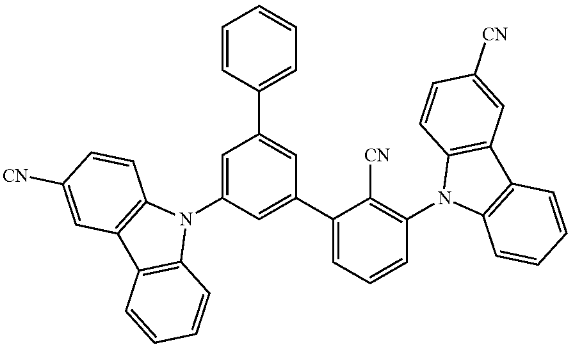
71
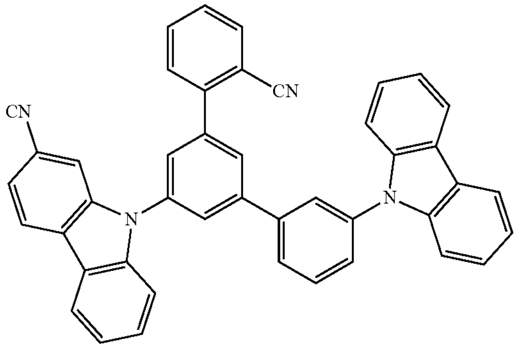
72
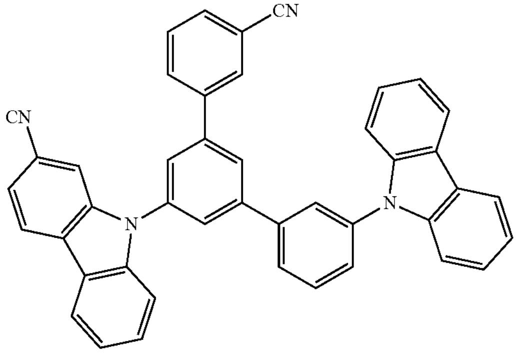
-continued
73
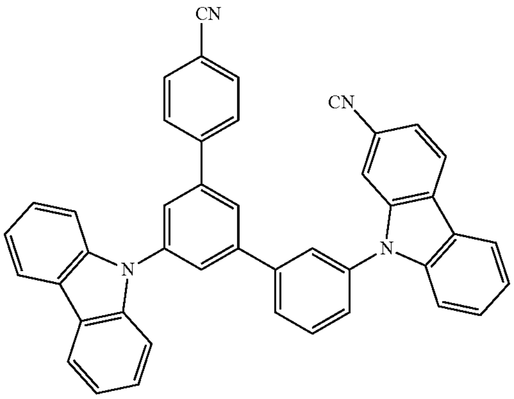
74
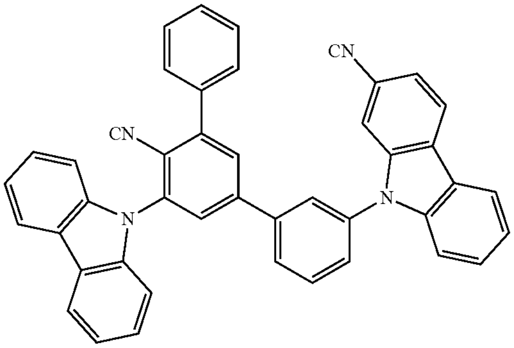
75
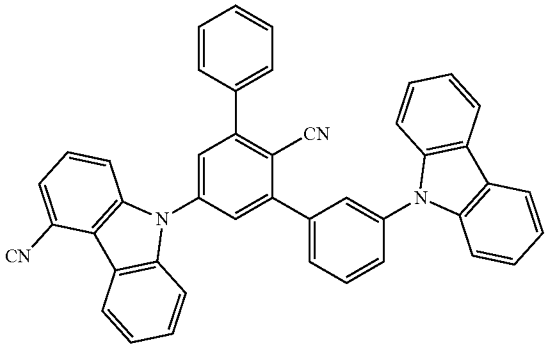
76
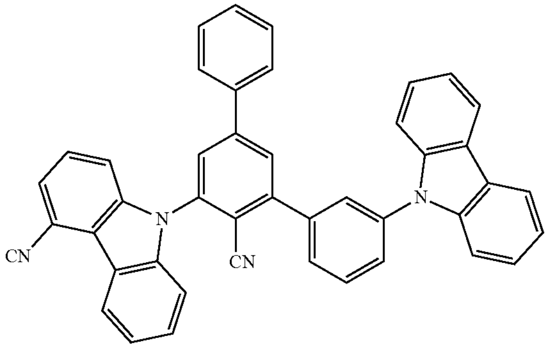

77
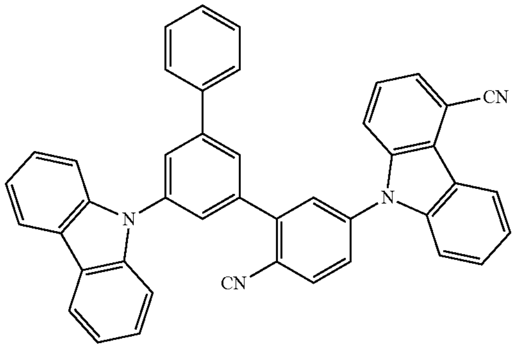
78
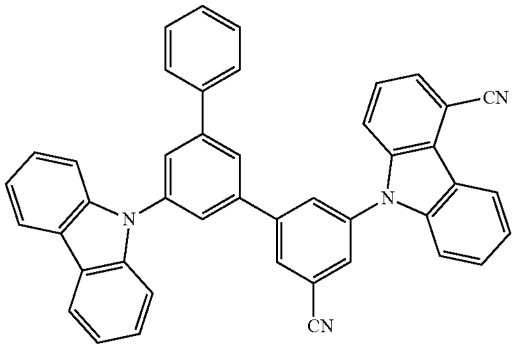
79
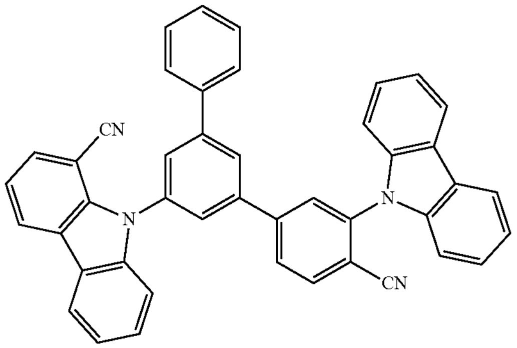
80
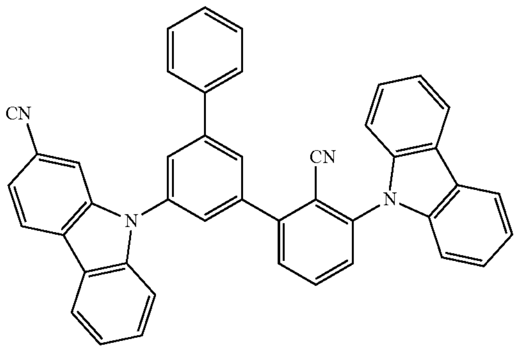
81
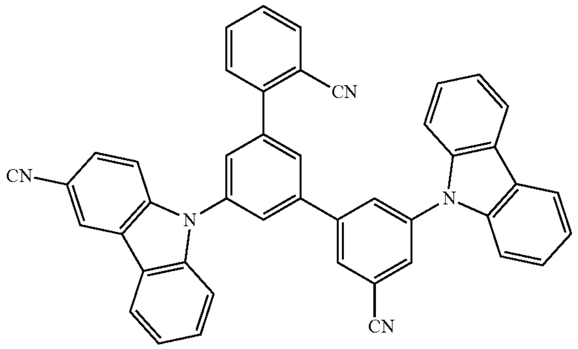
82
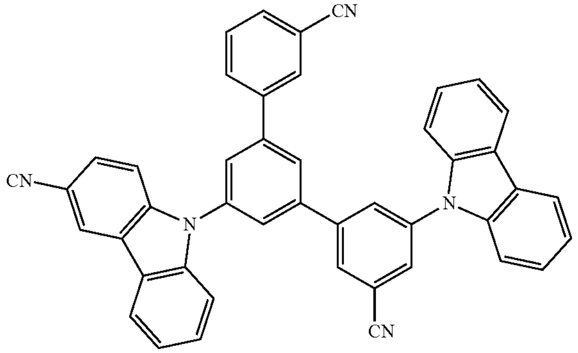
83
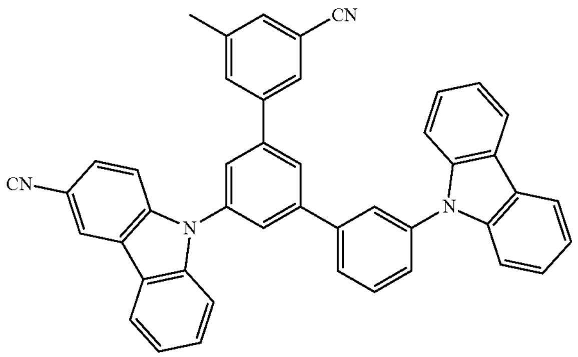
84
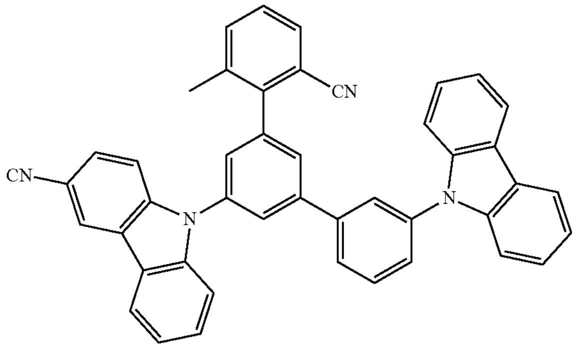

-continued
85
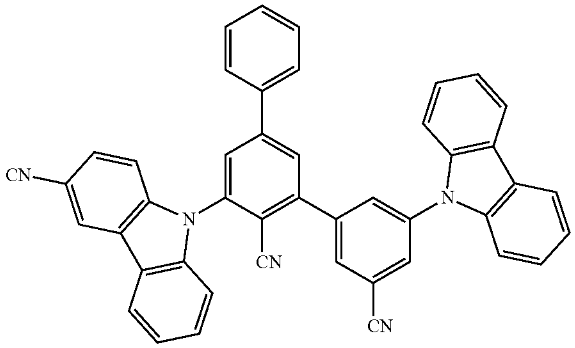
86
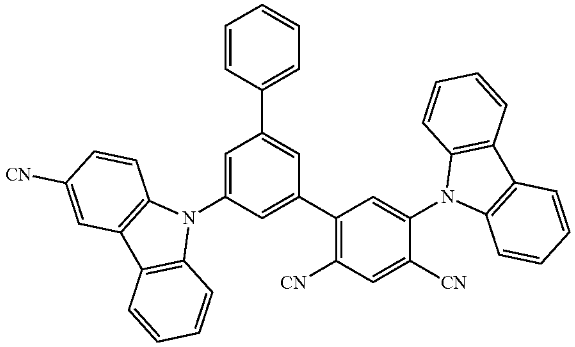
87
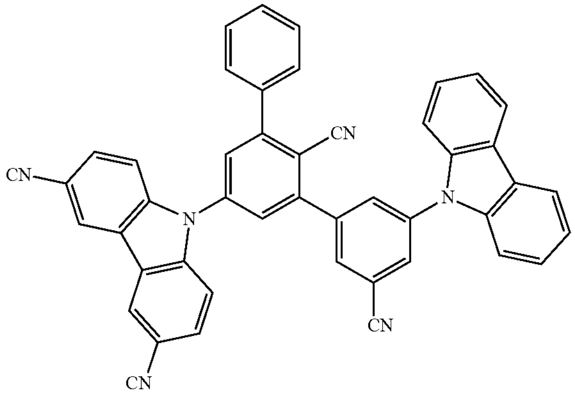
88
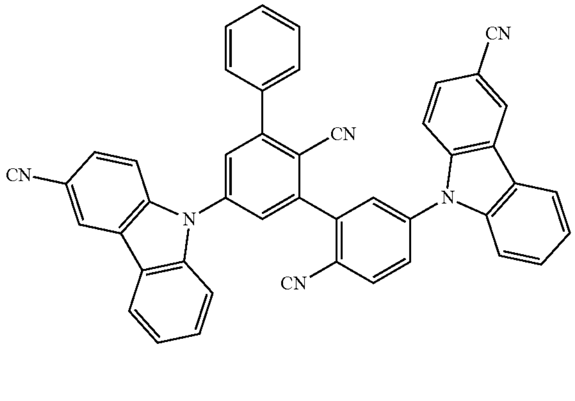
-continued
89
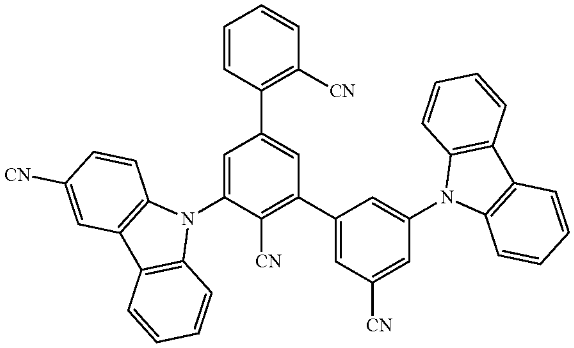
90
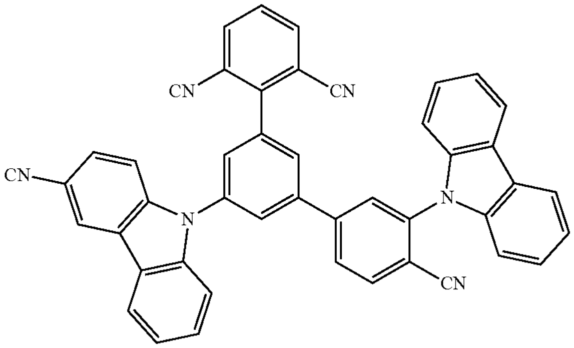
91
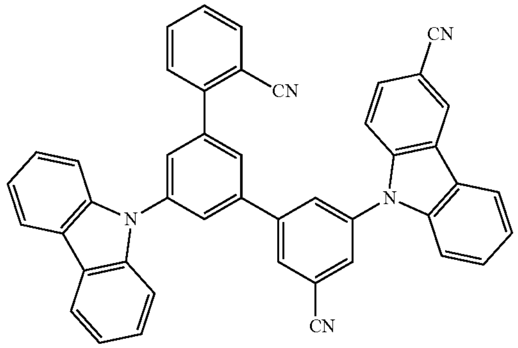
92
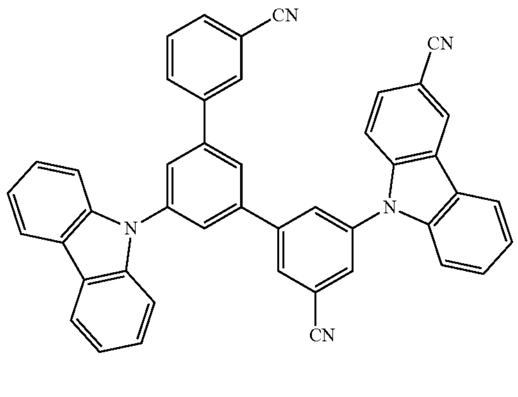

-continued
93
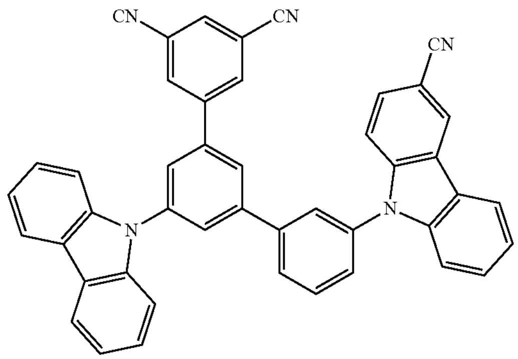
94
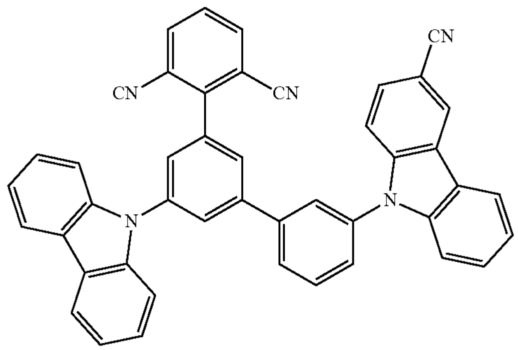
95
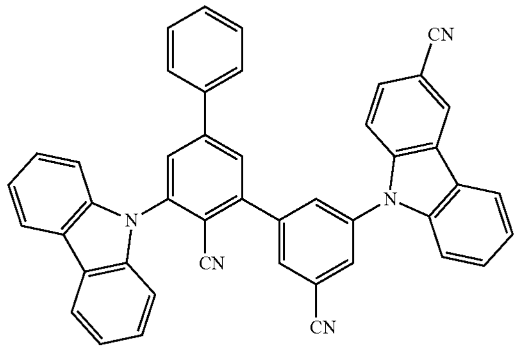
96
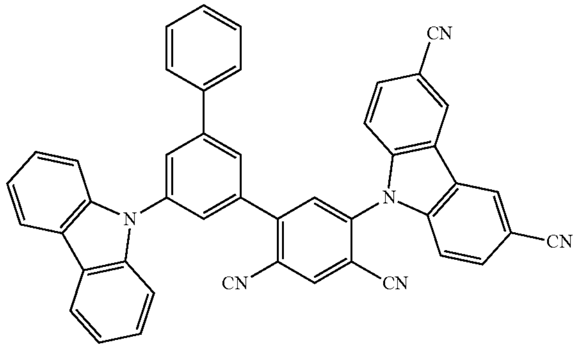
-continued
97
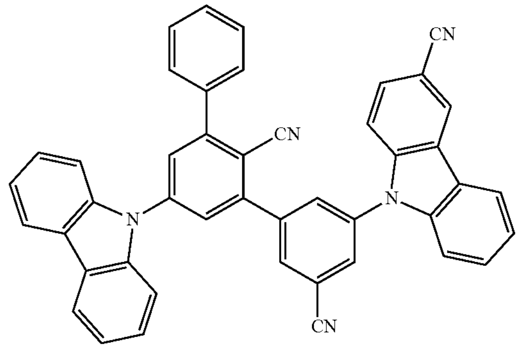
98
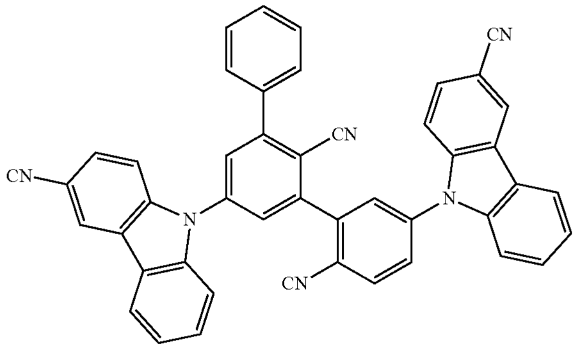
99
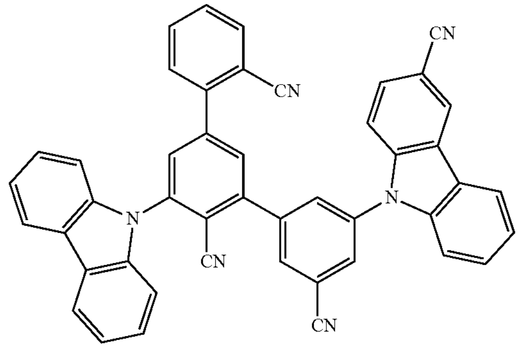
100
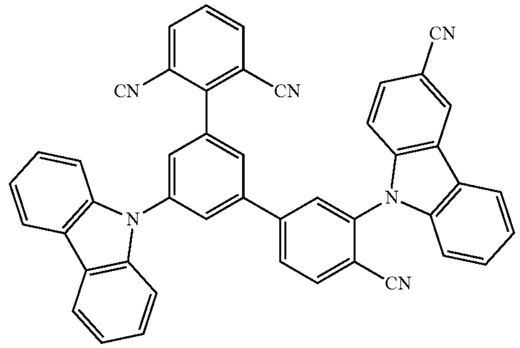

-continued
101
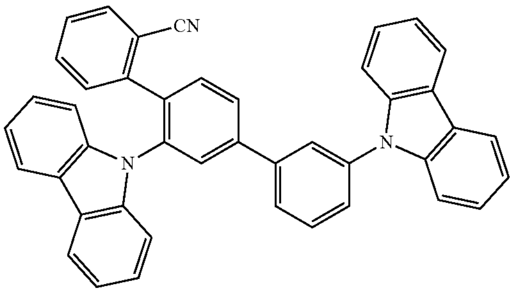
102
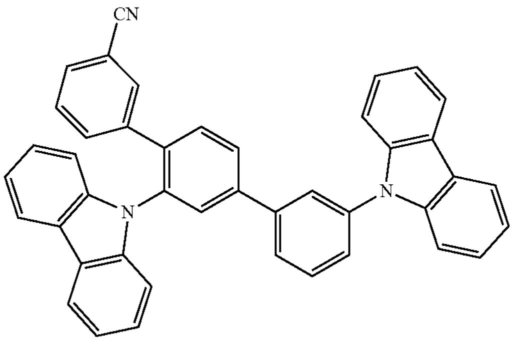
103
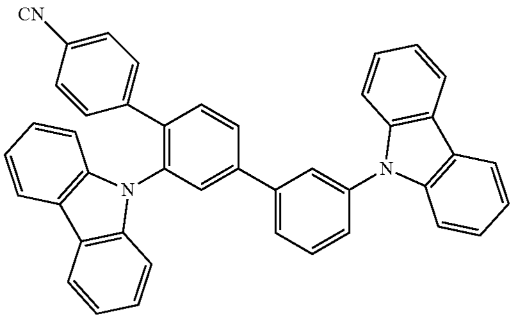
104
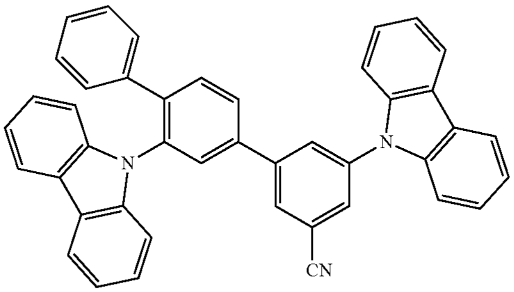
105
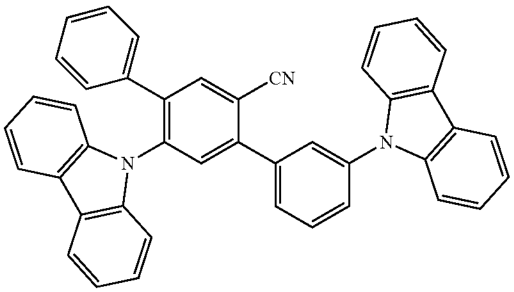
-continued
106
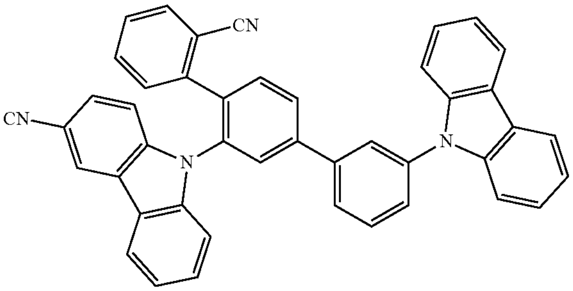
107
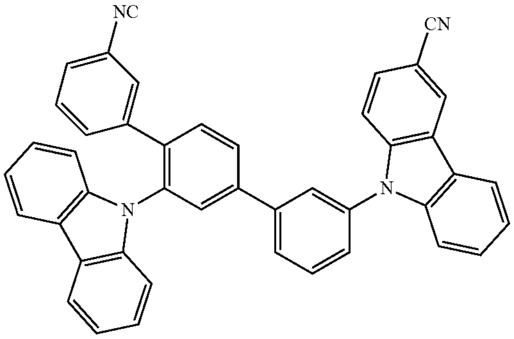
108
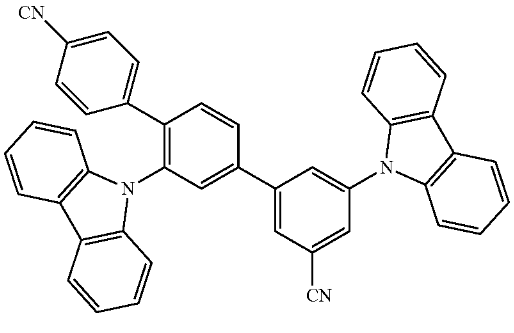
109
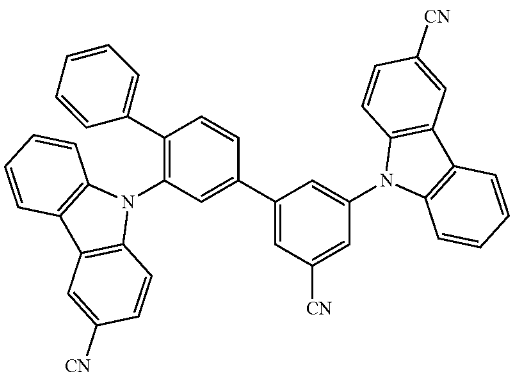

-continued
110
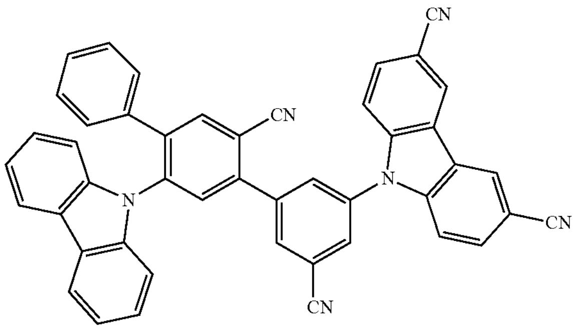
111
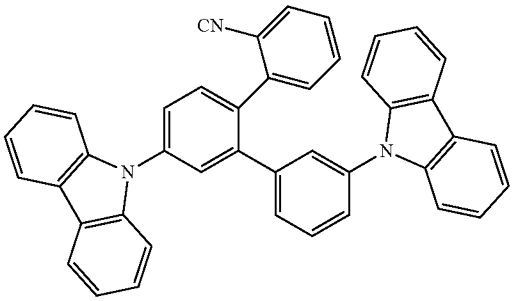
112
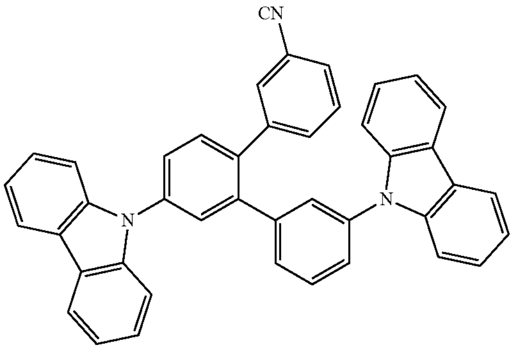
113
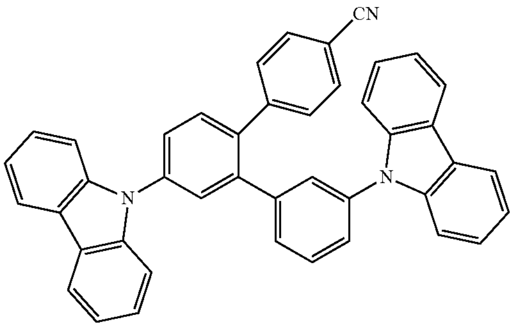
-continued
114
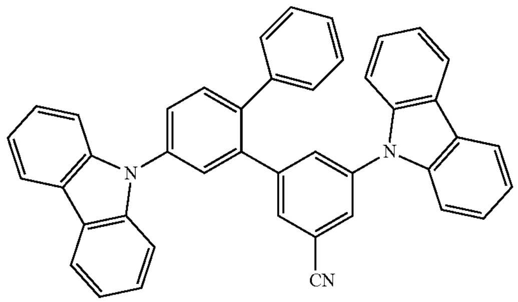
115
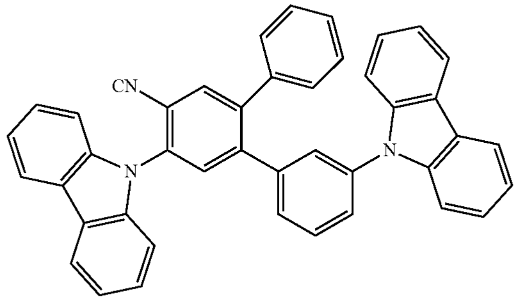
116
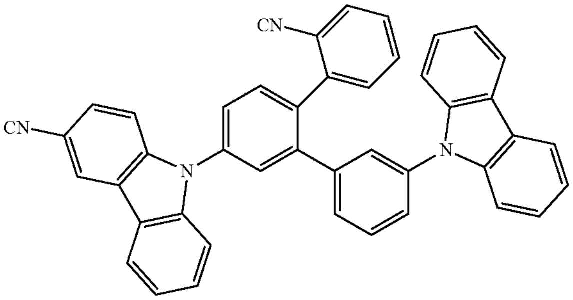
117
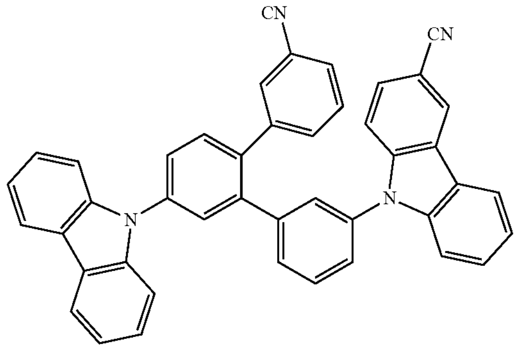

-continued
118
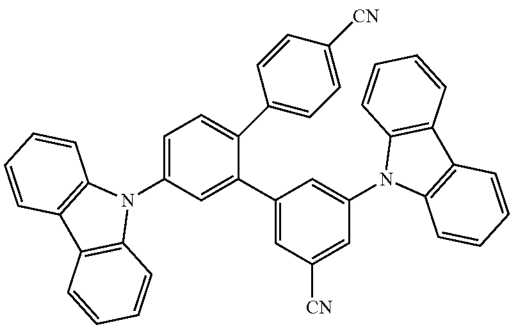
119
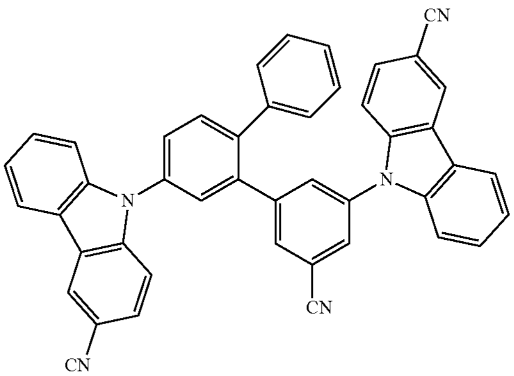
120
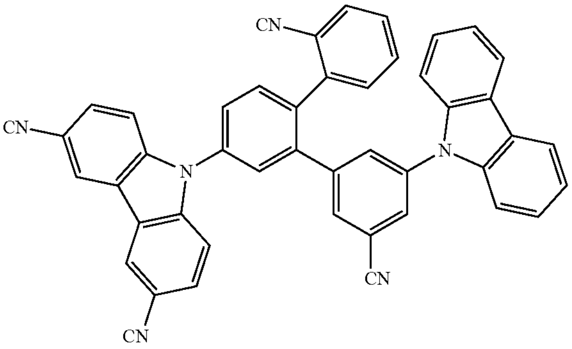
121
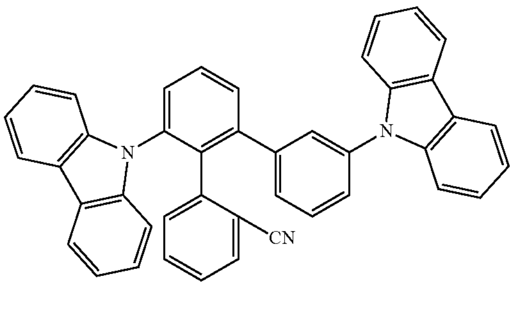
-continued
122
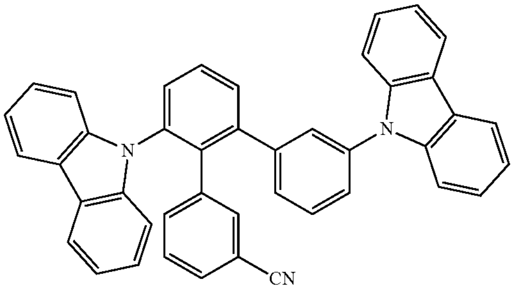
123
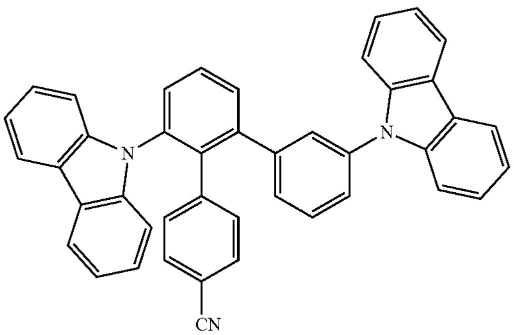
124
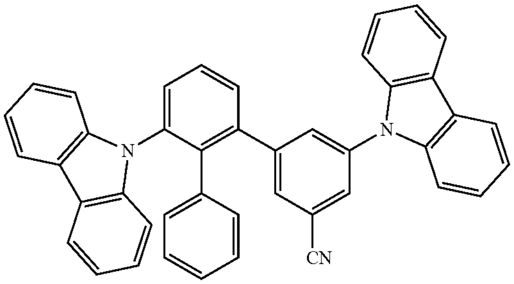
125
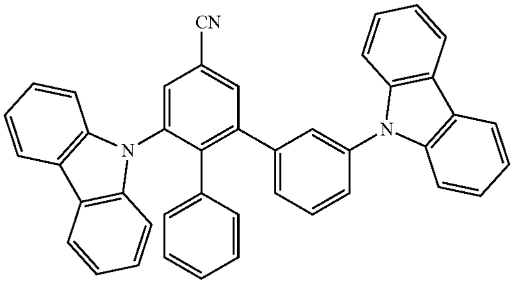
126
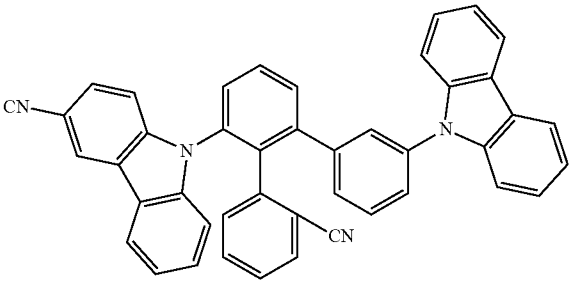

-continued
127
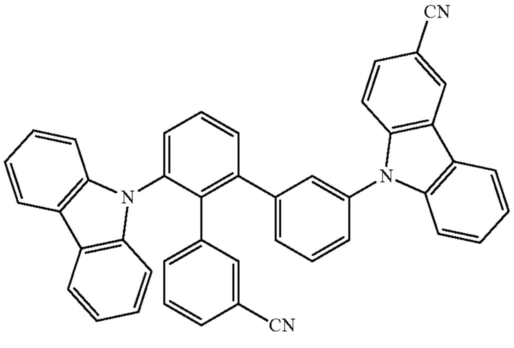
128
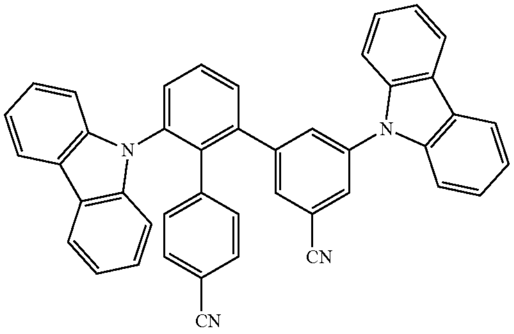
129
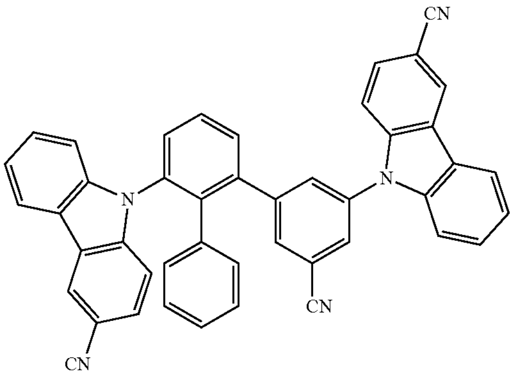
130
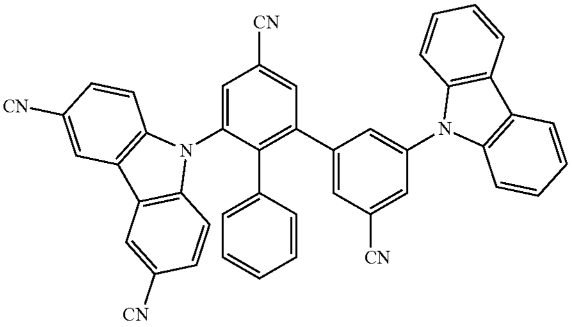
-continued
131
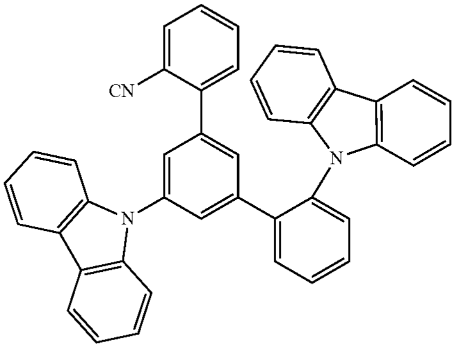
132
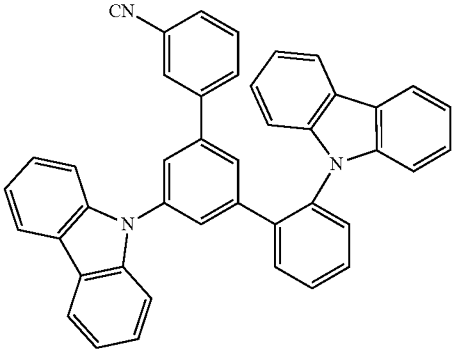
133
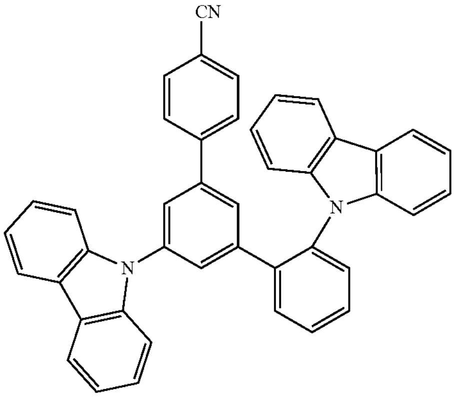
134
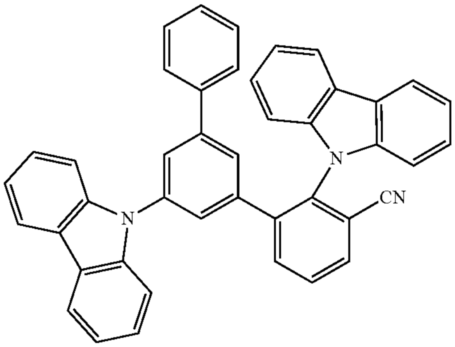

-continued
135
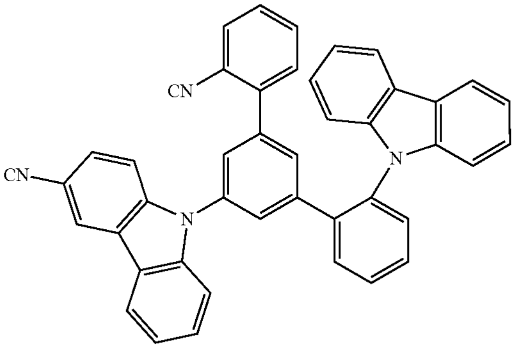
136
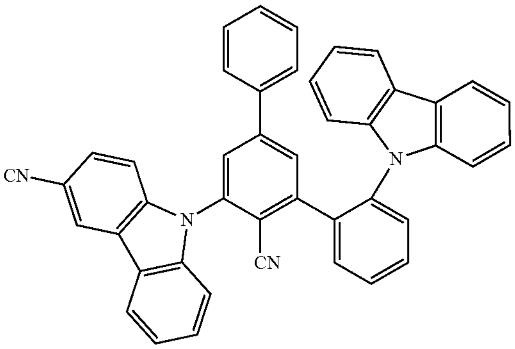
137
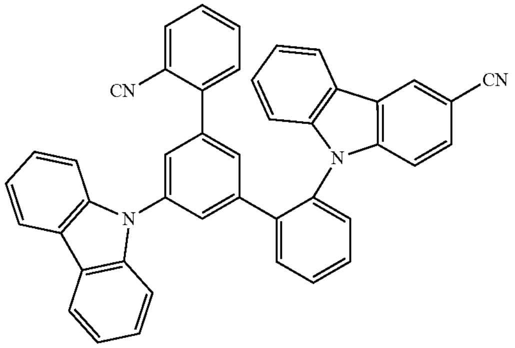
138
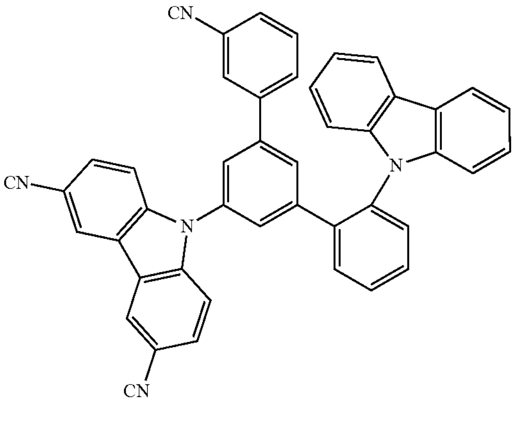
-continued
139
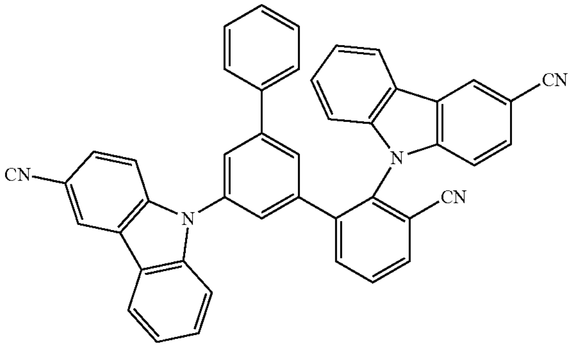
140
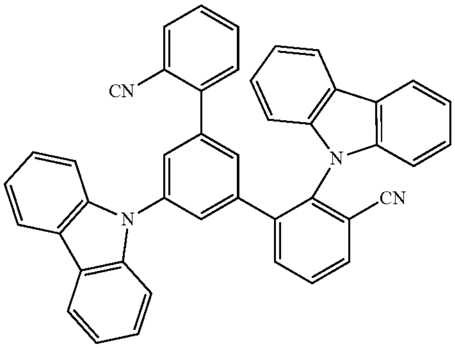
141
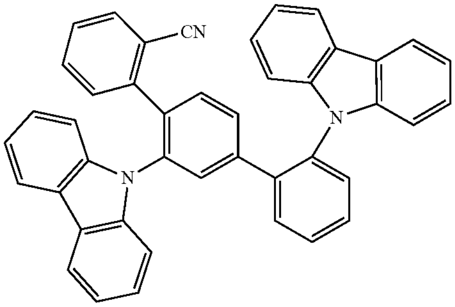
142
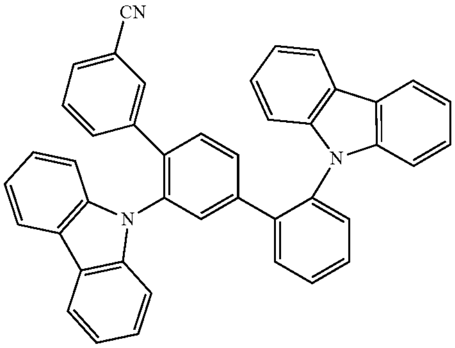

-continued
143
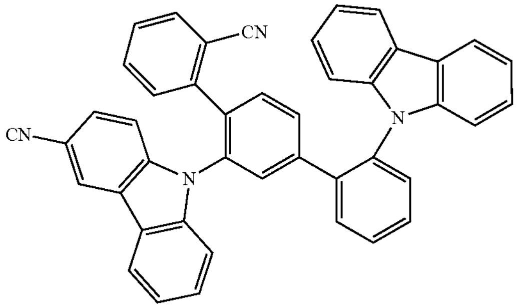
144
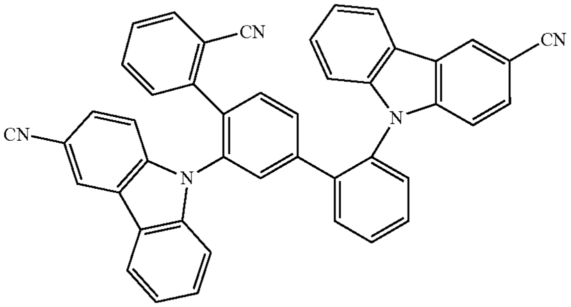
145
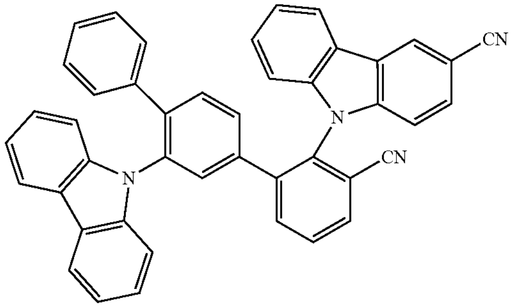
146
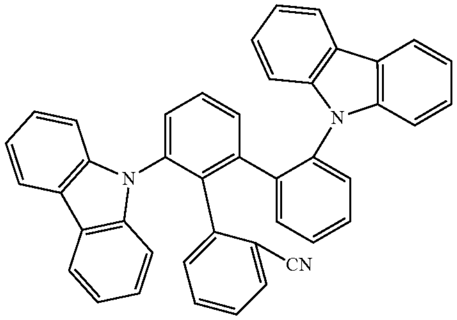
147
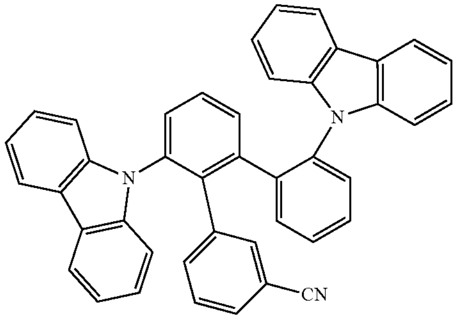
-continued
148
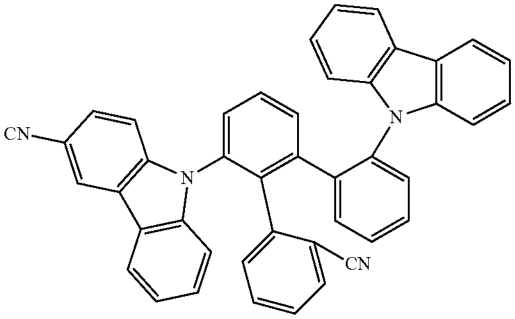
149
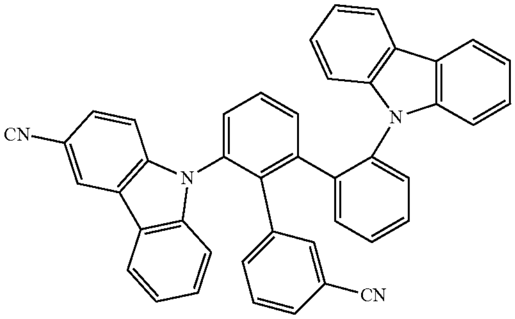
150
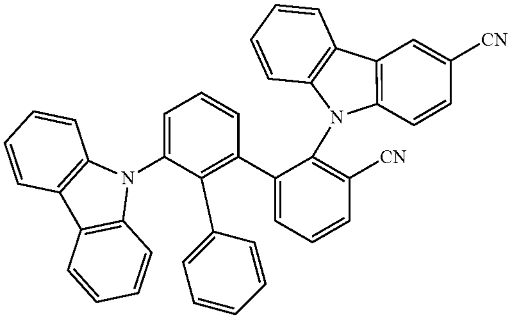
151
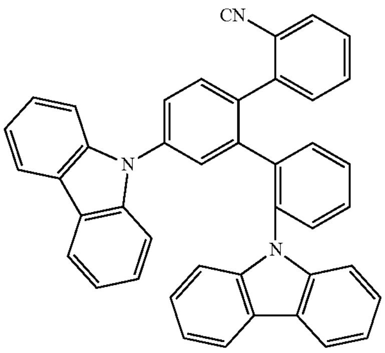

-continued
152
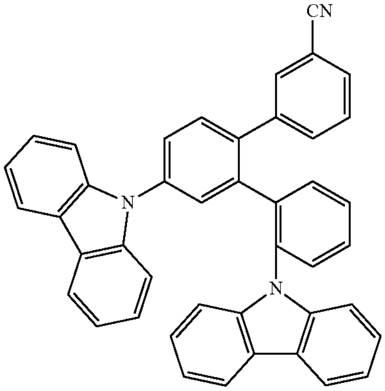
153
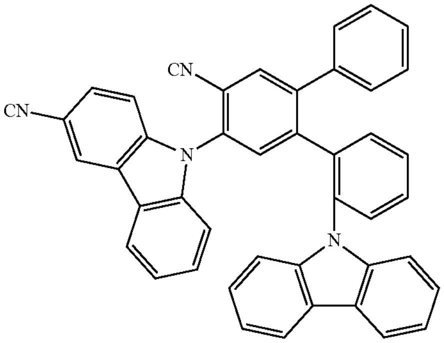
154
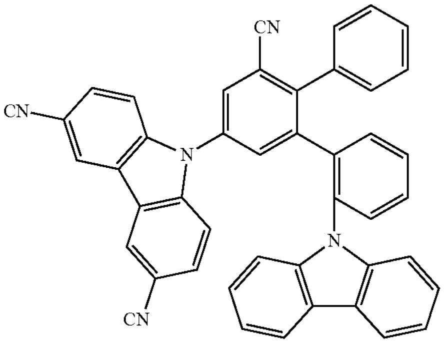
155
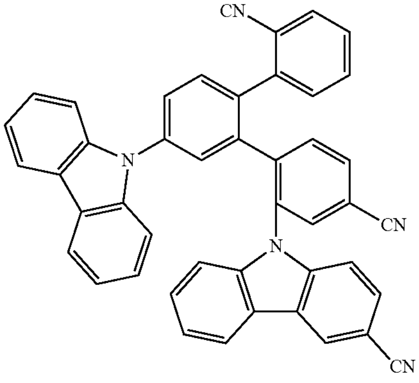
-continued
156
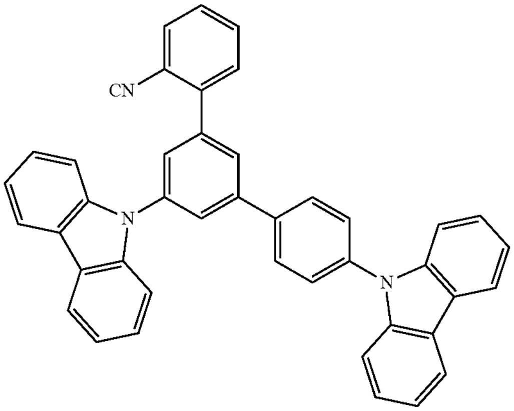
157
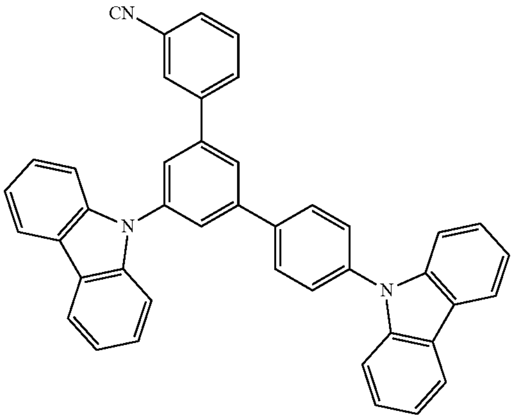
158
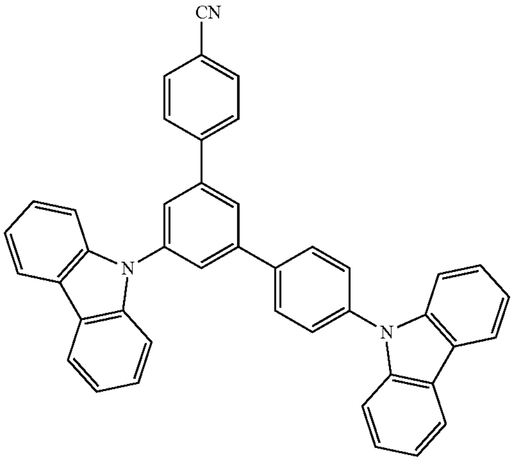

-continued
159
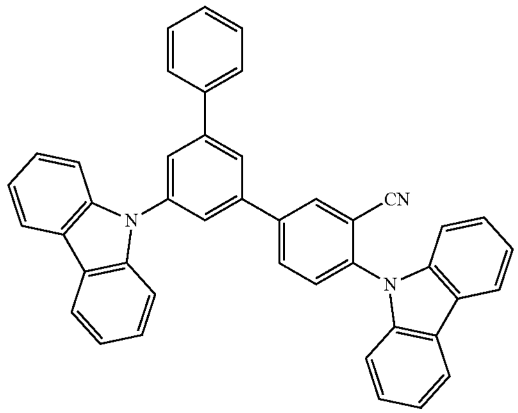
160
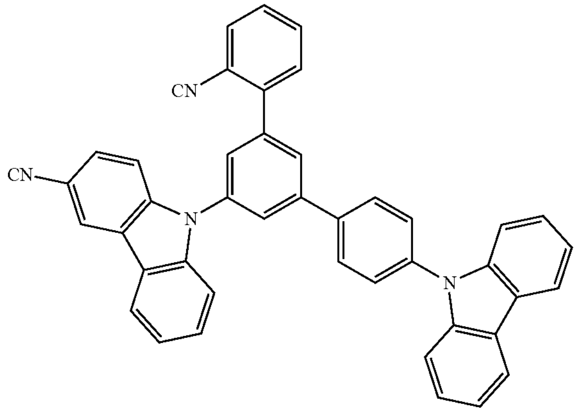
161
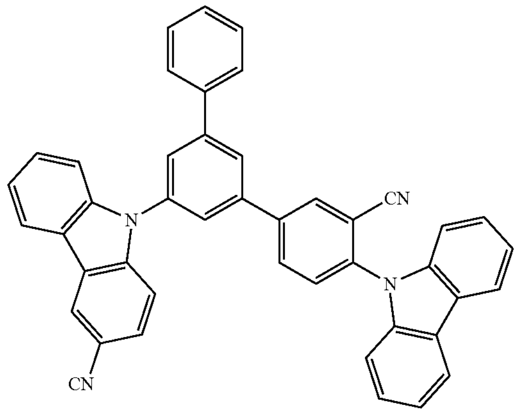
-continued
162
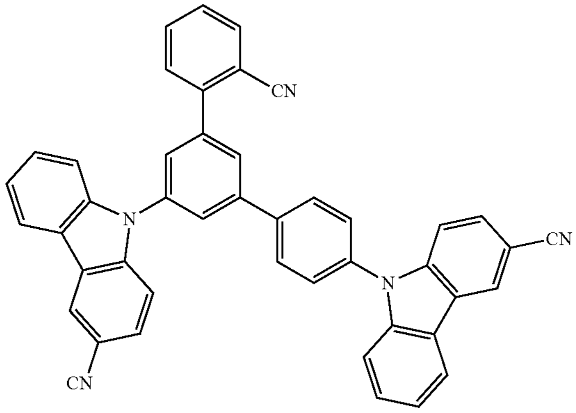
163
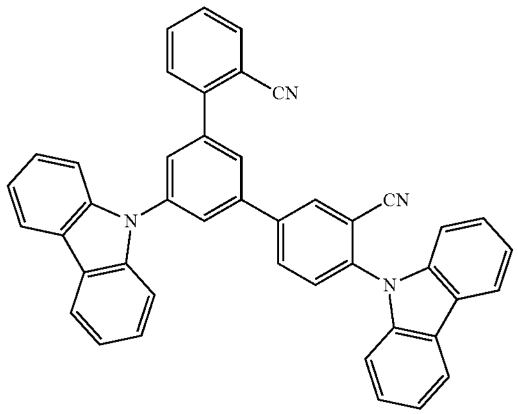
164
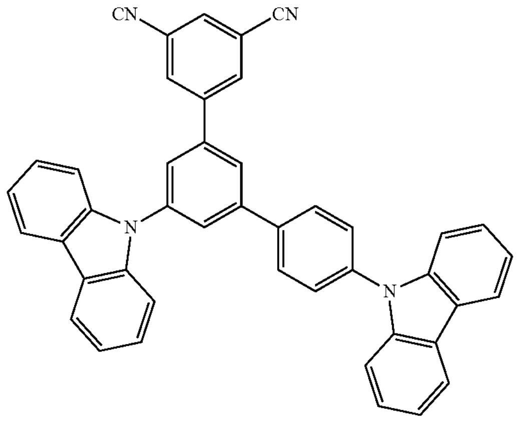

-continued
165
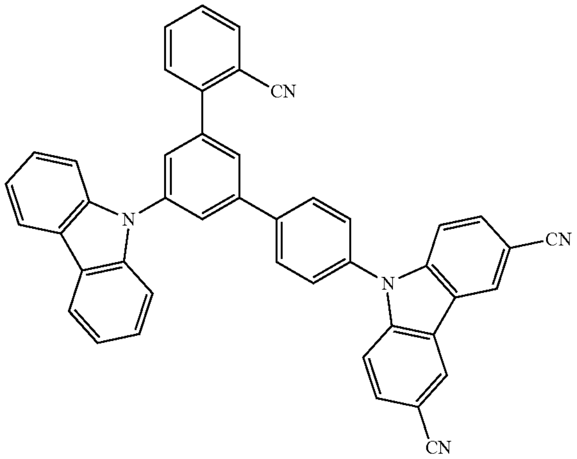
166
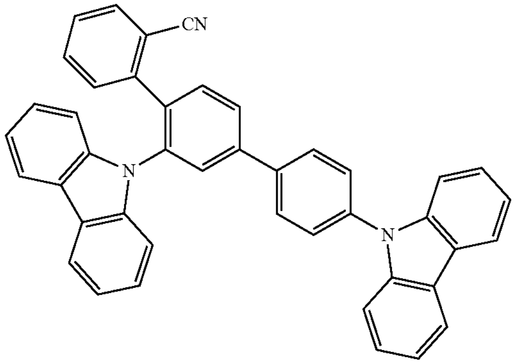
167
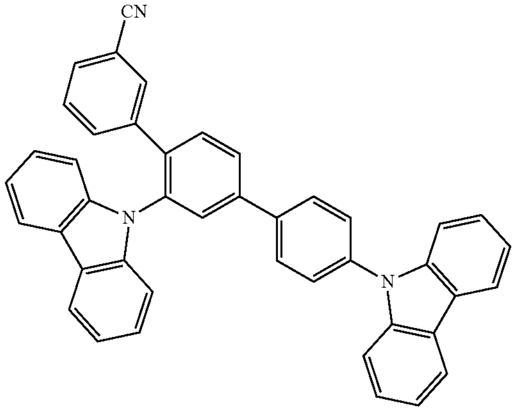
-continued
168
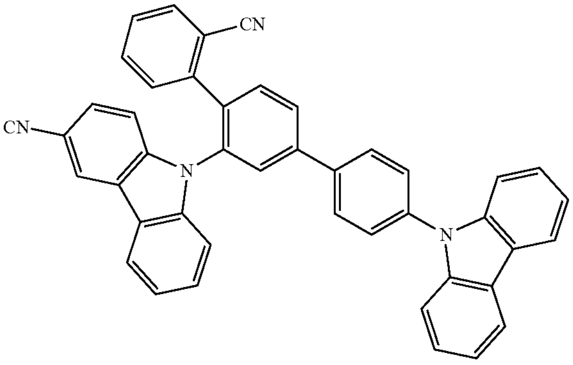
169
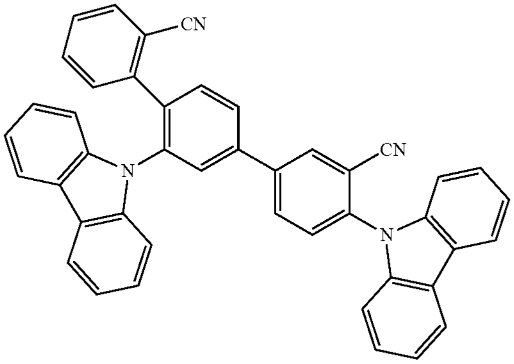
170
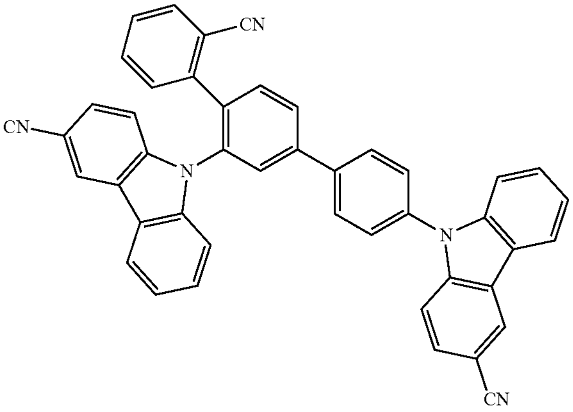
171
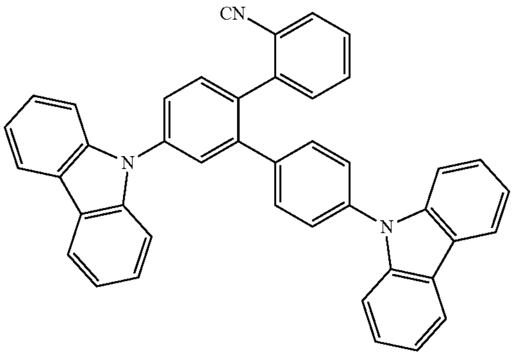

-continued
172
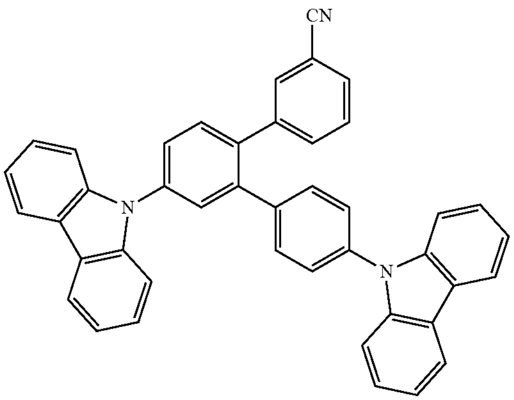
173
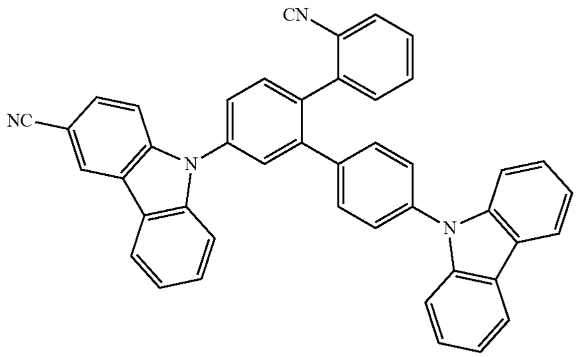
174
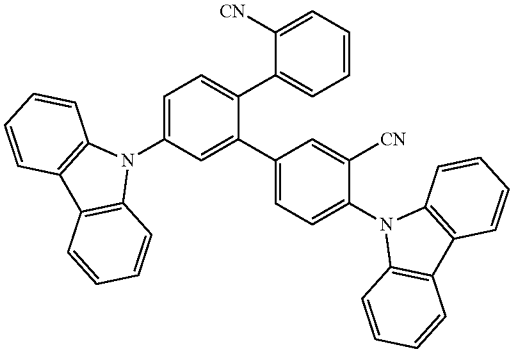
175
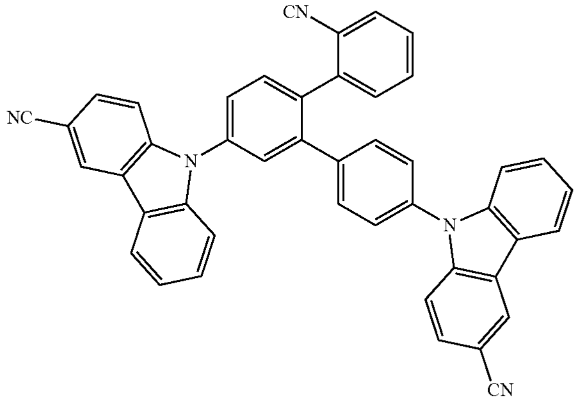
-continued
176
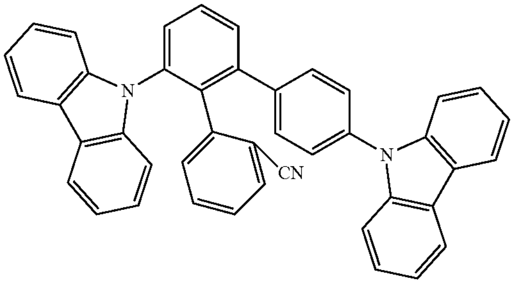
177
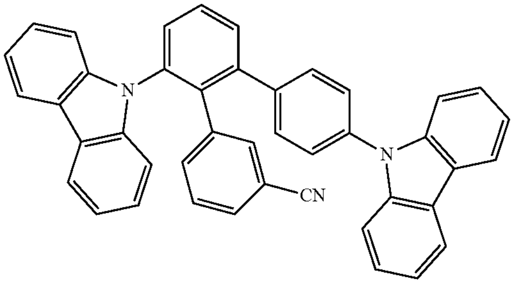
178
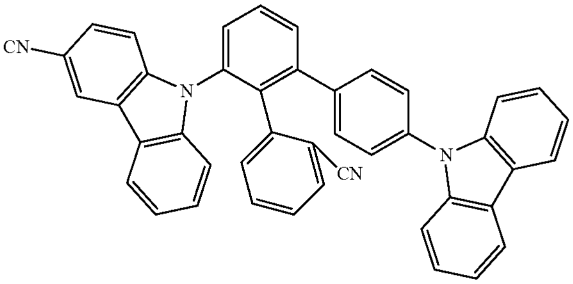
179
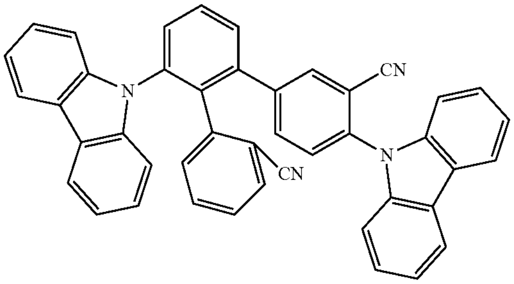
180
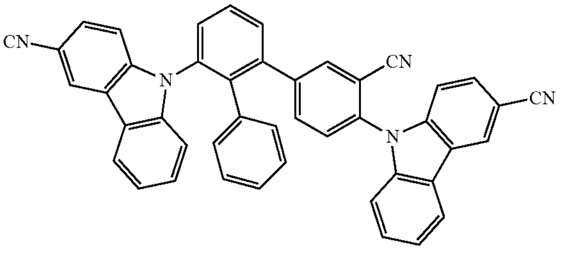

-continued
181
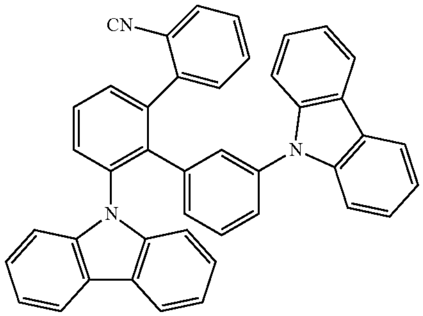
182
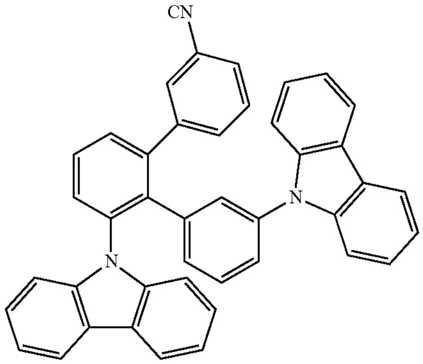
183
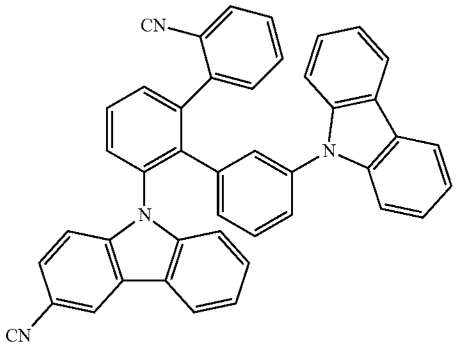
184
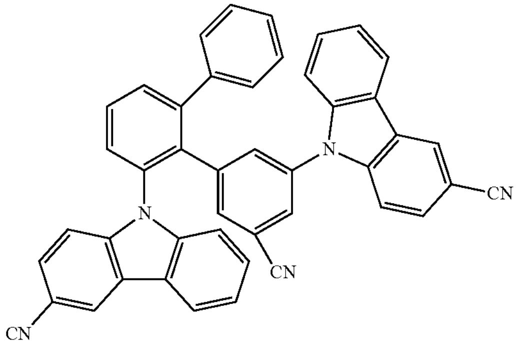
-continued
185
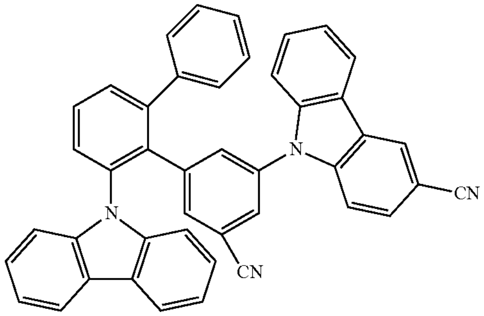
186
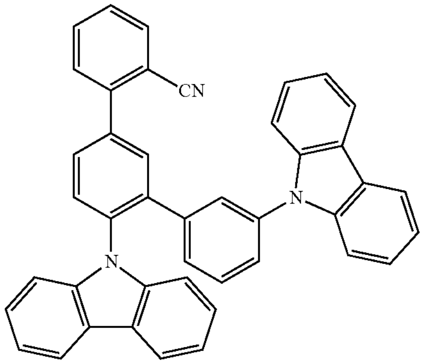
187
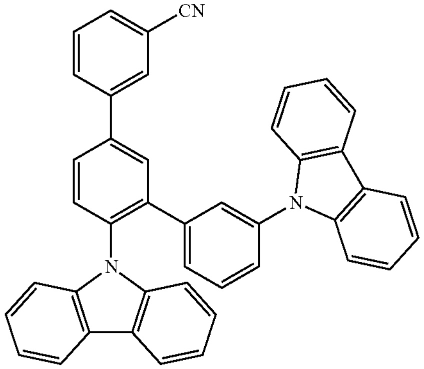
188
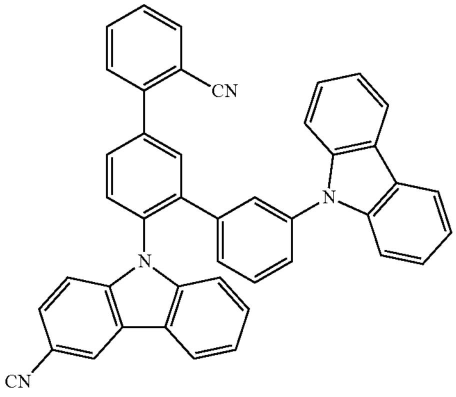

-continued
189
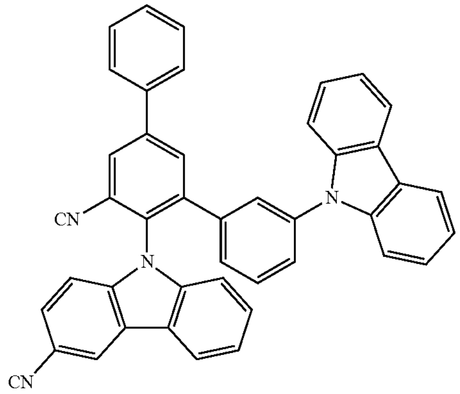
190
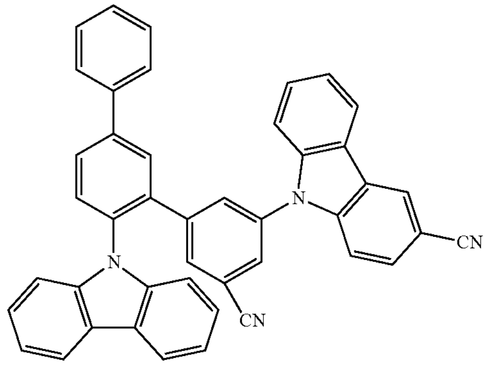
191
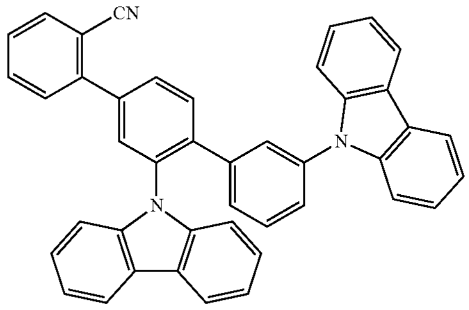
192
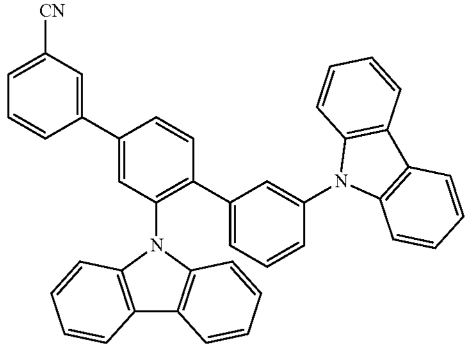
-continued
193
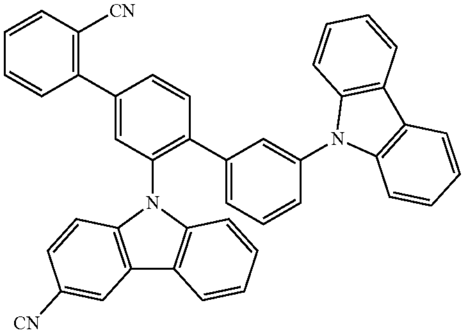
194
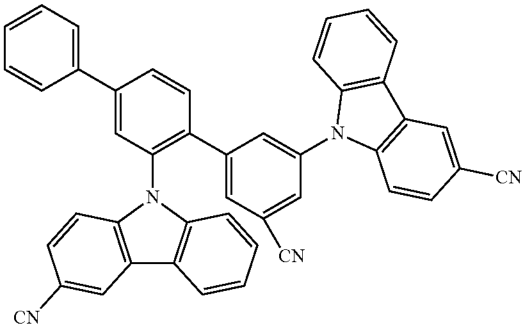
195
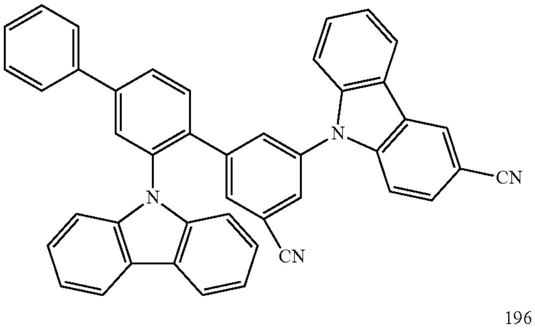
196
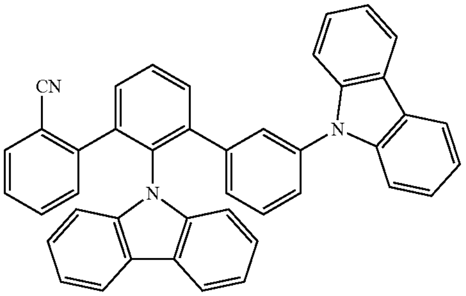
197
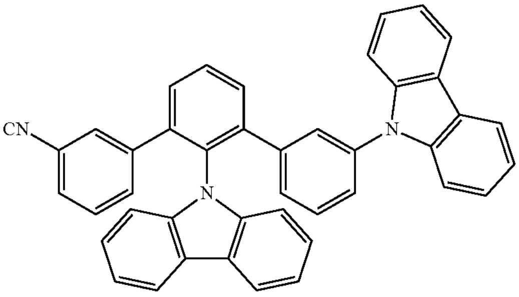

-continued
198
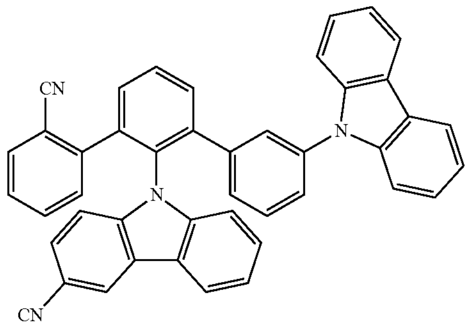
199
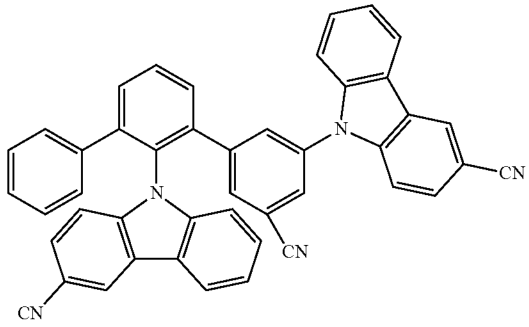
200
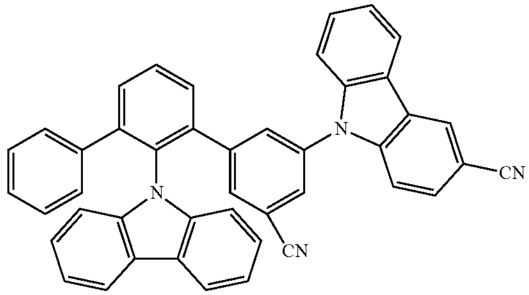
201
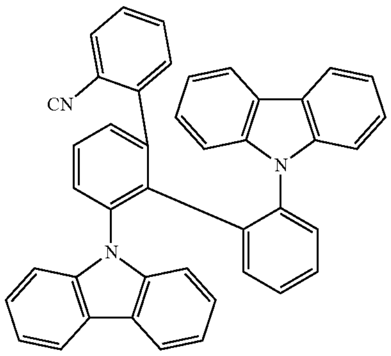
-continued
202
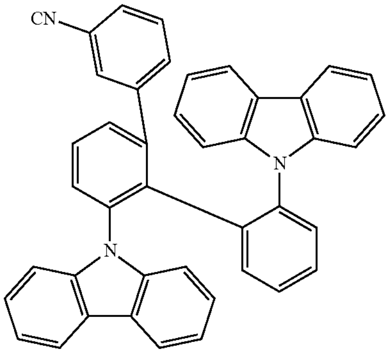
203
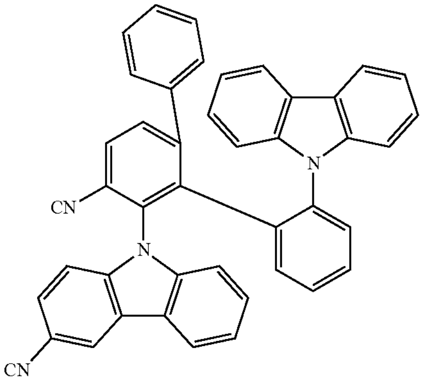
204
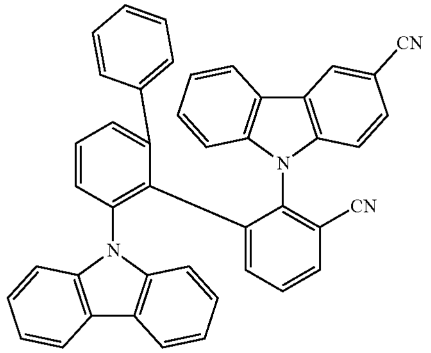
205
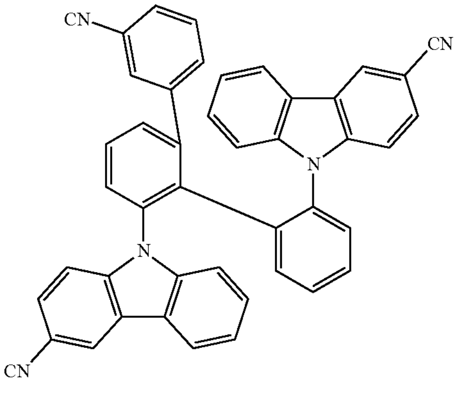

-continued
206
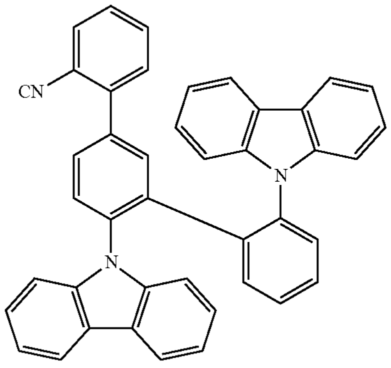
207
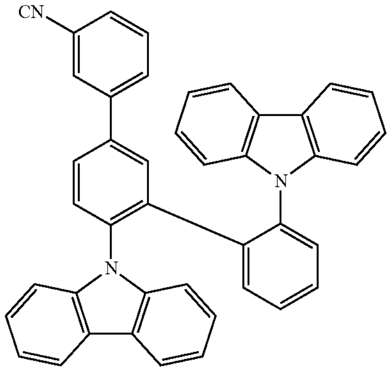
208
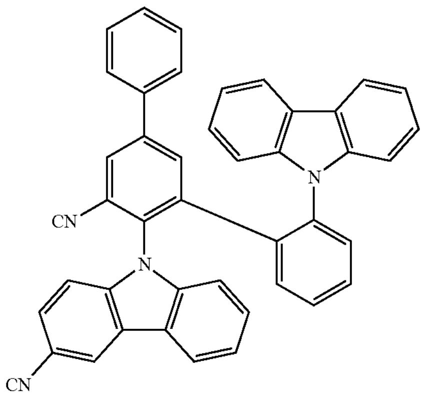
209
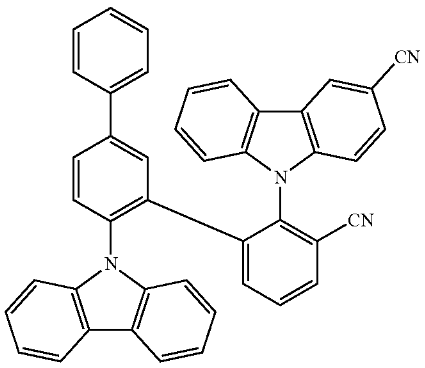
-continued
210
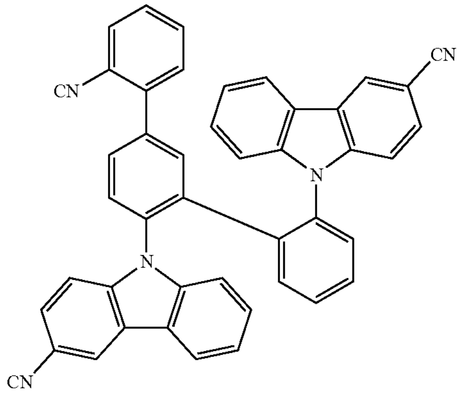
211
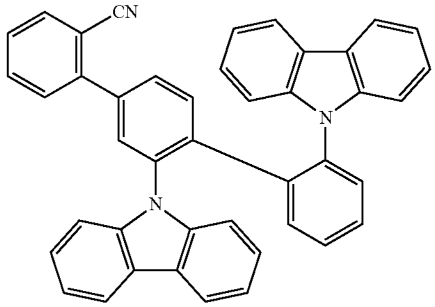
212
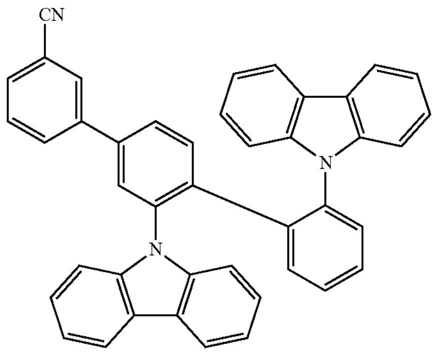
213
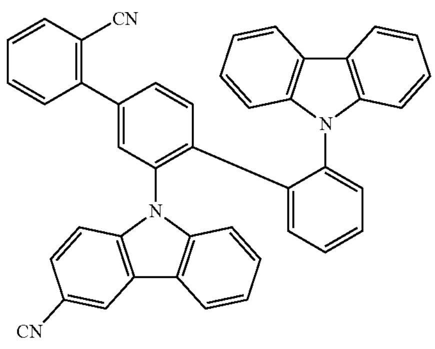

-continued
214
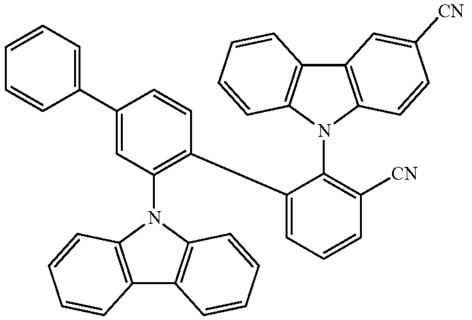
215
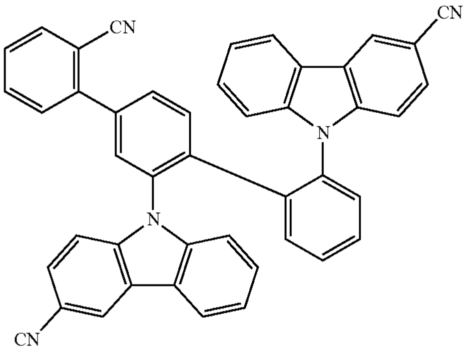
216
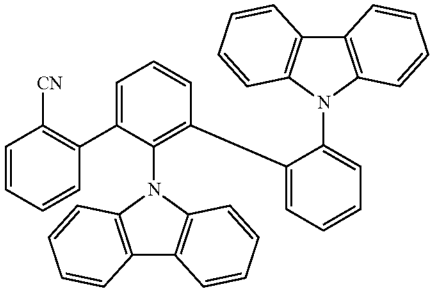
217
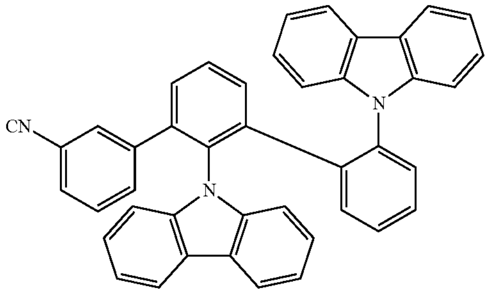
218
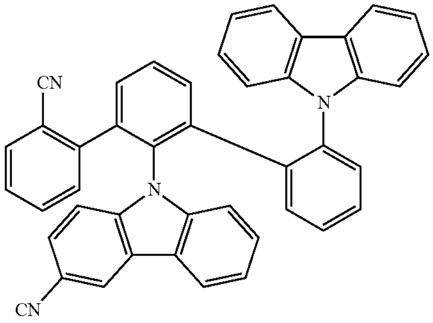
-continued
219
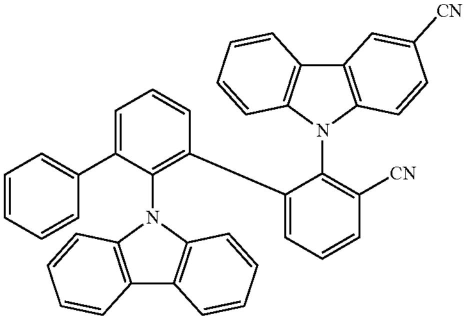
220
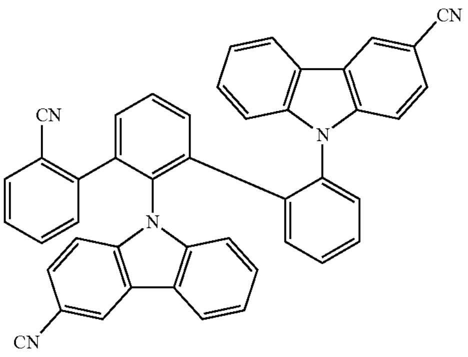
221
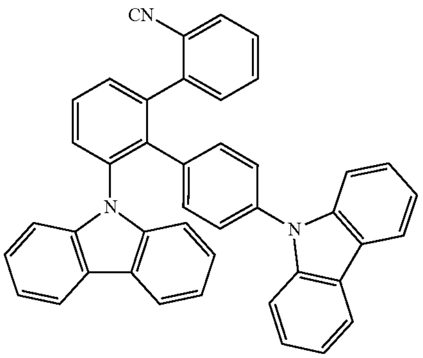
222
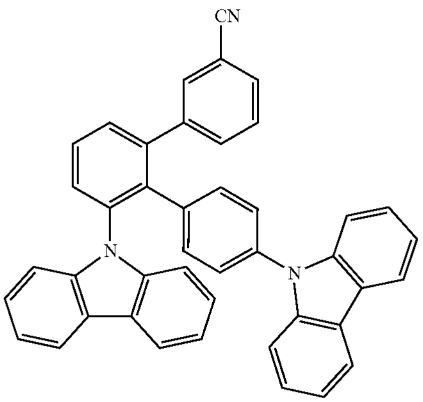

-continued
223
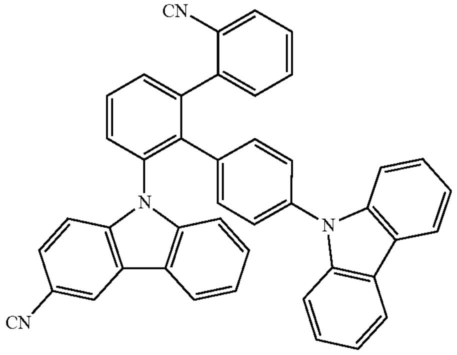
224
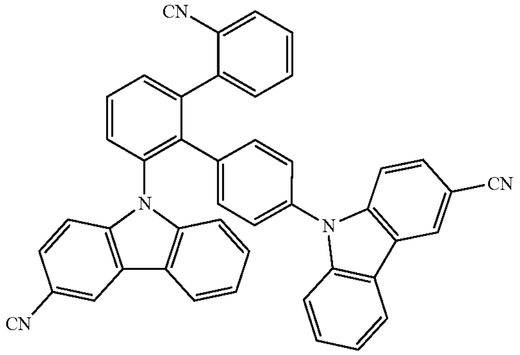
225
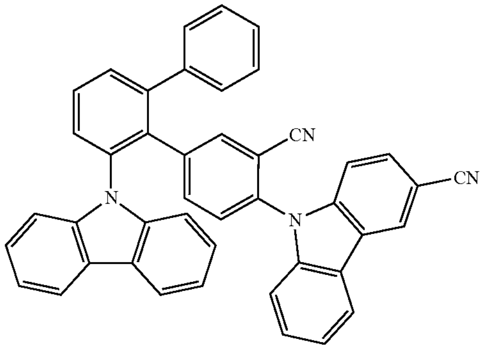
226
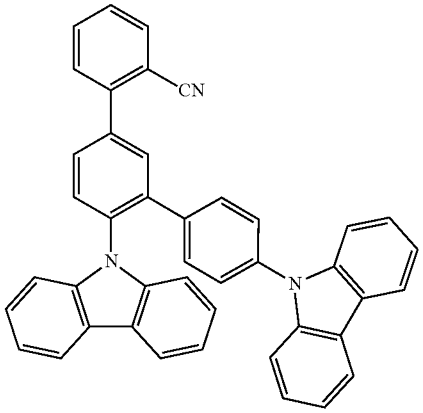
-continued
227
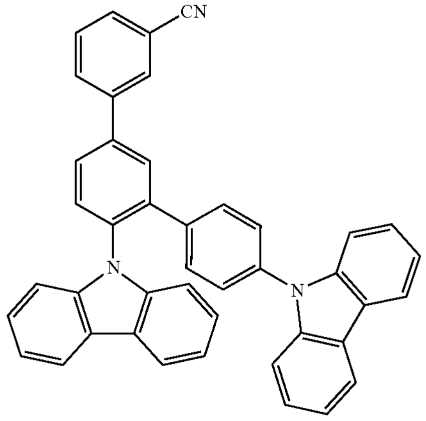
228
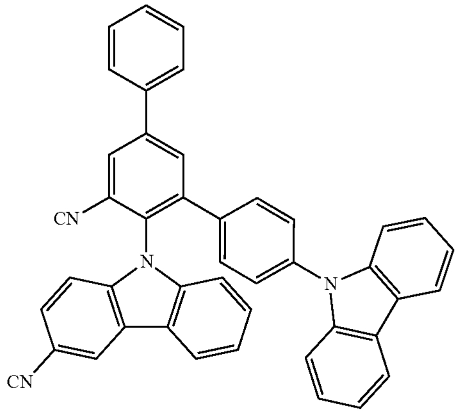
229
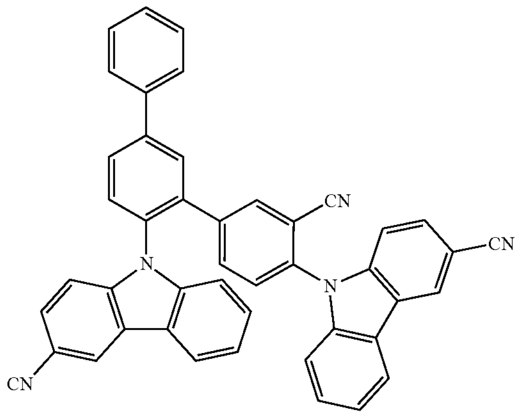

-continued
230
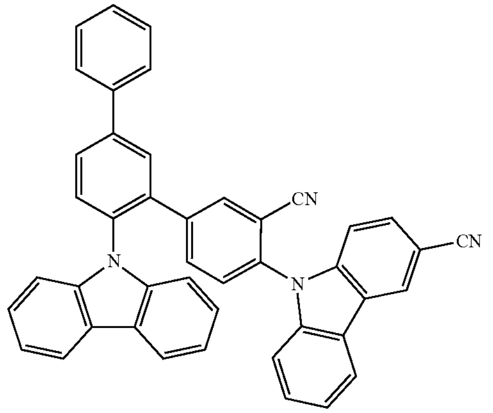
231
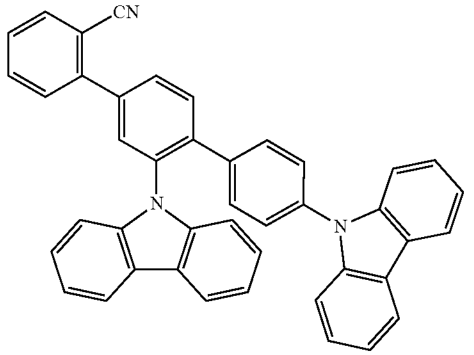
232
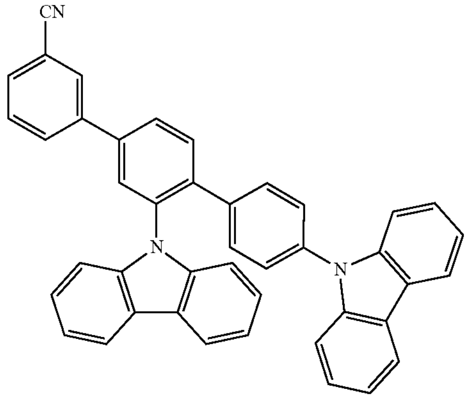
233
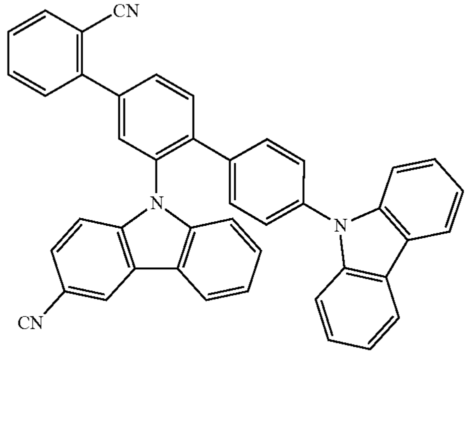
-continued
234
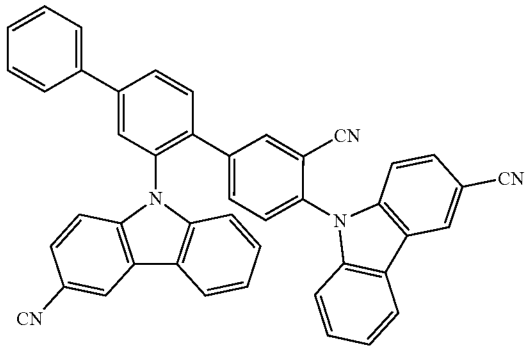
235
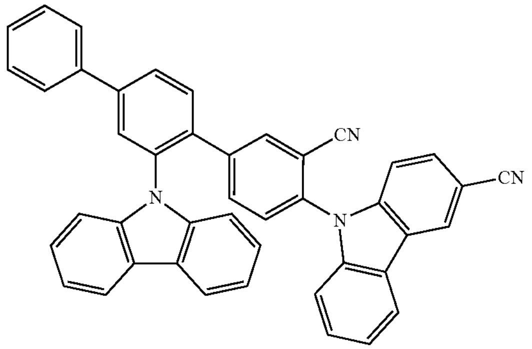
236
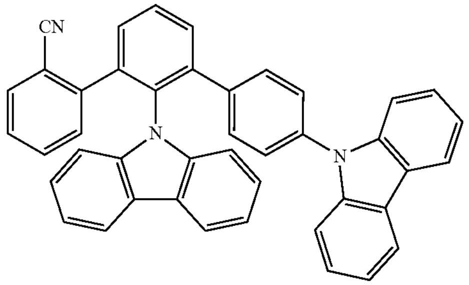
237
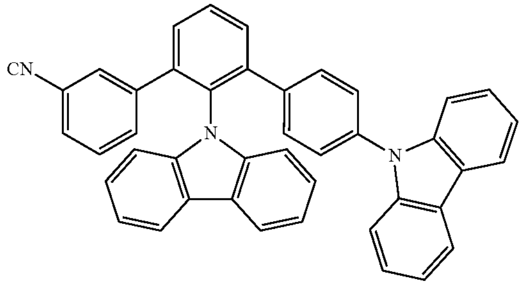
238
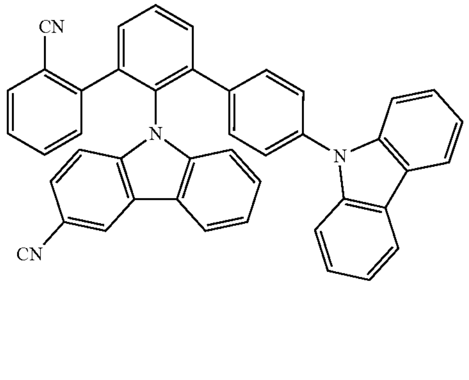

-continued
239
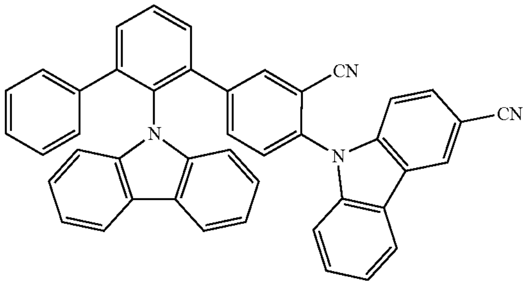
240
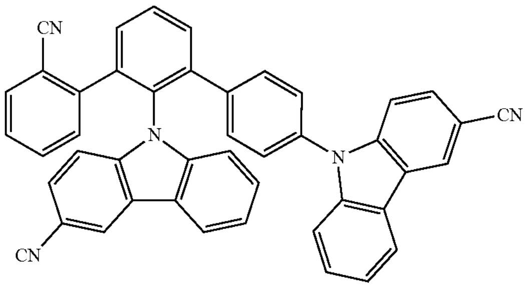
241
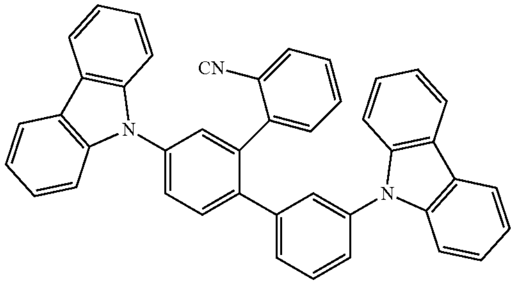
242
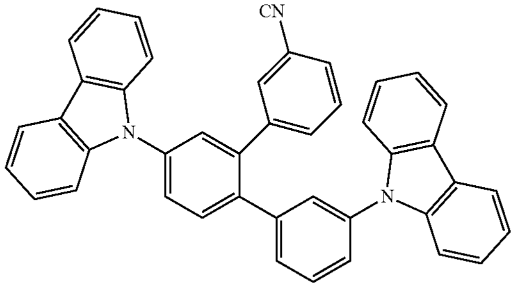
243
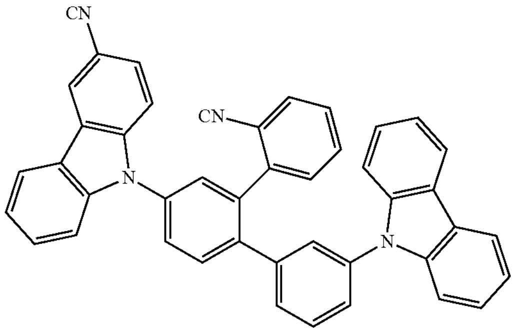
-continued
244
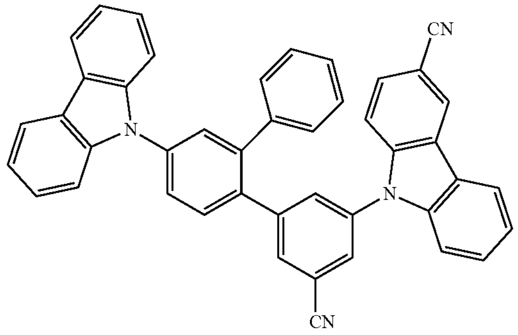
245
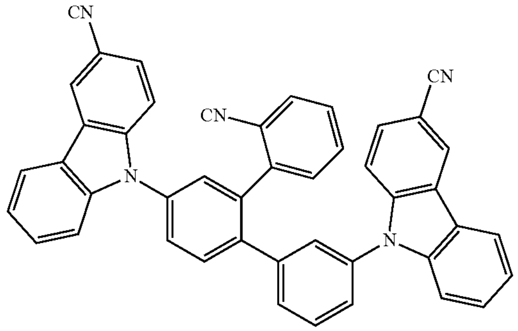
246
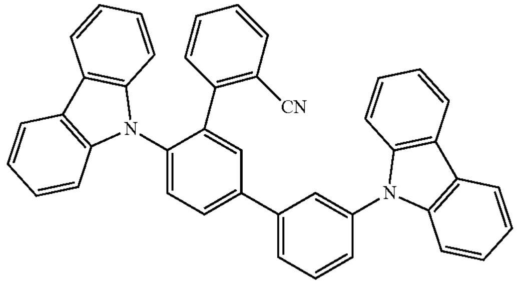
247
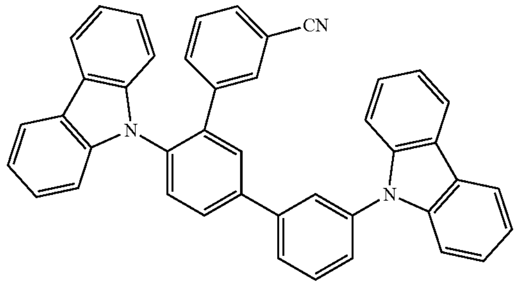

-continued
248
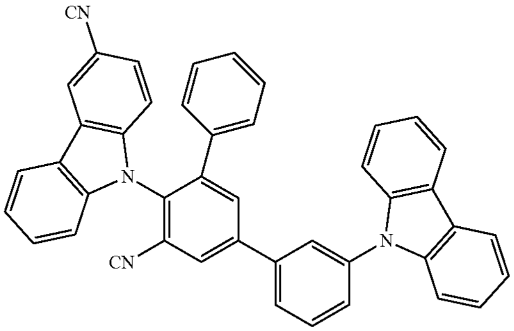
249
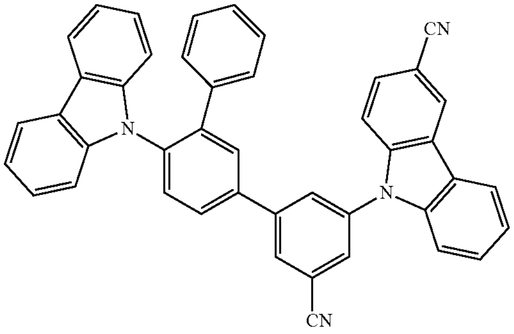
250
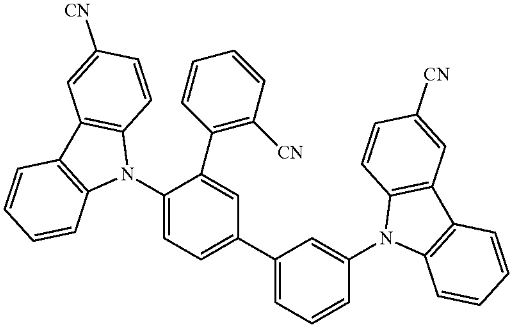
251
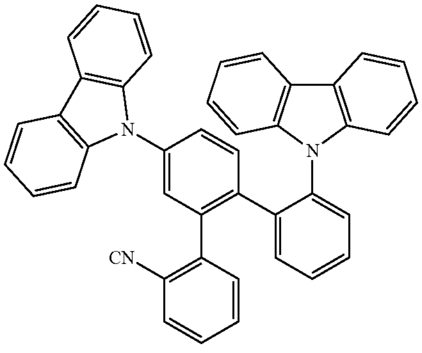
-continued
252
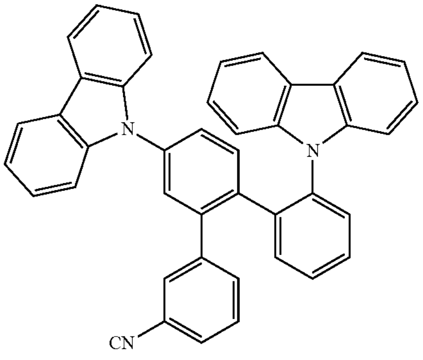
253
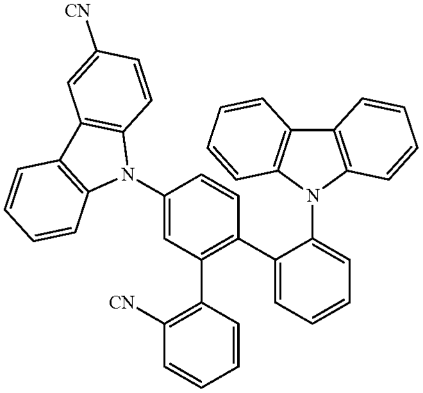
254
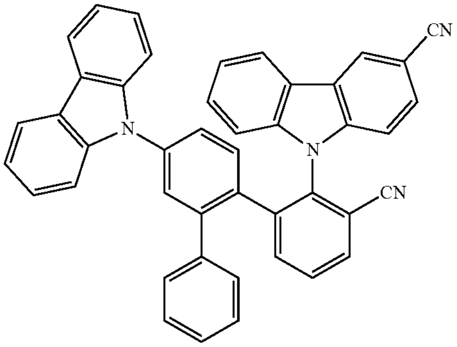
255
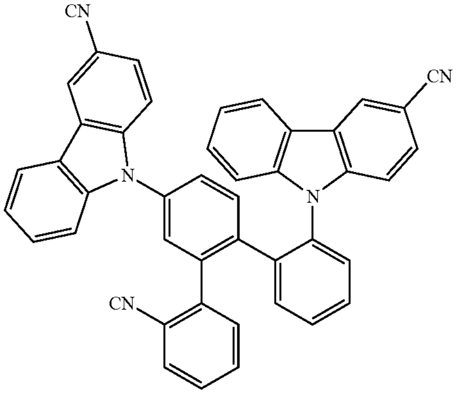

-continued
256
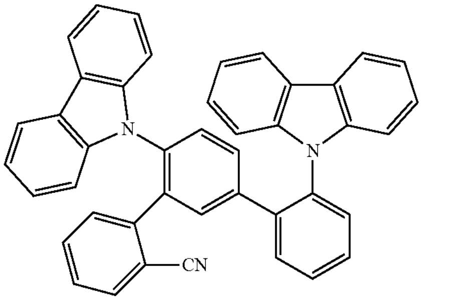
257
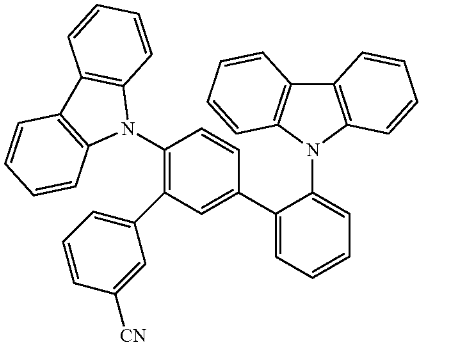
258
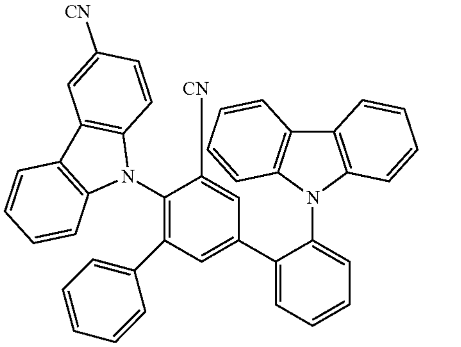
259
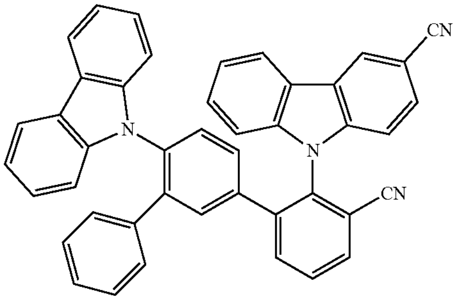
260
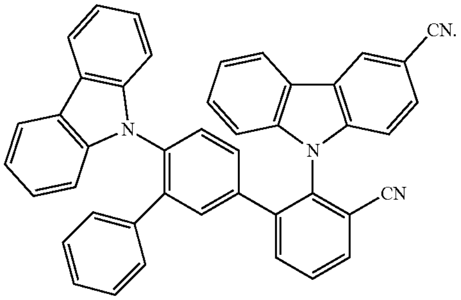
In some embodiments, the hole transporting host may include at least one of Compounds H-H1 to H-H103:
H-H1
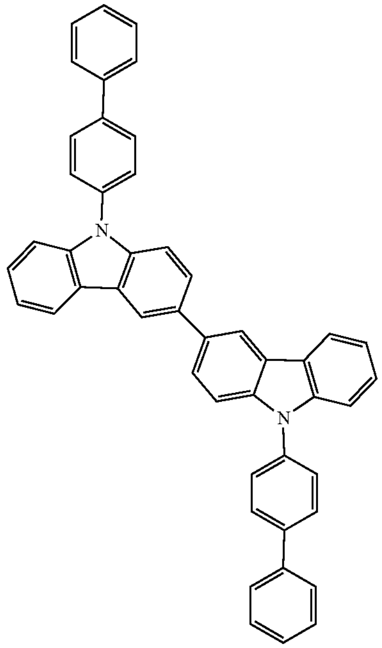
H-H2
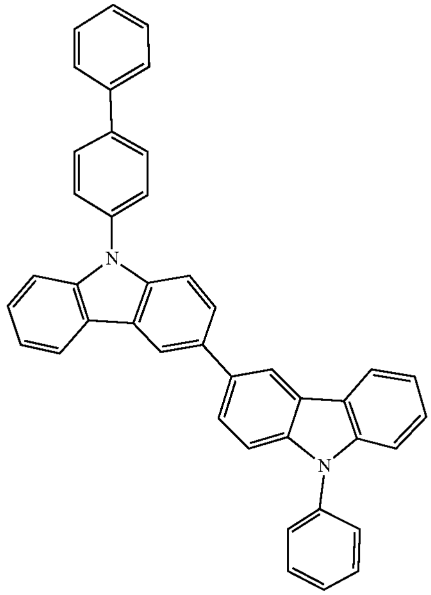

-continued
H-H3
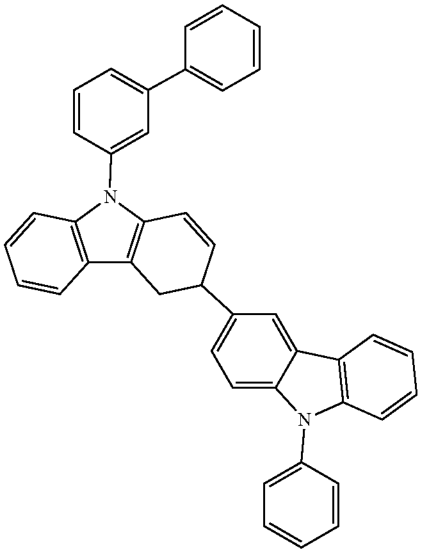
H-H4
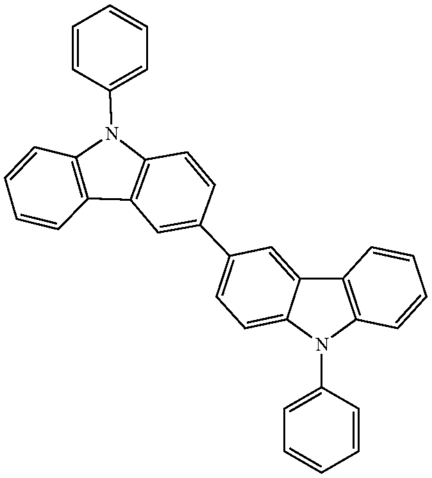
H-H5
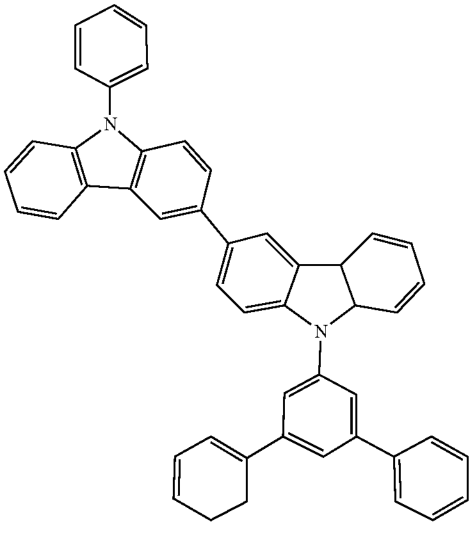
-continued
H-H6
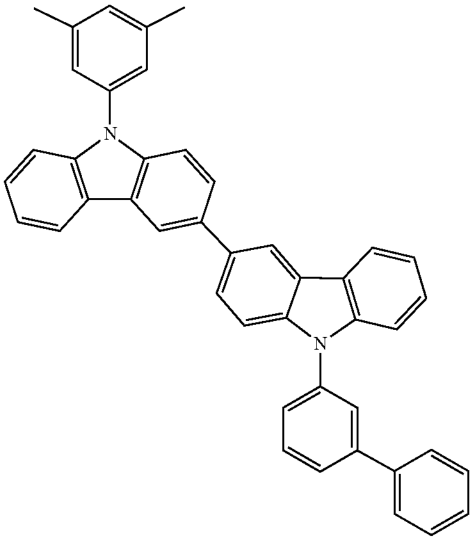
H-H7
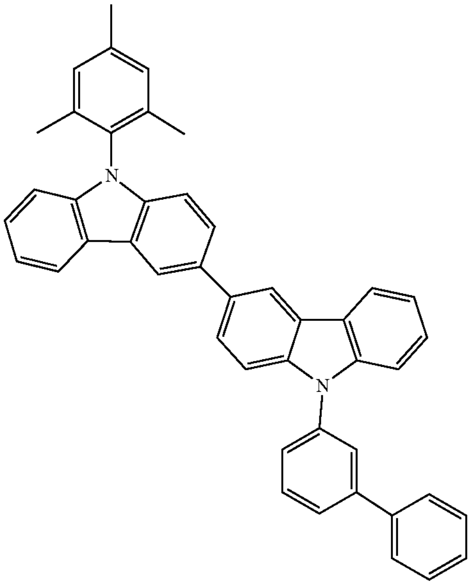

-continued
H-H8
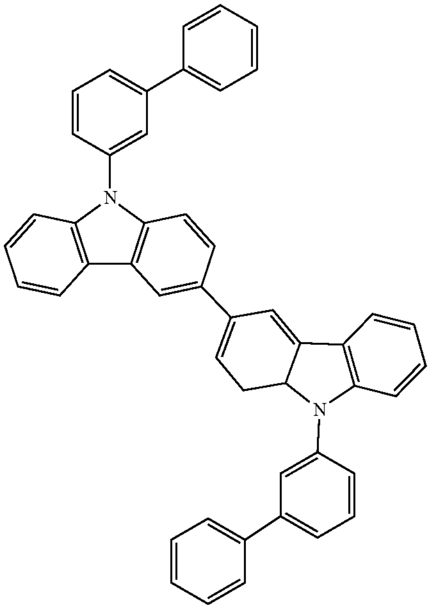
H-H9
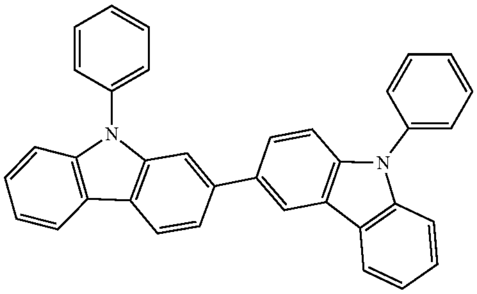
H-H10
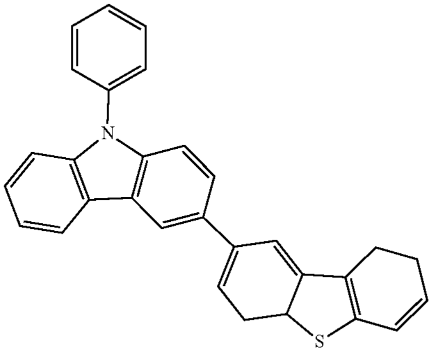
H-H11
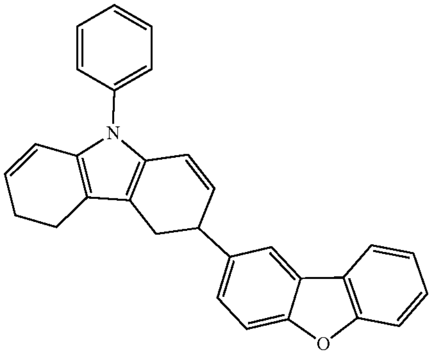
-continued
H-H12
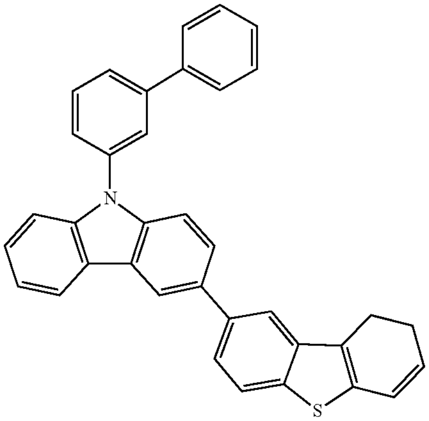
H-H13
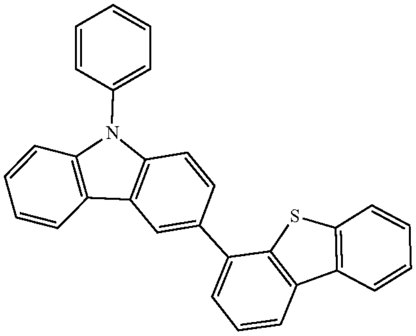
H-H14
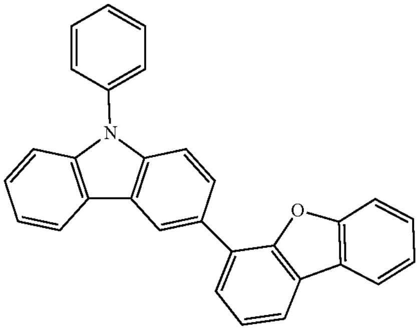
H-H15
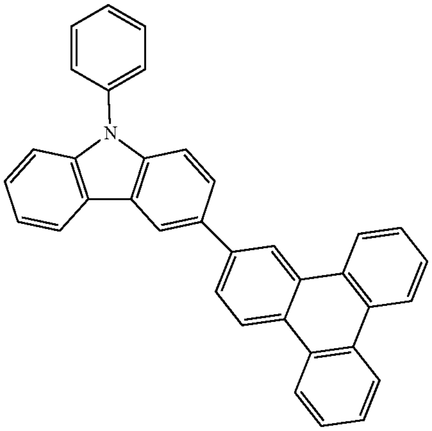

-continued
H-H16
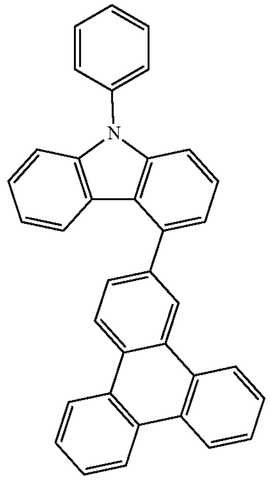
H-H17
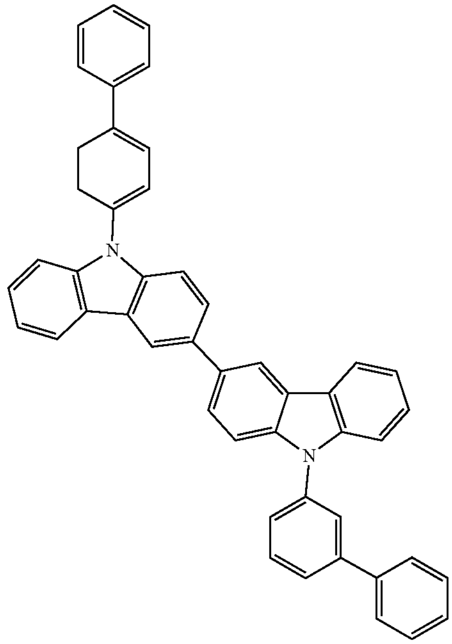
H-H18
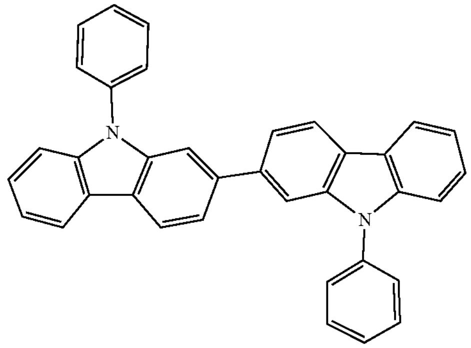
-continued
H-H19
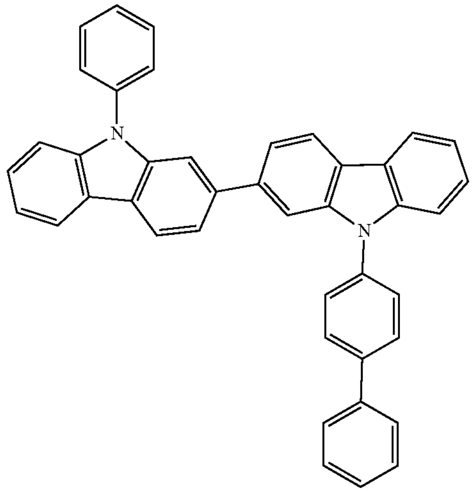
H-H20
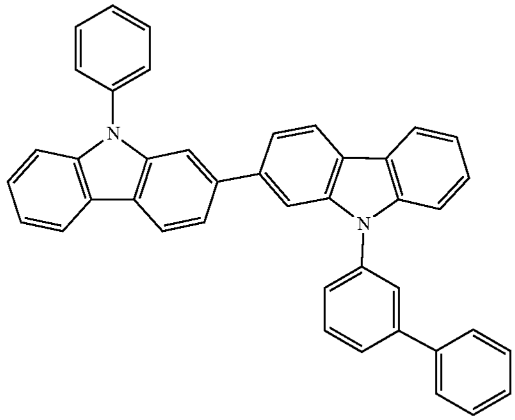
H-H21
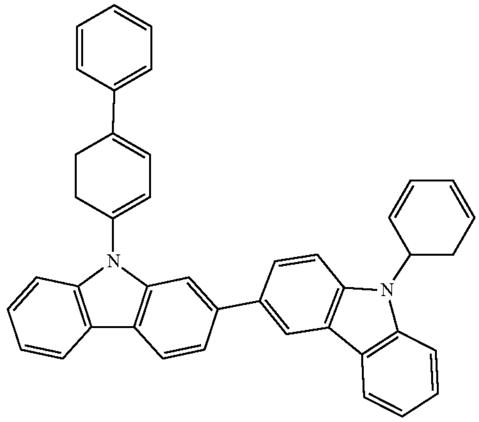

-continued
H-H22
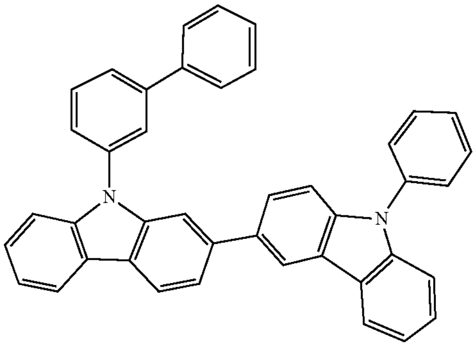
H-H23
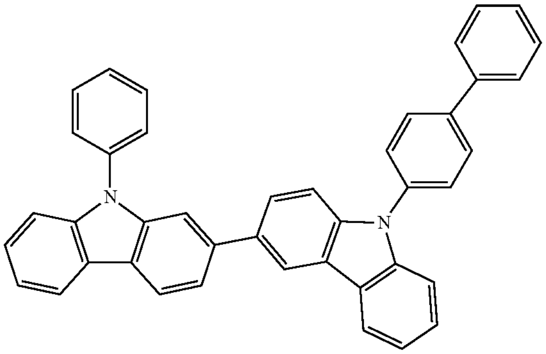
H-H24
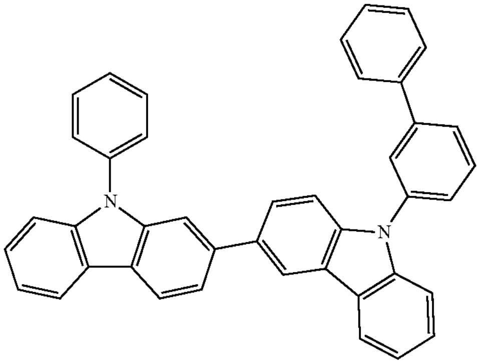
H-H25
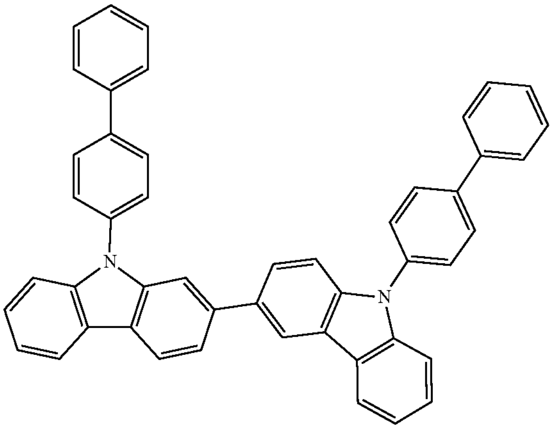
-continued
H-H26
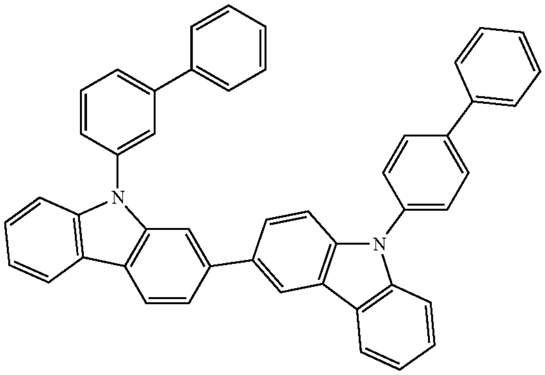
H-H27
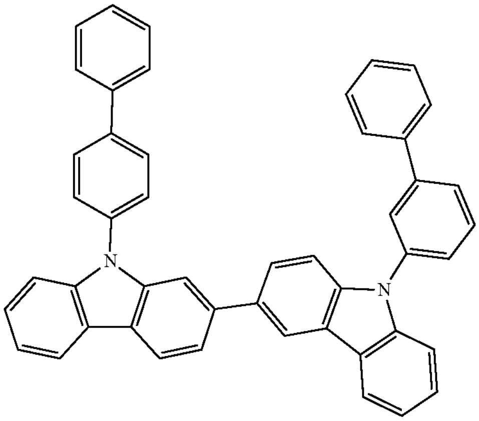
H-H28
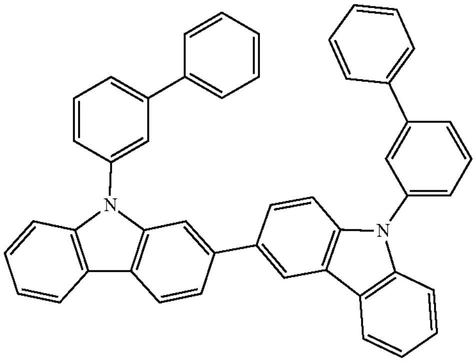

-continued
H-H29
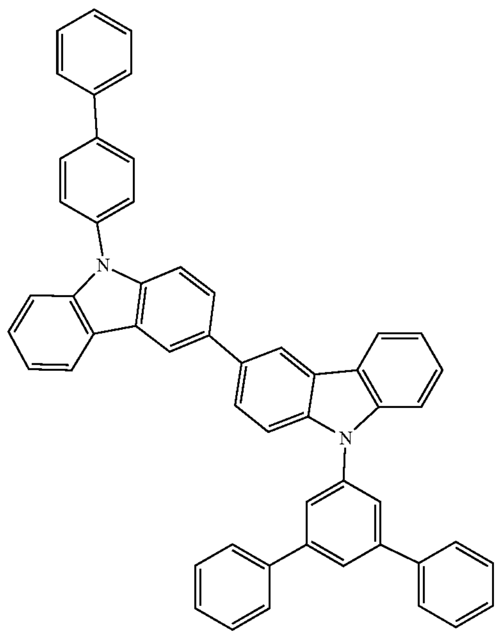
H-H30
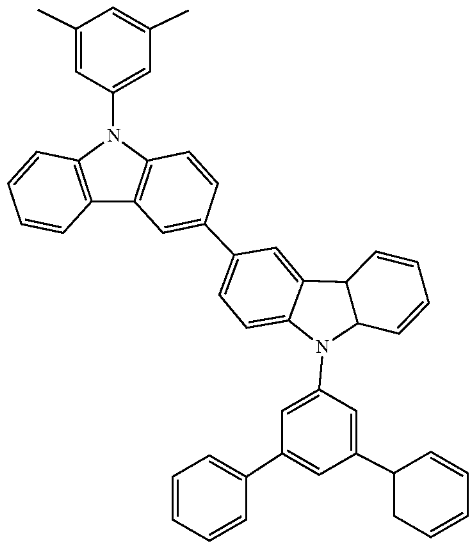
-continued
H-H31
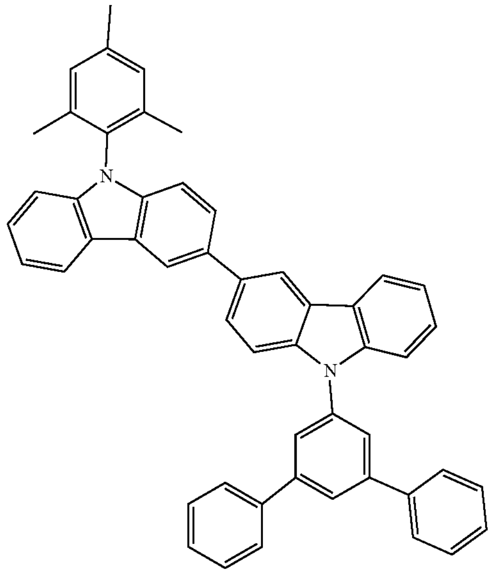
H-H32
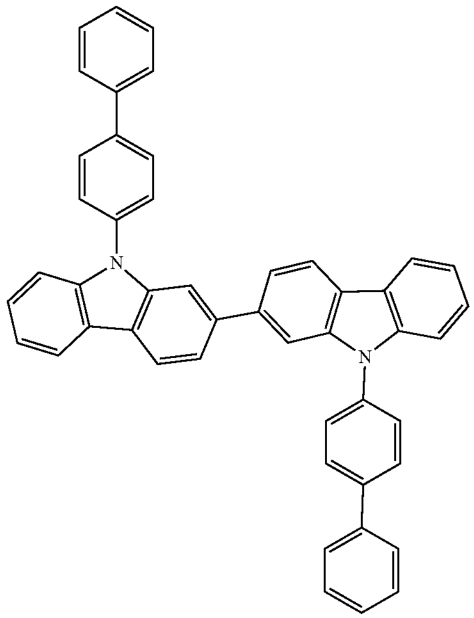

-continued
H-H33
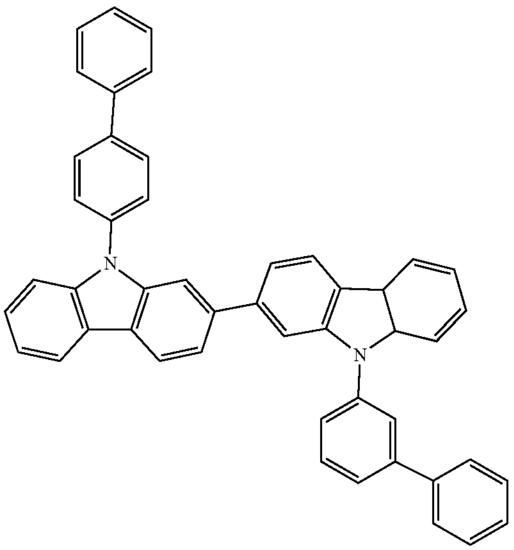
H-H34
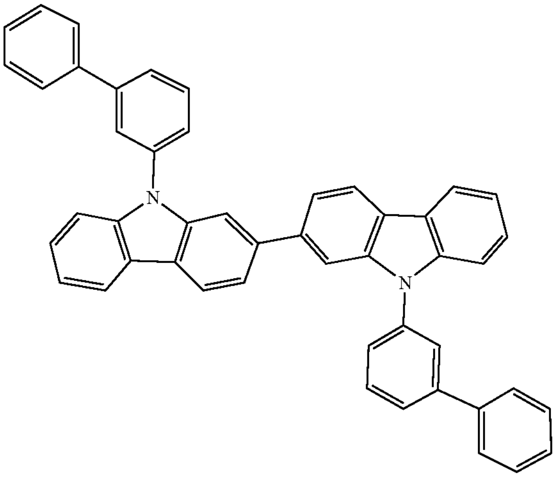
H-H35
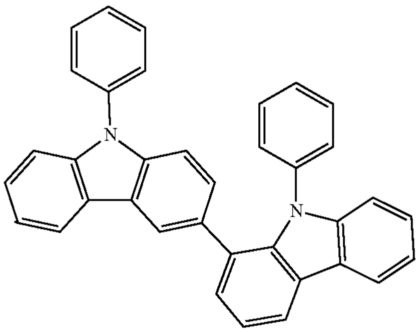
-continued
H-H36
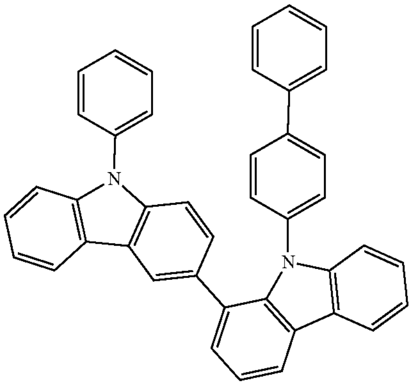
H-H37
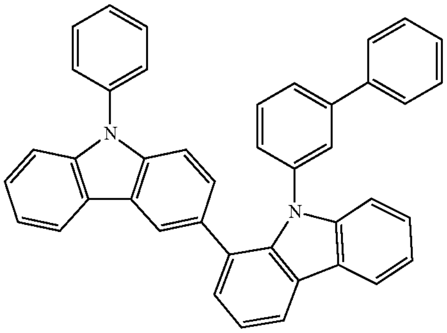
H-H38
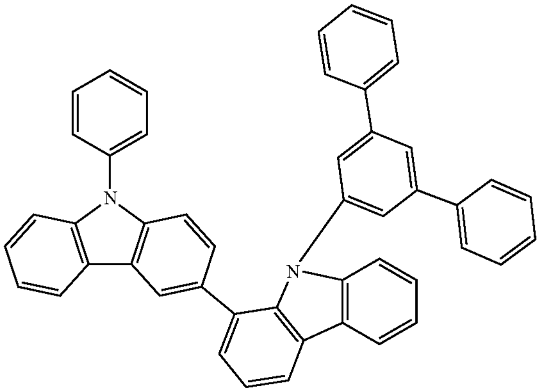
H-H39
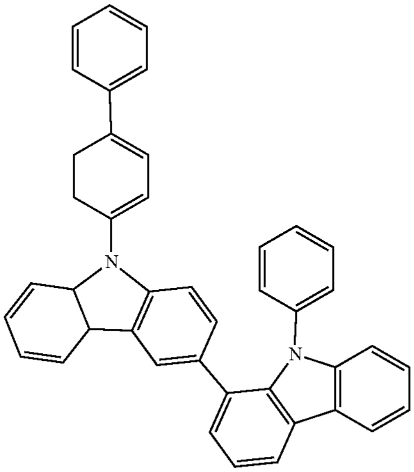

H-H40
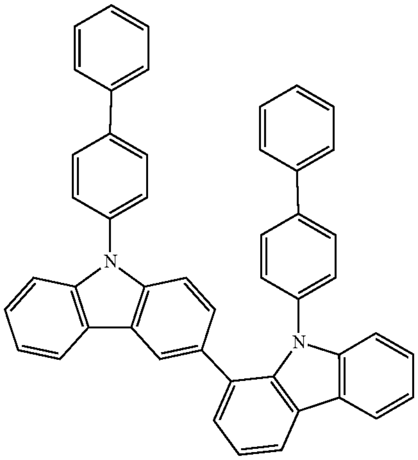
H-H41
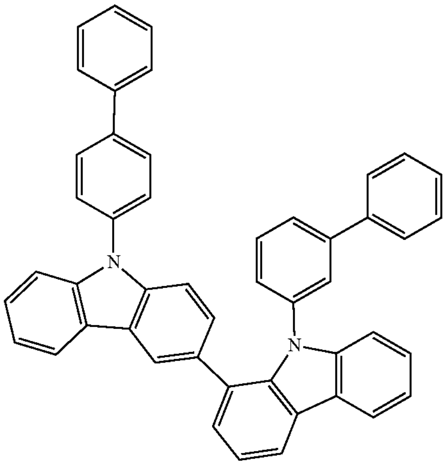
H-H42
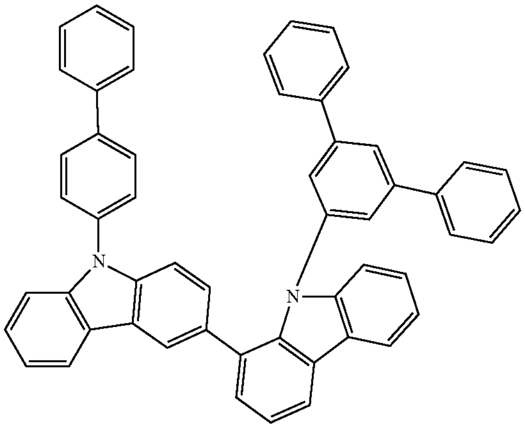
H-H43
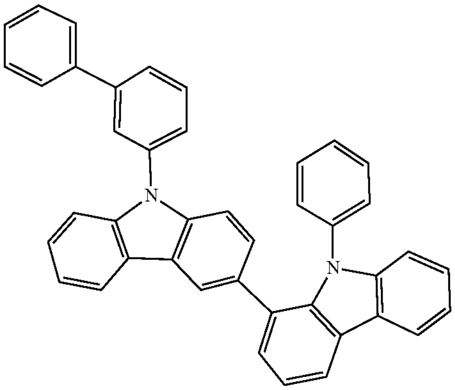
H-H44
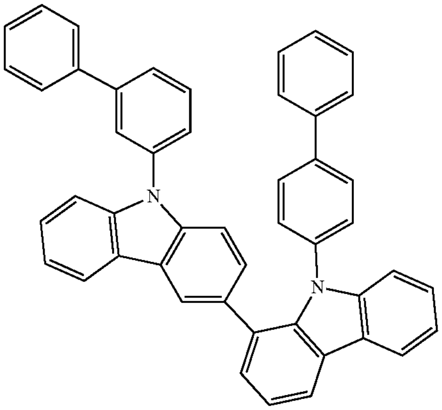
H-H45
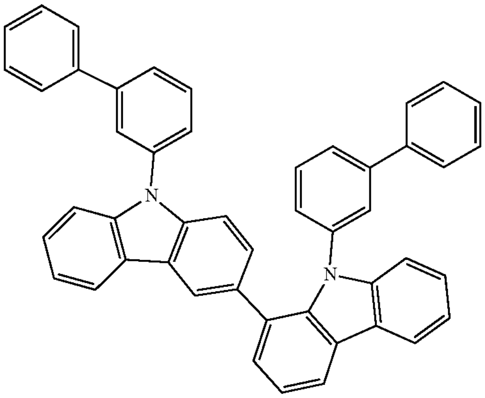
H-H46
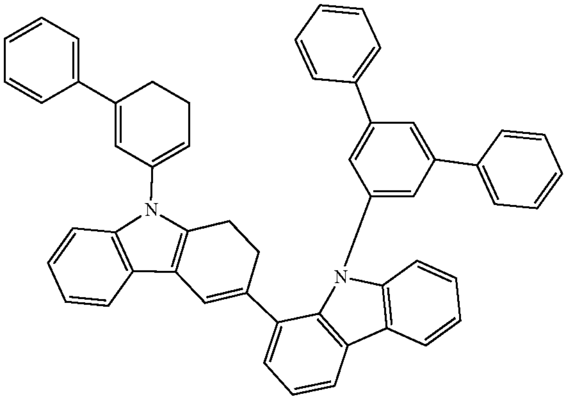

-continued
H-H47
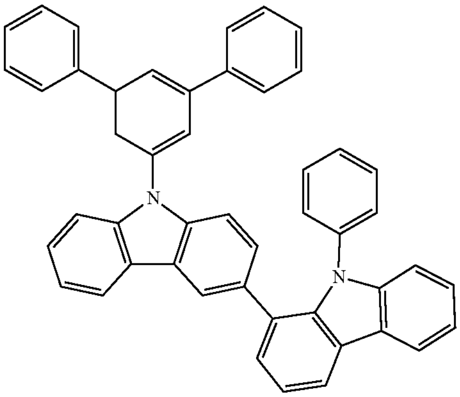
H-H48
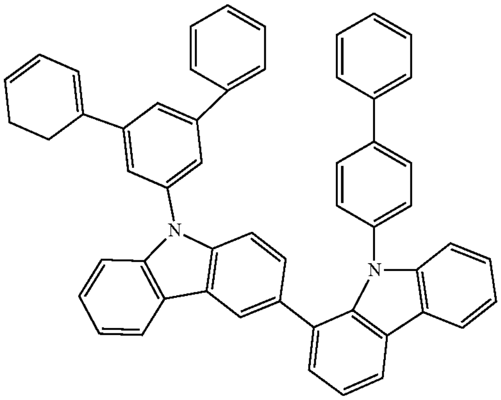
H-H49
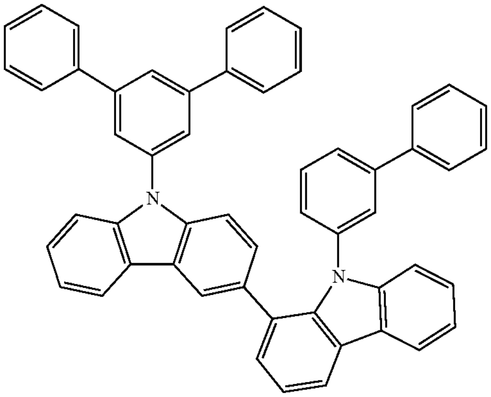
-continued
H-H50
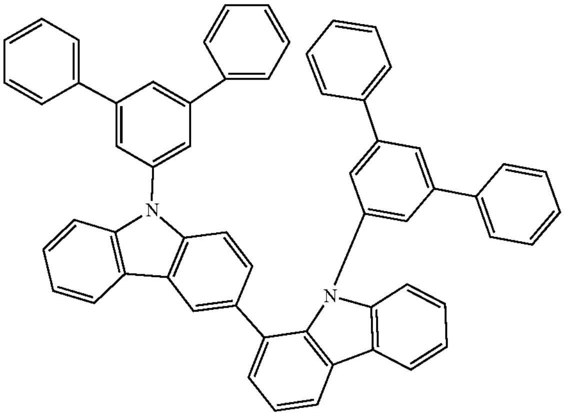
H-H51
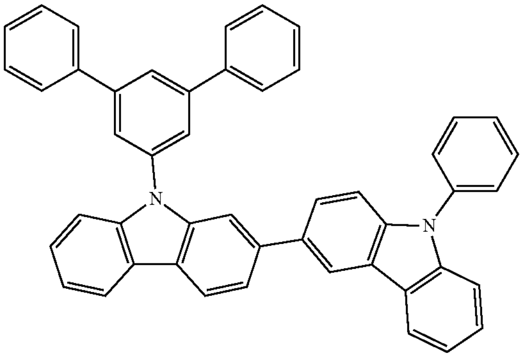
H-H52
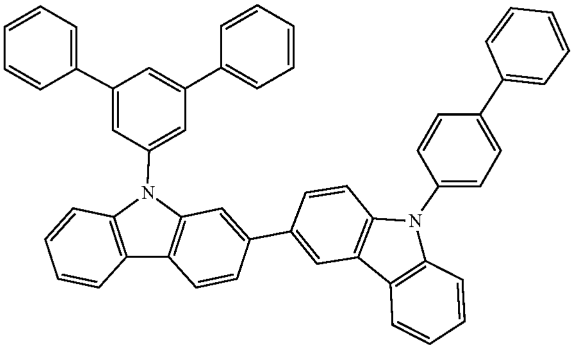
H-H53
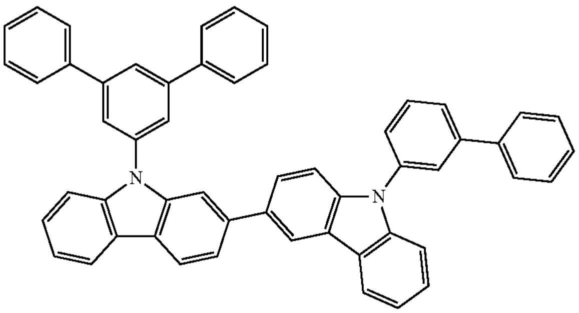

H-H54
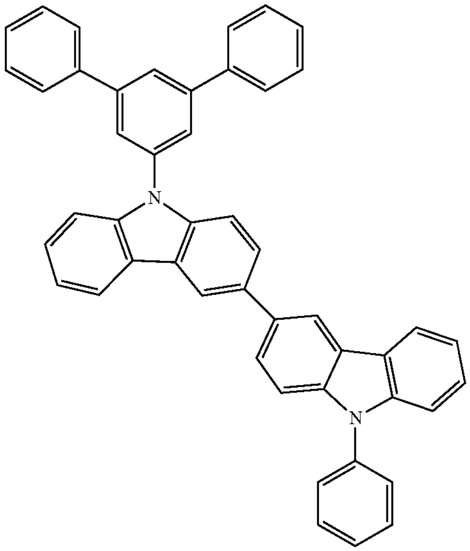
H-H55
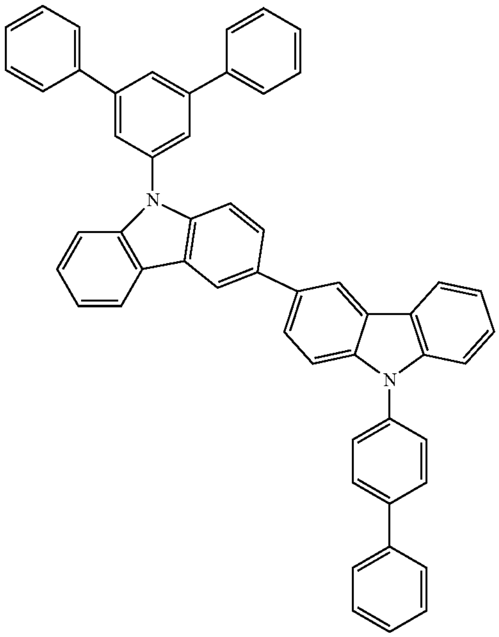
H-H56
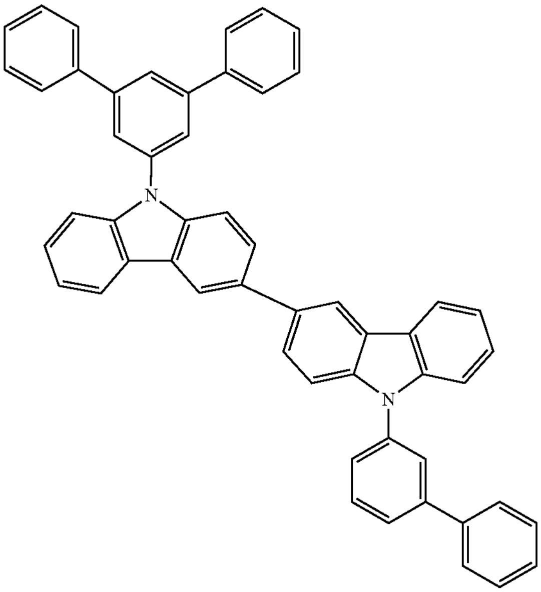
H-H57
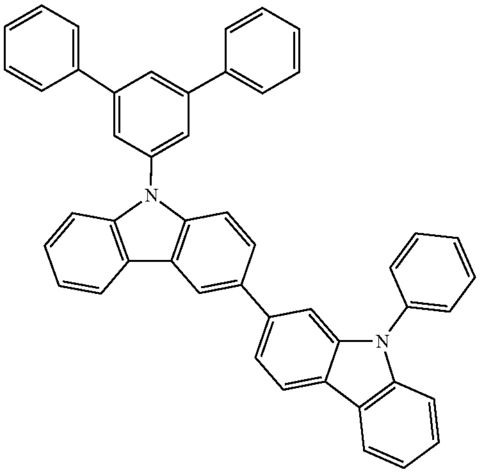
H-H58
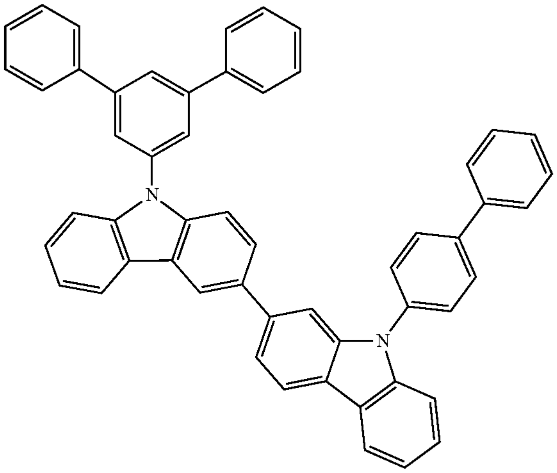

-continued
H-59
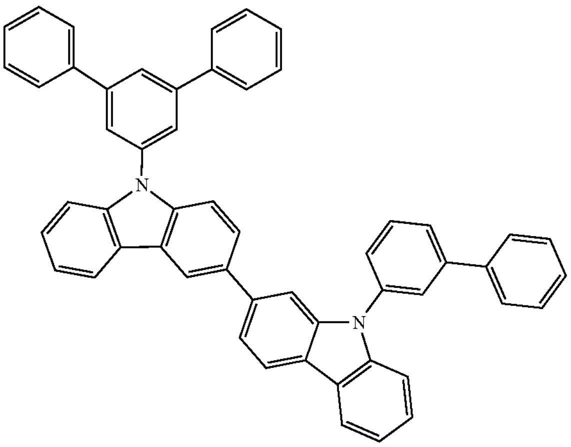
H-60
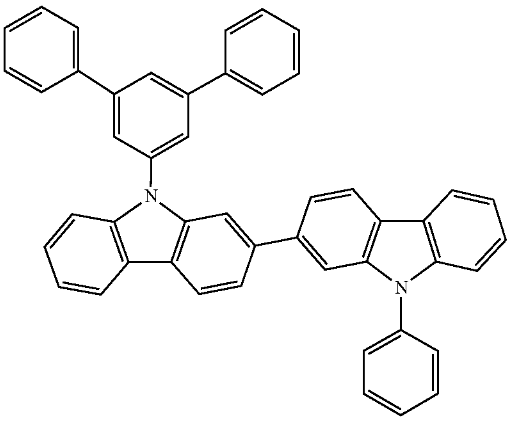
H-61
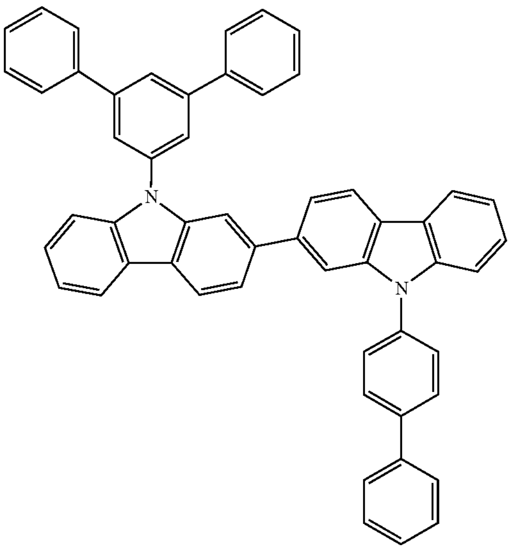
-continued
H-H62
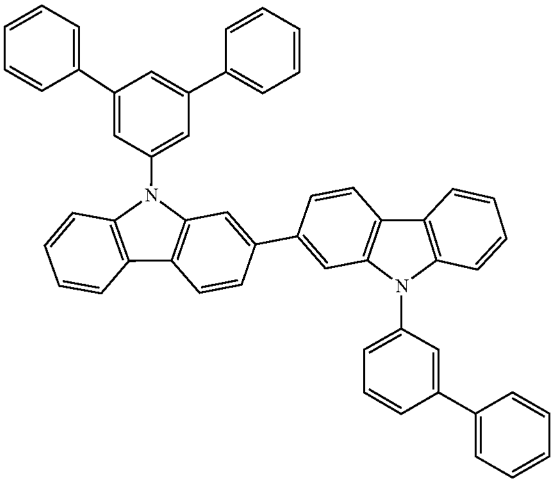
H-H63
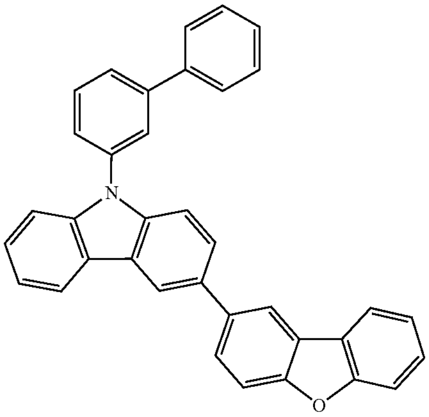
H-H64
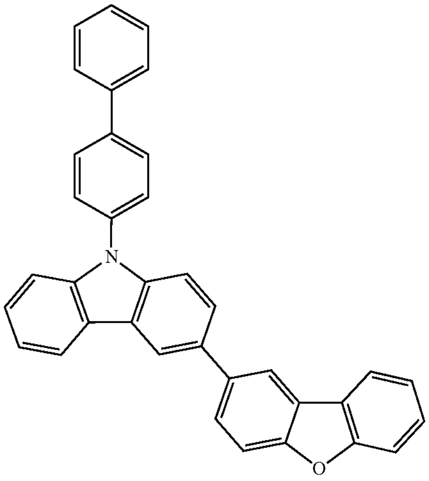

H-H65
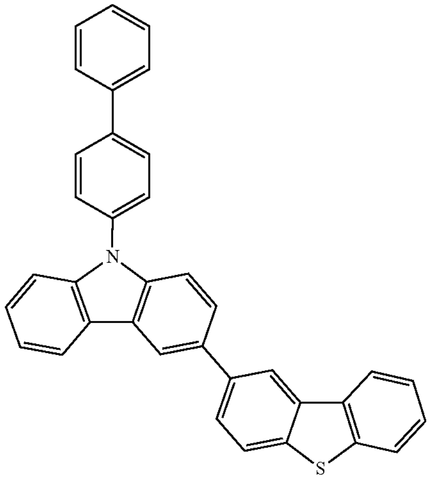
H-H66
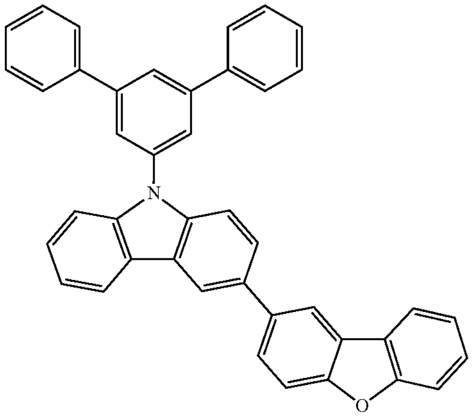
H-H67
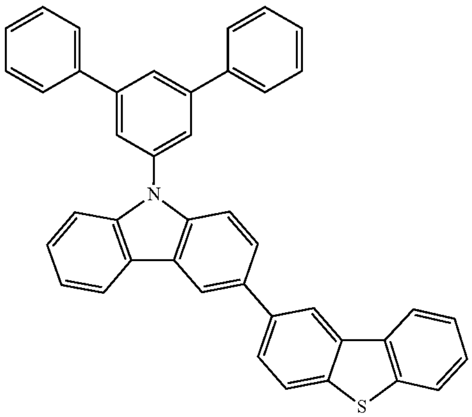
H-68
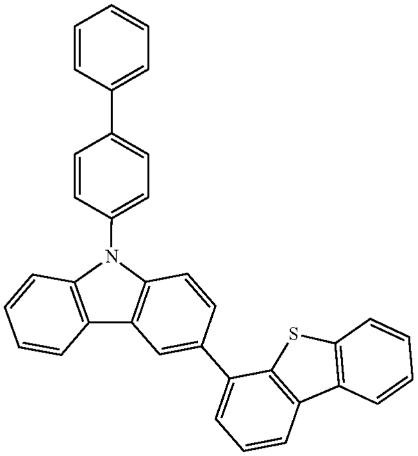
H-69
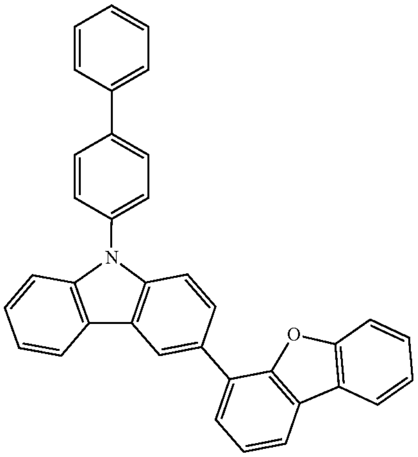
H-H70
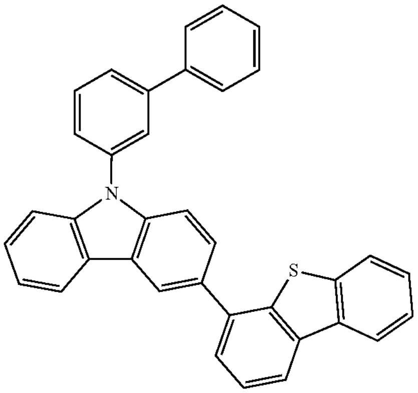

-continued
H-H71
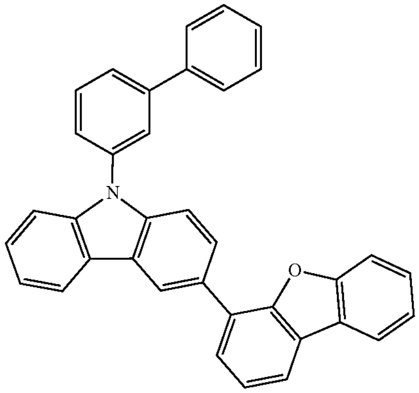
H-H72
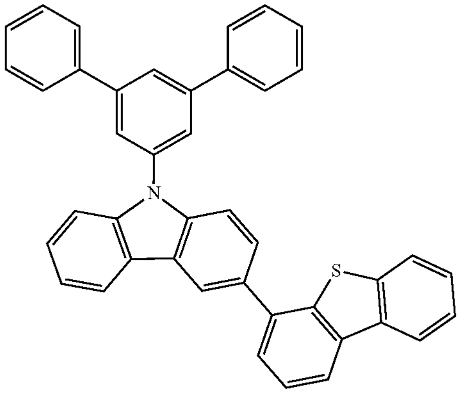
H-H73
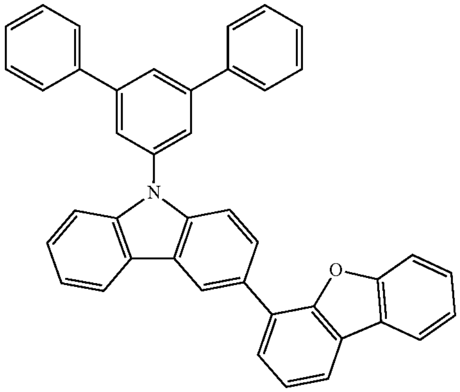
H-H74
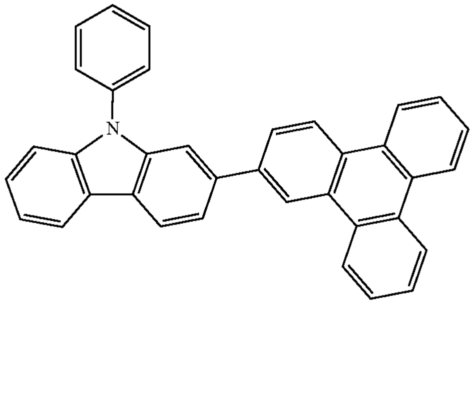
-continued
H-H75
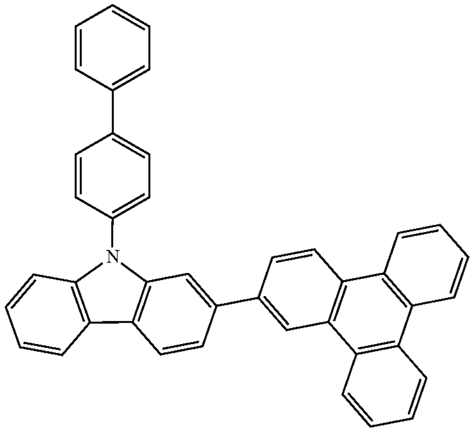
H-H76
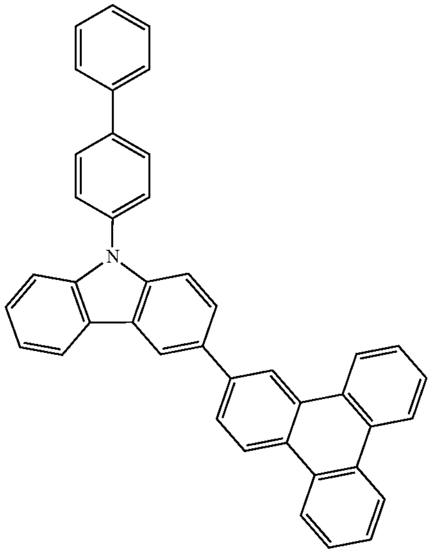
H-H77
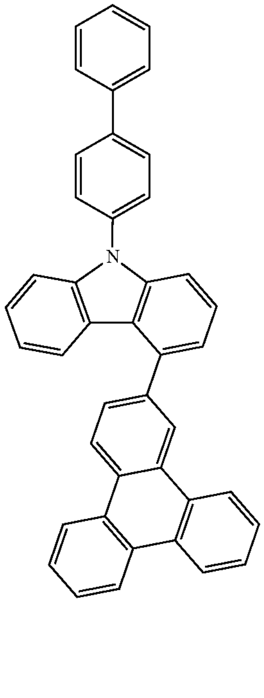

-continued
H-H78
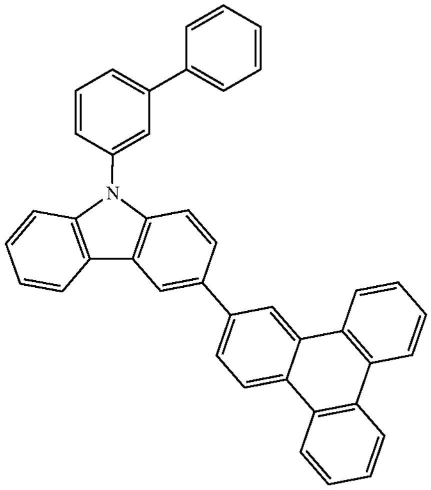
H-H79
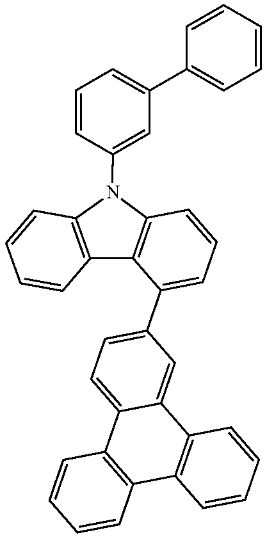
H-H80
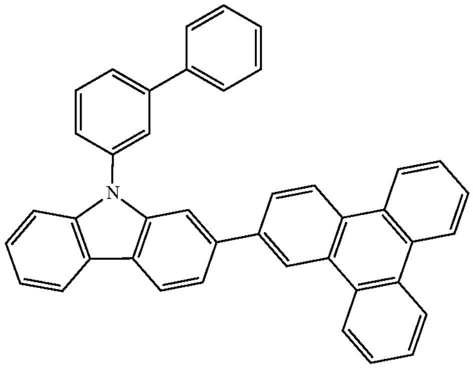
-continued
H-H81
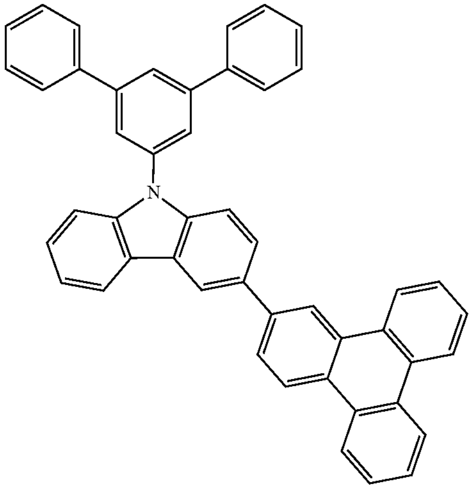
H-H82
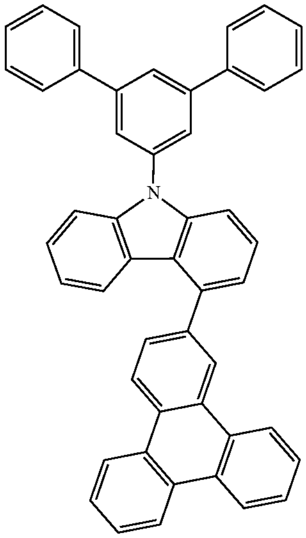
H-H83
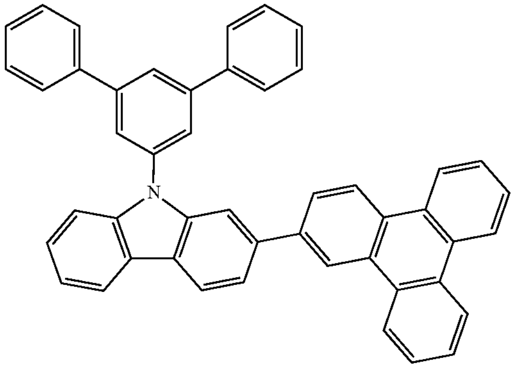

-continued
H-H84
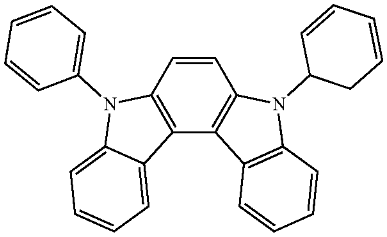
H-H85
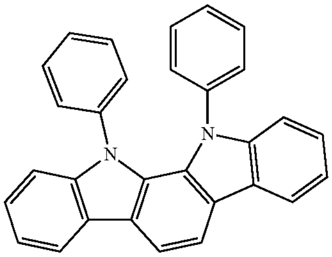
H-H86
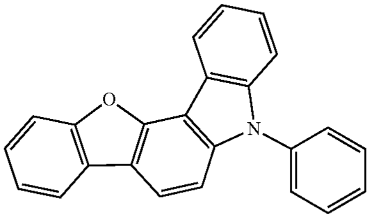
H-H87
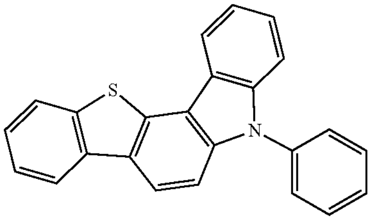
H-H88
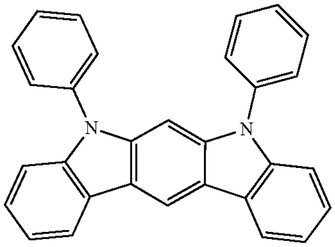
H-H89
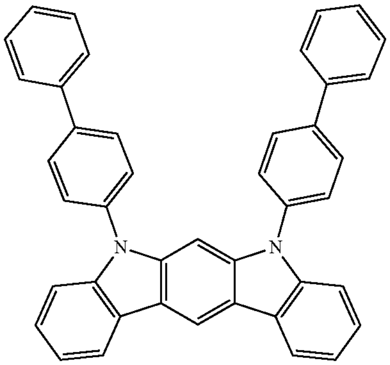
-continued
H-H90
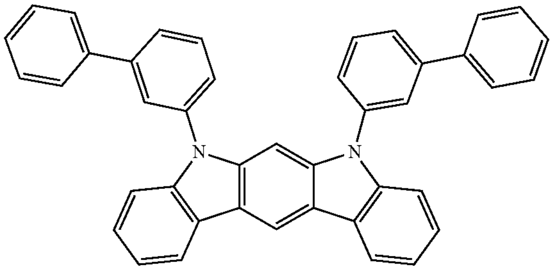
H-H91
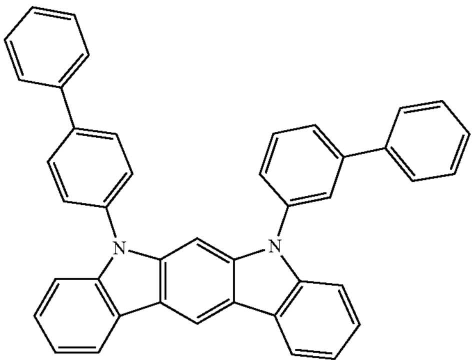
H-H92
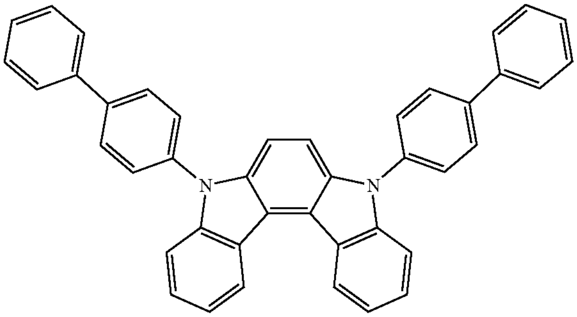
H-H93
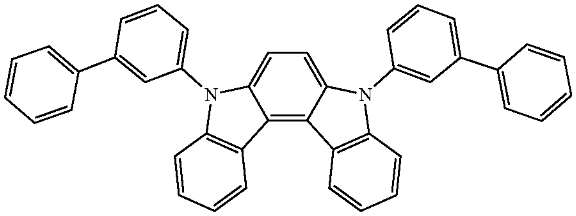

-continued
H-H94
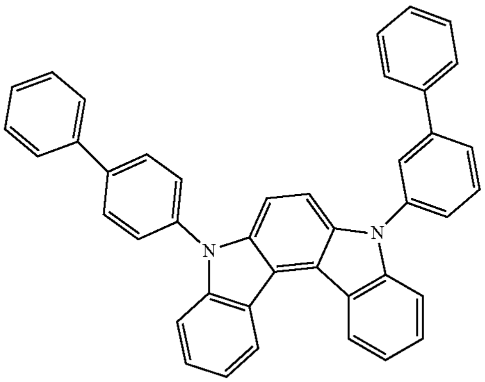
H-H95
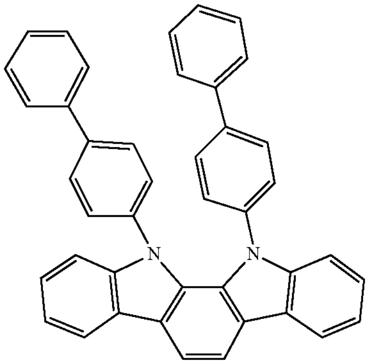
H-H96
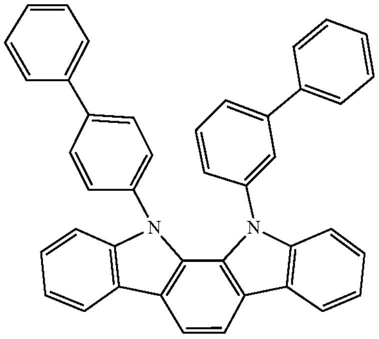
H-H97
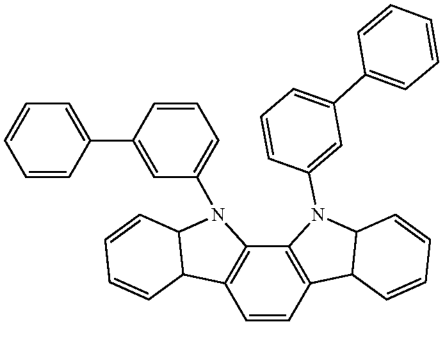
-continued
H-H98
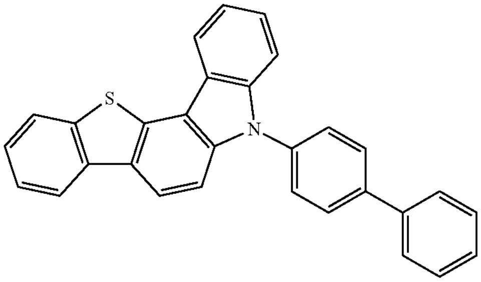
H-H99
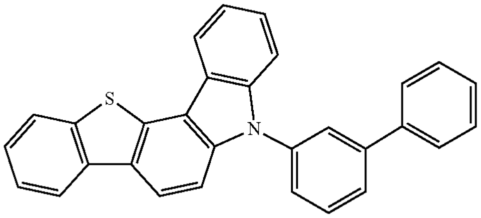
H-H100
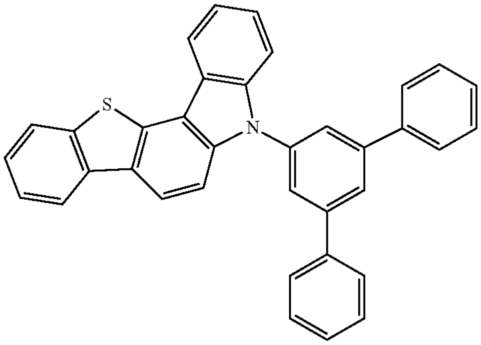
H-H101
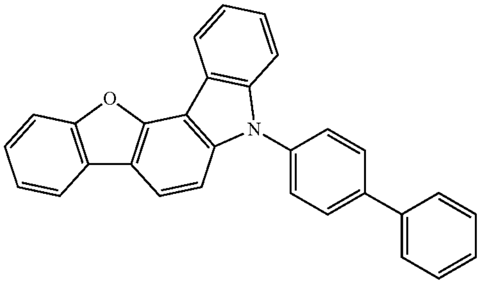
H-H102
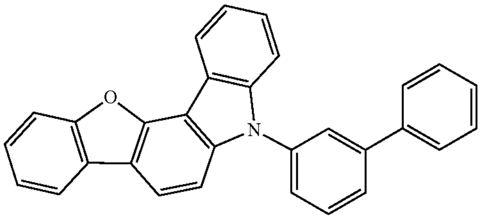

-continued
H-H103
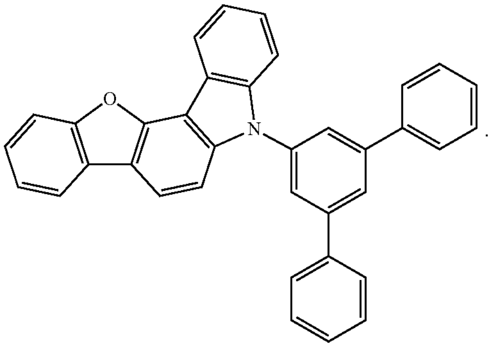
In some embodiments, the bipolar host may include a compound of Group HEH1:
Group HEH1
1
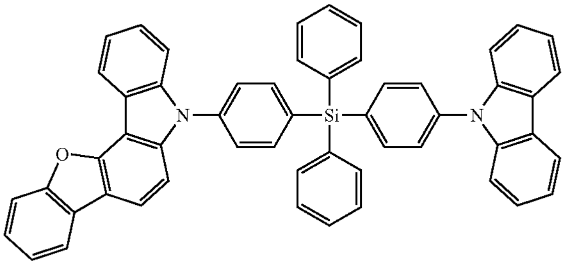
2
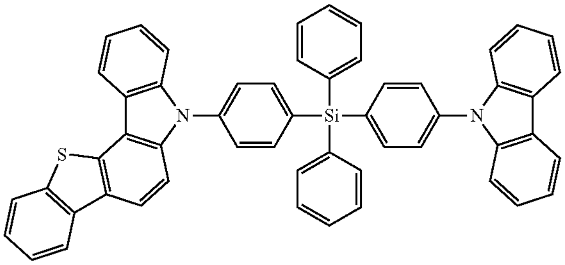
3
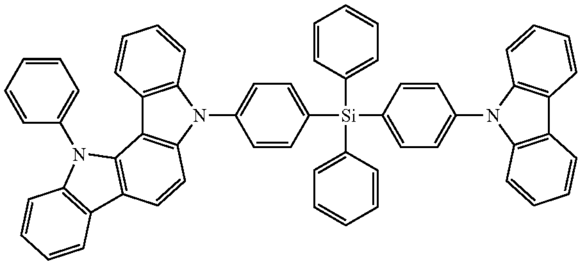
-continued
4
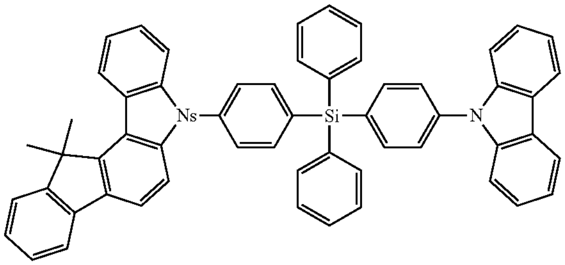
5
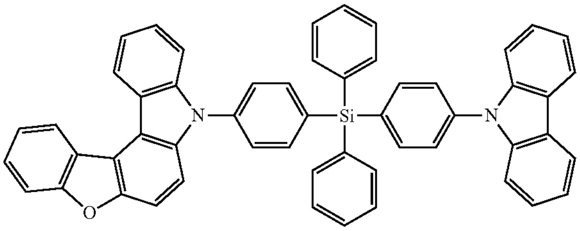
6
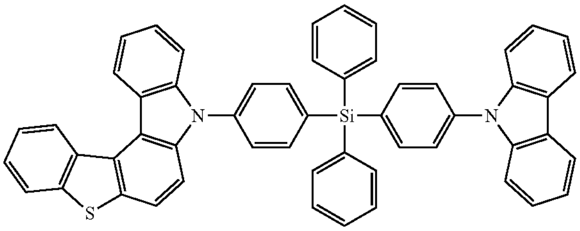
7
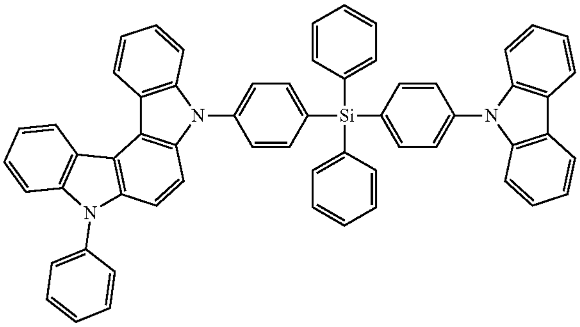
8
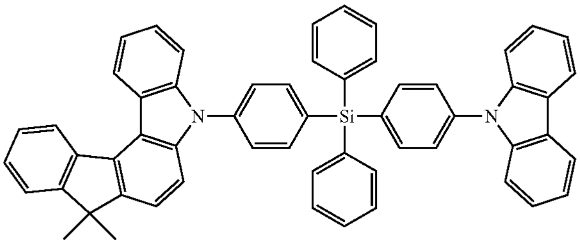

-continued
9
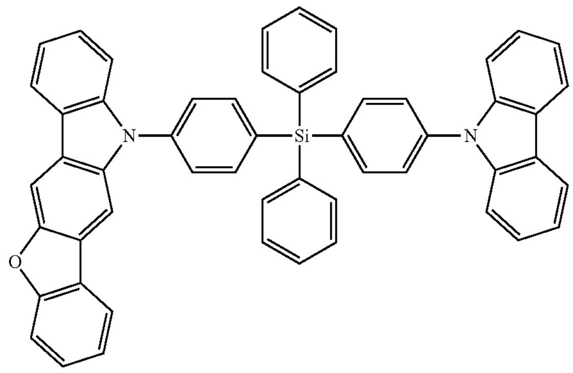
10
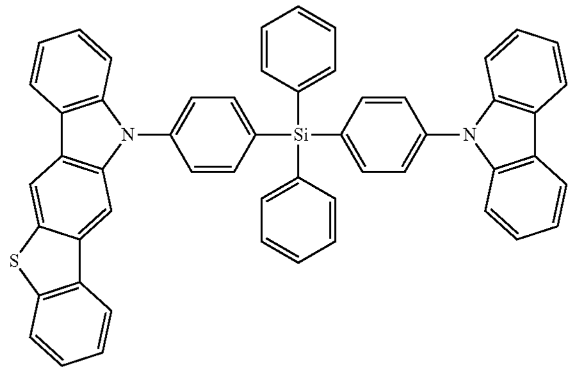
11
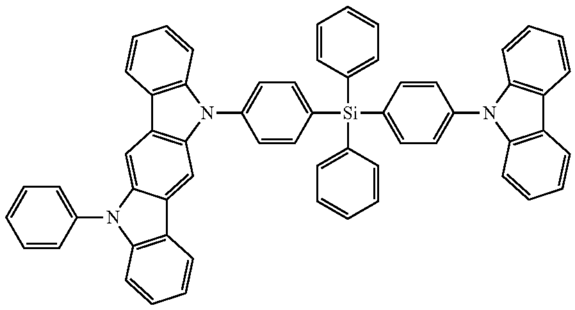
12
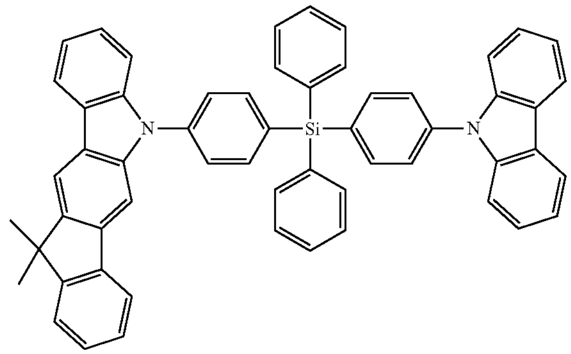
-continued
13
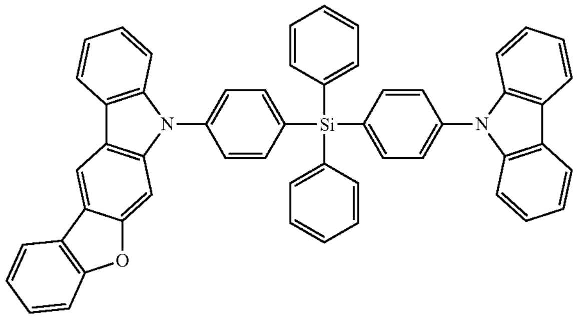
14
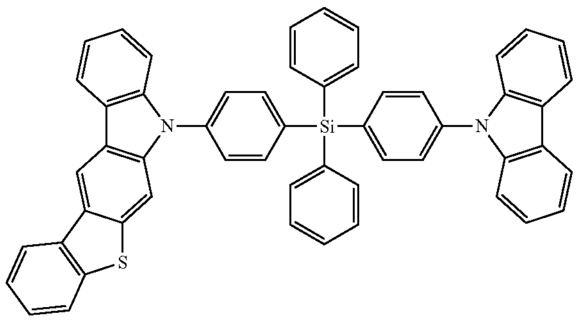
15
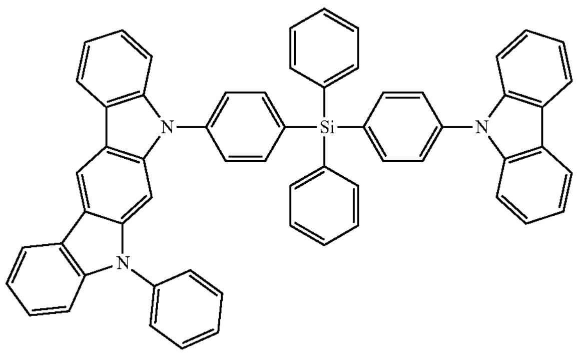
16
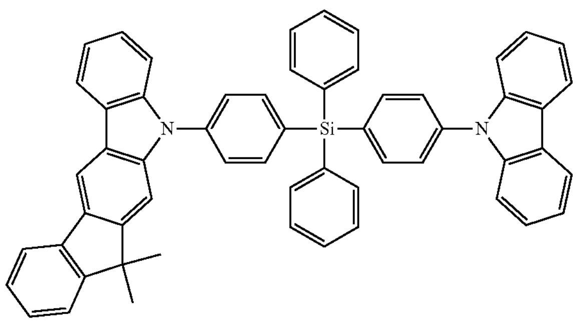

-continued
17
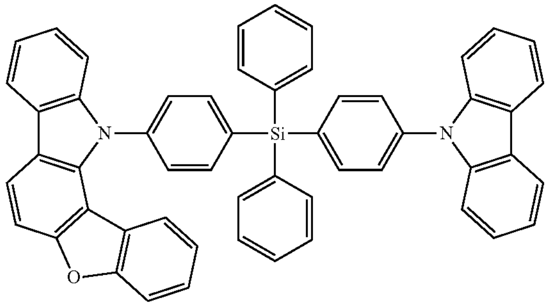
18
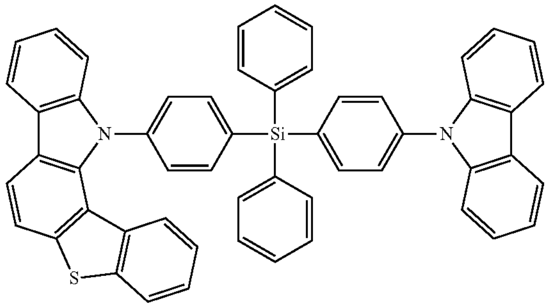
19
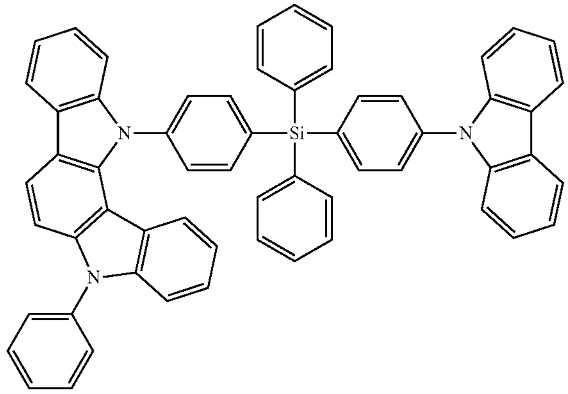
20
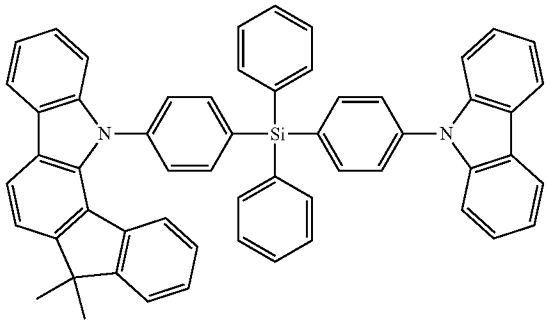
-continued
21
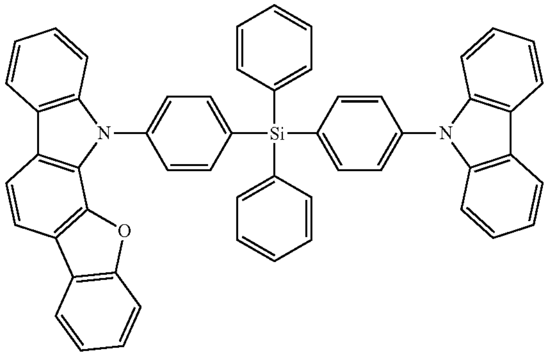
22
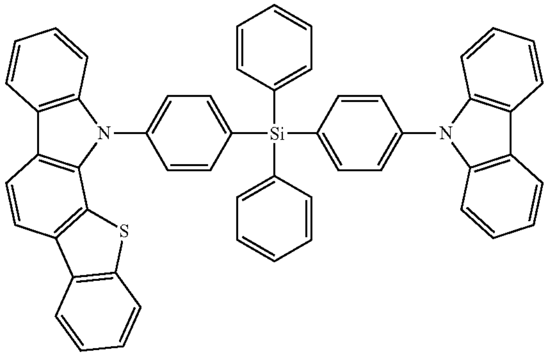
23
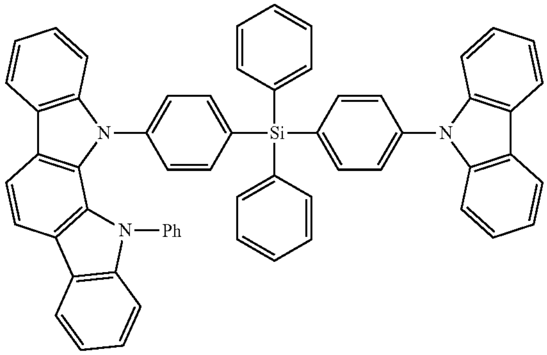
24
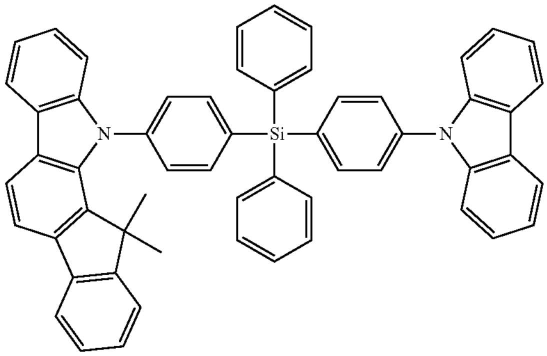

-continued
25
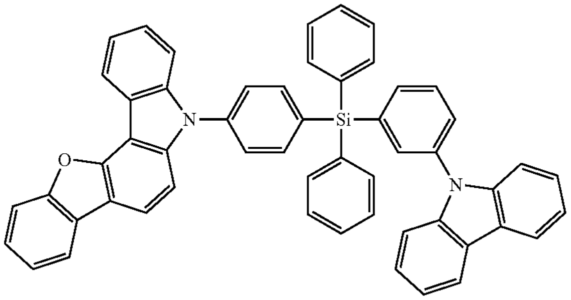
26
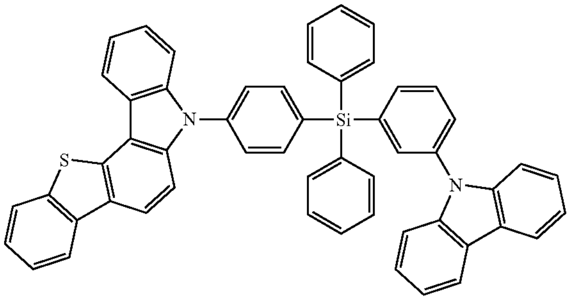
27
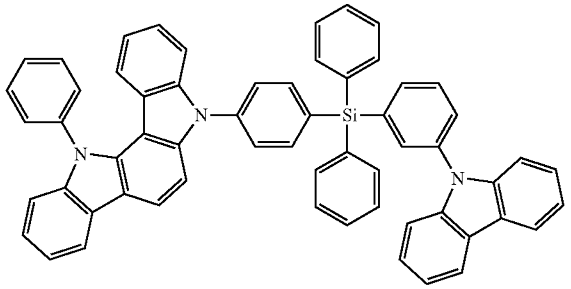
28
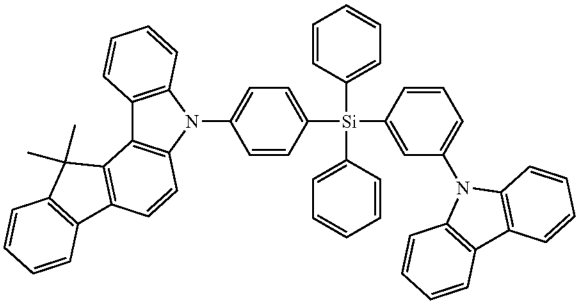
29
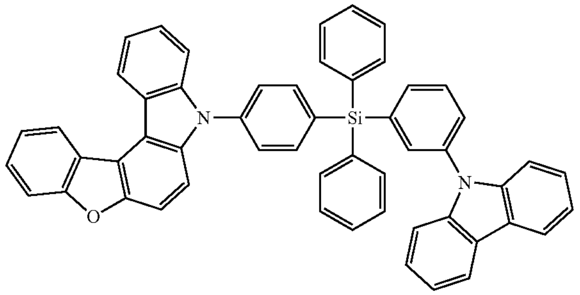
-continued
30
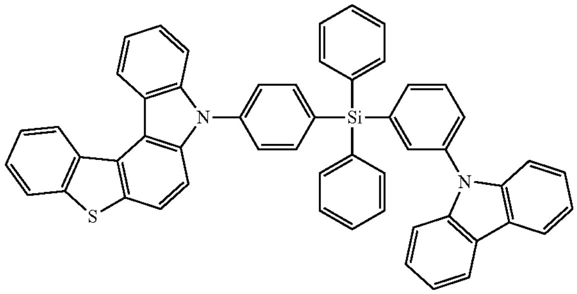
31
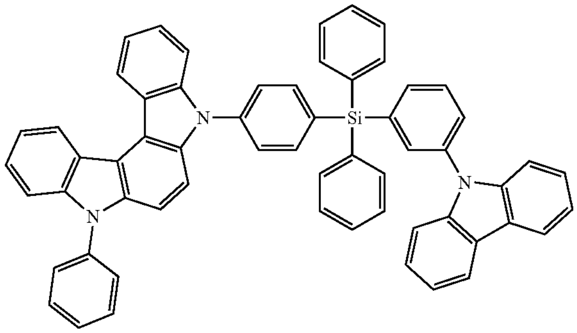
32
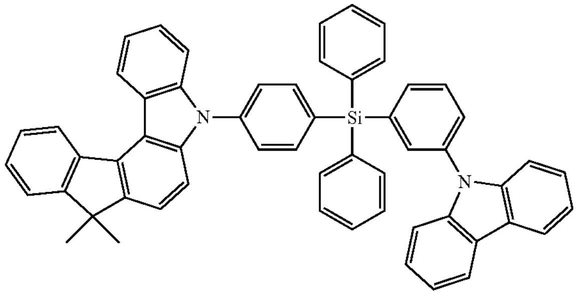
33
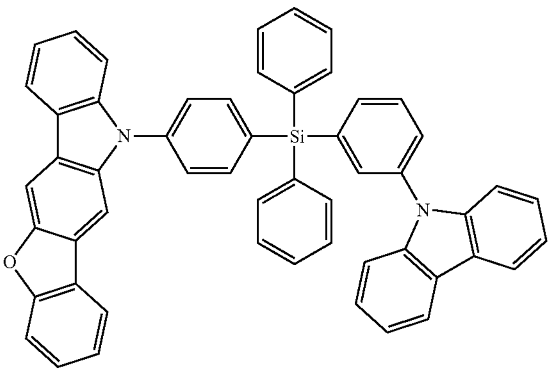

-continued
34
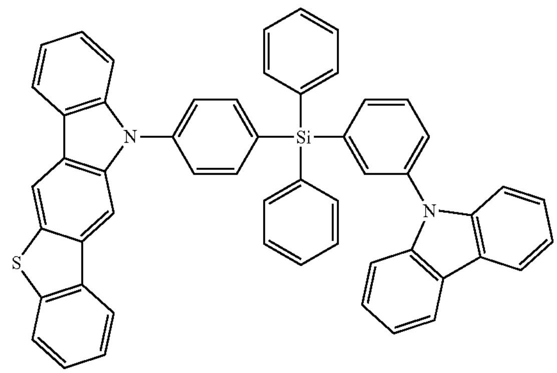
35
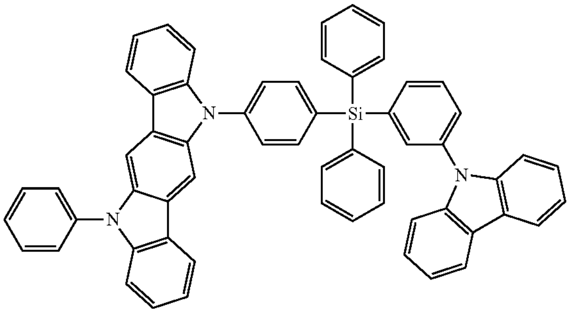
36
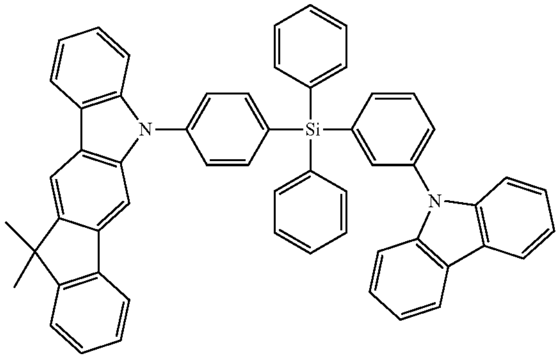
37
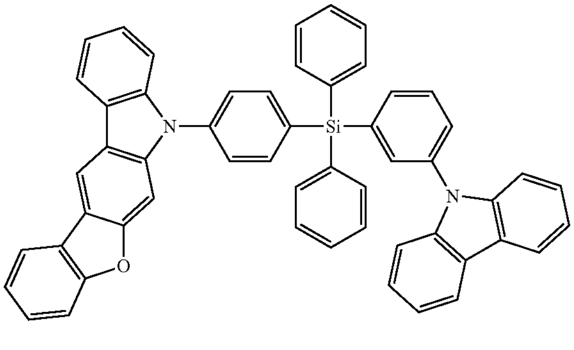
-continued
38
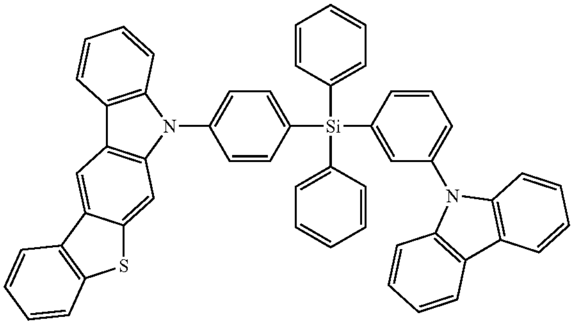
39
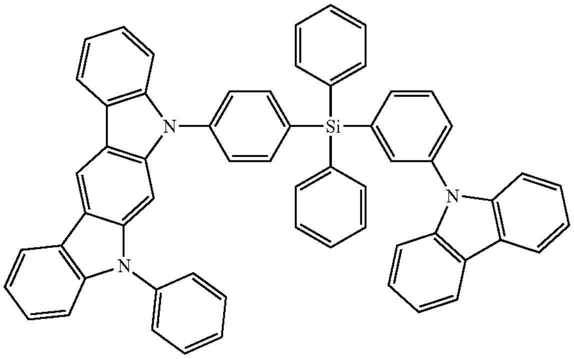
40
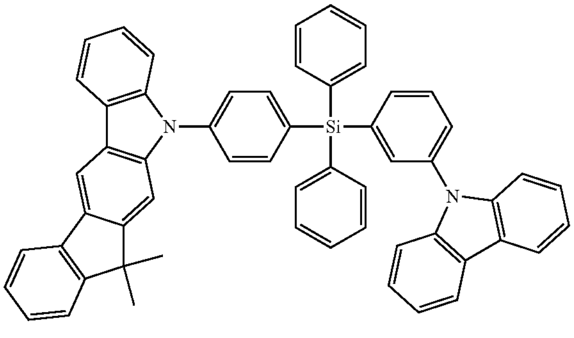
41
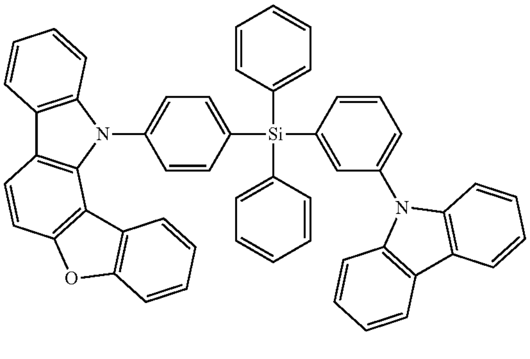

42
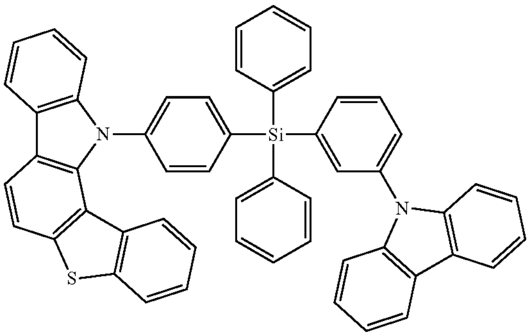
43
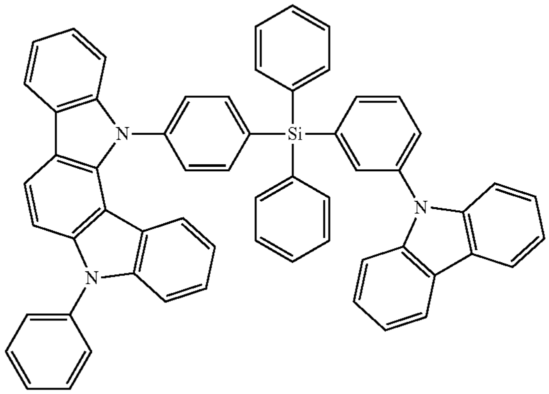
44
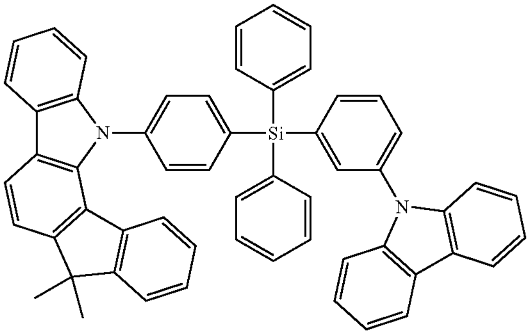
45
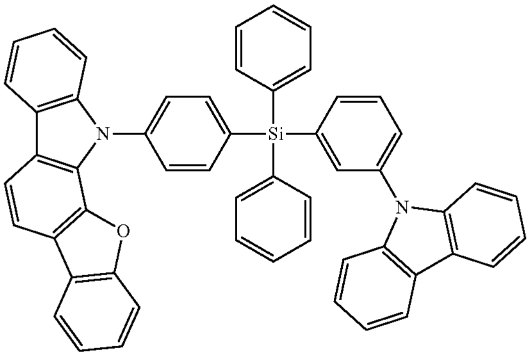
46
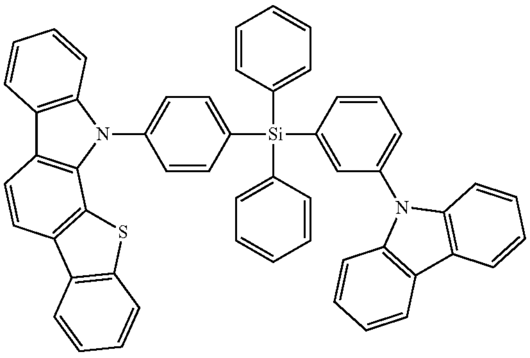
47
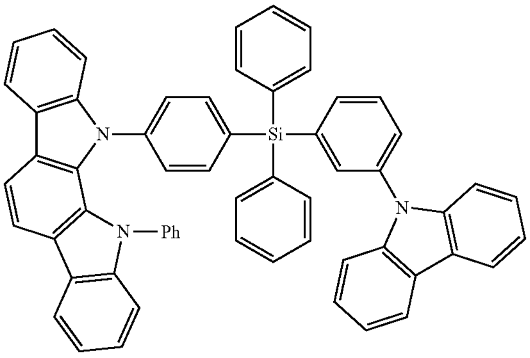
48
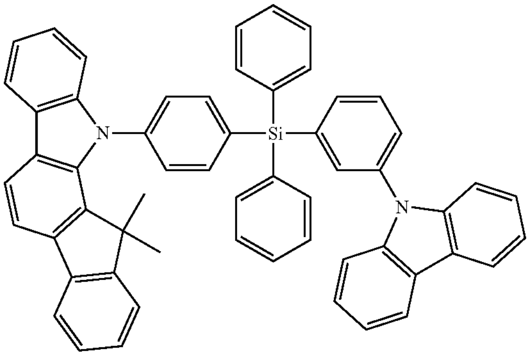
49
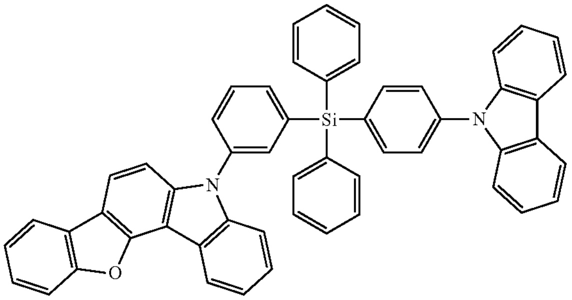

-continued
50
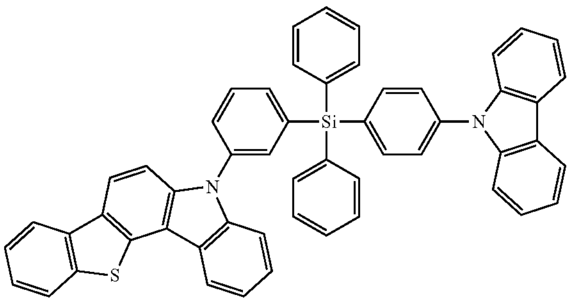
51
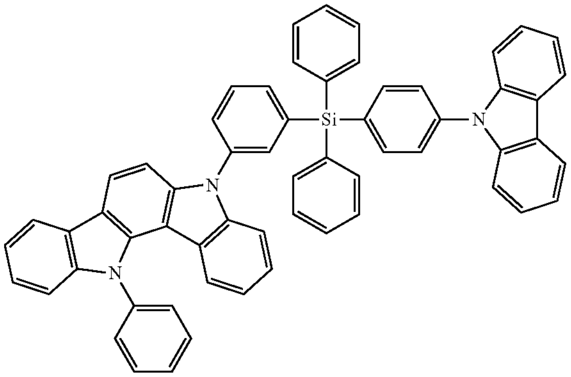
52
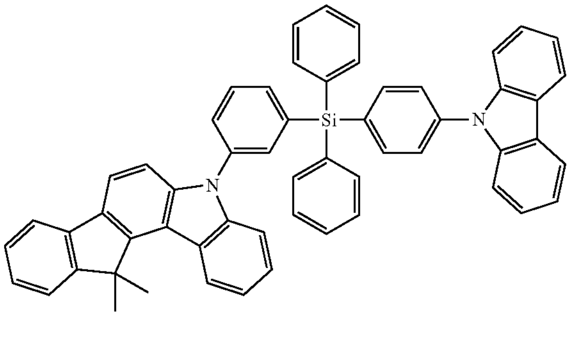
53
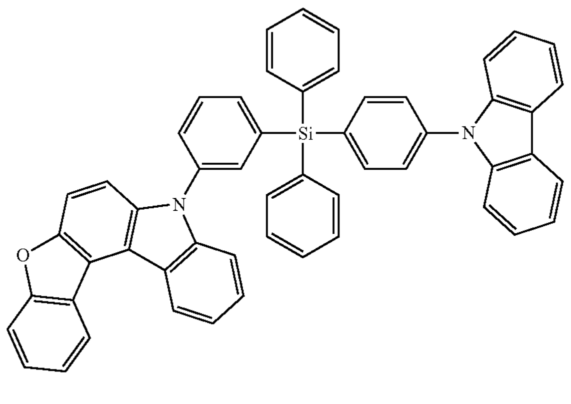
-continued
54
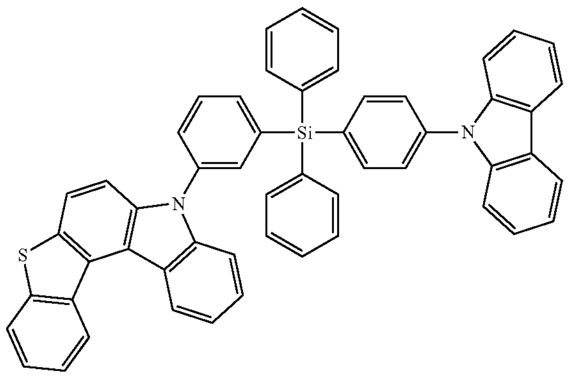
55
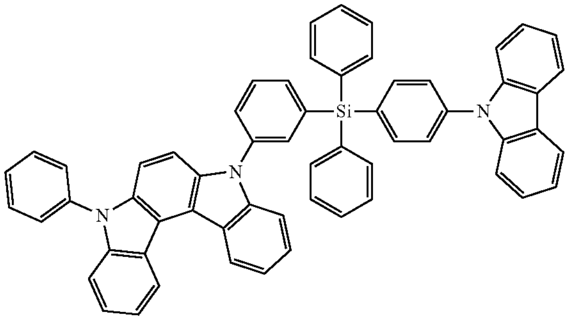
56
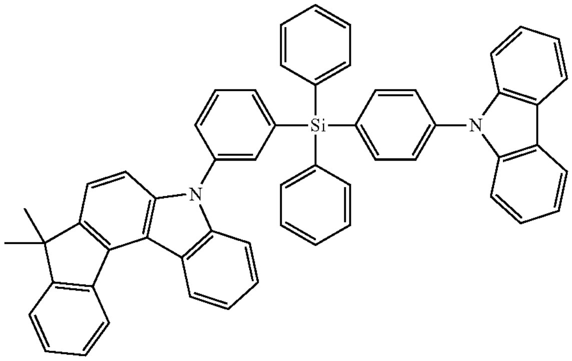
57
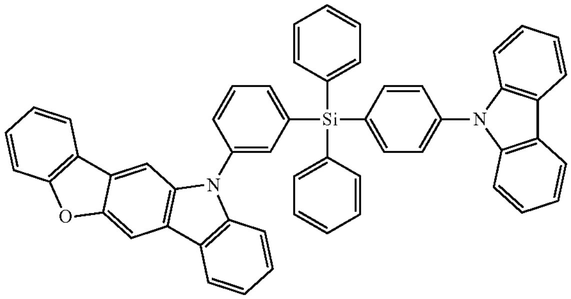

-continued
58
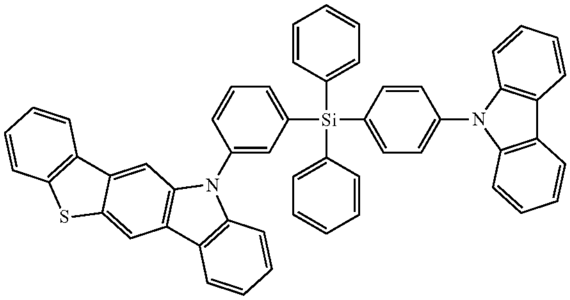
59
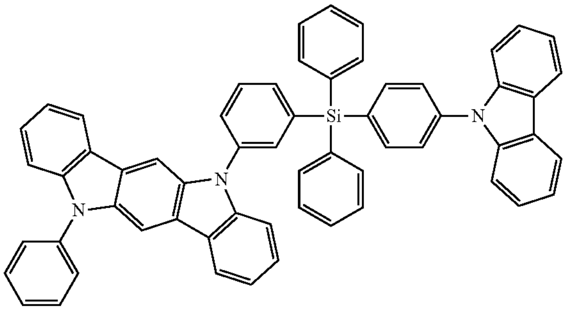
60
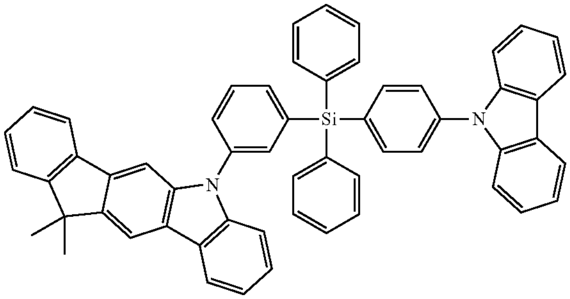
61
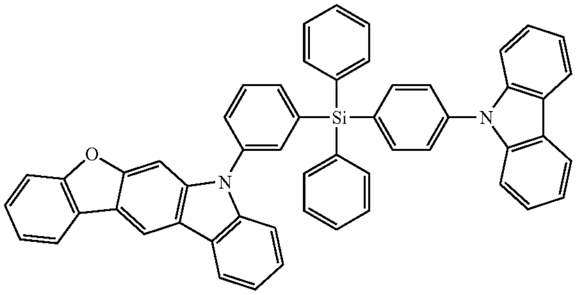
62
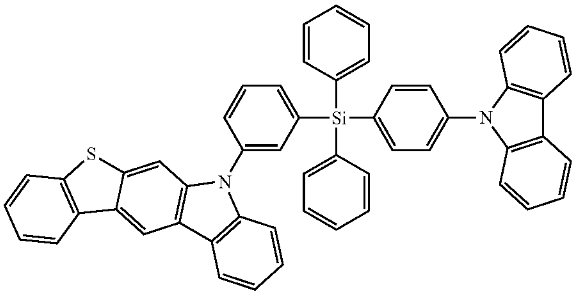
-continued
63
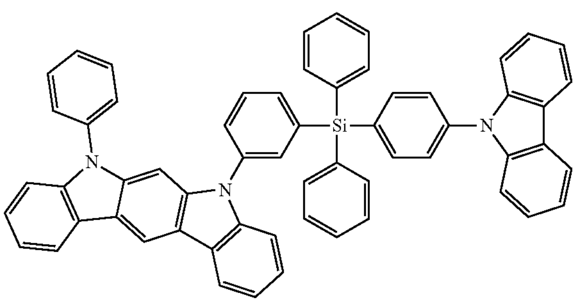
64
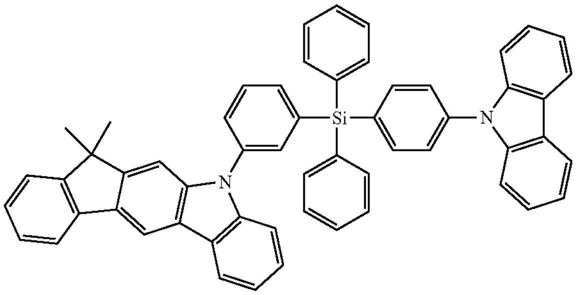
65
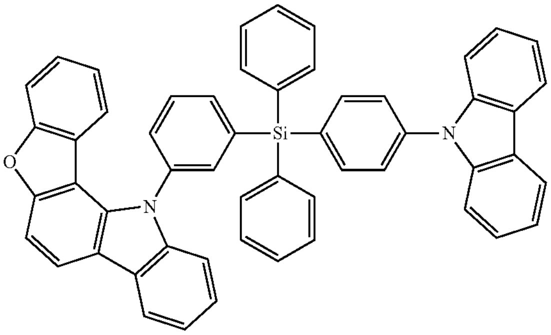
66
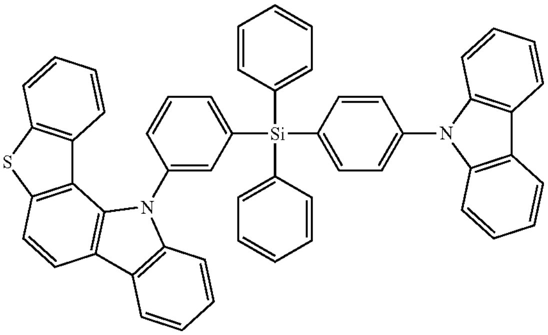

67
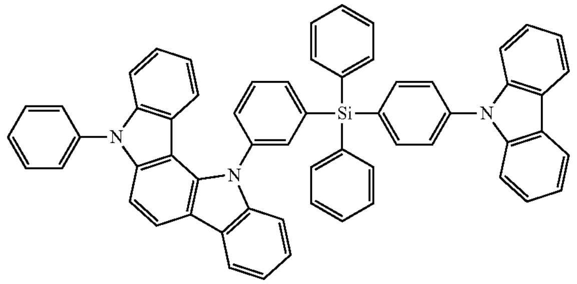
68
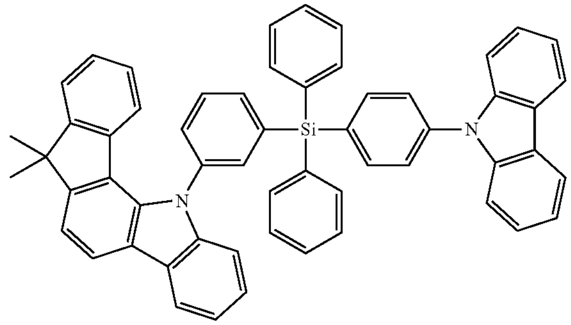
69
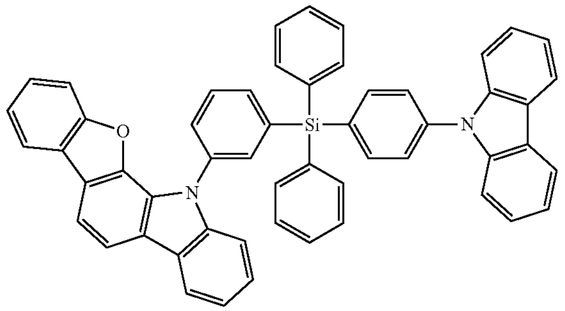
70
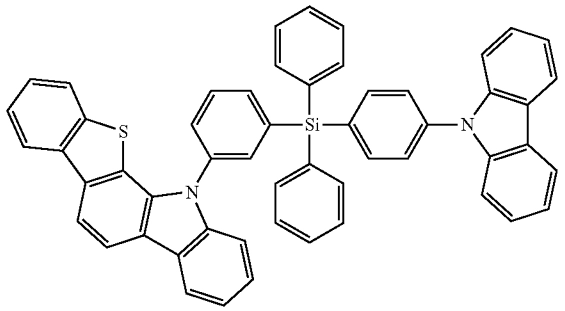
71
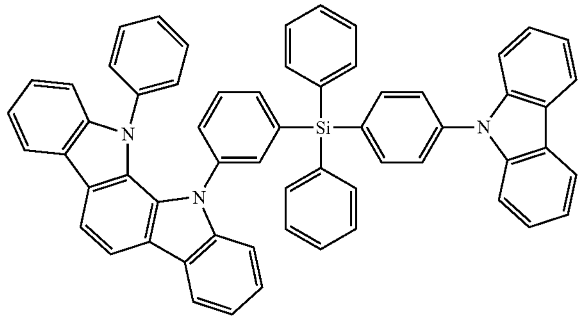
72
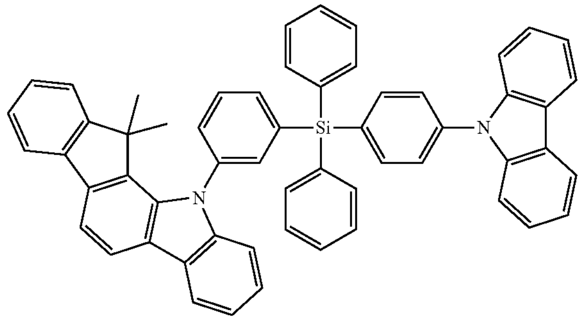
73
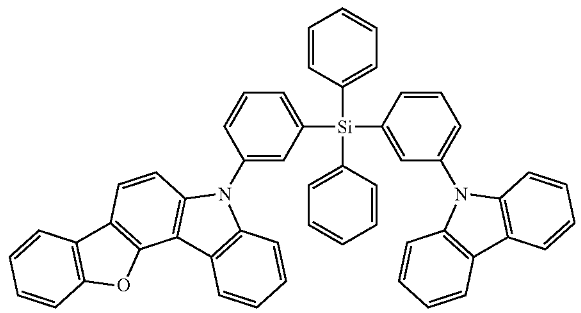
74
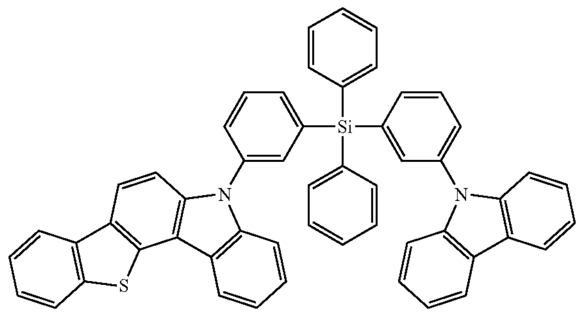

-continued
75
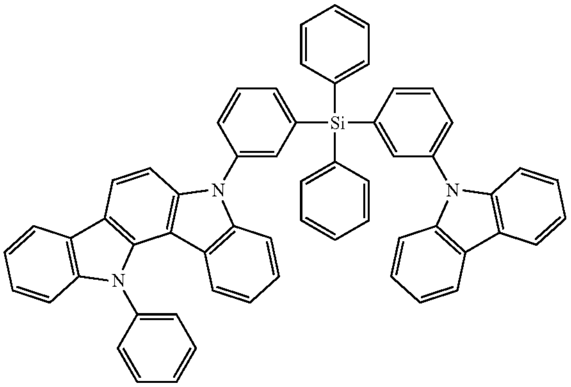
76
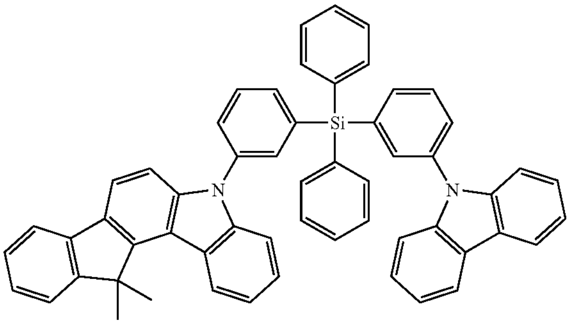
77
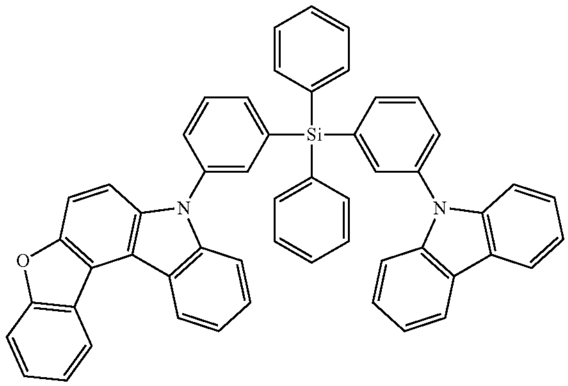
78
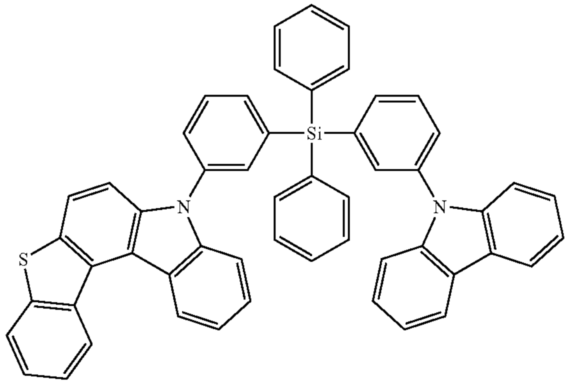
-continued
79
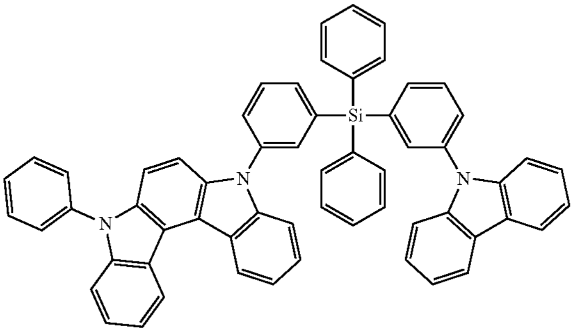
80
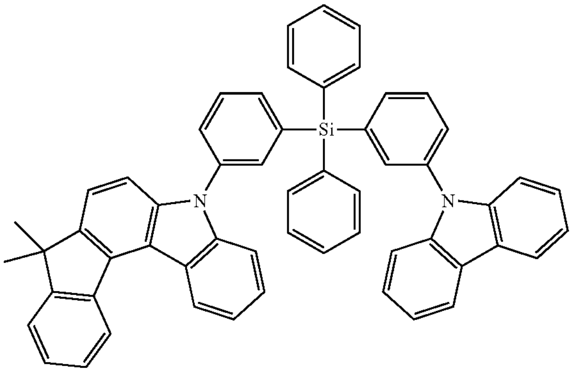
81
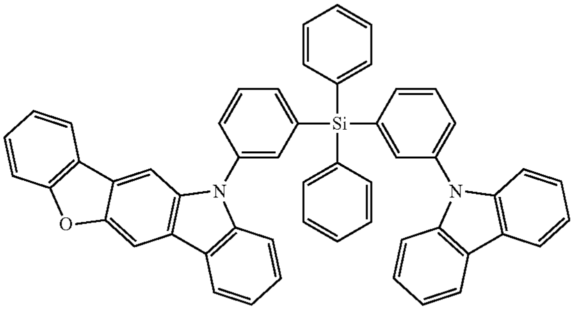
82
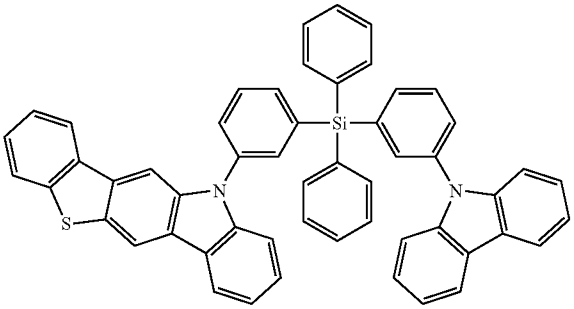

-continued
83
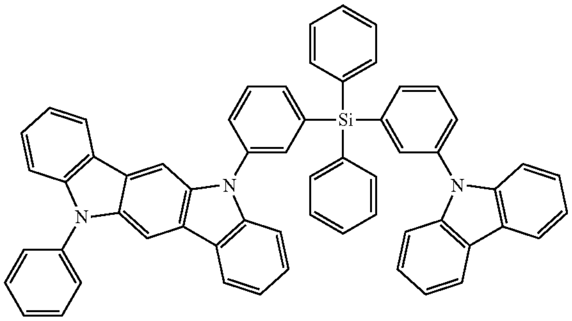
84
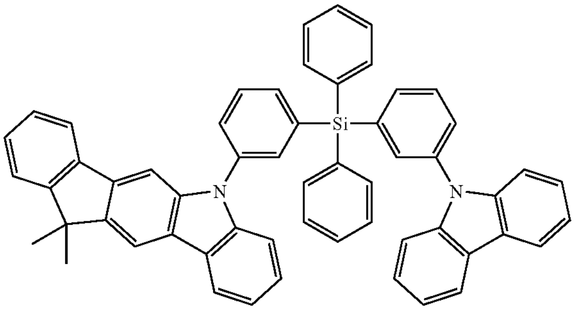
85
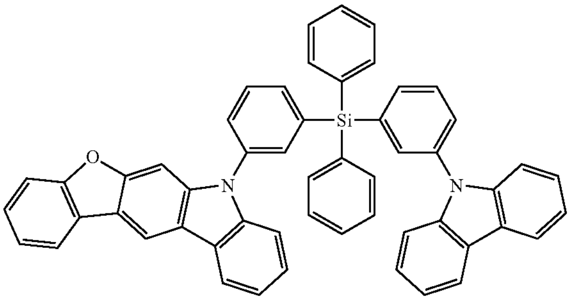
86
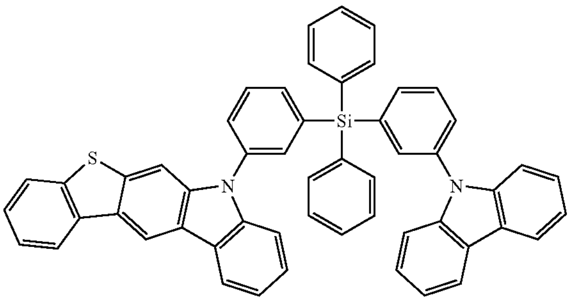
87
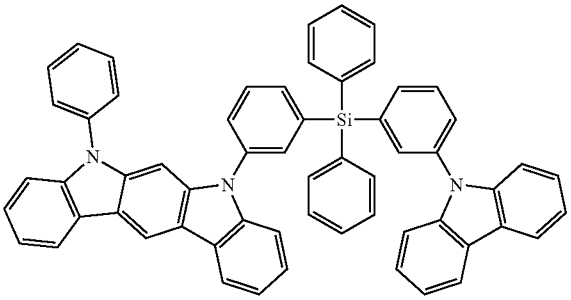
-continued
88
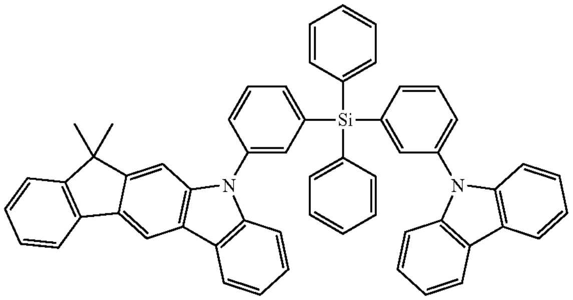
89
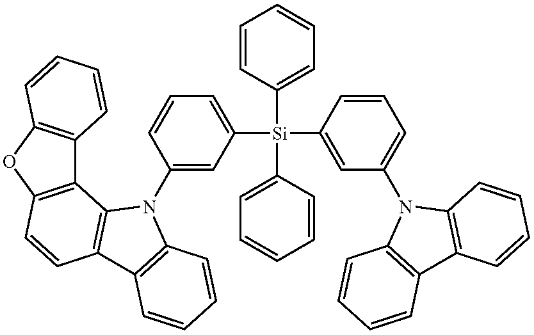
90
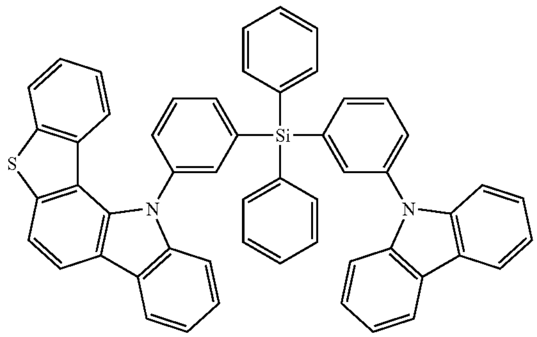
91
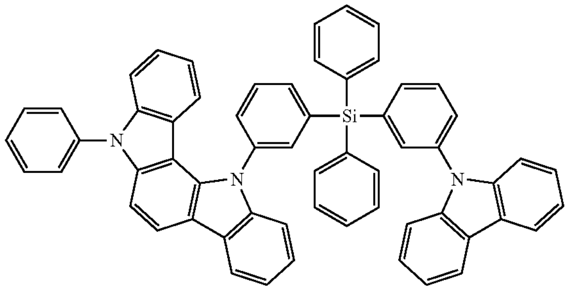

-continued
92
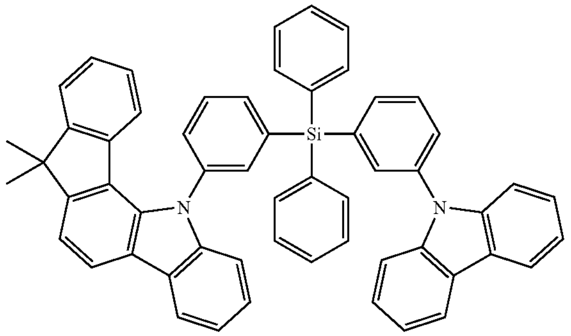
93
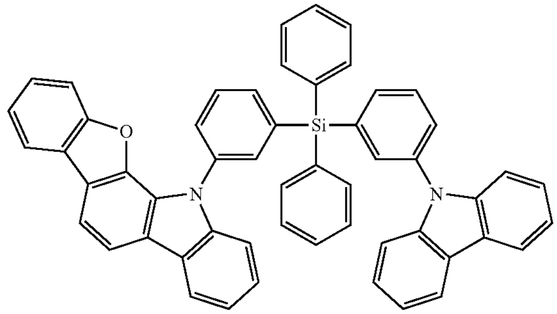
94
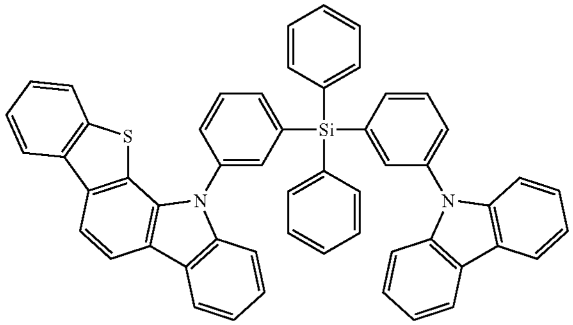
95
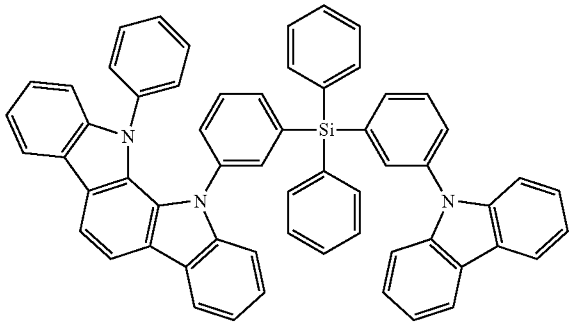
-continued
96
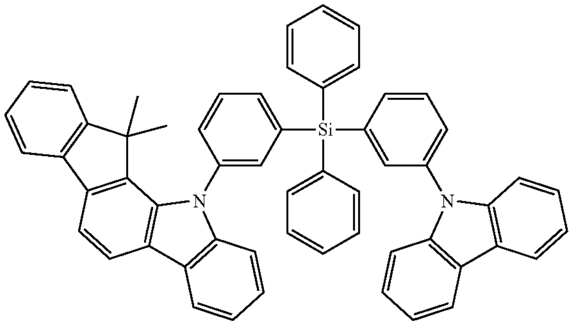
97
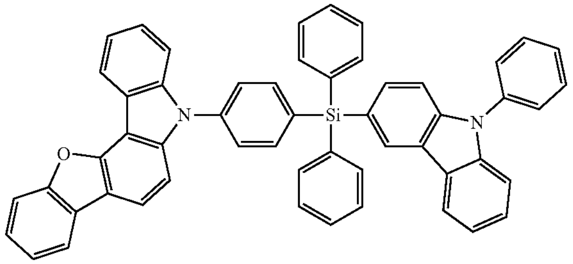
98
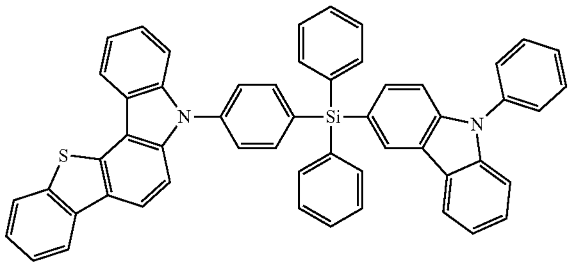
99
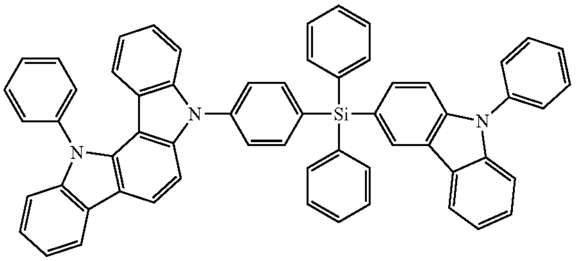
100
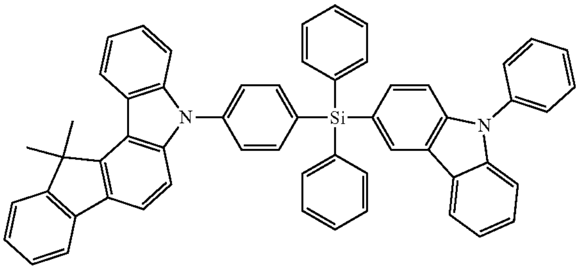

-continued
101
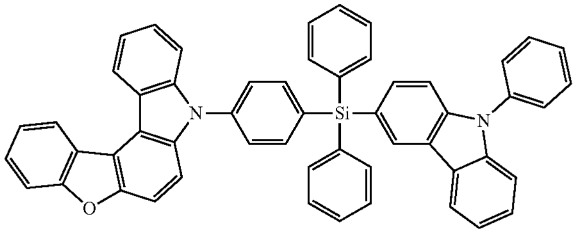
102
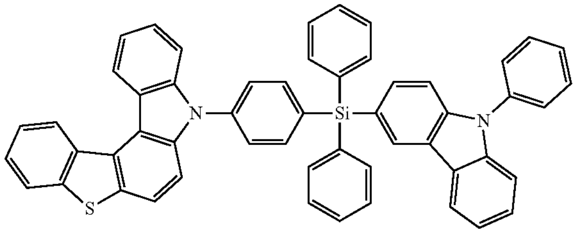
103
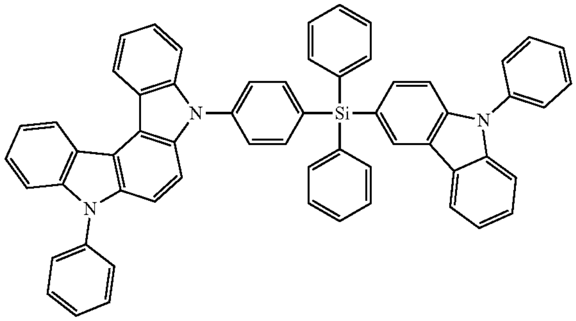
104
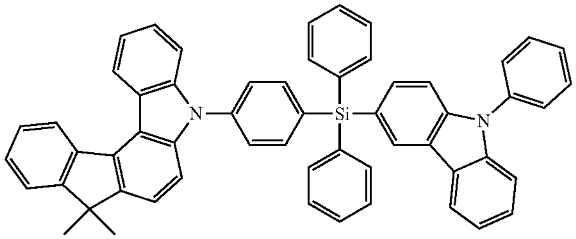
105
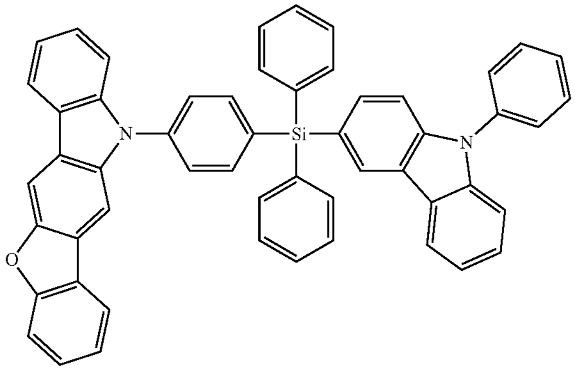
-continued
106
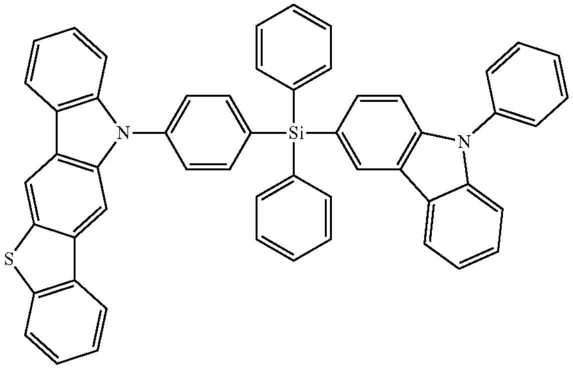
107
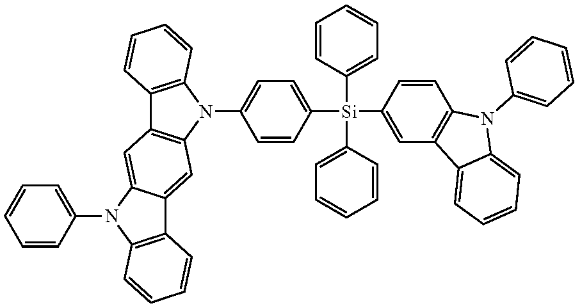
108
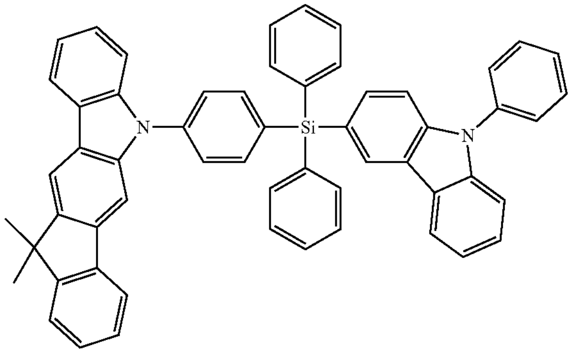
109
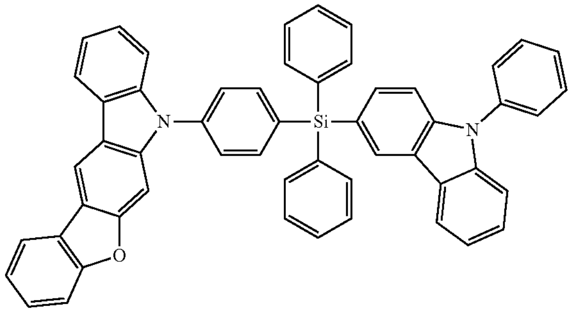

-continued
110
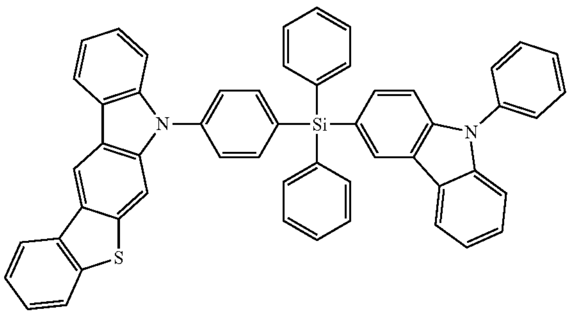
111
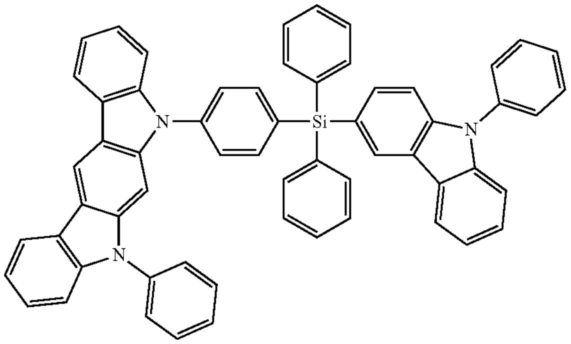
112
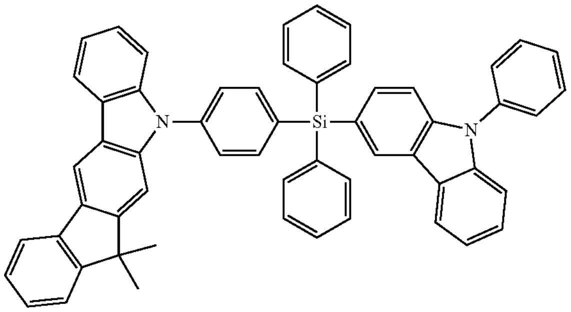
113
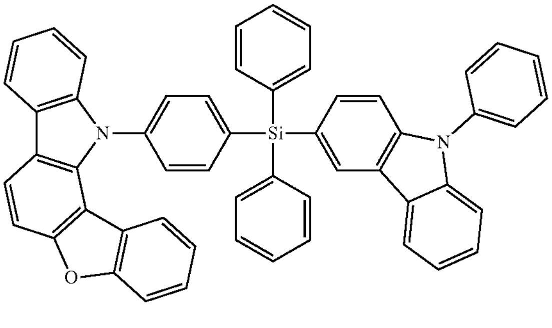
-continued
114
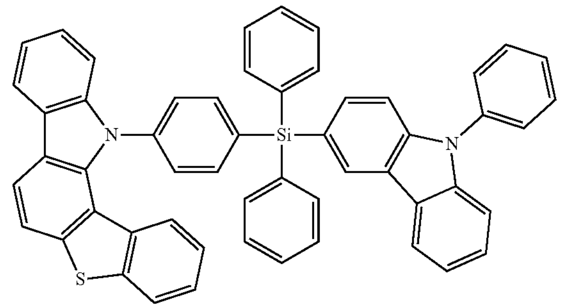
115
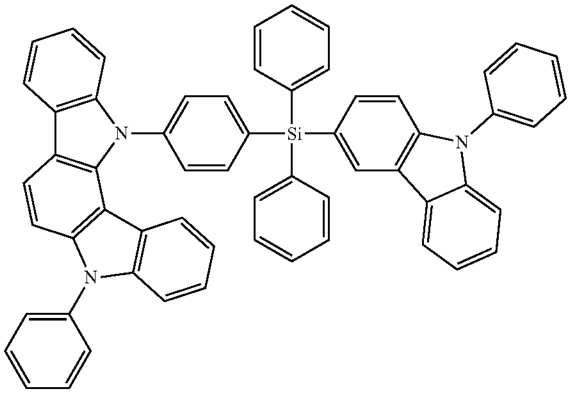
116
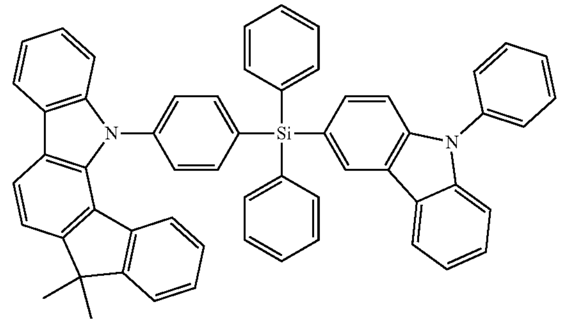
117
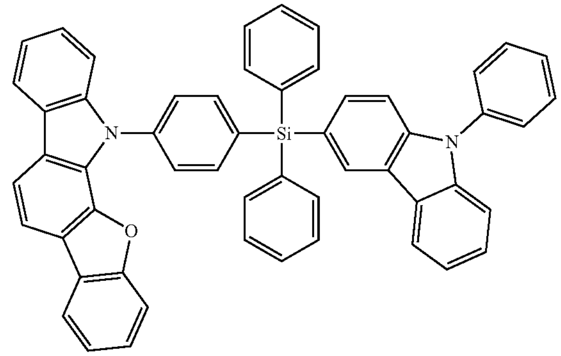

-continued
118
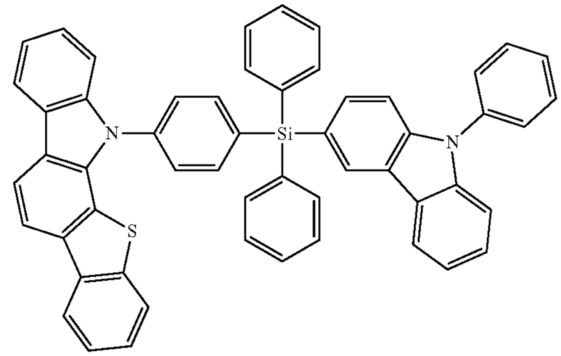
119
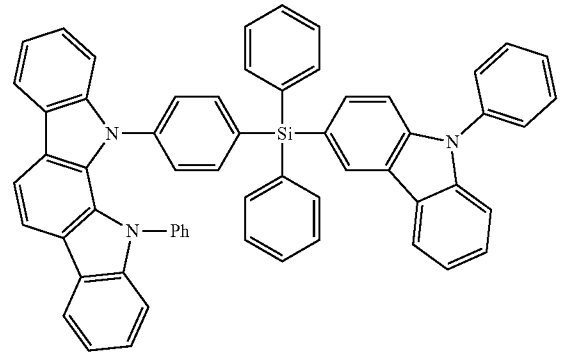
120
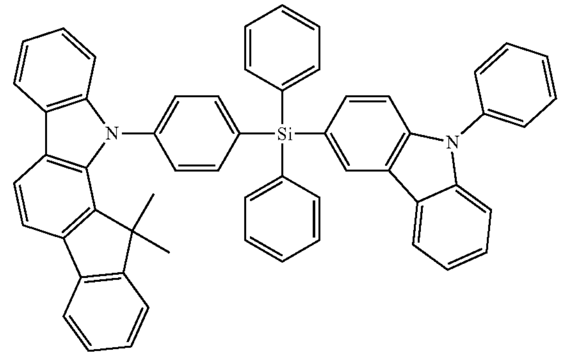
121
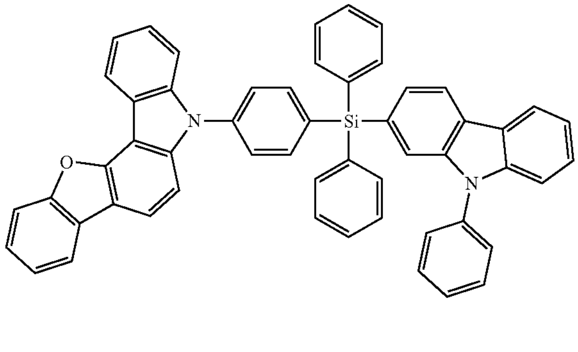
-continued
122
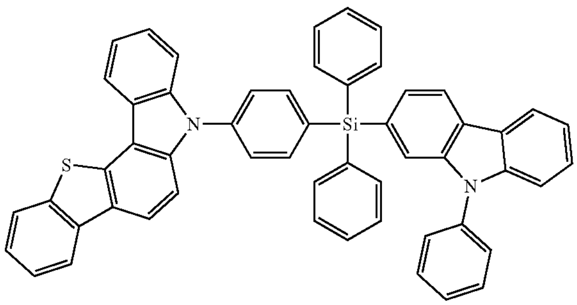
123
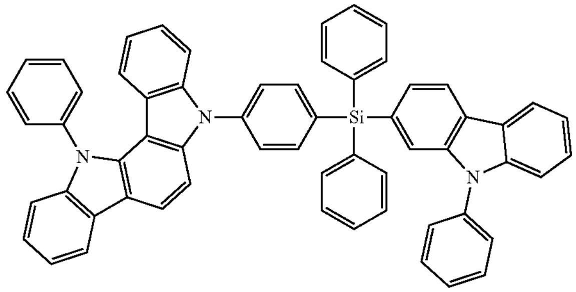
124
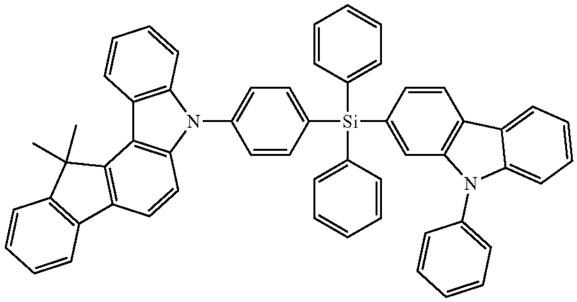
125
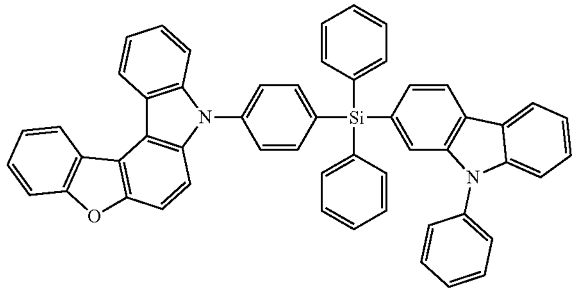
126
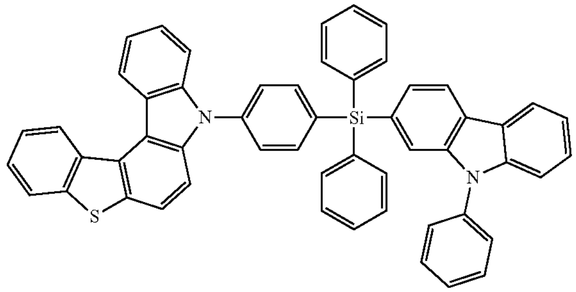

-continued
127
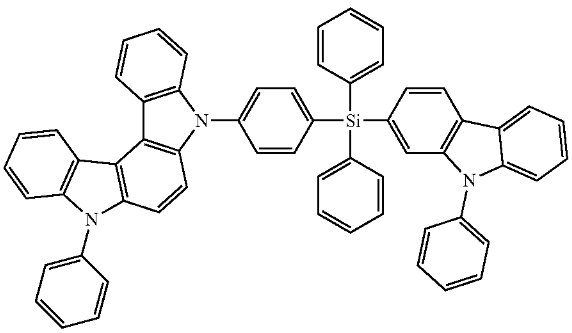
128
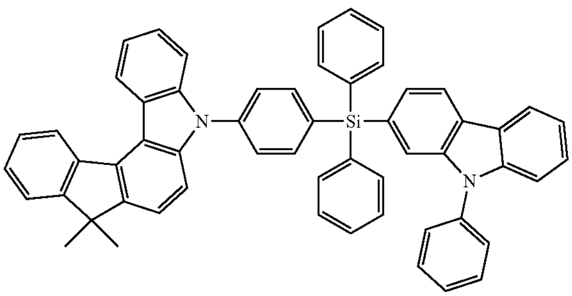
129
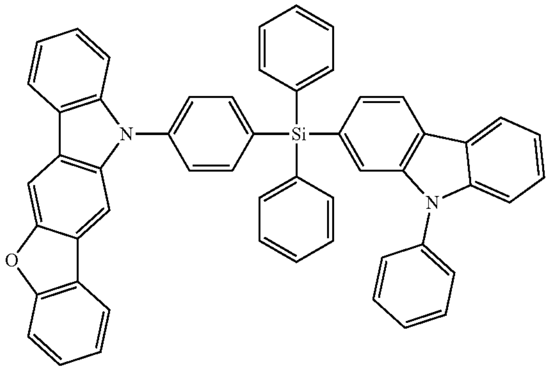
130
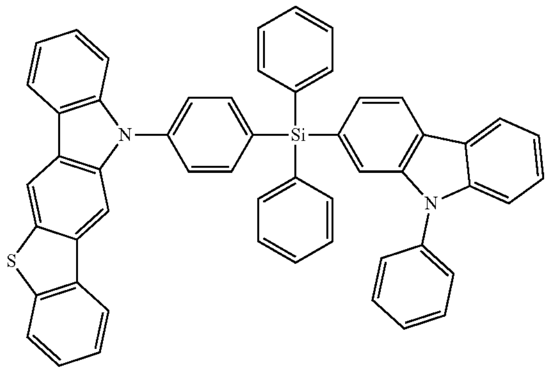
-continued
131
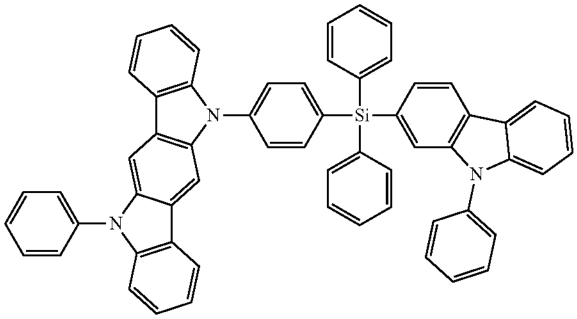
132
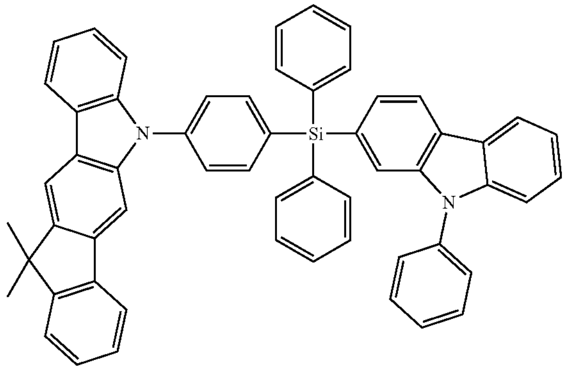
133
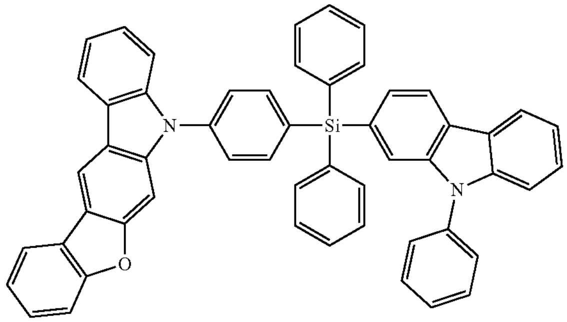
134
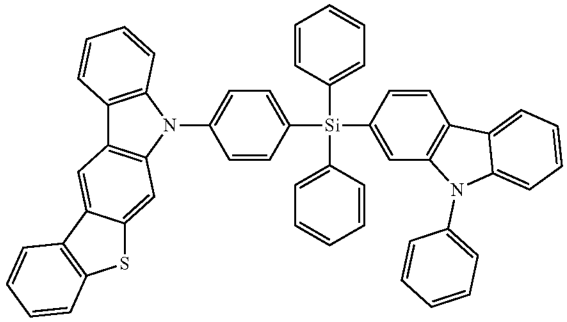

135
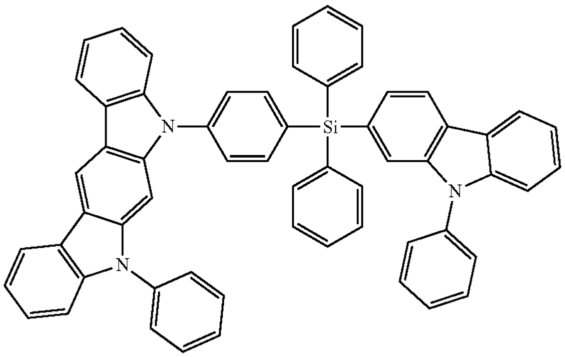
136
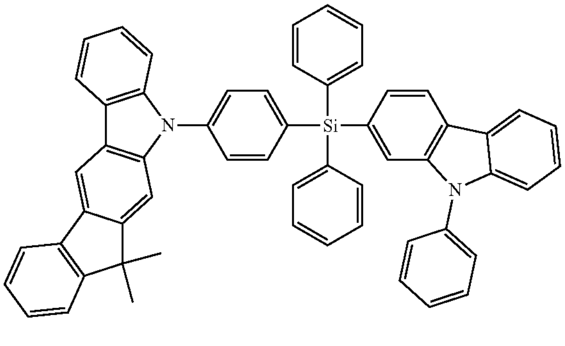
137
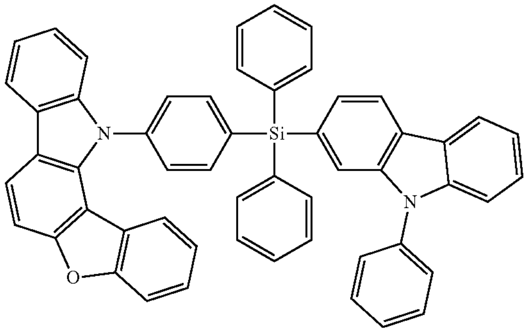
138
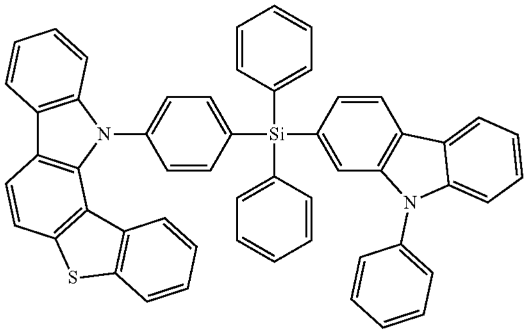
139
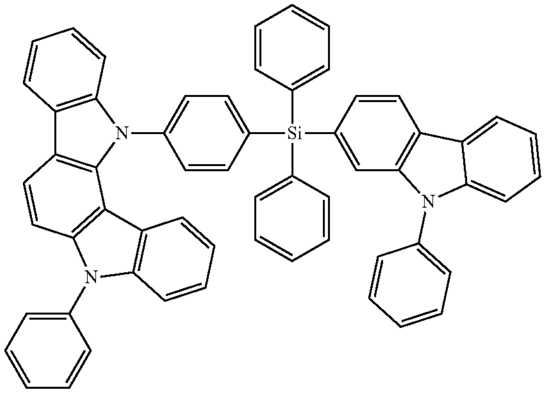
140
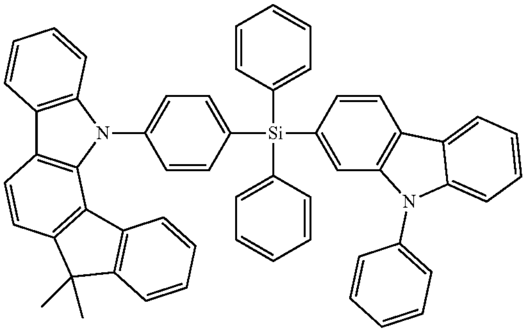
141
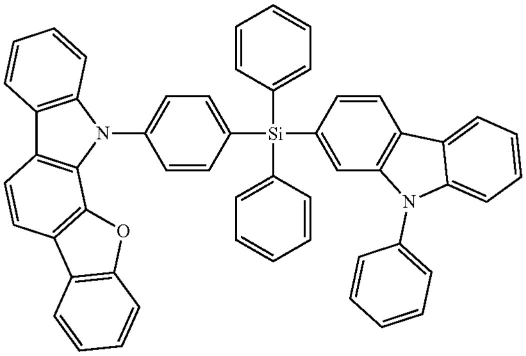
142
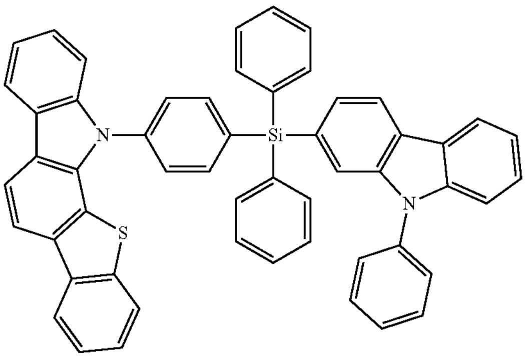

-continued
143
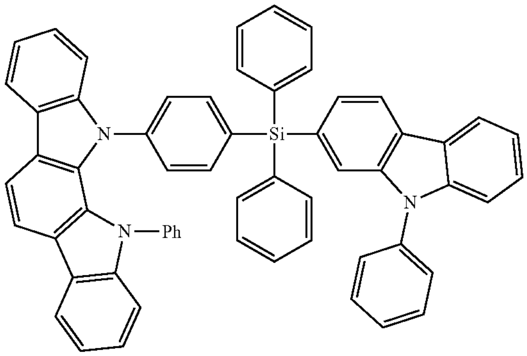
144
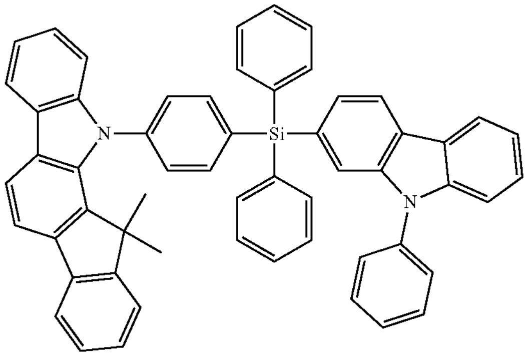
145
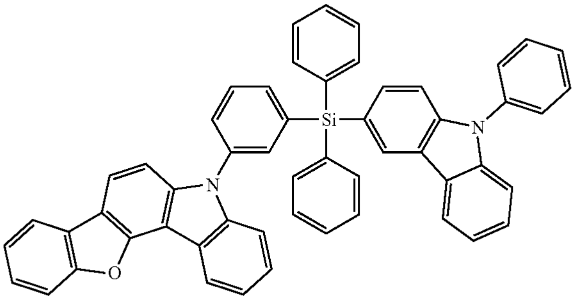
146
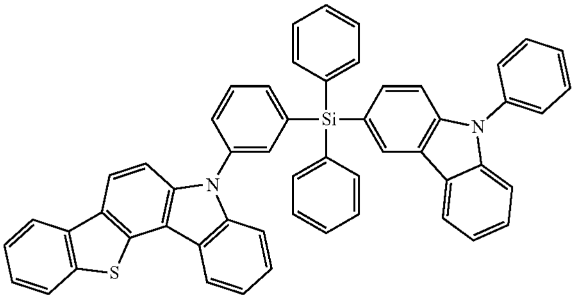
-continued
147
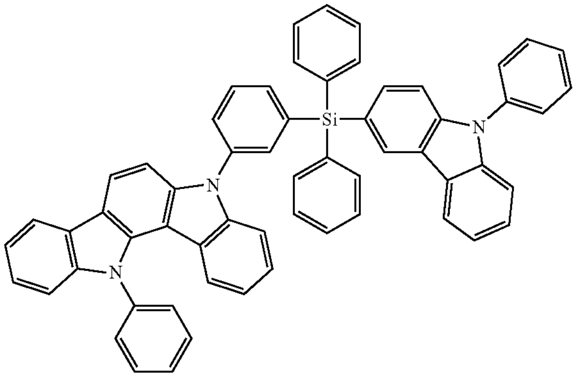
148
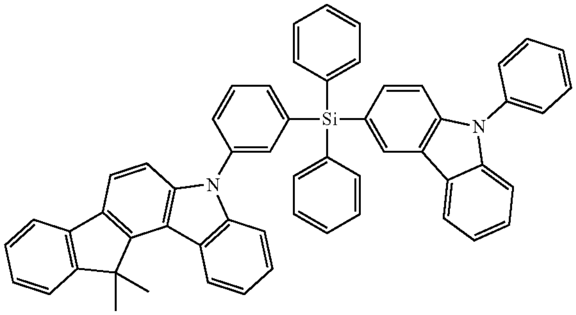
149
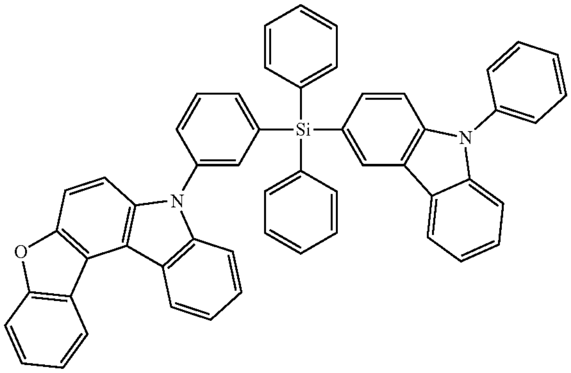
150
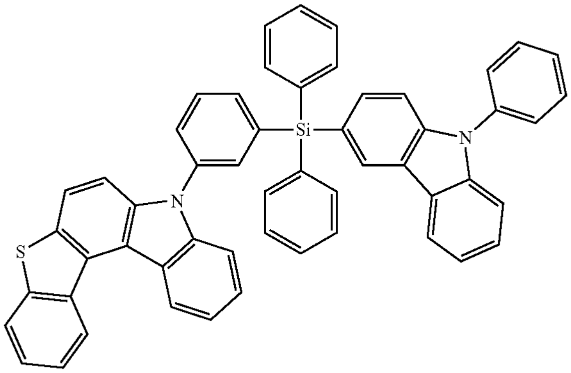

-continued
151
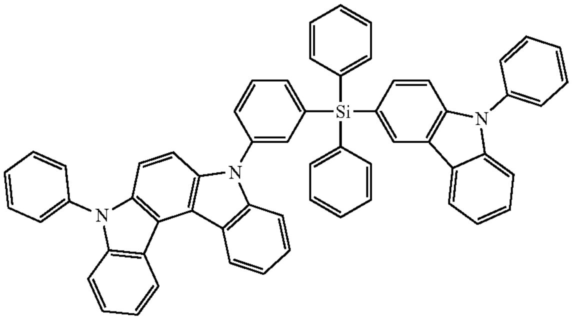
152
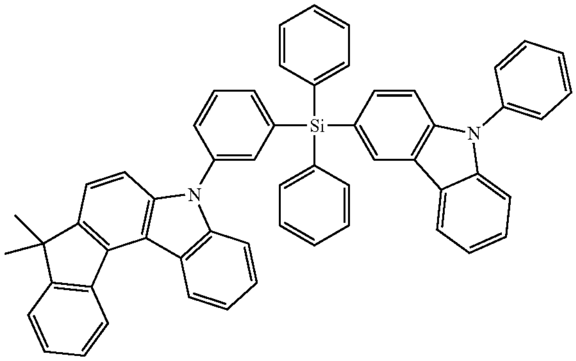
153
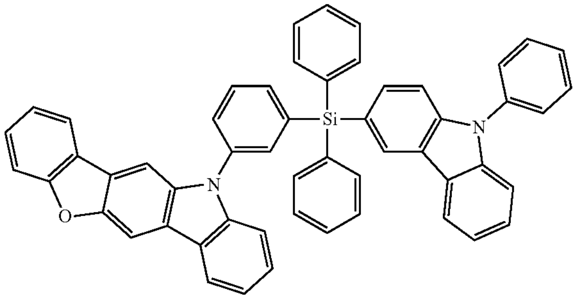
154
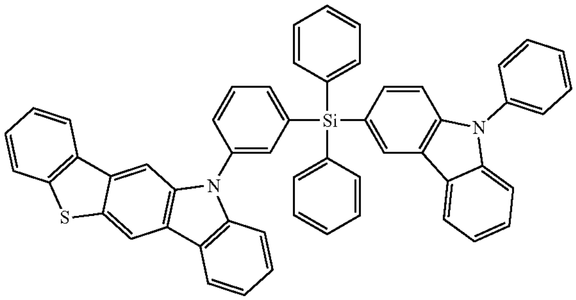
-continued
155
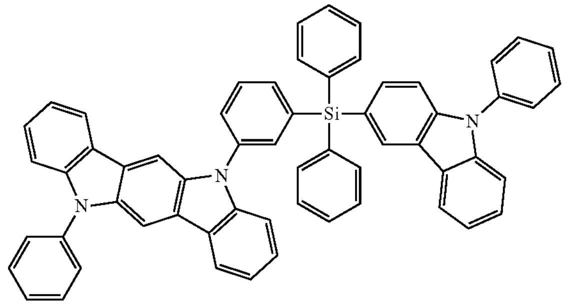
156
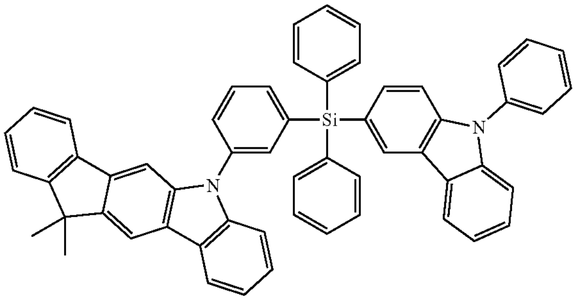
157
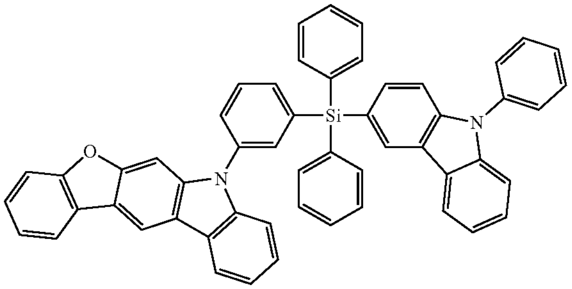
158
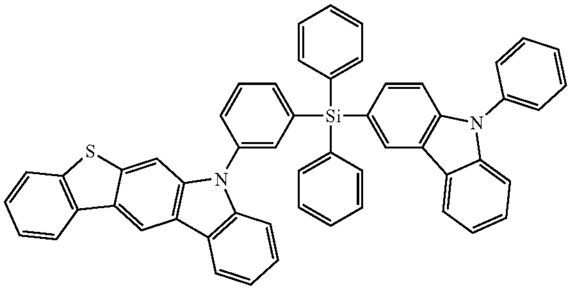
159
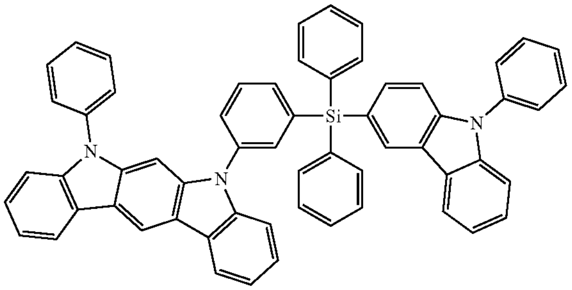

-continued
160
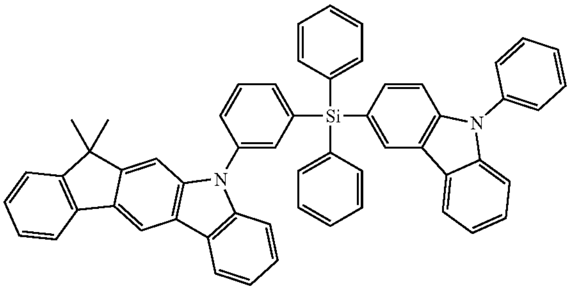
161
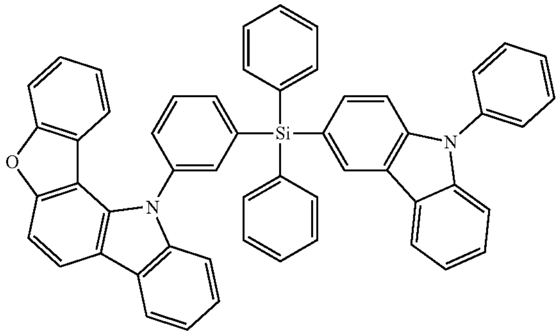
162
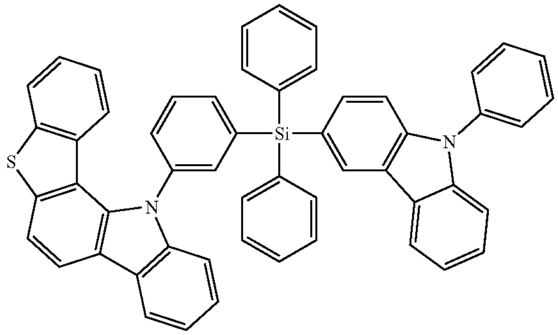
163
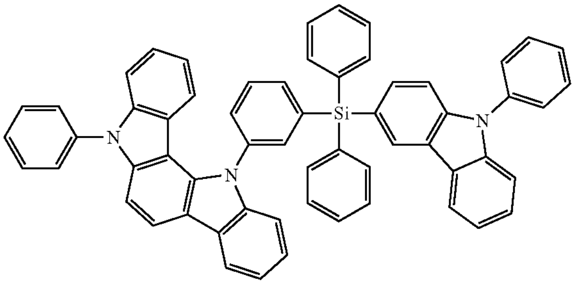
-continued
164
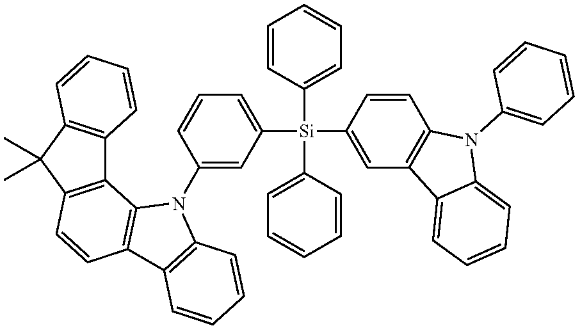
165
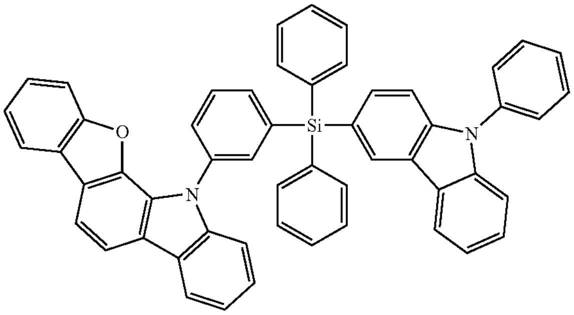
166
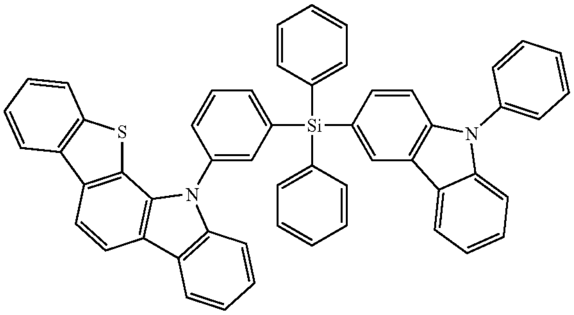
167
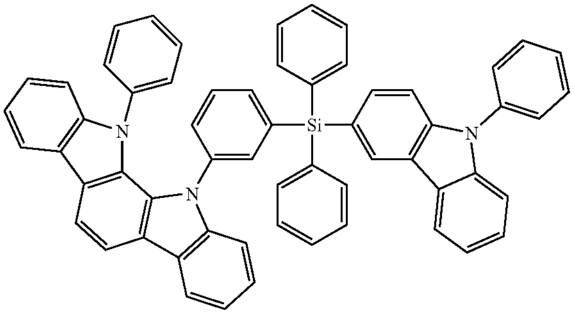

-continued
168
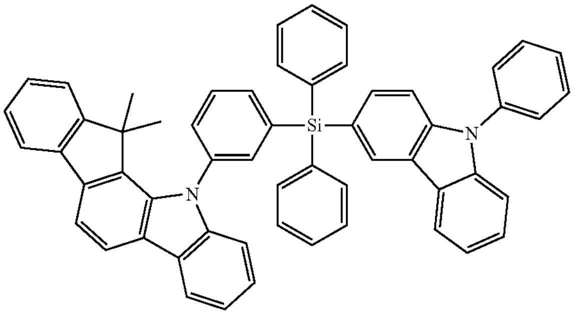
169
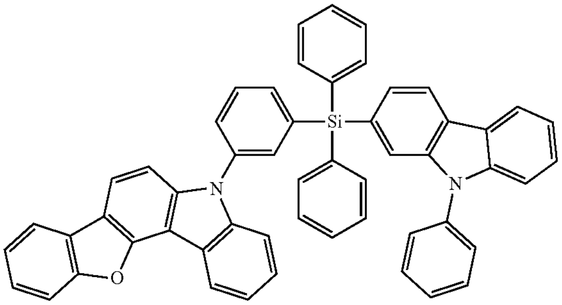
170
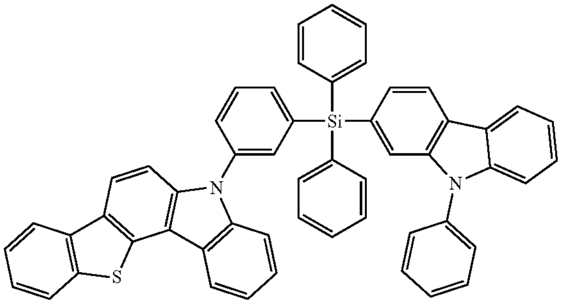
171
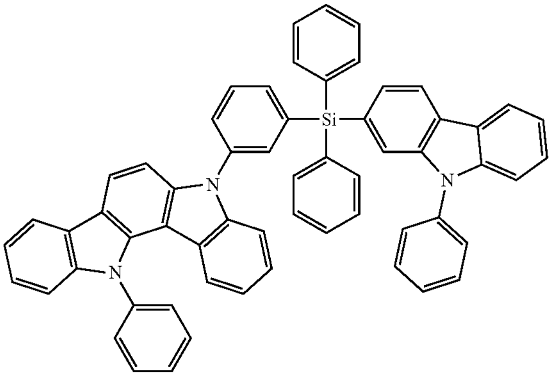
-continued
172
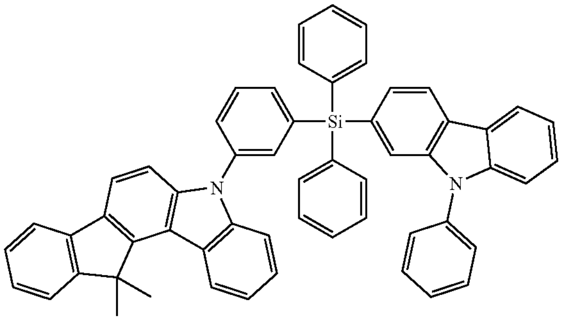
173
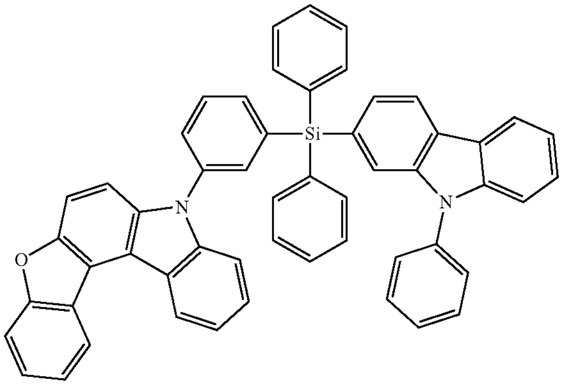
174
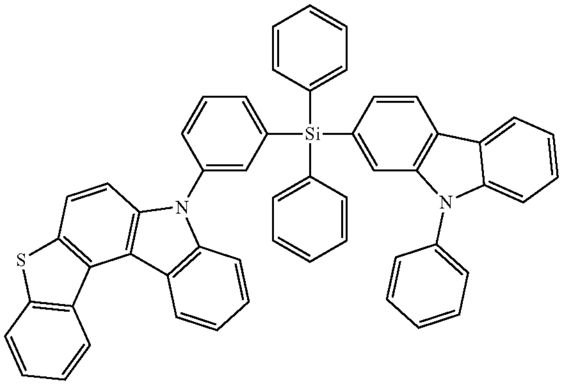
175
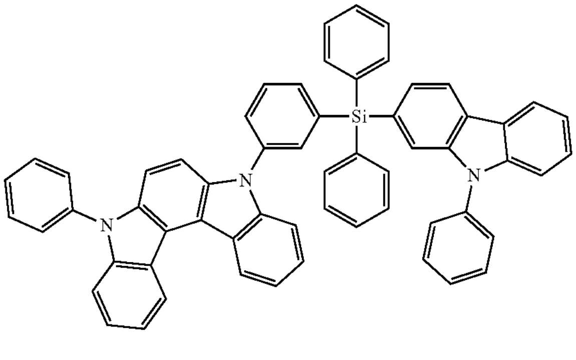

-continued
176
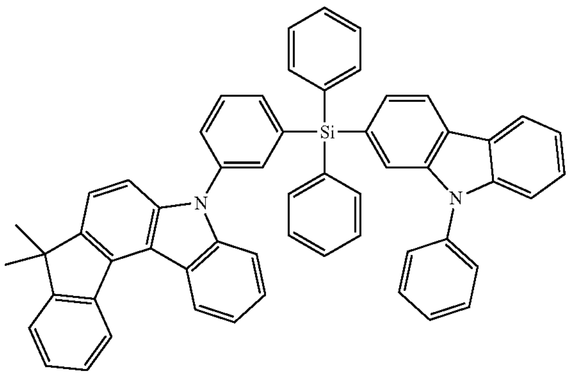
177
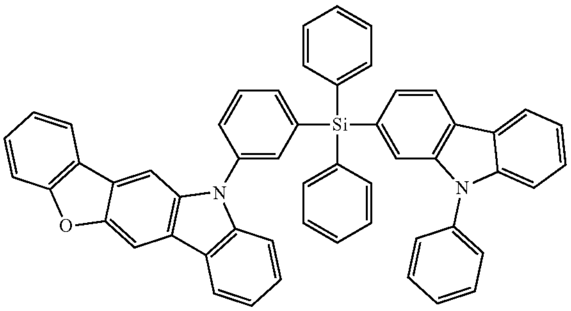
178
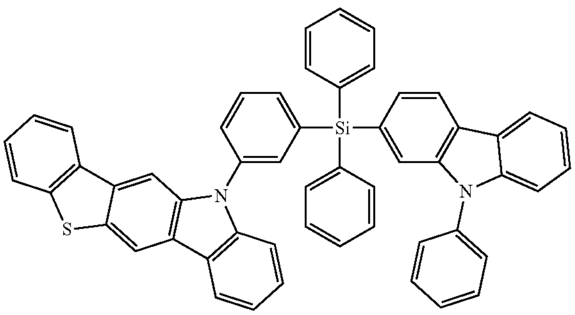
179
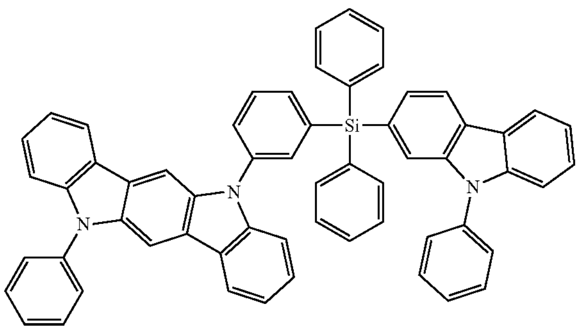
-continued
180
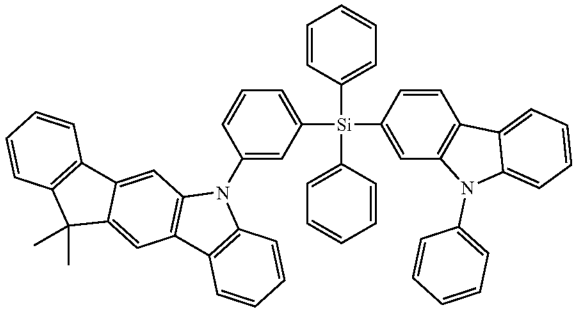
181
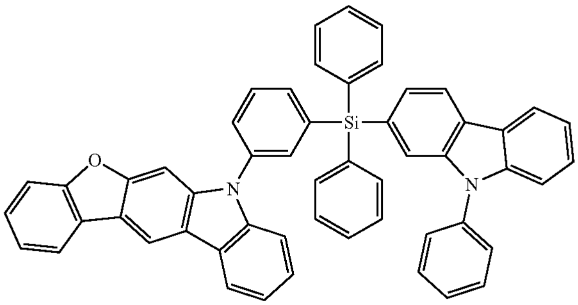
182
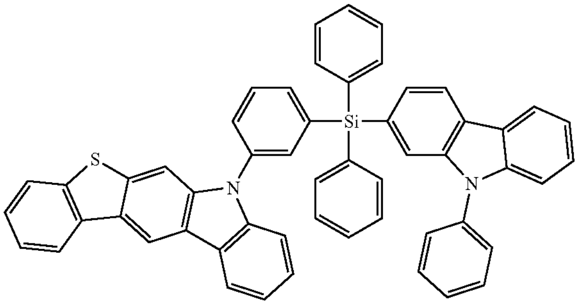
183
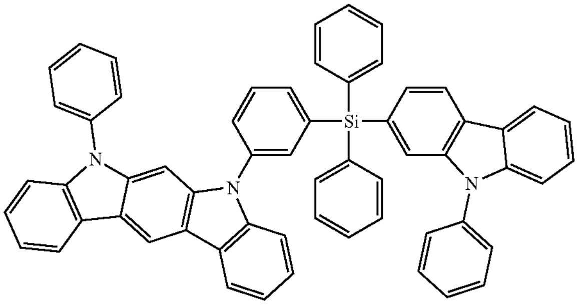

-continued
184
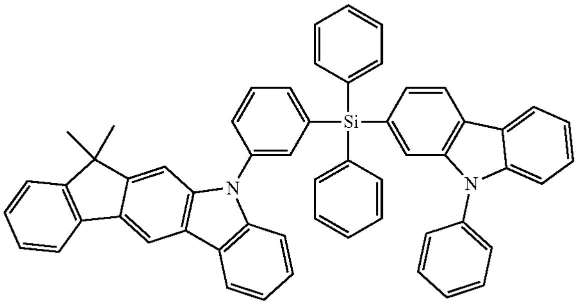
185
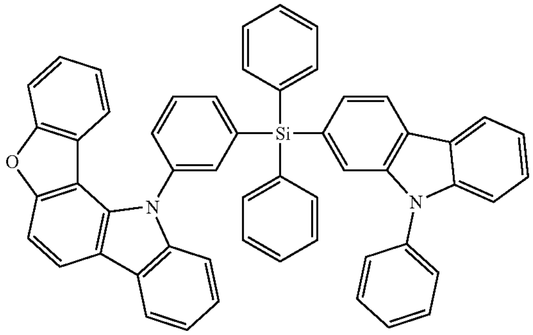
186
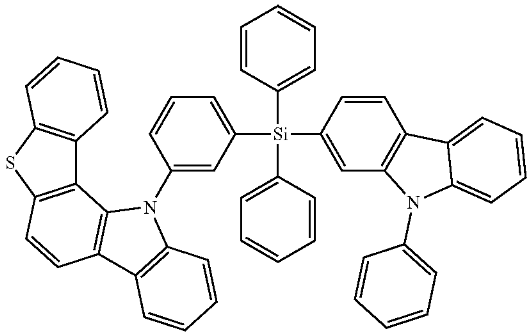
187
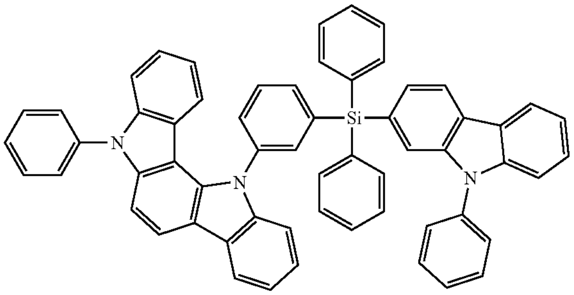
-continued
188
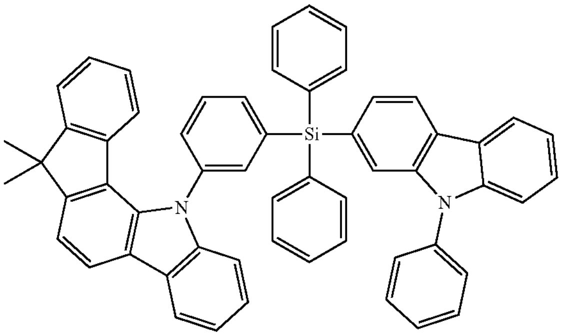
189
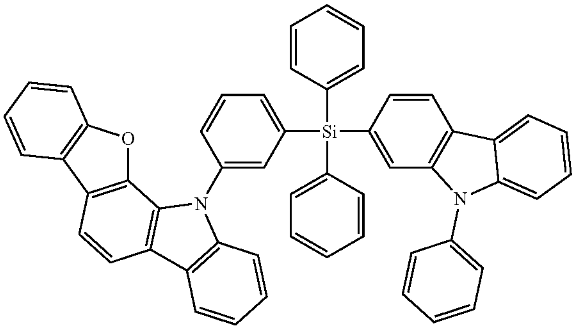
190
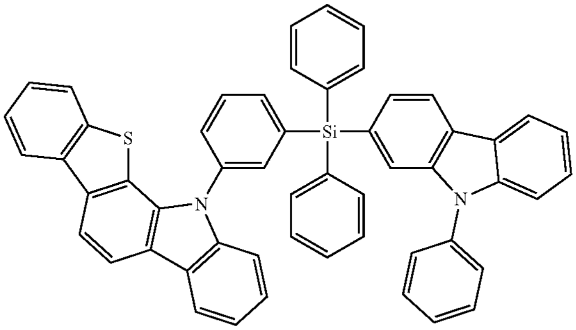
191
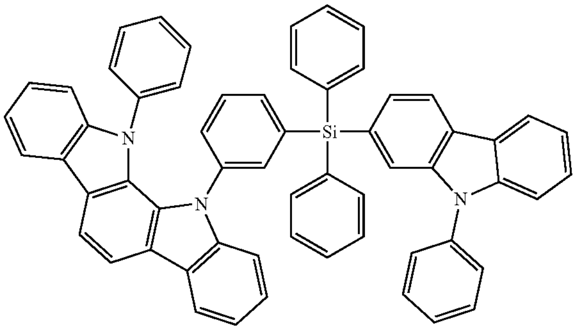

192
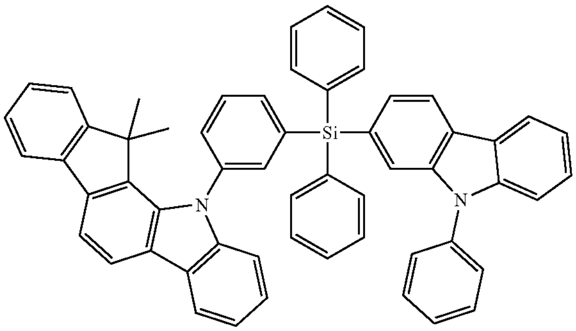
193
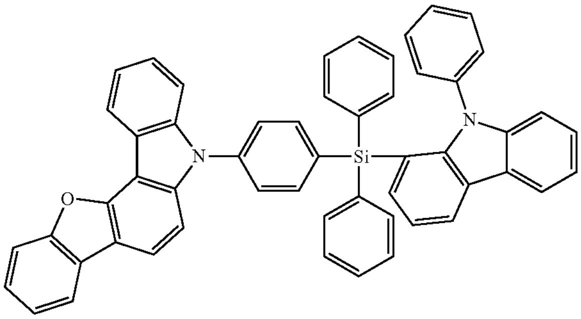
194
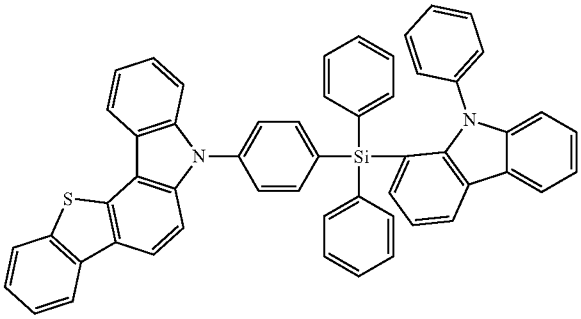
195
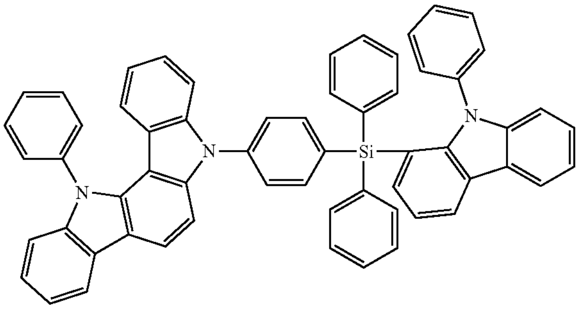
196
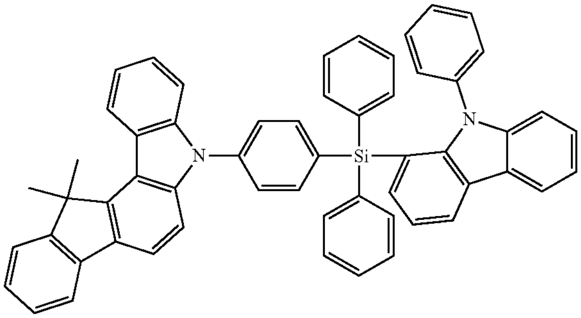
197
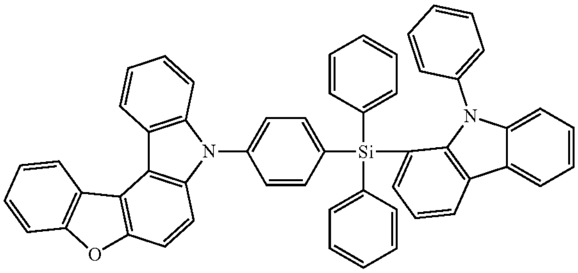
198
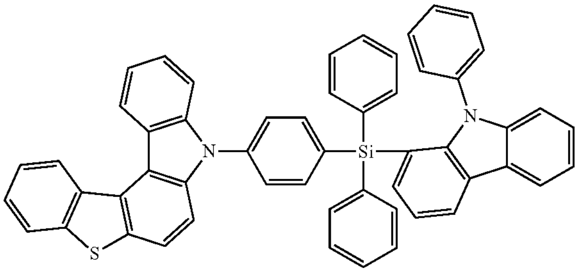
199
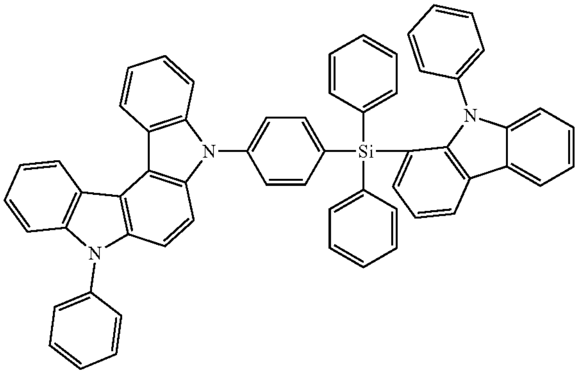
200
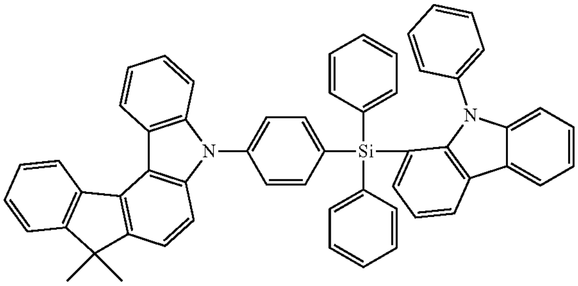

-continued
201
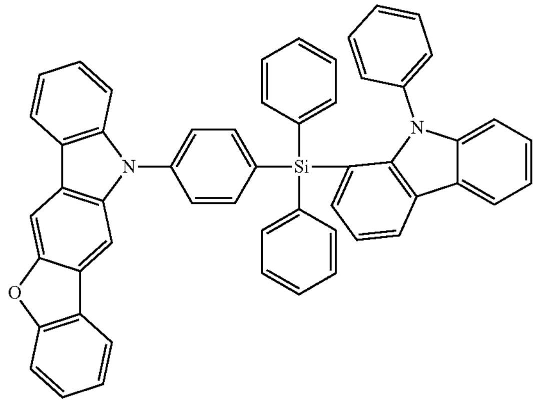
202
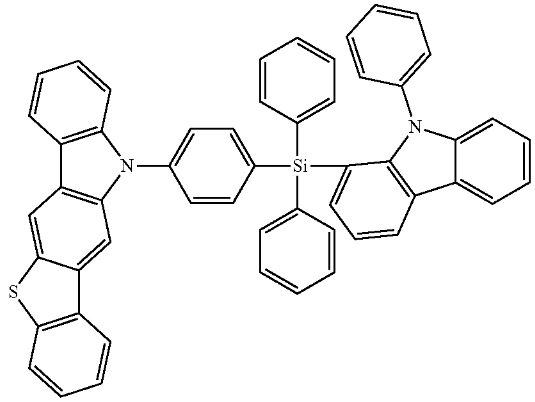
203
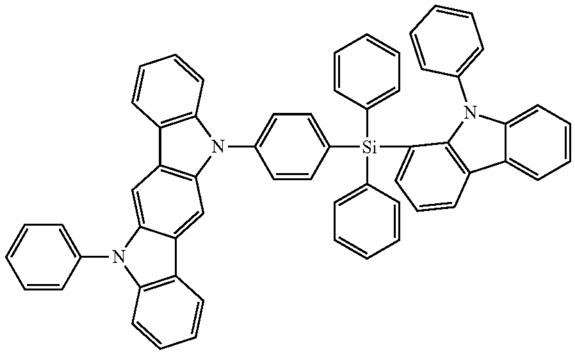
204
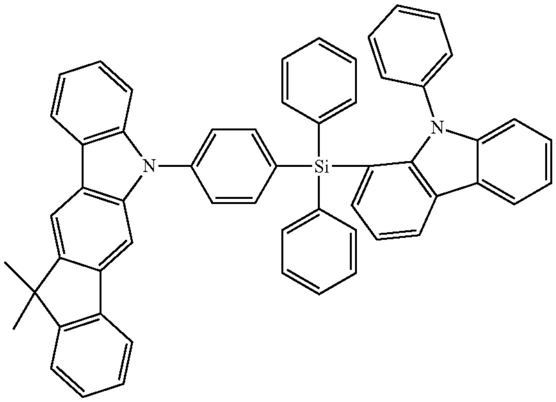
-continued
205
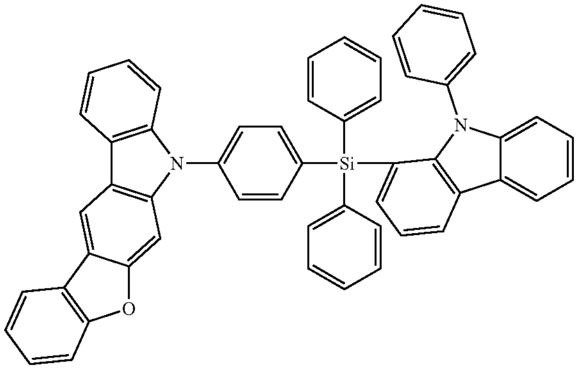
206
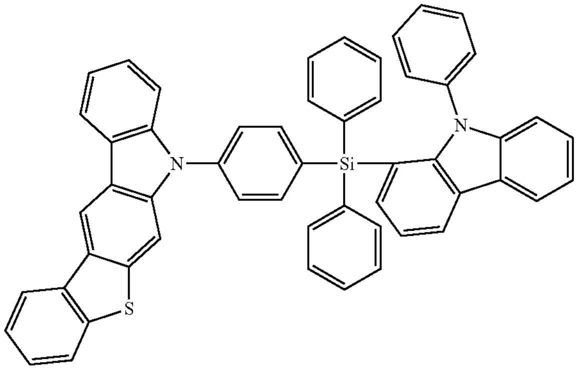
207
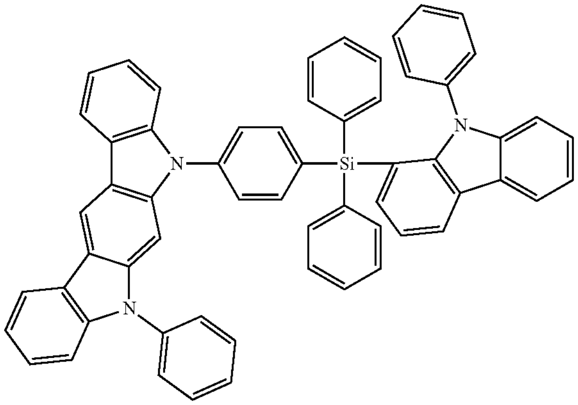
208
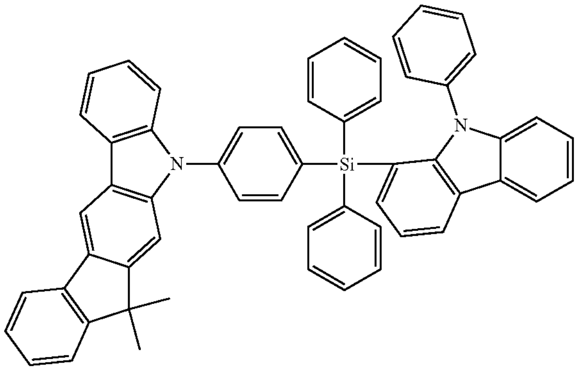

-continued
209
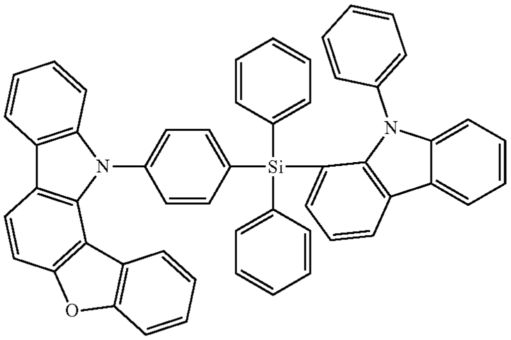
210
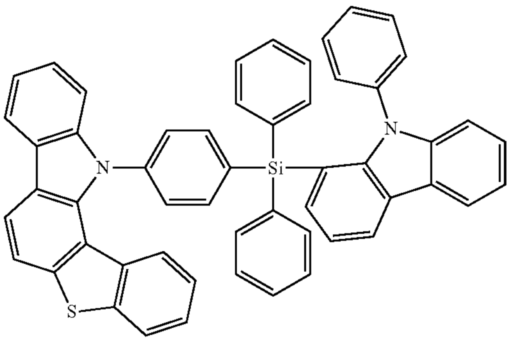
211
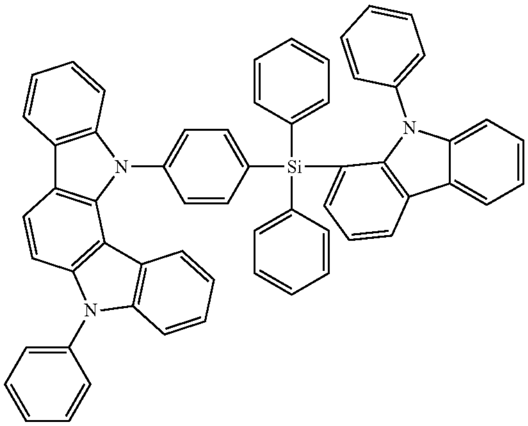
212
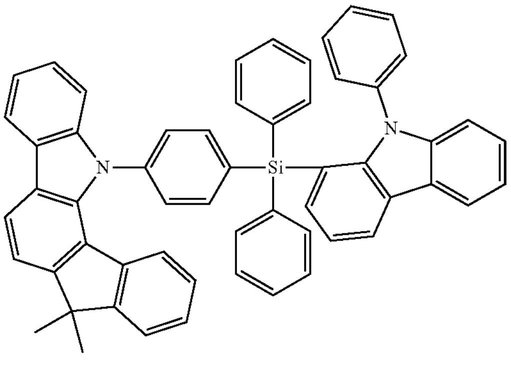
-continued
213
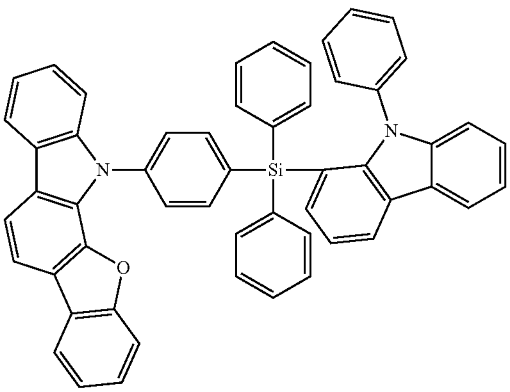
214
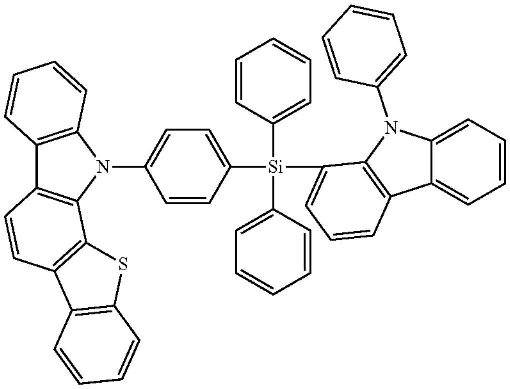
215
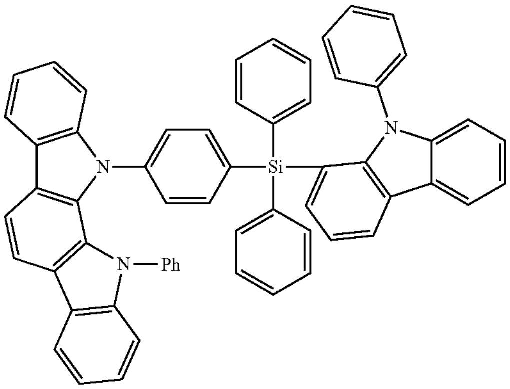
216
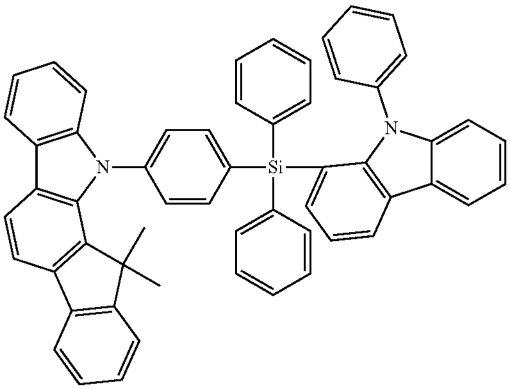

-continued
217
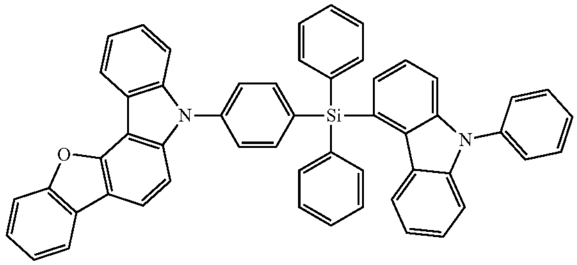
218
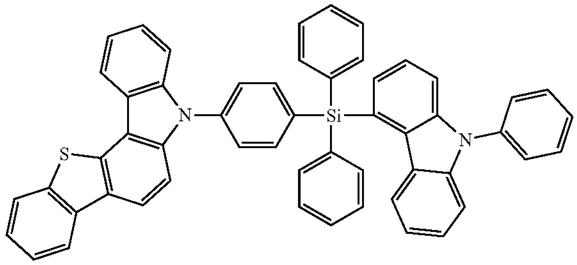
219
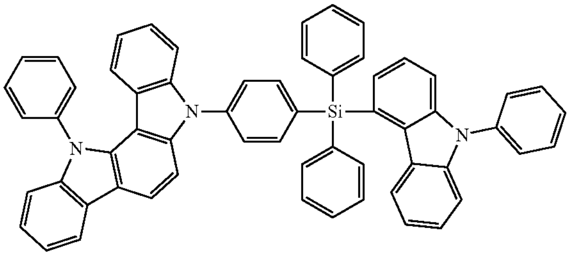
220
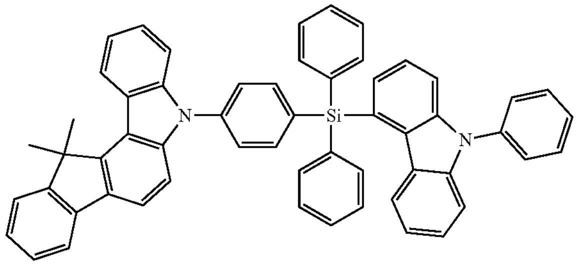
-continued
221
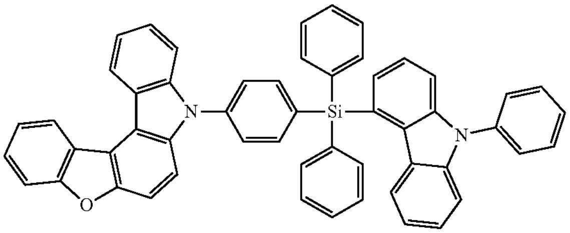
222
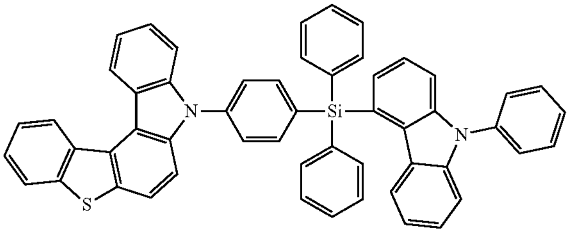
223
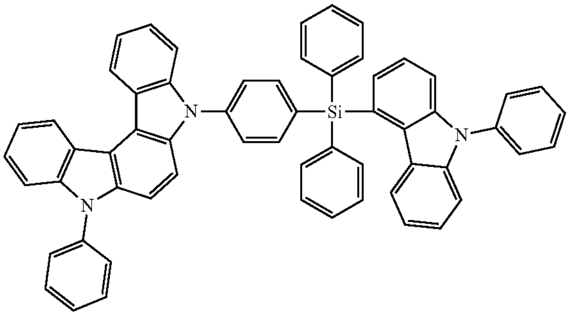
224
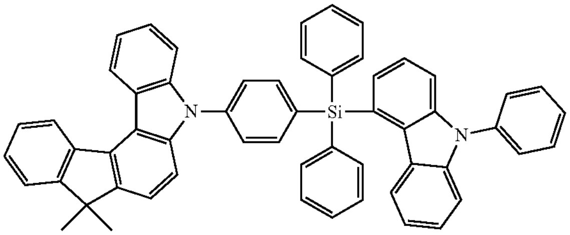
225
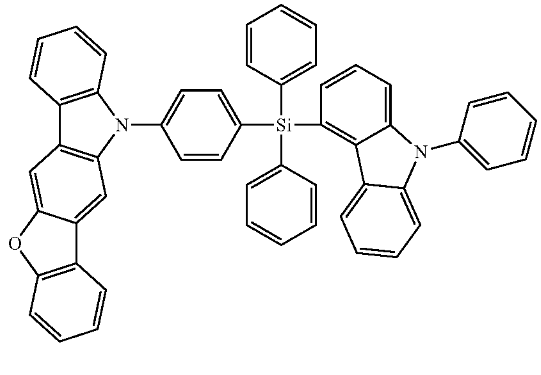
226
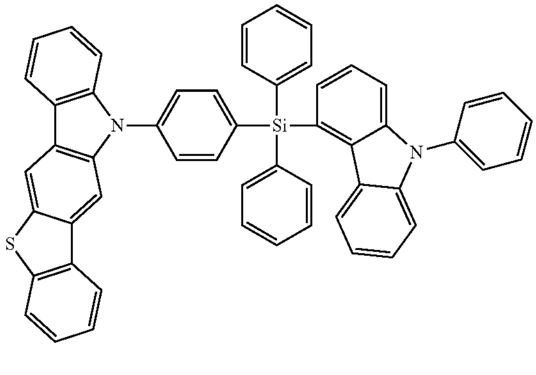

-continued
227
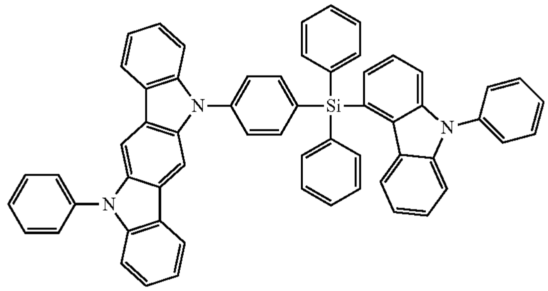
228
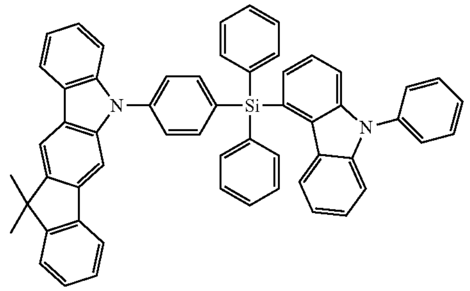
229
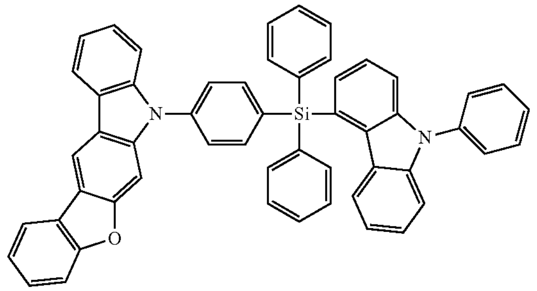
230
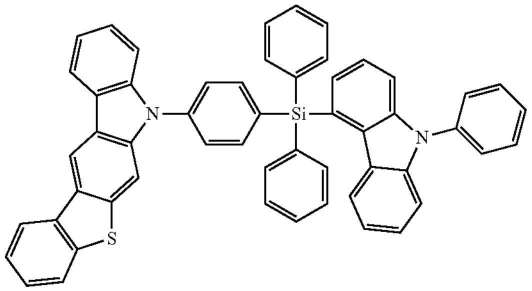
231
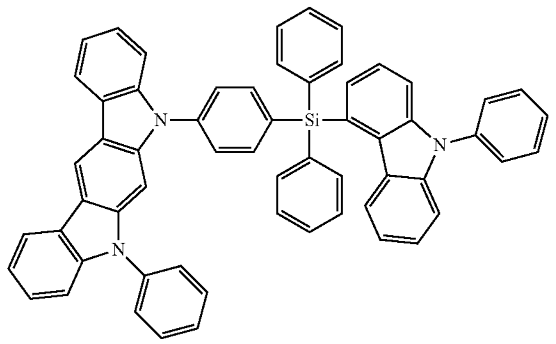
232
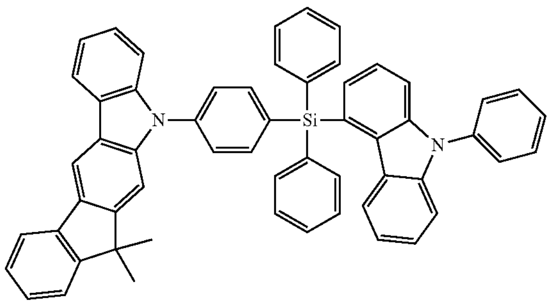
233
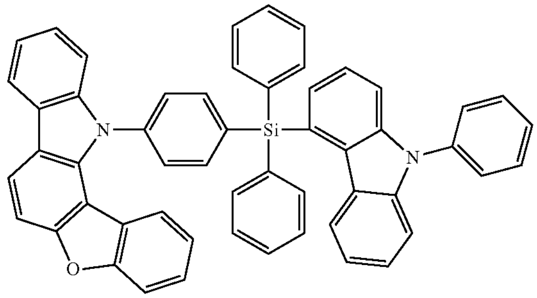
234
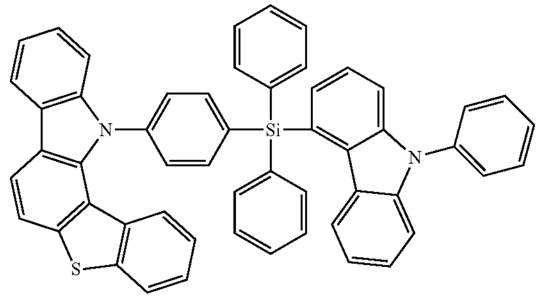

-continued
235
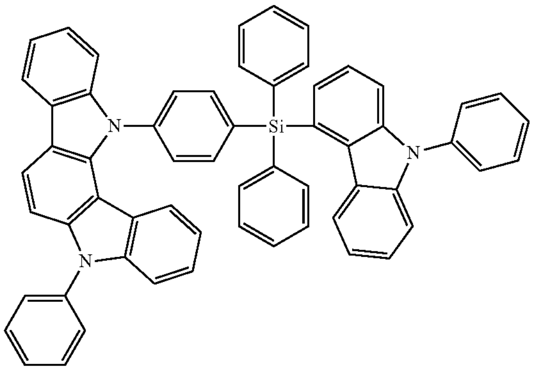
236
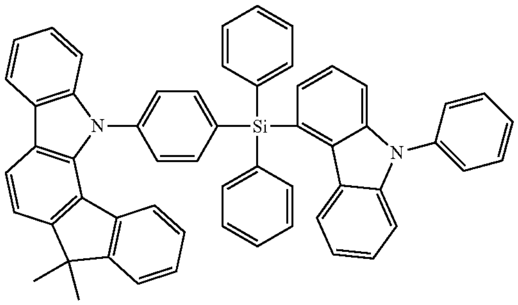
237
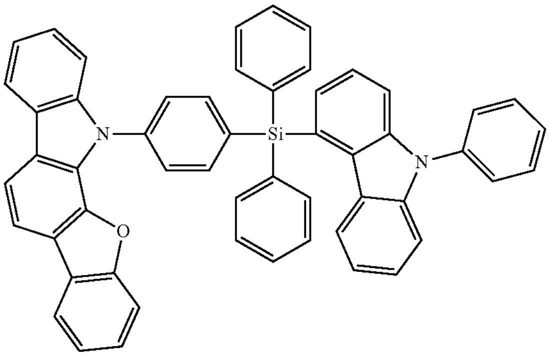
238
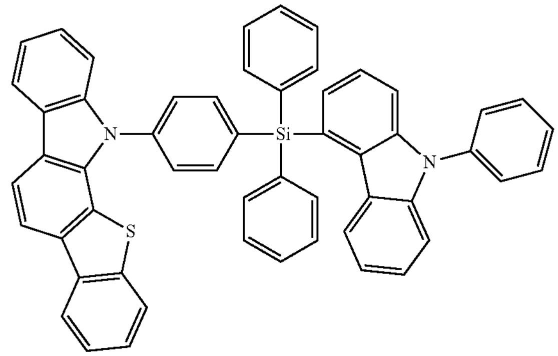
239
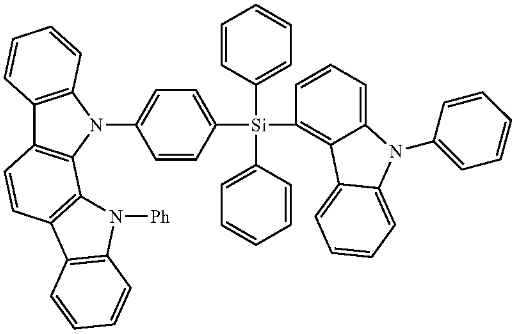
240
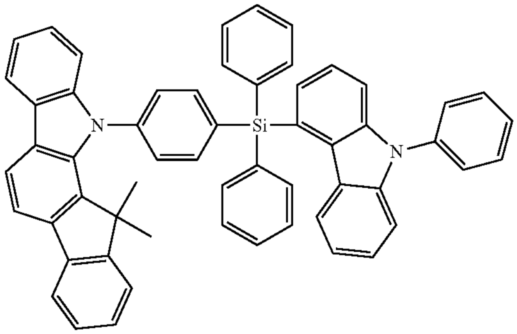
241
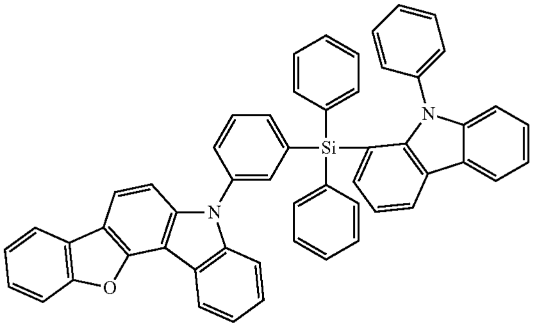
242
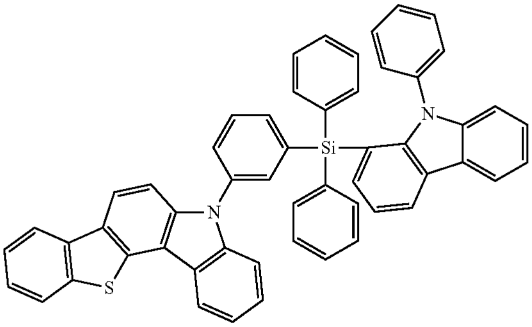

-continued
243
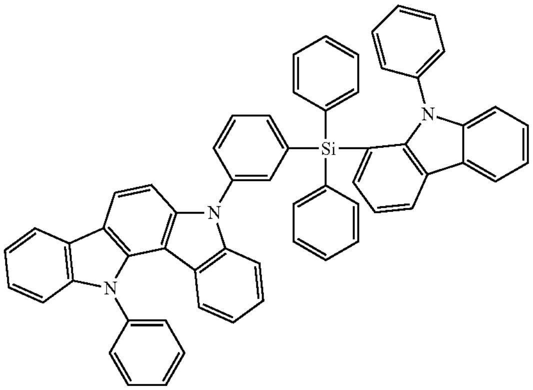
244
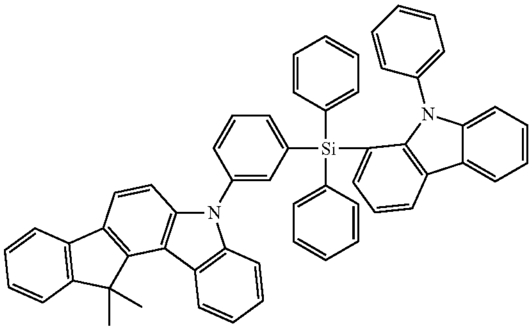
245
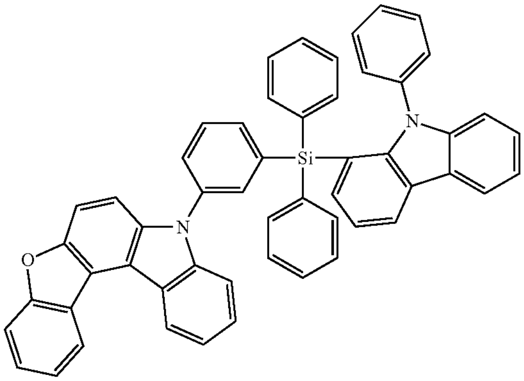
246
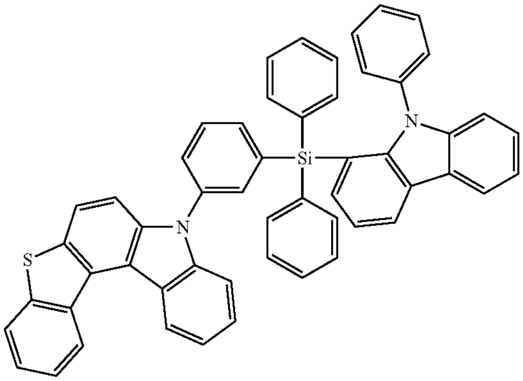
247
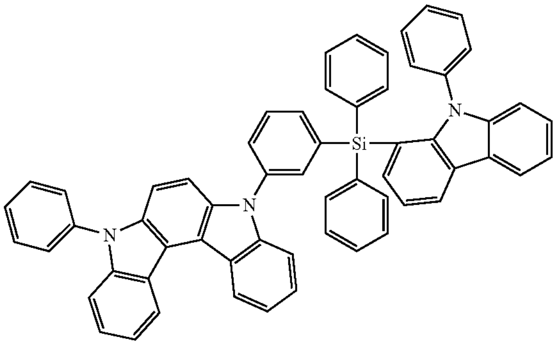
248
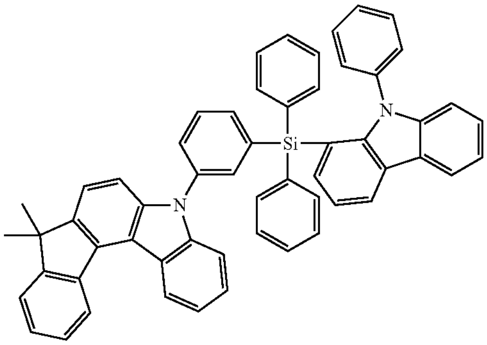
249
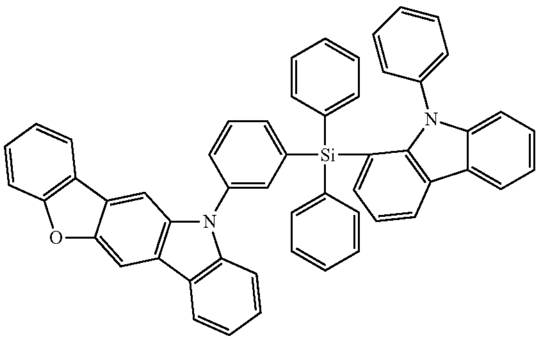
250
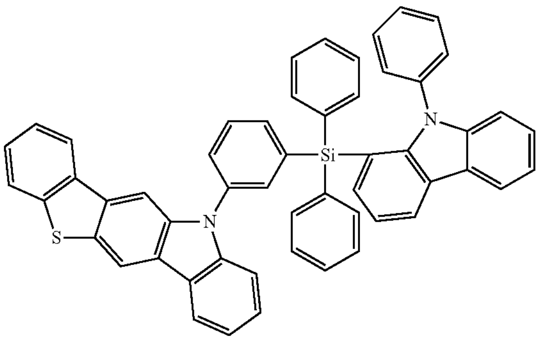

-continued
251
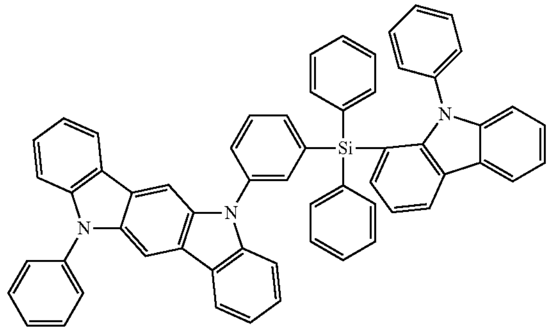
252
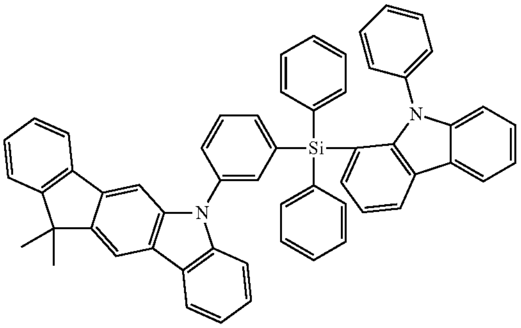
253
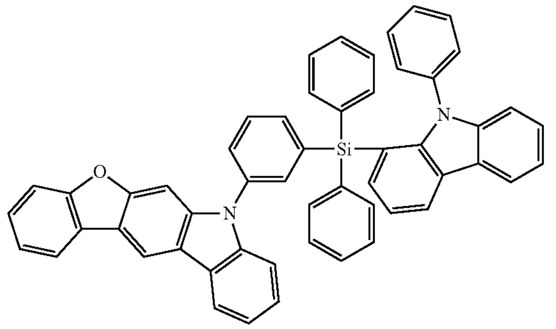
254
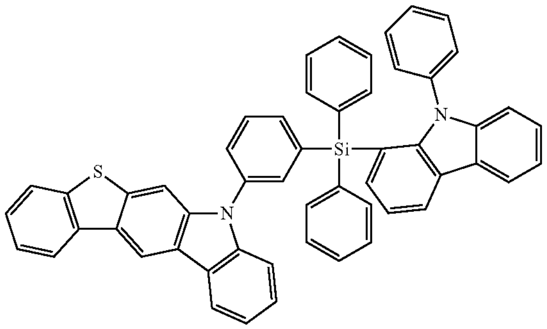
255
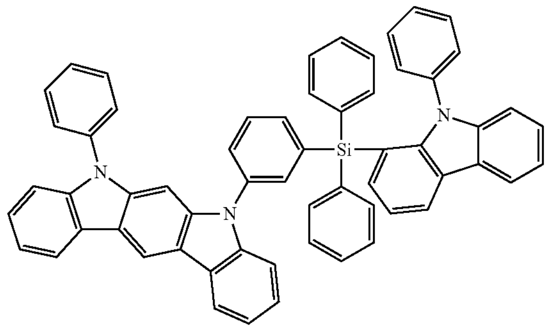
256
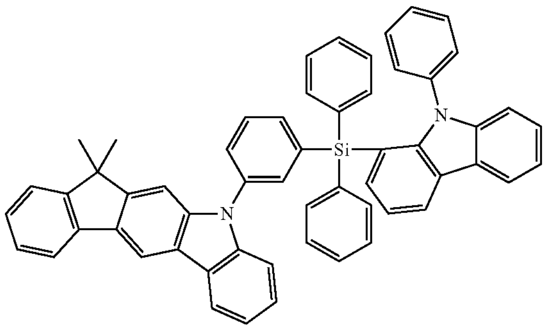
257
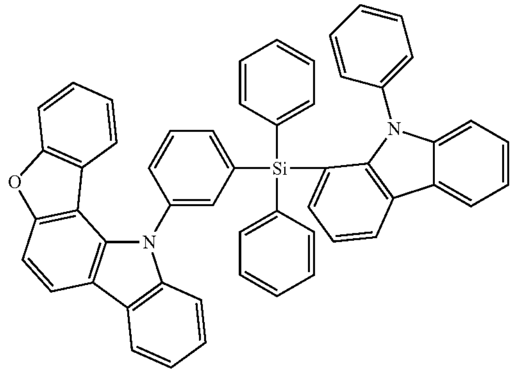
258
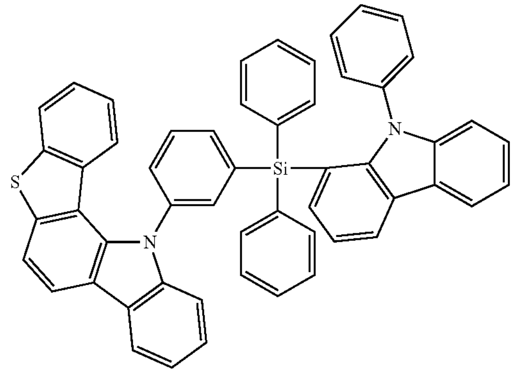

-continued
259
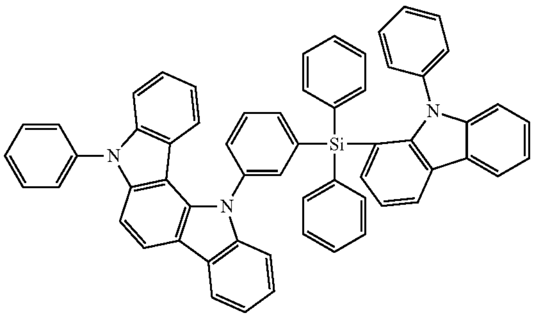
260
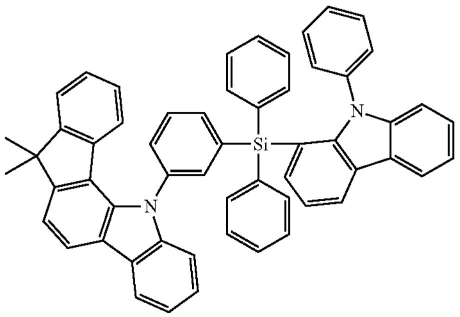
261
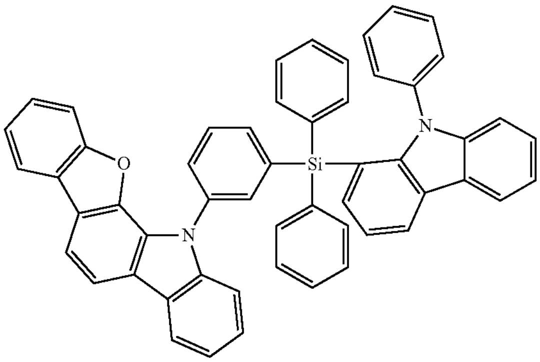
262
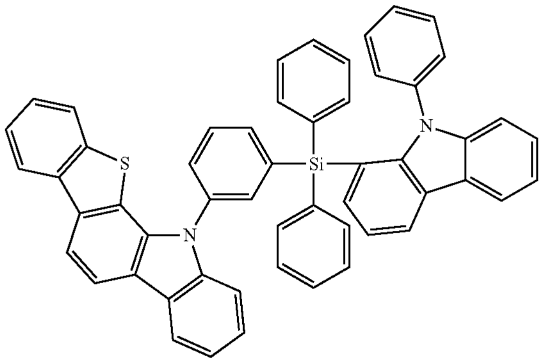
263
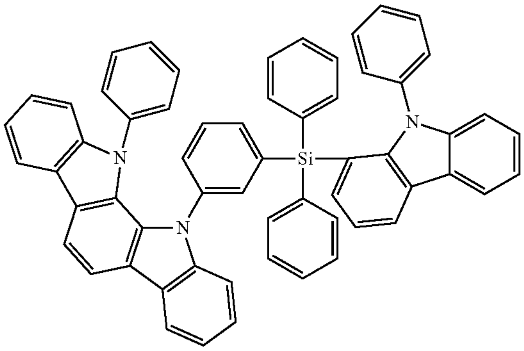
264
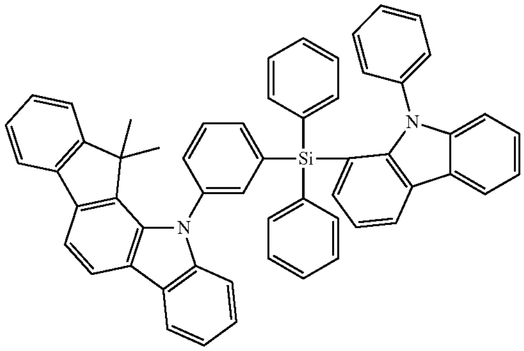
265
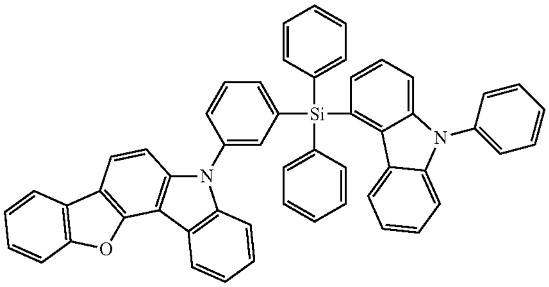
266
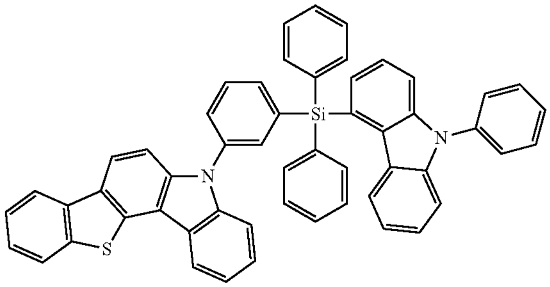

-continued
267
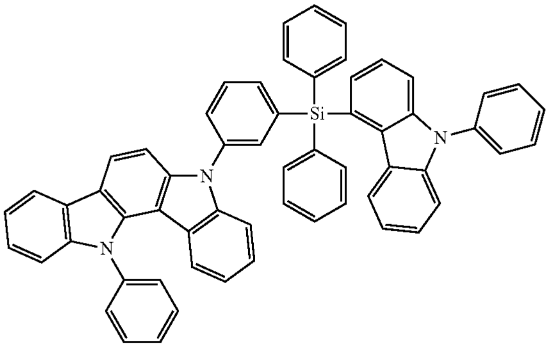
268
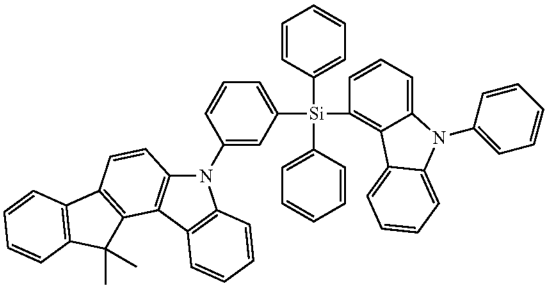
269
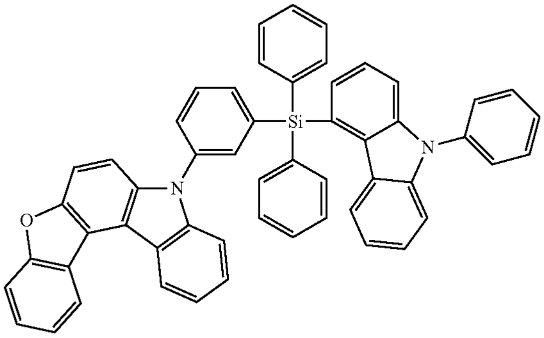
270
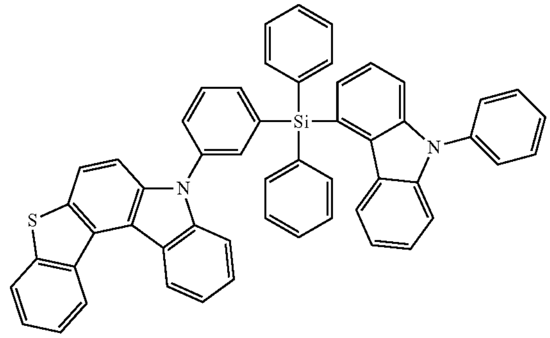
271
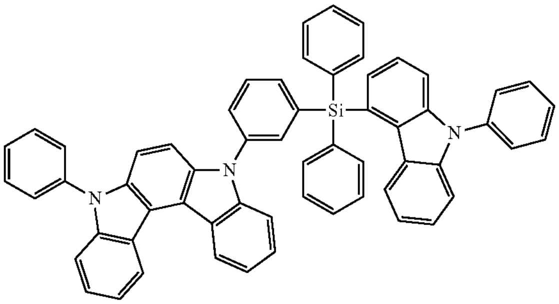
272
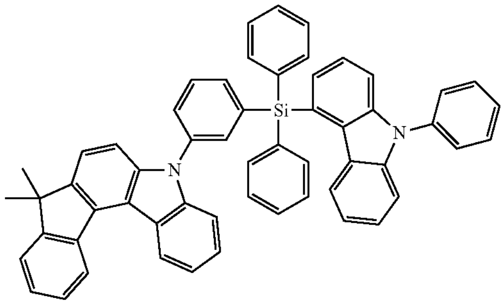
273
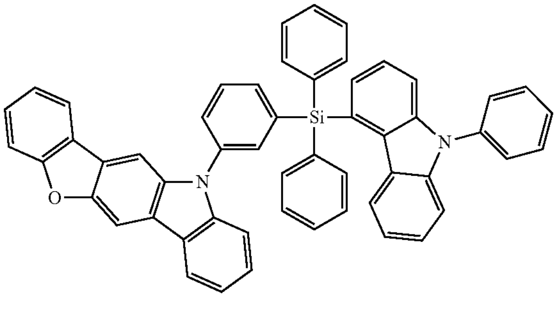
274
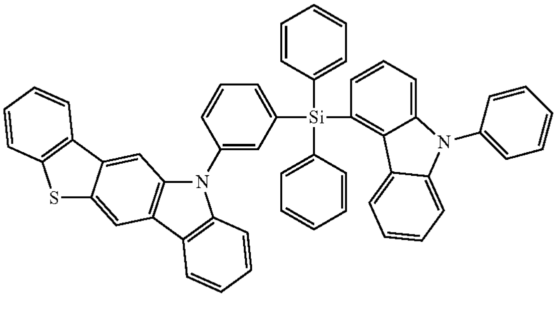

-continued
275
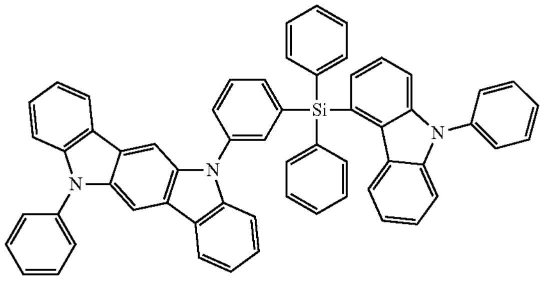
276
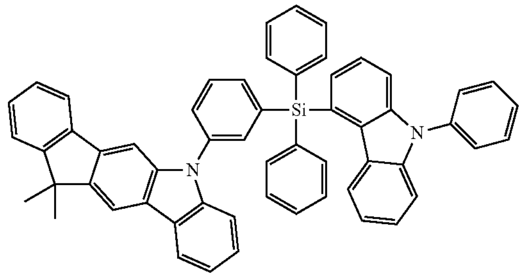
277
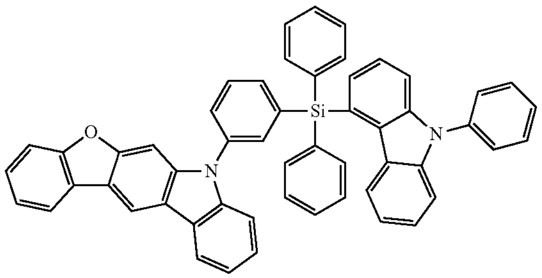
278
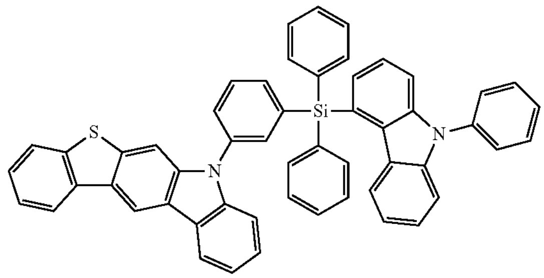
279
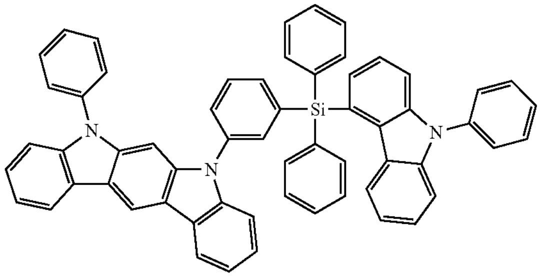
280
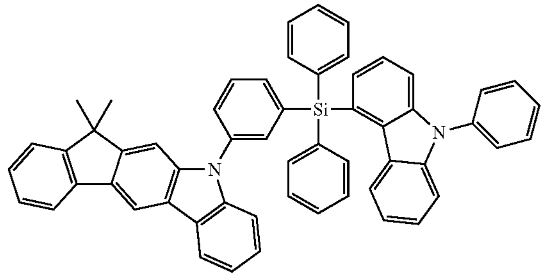
281
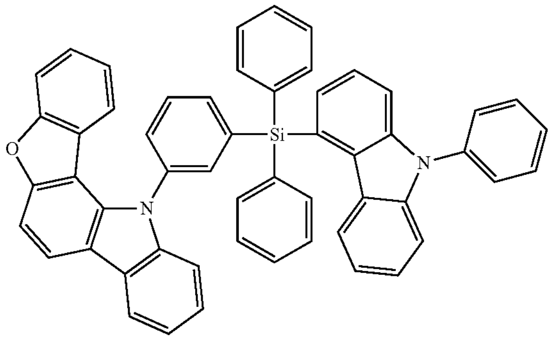
282
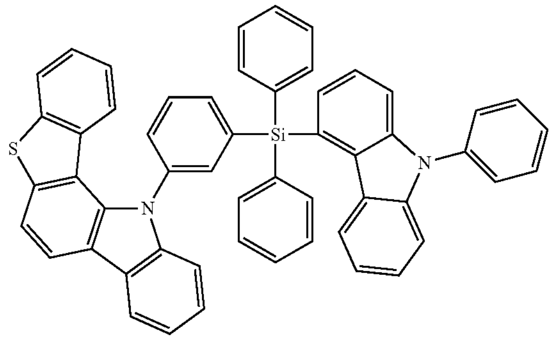
283
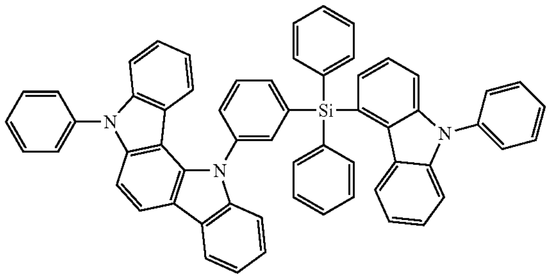
284
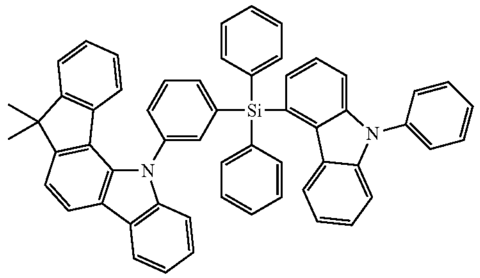

-continued
285
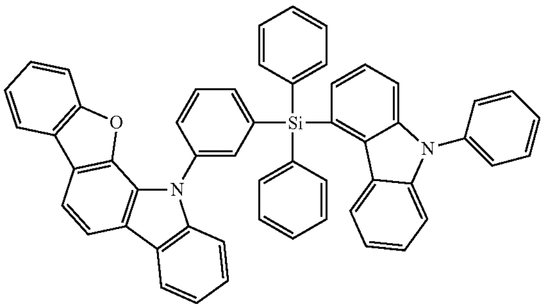
286
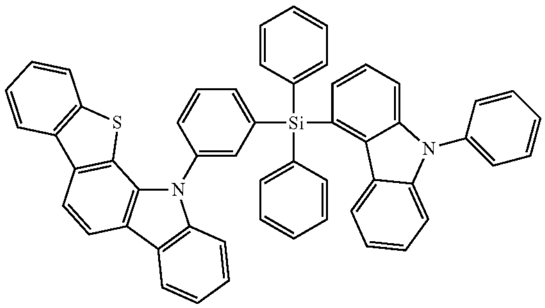
287
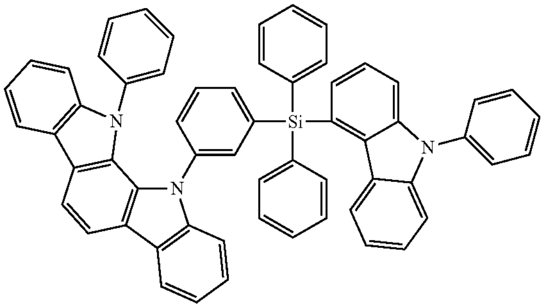
288
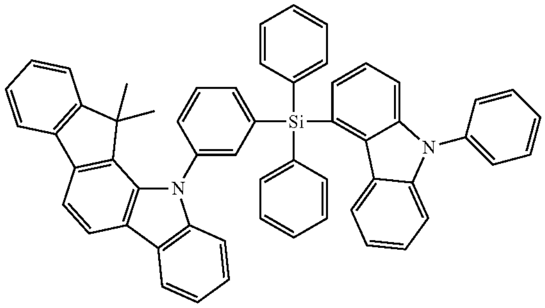
289
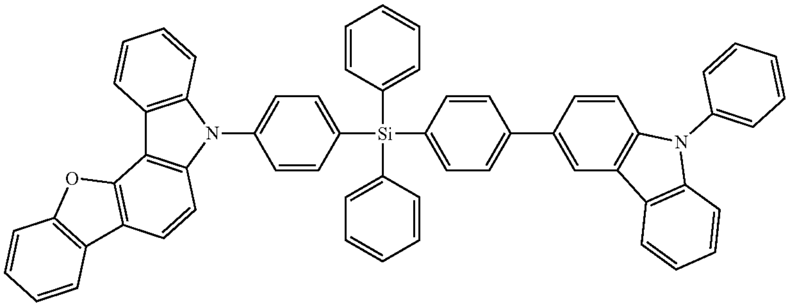
290
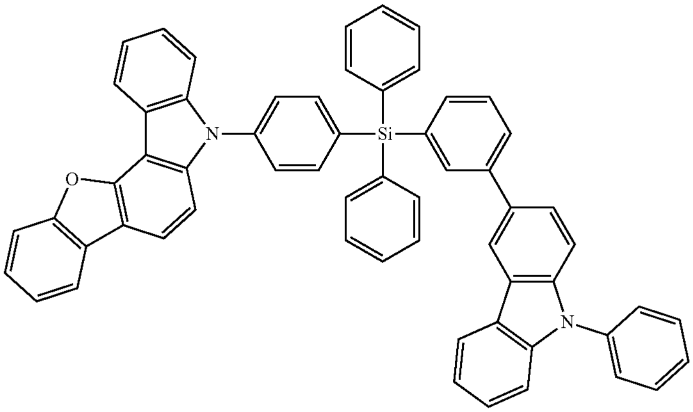

-continued
291
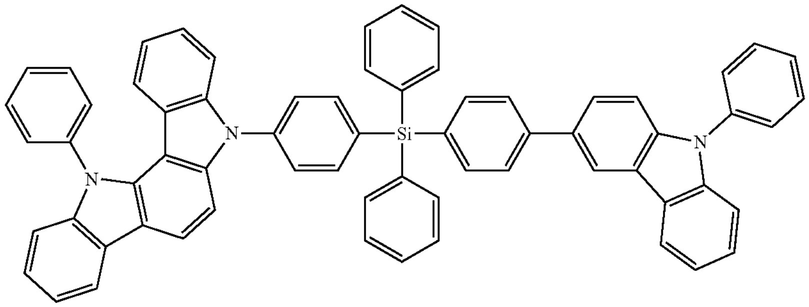
292
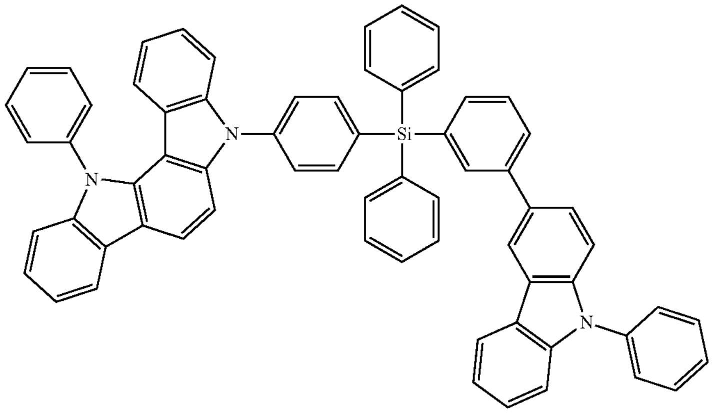
293
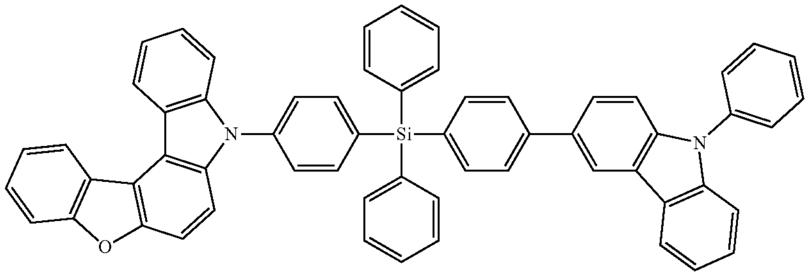
294
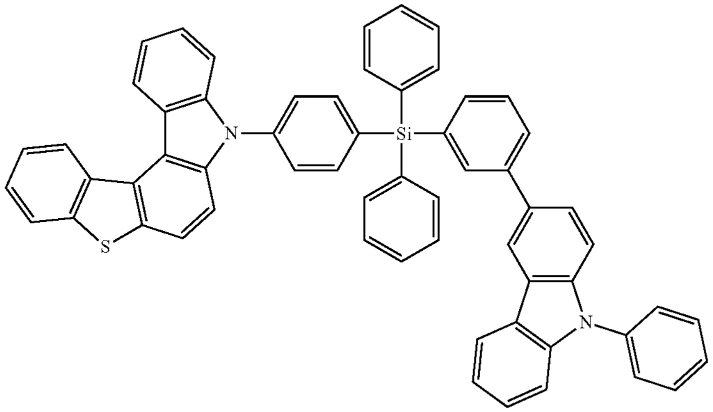

-continued
295
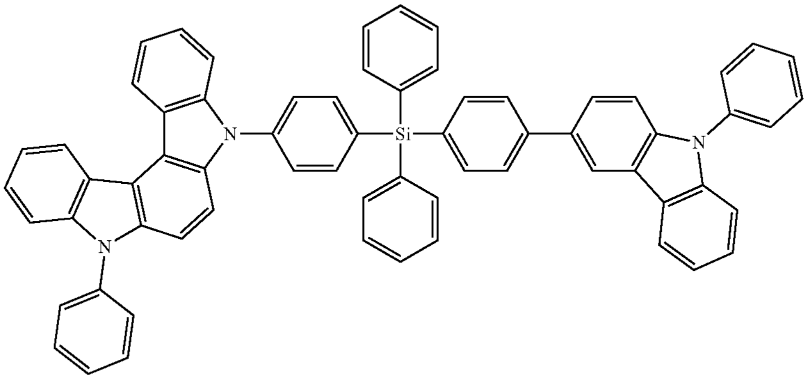
296
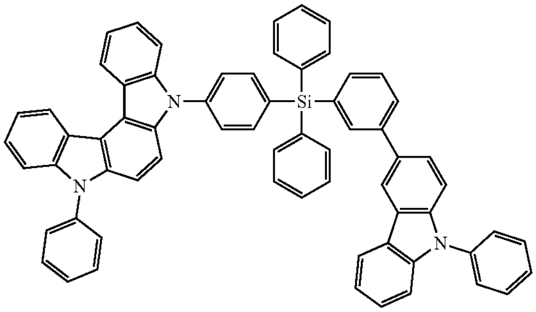
297
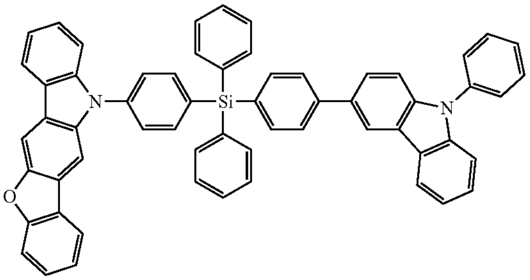
298
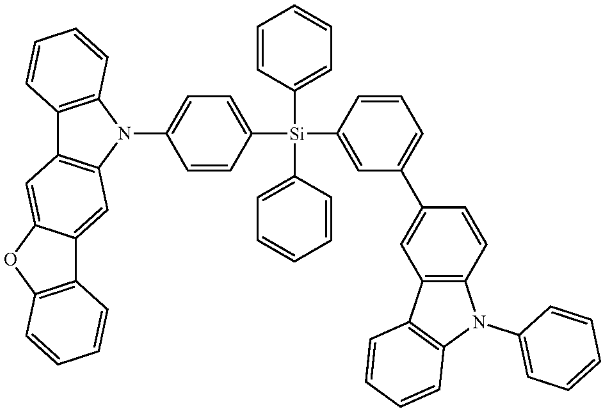
299
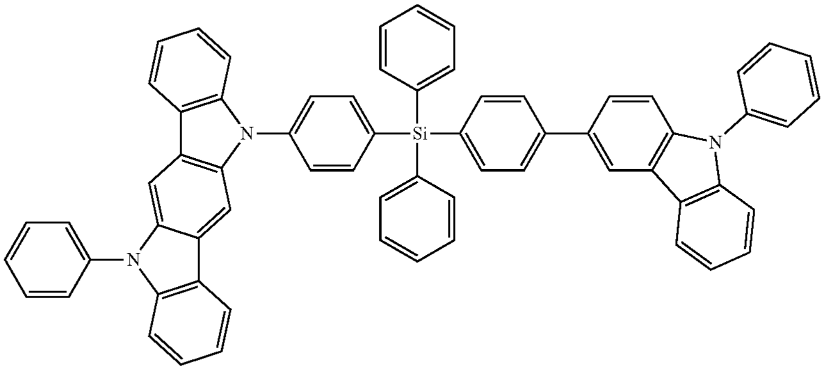

-continued
300
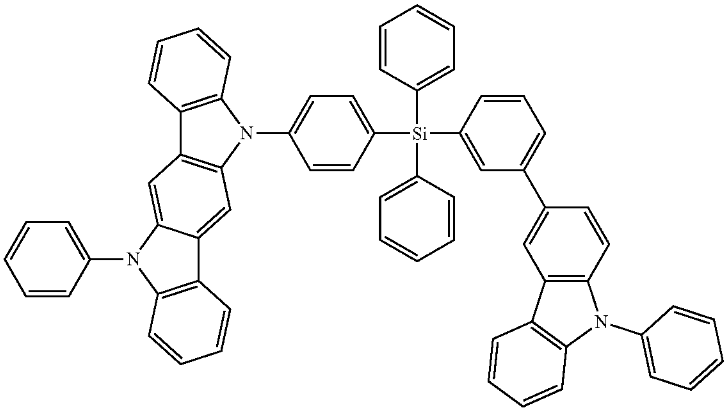
301
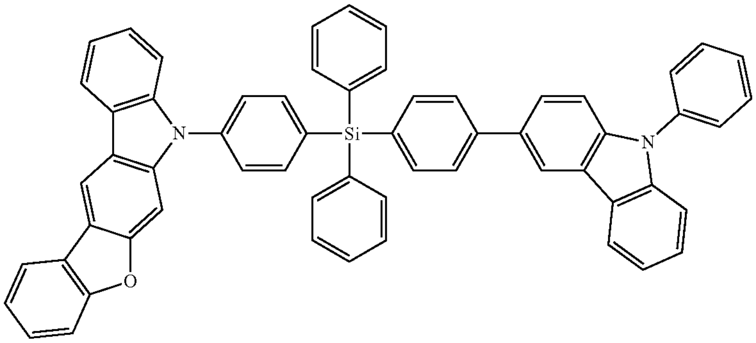
302
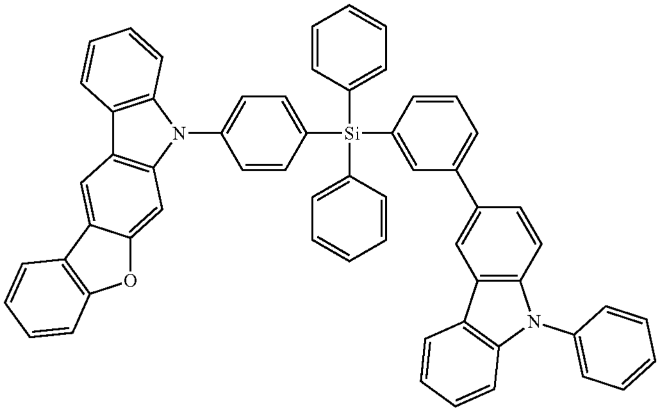
303
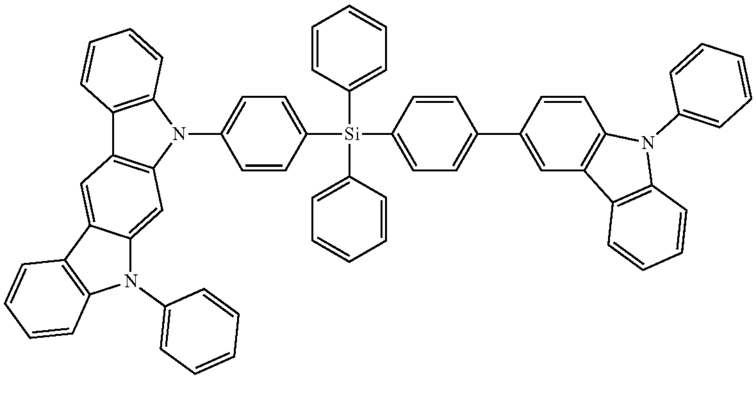

-continued
304
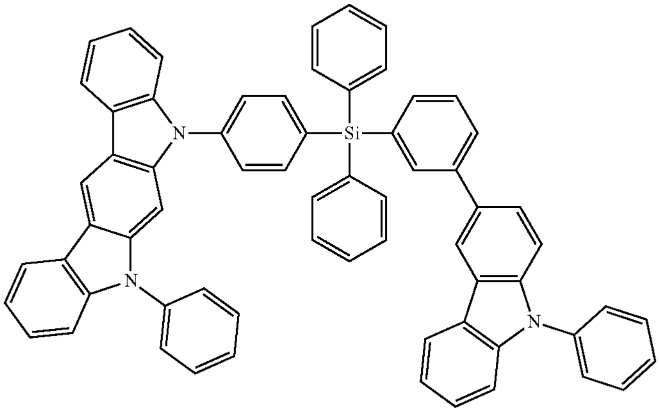
305
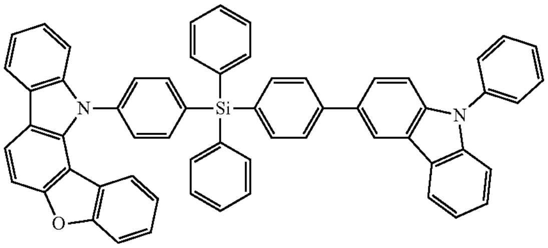
306
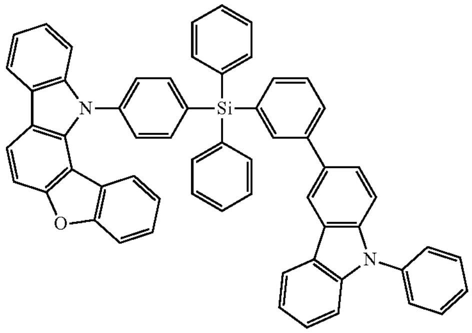
307
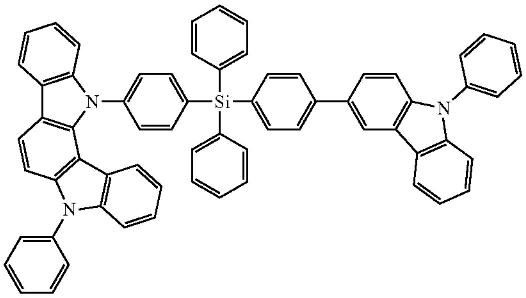
308
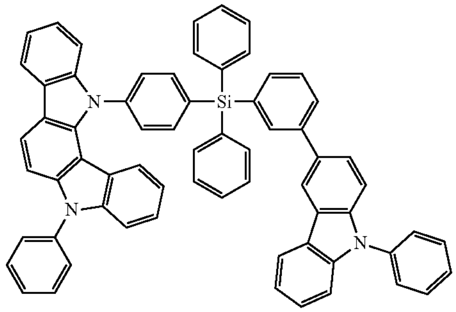
309
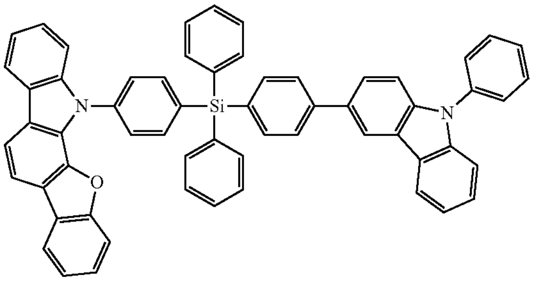
310
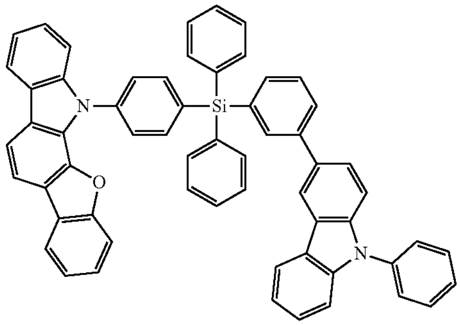

-continued
311
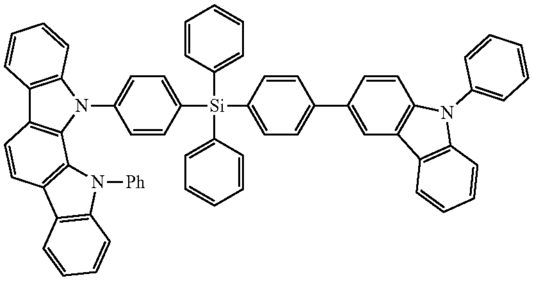
312
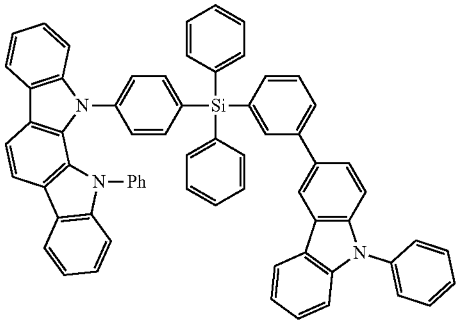
313
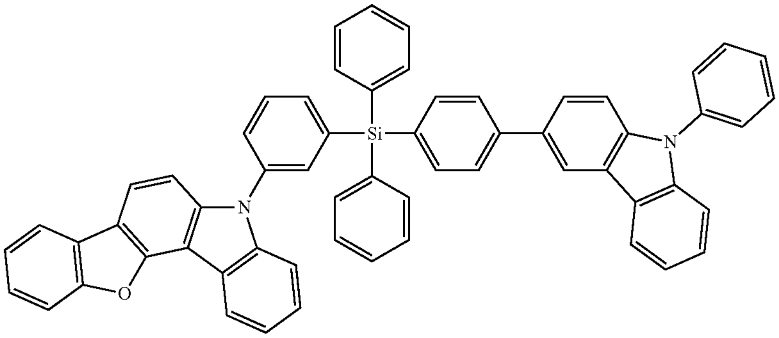
314
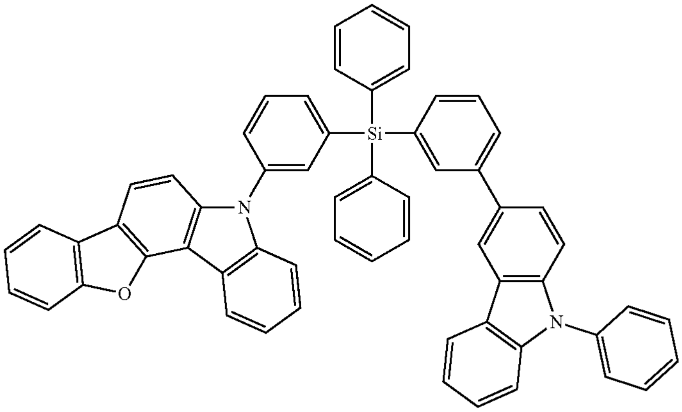
315
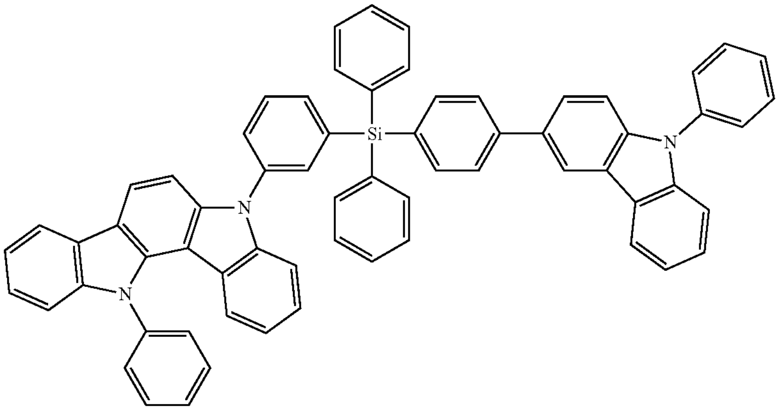

-continued
316
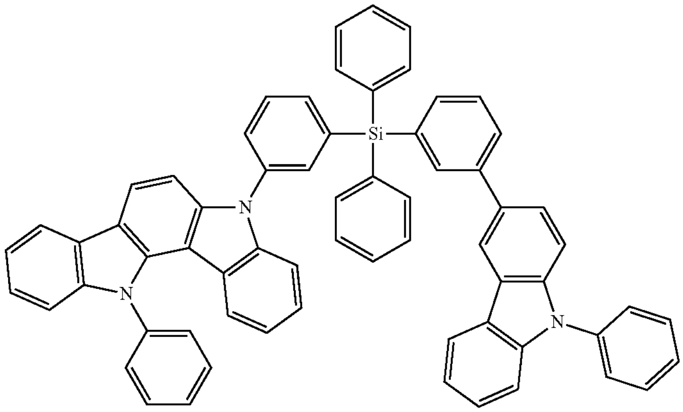
317
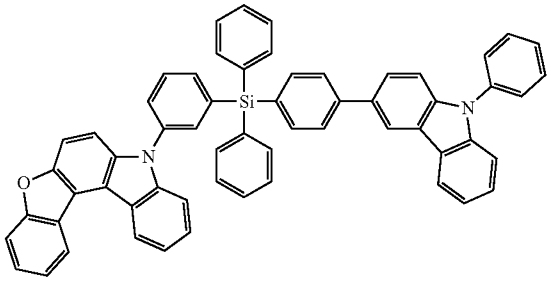
318
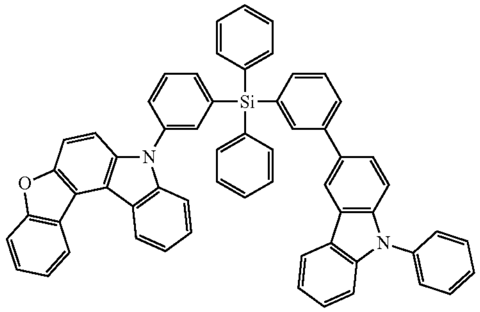
319
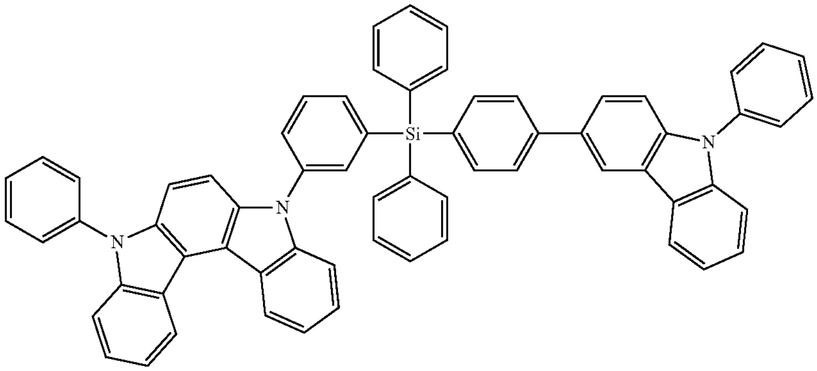
320
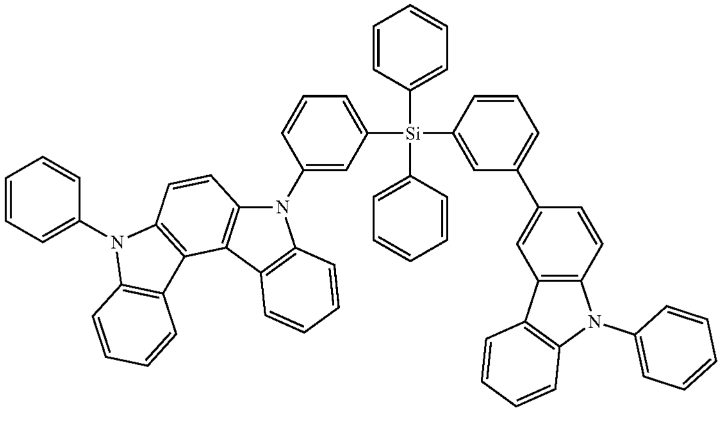

-continued
321
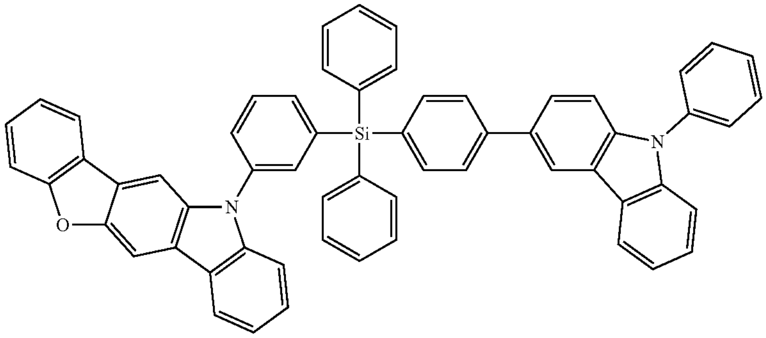
322
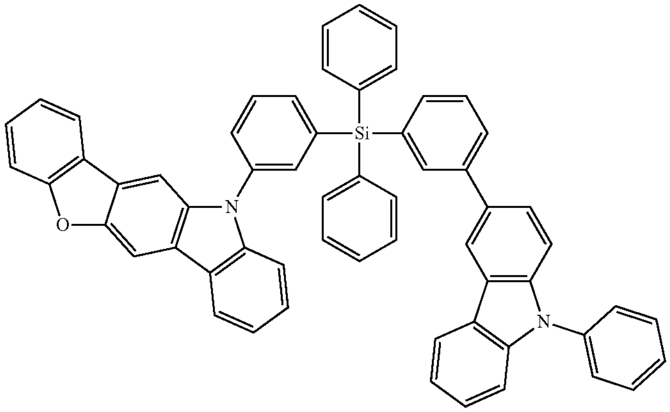
323
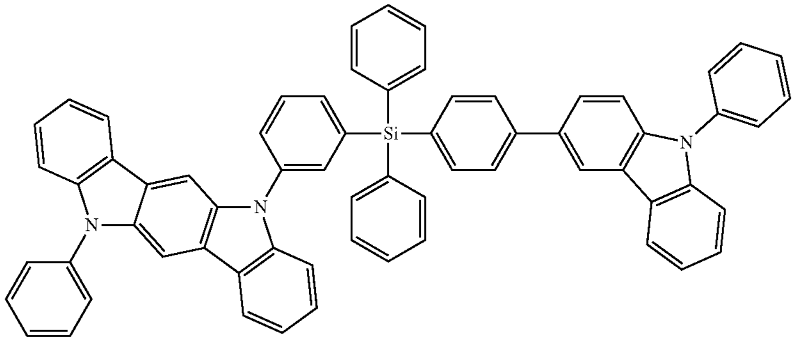
324
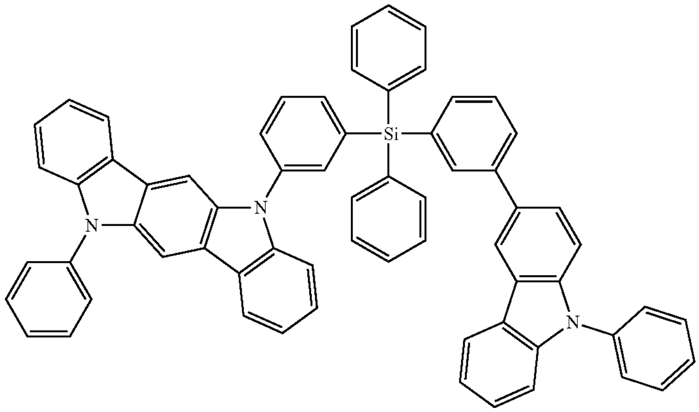

-continued
325
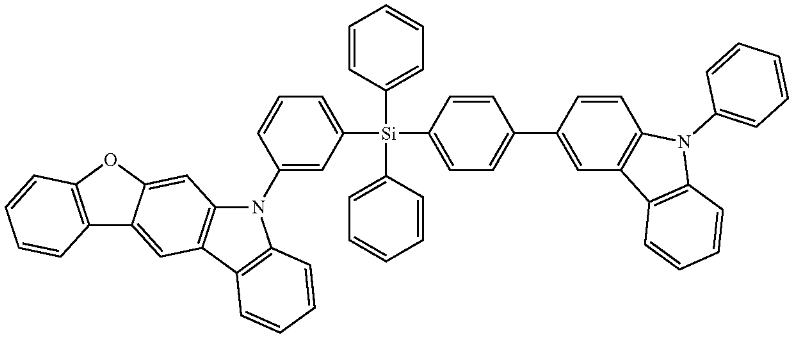
326
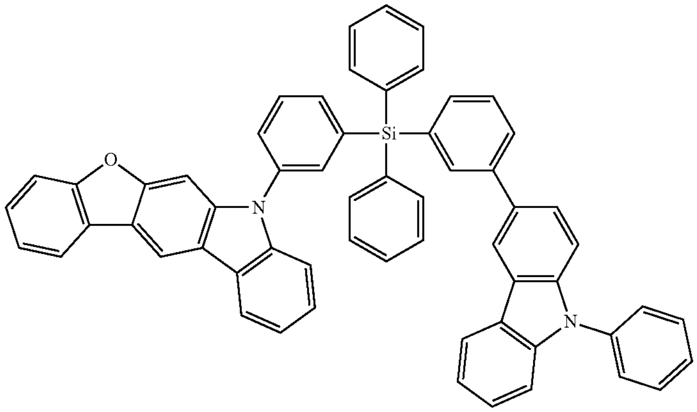
327
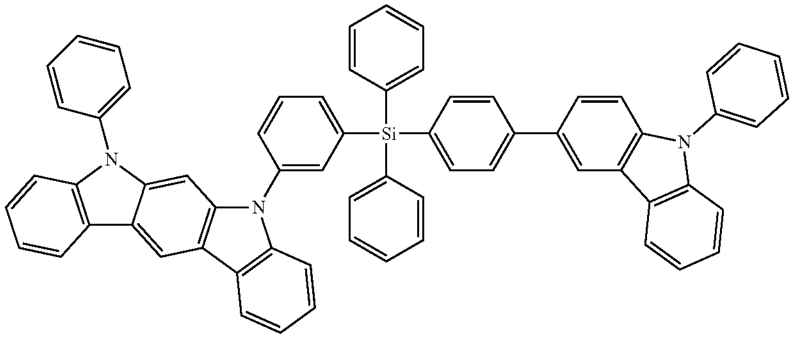
328
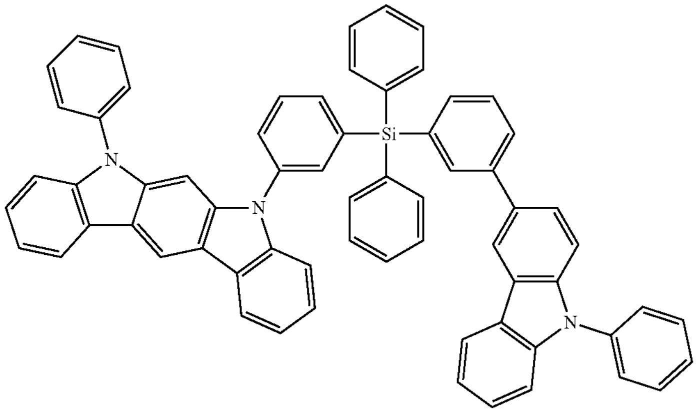

-continued
329
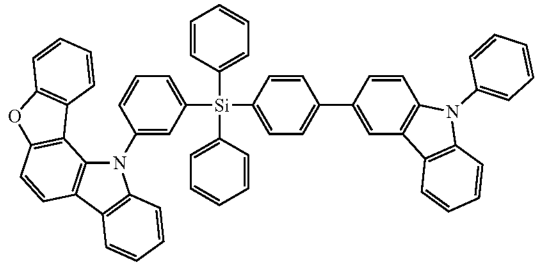
330
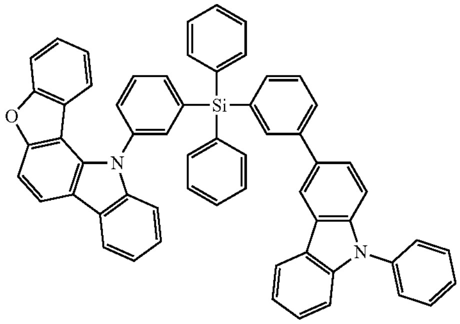
331
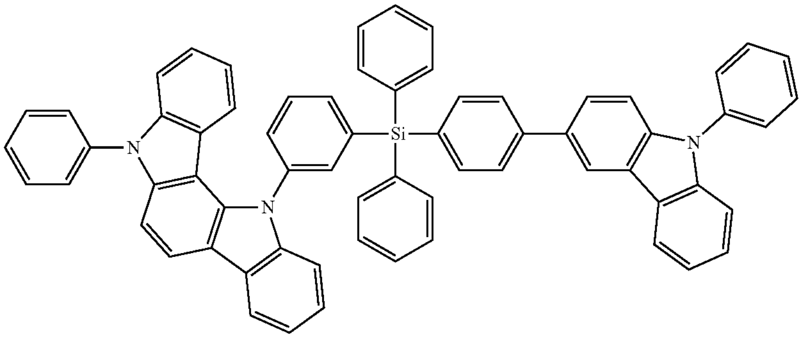
332
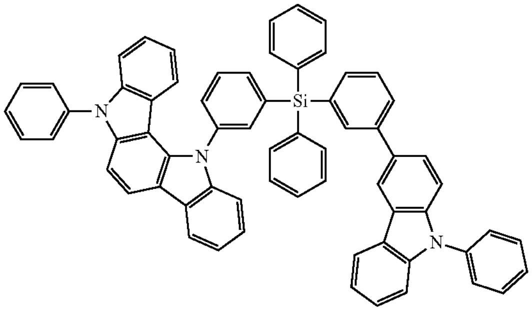
333
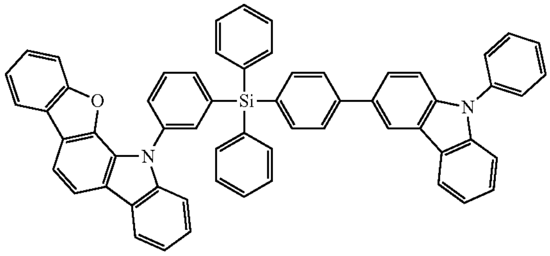
334
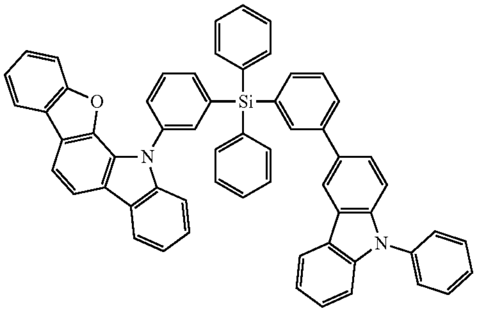
335
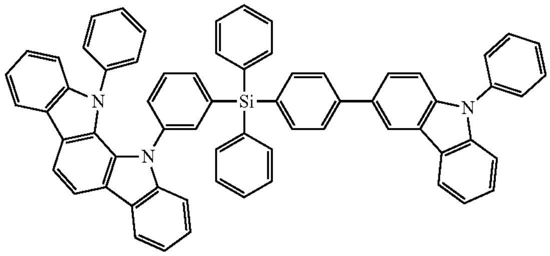

-continued
336
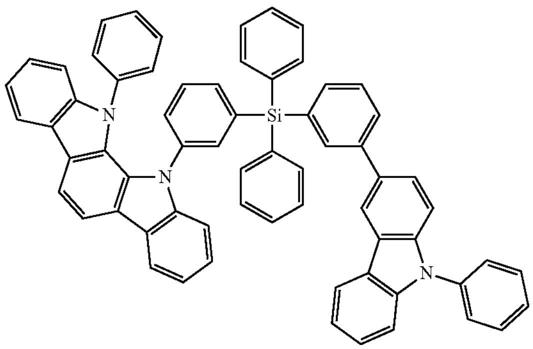
337
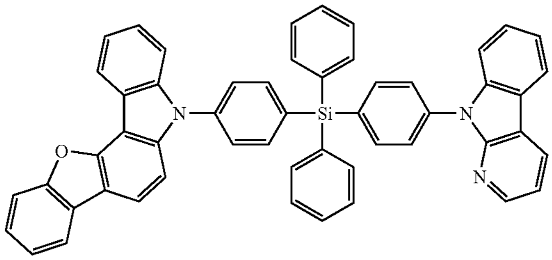
338
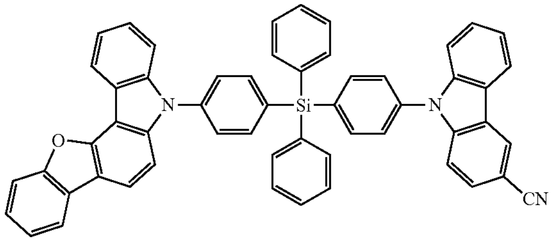
339
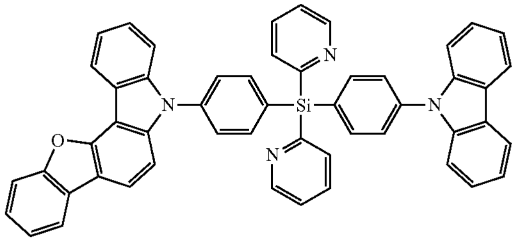
340
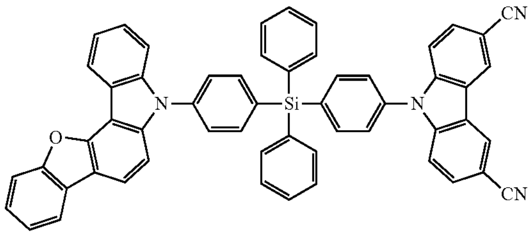
341
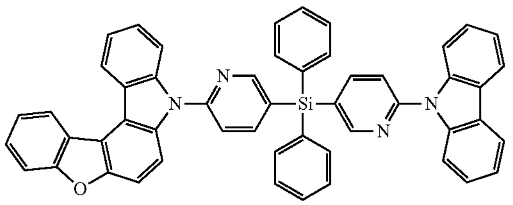
342
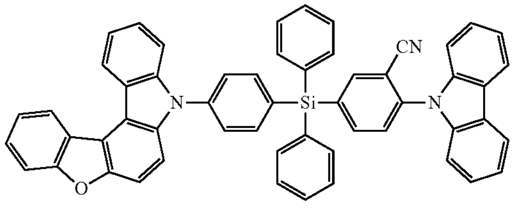
343
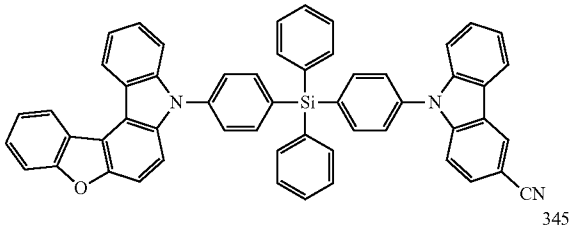
344
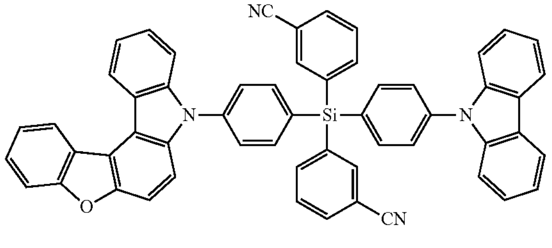
345
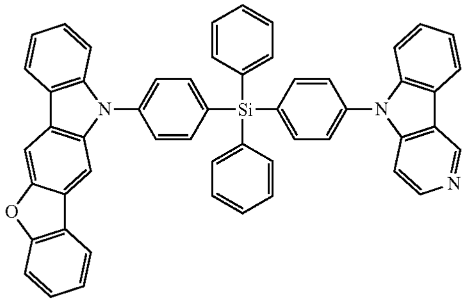

-continued
346
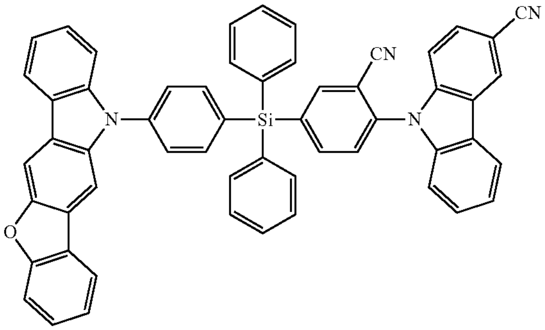
347
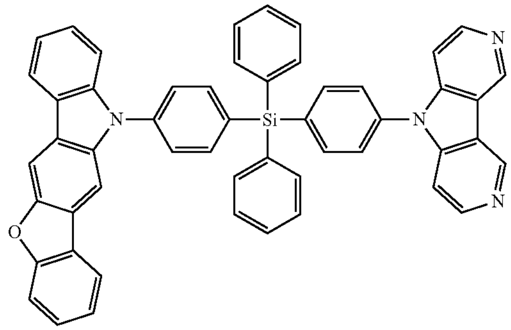
348
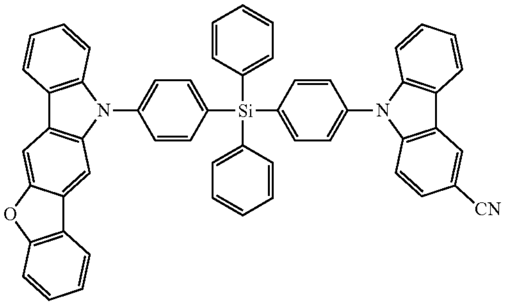
349
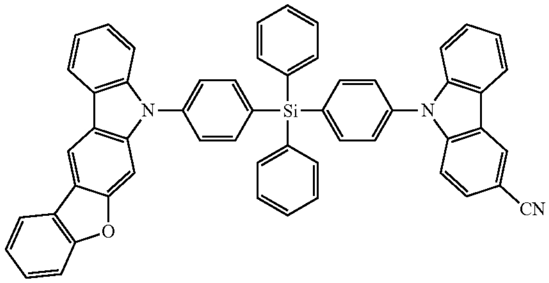
350
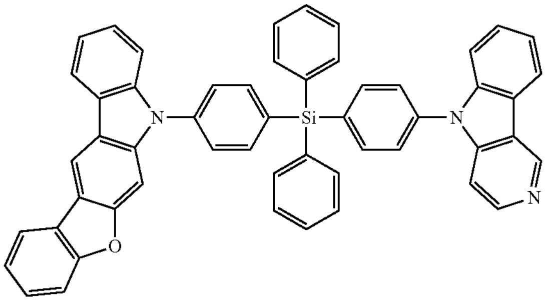
351
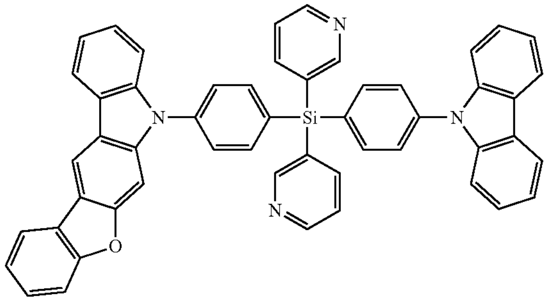
352
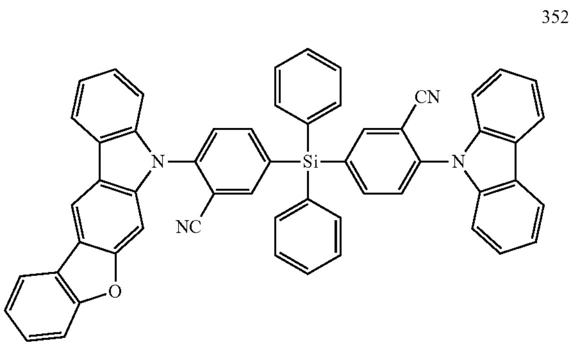
353
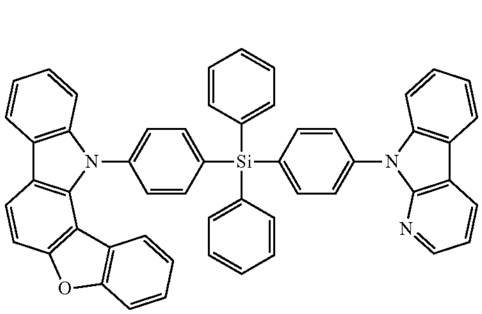

-continued
354
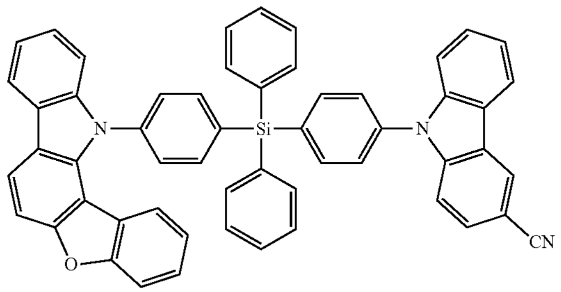
355
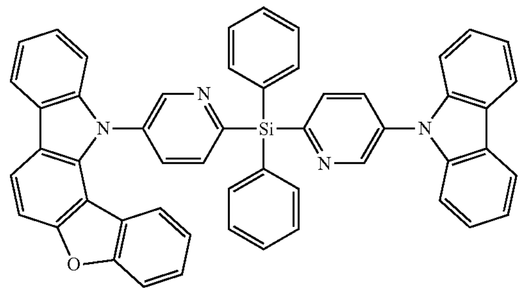
356
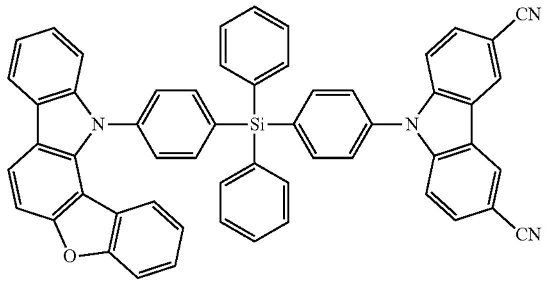
357
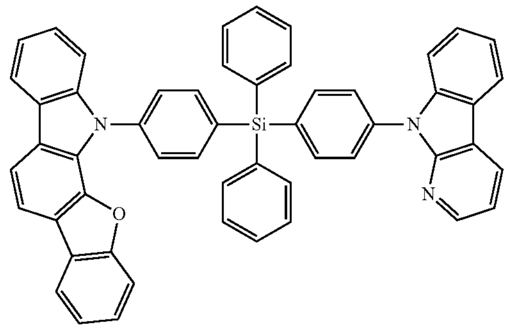
358
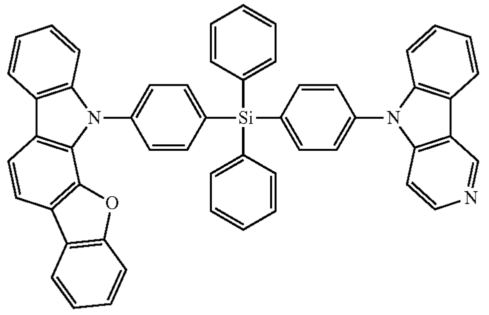
359
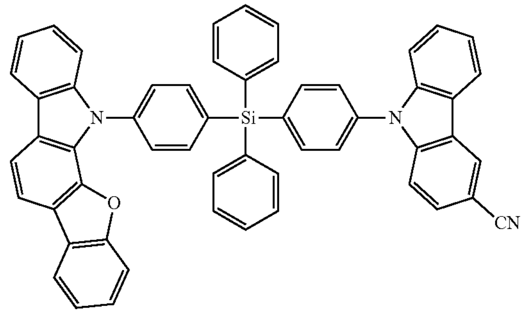
360
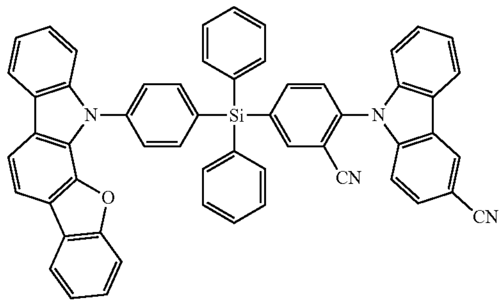
361
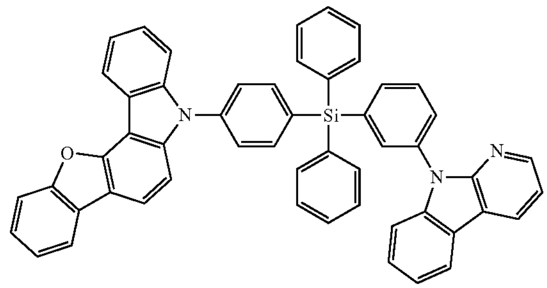
362
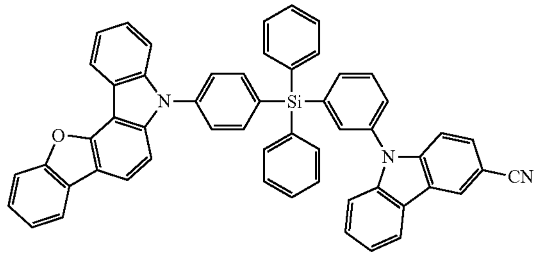
363
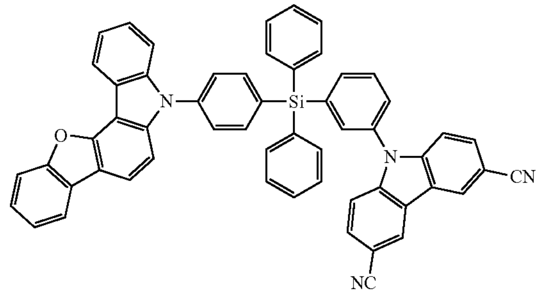

-continued
364
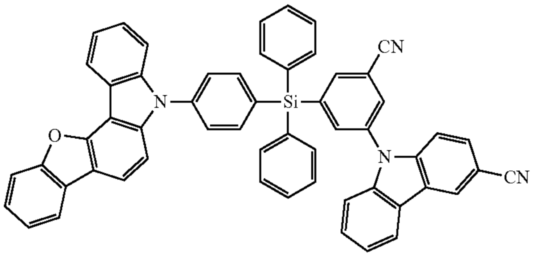
365
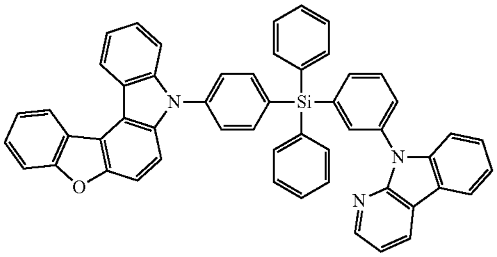
366
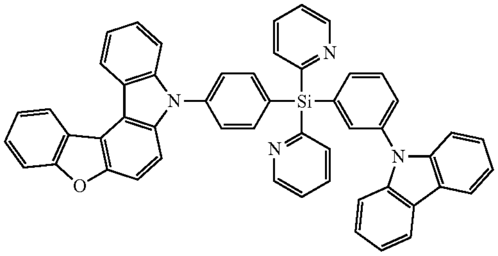
367
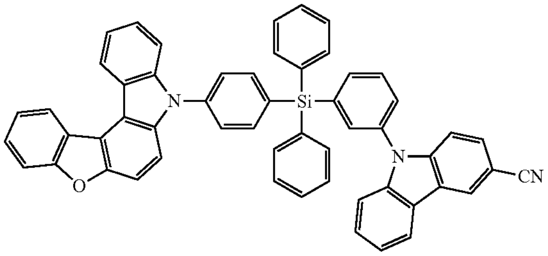
368
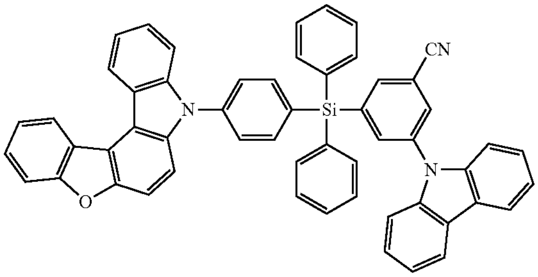
369
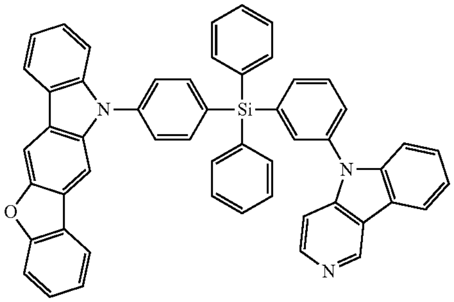
370
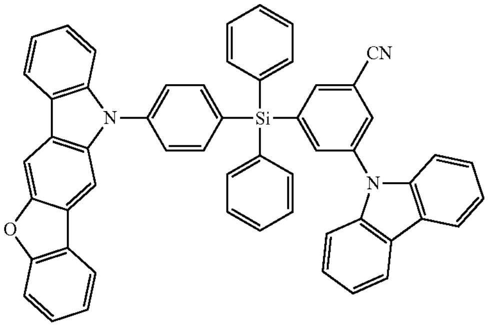
371
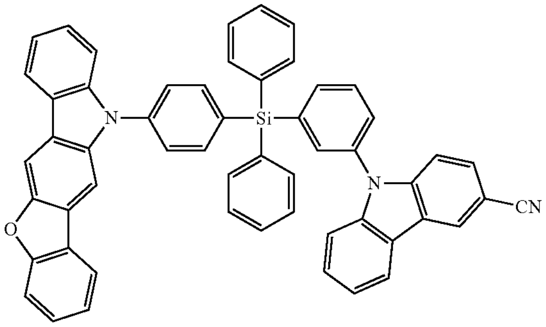
372
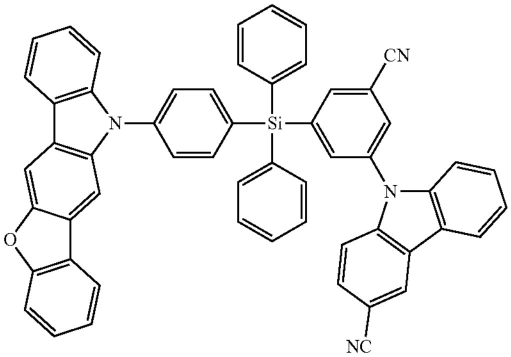
373
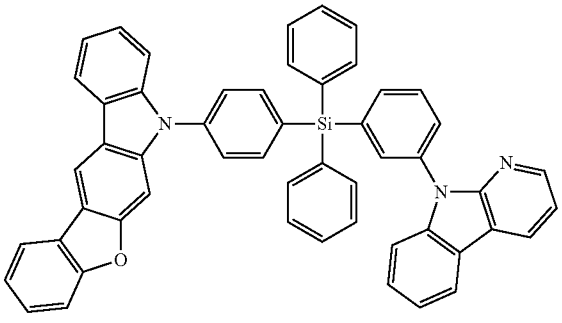

-continued
374
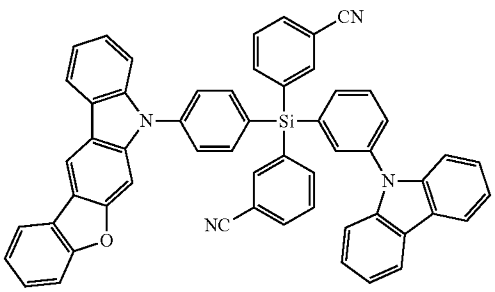
375
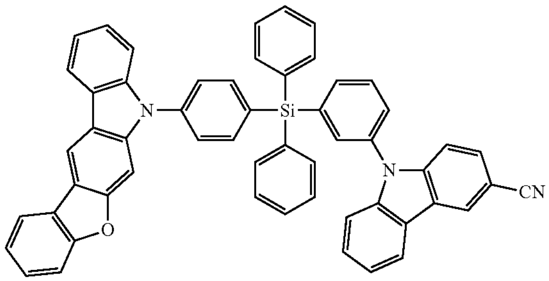
376
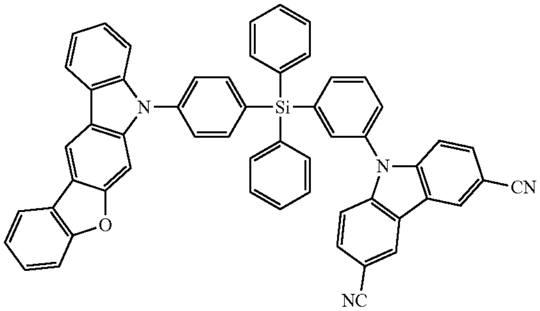
377
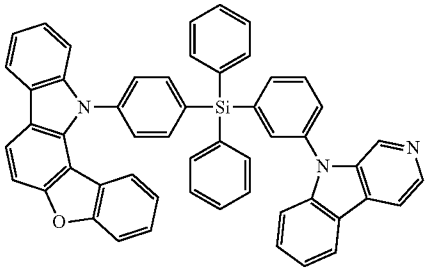
378
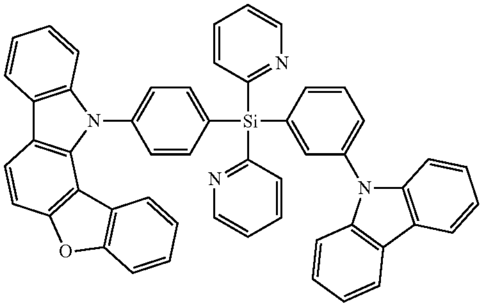
379
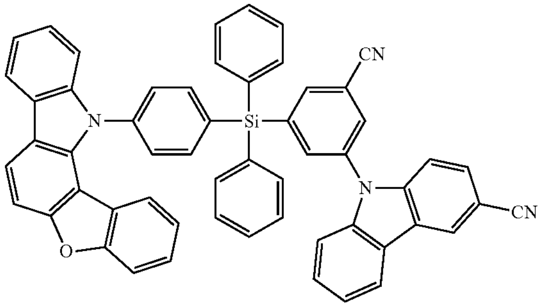
380
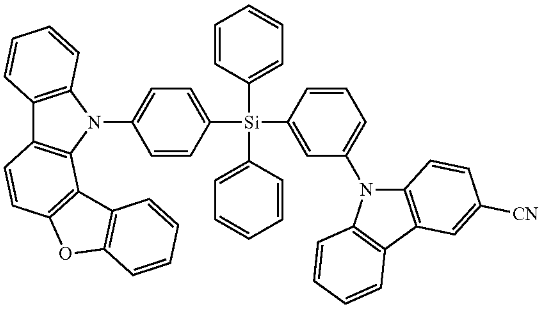
381
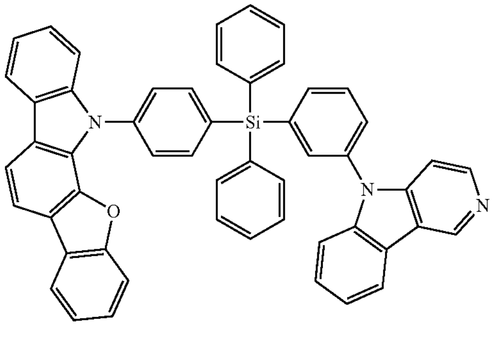

-continued
382
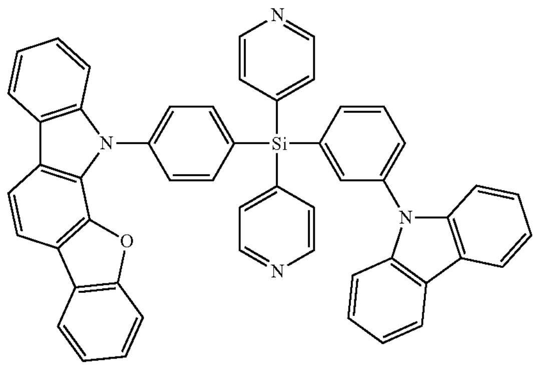
383
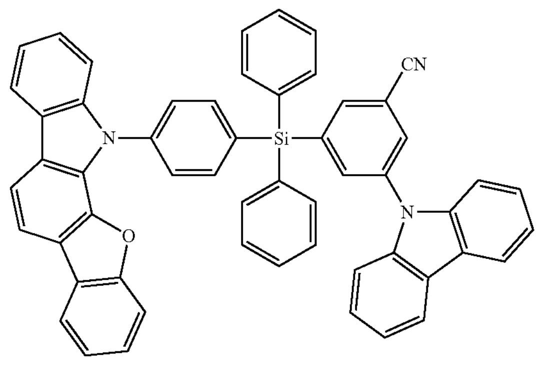
384
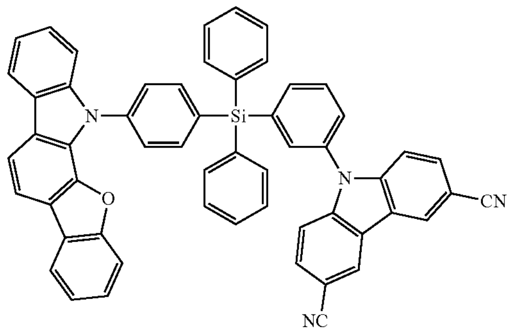
385
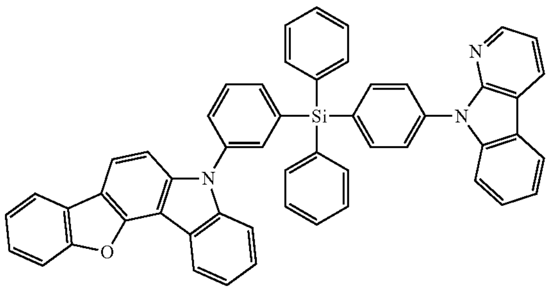
386
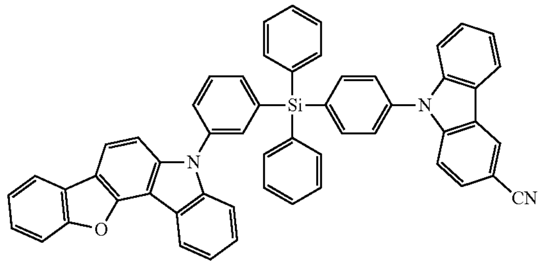
387
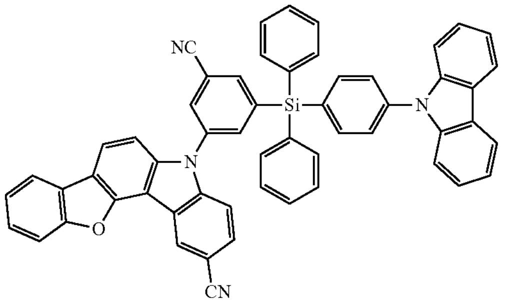
388
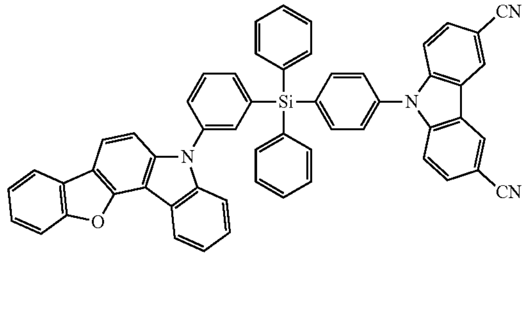
389
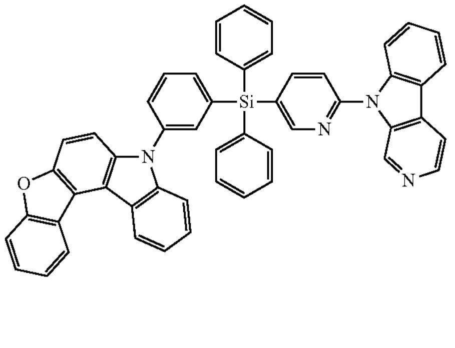

-continued
390
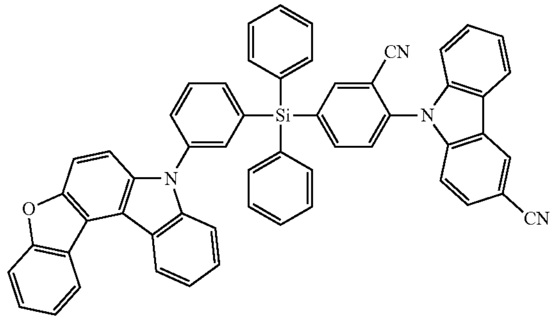
391
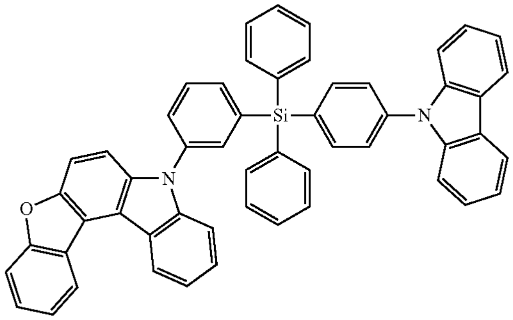
392
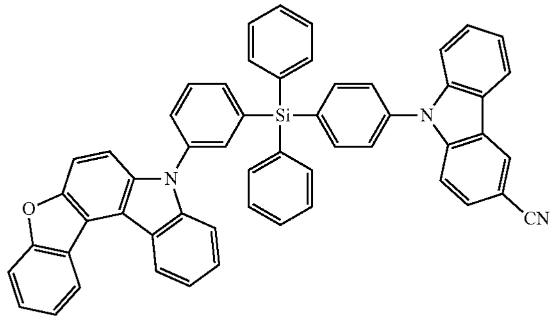
393
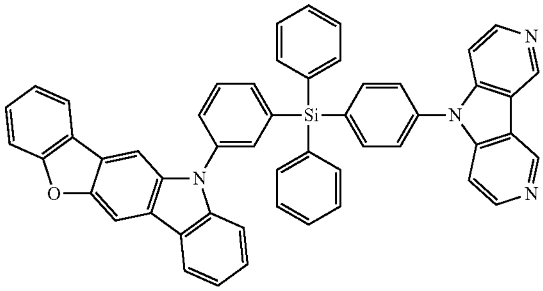
394
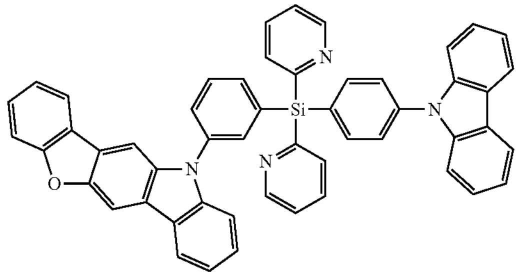
395
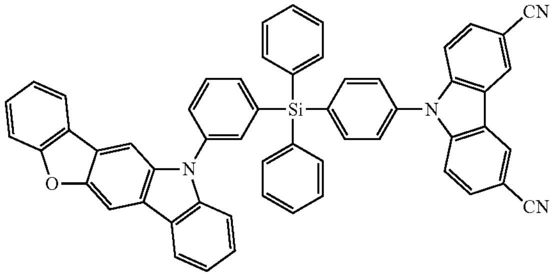
396
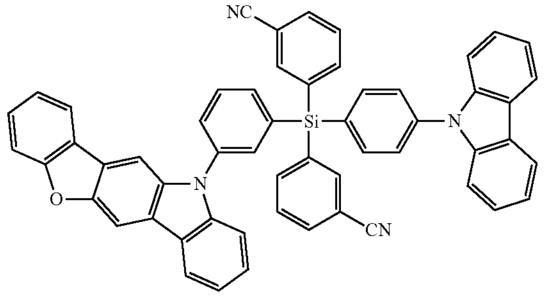
397
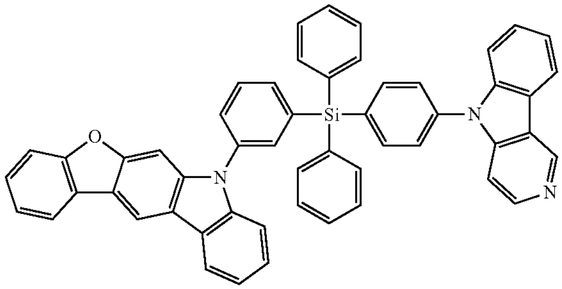
398
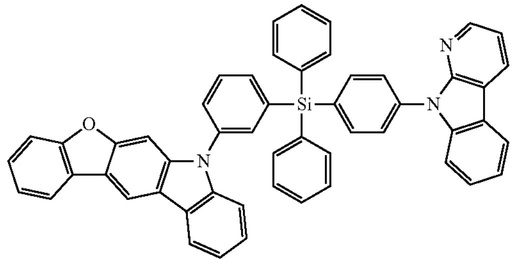
399
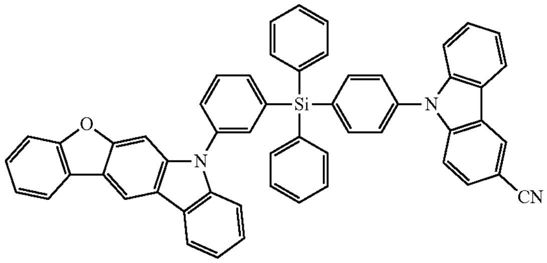

-continued
400
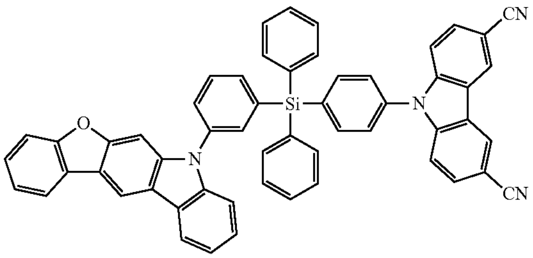
401
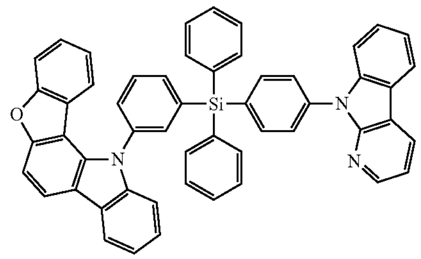
402
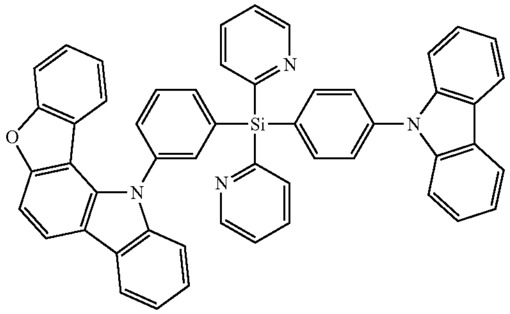
403
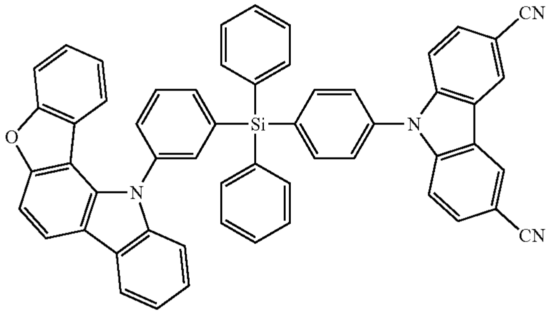
404
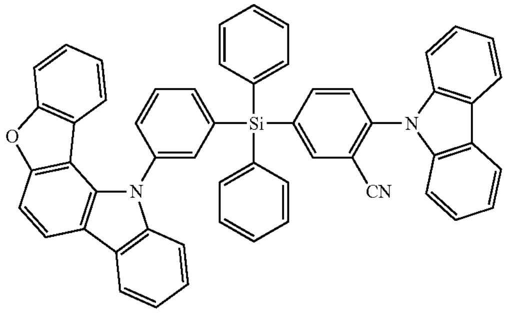
405
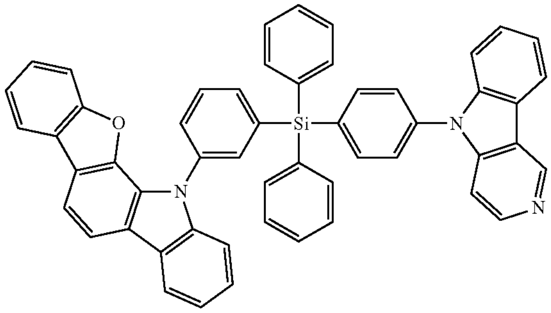
406
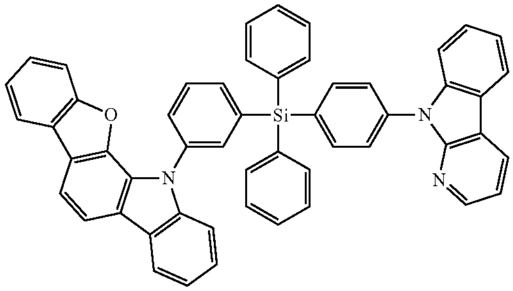
407
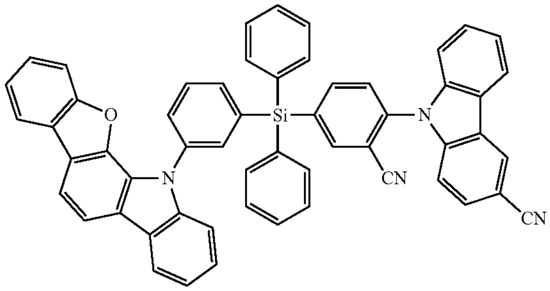
408
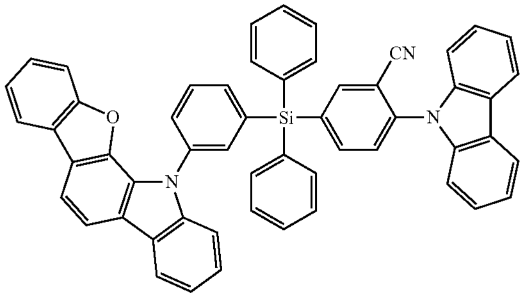
409
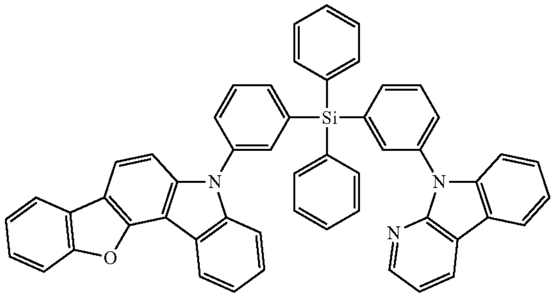

-continued
410
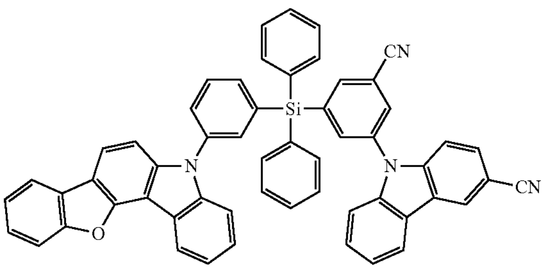
411
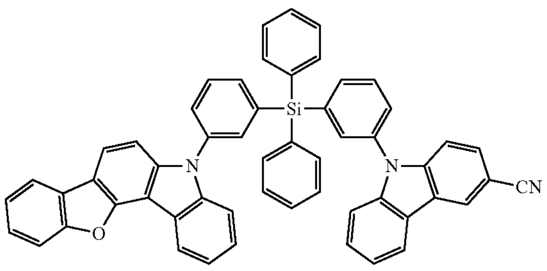
412
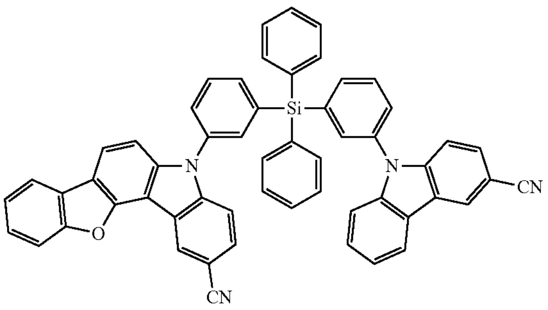
413
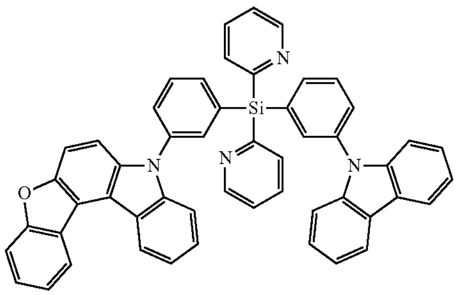
414
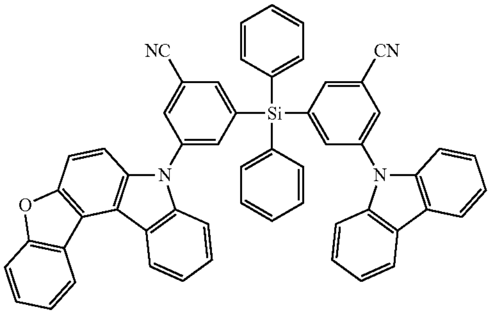
415
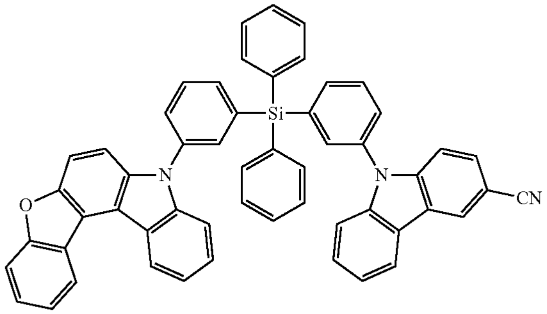
416
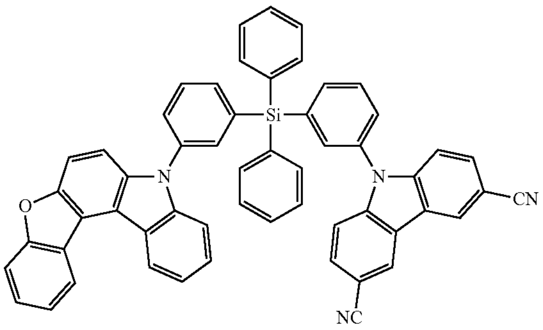
417
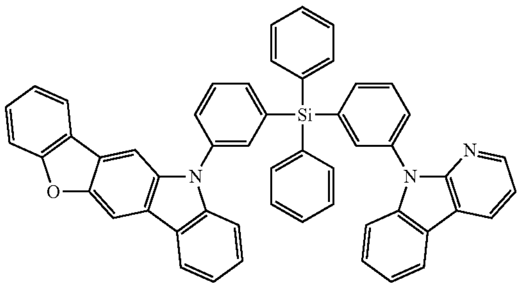
418
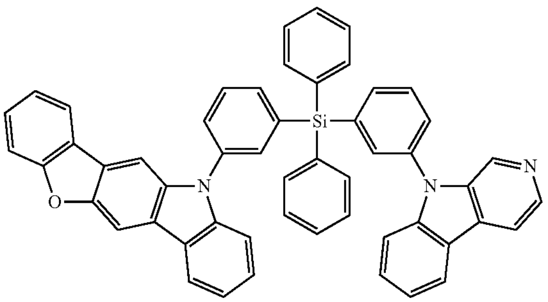
419
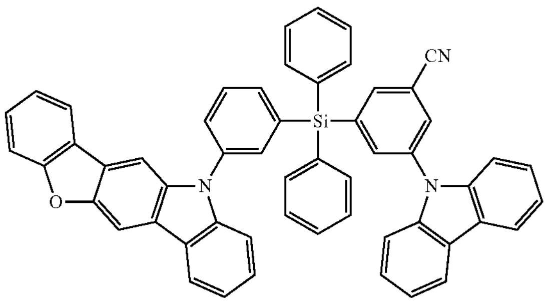

-continued
420
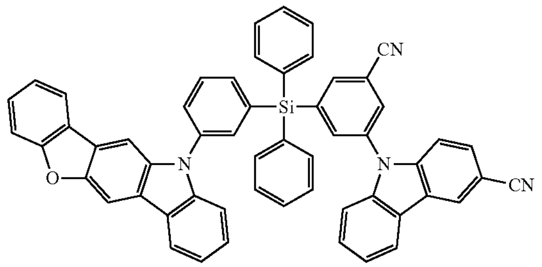
421
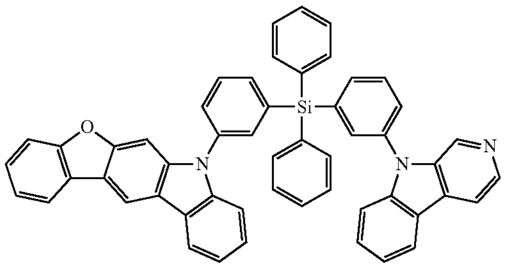
422
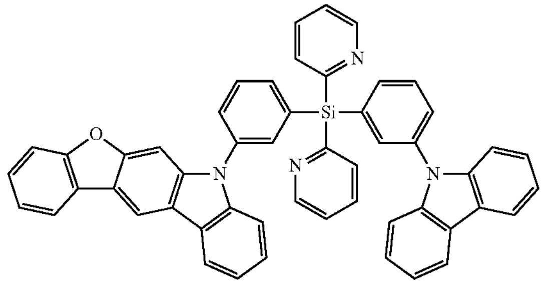
423
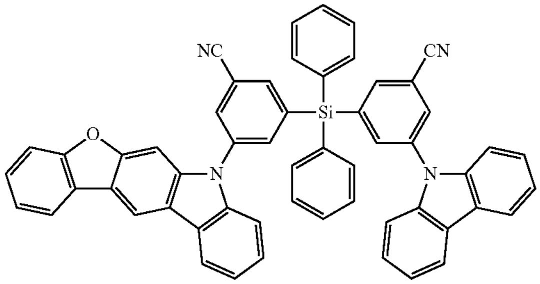
424
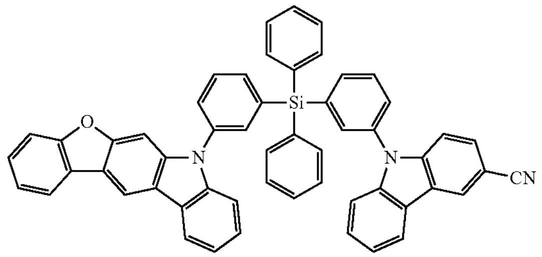
425
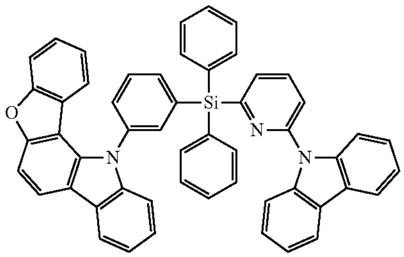
426
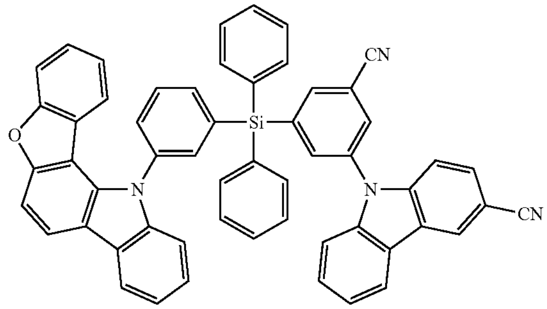
427
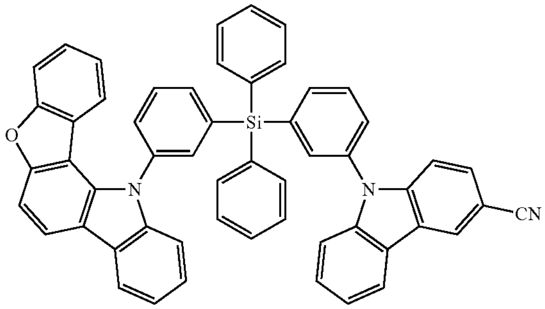
428
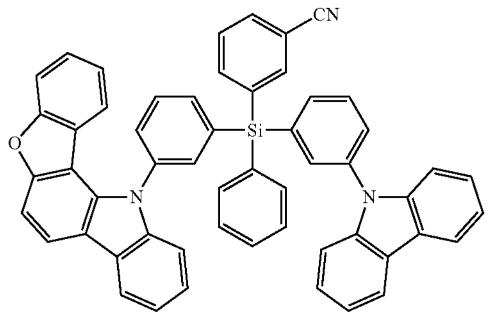
429
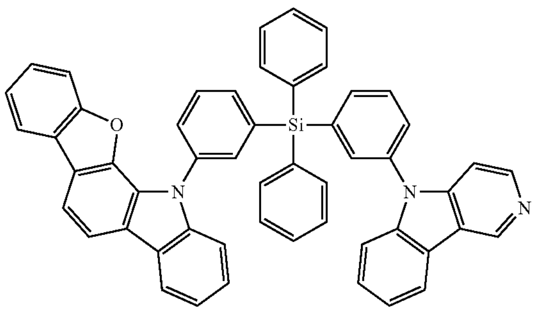

-continued

430

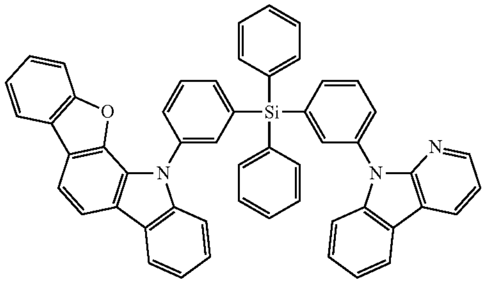

431

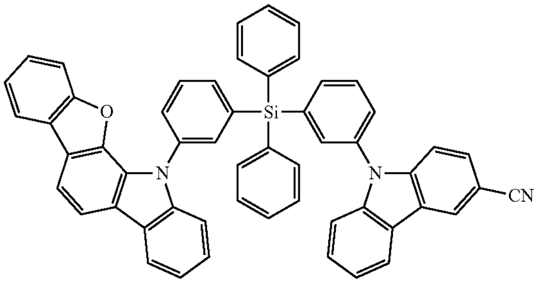

432

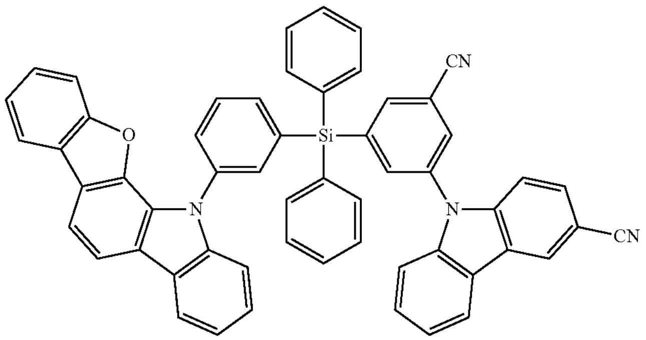

wherein, in Group HEH1, "Ph" represents a phenyl group.

In some embodiments, Compound H1 may be used as the hole transporting host. In one or more embodiments, Compound H2 may be used as the electron transporting host:

H1

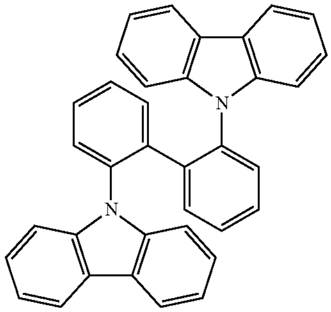

H2

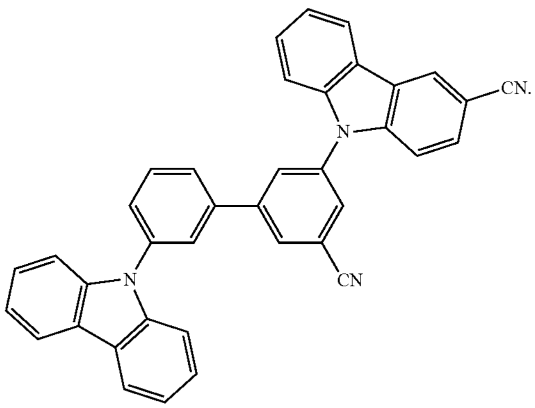

When the host is a mixture of an electron transporting host and a hole transporting host, a weight ratio of the electron transporting host to the hole transporting host may be in a range of about 1:9 to about 9:1, for example, about 2:8 to about 8:2, for example, about 4:6 to about 6:4, or for example, about 5:5. When a weight ratio of the electron transporting host to the hole transporting host is within any of these ranges, holes and electrons transport balance into the emission layer 15 may be achieved.

Emitter in Emission Layer 15

The emitter may be a phosphorescence emitter or a fluorescence emitter.

The phosphorescence emitter may include a transition metal.

In some embodiments, the emitter may be a fluorescence emitter. In some embodiments, the fluorescence emitter may be a prompt fluorescence emitter, not a delayed fluorescence emitter. When the emitter is a prompt emitter, the emission layer according to the Third Embodiment may be a prompt fluorescence emission layer. The prompt fluorescence emission layer is different from a delayed fluorescence emission layer that may include a delayed fluorescence emitter and have a ratio of delayed fluorescence components emitted from the delayed fluorescence emitter in a range of about 70% to about 100%, based on the total emission components.

An absolute value of a difference between the HOMO energy level of the fluorescence emitter and the HOMO energy level of the sensitizer may be about 0.5 eV or lower, about 0.45 eV or lower, about 0.4 eV or lower, about 0.35 eV or lower, about 0.3 eV or lower, about 0.25 eV or lower, about 0.2 eV or lower, or about 0.15 eV or lower. For example, an absolute value of a difference between the HOMO energy level of the fluorescence emitter and the HOMO energy level of the sensitizer may be in a range of about 0 eV to about 0.5 eV, about 0 eV to about 0.45 eV, about 0 eV to about 0.4 eV, about 0 eV to about 0.35 eV, about 0 eV to about 0.3 eV, about 0 eV to about 0.25 eV, about 0 eV to about 0.2 eV, or about 0 eV to about 0.15 eV. In this embodiment, the HOMO energy level of the fluorescence emitter and the HOMO energy level of the sensitizer may each be, for example, evaluated using Gaussian 09 program according to the DFT method. In some embodiments, the DFT method was according to 6-31G(d,p) basis set.

The fluorescence emitter may be any compound that emits fluorescence.

The maximum emission wavelength of an emission spectrum of the fluorescence emitter may be about 400 nm or greater and about 550 nm or lower. In some embodiments, the maximum emission wavelength of an emission spectrum of the fluorescence emitter may be about 400 nm or greater and about 495 nm or lower or about 450 nm or greater and about 495 nm or lower. That is, the fluorescence emitter may emit blue light. The "maximum emission wavelength" as used herein refers to a wavelength of which the emission intensity is greatest. In other words, the "maximum emission wavelength" may be referred to as "peak emission wavelength".

In some embodiments, the fluorescence emitter may not include a metal atom.

In one or more embodiments, the fluorescence emitter may not include a transition metal.

In some embodiments, the fluorescence emitter may be a condensed polycyclic compound, a styryl-based compound, or any combination thereof.

In an embodiment, the fluorescence emitter may include a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group (a tetracene group), a picene group, a perylene group, a pentaphene group, an indenoanthracene group, a group represented by one of Formulae 501-1 to 501-18, or any combination thereof:

501-1

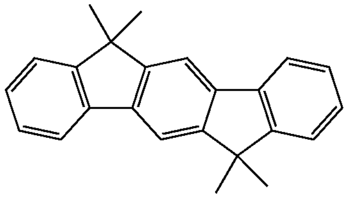

501-2

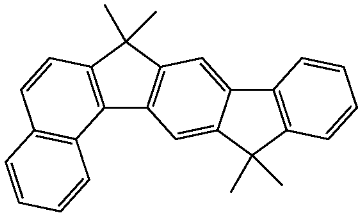

501-3

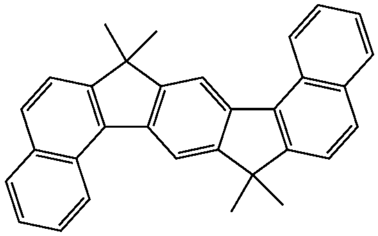

-continued 501-4

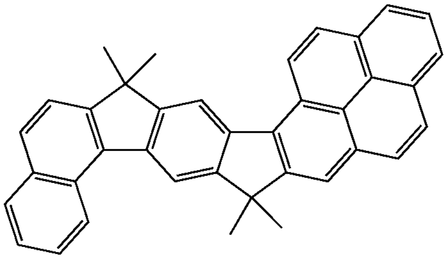

501-5

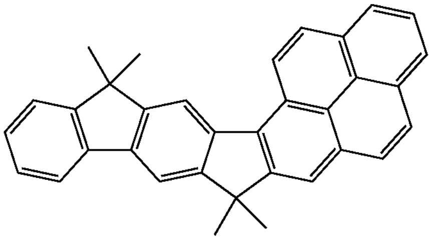

501-6

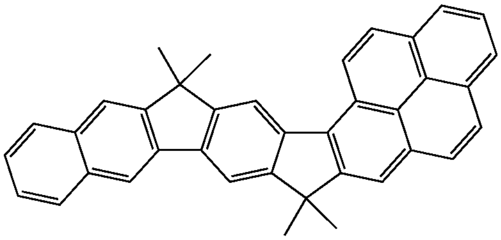

501-7

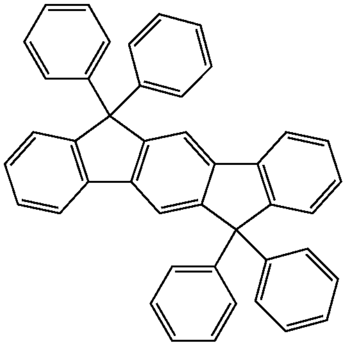

501-8

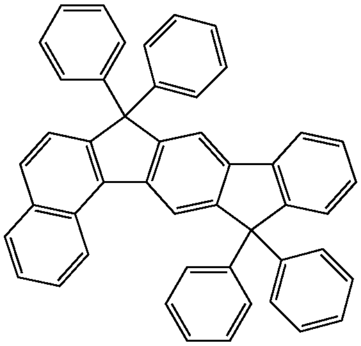

-continued 501-9

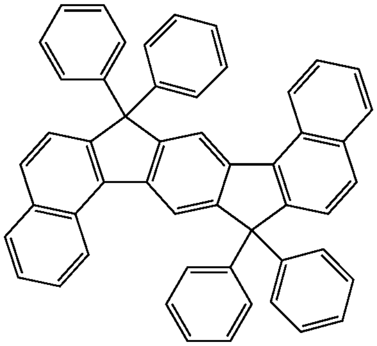

501-10

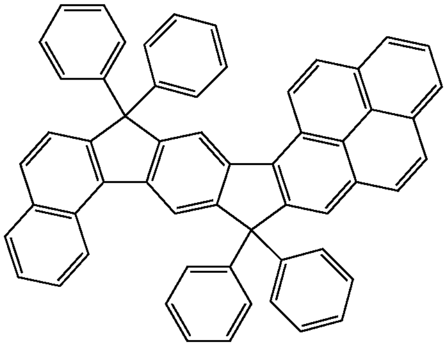

501-11

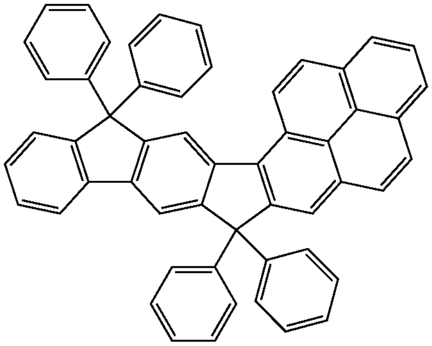

501-12

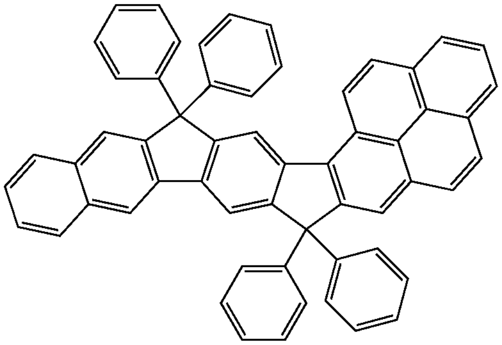

-continued 501-13

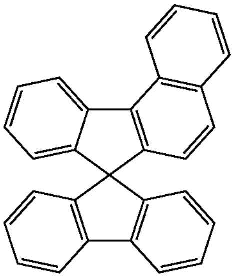

501-14

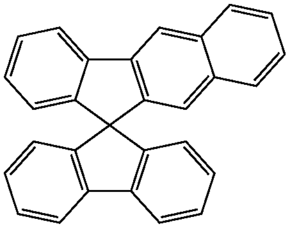

501-15

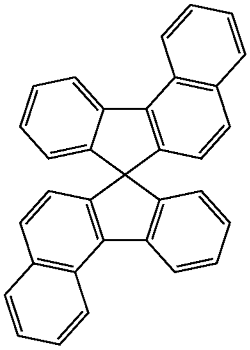

501-16

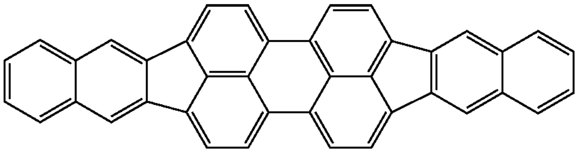

501-17

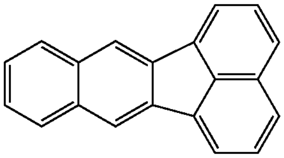

501-18

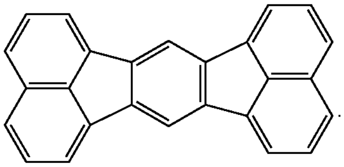

In one or more embodiments, the fluorescence emitter may include at least one of an amine-containing compound and a carbazole-containing compound.

In some embodiments, the fluorescence emitter may include a styryl-amine-based compound, a styryl-carbazole-based compound, or any combination thereof.

In some embodiments, the fluorescence emitter may include a compound represented by Formula 501 or Formula 502:

Formula 501

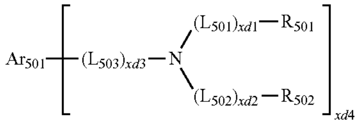

Formula 502

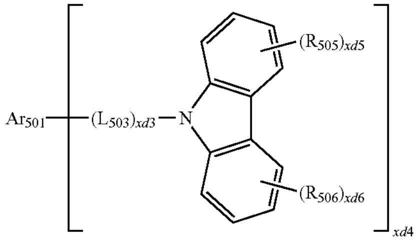

wherein, in Formulae 501 and 502, $Ar_{501}$ may be a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, or a group represented by one of Formulae 501-1 to 501-18, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{16}$ alkyl group, a $C_2$-$C_{60}$ alkenyl group, a $C_2$-$C_{60}$ alkynyl group, a $C_1$-$C_{16}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{10}$ heteroaryl group, a monovalent non-aromatic condensed polycyclic group, a monovalent non-aromatic condensed heteropolycyclic group, —Si($Q_{501}$)($Q_{502}$)($Q_{503}$), or any combination thereof, $L_{501}$ to $L_{503}$ may each independently be:

a single bond, or a $C_5$-$C_{60}$ carbocyclic group or a $C_1$-$C_{10}$ heterocyclic group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{10}$ heteroaryl group, a monovalent non-aromatic condensed polycyclic group, a monovalent non-aromatic condensed heteropolycyclic group, —Si($Q_{501}$)($Q_{502}$)($Q_{503}$), or any combination thereof, xd1 to xd3 may each independently be an integer from 1 to 10, $R_{501}$ and $R_{502}$ may each independently be a $C_5$-$C_{60}$ carbocyclic group or a $C_1$-$C_{60}$ heterocyclic group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{10}$ heteroaryl group, a monovalent non-aromatic condensed polycyclic group, a monovalent non-aromatic condensed heteropolycyclic group, —Si($Q_{501}$)($Q_{502}$)($Q_{503}$), or any combination thereof, $R_{505}$ and $R_{506}$ may be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or —Si($Q_{501}$)($Q_{502}$)($Q_{503}$), xd5 and xd6 may each independently be an integer from 1 to 4, and xd4 may be an integer from 1 to 6, wherein $Q_{501}$ to $Q_{503}$ may each independently be hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

In some embodiments, $R_{501}$ and $R_{502}$ may each independently be a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, or a dibenzothiophenyl group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, or any combination thereof.

In some embodiments, xd4 may be an integer from 2 to 6 (or, 2, 3, or 4).

In some embodiments, the fluorescence emitter may include a compound represented by one of Formulae 502-1 to 502-5:

Formula 502-1

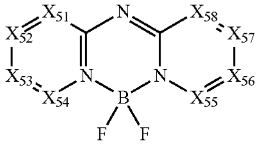

Formula 502-2

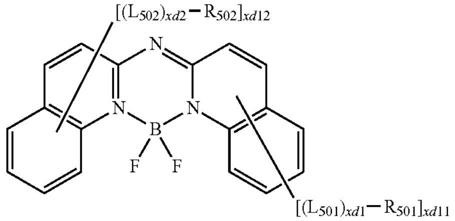

Formula 502-3

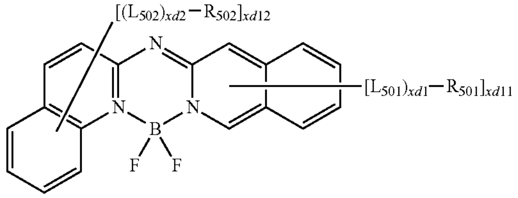

Formula 502-4

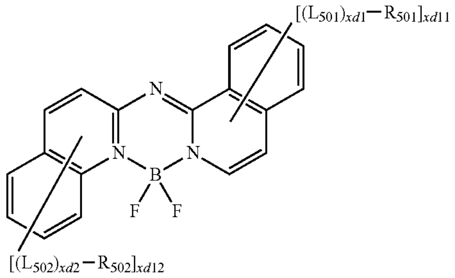

Formula 502-5

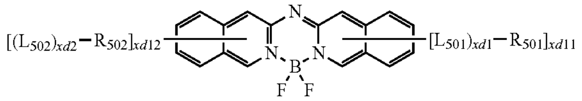

wherein, in Formulae 502-1 to 502-5, $X_{51}$ may be N or C-[$(L_{501})_{xd1}$-$R_{501}$], $X_{52}$ may be N or C-[$(L_{502})_{xd2}$-$R_{502}$], $X_{53}$ may be N or C-[$(L_{503})_{xd3}$-$R_{503}$], $X_{54}$ may be N or C-[$(L_{504})_{xd4}$-$R_{504}$], $X_{55}$ may be N or C-[$(L_{505})_{xd5}$-$R_{505}$], $X_{56}$ may be N or C-[$(L_{506})_{xd6}$-$R_{506}$], $X_{57}$ may be N or C-[$(L_{507})_{xd7}$-$R_{507}$], $X_{58}$ may be N or C-[$(L_{508})_{xd8}$-$R_{508}$], $L_{501}$ to $L_{508}$ may each be understood by referring to the description of $L_{501}$ in Formula 501, xd1 to xd8 may each be understood by referring to the description of xd1 in Formula 501, $R_{501}$ to $R_{508}$ may be each independently:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group; or a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each unsubstituted or substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, or any combination thereof, xd11 and xd12 may each independently be an integer from 0 to 5, two of $R_{501}$ to $R_{504}$ may optionally be bound to form a saturated or unsaturated ring, and two of $R_{505}$ to $R_{508}$ may optionally be bound to form a saturated or unsaturated ring.

The fluorescence emitter may include, e.g., one of Compounds FD(1) to FD(16), one of Compounds FD1 to FD19, or any combination thereof:

FD(1)

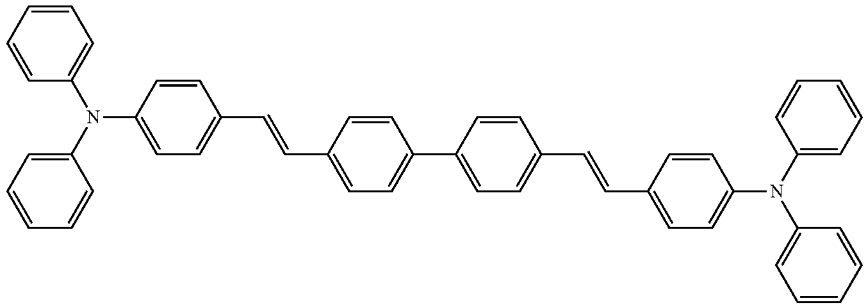

-continued
FD(2)
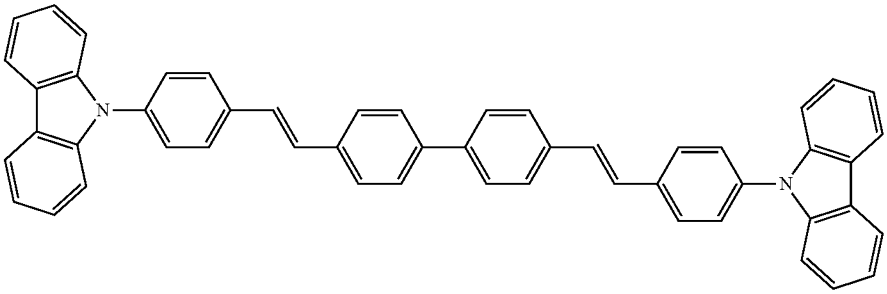
FD(3)
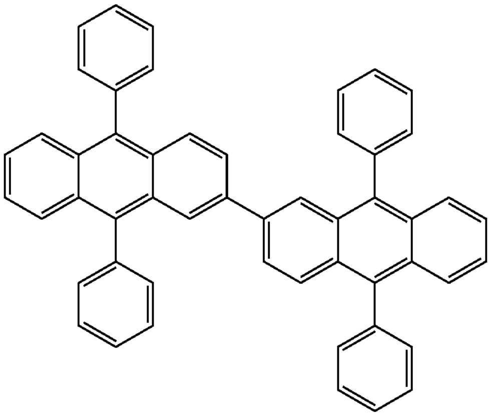
FD(4)
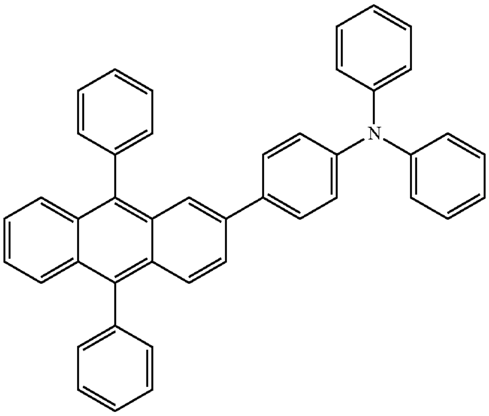
FD(5)
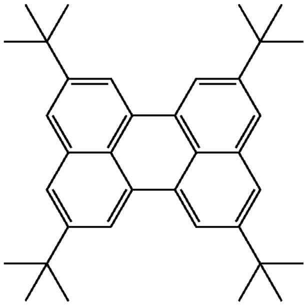
FD(6)
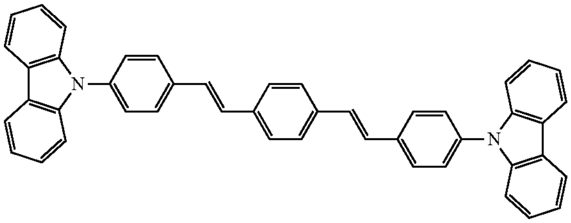
FD(7)
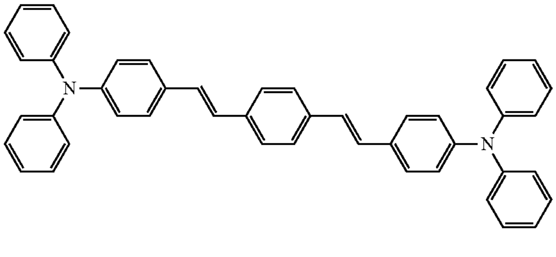
FD(8)
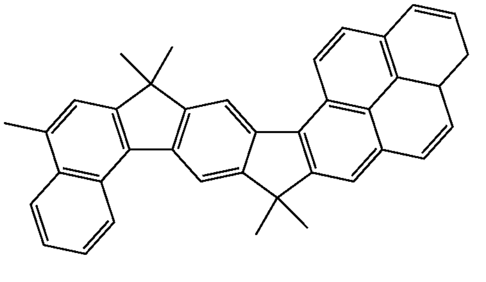

-continued
FD(9)
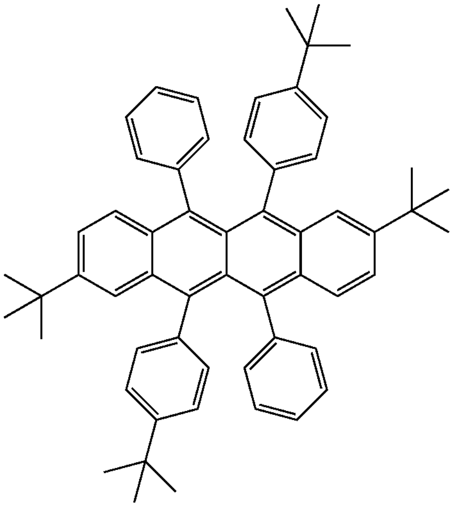
FD(10)
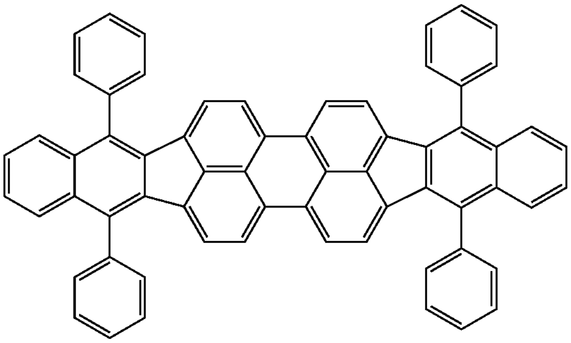
FD(11)
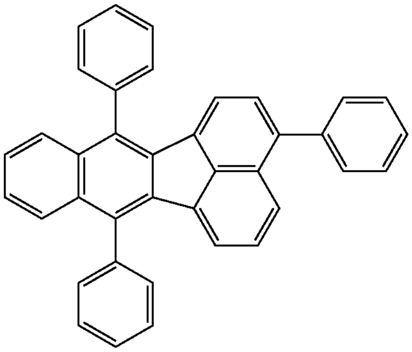
FD(12)
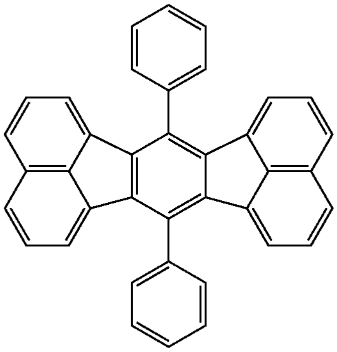
FD(13)
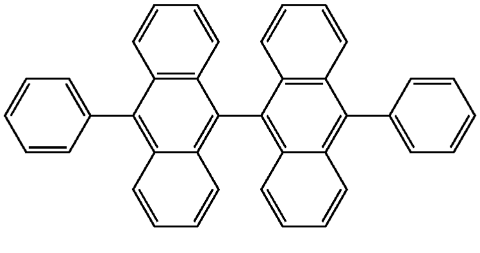
FD(14)
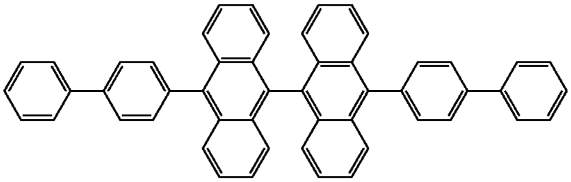
FD(15)
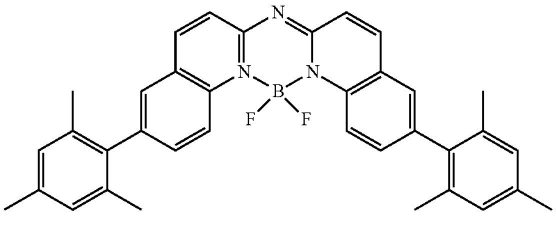
FD(16)
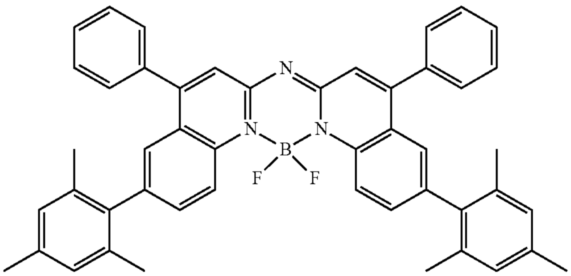

-continued
FD1
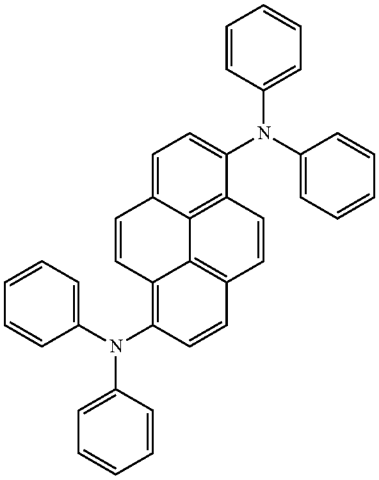
FD2
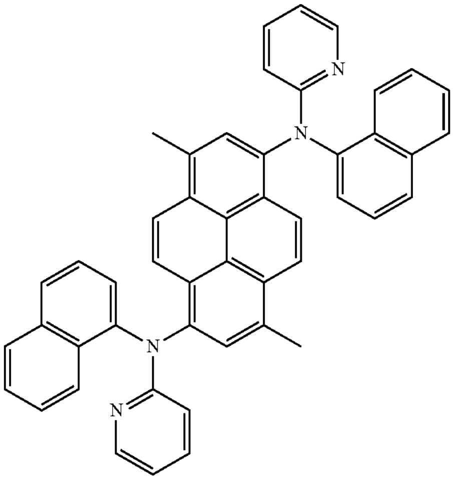
FD3
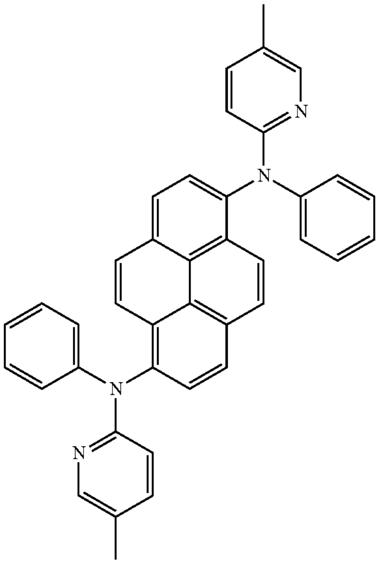
FD4
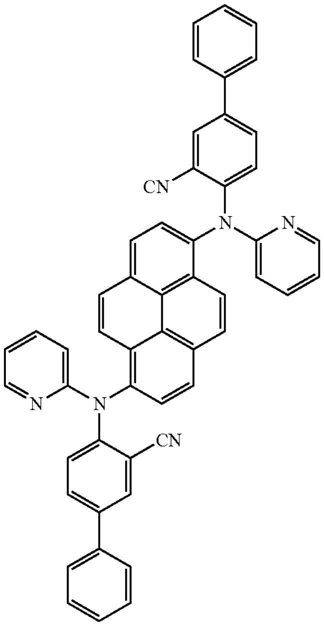
FD5
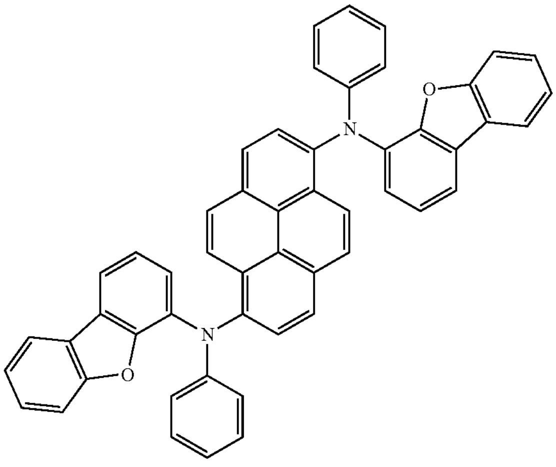
FD6
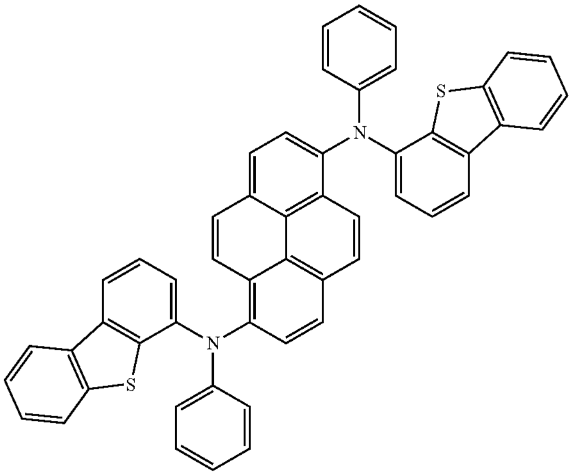

-continued
FD7
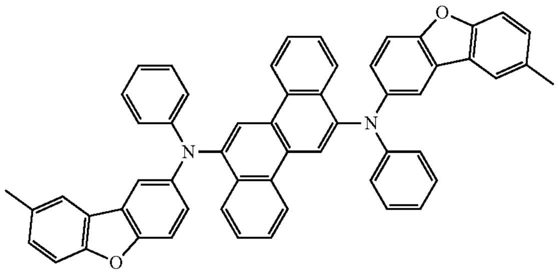
FD8
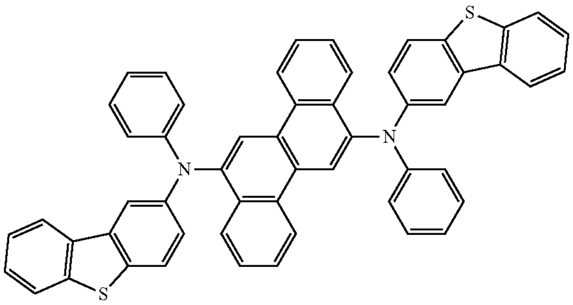
FD9
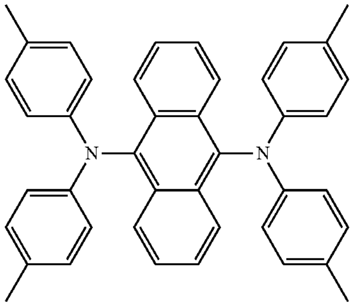
FD10
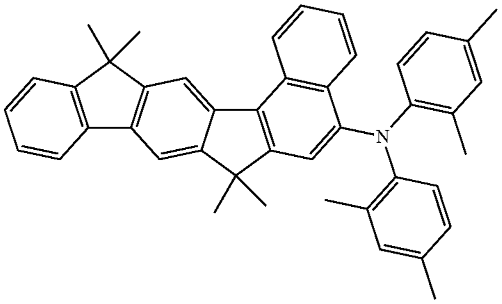
FD11
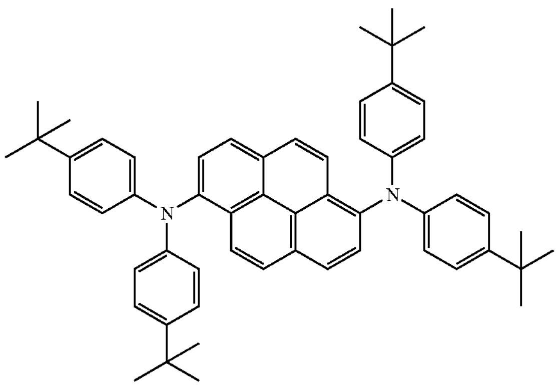
FD12
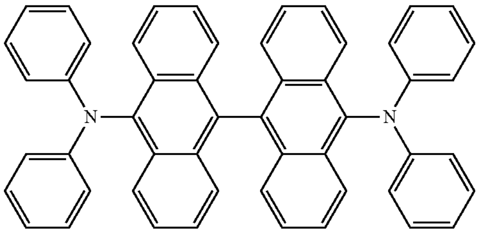
FD13
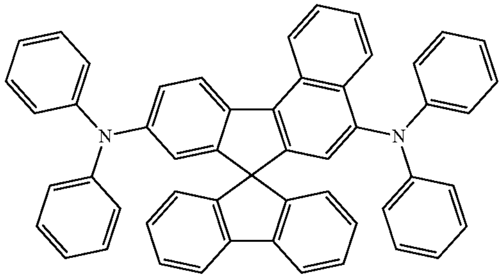
FD14
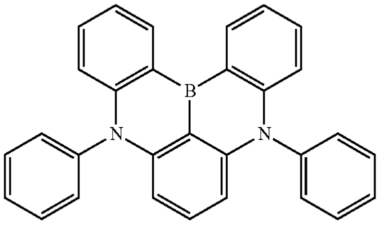

-continued

FD15

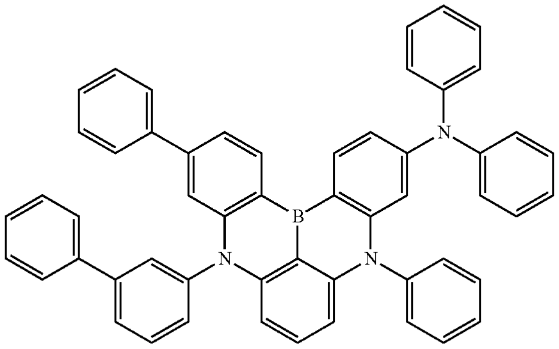

FD16

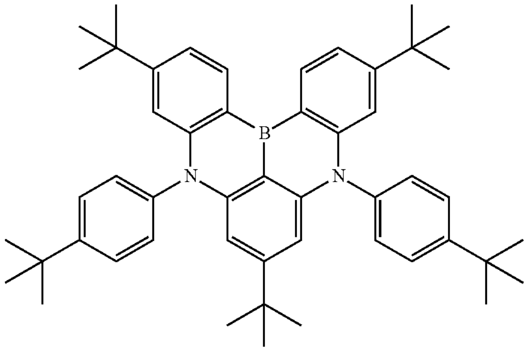

FD17

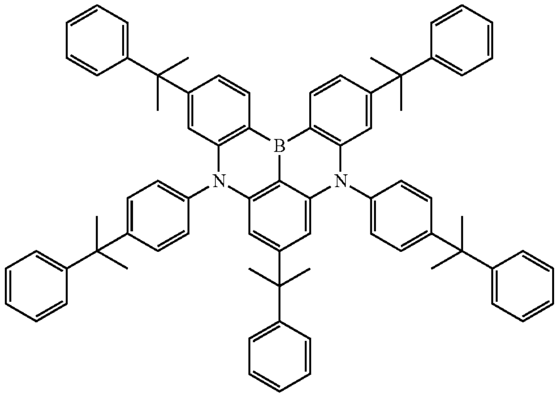

FD18

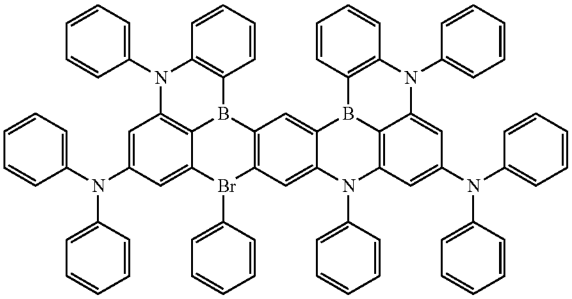

FD19

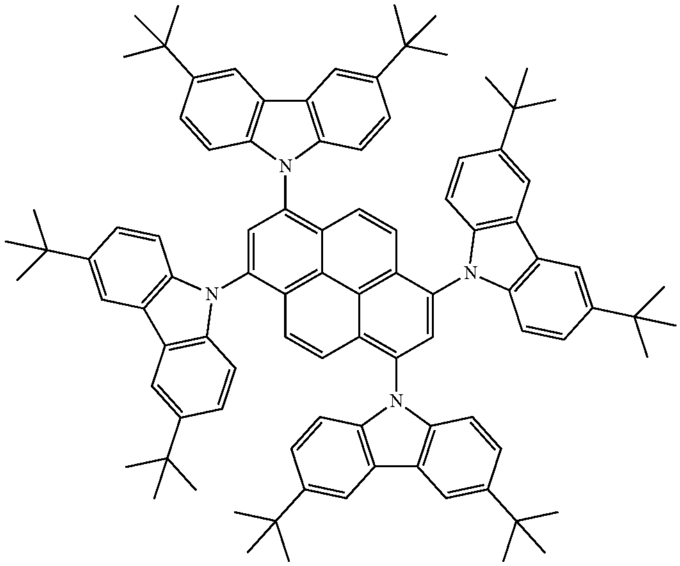

Hole Transport Region 12

In the organic light-emitting device 10, the hole transport region 12 may be between the first electrode 11 and the emission layer 15.

The hole transport region 12 may have a single-layered structure or a multi-layered structure.

For example, the hole transport region 12 may have a structure of hole injection layer, a structure of hole transport layer, a structure of hole injection layer/hole transport layer, a structure of hole injection layer/first hole transport layer/second hole transport layer, a structure of hole injection layer/first hole transport layer/second hole transport layer/electron blocking layer, a structure of hole transport layer/intermediate layer, a structure of hole injection layer/hole transport layer/intermediate layer, a structure of hole transport layer/electron blocking layer, or a structure of hole injection layer/hole transport layer/electron blocking layer.

The hole transport region 12 may include a compound having hole transport characteristics.

For example, the hole transport region 12 may include an amine-based compound.

In some embodiments, the hole transport region 12 may include m-MTDATA, TDATA, 2-TNATA, NPB, R-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor-sulfonic acid (PANI/CSA), polyaniline/poly(4-styrene sulfonate) (PANI/PSS), a compound represented by one of Formulae 201 to 205, or any combination thereof:

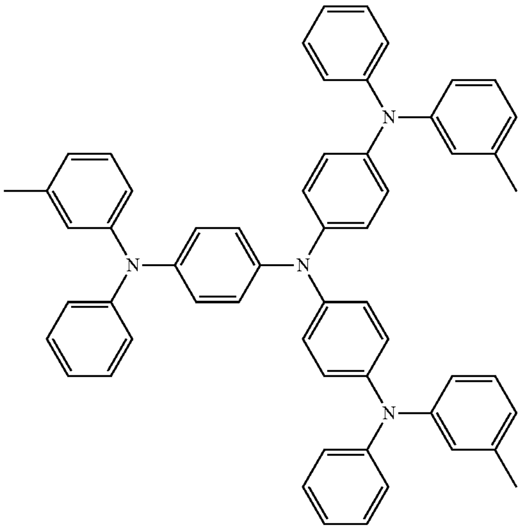

m-MTDATA

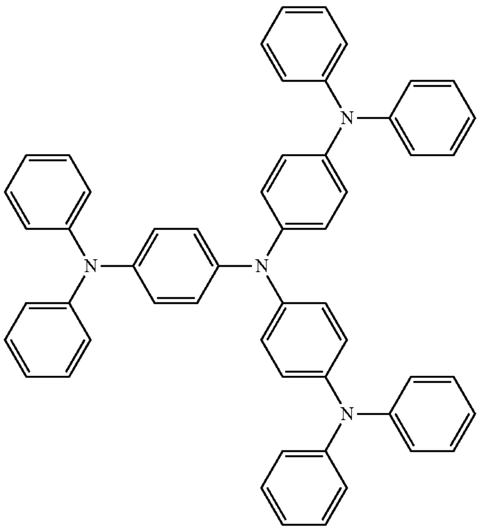

TDATA

-continued

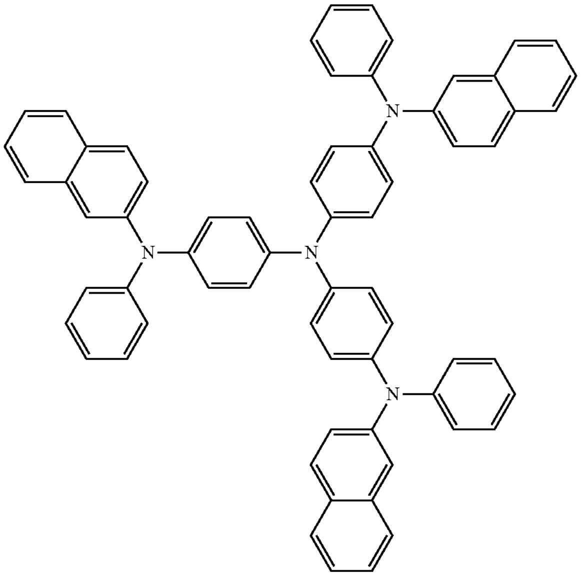

2-TNATA

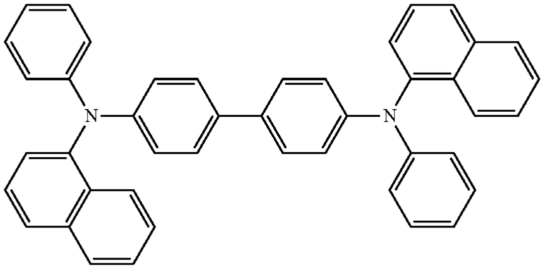

NPB

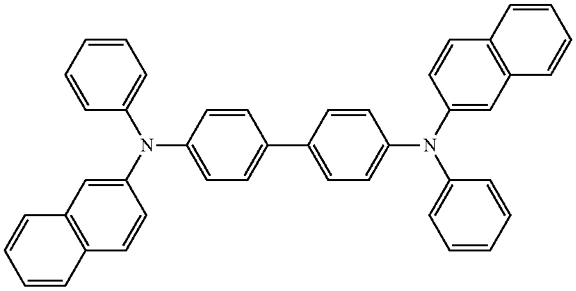

β-NPB

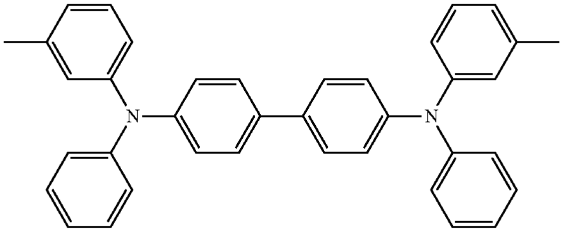

TPD

-continued

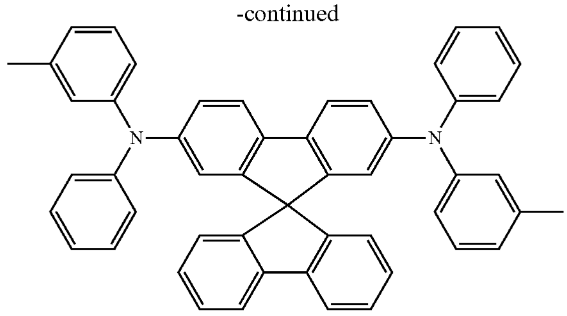

Spiro-TPD

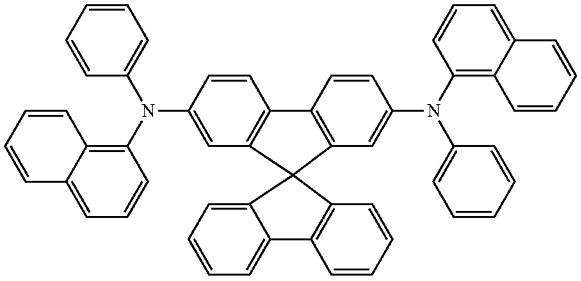

Spiro-NPB

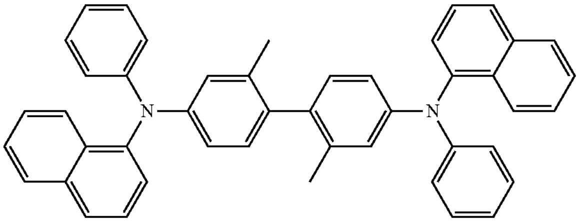

methylated NPB

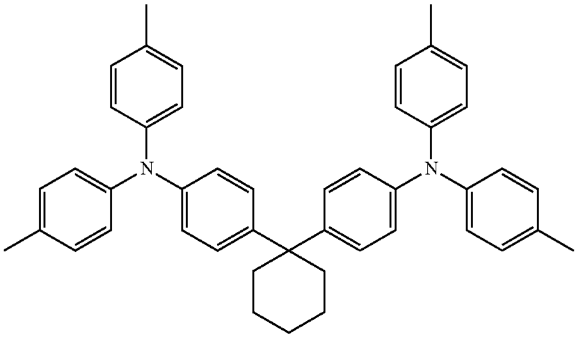

TAPC

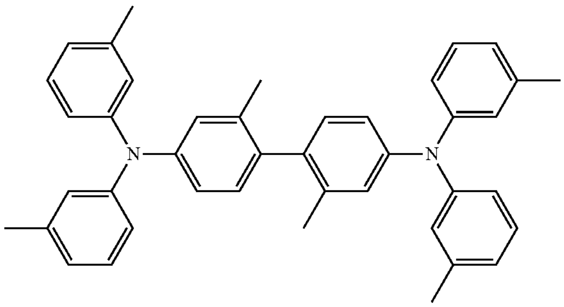

HMTPD

Formula 201

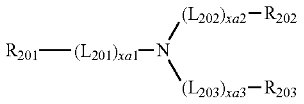

-continued

Formula 202

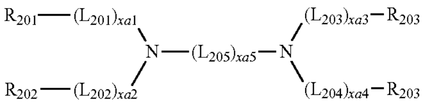

Formula 203

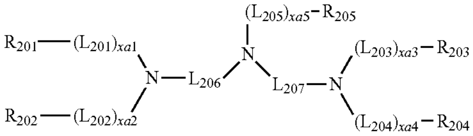

Formula 204

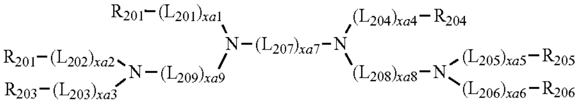

Formula 205

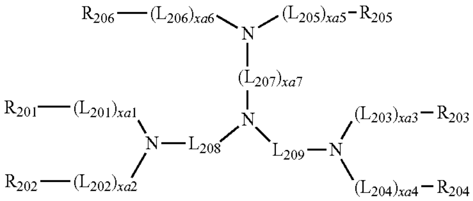

wherein, in Formulae 201 to 205, $L_{201}$ to $L_{209}$ may each independently be *—O—*', *—S—*', a substituted or unsubstituted $C_5$-$C_{60}$ carbocyclic group or a substituted or unsubstituted $C_1$-$C_{60}$ heterocyclic group, xa1 to xa9 may each independently be an integer from 0 to 5, $R_{201}$ to $R_{206}$ may each independently be a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, and adjacent two groups of $R_{201}$ to $R_{206}$ may optionally be bound to each other via a single bond, a dimethyl-methylene group or a diphenyl-methylene group.

In some embodiments, $L_{201}$ to $L_{209}$ may be a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a coronene group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, or a triindolobenzene group, each unsubstituted or substituted with deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, a tetraphenyl group, —$Si(Q_{11})(Q_{12})(Q_{13})$, or any combination thereof, xa1 to xa9 may each independently be 0, 1, or 2, and $R_{201}$ to $R_{206}$ may each independently be a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an indenocarbazolyl group, an indolocarbazolyl group, a benzofurocarbazolyl group, or a benzothienocarbazolyl group, each unsubstituted or substituted with deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —$Si(Q_{31})(Q_{32})(Q_{33})$, —$N(Q_{31})(Q_{32})$, or any combination thereof, wherein $Q_{11}$ to $Q_{13}$ and $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group.

According to an embodiment, the hole transport region 12 may include a carbazole-containing amine-based compound.

In one or more embodiments, the hole transport region 12 may include a carbazole-containing amine-based compound and a carbazole-free amine-based compound.

The carbazole-containing amine-based compound may include, for example, a compound represented by Formula 201 including a carbazole group and further including at least one of a dibenzofuran group, a dibenzothiophene group, a fluorene group, a spirofluorene group, an indenocarbazole group, an indolocarbazole group, a benzofurocarbazole group, a benzothienocarbazole group, or any combination thereof.

The carbazole-free amine-based compound may include, for example, a compound represented by Formula 201 not including a carbazole group and including at least one of a dibenzofuran group, a dibenzothiophene group, a fluorene group, a spirofluorene group, an indenocarbazole group, an indolocarbazole group, a benzofurocarbazole group, a benzothienocarbazole group, or any combination thereof.

In one or more embodiments, the hole transport region 12 may include a compound represented by Formula 201, a compound represented by Formula 202, or any combination thereof.

In some embodiments, the hole transport region 12 may include a compound represented by Formula 201-1, 202-1, or 201-2 or any combination thereof:

Formula 201-1

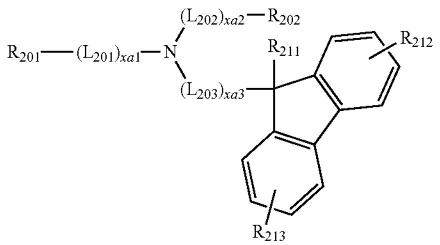

Formula 202-1

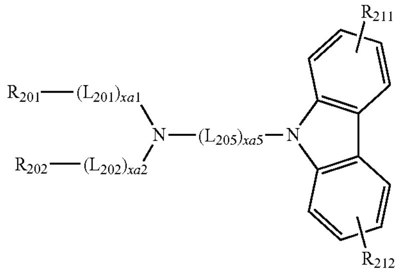

Formula 201-2

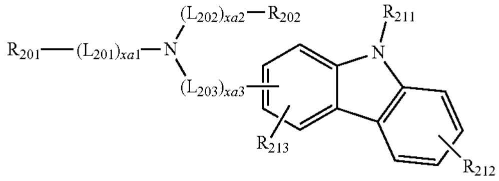

wherein in Formulae 201-1, 202-1, and 201-2, $L_{201}$ to $L_{203}$, $L_{205}$, xa1 to xa3, xa5, $R_{201}$ and $R_{202}$ may respectively be understood by referring to the descriptions of $L_{201}$ to $L_{203}$, $L_{205}$, xa1 to xa3, xa5, $R_{201}$ and $R_{202}$ provided herein, and $R_{211}$ to $R_{213}$ may each independently be hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a dimethylfluorenyl group, a diphenylfluorenyl group, a triphenylenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, or a pyridinyl group.
In some embodiments, the hole transport region 12 may include one of Compounds HT1 to HT39 or any combination thereof:
HT1
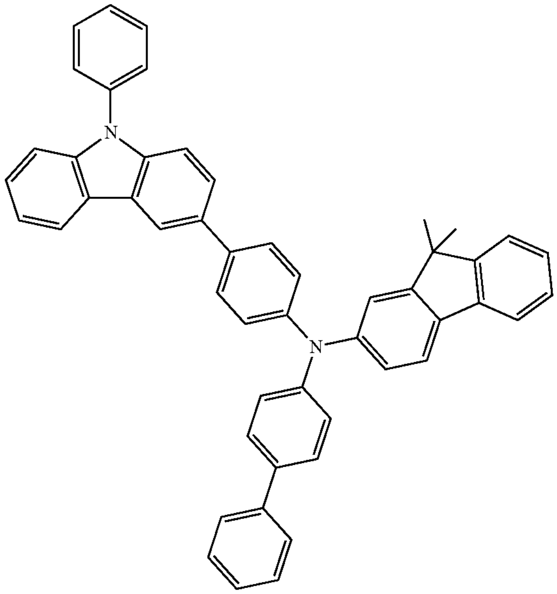
HT2
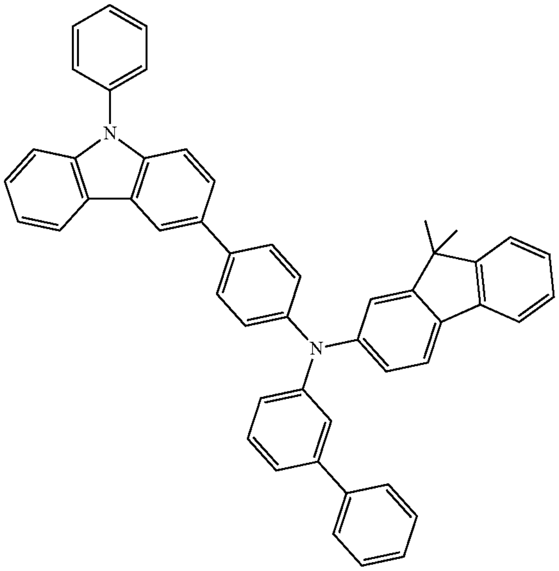
HT3
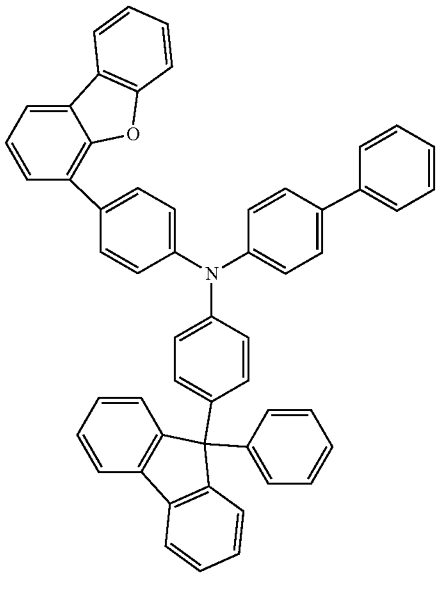
HT4
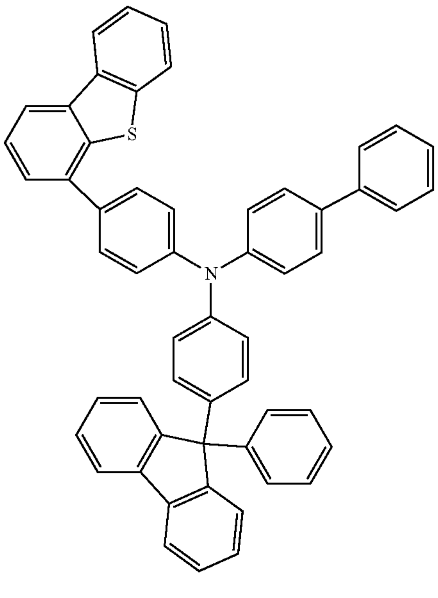

-continued
HT5
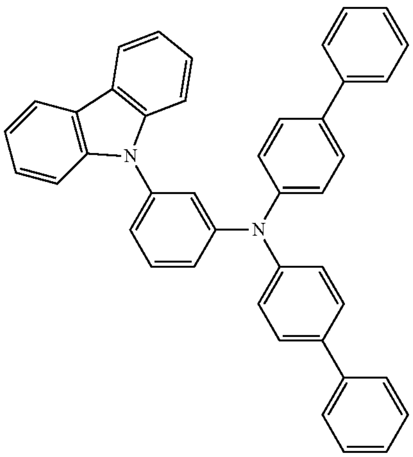
HT6
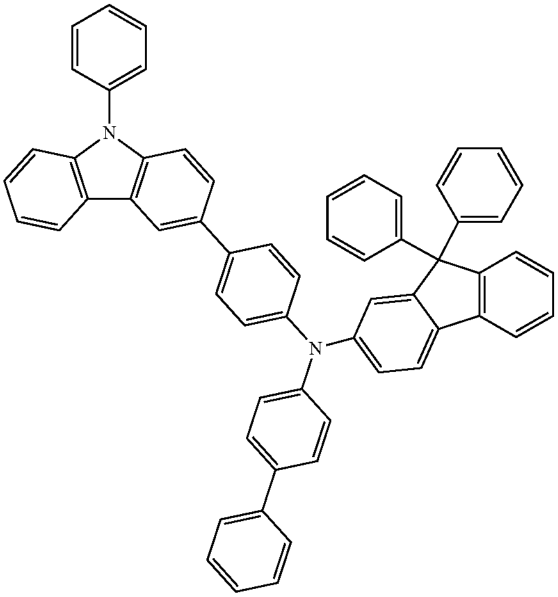
HT7
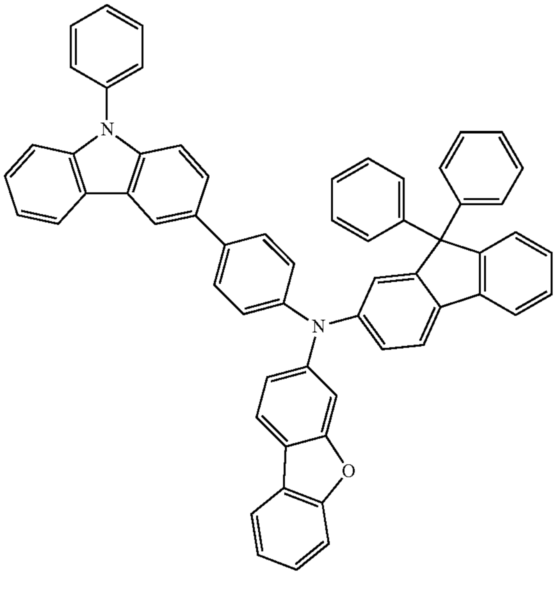
HT8
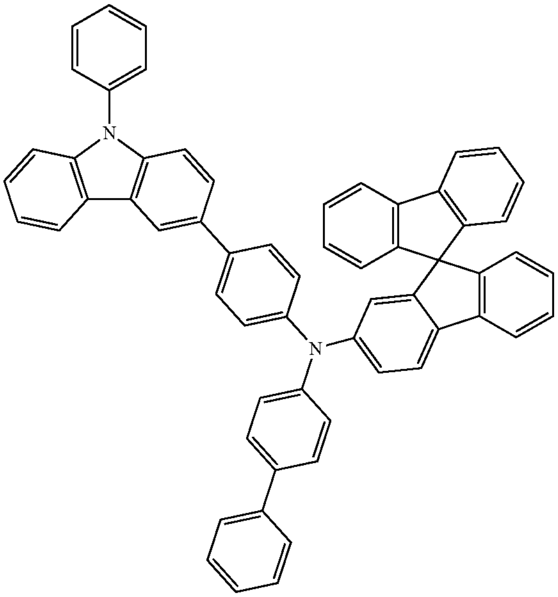

-continued
HT9
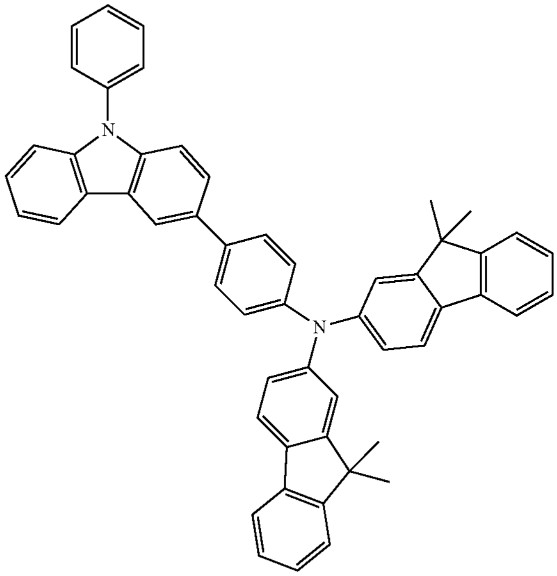
HT10
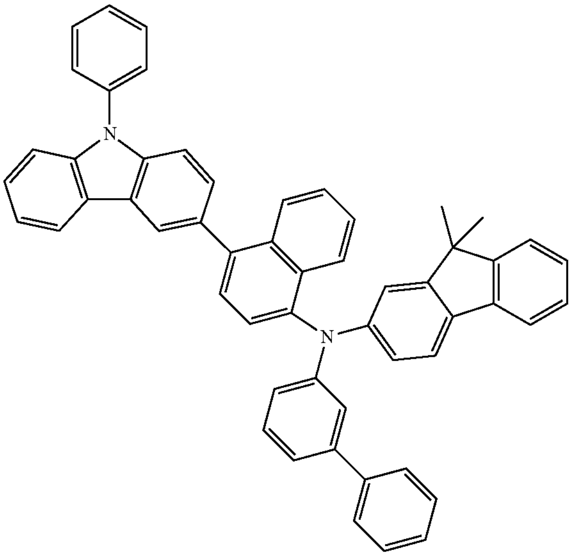
HT11
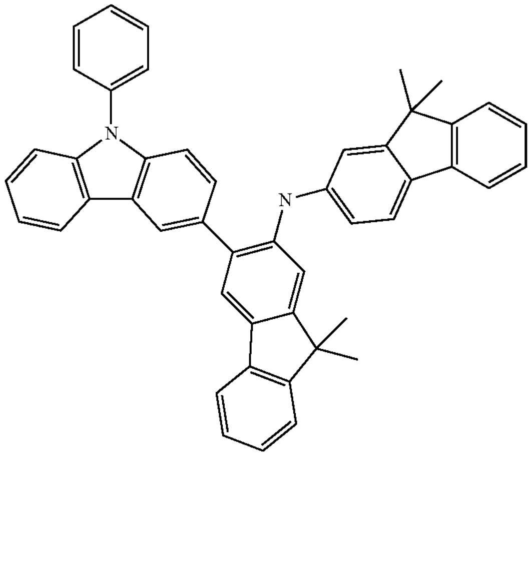
HT12
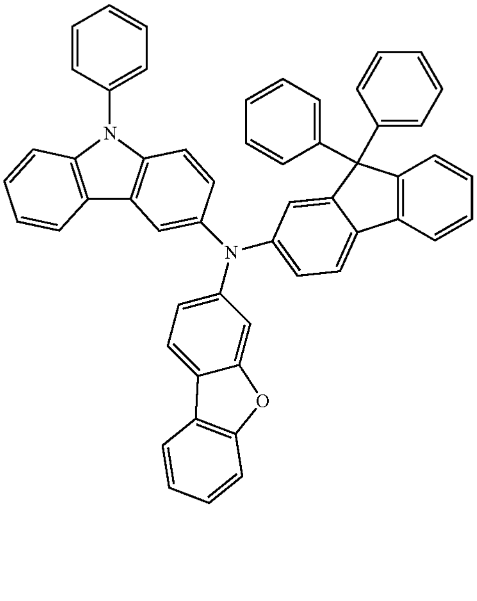

-continued
HT13
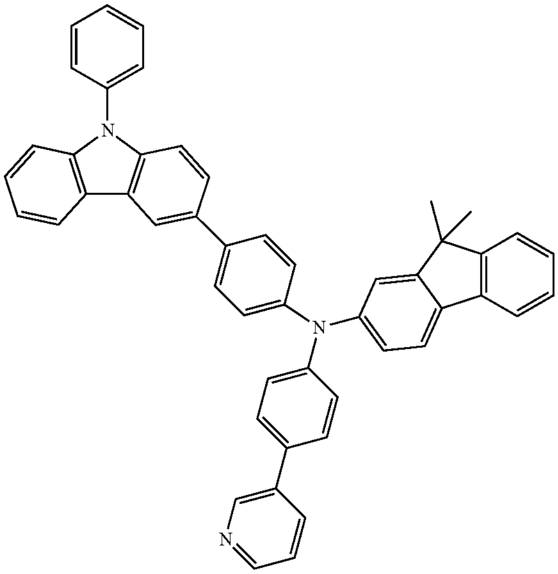
HT14
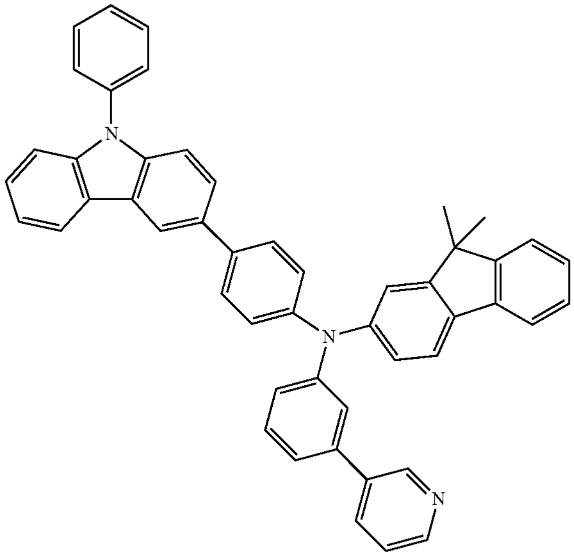
HT15
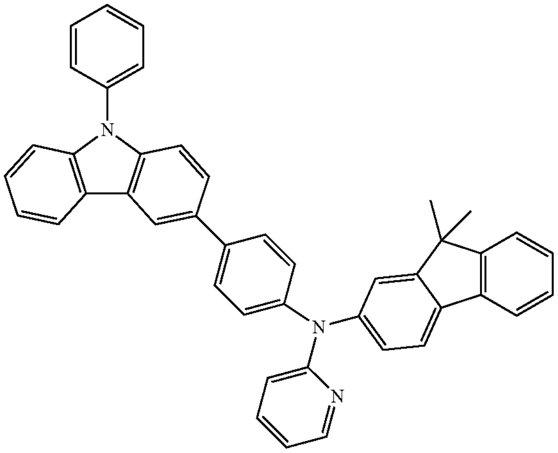
HT16
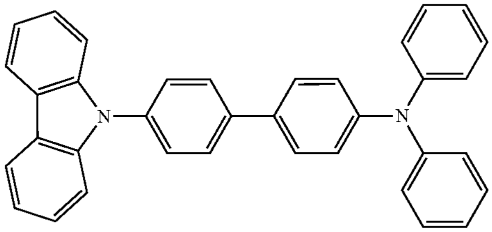
HT17
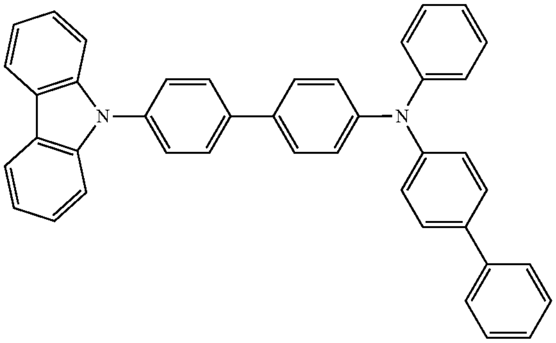
HT18
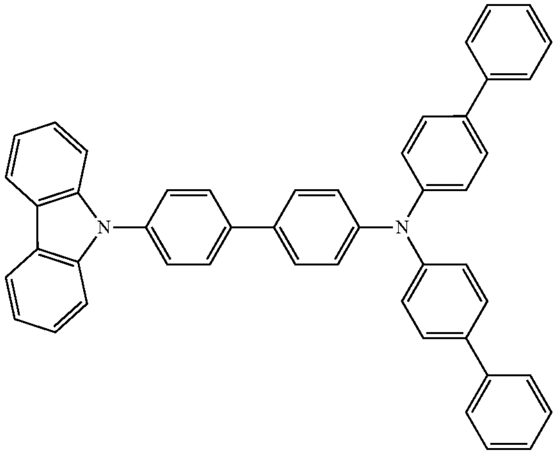

-continued
HT19
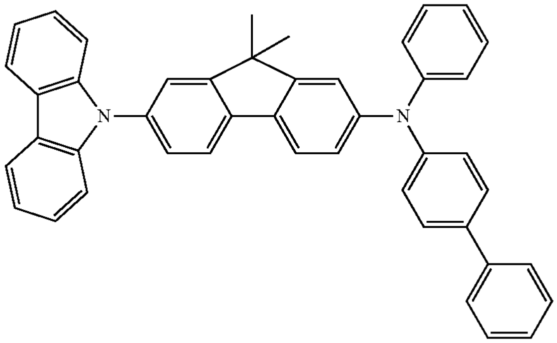
HT20
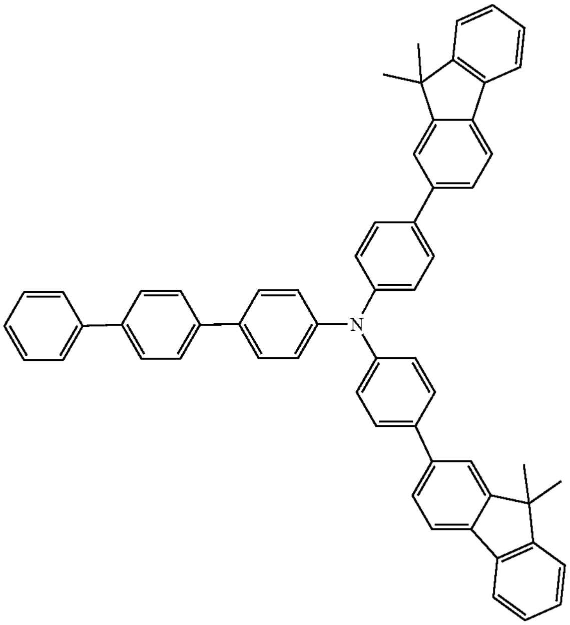
HT21
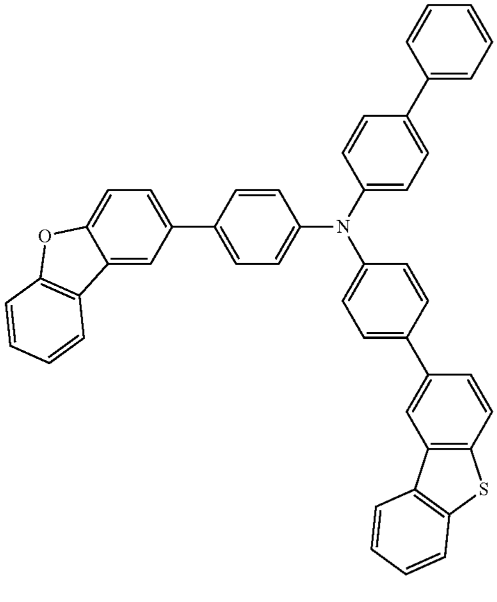
HT22
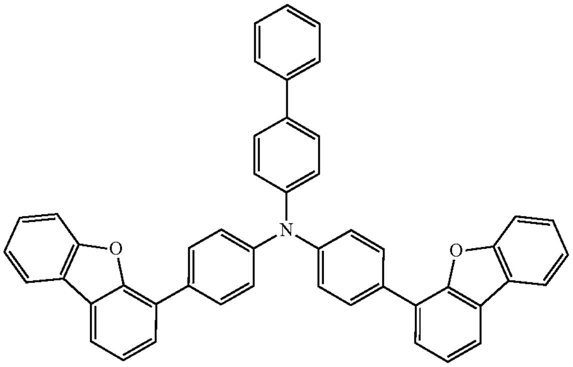

-continued
HT23
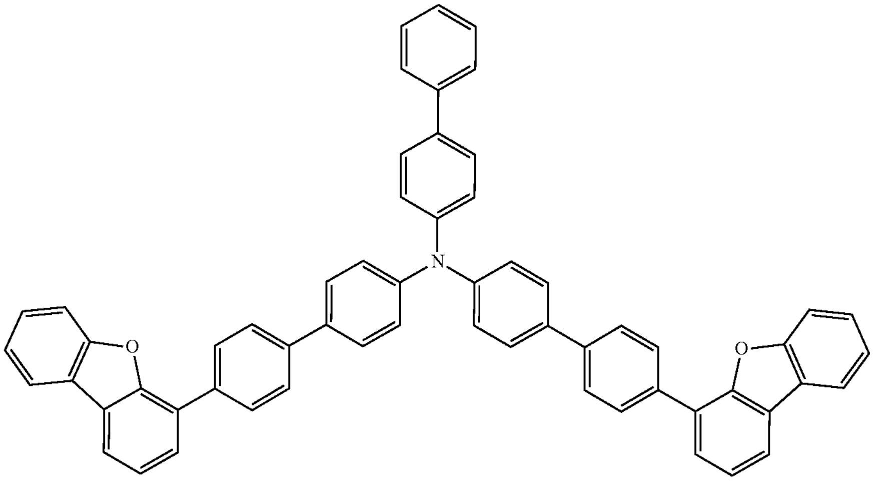
HT24
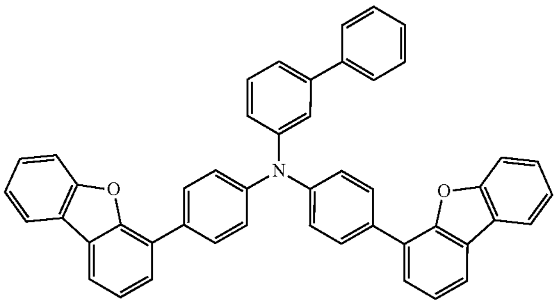
HT25
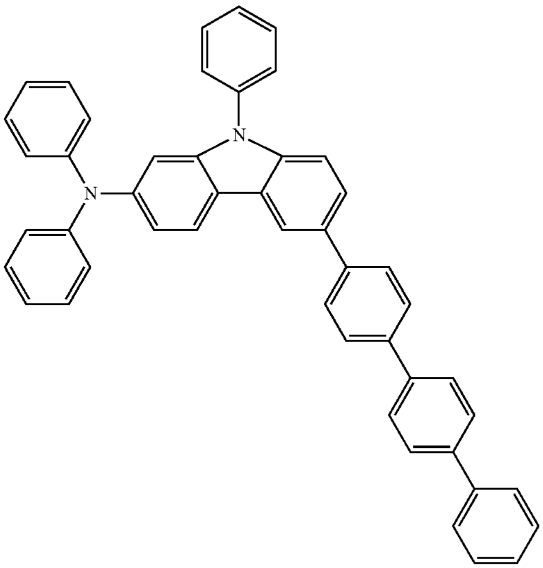
HT26
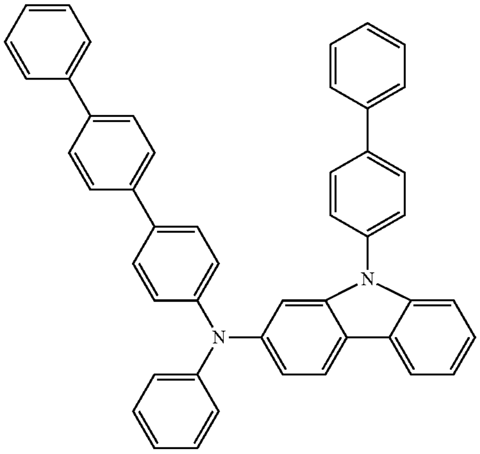
HT27
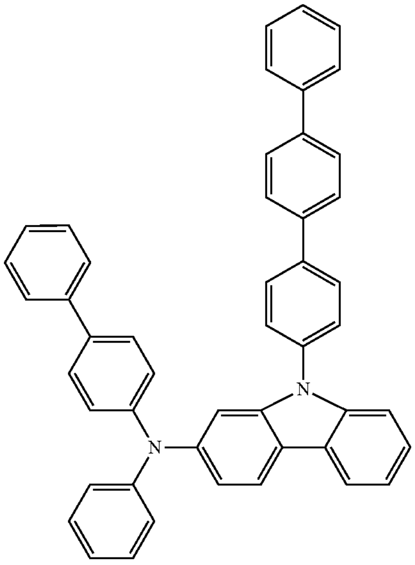

-continued
HT28
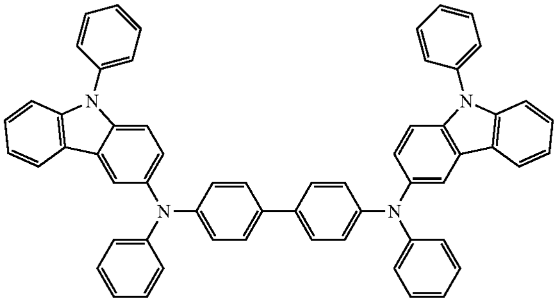
HT29
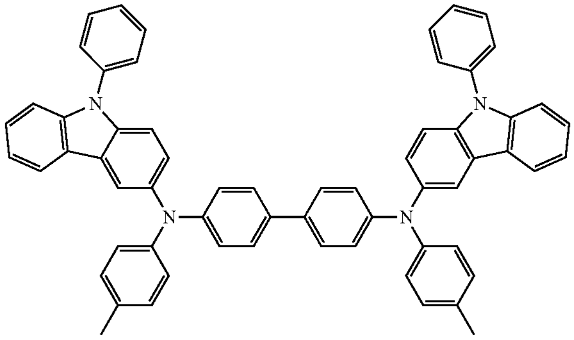
HT30
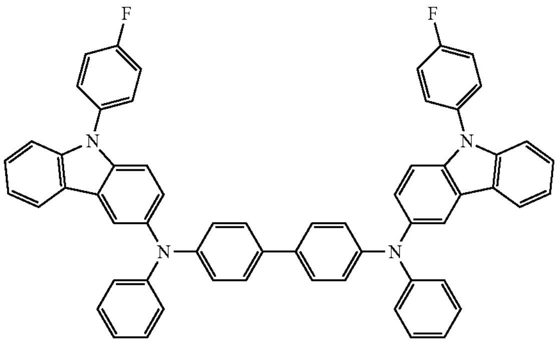
HT31
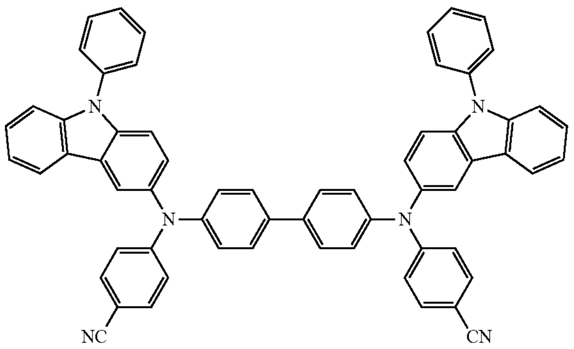
HT32
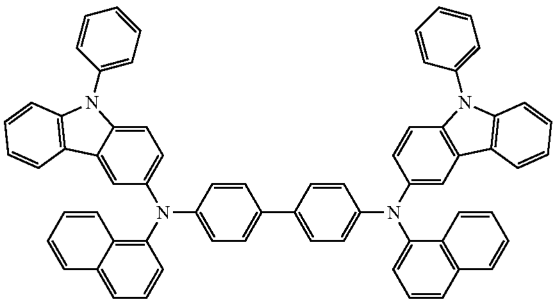
HT33
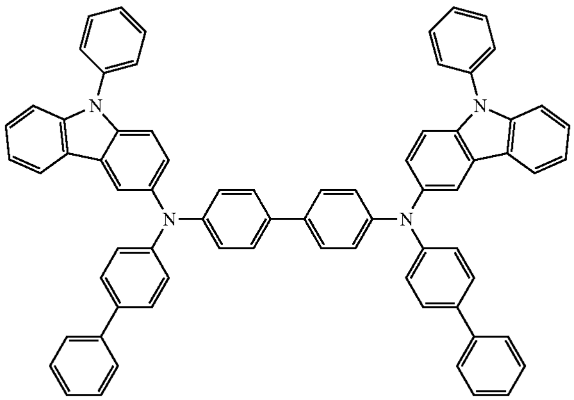

-continued
HT34
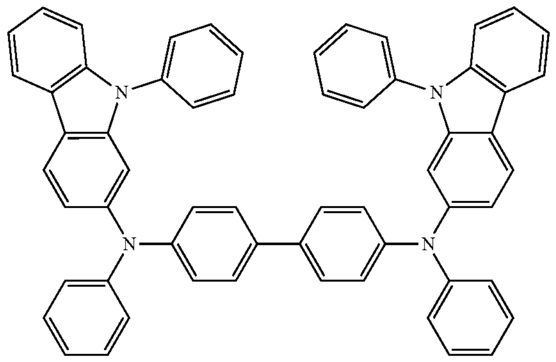
HT35
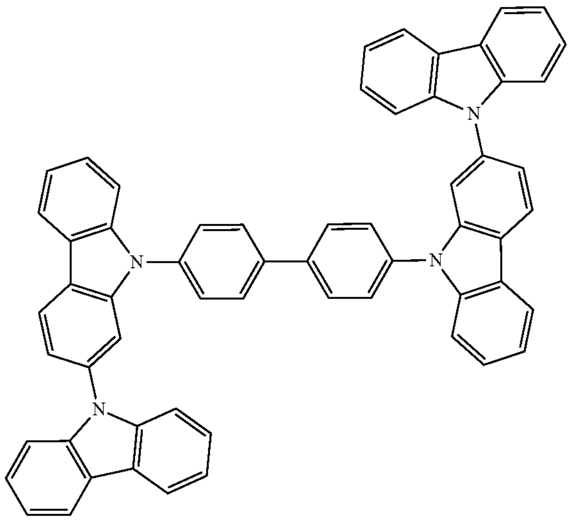
HT36
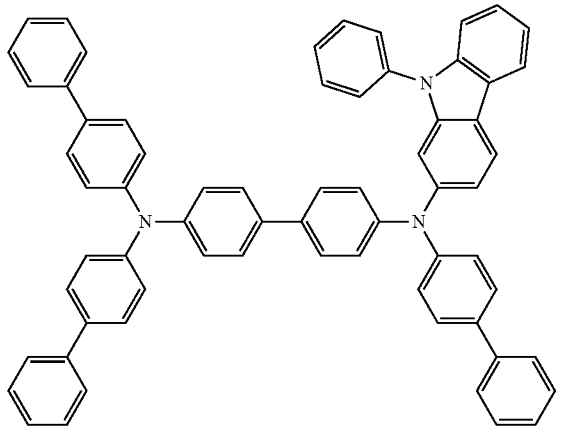
HT37
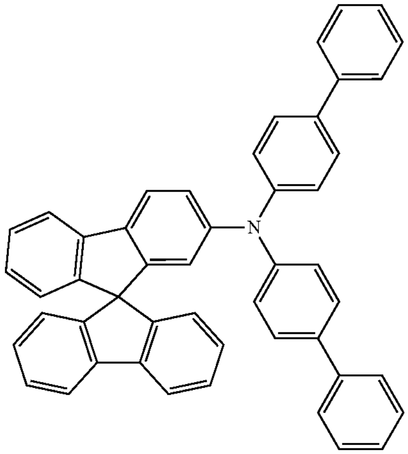
HT38
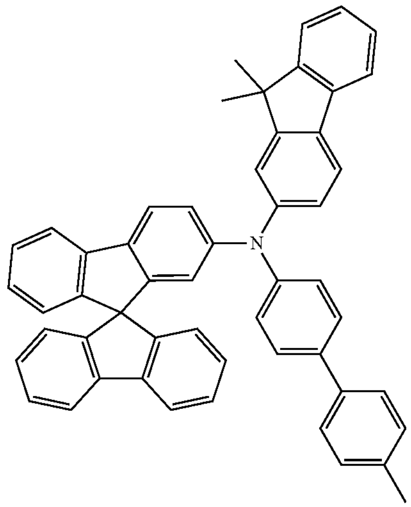
HT39
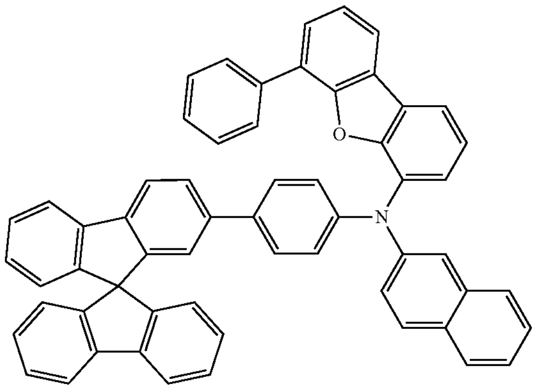
The hole transport region 12 of the organic light-emitting device 10 may further include a p-dopant. When the hole transport region 12 further includes a p-dopant, the hole transport region 12 may have a structure including a matrix (for example, at least one compound represented by Formulae 201 to 205) and a p-dopant included in the matrix. The p-dopant may be homogeneously or non-homogeneously doped in the hole transport region 12.

In some embodiments, a LUMO energy level of the p-dopant may be about −3.5 eV or less.

The p-dopant may include a quinone derivative, a metal oxide, a compound containing a cyano group, or any combination thereof.

In some embodiments, the p-dopant may include:

a quinone derivative such as tetracyanoquinodimethane (TCNQ), 2,3,5,6-tetrafluoro-7,7,8,8-tetracyanoquinodimethane (F4-TCNQ), or F6-TCNNQ;

a metal oxide such as tungsten oxide or molybdenum oxide;

1,4,5,8,9,12-hexaazatriphenylene-hexacarbonitrile (HAT-CN);

a compound represented by Formula 221, or any combination thereof:

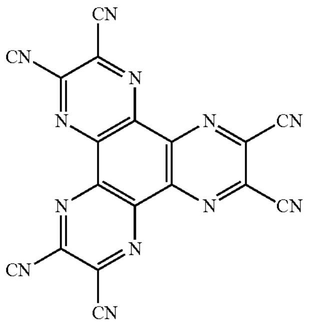

HAT-CN

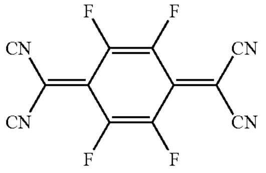

F4-TCNQ

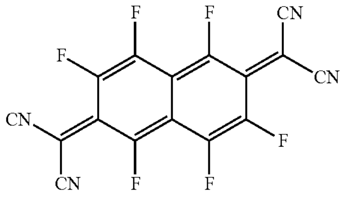

F6-TCNNQ

Formula 221

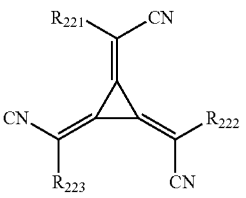

wherein, in Formula 221, $R_{221}$ to $R_{223}$ may each independently be a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, wherein at least one substituent of $R_{221}$ to $R_{223}$ may be: a cyano group; —F; —Cl; —Br; —I; a $C_1$-$C_{20}$ alkyl group substituted with —F; a $C_1$-$C_{20}$ alkyl group substituted with —Cl; a $C_1$-$C_{20}$ alkyl group substituted with —Br; a $C_1$-$C_{20}$ alkyl group substituted with —I; or any combination thereof.

The compound represented by Formula 221 may include, for example, Compound HT-D2:

HT-D2

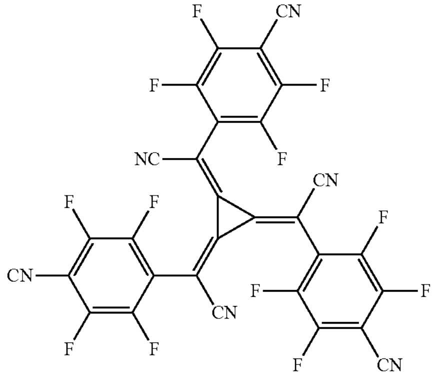

A thickness of the hole transport region 12 may be in a range of about 100 Å to about 10,000 Å, e.g., about 400 Å to about 2,000 Å, and a thickness of the emission layer 15 may be in a range of about 100 Å to about 3,000 Å, e.g., about 300 Å to about 1,000 Å. When the thicknesses of the hole transport region 12 and the emission layer 15 are within any of these ranges, satisfactory hole transporting characteristics and/or luminescence characteristics may be obtained without a substantial increase in driving voltage.

The hole transport region 12 may further include a buffer layer.

The buffer layer may compensate for an optical resonance distance depending on a wavelength of light emitted from the emission layer to improve the emission efficiency of an organic light-emitting device.

The hole transport region 12 may further include an electron blocking layer. The electron blocking layer may include a known material, e.g., mCP or DBFPO:

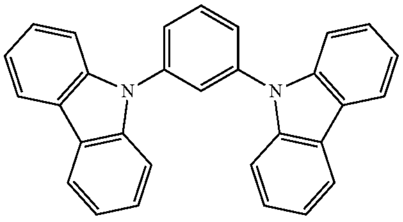

mCP

-continued

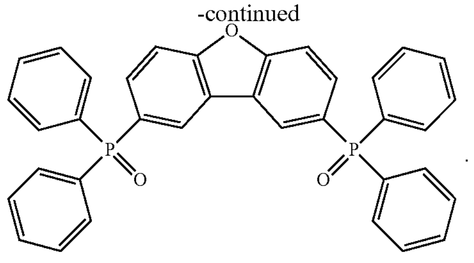

DBFPO

Electron Transport Region 17

In the organic light-emitting device 10, the electron transport region 17 may be between the emission layer 15 and the second electrode 19.

The electron transport region 17 may have a single-layered structure or a multi-layered structure.

For example, the electron transport region 17 may have a structure of an electron transport layer, a structure of an electron transport layer/an electron injection layer, a structure of a buffer layer/an electron transport layer, a structure of a hole blocking layer/an electron transport layer, a structure of a buffer layer/an electron transport layer/an electron injection layer, or a structure of hole blocking layer/an electron transport layer/an electron injection layer. The electron transport region 17 may include an electron control layer.

The electron transport region 17 may include a known electron transport material.

The electron transport region 17 (for example, a buffer layer, a hole blocking layer, an electron control layer, or an electron transport layer in the electron transport region) may include a metal-free compound including at least one π electron-depleted nitrogen-containing $C_1$-$C_{60}$ cyclic group. The π electron-depleted nitrogen-containing $C_1$-$C_{60}$ cyclic group may be understood by referring to the description of the π electron-depleted nitrogen-containing $C_1$-$C_{60}$ cyclic group provided herein.

In some embodiments, the electron transport region 17 may include a compound represented by Formula 601:

$$[Ar_{601}]_{xe11}\text{-}[(L_{601})_{xe1}\text{-}R_{601}]_{xe21} \quad \text{Formula 601}$$

wherein, in Formula 601, $Ar_{601}$ and $L_{601}$ may each independently be a $C_5$-$C_{60}$ carbocyclic group unsubstituted or substituted with at least one $R_{601a}$ or a $C_1$-$C_{60}$ heterocyclic group unsubstituted or substituted with at least one $R_{601a}$, xe11 may be 1, 2, or 3, xe1 may be an integer from 0 to 5, $R_{601a}$ and $R_{601}$ may each independently be a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(═O)($Q_{601}$), —S(═O)$_2$($Q_{601}$), or —P(═O)($Q_{601}$)($Q_{602}$), wherein $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In some embodiments, at least one of $Ar_{601}$(s) in the number of xe11 and $R_{601}$(s) in the number of xe21 may include a π electron-depleted nitrogen-containing $C_1$-$C_{60}$ cyclic group.

In some embodiments, in Formula 601, ring $Ar_{601}$ and $L_{601}$ may each independently be a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, or an azacarbazole group, each unsubstituted or substituted with deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(═O)$_2$($Q_{31}$), —P(═O)($Q_{31}$)($Q_{32}$), or any combination thereof, wherein $Q_{31}$ to $Q_{33}$ may each independently be a $C_1$-$C_{10}$ alkyl group, a $C_1$-$C_{10}$ alkoxy group, a phenyl group, a biphenyl group, a terphenyl group, or a naphthyl group.

When xe11 in Formula 601 is 2 or greater, at least two $Ar_{601}$(s) may be bound via a single bond.

In one or more embodiments, $A_{601}$ in Formula 601 may be an anthracene group.

In some embodiments, the compound represented by Formula 601 may be represented by Formula 601-1:

Formula 601-1

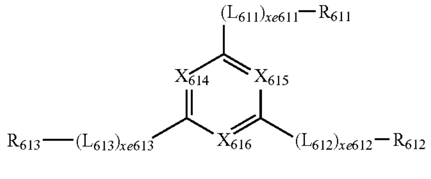

wherein, in Formula 601-1, $X_{614}$ may be N or C($R_{614}$), $X_{615}$ may be N or C($R_{615}$), $X_{616}$ may be N or C($R_{616}$), at least one of $X_{614}$ to $X_{616}$ may be N, $L_{611}$ to $L_{613}$ may each independently be understood by referring to the description of $L_{601}$ provided herein, xe611 to xe613 may each independently be understood by referring to the description of xe1 provided herein, $R_{611}$ to $R_{613}$ may each independently be understood by referring to the description of $R_{601}$ provided herein, and $R_{614}$ to $R_{616}$ may each independently be hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, or a naphthyl group.

In one or more embodiments, in Formulae 601 and 601-1, xe1 and xe611 to xe613 may each independently be 0, 1, or 2.

In one or more embodiments, in Formulae 601 and 601-1, $R_{601}$ and $R_{611}$ to $R_{613}$ may each independently be a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, or an azacarbazolyl group, each unsubstituted or substituted with deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, or any combination thereof; or $-S(=O)_2(Q_{601})$ or $-P(=O)(Q_{601})(Q_{602})$, wherein $Q_{601}$ and $Q_{602}$ may respectively be understood by referring to the descriptions of $Q_{601}$ and $Q_{602}$ provided herein.

The electron transport region 17 may include one of Compounds ET1 to ET36 or any combination thereof:

ET1

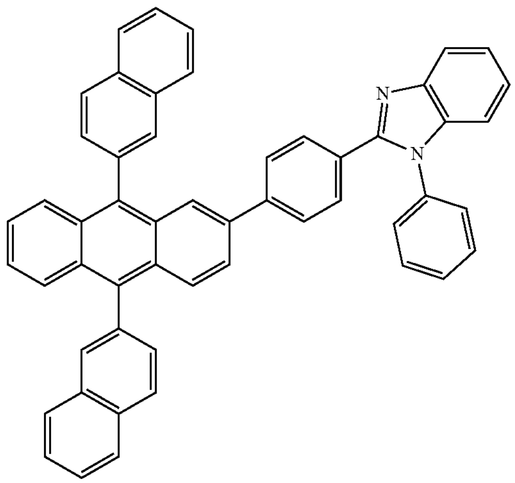

ET2

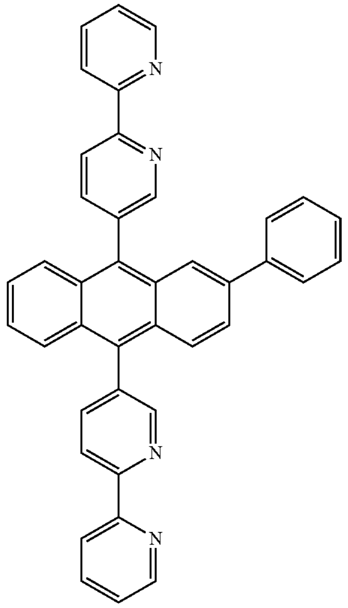

ET3

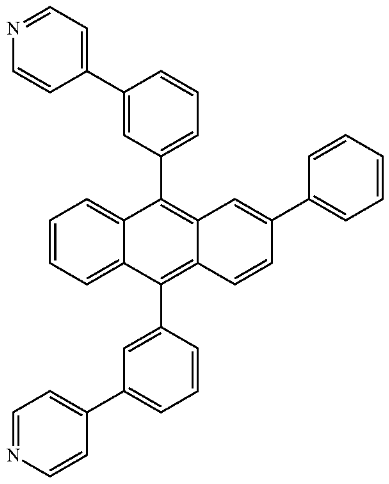

-continued
ET4
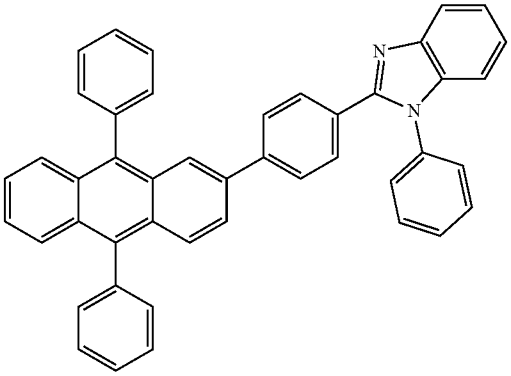
ET5
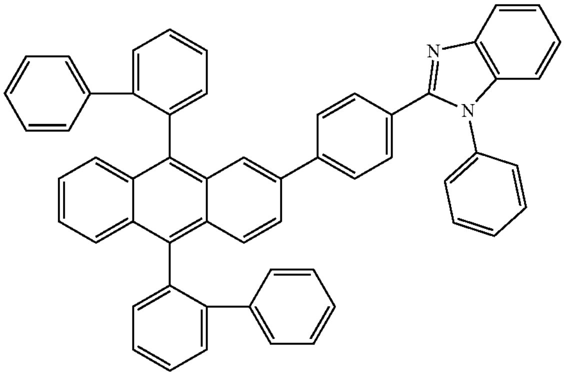
ET6
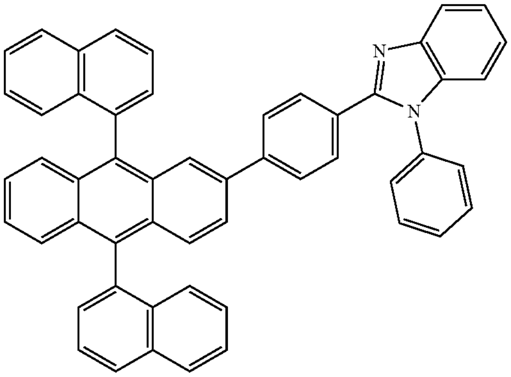
-continued
ET7
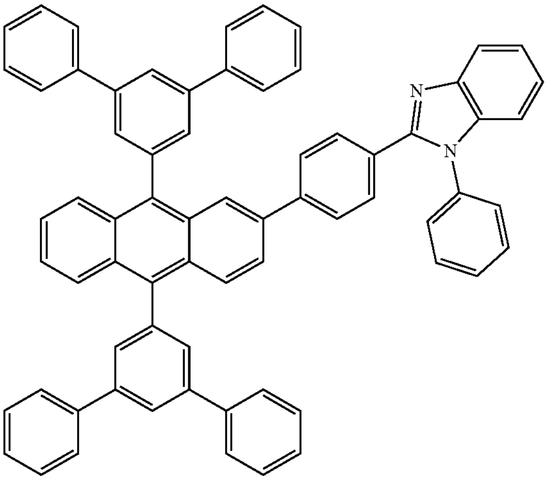
ET8
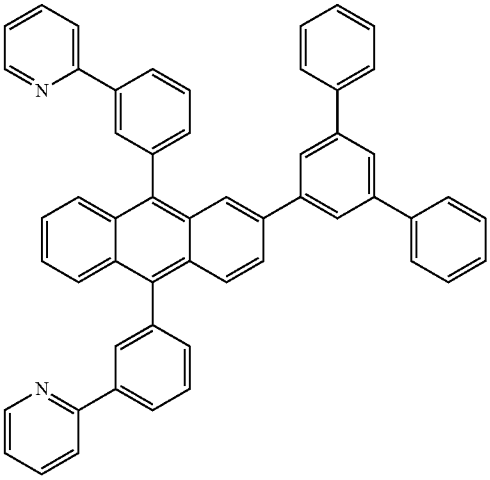
ET9
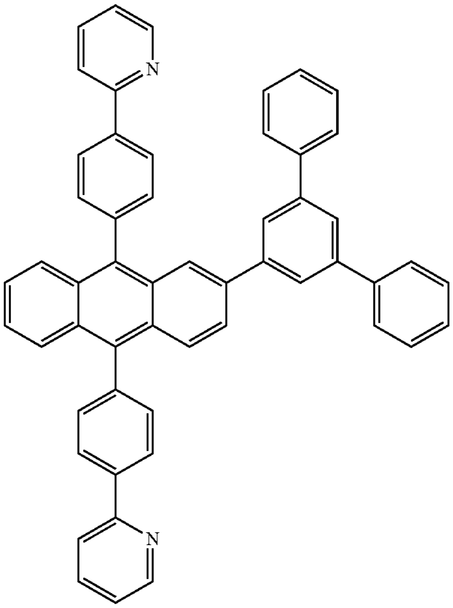

-continued
ET10
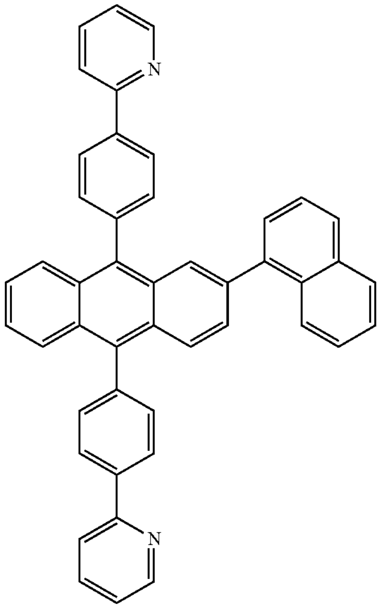
HT11
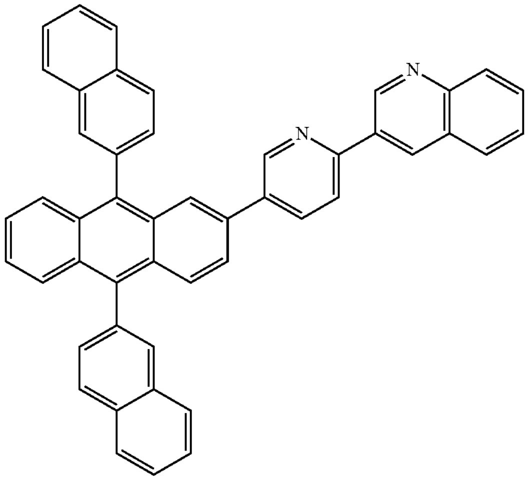
HT12
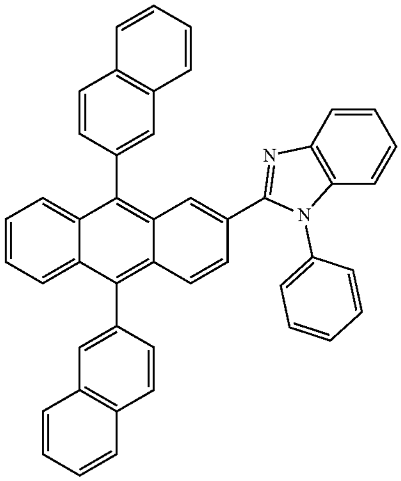
-continued
HT13
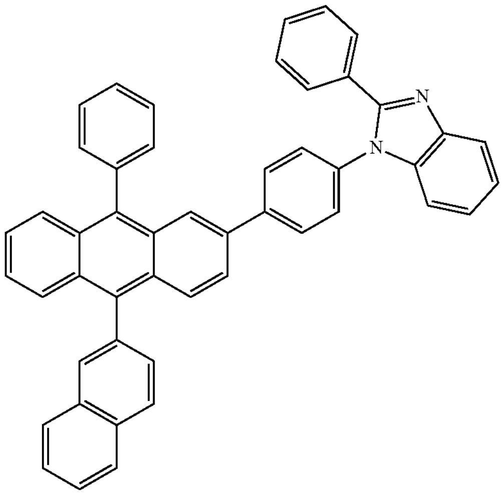
ET14
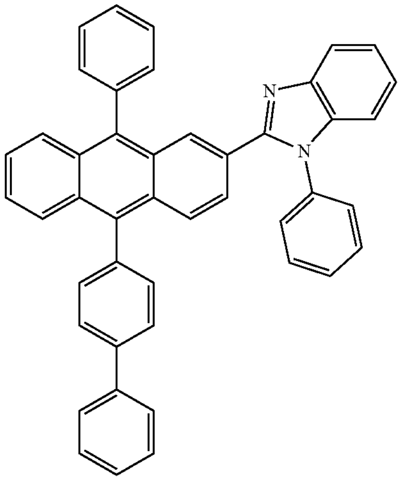
ET15
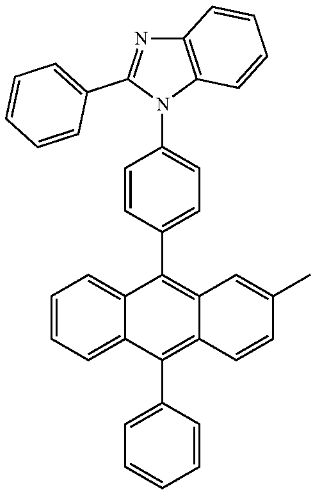

-continued
ET16
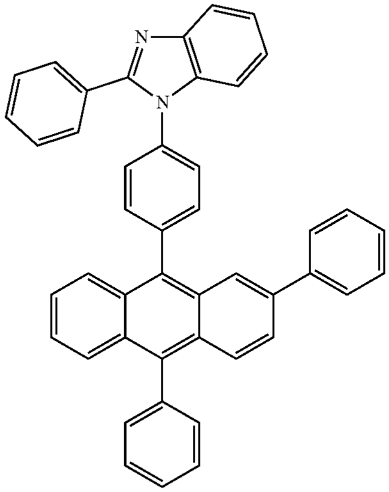
ET17
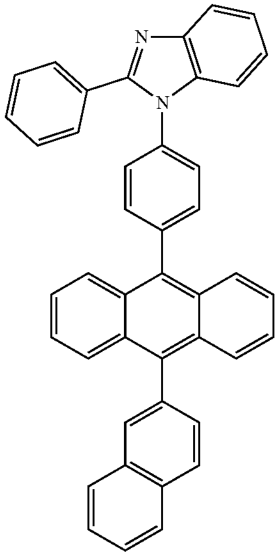
ET18
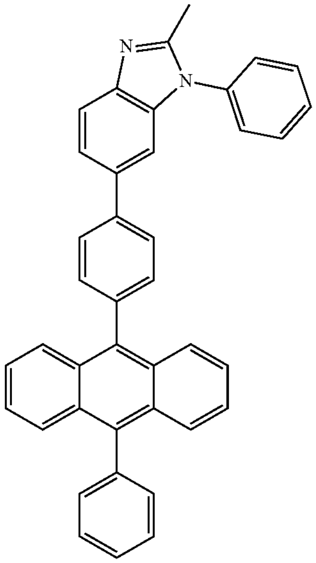
-continued
ET19
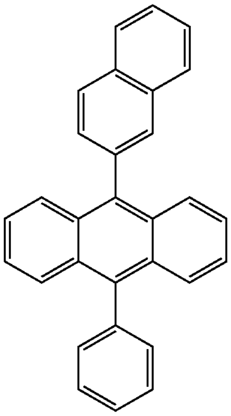
ET20
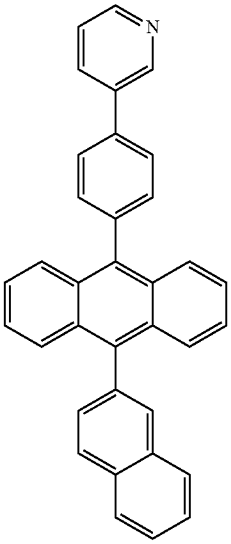
ET21
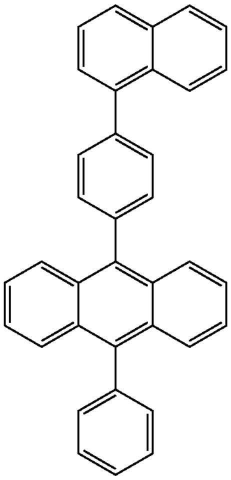

-continued
ET22
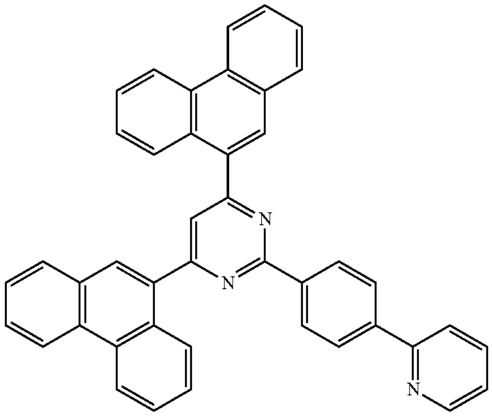
ET23
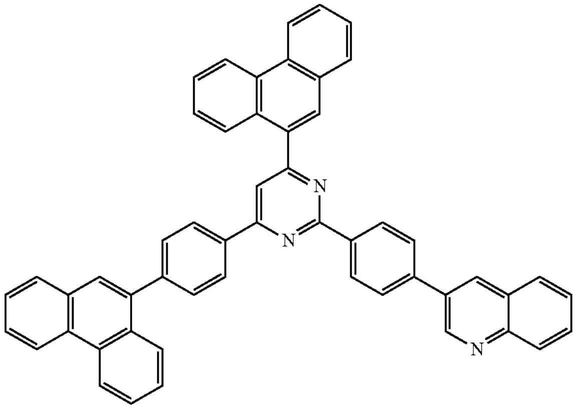
ET24
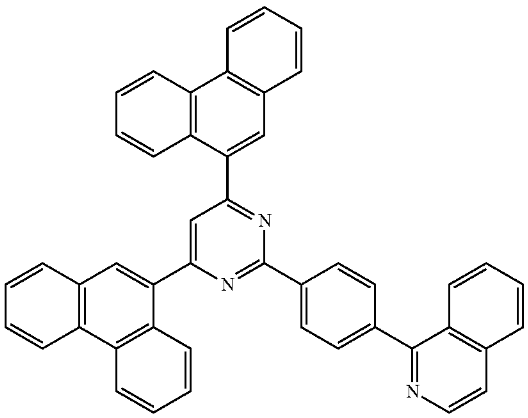
-continued
ET25
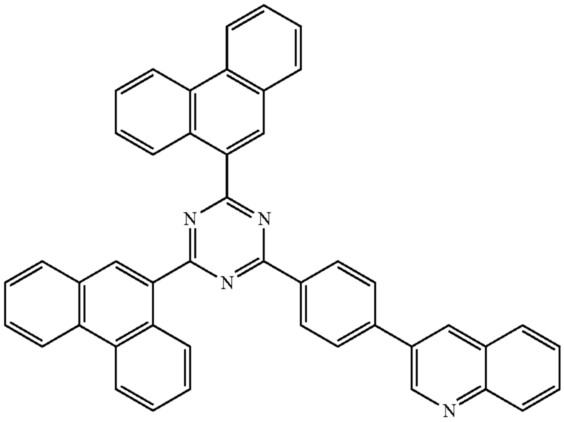
ET26
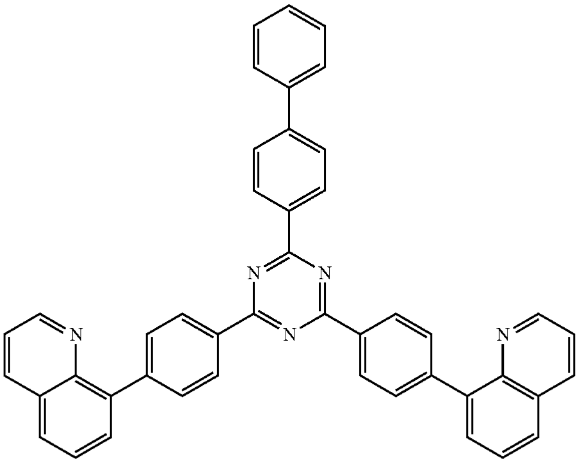
ET27
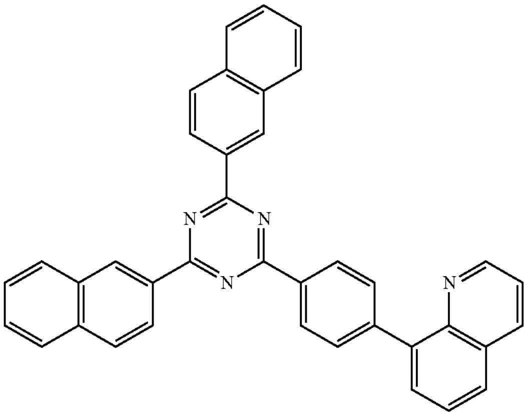

-continued
ET28
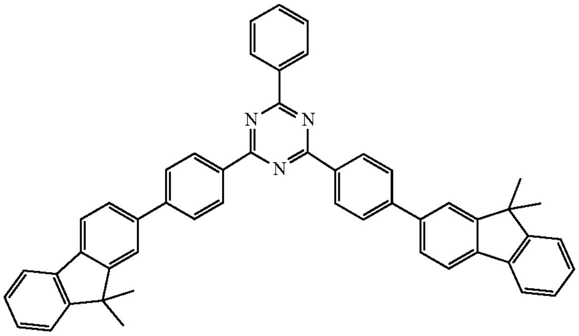
ET29
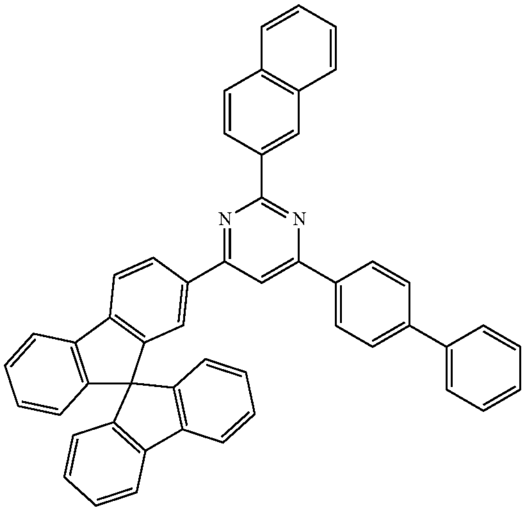
ET30
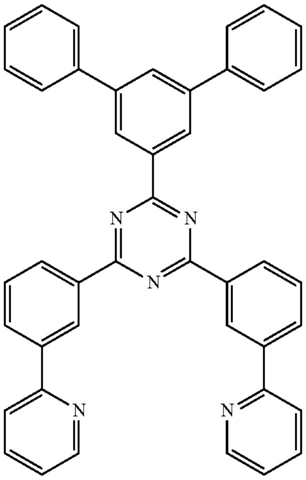
-continued
ET31
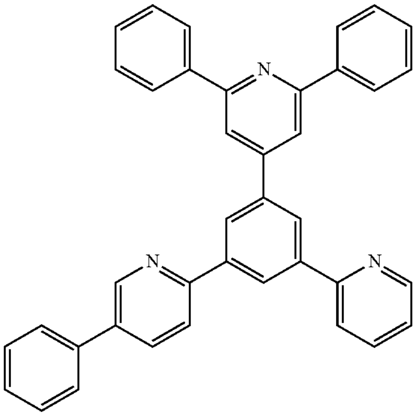
ET32
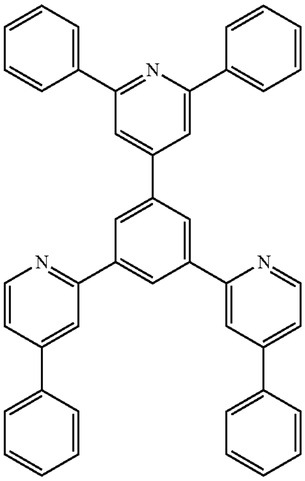
ET33
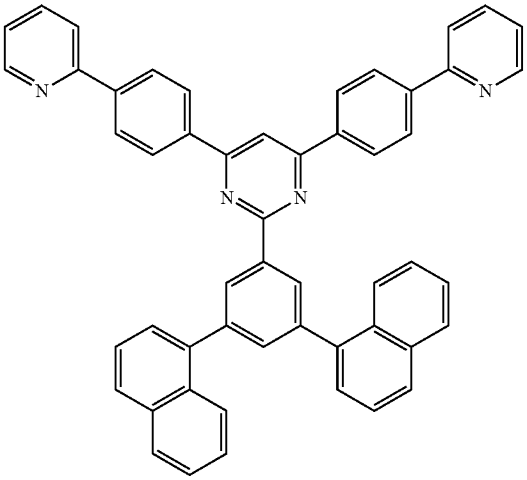

-continued

ET34

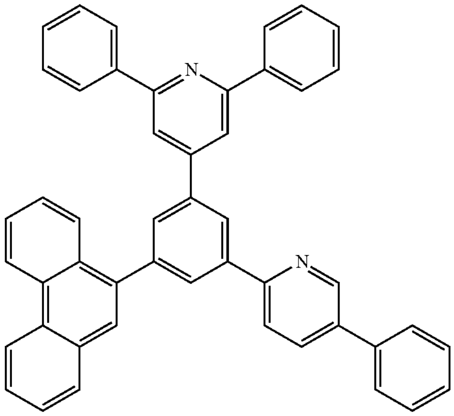

ET35

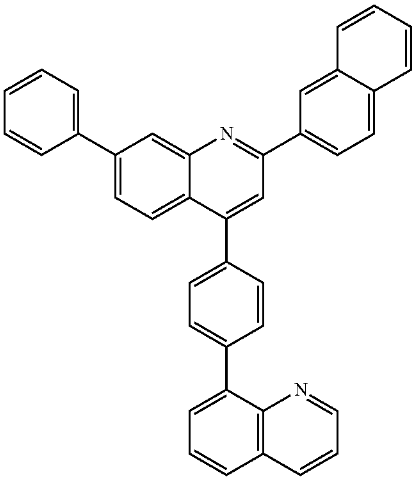

ET36

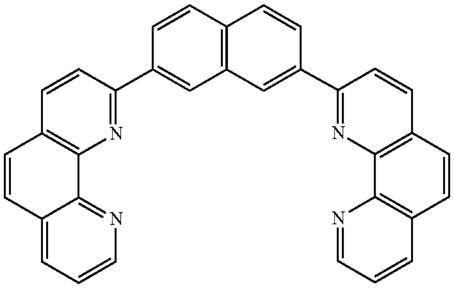

In some embodiments, the electron transport region 17 may include 2,9-dimethyl-4,7-diphenyl-1,10-phenanthroline (BCP), 4,7-diphenyl-1,10-phenanthroline (Bphen), Alq3, BAlq, 3-(biphenyl-4-yl)-5-(4-tert-butylphenyl)-4-phenyl-4H-1,2,4-triazole (TAZ), NTAZ, DBFPO, or any combination thereof. In some embodiments, when the electron transport region 17 includes a hole blocking layer, the hole blocking layer may include BCP or Bphen.

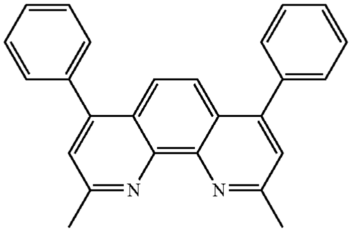

BCP

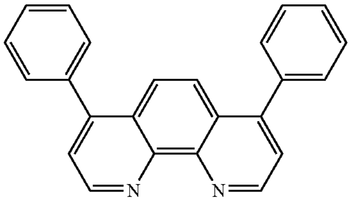

Bphen

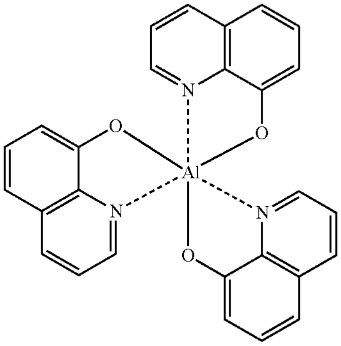

$Alq_3$

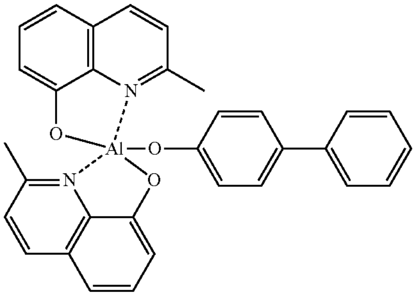

BAlq

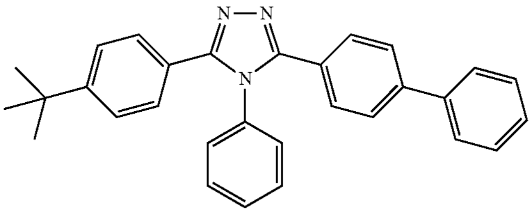

TAZ

-continued

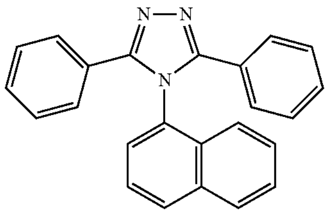

NTAZ

The thicknesses of the buffer layer, the hole blocking layer, or the electron control layer may each independently be in a range of about 20 Å to about 1,000 Å, and in some embodiments, about 30 Å to about 300 Å. When the thicknesses of the buffer layer, the hole blocking layer or the electron control layer are within any of these ranges, excellent hole blocking characteristics or excellent electron controlling characteristics may be obtained without a substantial increase in driving voltage.

The thickness of the electron transport layer may be in a range of about 100 Å to about 1,000 Å, and in some embodiments, about 150 Å to about 500 Å. When the thickness of the electron transport layer is within any of these ranges, excellent electron transport characteristics may be obtained without a substantial increase in driving voltage.

The electron transport region 17 (e.g., the electron transport layer in the electron transport region 17) may further include, in addition to the materials described above, a material including metal.

The metal-containing material may include an alkali metal complex, an alkaline earth metal complex, or any combination thereof. A metal ion of the alkali metal complex may be a lithium (Li) ion, a sodium (Na) ion, a potassium (K) ion, a rubidium (Rb) ion, a cesium (Cs) ion, or any combination thereof. A metal ion of the alkaline earth metal complex may be a beryllium (Be) ion, a magnesium (Mg) ion, a calcium (Ca) ion, a strontium (Sr) ion, a barium (Ba) ion, or any combination thereof. Each ligand coordinated with the metal ion of the alkali metal complex and the alkaline earth metal complex may independently be hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, cyclopentadiene, or any combination thereof.

For example, the metal-containing material may include a Li complex. The Li complex may include, e.g., Compound ET-D1 (LiQ) or Compound ET-D2:

ET-D1

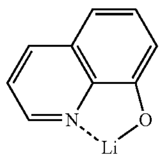

-continued

ET-D2

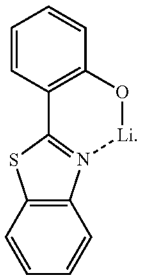

The electron transport region 17 may include an electron injection layer that facilitates injection of electrons from the second electrode 19. The electron injection layer may be in direct contact with the second electrode 19.

The electron injection layer may have i) a single-layered structure consisting of a single layer consisting of a single material, ii) a single-layered structure consisting of a single layer including a plurality of different materials, or iii) a multi-layered structure having a plurality of layers, each including a plurality of different materials.

The electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof.

The alkali metal may be Li, Na, K, Rb, Cs or any combination thereof. In some embodiments, the alkali metal may be Li, Na, or Cs. In an embodiment, the alkali metal may be Li or Cs.

The alkaline earth metal may be Mg, Ca, Sr, Ba, or any combination thereof.

The rare earth metal may be Sc, Y, Ce, Tb, Yb, Gd, or any combination thereof.

The alkali metal compound, the alkaline earth metal compound, and the rare earth metal compound may respectively be oxides, halides (e.g., fluorides, chlorides, bromides, or iodides), or any combination thereof of each of the alkali metal, the alkaline earth metal, and the rare earth metal.

The alkali metal compound may be one of alkali metal oxides such as $Li_2O$, $Cs_2O$, or $K_2O$, one of alkali metal halides such as LiF, NaF, CsF, KF, LiI, NaI, CsI, or KI, or any combination thereof. In some embodiments, the alkali metal compound may include LiF, $Li_2O$, NaF, LiI, NaI, CsI, KI, or any combination thereof.

The alkaline earth-metal compound may include one of alkaline earth-metal compounds, such as BaO, SrO, CaO, $BaxSr_{1-x}O$ (wherein $0<x<1$), or $Ba_xCa_{1-x}O$ (wherein $0<x<1$), or any combination thereof. In some embodiments, the alkaline earth metal compound may include BaO, SrO, CaO, or any combination thereof.

The rare earth metal compound may include $YbF_3$, $ScF_3$, $ScO_3$, $Y_2O_3$, $Ce_2O_3$, $GdF_3$, $TbF_3$, or any combination thereof. In some embodiments, the rare earth metal compound may include $YbF_3$, $ScF_3$, $TbF_3$, $YbI_3$, $ScI_3$, $TbI_3$, or any combination thereof.

The alkali metal complex, the alkaline earth metal complex, and the rare earth metal complex may each include ions of the above-described alkali metal, alkaline earth metal, and rare earth metal. Each ligand coordinated with the metal ion of the alkali metal complex, the alkaline earth metal complex, and the rare earth metal complex may independently be hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, cyclopentadiene, or any combination thereof.

The electron injection layer may consist of an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof, as described above. In some embodiments, the electron injection layer may further include an organic material. When the electron injection layer further includes an organic material, the alkali metal, the alkaline earth metal, the rare earth metal, the alkali metal compound, the alkaline earth metal compound, the rare earth metal compound, the alkali metal complex, the alkaline earth metal complex, the rare earth metal complex, or a combination thereof may be homogeneously or non-homogeneously dispersed in a matrix including the organic material.

The thickness of the electron injection layer may be in a range of about 1 Å to about 100 Å, and in some embodiments, about 3 Å to about 90 Å. When the thickness of the electron injection layer is within any of these ranges, excellent electron injection characteristics may be obtained without a substantial increase in driving voltage.

Second Electrode 19

The second electrode 19 may be disposed on the organic layer 10A. In an embodiment, the second electrode 19 may be a cathode that is an electron injection electrode. In this embodiment, a material for forming the second electrode 19 may be a material having a low work function, for example, a metal, an alloy, an electrically conductive compound, or a combination thereof.

The second electrode 19 may include lithium (Li), silver (Ag), magnesium (Mg), aluminum (Al), aluminum-lithium (Al—Li), calcium (Ca), magnesium-indium (Mg—In), magnesium-silver (Mg—Ag), ITO, IZO, or any combination thereof. The second electrode 19 may be a transmissive electrode, a semi-transmissive electrode, or a reflective electrode.

The second electrode 19 may have a single-layered structure, or a multi-layered structure including two or more layers.

General Definitions of Terms

The term "$C_1$-$C_{60}$ alkyl group" as used herein refers to a linear or branched saturated aliphatic hydrocarbon monovalent group having 1 to 60 carbon atoms, and the term "$C_1$-$C_{60}$ alkylene group" as used herein refers to a divalent group having the same structure as the $C_1$-$C_{60}$ alkyl group.

Examples of the $C_1$-$C_{60}$ alkyl group, the $C_1$-$C_{20}$ alkyl group, and/or the $C_1$-$C_{10}$ alkyl group may include a methyl group, an ethyl group, an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, or a tert-decyl group, each unsubstituted or substituted with a methyl group, an ethyl group, an n-propyl group, an iso-propyl group, an n-butyl group, a sec-butyl group, an isobutyl group, a tert-butyl group, an n-pentyl group, a tert-pentyl group, neopentyl group, an isopentyl group, a sec-pentyl group, a 3-pentyl group, a sec-isopentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, or any combination thereof.

The term "$C_1$-$C_{60}$ alkoxy group" as used herein refers to a monovalent group represented by —$OA_{101}$ (wherein $A_{101}$ is a $C_1$-$C_1$ alkyl group). Examples thereof include a methoxy group, an ethoxy group, a propoxy group, a butoxy group, and a pentoxy group.

The term "$C_2$-$C_{60}$ alkenyl group" as used herein refers to a group formed by placing at least one carbon-carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a group formed by placing at least one carbon-carbon triple bond in the middle or at the terminus of the $C_2$-$C_{60}$ alkyl group. Examples thereof include an ethenyl group and a propenyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon cyclic group having 3 to 10 carbon atoms. The term "$C_3$-$C_{10}$ cycloalkylene group" as used herein refers to a divalent group having the same structure as the $C_3$-$C_{10}$ cycloalkyl group.

Examples of the $C_3$-$C_{10}$ cycloalkyl group as used herein include a cyclopropyl group, a cyclobutyl group, a cyclopentyl group, a cyclohexyl group, a cycloheptyl group, a cyclooctyl group, an adamantanyl group, a norbornanyl (bicyclo[2.2.1]heptyl) group, a bicyclo[1.1.1]pentyl group, a bicyclo[2.1.1]hexyl group, and a bicyclo[2.2.2]octyl group.

The term "$C_1$-$C_{10}$ heterocycloalkyl group" as used herein refers to a monovalent monocyclic group having 1 to 10 carbon atoms and at least one heteroatom of N, O, P, Si, S, Se, Ge, B, or any combination thereof as a ring-forming atom. The term "$C_1$-$C_{10}$ heterocycloalkylene group" as used herein refers to a divalent group having the same structure as the $C_1$-$C_{10}$ heterocycloalkyl group.

Examples of the $C_1$-$C_{10}$ heterocycloalkyl group as used herein may include a silolanyl group, a silinanyl group, a tetrahydrofuranyl group, a tetrahydro-2H-pyranyl group, or a tetrahydrothiophenyl group.

The term "$C_3$-$C_{10}$ cycloalkenyl group" as used herein refers to a monovalent monocyclic group that has 3 to 10 carbon atoms and at least one carbon-carbon double bond in its ring, wherein the molecular structure as a whole is non-aromatic. Examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group including at least one heteroatom of N, O, P, Si, S, Se, Ge, B, or any combination thereof as a ring-forming atom, 1 to 10 carbon atoms, and at least one double bond in its ring. Examples of the $C_1$-$C_{10}$ heterocycloalkenyl group include a 2,3-dihydrofuranyl group and a 2,3-dihydrothiophenyl group. The term "$C_1$-$C_{10}$ heterocycloalkylene group" as used herein refers to a divalent group having the same structure as the $C_1$-$C_{10}$ heterocycloalkyl group.

The term "$C_6$-$C_{60}$ aryl group" as used herein refers to a monovalent group having a carbocyclic aromatic system having 6 to 60 carbon atoms. The term "$C_6$-$C_{60}$ arylene group" as used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include a plurality of rings, the plurality of rings may be fused to each other.

The term "$C_1$-$C_{60}$ heteroaryl group" as used herein refers to a monovalent group having a heterocyclic aromatic system having at least one heteroatom of N, O, P, Si, S, Se, Ge, B, or any combination thereof as a ring-forming atom and 1 to 60 carbon atoms. The term "$C_1$-$C_{60}$ heteroarylene group" as used herein refers to a divalent group having a heterocyclic aromatic system having at least one heteroatom of N, O, P, Si, S, Se, Ge, or any combination thereof as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include a plurality of rings, the plurality of rings may be fused to each other.

The term "$C_6$-$C_{60}$ aryloxy group" as used herein is represented by $-OA_{102}$ (wherein $A_{102}$ is the $C_6$-$C_{60}$ aryl group). The term "$C_6$-$C_{60}$ arylthio group" as used herein is represented by $-SA_{103}$ (wherein $A_{103}$ is the $C_6$-$C_{60}$ aryl group).

The term "monovalent non-aromatic condensed polycyclic group" as used herein refers to a monovalent group having two or more rings condensed and only carbon atoms (for example, the number of carbon atoms may be in a range of 8 to 60) as ring-forming atoms, wherein the molecular structure as a whole is non-aromatic. Examples of the non-aromatic condensed polycyclic group include a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group having at least two rings condensed and a heteroatom N, O, P, Si, S, Se, Ge, B, or any combination thereof as well as carbon atoms (for example, the number of carbon atoms may be in a range of 1 to 60) as ring-forming atoms, wherein the molecular structure as a whole is non-aromatic. Examples of the monovalent non-aromatic condensed heteropolycyclic group include a carbazolyl group. The term "divalent non-aromatic condensed heteropolycyclic group" as used herein refers to a divalent group having substantially the same structure as the monovalent non-aromatic condensed heteropolycyclic group.

The term "π electron-depleted nitrogen-containing $C_1$-$C_{60}$ cyclic group" as used herein refers to a cyclic group having 1 to 60 carbon atoms and including at least one *—N=*' (wherein * and *' each indicate a binding site to an adjacent atom) as a ring-forming moiety. For example, the π electron-depleted nitrogen-containing $C_1$-$C_{60}$ cyclic group may be a) a first ring, b) a condensed ring in which at least two first rings are condensed, or c) a condensed ring in which at least one first ring and at least one second ring are condensed.

The term "π electron-rich $C_3$-$C_{60}$ cyclic group" as used herein refers to a cyclic group having 3 to 60 carbon atoms and not including at least one *—N=*' (wherein * and *' each indicate a binding site to an adjacent atom) as a ring-forming moiety. For example, the π electron-rich $C_3$-$C_{60}$ cyclic group may be a) a second ring or b) a condensed ring in which at least two second rings are condensed.

The "$C_5$-$C_{60}$ cyclic group" as used herein refers to a monocyclic or polycyclic group having 5 to 60 carbon atoms, e.g., a) a third ring or b) a condensed ring in which at least two third rings are condensed.

The "$C_1$-$C_{60}$ heterocyclic group" as used herein refers to a monocyclic or polycyclic group including at least one heteroatom and 1 to 60 carbon atoms, e.g., a) a fourth ring, b) a condensed ring in which at least two fourth rings are condensed, or c) a condensed ring in which at least one third ring is condensed with at least one fourth ring.

The "first ring" as used herein may be an imidazole group, a pyrazole group, a thiazole group, an isothiazole group, an oxazole group, an isoxazole group, a pyridine group, a pyrazine group, a pyridazine group, a pyrimidine group, a triazole group, a tetrazole group, an oxadiazole group, a triazine group, or a thiadiazole group.

The "second ring" as used herein may be a benzene group, a cyclopentadiene group, a pyrrole group, a furan group, a thiophene group, or a silole group.

The "third ring" as used herein may be a cyclopentane group, a cyclopentadiene group, an indene group, an adamantane group, a norbornene group, a bicyclo[1.1.1]pentane group, a bicyclo[2.1.1]hexane group, a bicyclo[2.2.1]heptane group (a norbornane group), a bicyclo[2.2.2]octane group, a cyclohexane group, a cyclohexene group, or a benzene group.

The "fourth ring" as used herein may be a furan group, a thiophene group, a pyrrole group, a silole group, an oxazole group, an isoxazole group, an oxadiazole group, an isooxadiazole group, oxatriazole group, an isooxatriazole group, a thiazole group, an isothiazole group, a thiadiazole group, an isothiadiazole group, a thiatriazole group, an isotriazole group, a pyrazole group, an imidazole group, a triazole group, a tetrazole group, an azasilole group, a diazasilole group, a trazasilole group, a pyridine group, a pyrimidine group, a pyrazine group, a pyridazine group, or a triazine group.

In some embodiments, the π electron-depleted nitrogen-containing $C_1$-$C_{60}$ cyclic group may be an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azacarbazole group, an azadibenzofuran group, an azadibenzothiophene group, an azadibenzosilole group, an acridine group, or a pyridopyrazine group.

In one or more embodiments, the π electron-rich $C_3$-$C_{60}$ cyclic group may be a benzene group, a heptalene group, an indene group, a naphthalene group, an azulene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, a furan group, a thiophene group, an isoindole group, an indole group, an indene group, a benzofuran group, a benzothiophene group, a benzosilole group, a naphthopyrrole group, a naphthofuran group, a naphthothiophene group, a naphthosilole group, a benzocarbazole group, a dibenzocarbazole group, a dibenzofuran group, a dibenzothiophene group, a carbazole group, a dibenzosilole group, an indenocarbazole group, an indolocarbazole group, a benzofurocarbazole group, a benzothienocarbazole group, a benzosilolocarbazole group, a triindolobenzene group, a pyrrolophenanthrene group, a furanophenanthrene group, a thienophenanthrene group, a benzonaphthofuran group, a benzonapthothiophene group, an (indolo)phenanthrene group, a (benzofurano)phenanthrene group, or a (benzothieno)phenanthrene group.

For example, the $C_5$-$C_{60}$ carbocyclic group may be a cyclopentane group, a cyclohexane group, a cyclohexene group, a benzene group, a naphthalene group, an anthracene group, a phenanthrene group, a triphenylene group, a pyrene group, a chrysene group, a 1,2,3,4-tetrahydronaphthalene group, a cyclopentadiene group, an indene group, a fluorene group, a 5,6,7,8-tetrahydroisoquinoline group, a 5,6,7,8-tetrahydroquinoline group, an adamantane group, a norbornane group, or a norbornene group.

For example, the $C_1$-$C_{60}$ heterocyclic group may be a thiophene group, a furan group, a pyrrole group, a cyclopentadiene group, a silole group, a borole group, a phosphole group, a selenophene group, a germole group, a benzothiophene group, a benzofuran group, an indole group, an indene group, a benzosilole group, a benzoborole group, a benzophosphole group, a benzoselenophene group, a benzogermole group, a dibenzothiophene group, a dibenzofuran group, a carbazole group, a dibenzosilole group, a dibenzoborole group, a dibenzophosphole group, a dibenzoselenophene group, a dibenzogermole group, a dibenzothiophene 5-oxide group, a 9H-fluorene-9-one group, a dibenzothiophene 5,5-dioxide group, an azabenzothiophene group, an azabenzofuran group, an azaindole group, an azaindene group, an azabenzosilole group, an azabenzoborole group, an azabenzophosphole group, an azabenzoselenophene group, an azabenzogermole group, an azadibenzothiophene group, an azadibenzofuran group, an azacarbazole group, an azafluorene group, an azadibenzosilole group, an azadibenzoborole group, an azadibenzophosphole group, an azadibenzoselenophene group, an azadibenzogermole group, an azadibenzothiophene 5-oxide group, an aza-9H-fluoren-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrazole group, an imidazole group, a triazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, or a benzothiadiazole group.

The π electron-depleted nitrogen-containing $C_1$-$C_{60}$ cyclic group, a the π electron-rich $C_3$-$C_{60}$ cyclic group, the $C_5$-$C_{60}$ cyclic group, and the $C_1$-$C_{60}$ heterocyclic group may each be a part of a condensed ring or a monovalent, divalent, trivalent, quadrivalent, pentavalent, or hexavalent, group, depending on the structure of the formula.

A substituent of the substituted π electron-depleted nitrogen-containing $C_1$-$C_{60}$ cyclic group, the substituted π electron-rich $C_3$-$C_{60}$ cyclic group, the substituted $C_6$-$C_{60}$ cyclic group, the substituted $C_1$-$C_{60}$ heterocyclic group, the substituted $C_1$-$C_{60}$ alkylene group, the substituted $C_2$-$C_{60}$ alkenylene group, the substituted $C_2$-$C_{60}$ alkynylene group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may each independently be:

deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, $—CD_3$, $—CD_2H$, $—CDH_2$, $—CF_3$, $—CF_2H$, $—CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkylheteroaryl group, a monovalent non-aromatic condensed polycyclic group, a monovalent non-aromatic condensed heteropolycyclic group, $—N(Q_{11})(Q_{12})$, $—Si(Q_{13})(Q_{14})(Q_{15})$, $—Ge(Q_{13})(Q_{14})(Q_{15})$, $—B(Q_{16})(Q_{17})$, $—P(=O)(Q_{18})(Q_{19})$, $—P(Q_{18})(Q_{19})$, or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a monovalent non-aromatic condensed polycyclic group, or a monovalent non-aromatic condensed heteropolycyclic group, each unsubstituted or substituted with deuterium, —F, —Cl, —Br, —I, $-CD_3$, $-CD_2H$, $-CDH_2$, $-CF_3$, $-CF_2H$, $-CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkyl heteroaryl group, a monovalent non-aromatic condensed polycyclic group, a monovalent non-aromatic condensed heteropolycyclic group, $-N(Q_{21})(Q_{22})$, $-Si(Q_{23})(Q_{24})(Q_{25})$, $-Ge(Q_{23})(Q_{24})(Q_{25})$, $-B(Q_{26})(Q_{27})$, $-P(=O)(Q_{28})(Q_{29})$, $-P(Q_{28})(Q_{29})$, or any combination thereof;

$-N(Q_{31})(Q_{32})$, $-Si(Q_{33})(Q_{34})(Q_{35})$, $-Ge(Q_{33})(Q_{34})(Q_{35})$, $-B(Q_{36})(Q_{37})$, $-P(=O)(Q_{38})(Q_{39})$, or $-P(Q_{38})(Q_{39})$; or any combination thereof.

$Q_1$ to $Q_9$, $Q_{11}$ to $Q_{19}$, $Q_{21}$ to $Q_{29}$, and $Q_{31}$ to $Q_{39}$ may each independently be: hydrogen; deuterium; —F; —Cl; —Br; —I; a hydroxyl group; a cyano group; a nitro group; an amidino group; a hydrazine group; a hydrazone group; a carboxylic acid group or a salt thereof; a sulfonic acid group or a salt thereof; a phosphoric acid group or a salt thereof; a $C_1$-$C_{60}$ alkyl group unsubstituted or substituted with deuterium, a $C_1$-$C_{60}$ alkyl group, a $C_6$-$C_{60}$ aryl group, or any combination thereof; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group unsubstituted or substituted with deuterium, a $C_1$-$C_{60}$ alkyl group, a $C_6$-$C_{60}$ aryl group, or any combination thereof; a $C_6$-$C_{60}$ aryloxy group; a $C_6$-$C_{60}$ arylthio group; a $C_1$-$C_{60}$ heteroaryl group; a monovalent non-aromatic condensed polycyclic group; or a monovalent non-aromatic condensed heteropolycyclic group.

For example, $Q_1$ to $Q_9$, $Q_{11}$ to $Q_{19}$, $Q_{21}$ to $Q_{29}$, and $Q_{31}$ to $Q_{39}$ may each independently be:

$-CH_3$, $-CD_3$, $-CD_2H$, $-CDH_2$, $-CH_2CH_3$, $-CH_2CD_3$, $-CH_2CD_2H$, $-CH_2CDH_2$, $-CHDCH_3$, $-CHDCD_2H$, $-CHDCDH_2$, $-CHDCD_3$, $-CD_2CD_3$, $-CD_2CD_2H$, or $-CD_2CDH_2$; an n-propyl group, an isopropyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, a phenyl group, a biphenyl group, or a naphthyl group, each unsubstituted or substituted with deuterium, a $C_1$-$C_{10}$ alkyl group, a phenyl group, or any combination thereof.

The term "room temperature" as used herein refers to a temperature of about 25° C.

The terms "a biphenyl group, a terphenyl group, and a tetraphenyl group" as used herein each refer to a monovalent group having two, three, and four phenyl groups linked via a single bond, respectively.

The terms "a cyano group-containing phenyl group, a cyano group-containing biphenyl group, a cyano group-containing terphenyl group, and a cyano group-containing tetraphenyl group" as used herein each refer to a phenyl group, a biphenyl group, a terphenyl group, and a tetraphenyl group, each substituted with at least one cyano group. In "the cyano group-containing phenyl group, the cyano group-containing biphenyl group, the cyano group-containing terphenyl group, and the cyano group-containing tetraphenyl group", a cyano group may be substituted at any position, and "the cyano group-containing phenyl group, the cyano group-containing biphenyl group, the cyano group-containing terphenyl group, and the cyano group-containing tetraphenyl group" may further include a substituent in addition to a cyano group. For example, 'a phenyl group substituted with a cyano group' and 'a phenyl group substituted with a methyl group' all belong to "a cyano group-containing phenyl group".

Hereinafter, a compound and an organic light-emitting device according to an embodiment will be described in detail with reference to Synthesis Examples and Embodiments, however, the present disclosure is not limited thereto. The wording "B was used instead of A" used in describing Synthesis Examples means that an identical molar equivalent of B was used in place of A.

EXAMPLES

Synthesis Example 1 (Compound 119)

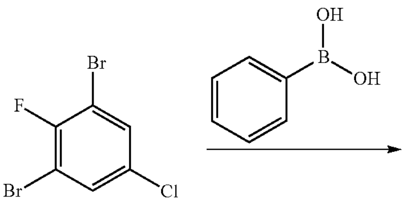

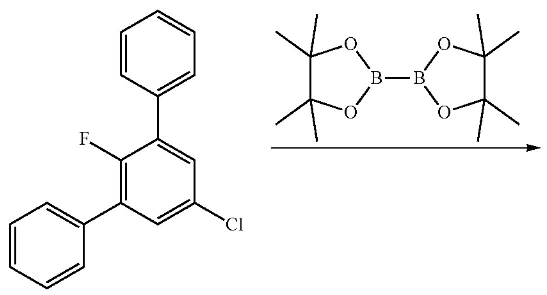

119a

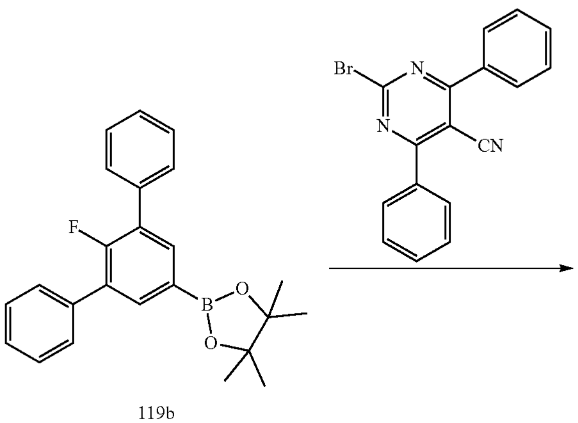

119b

-continued

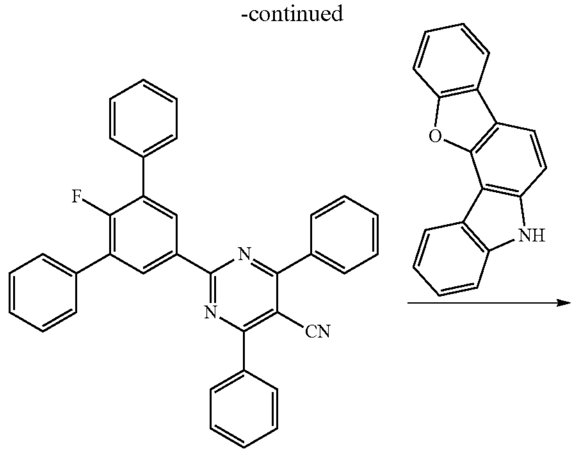

119c

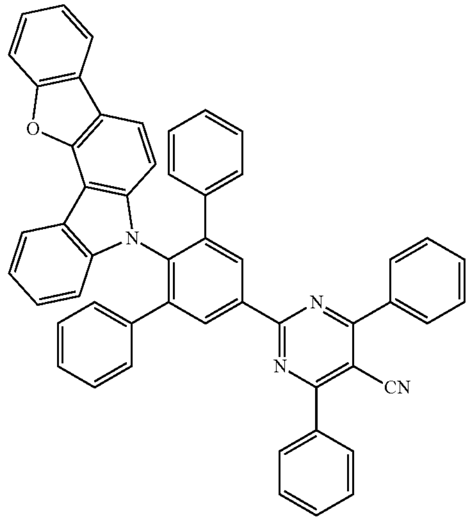

119

Synthesis of Intermediate 119a 63.43 grams (g) (520.22 millimole (mmol)) of phenylboronic acid, 50 g (173.41 mmol) of 1,3-dibromo-5-chloro-2-fluorobenzonitrile, 20.04 g (17.34 mmol) of palladium tetrakis(triphenylphosphine) ($Pd(PPh_3)_4$), 95.87 g (693.63 mmol) of potassium carbonate ($K_2CO_3$) and 14.24 g (34.68 mmol) of S-phos were added to 300 milliliters (mL) of tetrahydrofuran and 300 mL of distilled water, followed by heating under reflux. Once the reaction was complete, the resulting mixture was cooled to room temperature. Then an organic layer was extracted therefrom using ethyl acetate, and the resulting organic layer was dried using anhydrous sodium sulfate ($Na_2SO_4$) for concentration, followed by separation through silica gel column chromatography (dichloromethane/hexane). The solid resulting therefrom was recrystallized using hexane to thereby obtain 40.7 g (143.81 mmol) of white solid, Intermediate 119a (yield: 83%).

Synthesis of Intermediate 119b 40.7 g (143.81 mmol) of Intermediate 119a, 54.78 g (215.71 mmol) of bis(pinacolato)diboron, 35.29 g (359.52 mmol) of potassium acetate, 13.17 g (14.38 mmol) of tris(dibenzylideneacetone)dipalladium(0) ($Pd_2(dba)_3$), and 4.03 g (14.38 mmol) of tricyclohexylphosphine were added to 290 mL of dioxane, followed by heating under reflux. Once the reaction was complete, the resulting mixture was cooled to room temperature, followed by adding excess toluene for dissolution. Then, the solution was passed through a silica gel column. The eluent resulting therefrom was concentrated, followed by adding hexane thereto for precipitation. Then, the mixture was filtered to thereby obtain 47.0 g (125.58 mmol) of a white solid, Intermediate 119b (yield: 87%).

Synthesis of Intermediate 119c 18.0 g (53.54 mmol) of 2-bromo-4,6-diphenylpyrimidine-5-carbonitrile, 24.04 g (64.25 mmol) of Intermediate 119b, 3.09 g (2.68 mmol) of palladium tetrakis(triphenylphosphine) ($Pd(PPh_3)_4$), 14.80 g (107.08 mmol) of potassium carbonate ($K_2CO_3$) and 4.39 g (10.71 mmol) of S-phos were added to 90 mL of tetrahydrofuran and 90 mL of distilled water, followed by heating under reflux. Once the reaction was complete, the resulting mixture was cooled to room temperature, followed by adding methanol thereto. Then, the solution was passed through a silica gel column. The eluent was concentrated, followed by adding methanol thereto for precipitation. Then, a filtration process was performed thereon to thereby obtain 25.3 g (53.54 mmol) of a white solid, Intermediate 119c (yield: 94%).

Synthesis of Compound 119

5.20 g (10.33 mmol) of Intermediate 119c, 2.92 g (11.36 mmol) of 5H-benzofuro[3,2-c]carbazole, and 6.73 g (20.65 mmol) of cesium carbonate ($CS_2CO_3$) were added to 30 mL of N,N-dimethylformamide, followed by stirring at a temperature of 160° C. for 12 hours. Once the reaction was complete, the resulting mixture was cooled to room temperature, followed by adding methanol thereto. Then, the solution was passed through a silica gel column. The eluent was concentrated, followed by dissolution by toluene again, and then the solution was passed through another silica gel column and for concentrated. The resulting product was recrystallized using toluene to thereby synthesize a yellow solid, 3.56 g of Compound 119 (yield: 47%).

LC-Mass (calculated value: 740.87 g/mol, found value: 740.9 g/mol ($M^{+1}$))

Synthesis Example 2 (Compound 95)

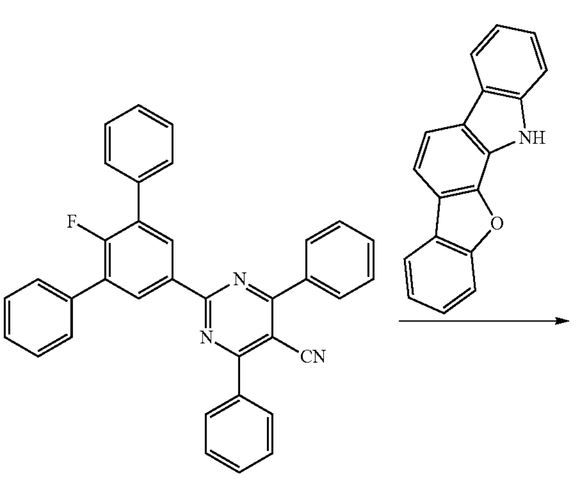

119c

-continued

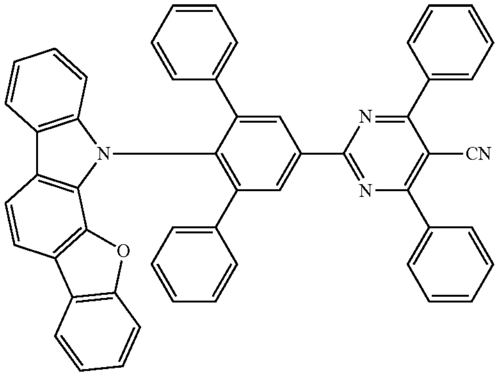

95

2.4 g of Compound 95 (yield: 31%) was synthesized in substantially the same manner as in Synthesis of Compound 119 in Synthesis Example 1, except that 12H-benzofuro[2,3-a]carbazole was used instead of 5H-benzofuro[3,2-c]carbazole).

LC-Mass (calculated value: 740.87 g/mol, found value: 740.9 g/mol ($M^{+1}$))

Synthesis Example 3 (Compound 201)

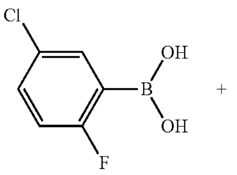

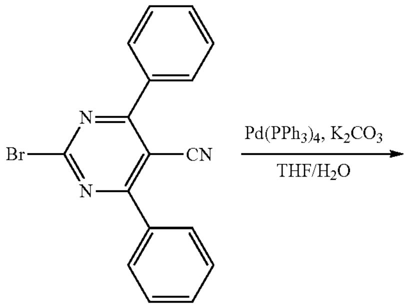

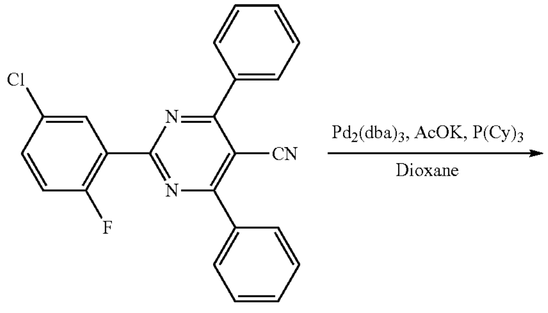

201a

-continued

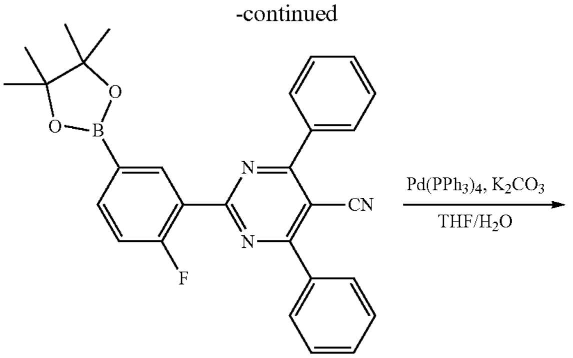

201b

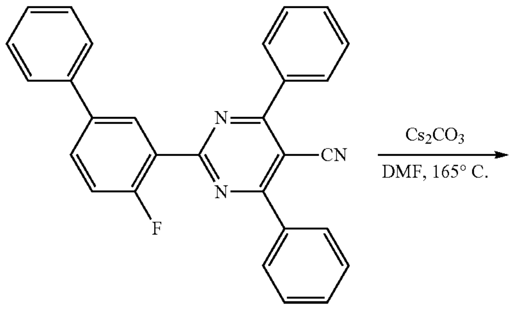

201c

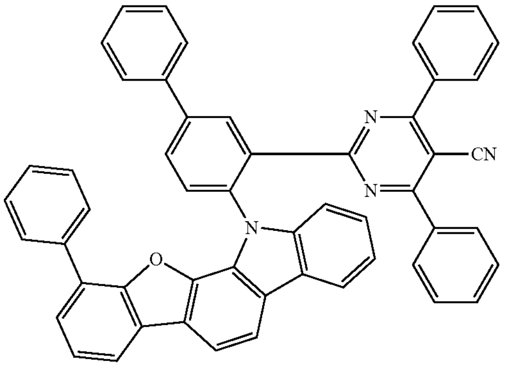

201

Synthesis of Intermediate 201(a)

15.30 g of Intermediate 201a (yield: 74%) was synthesized in substantially the same manner as in Synthesis of Intermediate 119c in Synthesis Example 1, except that (5-chloro-2-fluorophenyl)boronic acid was used instead of Intermediate 119b.

LC-Mass (calculated value: 385.8 g/mol, found value: 386.9 g/mol ($M^{-1}$)) Synthesis of Intermediate 201b 15.0 g (38.88 mmol) of Intermediate 201a, 14.8 g (58.32 mmol) of bis(pinacolato)diboron, 9.54 g (97.19 mmol) of potassium acetate (AcOK), 3.56 g (3.89 mmol) of tris (dibenzylideneacetone)dipalladium ($Pd_2(dba)_3$), and 1.09 g (3.89 mmol) of tricyclohexylphosphine ($P(Cy)_3$)) were added to a reaction vessel, followed by dissolution by 80 mL of dioxane and stirring at a temperature of 120° C. Once the reaction was complete, the resulting mixture was cooled to room temperature, and an extraction process was performed by using ethyl acetate and water to thereby obtain an organic layer. The obtained organic layer was subjected to filtration through silica gel column chromatography and concentrated. The resulting solid compound (Intermediate 201 b) was used in the following reaction without any further purification process. (17.1 g, yield: 92%)

LC-Mass (calculated value: 477.3 g/mol, found value: 477.4 g/mol (M+1))

Synthesis of Intermediate 201c 12.8 g of Compound 201c (yield: 83%) was synthesized in the same manner as in Synthesis of Intermediate 119a in Synthesis Example 1, except that Intermediate 201b was used instead of 1,3-dibromo-5-chloro-2-fluorobenzonitrile.

LC-Mass (calculated value: 427.4 g/mol, found value: 427.5 g/mol (M+1))

Synthesis of Compound 201

3.1 g of Compound 201 (yield: 34%) was synthesized in substantially the same manner as in Synthesis of Compound 119 in Synthesis Example 1, except that 10-phenyl-12H-benzofuro[2,3-a]carbazole and Intermediate 201c were respectively used instead of 5H-benzofuro[3,2-c]carbazole and Intermediate 119c.

LC-Mass (calculated value: 740.87 g/mol, found value: 741.8 g/mol ($M^{+1}$))

Evaluation Example 1: Evaluation on HOMO, LUMO, $T_1$, and $S_1$ Energy Levels The HOMO, LUMO, $T_1$ and $S_1$ energy levels of the compounds shown in Table 2 were measured according to the method described in Table 1. The results thereof are shown in Table 2:

TABLE 1

| | |
|---|---|
| HOMO energy level evaluation method | A potential (Volts, V) versus current (Amperes, A) graph of each compound was obtained by using cyclic voltammetry (CV) (electrolyte: 0.1 molar (M) $Bu_4NPF_6$/solvent: $CH_2Cl_2$/ electrode: 3-electrode system (working electrode: glassy carbon, reference electrode: Ag/AgCl, auxiliary electrode: Pt)). Subsequently, from oxidation onset of the graph, a HOMO energy level of the compound was calculated. |
| LUMO energy level evaluation method | Each compound was diluted at a concentration of 1 × $10^{-5}$M in Toluene, and an UV absorption spectrum thereof was measured at room temperature by using a Shimadzu UV-350 spectrometer. A LUMO energy level thereof was calculated by using an optical band gap (Eg) from an edge of the absorption spectrum and a HOMO energy level. |
| $T_1$ energy level evaluation method | A mixture (each compound was dissolved in 3 mL of toluene such that the concentration of each compound was 1 × $10^{-4}$M) of toluene and each compound was loaded into a quartz cell. Subsequently, the resultant quartz cell was loaded into liquid nitrogen (77 Kelvins (K)), a photoluminescence spectrum thereof was measured by using a device for measuring photoluminescence. The obtained spectrum was compared with a photoluminescence spectrum measured at room temperature, and peaks observed only at a low temperature were analyzed to calculate onset $T_1$ energy levels. |
| $S_1$ energy level evaluation method | A photoluminescence spectrum of a mixture of each compound, diluted with toluene at a concentration of about 1 × $10^{-4}$M, was measured by using a device for measuring photoluminescence at room temperature. The observed peaks were analyzed to calculate onset S1 energy levels. |

TABLE 2

| Compound No. | HOMO (eV) | LUMO (eV) | $T_1$ (eV) | $S_1$ (eV) | $\Delta E_{ST}$ (eV) |
|---|---|---|---|---|---|
| 119 | −5.265 | −2.349 | 2.594 | 2.627 | 0.033 |
| 95 | −5.38 | −2.285 | 2.599 | 2.768 | 0.169 |
| 201 | −5.37 | −2.08 | 2.5 | 2.535 | 0.035 |

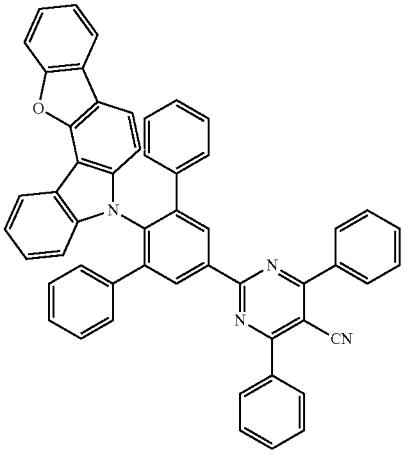

119

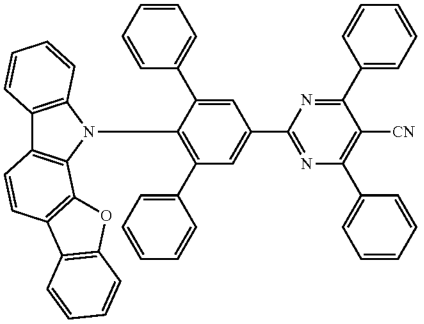

95

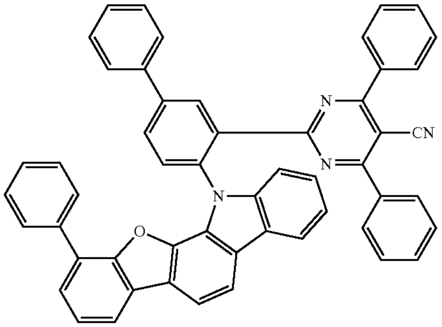

201

Referring to the results of Table 2, the compounds shown in Table 2 are found to have excellent electrical characteristics.

Evaluation Example 2: Evaluation of Full Width at Half Maximum (FWHM)

As the method described in Table 3, photoluminescence spectra of the compounds shown in Table 4 were measured, and the FWHM of each compound was evaluated. The results thereof are shown in Table 4.

TABLE 3

| | |
|---|---|
| Measurement of photoluminescence (PL) spectrum | Each compound was dissolved at a concentration of $10^{-4}$M, and then a F7000 spectrofluorometer (available from Hitachi) in which a Xenon lamp was mounted was used to measure a PL spectrum (@ 298K) of each compound. |

TABLE 4

| Compound No. | FWHM (nm) |
|---|---|
| 119 | 70 |
| 95 | 64 |
| 201 | 82 |

Referring to the results of Table 4, the compounds shown in Table 4 are found to have excellent emission characteristics.

Evaluation Example 3: Evaluation of Photoluminescent Quantum Yield (PLQY) and Decay Time (1) Preparation of Thin Film A quartz substrate was prepared by washing with chloroform and distilled water. Then, the compounds shown in Table 5 were each co-deposited with Compound H3 (Compound 3 in Group HE4) at a weight ratio of 5:5 at a vacuum pressure of $10^{-7}$ torr to prepare a thin film having a thickness of 50 nm.

(2) Evaluation of Photoluminescent Quantum Yield

Photoluminescent quantum yields in the thin film was evaluated by using Hamamatsu Photonics absolute PL quantum yield measurement system employing PLQY measurement software (Hamamatsu Photonics, Ltd., Shizuoka, Japan), in which a xenon light source, a monochromator, a photonic multichannel analyzer, and an integrating sphere are mounted. Thus, PLQY in film of the compounds shown in Table 5 were measured accordingly.

(3) Decay Time Evaluation

The PL spectrum of each thin film was evaluated at room temperature by using a time-resolved photoluminescence (TRPL) measurement system, FluoTime 300 (available from PicoQuant), and a pumping source, PLS340 (available from PicoQuant, excitation wavelength=340 nm, spectral width=20 nm). Then, a wavelength of the main peak in the PL spectrum was determined, and upon photon pulses (pulse width=500 picoseconds, ps) applied to the thin film by PLS340, the number of photons emitted at the wavelength of the main peak for each thin film was repeatedly measured over time by time-correlated single photon counting (TCSPC), thereby obtaining TRPL curves available for the sufficient fitting. $T_{decay}$(Ex) (decay time) of the thin film was obtained by fitting at least two exponential decay functions to the results thereof. The functions used for the fitting are as described in Equation 1, and a decay time $T_{decay}$ having the largest value among values for each of the exponential decay functions used for the fitting was taken as $T_{decay}$(Ex), i.e., a decay time. The results thereof are shown in Table 5. The remaining decay time $T_{decay}$ values were used to determine the lifetime of typical fluorescence to be decayed. Here, during the same measurement time as the measurement time for obtaining TRPL curves, the same measurement was repeated once more in a dark state (i.e., a state where a pumping signal incident on each of the films was blocked), thereby obtaining a baseline or a background signal curve available as a baseline for the fitting:

$$f(t) = \sum_{i=1}^{n} A_i \exp(-t / T_{decay,i}) \quad \text{Equation 1}$$

TABLE 5

| Compound No. | PLQY | $T_{decay}$(Ex) (μs) (decay time) |
|---|---|---|
| 119 | 80 | 21.4 |
| 95 | 63 | 31.6 |
| 201 | 32 | 5.12 |

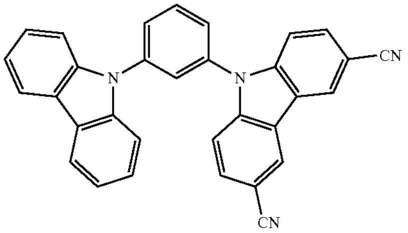

H3

Referring to the results of Table 5, the compounds shown in Table 5 are found to have excellent PLQY (in film) and decay time characteristics.

Example 1

A glass substrate having an indium tin oxide (ITO) electrode (a first electrode, an anode) deposited thereon at a thickness of 1,500 Å was washed with distilled water in the presence of ultrasound waves. Once the washing with distilled water was complete, ultrasound wave washing was performed on the substrate using solvents, such as isopropyl alcohol, acetone, and methanol. Subsequently, the substrate was dried, transferred to a plasma washer, washed for 5 minutes using oxygen plasma, and mounted in a vacuum depositor.

Compound HT1 and Compound HT-D2 were co-deposited on the ITO electrode of the glass substrate to form a hole injection layer having a thickness of 100 Å. Subsequently, Compound HT1 was deposited on the hole injection layer to form a hole transport layer having a thickness of 1,350 Å. mCP was next deposited on the hole transport layer to form an electron blocking layer having a thickness of 100 Å, thereby forming a hole transport region.

A host (Compound H3 (Compound 3 in Group HE4)) and an emitter (Compound 119) were co-deposited on the hole transport region at a volumetric ratio of 85:15 to form an emission layer having a thickness of 300 Å.

BCP was vacuum deposited on the emission layer to form a hole blocking layer having a thickness of about 100 Å. Compound ET27 and Liq were then co-deposited on the hole blocking layer to form an electron transport layer having a thickness of about 300 Å. Next, Liq was deposited on the electron transport layer to form an electron injection layer having a thickness of about 10 Å, and then, aluminum (Al) second electrode (a cathode) having a thickness of 1,000 Å was formed on the electron injection layer, thereby completing the manufacture of an organic light-emitting device.

HT1

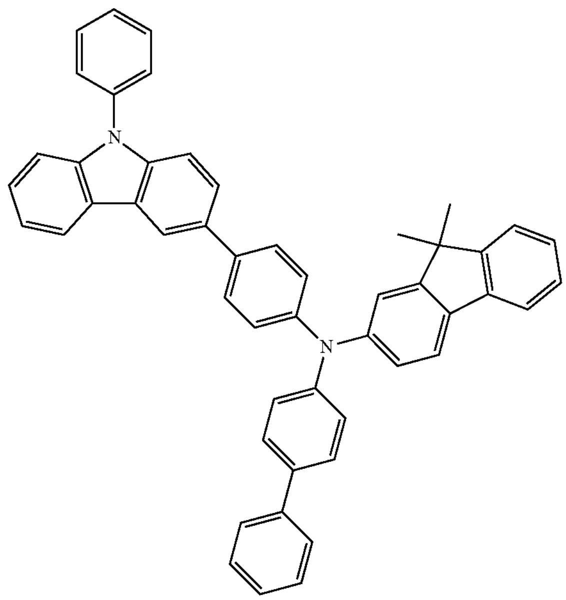

HT-D2

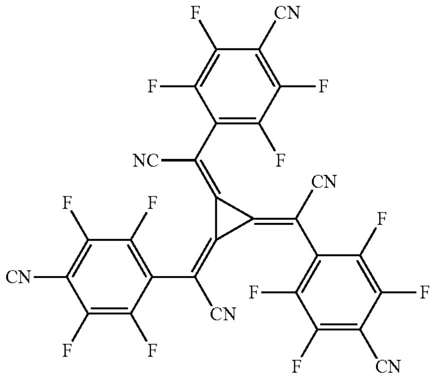

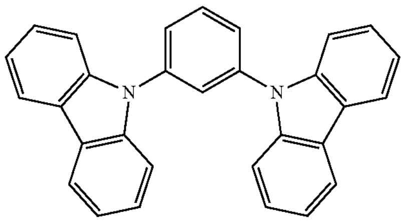

mCP

H3

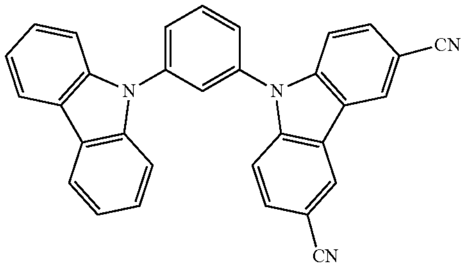

-continued

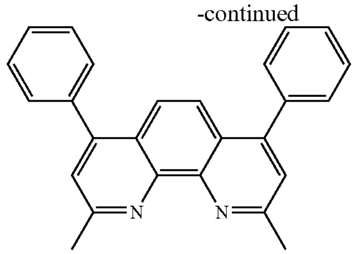

BCP

ET27

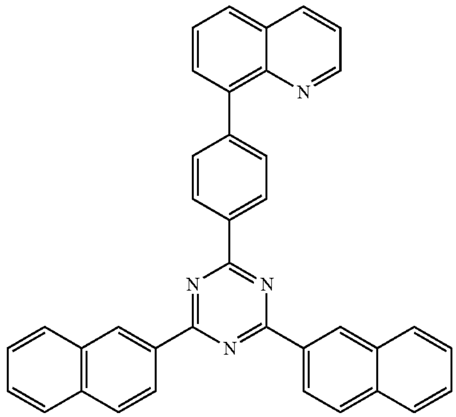

Examples 2 and 3 and Comparative Examples A, B1, and B2

Organic light-emitting devices were manufactured in substantially the same manner as in Example 1, except that materials shown in Table 6 were used in the formation of emission layer as an emitter.

Evaluation Example 4: Device Data Evaluation

The driving voltage, emission efficiency, lifespan ($T_{95}$) of the organic light-emitting devices manufactured in Examples 1 to 3 and Comparative Examples A, B1, and B2 were measured by using a current voltmeter (Keithley 2400) and a luminance meter (Minolta Cs-1000A). The evaluation results are shown in Table 6. In Table 6, $T_{95}$ is lifespan data evaluating a period (hours) taken for the luminance (at 500 candelas per square meter (cd/$m^2$)) to reach 95% with respect to 100% of the initial luminance. The emission efficiency and lifespan are shown in relative values based on the emission efficiency and lifespan of the organic light-emitting device prepared in Comparative Example A.

TABLE 6

| | Emitter No. | Driving voltage (V) | Emission efficiency (relative value, %) | Lifespan ($T_{95}$) (relative value, %) |
|---|---|---|---|---|
| Example 1 | 119 | 4.81 | 161 | 625 |
| Example 2 | 95 | 6.23 | 100 | 100 |
| Example 3 | 201 | 4.05 | 107 | 48 |
| Comparative Example A | A | 6.03 | 36 | 2.44 |
| Comparative Example B1 | B1 | 4.04 | 76 | 39 |
| Comparative Example B2 | B2 | 7.59 | 74 | 1.1 |

TABLE 6-continued

| Emitter No. | Driving voltage (V) | Emission efficiency (relative value, %) | Lifespan ($T_{95}$) (relative value, %) |
|---|---|---|---|
| 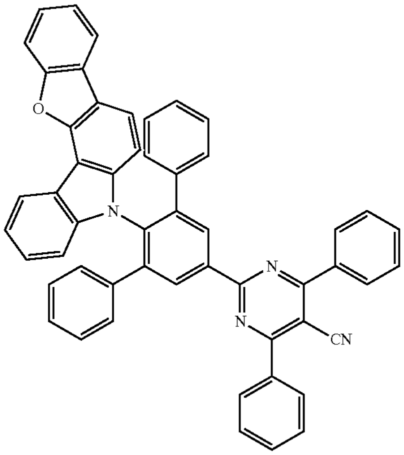 119 | | | |
| 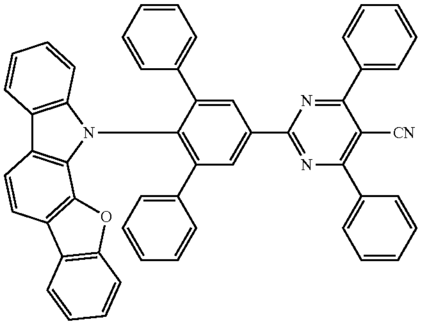 95 | | | |
| 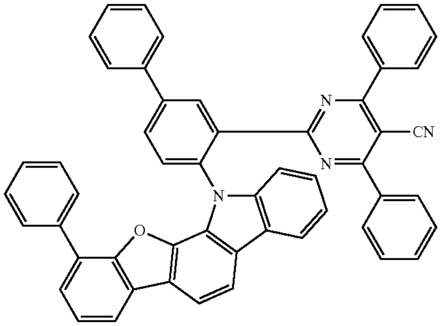 201 | | | |
| 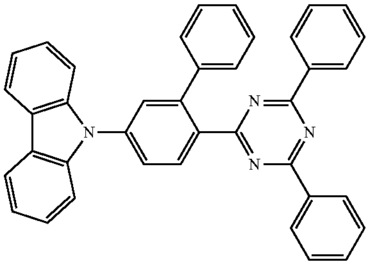 A | | | |
| 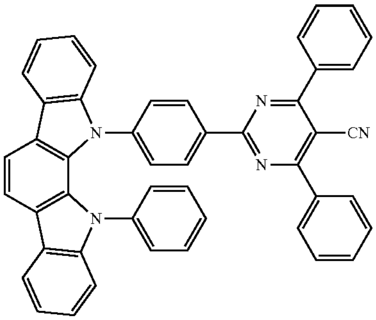 B1 | | | |
| 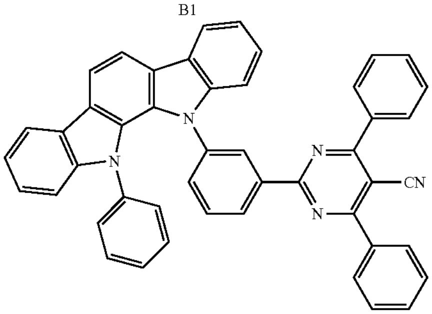 B2 | | | |

Referring to the results of Table 6, the organic light-emitting devices prepared in Examples 1 to 3 were found to have improved emission efficiency and lifespan, as compared with the organic light-emitting devices prepared in Comparative Examples A, B1, and B2.

Example 11

A glass substrate, on which an ITO electrode was formed, was cut to a size of 50 millimeters (mm)×50 mm×0.5 mm. Then the glass substrate was sonicated in acetone isopropyl alcohol and pure water for about 15 minutes in each solvent and cleaned by exposure to ultraviolet rays with ozone for 30 minutes.

Subsequently, HAT-CN was deposited on the ITO electrode (anode) of the glass substrate to form a hole injection layer having a thickness of 100 Å, NPB was deposited on the hole injection layer to form a first hole transport layer having a thickness of 500 Å, TCTA was deposited on the first hole transport layer to form a second hole transport layer having a thickness of 50 Å, and mCP was deposited on the second hole transport layer to form an electron blocking layer having a thickness of 50 Å.

A first host (H1), a second host (H2), a sensitizer (Compound 119), and a fluorescence emitter (FD11) were co-deposited on the electron blocking layer to form an emission layer having a thickness of 400 Å. Here, a weight ratio of the first host to the second host to the sensitizer was 60:40:10, and the content of the fluorescence emitter was controlled to be 1.5 wt %, based on the total weight of the first host, the second host, the sensitizer, and the fluorescence emitter.

DBFPO was deposited on the emission layer to form a hole blocking layer having a thickness of 100 Å. DBFPO and LiQ were co-deposited on the hole blocking layer at a weight ratio of 5:5 to form an electron transport layer having a thickness of 300 Å. LiQ was deposited on the electron transport layer to form an electron injection layer having a thickness of 10 Å. Aluminum (Al) was deposited on the electron injection layer to form cathode having a thickness of 1000 Å, thereby completing the manufacture of an organic light-emitting device.

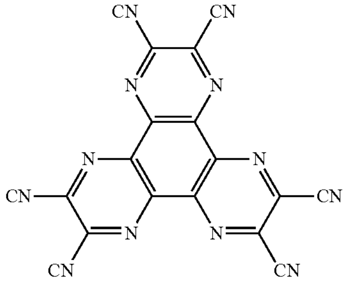

HT-D1(HAT-CN)

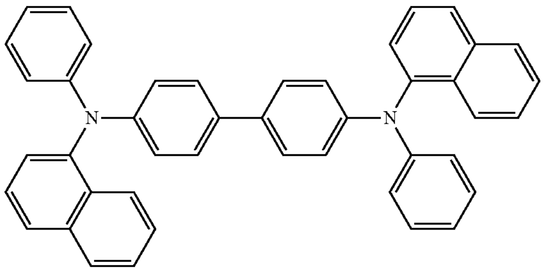

NPB

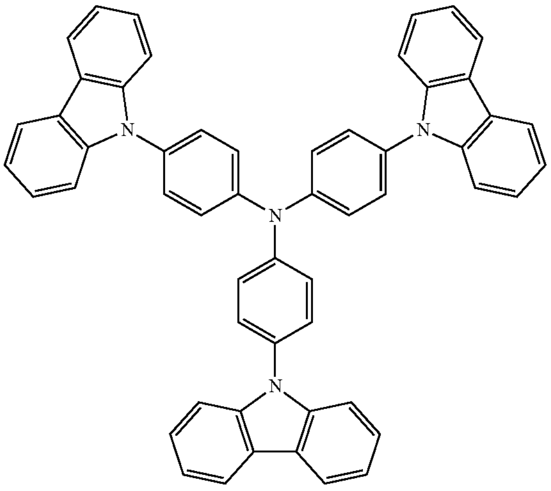

TCTA

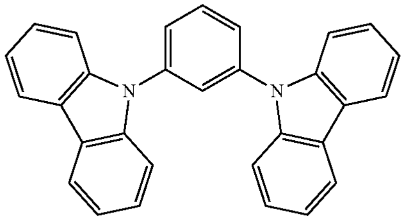

mCP

-continued

H1

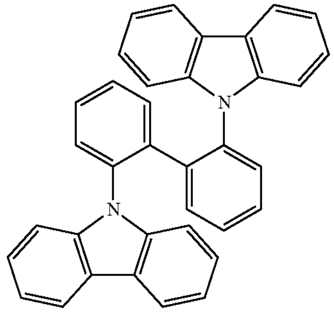

H2

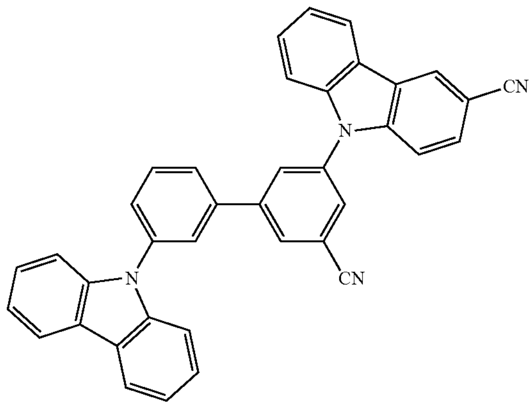

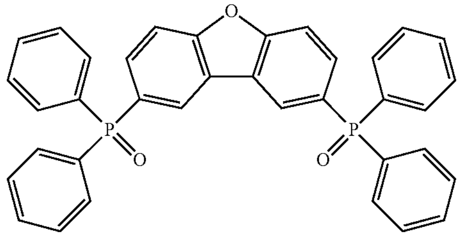

DBFPO

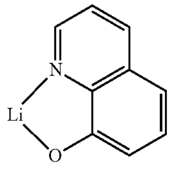

Liq

Examples 12 to 13

Organic light-emitting devices were manufactured in substantially the same manner as in Example 11, except that sensitizers shown in Table 7 were used in the emission layer.

Evaluation Example 5: Device Data Evaluation

The driving voltage, emission efficiency, lifespan ($T_{95}$) of the organic light-emitting devices manufactured in Examples 11 to 13 were measured in the same manner as in Evaluation Example 4 by using a current voltmeter (Keithley 2400) and a luminance meter (Minolta Cs-1000A). The evaluation results are shown in Table 7. The emission efficiency and lifespan shown in Table 7 are shown in relative values based on the emission efficiency and lifespan of the organic light-emitting device prepared in Comparative Example A.

TABLE 7

| | Sensitizer No. | Emitter No. | Driving voltage (V) | Emission efficiency (relative value, %) | Lifespan ($T_{95}$) (relative value, %) |
|---|---|---|---|---|---|
| Example 11 | 119 | FD11 | 7.73 | 100 | 241 |
| Example 12 | 95 | FD11 | 8.34 | 66 | 100 |
| Example 13 | 201 | FD11 | 4.03 | 460 | 13 |

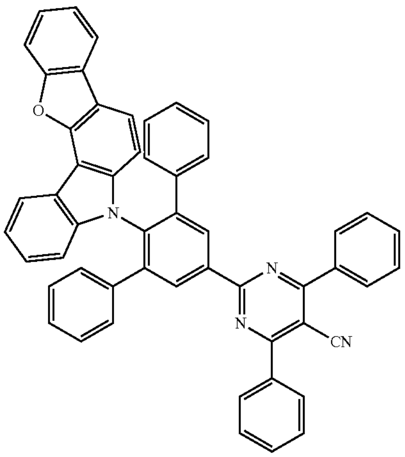

119

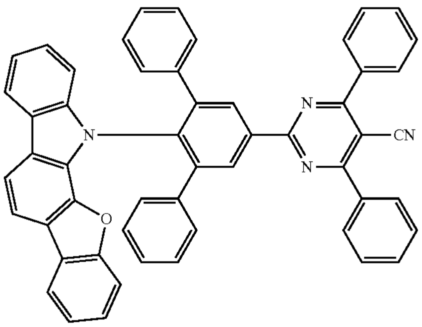

95

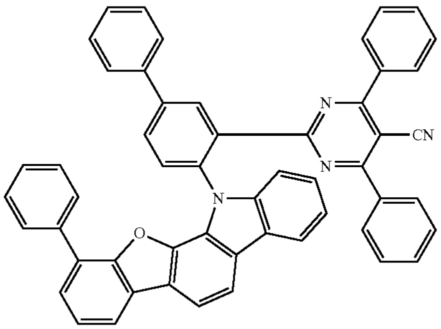

201

TABLE 7-continued

| Sensitizer No. | Emitter No. | Driving voltage (V) | Emission efficiency (relative value, %) | Lifespan ($T_{95}$) (relative value, %) |
|---|---|---|---|---|

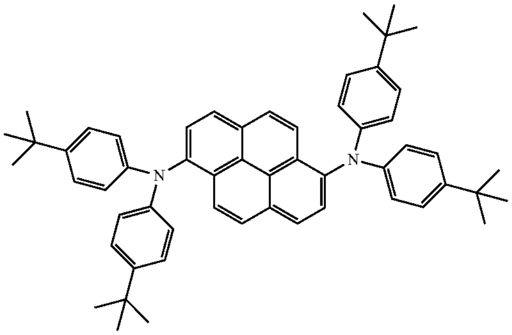

FD11

Referring to the results of Table 7, the organic light-emitting devices prepared in Examples 11 to 13 were found to have improved emission efficiency and lifespan simultaneously.

As apparent from the foregoing description, when the heterocyclic compound represented by Formula 1 is used, an organic light-emitting device having high emission efficiency and long lifespan characteristics and an electronic apparatus including the organic light-emitting device may be provided.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A heterocyclic compound represented by Formula 1:

Formula 1

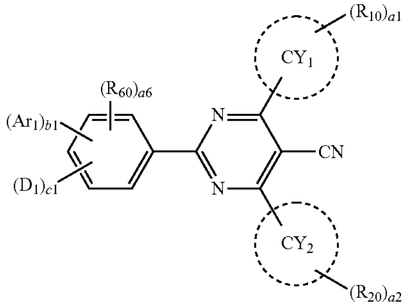

Formula 2

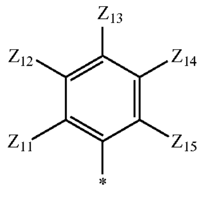

-continued

Formula 3

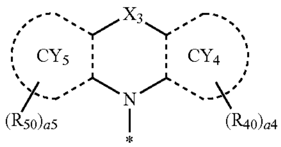

wherein, in Formula 1, $Ar_1$ is a group represented by Formula 2, and b1 is an integer from 1 to 3, in Formula 1, $D_1$ is a group represented by Formula 3, and c1 is an integer from 1 to 3, in Formulae 1 and 3, ring $CY_1$, ring $CY_2$, ring $CY_4$, and ring $CY_5$ are each independently a π electron-rich $C_3$-$C_{60}$ cyclic group, in Formula 3, $X_3$ is a single bond, O, S, $N(R_{31})$, $C(R_{31})(R_{32})$, $Si(R_{31})(R_{32})$, or $Ge(R_{31})(R_{32})$, wherein a group represented by

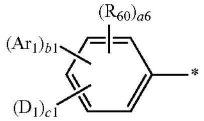

in Formula 1 is represented by Formula 1-19 or 1-24:

1-19

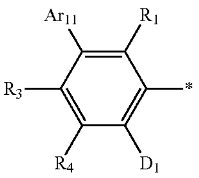

1-24

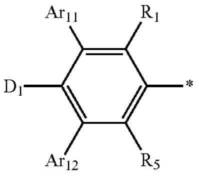

wherein, in Formulae 19 and 1-24, $R_1$, $R_3$, $R_4$ and $R_5$ are each understood by referring to the description of $R_{60}$, $Ar_{11}$ and $Ar_{12}$ are each understood by referring to the description of $Ar_1$, and

* indicates a binding site to an adjacent atom, wherein a group represented by Formula 3 is represented by one of Formulae 3-1 to 3-6:

3-1

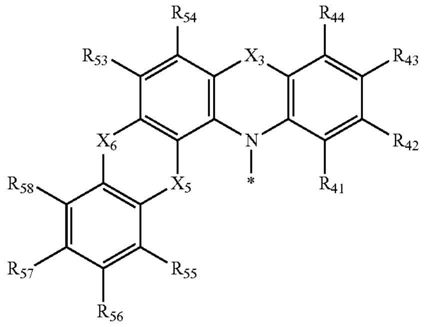

3-2

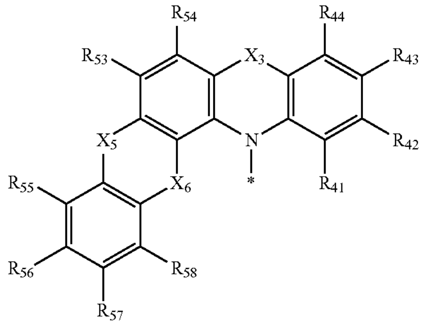

3-3

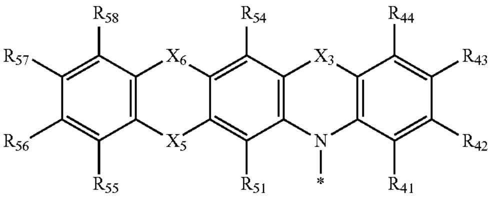

3-4

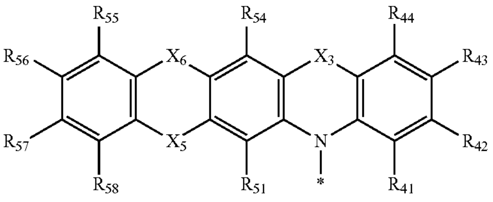

3-5

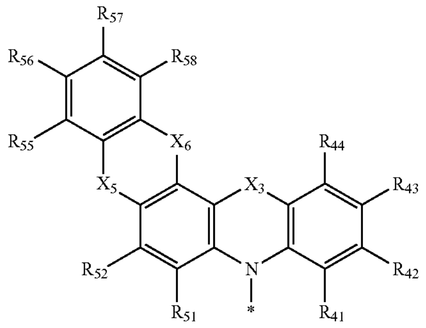

-continued

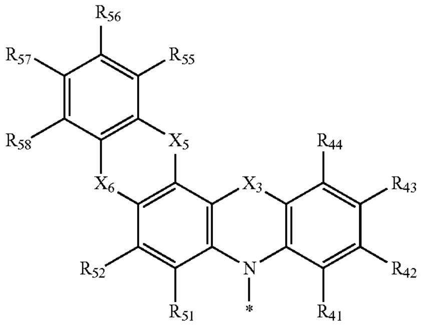

3-6 wherein, in Formulae 3-1 to 3-6, $X_5$ is O, S, $N(R_{59})$, $Si(R_{59a})(R_{59b})$, or $Ge(R_{59a})(R_{59b})$, $X_6$ is a single bond, O, S, $N(R_{59c})$, $C(R_{59a})(R_{59e})$, $Si(R_{59a})(R_{59e})$, or $Ge(R_{59a})(R_{59e})$, $R_{41}$ to $R_{44}$ are each understood by referring to the description of $R_{40}$, $R_{51}$ to $R_{59}$, and $R_{59a}$ to $R_{59e}$ are each understood by referring to the description of $R_{50}$, and

* indicates a binding site to an adjacent atom, in Formulae 1 and 2, $R_{10}$, $R_{20}$, $R_{60}$, and $Z_{11}$ to $Z_{15}$ are each independently hydrogen, deuterium, —F, —Cl, —Br, —I, —$SF_5$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$Ge(Q_3)(Q_4)(Q_5)$, —$B(Q_6)(Q_7)$, —$P(=O)(Q_8)(Q_9)$, or —$P(Q_8)(Q_9)$, in Formula 3, $R_{31}$, $R_{32}$, $R_{40}$, and $R_{50}$ are each independently:

hydrogen, deuterium, —F, or a cyano group; or a $C_1$-$C_{60}$ alkyl group, a $C_1$-$C_{60}$ alkoxy group, a n electron-rich $C_3$-$C_{60}$ cyclic group, or a pyridinyl group, each unsubstituted or substituted with deuterium, —F, a cyano group, a $C_1$-$C_{60}$ alkyl group, a $C_1$-$C_{60}$ alkoxy group, a π electron-rich $C_3$-$C_{60}$ cyclic group, a pyridinyl group, a biphenyl group, a terphenyl group, or any combination thereof, in Formulae 1 and 3, a1, a2, a4, and a5 are each independently an integer from 0 to 20, in Formula 1, a6 is an integer from 0 to 3, in Formulae 2 and 3, * indicates a binding site to an adjacent atom, and a substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$Ge(Q_{13})(Q_{14})(Q_{15})$, —$B(Q_{16})(Q_{17})$, —$P(=O)(Q_{18})(Q_{19})$, —$P(Q_{18})(Q_{19})$, or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$Ge(Q_{23})(Q_{24})(Q_{25})$, —$B(Q_{26})(Q_{27})$, —$P(=O)(Q_{28})(Q_{29})$, —$P(Q_{28})(Q_{29})$, or any combination thereof;

—N($Q_{31}$)($Q_{32}$), —Si($Q_{33}$)($Q_{34}$)($Q_{35}$), —Ge($Q_{33}$)($Q_{34}$)($Q_{35}$), —B($Q_{36}$)($Q_{37}$), —P(=O)($Q_{38}$)($Q_{39}$), or —P($Q_{38}$)($Q_{39}$); or any combination thereof, wherein $Q_1$ to $Q_9$, $Q_{11}$ to $Q_{19}$, $Q_{21}$ to $Q_{29}$, and $Q_{31}$ to $Q_{39}$ are each independently: hydrogen; deuterium; —F; —Cl; —Br; —I; a hydroxyl group; a cyano group; a nitro group; an amidino group; a hydrazine group; a hydrazone group; a carboxylic acid group or a salt thereof; a sulfonic acid group or a salt thereof; a phosphoric acid group or a salt thereof; a $C_1$-$C_{60}$ alkyl group unsubstituted or substituted with deuterium, a $C_1$-$C_{60}$ alkyl group, a $C_6$-$C_{60}$ aryl group, or any combination thereof; a $C_2$-$C_{60}$ alkenyl group; a $C_2$-$C_{60}$ alkynyl group; a $C_1$-$C_{60}$ alkoxy group; a $C_3$-$C_{10}$ cycloalkyl group; a $C_1$-$C_{10}$ heterocycloalkyl group; a $C_3$-$C_{10}$ cycloalkenyl group; a $C_1$-$C_{10}$ heterocycloalkenyl group; a $C_6$-$C_{60}$ aryl group unsubstituted or substituted with deuterium, a $C_1$-$C_{60}$ alkyl group, a $C_6$-$C_{60}$ aryl group, or any combination thereof; a $C_6$-$C_{60}$ aryloxy group; a $C_6$-$C_{60}$ arylthio group; a $C_1$-$C_{60}$ heteroaryl group; a monovalent non-aromatic condensed polycyclic group; or a monovalent non-aromatic condensed heteropolycyclic group.

2. The heterocyclic compound of claim 1, wherein b1 in Formula 1 is 1 or 2.

3. The heterocyclic compound of claim 1, wherein c1 in Formula 1 is 1.

4. The heterocyclic compound of claim 1, wherein ring $CY_1$, ring $CY_2$, ring $CY_4$, and ring $CY_5$ in Formulae 1 and 3 are each independently a benzene group, a naphthalene group, a phenanthrene group, a furan group, a thiophene group, a pyrrole group, a cyclopentene group, a silole group, a germole group, a benzofuran group, a benzothiophene group, an indole group, an indene group, a benzosilole group, a benzogermole group, a dibenzofuran group, a dibenzothiophene group, a carbazole group, a fluorene group, a dibenzosilole group, a dibenzogermole group, an indolodibenzofuran group, an indolodibenzothiophene group, an indolocarbazole group, an indolofluorene group, an indolodibenzosilole group, an indolodibenzogermole group, or a 9,10-dihydroacridine group.

5. The heterocyclic compound of claim 1, wherein $X_3$ in Formula 3 is a single bond or C($R_{31}$)($R_{32}$).

6. The heterocyclic compound of claim 1, wherein $R_{10}$, $R_{20}$, $R_{60}$, and $Z_{11}$ to $Z_{15}$ in Formulae 1 and 2 are each independently:

hydrogen, deuterium, —F, or a cyano group; or a $C_1$-$C_{60}$ alkyl group, a $C_1$-$C_{60}$ alkoxy group, a π electron-rich $C_3$-$C_{60}$ cyclic group, or a pyridinyl group, each unsubstituted or substituted with deuterium, —F, a cyano group, a $C_1$-$C_{60}$ alkyl group, a $C_1$-$C_{60}$ alkoxy group, a π electron-rich $C_3$-$C_{60}$ cyclic group, a pyridinyl group, a biphenyl group, a terphenyl group, or any combination thereof.

7. An organic light-emitting device comprising:

a first electrode;

a second electrode; and an organic layer located between the first electrode and the second electrode and comprising an emission layer, wherein the organic layer comprises the heterocyclic compound of claim 1.

8. The organic light-emitting device of claim 7, wherein the heterocyclic compound is included in the emission layer.

9. The organic light-emitting device of claim 8, wherein the emission layer comprises a host and an emitter, the host is different from the emitter, and the heterocyclic compound is included in the emitter.

10. The organic light-emitting device of claim 9, wherein a ratio of emission components emitted from the heterocyclic compound is in a range of about 70 percent (%) to about 100%, based on total emission components emitted from the emission layer.

11. The organic light-emitting device of claim 9, wherein the emission layer emits blue light.

12. The organic light-emitting device of claim 9, wherein the host does not comprise a transition metal.

13. The organic light-emitting device of claim 8, wherein the emission layer comprises a host, an emitter, and a sensitizer, wherein the host, the emitter, and the sensitizer are different from each other, and the heterocyclic compound is included in the sensitizer.

14. The organic light-emitting device of claim 13, wherein a ratio of emission components emitted from the emitter is in a range of about 70% to about 100%, based on total emission components emitted from the emission layer.

15. The organic light-emitting device of claim 13, wherein the emitter is a fluorescence emitter.

16. An electronic apparatus comprising the organic light-emitting device of claim 7.

17. The heterocyclic compound of claim 1, represented by one of the following compounds:

95

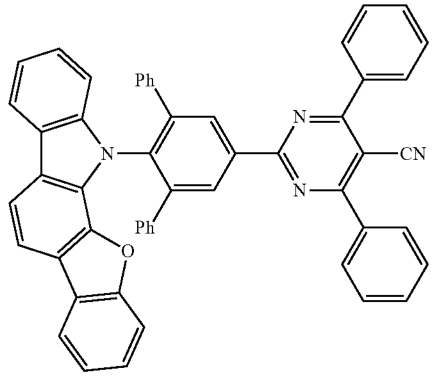

119

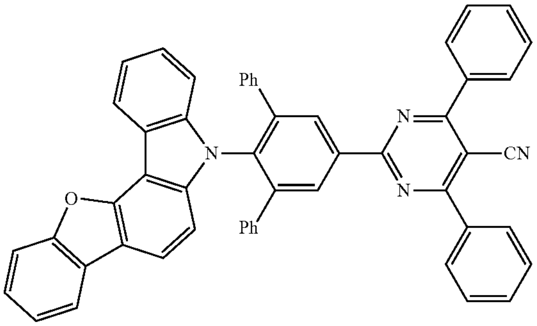

-continued
143
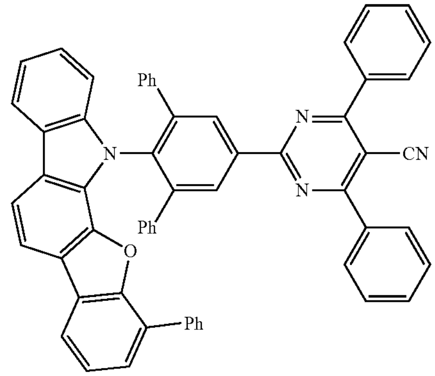
167
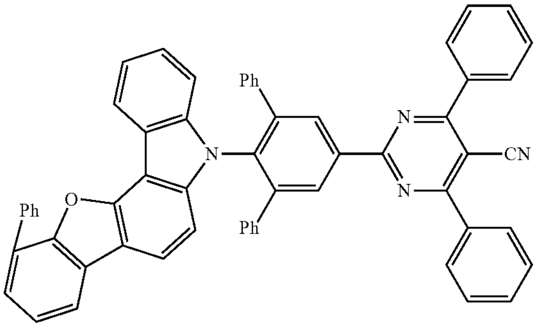
169
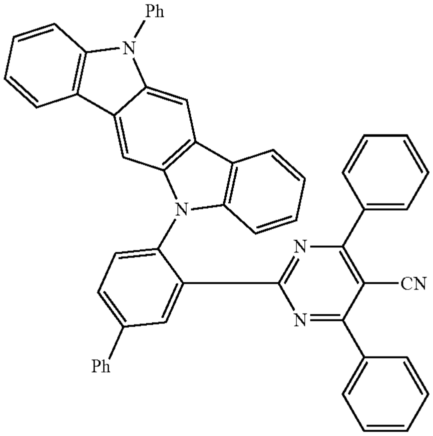
171
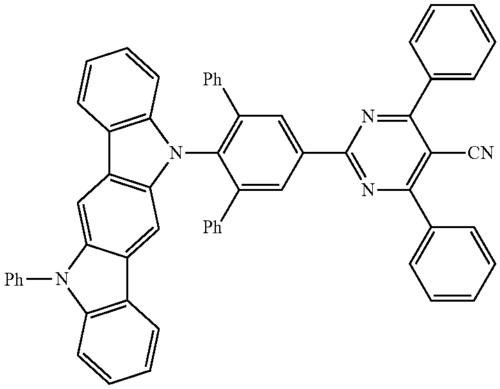
-continued
172
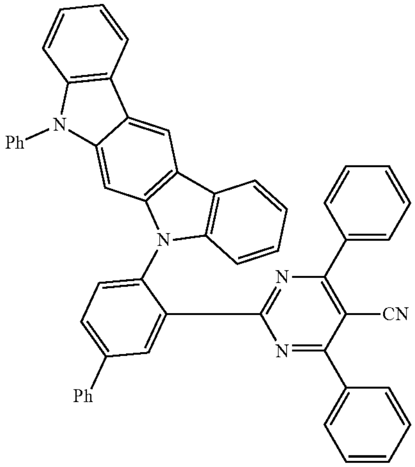
174
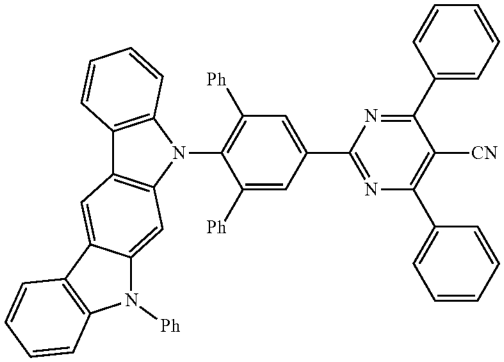
175
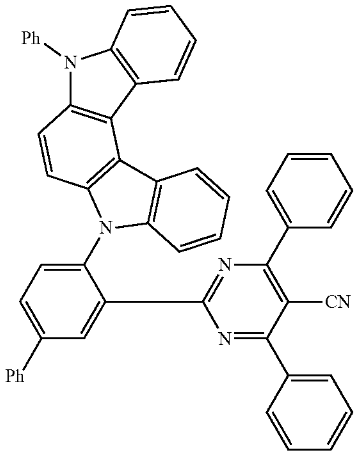
177
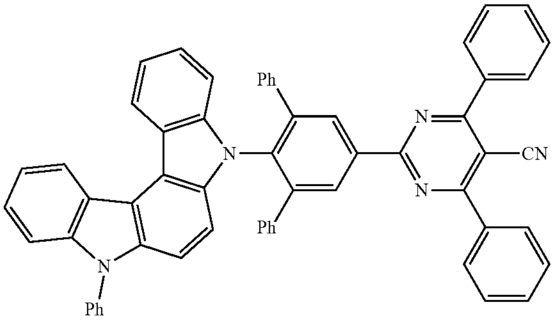

178
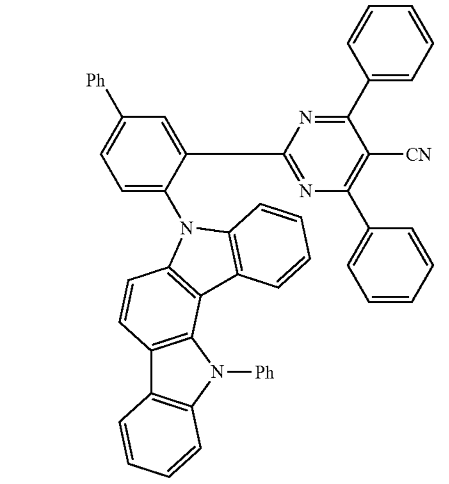
180
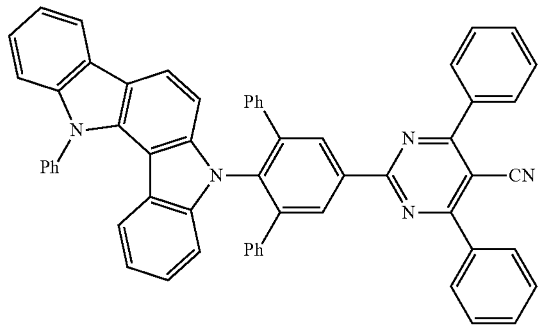
181
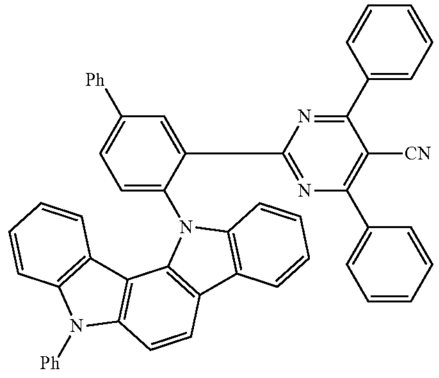
183
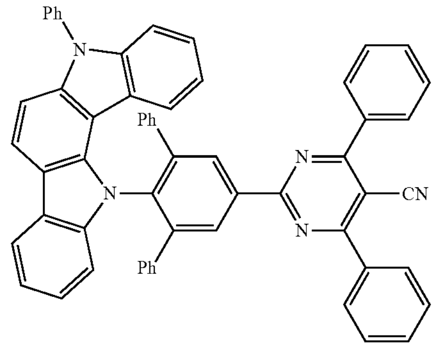
184
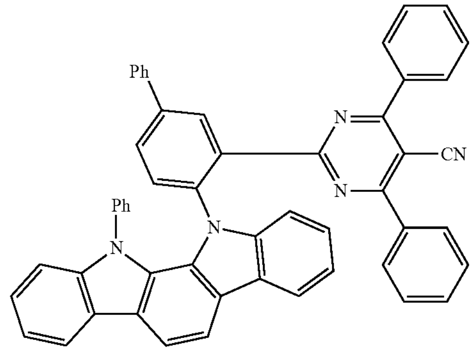
186
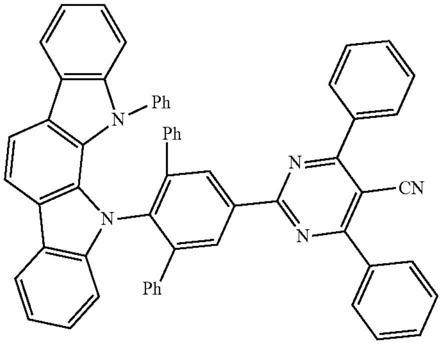
187
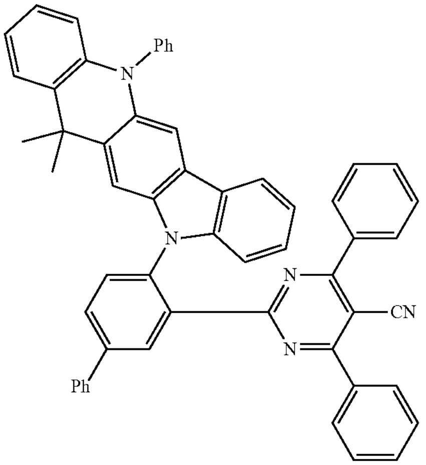
189
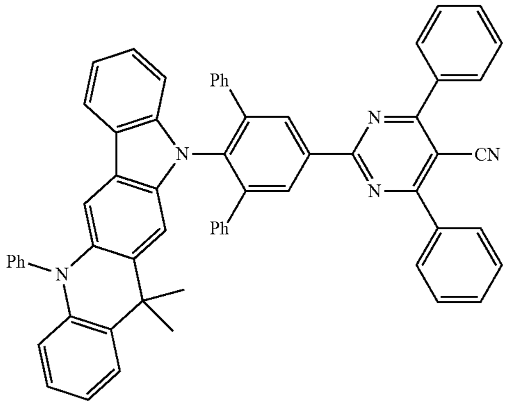

-continued
190
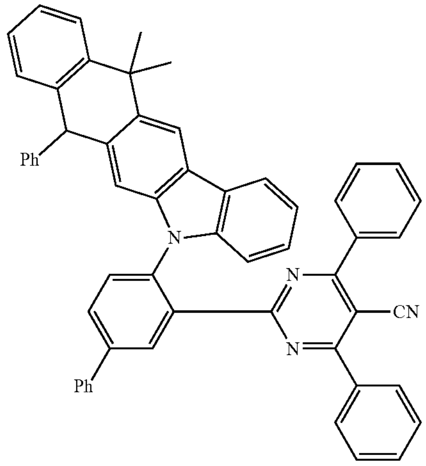
192
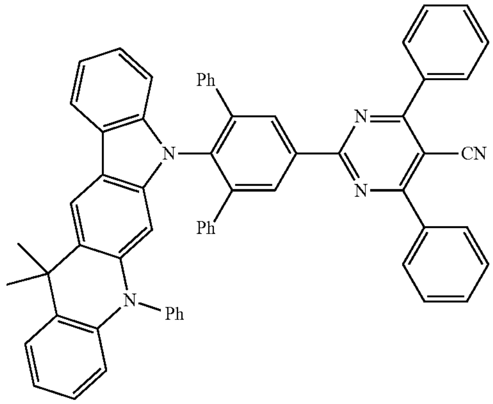
195
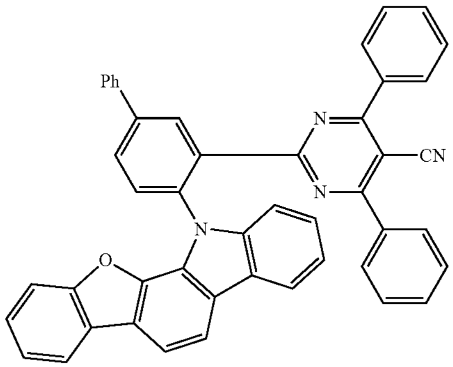
-continued
199
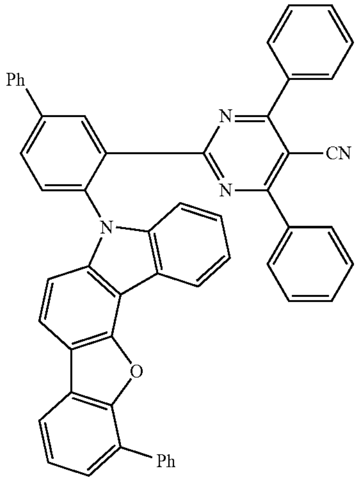
201
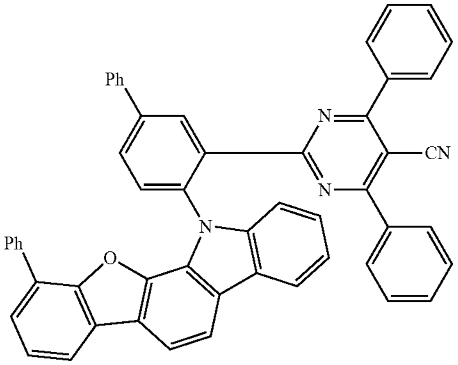
203
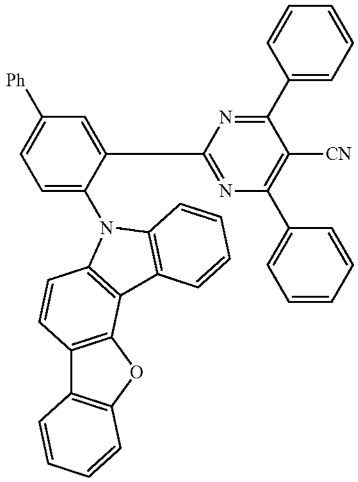

-continued
207
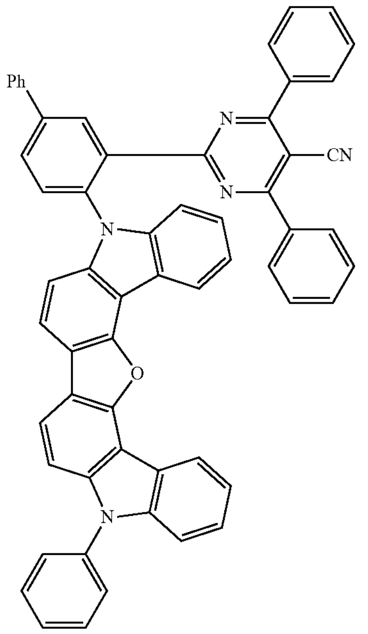
209
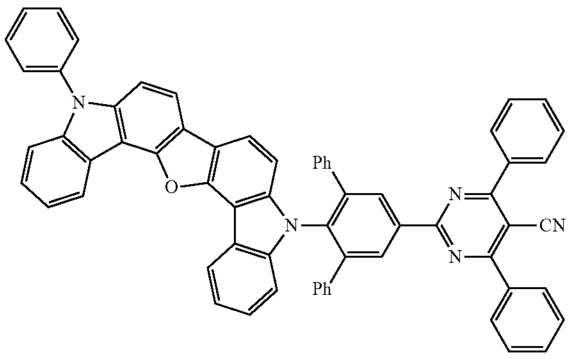
210
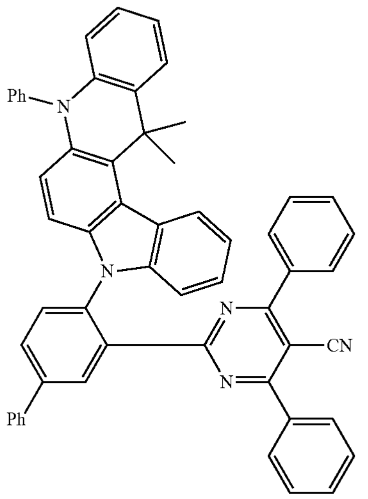
-continued
212
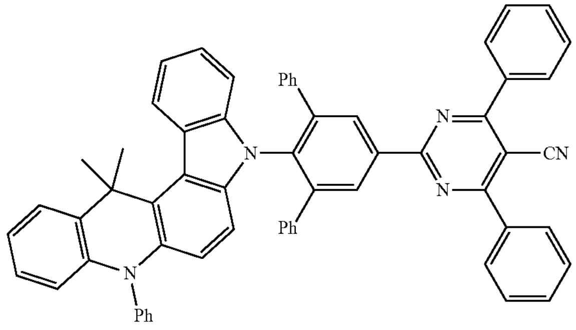
213
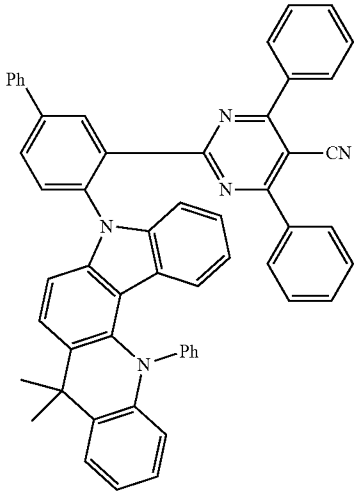
215
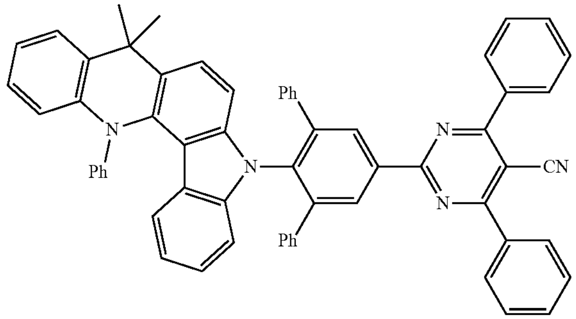
216
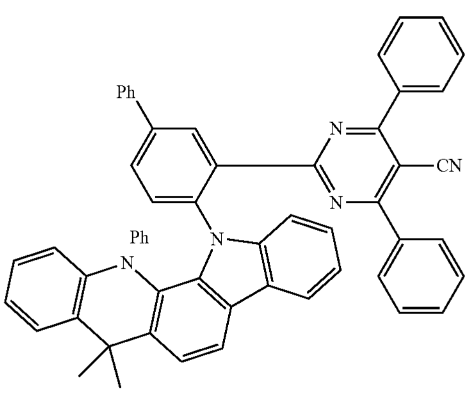

-continued
218
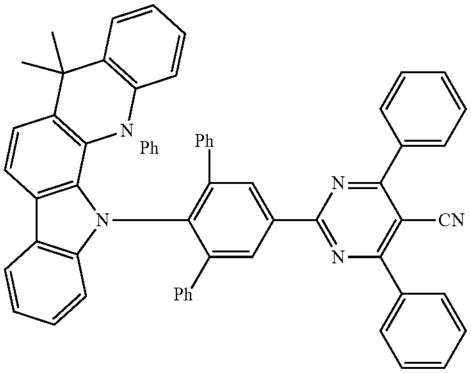
219
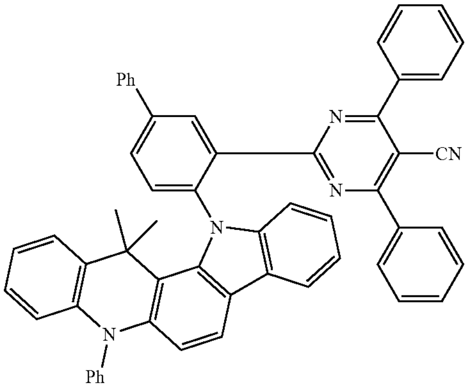
221
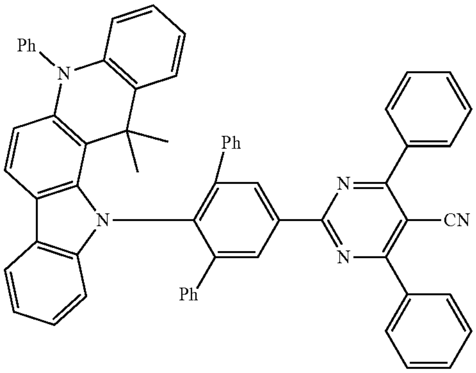
222
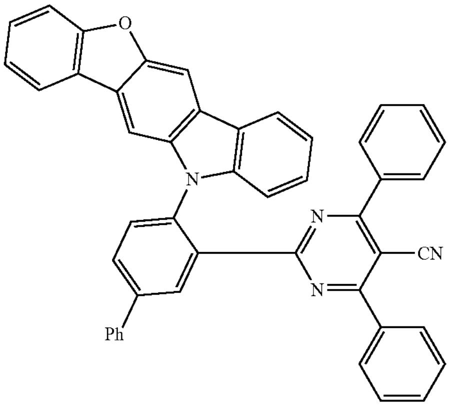
-continued
224
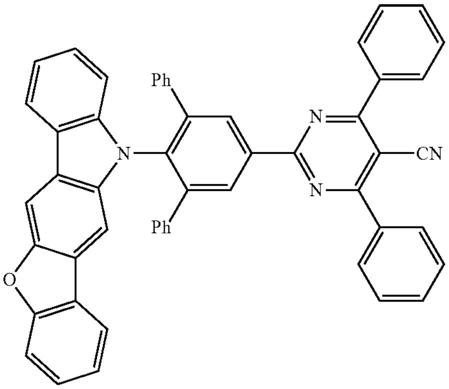
225
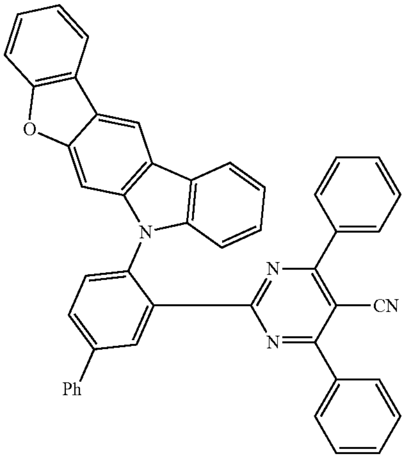
227
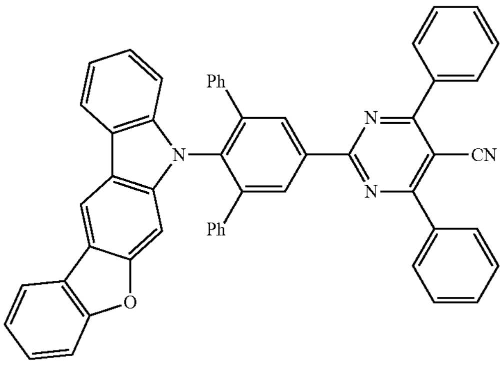

-continued
228
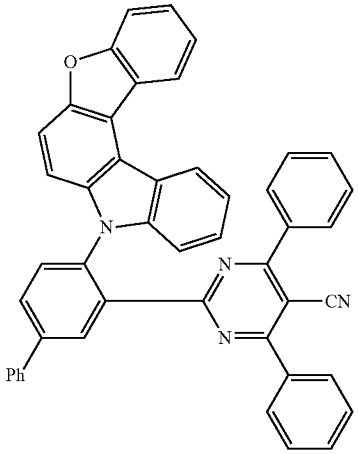
230
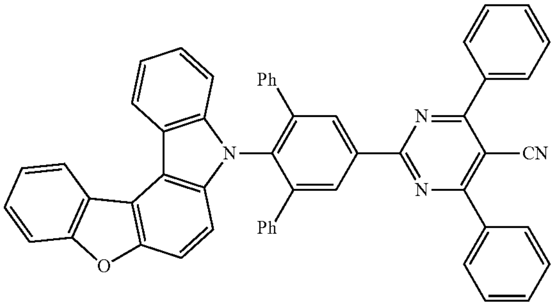
231
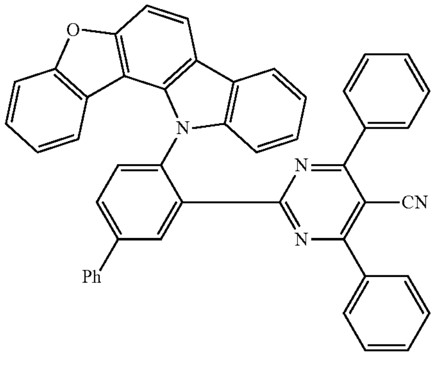
233
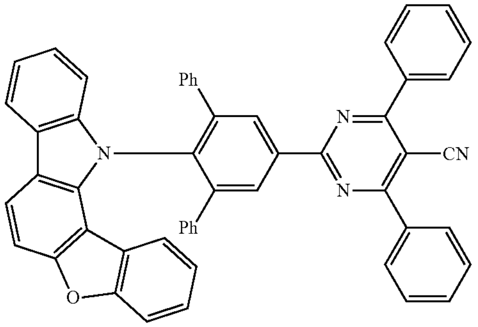
-continued
234
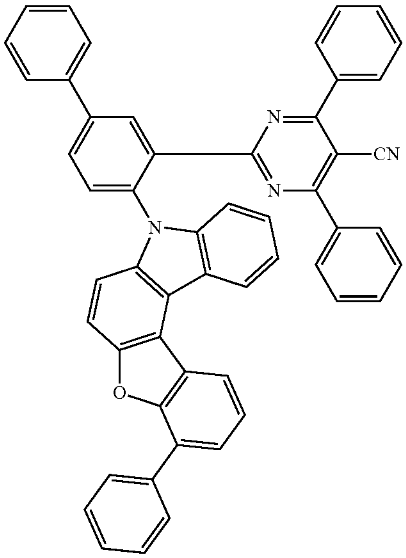
235
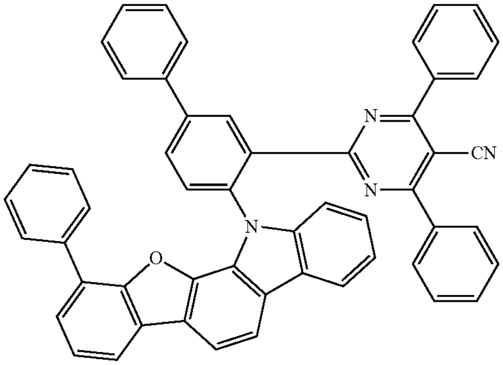
236
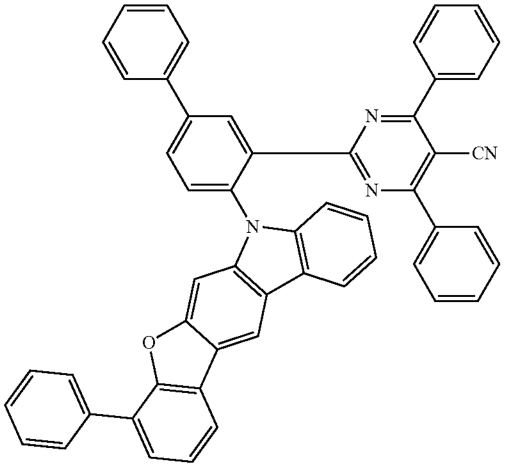

-continued
237
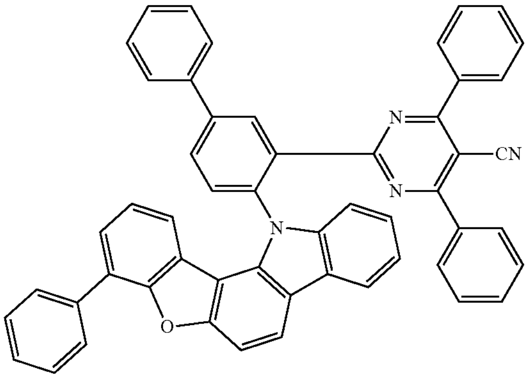
-continued
238
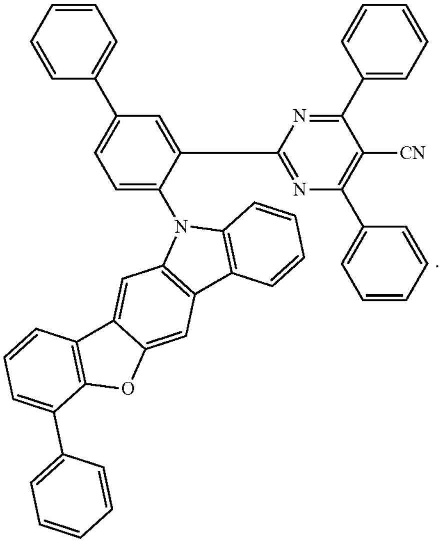
.
* * * * *